US010766869B2

(12) United States Patent
Davies et al.

(10) Patent No.: US 10,766,869 B2
(45) Date of Patent: Sep. 8, 2020

(54) TRIAZOLES FOR THE TREATMENT OF DEMYELINATING DIEASES

(71) Applicant: Vertex Pharmaceuticals Incorporated, Boston, MA (US)

(72) Inventors: Robert J. Davies, Arlington, MA (US); Jingrong Cao, Newton, MA (US); Meghan Elise Cockerill, Boston, MA (US); Philip Noel Collier, Hingham, MA (US); Elisabeth Doyle, Worcester, MA (US); James Daniel Frantz, Belmont, MA (US); Huai Gao, Arlington, MA (US); Brian Anthony Goldman, Brookline, MA (US); Ronald Lee Grey, Jr., Mansfield, MA (US); Anne-Laure Grillot, Milton, MA (US); Wenxin Gu, Concord, MA (US); James A. Henderson, Cambridge, MA (US); Raul Eduardo Krauss, Chestnut Hill, MA (US); Adrianne Lynn Kolpak, Watertown, MA (US); Yusheng Liao, Lexington, MA (US); Sanjay Shivayogi Magavi, Cambridge, MA (US); David Messersmith, Somerville, MA (US); Albert Charles Pierce, Cambridge, MA (US); Emanuele Perola, Brookline, MA (US); Elizabeth Jin-Sun Ryu, Newton, MA (US); Joshua Syken, Jamaica Plain, MA (US); Jian Wang, Newton, MA (US); Michael Paul DeNinno, Gales Ferry, CT (US); Francois Maltais, Tewksbury, MA (US)

(73) Assignee: VERTEX PHARMACEUTCALS INCORPORATED, Boston, MA (US)

(*) Notice: Subject to any disclaimer, the term of this patent is extended or adjusted under 35 U.S.C. 154(b) by 0 days.

(21) Appl. No.: 16/162,835

(22) Filed: Oct. 17, 2018

(65) Prior Publication Data
US 2019/0185436 A1    Jun. 20, 2019

Related U.S. Application Data

(62) Division of application No. 15/173,177, filed on Jun. 3, 2016, now Pat. No. 10,118,904.
(Continued)

(51) Int. Cl.
*A61K 31/496* (2006.01)
*A61K 31/4196* (2006.01)
(Continued)

(52) U.S. Cl.
CPC ........ *C07D 249/14* (2013.01); *A61K 31/4196* (2013.01); *A61K 31/4439* (2013.01);
(Continued)

(58) Field of Classification Search
CPC ........ A61P 43/00; A61P 25/28; A61K 31/496; A61K 31/4196; A61K 31/454; A61K 31/5377
See application file for complete search history.

(56) References Cited

U.S. PATENT DOCUMENTS 6,596,747 B2   7/2003  Liu
7,226,920 B2   6/2007  Arnost
(Continued)

FOREIGN PATENT DOCUMENTS

EP     1921073 A1      5/2008
WO   WO0222601 A1     3/2002
(Continued)

OTHER PUBLICATIONS

Murphy et al. Bioengineered 4:3, 140-146; May/Jun. 2013; (Year: 2013).*
(Continued)

*Primary Examiner* — Emily A Bernhardt
(74) *Attorney, Agent, or Firm* — Barnes & Thornburg LLP

(57) ABSTRACT

The invention relates to triazole compounds of formula I and I' or pharmaceutically acceptable salts thereof, useful as modulators of demyelinating diseases:

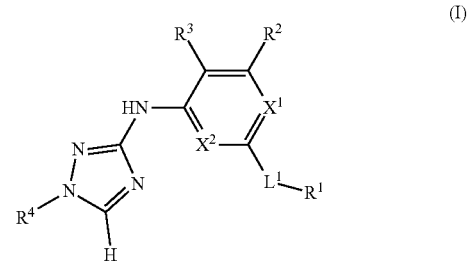

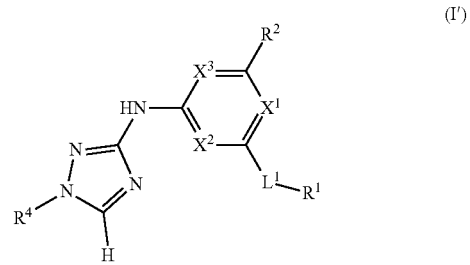

The invention also provides pharmaceutically acceptable compositions comprising the compounds of the invention, methods of using the compositions and kits thereof in the treatment of various demyelinating and neurodegenerative diseases, including multiple sclerosis.

22 Claims, No Drawings

Related U.S. Application Data

(60) Provisional application No. 62/171,784, filed on Jun. 5, 2015, provisional application No. 62/326,471, filed on Apr. 22, 2016.

(51) Int. Cl.
| | |
|---|---|
| *A61K 31/454* | (2006.01) |
| *A61K 31/5377* | (2006.01) |
| *A61P 25/28* | (2006.01) |
| *C07D 249/14* | (2006.01) |
| *C07D 405/14* | (2006.01) |
| *C07D 401/04* | (2006.01) |
| *C07D 401/12* | (2006.01) |
| *C07D 403/04* | (2006.01) |
| *C07D 403/14* | (2006.01) |
| *C07D 405/12* | (2006.01) |
| *A61K 31/4439* | (2006.01) |
| *A61K 31/497* | (2006.01) |
| *C07D 403/12* | (2006.01) |

(52) U.S. Cl.
CPC .......... *A61K 31/454* (2013.01); *A61K 31/496* (2013.01); *A61K 31/497* (2013.01); *A61K 31/5377* (2013.01); *C07D 401/04* (2013.01); *C07D 401/12* (2013.01); *C07D 403/04* (2013.01); *C07D 403/12* (2013.01); *C07D 403/14* (2013.01); *C07D 405/12* (2013.01); *C07D 405/14* (2013.01)

(56) References Cited

U.S. PATENT DOCUMENTS

| | | | |
|---|---|---|---|
| 7,598,245 B2 | 10/2009 | Arnost | |
| 10,118,904 B2 * | 11/2018 | Davies | ............... A61K 31/4439 |
| 2014/0088099 A1 | 3/2014 | Ren | |

FOREIGN PATENT DOCUMENTS

| | | |
|---|---|---|
| WO | WO0222607 A1 | 3/2002 |
| WO | WO05013982 A1 | 2/2005 |
| WO | WO06047256 A1 | 5/2006 |
| WO | WO07056221 A2 | 5/2007 |
| WO | WO07059299 A1 | 5/2007 |
| WO | WO08057940 A1 | 5/2008 |
| WO | WO08077086 A1 | 6/2008 |
| WO | WO08083356 A1 | 7/2008 |
| WO | WO08137619 A2 | 11/2008 |
| WO | WO08147626 A2 | 12/2008 |
| WO | WO09145814 A2 | 12/2009 |
| WO | WO13052394 A1 | 4/2013 |
| WO | WO14070978 A1 | 5/2014 |
| WO | WO15094997 A1 | 6/2015 |

OTHER PUBLICATIONS

Blakemore et al. "The origin of remyelinating cells in the central nervous system", J. of Neuroimmunology, 98, 69-76, 1999.

Compston, A., et al., "Multiple sclerosis", The Lancet, vol. 359, 1221-1231, 2002.

Kremer, D. et al., "Pushing Forward: Remyelination as the New Frontier in CNS Diseases", Trends in Neurosciences, vol. 39, No. 4, 246-263, 2016.

Franklin, R., et al., "Remyelination in the CNS: from biology to therapy" Nature Reviews/Neuroscience, vol. 9, 839-855, 2008.

Stangel, M. et al., "Remyelinating strategies for the treatment of multiple sclerosis", Progress in Neurobiology, 68, 361-376, 2002.

Najm, F. J. et al., "Drug-based modulation of endogenous stem cells promotes functional remyelination in vivo", Nature (Letter), published online Apr. 20, 2015, doi:10.1038/nature14335.

Mei, F. et al. "Micropillar arrays as a high-throughput screening platform for therapeutics in multiple sclerosis", Nature Medicine, vol. 20, No. 8, 954-961, 2014.

Merrill, J.E., et al. "Mechanisms of damage to myelin and oligodendrocytes and their relevance to disease", Neuropathology and Applied Neurobiology (1999), 25, 435-458.

\* cited by examiner

TRIAZOLES FOR THE TREATMENT OF DEMYELINATING DIEASES

RELATED APPLICATIONS

This application is a divisional of U.S. patent application Ser. No. 15/173,177, filed Jun. 3, 2016, the entire contents of which is hereby incorporated herein by reference. U.S. application Ser. No. 15/173,177 claims the benefit of the filing date under 35 U.S.C. § 119(e) of Provisional U.S. Patent Application Ser. No. 62/171,784, filed Jun. 5, 2015, and Provisional U.S. Patent Application Ser. No. 62/326,471, filed Apr. 22, 2016, and which are hereby incorporated by reference.

BACKGROUND OF THE INVENTION

Multiple sclerosis (MS) is an inflammatory neurodegenerative disease of the central nervous system, characterized by myelin loss and degeneration of axons (see, Blakemore, et al., *J. of Neuroimmunology*, 98, 69-76, 1999). Activation and CNS infiltration of the peripheral immune system is typical in early stages of the disease, but can become less prevalent as disease progresses.

A hallmark of MS is loss of myelin, accompanied by the death of associated oligodendrocytes (see, Merrill, J. E. et al., *Neuropathology and Applied Neurobiology*, 25, 435-458, 1999). Myelin, which is produced by oligodendrocytes, ensheathes axons and dramatically increases conduction velocity of neural impulses while providing trophic support to the neuron. Myelin is thought to regenerate early in disease, as oligodendrocyte progenitor cells (OPCs) proliferate and generate new myelinating oligodendrocytes in response to demyelination events. As the disease progresses the regenerative capacity of the OPCs becomes less robust, and axons remain chronically demyelinated. Chronic demyelination is thought to underlie axon loss, as loss of trophic support combined with the metabolic stress of transmitting impulses along a demyelinated membrane can lead to a breakdown of axonal integrity and permanent damage to the demyelinated circuit. In addition, exposure of a demyelinated axon to an inflammatory milieu, including infiltrating immune cells and activated microglia cells, is also thought to produce permanent damage and axonal loss. Axon loss as a result of demyelination is thought to underlie long term disease progression and disability in MS patients (see, Compston, et al., *The Lancet*, Vol. 359, 1221-1231, 2002 and D. Kremer et al, *Trends in Neurosciences*, Vol. 39, No. 4, 246-263, 2016).

The loss of remyelinating capacity in MS is not well understood, but is thought to involve a block in the differentiation capacity of OPCs, or the absence of a necessary signal present in the cell environment of the demyelinating lesion or in the demyelinated axons (see, R. Franklin et al., *Nature Reviews/Neuroscience*, Vol. 9, 839-855, 2008). The OPC cell population is prevalent in MS patients, but fails to generate new myelin in response to demyelination. Thus, a compound that can promote differentiation and myelination of OPCs should function to restore this regenerative capacity and blunt or reverse the degenerative effects of MS (see, Stangel, M. et al., *Progress in Neurobiology*, 68, 361-376, 2002, Nalm, F. J. et al., *Nature* (Letter), published online 20 Apr. 2015, doi:10.1038/nature14335). Such an agent could both increase the function of neurons and provide trophic support to enhance their survival (see, Mei, F. et al. *Nature Medicine*, Vol. 20, No. 8, 954-961, 2014).

Leukodystrophies are degenerative white matter diseases characterized by dysmyelination or demyelination. Multiple genetic or metabolic disorders can lead to progressive white matter damage in pediatric or adult populations resulting in severe motor or cognitive deficits, mental retardation or death. A compound that can delay myelin damage or promote repair of demyelinated axons could significantly alter the course of leukodystrophies and improve their outcome. Such a compound could be also useful in combination with other therapies that can correct the disease-specific defect, metabolic, genetic or other, responsible for initiating or maintaining the disease in order to accelerate repair, restore function or prevent further damage.

Hypoxic-ischemic insults leading to reduced oxygenation and blood supply into the brain can cause severe damage to OPCs, and demyelination. Periventricular leukomalacia is a condition characterized by toxic death of OPCs in the periventricular region and leading to severe dysmyelination and demyelination. This pathology has been proposed as the root cause of cerebral palsy, a life-long debilitating CNS disorder characterized by various motor and/or cognitive deficits of variable intensity. A compound promoting differentiation of surviving OPCs and remyelination of damaged areas could be used for the treatment or prevention of cerebral palsy in vulnerable infant populations.

Current therapies for MS are immunomodulatory in nature and do not directly promote repair. In addition, some of these immunomodulatory agents can leave patients vulnerable to opportunistic infection or neoplasia. Thus, there remains a need for compounds, such as those of the present invention, that can promote differentiation and myelination of OPCs and lead to the repair of demyelinated axons. Such a compound could also be useful in combination with existing or experimental immunomodulating and other relevant therapies to treat MS and other neurological and demyelinating diseases.

SUMMARY OF THE INVENTION

The present invention provides compounds or a pharmaceutically acceptable salt thereof and the methods, compositions and kits disclosed herein for treating or lessening the severity of, in a subject, a disease or disorder selected from a demyelinating disease, central pontine myelinolysis, a nerve injury disease or disorder, a leukoencephalopathy or a leukodystrophy. These compounds have the general formula I and I':

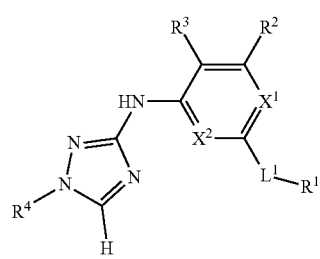

I

-continued

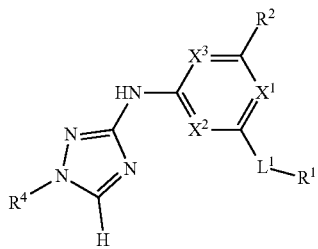

or a pharmaceutically acceptable salt thereof.

In one aspect, the present invention provides compounds of formula (I')

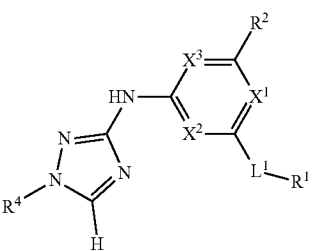

or a pharmaceutically acceptable salt thereof, wherein:

$X^1$ is CH or N;

$X^2$ is $CR^{X2}$ or N;

$X^3$ is $CR^3$ or N;

where $R^3$ and $R^{X2}$ are each independently selected from the group consisting of hydrogen, halogen, $C_{1-4}$alkyl, $C_{1-4}$haloalkyl, —$OC_{1-4}$alkyl, and cyano;

provided that $X^1$, $X^2$, and $X^3$ are not simultaneously N, $X^2$ and $X^3$ are not simultaneously N, and $X^1$ and $X^3$ are not simultaneously N;

$L^1$ is a bond, —O—, —$NR^5$—, —$NR^5$—$C_{1-4}$alkylene-, —O—$C_{1-4}$alkylene-, —$C_{1-4}$alkylene-, or —C(O)—, wherein $R^5$ is hydrogen or $C_{1-4}$alkyl;

$R^1$ is -$G^1$-$L^2$-$R^6$, -$G^1$-$L^2$-$R^7$, $G^2$, $G^3$, $G^4$, $G^5$, $G^6$, or -=-$G^5$;

$G^1$ is i) a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms, $G^1$ being optionally substituted with 1-4 substituents independently selected from the group consisting of $C_{1-4}$alkyl, $C_{1-4}$haloalkyl, halogen, hydroxyl, and oxo; or ii) a 3- to 8-membered cycloalkyl optionally substituted with 1-4 substituents independently selected from the group consisting of $C_{1-4}$alkyl, $C_{1-4}$haloalkyl, halogen, hydroxyl, and oxo;

$L^2$ is a bond, a —$C_{1-3}$alkylene-, or —C(O)—;

$R^6$ is a) a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms and being optionally substituted with 1-4 substituents independently selected from the group consisting of $C_{1-4}$alkyl, $C_{1-4}$haloalkyl, —$CH_2S(O)_2$phenyl, halogen, hydroxyl, and oxo; b) a 5- or 6-membered monocyclic heteroaryl containing 1-3 heteroatoms independently selected from nitrogen, oxygen, and sulfur, the monocyclic heteroaryl being optionally substituted with 1-3 substituents independently selected from the group consisting of $C_{1-4}$alkyl, $C_{1-4}$haloalkyl, halogen, and hydroxyl; c) a 7- to 12-membered spiro heterocycle comprising a first ring and a second ring, the first ring being a 4- to 8-membered monocyclic heterocycle containing 1-2 heteroatoms independently selected from nitrogen and oxygen and being attached to $L^2$, the second ring being a $C_{3-8}$cycloalkyl or a 4- to 8-membered monocyclic heterocycle containing 1-2 oxygen atoms wherein two atoms of the second ring are attached to one carbon of the first ring to form a spirocycle optionally substituted with 1-4 substituents independently selected from the group consisting of $C_{1-4}$alkyl, $C_{1-4}$haloalkyl, halogen, hydroxyl, and oxo; or d) a 7- to 12-membered fused bicyclic heterocycle containing 1-3 heteroatoms independently selected from oxygen, nitrogen, and sulfur and being optionally substituted with 1-4 substituents independently selected from the group consisting of $C_{1-4}$alkyl, $C_{1-4}$haloalkyl, halogen, hydroxyl, and oxo;

$R^7$ is a) a 3- to 8-membered cycloalkyl optionally substituted with 1-4 substituents independently selected from the group consisting of $C_{1-4}$alkyl, $C_{1-4}$haloalkyl, halogen, hydroxyl, —C(O)O$C_{1-4}$alkyl, —C(O)OH, and oxo; or b) phenyl optionally substituted with 1-4 substituents independently selected from the group consisting of $C_{1-4}$alkyl, $C_{1-4}$haloalkyl, halogen, hydroxyl, —C(O)O$C_{1-4}$alkyl, and —C(O)OH;

$G^2$ is a 4- to 8-membered monocyclic heterocycle containing 1-3 heteroatoms independently selected from oxygen, nitrogen, and sulfur, the monocyclic heterocycle optionally containing one double bond and/or a $C_{1-3}$alkylene bridge between two non-adjacent ring atoms, $G^2$ being optionally substituted with 1-4 substituents independently selected from the group consisting of $C_{1-4}$alkyl, $C_{1-4}$haloalkyl, halogen, hydroxyl, oxo, cyano, —C(O)$C_{1-4}$alkyl, —C(O)$C_{3-6}$cycloalkyl, —C(O)O$C_{1-4}$alkyl, —C(O)O$C_{1-4}$haloalkyl, —C(O)$NH_2$, —C(O)NH($C_{1-4}$alkyl), —C(O)N($C_{1-4}$alkyl)($C_{1-4}$alkyl), —C(O)NH(—$C_{1-6}$alkylene-O$C_{1-4}$alkyl), —C(O)N($C_{1-4}$alkyl)(—$C_{1-6}$alkylene-O$C_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-O$C_{1-4}$alkyl), —N($C_{1-4}$alkyl)(—$C_{1-6}$alkylene-O$C_{1-4}$alkyl), —NH(—$C_{1-6}$alkylene-OH), —N($C_{1-4}$alkyl)(—$C_{1-6}$alkylene-OH), —C(O)$C_{1-4}$haloalkyl, —O$C_{1-4}$alkyl, —$C_{1-6}$alkylene-O$C_{1-4}$alkyl, —$C_{1-6}$alkylene-OH, —$C_{1-6}$alkylene substituted by 2 groups independently selected from hydroxyl and —OC(O)$C_{1-4}$alkyl, —$C_{1-6}$alkylene-$NH_2$, —$C_{1-6}$alkylene-NH($C_{1-4}$alkyl), —$C_{1-6}$alkylene-N($C_{1-4}$alkyl)($C_{1-4}$alkyl), —$C_{1-4}$alkylene-C(O)O$C_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —$NH_2$, —NH($C_{1-4}$alkyl), and —N($C_{1-4}$alkyl)($C_{1-4}$alkyl);

$G^3$ is a 7- to 12-membered spiro heterocycle comprising a first ring and a second ring, the first ring being a 4- to 8-membered monocyclic heterocycle containing 1-2 heteroatoms independently selected from nitrogen and oxygen and being attached to $L^1$, the second ring being a $C_{3-8}$cycloalkyl or a 4- to 8-membered monocyclic heterocycle containing 1-2 oxygen atoms wherein two atoms of the second ring are attached to one carbon of the first ring to form a spirocycle, and wherein $G^3$ is optionally substituted with 1-4 substituents independently selected from the group consisting of $C_{1-4}$alkyl, $C_{1-4}$haloalkyl, halogen, hydroxyl, and oxo;

$G^4$ is a 7- to 12-membered fused bicyclic heterocycle containing 1-3 heteroatoms independently selected from oxygen, nitrogen, and sulfur, $G^4$ being optionally substituted with 1-4 substituents independently selected from the group consisting of $C_{1-4}$alkyl, $C_{1-4}$haloalkyl, halogen, hydroxyl, and oxo;

$G^5$ is 3- to 8-membered cycloalkyl optionally substituted with 1-4 substituents independently selected from the group consisting of $C_{1-4}$alkyl, $C_{1-4}$haloalkyl, halogen, hydroxyl, oxo, cyano, —C(O)$C_{1-4}$alkyl, —C(O)$C_{3-6}$cycloalkyl, —C(O)O$C_{1-4}$alkyl, —C(O)O$C_{1-4}$haloalkyl, —C(O)NH$_2$, —C(O)NH($C_{1-4}$alkyl), —C(O)N($C_{1-4}$alkyl)($C_{1-4}$alkyl), —C(O)NH(—$C_{1-6}$alkylene-O$C_{1-4}$alkyl), —C(O)N($C_{1-4}$alkyl)(—$C_{1-6}$alkylene-O$C_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-O$C_{1-4}$alkyl), —N($C_{1-4}$alkyl)(—$C_{1-6}$alkylene-O$C_{1-4}$alkyl), —NH(—$C_{1-6}$alkylene-OH), —N($C_{1-4}$alkyl)(—$C_{1-6}$alkylene-OH), —C(O)$C_{1-4}$haloalkyl, —O$C_{1-4}$alkyl, —$C_{1-4}$alkylene-O$C_{1-4}$alkyl, —$C_{1-6}$alkylene-OH, —$C_{1-6}$alkylene substituted by 2 groups independently selected from hydroxyl and —OC(O)$C_{1-4}$alkyl, —$C_{1-4}$alkylene-C(O)O$C_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —NH$_2$, —NH($C_{1-4}$alkyl), and —N($C_{1-4}$alkyl)($C_{1-4}$alkyl);

$G^6$ is a monocyclic or bicyclic heteroaryl containing 1-4 heteroatoms independently selected from oxygen, nitrogen, and sulfur, $G^6$ being optionally substituted with 1-4 substituents independently selected from the group consisting of $C_{1-4}$alkyl, $C_{1-4}$haloalkyl, halogen, hydroxyl, cyano, phenyl, —C(O)$C_{1-4}$alkyl, —C(O)$C_{3-6}$cycloalkyl, —C(O)O$C_{1-4}$alkyl, —C(O)O$C_{1-4}$haloalkyl, —C(O)NH$_2$, —C(O)NH($C_{1-4}$alkyl), —C(O)N($C_{1-4}$alkyl)($C_{1-4}$alkyl), —C(O)NH(—$C_{1-6}$alkylene-O$C_{1-4}$alkyl), —C(O)N($C_{1-4}$alkyl)(—$C_{1-6}$alkylene-O$C_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-O$C_{1-4}$alkyl), —N($C_{1-4}$alkyl)(—$C_{1-6}$alkylene-O$C_{1-4}$alkyl), —NH(—$C_{1-6}$alkylene-OH), —N($C_{1-4}$alkyl)(—$C_{1-6}$alkylene-OH), —C(O)$C_{1-4}$haloalkyl, —O$C_{1-4}$alkyl, —$C_{1-4}$alkylene-O$C_{1-4}$alkyl, —$C_{1-6}$alkylene-OH, —$C_{1-6}$alkylene substituted by 2 groups independently selected from hydroxyl and —OC(O)$C_{1-4}$alkyl, —$C_{1-4}$alkylene-C(O)O$C_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —NH$_2$, —NH($C_{1-4}$alkyl), and —N($C_{1-4}$alkyl)($C_{1-4}$alkyl);

$R^2$ is $C_{1-4}$alkyl, $C_{1-4}$haloalkyl, halogen, hydroxyl, cyano, —S(O)$_2C_{1-4}$alkyl, —S(O)$C_{1-4}$alkyl, —S$C_{1-4}$alkyl, —O$C_{1-4}$alkyl, —O$C_{1-4}$haloalkyl, —C(O)$C_{1-4}$alkyl, —C(O)O$C_{1-4}$alkyl, —C(O)NH$_2$, —C(O)NH($C_{1-4}$alkyl), —C(O)N($C_{1-4}$alkyl)($C_{1-4}$alkyl), —$C_{1-4}$alkylene-O$C_{1-4}$alkyl, —$C_{1-4}$alkylene-OH, or $G^{10}$, $G^{10}$ being a $C_{3-6}$cycloalkyl, $C_{5-6}$cycloalkenyl, or a 4- to 8-membered monocyclic heterocycle containing 1 to 2 heteroatoms independently selected from nitrogen and oxygen and optionally containing 1 double bond, $G^{10}$ being optionally substituted with 1-2 substituents independently selected from oxo, halogen, $C_{1-4}$alkyl, $C_{1-4}$haloalkyl, and $G^{20}$, $G^{20}$ being a $C_{3-6}$cycloalkyl or a 4- to 8-membered monocyclic heterocycle containing 1 to 2 heteroatoms independently selected from nitrogen and oxygen, $G^{20}$ being optionally substituted with 1-4 substituents independently selected from the group consisting of $C_{1-4}$alkyl, $C_{1-4}$haloalkyl, halogen, hydroxyl, and oxo; and $R^4$ is phenyl or a 6-membered heteroaryl containing 1-3 nitrogen atoms, $R^4$ being optionally substituted with 1-3 substituents independently selected from the group consisting of halogen, hydroxyl, cyano, —S(O)$_2C_{1-4}$alkyl, —S(O)$C_{1-4}$alkyl, —S$C_{1-4}$alkyl, $C_{1-4}$alkyl, $C_{1-4}$haloalkyl, —O$C_{1-4}$alkyl, —O$C_{1-4}$haloalkyl, —$C_{1-4}$alkylene-O$C_{1-4}$alkyl, —$C_{1-4}$alkylene-N($C_{1-4}$alkyl)($C_{1-4}$alkyl), —NH(—$C_{1-4}$alkylene-O$C_{1-4}$alkyl), —NH(—$C_{1-4}$alkylene-OH), —N($C_{1-4}$alkyl)(—$C_{1-4}$alkylene-O$C_{1-4}$alkyl), —N($C_{1-4}$alkyl)(—$C_{1-4}$alkylene-OH), —NH$_2$, —NH($C_{1-4}$alkyl), —N($C_{1-4}$alkyl)($C_{1-4}$alkyl), $C_{3-6}$cycloalkyl, $C_{5-6}$cycloalkenyl, or a 4- to 8-membered monocyclic heterocycle containing 1-2 nitrogen atoms, the $C_{3-6}$cycloalkyl, the $C_{5-6}$cycloalkenyl, and the 4- to 8-membered monocyclic heterocycle being independently optionally substituted with 1-2 substituents independently selected from the group consisting of halogen, hydroxyl, —O$C_{1-4}$alkyl, $C_{1-4}$alkyl, $C_{1-4}$haloalkyl, —$C_{1-4}$alkylene-O$C_{1-4}$alkyl, and —$C_{1-4}$alkylene-OH.

In another aspect, the present invention provides compounds of formula (I'), or a pharmaceutically acceptable salt thereof, wherein:

$X^1$ is CH or N;
$X^2$ is $CR^{X2}$ or N;
$X^3$ is $CR^3$ or N;
where $R^3$ and $R^{X2}$ are each independently selected from the group consisting of hydrogen, halogen, $C_{1-4}$alkyl, $C_{1-4}$haloalkyl, —O$C_{1-4}$alkyl, and cyano;
provided that $X^1$, $X^2$, and $X^3$ are not simultaneously N, $X^2$ and $X^3$ are not simultaneously N, and $X^1$ and $X^3$ are not simultaneously N;

$L^1$ is a bond, —O—, —NR$^5$—, —NR$^5$—$C_{1-4}$alkylene-, —O—$C_{1-4}$alkylene-, —$C_{1-4}$alkylene-, —C(O)—, —NR$^5$C(O)—, —OC(O)—, —NR$^5$C(O)NR$^5$—, —NR$^5$C(O)O—, —NR$^5$—$C_{1-4}$alkylene-C(O)—, —O—$C_{1-4}$alkylene-C(O)—, —$C_{1-4}$alkylene-C(O)—, —NR$^5$C(O)—$C_{1-4}$alkylene-, —OC(O)—$C_{1-4}$alkylene-, —NR$^5$C(O)NR$^5$—$C_{1-4}$alkylene-, —NR$^5$C(O)O—$C_{1-4}$alkylene-, or —NR$^5$—$C_{1-4}$alkylene-O—, wherein each R$^5$ is independently hydrogen or $C_{1-4}$alkyl, and the $C_{1-4}$alkylene of —NR$^5$—$C_{1-4}$alkylene-, —O—$C_{1-4}$alkylene-, —$C_{1-4}$alkylene-, —NR$^5$—$C_{1-4}$alkylene-C(O)—, —O—$C_{1-4}$alkylene-C(O)—, —$C_{1-4}$alkylene-C(O)—, —NR$^5$C(O)—$C_{1-4}$alkylene-, —OC(O)—$C_{1-4}$alkylene-, —NR$^5$C(O)NR$^5$—$C_{1-4}$alkylene-, —NR$^5$C(O)O—$C_{1-4}$alkylene-, or —NR$^5$—$C_{1-4}$alkylene-O— is optionally substituted with 1-6 halogens;

$R^1$ is -$G^1$-$L^2$-$R^6$, -$G^1$-$L^2$-$R^7$, $G^2$, $G^3$, $G^4$, $G^5$, $G^6$, $G^7$, or -=$G^5$;

$G^1$ is i) a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms, $G^1$ being optionally substituted with 1-4 substituents independently selected from the group consisting of $C_{1-4}$alkyl, $C_{1-4}$haloalkyl, halogen, hydroxyl, and oxo; or ii) a 3- to 8-membered cycloalkyl optionally substituted with 1-4 substituents independently selected from the group consisting of $C_{1-4}$alkyl, $C_{1-4}$haloalkyl, halogen, hydroxyl, and oxo;

$L^2$ is a bond, a —$C_{1-6}$alkylene-, —C(O)—, —O—, or —NR$^{5'}$—, wherein the —$C_{1-6}$alkylene- is optionally substituted with 1-6 halogens and 1-2 $C_1$alkylene units of the —$C_{1-6}$alkylene- are optionally replaced with —C(O)—, —O—, or —NR$^{5'}$—, wherein each $R^{5'}$ is independently hydrogen or $C_{1-4}$alkyl;

$R^6$ is a) a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms and being optionally substituted with 1-4 substituents independently selected from the group consisting of $C_{1-4}$alkyl, $C_{1-4}$haloalkyl, —CH$_2$S(O)$_2$phenyl, halogen, hydroxyl, oxo, —O$C_{1-4}$alkyl, —$C_{1-6}$alkylene-O$C_{1-4}$alkyl, and —$C_{1-6}$alkylene-OH; b) a 5- or 6-membered monocyclic heteroaryl containing 1-3 heteroatoms independently selected from nitrogen, oxygen, and sulfur, the monocyclic heteroaryl being optionally substituted with 1-3 substituents independently selected from the group consisting of $C_{1-4}$alkyl, $C_{1-4}$haloalkyl, halogen, hydroxyl, —$OC_{1-4}$alkyl, —$C_{1-6}$alkylene-$OC_{1-4}$alkyl, and —$C_{1-6}$alkylene-OH; c) a 7- to 12-membered spiro heterocycle comprising a first ring and a second ring, the first ring being a 4- to 8-membered monocyclic heterocycle containing 1-2 heteroatoms independently selected from nitrogen and oxygen and being attached to $L^2$, the second ring being a $C_{3-8}$cycloalkyl or a 4- to 8-membered monocyclic heterocycle containing 1-2 oxygen atoms wherein two atoms of the second ring are attached to one carbon of the first ring to form a spirocycle optionally substituted with 1-4 substituents independently selected from the group consisting of $C_{1-4}$alkyl, $C_{1-4}$haloalkyl, halogen, hydroxyl, oxo, —$OC_{1-4}$alkyl, —$C_{1-6}$alkylene-$OC_{1-4}$alkyl, and —$C_{1-6}$alkylene-OH; or d) a 7- to 12-membered fused bicyclic heterocycle containing 1-3 heteroatoms independently selected from oxygen, nitrogen, and sulfur and being optionally substituted with 1-4 substituents independently selected from the group consisting of $C_{1-4}$alkyl, $C_{1-4}$haloalkyl, halogen, hydroxyl, oxo, —$OC_{1-4}$alkyl, —$C_{1-6}$alkylene-$OC_{1-4}$alkyl, and —$C_{1-6}$alkylene-OH;

$R^7$ is a) a 3- to 8-membered cycloalkyl optionally substituted with 1-4 substituents independently selected from the group consisting of $C_{1-4}$alkyl, $C_{1-4}$haloalkyl, halogen, hydroxyl, —$C(O)OC_{1-4}$alkyl, —C(O)OH, oxo, —$OC_{1-4}$alkyl, —$C_{1-6}$alkylene-$OC_{1-4}$alkyl, and —$C_{1-6}$alkylene-OH; or b) phenyl optionally substituted with 1-4 substituents independently selected from the group consisting of $C_{1-4}$alkyl, $C_{1-4}$haloalkyl, halogen, hydroxyl, —$C(O)OC_{1-4}$alkyl, —C(O)OH, —$OC_{1-4}$alkyl, —$C_{1-6}$alkylene-$OC_{1-4}$alkyl, and —$C_{1-6}$alkylene-OH;

$G^2$ is a 4- to 8-membered monocyclic heterocycle containing 1-3 heteroatoms independently selected from oxygen, nitrogen, and sulfur, the monocyclic heterocycle optionally containing one double bond and/or a $C_{1-3}$alkylene bridge between two non-adjacent ring atoms, $G^2$ being optionally substituted with 1-4 substituents independently selected from the group consisting of $C_{1-4}$alkyl, $C_{1-4}$haloalkyl, halogen, hydroxyl, oxo, cyano, —$C_{1-6}$alkylene-cyano, —$C(O)C_{1-4}$alkyl, —C(O)—$C_{1-6}$alkylene-$OC_{1-4}$alkyl, —C(O)—$C_{1-6}$alkylene-OH, —$C(O)C_{3-6}$cycloalkyl, —$C(O)OC_{1-4}$alkyl, —$C(O)OC_{1-4}$haloalkyl, —$C(O)NH_2$, —$C(O)NH(C_{1-4}$alkyl), —$C(O)N(C_{1-4}$alkyl)($C_{1-4}$alkyl), —C(O)NH(—$C_{1-6}$alkylene-$OC_{1-4}$alkyl), —C(O)N($C_{1-4}$alkyl)(—$C_{1-6}$alkylene-$OC_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-$OC_{1-4}$alkyl), —N($C_{1-4}$alkyl)(—$C_{1-6}$alkylene-$OC_{1-4}$alkyl), —NH(—$C_{1-6}$alkylene-OH), —N($C_{1-4}$alkyl)(—$C_{1-6}$alkylene-OH), —$C(O)C_{1-4}$haloalkyl, —$OC_{1-4}$alkyl, —$OC_{1-4}$haloalkyl, —$C_{1-6}$alkylene-$OC_{1-4}$alkyl, —$C_{1-6}$alkylene-OH, —$C_{1-6}$alkylene-$NH_2$, —$C_{1-6}$alkylene-NH($C_{1-4}$alkyl), —$C_{1-6}$alkylene-N($C_{1-4}$alkyl)($C_{1-4}$alkyl), —O—$C_{1-6}$alkylene-$NH_2$, —O—$C_{1-6}$alkylene-NH($C_{1-4}$alkyl), —O—$C_{1-6}$alkylene-N($C_{1-4}$alkyl)($C_{1-4}$alkyl), —O—$C_{1-6}$alkylene-$OC_{1-4}$alkyl, —O—$C_{1-6}$alkylene-OH, —$C_{1-4}$alkylene-O—$C_{1-4}$alkylene-$OC_{1-4}$alkyl, —$C_{1-4}$alkylene-O—$C_{1-4}$alkylene-OH, —$C_{1-4}$alkylene-$C(O)OC_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —$NH_2$, —NH($C_{1-4}$alkyl), —N($C_{1-4}$alkyl)($C_{1-4}$alkyl), —$S(O)_{1-2}C_{1-4}$alkyl, —$C_{1-6}$alkylene-$S(O)_{1-2}C_{1-4}$alkyl, and a —$C_{1-6}$alkylene substituted by 2 groups independently selected from hydroxyl, —$OC(O)C_{1-4}$alkyl, —$OC_{1-4}$alkyl, —$NH_2$, —NH($C_{1-4}$alkyl), and —N($C_{1-4}$alkyl)($C_{1-4}$alkyl);

$G^3$ is a 7- to 12-membered spiro heterocycle comprising a first ring and a second ring, the first ring being a 4- to 8-membered monocyclic heterocycle containing 1-2 heteroatoms independently selected from nitrogen and oxygen and being attached to $L^1$, the second ring being a $C_{3-8}$cycloalkyl or a 4- to 8-membered monocyclic heterocycle containing 1-2 oxygen atoms wherein two atoms of the second ring are attached to one carbon of the first ring to form a spirocycle, and wherein $G^3$ is optionally substituted with 1-4 substituents independently selected from the group consisting of $C_{1-4}$alkyl, $C_{1-4}$haloalkyl, halogen, hydroxyl, and oxo;

$G^4$ is a 7- to 12-membered fused bicyclic heterocycle containing 1-3 heteroatoms independently selected from oxygen, nitrogen, and sulfur, $G^4$ being optionally substituted with 1-4 substituents independently selected from the group consisting of $C_{1-4}$alkyl, $C_{1-4}$haloalkyl, halogen, hydroxyl, and oxo;

$G^5$ is 3- to 8-membered cycloalkyl optionally substituted with 1-4 substituents independently selected from the group consisting of $C_{1-4}$alkyl, $C_{1-4}$haloalkyl, halogen, hydroxyl, oxo, cyano, —$C(O)C_{1-4}$alkyl, —$C(O)C_{3-6}$cycloalkyl, —$C(O)OC_{1-4}$alkyl, —$C(O)OC_{1-4}$haloalkyl, —$C(O)NH_2$, —$C(O)NH(C_{1-4}$alkyl), —$C(O)N(C_{1-4}$alkyl)($C_{1-4}$alkyl), —C(O)NH(—$C_{1-6}$alkylene-$OC_{1-4}$alkyl), —C(O)N($C_{1-4}$alkyl)(—$C_{1-6}$alkylene-$OC_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-$OC_{1-4}$alkyl), —N($C_{1-4}$alkyl)(—$C_{1-6}$alkylene-$OC_{1-4}$alkyl), —NH(—$C_{1-6}$alkylene-OH), —N($C_{1-4}$alkyl)(—$C_{1-6}$alkylene-OH), —$C(O)C_{1-4}$haloalkyl, —$OC_{1-4}$alkyl, —$C_{1-4}$alkylene-$OC_{1-4}$alkyl, —$C_{1-6}$alkylene-OH, —$C_{1-6}$alkylene substituted by 2 groups independently selected from hydroxyl and —$OC(O)C_{1-4}$alkyl, —$C_{1-4}$alkylene-$C(O)OC_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —$NH_2$, —NH($C_{1-4}$alkyl), and —N($C_{1-4}$alkyl)($C_{1-4}$alkyl);

$G^6$ is a monocyclic or bicyclic heteroaryl containing 1-4 heteroatoms independently selected from oxygen, nitrogen, and sulfur, $G^6$ being optionally substituted with 1-4 substituents independently selected from the group consisting of $C_{1-4}$alkyl, $C_{1-4}$haloalkyl, halogen, hydroxyl, cyano, phenyl, —$C(O)C_{1-4}$alkyl, —$C(O)C_{3-6}$cycloalkyl, —$C(O)OC_{1-4}$alkyl, —$C(O)OC_{1-4}$haloalkyl, —$C(O)NH_2$, —$C(O)NH(C_{1-4}$alkyl), —$C(O)N(C_{1-4}$alkyl)($C_{1-4}$alkyl), —C(O)NH(—$C_{1-6}$alkylene-$OC_{1-4}$alkyl), —C(O)N($C_{1-4}$alkyl)(—$C_{1-6}$alkylene-$OC_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-$OC_{1-4}$alkyl), —N($C_{1-4}$alkyl)(—$C_{1-6}$alkylene-$OC_{1-4}$alkyl), —NH(—$C_{1-6}$alkylene-OH), —N($C_{1-4}$alkyl)(—$C_{1-6}$alkylene-OH), —$C(O)C_{1-4}$haloalkyl, —$OC_{1-4}$alkyl, —$C_{1-4}$alkylene-$OC_{1-4}$alkyl, —$C_{1-6}$alkylene-OH, —$C_{1-6}$alkylene substituted by 2 groups independently selected from hydroxyl and —$OC(O)C_{1-4}$alkyl, —$C_{1-4}$alkylene-$C(O)OC_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —$NH_2$, —NH($C_{1-4}$alkyl), and —N($C_{1-4}$alkyl)($C_{1-4}$alkyl);

$G^7$ is aryl optionally substituted with 1-4 substituents independently selected from the group consisting of $C_{1-4}$alkyl, $C_{1-4}$haloalkyl, halogen, hydroxyl, cyano, phenyl, —$C(O)C_{1-4}$alkyl, —$C(O)C_{3-6}$cycloalkyl, —$C(O)OC_{1-4}$alkyl, —$C(O)OC_{1-4}$haloalkyl, —$C(O)NH_2$, —C(O)NH($C_{1-4}$alkyl), —$C(O)N(C_{1-4}$alkyl)($C_{1-4}$alkyl), —C(O)NH(—$C_{1-6}$alkylene-$OC_{1-4}$alkyl), —C(O)N($C_{1-4}$alkyl)(—$C_{1-6}$alkylene-$OC_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-$OC_{1-4}$alkyl), —N($C_{1-4}$alkyl)(—$C_{1-6}$alkylene-$OC_{1-4}$alkyl), —NH(—$C_{1-6}$alkylene-OH), —N($C_{1-4}$alkyl)(—$C_{1-6}$alkylene-OH), —$C(O)C_{1-4}$haloalkyl, —$OC_{1-4}$alkyl, —$C_{1-4}$alkylene-$OC_{1-4}$alkyl, —$C_{1-6}$alkylene-OH, —$C_{1-6}$alkylene substituted by 2 groups independently selected from hydroxyl and —OC(O)C$_{1-4}$alkyl, —C$_{1-4}$alkylene-C(O)OC$_{1-4}$alkyl, —C$_{1-4}$alkylene-C(O)OH, —NHC(O)(C$_{1-4}$alkyl), —N(C$_{1-4}$alkyl)C(O)(C$_{1-4}$alkyl), —NH$_2$, —NH(C$_{1-4}$alkyl), and —N(C$_{1-4}$alkyl)(C$_{1-4}$alkyl);

R$^2$ is C$_{1-4}$alkyl, C$_{1-4}$haloalkyl, halogen, hydroxyl, cyano, —S(O)$_2$C$_{1-4}$alkyl, —S(O)C$_{1-4}$alkyl, —SC$_{1-4}$alkyl, —OC$_{1-4}$alkyl, —OC$_{1-4}$haloalkyl, —C(O)C$_{1-4}$alkyl, —C(O)OC$_{1-4}$alkyl, —C(O)NH$_2$, —C(O)NH(C$_{1-4}$alkyl), —C(O)N(C$_{1-4}$alkyl)(C$_{1-4}$alkyl), —C$_{1-4}$alkylene-OC$_{1-4}$alkyl, —C$_{1-4}$alkylene-OH, or G$^{10}$, G$^{10}$ being a C$_{3-6}$cycloalkyl, C$_{5-6}$cycloalkenyl, or a 4- to 8-membered monocyclic heterocycle containing 1 to 2 heteroatoms independently selected from nitrogen and oxygen and optionally containing 1 double bond, G$^{10}$ being optionally substituted with 1-2 substituents independently selected from oxo, halogen, C$_{1-4}$alkyl, C$_{1-4}$haloalkyl, and G$^{20}$, G$^{20}$ being a C$_{3-6}$cycloalkyl or a 4- to 8-membered monocyclic heterocycle containing 1 to 2 heteroatoms independently selected from nitrogen and oxygen, G$^{20}$ being optionally substituted with 1-4 substituents independently selected from the group consisting of C$_{1-4}$alkyl, C$_{1-4}$haloalkyl, halogen, hydroxyl, and oxo; and R$^4$ is phenyl or a 6-membered heteroaryl containing 1-3 nitrogen atoms, R$^4$ being optionally substituted with 1-3 substituents independently selected from the group consisting of halogen, hydroxyl, cyano, —S(O)$_2$C$_{1-4}$alkyl, —S(O)C$_{1-4}$alkyl, —SC$_{1-4}$alkyl, C$_{1-4}$alkyl, C$_{1-4}$haloalkyl, —OC$_{1-4}$alkyl, —OC$_{1-4}$haloalkyl, —C$_{1-4}$alkylene-OC$_{1-4}$alkyl, —C$_{1-4}$alkylene-N(C$_{1-4}$alkyl)(C$_{1-4}$alkyl), —NH(C$_{1-4}$alkylene-OC$_{1-4}$alkyl), —NH(C$_{1-4}$alkylene-OH), —N(C$_{1-4}$alkyl)(C$_{1-4}$alkylene-OC$_{1-4}$alkyl), —N(C$_{1-4}$alkyl)(C$_{1-4}$alkylene-OH), —NH$_2$, —NH(C$_{1-4}$alkyl), —N(C$_{1-4}$alkyl)(C$_{1-4}$alkyl), C$_{3-6}$cycloalkyl, C$_{5-6}$cycloalkenyl, or a 4- to 8-membered monocyclic heterocycle containing 1-2 nitrogen atoms, the C$_{3-6}$cycloalkyl, the C$_{5-6}$cycloalkenyl, and the 4- to 8-membered monocyclic heterocycle being independently optionally substituted with 1-2 substituents independently selected from the group consisting of halogen, hydroxyl, —OC$_{1-4}$alkyl, C$_{1-4}$alkyl, C$_{1-4}$haloalkyl, —C$_{1-4}$alkylene-OC$_{1-4}$alkyl, and —C$_{1-4}$alkylene-OH.

In another aspect, the present invention provides compounds of formula (I)

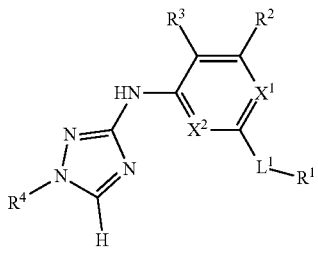

(I)

or a pharmaceutically acceptable salt thereof, wherein:

X$^1$ and X$^2$ are independently CH or N, provided that both X$^1$ and X$^2$ are not simultaneously N;

L$^1$ is a bond, —O—, —NR$^5$—, or —NR$^5$—C$_{1-4}$alkylene-, wherein R$^5$ is hydrogen or C$_{1-4}$alkyl;

R$^1$ is -G$^1$-L$^2$-R$^6$, -G$^1$-L$^2$-R$^7$, G$^2$, G$^3$, G$^4$ or G$^5$;

G$^1$ is a 4- to 8-membered monocyclic heterocycle containing 1 or 2 nitrogen atoms, the monocyclic heterocycle optionally containing one double bond and/or a C$_{1-3}$alkylene bridge between two non-adjacent ring atoms, G$^1$ being optionally substituted with 1-4 substituents independently selected from the group consisting of C$_{1-4}$alkyl, C$_{1-4}$haloalkyl, halogen, hydroxyl, and oxo;

L$^2$ is a bond or a —C$_{1-3}$alkylene-;

R$^6$ is: a) a 4- to 8-membered monocyclic heterocycle containing 1-2 heteroatoms independently selected from oxygen, nitrogen, and sulfur, the monocyclic heterocycle being optionally substituted with 1-4 substituents independently selected from the group consisting of C$_{1-4}$alkyl, C$_{1-4}$haloalkyl, —CH$_2$S(O)$_2$phenyl, halogen, hydroxyl, and oxo; or b) a 5- or 6-membered monocyclic heteroaryl containing 1-3 heteroatoms independently selected from nitrogen, oxygen, and sulfur, the monocyclic heteroaryl being optionally substituted with 1-3 substituents independently selected from C$_{1-4}$alkyl, C$_{1-4}$haloalkyl, halogen, and hydroxyl;

R$^7$ is: a) a 3- to 8-membered cycloalkyl optionally substituted with 1-4 substituents independently selected from the group consisting of C$_{1-4}$alkyl, C$_{1-4}$haloalkyl, halogen, hydroxyl, —C(O)OC$_{1-4}$alkyl, —C(O)OH, and oxo; or b) phenyl optionally substituted with 1-4 substituents independently selected from the group consisting of C$_{1-4}$alkyl, C$_{1-4}$haloalkyl, halogen, hydroxyl, —C(O)OC$_{1-4}$alkyl, and —C(O)OH;

G$^2$ is a 4- to 8-membered monocyclic heterocycle containing 1-3 heteroatoms independently selected from oxygen, nitrogen, and sulfur, the monocyclic heterocycle optionally containing one double bond and/or a C$_{1-3}$alkylene bridge between two non-adjacent ring atoms, G$^2$ being optionally substituted with 1-4 substituents independently selected from the group consisting of C$_{1-4}$alkyl, C$_{1-4}$haloalkyl, halogen, hydroxyl, oxo, cyano, —C(O)C$_{1-4}$alkyl, —C(O)C$_{3-6}$cycloalkyl, —C(O)OC$_{1-4}$alkyl, —C(O)OC$_{1-4}$haloalkyl, —C(O)NH$_2$, —C(O)NH(C$_{1-4}$alkyl), and —C(O)N(C$_{1-4}$alkyl)(C$_{1-4}$alkyl), —C(O)C$_{1-4}$haloalkyl, —OC$_{1-4}$alkyl, —C$_{1-4}$alkylene-OC$_{1-4}$alkyl, —C$_{1-6}$alkylene-OH, —C$_{1-6}$alkylene substituted by 2 groups independently selected from hydroxyl and —OC(O)C$_{1-4}$alkyl, —C$_{1-4}$alkylene-C(O)OC$_{1-4}$alkyl, —C$_{1-4}$alkylene-C(O)OH, —NHC(O)(C$_{1-4}$alkyl), —N(C$_{1-4}$alkyl)C(O)(C$_{1-4}$alkyl), —NH$_2$, —NH(C$_{1-4}$alkyl), and —N(C$_{1-4}$alkyl)(C$_{1-4}$alkyl);

G$^3$ is a 7- to 12-membered spiro heterocycle comprising a first ring and a second ring, the first ring being a 4- to 8-membered monocyclic heterocycle containing 1-2 heteroatoms independently selected from nitrogen and oxygen and being attached to L$^1$, the second ring being a C$_{3-8}$cycloalkyl or a 4- to 8-membered monocyclic heterocycle containing 1-2 oxygen atoms wherein two atoms of the second ring are attached to one carbon of the first ring to form a spirocycle, and wherein G$^3$ is optionally substituted with 1-4 substituents independently selected from the group consisting of C$_{1-4}$alkyl, C$_{1-4}$haloalkyl, halogen, and oxo;

G$^4$ is a 7- to 12-membered fused bicyclic heterocycle containing 1-3 heteroatoms independently selected from oxygen, nitrogen, and sulfur, G$^4$ being optionally substituted with 1-4 substituents independently selected from the group consisting of C$_{1-4}$alkyl, C$_{1-4}$haloalkyl, halogen, and oxo;

G$^5$ is 3- to 8-membered cycloalkyl optionally substituted with 1-4 substituents independently selected from the group consisting of C$_{1-4}$alkyl, C$_{1-4}$haloalkyl, halogen, hydroxyl, oxo, cyano, —C(O)C$_{1-4}$alkyl, —C(O)C$_{3-6}$cycloalkyl, —C(O)OC$_{1-4}$alkyl, —C(O)OC$_{1-4}$haloalkyl, —C(O)C$_{1-4}$haloalkyl, —OC$_{1-4}$alkyl, —C$_{1-4}$alkylene-OC$_{1-4}$alkyl, —C$_{1-6}$alkylene-OH, —C$_{1-6}$alkylene substituted by 2 groups independently selected from hydroxyl and —OC(O)C$_{1-4}$alkyl, —C$_{1-4}$alkylene-C(O)OC$_{1-4}$alkyl, —C$_{1-4}$alkylene-C(O)OH, —NHC(O)(C$_{1-4}$alkyl), —N(C$_{1-4}$alkyl)C(O)(C$_{1-4}$alkyl), —NH$_2$, —NH(C$_{1-4}$alkyl), and —N(C$_{1-4}$alkyl)(C$_{1-4}$alkyl);

$R^2$ is $C_{1-4}$alkyl, $C_{1-4}$haloalkyl, halogen, cyano, —S(O)$_2$C$_{1-4}$alkyl, —S(O)C$_{1-4}$alkyl, —SC$_{1-4}$alkyl, —OC$_{1-4}$alkyl, —OC$_{1-4}$haloalkyl, —C(O)C$_{1-4}$alkyl, C$_{3-6}$cycloalkyl, C$_{5-6}$cycloalkenyl, or a 4- to 8-membered monocyclic heterocycle containing 1 to 2 heteroatoms independently selected from nitrogen and oxygen and optionally containing 1 double bond, the C$_{3-6}$cycloalkyl, the C$_{5-6}$cycloalkenyl, and the 4- to 8-membered monocyclic heterocycle being optionally substituted with 1-2 substituents independently selected from oxo, halogen, C$_{1-4}$alkyl C$_{1-4}$haloalkyl, C$_{3-6}$cycloalkyl, and a 4- to 8-membered monocyclic heterocycle containing 1 to 2 heteroatoms independently selected from nitrogen and oxygen;

$R^3$ is hydrogen, halogen, C$_{1-4}$alkyl, C$_{1-4}$haloalkyl, —OC$_{1-4}$alkyl, or cyano; and $R^4$ is phenyl or a 6-membered heteroaryl containing 1-3 nitrogen atoms, $R^4$ being optionally substituted with 1-3 substituents independently selected from the group consisting of halogen, hydroxyl, cyano, —S(O)$_2$C$_{1-4}$alkyl, —S(O)C$_{1-4}$alkyl, —SC$_{1-4}$alkyl, C$_{1-4}$alkyl, C$_{1-4}$haloalkyl, —OC$_{1-4}$alkyl, —OC$_{1-4}$haloalkyl, —C$_{1-4}$alkylene-OC$_{1-4}$alkyl, —C$_{1-4}$alkylene-N(C$_{1-4}$alkyl)(C$_{1-4}$alkyl), —N(C$_{1-4}$alkyl)(C$_{1-4}$alkylene-OC$_{1-4}$alkyl), C$_{3-6}$cycloalkyl, C$_{5-6}$cycloalkenyl, or a 4- to 8-membered monocyclic heterocycle containing 1-2 nitrogen atoms, the C$_{3-6}$cycloalkyl, the C$_{5-6}$cycloalkenyl, and the 4- to 8-membered monocyclic heterocycle being independently optionally substituted with 1-2 substituents independently selected from the group consisting of halogen, hydroxyl, —OC$_{1-4}$alkyl, C$_{1-4}$alkyl, C$_{1-4}$haloalkyl, —C$_{1-4}$alkylene-OC$_{1-4}$alkyl, and —C$_{1-4}$alkylene-OH.

Another aspect of the present invention provides pharmaceutical compositions comprising a pharmaceutically acceptable carrier and therapeutically effective amounts of a compound of formula (I), or a pharmaceutically acceptable salt thereof.

In another aspect, the invention provides compounds of formula (I), or a pharmaceutically acceptable salt thereof, which promote remyelination of demyelinated axons.

In another aspect, the invention provides compounds of formula (I), or a pharmaceutically acceptable salt thereof, which differentiate endogenous oligodendrocyte precursor cells.

In another aspect, the invention provides methods of treating multiple sclerosis by administering to a patient in need thereof a therapeutically effective amount of a compound or composition of formula (I), or a pharmaceutically acceptable salt thereof.

In another aspect, the present invention provides a method of treating, preventing or ameliorating one or more symptoms of a subject with multiple sclerosis or another neurological disease.

In another aspect, the invention provides the use of a compound of formula (I), or a pharmaceutically acceptable salt thereof, for the manufacture of a medicament for the treatment of multiple sclerosis, the promotion of remyelination of demyelinated axons, or the differentiation of endogenous oligodendrocyte precursor cells.

In another aspect, the invention provides compounds of formula (I), or a pharmaceutically acceptable salt thereof, for use in treating multiple sclerosis, promoting remyelination of demyelinated axons, or differentiating endogenous oligodendrocyte precursor cells.

In another aspect, the invention provides compounds of formula (I), or a pharmaceutically acceptable salt thereof for treating or lessening the severity of, in a subject, a disease or disorder selected from a demyelinating disease, central pontine myelinolysis, a nerve injury disease or disorder, a leukoencephalopathy or a leukodystrophyin.

In another aspect, the invention provides compounds of formula (I), or a pharmaceutically acceptable salt thereof.

In another aspect, the invention provides compounds of formula (I), or a pharmaceutically acceptable salt thereof can be employed in combination therapies, that is, the compounds and pharmaceutically acceptable compositions can be administered concurrently with, prior to, or subsequent to, one or more other desired therapeutics or medical procedures.

The present invention also features kits comprising compounds of formula I or I'.

DETAILED DESCRIPTION OF THE INVENTION

1. Definitions

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference.

As described herein, compounds of the invention can optionally be substituted with one or more substituents, such as are illustrated generally above, or as exemplified by particular classes, subclasses, and species of the invention. As described herein, the variables in formula I or I' encompass specific groups, such as, for example, alkyl and cycloalkyl. As one of ordinary skill in the art will recognize, combinations of substituents envisioned by this invention are those combinations that result in the formation of stable or chemically feasible compounds. The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The phrase "optionally substituted" may be used interchangeably with the phrase "substituted or unsubstituted." In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The compounds of the invention are defined according to the terms in the claims and the embodiments. The following definitions are provided as a general guide to understanding the claims and embodiments and are applicable where specific definitions are absent.

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene," as used herein, means a divalent group derived from a straight or branched chain saturated hydrocarbon. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, and —CH$_2$CH(CH$_3$)CH(CH$_3$)CH$_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "halogen" means a chlorine, bromine, iodine, or fluorine atom.

The term "haloalkyl," as used herein, means an alkyl, as defined herein, in which one, two, three, four, five, six, or seven hydrogen atoms are replaced by halogen. For example, representative examples of haloalkyl include, but are not limited to, 2-fluoroethyl, difluoromethyl, trifluoromethyl, 2,2,2-trifluoroethyl, 2,2,2-trifluoro-1,1-dimethylethyl, and the like.

The term "haloalkoxy," as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "heteroaryl," as used herein, means an aromatic heterocycle, i.e., an aromatic ring that contains at least one heteroatom. A heteroaryl may contain from 5 to 12 ring atoms. A heteroaryl may be a 5- to 6-membered monocyclic heteroaryl or an 8- to 12-membered bicyclic heteroaryl. A 5-membered monocyclic heteroaryl ring contains two double bonds, and one, two, three, or four heteroatoms as ring atoms. Representative examples of 5-membered monocyclic heteroaryls include, but are not limited to, furanyl, imidazolyl, isoxazolyl, isothiazolyl, oxadiazolyl, oxazolyl, pyrazolyl, pyrrolyl, tetrazolyl, thiadiazolyl, thiazolyl, thienyl, and triazolyl. A 6-membered heteroaryl ring contains three double bonds, and one, two, three or four heteroatoms as ring atoms. Representative examples of 6-membered monocyclic heteroaryls include, but are not limited to, pyridinyl, pyridazinyl, pyrimidinyl, pyrazinyl, and triazinyl. The bicyclic heteroaryl is an 8- to 12-membered ring system having a monocyclic heteroaryl fused to an aromatic, saturated, or partially saturated carbocyclic ring, or fused to a second monocyclic heteroaryl ring. Representative examples of bicyclic heteroaryl include, but are not limited to, benzofuranyl, benzoxadiazolyl, 1,3-benzothiazolyl, benzimidazolyl, benzothienyl, indolyl, indazolyl, isoquinolinyl, naphthyridinyl, oxazolopyridine, quinolinyl, thienopyridinyl, 5,6,7,8-tetrahydroquinolinyl, and 6,7-dihydro-5H-cyclopenta[b]pyridinyl. The heteroaryl groups are connected to the parent molecular moiety through any substitutable carbon atom or any substitutable nitrogen atom contained within the groups.

The term "cycloalkyl" as used herein, means a monocyclic all-carbon ring containing zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups described herein can be appended to the parent molecular moiety through any substitutable carbon atom.

The term "cycloalkenyl" as used herein, means a monocyclic non-aromatic all-carbon 5- to 6-membered ring containing zero heteroatoms as ring atoms and one double bond. Examples of cycloalkenyl include cyclopentenyl and cyclohexenyl. The cycloalkenyl groups described herein can be appended to the parent molecular moiety through any substitutable carbon atom.

The terms "heterocycle" or "heterocyclic" refer generally to ring systems containing at least one heteroatom as a ring atom where the heteroatom is selected from oxygen, nitrogen, and sulfur. In some embodiments, a nitrogen or sulfur atom of the heterocycle is optionally substituted with oxo. Heterocycles may be a monocyclic heterocycle, a fused bicyclic heterocycle, or a spiro heterocycle. The monocyclic heterocycle is generally a 4, 5, 6, 7, or 8-membered non-aromatic ring containing at least one heteroatom selected from O, N, or S. The 4-membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The fused bicyclic heterocycle is a 7-12-membered ring system having a monocyclic heterocycle fused to a phenyl, to a saturated or partially saturated carbocyclic ring, or to another monocyclic heterocyclic ring, or to a monocyclic heteroaryl ring. Representative examples of fused bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, 5,6,7,8-tetrahydroimidazo[1,2-a]pyrazinyl, and 1,2,3,4-tetrahydroquinolinyl. Spiro heterocycle means a 4, 5-, 6-, 7-, or 8-membered monocyclic heterocycle ring wherein two of the substituents on the same carbon atom form a second ring having 3, 4, 5, 6, 7, or 8-members. Examples of a spiro heterocycle include, but are not limited to, 1,4-dioxa-8-azaspiro[4.5]decanyl, 2-oxa-7-azaspiro[3.5]nonanyl, 2-oxa- 6-azaspiro[3.3]heptanyl, and 8-azaspiro[4.5]decane. The monocyclic heterocycle groups of the present invention may contain an alkylene bridge of 1, 2, or 3 carbon atoms, linking two non-adjacent atoms of the group. Examples of such a bridged heterocycle include, but are not limited to, 2,5-diazabicyclo[2.2.1]heptanyl, 2-azabicyclo[2.2.1]heptanyl, 2-azabicyclo[2.2.2]octanyl, and oxabicyclo[2.2.1]heptanyl. The monocyclic, fused bicyclic, and spiro heterocycle groups are connected to the parent molecular moiety through any substitutable carbon atom or any substitutable nitrogen atom contained within the group. The foregoing description of heterocycles is merely illustrative. In the embodiments of the invention are set forth definitions for types of heterocycles at $G^1$, $G^2$, $G^3$, $G^4$, $R^2$, $R^4$, and $R^6$, and the substituents contained therein.

The term "oxo" as used herein refers to an oxygen atom bonded to the parent molecular moiety. An oxo may be attached to a carbon atom or a sulfur atom by a double bond. Alternatively, an oxo may be attached to a nitrogen atom by a single bond, i.e., an N-oxide.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I or I'. The structures also include zwitterioinc forms of the compounds or salts of formula I or I' where appropriate.

2. Compounds

In a first aspect of the invention are provided compounds of formula (I')

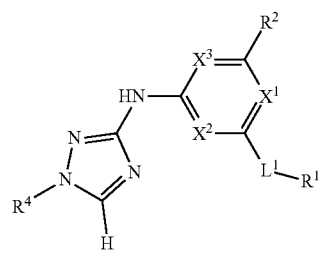

or a pharmaceutically acceptable salt thereof, wherein $L^1$, $R^1$, $R^2$, $R^4$, $X^1$, $X^2$, and $X^3$ are as defined herein.

In a second aspect of the invention are provided compounds of formula (I)

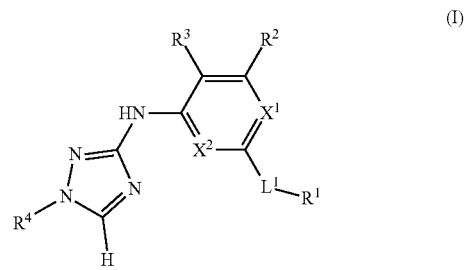

or a pharmaceutically acceptable salt thereof, wherein $L^1$, $R^1$, $R^2$, $R^3$, $R^4$, $X^1$, and $X^2$ are as defined herein.

In some embodiments of the invention, $L^1$-$R^1$ is $L^1$-$G^1$-$L^2$-$R^6$, wherein $L^1$, $G^1$, $L^2$, and $R^6$ are as defined herein. $L^1$ and $L^2$ may be bonded to the same atom in $G^1$

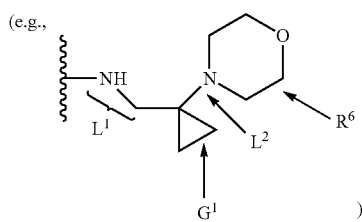

or $L^1$ and $L^2$ may be bonded to different atoms in $G^1$

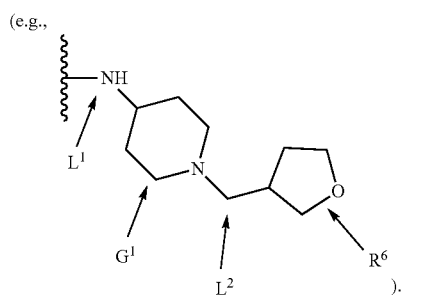

In some embodiments of the invention, $R^1$ is -$G^1$-$L^2$-$R^6$, wherein $G^1$, $L^2$, and $R^6$ are as defined herein. $R^6$ may be unsubstituted or substituted. Unless substitution is indicated as present or optional for a specific $R^6$, then $R^6$ is unsubstituted.

In some embodiments $R^6$ is a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms and being optionally substituted with 1-4 substituents independently selected from the group consisting of $C_{1-4}$alkyl, $C_{1-4}$haloalkyl, —$CH_2S(O)_2$phenyl, halogen, hydroxyl, and oxo. In some embodiments $R^6$ is a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms and being optionally substituted with 1-4 substituents independently selected from the group consisting of $C_{1-4}$alkyl, $C_{1-4}$haloalkyl, —$CH_2S(O)_2$phenyl, halogen, hydroxyl, oxo, —$OC_{1-4}$alkyl, —$C_{1-6}$alkylene-$OC_{1-4}$alkyl, and —$C_{1-6}$alkylene-OH. For example, in some embodiments, $R^6$ is an oxetanyl, a tetrahydrofuranyl, a tetrahydropyranyl, a morpholinyl, 2-oxa-5-azabicyclo[2.2.1]heptanyl, 6-oxa-3-azabicyclo[3.1.1]heptanyl, 1,4-oxazepanyl, 3-oxa-8-azabicyclo[3.2.1]octanyl, 8-oxa-3-azabicyclo[3.2.1]octanyl, a pyrrolidinyl, piperidinyl, thiomorpholinyl, a thietanyl, piperazinyl, or azetidinyl, each being optionally substituted as described herein. In other embodiments, $R^6$ is oxetanyl, tetrahydrofuranyl, tetrahydropyranyl, morpholinyl, pyrrolidinyl, or thietanyl, each being optionally substituted with 1-4 substituents independently selected from $C_{1-4}$alkyl and oxo. In some embodiments, the oxetanyl, tetrahydrofuranyl, tetrahydropyranyl, morpholinyl, pyrrolidinyl, thietanyl, piperazinyl, and azetidinyl, are each optionally substituted with 1-4 substituents independently selected from halogen, $C_{1-4}$alkyl and oxo. In some embodiments, the oxetanyl, tetrahydrofuranyl, tetrahydropyranyl, morpholinyl, pyrrolidinyl, thietanyl, and piperazinyl are each optionally substituted with $C_{1-4}$alkyl, and the pyrrolidinyl, piperazinyl, and thietanyl further optionally substituted with 1-2 oxo groups. In other embodiments, $R^6$ is a 4- to 8-membered monocyclic heterocycle containing 1 oxygen atom (e.g., an oxetanyl, a tetrahydrofuranyl, a tetrahydropyranyl). In other embodiments, $R^6$ is a 4-membered monocyclic heterocycle containing 1 oxygen atom and optionally substituted with $C_{1-4}$alkyl or —$CH_2S(O)_2$phenyl. In other embodiments, $R^6$ is a 4-membered monocyclic heterocycle containing 1 oxygen atom and optionally substituted with $C_{1-4}$alkyl. In other embodiments, $R^6$ is a 4- to 8-membered monocyclic heterocycle containing 1 sulfur atom (e.g., thietanyl, tetrahydrothiophenyl, tetrahydro-2H-thiopyranyl). In other embodiments, $R^6$ is a 4-membered monocyclic heterocycle containing 1 sulfur atom and optionally substituted with 1-2 oxo groups. In other embodiments, $R^6$ is a 4- to 8-membered monocyclic heterocycle containing 1 nitrogen atom and optionally 1 oxygen atom or 1 sulfur atom (e.g., azetidinyl, pyrrolidinyl, morpholinyl, homomorpholinyl, thiomorpholinyl, piperazinyl) and optionally substituted with oxo (e.g., 2-oxopyrrolidin-1-yl). The heterocycles of $R^6$ may be appended to the parent molecule (i.e., at $L^2$) by any substitutable carbon atom or nitrogen atom. Thus, in some embodiments, the oxygen-containing heterocycle is oxetan-3-yl, tetrahydrofuran-3-yl, tetrahydropyran-3-yl, or tetrahydropyran-4-yl. In other embodiments, the sulfur-containing heterocycle is thietan-3-yl, tetrahydrothiophen-3-yl, tetrahydro-2H-thiopyran-3-yl, or tetrahydro-2H-thiopyran-4-yl. In other embodiments, the heterocycle containing 1 nitrogen atom and optionally 1 oxygen or sulfur atom is e.g., piperidin-1-yl, morpholin-4-yl, azetidin-1-yl, piperazin-1-yl, 2-oxa-5-azabicyclo[2.2.1]heptan-5-yl, 6-oxa-3-azabicyclo[3.1.1]heptan-3-yl, 1,4-oxazepan-4-yl, 3-oxa-8-azabicyclo[3.2.1]octan-8-yl, 8-oxa-3-azabicyclo[3.2.1]octan-3-yl, thiomorpholin-4-yl, or 2-oxopyrrolidin-1-yl. In the embodiments of the invention, the oxygen- and sulfur-containing heterocycles may be unsubstituted or substituted as described herein. For example, the oxygen-containing heterocycle may be oxetan-3-yl, 3-methyloxetan-3-yl or 3-((phenylsulfonyl)methyl)oxetan-3-yl and the sulfur-containing heterocycle may be thietan-3-yl or 1,1-dioxothietan-3-yl.

In other embodiments, $R^6$ is a 5- or 6-membered monocyclic heteroaryl containing 1-3 heteroatoms independently selected from nitrogen, oxygen, and sulfur, the monocyclic heteroaryl being optionally substituted with 1-3 substituents independently selected from $C_{1-4}$alkyl, $C_{1-4}$haloalkyl, halogen, or hydroxyl. In other embodiments, $R^6$ is a 5- or 6-membered monocyclic heteroaryl containing 1-3 heteroatoms independently selected from nitrogen, oxygen, and sulfur, the monocyclic heteroaryl being optionally substituted with 1-3 substituents independently selected from $C_{1-4}$alkyl, $C_{1-4}$haloalkyl, halogen, hydroxyl, —$OC_{1-4}$alkyl, —$C_{1-6}$alkylene-$OC_{1-4}$alkyl, and —$C_{1-6}$alkylene-OH. For example, in some embodiments, $R^6$ is a 5-membered heteroaryl containing 1-3 nitrogen atoms (e.g., pyrrolyl, imidazolyl, pyrazolyl, triazolyl). In certain embodiments, $R^6$ is pyrazol-1-yl. In other embodiments, $R^6$ is a 6-membered heteroaryl containing 1-3 nitrogen atoms (e.g., pyridine, pyrimidine, etc.).

In other embodiments, $R^6$ is a 7- to 12-membered spiro heterocycle comprising a first ring and a second ring, the first ring being a 4- to 8-membered monocyclic heterocycle containing 1-2 heteroatoms independently selected from nitrogen and oxygen and being attached to $L^2$, the second ring being a $C_{3-8}$cycloalkyl or a 4- to 8-membered monocyclic heterocycle containing 1-2 oxygen atoms wherein two atoms of the second ring are attached to one carbon of the first ring to form a spirocycle optionally substituted with 1-4 substituents independently selected from the group consisting of $C_{1-4}$alkyl, $C_{1-4}$haloalkyl, halogen, hydroxyl, and oxo. In some embodiments, the spirocyclic $R^6$ is optionally substituted with 1-4 substituents independently selected from the group consisting of $C_{1-4}$alkyl, $C_{1-4}$haloalkyl, —$CH_2S(O)_2$phenyl, halogen, hydroxyl, oxo, —$OC_{1-4}$alkyl, —$C_{1-6}$alkylene-$OC_{1-4}$alkyl, and —$C_{1-6}$alkylene-OH. In some embodiments, $R^6$ is a 7- to 12-membered spiro heterocycle consisting of the first ring and a second ring, as described herein. The first ring is attached to $L^2$ through any substitutable carbon or nitrogen atom. In one embodiment, the first ring is attached to $L^2$ through a nitrogen atom. The first ring of $R^6$ includes, but is not limited to, heterocycles such as azetidine, pyrrolidine, piperidine, azepane, morpholine, azocane, piperazine, and homopiperazine. In some embodiments, the first ring of $R^6$ is a 4- to 8-membered monocyclic heterocycle containing 1-2 nitrogen atoms or 1 nitrogen atom and 1 oxygen atom. For example, in some embodiments, the first ring is morpholino, piperazin-1-yl, or piperidin-1-yl. The second ring includes a $C_{3-8}$cycloalkyl, e.g., cyclopropyl, cyclobutyl cyclopentyl. The second ring is formed by the attachment of two atoms of the second ring to a single carbon atom of the first ring such that the first ring and the second ring share one carbon atom in common. For example, in some embodiments, $R^6$ is 4-oxa-7-azaspiro[2.5]octanyl (e.g., 4-oxa-7-azaspiro[2.5]octan-7-yl).

In other embodiments, $R^6$ is a 7- to 12-membered fused bicyclic heterocycle containing 1-3 heteroatoms independently selected from oxygen, nitrogen, and sulfur and being optionally substituted with 1-4 substituents independently selected from the group consisting of $C_{1-4}$alkyl, $C_{1-4}$haloalkyl, halogen, hydroxyl, and oxo. In other embodiments, $R^6$ is a 7- to 12-membered fused bicyclic heterocycle containing 1-3 heteroatoms independently selected from oxygen, nitrogen, and sulfur and being optionally substituted with 1-4 substituents independently selected from the group consisting of $C_{1-4}$alkyl, $C_{1-4}$haloalkyl, halogen, hydroxyl, oxo, —$OC_{1-4}$alkyl, —$C_{1-6}$alkylene-$OC_{1-4}$alkyl, and —$C_{1-6}$alkylene-OH. For example, in some embodiments, $R^6$ is 2-oxa-5-azabicyclo[4.1.0]heptanyl (e.g., 2-oxa-5-azabicyclo[4.1.0]heptan-5-yl).

In some embodiments of the invention, $L^1$-$R^1$ is $L^1$-$G^1$-$L^2$-$R^7$, wherein $L^1$, $G^1$, $L^2$, and $R^7$ are as defined herein. $L^1$ and $L^2$ may be bonded to the same atom in $G^1$, or $L^1$ and $L^2$ may be bonded to different atoms in $G^1$. In some embodiments of the invention, $R^1$ is -$G^1$-$L^2$-$R^7$. Unless substitution is indicated as present or optional for a specific $R^7$, $R^7$ is unsubstituted.

In some embodiments, $R^7$ is a 3- to 8-membered cycloalkyl optionally substituted with 1-4 substituents independently selected from the group consisting of $C_{1-4}$alkyl, $C_{1-4}$haloalkyl, halogen, hydroxyl, —C(O)O$C_{1-4}$alkyl, —C(O)OH, and oxo. In other embodiments, $R^7$ is optionally substituted with 1-4 substituents independently selected from the group consisting of $C_{1-4}$alkyl, $C_{1-4}$haloalkyl, halogen, hydroxyl, —C(O)O$C_{1-4}$alkyl, —C(O)OH, oxo, —O$C_{1-4}$alkyl, —$C_{1-6}$alkylene-O$C_{1-4}$alkyl, and —$C_{1-6}$alkylene-OH. For example, in some embodiments, $R^7$ is cyclopropyl, cyclobutyl, or cyclopentyl, each being optionally substituted with —C(O)O$C_{1-4}$alkyl, —C(O)OH, hydroxyl or 1-2 halogen. In one group of compounds, $R^7$ is cyclopropyl. In another group of compounds $R^7$ is cyclobutyl. In other embodiments, $R^7$ is 3,3-difluorocyclobutyl. In other embodiments, $R^7$ is a cyclobutane carboxylic acid.

In other embodiments, $R^7$ is phenyl optionally substituted with 1-4 substituents independently selected from the group consisting of $C_{1-4}$alkyl, $C_{1-4}$haloalkyl, halogen, hydroxyl, —C(O)O$C_{1-4}$alkyl, and —C(O)OH. In other embodiments, $R^7$ is phenyl optionally substituted with 1-4 substituents independently selected from the group consisting of $C_{1-4}$alkyl, $C_{1-4}$haloalkyl, halogen, hydroxyl, —C(O)O$C_{1-4}$alkyl, —C(O)OH, oxo, —O$C_{1-4}$alkyl, —$C_{1-6}$alkylene-O$C_{1-4}$alkyl, and —$C_{1-6}$alkylene-OH.

In some embodiments, $G^1$ is a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms, $G^1$ being optionally substituted with 1-4 substituents independently selected from the group consisting of $C_{1-4}$alkyl, $C_{1-4}$haloalkyl, halogen, hydroxyl, and oxo. In some embodiments, $G^1$ is a 4- to 8-membered monocyclic heterocycle containing 1 or 2 nitrogen atoms, the monocyclic heterocycle optionally containing one double bond and/or a $C_{1-3}$alkylene bridge between two non-adjacent ring atoms, $G^1$ being optionally substituted with 1-4 substituents independently selected from the group consisting of $C_{1-4}$alkyl, $C_{1-4}$haloalkyl, halogen, hydroxyl, and oxo. In some embodiments, $G^1$ contains one nitrogen atom. In other embodiments, $G^1$ contains two nitrogen atoms. In some embodiments, $G^1$ is a 6-membered monocyclic heterocycle containing 1 or 2 nitrogen atoms. The heterocycles at $G^1$ may be unsubstituted or substituted. Unless substitution is indicated as present or optional for a specific heterocyclic $G^1$, the heterocycle is unsubstituted. For example, in some embodiments, $G^1$ may be piperazinyl, homopiperazinyl, azetidinyl, pyrrolidinyl, piperidinyl, azepanyl, 2,5-diazabicyclo[2.2.1]heptanyl, 2,5-dihydro-1H-pyrrolyl, oxetanyl, morpholino, tetrahydropyranyl, or 1,2,3,6-tetrahydropyridinyl, each unsubstituted or substituted as described herein. In other embodiments, the piperazinyl, homopiperazinyl, azetidinyl, pyrrolidinyl, piperidinyl, azepanyl, 2,5-diazabicyclo[2.2.1]heptanyl, 2,5-dihydro-1H-pyrrolyl, oxetanyl, morpholino, tetrahydropyranyl, or 1,2,3,6-tetrahydropyridinyl are optionally substituted with 1-4 substituents independently selected from 1 hydroxyl, 1-2 halogen, 1 oxo, and 1-4 $C_{1-4}$alkyl groups. In some embodiments, pyrrolidinyl and/or piperidinyl is optionally substituted with halogen, 1 hydroxyl, or 1 oxo and the piperazinyl is optionally substituted with oxo. In some embodiments, $G^1$ is piperazin-1-yl optionally substituted with oxo. In some embodiments, $G^1$ may have a $C_{1-3}$alkylene bridge between two non-adjacent ring atoms (e.g., 2,5-diazabicyclo[2.2.1]heptanyl). In other embodiments, $G^1$ is without a $C_{1-3}$alkylene bridge between two non-adjacent ring atoms. The heterocycles of $G^1$ may be appended to the parent molecule (i.e., at $L^1$) by any substitutable carbon or nitrogen atom. For example, non-limiting examples of $G^1$ include piperazin-1-yl, 2-oxo-piperazin-1-yl, homopiperazin-1-yl, azetidin-1-yl, azetidin-3-yl, pyrrolidin-3-yl, 3-hydroxy-pyrrolidin-3-yl, 3-fluoro-pyrrolidin-3-yl, piperidin-1-yl, piperidin-3-yl, piperidin-4-yl, 3-hydroxypiperidin-4-yl, 4-hydroxypiperidin-4-yl, 3-fluoropiperidin-4-yl, 4-fluoropiperidin-4-yl, 3,3-difluoropiperidin-4-yl, azepan-3-yl, 2,5-diazabicyclo[2.2.1]heptan-2-yl, 2,5-dihydro-1H-pyrrol-3-yl, or 1,2,3,6-tetrahydropyridin-4-yl.

$L^2$ is a bond, a —$C_{1-3}$alkylene- (e.g., CH$_2$), or a —C(O)— that links $G^1$ with $R^6$ or $R^7$. $L^2$ may be attached at any substitutable nitrogen or carbon atom of $G^1$ and any substitutable carbon or nitrogen atom of $R^6$ or carbon atom of $R^7$.

In other embodiments, $L^2$ is a bond, a —$C_{1-6}$alkylene- (e.g., —CH$_2$—, —CH$_2$CH$_2$—), —C(O)—, —O—, or —NR$^{5'}$—, wherein the —$C_{1-6}$alkylene- is optionally substituted with 1-6 halogens (e.g., fluoro) and 1-2 $C_1$alkylene units of the —$C_{1-6}$alkylene- are optionally replaced with —C(O)—, —O—, or —NR$^{5'}$— (e.g., —CH$_2$OCH$_2$—, —OCH$_2$CH$_2$—), wherein each $R^{5'}$ is independently hydrogen or $C_{1-4}$alkyl. In some embodiments, $L^2$ is $C_{1-3}$alkylene.

In other embodiments, $G^1$ is a 3- to 8-membered cycloalkyl optionally substituted with 1-4 substituents independently selected from the group consisting of $C_{1-4}$alkyl, $C_{1-4}$haloalkyl, halogen, hydroxyl, and oxo. For example, in some embodiments, $G^1$ may be cyclopropyl, cyclobutyl, cyclopentyl, cyclohexyl, cycloheptyl, or cyclooctyl.

In some embodiments, $R^1$ is -$G^1$-$L^2$-$R^6$ where $G^1$ is the monocyclic heterocycle and $R^6$ is one of the heterocyclic groups a), b), c) or d). In other embodiments, $G^1$ is the cycloalkyl and $R^6$ is one of the heterocyclic groups a), b), c) or d).

For example, in some embodiments -$G^1$-$L^2$-$R^6$ together may represent 4-(oxetan-3-yl)piperazin-1-yl, 4-(3-methyloxetan-3-yl)piperazin-1-yl, 4-(tetrahydrofuran-3-yl)piperazin-1-yl, 4-(2-methyltetrahydrofuran-3-yl)piperazin-1-yl, 4-(tetrahydro-2H-pyran-3-yl)piperazin-1-yl, 4-(tetrahydro-2H-pyran-4-yl)piperazin-1-yl, 4-((3-methyloxetan-3-yl)methyl)piperazin-1-yl, 4-(oxetan-3-yl)-2-oxo-piperazin-1-yl, 4-(oxetan-3-yl)piperidin-1-yl, 1-(oxetan-3-yl)piperidin-3-yl, 1-(oxetan-3-yl)piperidin-4-yl, 1-(3-methyloxetan-3-yl)piperidin-4-yl, 1-((3-methyloxetan-3-yl)methyl)piperidin-4-yl, 3-hydroxy-1-(oxetan-3-yl)piperidin-4-yl, 3-fluoro-1-(oxetan-3-yl)piperidin-4-yl, 4-hydroxy-1-(oxetan-3-yl)piperidin-4-yl, 4-fluoro-1-(oxetan-3-yl)piperidin-4-yl, 3,3-difluoro-1-(oxetan-3-yl)piperidin-4-yl, 4-(2-oxopyrrolidin-1-yl)piperidin-1-yl, 3-(2-oxopyrrolidin-1-yl)piperidin-1-yl, 4-morpholinopiperidin-1-yl, (4-methylpiperazin-1-yl)piperidin-1-yl, 4-(3,3-difluoroazetidin-1-yl)piperidin-1-yl, 3-morpholinopyrrolidin-1-yl, 1-(oxetan-3-yl)pyrrolidin-3-yl, 5-(oxetan-3-yl)-2,5-diazabicyclo[2.2.1]heptan-2-yl, 1-(oxetan-3-yl)-1,2,3,6-tetrahydropyridin-4-yl, 3-hydroxy-1-(oxetan-3-yl)-pyrrolidin-3-yl, 3-fluoro-1-(oxetan-3-yl)pyrrolidin-3-yl, 1-(oxetan-3-yl)azetidin-3-yl, 3-(oxetan-3-yl)azetidin-1-yl, 3-(pyrrolidin-1-yl)azetidin-1-yl, 3-(4-fluoropiperidin-1-yl)azetidin-1-yl, 3-morpholinoazetidin-1-yl, 3-methyl-3-morpholinoazetidin-1-yl, 3-(2-methylmorpholino)azetidin-1-yl, 3-(3-methylmorpholino)

azetidin-1-yl, dimethylmorpholino)azetidin-1-yl, 3-(2,6-dimethylmorpholino)azetidin-1-yl, 3-(morpholine-4-carbonyl)azetidin-1-yl, 3-(pyrrolidine-1-carbonyl)azetidin-1-yl, 3-(1,4-oxazepan-4-yl)azetidin-1-yl, 3-(6-oxa-3-azabicyclo[3.1.1]heptan-3-yl)azetidin-1-yl, (3-(2-oxa-5-azabicyclo[2.2.1]heptan-5-yl)azetidin-1-yl, 3-(8-oxa-3-azabicyclo[3.2.1]octan-3-yl)azetidin-1-yl, 3-(3-oxa-8-azabicyclo[3.2.1]octan-8-yl)azetidin-1-yl, 3-(4-oxa-7-azaspiro[2.5]octan-7-yl)azetidin-1-yl, 3-(2-oxa-5-azabicyclo[4.1.0]heptan-5-yl)azetidin-1-yl, 3-(morpholinomethyl)azetidin-1-yl), 3-(1,1-dioxidothiomorpholino)azetidin-1-yl, 4-(thietan-3-yl)piperazin-1-yl, 4-(piperazin-1-yl)thietane 1,1-dioxide, or 4-(oxetan-3-yl)-4-($\lambda^1$-oxidanyl)-4$\lambda^4$-piperazin-1-yl, 3-(1H-pyrazol-1-yl)azetidin-1-yl, 4-(oxetan-3-yl)morpholin-2-yl, 6-methyl-4-(oxetan-3-yl)morpholin-2-yl, 5-methyl-4-(oxetan-3-yl)morpholin-2-yl, 2-methyl-4-(oxetan-3-yl)morpholin-2-yl, 4-(oxetan-3-yl)-1,4-diazepan-1-yl, or 3-morpholinocyclobutyl.

In some embodiments, $R^1$ is -$G^1$-$L^2$-$R^7$ where $G^1$ is the monocyclic heterocycle and $R^7$ is the cycloalkyl group a) or the phenyl group.

In other embodiments, -$G^1$-$L^2$-$R^7$ together may represent 3-(1-hydroxycyclobutyl)piperazin-1-yl; 4-cyclopropylpiperazin-1-yl; 4-cyclobutylpiperazin-1-yl; 4-cyclopentylpiperazin-1-yl; 1-cyclopropylpiperidin-4-yl; 1-cyclopropylpiperidin-3-yl; 1-cyclobutylpiperidin-4-yl, 1-cyclopentylpiperidin-4-yl, 4-(3,3-difluorocyclobutyl)piperazin-1-yl; or 5-cyclopropyl-2,5-diazabicyclo[2.2.1]heptan-2-yl.

In other embodiments of the invention, $R^1$ is $G^2$, where $G^2$ is as described above. The heterocycles at $G^2$ may be unsubstituted or substituted. Unless substitution is indicated as present or optional for a specific heterocyclic $G^2$, the heterocycle is unsubstituted. The optional $G^2$ substituent may be bonded to the same atom, or a different atom, in $G^2$, to which $L^1$ is bonded. For example, in some embodiments, $G^2$ may be morpholinyl, homomorpholinyl, thiomorpholinyl, piperazinyl, homopiperazinyl, azetidinyl, pyrrolidinyl, oxazolidinyl, piperidinyl, azepanyl, 2,5-diazabicyclo[2.2.1]heptanyl, 6-oxa-3-azabicyclo[3.1.1]heptanyl, 2-oxa-5-azabicyclo[2.2.1]heptanyl, 3-oxa-8-azabicyclo[3.2.1]octanyl, 8-oxa-3-azabicyclo[3.2.1]octanyl, 2,5-dihydro-1H-pyrrolyl, 1,2,3,6-tetrahydropyridinyl, oxetanyl, tetrahydrofuranyl, tetrahydropyranyl, 2,5-dihydrofuranyl, or 3,6-dihydro-2H-pyranyl, each being optionally substituted with 1-4 substituents independently selected from the group consisting of $C_{1-4}$alkyl (e.g., methyl, ethyl, isopropyl), $C_{1-4}$haloalkyl (e.g., —$CF_3$, —$CH_2CF_3$, —$CH_2CHF_2$), halogen (e.g., fluoro), hydroxyl, oxo, cyano, —C(O)$C_{1-4}$alkyl (e.g., —C(O)$CH_3$), —C(O)$C_{3-6}$cycloalkyl (e.g., —C(O)cyclopropyl), —C(O)O$C_{1-4}$alkyl (e.g., —C(O)O$CH_3$, —C(O)O$CH_2CH_3$, —C(O)OC($CH_3$)$_3$), —C(O)O$C_{1-4}$haloalkyl (e.g., —C(O)O$CH_2CF_3$), —C(O)$NH_2$, —C(O)NH($C_{1-4}$alkyl) (e.g., —C(O)NH$CH_2CH_3$), —C(O)N($C_{1-4}$alkyl)($C_{1-4}$alkyl) (e.g., —C(O)N($CH_3$)$_2$), —C(O)NH(—$C_{1-6}$alkylene-O$C_{1-4}$alkyl) (e.g., —C(O)NH($CH_2CH_2OCH_3$)), —C(O)N($C_{1-4}$alkyl)(—$C_{1-6}$alkylene-O$C_{1-4}$alkyl) (e.g., —C(O)N$CH_3$($CH_2CH_2OCH_3$)), —C(O)NH(—$C_{1-6}$alkylene-OH) (e.g., —C(O)NH($CH_2CH_2OH$)), —C(O)N($C_{1-4}$alkyl)(—$C_{1-6}$alkylene-OH) (e.g., —C(O)N$CH_3$($CH_2CH_2OH$)), —NH(—$C_{1-6}$alkylene-O$C_{1-4}$alkyl) (e.g., —NH($CH_2CH_2OCH_3$)), —N($C_{1-4}$alkyl)(—$C_{1-6}$alkylene-O$C_{1-4}$alkyl) (e.g., —N$CH_3$($CH_2CH_2OCH_3$)), —NH(—$C_{1-6}$alkylene-OH) (e.g., —NH($CH_2CH_2OH$)), —N($C_{1-4}$alkyl)(—$C_{1-6}$alkylene-OH) (e.g., —N$CH_3$($CH_2CH_2OH$)), —C(O)$C_{1-4}$haloalkyl (e.g., —C(O)$CF_3$), —O$C_{1-4}$alkyl (e.g., —O$CH_3$), —$C_{1-6}$alkylene-O$C_{1-4}$alkyl (e.g., —$CH_2OCH_3$, —$CH_2CH_2OCH_3$, —$CH_2CH_2CH_2OCH_3$), —$C_{1-6}$alkylene-OH (e.g., —$CH_2OH$, —C(OH)($CH_3$)$_2$, —$CH_2$C(OH)($CH_3$)$_2$, —C(OH)($CH_3$)($CH($CH_3$)$_2$), —$C_{1-6}$alkylene substituted by 2 groups independently selected from hydroxyl and —OC(O)$C_{1-4}$alkyl (e.g., —CH($CH_2OH$)$_2$, —C($CH_3$)($CH_2OH$)$_2$, —C($CH_3$)($CH_2OC(O)CH_3$)$_2$, —C($CH_3$)($CH_2OH$)($CH_2OC(O)CH_3$)), —$C_{1-6}$alkyl-$NH_2$, —$C_{1-6}$alkyl-NH($C_{1-4}$alkyl), —$C_{1-6}$alkyl-N($C_{1-4}$alkyl)($C_{1-4}$alkyl) (e.g., —$CH_2CH_2$—N($CH_3$)$_2$, —$CH_2CH_2CH_2$—N($CH_3$)$_2$), —$C_{1-4}$alkylene-C(O)O$C_{1-4}$alkyl (e.g., —$CH_2$C(O)O$CH_2CH_3$), —$C_{1-4}$alkylene-C(O)OH (e.g., —$CH_2$C(O)OH), —C($CH_3$)$_2$C(O)OH), —NHC(O)($C_{1-4}$alkyl), —N($C_{1-4}$alkyl)C(O)($C_{1-4}$alkyl) (e.g., —N($CH_3$)C(O)$CH_3$), —$NH_2$, —NH($C_{1-4}$alkyl) (e.g., —NH$CH_3$), and —N($C_{1-4}$alkyl)($C_{1-4}$alkyl) (e.g., —N($CH_3$)$_2$). In some embodiments, $G^2$ may be substituted with one substituent selected from the foregoing group and further optionally substituted with 1-3 substituents selected from the group consisting of $C_{1-4}$alkyl and halogen. In some embodiments, $G^2$ is a 6-membered monocyclic heterocycle containing 1 or 2 nitrogen atoms and substituted with $C_{1-4}$alkyl. In some embodiments, $G^2$ is piperazin-1-yl optionally substituted with $C_{1-4}$alkyl. For example, $G^2$ may be 4-$C_{1-4}$alkyl-piperazin-1-yl. In other embodiments, $G^2$ may be unsubstituted. In some embodiments, $G^2$ may be an optionally substituted 4- to 8-membered monocyclic heterocycle containing one oxygen atom and optionally one double bond (e.g., oxetanyl, tetrahydrofuranyl, 2,5-dihydrofuranyl). In other embodiments, $G^2$ may be an optionally substituted 4- to 8-membered monocyclic heterocycle containing one nitrogen and optionally a second nitrogen atom, an oxygen or sulfur atom, and optionally containing one double bond and/or a $C_{1-3}$alkylene bridge between two non-adjacent ring atoms (e.g., azetidinyl, piperidinyl, piperazinyl, 2,5-diazabicyclo[2.2.1]heptanyl, 2-oxa-5-azabicyclo[2.2.1]heptanyl, 3-oxa-8-azabicyclo[3.2.1]octanyl, 8-oxa-3-azabicyclo[3.2.1]octanyl, 6-oxa-3-azabicyclo[3.1.1]heptanyl, 2,5-dihydro-1H-pyrrolyl, morpholinyl). For example, $G^2$ may be morpholinyl, homomorpholinyl, thiomorpholinyl, piperazinyl, homopiperazinyl, azetidinyl, pyrrolidinyl, piperidinyl, azepanyl, 2,5-diazabicyclo[2.2.1]heptanyl, 2,5-dihydro-1H-pyrrolyl, 6-oxa-3-azabicyclo[3.1.1]heptanyl, 2-oxa-5-azabicyclo[2.2.1]heptanyl, 3-oxa-8-azabicyclo[3.2.1]octanyl, 8-oxa-3-azabicyclo[3.2.1]octanyl, 1,2,3,6-tetrahydropyridinyl, oxetanyl, tetrahydrofuranyl, tetrahydropyranyl, 2,5-dihydrofuranyl, or 3,6-dihydro-2H-pyranyl. In some embodiments, $G^2$ may have a $C_{1-3}$alkylene bridge between two non-adjacent ring atoms (e.g., 2,5-diazabicyclo[2.2.1]heptanyl, 2-oxa-5-azabicyclo[2.2.1]heptanyl, 3-oxa-8-azabicyclo[3.2.1]octanyl, 8-oxa-3-azabicyclo[3.2.1]octanyl). In other embodiments, $G^2$ is without a $C_{1-3}$alkylene bridge between two non-adjacent ring atoms. The heterocycles of $G^2$ may be appended to the parent molecule (i.e., at $L^1$) by any substitutable carbon or nitrogen atom (e.g., morpholin-4-yl, homomorpholin-4-yl, thiomorpholin-4-yl, 4-thiomorpholine 1,1-dioxide, piperazin-1-yl, homopiperazin-1-yl, azetidin-1-yl, azetidin-3-yl, pyrrolidin-1-yl, pyrrolidin-3-yl, 2-oxooxazolidin-3-yl, 2-oxooxazolidin-5-yl, piperidin-1-yl, piperidin-3-yl, piperidin-4-yl, azepan-1-yl, azepan-3-yl, 2,5-diazabicyclo[2.2.1]heptan-2-yl, 6-oxa-3-azabicyclo[3.1.1]heptan-3-yl, 2-oxa-5-azabicyclo[2.2.1]heptan-5-yl, 3-oxa-8-azabicyclo[3.2.1]octan-8-yl, 8-oxa-3-azabicyclo[3.2.1]octan-3-yl, 2,5-dihydro-1H-pyrrol-3-yl, 1,2,3,6-tetrahydropyridin-4-yl, oxetan-3-yl, tetrahydrofuran-3-yl, tetrahydropyran-4-yl, 2,5-dihydrofuran-3-yl, and 3,6-dihydro-2H-pyran-4-yl).

In some embodiments, $G^2$ is morpholinyl, homomorpholinyl, thiomorpholinyl, piperazinyl, homopiperazinyl, azetidinyl, pyrrolidinyl, oxazolidinyl, piperidinyl, azepanyl, 2,5-diazabicyclo[2.2.1]heptanyl, 6-oxa-3-azabicyclo[3.1.1]heptanyl, 2-oxa-5-azabicyclo[2.2.1]heptanyl, 3-oxa-8-azabicyclo[3.2.1]octanyl, 8-oxa-3-azabicyclo[3.2.1]octanyl, 2,5-dihydro-1H-pyrrolyl, 1,2,3,6-tetrahydropyridinyl, oxetanyl, tetrahydrofuranyl, tetrahydropyranyl, 2,5-dihydrofuranyl, or 3,6-dihydro-2H-pyranyl, each being optionally substituted with one substituent selected from the group consisting of $C_{1-4}$alkyl, $C_{1-4}$haloalkyl, halogen, hydroxyl, oxo, cyano, —C(O)$C_{1-4}$alkyl, —C(O)$C_{3-6}$cycloalkyl, —C(O)O$C_{1-4}$alkyl, —C(O)O$C_{1-4}$haloalkyl, —C(O)NH$_2$, —C(O)NH($C_{1-4}$alkyl), —C(O)N($C_{1-4}$alkyl)($C_{1-4}$alkyl), —C(O)NH(—$C_{1-6}$alkylene-O$C_{1-4}$alkyl), —C(O)N($C_{1-4}$alkyl)(—$C_{1-6}$alkylene-O$C_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-O$C_{1-4}$alkyl), —N($C_{1-4}$alkyl)(—$C_{1-6}$alkylene-O$C_{1-4}$alkyl), —NH(—$C_{1-6}$alkylene-OH), —N($C_{1-4}$alkyl)(—$C_{1-6}$alkylene-OH), —C(O)$C_{1-4}$haloalkyl, —O$C_{1-4}$alkyl, —$C_{1-6}$alkylene-O$C_{1-4}$alkyl, —$C_{1-6}$alkylene-OH, —$C_{1-6}$alkylene substituted by 2 groups independently selected from hydroxyl and —OC(O)$C_{1-4}$alkyl, —$C_{1-6}$alkylene-NH$_2$, —$C_{1-6}$alkylene-NH($C_{1-4}$alkyl), —$C_{1-6}$alkylene-N($C_{1-4}$alkyl)($C_{1-4}$alkyl), —$C_{1-4}$alkylene-C(O)O$C_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —NH$_2$, —NH($C_{1-4}$alkyl), and —N($C_{1-4}$alkyl)($C_{1-4}$alkyl), and further optionally substituted with 1-3 substituents selected from the group consisting of $C_{1-4}$alkyl and halogen.

In some embodiments, $G^2$ is morpholinyl, homomorpholinyl, thiomorpholinyl, piperazinyl, homopiperazinyl, azetidinyl, pyrrolidinyl, oxazolidinyl, piperidinyl, azepanyl, 2,5-diazabicyclo[2.2.1]heptanyl, 6-oxa-3-azabicyclo[3.1.1]heptanyl, 2-oxa-5-azabicyclo[2.2.1]heptanyl, 3-oxa-8-azabicyclo[3.2.1]octanyl, 8-oxa-3-azabicyclo[3.2.1]octanyl, 2,5-dihydro-1H-pyrrolyl, 1,2,3,6-tetrahydropyridinyl, oxetanyl, tetrahydrofuranyl, tetrahydropyranyl, 2,5-dihydrofuranyl, or 3,6-dihydro-2H-pyranyl, each being optionally substituted with one substituent selected from the group consisting of $C_{1-4}$alkyl, $C_{1-4}$haloalkyl, halogen, hydroxyl, oxo, cyano, —$C_{1-6}$alkylene-cyano (e.g., —CH$_2$CN), —C(O)$C_{1-4}$alkyl, —C(O)—$C_{1-6}$alkylene-O$C_{1-4}$alkyl (e.g., —C(O)CH$_2$OCH$_3$), —C(O)—$C_{1-6}$alkylene-OH, —C(O)$C_{3-6}$cycloalkyl, —C(O)O$C_{1-4}$alkyl, —C(O)O$C_{1-4}$haloalkyl, —C(O)NH$_2$, —C(O)NH($C_{1-4}$alkyl), —C(O)N($C_{1-4}$alkyl)($C_{1-4}$alkyl), —C(O)NH(—$C_{1-6}$alkylene-O$C_{1-4}$alkyl), —C(O)N($C_{1-4}$alkyl)(—$C_{1-6}$alkylene-O$C_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-O$C_{1-4}$alkyl), —N($C_{1-4}$alkyl)(—$C_{1-6}$alkylene-O$C_{1-4}$alkyl), —NH(—$C_{1-6}$alkylene-OH), —N($C_{1-4}$alkyl)(—$C_{1-6}$alkylene-OH), —C(O)$C_{1-4}$haloalkyl, —O$C_{1-4}$alkyl, —O$C_{1-4}$haloalkyl (e.g., —OCH$_2$CH$_2$F, —OCF$_3$), —$C_{1-6}$alkylene-O$C_{1-4}$alkyl, —$C_{1-6}$alkylene-OH, —$C_{1-6}$alkylene-NH$_2$, —$C_{1-6}$alkylene-NH($C_{1-4}$alkyl), —$C_{1-6}$alkylene-N($C_{1-4}$alkyl)($C_{1-4}$alkyl), —O—$C_{1-6}$alkylene-NH$_2$, —O—$C_{1-6}$alkylene-NH($C_{1-4}$alkyl), —O—$C_{1-6}$alkylene-N($C_{1-4}$alkyl)($C_{1-4}$alkyl) (e.g., —OCH$_2$CH$_2$N(CH$_3$)$_2$), —O—$C_{1-6}$alkylene-O$C_{1-4}$alkyl (e.g., —OCH$_2$CH$_2$OCH$_2$CH$_3$), —O—$C_{1-6}$alkylene-OH, —$C_{1-4}$alkylene-O—$C_{1-4}$alkyl, —$C_{1-4}$alkylene-O—$C_{1-4}$alkylene-O$C_{1-4}$alkyl, —$C_{1-4}$alkylene-O—$C_{1-4}$alkylene-OH (e.g., —CH$_2$CH$_2$OCH$_2$CH$_2$OH), —$C_{1-4}$alkylene-C(O)O$C_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —NH$_2$, —NH($C_{1-4}$alkyl), —N($C_{1-4}$alkyl)($C_{1-4}$alkyl), —S(O)$_{1-2}$$C_{1-4}$alkyl (e.g., S(O)$_2$CH$_3$), —$C_{1-6}$alkylene-S(O)$_{1-2}$$C_{1-4}$alkyl (e.g., —CH$_2$S(O)$_2$CH$_3$), and a —$C_{1-6}$alkylene substituted by 2 groups independently selected from hydroxyl, —OC(O)$C_{1-4}$alkyl, —O$C_{1-4}$alkyl, —NH$_2$, —NH($C_{1-4}$alkyl), and —N($C_{1-4}$alkyl)($C_{1-4}$alkyl) (e.g., CH$_2$CH(OH)CH$_2$N(CH$_3$)$_2$, CH$_2$CH(OH)CH$_2$OCH$_2$CH$_3$), and further optionally substituted with 1-3 substituents selected from the group consisting of $C_{1-4}$alkyl and halogen.

In some embodiments, $G^2$ may be morpholinyl, homomorpholinyl, thiomorpholinyl, piperazinyl, homopiperazinyl, azetidinyl, pyrrolidinyl, oxazolidinyl, piperidinyl, azepanyl, 2,5-diazabicyclo[2.2.1]heptanyl, 6-oxa-3-azabicyclo[3.1.1]heptanyl, 2,5-dihydro-1H-pyrrolyl, 1,2,3,6-tetrahydropyridinyl, oxetanyl, tetrahydrofuranyl, tetrahydropyranyl, 2,5-dihydrofuranyl, or 3,6-dihydro-2H-pyranyl, each being optionally substituted with one substituent selected from the group consisting of $C_{1-4}$alkyl, $C_{1-4}$haloalkyl, halogen, hydroxyl, oxo, cyano, —C(O)$C_{1-4}$alkyl, —C(O)$C_{3-6}$cycloalkyl, —C(O)O$C_{1-4}$alkyl, —C(O)O$C_{1-4}$haloalkyl, —C(O)NH$_2$, —C(O)NH($C_{1-4}$alkyl), —C(O)N($C_{1-4}$alkyl)($C_{1-4}$alkyl), —C(O)$C_{1-4}$haloalkyl, —O$C_{1-4}$alkyl, —$C_{1-4}$alkylene-O$C_{1-4}$alkyl, —$C_{1-6}$alkylene-OH, —$C_{1-6}$alkylene substituted by 2 groups independently selected from hydroxyl and —OC(O)$C_{1-4}$alkyl, —$C_{1-4}$alkylene-C(O)O$C_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —NH$_2$, —NH($C_{1-4}$alkyl), and —N($C_{1-4}$alkyl)($C_{1-4}$alkyl), and further optionally substituted with 1-3 substituents selected from the group consisting of $C_{1-4}$alkyl and halogen.

In other embodiments, $G^2$ may be piperidin-1-yl, piperidin-3-yl, piperidin-4-yl, 3-fluoropiperidin-1-yl, 4-fluoropiperidin-1-yl, 3-methoxypiperidin-1-yl, 3-(methoxymethyl)piperidin-1-yl, 4-(methoxymethyl)piperidin-1-yl, 4-methylpiperidin-1-yl, 4-hydroxy-4-methylpiperidin-1-yl, 1-acetylpiperidin-3-yl, 4-(ethoxycarbonyl)piperidin-1-yl, 4-(tert-butoxycarbonyl)piperidin-1-yl, 4-(ethylcarbamoyl)piperidin-1-yl, 1-methylpiperidin-3-yl, 3-cyanopiperidin-1-yl, 4-cyanopiperidin-1-yl, 1-(methoxycarbonyl)piperidin-3-yl, 1-(methoxycarbonyl)piperidin-4-yl, 3-hydroxypiperidin-1-yl, 4-hydroxypiperidin-1-yl, 3-(hydroxymethyl)piperidin-1-yl, 1-(3-methoxypropyl)piperidin-4-yl, 4-(2-methoxyethyl)piperidin-1-yl, 1-acetylpiperidin-4-yl, 3-hydroxypiperidin-4-yl, pyrrolidin-1-yl, 3-fluoropyrrolidin-1-yl, 3-fluoro-1-methylpyrrolidin-3-yl, 3-hydroxy-1-methylpyrrolidin-3-yl, 1-acetylpyrrolidin-3-yl, 1-(2,2-difluoroethyl)pyrrolidin-3-yl, 3-(2-hydroxypropan-2-yl)pyrrolidin-1-yl, 3-(methylamino)pyrrolidin-1-yl, 3-(dimethylamino)pyrrolidin-1-yl, 3-hydroxy-3-methylpyrrolidin-1-yl, 3-(N-methylacetamido)pyrrolidin-1-yl, 2-oxooxazolidin-3-yl, 5-methyl-2-oxooxazolidin-5-yl, 3,5-dimethyl-2-oxooxazolidin-5-yl, 4-methylpiperazin-1-yl, 4-ethylpiperazin-1-yl, 4-isopropylpiperazin-1-yl, 4-(tert-butyl)piperazin-1-yl, 3-(2-hydroxypropan-2-yl)piperazin-1-yl, 4-(ethoxycarbonyl)piperazin-1-yl, 4-(methoxycarbonyl)piperazin-1-yl, 4-((2,2,2-trifluoroethoxy)carbonyl)piperazin-1-yl, 4-acetylpiperazin-1-yl, 4-(ethylcarbamoyl)piperazin-1-yl, 2,4,5-trimethylpiperazin-1-yl, 3,3,4-trimethylpiperazin-1-yl, 4-(2,2,2-trifluoroacetyl)piperazin-1-yl, piperazin-1-yl, 3-(trifluoromethyl)piperazin-1-yl, 4-(2-carboxypropan-2-yl)piperazin-1-yl, 4-(2-methoxyethyl)piperazin-1-yl, 4-(2,2,2-trifluoroethyl)piperazin-1-yl, 3,4,5-trimethylpiperazin-1-yl, 3-(2-hydroxy-3-methylbutan-2-yl)piperazin-1-yl, 2,5-dimethylpiperazin-1-yl, 3,4-dimethylpiperazin-1-yl, 3-methylpiperazin-1-yl, 4-(2-hydroxy-2-methylpropyl)piperazin-1-yl, 3-(hydroxymethyl)-4-methylpiperazin-1-yl, 4-(1-acetoxy-3-hydroxy-2-methylpropan-2-yl)piperazin-1-yl, 4-(1,3-diacetoxy-2-methylpropan-2-yl)piperazin-1-yl, 4-(1,3-dihydroxy-2-methylpropan-2-yl)piperazin-1-yl, 3-(hydroxymethyl)piperazin-1-yl, 4-(tert-butoxycarbonyl)piperazin-1-yl, 2-oxopiperazin-1-yl, 3-methylpiperazin-1-yl, 4-(cyclopropanecarbonyl)piperazin-1-yl, 4-(1,3-dihydroxypropan-2-yl)piperazin-1-yl, 4-(carboxymethyl)piperazin-1-yl, 4-(2-ethoxy-2-oxoethyl)piperazin-1-yl, (3-methoxypropyl)piperazin-1-yl, 2-(dimethylamino)ethyl)piperazin-1-yl, 3-(dimethylamino)propyl)piperazin-1-yl, 4-methyl-1,4-diazepan-1-yl, 4-acetyl-1,4-diazepan-1-yl, 1,4-oxazepan-4-yl, morpholin-4-yl, 2,6-dimethylmorpholino, 2-(methoxymethyl)morpholino, 1,1-dioxidothiomorpholino, tetrahydropyran-4-yl, tetrahydropyran-3-yl, 3,6-dihydro-2H-pyran-4-yl, 2,5-dihydrofuran-3-yl, tetrahydrofuran-3-yl, 2-methyltetrahydrofuran-2-yl, oxetan-3-yl, 3-hydroxyoxetan-3-yl, 3-methyloxetan-3-yl, azetidin-1-yl, azetidin-3-yl, 3-aminoazetidin-1-yl, 3-methylazetidin-1-yl, 3-hydroxy-3-methylazetidin-1-yl, 3-ethyl-3-hydroxyazetidin-1-yl, 3-hydroxy-3-isopropylazetidin-1-yl, 3-fluoroazetidin-1-yl, 3-(methoxymethyl)azetidin-1-yl, 3-(hydroxymethyl)azetidin-1-yl, 3-methoxyazetidin-1-yl, 3-hydroxyazetidin-1-yl, 3-(2-hydroxypropan-2-yl)azetidin-1-yl, 3-cyanoazetidin-1-yl, 3-(dimethylcarbamoyl)azetidin-1-y, 3-(diethylcarbamoyl)azetidin-1-y, 3-((2-methoxyethyl)(methyl)carbamoyl) azetidin-1-yl, 3-((1-methoxypropan-2-yl)carbamoyl) azetidin-1-yl, 3-((2-hydroxyethyl)amino)azetidin-1-yl, 3-((2-methoxyethyl)amino)azetidin-1-yl, 6-oxa-3-azabicyclo[3.1.1]heptan-3-yl, 2-oxa-5-azabicyclo[2.2.1]heptan-5-yl, 3-oxa-8-azabicyclo[3.2.1]octan-8-yl, 8-oxa-3-azabicyclo[3.2.1]octan-3-yl, or 5-methyl-2,5-diazabicyclo[2.2.1]heptan-2-yl.

In other embodiments of the invention, $R^1$ is $G^3$, where $G^3$ is a 7- to 12-membered spiro heterocycle comprising a first ring and a second ring, the first ring being a 4- to 8-membered monocyclic heterocycle containing 1-2 heteroatoms independently selected from nitrogen and oxygen and being attached to $L^1$, the second ring being a $C_{3-8}$cycloalkyl or a 4- to 8-membered monocyclic heterocycle containing 1-2 oxygen atoms wherein two atoms of the second ring are attached to one carbon of the first ring to form a spirocycle, and wherein $G^3$ is optionally substituted with 1-4 substituents independently selected from the group consisting of $C_{1-4}$alkyl, $C_{1-4}$haloalkyl, halogen, hydroxyl, and oxo. Unless substitution is indicated as present or optional for a specific spiro heterocyclic $G^3$, the spiro heterocycle is unsubstituted. In some embodiments, $G^3$ is a 7- to 12-membered spiro heterocycle consisting of the first ring and a second ring, as described herein. The first ring of $G^3$ includes, but is not limited to, heterocycles such as azetidine, pyrrolidine, piperidine, azepane, morpholine, azocane, piperazine, and homopiperazine. In a preferred embodiment, the first ring of $G^3$ is a 4- to 8-membered monocyclic heterocycle containing 1-2 nitrogen atoms or 1 nitrogen atom and 1 oxygen atom. In another embodiment, the first ring of $G^3$ is a 4- to 6-membered monocyclic heterocycle containing 1-2 nitrogen atoms. The first ring is attached to $L^1$ through any substitutable carbon or nitrogen atom. In one embodiment, the first ring is attached to $L^1$ through a nitrogen atom. For example, in some embodiments, the first ring is azetidin-1-yl, pyrrolidin-1-yl, piperazin-1-yl, or piperidin-1-yl. The second ring of $G^3$ includes, but is not limited to, heterocycles such as oxetane, tetrahydrofuran, tetrahydropyran, dioxolane, etc. In some embodiments, the second ring has one oxygen atom. In other embodiments, the second ring has two oxygen atoms. In other embodiments, the second ring is a $C_{3-8}$cycloalkyl, e.g., cyclopropyl, cyclobutyl cyclopentyl. The second ring is formed by the attachment of two atoms of the second ring to a single carbon atom of the first ring such that the first ring and the second ring share one carbon atom in common. For example, the second ring may be joined with the first ring at the 4-position of a first ring piperidin-1-yl or the 3-position of a first ring azetidin-1-yl, pyrrolidin-1-yl, piperidin-1-yl, or piperazin-1-yl. In certain embodiments, $G^3$ is 1,4-dioxa-8-azaspiro[4.5]decanyl, 2-oxa-6-azaspiro[3.5]nonanyl, 2-oxa-7-azaspiro[3.5]nonanyl, 2-oxa-5,8-diazaspiro[3.5]nonanyl, 2,5-dioxa-8-azaspiro[3.5]nonanyl, 1-oxa-8-azaspiro[4.5]decanyl, 5-oxa-8-azaspiro[3.5]nonanyl, 2-oxa-6-azaspiro[3.4]octanyl, 6-oxa-2-azaspiro[3.4]octanyl, 1-oxa-6-azaspiro[3.3]heptanyl, or 2-oxa-6-azaspiro[3.3]heptanyl, 2-oxa-8-azaspiro[4.5]decanyl, or 2,6-diazaspiro[3.3]heptanyl, where the 2-oxa-5,8-diazaspiro[3.5]nonanyl is optionally substituted with $C_{1-4}$alkyl and/or oxo. In other embodiments, $G^3$ is 1,4-dioxa-8-azaspiro[4.5]decanyl, 2-oxa-6-azaspiro[3.5]nonanyl, 2-oxa-7-azaspiro[3.5]nonanyl, 2-oxa-5,8-diazaspiro[3.5]nonanyl, 5-oxa-8-azaspiro[3.5]nonanyl, 2-oxa-6-azaspiro[3.4]octanyl, 6-oxa-2-azaspiro[3.4]octanyl, 1-oxa-6-azaspiro[3.3]heptanyl, or 2-oxa-6-azaspiro[3.3]heptanyl, the 2-oxa-5,8-diazaspiro[3.5]nonanyl being optionally substituted with $C_{1-4}$alkyl and oxo. The heterocycles of $G^3$ may be appended to the parent molecule (i.e., at $L^1$) by any substitutable carbon or nitrogen atom. Other embodiments include 1,4-dioxa-8-azaspiro[4.5]decan-8-yl, 2-oxa-7-azaspiro[3.5]nonan-7-yl, 5-methyl-2-oxa-5,8-diazaspiro[3.5]nonan-8-yl, 2-oxa-6-azaspiro[3.4]octan-6-yl, 1-oxa-6-azaspiro[3.3]heptan-6-yl, 2-oxa-6-azaspiro[3.5]nonan-6-yl, 2,5-dioxa-8-azaspiro[3.5]nonan-8-yl, 1-oxa-8-azaspiro[4.5]decan-8-yl, 5-oxa-8-azaspiro[3.5]nonan-8-yl, 6-oxa-2-azaspiro[3.4]octan-2-yl, 2-oxa-6-azaspiro[3.3]heptan-6-yl, 2-oxa-8-azaspiro[4.5]decan-8-yl, or 2,6-diazaspiro[3.3]heptan-2-yl.

In other embodiments of the invention, $R^1$ is $G^4$, where $G^4$ is as described above. The heterocycles at $G^4$ may be unsubstituted or substituted. Unless substitution is indicated as present or optional for a specific heterocyclic $G^4$, the heterocycle is unsubstituted. For example, in some embodiments, $G^4$ may be

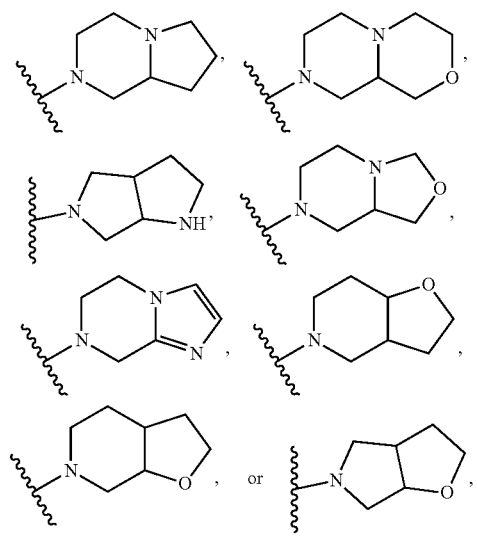

each being optionally substituted with 1-4 substituents selected from the group consisting of $C_{1-4}$alkyl (e.g., methyl, ethyl, isobutyl), $C_{1-4}$haloalkyl (e.g., —$CF_3$, —$CH_2CF_3$), halogen (e.g., fluoro), hydroxyl, and oxo. In other embodiments $G^4$ may be

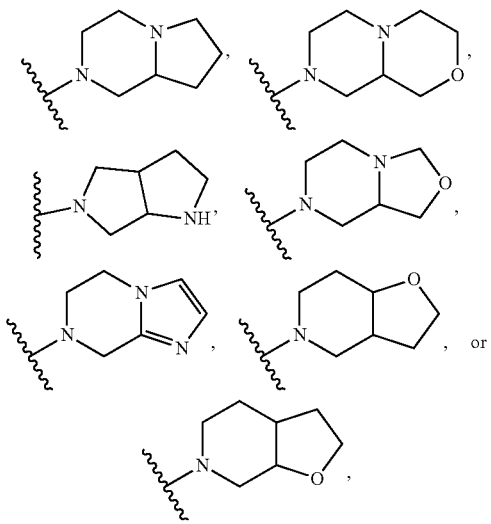

each being optionally substituted with one $C_{1-4}$alkyl, $C_{1-4}$haloalkyl, halogen, or oxo. In some embodiments, $G^4$ may be substituted with one substituent selected from the foregoing group. For example, in some embodiments, $G^4$ is

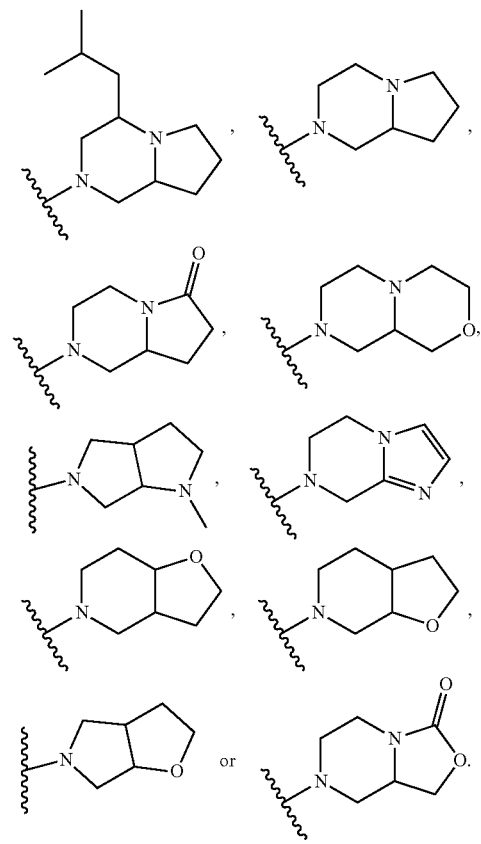

In other embodiments of the invention, $R^1$ is $G^5$, where $G^5$ is as described above. In some embodiments, $G^5$ is cyclopropyl, cyclobutyl, or cyclopentyl, each optionally substituted as defined herein. For example, in some embodiments $G^5$ is substituted with $C_{1-4}$alkoxy (e.g., 3-methoxycyclobutane). The optional $G^5$ substituent may be bonded to the same atom, or a different atom, in $G^5$, to which $L^1$ is bonded.

In some embodiments, $R^1$ is -≡-$G^5$, where $G^5$ is as described above. For example, in some embodiments, $R^1$ is -≡-cyclopropyl.

In some embodiments, $R^1$ is $G^6$, where $G^6$ is as described above. The heteroaryls at $G^6$ may be unsubstituted or substituted. Unless substitution is indicated as present or optional for a specific $G^6$, the heteroaryl is unsubstituted. For example, in some embodiments, $G^6$ may be optionally substituted with 1-4 substituents independently selected from the group consisting of $C_{1-4}$alkyl, $C_{1-4}$haloalkyl, halogen, hydroxyl, cyano, phenyl, —C(O)$C_{1-4}$alkyl, —C(O)$C_{3-6}$cycloalkyl, —C(O)O$C_{1-4}$alkyl, —C(O)O$C_{1-4}$haloalkyl, —C(O)NH$_2$, —C(O)NH($C_{1-4}$alkyl), —C(O)N($C_{1-4}$alkyl)($C_{1-4}$alkyl), —C(O)NH(—$C_{1-6}$alkylene-O$C_{1-4}$alkyl), —C(O)N($C_{1-4}$alkyl)(—$C_{1-6}$alkylene-O$C_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-O$C_{1-4}$alkyl), —N($C_{1-4}$alkyl)(—$C_{1-6}$alkylene-O$C_{1-4}$alkyl), —NH(—$C_{1-6}$alkylene-OH), —N($C_{1-4}$alkyl)(—$C_{1-6}$alkylene-OH), —C(O)$C_{1-4}$haloalkyl, —O$C_{1-4}$alkyl, —$C_{1-4}$alkylene-O$C_{1-4}$alkyl, —$C_{1-6}$alkylene-OH, —$C_{1-6}$alkylene substituted by 2 groups independently selected from hydroxyl and —OC(O)$C_{1-4}$alkyl, —$C_{1-4}$alkylene-C(O)O$C_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —NH$_2$, —NH($C_{1-4}$alkyl), and —N($C_{1-4}$alkyl)($C_{1-4}$alkyl). For example, in some embodiments $G^6$ may be a thiazole, oxazole, triazole or pyrazole optionally substituted with $C_{1-4}$alkyl or phenyl. Further exemplary $G^6$ include 1-methyl-1H-1,2,4-triazol-3-yl, 1-ethyl-1H-1,2,4-triazol-3-yl, 1-phenyl-1H-1,2,4-triazol-3-yl, 1-methyl-1H-pyrazol-3-yl, 1-ethyl-1H-pyrazol-3-yl, 1-phenyl-1H-pyrazol-3-yl, oxazol-2-yl, and thiazol-2-yl.

In some embodiments, $R^1$ is $G^7$, where $G^7$ is as described above. $G^7$ may be unsubstituted or substituted. Unless substitution is indicated as present or optional for a specific $G^7$, is unsubstituted. In some embodiments, $G^7$ is phenyl.

According to the embodiments described herein above and below are further combinations of embodiments wherein $L^1$ is a bond. In alternative combinations of embodiments, $L^1$ is —O—. In still further alternative combinations, $L^1$ is —$NR^5$— and $R^5$ is hydrogen or $C_{1-4}$alkyl. In still other embodiments, $L^1$ is —$NR^5$—$C_{1-4}$alkylene-, wherein $R^5$ is hydrogen or $C_{1-4}$alkyl. In other embodiments, $L^1$ is —O—$C_{1-4}$alkylene-. In other embodiments, $L^1$ is —$C_{1-4}$alkylene-. In other embodiments, $L^1$ is —C(O)—.

In still other embodiments, and combinations thereof, $L^1$ is a bond, —O—, —$NR^5$—, —$NR^5$—$C_{1-4}$alkylene-, —O—$C_{1-4}$alkylene-, —$C_{1-4}$alkylene-, —C(O)—, —$NR^5$C(O)—, —OC(O)—, —$NR^5$C(O)$NR^5$—, —$NR^5$C(O)O—, —$NR^5$—$C_{1-4}$alkylene-C(O)—, —O—$C_{1-4}$alkylene-C(O)—, —$C_{1-4}$alkylene-C(O)—, —$NR^5$C(O)—$C_{1-4}$alkylene-, —OC(O)—$C_{1-4}$alkylene-, —$NR^5$C(O)$NR^5$—$C_{1-4}$alkylene-, —$NR^5$C(O)O—$C_{1-4}$alkylene-, or —$NR^5$—$C_{1-4}$alkylene-O—, wherein each $R^5$ is independently hydrogen or $C_{1-4}$alkyl, and the $C_{1-4}$alkylene of —$NR^5$—$C_{1-4}$alkylene-, —O—$C_{1-4}$alkylene-, —$C_{1-4}$alkylene-, $NR^5$—$C_{1-4}$alkylene-C(O)—, —O—$C_{1-4}$alkylene-C(O)—, —$C_{1-4}$alkylene-C(O)—, —$NR^5$C(O)—$C_{1-4}$alkylene-, —OC(O)—$C_{1-4}$alkylene-, —$NR^5$C(O)$NR^5$—$C_{1-4}$alkylene-, —$NR^5$C(O)O—$C_{1-4}$alkylene-, or —$NR^5$—$C_{1-4}$alkylene-O— is optionally substituted with 1-6 halogens (e.g., fluoro). For example, in some embodiments, each of the foregoing $C_{1-4}$alkylenes is optionally substituted with three fluoros.

In some embodiments, $L^1$-$R^1$ is —$NR^5$—$C_{1-4}$alkylene-$R^1$, —O—$C_{1-4}$alkylene-$R^1$, —$NR^5$C(O)—$R^1$, —OC(O)—

$R^1$, —$NR^5C(O)O$—$R^1$, —$NR^5$—$C_{1-4}$alkylene-$C(O)$—$R^1$, —$O$—$C_{1-4}$alkylene-$C(O)$—$R^1$, —$C_{1-4}$alkylene-$C(O)$—$R^1$, —$NR^5C(O)$—$C_{1-4}$alkylene-$R^1$, —$OC(O)$—$C_{1-4}$alkylene-$R^1$, —$NR^5C(O)NR^5$—$C_{1-4}$alkylene-$R^1$, —$NR^5C(O)O$—$C_{1-4}$alkylene-$R^1$, or —$NR^5$—$C_{1-4}$alkylene-$O$—$R^1$, wherein each $R^5$ is independently hydrogen or $C_{1-4}$alkyl, and the $C_{1-4}$alkylene of —$NR^5$—$C_{1-4}$alkylene-, —$O$—$C_{1-4}$alkylene-, —$C_{1-4}$alkylene-, $NR^5$—$C_{1-4}$alkylene-$C(O)$—, —$O$—$C_{1-4}$alkylene-$C(O)$—, —$C_{1-4}$alkylene-$C(O)$—, —$NR^5C(O)$—$C_{1-4}$alkylene-, —$OC(O)$—$C_{1-4}$alkylene-, —$NR^5C(O)NR^5$—$C_{1-4}$alkylene-, —$NR^5C(O)O$—$C_{1-4}$alkylene-, or —$NR^5$—$C_{1-4}$alkylene-$O$— is optionally substituted with 1-6 halogens. In other embodiments, the $L^1$ is reversed such that $L^1$-$R^1$ is $R^1$—$NR^5$—$C_{1-4}$alkylene-, $R^1$—$O$—$C_{1-4}$alkylene-, $R^1$—$NR^5C(O)$—, $R^1$—$OC(O)$—, $R^1$—$NR^5C(O)O$—, $R^1$—$NR^5$—$C_{1-4}$alkylene-$C(O)$—, $R^1$—$O$—$C_{1-4}$alkylene-$C(O)$—, $R^1$—$C_{1-4}$alkylene-$C(O)$—, $R^1$—$NR^5C(O)$—$C_{1-4}$alkylene-, $R^1$—$OC(O)$—$C_{1-4}$alkylene-, $R^1$—$NR^5C(O)NR$—$C_{1-4}$alkylene-, $R^1$—$NR^5C(O)O$—$C_{1-4}$alkylene-, or $R^1$—$NR^5$—$C_{1-4}$alkylene-$O$—, wherein each $R^5$ is independently hydrogen or $C_{1-4}$alkyl, and the $C_{1-4}$alkylene of —$NR^5$—$C_{1-4}$alkylene-, —$O$—$C_{1-4}$alkylene-, —$C_{1-4}$alkylene-, $NR^5$—$C_{1-4}$alkylene-$C(O)$—, —$O$—$C_{1-4}$alkylene-$C(O)$—, —$C_{1-4}$alkylene-$C(O)$—, —$NR^5C(O)$—$C_{1-4}$alkylene-, —$OC(O)$—$C_{1-4}$alkylene-, —$NR^5C(O)NR^5$—$C_{1-4}$alkylene-, —$NR^5C(O)O$—$C_{1-4}$alkylene-, or —$NR^5$—$C_{1-4}$alkylene-$O$— is optionally substituted with 1-6 halogens.

Further in accordance with the embodiments described herein above and below are embodiments where $X^1$ and $X^2$ are each CH. In alternative embodiments, $X^1$ is N and $X^2$ is CH. In still other embodiments, $X^1$ is CH and $X^2$ is N. In other embodiments, $X^1$, $X^2$, and $X^3$ are each CH. In other embodiments, $X^1$ is CH, $X^2$ is $CR^{X2}$, and $X^3$ is $CR^3$. In other embodiments, $X^1$ is CH, $X^2$ is $CR^{X2}$, and $X^3$ is CH. In other embodiments, $X^1$ is CH, $X^2$ is C—F, and $X^3$ is CH. In other embodiments, $X^1$ is CH, $X^2$ is CH, and $X^3$ is $CR^3$. In other embodiments, $X^1$ is N and $X^2$ and $X^3$ and are CH. In other embodiments, $X^1$ is N, $X^2$ is $CR^{X2}$, and $X^3$ is $CR^3$. In other embodiments, $X^1$ is CH, $X^2$ is N, and $X^3$ is CH. In other embodiments, $X^1$ is CH, $X^2$ is N, and $X^3$ is $CR^3$. In other embodiments, $X^1$ and $X^2$ are CH, and $X^3$ is N. In other embodiments, $X^1$ is CH, $X^2$ is $CR^{X2}$, and $X^3$ is N. In other embodiments, $X^1$ and $X^2$ are N, and $X^3$ is CH. In other embodiments, $X^1$ and $X^2$ are N, and $X^3$ is $CR^3$.

$R^3$ and $R^{X2}$ are each independently selected from the group consisting of hydrogen, halogen (e.g, fluoro), $C_{1-4}$alkyl (methyl), $C_{1-4}$haloalkyl, —$OC_{1-4}$alkyl, or cyano.

Further according to each of the foregoing embodiments, $R^4$ is phenyl or a 6-membered heteroaryl containing 1-3 nitrogen atoms, $R^4$ being optionally substituted with 1-3 substituents independently selected from the group consisting of halogen (e.g., fluoro, chloro), hydroxyl, cyano, —$S(O)_2C_{1-4}$alkyl (e.g., —$SO_2CH_3$), —$S(O)C_{1-4}$alkyl (e.g., —$SOCH_3$), —$SC_{1-4}$alkyl (e.g., —$SCH_3$), $C_{1-4}$alkyl (e.g., methyl, ethyl), $C_{1-4}$haloalkyl (e.g., —$CF_3$), —$OC_{1-4}$alkyl (e.g., —$OCH_3$, —$OCH_2CH_3$, —$OCH(CH_3)_2$), —$OC_{1-4}$haloalkyl (e.g., —$OCF_3$), —$C_{1-4}$alkylene-$OC_{1-4}$alkyl (e.g., —$CH_2OCH_3$), —$C_{1-4}$alkylene-$N(C_{1-4}$alkyl)($C_{1-4}$alkyl) (e.g., —$CH_2N(CH_3)(CH_2CH_3)$), —$NH(C_{1-4}$alkylene-$OC_{1-4}$alkyl) (e.g., —$NH(CH_2CH_2OCH_3)$), —$NH(C_{1-4}$alkylene-OH) (e.g., —$NH(CH_2CH_2OH)$), —$N(C_{1-4}$alkyl)($C_{1-4}$alkylene-$OC_{1-4}$alkyl) (e.g., —$N(CH_3)(CH_2CH_2OCH_3)$), —$N(C_{1-4}$alkyl)($C_{1-4}$alkylene-OH)(e.g., —$N(CH_3)(CH_2CH_2OH)$), —$NH_2$, —$NH(C_{1-4}$alkyl), —$N(C_{1-4}$alkyl)($C_{1-4}$alkyl)), $C_{3-6}$cycloalkyl, $C_{5-6}$cycloalkenyl, or a 4- to 8-membered monocyclic heterocycle containing 1-2 nitrogen atoms (e.g., azetidin-1-yl, pyrrolidin-1-yl, azepan-1-yl), the $C_{3-6}$cycloalkyl, the $C_{5-6}$cycloalkenyl, and the 4- to 8-membered monocyclic heterocycle being independently optionally substituted with 1-2 substituents independently selected from the group consisting of halogen (e.g., fluoro), hydroxyl, —$OC_{1-4}$alkyl (e.g., —$OCH_3$), $C_{1-4}$alkyl (e.g., ethyl), $C_{1-4}$haloalkyl, —$C_{1-4}$alkylene-$OC_{1-4}$alkyl (e.g., —$CH_2OCH_3$, —$CH_2OCH_2CH_3$), and —$C_{1-4}$alkylene-OH (e.g., —$CH_2OH$, —$C(OH)(CH_3)_2$). In further embodiments, $R^4$ is phenyl, or a 6-membered heteroaryl such as pyrazinyl, pyrimidinyl, pyridazinyl, or pyridinyl, each optionally substituted as defined above. The 6-membered heteroaryl at $R^4$ includes a pyridone ring, which is defined herein by the tautomeric hydroxypyridine form, whether or not the pyridone or the hydroxypyridine tautomer predominates. In some embodiments, $R^4$ is phenyl, the phenyl being optionally substituted with one substituent selected from the group consisting of halogen, hydroxyl, cyano, —$S(O)_2C_{1-4}$alkyl, —$S(O)C_{1-4}$alkyl, —$SC_{1-4}$alkyl, $C_{1-4}$alkyl, $C_{1-4}$haloalkyl, —$OC_{1-4}$alkyl, —$OC_{1-4}$haloalkyl, —$C_{1-4}$alkylene-$OC_{1-4}$alkyl, —$C_{1-4}$alkylene-$N(C_{1-4}$alkyl)($C_{1-4}$alkyl), —$NH(C_{1-4}$alkylene-$OC_{1-4}$alkyl), —$NH(C_{1-4}$alkylene-OH), —$N(C_{1-4}$alkyl)($C_{1-4}$alkylene-$OC_{1-4}$alkyl), —$N(C_{1-4}$alkyl)($C_{1-4}$alkylene-OH), —$NH_2$, —$NH(C_{1-4}$alkyl), —$N(C_{1-4}$alkyl)($C_{1-4}$alkyl), $C_{3-6}$cycloalkyl, $C_{5-6}$cycloalkenyl, or a 4- to 8-membered monocyclic heterocycle containing 1-2 nitrogen atoms, the $C_{3-6}$cycloalkyl, the $C_{5-6}$cycloalkenyl, and the 4- to 8-membered monocyclic heterocycle being independently optionally substituted with 1-2 substituents independently selected from the group consisting of halogen, hydroxyl, —$OC_{1-4}$alkyl, $C_{1-4}$alkyl, $C_{1-4}$haloalkyl, —$C_{1-4}$alkylene-$OC_{1-4}$alkyl, and —$C_{1-4}$alkylene-OH, and the phenyl being further optionally substituted with 1-2 substituents independently selected from the group consisting of halogen and $C_{1-4}$alkyl. In yet additional embodiments, $R^4$ is phenyl, the phenyl being optionally substituted with one substituent selected from the group consisting of halogen, cyano, —$S(O)_2C_{1-4}$alkyl, —$S(O)C_{1-4}$alkyl, —$SC_{1-4}$alkyl, $C_{1-4}$alkyl, $C_{1-4}$haloalkyl, —$OC_{1-4}$alkyl, —$OC_{1-4}$haloalkyl, —$C_{1-4}$alkylene-$OC_{1-4}$alkyl, —$C_{1-4}$alkylene-$N(C_{1-4}$alkyl)($C_{1-4}$alkyl), —$N(C_{1-4}$alkyl)($C_{1-4}$alkylene-$OC_{1-4}$alkyl), or a 4- to 8-membered monocyclic heterocycle containing 1-2 nitrogen atoms, the 4- to 8-membered monocyclic heterocycle being independently optionally substituted with 1-2 substituents independently selected from the group consisting of halogen, —$OC_{1-4}$alkyl, $C_{1-4}$alkyl, —$C_{1-4}$alkylene-$OC_{1-4}$alkyl, and —$C_{1-4}$alkylene-OH, and the phenyl being further optionally substituted with 1-2 substituents independently selected from the group consisting of halogen and $C_{1-4}$alkyl. Alternatively, $R^4$ is pyrazinyl, the pyrazinyl being optionally substituted with 1-3 $C_{1-4}$alkyl groups. In another alternative, $R^4$ is pyrimidinyl (e.g., pyrimidin-4-yl, pyrimidin-5-yl), the pyrimidinyl being optionally substituted with one substituent selected from halogen, —$S(O)_2C_{1-4}$alkyl, —$S(O)C_{1-4}$alkyl, —$SC_{1-4}$alkyl, $C_{1-4}$alkyl, —$OC_{1-4}$alkyl, or —$C_{1-4}$alkylene-$OC_{1-4}$alkyl, the pyrimidinyl being further optionally substituted with $C_{1-4}$alkyl. In still a further alternative, $R^4$ is pyridazinyl (e.g., pyridazin-4-yl). In another alternative, $R^4$ is pyridinyl (e.g., pyridin-2-yl, pyridin-3-yl, pyridin-4-yl), the pyridinyl being optionally substituted with one substituent selected from the group consisting of halogen, hydroxyl, $C_{1-4}$alkyl, and a 4- to 8-membered monocyclic heterocycle containing 1-2 nitrogen atoms, the pyridinyl being further optionally substituted with 1-2 substituents selected from halogen and $C_{1-4}$alkyl.

In further embodiments according to the foregoing, $R^4$ is phenyl optionally substituted with 1-3 substituents independently selected from the group consisting of halogen and $C_{1-4}$alkyl. For example, in certain embodiments, $R^4$ is phenyl optionally substituted with 1-2 fluoro atoms or 1 fluoro and 1 methyl group. In certain embodiments, $R^4$ is independently any of phenyl, 3,5-difluorophenyl, 3-fluorophenyl, 3,4-difluorophenyl, 2,5-difluorophenyl, or 3-fluoro-5-methylphenyl.

In further embodiments according to the foregoing, $R^4$ is pyrazine, which is unsubstituted.

$R^2$ is $C_{1-4}$alkyl (e.g., methyl, ethyl, isopropyl, t-butyl), $C_{1-4}$haloalkyl (e.g., $CF_3$, $CHF_2$), halogen (e.g., fluoro, chloro, bromo), hydroxyl, cyano, —$S(O)_2C_{1-4}$alkyl (e.g., —$S(O)_2CH_3$), —$S(O)C_{1-4}$alkyl (e.g., —$S(O)CH_3$), —$SC_{1-4}$alkyl (e.g., —$SCH_3$), —$OC_{1-4}$alkyl (e.g., —$OCH_3$, —$OCH(CH_3)_2$), —$OC_{1-4}$haloalkyl (e.g., —$OCF_3$), —$C(O)C_{1-4}$alkyl (e.g., —$C(O)CH_3$), —$C(O)OC_{1-4}$alkyl (e.g., —$C(O)OCH_3$), —$C(O)NH_2$, —$C(O)NH(C_{1-4}$alkyl) (e.g., —$C(O)NHCH_3$), —$C(O)N(C_{1-4}$alkyl)($C_{1-4}$alkyl), —$C_{1-4}$alkylene-$OC_{1-4}$alkyl (e.g., —$CH_2OCH_3$), —$C_{1-4}$alkylene-OH (e.g., —$CH_2OH$), or $G^{10}$, $G^{10}$ being a $C_{3-6}$cycloalkyl (e.g., cyclopropyl), $C_{5-6}$cycloalkenyl (e.g., cyclopentenyl), or a 4- to 8-membered monocyclic heterocycle containing 1 to 2 heteroatoms selected from nitrogen and oxygen and optionally containing 1 double bond (e.g., tetrahydropyran-4-yl, 3,6-dihydro-2H-pyran-4-yl, tetrahydrofuran-3-yl, 2,5-dihydrofuran-3-yl, oxetan-3-yl, morpholin-4-yl, azetidin-1-yl, piperazin-1-yl), $G^{10}$ being optionally substituted with 1-2 substituents independently selected from oxo, halogen, $C_{1-4}$alkyl (e.g., methyl), $C_{1-4}$haloalkyl, and $G^{20}$, $G^{20}$ being a $C_{3-6}$cycloalkyl, or a 4- to 8-membered monocyclic heterocycle containing 1 to 2 heteroatoms selected from nitrogen and oxygen (e.g., oxetan-3-yl, morpholino), $G^{20}$ being optionally substituted with 1-4 substituents independently selected from the group consisting of $C_{1-4}$alkyl, $C_{1-4}$haloalkyl, halogen, hydroxyl, and oxo. In some embodiments, $R^2$ may be $G^{10}$-$G^{20}$, where $G^{10}$ and $G^{20}$ are optionally substituted as described herein. In some embodiments, $R^2$ is $C_{1-4}$alkyl, $C_{1-4}$haloalkyl, halogen or $C_{3-6}$cycloalkyl. In other embodiments, $R^2$ is $C_{1-4}$alkyl, $C_{1-4}$haloalkyl, or $C_{3-6}$cycloalkyl. In other embodiments, $R^2$ is $C_{1-4}$alkyl or $C_{1-4}$haloalkyl. In other embodiments, $R^2$ is a 4- to 8-membered monocyclic heterocycle containing 1 to 2 nitrogen atoms (e.g., azetidine, piperazine) optionally substituted with a 4- to 8-membered monocyclic heterocycle containing 1 to 2 heteroatoms selected from nitrogen and oxygen (e.g., oxetane, morpholine). In one group of compounds, $R^2$ is methyl, ethyl, fluoro, trifluoromethyl, difluoromethyl, or cyclopropyl. In another group of compounds, $R^2$ is methyl, ethyl, trifluoromethyl, difluoromethyl, or cyclopropyl.

In still other embodiments, $X^1$ and $X^2$ are each CH and $R^2$ is $C_{1-4}$alkyl, $C_{1-4}$haloalkyl, halogen, cyano, —$S(O)_2C_{1-4}$alkyl, —$S(O)C_{1-4}$alkyl, —$SC_{1-4}$alkyl, —$OC_{1-4}$alkyl, —$OC_{1-4}$haloalkyl, —$C(O)C_{1-4}$alkyl, $C_{3-6}$cycloalkyl, $C_{5-6}$cycloalkenyl, or a 4- to 8-membered monocyclic heterocycle containing 1 to 2 heteroatoms selected from nitrogen and oxygen and optionally containing 1 double bond, the $C_{3-6}$cycloalkyl, the $C_{5-6}$cycloalkenyl, and the 4- to 8-membered monocyclic heterocycle being optionally substituted with 1-2 substituents independently selected from oxo, halogen, $C_{1-4}$alkyl, and $C_{1-4}$haloalkyl; or $X^1$ is N, $X^2$ is CH and $R^2$ is $C_{1-4}$alkyl, halogen, $C_{3-6}$cycloalkyl, or a 4- to 8-membered monocyclic heterocycle containing 1 to 2 heteroatoms selected from nitrogen and oxygen and optionally containing 1 double bond, the $C_{3-6}$cycloalkyl, the $C_{5-6}$cycloalkenyl, and the 4- to 8-membered monocyclic heterocycle being optionally substituted with 1-2 substituents independently selected from oxo, halogen, $C_{1-4}$alkyl, and $C_{1-4}$haloalkyl; or $X^1$ is CH, $X^2$ is N, and $R^2$ is $C_{1-4}$alkyl.

In other embodiments, $X^1$ and $X^2$ are each CH and $R^2$ is $C_{1-4}$alkyl (e.g., methyl, ethyl, isopropyl, t-butyl), $C_{1-4}$haloalkyl (e.g., $CF_3$, $CHF_2$), halogen (e.g., fluoro, chloro, bromo), cyano, —$S(O)_2C_{1-4}$alkyl (e.g., —$S(O)_2CH_3$), —$SC_{1-4}$alkyl (e.g., —$SCH_3$), —$OC_{1-4}$alkyl (e.g., —$OCH_3$), —$OC_{1-4}$haloalkyl (e.g., —$OCF_3$), $C_{3-6}$cycloalkyl (e.g., cyclopropyl), or a 4- to 6-membered monocyclic heterocycle containing 1 to 2 heteroatoms selected from nitrogen and oxygen and optionally containing 1 double bond (e.g., tetrahydropyran-4-yl, 3,6-dihydro-2H-pyran-4-yl, tetrahydrofuran-3-yl, 2,5-dihydrofuran-3-yl, oxetan-3-yl, morpholin-4-yl); or $X^1$ is N, $X^2$ is CH, and $R^2$ is $C_{1-4}$alkyl (e.g. methyl), halogen (e.g., chloro), $C_{3-6}$cycloalkyl (e.g., cyclopropyl), or a 6-membered monocyclic heterocycle containing 1 to 2 heteroatoms selected from nitrogen and oxygen (e.g., morpholin-4-yl); or $X^1$ is CH, $X^2$ is N, and $R^2$ is $C_{1-4}$alkyl (e.g. methyl).

$R^3$ is hydrogen, halogen (e.g., fluoro, chloro, bromo), $C_{1-4}$alkyl (e.g., methyl, ethyl), $C_{1-4}$haloalkyl (e.g., $CF_3$, $CHF_2$), —$OC_{1-4}$alkyl (e.g., —$OCH_3$), or cyano. In some embodiments of formula (I), $X^1$ and $X^2$ are each CH and $R^3$ is hydrogen, halogen, $C_{1-4}$alkyl, $C_{1-4}$haloalkyl, —$OC_{1-4}$alkyl, or cyano. In other embodiments, $X^1$ and $X^2$ are each CH and $R^3$ is hydrogen, halogen, $C_{1-4}$alkyl, or —$OC_{1-4}$alkyl. In one group of compounds, $X^1$ and $X^2$ are each CH and $R^3$ is hydrogen, fluoro, methyl, or methoxy. In other embodiments, $X^1$ and $X^2$ are as defined herein and $R^3$ is hydrogen. In one group of compounds, $X^1$ and $X^2$ are each CH and $R^3$ is hydrogen. In another group of compounds, $X^1$ is N, $X^2$ is CH, and $R^3$ is hydrogen. In still another group of compounds, $X^1$ is CH, $X^2$ is N, and $R^3$ is hydrogen.

In yet other embodiments, the invention provides particular combinations of $L^1$, $R^1$, $R^2$, $R^3$, $R^4$, $X^1$ and $X^2$.

In one embodiment, $R^1$ is -$G^1$-$L^2$-$R^6$, -$G^1$-$L^2$-$R^7$, or $G^2$; $L^1$ is a bond; $G^1$ is a 6-membered monocyclic heterocycle containing 1 or 2 nitrogen atoms; $L^2$ is a bond; $R^6$ is a 4-membered monocyclic heterocycle containing 1 oxygen atom and optionally substituted with $C_{1-4}$alkyl; $R^7$ is a cyclopropyl; $G^2$ is a 6-membered monocyclic heterocycle containing 1 or 2 nitrogen atoms and substituted with $C_{1-4}$alkyl or $G^2$ is a 4-membered monocyclic heterocycle containing 1 oxygen atom; $R^2$ is $C_{1-4}$alkyl $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl; and $X^1$ and $X^2$ are each CH or $X^1$ is CH and $X^2$ is N. In one group of compounds, $G^1$ is piperazin-1-yl; $L^2$ is a bond; $R^6$ is oxetan-3-yl or 3-methyloxetan-3-yl, each attached to the 4-position of the piperazin-1-yl of $G^1$; $R^7$ is cyclopropyl attached to the 4-position of the piperazin-1-yl of $G^1$; $G^2$ is 4-methylpiperazin-1-yl or oxetan-3-yl; $R^2$ is methyl, ethyl, trifluoromethyl, difluoromethyl, or cyclopropyl; $R^3$ is hydrogen; $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl; and $X^1$ and $X^2$ are each CH, or $X^1$ is CH and $X^2$ is N.

In another embodiment, $R^1$ is -$G^1$-$L^2$-$R^6$; $L^1$ is a bond; $G^1$ is a 6-membered monocyclic heterocycle containing 1 or 2 nitrogen atoms; $L^2$ is a bond; $R^6$ is a 4-membered monocyclic heterocycle containing 1 oxygen atom and optionally substituted with $C_{1-4}$alkyl; $R^2$ is $C_{1-4}$alkyl, $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl; and $X^1$ and $X^2$ are each CH, or $X^1$ is CH and $X^2$ is N. In one group of compounds, $G^1$ is piperazin-1-yl; $L^2$ is a bond; $R^6$ is oxetan-3-yl or 3-methyloxetan-3-yl, each attached to the 4-position of the piperazin-1-yl of $G^1$; $R^2$ is methyl, ethyl, trifluoromethyl, difluoromethyl, or cyclopropyl; $R^3$ is hydrogen; $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl; and $X^1$ and $X^2$ are each CH, or $X^1$ is CH and $X^2$ is N.

In another embodiment, $R^1$ is -$G^1$-$L^2$-$R^7$; $L^1$ is a bond; $G^1$ is a 6-membered monocyclic heterocycle containing 1 or 2 nitrogen atoms; $L^2$ is a bond; $R^7$ is a cyclopropyl; $R^2$ is $C_{1-4}$alkyl, $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl; and $X^1$ and $X^2$ are each CH, or $X^1$ is CH and $X^2$ is N. In one group of compounds, $G^1$ is piperazin-1-yl; $L^2$ is a bond; $R^7$ is cyclopropyl attached to the 4-position of the piperazin-1-yl of $G^1$; $R^2$ is methyl, ethyl, trifluoromethyl, difluoromethyl, or cyclopropyl; $R^3$ is hydrogen; $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl; and $X^1$ and $X^2$ are each CH, or $X^1$ is CH and $X^2$ is N.

In another embodiment, $R^1$ is $G^2$; $L^1$ is a bond; $G^2$ is a 6-membered monocyclic heterocycle containing 1 or 2 nitrogen atoms and substituted with $C_{1-4}$alkyl or $G^2$ is a 4-membered monocyclic heterocycle containing 1 oxygen atom; $R^2$ is $C_{1-4}$alkyl, $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl; and $X^1$ and $X^2$ are each CH, or $X^1$ is CH and $X^2$ is N. In one group of compounds, $G^2$ is 4-methylpiperazin-1-yl or oxetan-3-yl; $R^2$ is methyl, ethyl, trifluoromethyl, difluoromethyl, or cyclopropyl; $R^3$ is hydrogen; $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl; and $X^1$ and $X^2$ are each CH, or $X^1$ is CH and $X^2$ is N.

In some embodiments are compounds of formula (II), formula (III), formula (IV) or formula (V), wherein $R^1$, $R^2$, $R^3$, $R^4$, $R^5$, $X^1$, and $X^2$ are as defined herein:

(II)
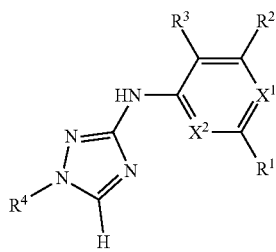

(III)
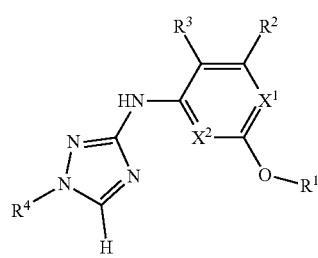

(IV)
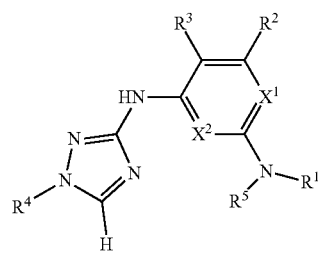

(V)
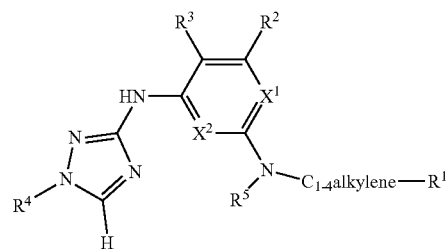

Included in compounds of formula (II) are compounds of formula (IIA), (IIB), (IIC), (IID), (IIE) and (IIF), wherein $G^1$, $G^2$, $G^3$, $G^4$, $G^5$, $R^2$, $R^3$, $R^4$, $R^6$, $R^7$, $X^1$, and $X^2$ are as defined herein:

(IIA)
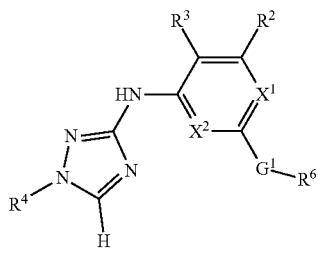

(IIB)
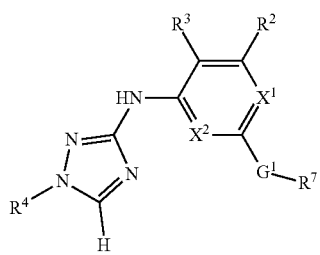

(IIC)
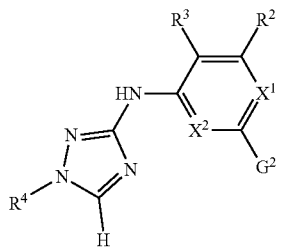

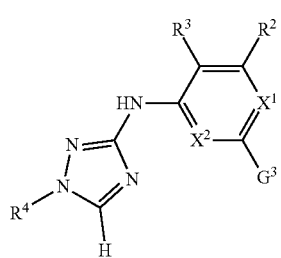 (IID)
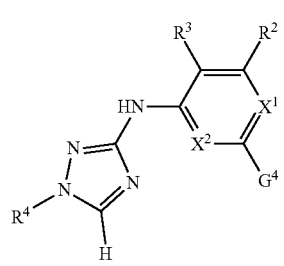 (IIE)
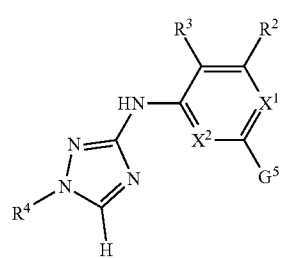 (IIF)
In some embodiments of formula (IIA), are compounds of formula (IIA-1), (IIA-2), (IIA-3), (IIA-4), (IIA-5), (IIA-6), (IIA-7), (IIA-8), or (IIA-9):
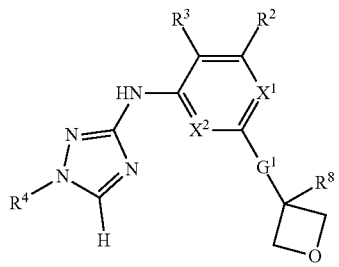 (IIA-1)
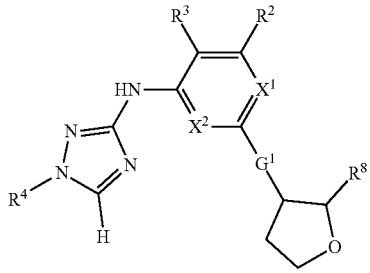 (IIA-2)
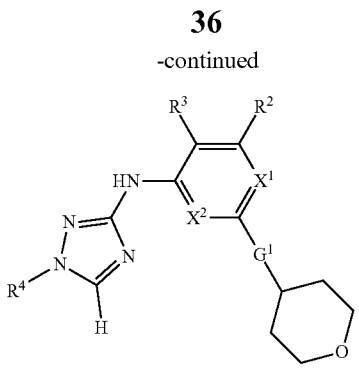 (IIA-3)
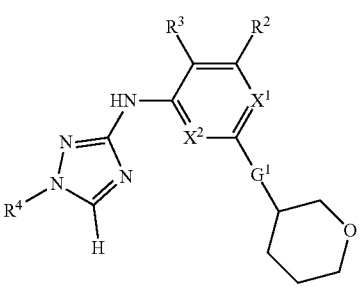 (IIA-4)
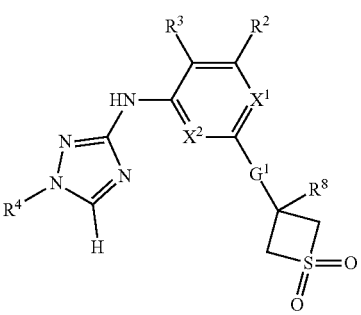 (IIA-5)
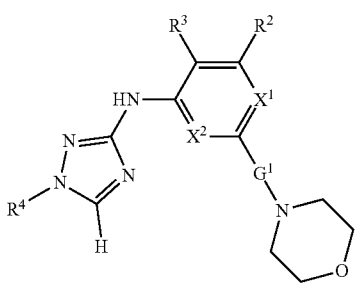 (IIA-6)
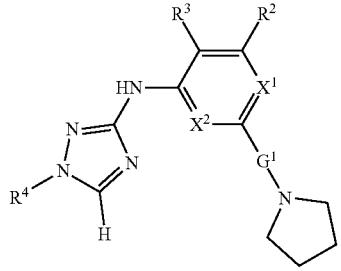 (IIA-7)

-continued (IIA-8)
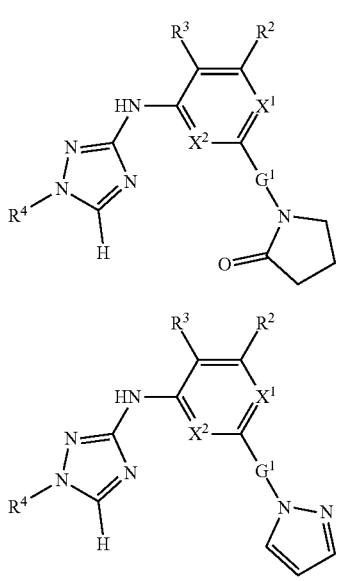

(IIA-9)
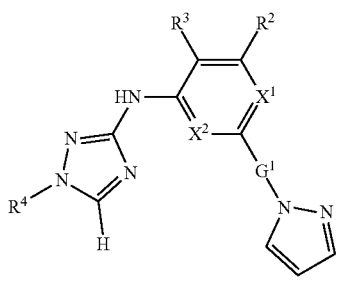

wherein R[8] is hydrogen or $C_{1-4}$alkyl and $G^1$, $R^2$, $R^3$, $R^4$, $X^1$, and $X^2$ are as defined herein.

In some embodiments according to formula (IIA), (IIA-1), (IIA-2), (IIA-3), (IIA-4), (IIA-5), (IIA-6), (IIA-7), (IIA-8), or (IIA-9), $G^1$ is

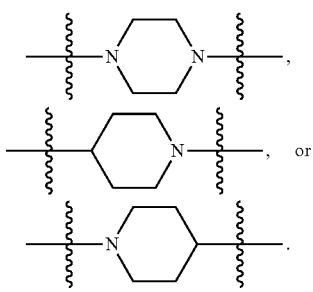

In another embodiment, $G^1$ is

and R[8] is hydrogen or $C_{1-4}$alkyl. In a further embodiment, $G^1$ is

and R[8] is hydrogen or methyl.

In another embodiment, the present invention features a compound of formula (IIA), (IIA-1), (IIA-2), (IIA-3), (IIA-4), (IIA-5), (IIA-6), (IIA-7), (IIA-8), or (IIA-9) and the attendant definitions, wherein one or more hydrogen atoms are replaced by a deuterium atom In other embodiments, compounds of formula (IIA-1) may be represented by the formulas (IIA-1.0) to (IIA-1.9):

(IIA-1.0)
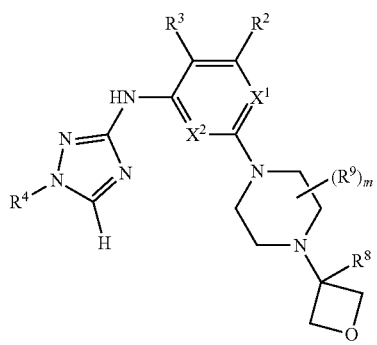

(IIA-1.1)
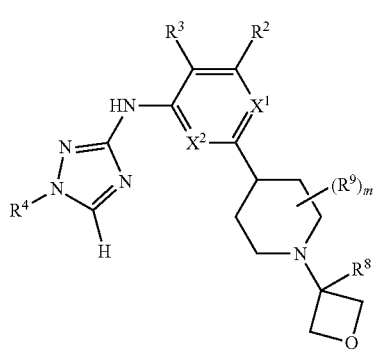

(IIA-1.2)
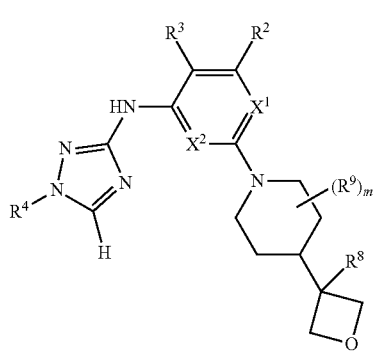

(IIA-1.3)
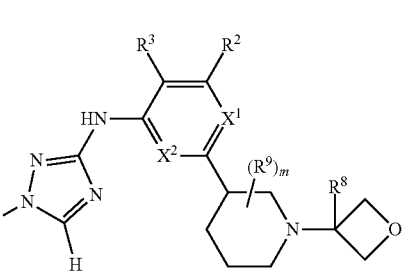

(IIA-1.4)
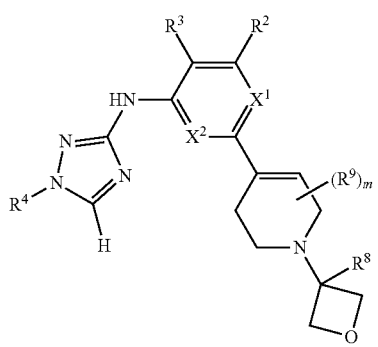

(IIA-1.5)
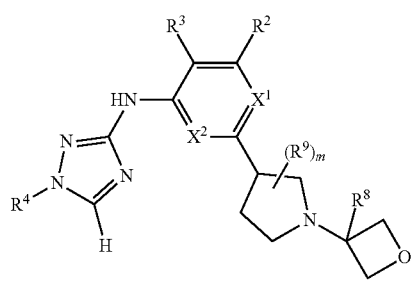

(IIA-1.6)
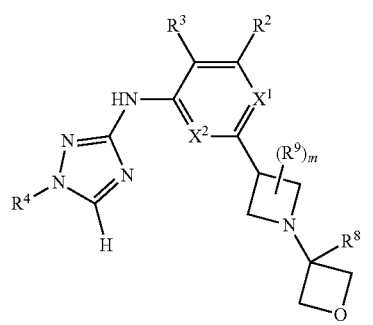

(IIA-1.7)
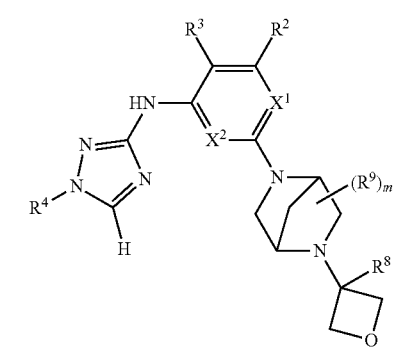

(IIA-1.8)
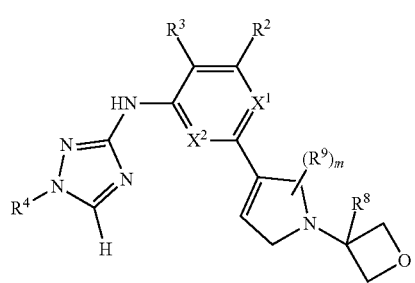

(IIA-1.9)
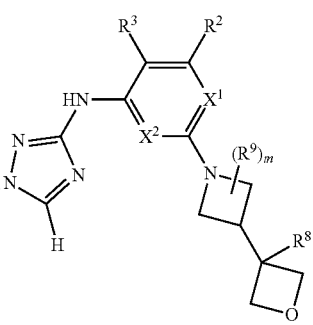

wherein $R^9$ is $C_{1-4}$alkyl, $C_{1-4}$haloalkyl, halogen, hydroxyl, or oxo, m is an integer from 0 to 4, and $R^2$, $R^3$, $R^4$, $R^8$, $X^1$, and $X^2$ are as defined herein.

In some embodiments, m is 0. In other embodiments, compounds of formulas (IIA-2), (IIA-3), (IIA-4), (IIA-5), (IIA-6), (IIA-7), (IIA-8), and (IIA-9) may be represented, respectively, by the formulas (IIA-2.0), (IIA-3.0), (IIA-4.0), (IIA-5.0), (IIA-6.0), (IIA-6.1), (IIA-6.2), (IIA-7.0), (IIA-8.0), (IIA-8.1), (IIA-8.2), and (IIA-9.0):

(IIA-2.0)
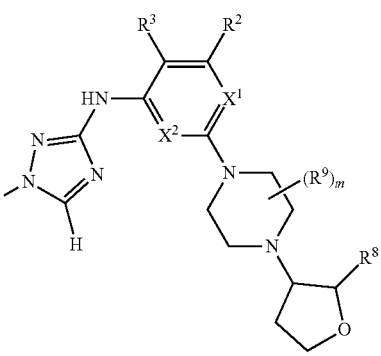

(IIA-3.0)
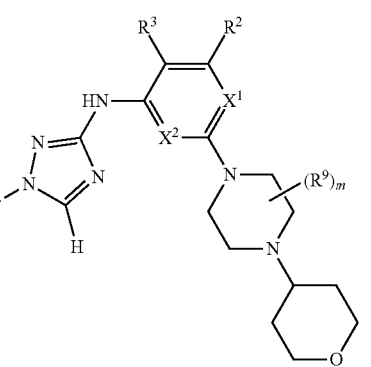

(IIA-4.0) 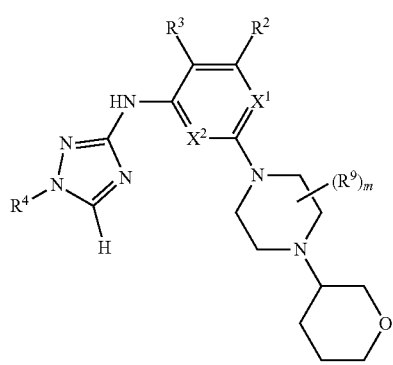
(IIA-5.0) 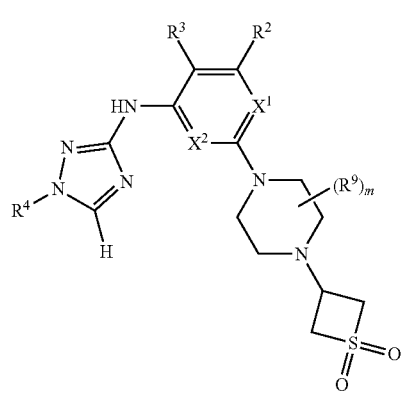
(IIA-6.0) 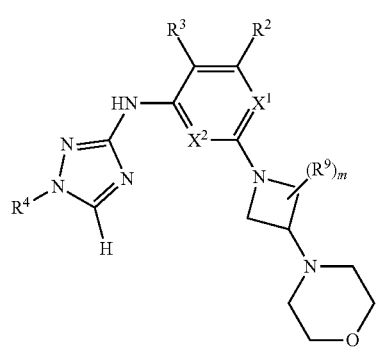
(IIA-6.1) 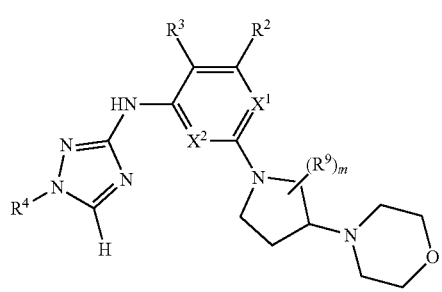
(IIA-6.2) 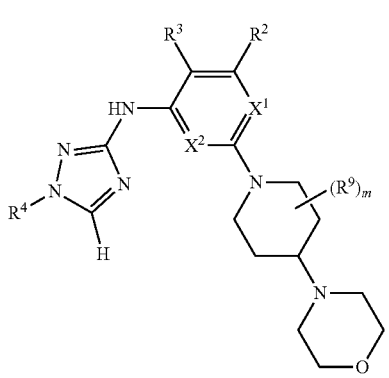
(IIA-7.0) 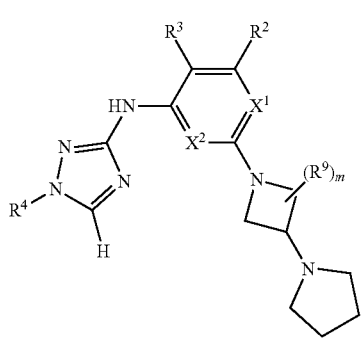
(IIA-8.0) 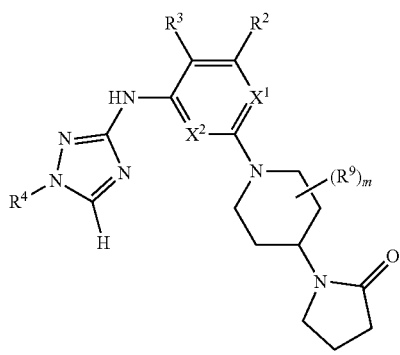
(IIA-8.1) 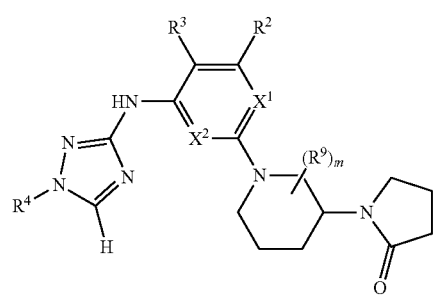

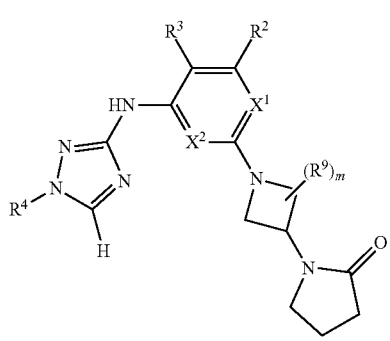

(IIA-8.2)

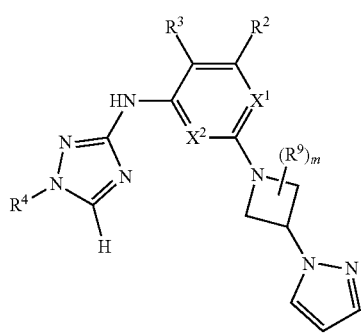

(IIA-9.0)

wherein m, $R^2$, $R^3$, $R^4$, $R^8$, $R^9$, X1, and $X^2$ are as defined herein.

In the compounds of formulas (IIA-1) to (IIA-9), (IIA-1.0) to (IIA-1.9), (IIA-2.0), (IIA-3.0), (IIA-4.0), (IIA-5.0), (IIA-6.0), (IIA-6.1), (IIA-6.2), (IIA-7.0), (IIA-8.0), (IIA-8.1), (IIA-8.2), and (IIA-9.0) are embodiments wherein $R^2$ is $C_{1-4}$alkyl $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl. In some embodiments, $R^2$ is methyl, ethyl, trifluoromethyl, difluoromethyl, or cyclopropyl; $R^3$ is hydrogen; $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl. In further embodiments, $X^1$ and $X^2$ are each CH; or $X^1$ is N and $X^2$ is CH; or $X^1$ is CH and $X^2$ is N.

In other embodiments, the present invention features compounds of formulas (IIA-1) to (IIA-9), (IIA-1.0) to (IIA-1.9), (IIA-2.0), (IIA-3.0), (IIA-4.0), (IIA-5.0), (IIA-6.0), (IIA-6.1), (IIA-6.2), (IIA-7.0), (IIA-8.0), (IIA-8.1), (IIA-8.2), and (IIA-9.0) and the attendant definitions, wherein one or more hydrogen atoms are replaced by a deuterium atom.

In some embodiments of formula (IIB), are compounds of formula (IIB-1), (IIB-2), (IIB-3), or (IIB-4):

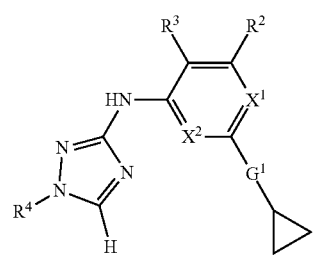

(IIB-1)

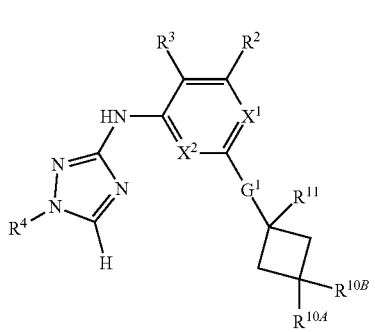

(IIB-2)

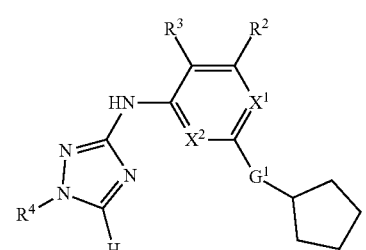

(IIB-3)

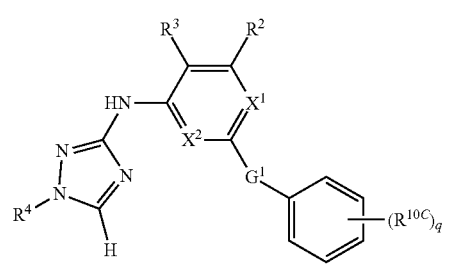

(IIB-4)

wherein $R^{10A}$ and $R^{10B}$ are each, independently hydrogen or halogen (e.g., fluoro), or COOH; $R^{10C}$ is $C_{1-4}$alkyl, $C_{1-4}$haloalkyl, halogen, hydroxyl, —C(O)O$C_{1-4}$alkyl, or —C(O)OH; q is an integer from 0 to 4; $R^{11}$ is hydrogen or hydroxyl; and $G^1$, $R^2$, $R^3$, $R^4$, $X^1$, and $X^2$ are as defined herein. In some embodiments of formula (IIB-2), each of $R^{10A}$, $R^{10B}$, and $R^{11}$ is hydrogen. In other embodiments of formula (IIB-2), $R^{11}$ is hydroxyl and each of $R^{10A}$ and $R^{10B}$ is hydrogen. In yet other embodiments, $R^{11}$ is hydrogen and each of $R^{10A}$ and $R^{10B}$ is fluoro. In some embodiments according to formula (IIB-1), (IIB-2), (IIB-3) or (IIB-4), $G^1$ is

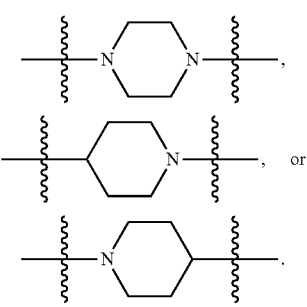

In one embodiment, $G^1$ is
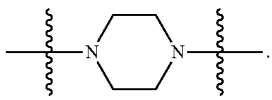
In other embodiments, compounds of formula (IIB-1), (IIB-2), (IIB-3) or (IIB-4) may be represented by the formulas (IIB-1.0) to (IIB-1.3), (IIB-2.0) to (IIB-2.3), (IIB-3.0) to (IIB-3.1) or (IIB-4.0):
(IIB-1.0)
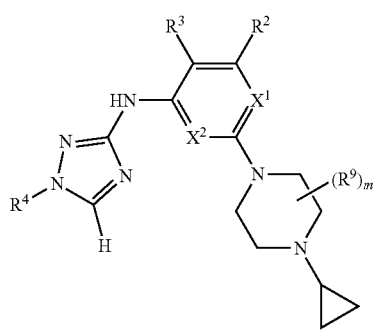
(IIB-1.1)
(IIB-1.2)
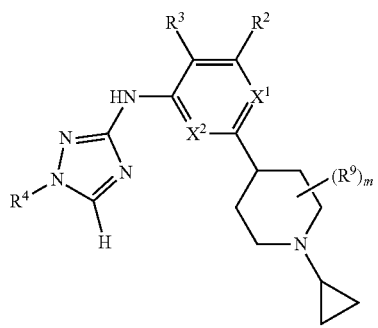
(IIB-1.3)
(IIB-2.0)
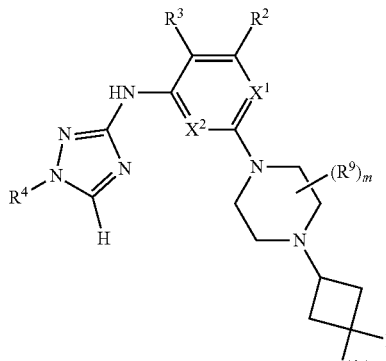
(IIB-2.1)
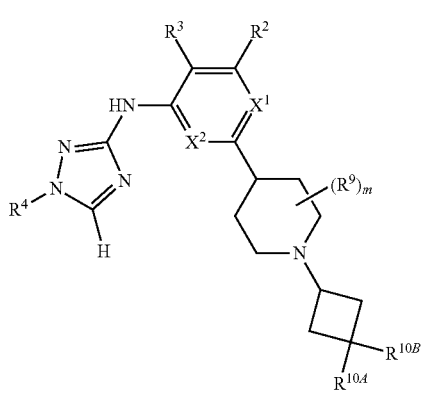
(IIB-2.2)
(IIB-2.3)
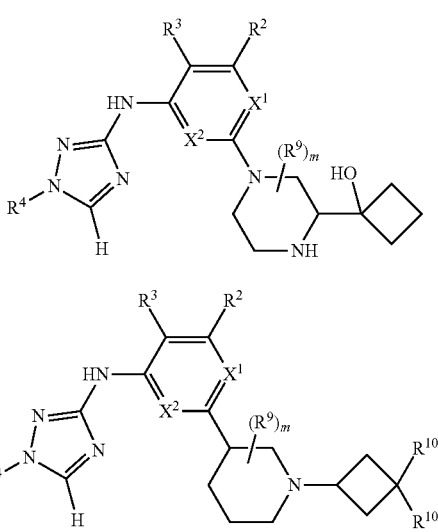
(IIB-3.0)
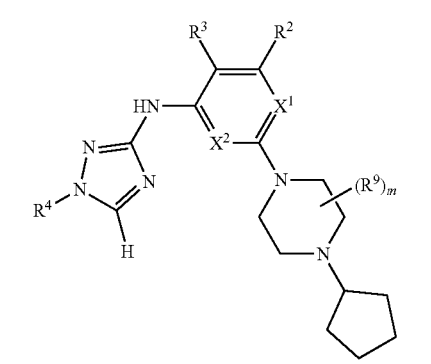

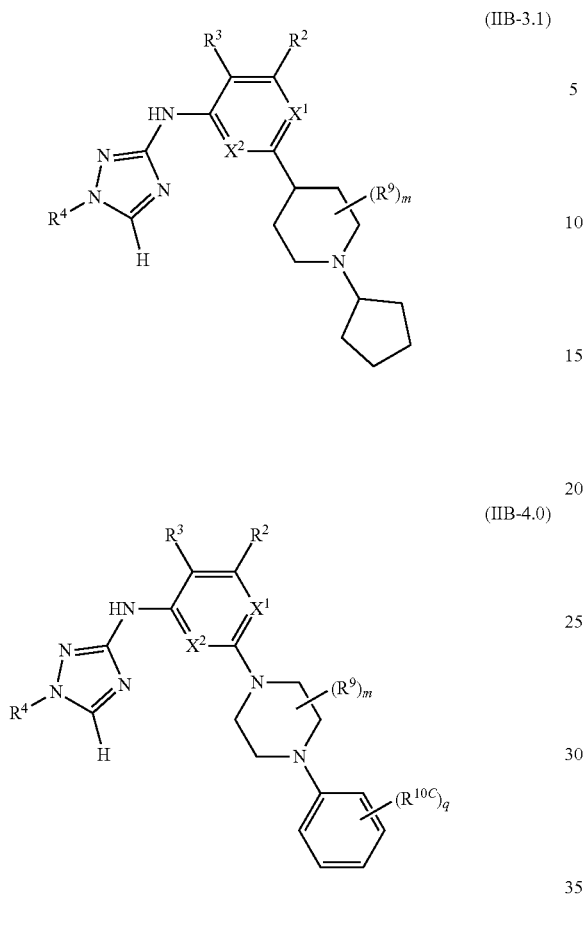

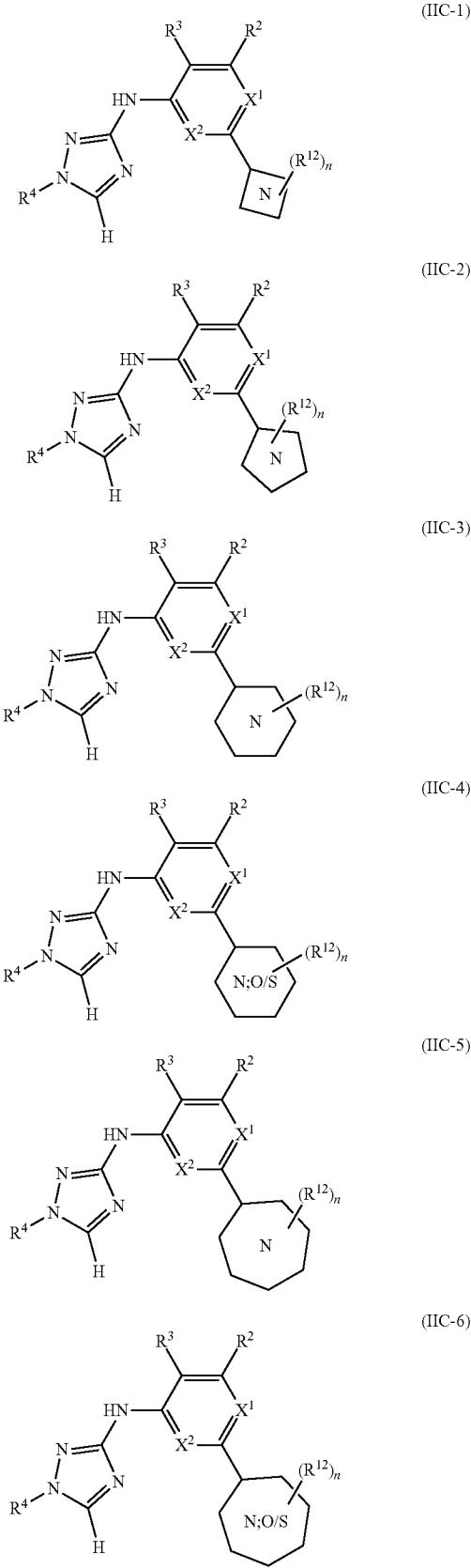

wherein R⁹ is $C_{1-4}$alkyl, $C_{1-4}$haloalkyl, halogen, hydroxyl, or oxo, m and q are each independently an integer from 0 to 4; and $R^2$, $R^3$, $R^4$, $R^{10A}$, $R^{10B}$, $X^1$, and $X^2$ are as defined herein.

In the compounds of formulas (IIB-1), (IIB-2), (IIB-3), (IIB-4), (IIB-1.0) to (IIB-1.3), (IIB-2.0) to (IIB-2.3), (IIB-3.0) to (IIB-3.1) and (IIB-4.0) are embodiments wherein $R^2$ is $C_{1-4}$alkyl, $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl. In some embodiments, $R^2$ is methyl, ethyl, trifluoromethyl, difluoromethyl, or cyclopropyl; $R^3$ is hydrogen; $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl. In further embodiments, $X^1$ and $X^2$ are each CH; or $X^1$ is N and $X^2$ is CH; or $X^1$ is CH and $X^2$ is N.

In other embodiments, the present invention features compounds of formulas (IIB-1), (IIB-2), (IIB-3), (IIB-4), (IIB-1.0) to (IIB-1.3), (IIB-2.0) to (IIB-2.3), (IIB-3.0) to (IIB-3.1) and (IIB-4.0) and the attendant definitions, wherein one or more hydrogen atoms are replaced by a deuterium atom.

In some embodiments of formula (IIC) are compounds of formula (IIC-1), (IIC-2), (IIC-3), (IIC-4), (IIC-5), (IIC-6), (IIC-7), (IIC-8), (IIC-9) and (IIC-10):

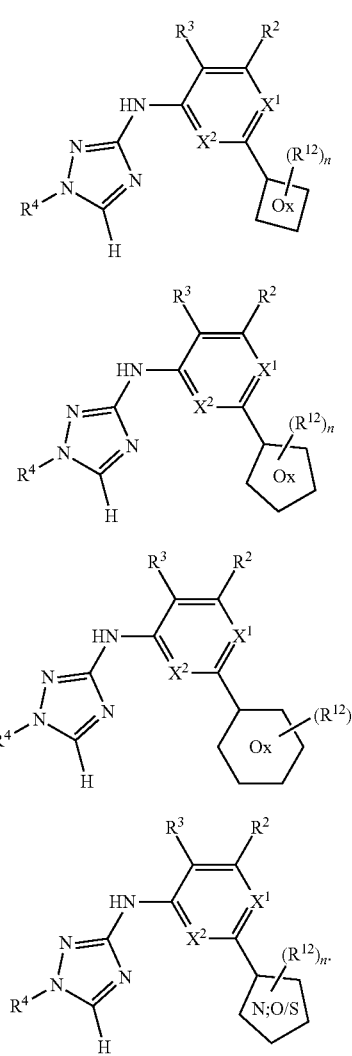

(IIC-7)

(IIC-8)

(IIC-9)

(IIC-10)

In each of formulas (IIC-1), (IIC-2), (IIC-3), (IIC-4), (IIC-5), (IIC-6), (IIC-7), (IIC-8), (IIC-9) and (IIC-10), $R^{12}$ represents the optional $G^2$ substitution, as defined herein, and n is an integer from 0-4. In the foregoing formulas, the illustrated $G^2$ groups having the following meanings: In compounds of formula (IIC-1),

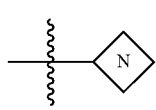

is a 4-membered monocyclic heterocycle containing one nitrogen atom. In compounds of formula (IIC-2),

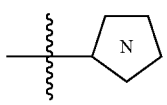

is a 5-membered monocyclic heterocycle containing one nitrogen atom and optionally one double bond. In compounds of formula (IIC-3),

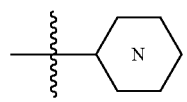

is a 6-membered monocyclic heterocycle containing one nitrogen and optionally a second nitrogen, one double bond, and/or a $C_{1-3}$alkylene bridge between two non-adjacent ring atoms. In compounds of formula (IIC-4),


is a 6-membered monocyclic heterocycle containing one nitrogen and one oxygen atom or sulfur atom, and optionally one double bond, and/or a $C_{1-3}$alkylene bridge between two non-adjacent ring atoms. In compounds of formula (IIC-5),

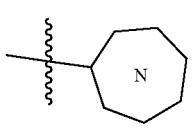

is a 7-membered monocyclic heterocycle containing one nitrogen and optionally a second nitrogen, one double bond, and/or a $C_{1-3}$alkylene bridge between two non-adjacent ring atoms. In compounds of formula (IIC-6),

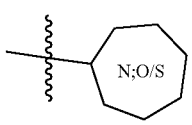

is a 7-membered monocyclic heterocycle containing one nitrogen and one oxygen atom or sulfur atom, and optionally one double bond, and/or a $C_{1-3}$alkylene bridge between two non-adjacent ring atoms. In compounds of formula (IIC-7),

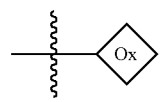 [SMILES: *C1CCC1]

is a 4-membered monocyclic heterocycle containing one oxygen atom. In compounds of formula (IIC-8),

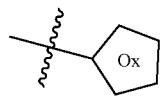

is a 5-membered monocyclic heterocycle containing one oxygen atom and optionally one double bond. In compounds of formula (IIC-9),

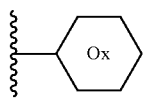

is a 6-membered monocyclic hetereocycle containing one oxygen atom and optionally one double bond and/or a $C_{1-3}$alkylene bridge between two non-adjacent ring atoms. In compounds of formula (IIC-10),

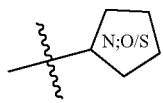 [SMILES: *C1CCCC1]

is a 5-membered monocyclic heterocycle containing one nitrogen and one oxygen atom or sulfur atom.

In other embodiments, the present invention features compounds of formulas (IIC-1), (IIC-2), (IIC-3), (IIC-4), (IIC-5), (IIC-6), (IIC-7), (IIC-8), (IIC-9) and (IIC-10) and the attendant definitions, wherein one or more hydrogen atoms are replaced by a deuterium atom.

In compounds of formula (IIC-1), are further compounds of formula (IIC-1.0) or (IIC-1.1), wherein $R^{12}$ and n are as defined herein:

(IIC-1.0)

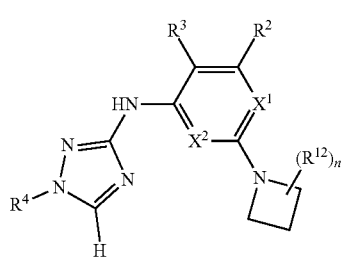

(IIC-1.1)

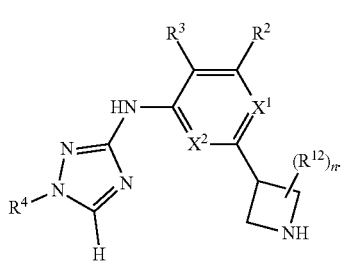

In compounds of formula (IIC-2), are further compounds of formula (IIC-2.0), (IIC-2.1), or (IIC-2.2), wherein $R^{12}$ and n are as defined herein:

(IIC-2.0)

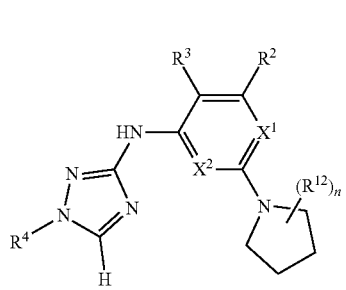

(IIC-2.1)

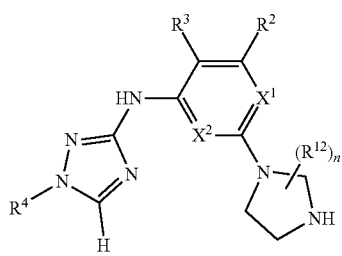

(IIC-2.2)

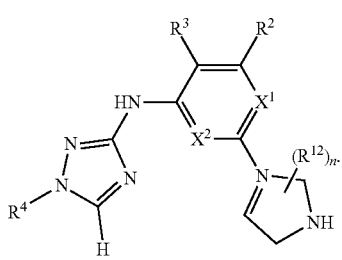

In compounds of formula (IIC-3), are further compounds of formula (IIC-3.0) to (IIC-3.5), wherein $R^{12}$ and n are as defined herein:

(IIC-3.0)

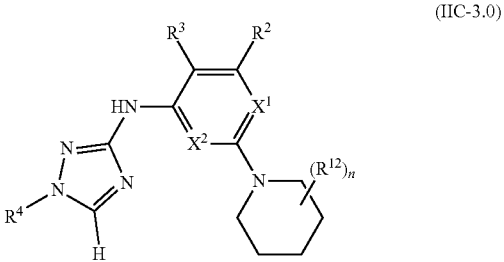

(IIC-3.1)

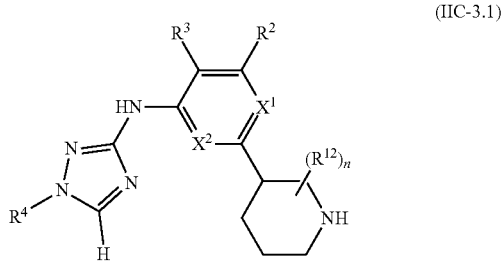

(IIC-3.2)

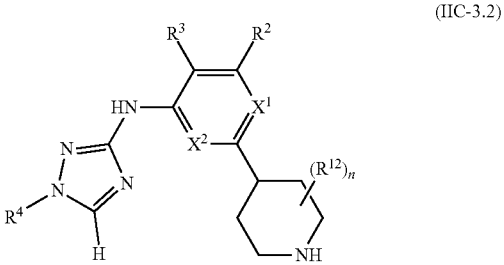

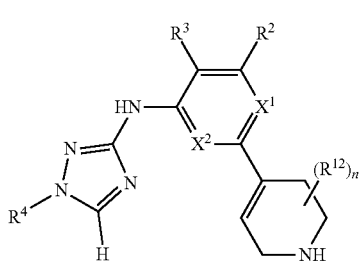
(IIC-3.3)

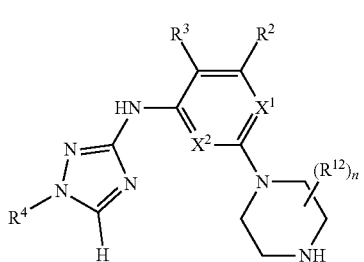
(IIC-3.4)

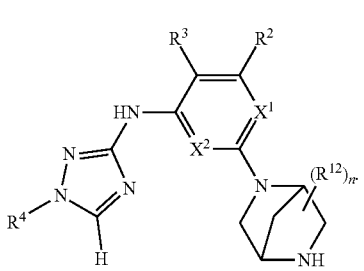
(IIC-3.5)

In compounds of formula (IIC-4), (IIC-5), and (IIC-6) are further compounds, respectively, of formula (IIC-4.0)-(IIC-4.2), (IIC-5.0), and (IIC-6.0), wherein $R^{12}$ and n are as defined herein:

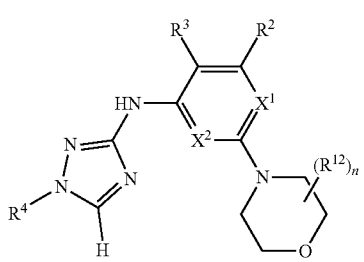
(IIC-4.0)

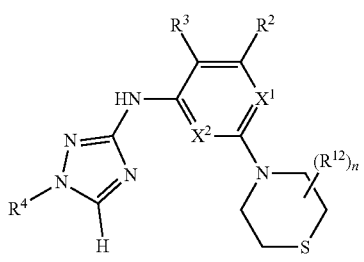
(IIC-4.1)

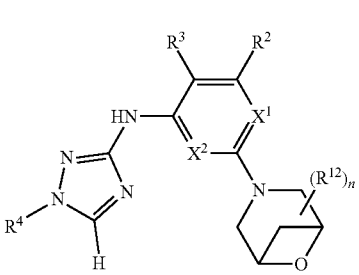
(IIC-4.2)

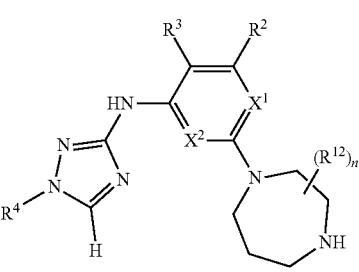
(IIC-5.0)

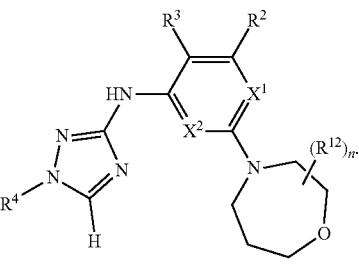
(IIC-6.0)

In compounds of formula (IIC-1.1), (IIC-2.1), (IIC-2.2), (IIC-3.1)-(IIC-3.5), and (IIC-5.0) are embodiments where n is 1 and $R^{12}$ is attached to the available ring nitrogen atom. In some embodiments, the single $R^{12}$ is $C_{1-4}$alkyl, $C_{1-4}$haloalkyl, —C(O)$C_{1-4}$alkyl, —C(O)$C_{3-6}$cycloalkyl, —C(O)O$C_{1-4}$alkyl, —C(O)O$C_{1-4}$haloalkyl, —C(O)$C_{1-4}$haloalkyl, —$C_{1-4}$alkylene-O$C_{1-4}$alkyl, —$C_{1-6}$alkylene-OH, —$C_{1-6}$alkylene substituted by 2 groups independently selected from hydroxyl and —OC(O)$C_{1-4}$alkyl, —$C_{1-4}$alkylene-C(O)O$C_{1-4}$alkyl, or —$C_{1-4}$alkylene-C(O)OH.

In compounds of formula (IIC-7), (IIC-8), (IIC-9) and (IIC-10) are further compounds, respectively, of formula (IIC-7.0), (IIC-8.0)-(IIC-8.1) (IIC-9.0)-(IIC-9.1) and (IIC-10.0)-(IIC-10.1), wherein $R^{12}$ and n are as defined herein:

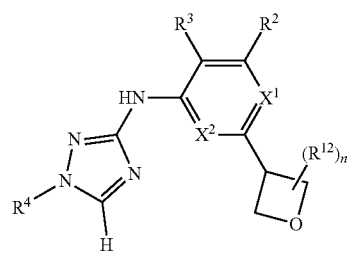
(IIC-7.0)

-continued

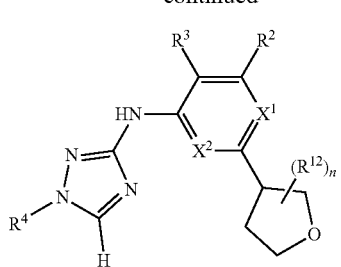
(IIC-8.0)

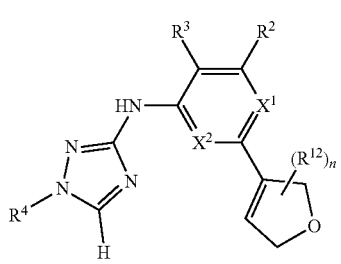
(IIC-8.1)

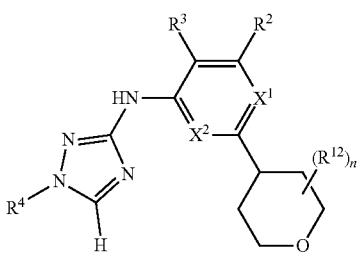
(IIC-9.0)

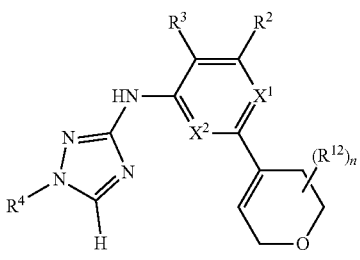
(IIC-9.1)

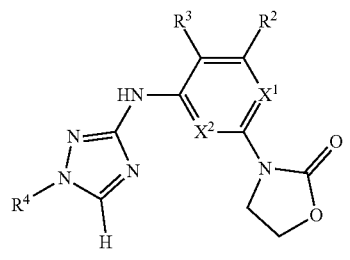
(IIC-10.0)

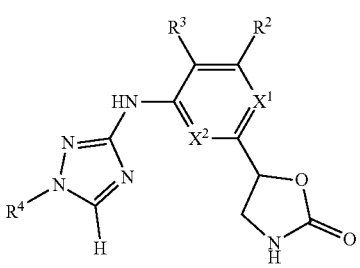
(IIC-10.1)

In the compounds of formulas (IIC-1) to (IIC-10), (IIC-1.0), (IIC-1.1), (IIC-2.0), (IIC-2.1), (IIC-2.2), (IIC-3.0) to (IIC-3.5), (IIC-4.0), (IIC-4.1), (IIC-5.0), (IIC-6.0), (IIC-7.0), (IIC-8.0), (IIC-8.1), (IIC-9.0), (IIC-9.1), (IIC-10.0), and (IIC-10.1) are embodiments wherein $R^2$ is $C_{1-4}$alkyl $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl. In some groups of compounds in these embodiments, $R^2$ is methyl, ethyl, trifluoromethyl, difluoromethyl, or cyclopropyl; $R^3$ is hydrogen; $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl. In further subgroups of compounds, $X^1$ and $X^2$ are each CH; or $X^1$ is N and $X^2$ is CH; or $X^1$ is CH and $X^2$ is N.

In some embodiments of formula (IIC), $G^2$ is

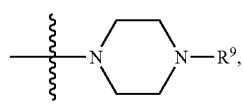

$R^9$ is $C_{1-4}$alkyl, $R^2$ is $C_{1-4}$alkyl $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl and $X^1$, and $X^2$ are as defined herein. In one embodiment, $G^2$ is

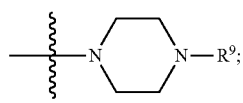

$R^9$ is methyl; $R^2$ is methyl, ethyl, trifluoromethyl, difluoromethyl, or cyclopropyl; $R^3$ is hydrogen; and $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl. In another embodiment, $X^1$ and $X^2$ are each CH; or $X^1$ is N and $X^2$ is CH; or $X^1$ is CH and $X^2$ is N.

In other embodiments of formula (IIC), $G^2$ is oxetan-3-yl; $R^2$ is $C_{1-4}$alkyl $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl and $X^1$, and $X^2$ are as defined herein. In some embodiment, $G^2$ is oxetan-3-yl; $R^2$ is methyl, ethyl, trifluoromethyl, difluoromethyl, or cyclopropyl; $R^3$ is hydrogen; and $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl. In other embodiments, $X^1$ and $X^2$ are each CH; or $X^1$ is N and $X^2$ is CH; or $X^1$ is CH and $X^2$ is N.

In some embodiments of formula (IID), $G^3$ is

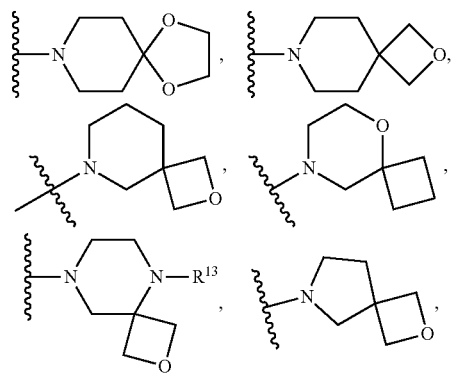

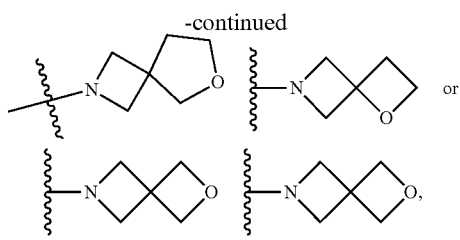

wherein R[13] is hydrogen or an optional substituent of G[3] (e.g., $C_{1-4}$alkyl such as methyl, ethyl). In some embodiments, R[2] is $C_{1-4}$alkyl $C_{1-4}$haloalkyl, or $C_{3-6}$cycloalkyl; R[3] is hydrogen; R[4] is phenyl optionally substituted with 1-2 substituents selected from halogen and $C_{1-4}$alkyl or R[4] is pyrazinyl and X[1], and X[2] are as defined herein. In some groups of compounds, G[3] is

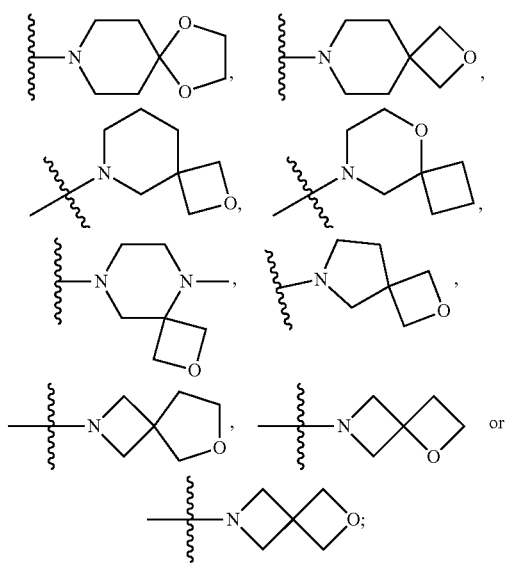

R[2] is methyl, ethyl, trifluoromethyl, difluoromethyl, or cyclopropyl; R[3] is hydrogen; and R[4] is phenyl, 3,5-difluorophenyl, 3-fluorophenyl, 3,4-difluorophenyl, 2,5-difluorophenyl, 3-fluoro-5-methylphenyl, or pyrazin-2-yl. In some embodiments, X[1] and X[2] are each CH; or X[1] is N and X[2] is CH; or X[1] is CH and X[2] is N.

In some embodiments of formula (IIE), G[4] is

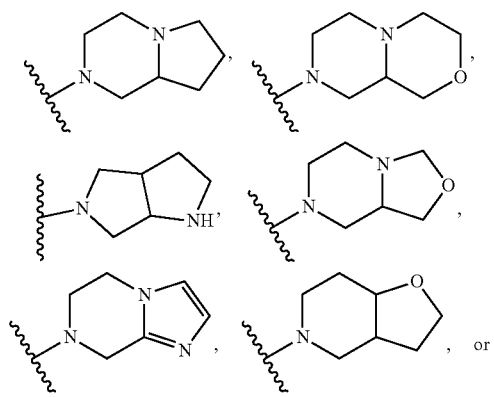

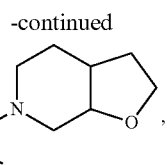

each being optionally substituted with 1-4 substituents selected from the group consisting of $C_{1-4}$alkyl (e.g., methyl, ethyl, isobutyl), $C_{1-4}$haloalkyl (e.g., —CF$_3$, —CH$_2$CF$_3$), halogen (e.g., fluoro), and oxo. In one embodiment, G[4] is

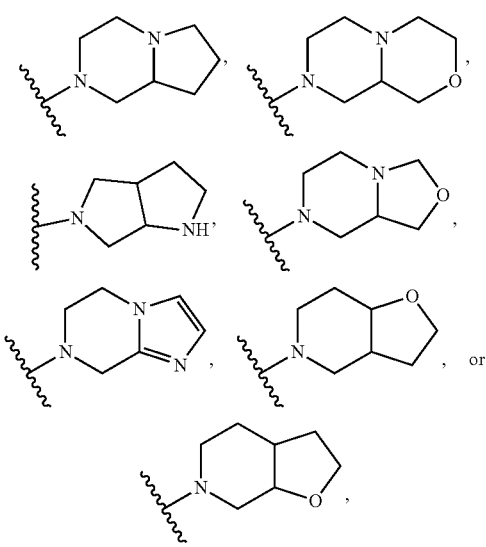

each being optionally substituted with one $C_{1-4}$alkyl, $C_{1-4}$haloalkyl, halogen, or oxo. In some embodiments, R[2] is $C_{1-4}$alkyl $C_{1-4}$haloalkyl, or $C_{3-6}$cycloalkyl; R[3] is hydrogen; R[4] is phenyl optionally substituted with 1-2 substituents selected from halogen and $C_{1-4}$alkyl or R[4] is pyrazinyl and X[1], and X[2] are as defined herein. In other embodiments, G[4] is

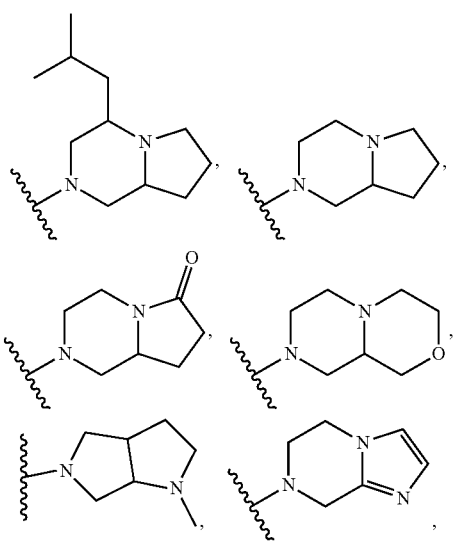

-continued

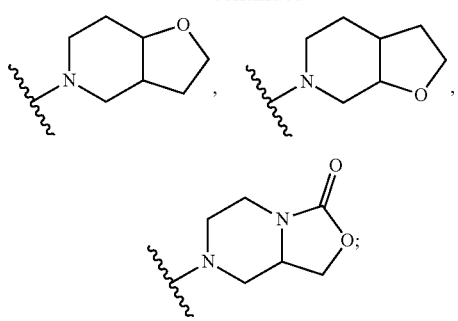

$R^2$ is methyl, ethyl, trifluoromethyl, difluoromethyl, or cyclopropyl; $R^3$ is hydrogen; and $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl. In some embodiment, $X^1$ and $X^2$ are each CH; or $X^1$ is N and $X^2$ is CH; or $X^1$ is CH and $X^2$ is N.

In other embodiments, the present invention features compounds of formulas (IIC-1) to (IIC-10), (IIC-1.0), (IIC-1.1), (IIC-2.0), (IIC-2.1), (IIC-2.2), (IIC-3.0) to (IIC-3.5), (IIC-4.0), (IIC-4.1), (IIC-5.0), (IIC-6.0), (IIC-7.0), (IIC-8.0), (IIC-8.1), (IIC-9.0), (IIC-9.1), (IIC-10.0), and (IIC-10.1) and the attendant definitions, wherein one or more hydrogen atoms are replaced by a deuterium atom.

Included in compounds of formula (III) are compounds of formula (IIIA), (IIIB), (IIIC), (IIID), (IIIE) and (IIIF), wherein $G^1$, $G^2$, $G^3$, $G^4$, $G^5$, $R^2$, $R^3$, $R^4$, $X^1$, and $X^2$ are as defined herein:

(IIIA)

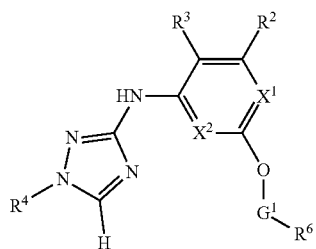

(IIIB)

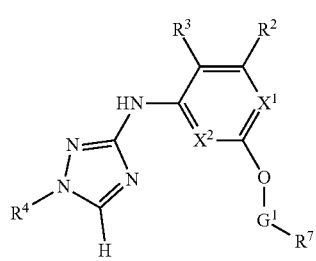

(IIIC)

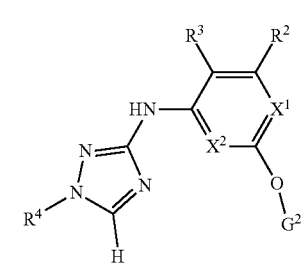

(IIID)

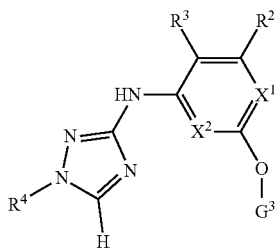

(IIIE)

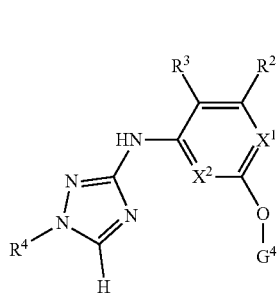

(IIIF)

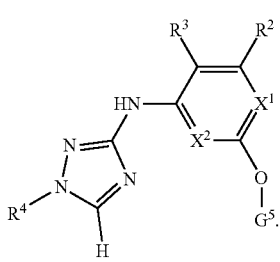

In some embodiments, the present invention features compounds of formulas (IIIA), (IIIB), (IIIC), (IIID), (IIIE) and (IIIF) and the attendant definitions, wherein one or more hydrogen atoms are replaced by a deuterium atom.

In some embodiments of formula (IIIA), are compounds of formula (IIIA-1), wherein $G^1$, $R^2$, $R^3$, $R^4$, $R^8$, $X^1$, and $X^2$ are as defined herein:

(IIIA-1)

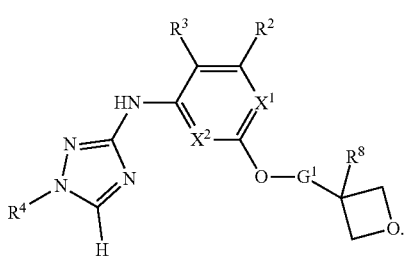

In some embodiments, compounds of formula (IIIA-1) may be represented by the formulas (IIIA-1.0) or (IIIA-1.1):

(IIIA-1.0)

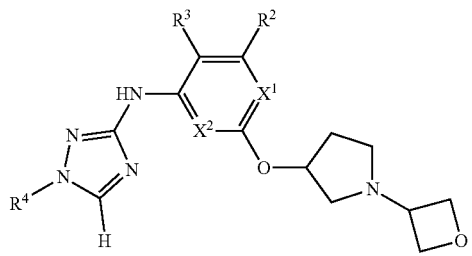

(IIIA-1.1)

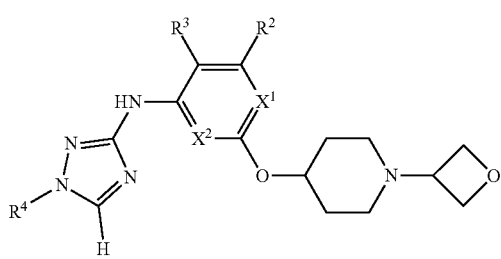

wherein $R^2$, $R^3$, $R^4$, $X^1$, and $X^2$ are as defined herein.

In some embodiments of formulas (IIIA) to (IIIF), (IIIA-1), (IIIA-1.0), or (IIIA-1.1), $R^2$ is $C_{1-4}$alkyl $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl and $X^1$, and $X^2$ are as defined herein. In some embodiments, $R^2$ is methyl, ethyl, trifluoromethyl, difluoromethyl, or cyclopropyl; $R^3$ is hydrogen; and $R^4$ is phenyl, 3,5-difluorophenyl, 3-fluorophenyl, 4-fluorophenyl, 3,4-difluorophenyl, 2,5-difluorophenyl, 3-fluoro-5-methylphenyl, or pyrazin-2-yl. In other embodiments, $X^1$ and $X^2$ are each CH; or $X^1$ is N and $X^2$ is CH; or $X^1$ is CH and $X^2$ is N.

Included in compounds of formula (IV) are compounds of formula (IVA), (IVB), (IVC), (IVD), (IVE) or (IVF), wherein $G^1$, $G^2$, $G^3$, $G^4$, $G^5$, $R^2$, $R^3$, $R^4$, $R^5$, $X^1$, and $X^2$ are as defined herein:

(IVA)

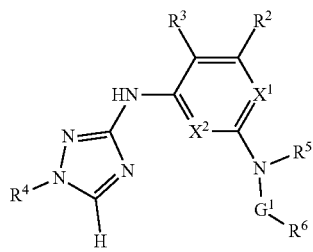

(IVB)

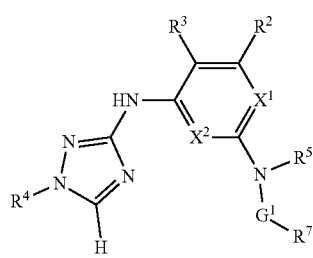

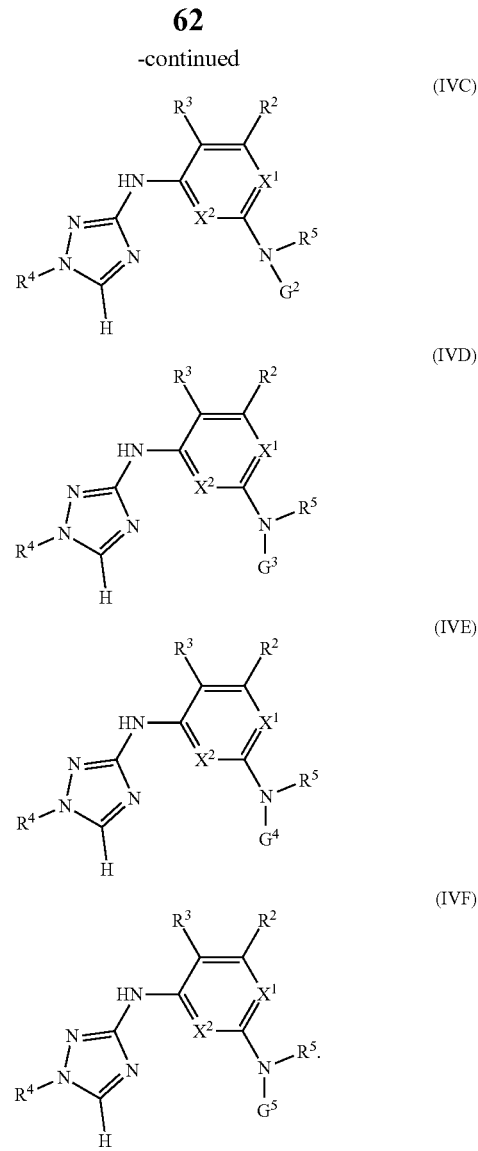

In some embodiments, the present invention features compounds of formulas (IVA), (IVB), (IVC), (IVD), (IVE) and (IVF) and the attendant definitions, wherein one or more hydrogen atoms are replaced by a deuterium atom.

In some embodiments of formula (IVA), are compounds of formula (IVA-1), wherein $G^1$, $R^2$, $R^3$, $R^4$, $R^5$, $R^8$, $X^1$, and $X^2$ are as defined herein:

(IVA-1)

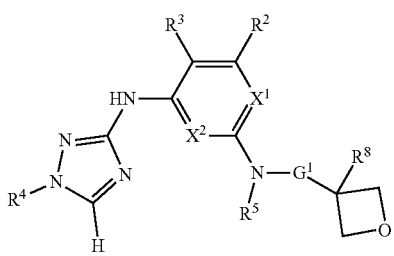

In some embodiments, compounds of formula (IVA-1) may be represented by the formulas (IVA-1.0) or (IVA-1.1):

(IVA-1.0)

(IVA-1.1)

In some embodiments of formulas (IVA) to (IVF), (IVA-1), (IVA-1.0), or (IVA-1.1), $R^5$ is H or methyl; $R^2$ is $C_{1-4}$alkyl $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl and $X^1$, and $X^2$ are as defined herein. In some embodiments, $R^5$ is H or methyl; $R^2$ is methyl, ethyl, trifluoromethyl, difluoromethyl, or cyclopropyl; $R^3$ is hydrogen; and $R^4$ is phenyl, 3,5-difluorophenyl, 3-fluorophenyl, 4-fluorophenyl, 3,4-difluorophenyl, 2,5-difluorophenyl, 3-fluoro-5-methylphenyl, pyridine-3-yl, 2-fluoropyridin-4-yl, or pyrazin-2-yl. In subgroups of compounds $X^1$ and $X^2$ are each CH; or $X^1$ is N and $X^2$ is CH; or $X^1$ is CH and $X^2$ is N.

In some embodiments of formula (IVC), are compounds of formula (IVC-1) (IVC-2), (IVC-3), or (IVC-4), wherein n, $R^2$, $R^3$, $R^4$, $R^5$, $R^{12}$, $X^1$, and $X^2$ are as defined herein:

(IVC-1)

(IVC-2)

(IVC-3)

(IVC-4)

wherein $R^{12}$ represents the optional $G^2$ substitution, as defined herein, and n is an integer from 0-4. In some embodiments, $R^{12}$ is —$C_{1-4}$alkylene-$OC_{1-4}$alkyl or —C(O)$C_{1-4}$alkyl and n is 1. In a subgroup of compounds, n is 1 and $R^{12}$ is —$C_{1-4}$alkylene-$OC_{1-4}$alkyl or —C(O)$C_{1-4}$alkyl and is bonded to an available ring nitrogen atom. In compounds of formula (IVC-1), is a 4-membered monocyclic heterocycle containing one nitrogen atom. In compounds of formula (IVC-2), is a 6-membered monocyclic hetereocycle containing one nitrogen and optionally a second nitrogen, one double bond, and/or a $C_{1-3}$alkylene bridge between two non-adjacent ring atoms. In compounds of (IVC-3), is a 4-membered monocyclic heterocycle containing one oxygen atom. In compounds of formula (IVC-4), is a 5-membered monocyclic heterocycle containing one oxygen atom and optionally one double bond.

In some embodiments, compounds of formula (IVC-1) (IVC-2), (IVC-3), and (IVC-4) may be represented by the formulas (IVC-1.0), (IVC-2.0), (IVC-2.1), (IVC-3.0), and (IVC-4.0):

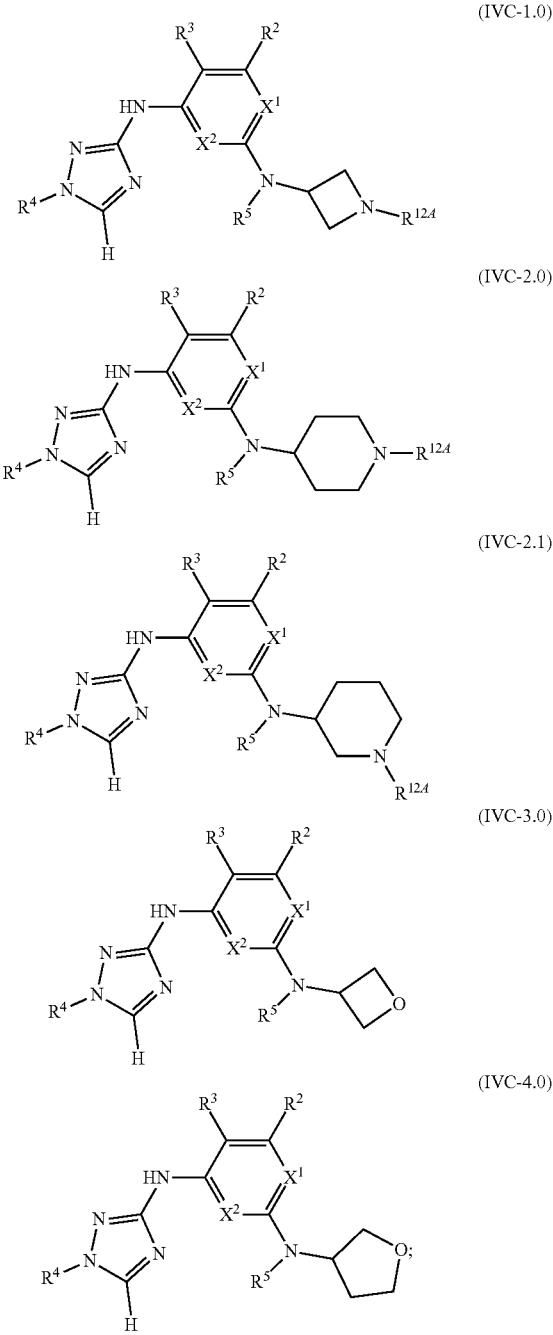

wherein $R^{12A}$ is H or $R^{12}$, and $R^2$, $R^3$, $R^4$, $R^5$, $R^{12}$, $X^1$, and $X^2$ are as defined herein.

In some embodiments of formulas (IVC-1), (IVC-2), (IVC-3), (IVC-4), (IV-1.0), (IVA-2.0), (IVC-2.1), (IVC-3.0), or (IVC-4.0), $R^5$ is H or methyl; $R^2$ is $C_{1-4}$alkyl $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl; and $X^1$ and $X^2$ are as defined herein. In some embodiments, $R^5$ is H or methyl;

$R^2$ is methyl, ethyl, trifluoromethyl, difluoromethyl, or cyclopropyl; $R^3$ is hydrogen; and $R^4$ is phenyl, 3,5-difluorophenyl, 3-fluorophenyl, 4-fluorophenyl, 2,4-difluorophenyl, 3,4-difluorophenyl, 2,5-difluorophenyl, 3-fluoro-5-methylphenyl, pyridine-3-yl, 2-fluoropyridin-4-yl, or pyrazin-2-yl. In subgroups of compounds $X^1$ and $X^2$ are each CH; or $X^1$ is N and $X^2$ is CH; or $X^1$ is CH and $X^2$ is N.

In some embodiments of formula (IVF), are compounds of formula (IVF-1) and (IVF-2), wherein $R^{14}$ is the optional substituent on $G^5$, p is an integer from 0-4, and $R^2$, $R^3$, $R^4$, $R^5$, $X^1$, and $X^2$ are as defined herein:

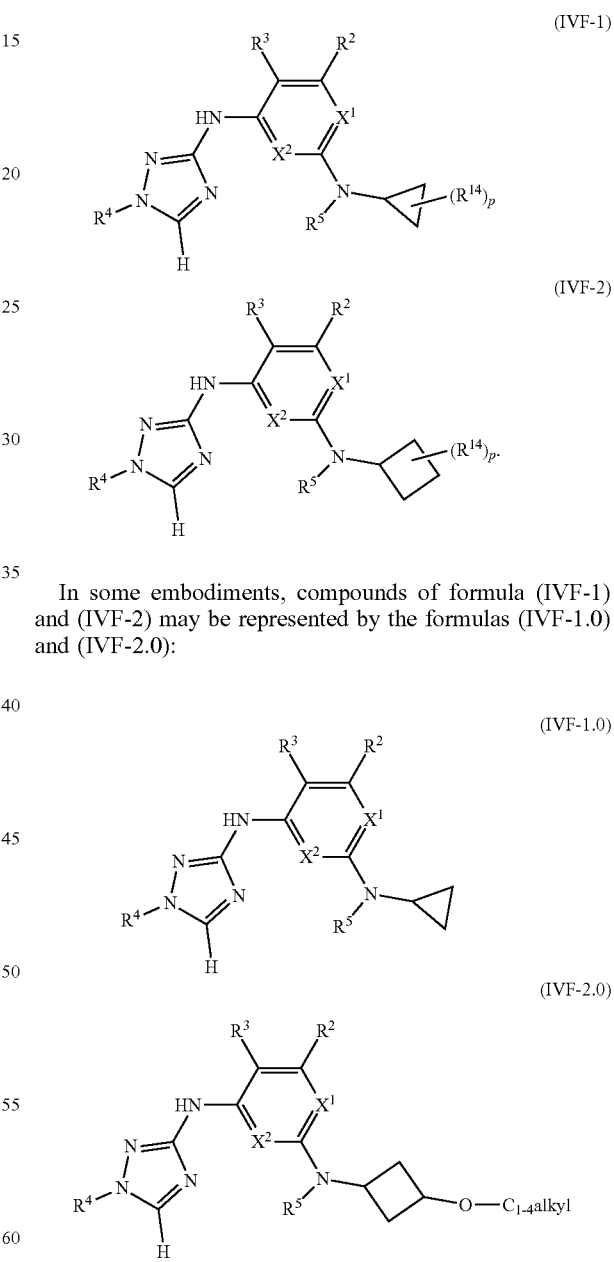

In some embodiments, compounds of formula (IVF-1) and (IVF-2) may be represented by the formulas (IVF-1.0) and (IVF-2.0):

In some embodiments of formulas (IVF-1), (IVF-2), (IVF-1.0) or (IVF-2.0), $R^5$ is H or methyl; $R^2$ is $C_{1-4}$alkyl, $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl; and $X^1$ and $X^2$ are as defined herein. In some embodiments, $R^5$ is H or methyl; $R^2$ is methyl, ethyl, trifluoromethyl, difluoromethyl, or cyclopropyl; $R^3$ is hydrogen; and $R^4$ is phenyl, 3,5-difluorophenyl, 3-fluorophenyl, 4-fluorophenyl, 2,4-difluorophenyl, 3,4-difluorophenyl, 2,5-difluorophenyl, 3-fluoro-5-methylphenyl, pyridine-3-yl, 2-fluoropyridin-4-yl, or pyrazin-2-yl. In other embodiments, $X^1$ and $X^2$ are each CH; or $X^1$ is N and $X^2$ is CH; or $X^1$ is CH and $X^2$ is N.

Included in compounds of formula (V) are compounds of formula (VA), (VB), (VC), (VD), (VE), or (VF), wherein $G^1$, $G^2$, $G^3$, $G^4$, $G^5$, $R^2$, $R^3$, $R^4$, $R^5$, $X^1$, and $X^2$ are as defined herein:

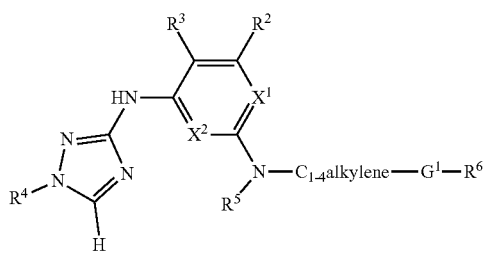

(VA)

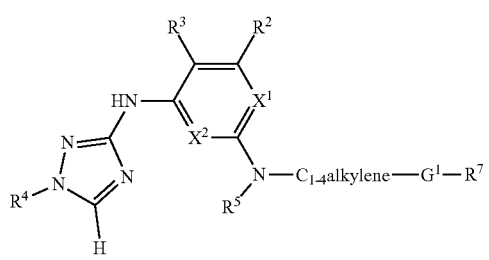

(VB)

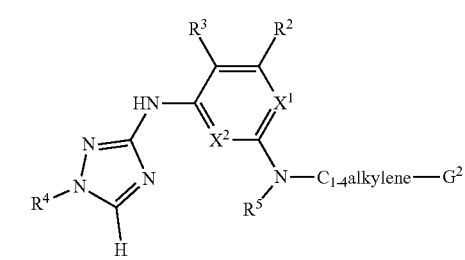

(VC)

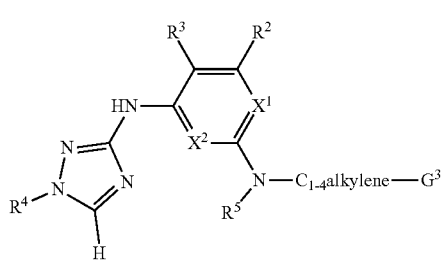

(VD)

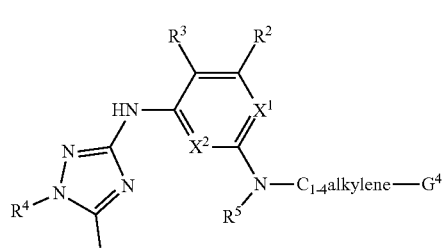

(VE)

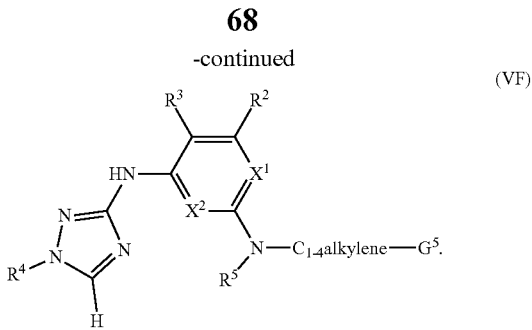

(VF)

In some embodiments, the present invention features compounds of formulas (VA), (VB), (VC), (VD), (VE), and (VF) and the attendant definitions, wherein one or more hydrogen atoms are replaced by a deuterium atom.

In some embodiments of formula (VC), are compounds of formula (VC-1)

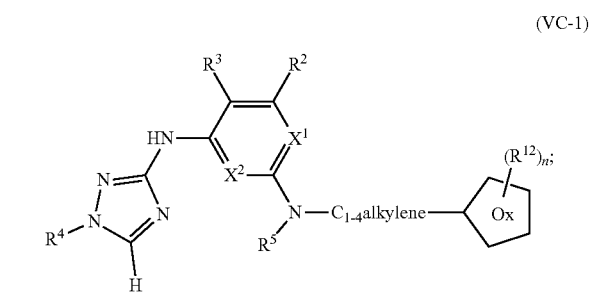

(VC-1)

wherein n, $R^2$, $R^3$, $R^4$, $R^5$, $R^{12}$, $X^1$, and $X^2$ are as defined herein. $R^{12}$ represents the optional $G^2$ substitution, as defined herein, and n is an integer from 0-4. In compounds of formula (VC-1),

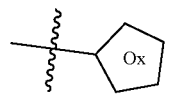

is a 5-membered monocyclic heterocycle containing one oxygen atom and optionally one double bond.

In some embodiments, compounds of formula (VC-1) may be represented by the formula (VC-1.0)

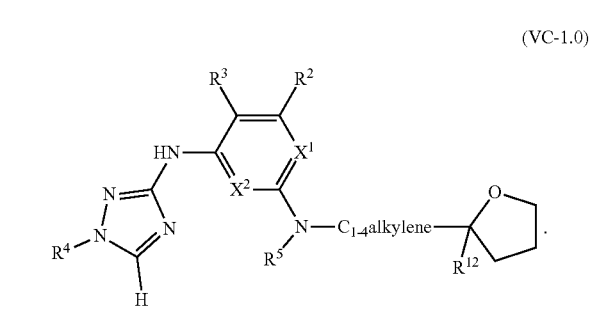

(VC-1.0)

In some embodiments of formulas (VA) to VF), (VC-1) or (VC-1.0), $R^5$ is H or methyl; $R^{12}$ is H or $C_{1-4}$alkyl, $R^2$ is $C_{1-4}$alkyl, $C_{1-4}$haloalkyl, or $C_{3-6}$cycloalkyl; $R^3$ is hydrogen; $R^4$ is phenyl optionally substituted with 1-2 substituents selected from halogen and $C_{1-4}$alkyl or $R^4$ is pyrazinyl; and $X^1$ and $X^2$ are as defined herein. In some embodiments, $R^5$ is H or methyl; $R^{12}$ is H or methyl, the $C_{1-4}$alkylene is —CH$_2$— or —CH$_2$CH$_2$—; $R^2$ is methyl, ethyl, trifluoromethyl, difluoromethyl, or cyclopropyl; $R^3$ is hydrogen; and $R^4$ is phenyl, 3,5-difluorophenyl, 3-fluorophenyl, 4-fluorophenyl, 2,4-difluorophenyl, 3,4-difluorophenyl, 2,5-difluorophenyl, 3-fluoro-5-methylphenyl, pyridine-3-yl, 2-fluoropyridin-4-yl, or pyrazin-2-yl. In other embodiments, $X^1$ and $X^2$ are each CH; or $X^1$ is N and $X^2$ is CH; or $X^1$ is CH and $X^2$ is N.

In still other embodiments, the invention provides particular combinations of $L^1$, $R^1$, $R^2$, $R^4$, $X^1$, $X^2$, and $X^3$.

In some embodiments are compounds of formula (II'), formula (III'), formula (IV'), formula (V'), formula (VI'), formula (VII'), or formula (VIII'), wherein —NR$^5$—C$_{1-4}$alkylene-, —O—C$_{1-4}$alkylene-, —C$_{1-4}$alkylene-, $R^1$, $R^2$, $R^4$, $X^1$, $X^2$, and $X^3$ are as defined herein:

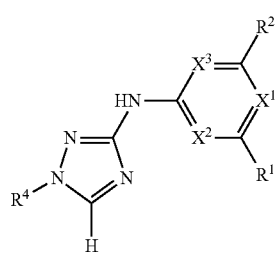

(II')

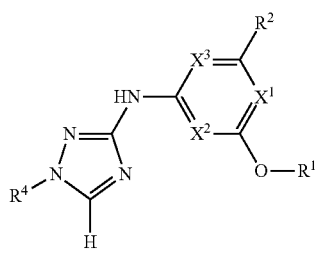

(III')

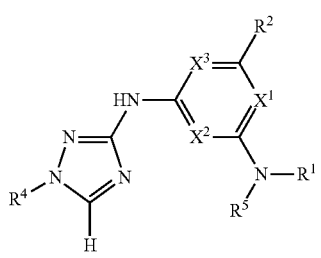

(IV')

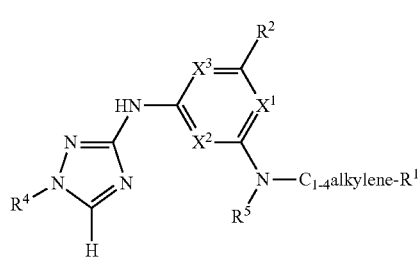

(V')

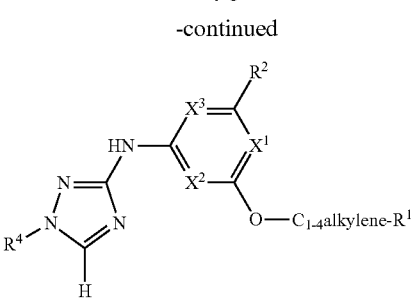

(VI')

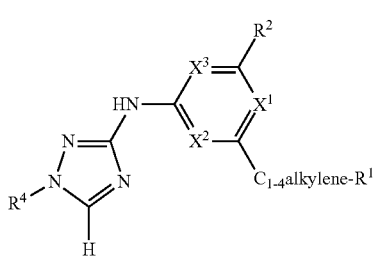

(VII')

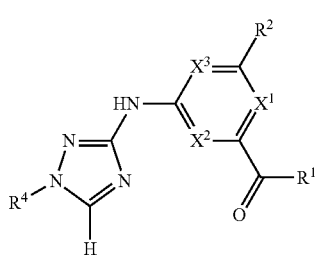

(VIII')

In some embodiments, the present invention features compounds of formulas (II'), formula (III'), formula (IV'), formula (V'), formula (VI'), formula (VII'), and formula (VIII') and the attendant definitions, wherein one or more hydrogen atoms are replaced by a deuterium atom.

In other embodiments, the present invention features compounds of formulas (IX'), (XI'), (XII'), (XIII'), and (XIV'), wherein —NR$^5$—C$_{1-4}$alkylene-, —O—C$_{1-4}$alkylene-, —C$_{1-4}$alkylene-, $R^1$, $R^2$, $R^4$, $X^1$, $X^2$, and $X^3$ are as defined herein and wherein one or more hydrogen atoms are optionally replaced by a deuterium atom.

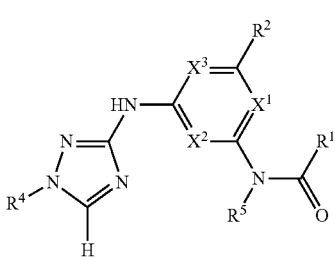

(IX')

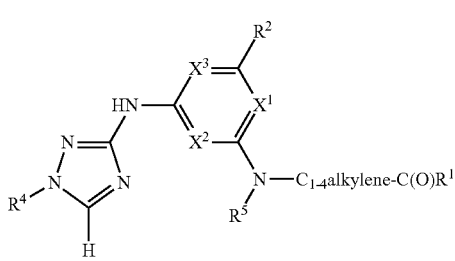

(XI')

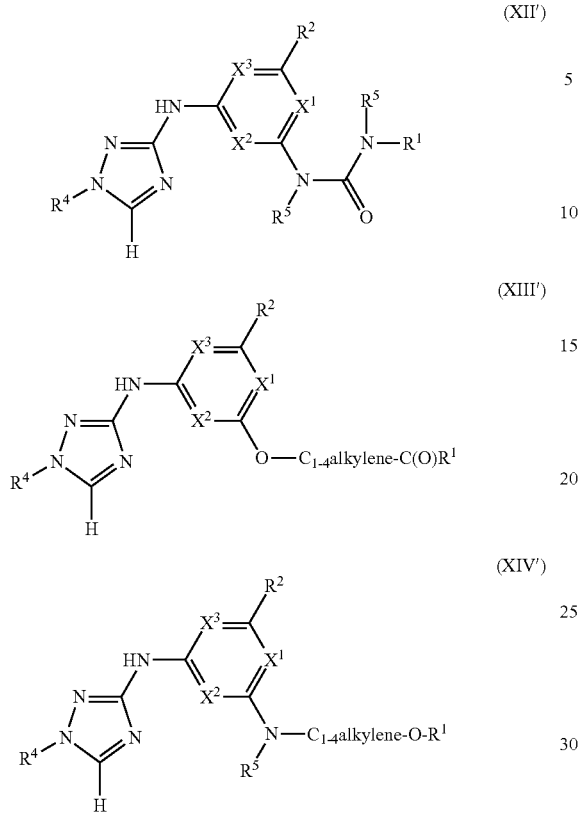

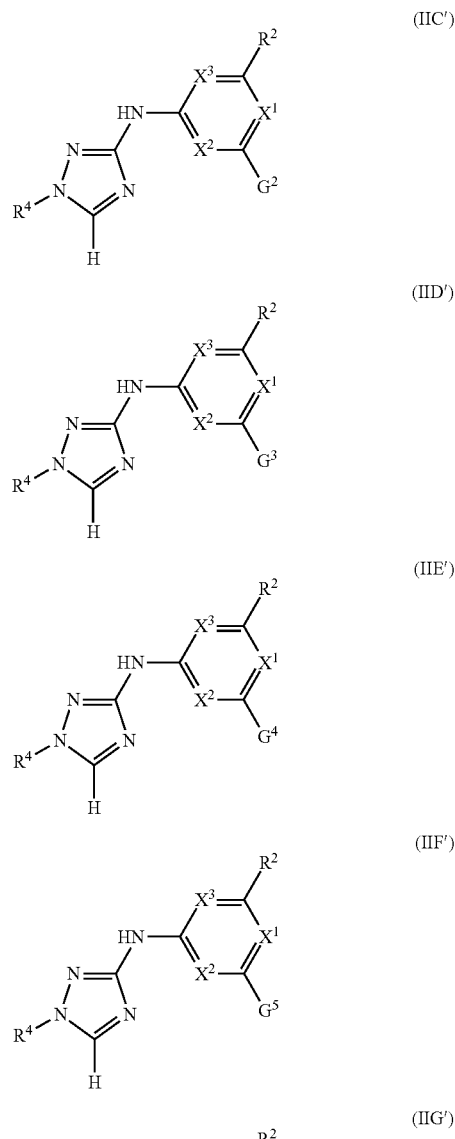

In some embodiments of formulas (II') to (VIII') and (IX'), (XI'), (XII'), (XIII'), and (XIV') are compounds where $X^2$ is $CR^{X2}$ and $R^{X2}$ is hydrogen or fluoro. In other embodiments, $R^{X2}$ is fluoro.

Included in compounds of formula (II') are compounds of formula (IIA'), (IIB'), (IIC'), (IID'), (IIE'), (IIF'), (IIG'), and (IIH'), wherein $L^2$, $G^1$, $G^2$, $G^3$, $G^4$, $G^5$, $G^6$, $R^2$, $R^4$, $R^6$, $R^7$, $X^1$, $X^2$, and $X^3$ are as defined herein:

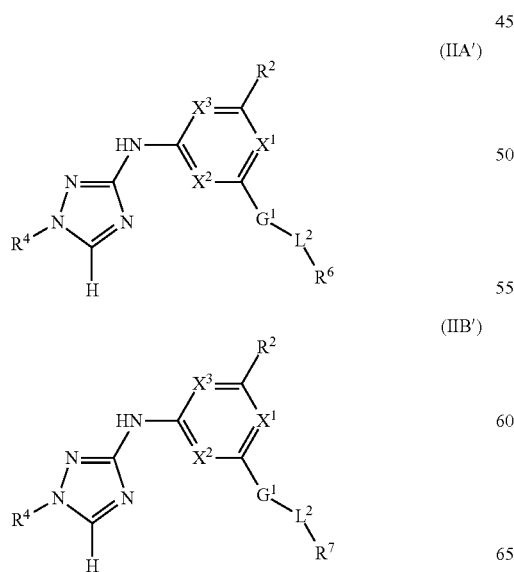

In some embodiments, the present invention features compounds of formulas (IIA'), (IIB'), (IIC'), (IID'), (IIE'), (IIF'), (IIG'), and (IIH') and the attendant definitions, wherein one or more hydrogen atoms are replaced by a deuterium atom.

In some embodiments of formula (IIA'), are compounds where $L^2$ is a bond having formula (IIA-1') to (IIA-20'), wherein $R^{8'}$ is $C_{1-4}$alkyl, $C_{1-4}$haloalkyl, —$CH_2S(O)_2$phenyl, halogen, hydroxyl, or oxo, s is an integer from 0-4, and $G^1$, $R^2$, $R^4$, $X^1$, $X^2$, and $X^3$, are as defined herein.

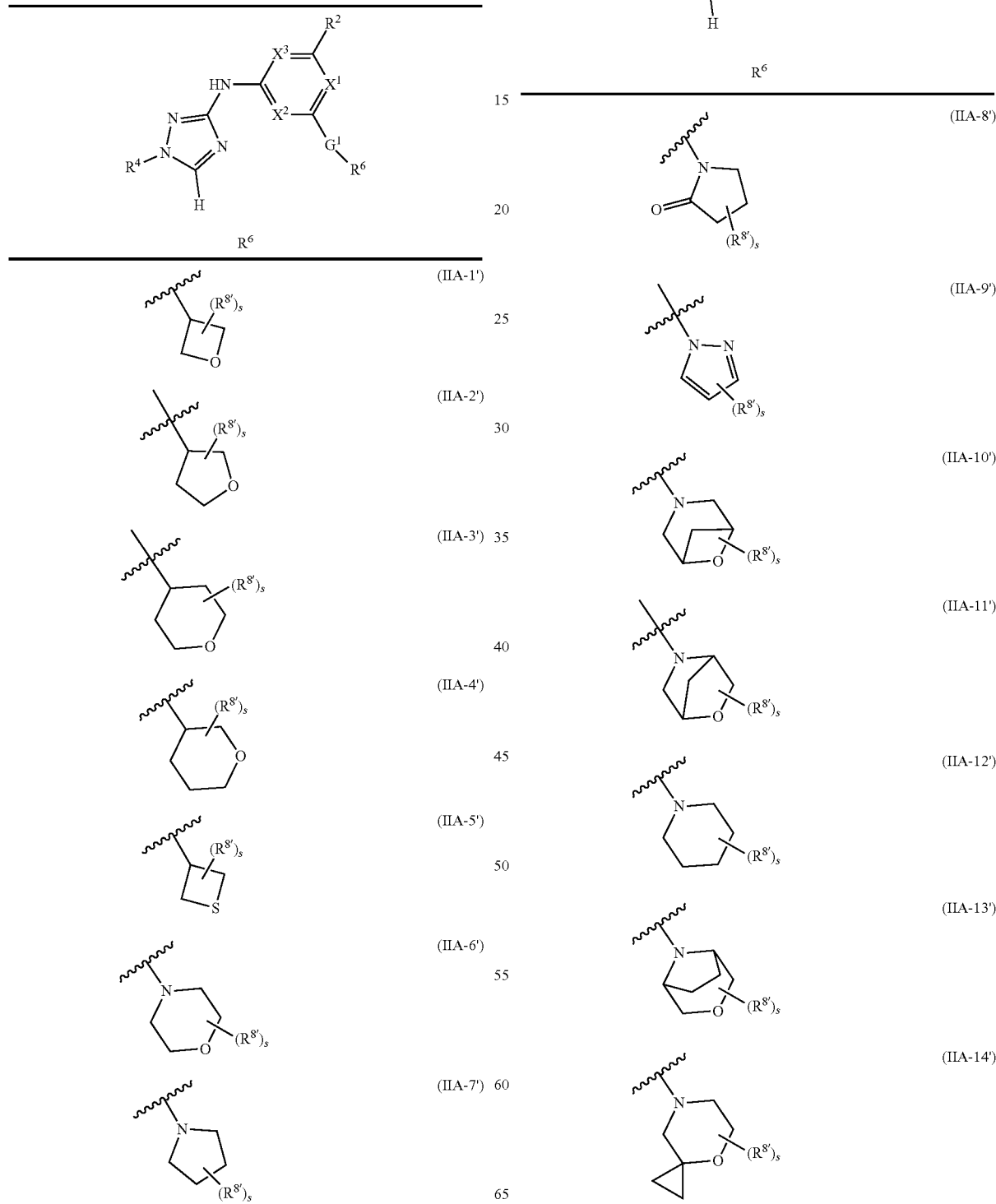

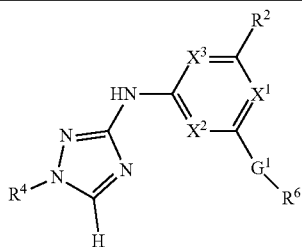

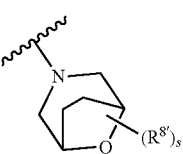
(IIA-15')

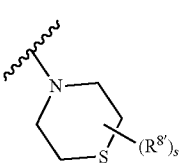
(IIA-16')

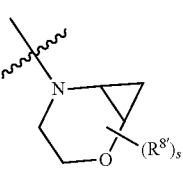
(IIA-17')

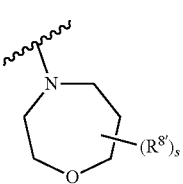
(IIA-18')

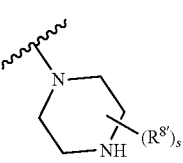
(IIA-19')

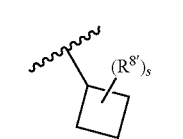
(IIA-20')

In some embodiments, the present invention features compounds of formulas (IIA-1') to (IIA-20') and the attendant definitions, wherein one or more hydrogen atoms are replaced by a deuterium atom.

In some embodiments according to formula (IIA'), and (IIA-1') to (IIA-20'), $G^1$ is

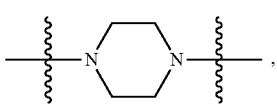

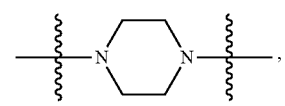 [SMILES: *N1CCN(*)CC1], or

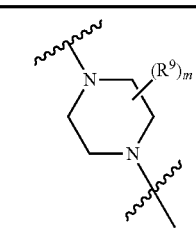.

In another embodiment, $G^1$ is

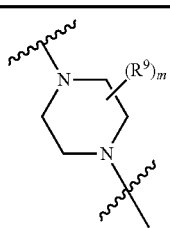;

$R^{8'}$ is $C_{1-4}$alkyl or oxo, and s is an integer from 0 to 2. In a further embodiment, $G^1$ is

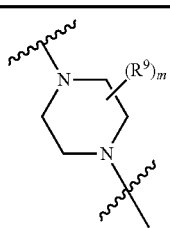;

$R^{8'}$ is methyl or oxo, and s is an integer from 0 to 2. In other embodiments, compounds of formula (IIA-1') may be represented by the formulas (IIA-1.0') to (IIA-1.11'), where $R^9$ is $C_{1-4}$alkyl, $C_{1-4}$haloalkyl, halogen, hydroxyl, or oxo, m is an integer from 0 to 4, and $R^2$, $R^4$, $R^{8'}$, $X^1$, $X^2$, and $X^3$, are as defined herein. In some embodiments, m is 0. In some embodiments, $R^{8'}$ is H or $C_{1-4}$alkyl (e.g., methyl). In some embodiments, $G^1$ is

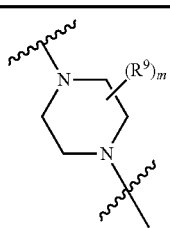, m is 0, $R^8$ is H, $R^2$ is $C_{1-4}$alkyl (e.g., methyl), $X^1$ is CH, $X^2$ is $CR^{X2}$, $R^{X2}$ is F, and $X^3$ is CH.

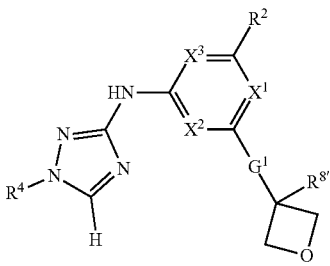

$G^1$ (IIA-1.0')

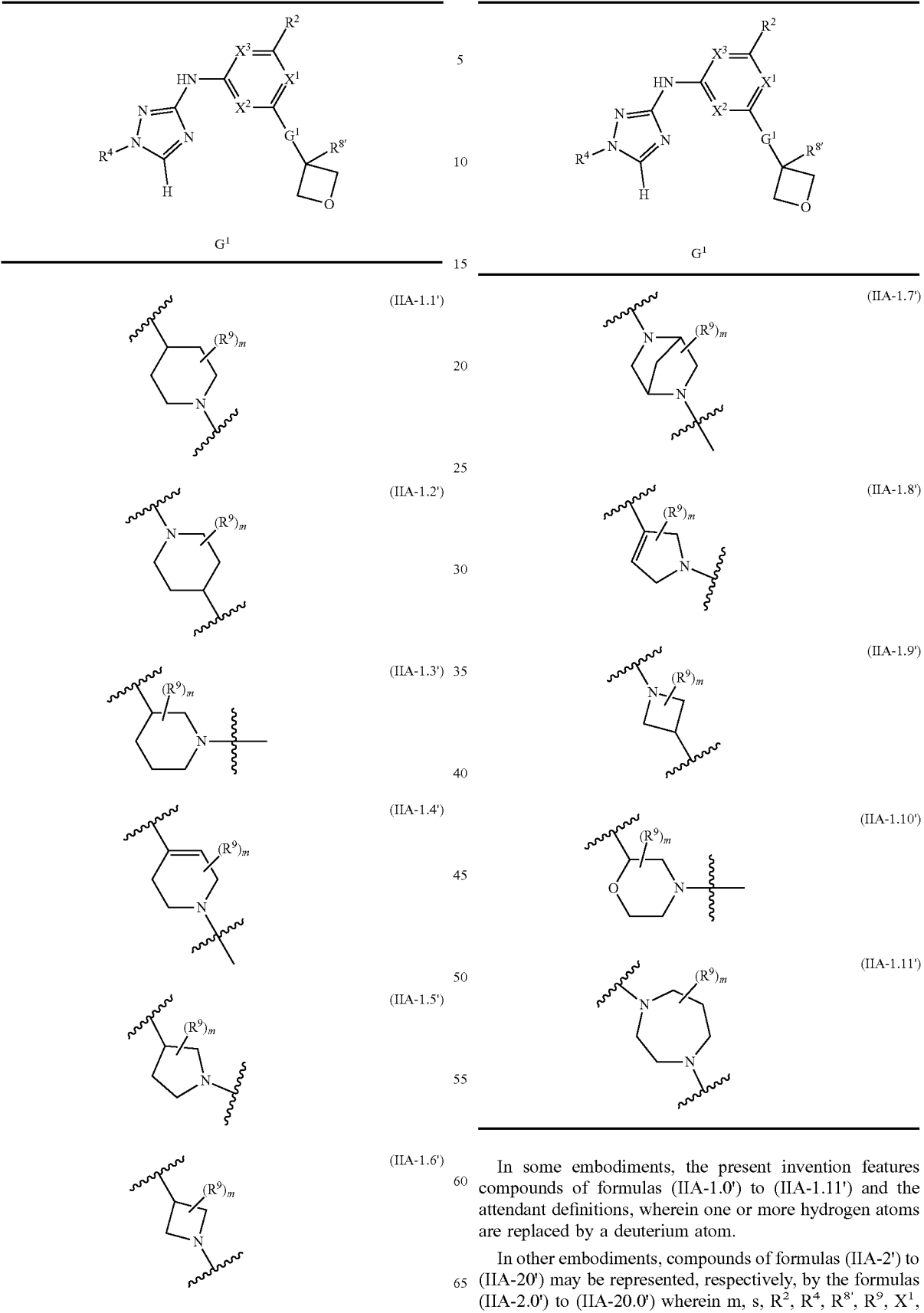

In some embodiments, the present invention features compounds of formulas (IIA-1.0') to (IIA-1.11') and the attendant definitions, wherein one or more hydrogen atoms are replaced by a deuterium atom.

In other embodiments, compounds of formulas (IIA-2') to (IIA-20') may be represented, respectively, by the formulas (IIA-2.0') to (IIA-20.0') wherein m, s, $R^2$, $R^4$, $R^{8'}$, $R^9$, $X^1$, $X^2$, and $X^3$ are as defined herein.

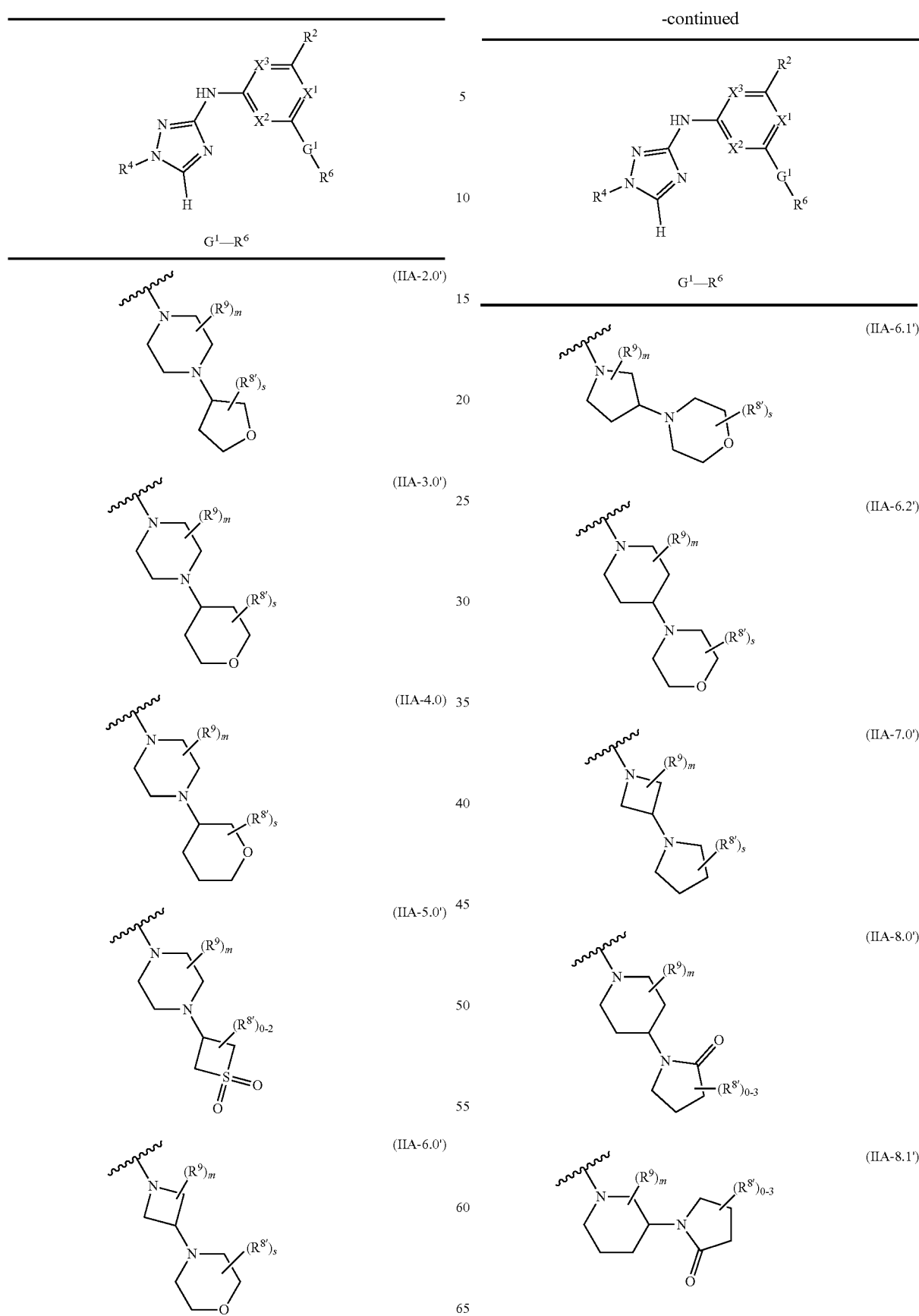

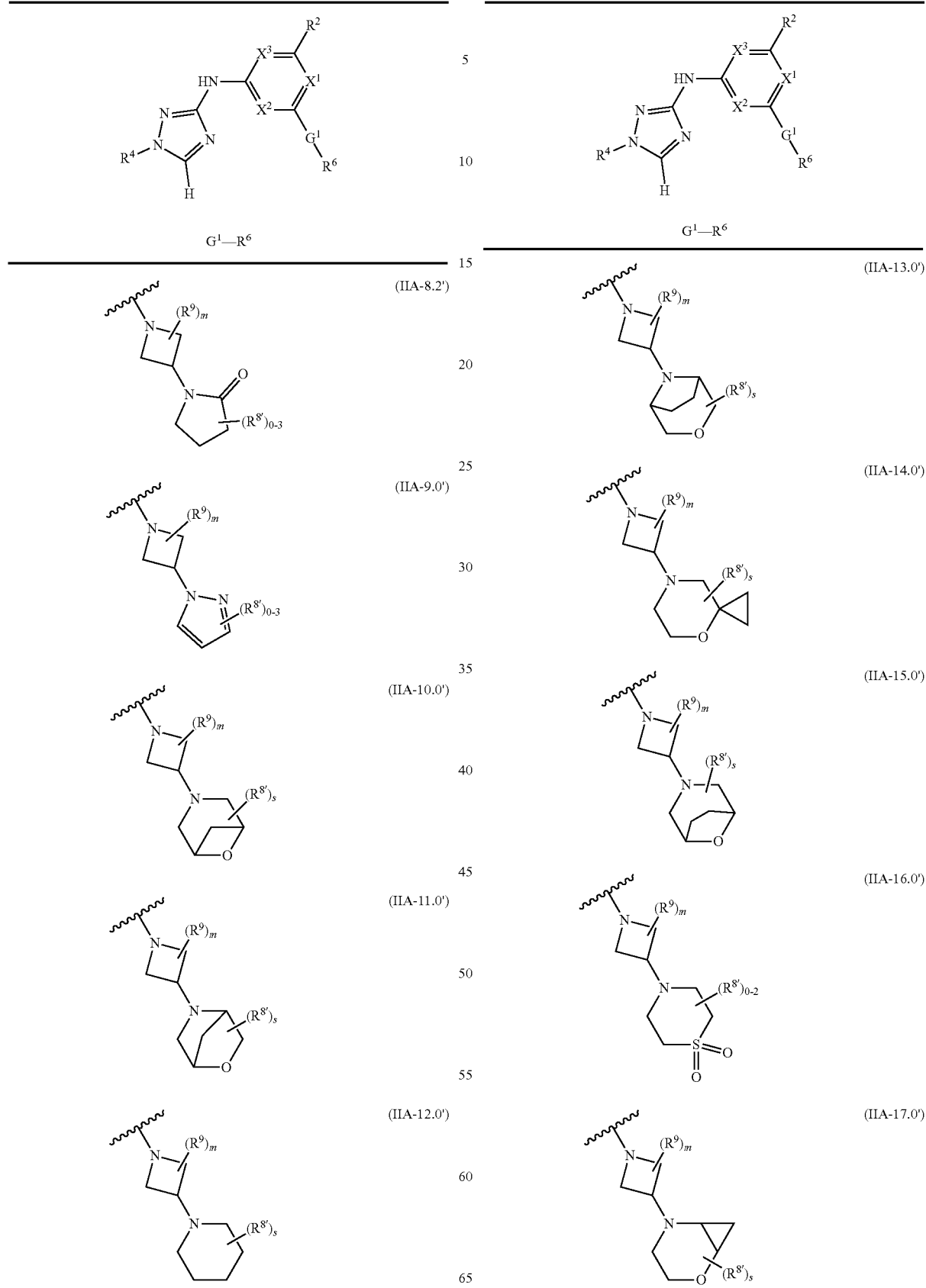

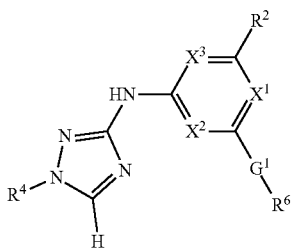
(IIA-200')

In some embodiments, the present invention features compounds of formula (IIA-100') and (IIA-200') and the attendant definitions, wherein one or more hydrogen atoms are replaced by a deuterium atom.

In some embodiments of formulas (IIA-100') and (IIA-200'), $G^1$ is piperazinyl, piperidinyl, or azetidinyl, and $R^6$ is oxetanyl, morpholino, or pyrrolidinyl. In other embodiments, $G^1$ is piperazin-1-yl, piperidin-1-yl, or azetidin-1-yl and $R^6$ is oxetan-3-yl, morpholin-4-yl, or pyrrolidin-1-yl. In each of the foregoing instances, $G^1$ and $R^6$ are optionally substituted as described herein.

In other embodiments, compounds of formulas (IIA-100') and (IIA-200'), where $L^2$ is methylene or carbonyl, may be represented, respectively, by the formulas (IIA-100.0') to (IIA-100.3') and (IIA-200.0') to (IIA-200.3') wherein m, s, $R^2$, $R^4$, $R^{8'}$, $R^9$, $X^1$, $X^2$, and $X^3$ are as defined herein.

$G^1—R^6$

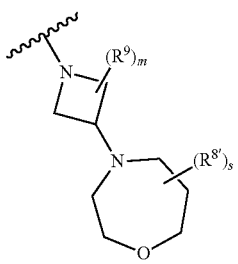
(IIA-18.0')

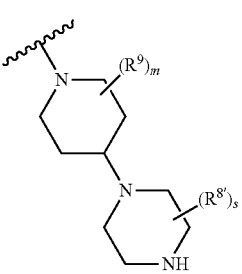
(IIA-19.0')

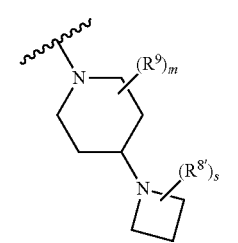
(IIA-20.0')

In some embodiments, the present invention features compounds of formulas (IIA-2.0') to (IIA-20.0') and the attendant definitions, wherein one or more hydrogen atoms are replaced by a deuterium atom.

In some embodiments of formula (IIA'), are compounds of formula (IIA-100') and (IIA-200').

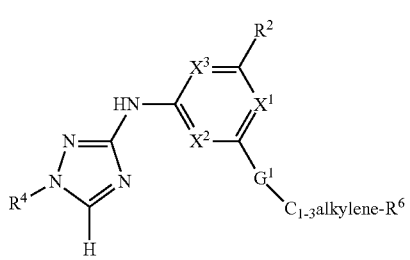
(IIA-100')

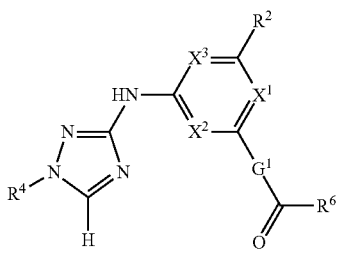

$G^1—L^2—R^6$

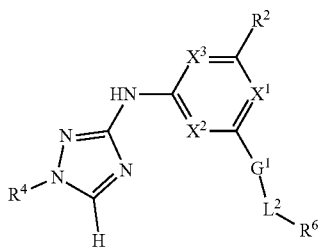
(IIA-100.0')

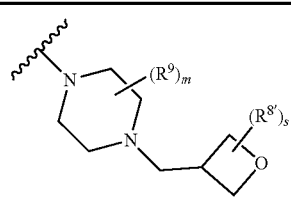
(IIA-100.1')

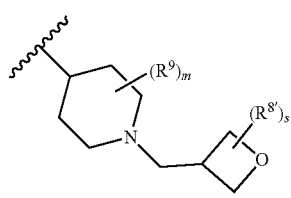
(IIA-100.2')

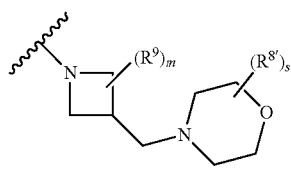

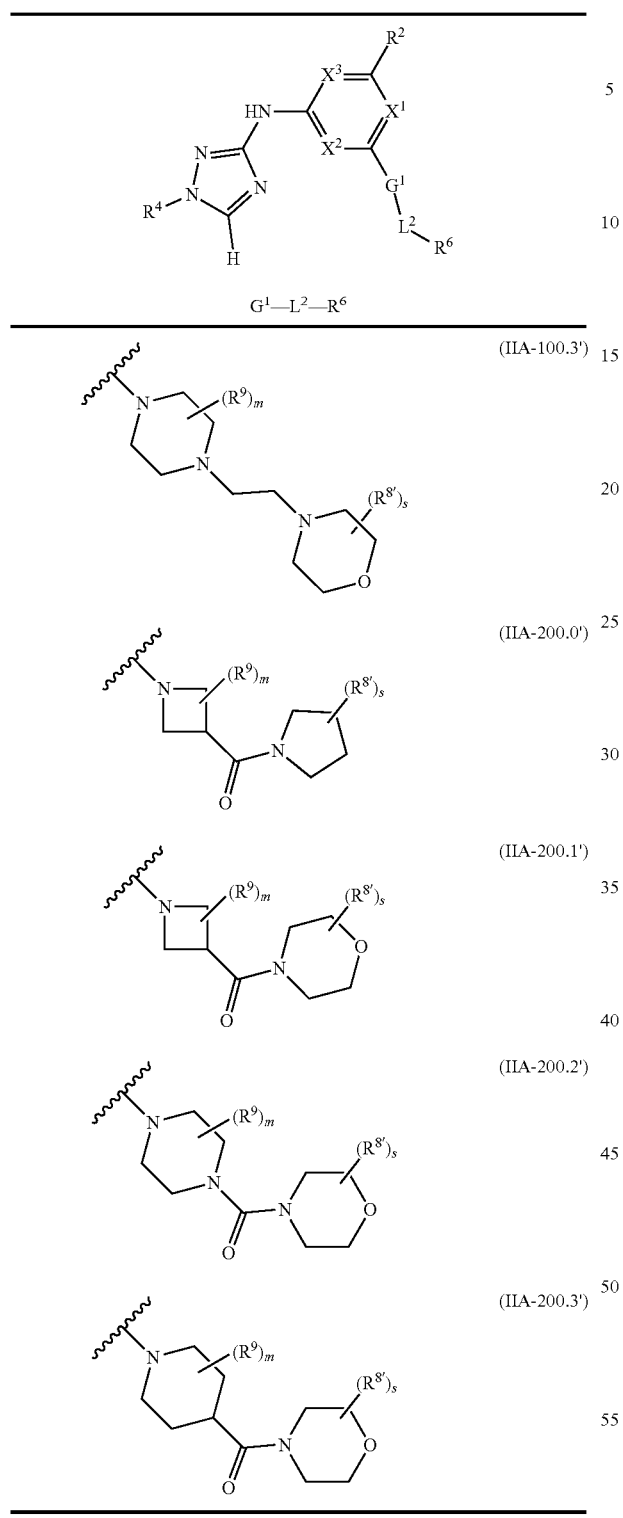

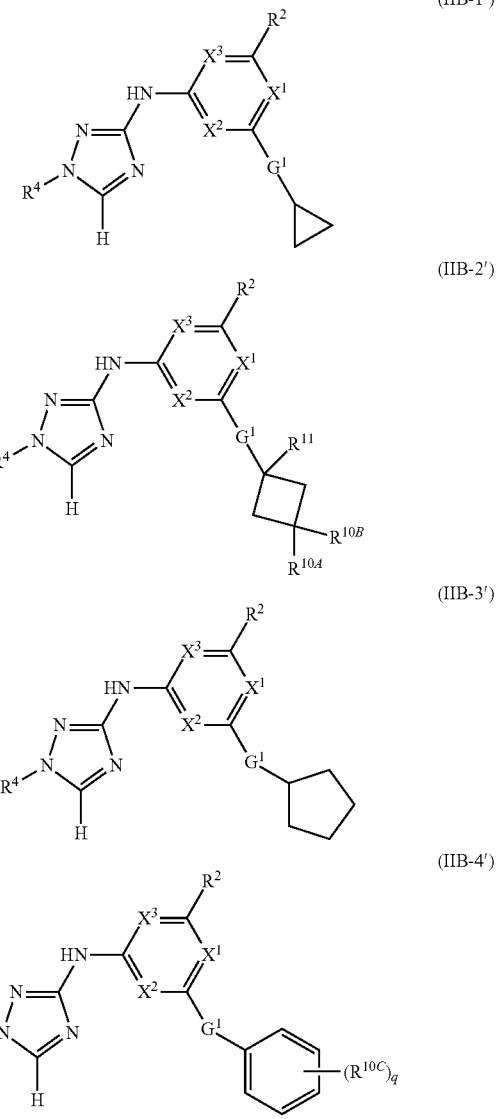

In some embodiments, the present invention features compounds of formulas (IIA-100.0') to (IIA-100.3') and (IIA-200.0') to (IIA-200.3') and the attendant definitions, wherein one or more hydrogen atoms are replaced by a deuterium atom.

In some embodiments of formula (IIB'), are compounds of formula (IIB-1'), (IIB-2'), (IIB-3'), or (IIB-4'):

wherein $R^{10A}$ and $R^{10B}$ are each independently hydrogen, halogen (e.g., fluoro), or COOH; $R^{10C}$ is $C_{1-4}$alkyl, $C_{1-4}$haloalkyl, halogen, hydroxyl, —C(O)O$C_{1-4}$alkyl, or —C(O)OH; q is an integer from 0 to 4; $R^{11}$ is hydrogen or hydroxyl; and $G^1$, $R^2$, $R^4$, $X^1$, $X^2$, and $X^3$ are as defined herein. In some embodiments of formula (IIB-2'), each of $R^{10A}$, $R^{10B}$, and $R^{11}$ is hydrogen. In other embodiments of formula (IIB-2'), $R^{11}$ is hydroxyl and each of $R^{10A}$ and $R^{10B}$ is hydrogen. In yet other embodiments, $R^{11}$ is hydrogen and each of $R^{10A}$ and $R^{10B}$ is fluoro. In some embodiments according to formula (IIB-1'), (IIB-2'), (IIB-3') or (IIB-4'), $G^1$ is

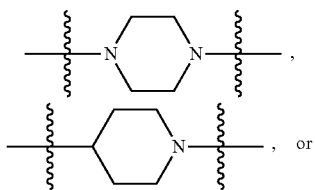

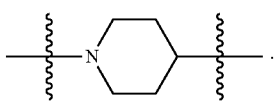

In one embodiment, $G^1$ is

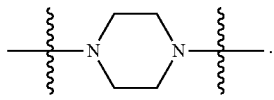

In some embodiments, the present invention features compounds of formulas (IIB-1'), (IIB-2'), (IIB-3'), and (IIB-4') and the attendant definitions, wherein one or more hydrogen atoms are replaced by a deuterium atom.

In other embodiments, compounds of formula (IIB-1') to (IIB-4') may be represented by the formulas (IIB-1.0') to (IIB-1.3'), (IIB-2.0') to (IIB-2.3'), (IIB-3.0') to (IIB-3.1') or (IIB-4.0'):

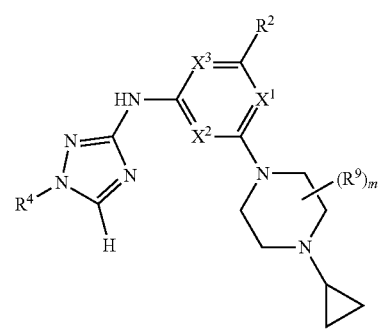

(IIB-1.0')

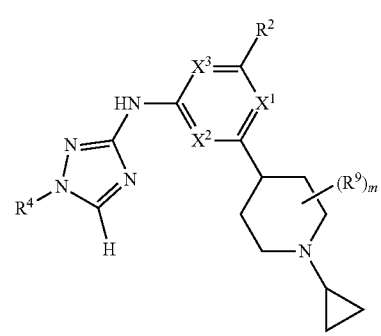

(IIB-1.1')

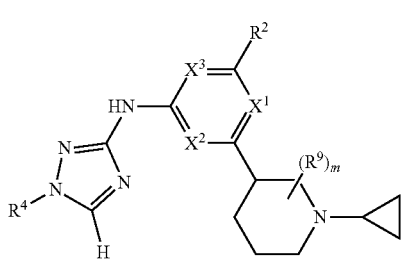

(IIB-1.2')

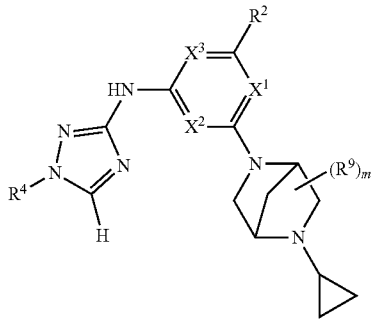

(IIB-1.3')

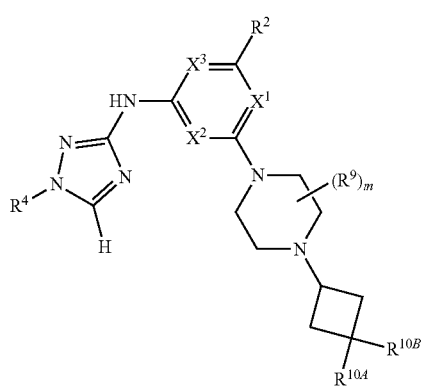

(IIB-2.0')

(IIB-2.1')

(IIB-2.2')

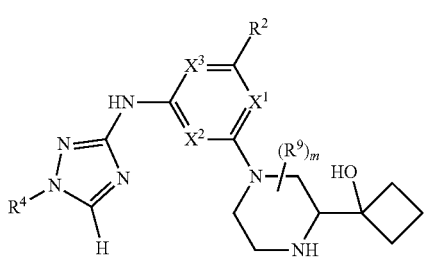

(IIB-2.3')

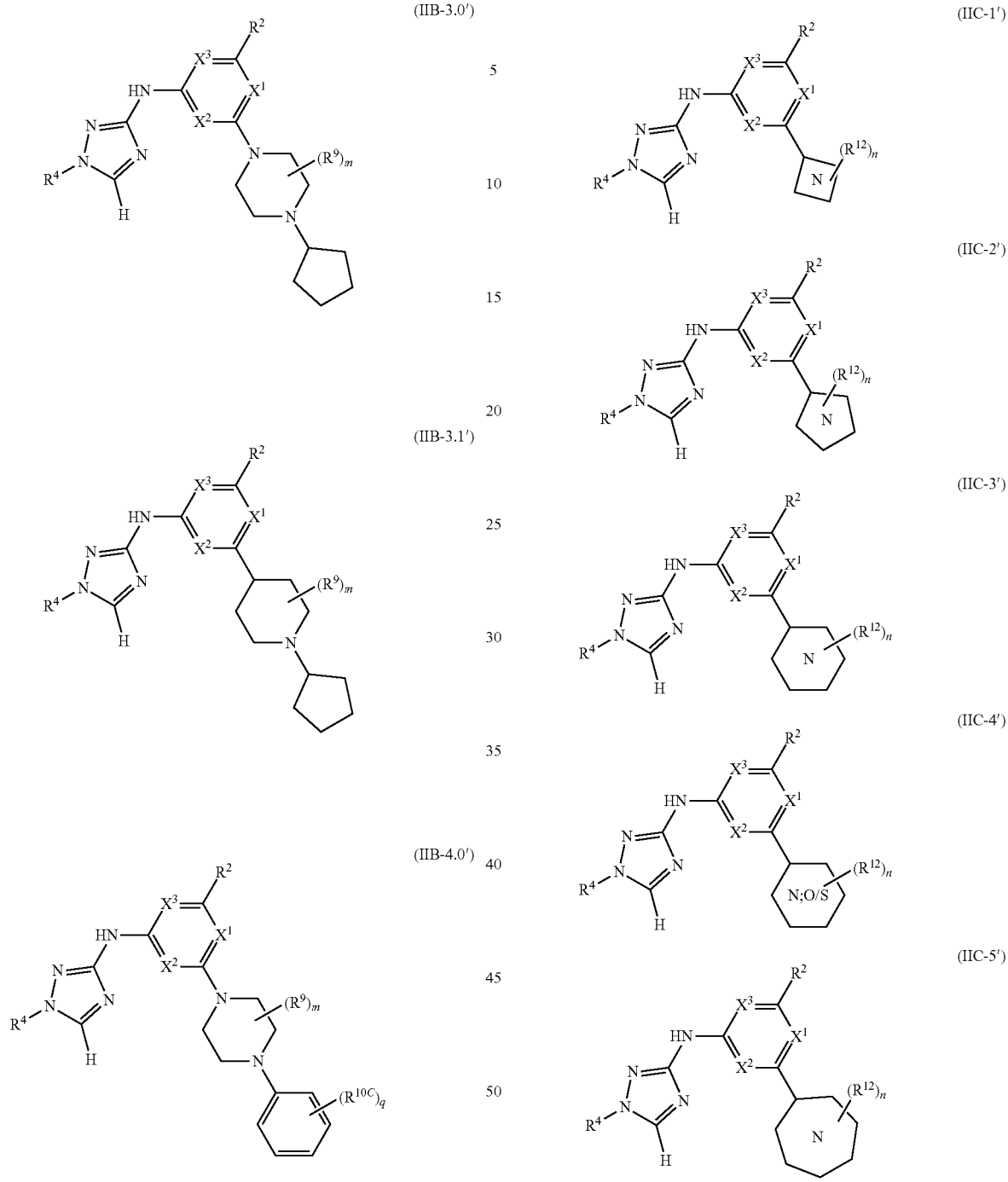

wherein R⁹ is $C_{1-4}$alkyl, $C_{1-4}$haloalkyl, halogen, hydroxyl, or oxo, m and q are each independently an integer from 0 to 4; and $R^2$, $R^4$, $R^{10A}$, $R^{10B}$, $R^{10C}$, $X^1$, $X^2$, and $X^3$ are as defined herein.

In some embodiments, the present invention features compounds of formulas (IIB-1.0') to (IIB-1.3'), (IIB-2.0') to (IIB-2.3'), (IIB-3.0') to (IIB-3.1') and (IIB-4.0') and the attendant definitions, wherein one or more hydrogen atoms are replaced by a deuterium atom.

In some embodiments of formula (IIC') are compounds of formula (IIC-1') to (IIC-10'):

(IIC-7')

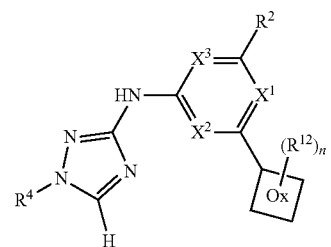

(IIC-8')

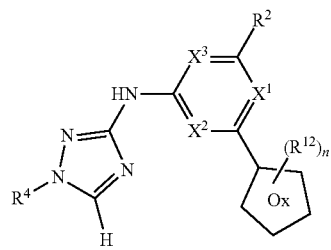

(IIC-9')

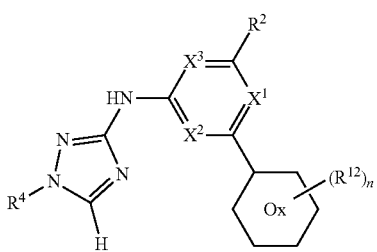

(IIC-10')

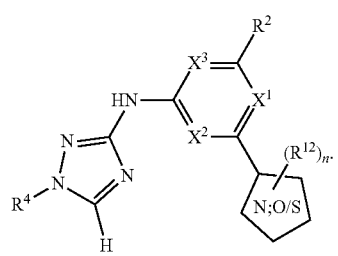

In some embodiments, the present invention features compounds of formulas (IIC-1'), (IIC-2'), (IIC-3'), (IIC-4'), (IIC-5'), (IIC-6'), (IIC-7'), (IIC-8'), (IIC-9') and (IIC-10') and the attendant definitions, wherein one or more hydrogen atoms are replaced by a deuterium atom.

In each of formulas (IIC-1'), (IIC-2'), (IIC-3'), (IIC-4'), (IIC-5'), (IIC-6'), (IIC-7'), (IIC-8'), (IIC-9') and (IIC-10'), $R^{12}$ represents the optional $G^2$ substitution, as defined herein, and n is an integer from 0-4. In the foregoing formulas, the illustrated $G^2$ groups having the following meanings: In compounds of formula (IIC-1'),

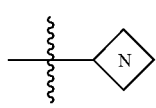

is a 4-membered monocyclic heterocycle containing one nitrogen atom. In compounds of formula (IIC-2'),

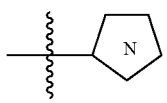

is a 5-membered monocyclic heterocycle containing one nitrogen atom and optionally one double bond. In compounds of formula (IIC-3'),

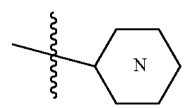

is a 6-membered monocyclic heterocycle containing one nitrogen and optionally a second nitrogen, one double bond, and/or a $C_{1-3}$alkylene bridge between two non-adjacent ring atoms. In compounds of formula (IIC-4'),

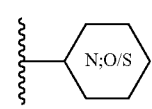

is a 6-membered monocyclic heterocycle containing one nitrogen and one oxygen atom or sulfur atom, and optionally one double bond, and/or a $C_{1-3}$alkylene bridge between two non-adjacent ring atoms. In compounds of formula (IIC-5'),

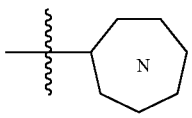

is a 7-membered monocyclic heterocycle containing one nitrogen and optionally a second nitrogen, one double bond, and/or a $C_{1-3}$alkylene bridge between two non-adjacent ring atoms. In compounds of formula (IIC-6'),

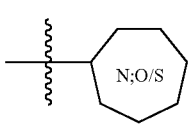

is a 7-membered monocyclic heterocycle containing one nitrogen and one oxygen atom or sulfur atom, and optionally one double bond, and/or a $C_{1-3}$alkylene bridge between two non-adjacent ring atoms. In compounds of formula (IIC-7'),

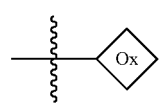 [SMILES: *C1CCC1]

is a 4-membered monocyclic heterocycle containing one oxygen atom. In compounds of formula (IIC-8'),

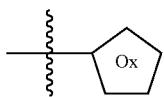 [SMILES: *C1CCCC1]

is a 5-membered monocyclic heterocycle containing one oxygen atom and optionally one double bond. In compounds of formula (IIC-9'),

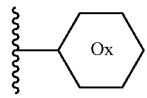

is a 6-membered monocyclic hetereocycle containing one oxygen atom and optionally one double bond and/or a $C_{1-3}$alkylene bridge between two non-adjacent ring atoms. In compounds of formula (IIC-10'),

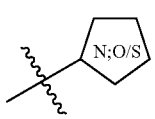 [SMILES: *C1CCCC1]

is a 5-membered monocyclic heterocycle containing one nitrogen and one oxygen atom or sulfur atom.

In compounds of formula (IIC-1'), are further compounds of formula (IIC-1.0') or (IIC-1.1'), wherein $R^{12}$ and n are as defined herein:

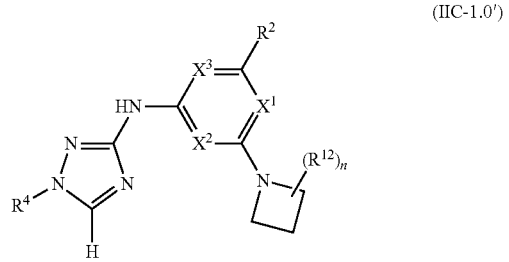

(IIC-1.0')

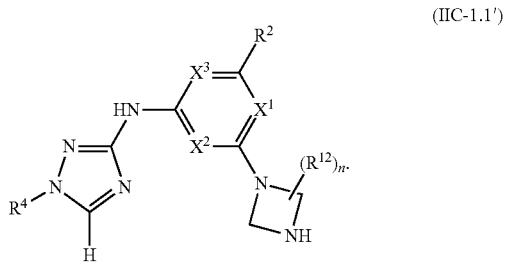

(IIC-1.1')

In some embodiments, the present invention features compounds of formulas (IIC-1.0') and (IIC-1.1') and the attendant definitions, wherein one or more hydrogen atoms are replaced by a deuterium atom.

In compounds of formula (IIC-2'), are further compounds of formula (IIC-2.0'), (IIC-2.1'), or (IIC-2.2'), wherein $R^{12}$ and n are as defined herein:

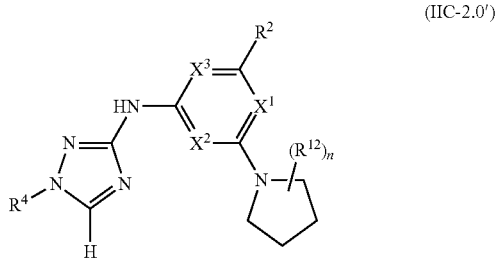

(IIC-2.0')

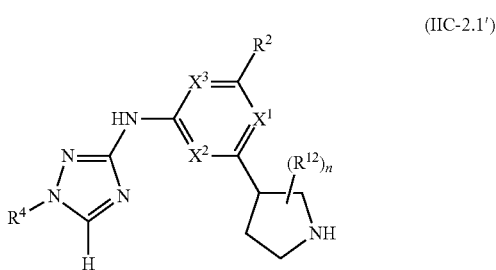

(IIC-2.1')

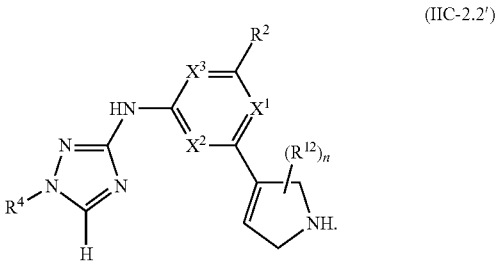

(IIC-2.2')

In some embodiments, the present invention features compounds of formulas (IIC-2.0'), (IIC-2.1'), and (IIC-2.2') and the attendant definitions, wherein one or more hydrogen atoms are replaced by a deuterium atom.

In compounds of formula (IIC-3'), are further compounds of formula (IIC-3.0') to (IIC-3.5'), wherein $R^{12}$ and n are as defined herein:

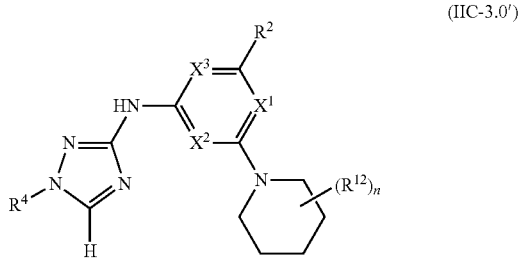

(IIC-3.0')

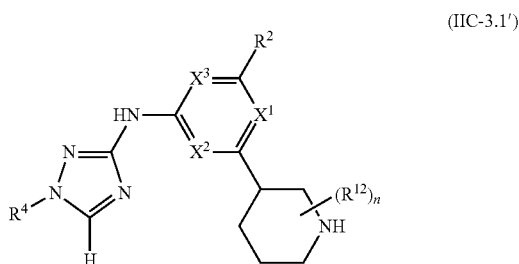

(IIC-3.1')

(IIC-3.2′)
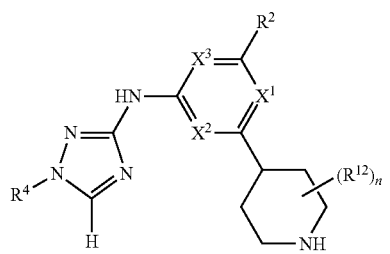

(IIC-3.3′)
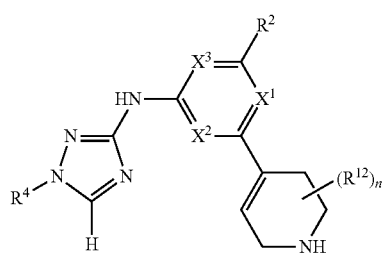

(IIC-3.4′)
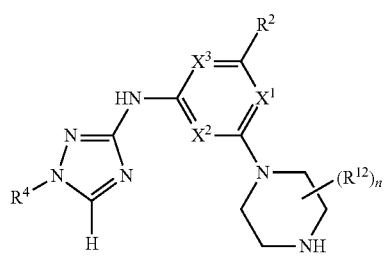

(IIC-3.5′)
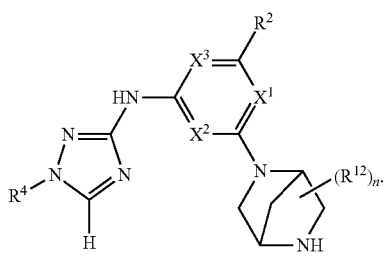

In some embodiments, the present invention features compounds of formulas (IIC-3.0′) to (IIC-3.5′) and the attendant definitions, wherein one or more hydrogen atoms are replaced by a deuterium atom.

In compounds of formula (IIC-4′), (IIC-5′), and (IIC-6′) are further compounds, respectively, of formula (IIC-4.0′)-(IIC-4.6′), (IIC-5.0′), and (IIC-6.0′), wherein $R^{12}$ and n are as defined herein:

(IIC-4.0′)
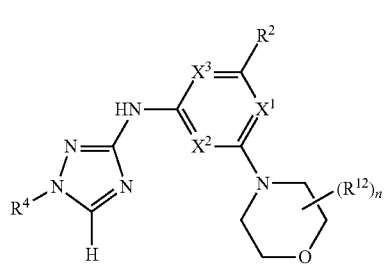

(IIC-4.1′)
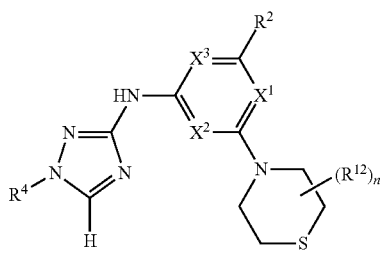

(IIC-4.2′)
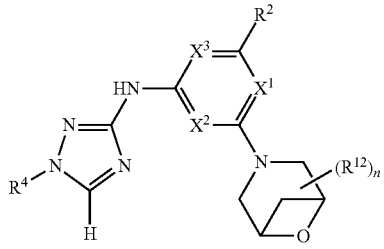

(IIC-4.3′)
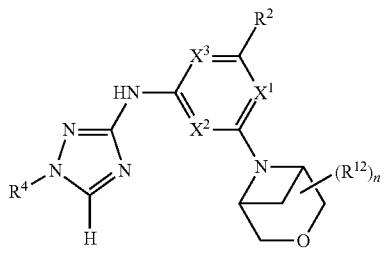

(IIC-4.4′)
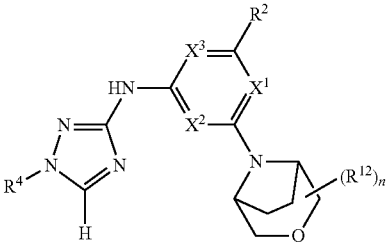

(IIC-4.5′)
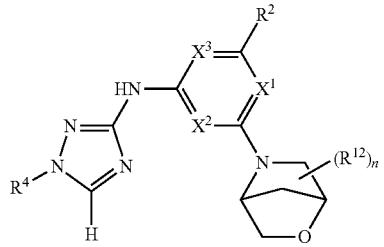

(IIC-4.6′)
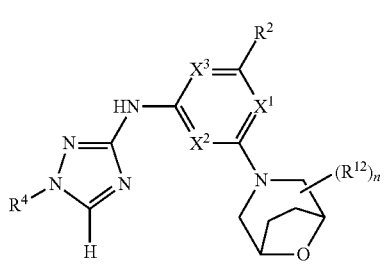

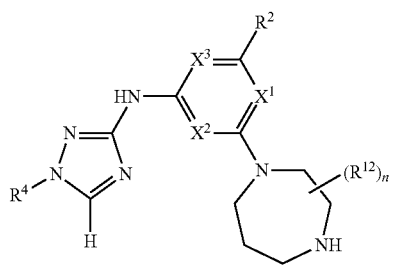
(IIC-5.0')

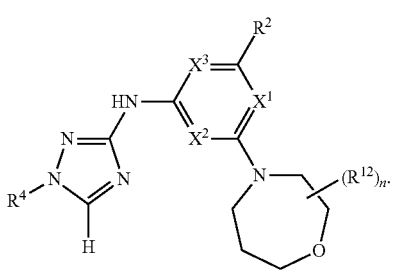
(IIC-6.0')

In some embodiments, the present invention features compounds of formulas (IIC-4.0')-(IIC-4.6'), (IIC-5.0'), and (IIC-6.0') and the attendant definitions, wherein one or more hydrogen atoms are replaced by a deuterium atom.

In compounds of formula (IIC-1.1'), (IIC-2.1'), (IIC-2.2'), (IIC-3.1')-(IIC-3.5'), and (IIC-5.0') are embodiments where n is 1 and R$^{12}$ is attached to the available ring nitrogen atom. In some embodiments, the single R$^{12}$ is C$_{1-4}$alkyl, C$_{1-4}$haloalkyl, —C(O)C$_{1-4}$alkyl, —C(O)C$_{3-6}$cycloalkyl, —C(O)OC$_{1-4}$alkyl, —C(O)OC$_{1-4}$haloalkyl, —C(O)C$_{1-4}$haloalkyl, —C$_{1-6}$alkylene-OC$_{1-4}$alkyl, —C$_{1-6}$alkylene-OH, —C$_{1-6}$alkylene substituted by 2 groups independently selected from hydroxyl and —OC(O)C$_{1-4}$alkyl, —C$_{1-6}$alkyl-N(C$_{1-4}$alkyl)(C$_{1-4}$alkyl), —C$_{1-4}$alkylene-C(O)OC$_{1-4}$alkyl, or —C$_{1-4}$alkylene-C(O)OH.

In compounds of formula (IIC-7'), (IIC-8'), (IIC-9') and (IIC-10') are further compounds, respectively, of formula (IIC-7.0'), (IIC-8.0')-(IIC-8.1') (IIC-9.0')-(IIC-9.1') and (IIC-10.0')-(IIC-10.1'), wherein R$^{12}$ and n are as defined herein:

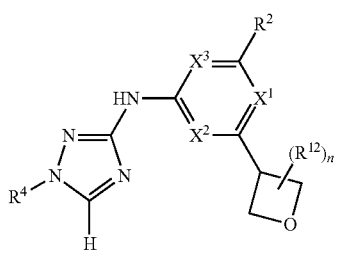
(IIC-7.0')

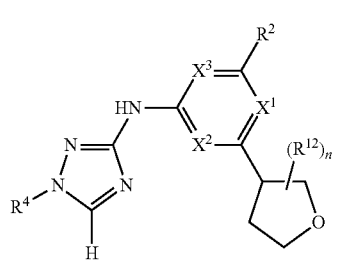
(IIC-8.0')

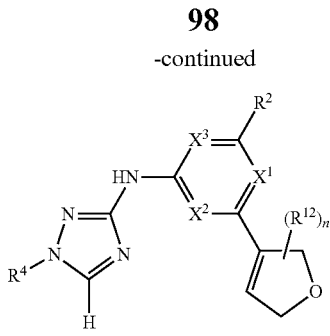
(IIC-8.1')

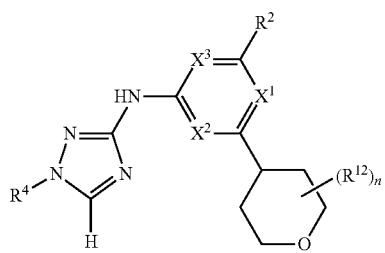
(IIC-9.0')

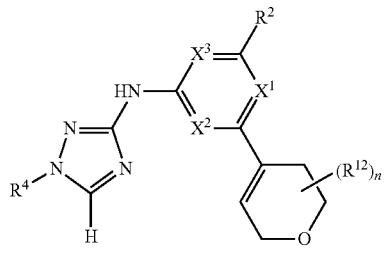
(IIC-9.1')

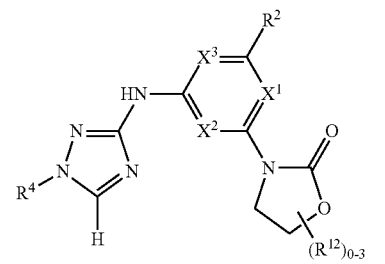
(IIC-10.0')

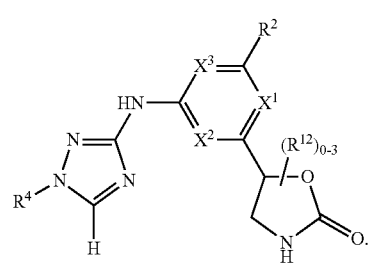
(IIC-10.1')

In some embodiments, the present invention features compounds of formulas (IIC-7.0'), (IIC-8.0')-(IIC-8.1') (IIC-9.0')-(IIC-9.1') and (IIC-10.0')-(IIC-10.1') and the attendant definitions, wherein one or more hydrogen atoms are replaced by a deuterium atom.

In some embodiments of formula (IIC'), G$^2$ is

$R^9$ is $C_{1-4}$alkyl, $R^2$ is $C_{1-4}$alkyl $C_{1-4}$haloalkyl, or $C_{3-6}$cycloalkyl; $R^4$ is phenyl optionally substituted with 1-2 substituents selected from halogen and $C_{1-4}$alkyl or $R^4$ is pyrazinyl and $X^1$, $X^2$, and $X^3$ are as defined herein. In one embodiment, $G^2$ is

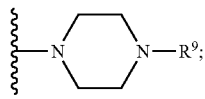

$R^9$ is methyl; $R^2$ is methyl, ethyl, trifluoromethyl, difluoromethyl, or cyclopropyl; and $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl.

In other embodiments of formula (IIC'), $G^2$ is oxetan-3-yl; $R^2$ is $C_{1-4}$alkyl $C_{1-4}$haloalkyl, or $C_{3-6}$cycloalkyl; $R^4$ is phenyl optionally substituted with 1-2 substituents selected from halogen and $C_{1-4}$alkyl or $R^4$ is pyrazinyl and $X^1$, $X^2$, and $X^3$ are as defined herein. In some embodiments, $G^2$ is oxetan-3-yl; $R^2$ is methyl, ethyl, trifluoromethyl, difluoromethyl, or cyclopropyl; and $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl.

In some embodiments of formula (IID'), $G^3$ is

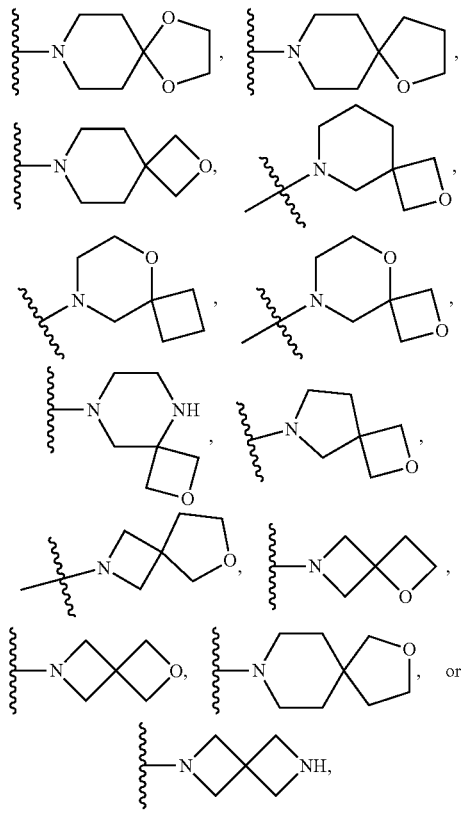

each being optionally substituted with 1-4 substituents selected from the group consisting of $C_{1-4}$alkyl (e.g., methyl, ethyl, isobutyl), $C_{1-4}$haloalkyl (e.g., —CF$_3$, —CH$_2$CF$_3$), halogen (e.g., fluoro), and oxo (i.e., the optional substituent of $G^3$). In some embodiments, $R^2$ is $C_{1-4}$alkyl, $C_{1-4}$haloalkyl, or $C_{3-6}$cycloalkyl; $R^4$ is phenyl optionally substituted with 1-2 substituents selected from halogen and $C_{1-4}$alkyl or $R^4$ is pyrazinyl and $X^1$, $X^2$, and $X^3$ are as defined herein. In some groups of compounds, $G^3$ is

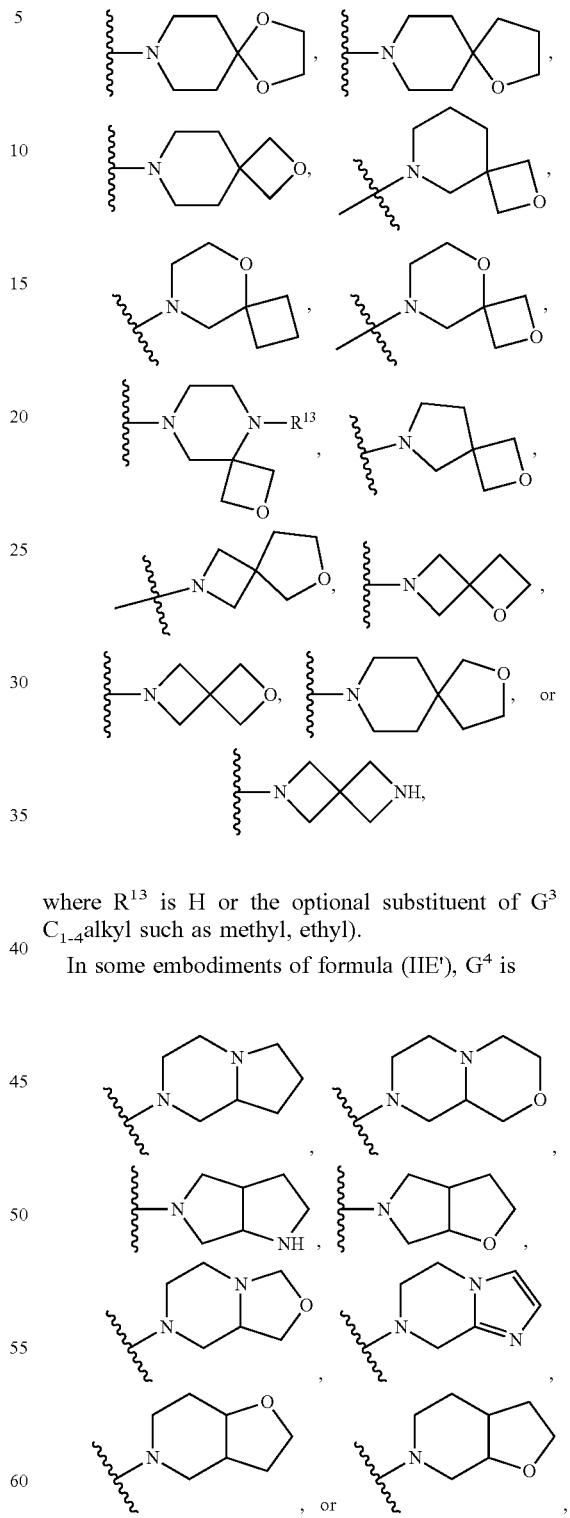

where $R^{13}$ is H or the optional substituent of $G^3$ (e.g., $C_{1-4}$alkyl such as methyl, ethyl).

In some embodiments of formula (IIE'), $G^4$ is

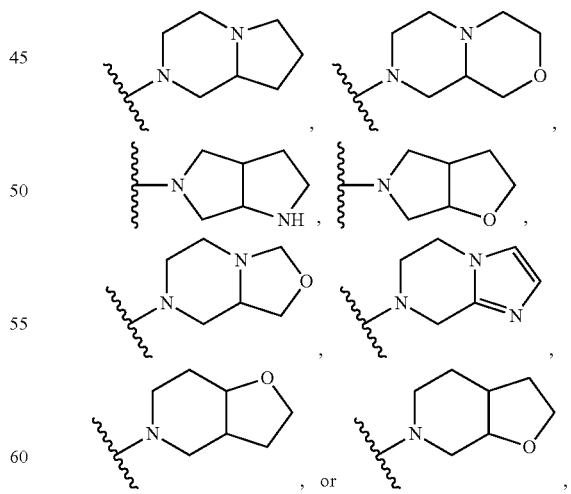

each being optionally substituted with 1-4 substituents selected from the group consisting of $C_{1-4}$alkyl (e.g., methyl, ethyl, isobutyl), $C_{1-4}$haloalkyl (e.g., —CF$_3$, —CH$_2$CF$_3$), halogen (e.g., fluoro), and oxo. In one embodiment, $G^4$ is

101

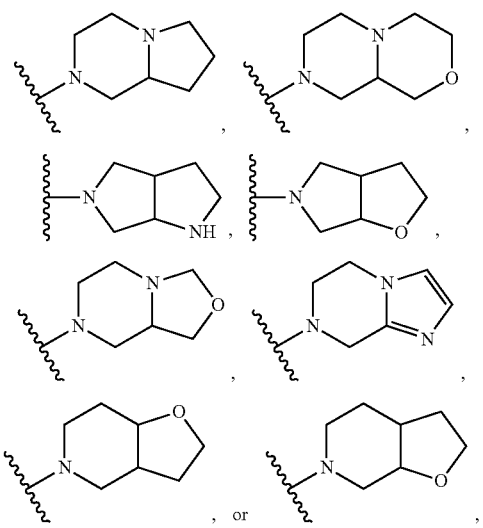

, or each being optionally substituted with one $C_{1-4}$alkyl, $C_{1-4}$haloalkyl, halogen, or oxo. In some embodiments, $R^2$ is $C_{1-4}$alkyl, $C_{1-4}$haloalkyl, or $C_{3-6}$cycloalkyl; $R^4$ is phenyl optionally substituted with 1-2 substituents selected from halogen and $C_{1-4}$alkyl or $R^4$ is pyrazinyl and $X^1$, $X^2$, and $X^3$ are as defined herein. In other embodiments, $G^4$ is

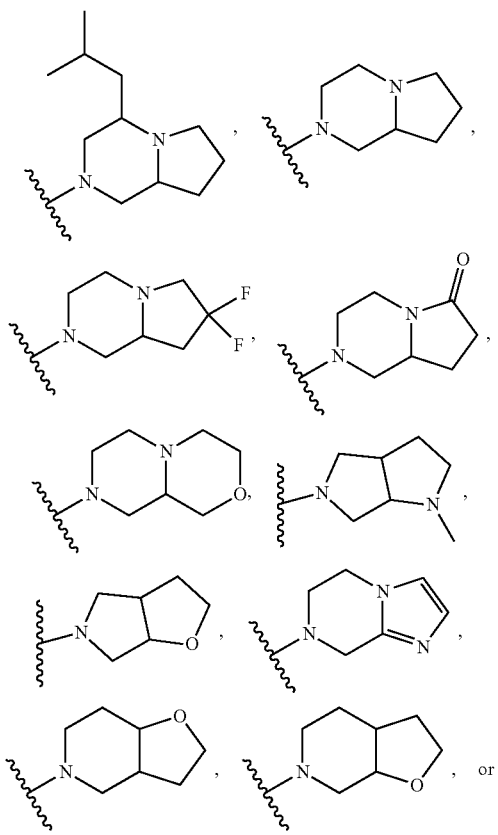

, or

102

-continued

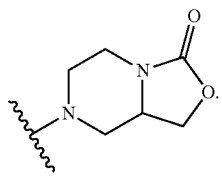

Included in compounds of formula (III') are compounds of formula (IIIA') to (IIIG'), wherein $G^1$, $G^2$, $G^3$, $G^4$, $G^5$, $G^6$, $R^2$, $R^4$, $R^6$, $R^7$, $X^1$, $X^2$, and $X^3$ are as defined herein.

(IIIA')

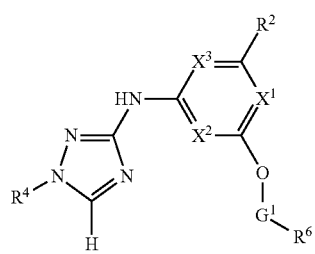

(IIIB')

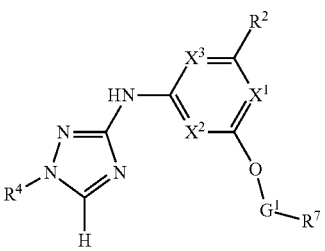

(IIIC')

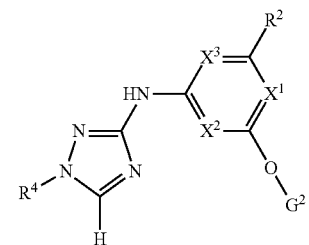

(IIID')

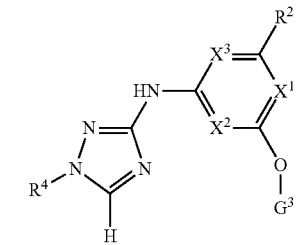

(IIIE')

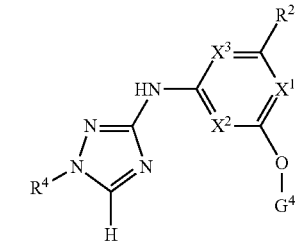

-continued (IIIF′)

(IIIG′)

In some embodiments, the present invention features compounds of formulas (IIIA′) to (IIIG′) and the attendant definitions, wherein one or more hydrogen atoms are replaced by a deuterium atom.

In some embodiments of formula (IIIA′), are compounds of formula (IIIA-1′) and (IIIA-2′), wherein s, $G^1$, $R^2$, $R^4$, $R^{8′}$, $X^1$, $X^2$, and $X^3$ are as defined herein.

(IIIA-1′)

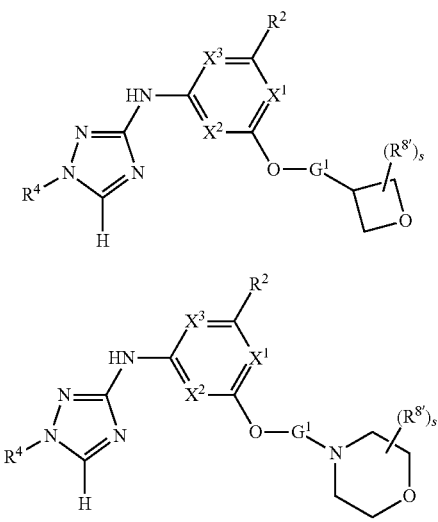

(IIIA-2′)

In some embodiments, the present invention features compounds of formulas (IIIA-1′) and (IIIA-2′) and the attendant definitions, wherein one or more hydrogen atoms are replaced by a deuterium atom.

In some embodiments, compounds of formula (IIIA-1′) and (IIIA-2′) may be represented by the formulas (IIIA-1.0′), (IIIA-1.1′), (IIIA-1.2′), or (IIIA-2.0′):

(IIIA-1.0′)

(IIIA-1.1′)

(IIIA-1.2′)

(IIIA-2.0′)

wherein $R^2$, $R^4$, $X^1$, $X^2$, and $X^3$ are as defined herein.

In some embodiments, the present invention features compounds of formulas (IIIA-1.0′), (IIIA-1.1′), (IIIA-1.2′), and (IIIA-2.0′) and the attendant definitions, wherein one or more hydrogen atoms are replaced by a deuterium atom.

In some embodiments of formula (IIIC′), are compounds of formula (IIIC-1′) to (IIIC-6′), wherein $R^{12}$ represents the optional $G^2$ substitution, as defined herein, n is an integer from 0-4, and $R^2$, $R^4$, $X^1$, $X^2$, and $X^3$ are as defined herein.

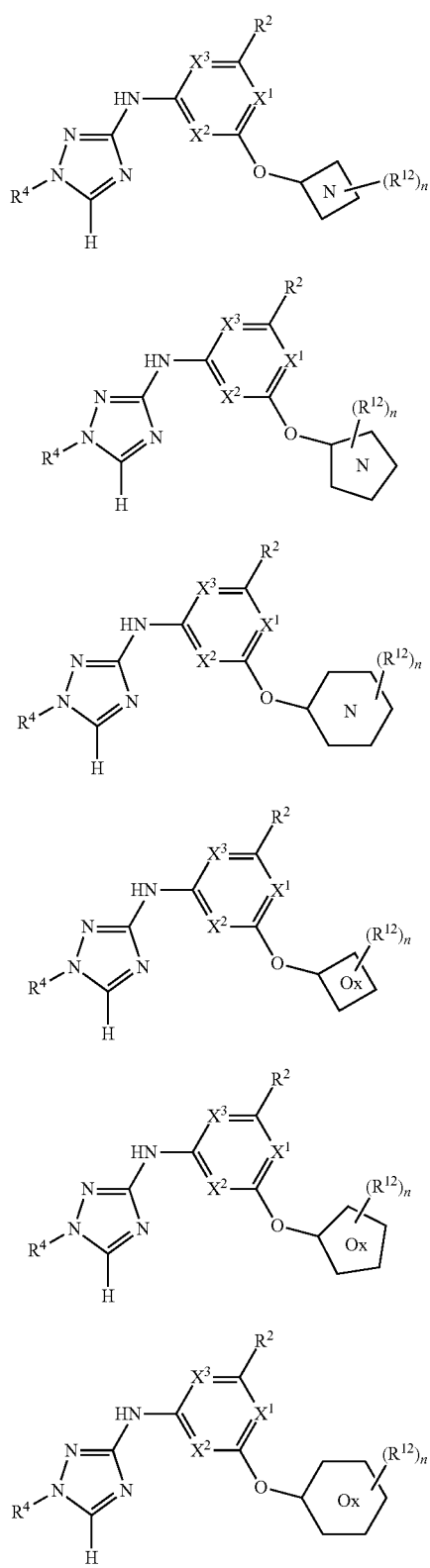

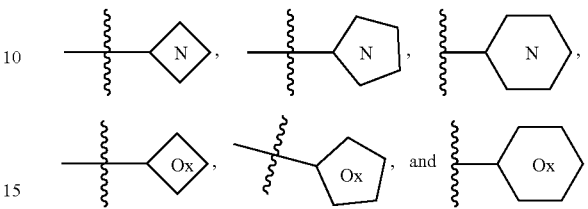

In some embodiments, $R^{12}$ is —$C_{1-4}$alkylene-O$C_{1-4}$alkyl or —C(O)$C_{1-4}$alkyl and n is 1. In a subgroup of compounds, n is 1 and $R^{12}$ is —$C_{1-4}$alkylene-O$C_{1-4}$alkyl or —C(O)$C_{1-4}$alkyl and is bonded to an available ring nitrogen atom. In compounds of formulas (IIIC-1') to (IIIC-6'), are as defined elsewhere herein.

In some embodiments of formula (IIIC-3'), (IIIC-5'), and (IIIC-6') are compounds of formula (IIIC-3.0'), (IIIC-5.0'), and (IIIC-6.0'), wherein $R^{12A}$ is H or $R^{12}$, and $R^2$, $R^4$, $R^{12}$, $X^1$, $X^2$, and $X^3$ are as defined herein.

In some embodiments, the present invention features compounds of formulas (IIIC-3.0'), (IIIC-5.0'), and (IIIC-6.0') and the attendant definitions, wherein one or more hydrogen atoms are replaced by a deuterium atom.

In some embodiments of formula (IIIF'), are compounds of formula (IIIF-1') and (IIIF-2'), wherein $R^{14}$ is the optional substituent on $G^5$, p is an integer from 0-4, and $R^2$, $R^4$, $X^1$, $X^2$, and $X^3$ are as defined herein.

In some embodiments, the present invention features compounds of formulas (IIIC-1') to (IIIC-6') and the attendant definitions, wherein one or more hydrogen atoms are replaced by a deuterium atom.

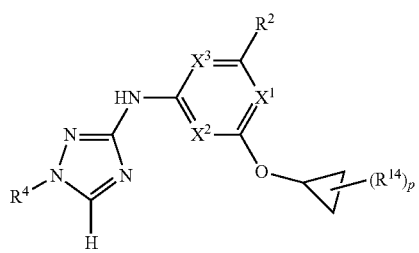
(IIIF-1')

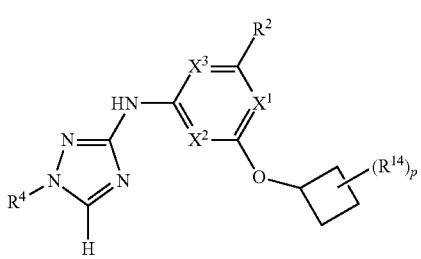
(IIIF-2')

In some embodiments, the present invention features compounds of formulas (IIIF-1') and (IIIF-2') and the attendant definitions, wherein one or more hydrogen atoms are replaced by a deuterium atom.

In some embodiments of formula (IIIF-2') are compounds of formula (IIIF-2.0'), wherein $R^{14A}$ is H or $R^{14}$. In some groups of compounds $R^{14A}$ is —NHC(O)($C_{1-4}$alkyl).

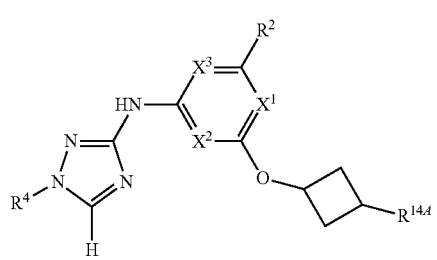
(IIIF-2.0')

In some embodiments, the present invention features compounds of formula (IIIF-2.0') and the attendant definitions, wherein one or more hydrogen atoms are replaced by a deuterium atom.

Included in compounds of formula (IV') are compounds of formula (IVA') to (IVH') and (IVJ'), wherein $L^2$, $G^1$, $G^2$, $G^3$, $G^4$, $G^5$, $G^6$, $R^2$, $R^4$, $R^5$, $R^6$, $R^7$, $X^1$, $X^2$, and $X^3$ are as defined herein:

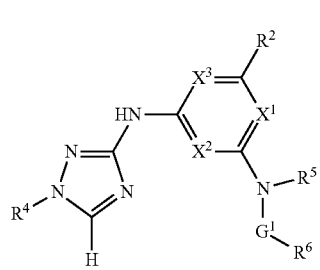
(IVA')

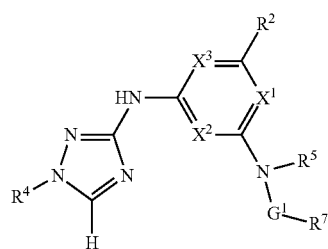
(IVB')

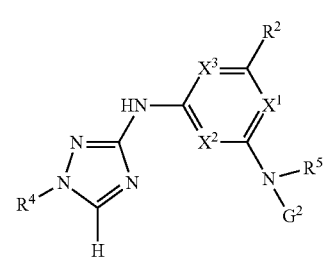
(IVC')

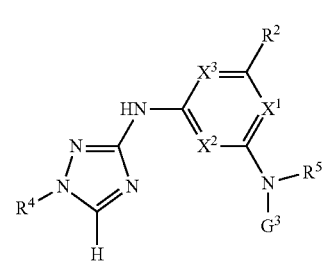
(IVD')

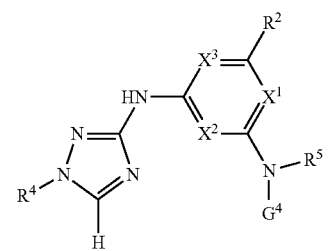
(IVE')

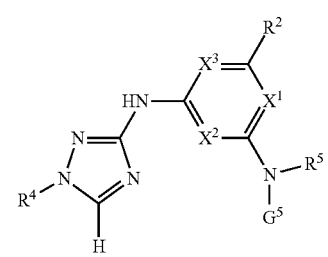
(IVF')

In one embodiment, $G^1$ is

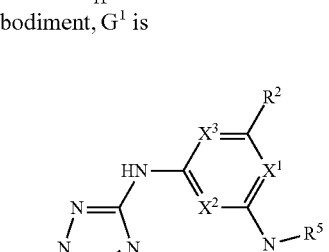
(IVG')

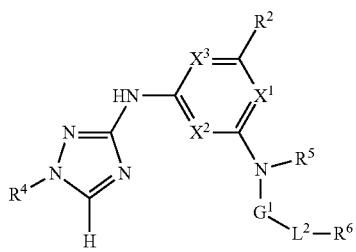
(IVH')

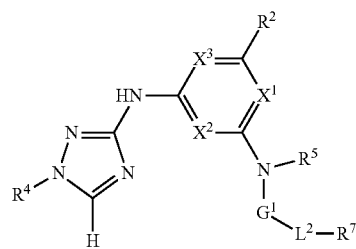
(IVJ')

In some embodiments, the present invention features compounds of formulas (IVA') to (IVH') and (IVJ') and the attendant definitions, wherein one or more hydrogen atoms are replaced by a deuterium atom.

In some embodiments of formula (IVA'), are compounds of formula (IVA-1') and (IVA-2'), wherein s, $G^1$, $R^2$, $R^4$, $R^5$, $R^8$, $X^1$, $X^2$, and $X^3$ are as defined herein.

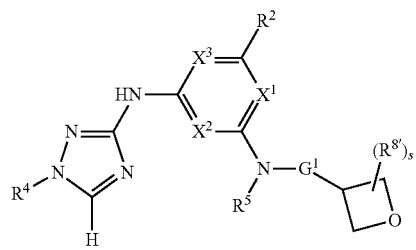
(IVA-1')

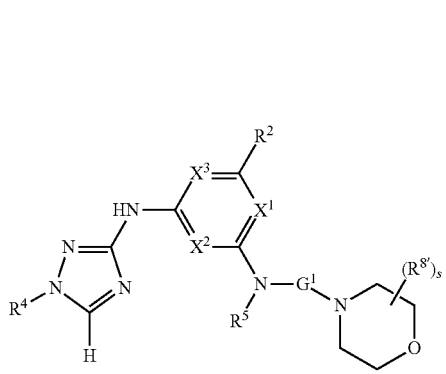
(IVA-2')

In some embodiments, the present invention features compounds of formulas (IVA-1') and (IVA-2') and the attendant definitions, wherein one or more hydrogen atoms are replaced by a deuterium atom.

In some embodiments, compounds of formula (IVA-1') and (IVA-2') may be represented by the formulas (IVA-1.0') to (IVA-2.0').

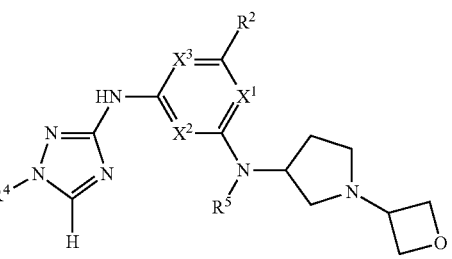
(IVA-1.0')

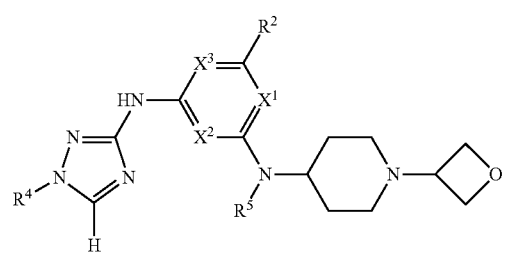
(IVA-1.1')

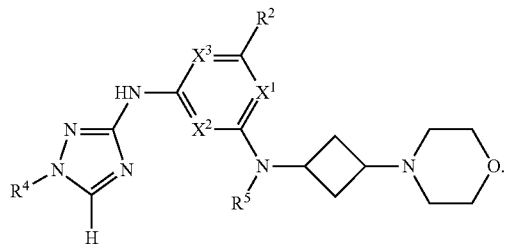
(IVA-2.0')

In some embodiments, the present invention features compounds of formulas (IVA-1.0') to (IVA-2.0') and the attendant definitions, wherein one or more hydrogen atoms are replaced by a deuterium atom.

In some embodiments of formulas (IVA') to (IVG'), (IVA-1'), (IVA-2'), (IVA-1.0'), (IVA-1.1'), or (IVA-2.0'), $R^5$ is H or methyl;

In some embodiments of formula (IVC'), are compounds of formula (IVC-1') to (IVC-6'), wherein n, $R^2$, $R^4$, $R^5$, $R^{12}$, $X^1$, $X^2$, and $X^3$ are as defined herein.

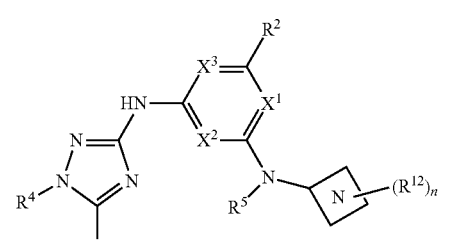
(IVC-1')

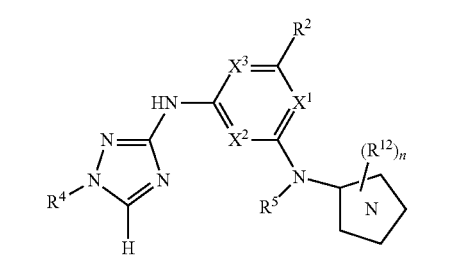
(IVC-2')

-continued

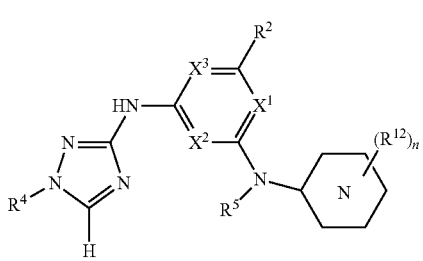
(IVC-3')

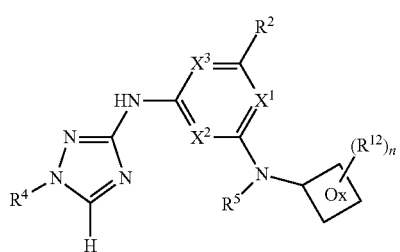
(IVC-4')

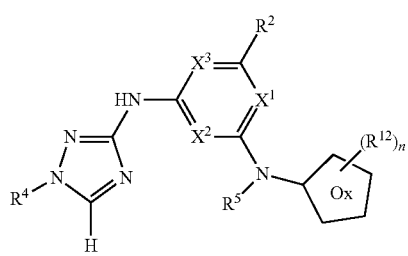
(IVC-5')

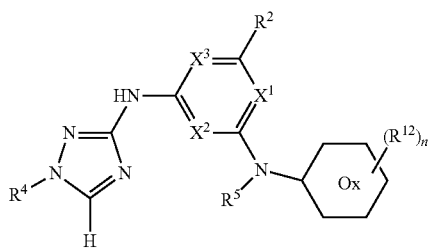
(IVC-6')

In some embodiments, the present invention features compounds of formulas (IVC-1') to (IVC-6') and the attendant definitions, wherein one or more hydrogen atoms are replaced by a deuterium atom.

In some embodiments, $R^{12}$ is —$C_{1-4}$alkylene-O$C_{1-4}$alkyl, —C(O)$C_{1-4}$alkyl, or $C_{1-4}$alkyl and n is 1. In a subgroup of compounds, n is 1 and $R^{12}$ is —$C_{1-4}$alkylene-O$C_{1-4}$alkyl or —C(O)$C_{1-4}$alkyl and is bonded to an available ring nitrogen atom. In compounds of formulas (IVC-1') to (IVC-6'),

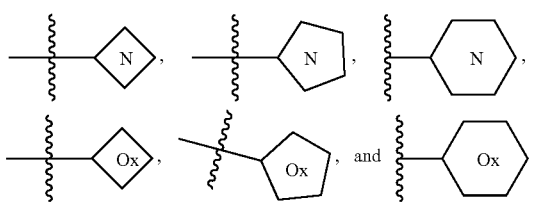

are as defined herein.

In some embodiments, compounds of formula (IVC-1') (IVC-3'), (IVC-4'), (IVC-5'), and (IVC-6') may be represented by the formulas (IVC-1.0'), (IVC-3.0'), (IVC-3.1'), (IVC-4.0'), (IVC-5.0'), and (IVC-6.0'), wherein $R^{12A}$ and $R^{12B}$ are independently H or $R^{12}$, and $R^2$, $R^4$, $R^5$, $R^{12}$, $X^1$, $X^2$, and $X^3$ are as defined herein. In some embodiments, $R^{12A}$ is —$C_{1-4}$alkylene-O$C_{1-4}$alkyl, or —C(O)$C_{1-4}$alkyl. In some embodiments, $R^{12B}$ is H or $C_{1-4}$alkyl.

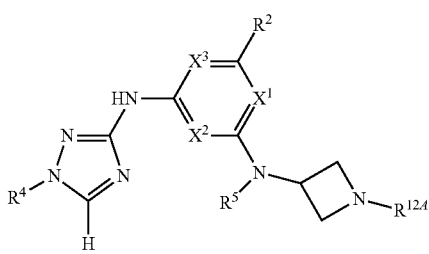
(IVC-1.0')

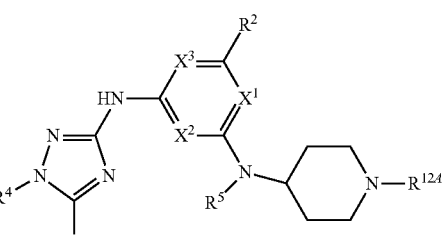
(IVC-2.0')

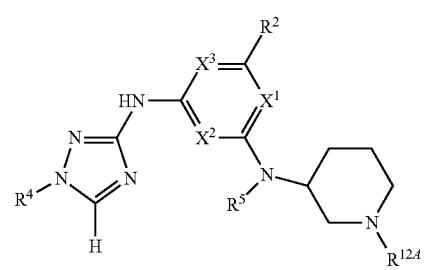
(IVC-3.0')

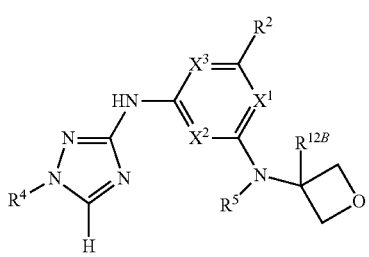
(IVC-4.0')

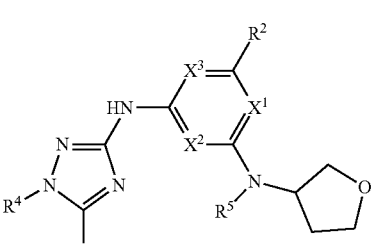
(IVC-5.0')

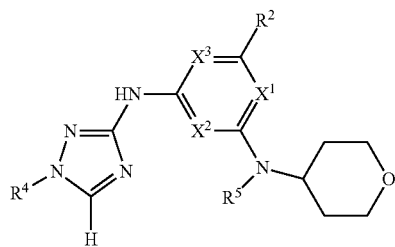

(IVC-6.0′)

In some embodiments, the present invention features compounds of formulas (IVC-1′) to (IVC-6′), (IV-1.0′), (IVA-3.0′), (IVC-3.1′), (IVC-4.0′), (IVC-5.0′), and (IVC-6.0′) and the attendant definitions, wherein one or more hydrogen atoms are replaced by a deuterium atom.

In some embodiments of formulas (IVC-1′) to (IVC-6′), (IV-1.0′), (IVA-3.0′), (IVC-3.1′), (IVC-4.0′), (IVC-5.0′), or (IVC-6.0′), $R^5$ is H or methyl;

In some embodiments of formula (IVF′), are compounds of formula (IVF-1′) and (IVF-2′), wherein $R^{14}$ is the optional substituent on $G^5$, p is an integer from 0-4, and $R^2$, $R^4$, $R^5$, $X^1$, $X^2$, and $X^3$ are as defined herein.

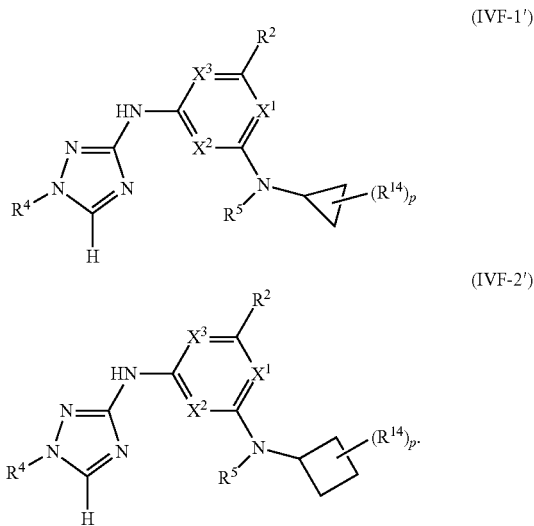

(IVF-1′)

(IVF-2′)

In some embodiments, the present invention features compounds of formulas (IVF-1′) and (IVF-2′) and the attendant definitions, wherein one or more hydrogen atoms are replaced by a deuterium atom.

In some embodiments, compounds of formula (IVF-1′) and (IVF-2′) may be represented by the formulas (IVF-1.0′) and (IVF-2.0′).

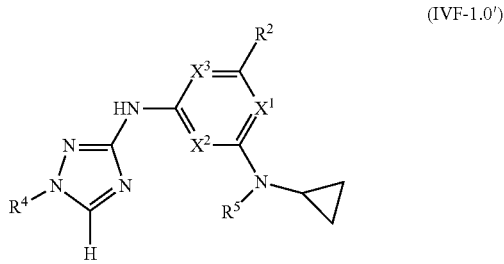

(IVF-1.0′)

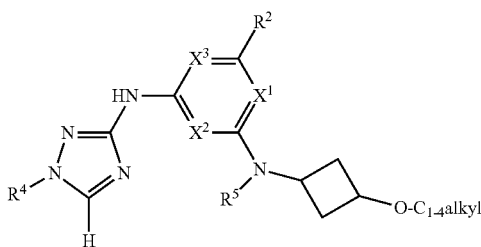

(IVF-2.0′)

In some embodiments, the present invention features compounds of formulas (IVF-1.0′) and (IVF-2.0′) and the attendant definitions, wherein one or more hydrogen atoms are replaced by a deuterium atom.

In some embodiments of formulas (IVF-1′), (IVF-2′), (IVF-1.0′) or (IVF-2.0′), $R^5$ is H or methyl.

In some embodiments of formula (IVG′), are compounds of formula (IVG-1′) to (IVG-4′), wherein $R^{15}$ is the optional substituent on $G^6$, t is an integer from 0-4, and $R^2$, $R^4$, $R^5$, $X^1$, $X^2$, and $X^3$ are as defined herein.

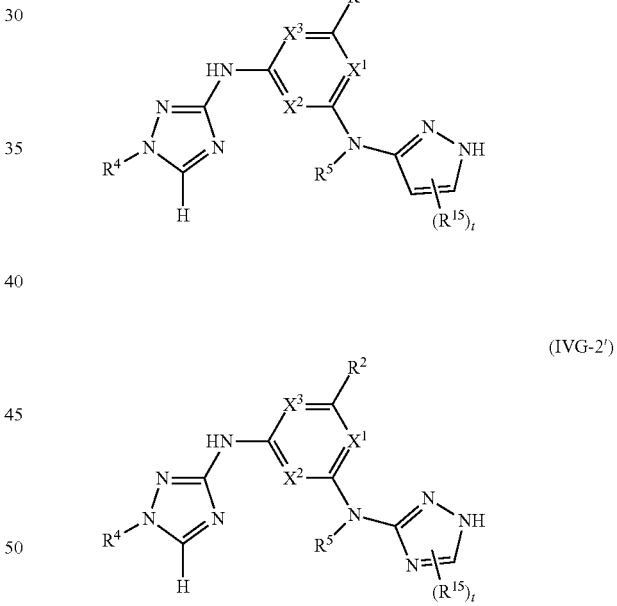

(IVG-1′)

(IVG-2′)

(IVG-3′)

(IVG-4') 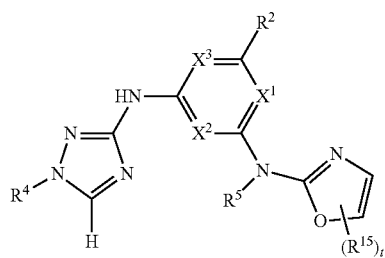

(IVG-4.0') 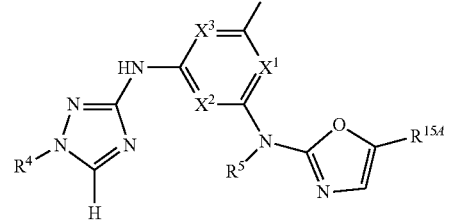

In some embodiments, the present invention features compounds of formulas (IVG-1') to (IVG-4') and the attendant definitions, wherein one or more hydrogen atoms are replaced by a deuterium atom.

In some embodiments, compounds of formula (IVG-1')-(IVG-4') may be represented by the formulas (IVG-1.0')-(IVG-4.0'), where $R^{15A}$ is H or $R^{15}$. In some embodiments, $R^{15A}$ is H, phenyl or $C_{1-4}$alkyl.

In some embodiments, the present invention features compounds of formulas (IVG-1.0') to (IVG-4.0') and the attendant definitions, wherein one or more hydrogen atoms are replaced by a deuterium atom.

In some embodiments of formulas (IVH') and (IVJ'), are compounds, respectively, of formulas (IVH-1') and (IVJ-1'), wherein $G^1$, $R^2$, $R^4$, $R^5$, $R^6$, $R^7$, $X^1$, $X^2$, and $X^3$ are as defined herein and wherein one or more hydrogen atoms are optionally replaced by a deuterium atom.

(IVG-1.0') 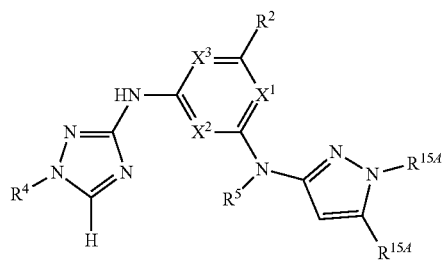

(IVH-1') 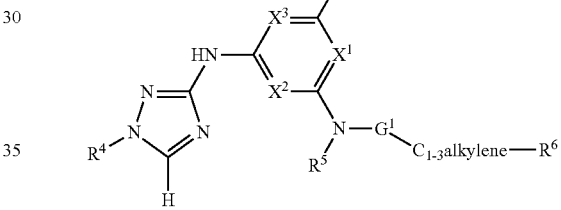

(IVG-2.0')

(IVJ-1') 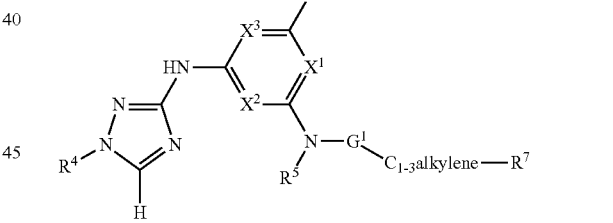

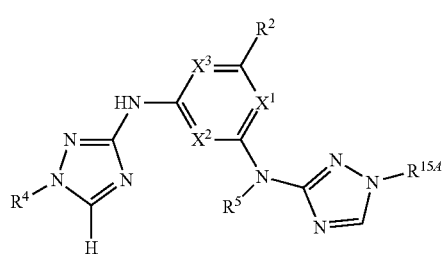

Included in compounds of formula (V') are compounds of formula (VA'), (VB'), (VC'), (VD'), (VE'), (VF'), (VG'), or (VH'), wherein —NR⁵—$C_{1-4}$alkylene-, $G^1$, $G^2$, $G^3$, $G^4$, $G^5$, $G^6$, $G^7$, $R^2$, $R^4$, $R^6$, $R^7$, $X^1$, $X^2$, and $X^3$ are as defined herein:

(IVG-3.0') 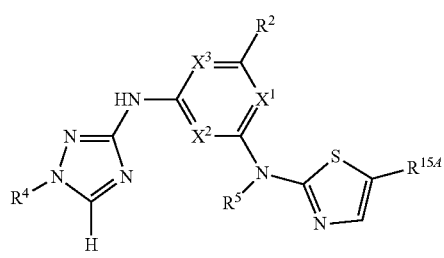

(VA') 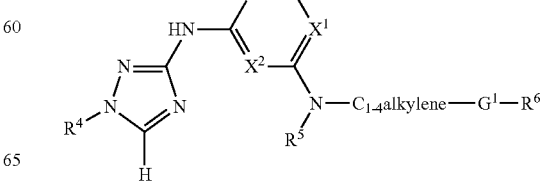

(VB') 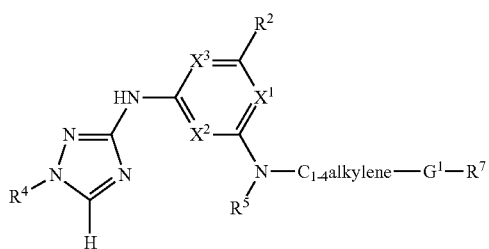

(VC') 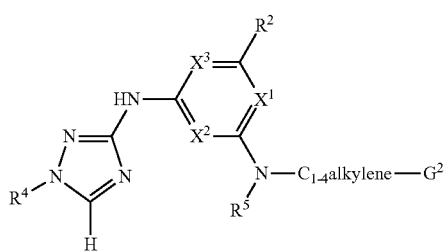

(VD') 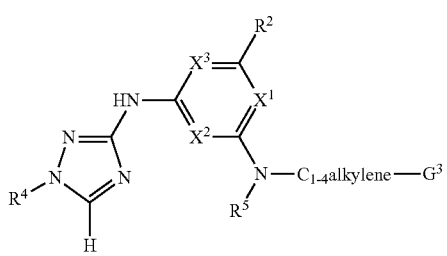

(VE') 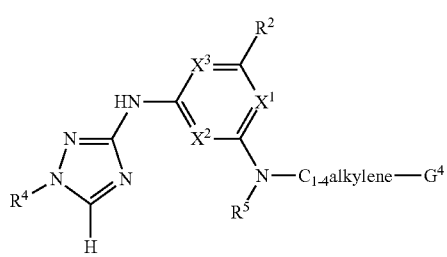

(VF') 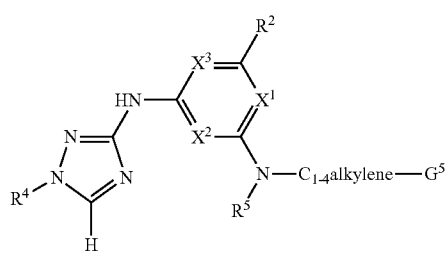

(VG') 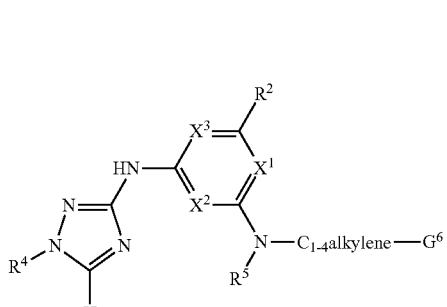

(VH') 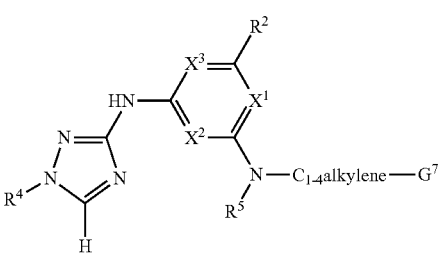

In some embodiments, the present invention features compounds of formulas (VA'), (VB'), (VC'), (VD'), (VE'), (VF'), (VG'), and (VH') and the attendant definitions, wherein one or more hydrogen atoms are replaced by a deuterium atom.

In some embodiments of formula (VA'), are compounds wherein $G^1$ is a 3-8 membered cycloalkyl optionally substituted as described herein. In subsets of these compounds, $R^6$ is the 4- to 8-membered monocyclic heterocyclic ring as described herein. In further subsets of compounds, the $C_{1-4}$alkylene is a methylene. In further subsets of compounds, $R^6$ is the 4- to 8-membered monocyclic heterocyclic ring as described herein and the $C_{1-4}$alkylene is a methylene.

In some embodiments of formula (VA'), are compounds wherein $G^1$ is a 4- to 8-membered monocyclic heterocyclic ring as described herein (e.g., oxetanyl, piperidinyl). In subsets of these compounds, $R^6$ is the 4- to 8-membered monocyclic heterocyclic ring as described herein (e.g., pyrrolidinyl, tetrahydropyranyl). In further subsets of compounds, the $C_{1-4}$alkylene is a methylene. In further subsets of compounds, $R^6$ is the 4- to 8-membered monocyclic heterocyclic ring as described herein and the $C_{1-4}$alkylene is a methylene. Representative examples include the Compound numbers 1020 and 1046.

In some embodiments of formula (VB'), are compounds wherein $G^1$ is a 4- to 8-membered monocyclic heterocyclic ring as described herein (e.g., morpholino). In subsets of these compounds, $R^7$ is a 3-8 membered cycloalkyl optionally substituted as described herein (e.g., cyclopropyl). In further subsets of compounds, the $C_{1-4}$alkylene is a methylene. In further subsets of compounds, $R^7$ is a 3-8 membered cycloalkyl optionally substituted as described herein and the $C_{1-4}$alkylene is a methylene. A representative example includes Compound number 968.

In some embodiments of formula (VC'), are compounds of formula (VC-1') and (VC-2') wherein

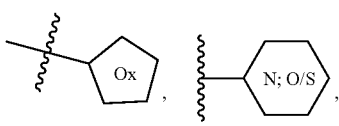

n, —NR$^5$—C$_{1-4}$alkylene-, R$^2$, R$^4$, R$^{12}$, X$^1$, X$^2$, and X$^3$ are as defined herein.

(VC-1')

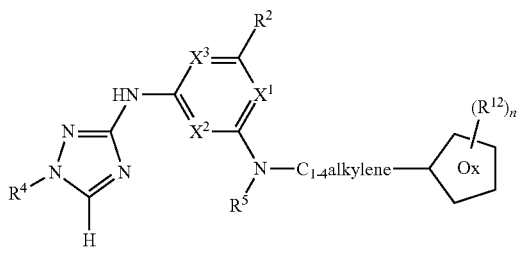

(VC-2')

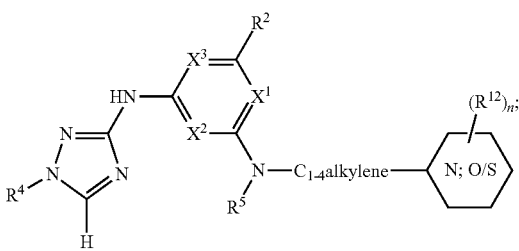

In some embodiments, the present invention features compounds of formulas (VC-1') and (VC-2') and the attendant definitions, wherein one or more hydrogen atoms are replaced by a deuterium atom.

In some embodiments, compounds of formula (VC-1') and (VC-2') may be represented by the formula (VC-1.0') and (VC-2.0'), where $R^{12B}$ is H or $R^{12}$. In some embodiments, $R^{12B}$ is H or $C_{1-4}$alkyl (e.g., methyl) and the $C_{1-4}$alkylene is methylene, ethylene, or propylene, optionally substituted with 1-3 fluoros.

(VC-1.0')

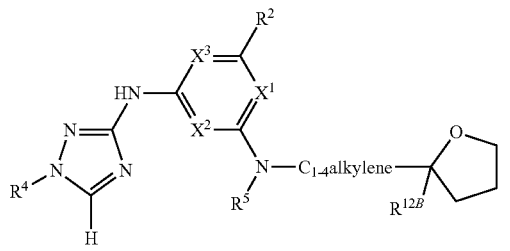

(VC-2.0')

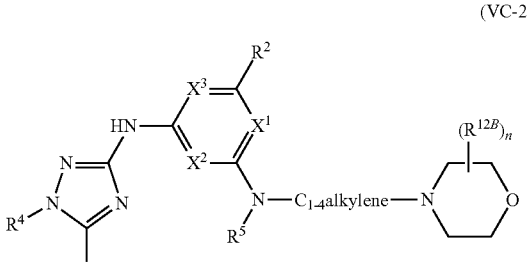

In some embodiments, the present invention features compounds of formulas (VC-1.0') and (VC-2.0') and the attendant definitions, wherein one or more hydrogen atoms are replaced by a deuterium atom.

In other embodiments of formula VC' are compounds where $G^2$ is an azetidinyl, 1,4-dioxanyl, or 4,5-dihydroisoxazolyl (i.e., isoxazoline), for example, as shown in Compound numbers 932, 1004 or 1084.

In some embodiments of formulas (VA') to (VH'), (VC-1'), (VC-2'), (VC-1.0'), or (VC-2.0'), $R^5$ is H or methyl.

Included in compounds of formula (VI') are compounds of formula (VIA'), (VIB'), (VIC'), (VID'), (VIE'), (VIF'), or (VIG'), wherein $G^1$, $G^2$, $G^3$, $G^4$, $G^5$, $G^6$, $R^2$, $R^4$, $R^6$, $R^7$, $X^1$, $X^2$, and $X^3$ are as defined herein.

(VIA')

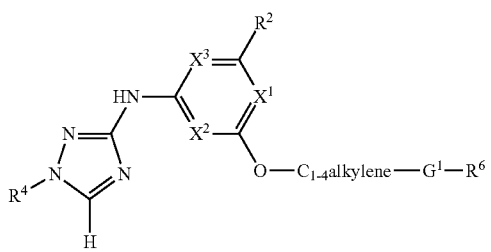

(VIB')

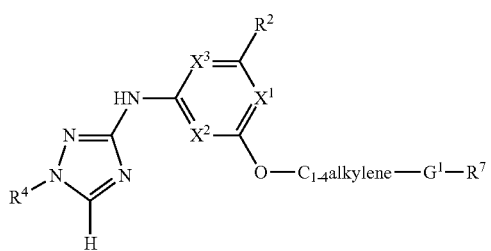

(VIC')


(VID')

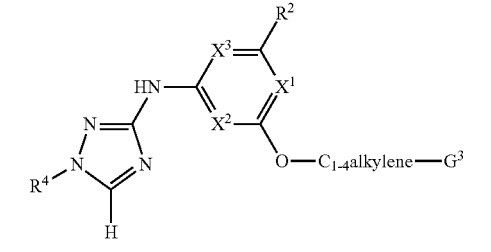

(VIE')

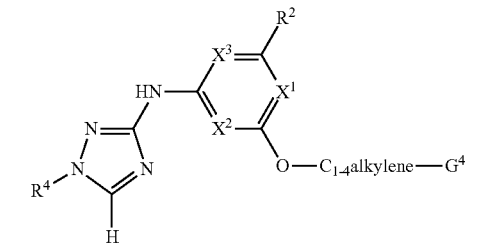

-continued (VIF')
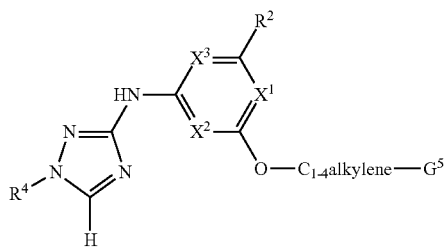

(VIG')
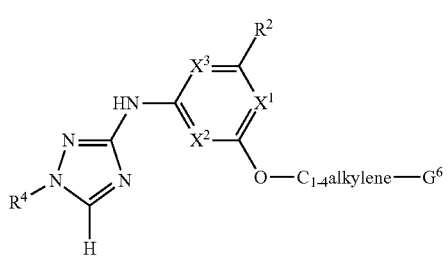

In some embodiments, the present invention features compounds of formulas (VIA'), (VIB'), (VIC'), (VID'), (VIE'), (VIF'), and (VIG') and the attendant definitions, wherein one or more hydrogen atoms are replaced by a deuterium atom.

In some embodiments of formula (VIC'), are compounds of formula (VIC-1') to (VIC-4'), wherein

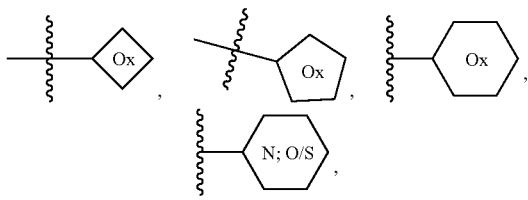

n, $R^2$, $R^4$, $R^{12}$, $X^1$, $X^2$, and $X^3$ are as defined herein.

(VIC-1')
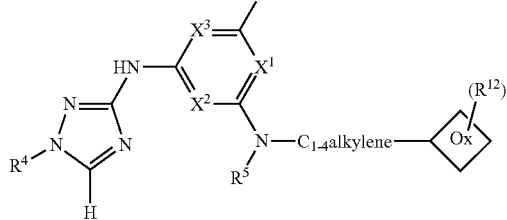

(VIC-2')
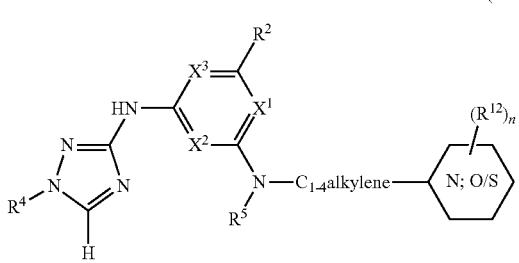

-continued (VIC-3')
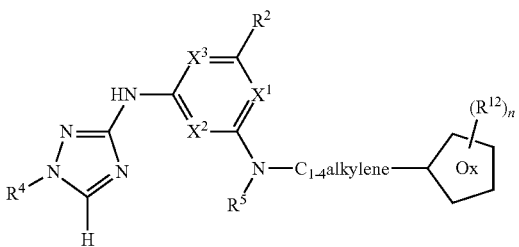

(VIC-4')
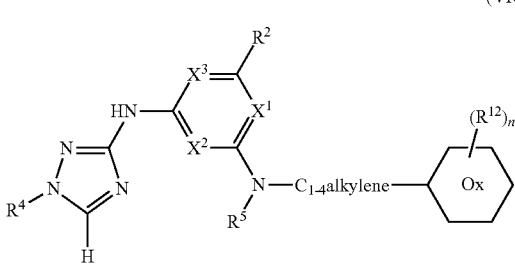

In some embodiments, the present invention features compounds of formulas (VIC-1') to (VIC-4') and the attendant definitions, wherein one or more hydrogen atoms are replaced by a deuterium atom.

In some embodiments, compounds of formula (VIC-1'), (VIC-2'), (VIC-3'), and (VIC-4') may be represented by the formulas (VIC-1.0')-(VIC-4.0'), wherein $R^{12B}$ is H or $R^{12}$. In some embodiments, $R^{12B}$ is H or $C_{1-4}$alkyl (e.g., methyl) and the $C_{1-4}$alkylene is methylene or ethylene.

(VIC-1.0')
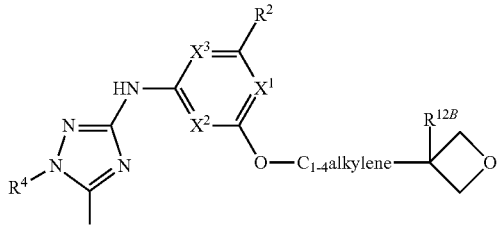

(VIC-2.0')
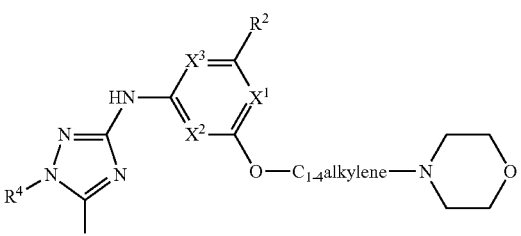

-continued

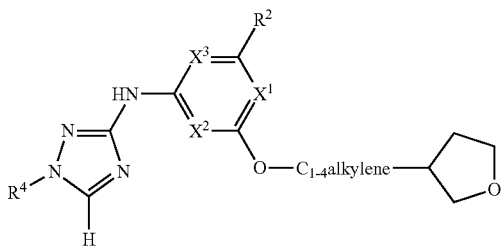
(VIC-3.0')

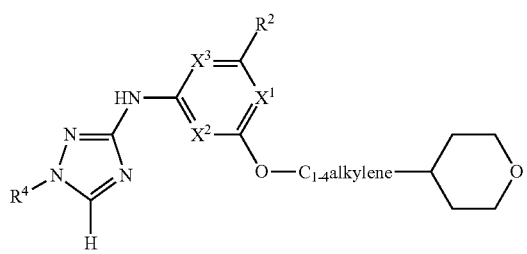
(VIC-4.0')

In some embodiments, the present invention features compounds of formulas (VIC-1.0') to (VIC-4.0') and the attendant definitions, wherein one or more hydrogen atoms are replaced by a deuterium atom.

In some embodiments of formula (VIF'), are compounds of formula (VIF-1'), wherein p, $R^2$, $R^4$, $R^{14}$, $X^1$, $X^2$, and $X^3$ are as defined herein.

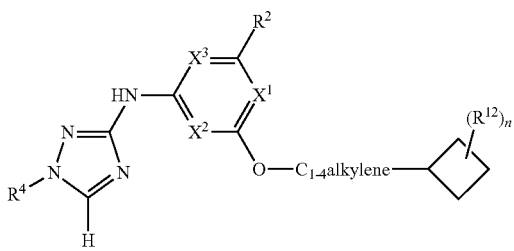
(VIF-1')

In some embodiments, the present invention features compounds of formula (VIF-1') and the attendant definitions, wherein one or more hydrogen atoms are replaced by a deuterium atom.

In some embodiments, compounds of formula (VIF-1') may be represented by the formulas (VIF-1.0'), wherein $R^{14A}$ is H or $R^{14}$. For example, in some cases $R^{14A}$ is halogen (e.g., fluoro).

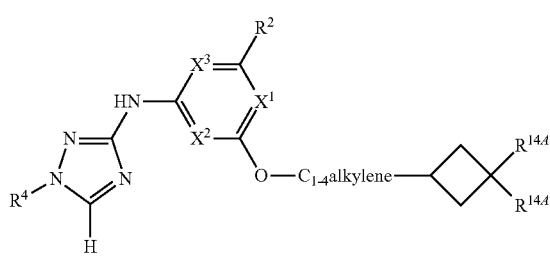
(VIF-1.0')

In some embodiments, the present invention features compounds of formula (VIF-1.0') and the attendant definitions, wherein one or more hydrogen atoms are replaced by a deuterium atom.

In some embodiments of formula (VIG'), are compounds of formula (VIG-1') and (VIG-2'), wherein $R^{15}$ is the optional substituent on $G^6$, t is an integer from 0-4, and $R^2$, $R^4$, $R^5$, $X^1$, $X^2$, and $X^3$ are as defined herein.

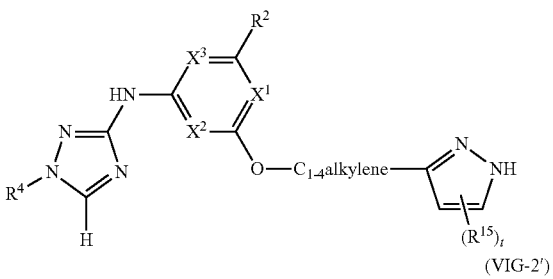
(VIG-1')

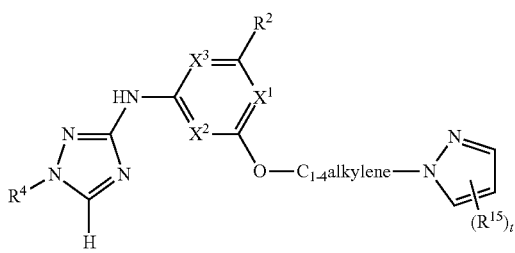
(VIG-2')

In some embodiments, the present invention features compounds of formulas (VIG-1') and (VIG-2') and the attendant definitions, wherein one or more hydrogen atoms are replaced by a deuterium atom.

In some embodiments, compounds of formula (VIG-1') may be represented by the formulas (VIG-1.0'), where $R^{15A}$ is H or $R^{15}$. In some embodiments, $R^{15A}$ is phenyl or $C_{1-4}$alkyl.

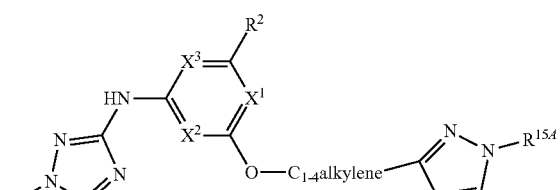
(VIG-1.0')

In some embodiments, the present invention features compounds of formula (VIG-1.0') and the attendant definitions, wherein one or more hydrogen atoms are replaced by a deuterium atom.

Included in compounds of formula (VII') are compounds of formula (VIIA') to (VIIG'), wherein $G^1$, $G^2$, $G^3$, $G^4$, $G^5$, $G^6$, $R^2$, $R^4$, $R^6$, $R^7$, $X^1$, $X^2$, and $X^3$ are as defined herein.

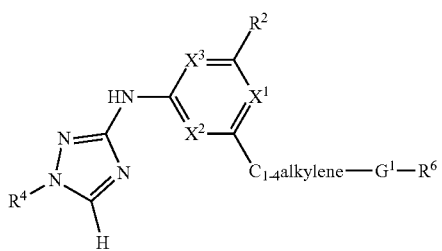
(VIIA')

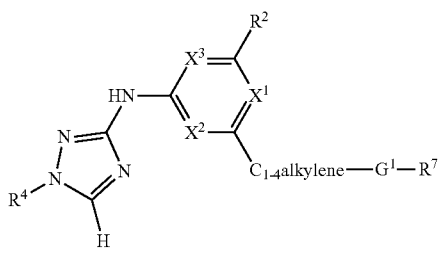
(VIIB')

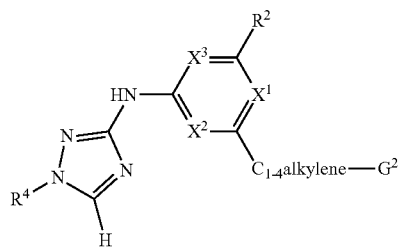
(VIIC')

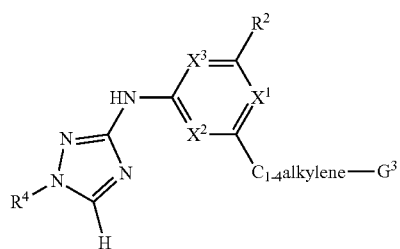
(VIID')

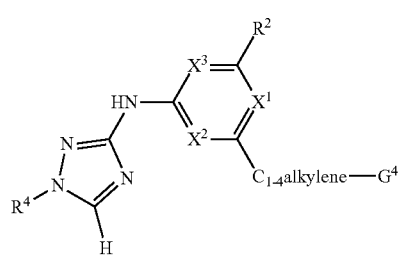
(VIIE')

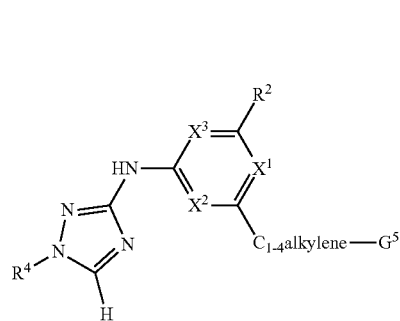
(VIIF')

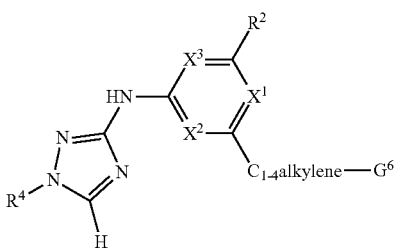
(VIIG')

In some embodiments, the present invention features compounds of formulas (VIIA') to (VIIG') and the attendant definitions, wherein one or more hydrogen atoms are replaced by a deuterium atom.

In some embodiments of formula (VIIA'), are compounds of formula (VIIA-1'), wherein s, $G^1$, $R^2$, $R^4$, $R^{8'}$, $X^1$, $X^2$, and $X^3$ are as defined herein.

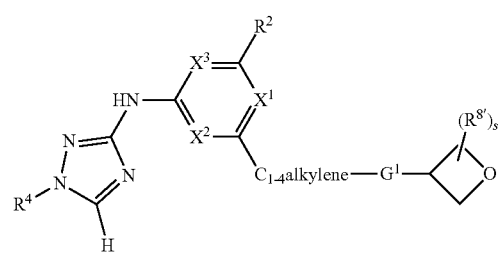
(VIIA-1')

In some embodiments, the present invention features compounds of formula (VIIA-1') and the attendant definitions, wherein one or more hydrogen atoms are replaced by a deuterium atom.

In some embodiments, compounds of formula (VIIA-1') may be represented by the formula (VIIA-1.0') or (VIIA-2.0'). As shown in (VIIA-2.0'), in some embodiments, the $C_{1-4}$alkylene is a $CH_2$ group.

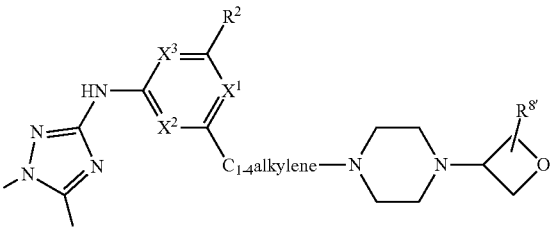
(VIIA-1.0')

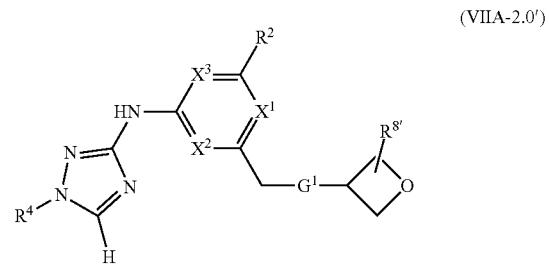
(VIIA-2.0')

In some embodiments, the present invention features compounds of formulas (VIIA-1.0') and (VIIA-2.0') and the attendant definitions, wherein one or more hydrogen atoms are replaced by a deuterium atom.

Included in compounds of formula (VIII') are compounds of formula (VIIIA') to (VIIIG'), wherein $G^1$, $G^2$, $G^3$, $G^4$, $G^5$, $G^6$, $R^2$, $R^4$, $R^6$, $R^7$, $X^1$, $X^2$, and $X^3$ are as defined herein.

(VIIIA')

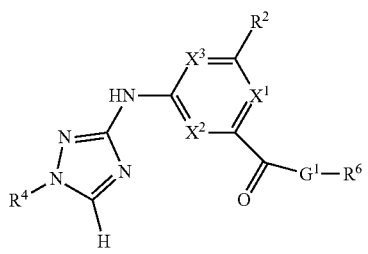

(VIIIB')

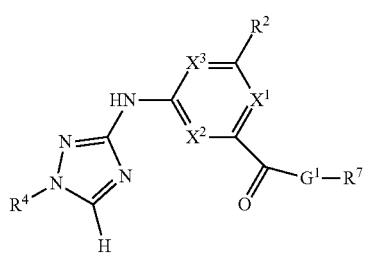

(VIIIC')

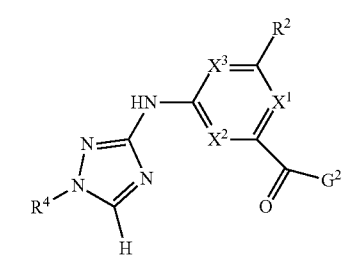

(VIIID')

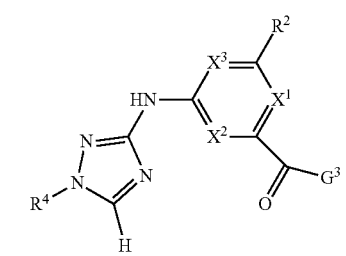

(VIIIE')

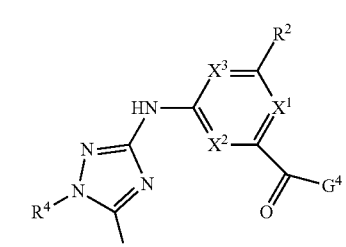

(VIIIF')

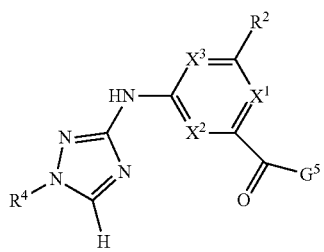

(VIIIG')

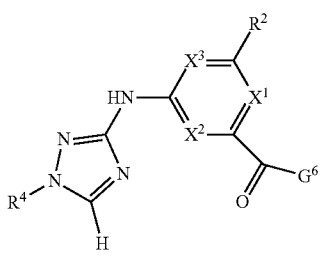

In some embodiments, the present invention features compounds of formulas (VIIIA') to (VIIIG') and the attendant definitions, wherein one or more hydrogen atoms are replaced by a deuterium atom.

In some embodiments of formula (VIIIA'), are compounds of formula (VIIIA-1'), wherein s, $G^1$, $R^2$, $R^4$, $R^8$, $X^1$, $X^2$, and $X^3$ are as defined herein.

(VIIIA-1')

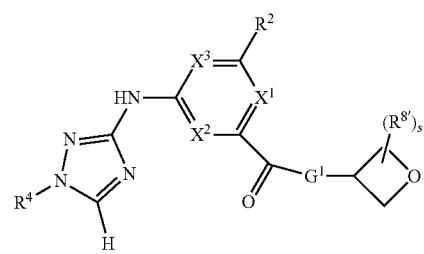

In some embodiments, the present invention features compounds of formula (VIIIA-1') and the attendant definitions, wherein one or more hydrogen atoms are replaced by a deuterium atom.

In some embodiments, compounds of formula (VIIIA-1') may be represented by the formula (VIIIA-1.0').

(VIIIA-1.0')

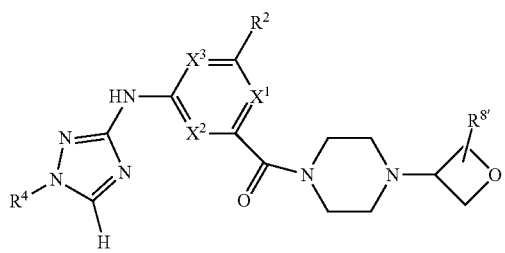

In some embodiments, the present invention features compounds of formula (VIIIA-1.0') and the attendant definitions, wherein one or more hydrogen atoms are replaced by a deuterium atom.

In each of the foregoing embodiments related to compounds of formulas (II') to (VIII'), and associated subformulas and compounds, are embodiments wherein $R^2$ is $C_{1-4}$alkyl $C_{1-4}$haloalkyl, or $C_{3-6}$cycloalkyl; $R^4$ is phenyl optionally substituted with 1-2 substituents selected from halogen and $C_{1-4}$alkyl or $R^4$ is pyrazinyl. In some embodiments, $R^2$ is methyl, ethyl, trifluoromethyl, difluoromethyl, or cyclopropyl; and $R^4$ is phenyl, 3,5-difluorophenyl, 3-fluorophenyl, 3,4-difluorophenyl, 2,5-difluorophenyl, 3-fluoro-5-methylphenyl, or pyrazin-2-yl. In further embodiments, $X^1$, $X^2$, and $X^3$ are each CH. In other embodiments, $X^1$ is CH, $X^2$ is $CR^{X2}$, and $X^3$ is $CR^3$. In other embodiments, $X^1$ is CH, $X^2$ is $CR^{X2}$, and $X^3$ is CH. In other embodiments, $X^1$ is CH, $X^2$ is C—F, and $X^3$ is CH. In other embodiments, $X^1$ is CH, $X^2$ is CH, and $X^3$ is $CR^3$. In other embodiments, $X^1$ is N and $X^2$ and $X^3$ are CH. In other embodiments, $X^1$ is N, $X^2$ is $CR^{X2}$, and $X^3$ is $CR^3$. In other embodiments, $X^1$ is CH, $X^2$ is N, and $X^3$ is CH. In other embodiments, $X^1$ is CH, $X^2$ is N, and $X^3$ is $CR^3$. In other embodiments, $X^1$ and $X^2$ are CH, and $X^3$ is N. In other embodiments, $X^1$ is CH, $X^2$ is $CR^{X2}$, and $X^3$ is N. In other embodiments, $X^1$ and $X^2$ are N, and $X^3$ is CH. In other embodiments, $X^1$ and $X^2$ are N, and $X^3$ is $CR^3$.

In some embodiments according to formulas (II') to (VIII'), and associated subformulas and compounds are further compounds where $X^1$ is H, $X^3$ is H, $X^2$ is $CR^{X2}$ and $R^{X2}$ is hydrogen or fluoro. In other embodiments, $R^{X2}$ is fluoro. For example, in some embodiments are compounds of formula (X'), wherein $R^1$, $R^2$, $R^4$, and $L^1$ are as defined in the description and embodiments herein.

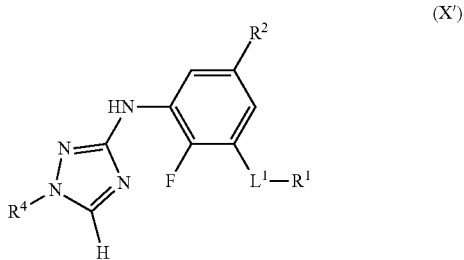

(X')

In some embodiments, the present invention features compounds of formula (X') and the attendant definitions, wherein one or more hydrogen atoms are replaced by a deuterium atom.

In another embodiment, the compounds of formula I or I' include isotope-labelled forms thereof. An isotope-labelled form of a compound of formula I or I' is identical to this compound apart from the fact that one or more atoms of the compound have been replaced by an atom or atoms having an atomic mass or mass number which differs from the atomic mass or mass number of the atom which usually occurs in greater natural abundance. Examples of isotopes which are readily commercially available and which can be incorporated into a compound of formula I or I' by well-known methods include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively.

In another embodiment, a compound of formula I or I' or a pharmaceutically acceptable salt thereof which contains one or more of the above-mentioned isotopes and/or other isotopes of other atoms is intended to be part of the present invention.

In another embodiment, the present invention features a compound of formula I or I' and the attendant definitions, wherein one or more hydrogen atoms are replaced by a deuterium atom.

In another embodiment, an isotope-labelled compound of formula I or I' can be used in a number of beneficial ways. In one embodiment, an isotope-labelled compound of formula I or I' into which, for example, a radioisotope, such as $^3$H or $^{14}$C, has been incorporated is suitable for a medicament and/or for substrate tissue distribution assays. In one embodiment, tritium ($^3$H) and carbon-14 ($^{14}$C) are particularly preferred owing to simple preparation and excellent detectability.

In yet another embodiment, incorporation of heavier isotopes, for example deuterium ($^2$H), into a compound of formula I or I' have therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of formula I or I' can usually be prepared by carrying out the procedures disclosed in the synthesis schemes and the related description, in the example part and in the preparation part in the present text, replacing a non-isotope-labelled reactant by a readily available isotope-labelled reactant.

In another embodiment, Deuterium ($^2$H) can also be incorporated into a compound of formula I or I' for the purpose of manipulating the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_{M/kD}=2-7$ are typical. If this rate difference is successfully applied to a compound of formula I or I' that is susceptible to oxidation, the profile of this compound in vivo can be drastically modified and result in improved pharmacokinetic properties. For a further discussion, see S. L. Harbeson and R. D. Tung, *Deuterium In Drug Discovery and Development*, Ann. Rep. Med. Chem. 2011, 46, 403-417, incorporated in its entirety herein by reference.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of formula I or I' with improved stability through resistance to such oxidative metabolism. Significant improvements in the pharmacokinetic profiles of compounds of formula I or I' are thereby obtained, and can be expressed quantitatively in terms of increases in the in vivo half-life ($t_{1/2}$), concentration at maximum therapeutic effect ($C_{max}$), area under the dose response curve (AUC), and bioavailability; and in terms of reduced clearance, dose and materials costs.

The following is intended to illustrate the above: a compound of formula I or I' which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

In another embodiment, deuterium-hydrogen exchange in a compound of formula I or I' can be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

In another embodiment, the invention features a compound of formula I or I', wherein the compound or a pharmaceutically acceptable salt thereof, is selected from Table 1 below. In the Table 1 below, compounds 92 and 473 are each single enantiomers with unknown stereochemistry and are arbitrarily assigned the "S" and "R" conformation, respectively. Compounds 101 and 487 are also each single enantiomers with unknown stereochemistry and are arbitrarily assigned the "S" and "R" conformation, respectively. Compound 208 is a racemic mixture of the (S,R) and (R,R) diastereomers where the stereocenters are in a cis configuration. Compound 282 is a racemic mixture of the (R,R) and (S,S) diastereomers where the stereocenters are in a trans configuration.

TABLE 1

Compound Table

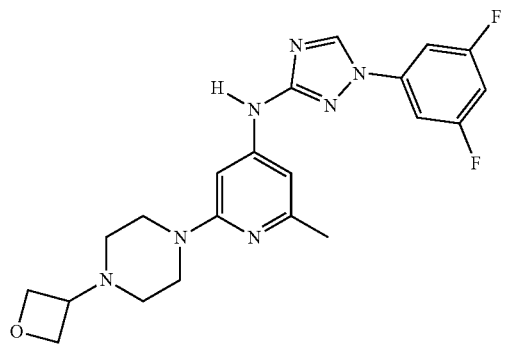 [SMILES: Cc1cc(Nc2ncn(-c3cc(F)cc(F)c3)n2)cc(N2CCN(C3COC3)CC2)n1]

1

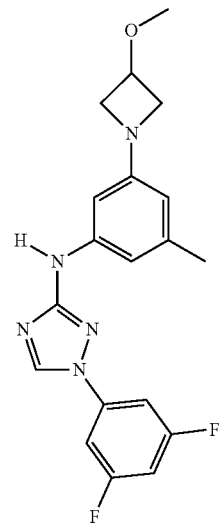

2

TABLE 1-continued
Compound Table
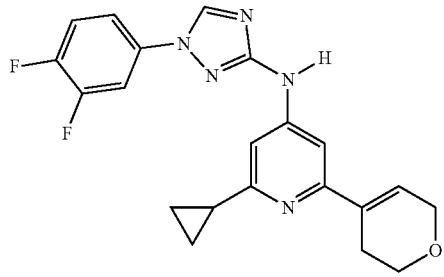 [SMILES: Fc1ccc(-n2cnc(Nc3cc(C4=CCOCC4)nc(C4CC4)c3)n2)cc1F]
3
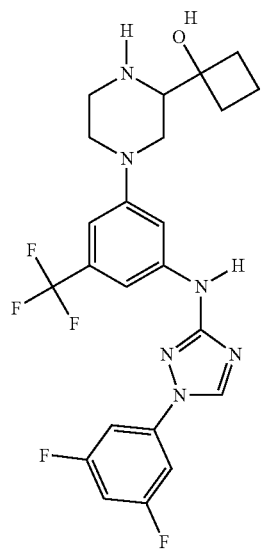
4
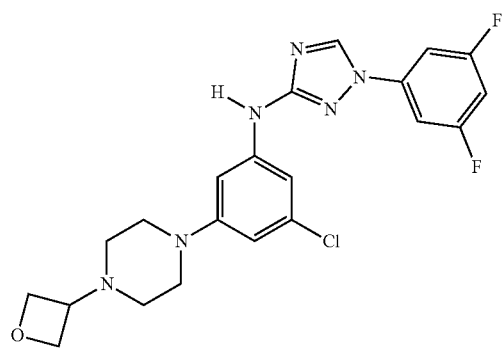
5

TABLE 1-continued
Compound Table
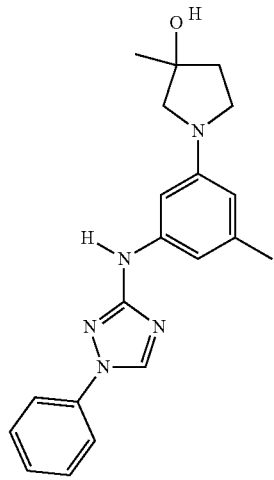
6
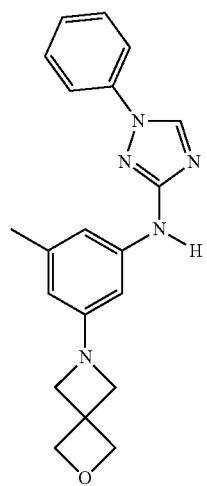 [SMILES: Cc1cc(Nc2ncn(-c3ccccc3)n2)cc(N2CC3(COC3)C2)c1]
7
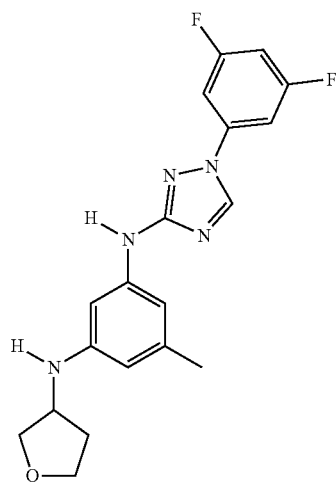 [SMILES: Cc1cc(Nc2ncn(-c3cc(F)cc(F)c3)n2)cc(NC2CCOC2)c1]
8

TABLE 1-continued
Compound Table
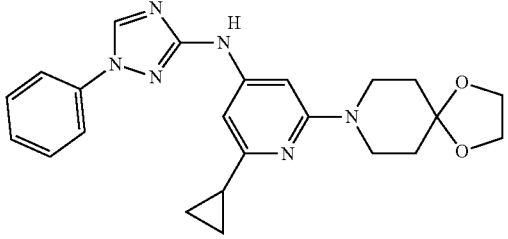
9
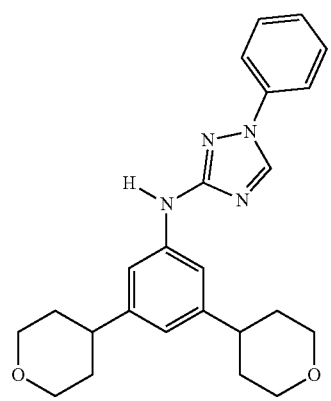 [SMILES: c1ccc(-n2cnc(Nc3cc(C4CCOCC4)cc(C4CCOCC4)c3)n2)cc1]
10
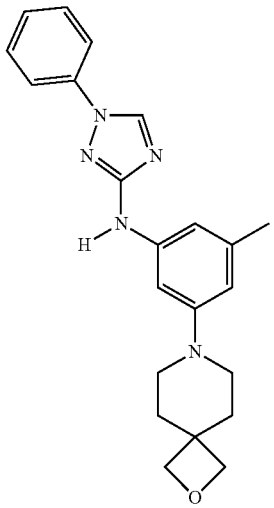 [SMILES: Cc1cc(Nc2ncn(-c3ccccc3)n2)cc(N2CCC3(CC2)COC3)c1]
11
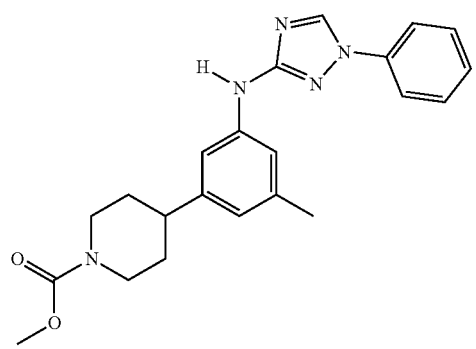 [SMILES: COC(=O)N1CCC(c2cc(C)cc(Nc3ncn(-c4ccccc4)n3)c2)CC1]
12

TABLE 1-continued
Compound Table
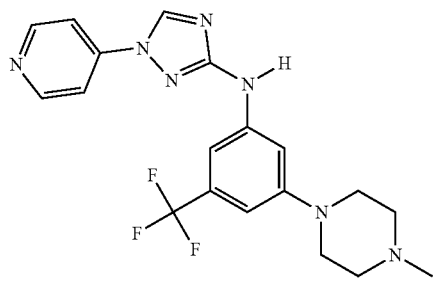 [SMILES: CN1CCN(c2cc(Nc3ncn(-c4ccncc4)n3)cc(C(F)(F)F)c2)CC1]
13
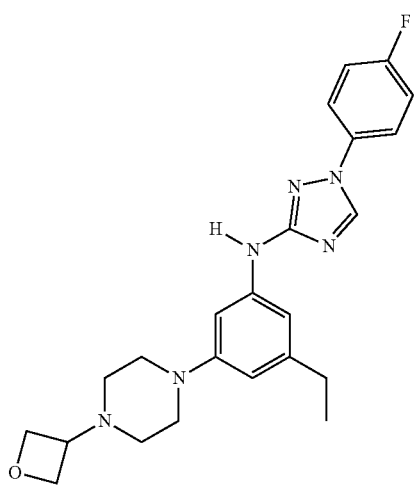
14
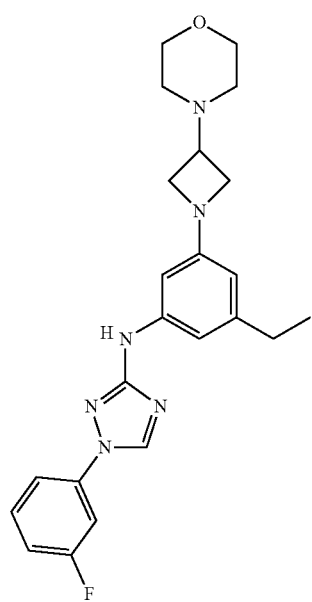
15

TABLE 1-continued
Compound Table
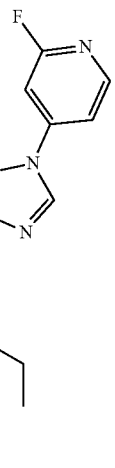 16
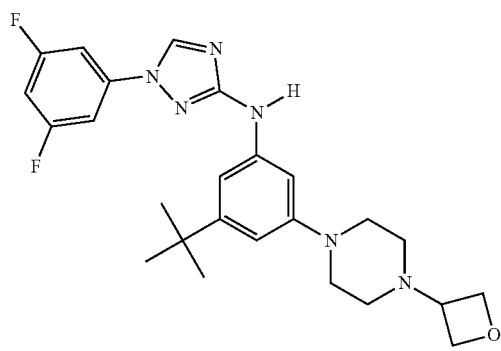 [SMILES: CC(C)(C)c1cc(Nc2ncn(-c3cc(F)cc(F)c3)n2)cc(N2CCN(C3COC3)CC2)c1] 17
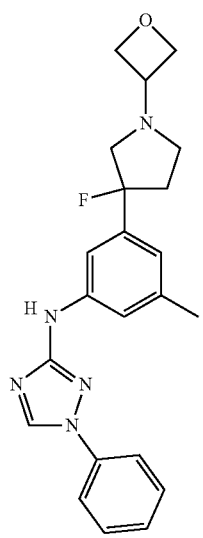 18
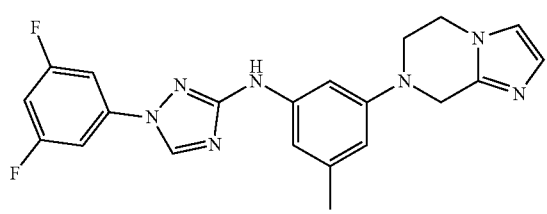 [SMILES: Cc1cc(Nc2ncn(-c3cc(F)cc(F)c3)n2)cc(N2CCn3ccnc3C2)c1] 19

TABLE 1-continued
Compound Table
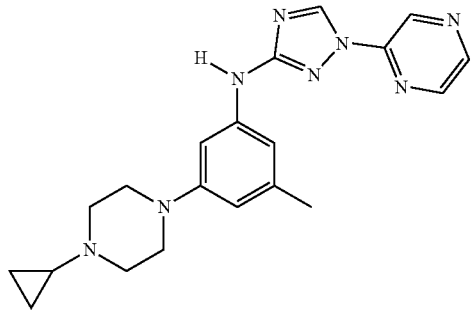 [SMILES: Cc1cc(Nc2ncn(-c3cnccn3)n2)cc(N2CCN(C3CC3)CC2)c1]
20
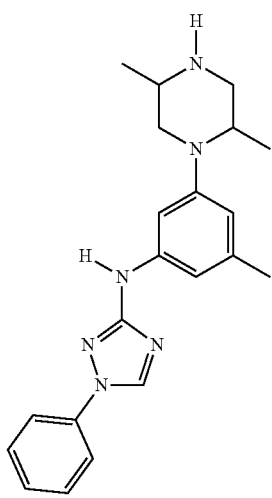 [SMILES: Cc1cc(Nc2ncn(-c3ccccc3)n2)cc(N2CC(C)NCC2C)c1]
21
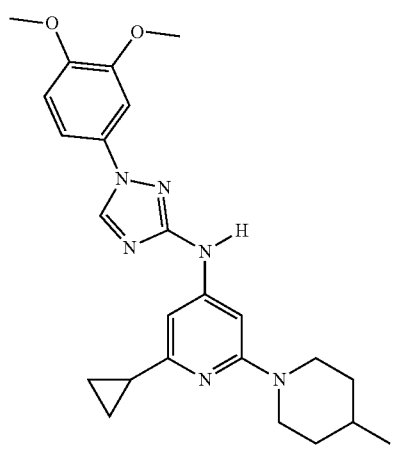
22

TABLE 1-continued
Compound Table
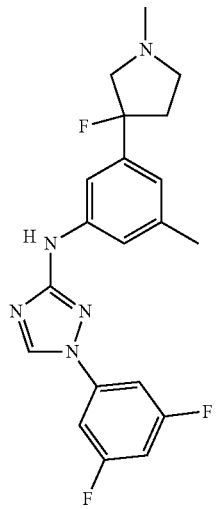
23
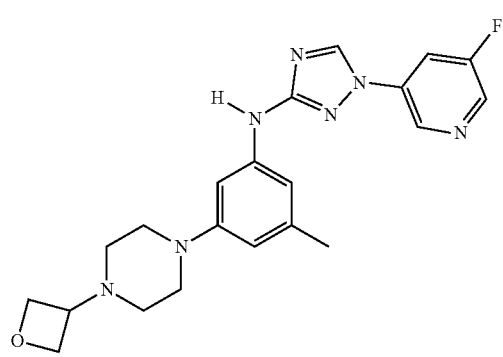 [SMILES: Cc1cc(Nc2ncn(-c3cncc(F)c3)n2)cc(N2CCN(C3COC3)CC2)c1]
24
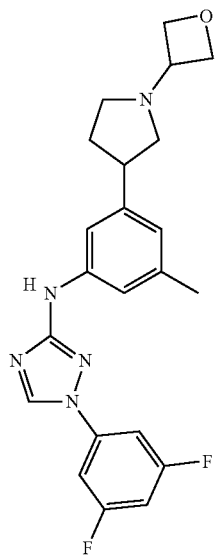
25

TABLE 1-continued
Compound Table
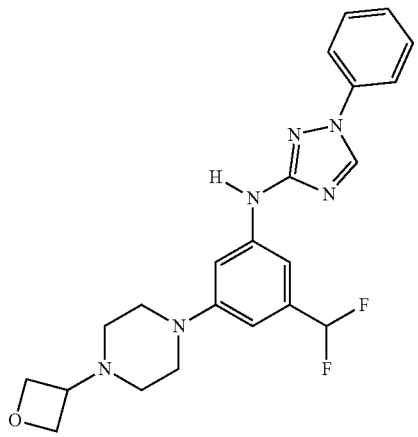 [SMILES: FC(F)c1cc(Nc2ncn(-c3ccccc3)n2)cc(N2CCN(C3COC3)CC2)c1]
26
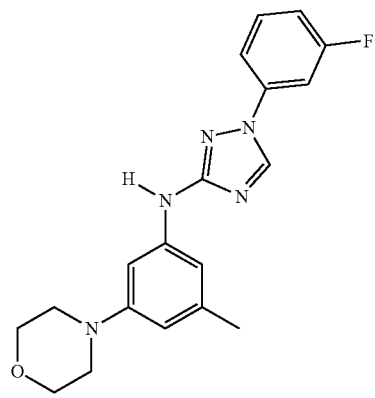 [SMILES: Cc1cc(Nc2ncn(-c3cccc(F)c3)n2)cc(N2CCOCC2)c1]
27
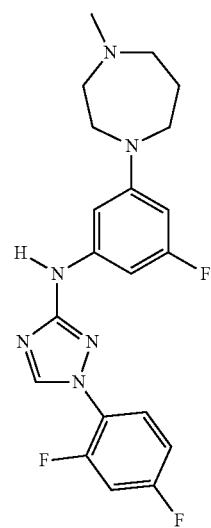 [SMILES: CN1CCCN(c2cc(F)cc(Nc3ncn(-c4ccc(F)cc4F)n3)c2)CC1]
28

TABLE 1-continued
Compound Table
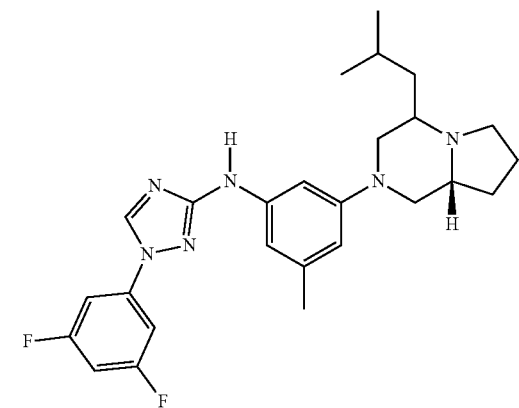 [SMILES: Cc1cc(Nc2ncn(-c3cc(F)cc(F)c3)n2)cc(N2CC(CC(C)C)N3CCC[C@@H]3C2)c1]
29
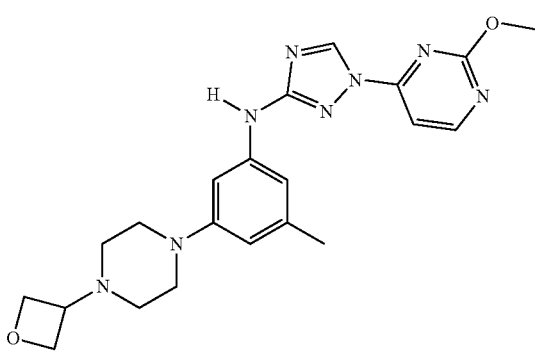
30
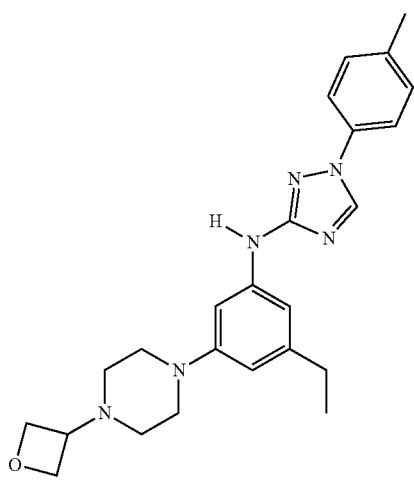 [SMILES: CCc1cc(Nc2ncn(-c3ccc(C)cc3)n2)cc(N2CCN(C3COC3)CC2)c1]
31
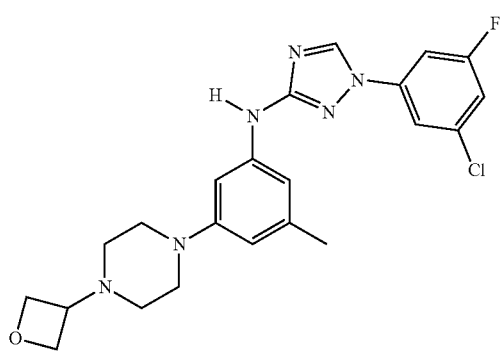 [SMILES: Cc1cc(Nc2ncn(-c3cc(F)cc(Cl)c3)n2)cc(N2CCN(C3COC3)CC2)c1]
32

TABLE 1-continued
Compound Table
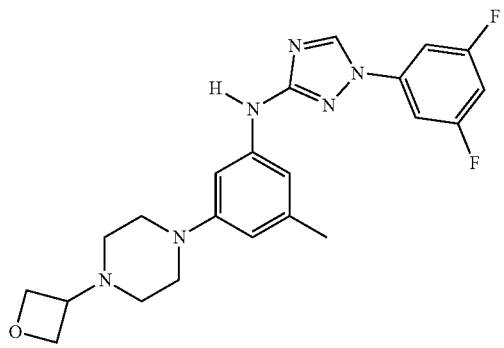 [SMILES: Cc1cc(Nc2ncn(-c3cc(F)cc(F)c3)n2)cc(N2CCN(C3COC3)CC2)c1]
33
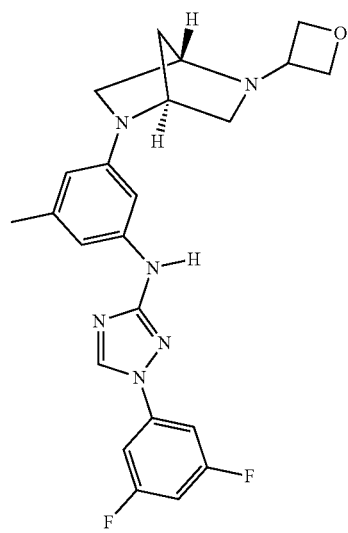 [SMILES: Cc1cc(Nc2ncn(-c3cc(F)cc(F)c3)n2)cc(N2C[C@@H]3C[C@H]2CN3C2COC2)c1]
34
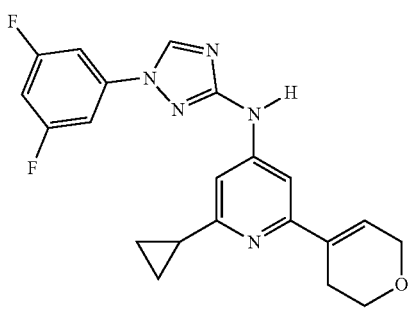 [SMILES: Fc1cc(F)cc(-n2cnc(Nc3cc(C4=CCOCC4)nc(C4CC4)c3)n2)c1]
35

TABLE 1-continued
Compound Table
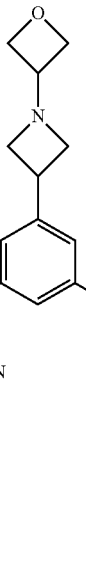
36
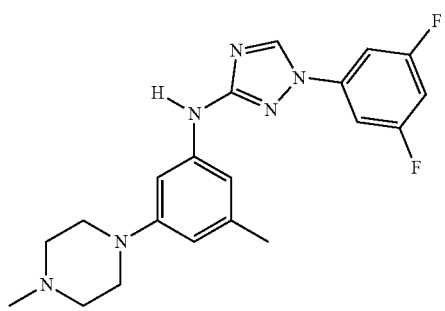
37
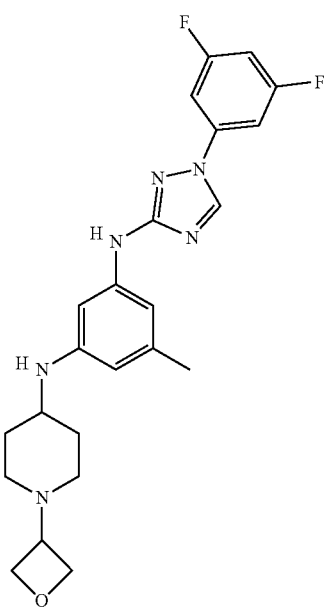
38

TABLE 1-continued
Compound Table
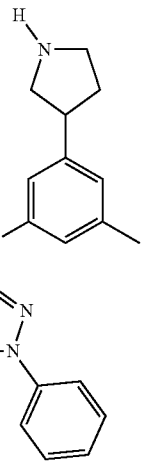
39
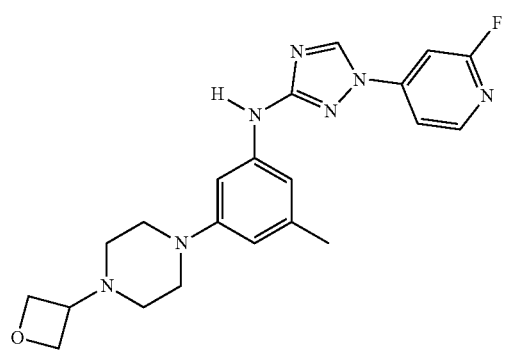 [SMILES: Cc1cc(Nc2ncn(-c3ccnc(F)c3)n2)cc(N2CCN(C3COC3)CC2)c1]
40
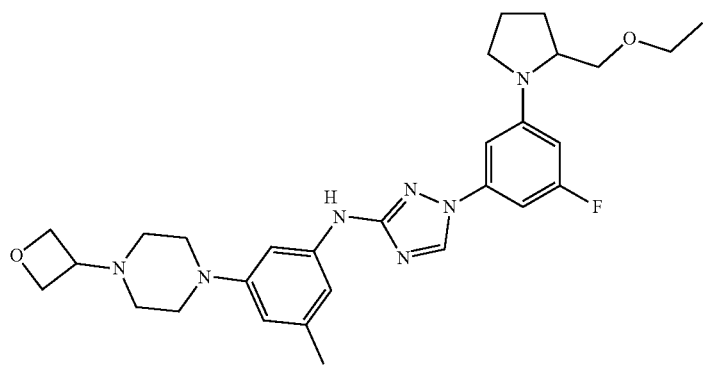
41
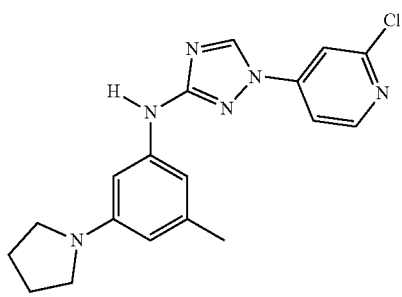
42

TABLE 1-continued
Compound Table
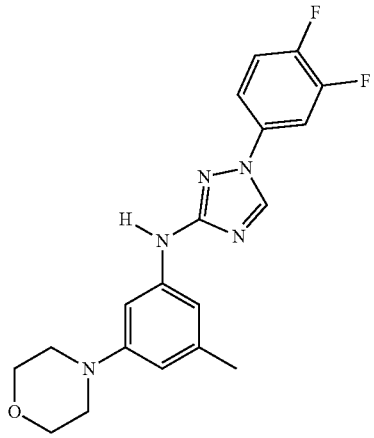 [SMILES: Cc1cc(Nc2ncn(-c3ccc(F)c(F)c3)n2)cc(N2CCOCC2)c1]
43
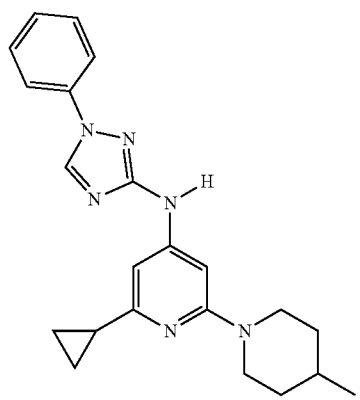 [SMILES: CC1CCN(c2cc(Nc3ncn(-c4ccccc4)n3)cc(C3CC3)n2)CC1]
44
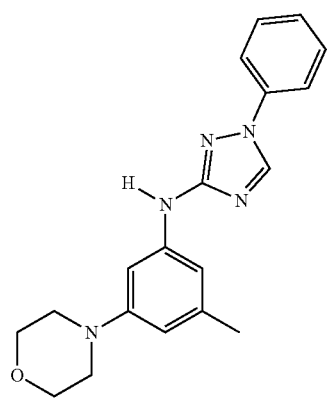 [SMILES: Cc1cc(Nc2ncn(-c3ccccc3)n2)cc(N2CCOCC2)c1]
45

TABLE 1-continued
Compound Table
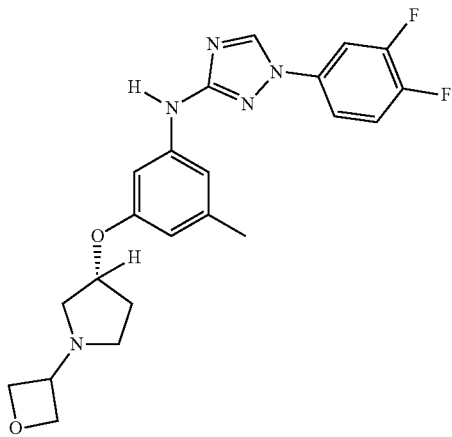 [SMILES: Cc1cc(Nc2ncn(-c3ccc(F)c(F)c3)n2)cc(O[C@@H]2CCN(C3COC3)C2)c1]
46
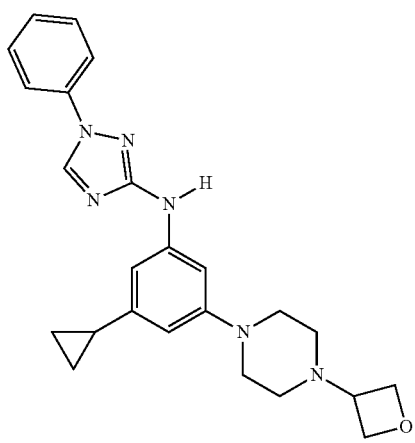 [SMILES: c1ccc(-n2cnc(Nc3cc(C4CC4)cc(N4CCN(C5COC5)CC4)c3)n2)cc1]
47
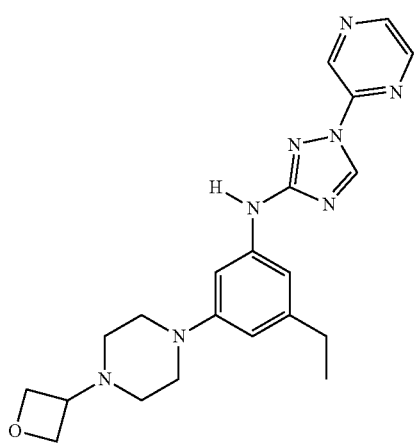 [SMILES: CCc1cc(Nc2ncn(-c3cnccn3)n2)cc(N2CCN(C3COC3)CC2)c1]
48

TABLE 1-continued
Compound Table
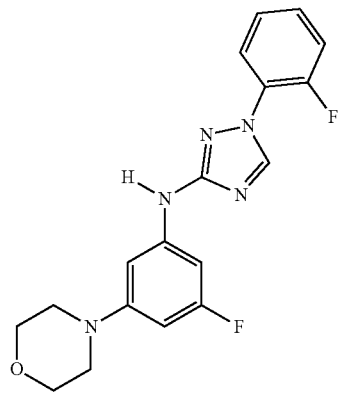 [SMILES: Fc1cc(Nc2ncn(-c3ccccc3F)n2)cc(N2CCOCC2)c1]
49
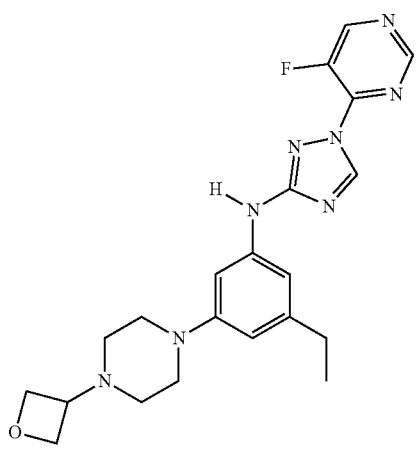 [SMILES: CCc1cc(Nc2ncn(-c3ncncc3F)n2)cc(N2CCN(C3COC3)CC2)c1]
50
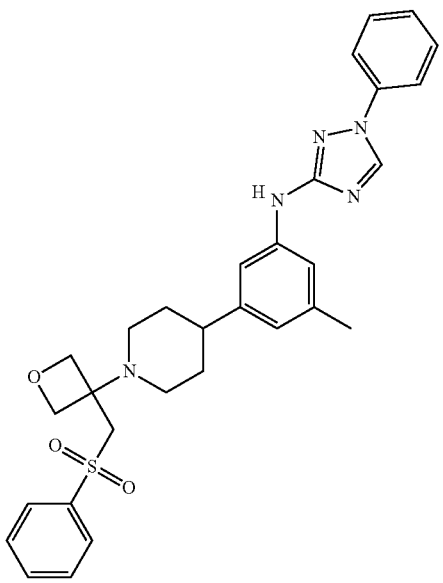
51

TABLE 1-continued
Compound Table
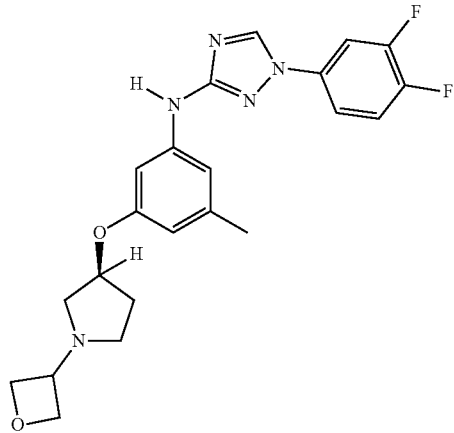 [SMILES: Cc1cc(Nc2ncn(-c3ccc(F)c(F)c3)n2)cc(O[C@H]2CCN(C3COC3)C2)c1]
52
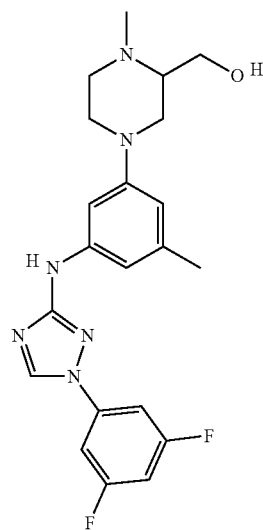
53
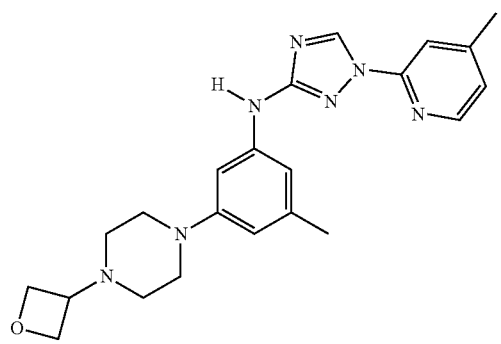 [SMILES: Cc1cc(Nc2ncn(-c3cc(C)ccn3)n2)cc(N2CCN(C3COC3)CC2)c1]
54

TABLE 1-continued
Compound Table
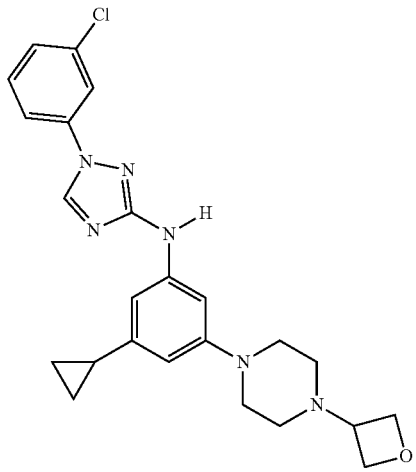
55
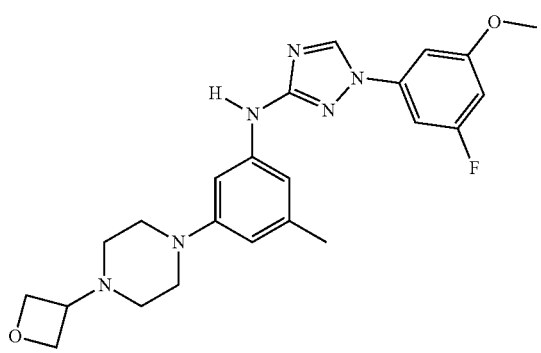 [SMILES: COc1cc(F)cc(-n2cnc(Nc3cc(C)cc(N4CCN(C5COC5)CC4)c3)n2)c1]
56
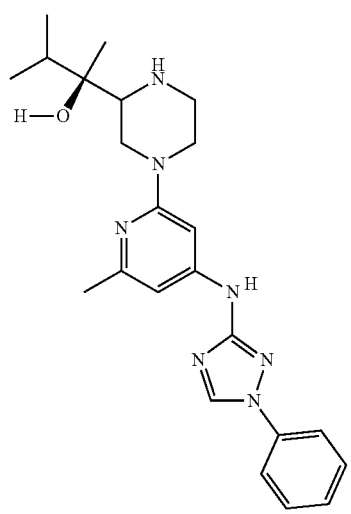
57

TABLE 1-continued
Compound Table
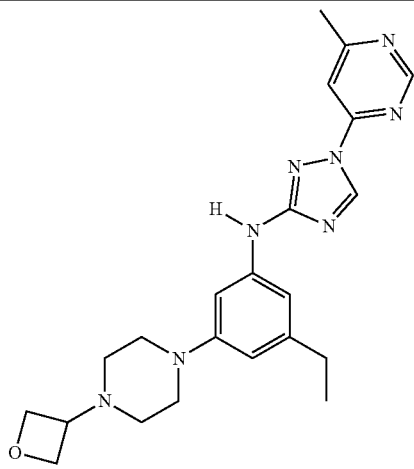
58
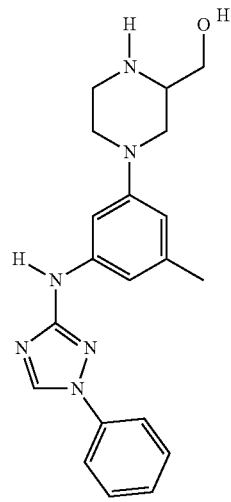
59
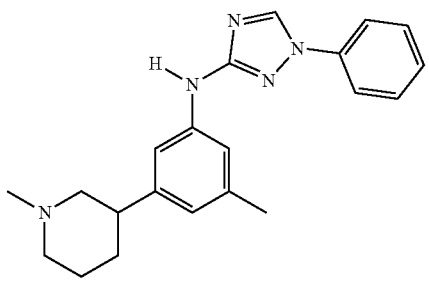 [SMILES: Cc1cc(Nc2ncn(-c3ccccc3)n2)cc(C2CCCN(C)C2)c1]
60
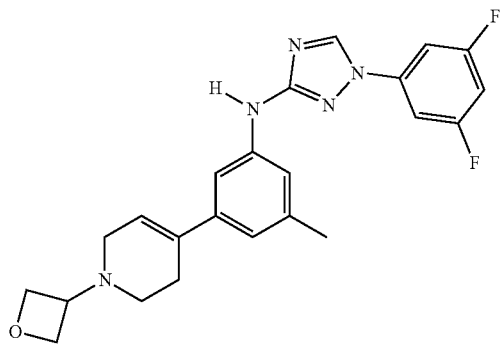 [SMILES: Cc1cc(Nc2ncn(-c3cc(F)cc(F)c3)n2)cc(C2=CCN(C3COC3)CC2)c1]
61

TABLE 1-continued
Compound Table
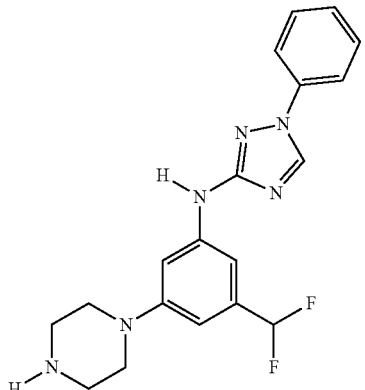
62
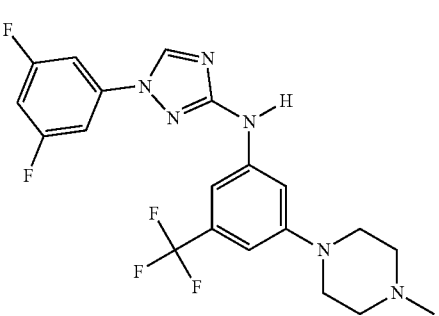 [SMILES: CN1CCN(c2cc(Nc3ncn(-c4cc(F)cc(F)c4)n3)cc(C(F)(F)F)c2)CC1]
63
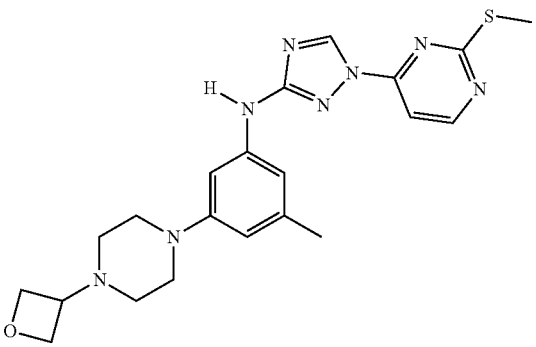 [SMILES: CSc1nccc(-n2cnc(Nc3cc(C)cc(N4CCN(C5COC5)CC4)c3)n2)n1]
64
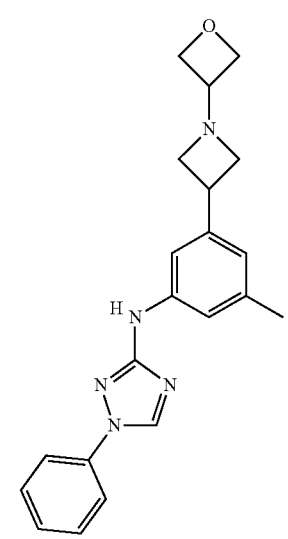
65

171
172
TABLE 1-continued
Compound Table
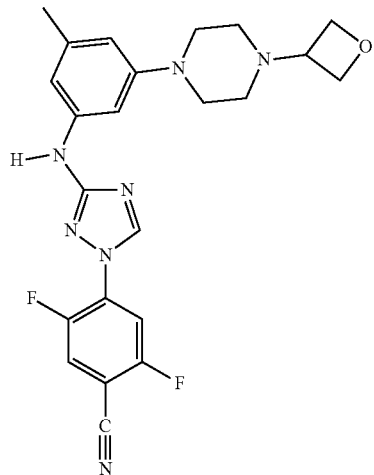 [SMILES: Cc1cc(Nc2ncn(-c3cc(F)c(C#N)cc3F)n2)cc(N2CCN(C3COC3)CC2)c1] 66
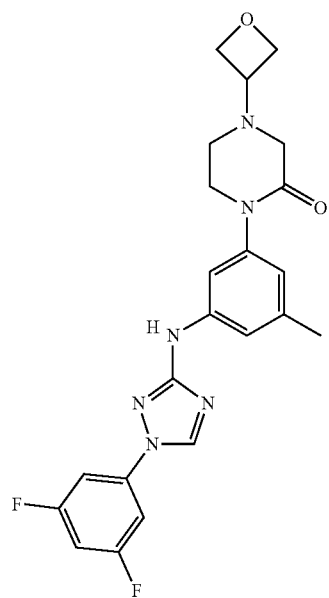 67
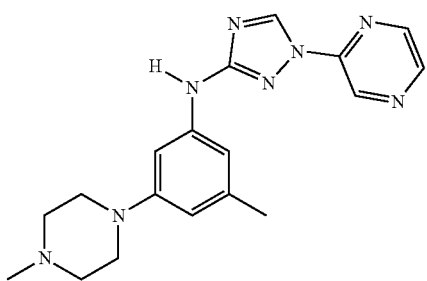 68

TABLE 1-continued
Compound Table
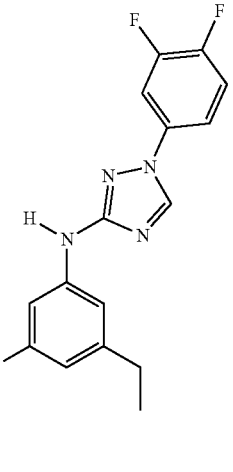
69
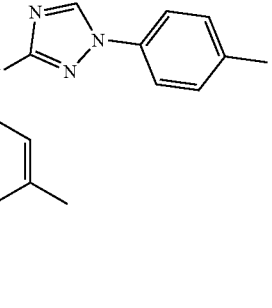
70
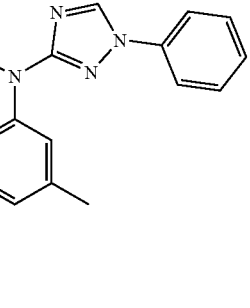
71
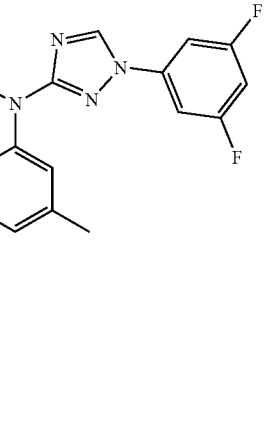
72

TABLE 1-continued
Compound Table
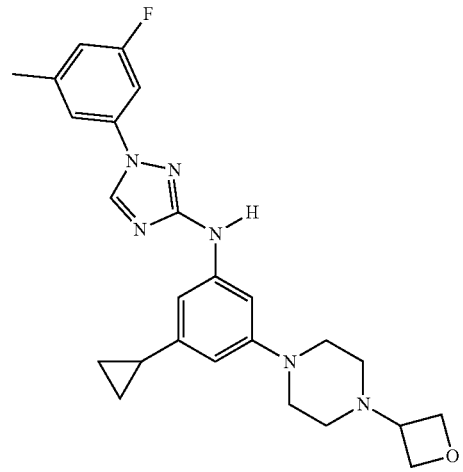 [SMILES: Cc1cc(F)cc(-n2cnc(Nc3cc(C4CC4)cc(N4CCN(C5COC5)CC4)c3)n2)c1]
73
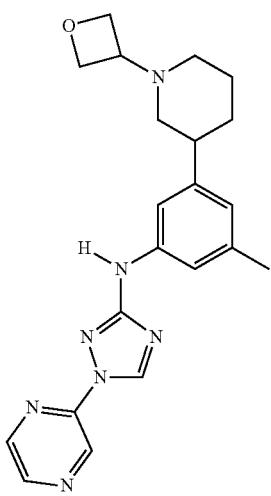 [SMILES: Cc1cc(Nc2ncn(-c3cnccn3)n2)cc(C2CCCN(C3COC3)C2)c1]
74
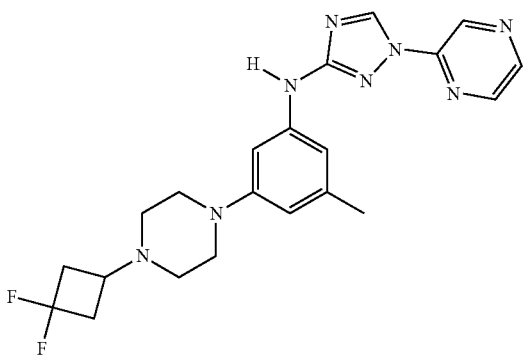 [SMILES: Cc1cc(Nc2ncn(-c3cnccn3)n2)cc(N2CCN(C3CC(F)(F)C3)CC2)c1]
75

TABLE 1-continued
Compound Table
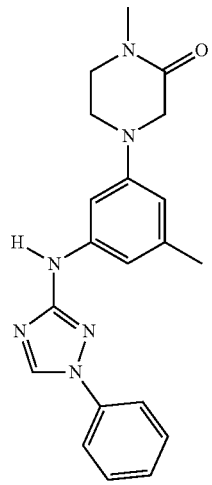 [SMILES: Cc1cc(Nc2ncn(-c3ccccc3)n2)cc(N2CCN(C)C(=O)C2)c1] 76
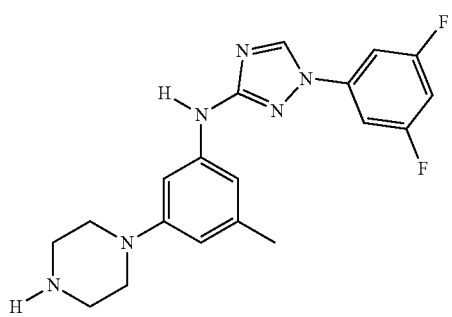 77
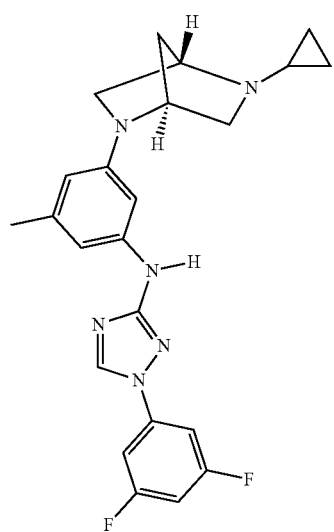 [SMILES: Cc1cc(Nc2ncn(-c3cc(F)cc(F)c3)n2)cc(N2C[C@@H]3C[C@H]2CN3C2CC2)c1] 78

TABLE 1-continued
Compound Table
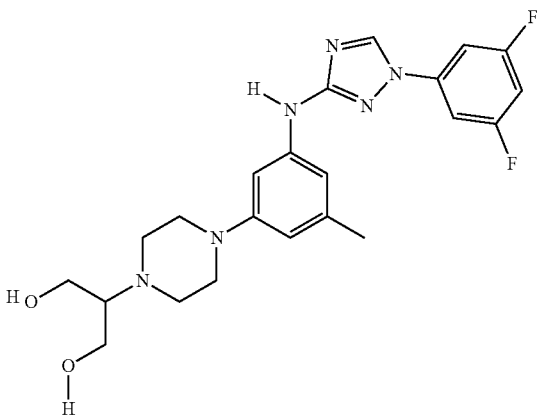
79
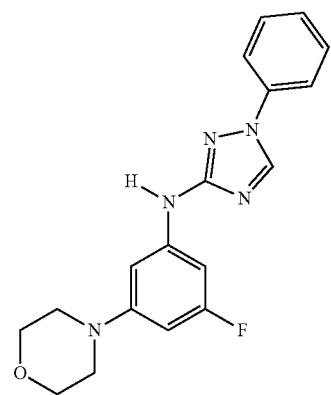 [SMILES: Fc1cc(Nc2ncn(-c3ccccc3)n2)cc(N2CCOCC2)c1]
80
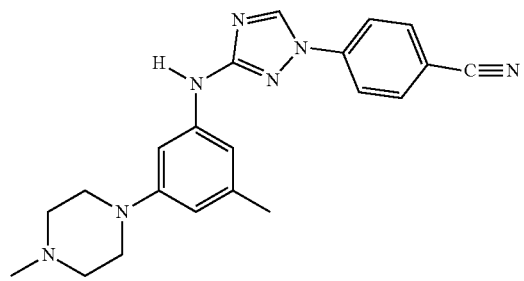 [SMILES: Cc1cc(Nc2ncn(-c3ccc(C#N)cc3)n2)cc(N2CCN(C)CC2)c1]
81
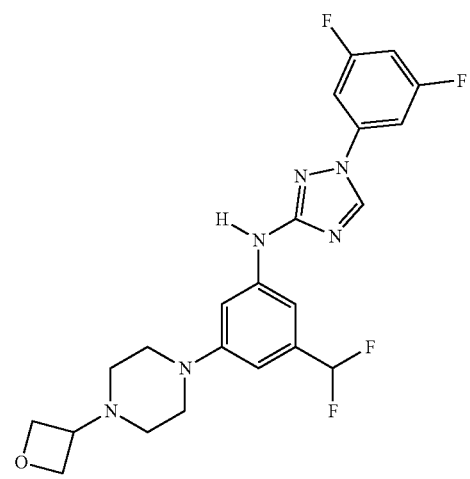 [SMILES: Fc1cc(F)cc(-n2cnc(Nc3cc(C(F)F)cc(N4CCN(C5COC5)CC4)c3)n2)c1]
82

TABLE 1-continued
Compound Table
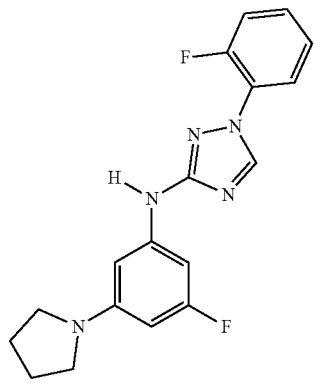 [SMILES: Fc1cc(Nc2ncn(-c3ccccc3F)n2)cc(N2CCCC2)c1]
83
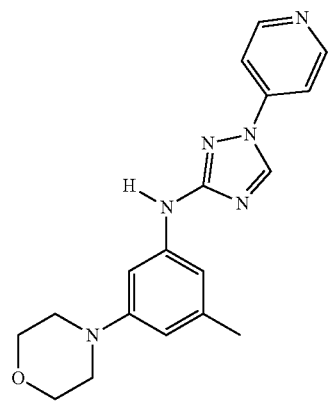 [SMILES: Cc1cc(Nc2ncn(-c3ccncc3)n2)cc(N2CCOCC2)c1]
84
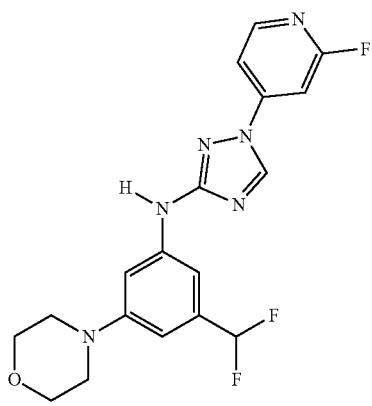 [SMILES: Fc1cc(-n2cnc(Nc3cc(C(F)F)cc(N4CCOCC4)c3)n2)ccn1]
85
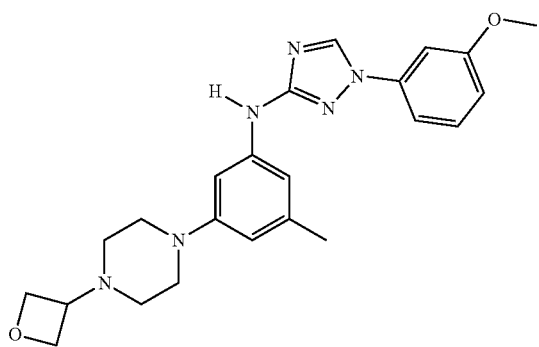 [SMILES: COc1cccc(-n2cnc(Nc3cc(C)cc(N4CCN(C5COC5)CC4)c3)n2)c1]
86

TABLE 1-continued
Compound Table
| | |
|---|---|
| 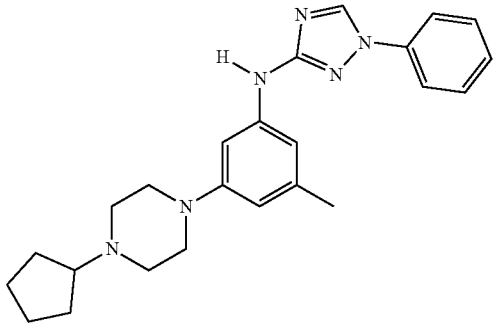 [SMILES: Cc1cc(Nc2ncn(-c3ccccc3)n2)cc(N2CCN(C3CCCC3)CC2)c1] | 87 |
| 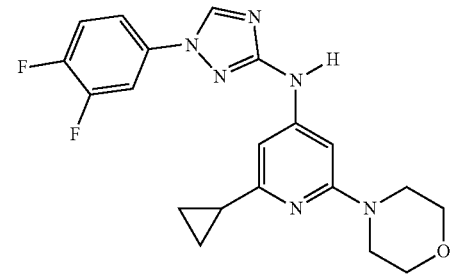 | 88 |
| 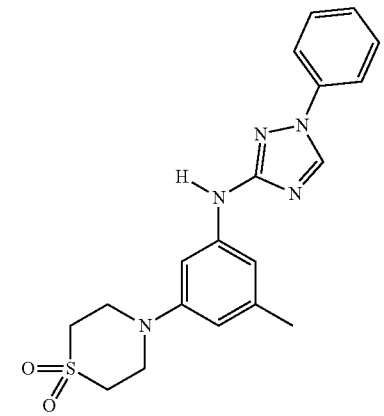 [SMILES: Cc1cc(Nc2ncn(-c3ccccc3)n2)cc(N2CCS(=O)(=O)CC2)c1] | 89 |
| 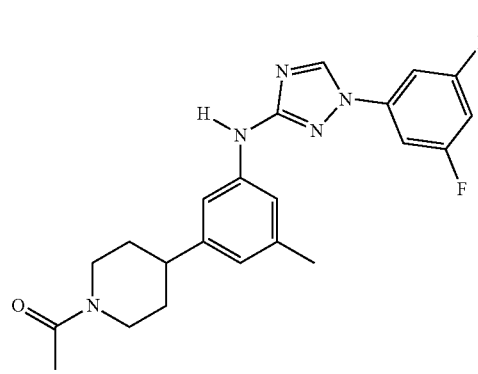 | 90 |

TABLE 1-continued
Compound Table
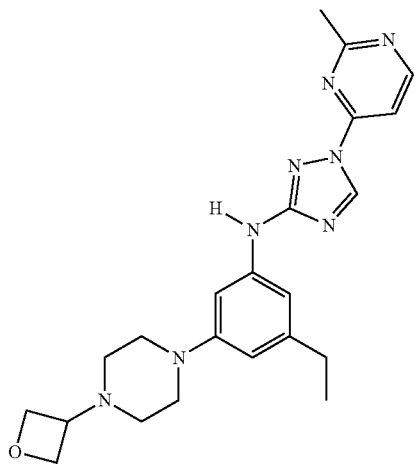 [SMILES: CCc1cc(Nc2ncn(-c3ccnc(C)n3)n2)cc(N2CCN(C3COC3)CC2)c1]
91
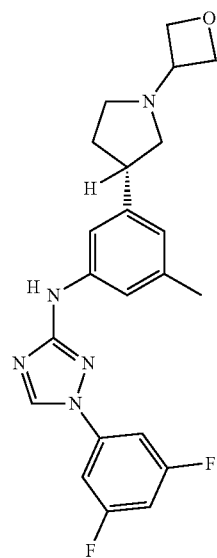
92
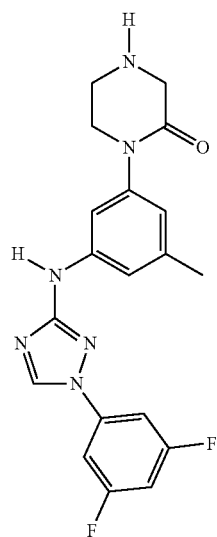 [SMILES: Cc1cc(Nc2ncn(-c3cc(F)cc(F)c3)n2)cc(N2CCNCC2=O)c1]
93

TABLE 1-continued
Compound Table
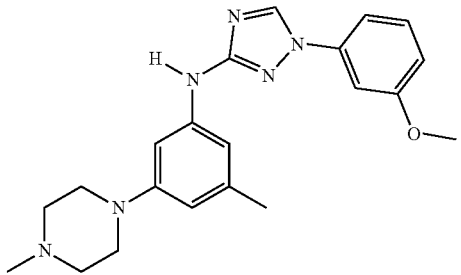
94
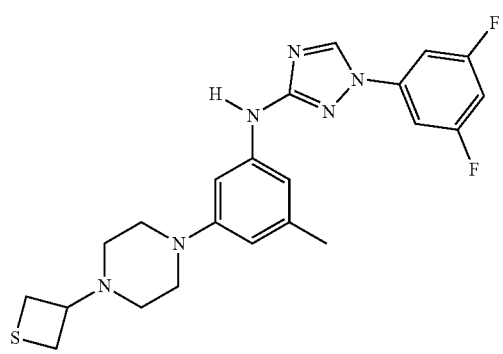 [SMILES: Cc1cc(Nc2ncn(-c3cc(F)cc(F)c3)n2)cc(N2CCN(C3CSC3)CC2)c1]
95
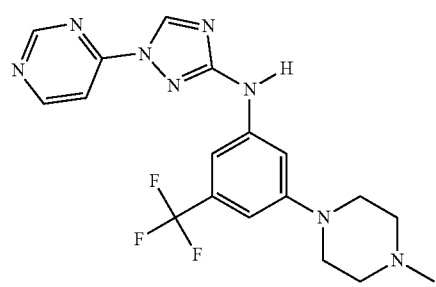 [SMILES: CN1CCN(c2cc(Nc3ncn(-c4ccncn4)n3)cc(C(F)(F)F)c2)CC1]
96
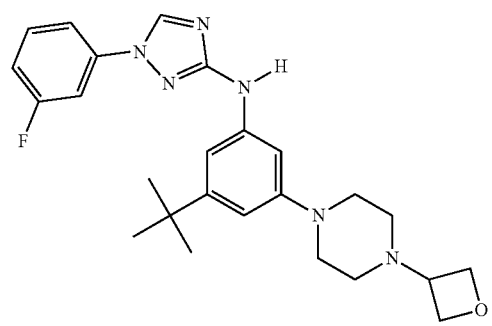 [SMILES: CC(C)(C)c1cc(Nc2ncn(-c3cccc(F)c3)n2)cc(N2CCN(C3COC3)CC2)c1]
97

TABLE 1-continued
Compound Table
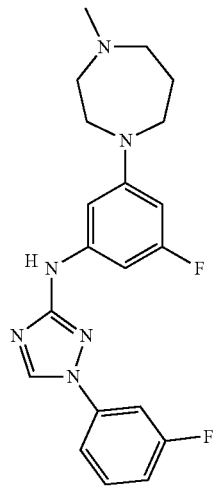
98
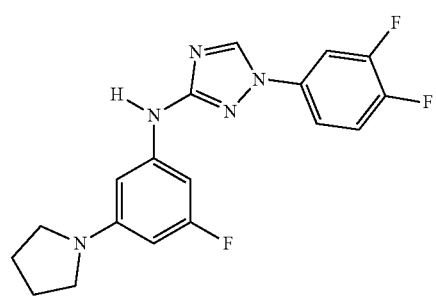 [SMILES: Fc1cc(Nc2ncn(-c3ccc(F)c(F)c3)n2)cc(N2CCCC2)c1]
99
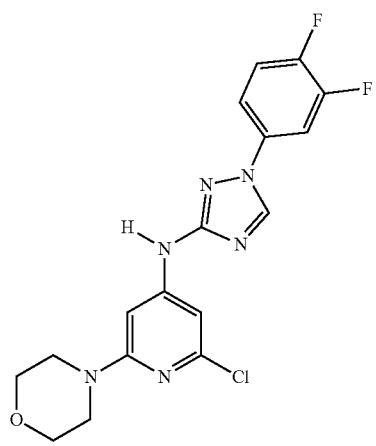
100

TABLE 1-continued
Compound Table
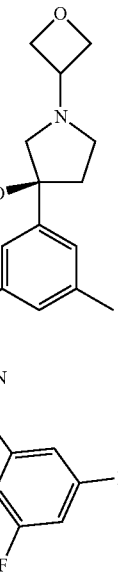
101
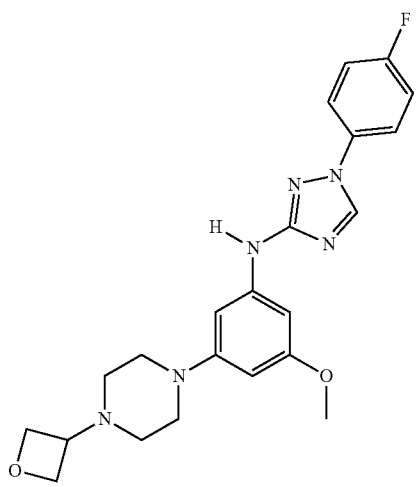 [SMILES: COc1cc(Nc2ncn(-c3ccc(F)cc3)n2)cc(N2CCN(C3COC3)CC2)c1]
102
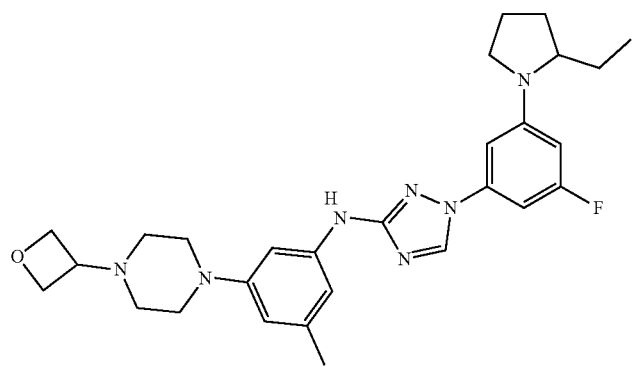
103

TABLE 1-continued
Compound Table
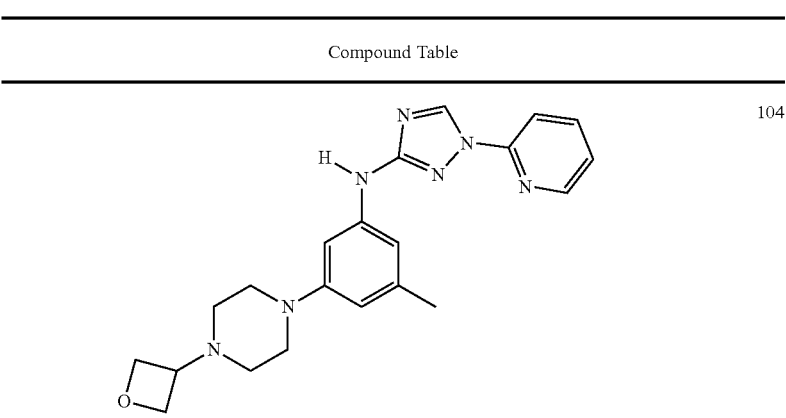
104
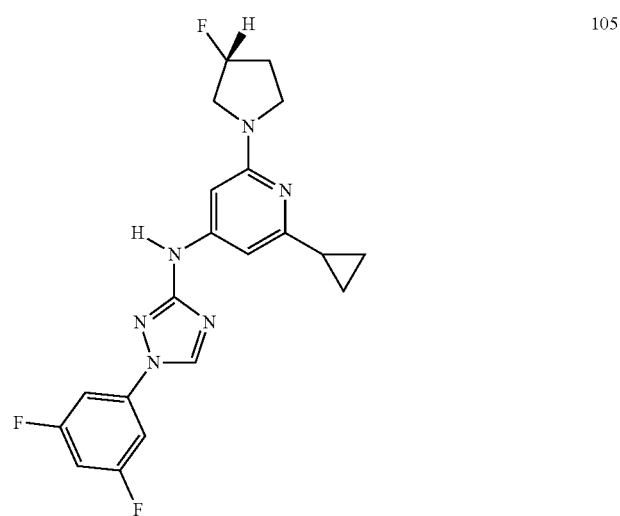
105
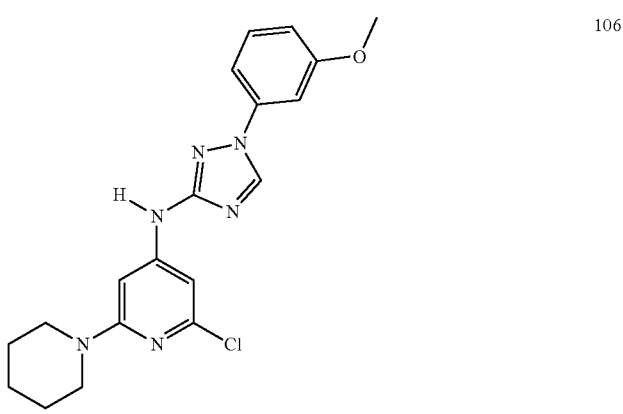
106

TABLE 1-continued
Compound Table
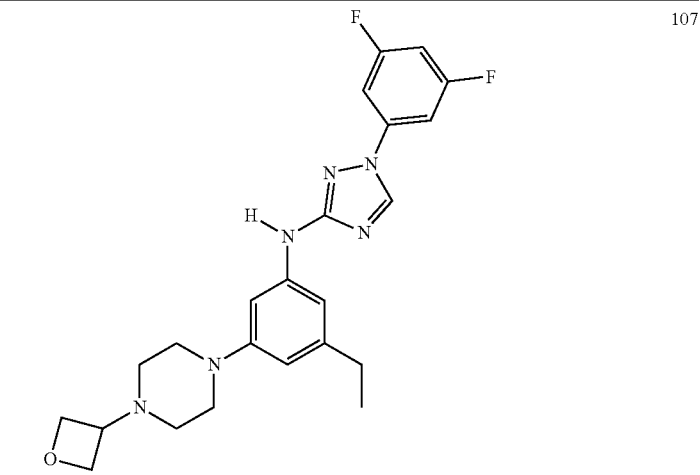
107
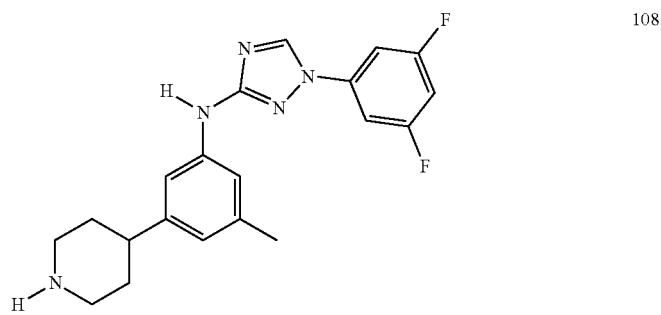
108
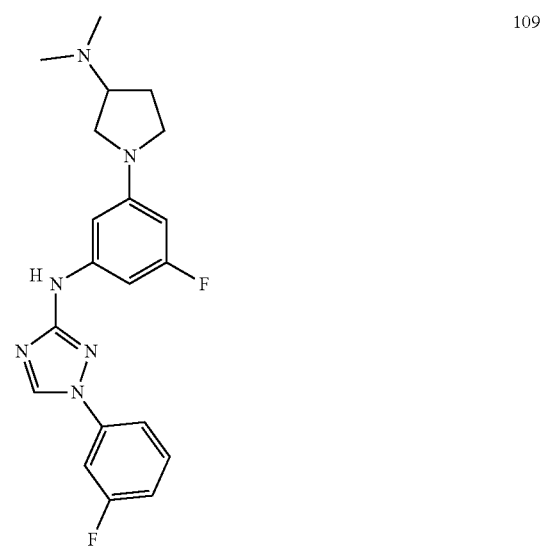
109
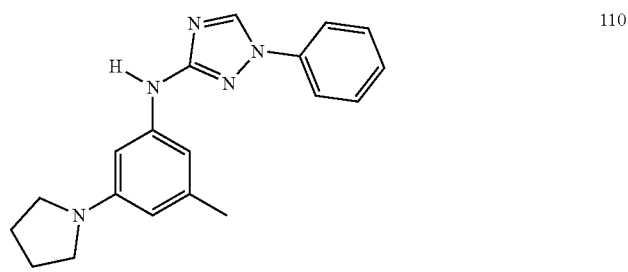
110

TABLE 1-continued
Compound Table
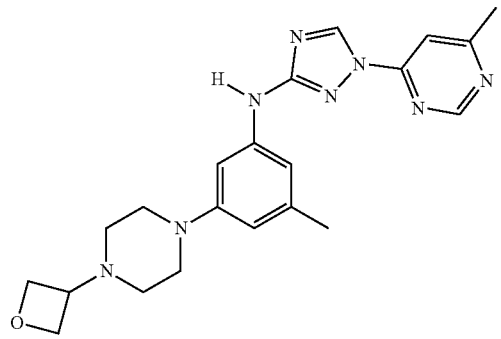 [SMILES: Cc1cc(Nc2ncn(-c3cc(C)ncn3)n2)cc(N2CCN(C3COC3)CC2)c1]
111
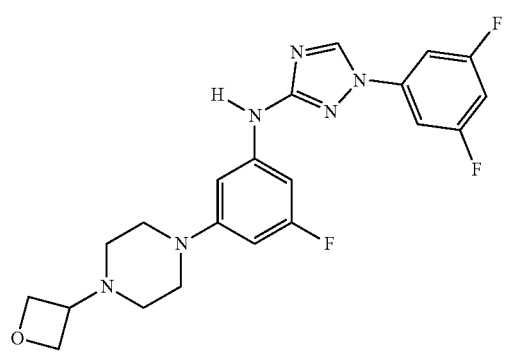
112
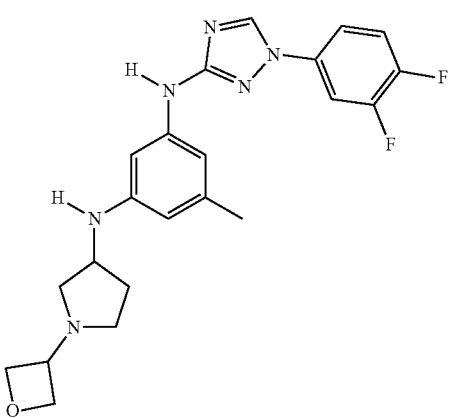 [SMILES: Cc1cc(Nc2ncn(-c3ccc(F)c(F)c3)n2)cc(NC2CCN(C3COC3)C2)c1]
113

TABLE 1-continued
Compound Table
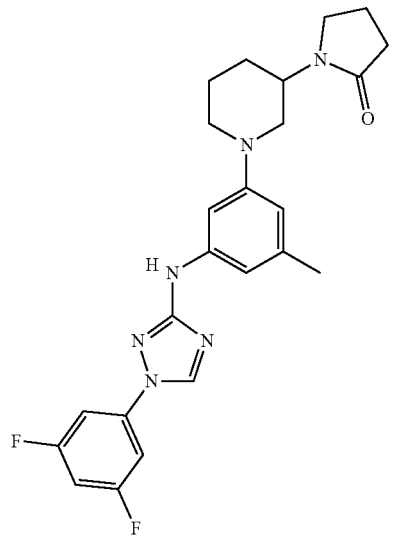
114
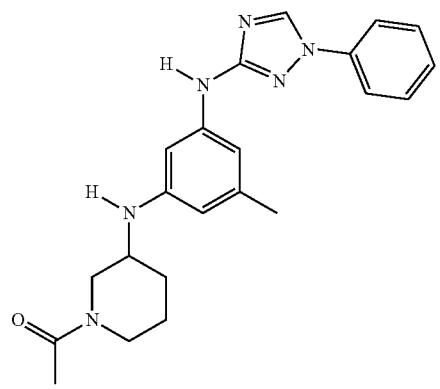 [SMILES: CC(=O)N1CCCC(Nc2cc(C)cc(Nc3ncn(-c4ccccc4)n3)c2)C1]
115
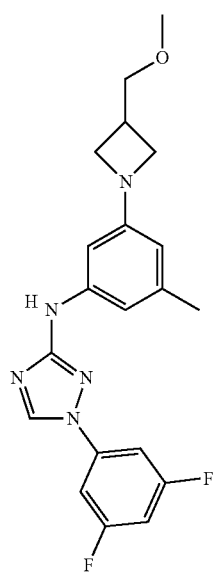
116

TABLE 1-continued
Compound Table
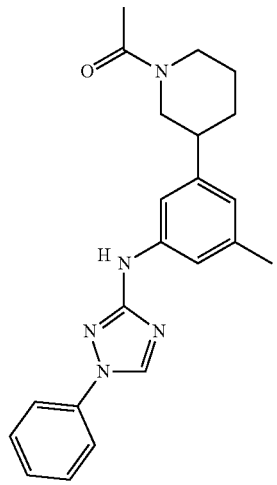
117
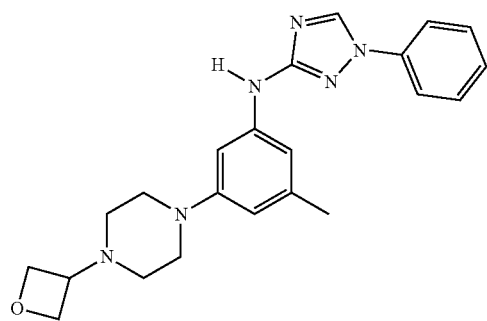 [SMILES: Cc1cc(Nc2ncn(-c3ccccc3)n2)cc(N2CCN(C3COC3)CC2)c1]
118
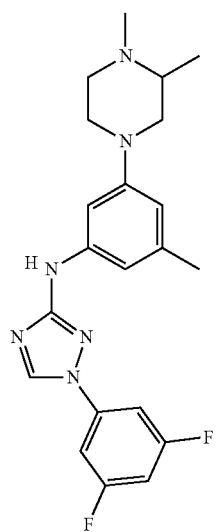
119

TABLE 1-continued
Compound Table
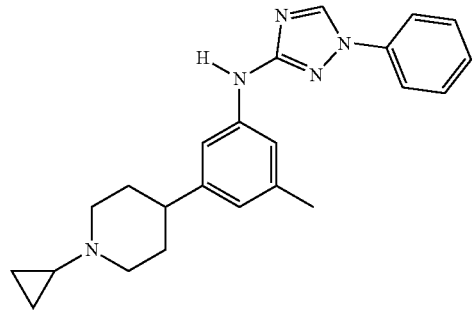 [SMILES: Cc1cc(Nc2ncn(-c3ccccc3)n2)cc(C2CCN(C3CC3)CC2)c1]
120
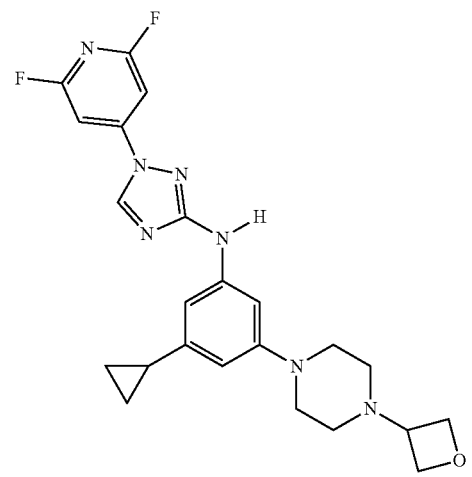
121
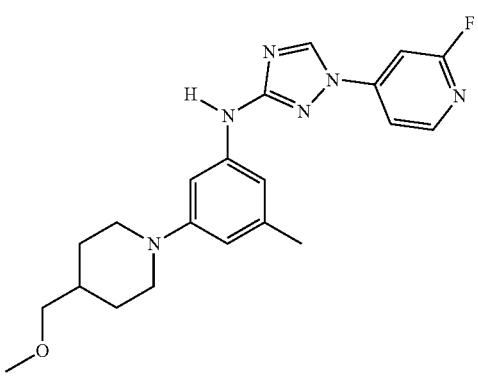 [SMILES: COCC1CCN(c2cc(C)cc(Nc3ncn(-c4ccnc(F)c4)n3)c2)CC1]
122

TABLE 1-continued
Compound Table
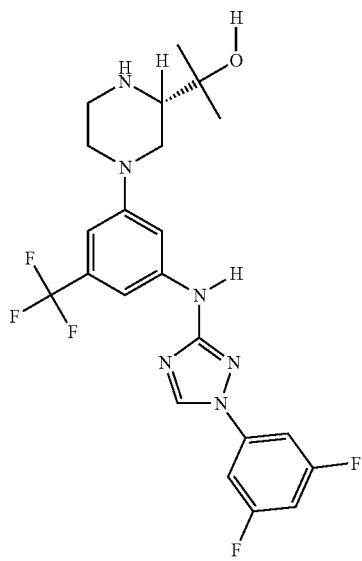 [SMILES: CC(C)(O)[C@@H]1CN(c2cc(Nc3ncn(-c4cc(F)cc(F)c4)n3)cc(C(F)(F)F)c2)CCN1]
123
124
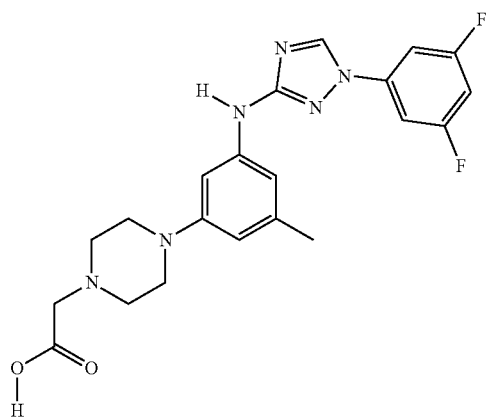 [SMILES: Cc1cc(Nc2ncn(-c3cc(F)cc(F)c3)n2)cc(N2CCN(CC(=O)O)CC2)c1]
125

TABLE 1-continued
Compound Table
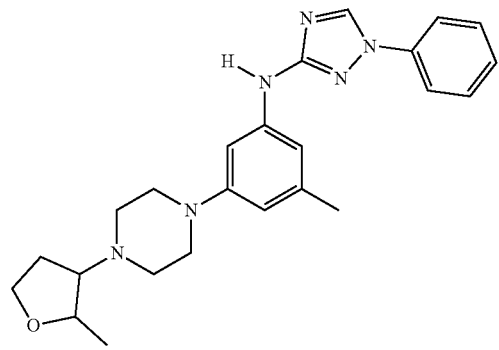 [SMILES: Cc1cc(Nc2ncn(-c3ccccc3)n2)cc(N2CCN(C3CCOC3C)CC2)c1]
127
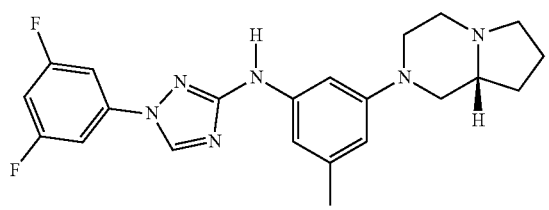 [SMILES: Cc1cc(Nc2ncn(-c3cc(F)cc(F)c3)n2)cc(N2CCN3CCC[C@@H]3C2)c1]
128
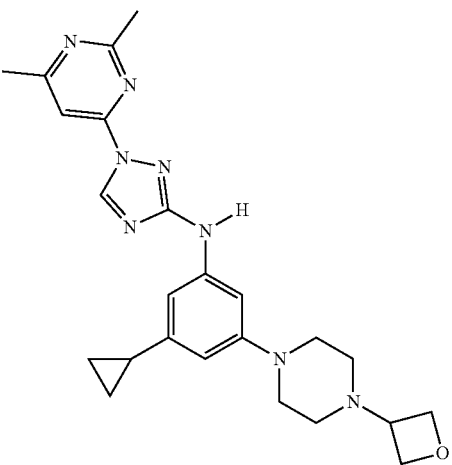 [SMILES: Cc1cc(-n2cnc(Nc3cc(C4CC4)cc(N4CCN(C5COC5)CC4)c3)n2)nc(C)n1]
129
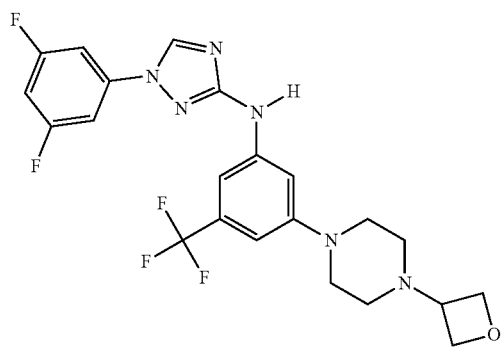
130

TABLE 1-continued
Compound Table
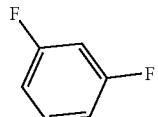
131
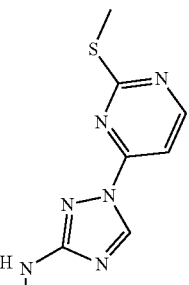
132
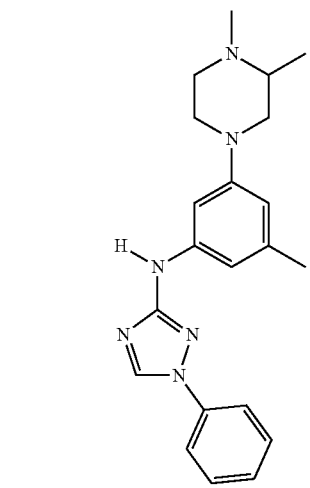 [SMILES: Cc1cc(Nc2ncn(-c3ccccc3)n2)cc(N2CCN(C)C(C)C2)c1]
133

TABLE 1-continued
Compound Table
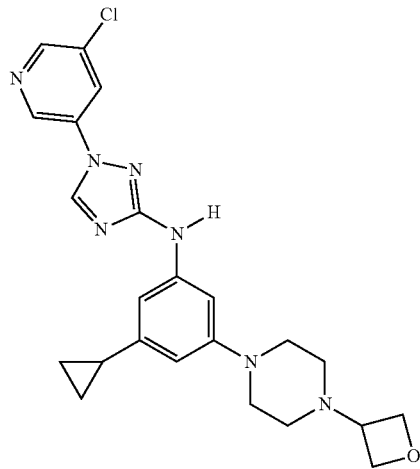 [SMILES: Clc1cncc(-n2cnc(Nc3cc(C4CC4)cc(N4CCN(C5COC5)CC4)c3)n2)c1]
134
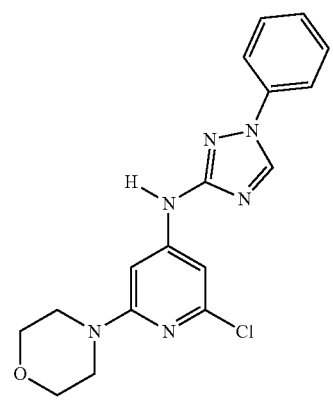 [SMILES: Clc1cc(Nc2ncn(-c3ccccc3)n2)cc(N2CCOCC2)n1]
135
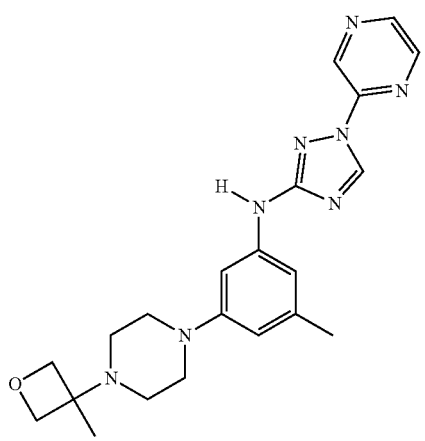 [SMILES: Cc1cc(Nc2ncn(-c3cnccn3)n2)cc(N2CCN(C3(C)COC3)CC2)c1]
136

TABLE 1-continued
Compound Table
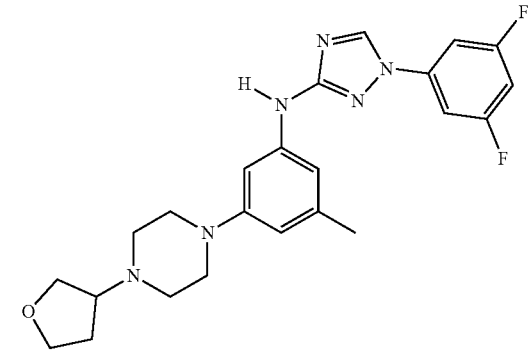 [SMILES: Cc1cc(Nc2ncn(-c3cc(F)cc(F)c3)n2)cc(N2CCN(C3CCOC3)CC2)c1]
137
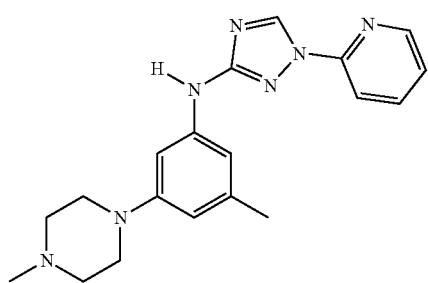 [SMILES: Cc1cc(Nc2ncn(-c3ccccn3)n2)cc(N2CCN(C)CC2)c1]
138
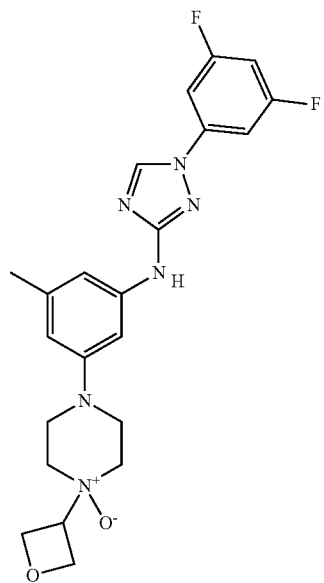
139
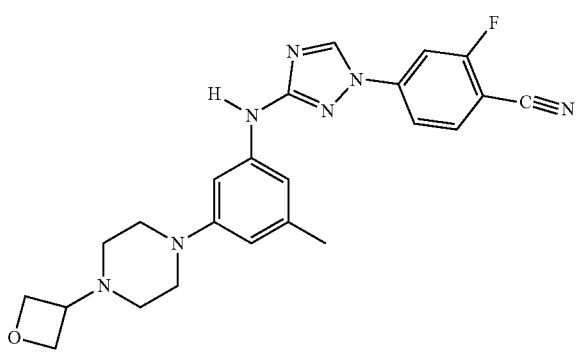 [SMILES: Cc1cc(Nc2ncn(-c3ccc(C#N)c(F)c3)n2)cc(N2CCN(C3COC3)CC2)c1]
140

TABLE 1-continued
Compound Table
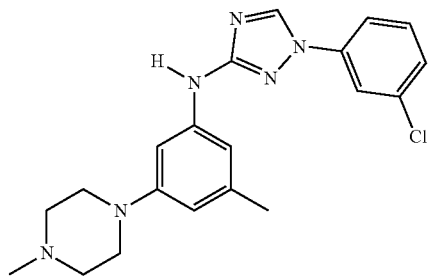 [SMILES: Cc1cc(Nc2ncn(-c3cccc(Cl)c3)n2)cc(N2CCN(C)CC2)c1]
141
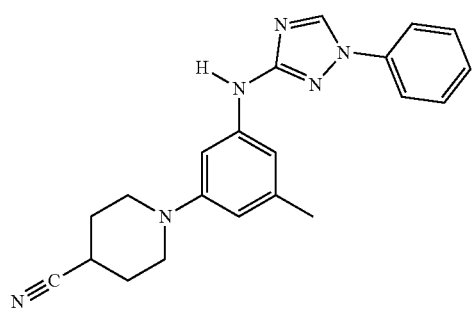 [SMILES: Cc1cc(Nc2ncn(-c3ccccc3)n2)cc(N2CCC(C#N)CC2)c1]
142
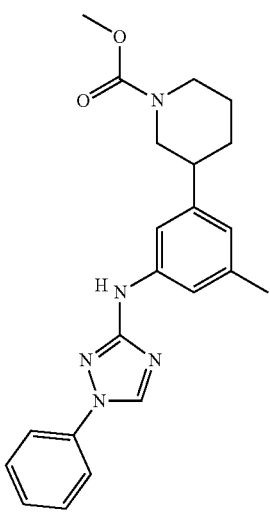
143
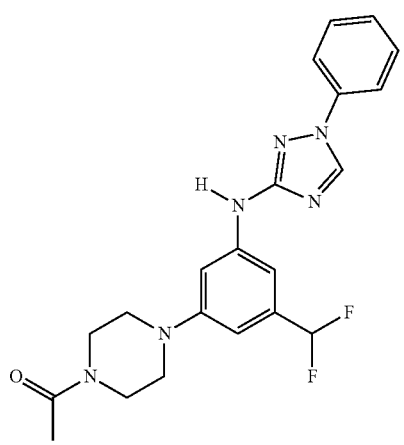 [SMILES: CC(=O)N1CCN(c2cc(Nc3ncn(-c4ccccc4)n3)cc(C(F)F)c2)CC1]
144

TABLE 1-continued
Compound Table
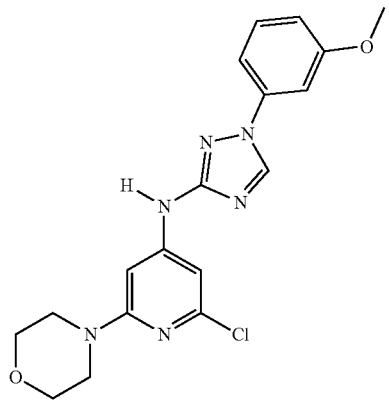 [SMILES: COc1cccc(-n2cnc(Nc3cc(Cl)nc(N4CCOCC4)c3)n2)c1]
145
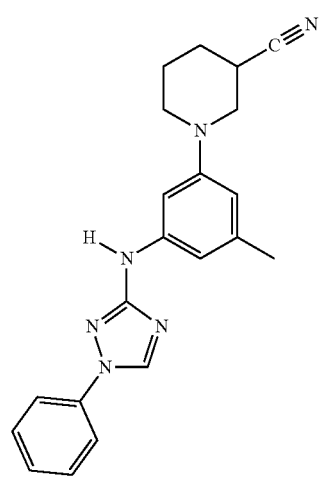 [SMILES: Cc1cc(Nc2ncn(-c3ccccc3)n2)cc(N2CCCC(C#N)C2)c1]
146
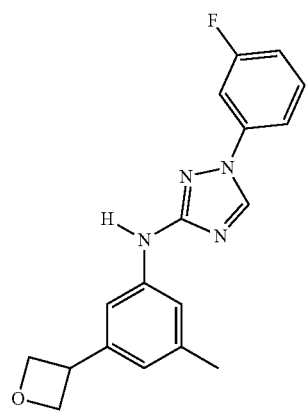 [SMILES: Cc1cc(Nc2ncn(-c3cccc(F)c3)n2)cc(C2COC2)c1]
147

TABLE 1-continued
Compound Table
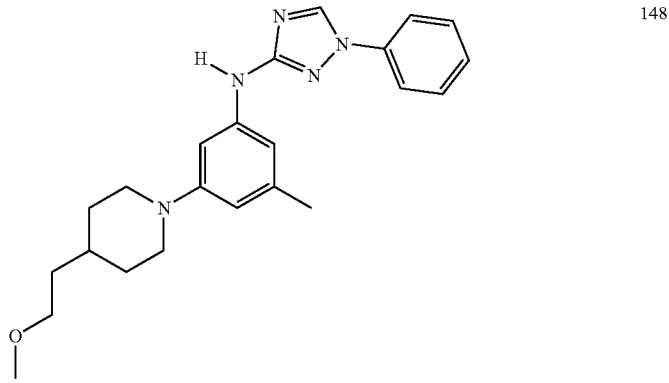
148
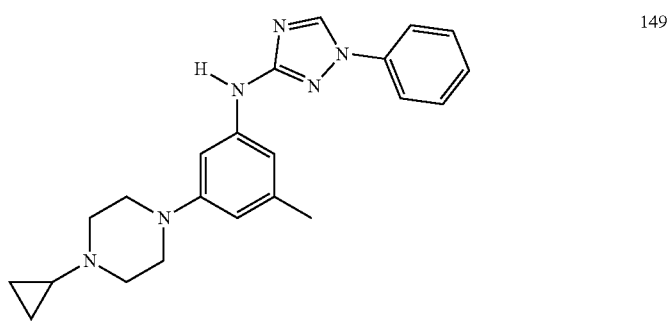
149
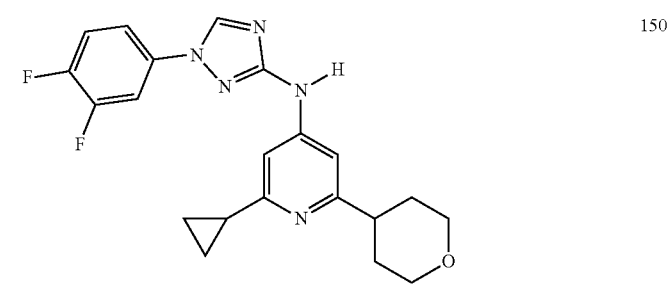
150
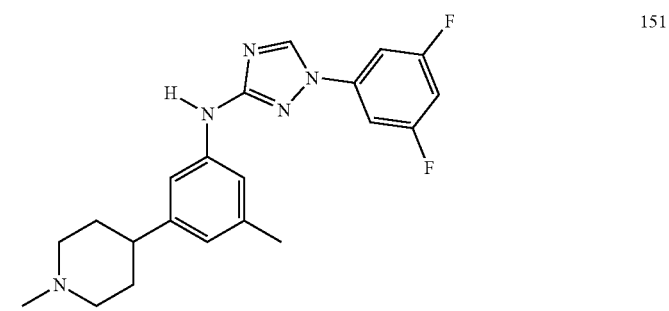
151

TABLE 1-continued
Compound Table
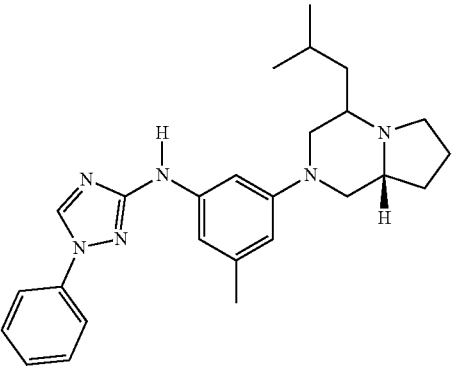 [SMILES: Cc1cc(Nc2ncn(-c3ccccc3)n2)cc(N2CC(CC(C)C)N3CCC[C@@H]3C2)c1]
152
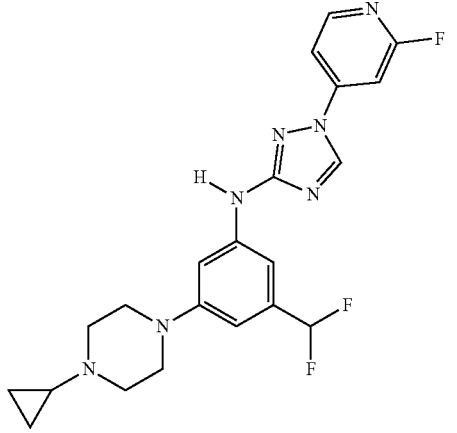 [SMILES: Fc1cc(-n2cnc(Nc3cc(C(F)F)cc(N4CCN(C5CC5)CC4)c3)n2)ccn1]
153
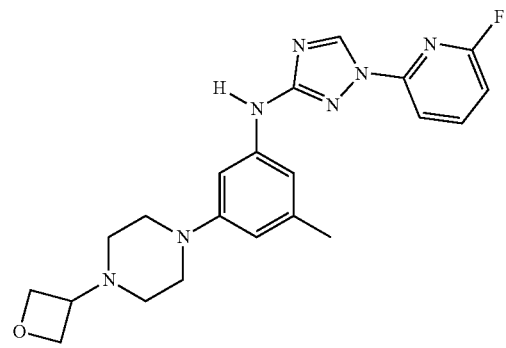
154
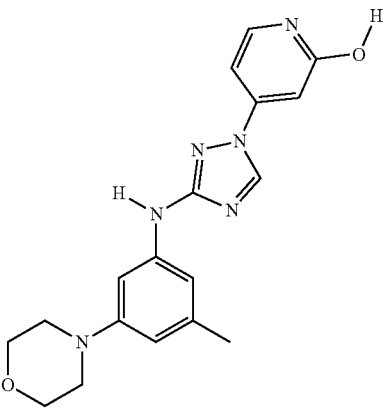 [SMILES: Cc1cc(Nc2ncn(-c3ccnc(O)c3)n2)cc(N2CCOCC2)c1]
155

TABLE 1-continued
Compound Table
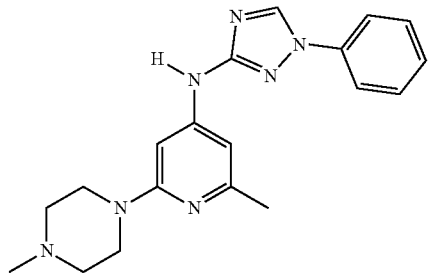 [SMILES: Cc1cc(Nc2ncn(-c3ccccc3)n2)cc(N2CCN(C)CC2)n1]
156
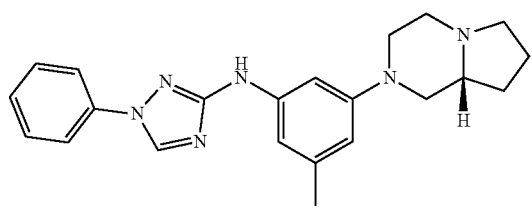 [SMILES: Cc1cc(Nc2ncn(-c3ccccc3)n2)cc(N2CCN3CCC[C@@H]3C2)c1]
157
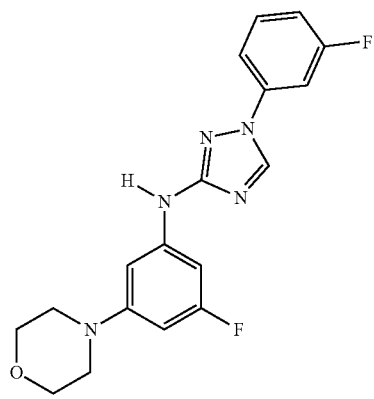 [SMILES: Fc1cc(Nc2ncn(-c3cccc(F)c3)n2)cc(N2CCOCC2)c1]
158
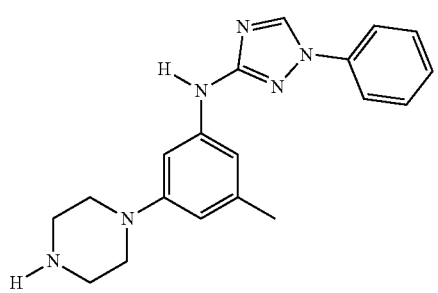
159

TABLE 1-continued
Compound Table
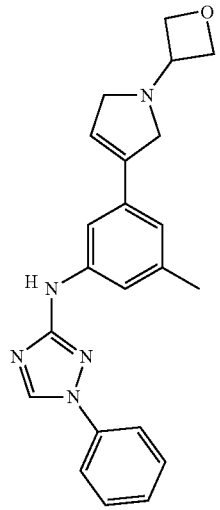
160
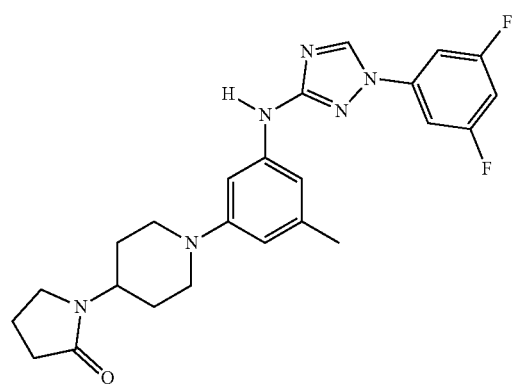 [SMILES: Cc1cc(Nc2ncn(-c3cc(F)cc(F)c3)n2)cc(N2CCC(N3CCCC3=O)CC2)c1]
161
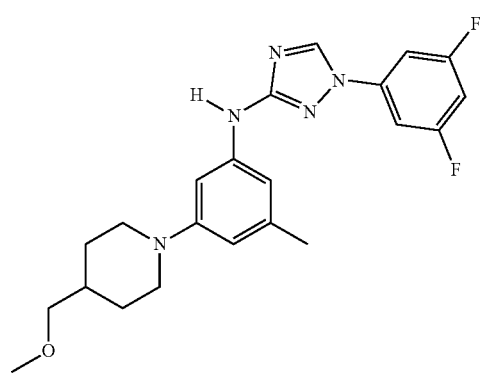 [SMILES: COCC1CCN(c2cc(C)cc(Nc3ncn(-c4cc(F)cc(F)c4)n3)c2)CC1]
162

TABLE 1-continued
Compound Table
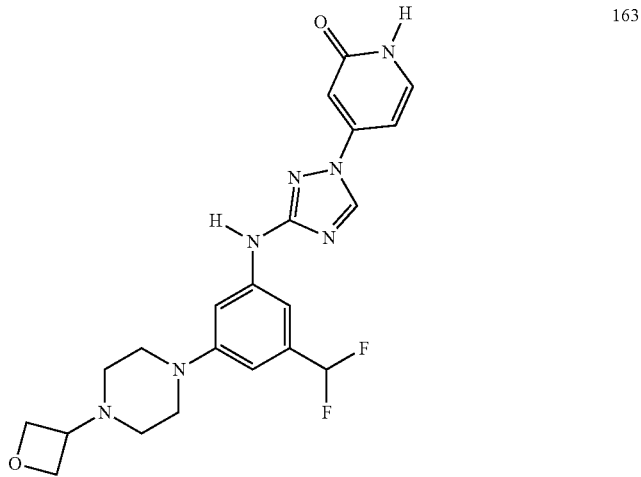
163
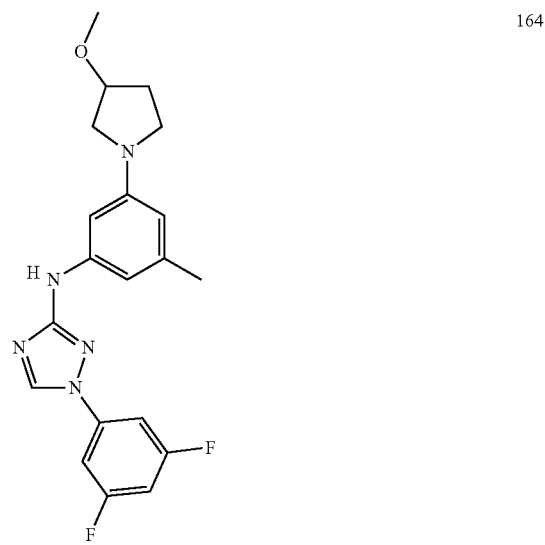
164
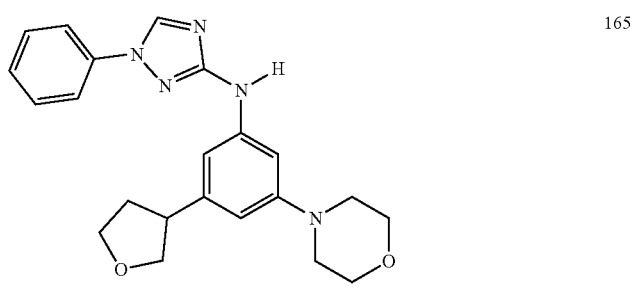
165

TABLE 1-continued
Compound Table
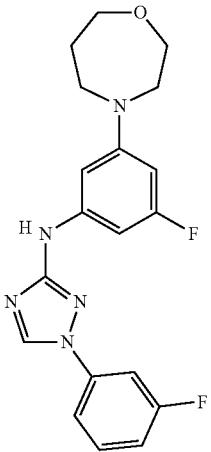
166
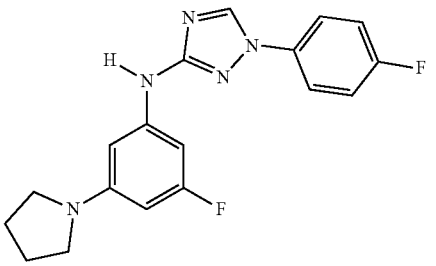 [SMILES: Fc1ccc(-n2cnc(Nc3cc(F)cc(N4CCCC4)c3)n2)cc1]
167
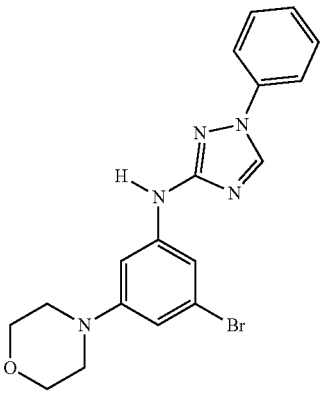 [SMILES: Brc1cc(Nc2ncn(-c3ccccc3)n2)cc(N2CCOCC2)c1]
168
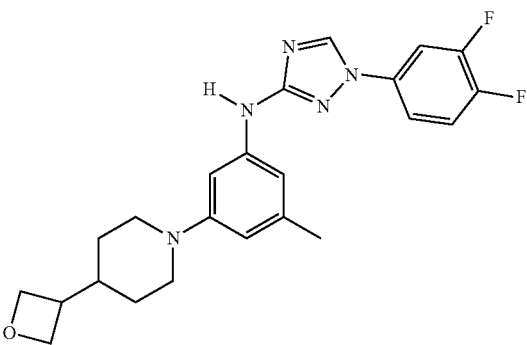 [SMILES: Cc1cc(Nc2ncn(-c3ccc(F)c(F)c3)n2)cc(N2CCC(C3COC3)CC2)c1]
169

TABLE 1-continued
Compound Table
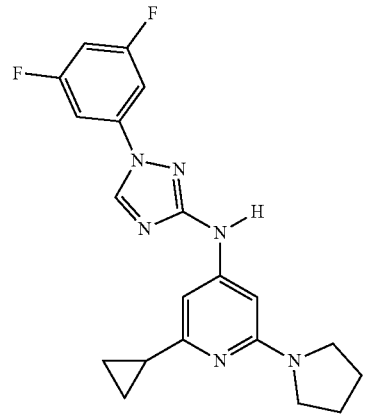 [SMILES: Fc1cc(F)cc(-n2cnc(Nc3cc(C4CC4)nc(N4CCCC4)c3)n2)c1]
170
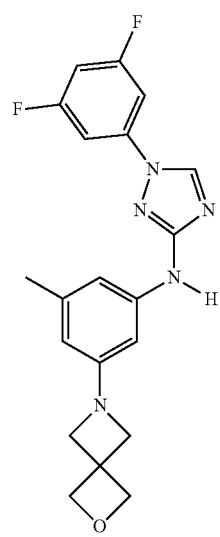 [SMILES: Cc1cc(Nc2ncn(-c3cc(F)cc(F)c3)n2)cc(N2CC3(COC3)C2)c1]
171
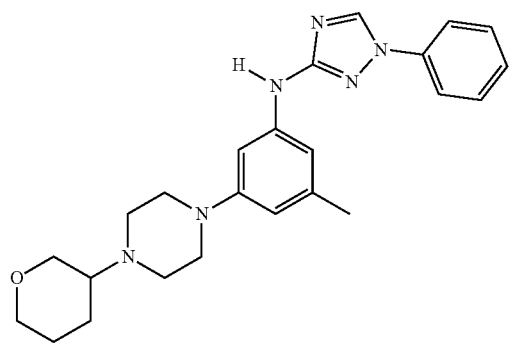 [SMILES: Cc1cc(Nc2ncn(-c3ccccc3)n2)cc(N2CCN(C3CCCOC3)CC2)c1]
172

TABLE 1-continued
Compound Table
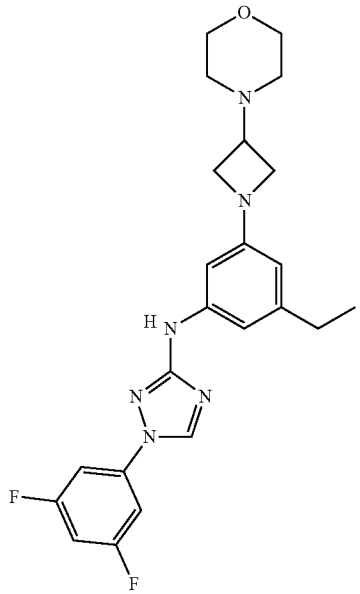
173
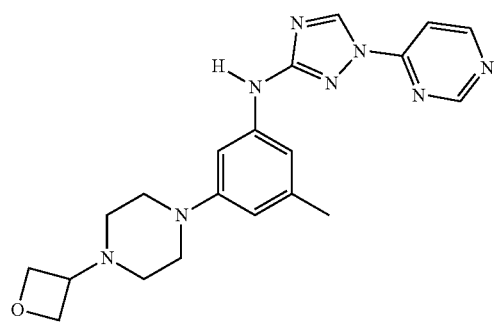 [SMILES: Cc1cc(Nc2ncn(-c3ccncn3)n2)cc(N2CCN(C3COC3)CC2)c1]
174
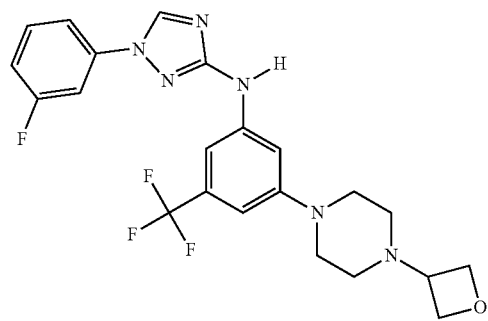 [SMILES: Fc1cccc(-n2cnc(Nc3cc(N4CCN(C5COC5)CC4)cc(C(F)(F)F)c3)n2)c1]
175
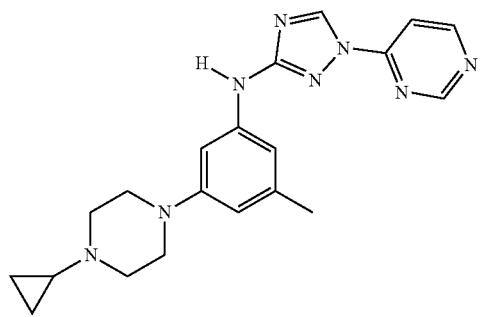 [SMILES: Cc1cc(Nc2ncn(-c3ccncn3)n2)cc(N2CCN(C3CC3)CC2)c1]
176

TABLE 1-continued
Compound Table
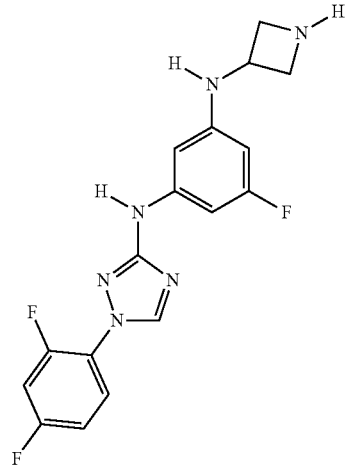 [SMILES: Fc1cc(Nc2ncn(-c3ccc(F)cc3F)n2)cc(NC2CNC2)c1] 177
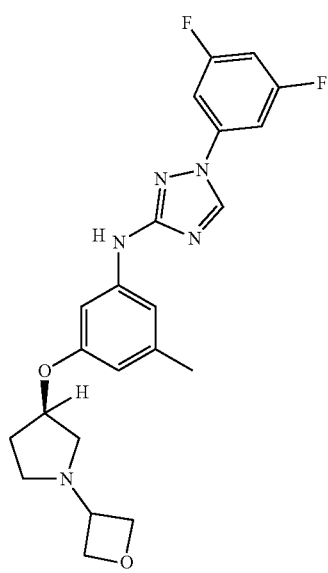 178
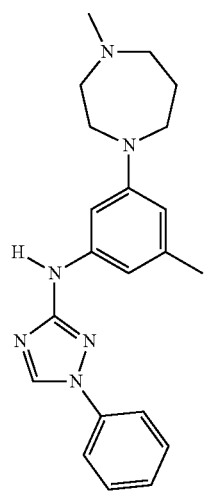 [SMILES: Cc1cc(Nc2ncn(-c3ccccc3)n2)cc(N2CCCN(C)CC2)c1] 179

TABLE 1-continued
Compound Table
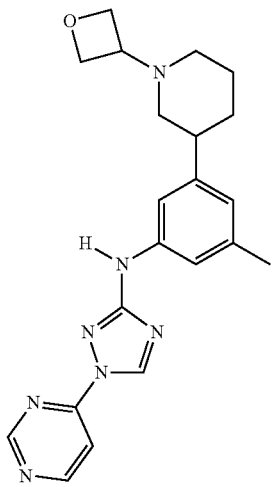 [SMILES: Cc1cc(Nc2ncn(-c3ccncn3)n2)cc(C2CCCN(C3COC3)C2)c1]
180
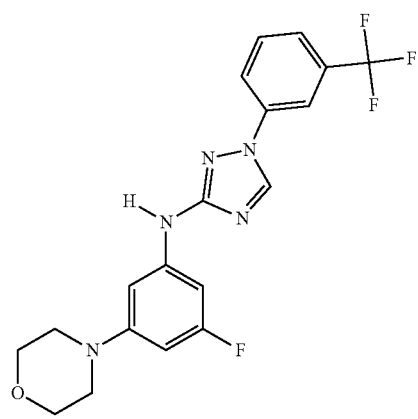 [SMILES: Fc1cc(Nc2ncn(-c3cccc(C(F)(F)F)c3)n2)cc(N2CCOCC2)c1]
181
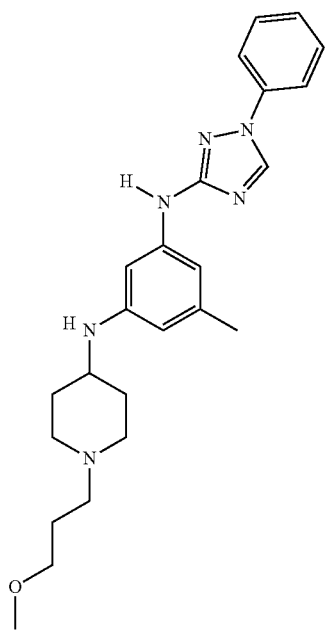
182

TABLE 1-continued
Compound Table
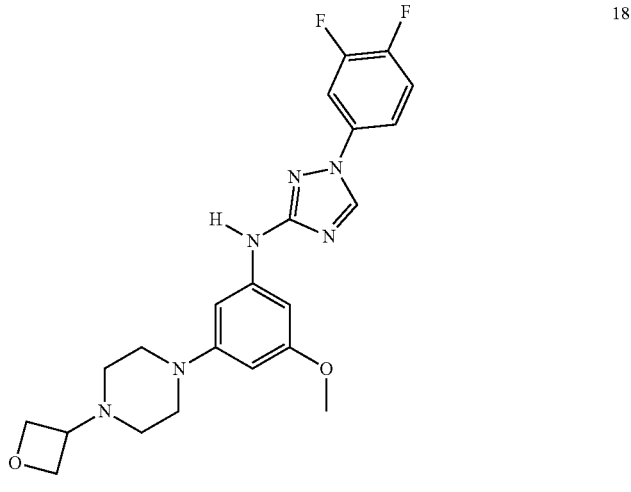
183
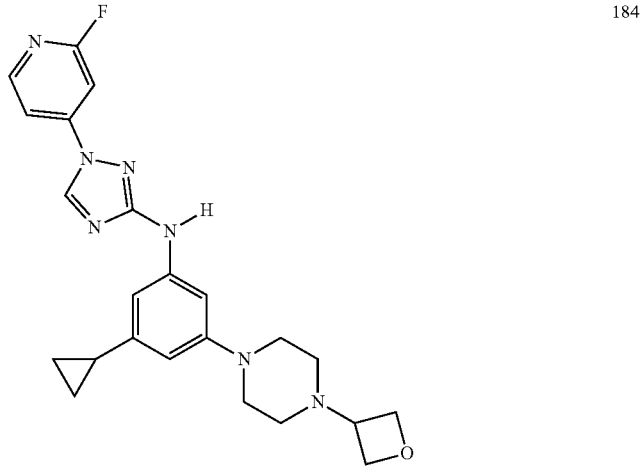
184
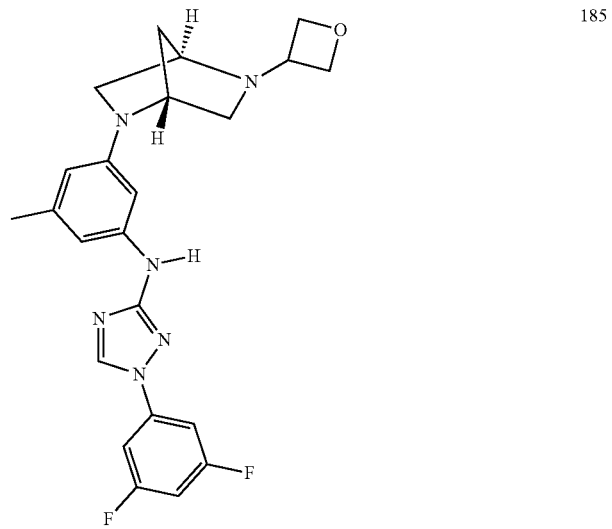
185

TABLE 1-continued
Compound Table
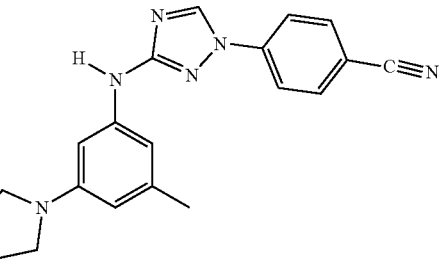 186
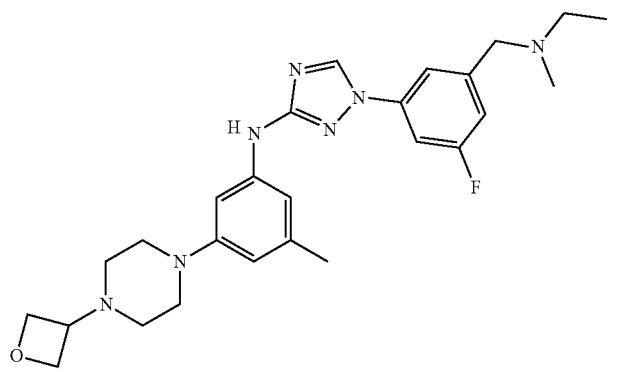 187
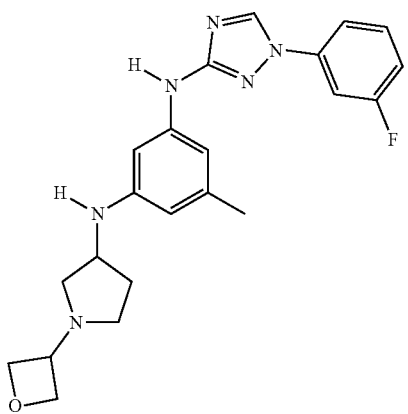 [SMILES: Cc1cc(Nc2ncn(-c3cccc(F)c3)n2)cc(NC2CCN(C3COC3)C2)c1] 188
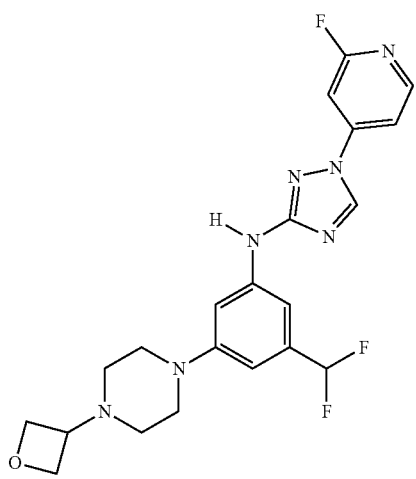 [SMILES: Fc1cc(-n2cnc(Nc3cc(C(F)F)cc(N4CCN(C5COC5)CC4)c3)n2)ccn1] 189

TABLE 1-continued
Compound Table
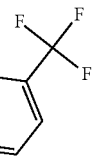
190
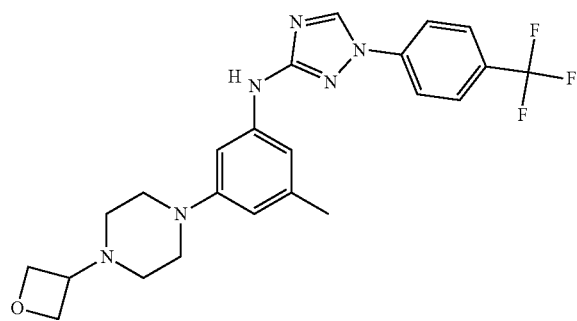
191
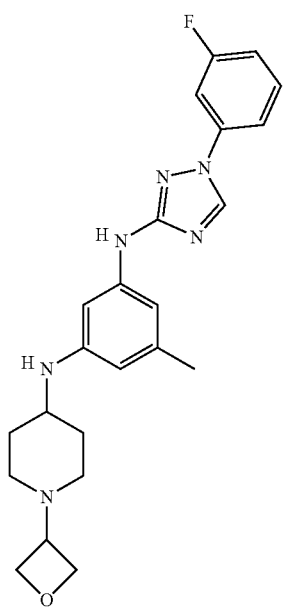
192

TABLE 1-continued
Compound Table
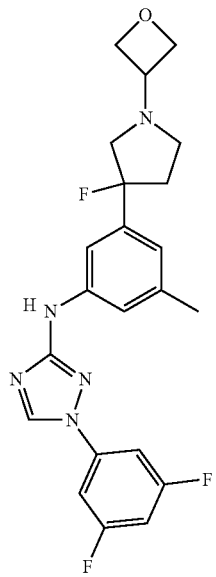
193
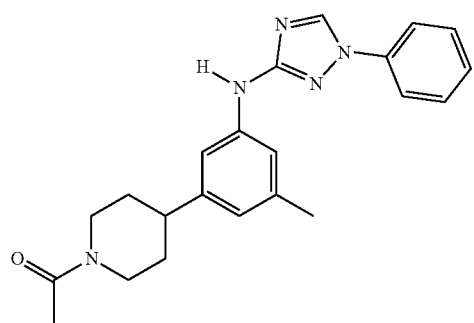 [SMILES: CC(=O)N1CCC(c2cc(C)cc(Nc3ncn(-c4ccccc4)n3)c2)CC1]
194
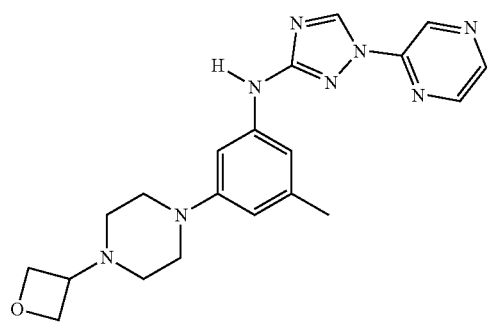 [SMILES: Cc1cc(Nc2ncn(-c3cnccn3)n2)cc(N2CCN(C3COC3)CC2)c1]
195

TABLE 1-continued
Compound Table
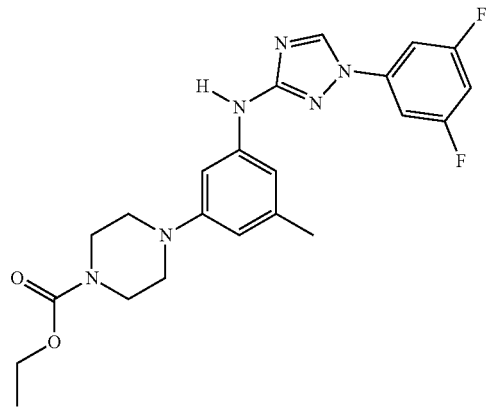 [SMILES: CCOC(=O)N1CCN(c2cc(C)cc(Nc3ncn(-c4cc(F)cc(F)c4)n3)c2)CC1]
196
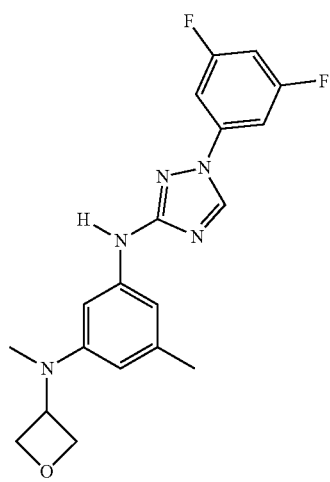 [SMILES: Cc1cc(Nc2ncn(-c3cc(F)cc(F)c3)n2)cc(N(C)C2COC2)c1]
197
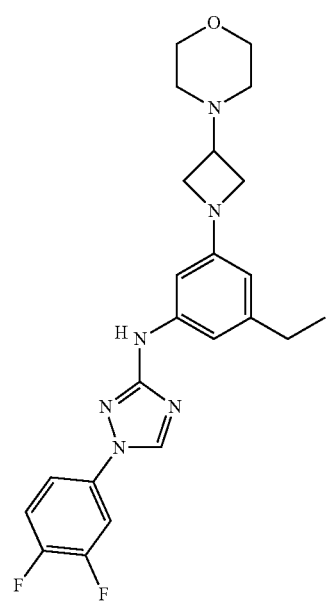
198

TABLE 1-continued
Compound Table
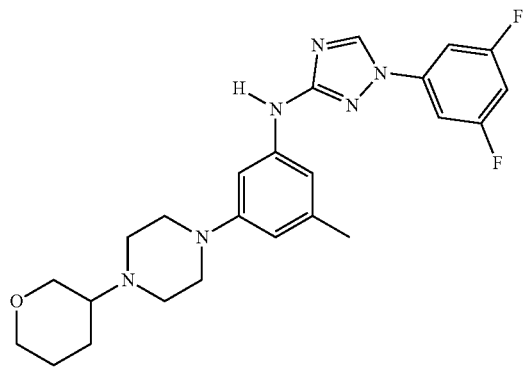 [SMILES: Cc1cc(Nc2ncn(-c3cc(F)cc(F)c3)n2)cc(N2CCN(C3CCCOC3)CC2)c1]
199
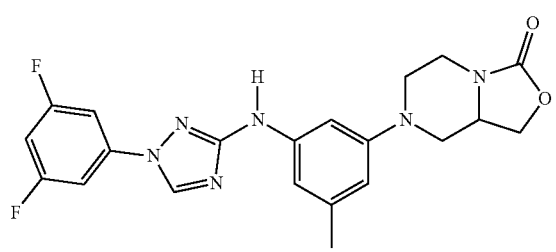 [SMILES: Cc1cc(Nc2ncn(-c3cc(F)cc(F)c3)n2)cc(N2CCN3C(=O)OCC3C2)c1]
200
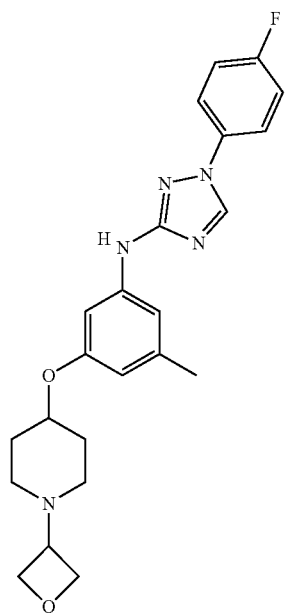
201

TABLE 1-continued
Compound Table
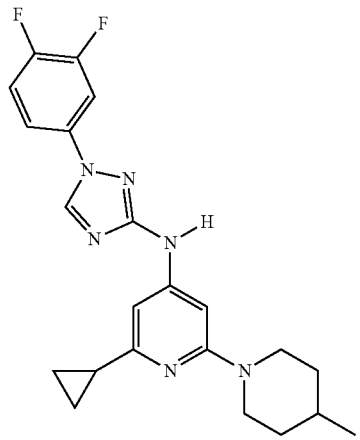 [SMILES: CC1CCN(c2cc(Nc3ncn(-c4ccc(F)c(F)c4)n3)cc(C3CC3)n2)CC1]
202
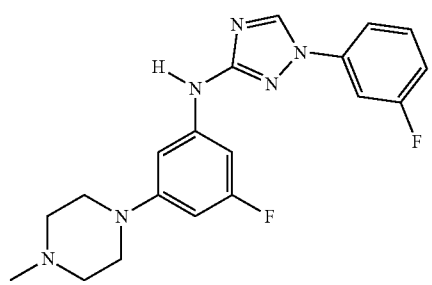 [SMILES: CN1CCN(c2cc(F)cc(Nc3ncn(-c4cccc(F)c4)n3)c2)CC1]
203
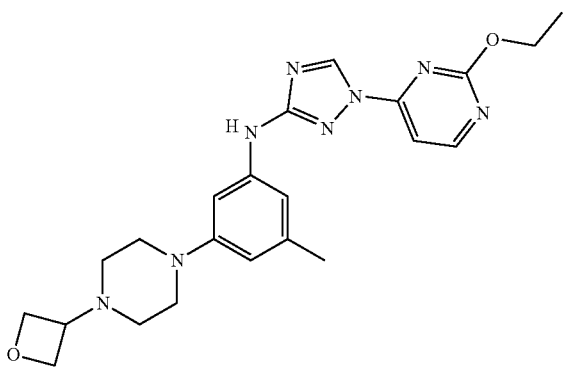
204
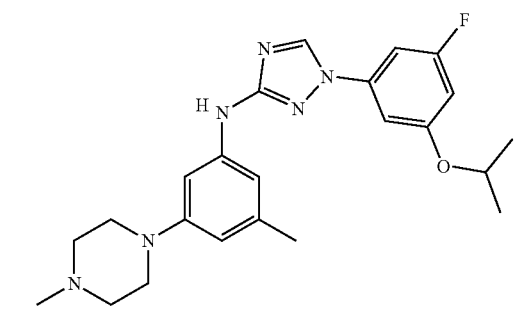
205

TABLE 1-continued
Compound Table
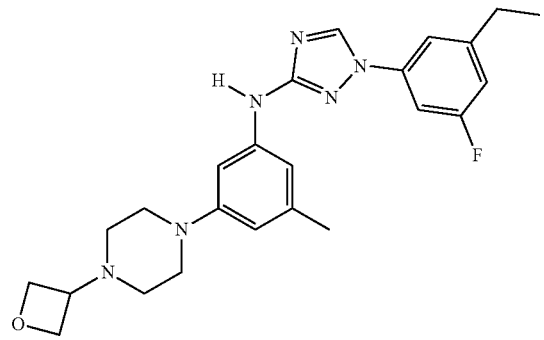 [SMILES: CCc1cc(F)cc(-n2cnc(Nc3cc(C)cc(N4CCN(C5COC5)CC4)c3)n2)c1]
206
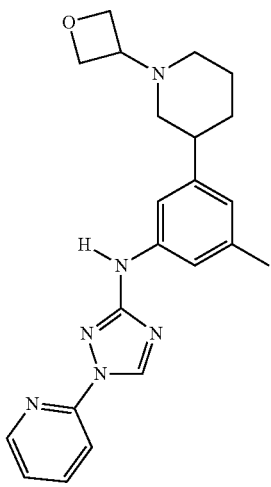 [SMILES: Cc1cc(Nc2ncn(-c3ccccn3)n2)cc(C2CCCN(C3COC3)C2)c1]
207
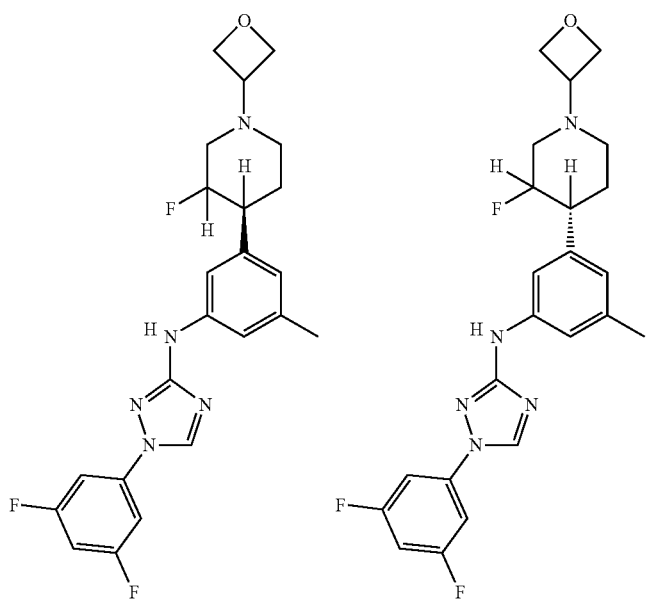
208

TABLE 1-continued
Compound Table
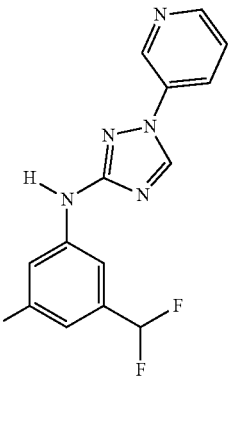
209
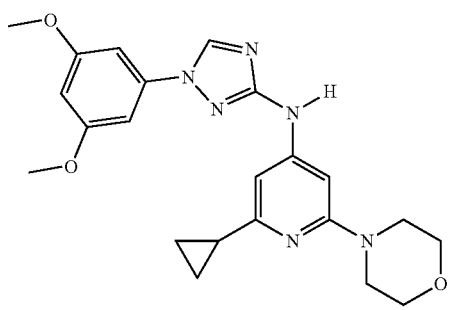 [SMILES: COc1cc(OC)cc(-n2cnc(Nc3cc(C4CC4)nc(N4CCOCC4)c3)n2)c1]
210
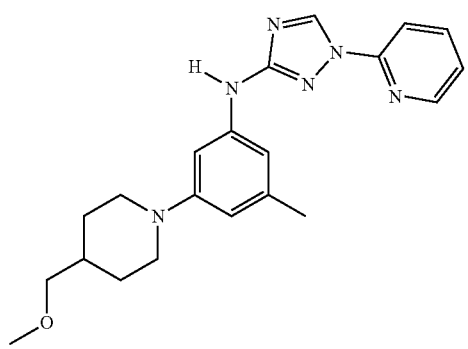 [SMILES: COCC1CCN(c2cc(C)cc(Nc3ncn(-c4ccccn4)n3)c2)CC1]
211
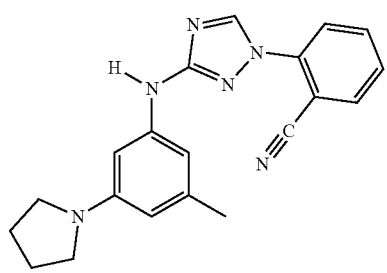 [SMILES: Cc1cc(Nc2ncn(-c3ccccc3C#N)n2)cc(N2CCCC2)c1]
212

TABLE 1-continued
Compound Table
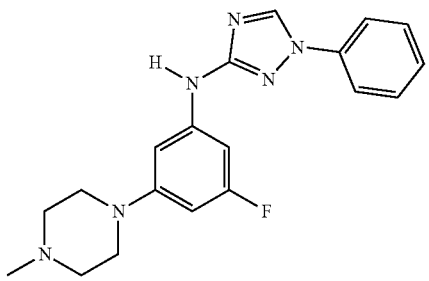 [SMILES: CN1CCN(c2cc(F)cc(Nc3ncn(-c4ccccc4)n3)c2)CC1]
213
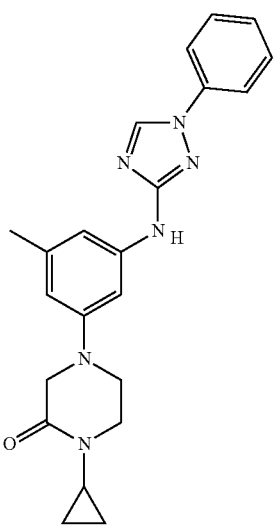
214
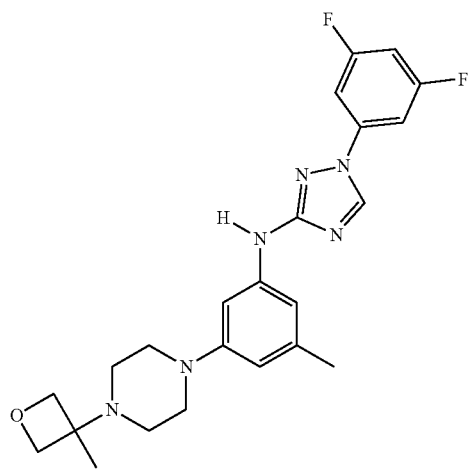 [SMILES: Cc1cc(Nc2ncn(-c3cc(F)cc(F)c3)n2)cc(N2CCN(C3(C)COC3)CC2)c1]
215
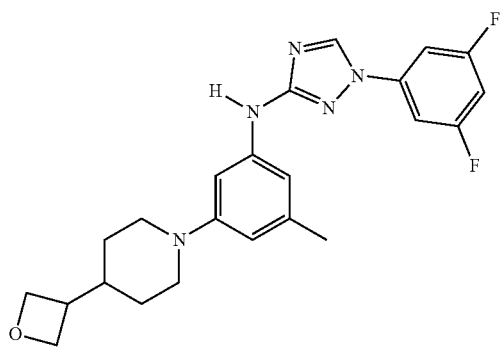
216

TABLE 1-continued
Compound Table
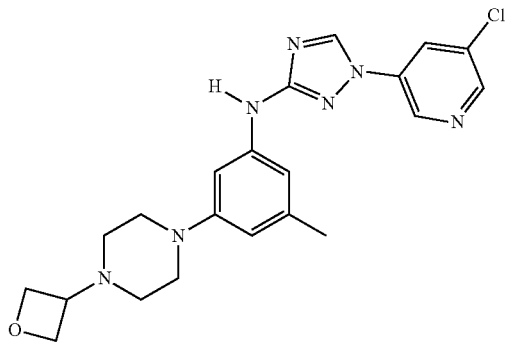 [SMILES: Cc1cc(Nc2ncn(-c3cncc(Cl)c3)n2)cc(N2CCN(C3COC3)CC2)c1]
217
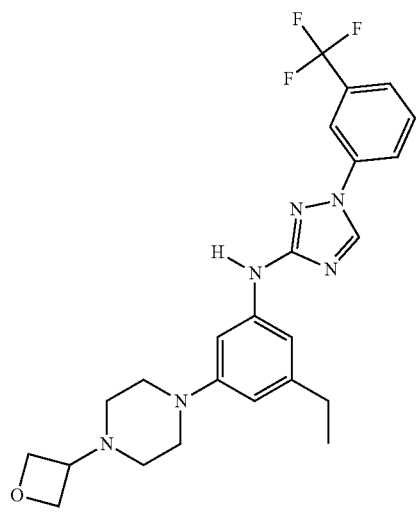 [SMILES: CCc1cc(Nc2ncn(-c3cccc(C(F)(F)F)c3)n2)cc(N2CCN(C3COC3)CC2)c1]
218
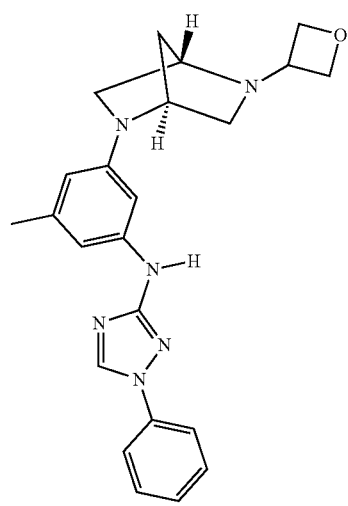 [SMILES: Cc1cc(Nc2ncn(-c3ccccc3)n2)cc(N2C[C@@H]3C[C@H]2CN3C2COC2)c1]
219

TABLE 1-continued
Compound Table
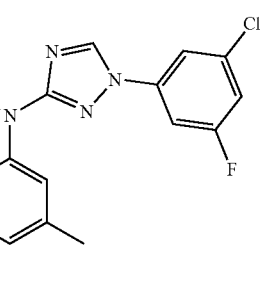
220
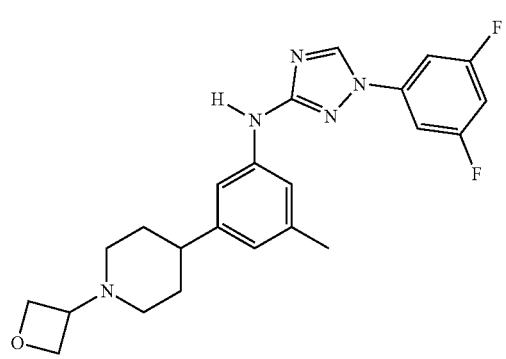 [SMILES: Cc1cc(Nc2ncn(-c3cc(F)cc(F)c3)n2)cc(C2CCN(C3COC3)CC2)c1]
221
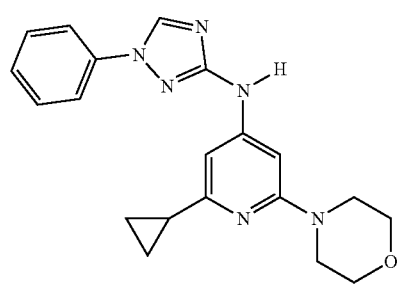 [SMILES: c1ccc(-n2cnc(Nc3cc(C4CC4)nc(N4CCOCC4)c3)n2)cc1]
222
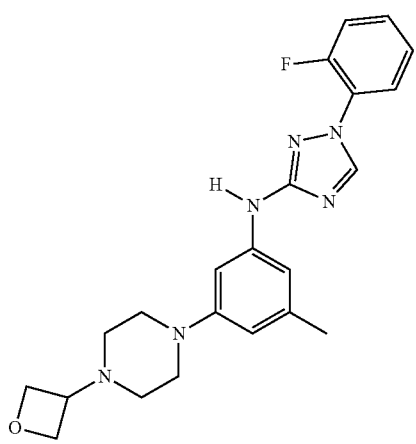 [SMILES: Cc1cc(Nc2ncn(-c3ccccc3F)n2)cc(N2CCN(C3COC3)CC2)c1]
223

TABLE 1-continued
Compound Table
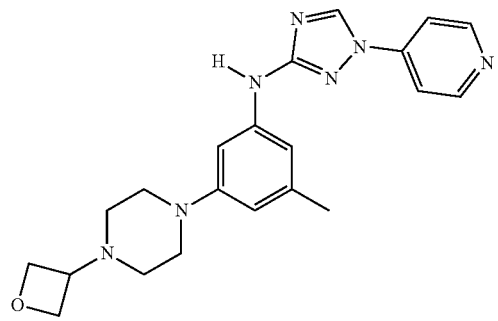 [SMILES: Cc1cc(Nc2ncn(-c3ccncc3)n2)cc(N2CCN(C3COC3)CC2)c1] 224
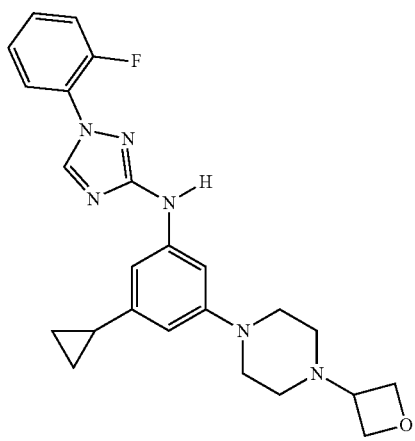 [SMILES: Fc1ccccc1-n1cnc(Nc2cc(C3CC3)cc(N3CCN(C4COC4)CC3)c2)n1] 225
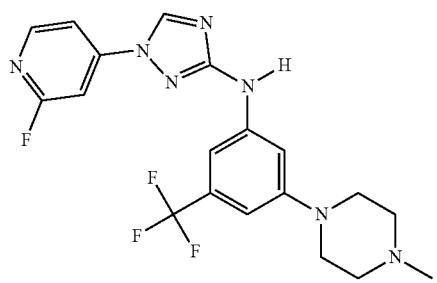 [SMILES: CN1CCN(c2cc(Nc3ncn(-c4ccnc(F)c4)n3)cc(C(F)(F)F)c2)CC1] 226
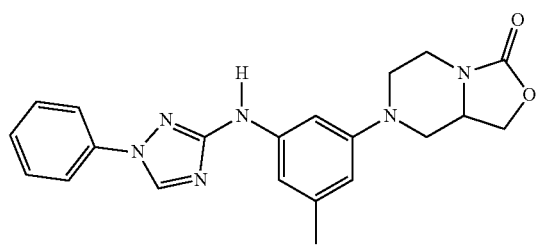 [SMILES: Cc1cc(Nc2ncn(-c3ccccc3)n2)cc(N2CCN3C(=O)OCC3C2)c1] 227

TABLE 1-continued
Compound Table
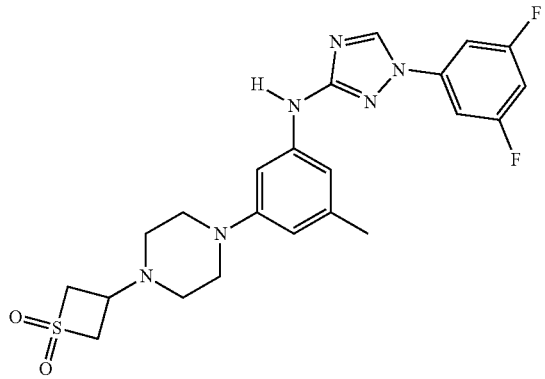 [SMILES: Cc1cc(Nc2ncn(-c3cc(F)cc(F)c3)n2)cc(N2CCN(C3CS(=O)(=O)C3)CC2)c1]
228
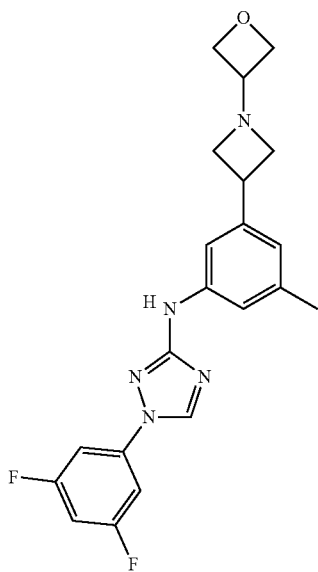
229
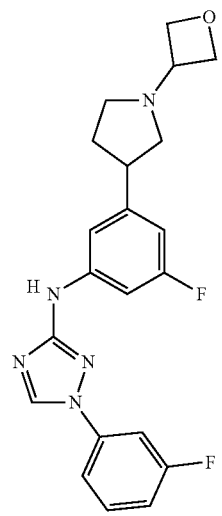
230

TABLE 1-continued
Compound Table
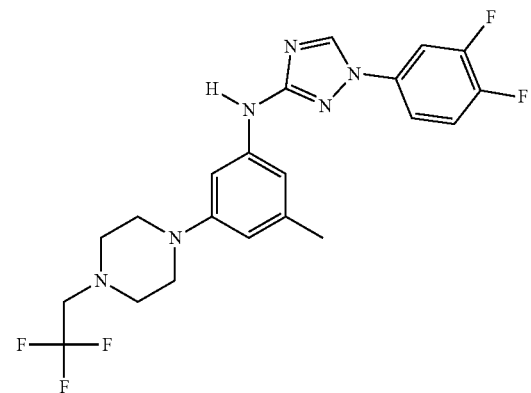 [SMILES: Cc1cc(Nc2ncn(-c3ccc(F)c(F)c3)n2)cc(N2CCN(CC(F)(F)F)CC2)c1]
231
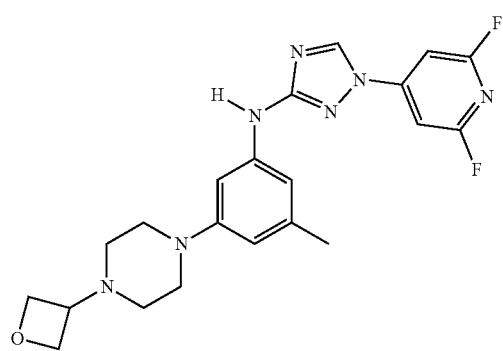 [SMILES: Cc1cc(Nc2ncn(-c3cc(F)nc(F)c3)n2)cc(N2CCN(C3COC3)CC2)c1]
232
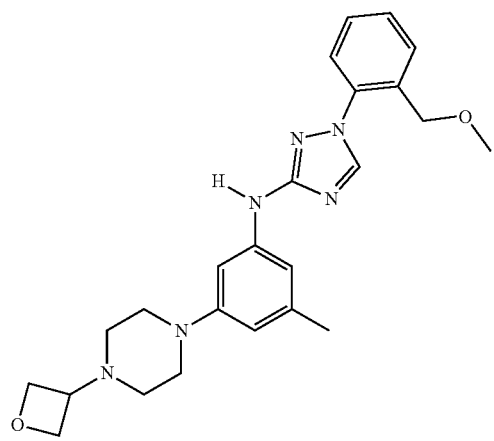 [SMILES: COCc1ccccc1-n1cnc(Nc2cc(C)cc(N3CCN(C4COC4)CC3)c2)n1]
233
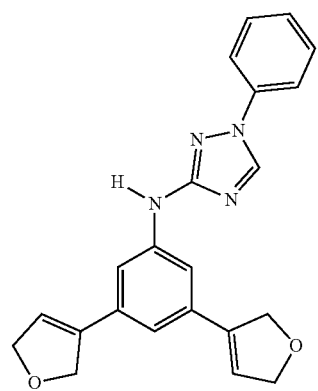 [SMILES: C1=C(c2cc(Nc3ncn(-c4ccccc4)n3)cc(C3=CCOC3)c2)COC1]
234

TABLE 1-continued
Compound Table
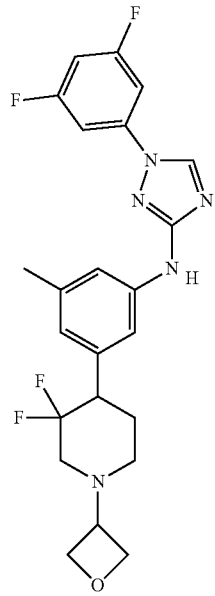
235
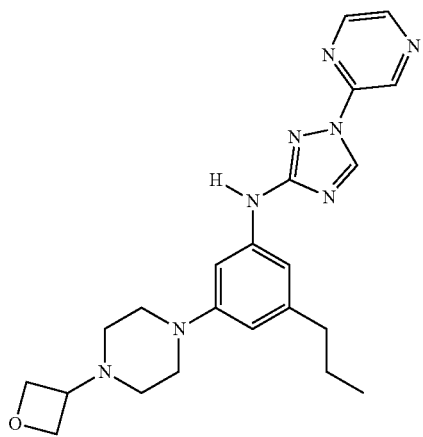 [SMILES: CCCc1cc(Nc2ncn(-c3cnccn3)n2)cc(N2CCN(C3COC3)CC2)c1]
236
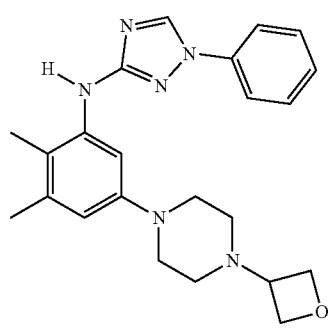 [SMILES: Cc1cc(N2CCN(C3COC3)CC2)cc(Nc2ncn(-c3ccccc3)n2)c1C]
237

TABLE 1-continued
Compound Table
| | |
|---|---|
| 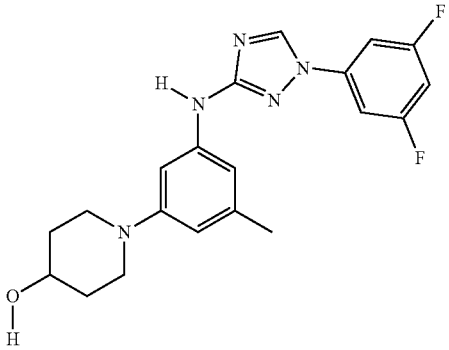 [SMILES: Cc1cc(Nc2ncn(-c3cc(F)cc(F)c3)n2)cc(N2CCC(O)CC2)c1] | 238 |
| 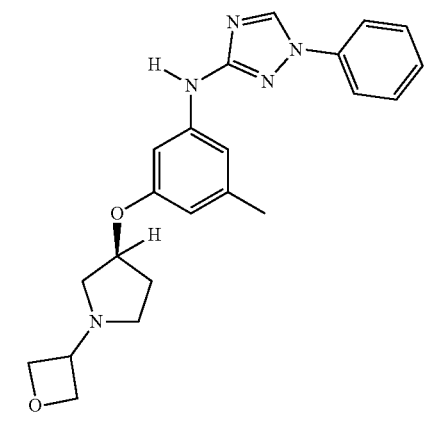 [SMILES: Cc1cc(Nc2ncn(-c3ccccc3)n2)cc(O[C@H]2CCN(C3COC3)C2)c1] | 239 |
| 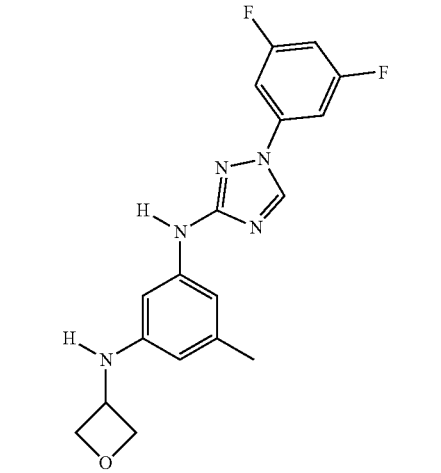 | 240 |
| 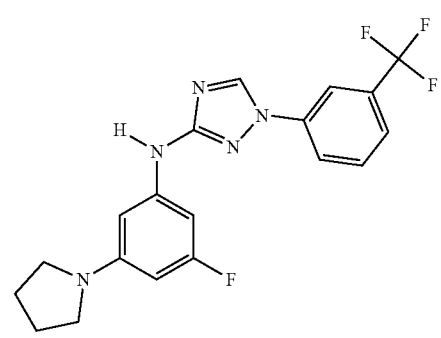 [SMILES: Fc1cc(Nc2ncn(-c3cccc(C(F)(F)F)c3)n2)cc(N2CCCC2)c1] | 241 |

TABLE 1-continued
Compound Table
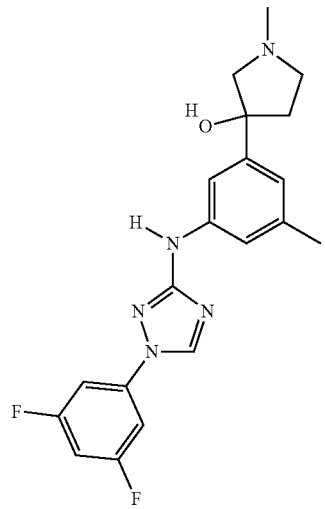
242
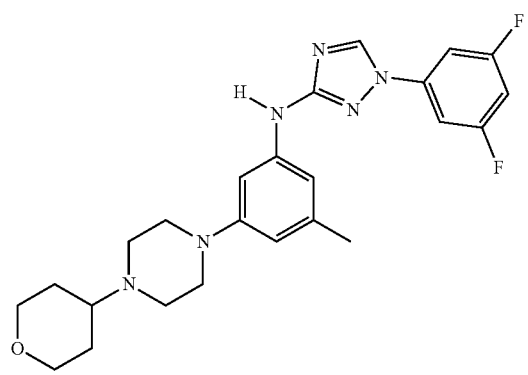 [SMILES: Cc1cc(Nc2ncn(-c3cc(F)cc(F)c3)n2)cc(N2CCN(C3CCOCC3)CC2)c1]
243
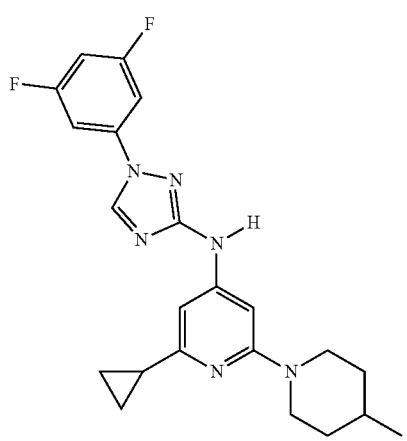 [SMILES: CC1CCN(c2cc(Nc3ncn(-c4cc(F)cc(F)c4)n3)cc(C3CC3)n2)CC1]
244

TABLE 1-continued
Compound Table
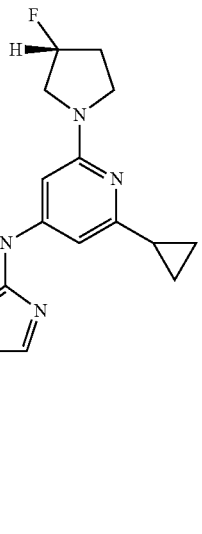
245
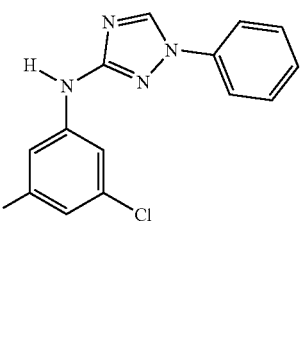
246
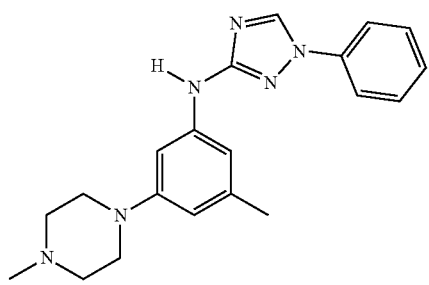 [SMILES: Cc1cc(Nc2ncn(-c3ccccc3)n2)cc(N2CCN(C)CC2)c1]
247

TABLE 1-continued
Compound Table
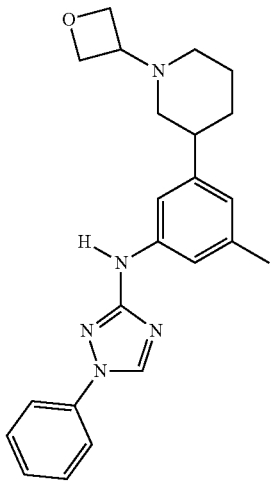 [SMILES: Cc1cc(Nc2ncn(-c3ccccc3)n2)cc(C2CCCN(C3COC3)C2)c1]
248
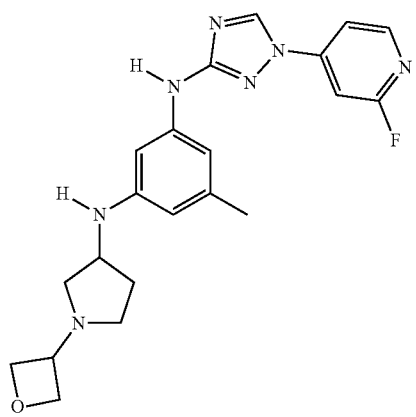 [SMILES: Cc1cc(Nc2ncn(-c3ccnc(F)c3)n2)cc(NC2CCN(C3COC3)C2)c1]
249
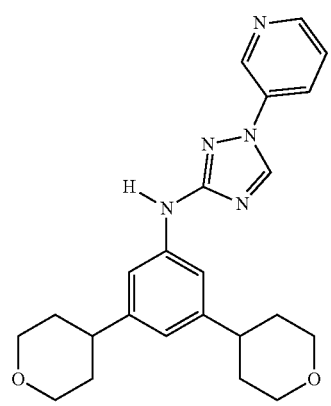 [SMILES: c1cncc(-n2cnc(Nc3cc(C4CCOCC4)cc(C4CCOCC4)c3)n2)c1]
250

TABLE 1-continued
Compound Table
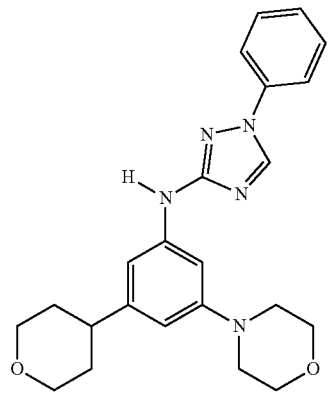 [SMILES: c1ccc(-n2cnc(Nc3cc(C4CCOCC4)cc(N4CCOCC4)c3)n2)cc1]
251
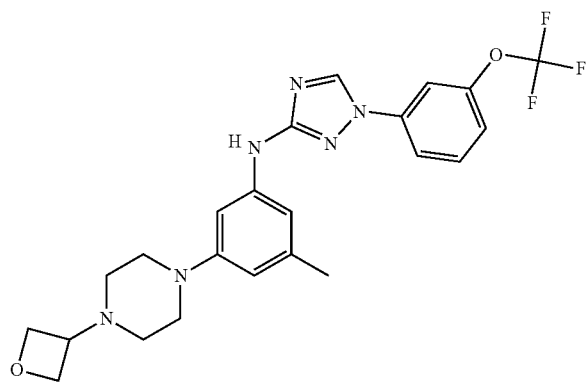
252
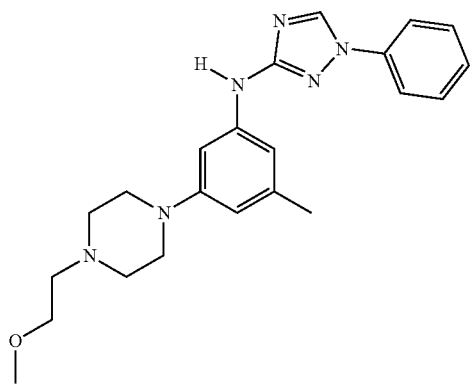 [SMILES: COCCN1CCN(c2cc(C)cc(Nc3ncn(-c4ccccc4)n3)c2)CC1]
253
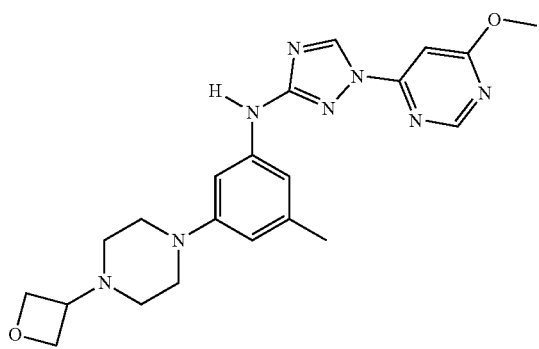 [SMILES: COc1cc(-n2cnc(Nc3cc(C)cc(N4CCN(C5COC5)CC4)c3)n2)ncn1]
254

TABLE 1-continued
Compound Table
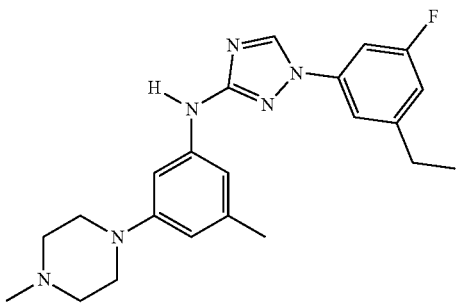 [SMILES: CCc1cc(F)cc(-n2cnc(Nc3cc(C)cc(N4CCN(C)CC4)c3)n2)c1]
255
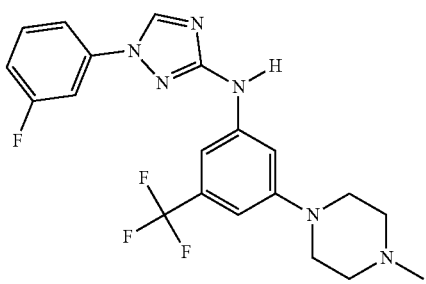 [SMILES: CN1CCN(c2cc(Nc3ncn(-c4cccc(F)c4)n3)cc(C(F)(F)F)c2)CC1]
257
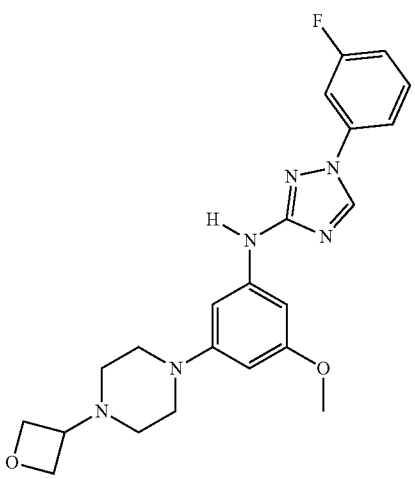 [SMILES: COc1cc(Nc2ncn(-c3cccc(F)c3)n2)cc(N2CCN(C3COC3)CC2)c1]
258
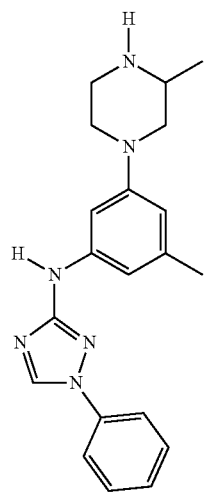 [SMILES: Cc1cc(Nc2ncn(-c3ccccc3)n2)cc(N2CCNC(C)C2)c1]
259

TABLE 1-continued
Compound Table
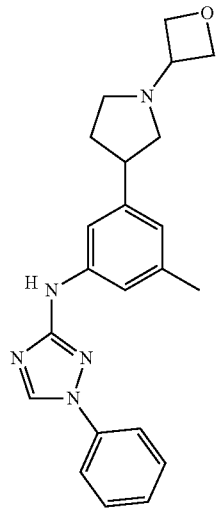
260
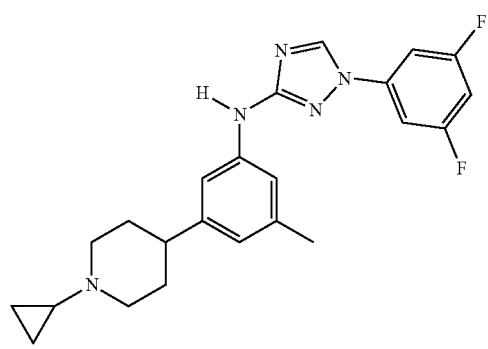 [SMILES: Cc1cc(Nc2ncn(-c3cc(F)cc(F)c3)n2)cc(C2CCN(C3CC3)CC2)c1]
261
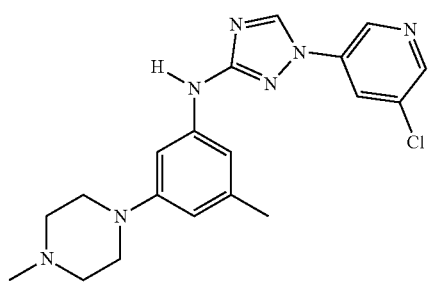
262
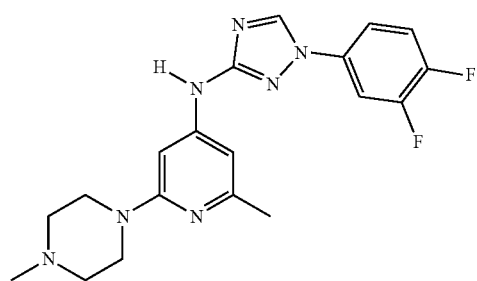 [SMILES: Cc1cc(Nc2ncn(-c3ccc(F)c(F)c3)n2)cc(N2CCN(C)CC2)n1]
263

TABLE 1-continued
Compound Table
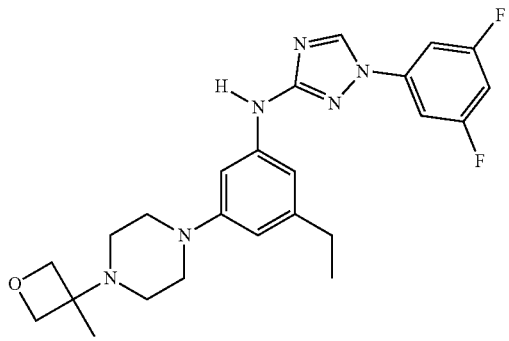 [SMILES: CCc1cc(Nc2ncn(-c3cc(F)cc(F)c3)n2)cc(N2CCN(C3(C)COC3)CC2)c1]
264
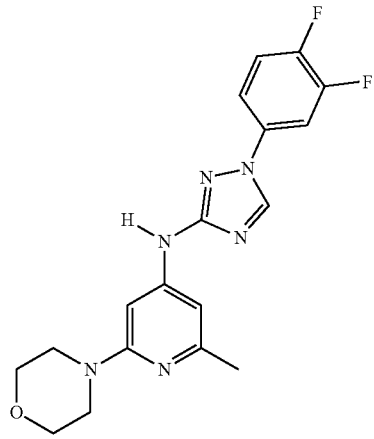 [SMILES: Cc1cc(Nc2ncn(-c3ccc(F)c(F)c3)n2)cc(N2CCOCC2)n1]
265
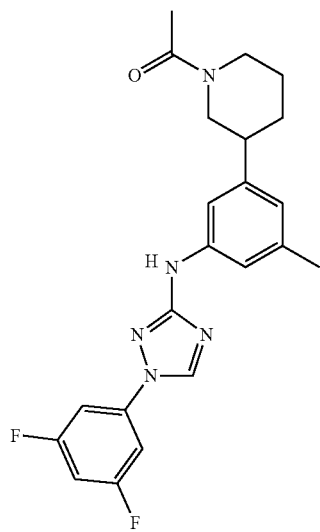
266

TABLE 1-continued
Compound Table
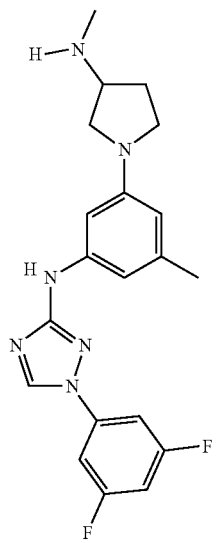
267
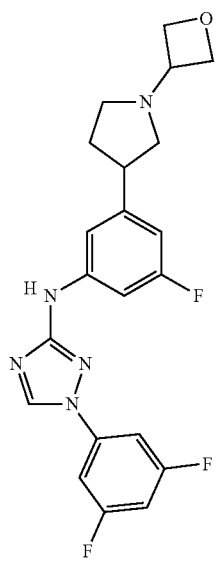
268
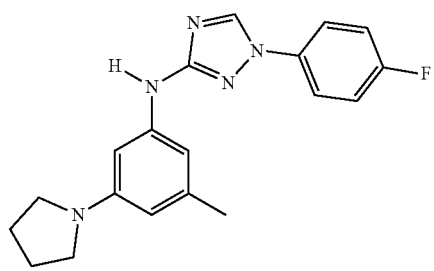 [SMILES: Cc1cc(Nc2ncn(-c3ccc(F)cc3)n2)cc(N2CCCC2)c1]
269

TABLE 1-continued
Compound Table
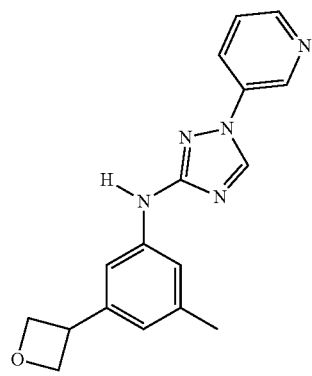 [SMILES: Cc1cc(Nc2ncn(-c3cccnc3)n2)cc(C2COC2)c1]
270
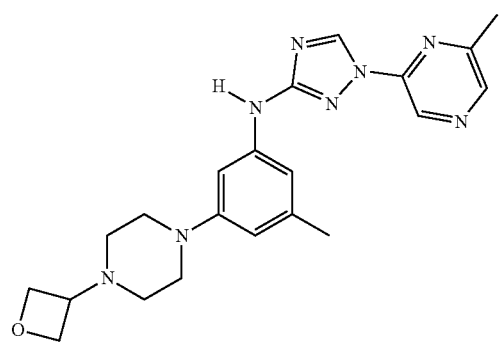 [SMILES: Cc1cc(Nc2ncn(-c3cncc(C)n3)n2)cc(N2CCN(C3COC3)CC2)c1]
271
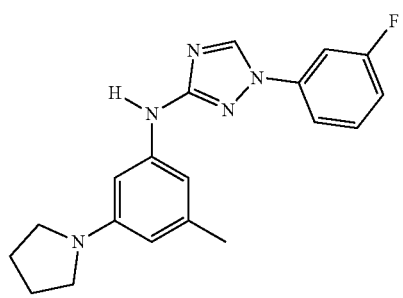 [SMILES: Cc1cc(Nc2ncn(-c3cccc(F)c3)n2)cc(N2CCCC2)c1]
272
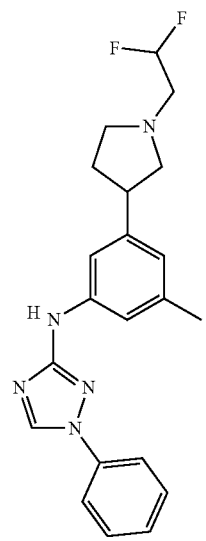
273

TABLE 1-continued
Compound Table
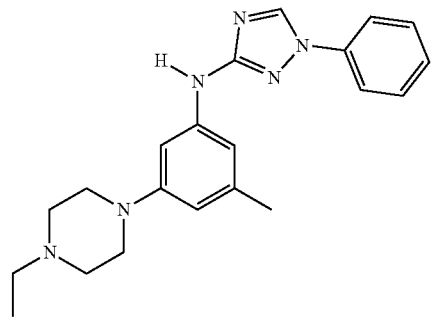 [SMILES: CCN1CCN(c2cc(C)cc(Nc3ncn(-c4ccccc4)n3)c2)CC1]
274
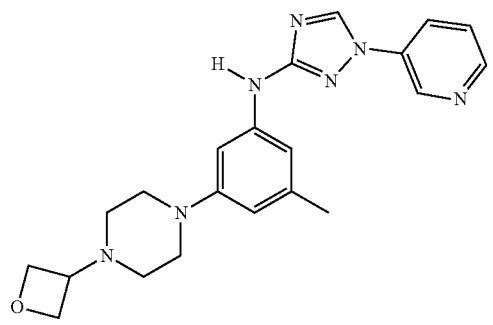 [SMILES: Cc1cc(Nc2ncn(-c3cccnc3)n2)cc(N2CCN(C3COC3)CC2)c1]
275
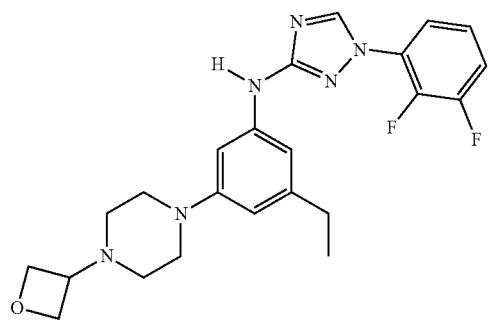 [SMILES: CCc1cc(Nc2ncn(-c3cccc(F)c3F)n2)cc(N2CCN(C3COC3)CC2)c1]
276
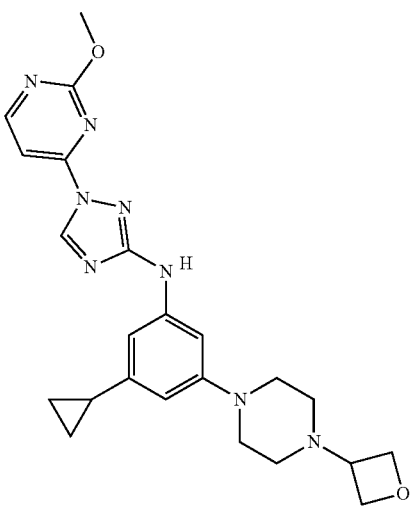
277

TABLE 1-continued
Compound Table
278
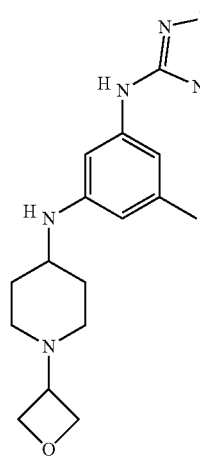
279
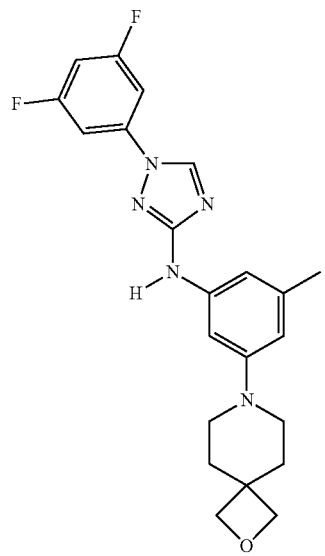 [SMILES: Cc1cc(Nc2ncn(-c3cc(F)cc(F)c3)n2)cc(N2CCC3(CC2)COC3)c1]

TABLE 1-continued
Compound Table
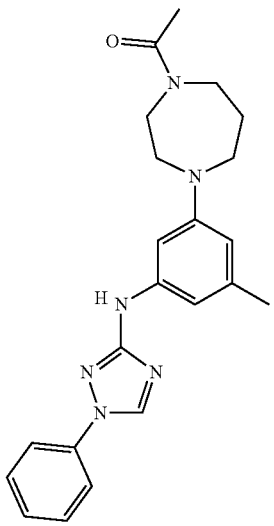
280
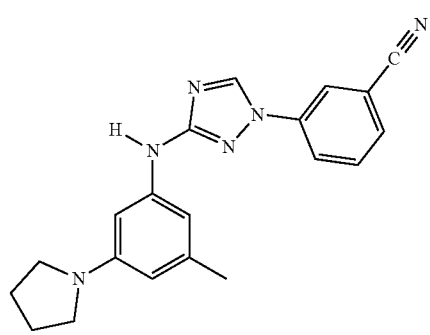 [SMILES: Cc1cc(Nc2ncn(-c3cccc(C#N)c3)n2)cc(N2CCCC2)c1]
281
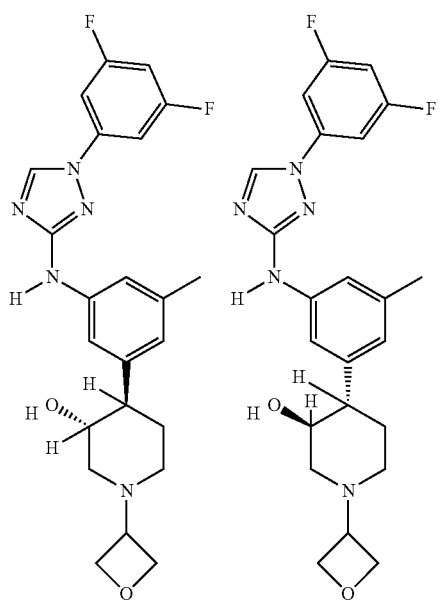
282

TABLE 1-continued
Compound Table
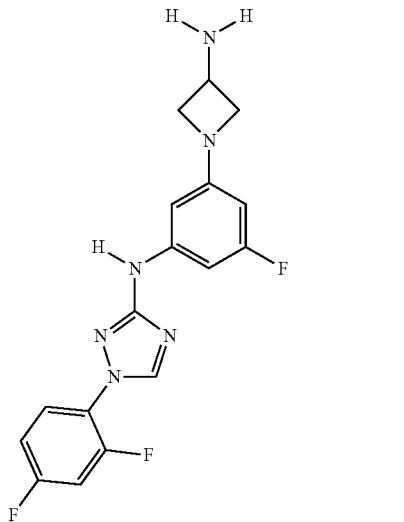 [SMILES: NC1CN(c2cc(F)cc(Nc3ncn(-c4ccc(F)cc4F)n3)c2)C1]
283
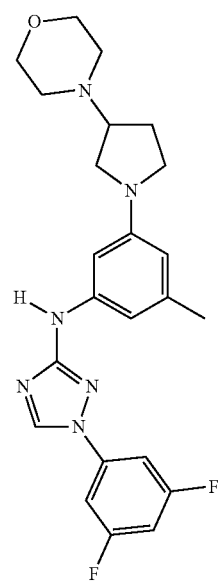 [SMILES: Cc1cc(Nc2ncn(-c3cc(F)cc(F)c3)n2)cc(N2CCC(N3CCOCC3)C2)c1]
284

TABLE 1-continued
Compound Table
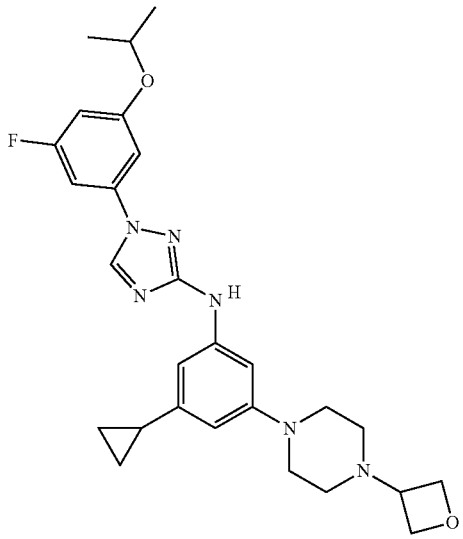
285
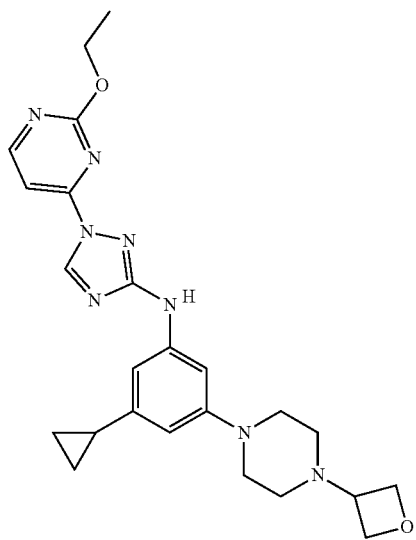
286
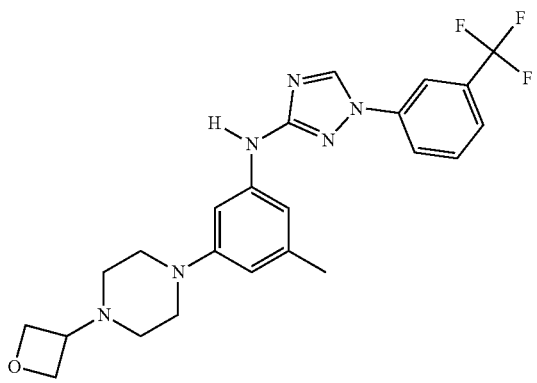 [SMILES: Cc1cc(Nc2ncn(-c3cccc(C(F)(F)F)c3)n2)cc(N2CCN(C3COC3)CC2)c1]
287

TABLE 1-continued
Compound Table
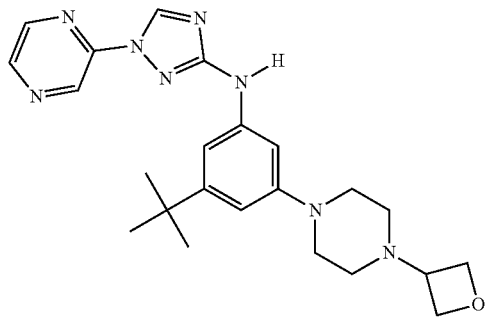 [SMILES: CC(C)(C)c1cc(Nc2ncn(-c3cnccn3)n2)cc(N2CCN(C3COC3)CC2)c1] 288
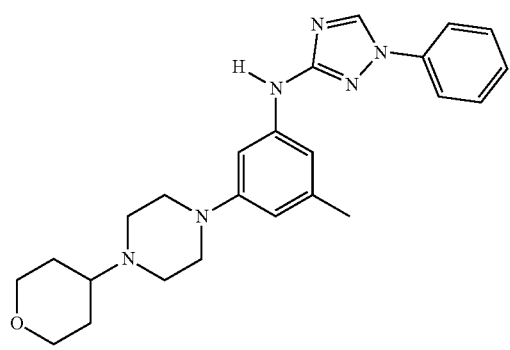 [SMILES: Cc1cc(Nc2ncn(-c3ccccc3)n2)cc(N2CCN(C3CCOCC3)CC2)c1] 289
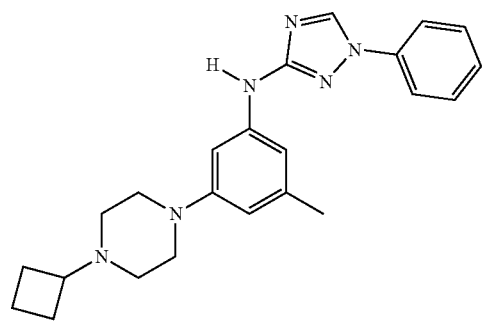 [SMILES: Cc1cc(Nc2ncn(-c3ccccc3)n2)cc(N2CCN(C3CCC3)CC2)c1] 290
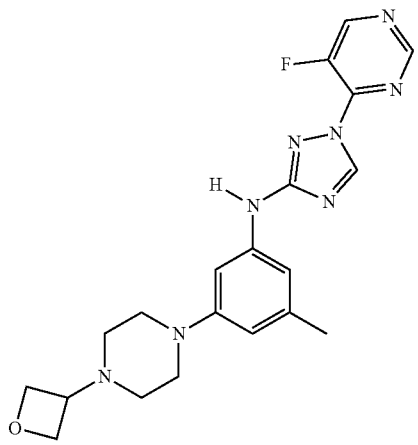 [SMILES: Cc1cc(Nc2ncn(-c3ncncc3F)n2)cc(N2CCN(C3COC3)CC2)c1] 291

TABLE 1-continued
Compound Table
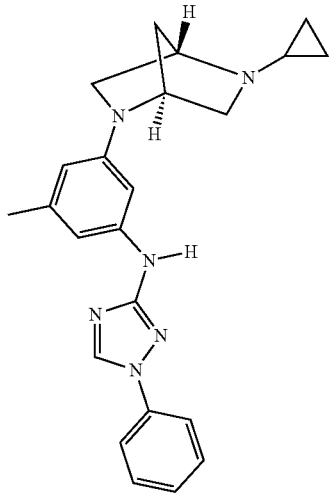 [SMILES: Cc1cc(Nc2ncn(-c3ccccc3)n2)cc(N2C[C@@H]3C[C@H]2CN3C2CC2)c1]
292
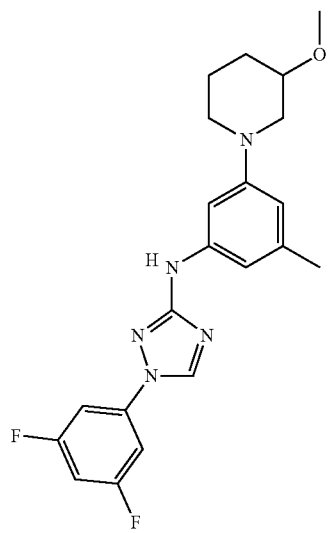
293
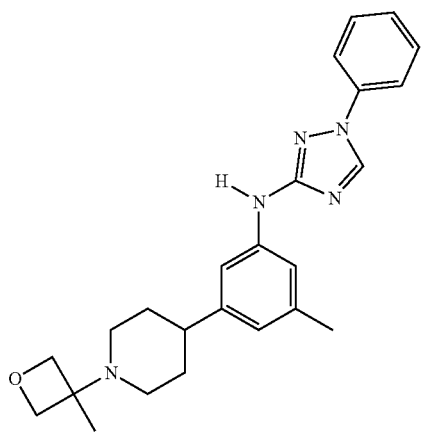 [SMILES: Cc1cc(Nc2ncn(-c3ccccc3)n2)cc(C2CCN(C3(C)COC3)CC2)c1]
294

TABLE 1-continued
Compound Table
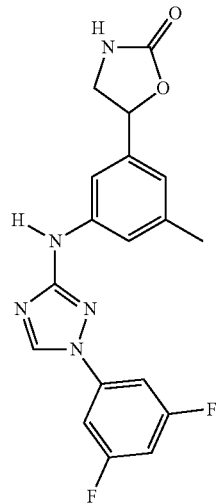
295
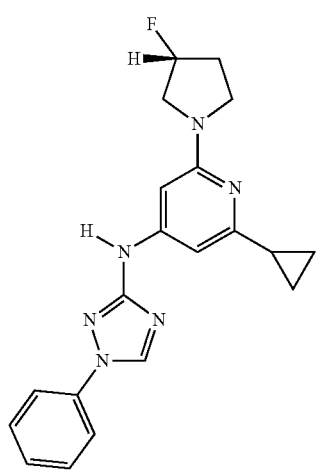 [SMILES: F[C@@H]1CCN(c2cc(Nc3ncn(-c4ccccc4)n3)cc(C3CC3)n2)C1]
296
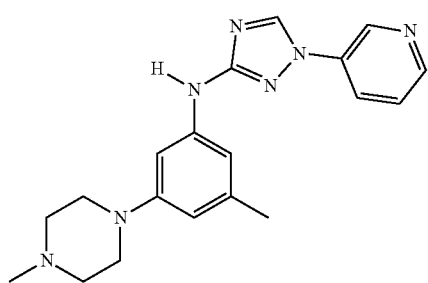 [SMILES: Cc1cc(Nc2ncn(-c3cccnc3)n2)cc(N2CCN(C)CC2)c1]
297
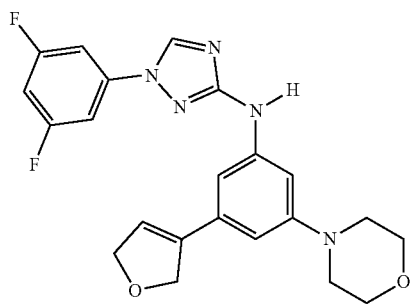 [SMILES: Fc1cc(F)cc(-n2cnc(Nc3cc(C4=CCOC4)cc(N4CCOCC4)c3)n2)c1]
298

TABLE 1-continued
Compound Table
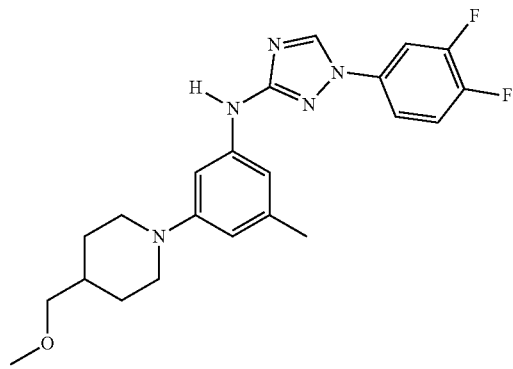 [SMILES: COCC1CCN(c2cc(C)cc(Nc3ncn(-c4ccc(F)c(F)c4)n3)c2)CC1]
299
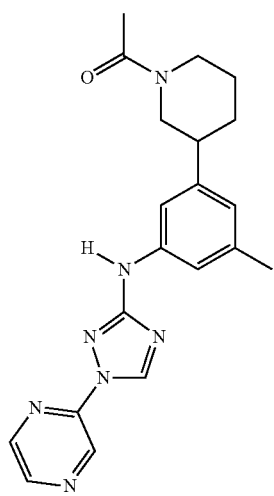 [SMILES: CC(=O)N1CCCC(c2cc(C)cc(Nc3ncn(-c4cnccn4)n3)c2)C1]
300
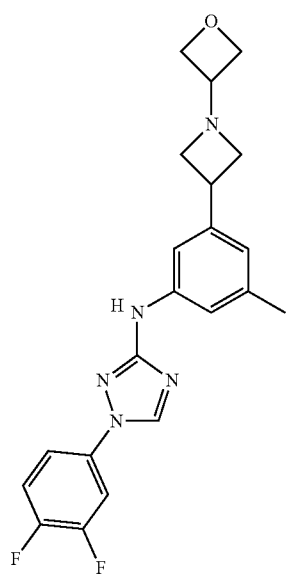
301

TABLE 1-continued
Compound Table
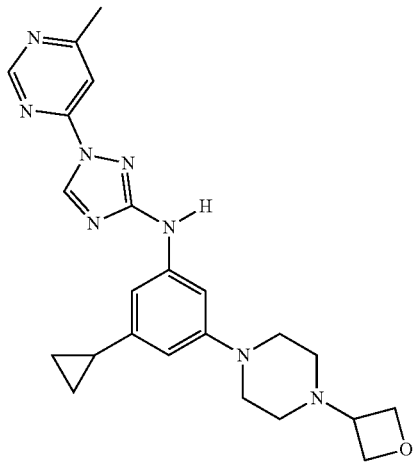 [SMILES: Cc1cc(-n2cnc(Nc3cc(C4CC4)cc(N4CCN(C5COC5)CC4)c3)n2)ncn1]
302
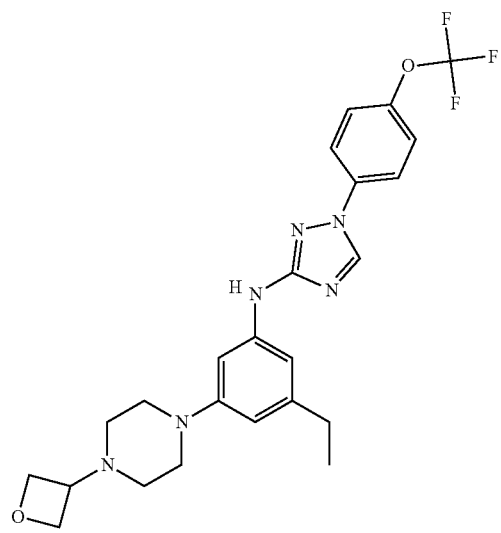
303
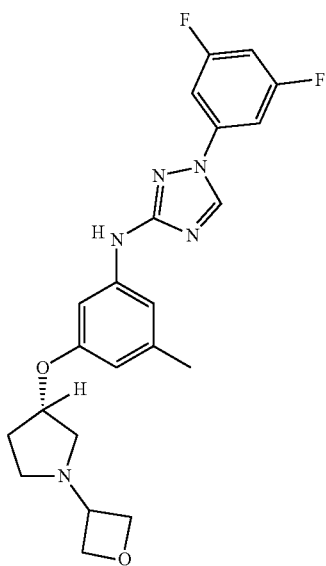
304

TABLE 1-continued
Compound Table
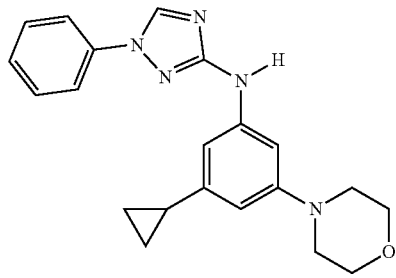 [SMILES: c1ccc(-n2cnc(Nc3cc(C4CC4)cc(N4CCOCC4)c3)n2)cc1]
305
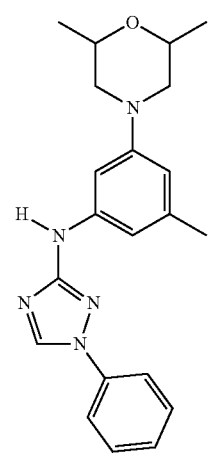 [SMILES: Cc1cc(Nc2ncn(-c3ccccc3)n2)cc(N2CC(C)OC(C)C2)c1]
306
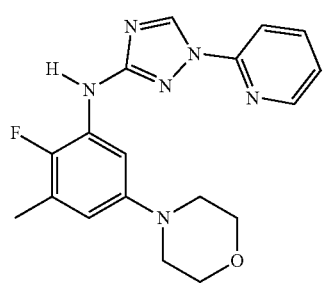 [SMILES: Cc1cc(N2CCOCC2)cc(Nc2ncn(-c3ccccn3)n2)c1F]
307
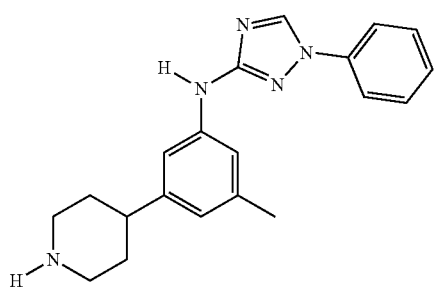 [SMILES: Cc1cc(Nc2ncn(-c3ccccc3)n2)cc(C2CCNCC2)c1]
308

TABLE 1-continued
Compound Table
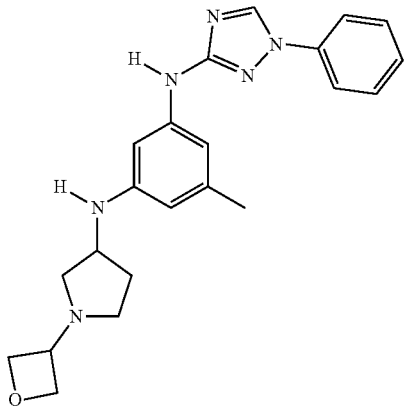 [SMILES: Cc1cc(Nc2ncn(-c3ccccc3)n2)cc(NC2CCN(C3COC3)C2)c1]
309
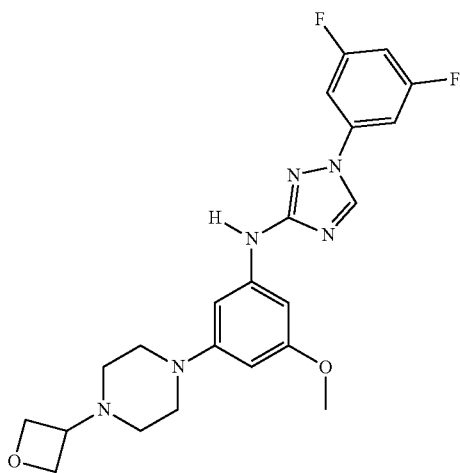
310
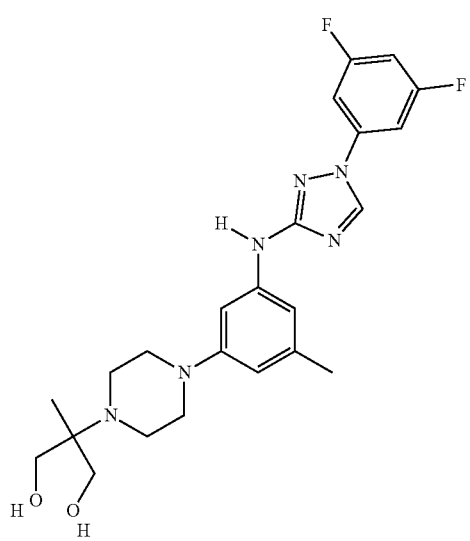
311

TABLE 1-continued
Compound Table
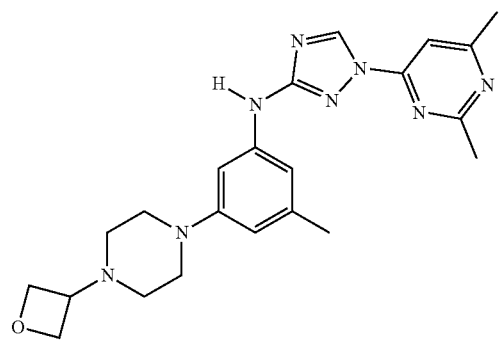 [SMILES: Cc1cc(Nc2ncn(-c3cc(C)nc(C)n3)n2)cc(N2CCN(C3COC3)CC2)c1] 312
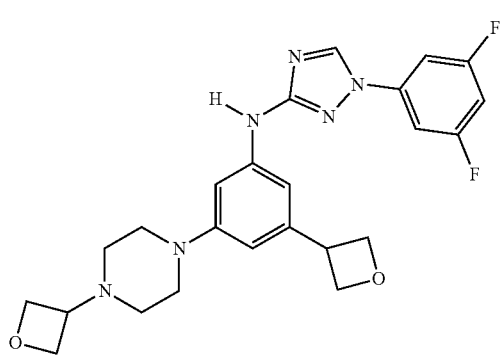 [SMILES: Fc1cc(F)cc(-n2cnc(Nc3cc(C4COC4)cc(N4CCN(C5COC5)CC4)c3)n2)c1] 313
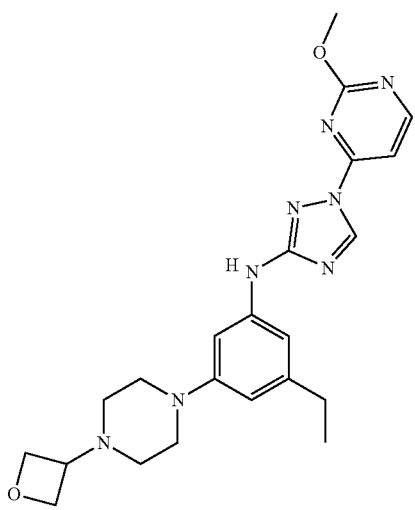 314
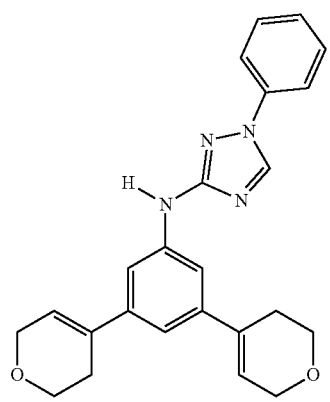 [SMILES: C1=C(c2cc(Nc3ncn(-c4ccccc4)n3)cc(C3=CCOCC3)c2)CCOC1] 315

TABLE 1-continued
Compound Table
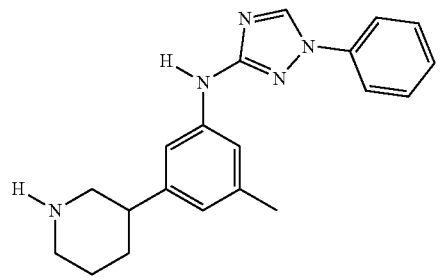 [SMILES: Cc1cc(Nc2ncn(-c3ccccc3)n2)cc(C2CCCNC2)c1] 316
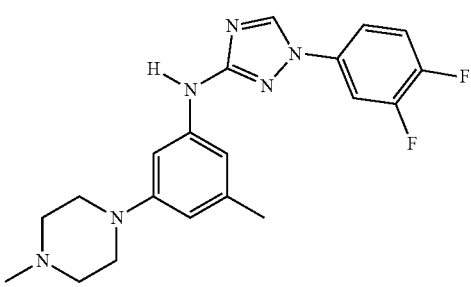 [SMILES: Cc1cc(Nc2ncn(-c3ccc(F)c(F)c3)n2)cc(N2CCN(C)CC2)c1] 317
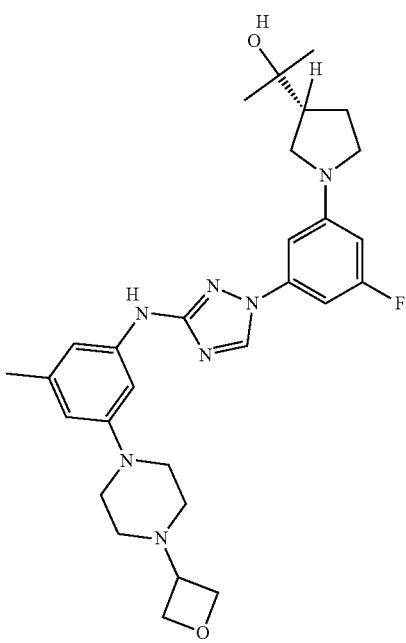 318
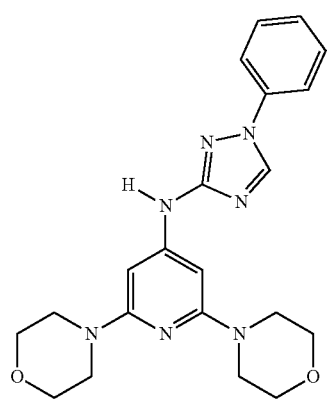 319

TABLE 1-continued
Compound Table
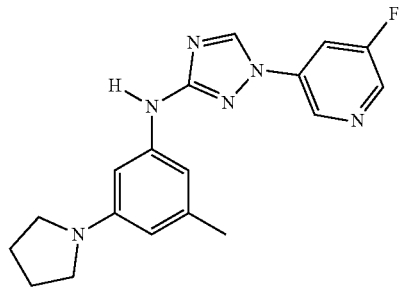 [SMILES: Cc1cc(Nc2ncn(-c3cncc(F)c3)n2)cc(N2CCCC2)c1]
320
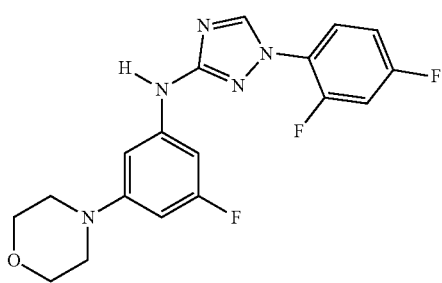 [SMILES: Fc1cc(Nc2ncn(-c3ccc(F)cc3F)n2)cc(N2CCOCC2)c1]
321
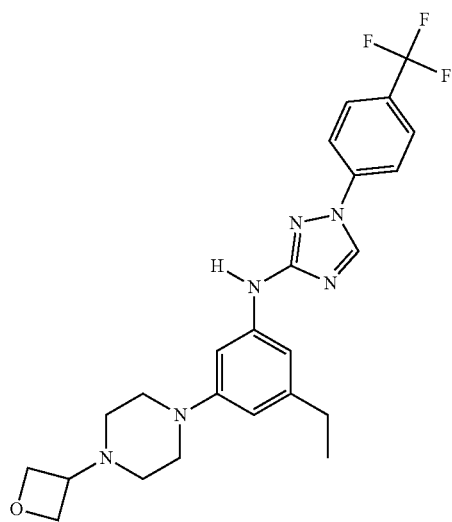 [SMILES: CCc1cc(Nc2ncn(-c3ccc(C(F)(F)F)cc3)n2)cc(N2CCN(C3COC3)CC2)c1]
322
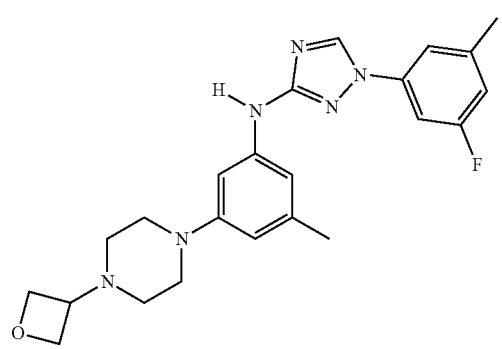 [SMILES: Cc1cc(Nc2ncn(-c3cc(C)cc(F)c3)n2)cc(N2CCN(C3COC3)CC2)c1]
323

TABLE 1-continued
Compound Table
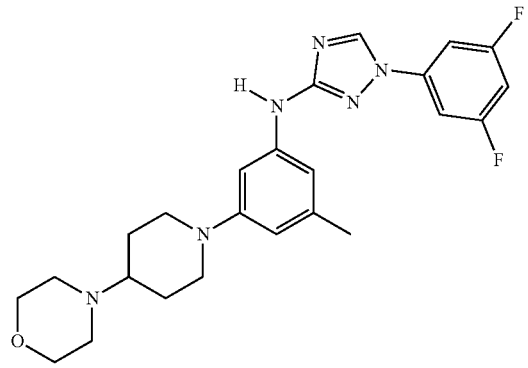 [SMILES: Cc1cc(Nc2ncn(-c3cc(F)cc(F)c3)n2)cc(N2CCC(N3CCOCC3)CC2)c1]
324
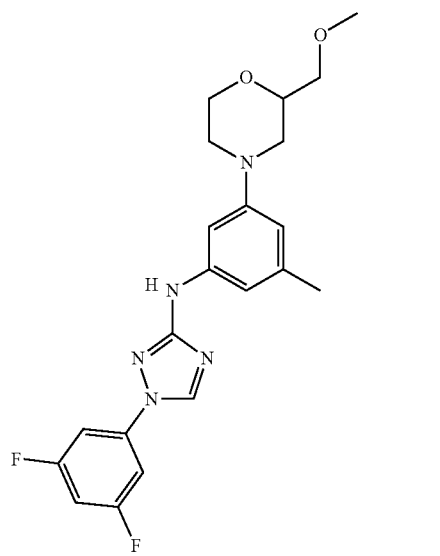
325
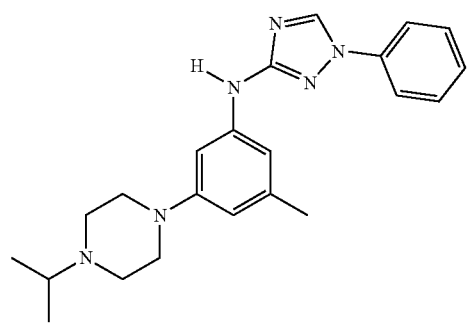 [SMILES: Cc1cc(Nc2ncn(-c3ccccc3)n2)cc(N2CCN(C(C)C)CC2)c1]
326
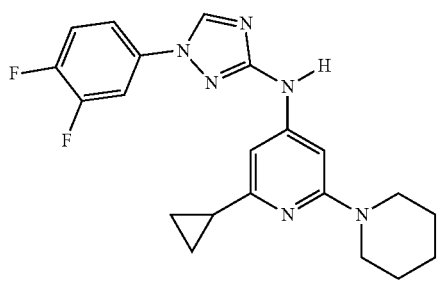 [SMILES: Fc1ccc(-n2cnc(Nc3cc(C4CC4)nc(N4CCCCC4)c3)n2)cc1F]
327

TABLE 1-continued
Compound Table
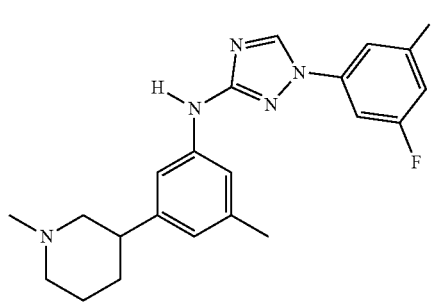
328
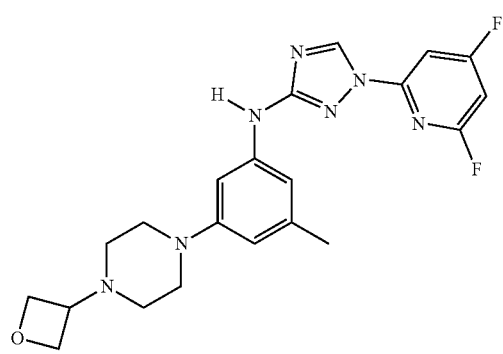 [SMILES: Cc1cc(Nc2ncn(-c3cc(F)cc(F)n3)n2)cc(N2CCN(C3COC3)CC2)c1]
329
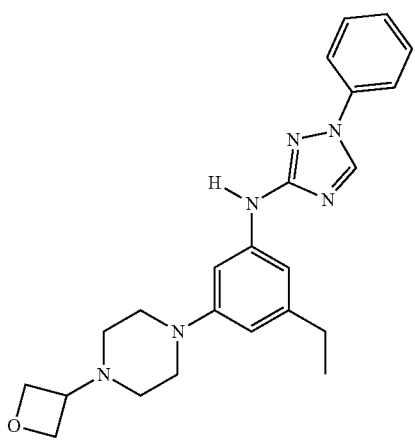 [SMILES: CCc1cc(Nc2ncn(-c3ccccc3)n2)cc(N2CCN(C3COC3)CC2)c1]
330
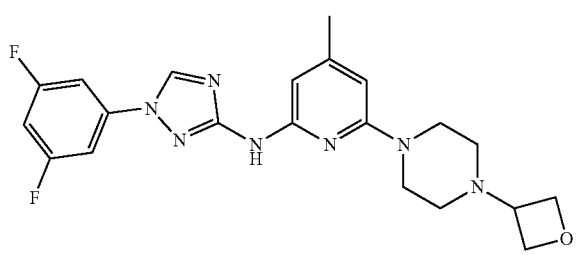 [SMILES: Cc1cc(Nc2ncn(-c3cc(F)cc(F)c3)n2)nc(N2CCN(C3COC3)CC2)c1]
331

TABLE 1-continued
Compound Table
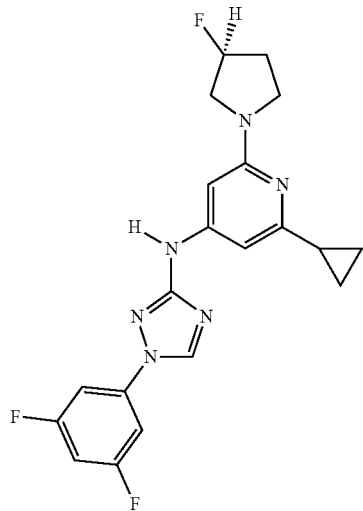 [SMILES: Fc1cc(F)cc(-n2cnc(Nc3cc(C4CC4)nc(N4CC[C@H](F)C4)c3)n2)c1]
332
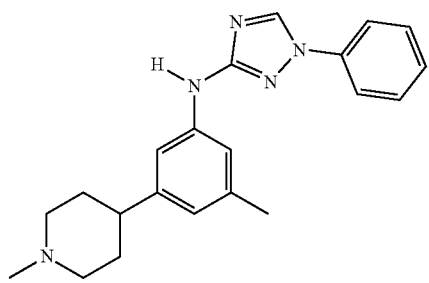 [SMILES: Cc1cc(Nc2ncn(-c3ccccc3)n2)cc(C2CCN(C)CC2)c1]
333
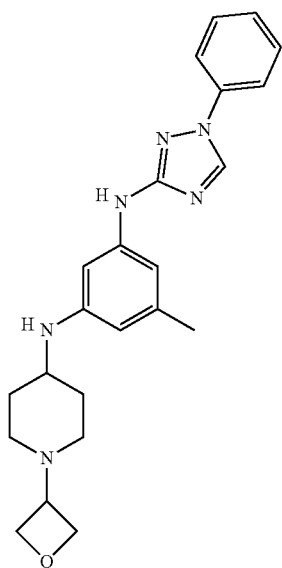
334

TABLE 1-continued
Compound Table
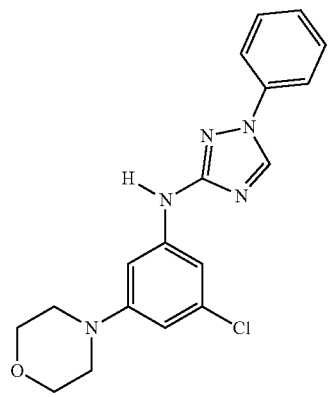 [SMILES: Clc1cc(Nc2ncn(-c3ccccc3)n2)cc(N2CCOCC2)c1]
335
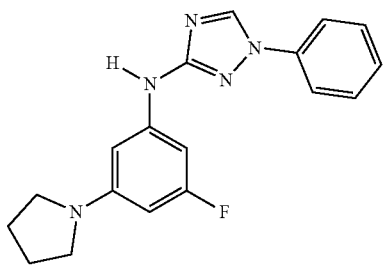 [SMILES: Fc1cc(Nc2ncn(-c3ccccc3)n2)cc(N2CCCC2)c1]
336
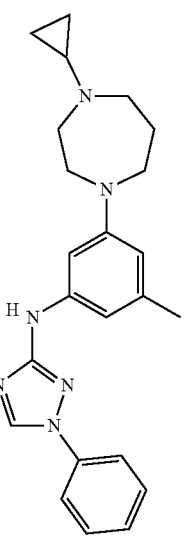
337
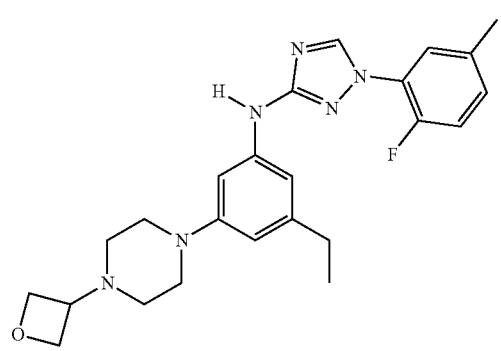 [SMILES: CCc1cc(Nc2ncn(-c3cc(C)ccc3F)n2)cc(N2CCN(C3COC3)CC2)c1]
338

TABLE 1-continued
Compound Table
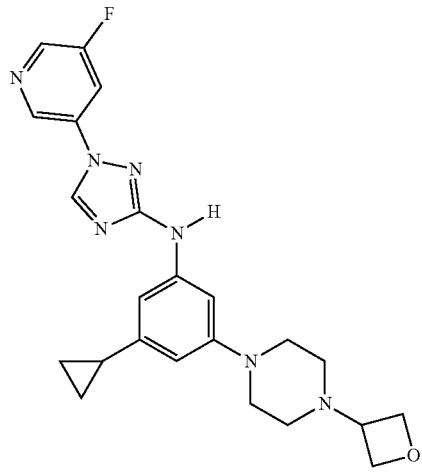 [SMILES: Fc1cncc(-n2cnc(Nc3cc(C4CC4)cc(N4CCN(C5COC5)CC4)c3)n2)c1]
339
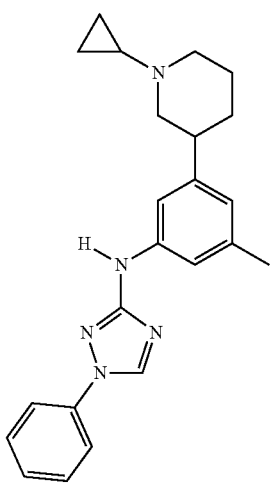 [SMILES: Cc1cc(Nc2ncn(-c3ccccc3)n2)cc(C2CCCN(C3CC3)C2)c1]
340
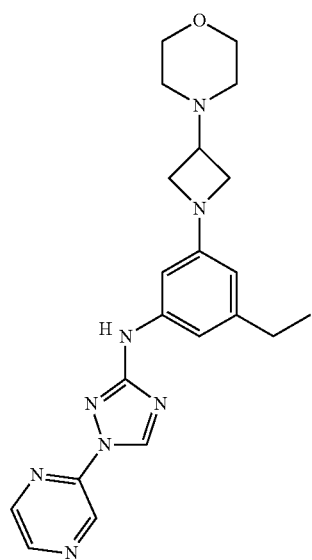
341

TABLE 1-continued
Compound Table
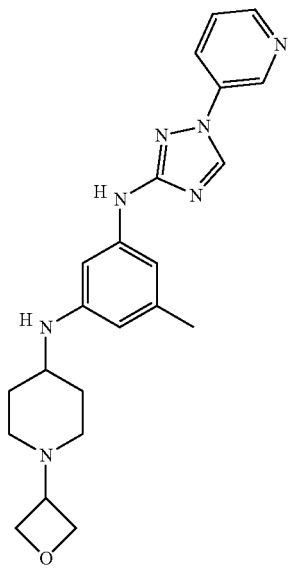
342
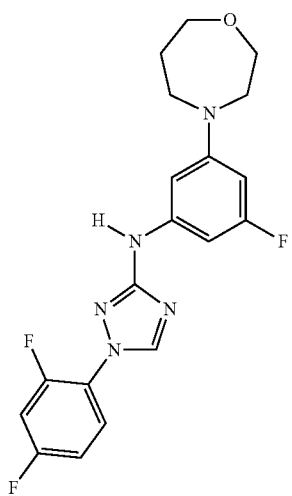 [SMILES: Fc1cc(Nc2ncn(-c3ccc(F)cc3F)n2)cc(N2CCCOCC2)c1]
343
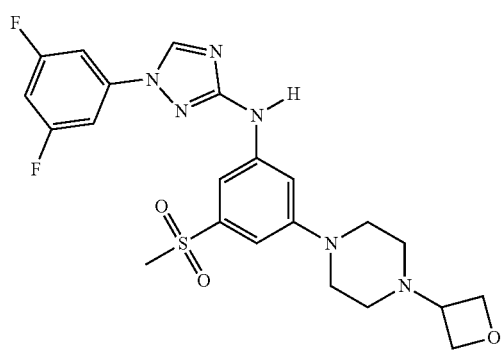 [SMILES: CS(=O)(=O)c1cc(Nc2ncn(-c3cc(F)cc(F)c3)n2)cc(N2CCN(C3COC3)CC2)c1]
344

TABLE 1-continued
Compound Table
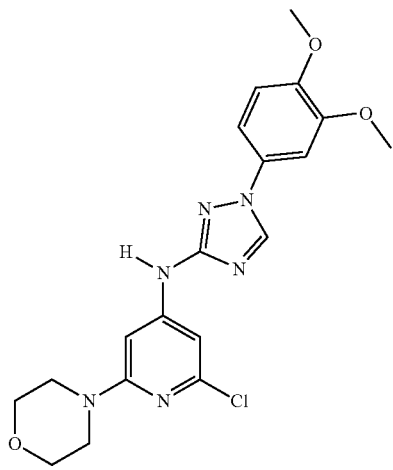 [SMILES: COc1ccc(-n2cnc(Nc3cc(Cl)nc(N4CCOCC4)c3)n2)cc1OC]
345
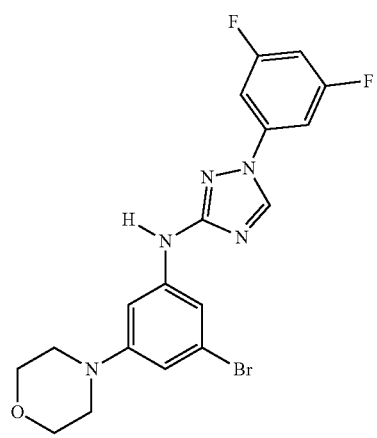
346
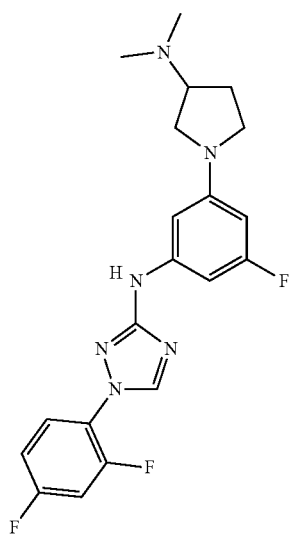
347

TABLE 1-continued
Compound Table
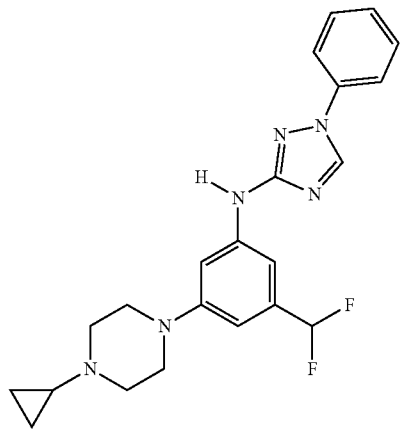 [SMILES: FC(F)c1cc(Nc2ncn(-c3ccccc3)n2)cc(N2CCN(C3CC3)CC2)c1]
348
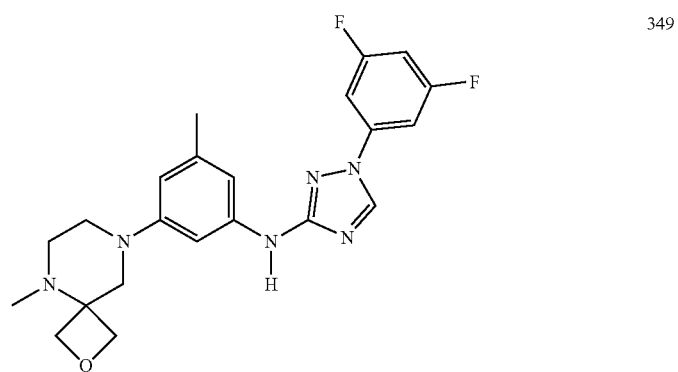
349
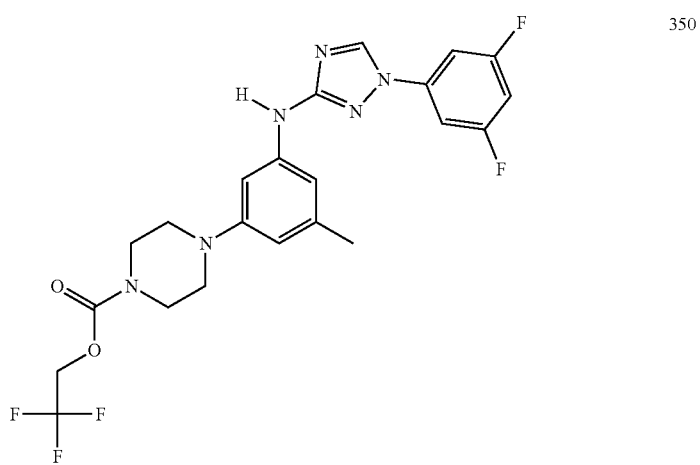
350

TABLE 1-continued
Compound Table
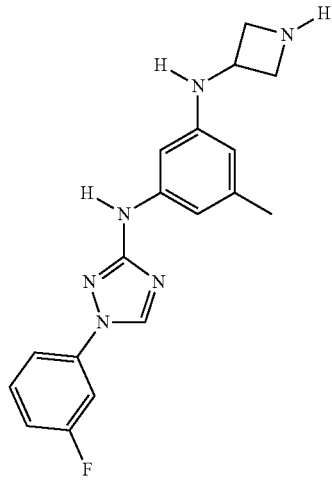 [SMILES: Cc1cc(Nc2ncn(-c3cccc(F)c3)n2)cc(NC2CNC2)c1]
351
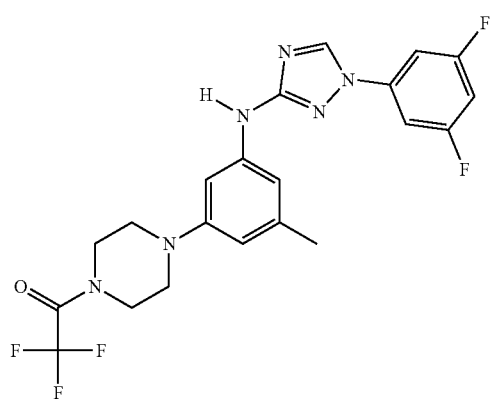 [SMILES: Cc1cc(Nc2ncn(-c3cc(F)cc(F)c3)n2)cc(N2CCN(C(=O)C(F)(F)F)CC2)c1]
352
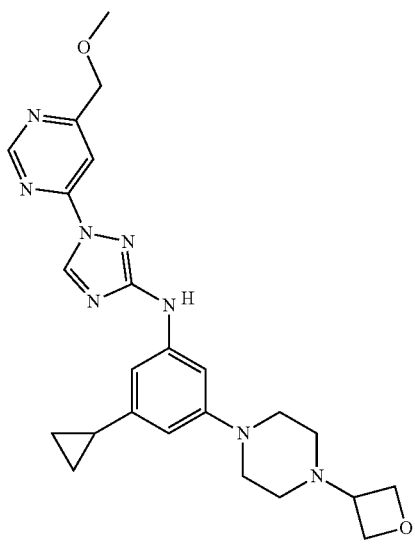
353

TABLE 1-continued
Compound Table
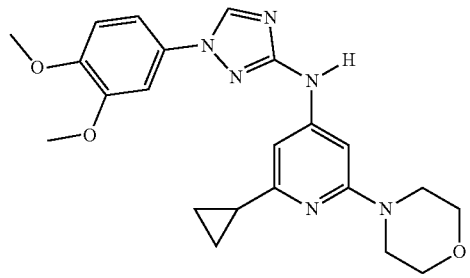 [SMILES: COc1ccc(-n2cnc(Nc3cc(C4CC4)nc(N4CCOCC4)c3)n2)cc1OC]
354
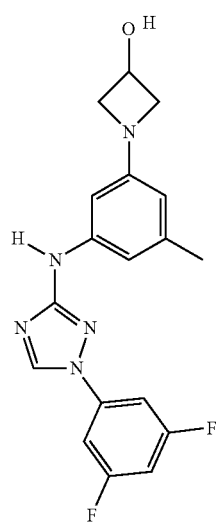
355
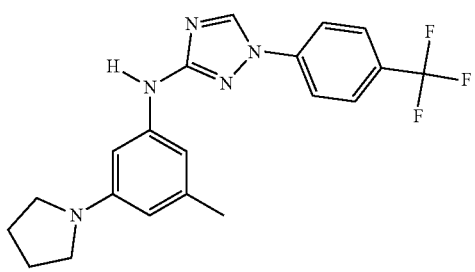
356
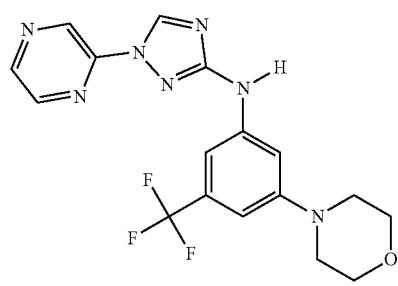 [SMILES: FC(F)(F)c1cc(Nc2ncn(-c3cnccn3)n2)cc(N2CCOCC2)c1]
357

TABLE 1-continued
Compound Table
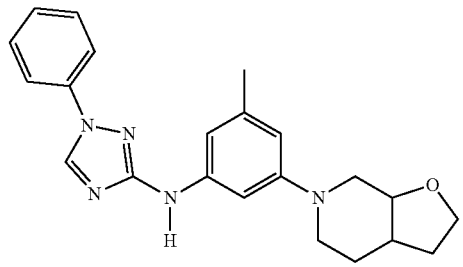 [SMILES: Cc1cc(Nc2ncn(-c3ccccc3)n2)cc(N2CCC3CCOC3C2)c1]
358
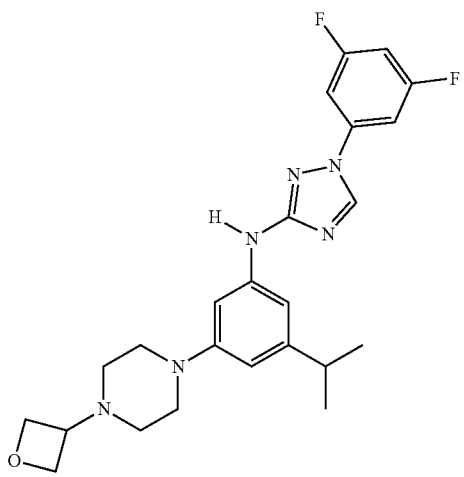 [SMILES: CC(C)c1cc(Nc2ncn(-c3cc(F)cc(F)c3)n2)cc(N2CCN(C3COC3)CC2)c1]
359
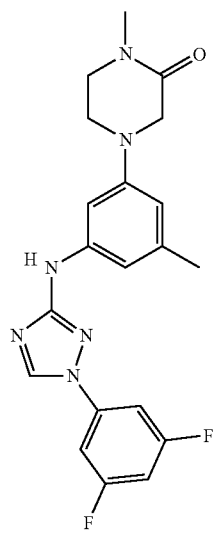
360
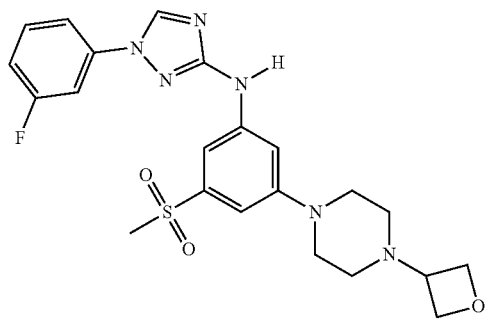 [SMILES: CS(=O)(=O)c1cc(Nc2ncn(-c3cccc(F)c3)n2)cc(N2CCN(C3COC3)CC2)c1]
361

TABLE 1-continued
Compound Table
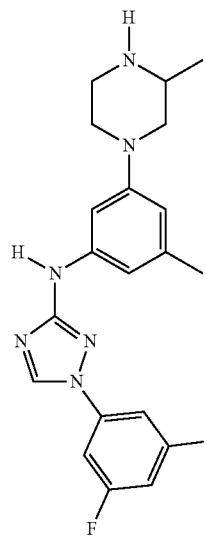
362
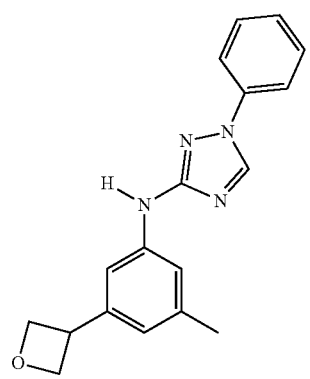 [SMILES: Cc1cc(Nc2ncn(-c3ccccc3)n2)cc(C2COC2)c1]
363
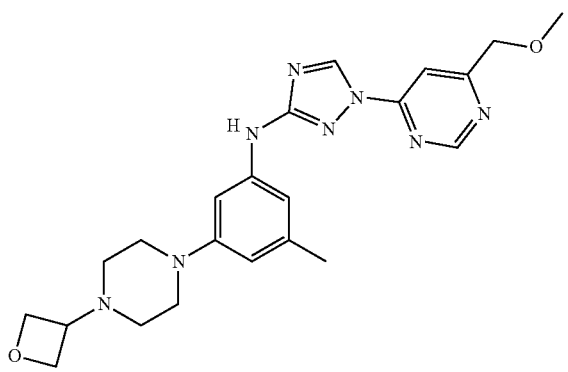
364
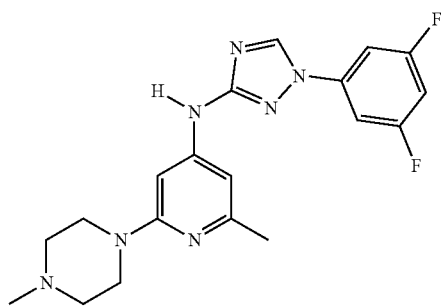 [SMILES: Cc1cc(Nc2ncn(-c3cc(F)cc(F)c3)n2)cc(N2CCN(C)CC2)n1]
365

TABLE 1-continued
Compound Table
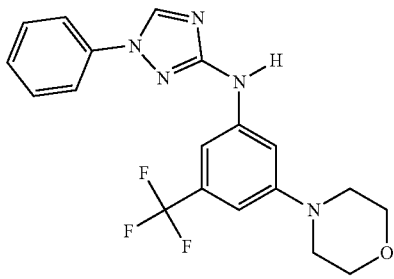 [SMILES: FC(F)(F)c1cc(Nc2ncn(-c3ccccc3)n2)cc(N2CCOCC2)c1]
366
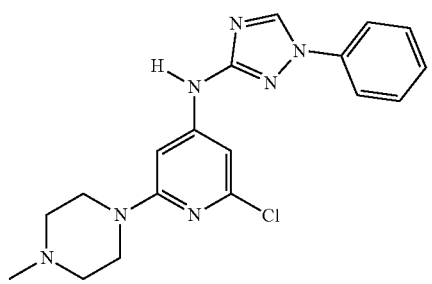
367
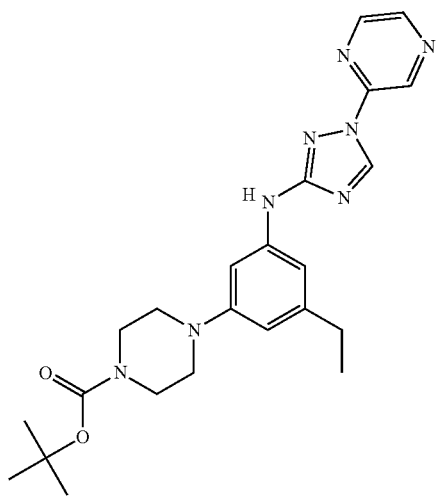
368
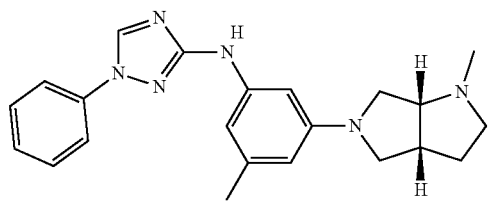
369
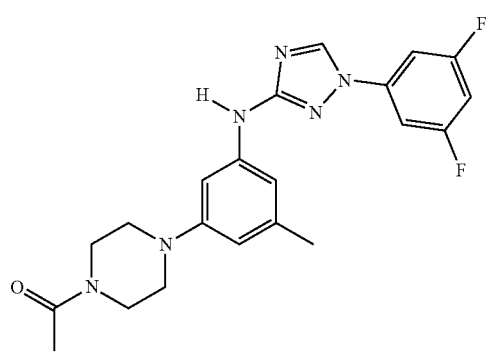 [SMILES: CC(=O)N1CCN(c2cc(C)cc(Nc3ncn(-c4cc(F)cc(F)c4)n3)c2)CC1]
370

TABLE 1-continued
Compound Table
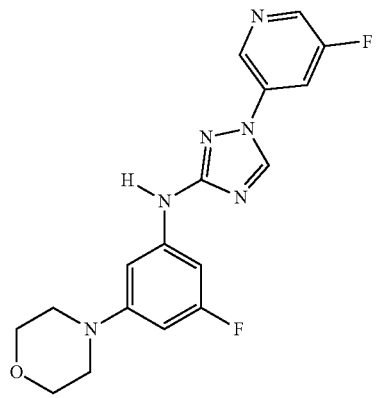 [SMILES: Fc1cc(Nc2ncn(-c3cncc(F)c3)n2)cc(N2CCOCC2)c1]
371
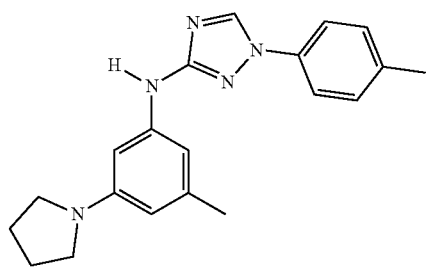 [SMILES: Cc1ccc(-n2cnc(Nc3cc(C)cc(N4CCCC4)c3)n2)cc1]
372
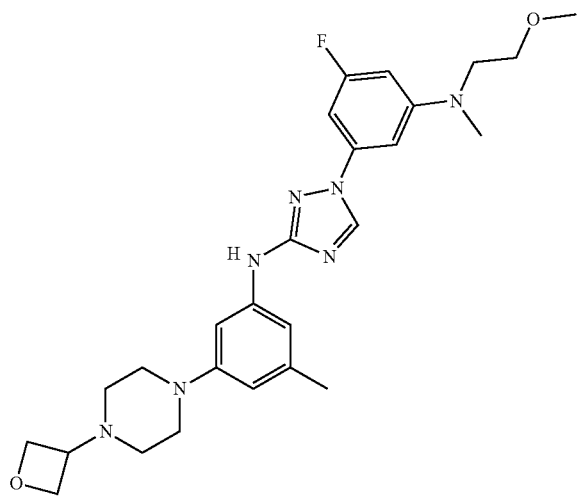
373
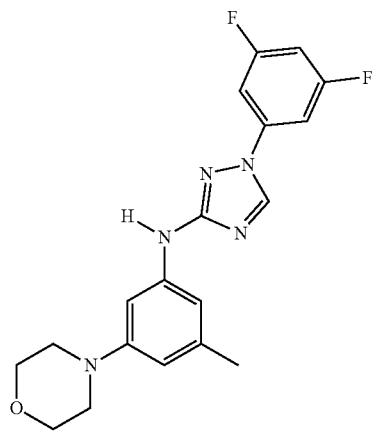 [SMILES: Cc1cc(Nc2ncn(-c3cc(F)cc(F)c3)n2)cc(N2CCOCC2)c1]
374

TABLE 1-continued
Compound Table
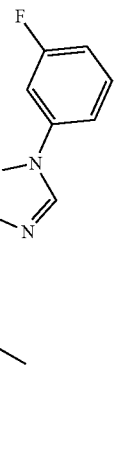 375
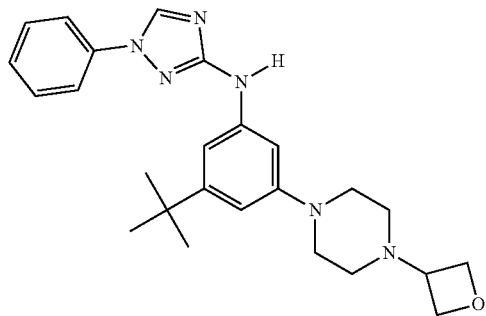 [SMILES: CC(C)(C)c1cc(Nc2ncn(-c3ccccc3)n2)cc(N2CCN(C3COC3)CC2)c1] 376
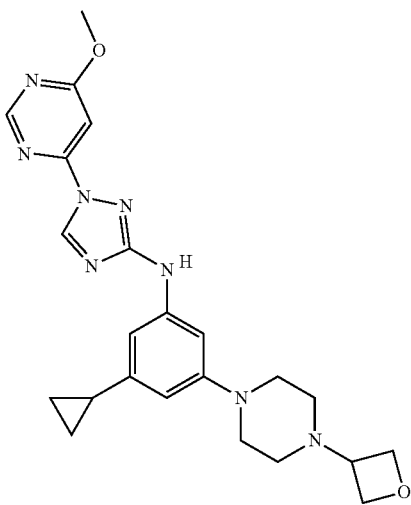 377
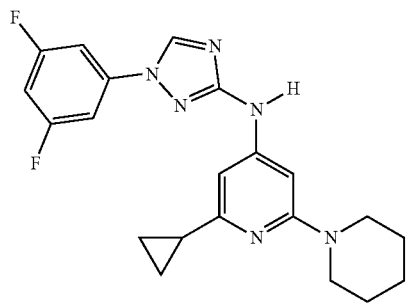 [SMILES: Fc1cc(F)cc(-n2cnc(Nc3cc(C4CC4)nc(N4CCCCC4)c3)n2)c1] 378

TABLE 1-continued
Compound Table
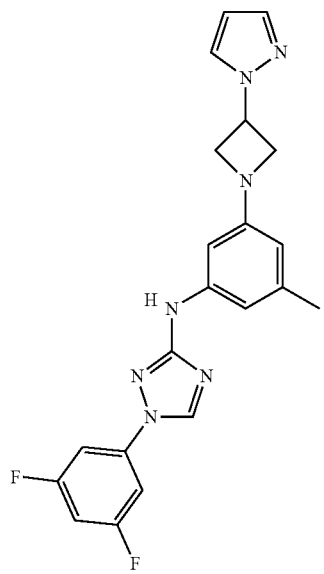
379
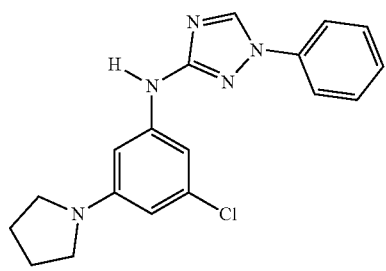 [SMILES: Clc1cc(Nc2ncn(-c3ccccc3)n2)cc(N2CCCC2)c1]
380
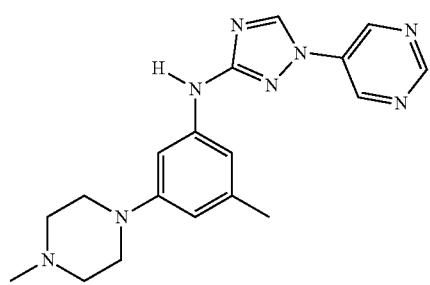 [SMILES: Cc1cc(Nc2ncn(-c3cncnc3)n2)cc(N2CCN(C)CC2)c1]
381

TABLE 1-continued
Compound Table
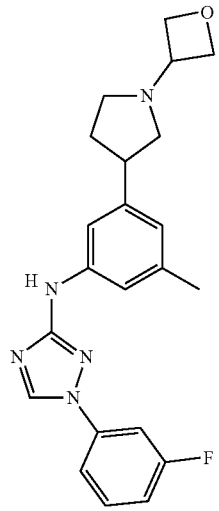
382
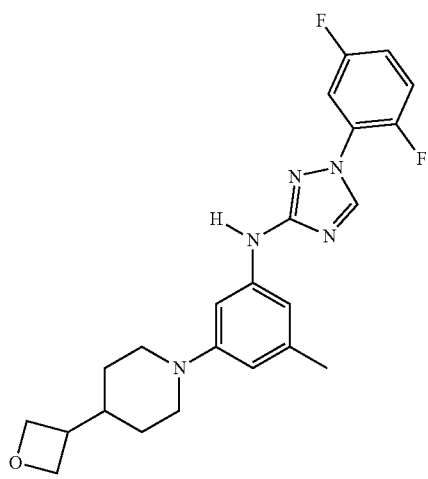
383
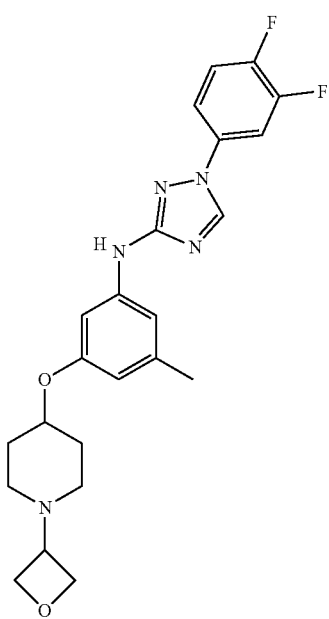
384

TABLE 1-continued
Compound Table
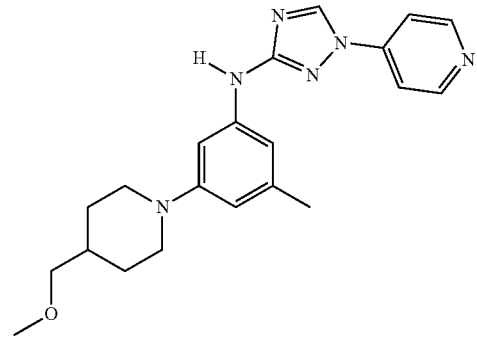 [SMILES: COCC1CCN(c2cc(C)cc(Nc3ncn(-c4ccncc4)n3)c2)CC1] 385
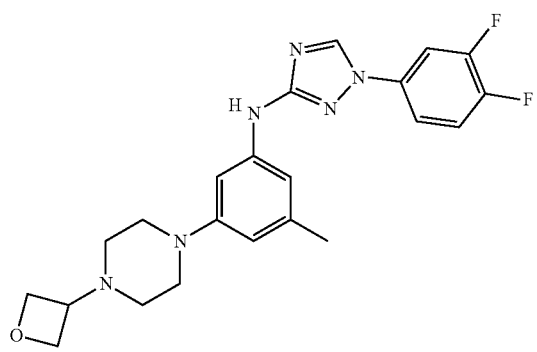 386
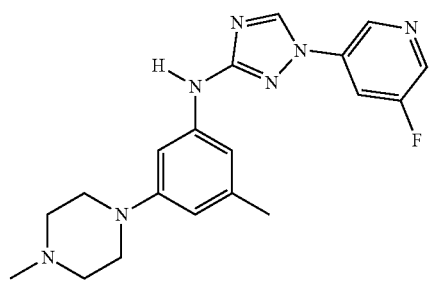 [SMILES: Cc1cc(Nc2ncn(-c3cncc(F)c3)n2)cc(N2CCN(C)CC2)c1] 387
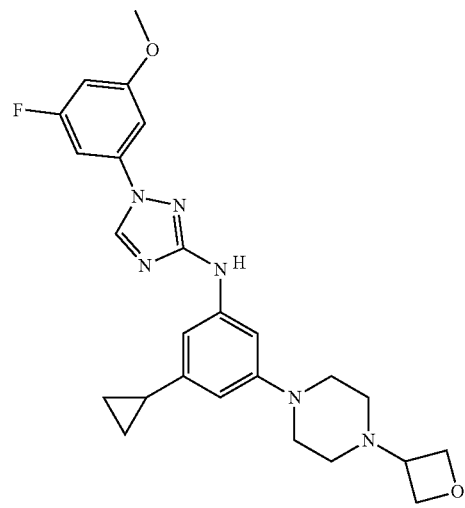 388

TABLE 1-continued
Compound Table
| | |
|---|---|
| 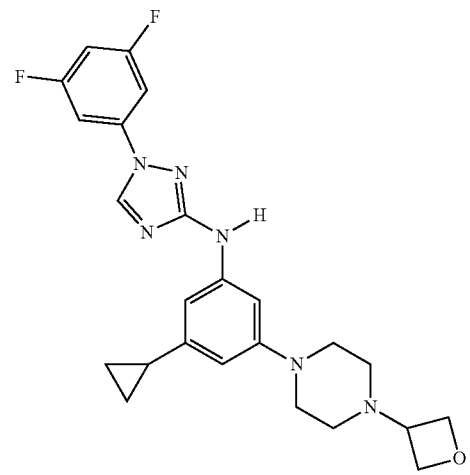 [SMILES: Fc1cc(F)cc(-n2cnc(Nc3cc(C4CC4)cc(N4CCN(C5COC5)CC4)c3)n2)c1] | 389 |
| 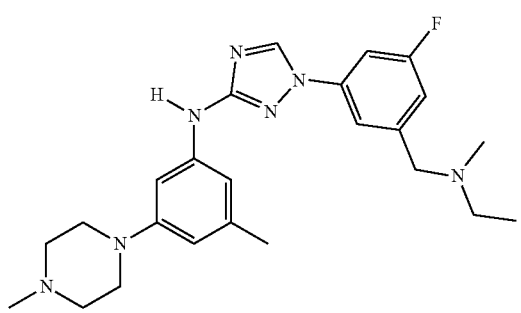 [SMILES: CCN(C)Cc1cc(F)cc(-n2cnc(Nc3cc(C)cc(N4CCN(C)CC4)c3)n2)c1] | 390 |
| 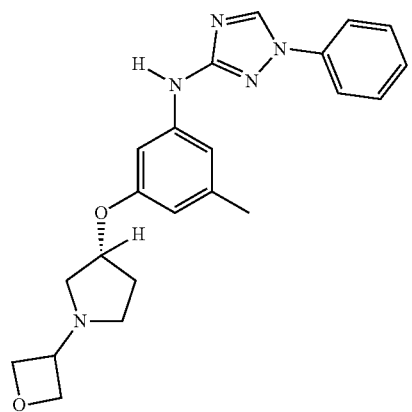 [SMILES: Cc1cc(Nc2ncn(-c3ccccc3)n2)cc(O[C@@H]2CCN(C3COC3)C2)c1] | 391 |
| 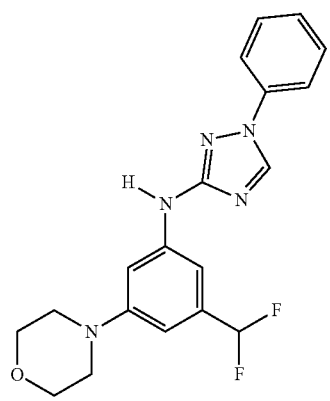 [SMILES: FC(F)c1cc(Nc2ncn(-c3ccccc3)n2)cc(N2CCOCC2)c1] | 392 |

TABLE 1-continued
Compound Table
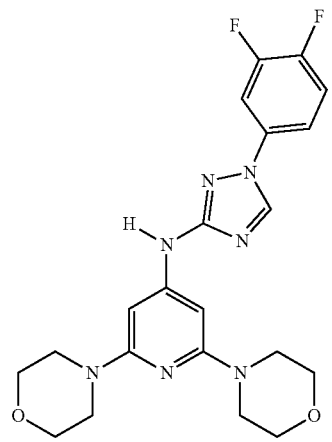 [SMILES: Fc1ccc(-n2cnc(Nc3cc(N4CCOCC4)nc(N4CCOCC4)c3)n2)cc1F]
393
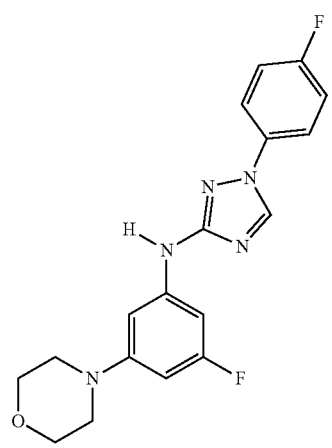 [SMILES: Fc1ccc(-n2cnc(Nc3cc(F)cc(N4CCOCC4)c3)n2)cc1]
394
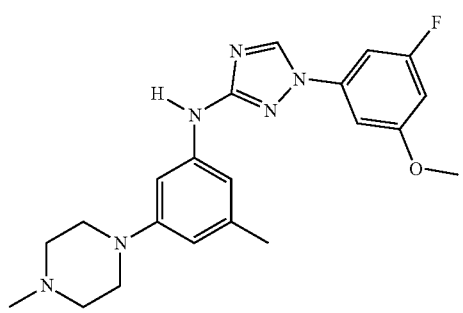
395

TABLE 1-continued
Compound Table
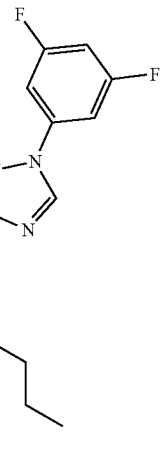 396
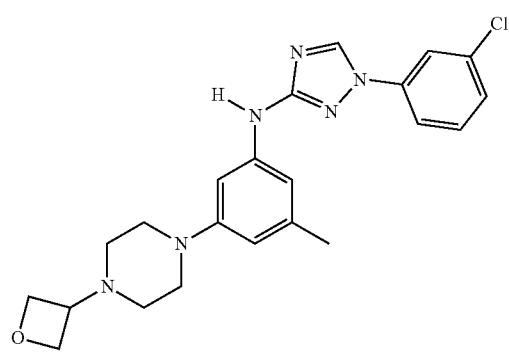 [SMILES: Cc1cc(Nc2ncn(-c3cccc(Cl)c3)n2)cc(N2CCN(C3COC3)CC2)c1] 397
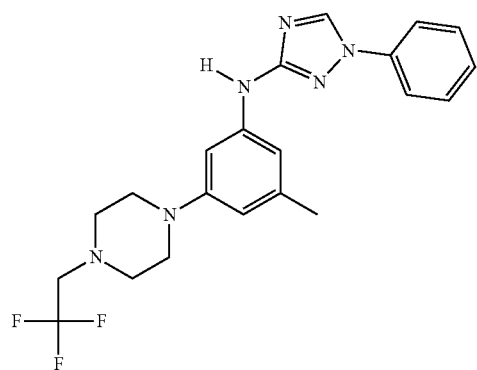 [SMILES: Cc1cc(Nc2ncn(-c3ccccc3)n2)cc(N2CCN(CC(F)(F)F)CC2)c1] 398
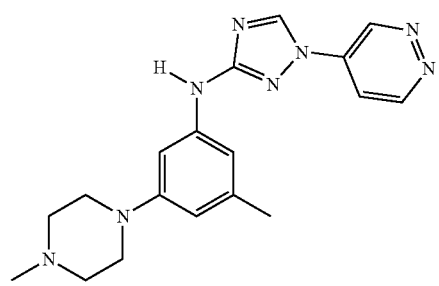 [SMILES: Cc1cc(Nc2ncn(-c3ccnnc3)n2)cc(N2CCN(C)CC2)c1] 399

TABLE 1-continued
Compound Table
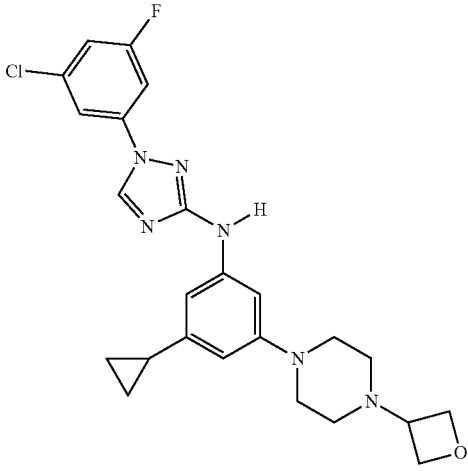 [SMILES: Fc1cc(Cl)cc(-n2cnc(Nc3cc(C4CC4)cc(N4CCN(C5COC5)CC4)c3)n2)c1]
400
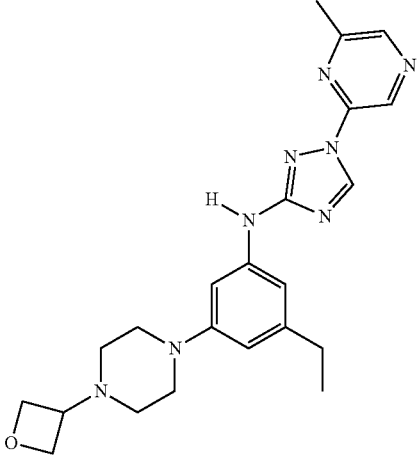 [SMILES: CCc1cc(Nc2ncn(-c3cncc(C)n3)n2)cc(N2CCN(C3COC3)CC2)c1]
401
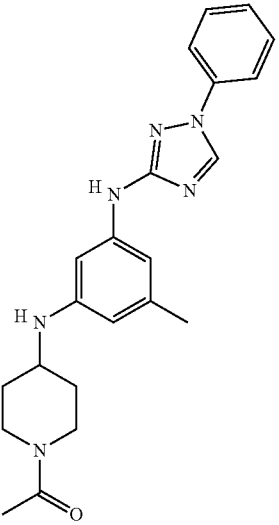
402

TABLE 1-continued
Compound Table
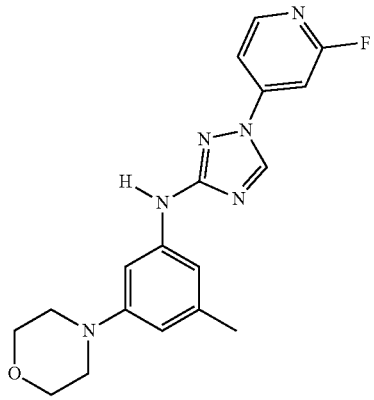 [SMILES: Cc1cc(Nc2ncn(-c3ccnc(F)c3)n2)cc(N2CCOCC2)c1]
403
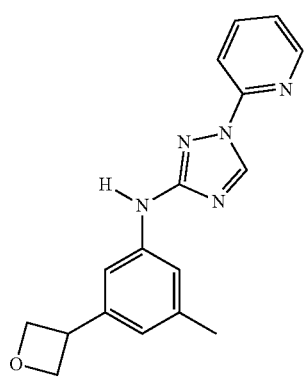 [SMILES: Cc1cc(Nc2ncn(-c3ccccn3)n2)cc(C2COC2)c1]
404
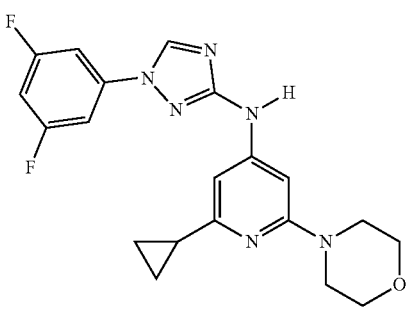 [SMILES: Fc1cc(F)cc(-n2cnc(Nc3cc(C4CC4)nc(N4CCOCC4)c3)n2)c1]
405
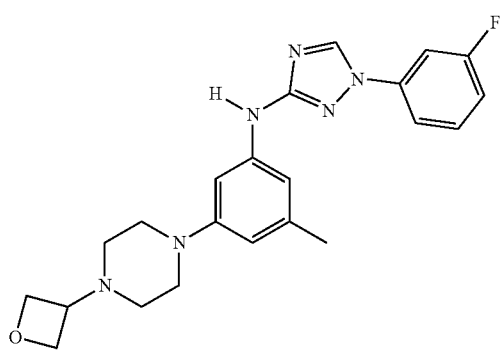 [SMILES: Cc1cc(Nc2ncn(-c3cccc(F)c3)n2)cc(N2CCN(C3COC3)CC2)c1]
406

TABLE 1-continued
Compound Table
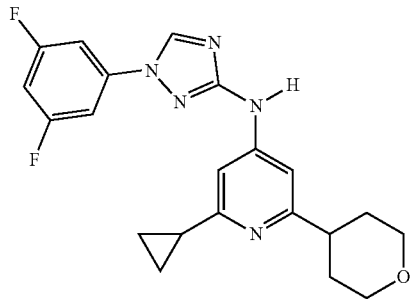 [SMILES: Fc1cc(F)cc(-n2cnc(Nc3cc(C4CCOCC4)nc(C4CC4)c3)n2)c1]
407
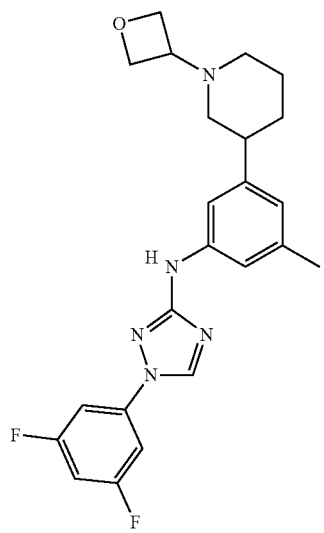
408
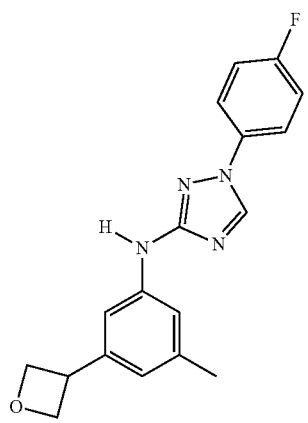 [SMILES: Cc1cc(Nc2ncn(-c3ccc(F)cc3)n2)cc(C2COC2)c1]
409

TABLE 1-continued
Compound Table
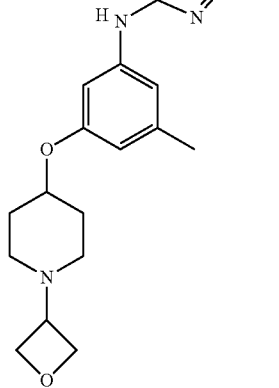
410
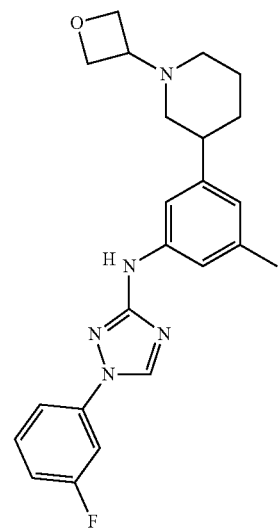
411
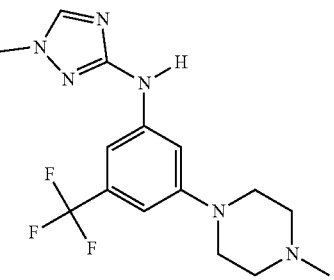
412

TABLE 1-continued
Compound Table
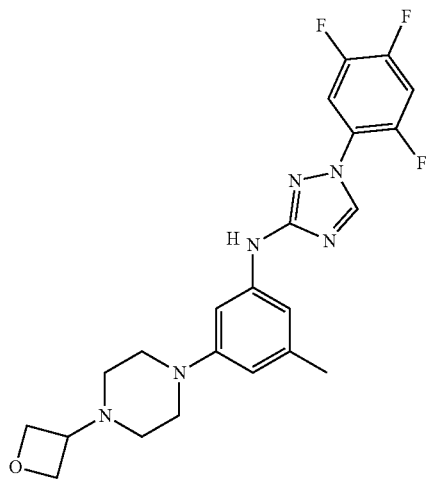
413
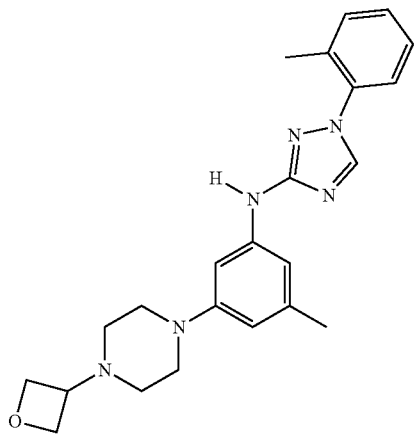 [SMILES: Cc1cc(Nc2ncn(-c3ccccc3C)n2)cc(N2CCN(C3COC3)CC2)c1]
414
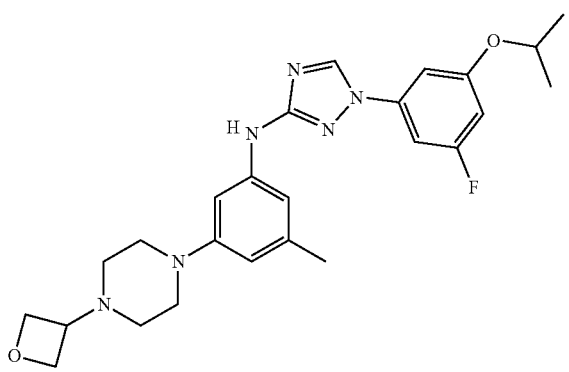
415

TABLE 1-continued
Compound Table
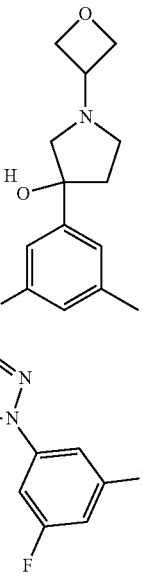 416
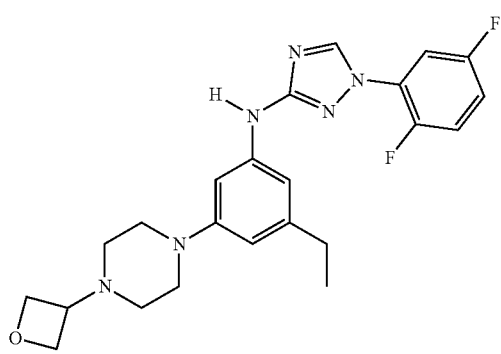 [SMILES: CCc1cc(Nc2ncn(-c3cc(F)ccc3F)n2)cc(N2CCN(C3COC3)CC2)c1] 417
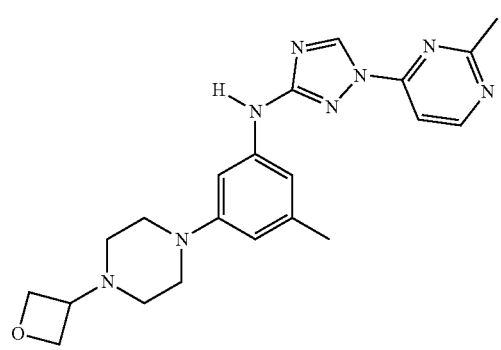 [SMILES: Cc1cc(Nc2ncn(-c3ccnc(C)n3)n2)cc(N2CCN(C3COC3)CC2)c1] 418

TABLE 1-continued
Compound Table
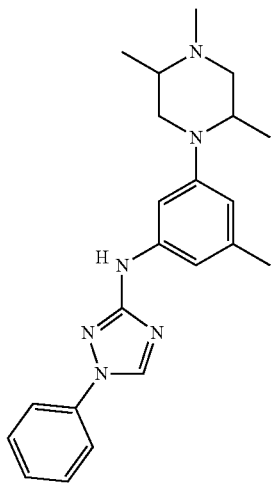
419
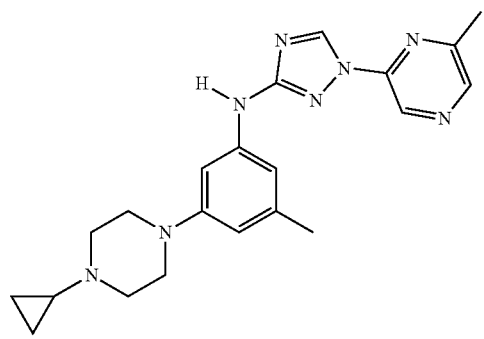 [SMILES: Cc1cc(Nc2ncn(-c3cncc(C)n3)n2)cc(N2CCN(C3CC3)CC2)c1]
420
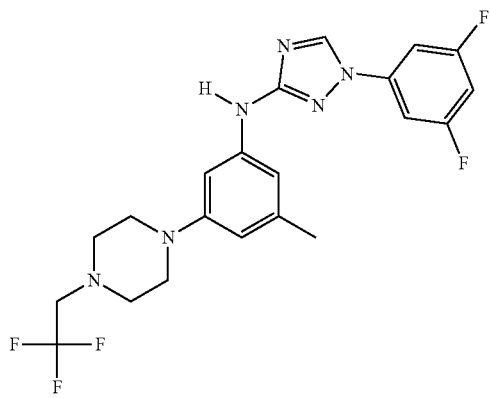 [SMILES: Cc1cc(Nc2ncn(-c3cc(F)cc(F)c3)n2)cc(N2CCN(CC(F)(F)F)CC2)c1]
421
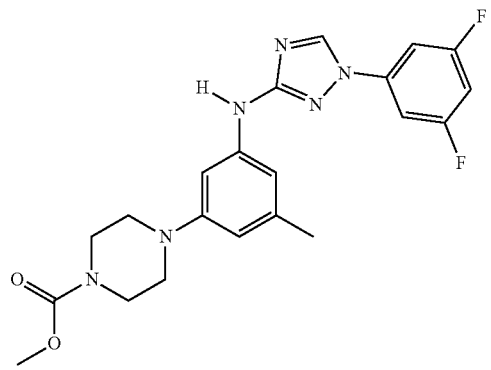 [SMILES: COC(=O)N1CCN(c2cc(C)cc(Nc3ncn(-c4cc(F)cc(F)c4)n3)c2)CC1]
422

TABLE 1-continued
Compound Table
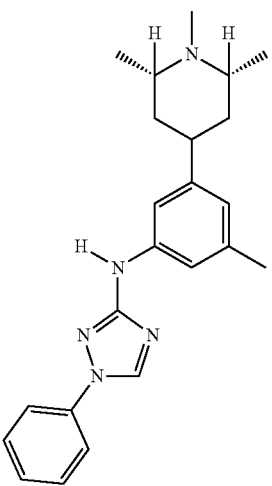 [SMILES: Cc1cc(Nc2ncn(-c3ccccc3)n2)cc(C2C[C@@H](C)N(C)[C@@H](C)C2)c1] 423
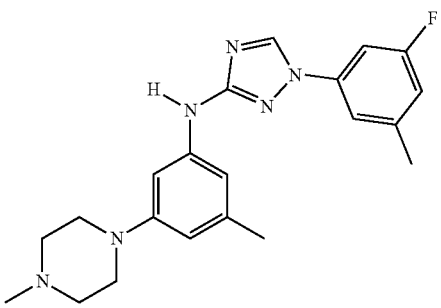 [SMILES: Cc1cc(Nc2ncn(-c3cc(C)cc(F)c3)n2)cc(N2CCN(C)CC2)c1] 424
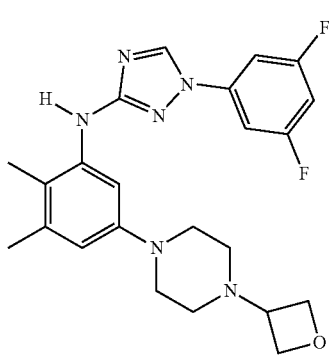 [SMILES: Cc1cc(N2CCN(C3COC3)CC2)cc(Nc2ncn(-c3cc(F)cc(F)c3)n2)c1C] 425
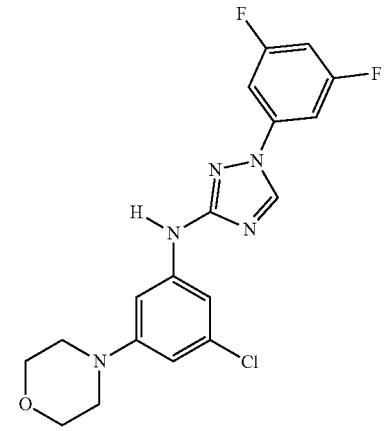 [SMILES: Fc1cc(F)cc(-n2cnc(Nc3cc(Cl)cc(N4CCOCC4)c3)n2)c1] 426

TABLE 1-continued
Compound Table
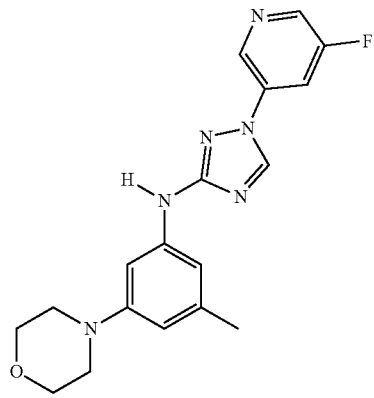 [SMILES: Cc1cc(Nc2ncn(-c3cncc(F)c3)n2)cc(N2CCOCC2)c1]
427
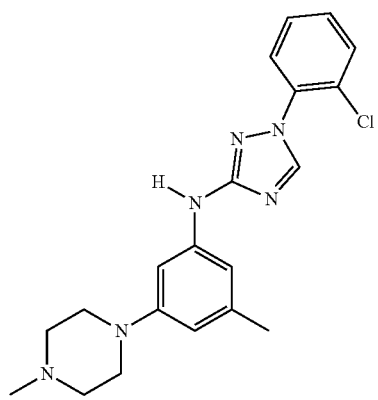 [SMILES: Cc1cc(Nc2ncn(-c3ccccc3Cl)n2)cc(N2CCN(C)CC2)c1]
428
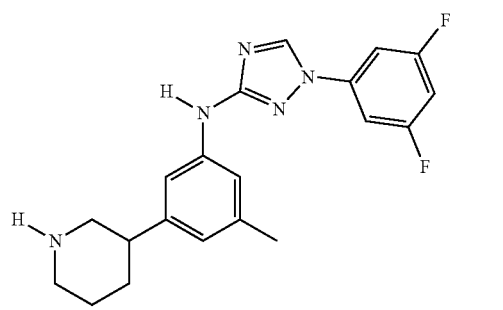 [SMILES: Cc1cc(Nc2ncn(-c3cc(F)cc(F)c3)n2)cc(C2CCCNC2)c1]
429
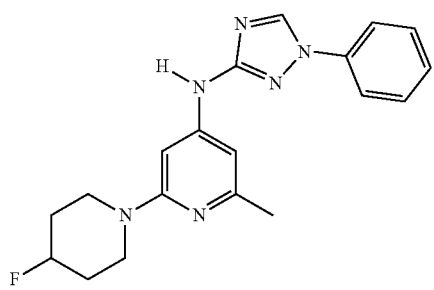 [SMILES: Cc1cc(Nc2ncn(-c3ccccc3)n2)cc(N2CCC(F)CC2)n1]
430

TABLE 1-continued
Compound Table
431
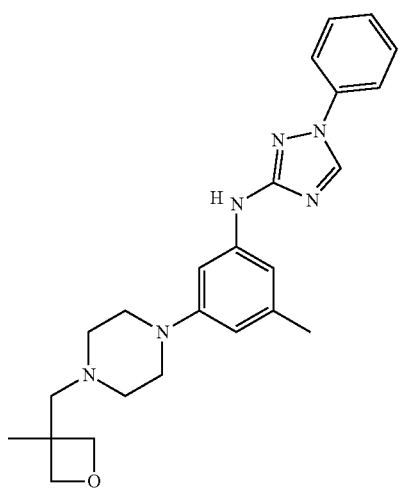
432
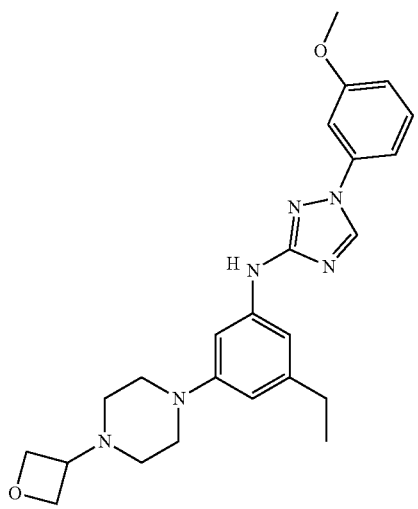
433
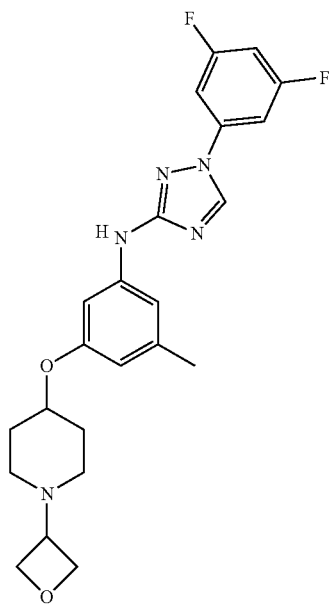

TABLE 1-continued
Compound Table
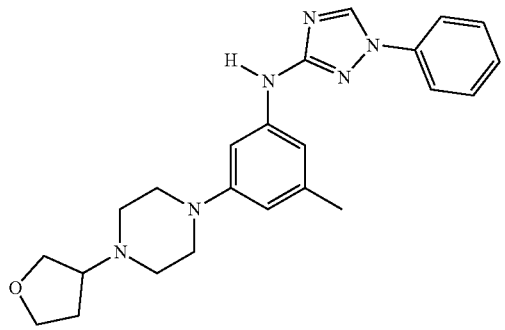 [SMILES: Cc1cc(Nc2ncn(-c3ccccc3)n2)cc(N2CCN(C3CCOC3)CC2)c1]   434
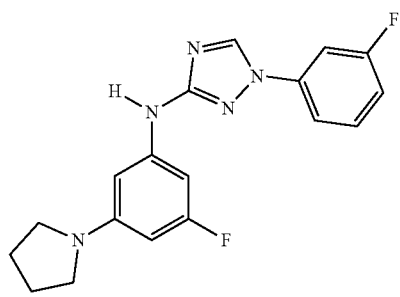 [SMILES: Fc1cc(Nc2ncn(-c3cccc(F)c3)n2)cc(N2CCCC2)c1]   435
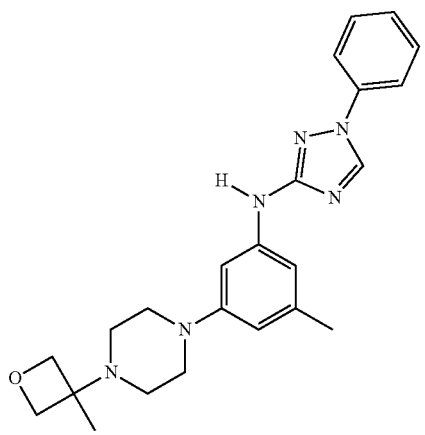 [SMILES: Cc1cc(Nc2ncn(-c3ccccc3)n2)cc(N2CCN(C3(C)COC3)CC2)c1]   436
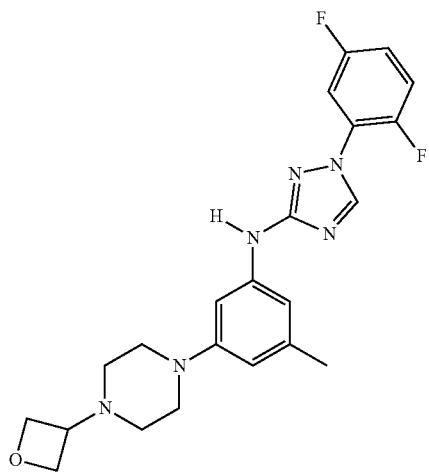 [SMILES: Cc1cc(Nc2ncn(-c3cc(F)ccc3F)n2)cc(N2CCN(C3COC3)CC2)c1]   437

TABLE 1-continued
Compound Table
| | |
|---|---|
| 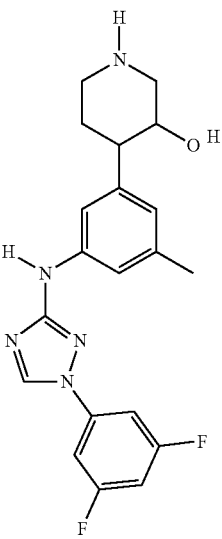 | 438 |
| 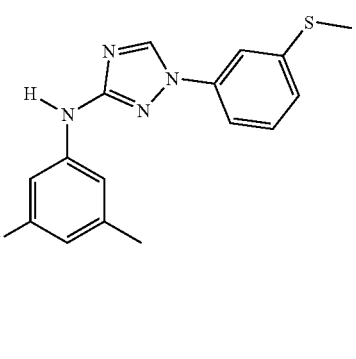 | 439 |
| 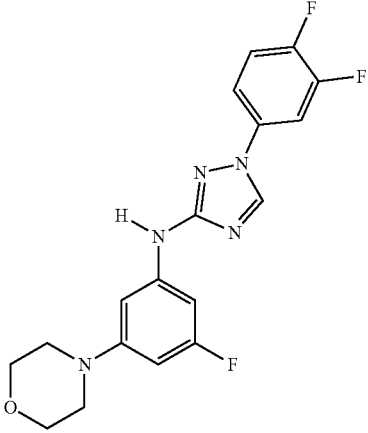 [SMILES: Fc1cc(Nc2ncn(-c3ccc(F)c(F)c3)n2)cc(N2CCOCC2)c1] | 440 |
| 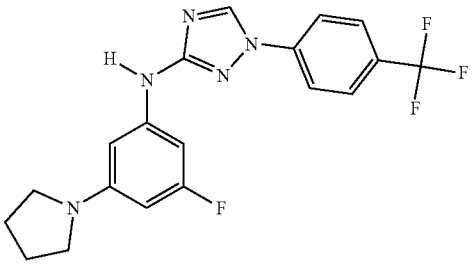 [SMILES: Fc1cc(Nc2ncn(-c3ccc(C(F)(F)F)cc3)n2)cc(N2CCCC2)c1] | 441 |

TABLE 1-continued
Compound Table
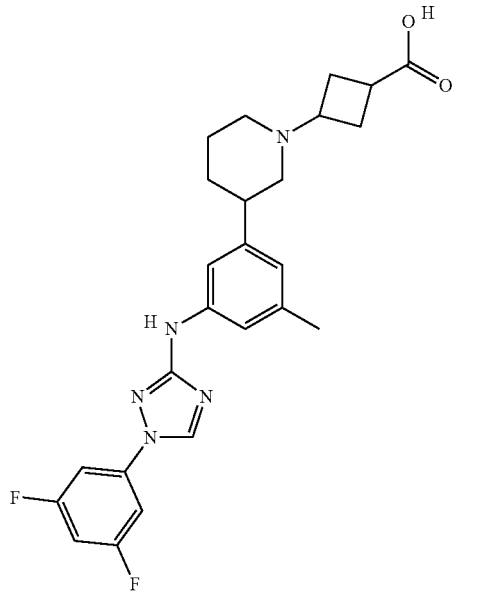 442
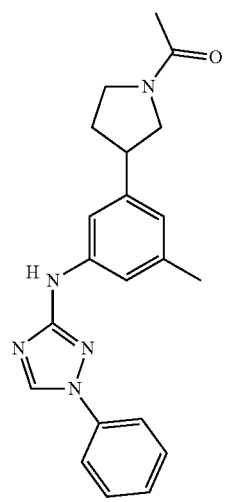 443
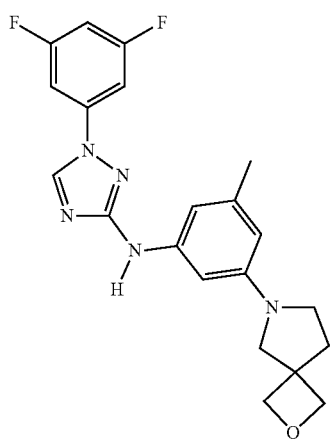 [SMILES: Cc1cc(Nc2ncn(-c3cc(F)cc(F)c3)n2)cc(N2CCC3(COC3)C2)c1] 444

TABLE 1-continued
Compound Table
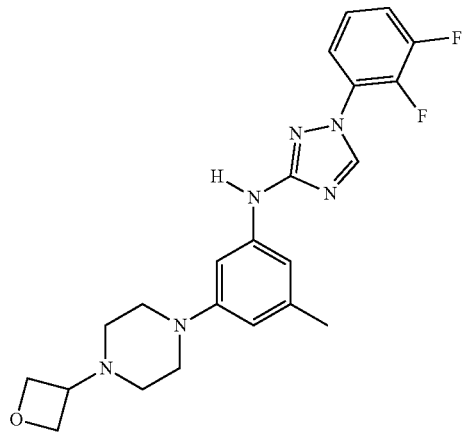 [SMILES: Cc1cc(Nc2ncn(-c3cccc(F)c3F)n2)cc(N2CCN(C3COC3)CC2)c1]
445
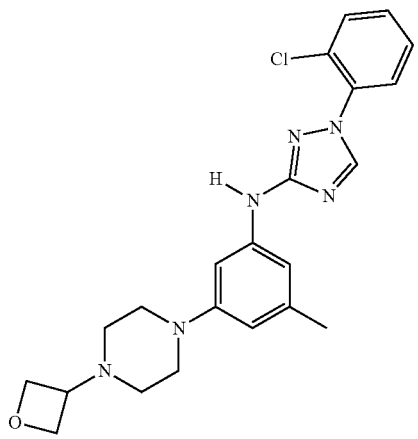 [SMILES: Cc1cc(Nc2ncn(-c3ccccc3Cl)n2)cc(N2CCN(C3COC3)CC2)c1]
446
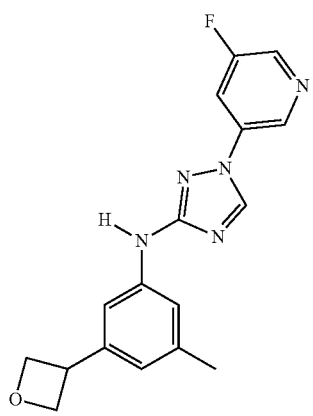 [SMILES: Cc1cc(Nc2ncn(-c3cncc(F)c3)n2)cc(C2COC2)c1]
447

TABLE 1-continued
Compound Table
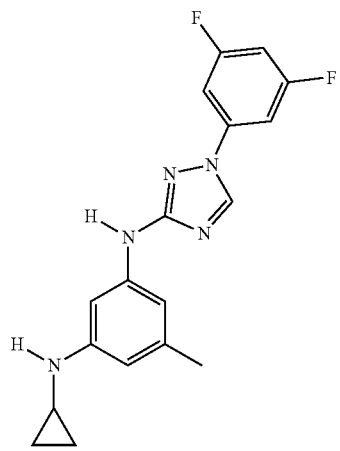 [SMILES: Cc1cc(Nc2ncn(-c3cc(F)cc(F)c3)n2)cc(NC2CC2)c1]
448
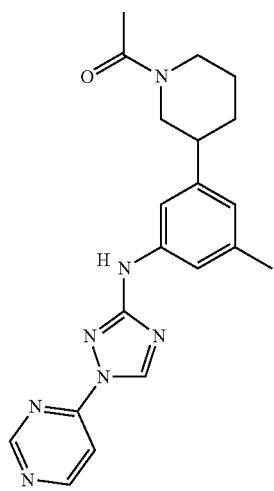
449
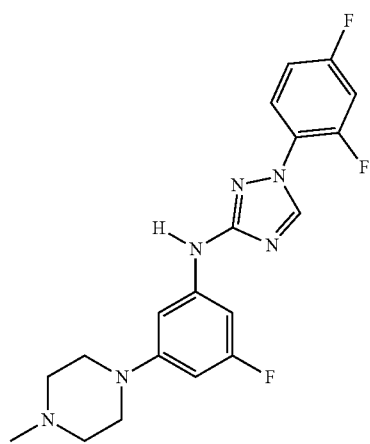 [SMILES: CN1CCN(c2cc(F)cc(Nc3ncn(-c4ccc(F)cc4F)n3)c2)CC1]
450

TABLE 1-continued
Compound Table
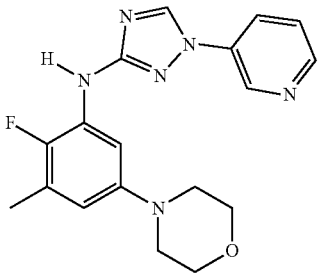 [SMILES: Cc1cc(N2CCOCC2)cc(Nc2ncn(-c3cccnc3)n2)c1F]
451
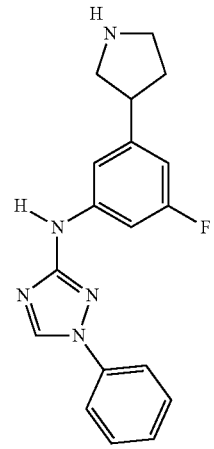
452
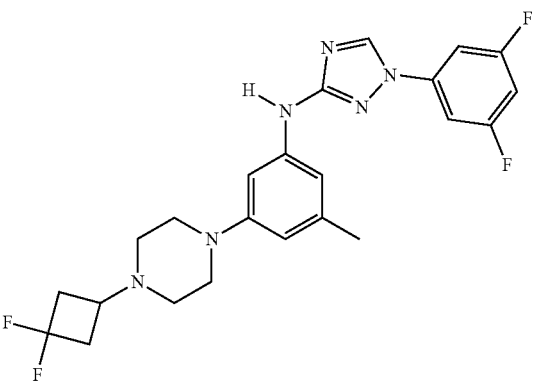 [SMILES: Cc1cc(Nc2ncn(-c3cc(F)cc(F)c3)n2)cc(N2CCN(C3CC(F)(F)C3)CC2)c1]
453
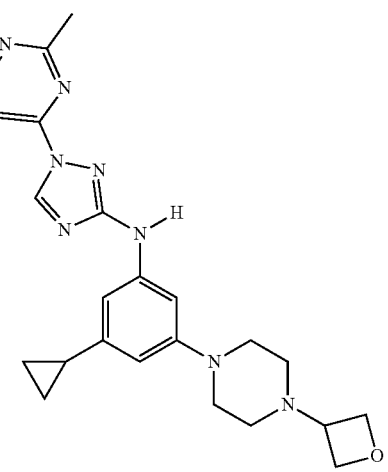
454

TABLE 1-continued
Compound Table
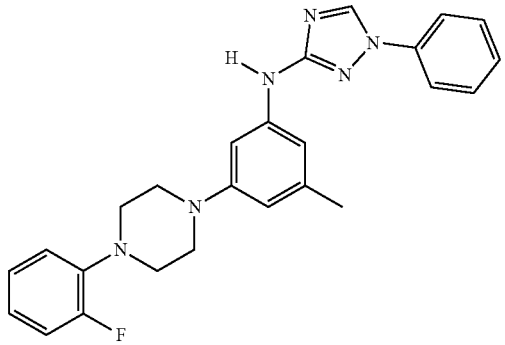 [SMILES: Cc1cc(Nc2ncn(-c3ccccc3)n2)cc(N2CCN(c3ccccc3F)CC2)c1]
455
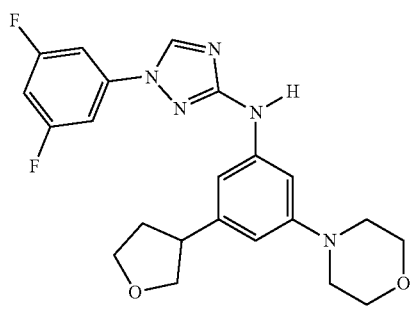
456
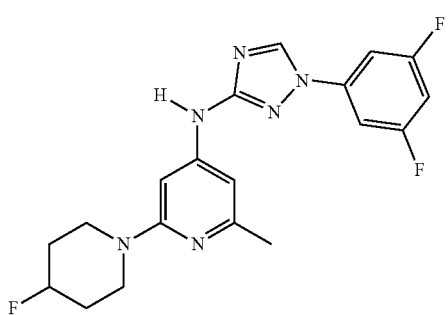 [SMILES: Cc1cc(Nc2ncn(-c3cc(F)cc(F)c3)n2)cc(N2CCC(F)CC2)n1]
457
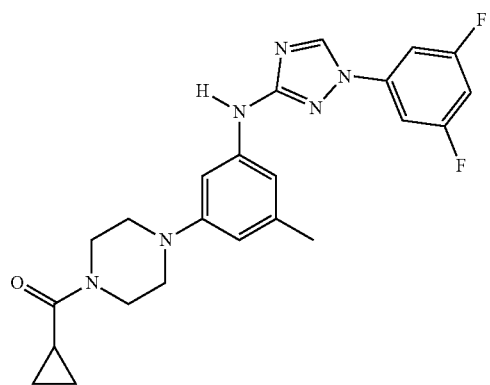 [SMILES: Cc1cc(Nc2ncn(-c3cc(F)cc(F)c3)n2)cc(N2CCN(C(=O)C3CC3)CC2)c1]
458

TABLE 1-continued
Compound Table
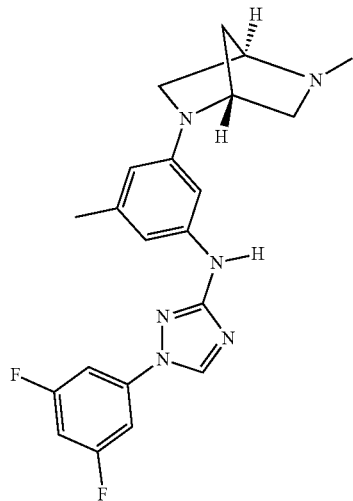 [SMILES: Cc1cc(Nc2ncn(-c3cc(F)cc(F)c3)n2)cc(N2C[C@H]3C[C@@H]2CN3C)c1]
459
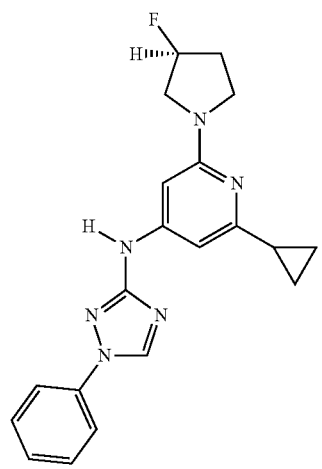 [SMILES: F[C@H]1CCN(c2cc(Nc3ncn(-c4ccccc4)n3)cc(C3CC3)n2)C1]
460
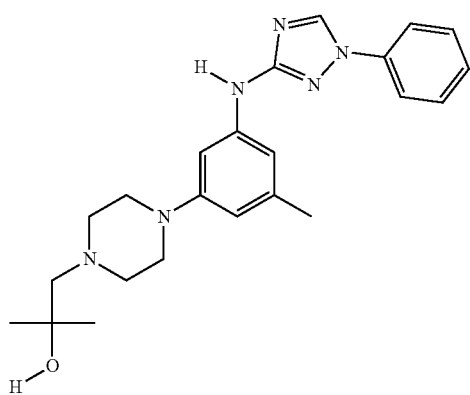 [SMILES: Cc1cc(Nc2ncn(-c3ccccc3)n2)cc(N2CCN(CC(C)(C)O)CC2)c1]
461

TABLE 1-continued
Compound Table
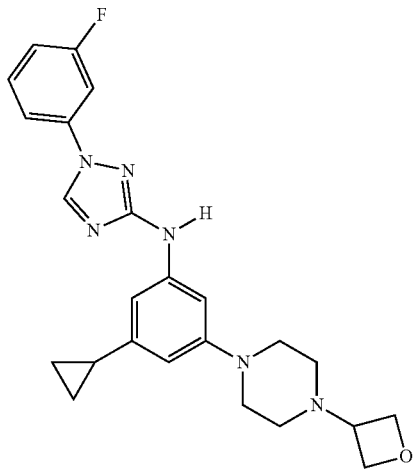 [SMILES: Fc1cccc(-n2cnc(Nc3cc(C4CC4)cc(N4CCN(C5COC5)CC4)c3)n2)c1]
462
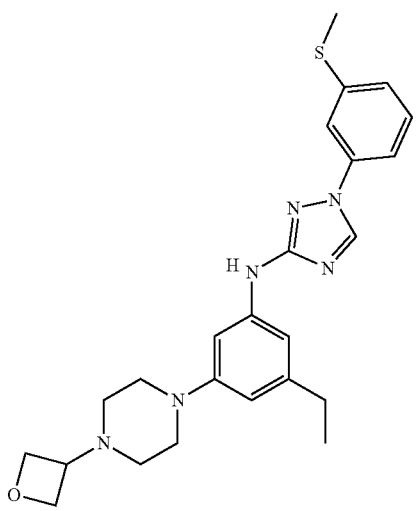
463
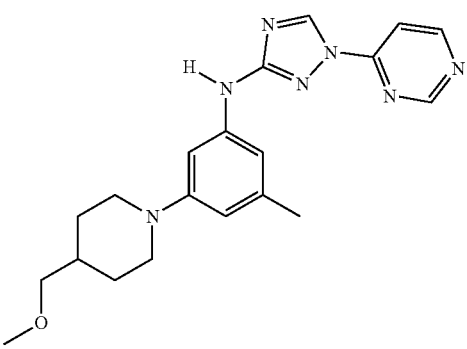 [SMILES: COCC1CCN(c2cc(C)cc(Nc3ncn(-c4ccncn4)n3)c2)CC1]
464
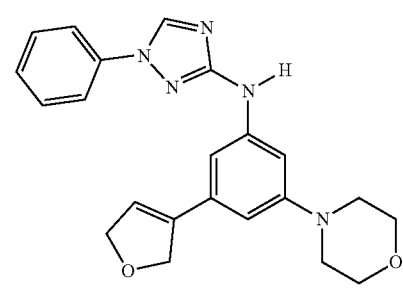 [SMILES: C1=C(c2cc(Nc3ncn(-c4ccccc4)n3)cc(N3CCOCC3)c2)COC1]
465

TABLE 1-continued
Compound Table
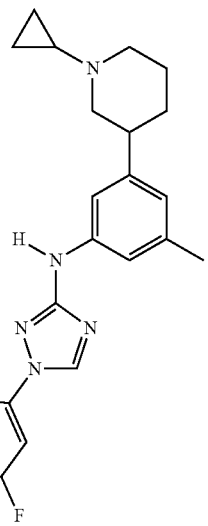
466
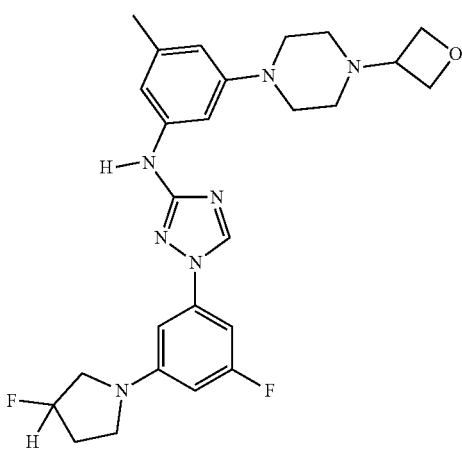 [SMILES: Cc1cc(Nc2ncn(-c3cc(F)cc(N4CCC(F)C4)c3)n2)cc(N2CCN(C3COC3)CC2)c1]
467
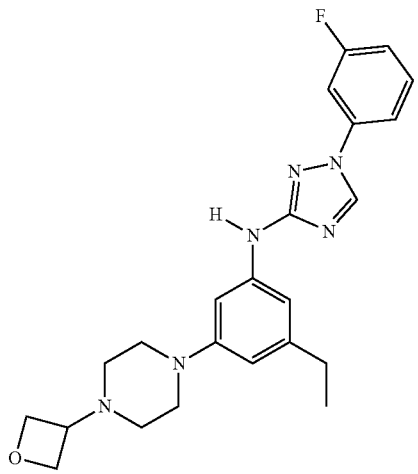
468

TABLE 1-continued
Compound Table
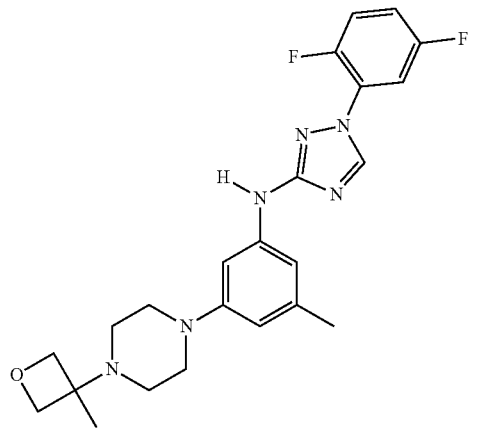 [SMILES: Cc1cc(Nc2ncn(-c3cc(F)ccc3F)n2)cc(N2CCN(C3(C)COC3)CC2)c1]
469
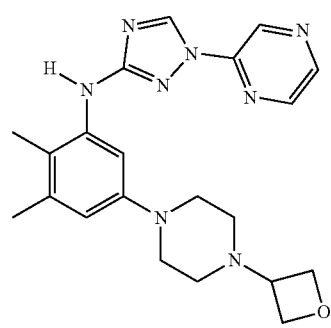 [SMILES: Cc1cc(N2CCN(C3COC3)CC2)cc(Nc2ncn(-c3cnccn3)n2)c1C]
470
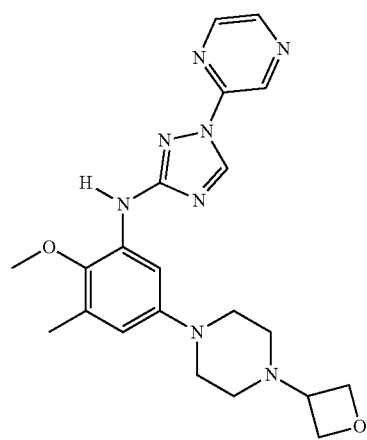 [SMILES: COc1c(C)cc(N2CCN(C3COC3)CC2)cc1Nc1ncn(-c2cnccn2)n1]
471

TABLE 1-continued
Compound Table
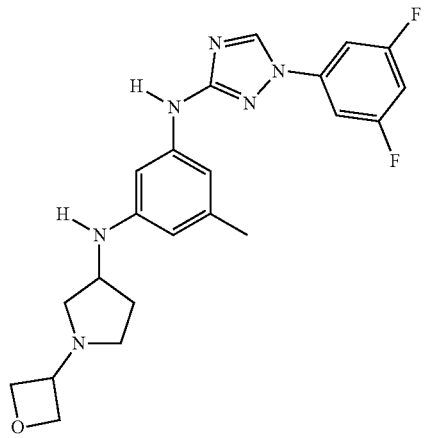 [SMILES: Cc1cc(Nc2ncn(-c3cc(F)cc(F)c3)n2)cc(NC2CCN(C3COC3)C2)c1]
472
473
475

TABLE 1-continued
Compound Table
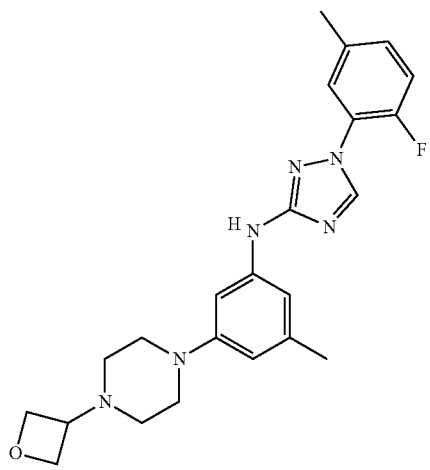
476
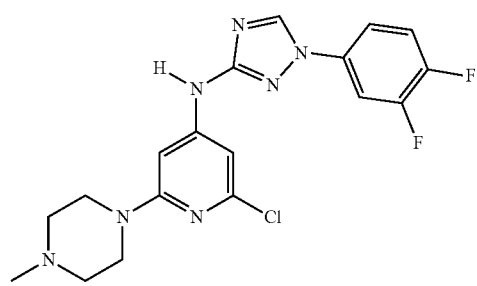 [SMILES: CN1CCN(c2cc(Nc3ncn(-c4ccc(F)c(F)c4)n3)cc(Cl)n2)CC1]
477
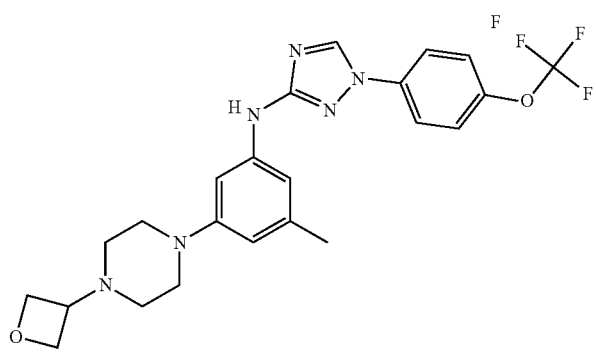
478
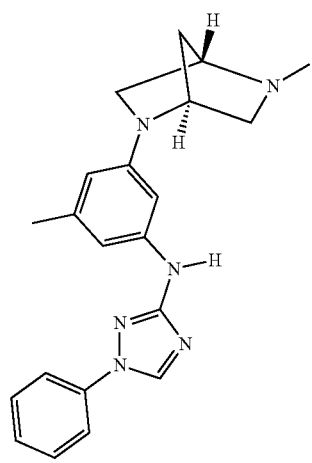 [SMILES: Cc1cc(Nc2ncn(-c3ccccc3)n2)cc(N2C[C@@H]3C[C@H]2CN3C)c1]
479

TABLE 1-continued
Compound Table
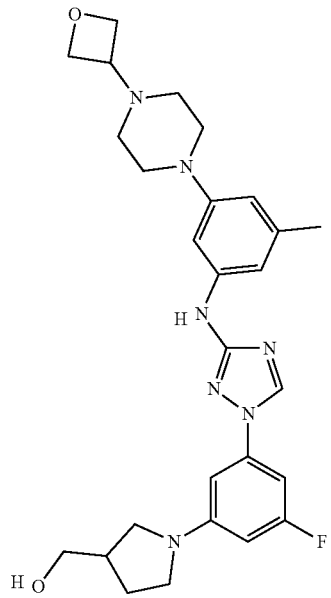
480
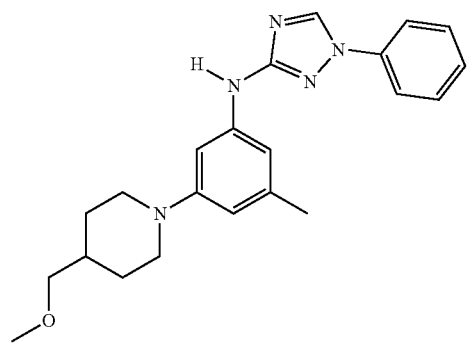 [SMILES: COCC1CCN(c2cc(C)cc(Nc3ncn(-c4ccccc4)n3)c2)CC1]
481
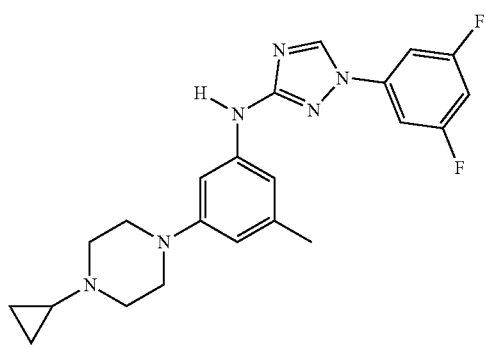 [SMILES: Cc1cc(Nc2ncn(-c3cc(F)cc(F)c3)n2)cc(N2CCN(C3CC3)CC2)c1]
482

TABLE 1-continued
Compound Table
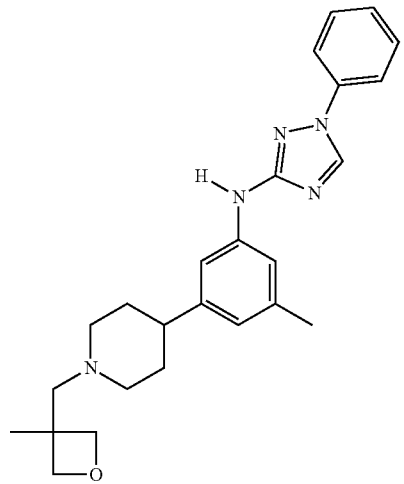 [SMILES: Cc1cc(Nc2ncn(-c3ccccc3)n2)cc(C2CCN(CC3(C)COC3)CC2)c1]
483
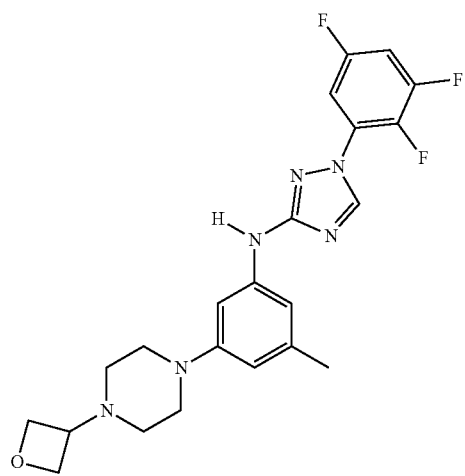 [SMILES: Cc1cc(Nc2ncn(-c3cc(F)cc(F)c3F)n2)cc(N2CCN(C3COC3)CC2)c1]
484
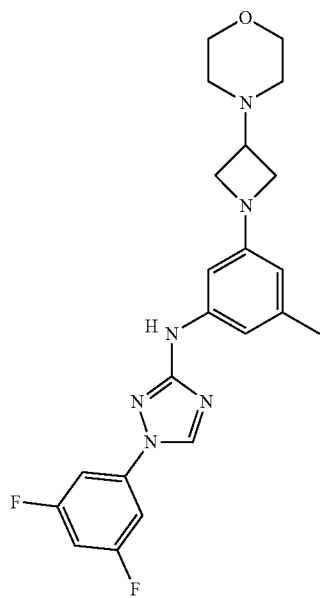
485

TABLE 1-continued
Compound Table
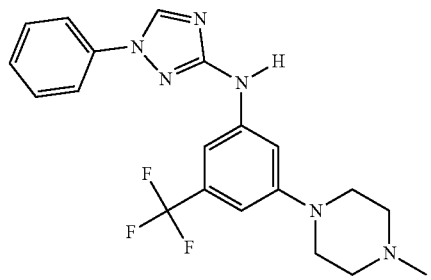 [SMILES: CN1CCN(c2cc(Nc3ncn(-c4ccccc4)n3)cc(C(F)(F)F)c2)CC1]
486
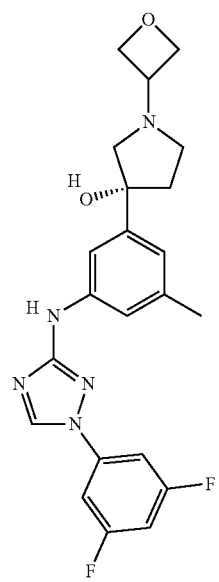
487
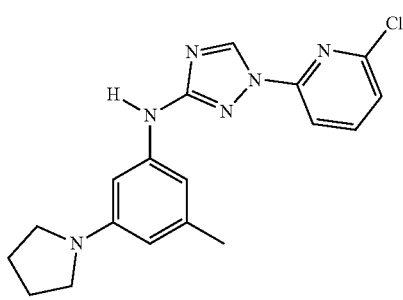 [SMILES: Cc1cc(Nc2ncn(-c3cccc(Cl)n3)n2)cc(N2CCCC2)c1]
488
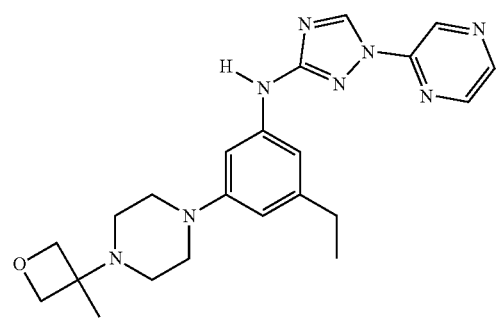 [SMILES: CCc1cc(Nc2ncn(-c3cnccn3)n2)cc(N2CCN(C3(C)COC3)CC2)c1]
489

TABLE 1-continued
Compound Table
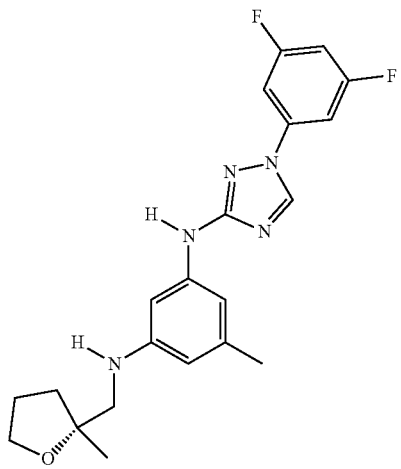 [SMILES: Cc1cc(NC[C@@]2(C)CCCO2)cc(Nc2ncn(-c3cc(F)cc(F)c3)n2)c1]
490
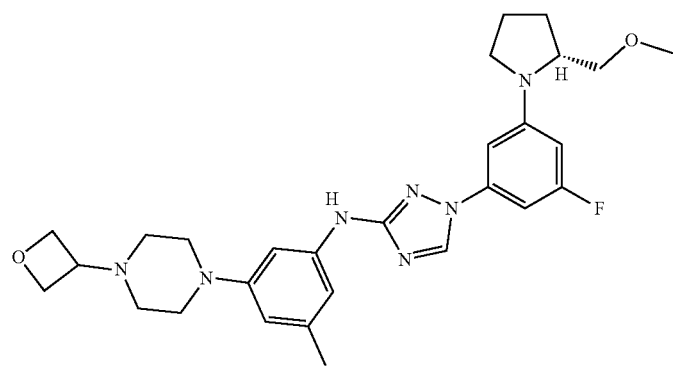
491
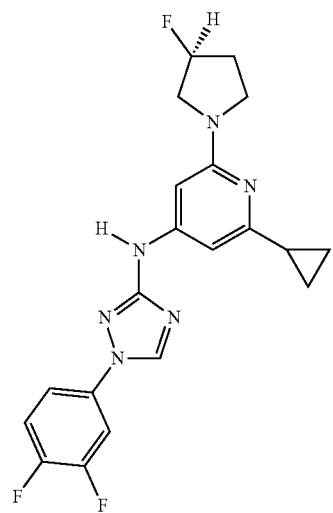 [SMILES: Fc1ccc(-n2cnc(Nc3cc(C4CC4)nc(N4CC[C@H](F)C4)c3)n2)cc1F]
492

US 10,766,869 B2
417
418
TABLE 1-continued
Compound Table
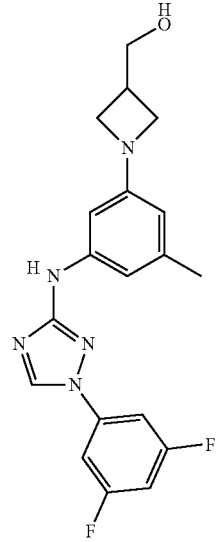
493
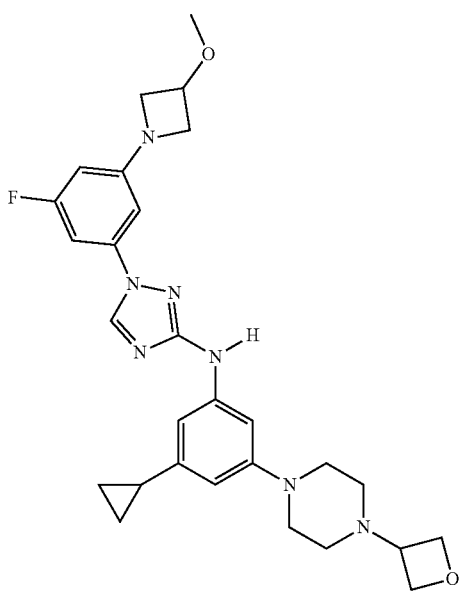 [SMILES: COC1CN(c2cc(F)cc(-n3cnc(Nc4cc(C5CC5)cc(N5CCN(C6COC6)CC5)c4)n3)c2)C1]
494
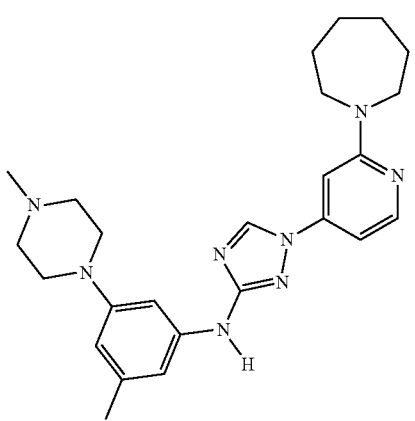 [SMILES: Cc1cc(Nc2ncn(-c3ccnc(N4CCCCCC4)c3)n2)cc(N2CCN(C)CC2)c1]
495

TABLE 1-continued
Compound Table
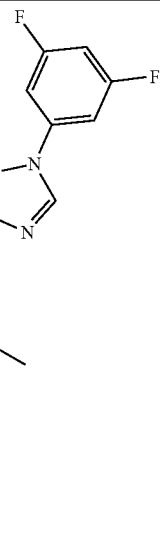
496
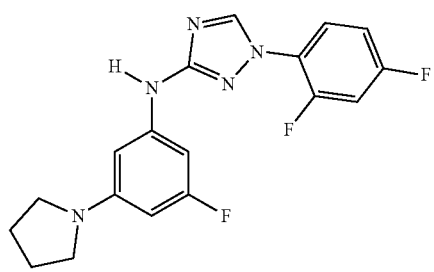 [SMILES: Fc1cc(Nc2ncn(-c3ccc(F)cc3F)n2)cc(N2CCCC2)c1]
497
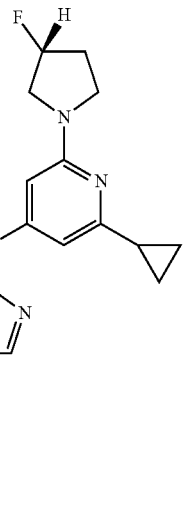
498
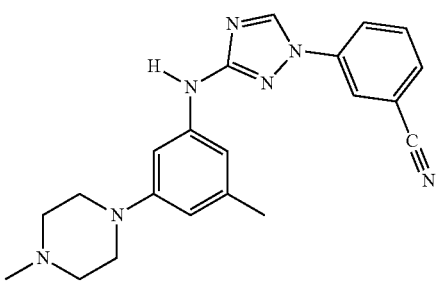 [SMILES: Cc1cc(Nc2ncn(-c3cccc(C#N)c3)n2)cc(N2CCN(C)CC2)c1]
499

TABLE 1-continued
Compound Table
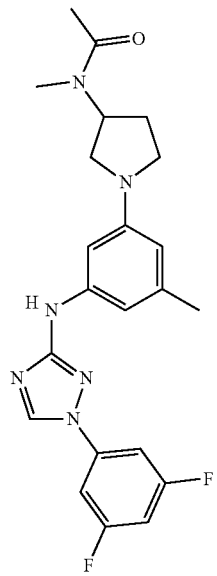
500
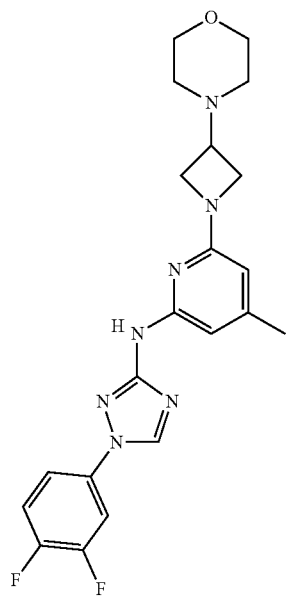
501

TABLE 1-continued
Compound Table
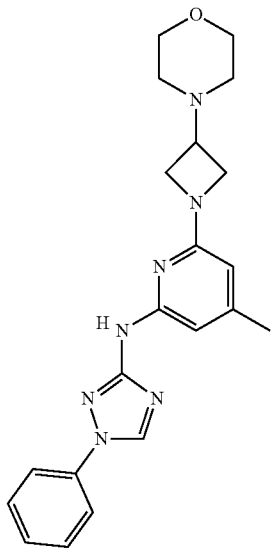
502
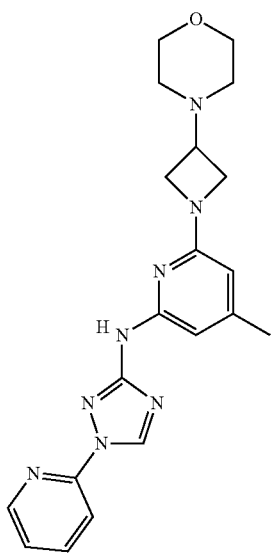
503

TABLE 1-continued
Compound Table
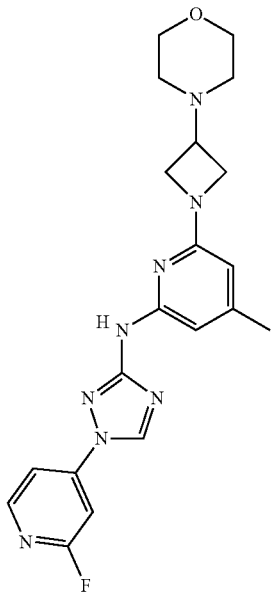
504
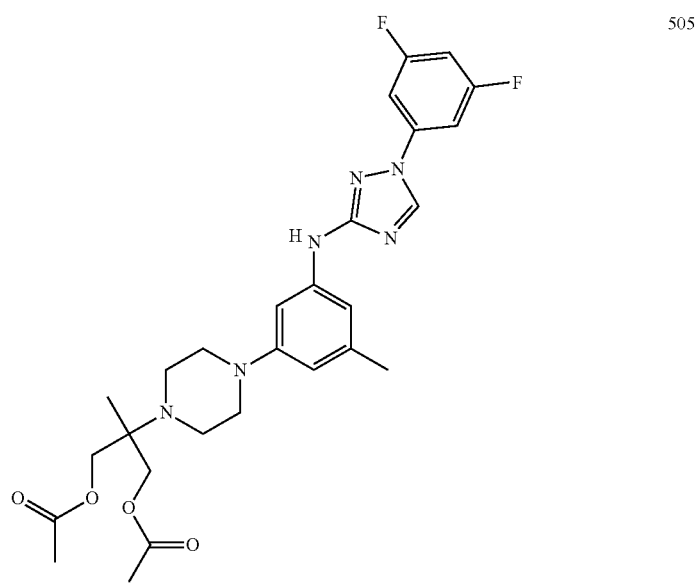
505

TABLE 1-continued
Compound Table
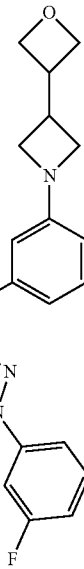
506
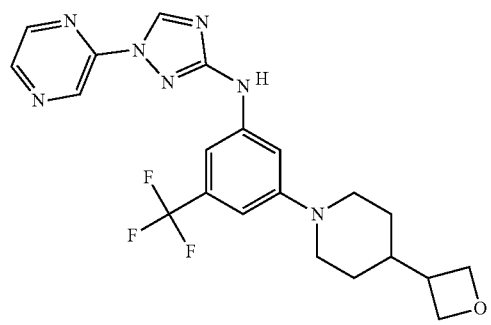
507
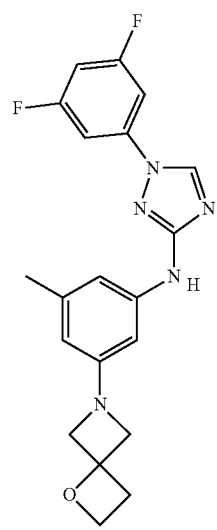
508

TABLE 1-continued
Compound Table
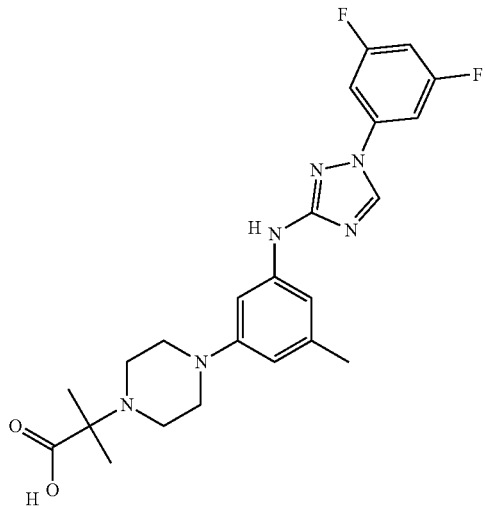
509
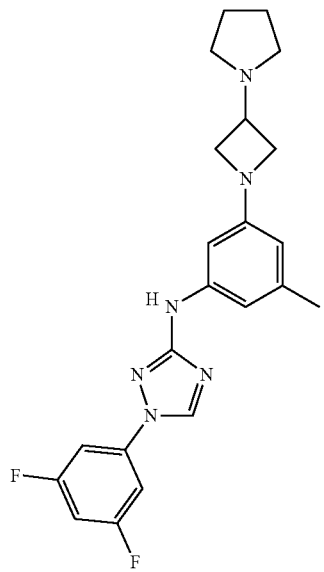
510
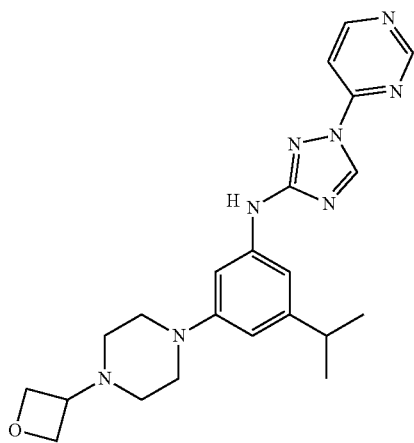
511

TABLE 1-continued
Compound Table
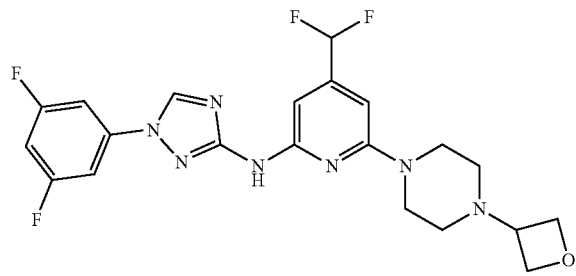 [SMILES: Fc1cc(F)cc(-n2cnc(Nc3cc(C(F)F)cc(N4CCN(C5COC5)CC4)n3)n2)c1]
512
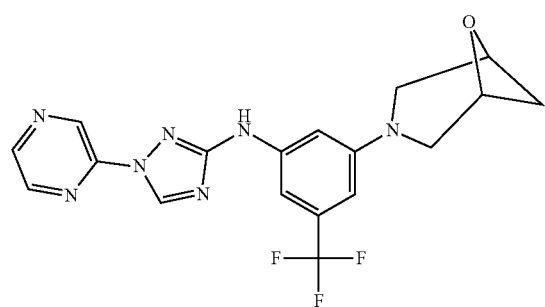 [SMILES: FC(F)(F)c1cc(Nc2ncn(-c3cnccn3)n2)cc(N2CC3CC(C2)O3)c1]
513
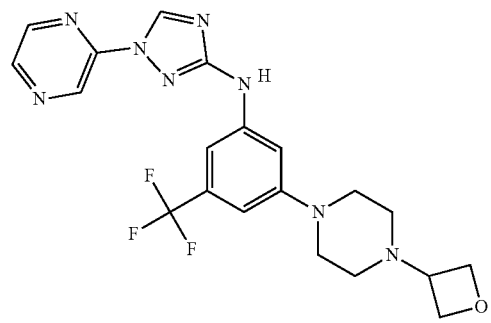
514
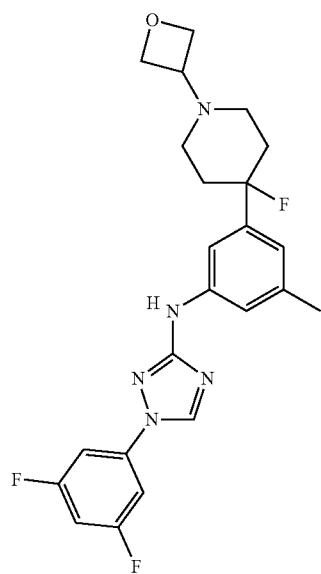
515

TABLE 1-continued
Compound Table
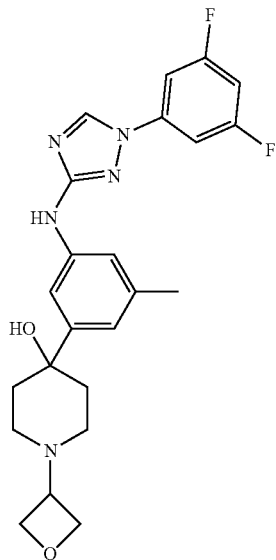 [SMILES: Cc1cc(Nc2ncn(-c3cc(F)cc(F)c3)n2)cc(C2(O)CCN(C3COC3)CC2)c1]
516
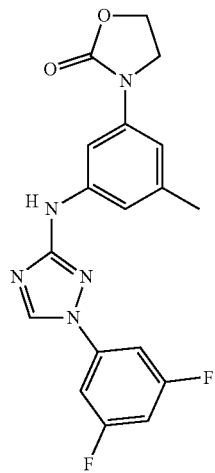
517
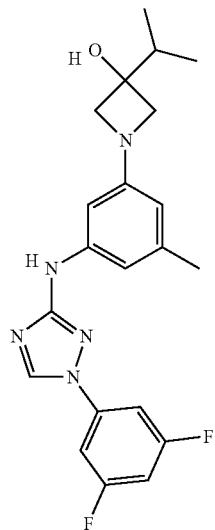
518

TABLE 1-continued
Compound Table
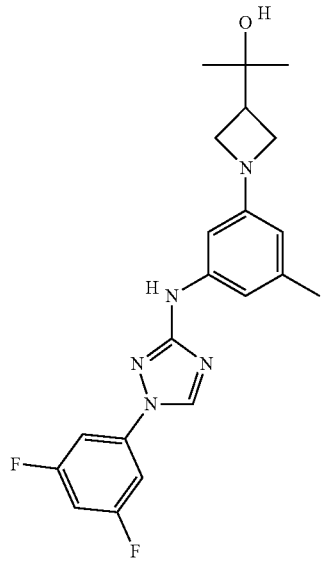
519
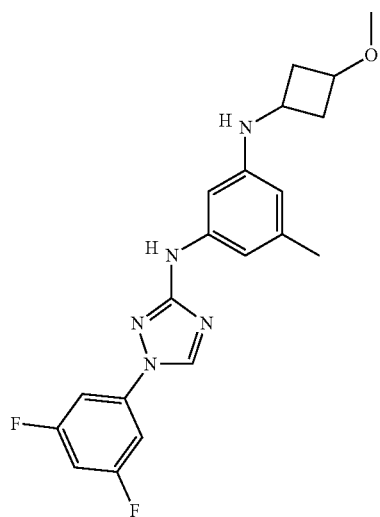
520
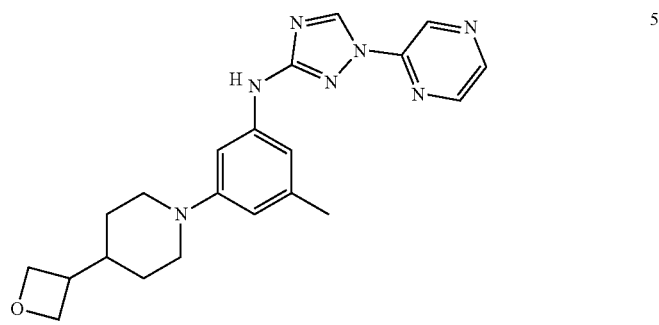
521

TABLE 1-continued
Compound Table
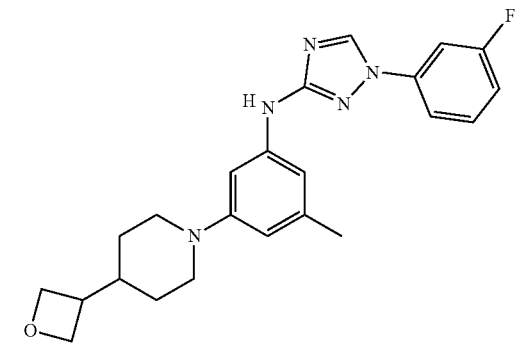
522
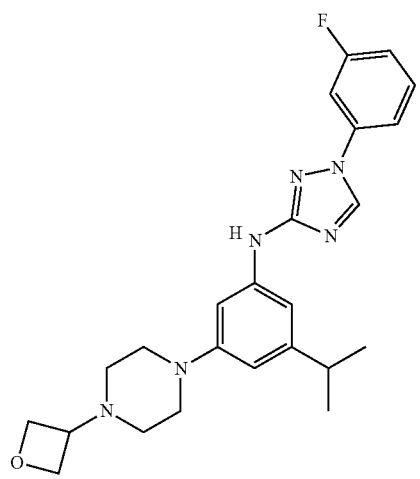
523
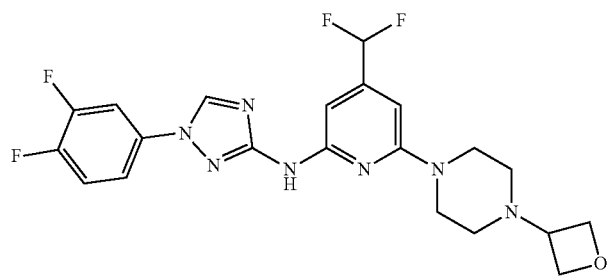 [SMILES: Fc1ccc(-n2cnc(Nc3cc(C(F)F)cc(N4CCN(C5COC5)CC4)n3)n2)cc1F]
524
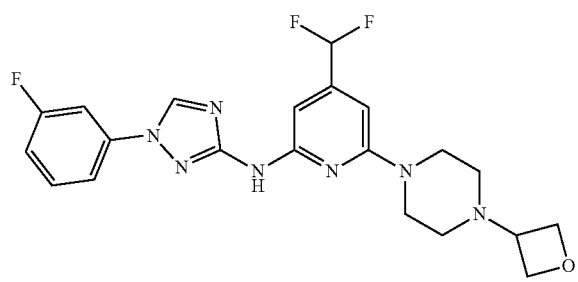 [SMILES: Fc1cccc(-n2cnc(Nc3cc(C(F)F)cc(N4CCN(C5COC5)CC4)n3)n2)c1]
525

US 10,766,869 B2
439                                                                                                               440
TABLE 1-continued
Compound Table
526
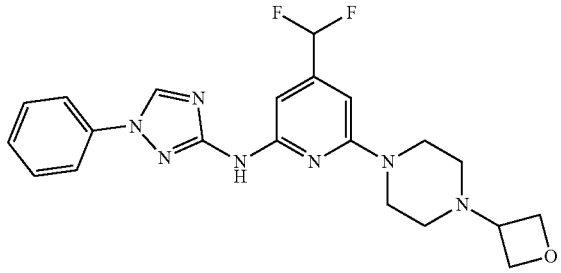 [SMILES: FC(F)c1cc(Nc2ncn(-c3ccccc3)n2)nc(N2CCN(C3COC3)CC2)c1]
527
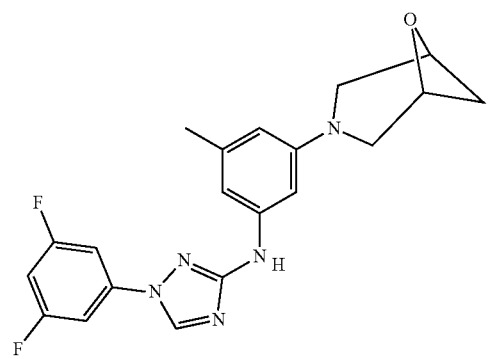
528
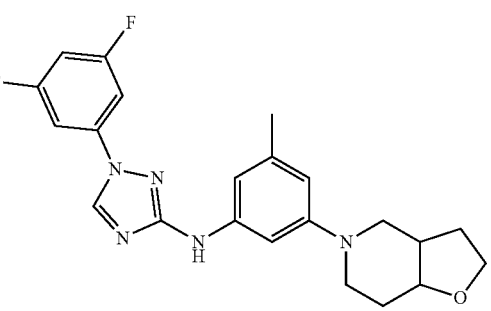
529
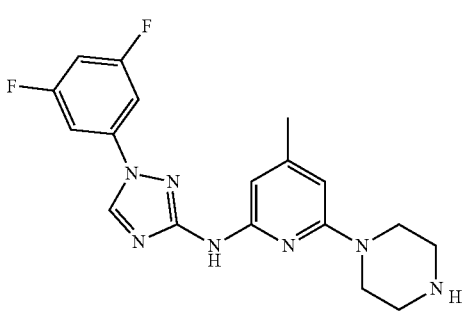
530
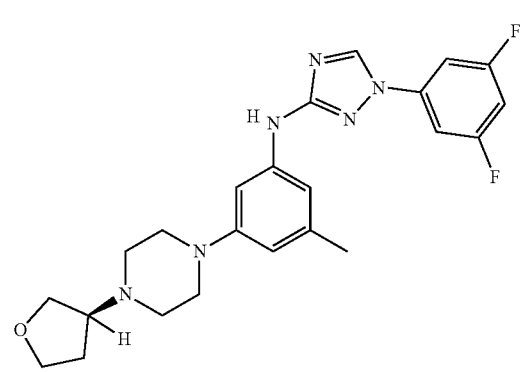

TABLE 1-continued
Compound Table
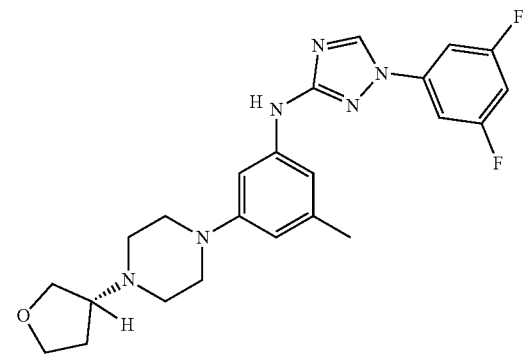 531
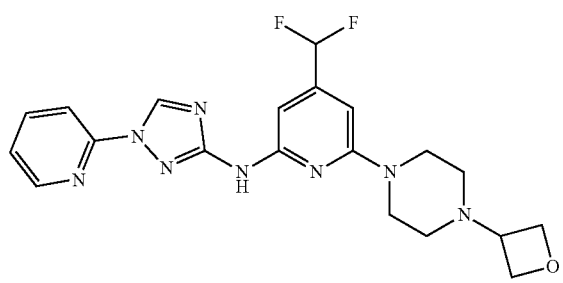 [SMILES: FC(F)c1cc(Nc2ncn(-c3ccccn3)n2)nc(N2CCN(C3COC3)CC2)c1] 532
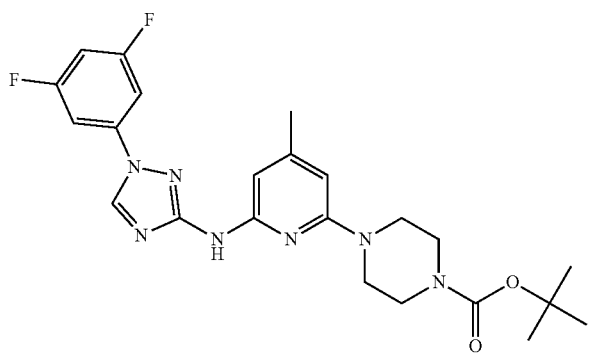 [SMILES: Cc1cc(Nc2ncn(-c3cc(F)cc(F)c3)n2)nc(N2CCN(C(=O)OC(C)(C)C)CC2)c1] 533
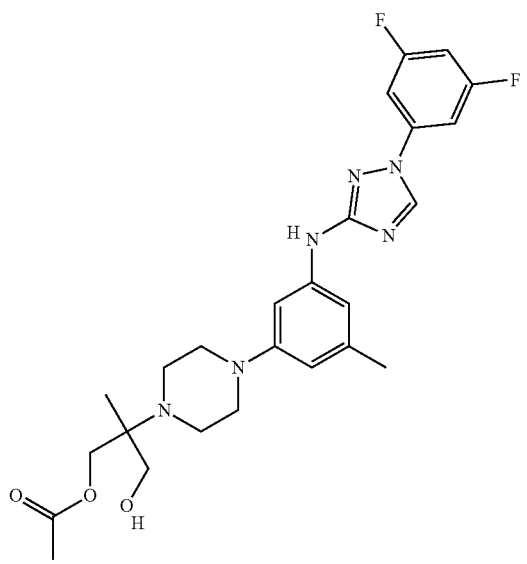 534

TABLE 1-continued
Compound Table
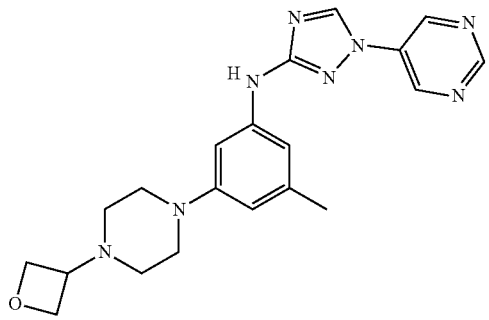
535
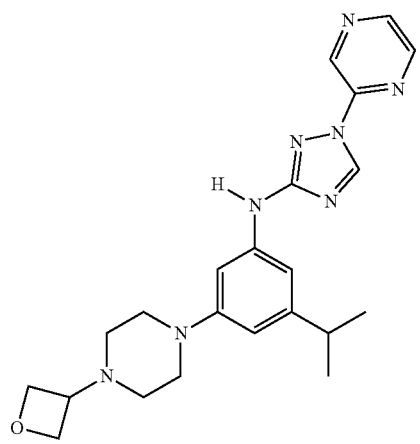 [SMILES: CC(C)c1cc(Nc2ncn(-c3cnccn3)n2)cc(N2CCN(C3COC3)CC2)c1]
536
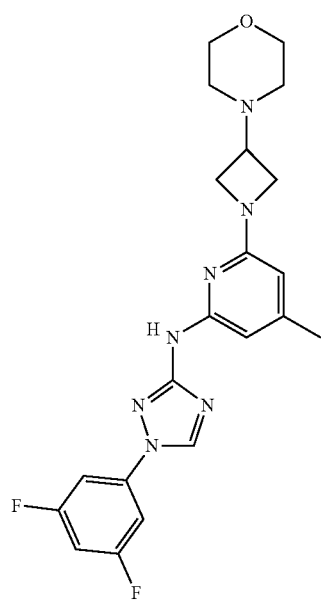
537

TABLE 1-continued
Compound Table
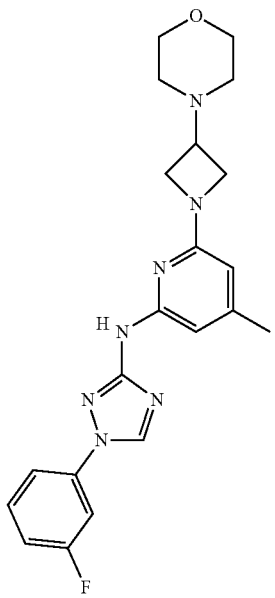
538
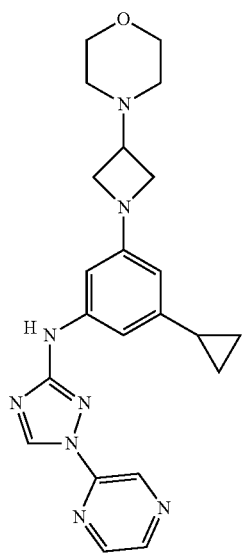
539
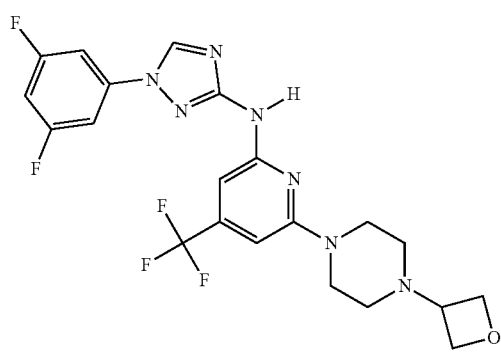
540

TABLE 1-continued
Compound Table
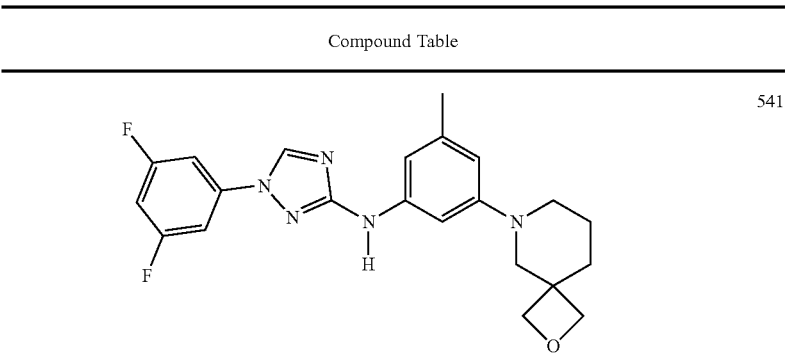
541
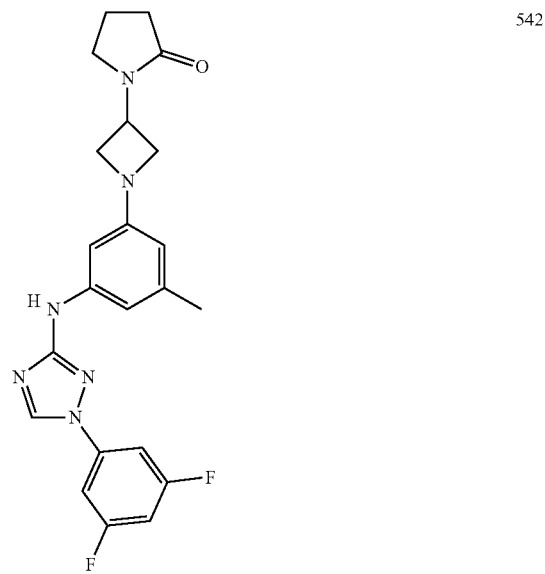
542
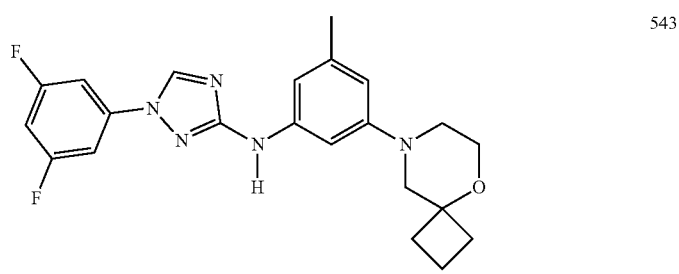
543

TABLE 1-continued
Compound Table
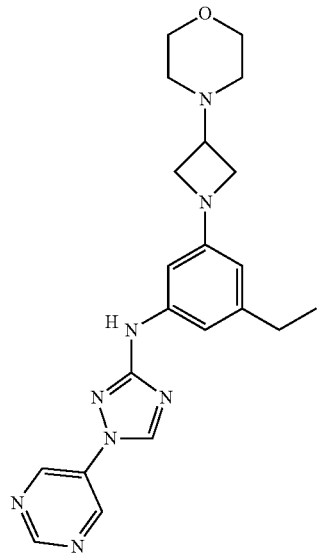
544
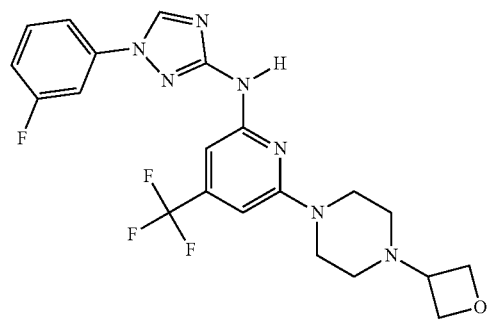 [SMILES: Fc1cccc(-n2cnc(Nc3cc(C(F)(F)F)cc(N4CCN(C5COC5)CC4)n3)n2)c1]
545
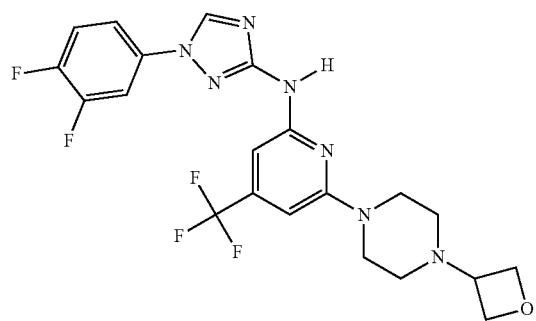 [SMILES: Fc1ccc(-n2cnc(Nc3cc(C(F)(F)F)cc(N4CCN(C5COC5)CC4)n3)n2)cc1F]
546
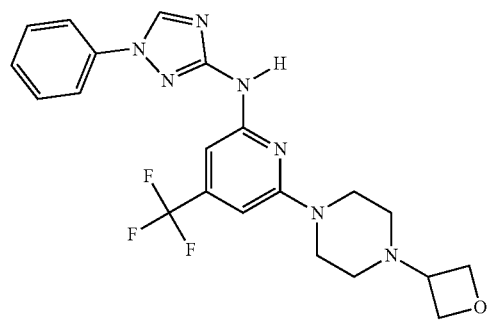 [SMILES: FC(F)(F)c1cc(Nc2ncn(-c3ccccc3)n2)nc(N2CCN(C3COC3)CC2)c1]
547

TABLE 1-continued
Compound Table
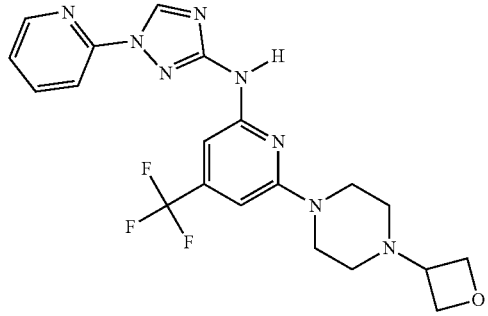 [SMILES: FC(F)(F)c1cc(Nc2ncn(-c3ccccn3)n2)nc(N2CCN(C3COC3)CC2)c1]
548
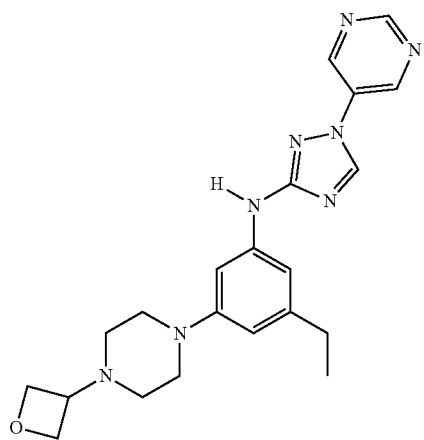 [SMILES: CCc1cc(Nc2ncn(-c3cncnc3)n2)cc(N2CCN(C3COC3)CC2)c1]
549
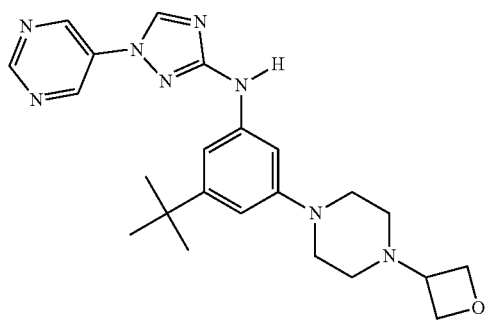 [SMILES: CC(C)(C)c1cc(Nc2ncn(-c3cncnc3)n2)cc(N2CCN(C3COC3)CC2)c1]
550
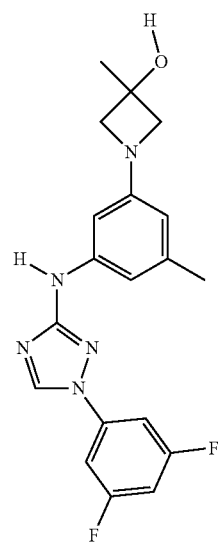 [SMILES: Cc1cc(Nc2ncn(-c3cc(F)cc(F)c3)n2)cc(N2CC(C)(O)C2)c1]
551

TABLE 1-continued
Compound Table
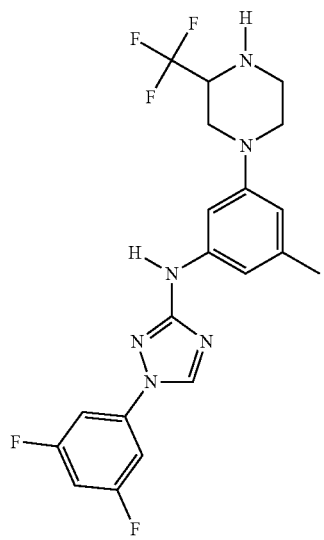 [SMILES: Cc1cc(Nc2ncn(-c3cc(F)cc(F)c3)n2)cc(N2CCNC(C(F)(F)F)C2)c1]
552
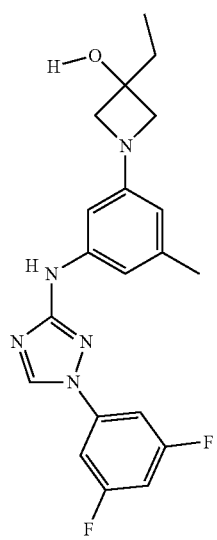
553
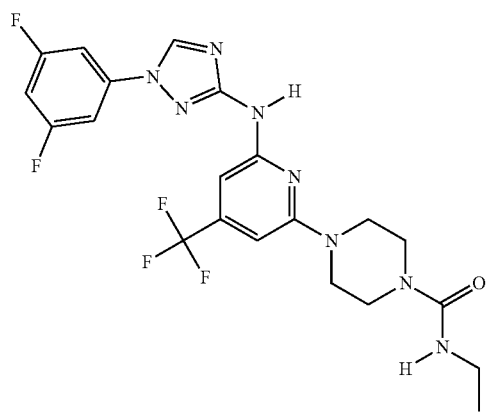 [SMILES: CCNC(=O)N1CCN(c2cc(C(F)(F)F)cc(Nc3ncn(-c4cc(F)cc(F)c4)n3)n2)CC1]
554

TABLE 1-continued
Compound Table
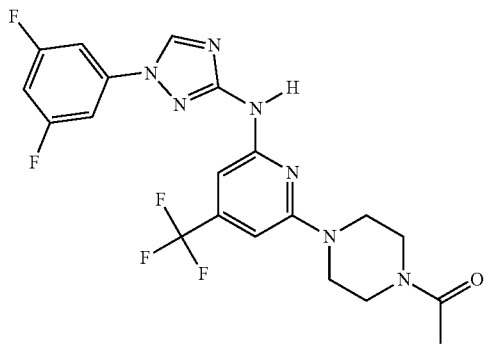 [SMILES: CC(=O)N1CCN(c2cc(C(F)(F)F)cc(Nc3ncn(-c4cc(F)cc(F)c4)n3)n2)CC1]
555
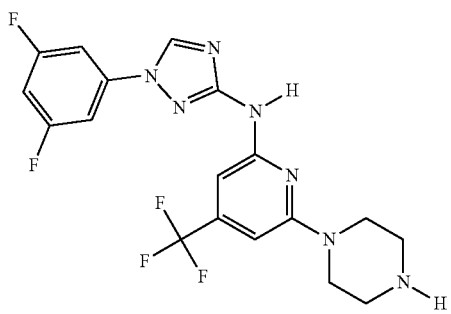 [SMILES: Fc1cc(F)cc(-n2cnc(Nc3cc(C(F)(F)F)cc(N4CCNCC4)n3)n2)c1]
556
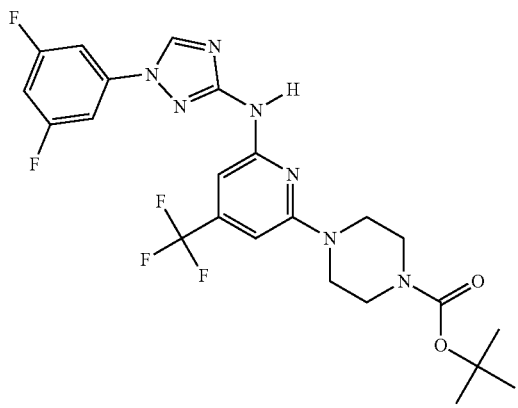 [SMILES: CC(C)(C)OC(=O)N1CCN(c2cc(C(F)(F)F)cc(Nc3ncn(-c4cc(F)cc(F)c4)n3)n2)CC1]
557
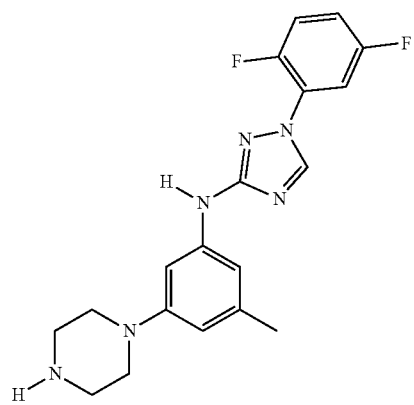 [SMILES: Cc1cc(Nc2ncn(-c3cc(F)ccc3F)n2)cc(N2CCNCC2)c1]
558

TABLE 1-continued
Compound Table
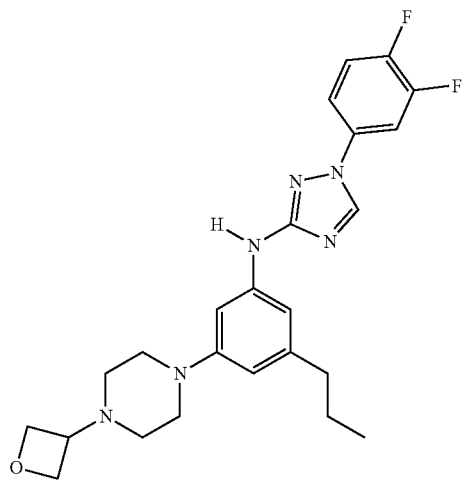 [SMILES: CCCc1cc(Nc2ncn(-c3ccc(F)c(F)c3)n2)cc(N2CCN(C3COC3)CC2)c1]
559
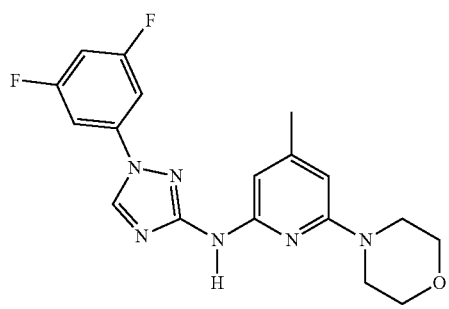 [SMILES: Cc1cc(Nc2ncn(-c3cc(F)cc(F)c3)n2)nc(N2CCOCC2)c1]
560
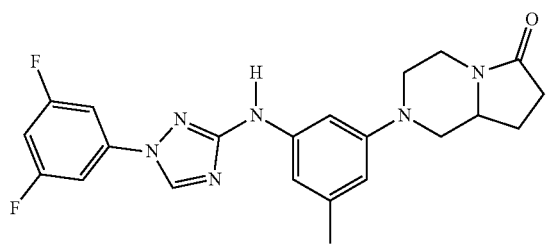 [SMILES: Cc1cc(Nc2ncn(-c3cc(F)cc(F)c3)n2)cc(N2CCN3C(=O)CCC3C2)c1]
561
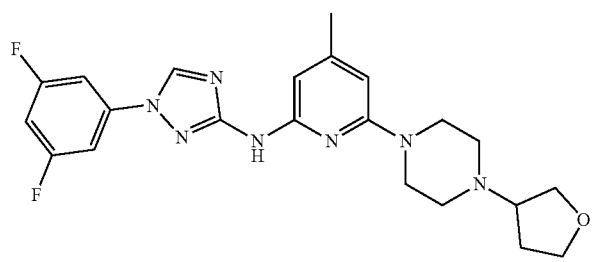 [SMILES: Cc1cc(Nc2ncn(-c3cc(F)cc(F)c3)n2)nc(N2CCN(C3CCOC3)CC2)c1]
562

TABLE 1-continued
Compound Table
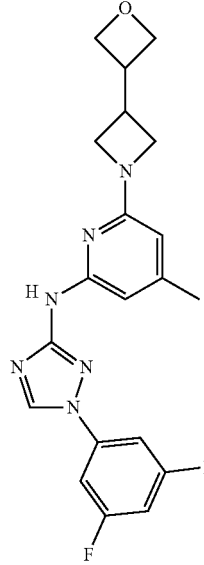
563
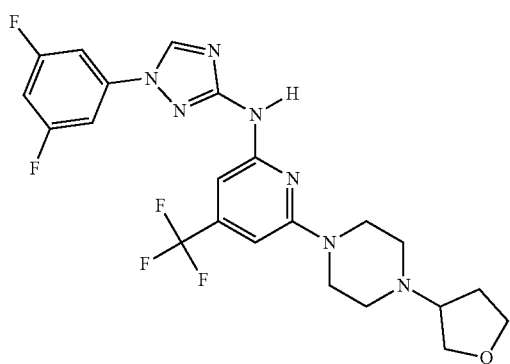 [SMILES: Fc1cc(F)cc(-n2cnc(Nc3cc(C(F)(F)F)cc(N4CCN(C5CCOC5)CC4)n3)n2)c1]
564
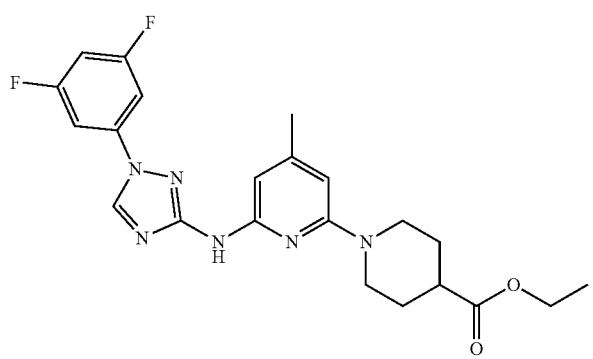 [SMILES: CCOC(=O)C1CCN(c2cc(C)cc(Nc3ncn(-c4cc(F)cc(F)c4)n3)n2)CC1]
565
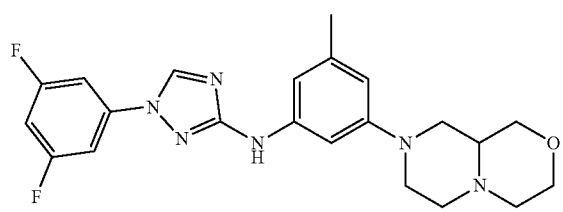 [SMILES: Cc1cc(Nc2ncn(-c3cc(F)cc(F)c3)n2)cc(N2CCN3CCOCC3C2)c1]
566

TABLE 1-continued
Compound Table
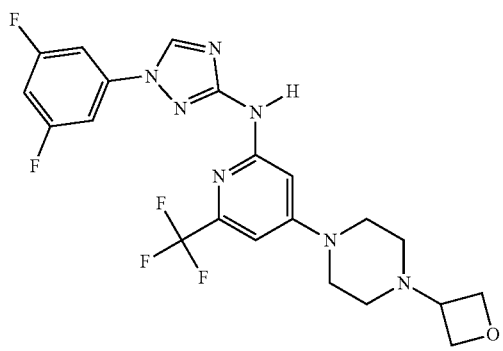 [SMILES: Fc1cc(F)cc(-n2cnc(Nc3cc(N4CCN(C5COC5)CC4)cc(C(F)(F)F)n3)n2)c1]
567
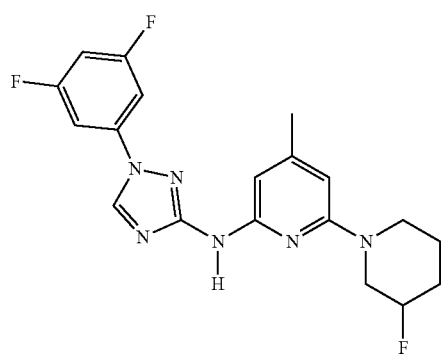 [SMILES: Cc1cc(Nc2ncn(-c3cc(F)cc(F)c3)n2)nc(N2CCCC(F)C2)c1]
568
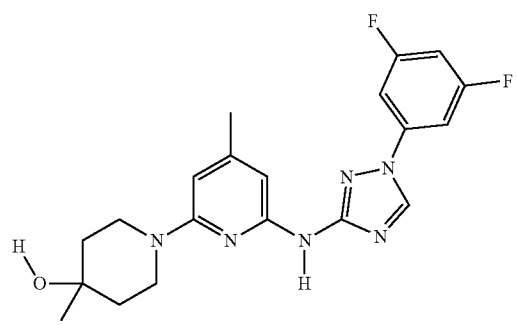 [SMILES: Cc1cc(Nc2ncn(-c3cc(F)cc(F)c3)n2)nc(N2CCC(C)(O)CC2)c1]
569
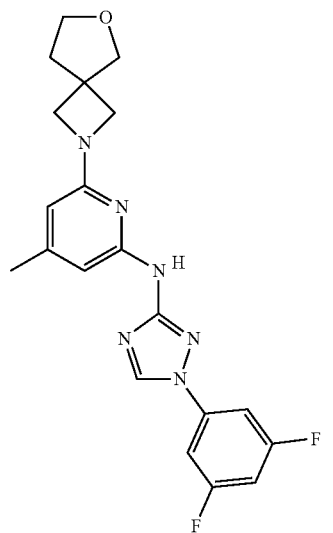
570

TABLE 1-continued
Compound Table
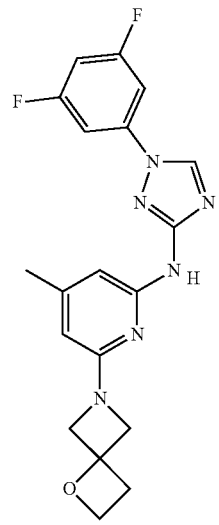
571
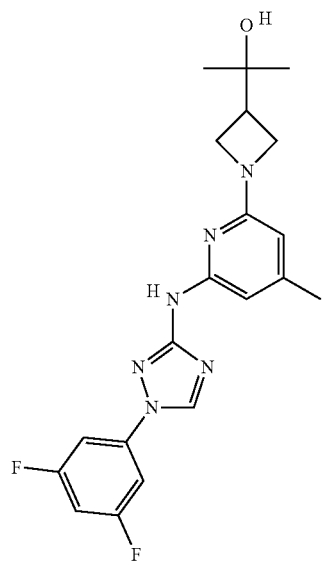
572
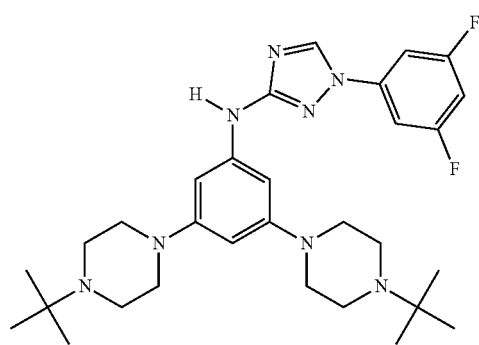 [SMILES: CC(C)(C)N1CCN(c2cc(Nc3ncn(-c4cc(F)cc(F)c4)n3)cc(N3CCN(C(C)(C)C)CC3)c2)CC1]
573

TABLE 1-continued

Compound Table

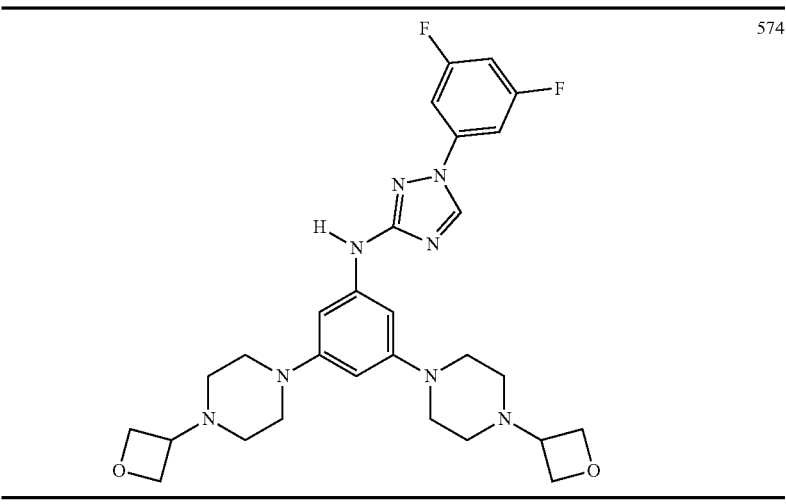

574

In Table 1A below, several compounds have stereocenters with either known (R or S) or unknown absolute configurations and/or known (cis or trans) or unknown configurations. For example, compounds 603, 611, 623, 632, 655, 665, 667, 672, 673, 679, 682, 696, 700, 740, 748, 750, 751, 787, 796 and 800 are each single enantiomers with unknown stereochemistry and are arbitrarily assigned the "S" or "R" conformation. Compounds 649 and 792 are each single enantiomers of unknown cis/trans configuration and are arbitrarily assigned a trans conformation. Compounds 826 and 861 are each single enantiomers of unknown cis/trans configuration and are arbitrarily assigned a cis conformation.

TABLE 1A

Compound Table

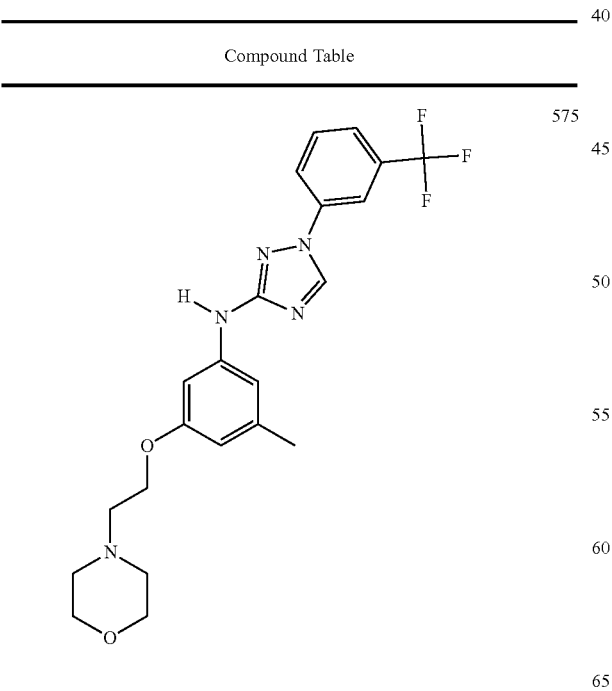

575

TABLE 1A-continued

Compound Table

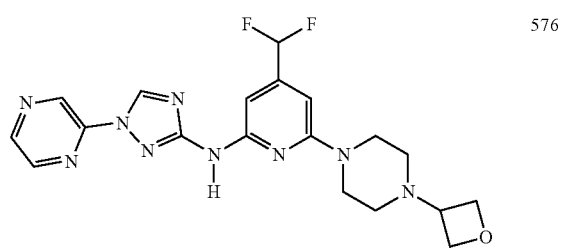

576

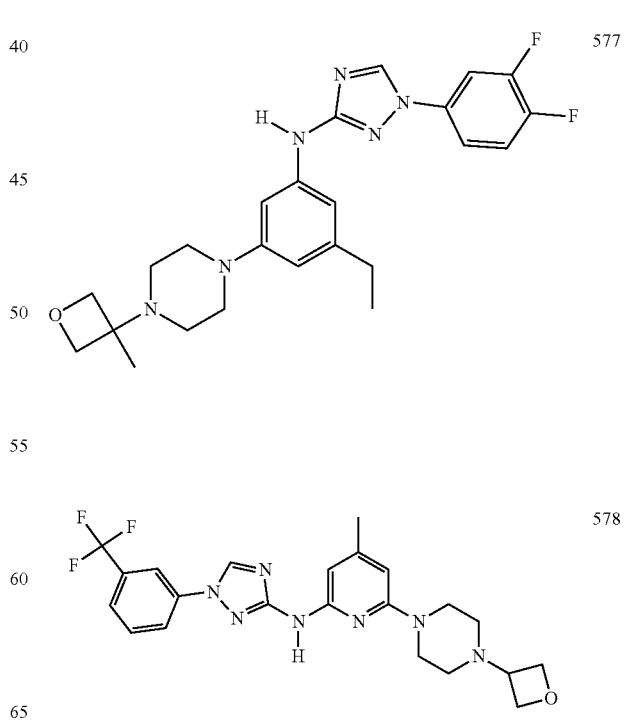

577

578

TABLE 1A-continued
Compound Table
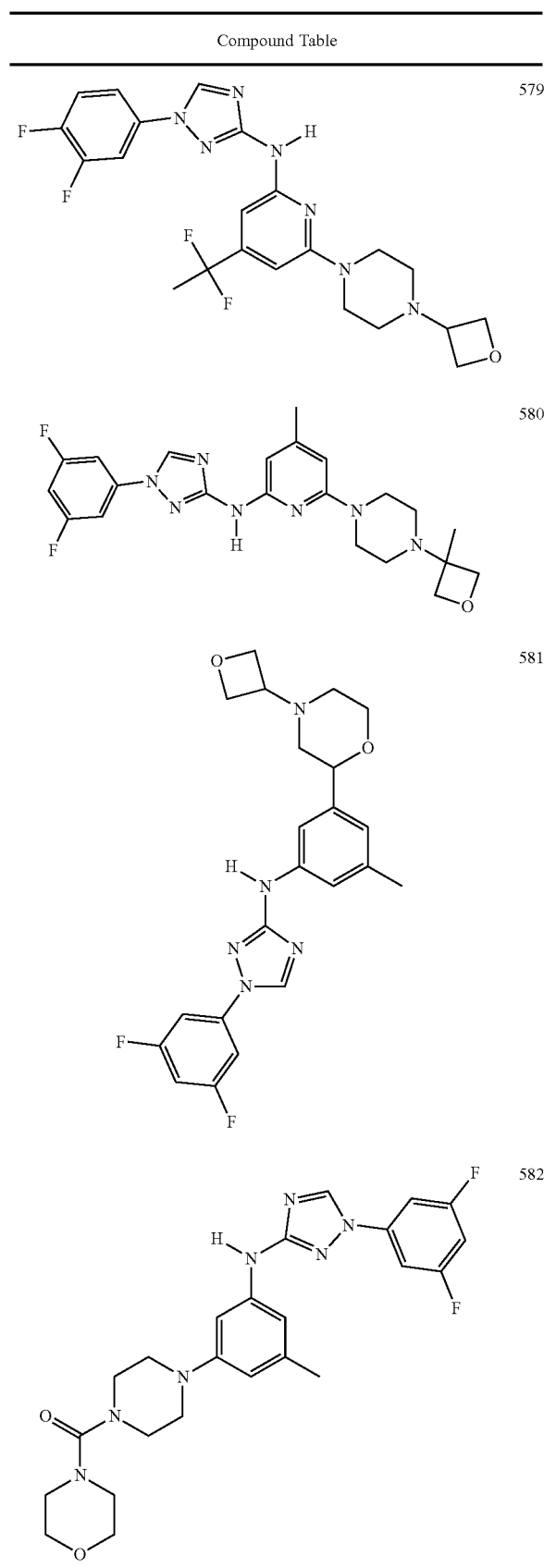
579
580
581
582
TABLE 1A-continued
Compound Table
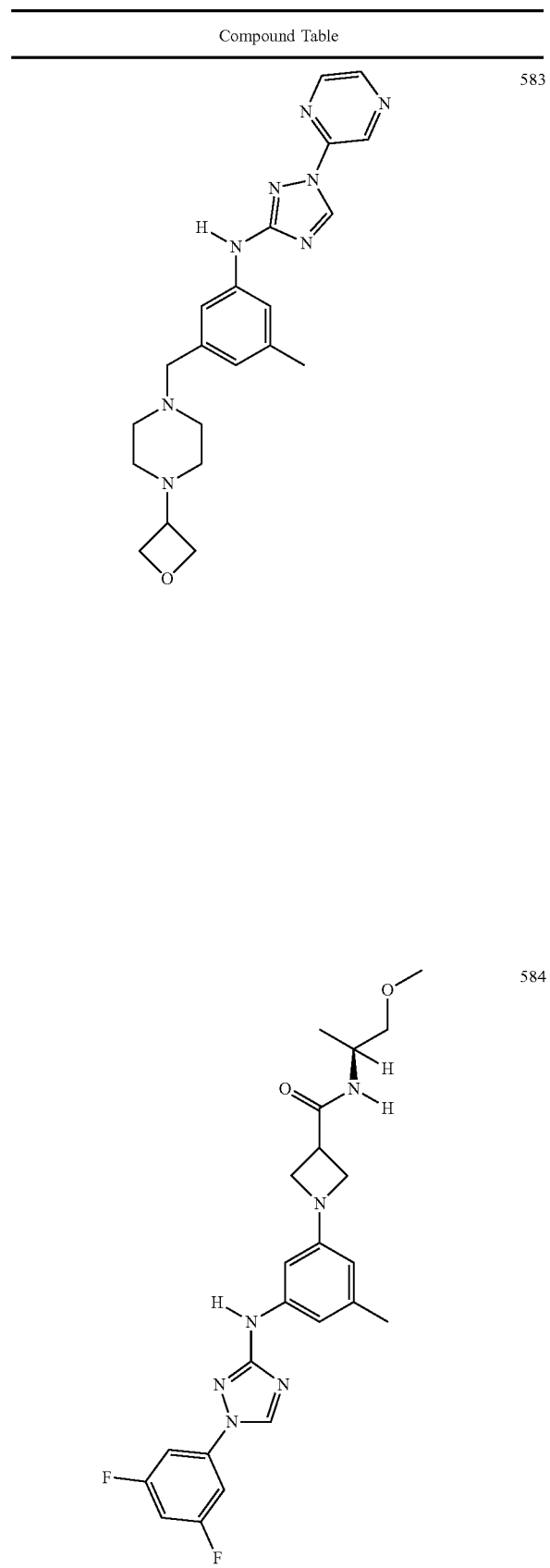
583
584

TABLE 1A-continued
Compound Table
585 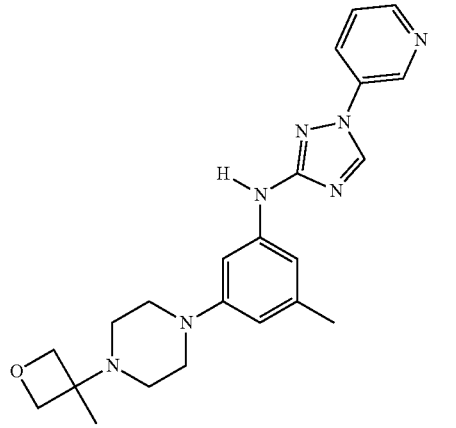 [SMILES: Cc1cc(Nc2ncn(-c3cccnc3)n2)cc(N2CCN(C3(C)COC3)CC2)c1]
586 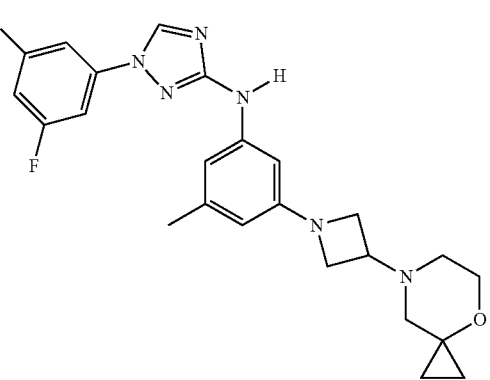
587 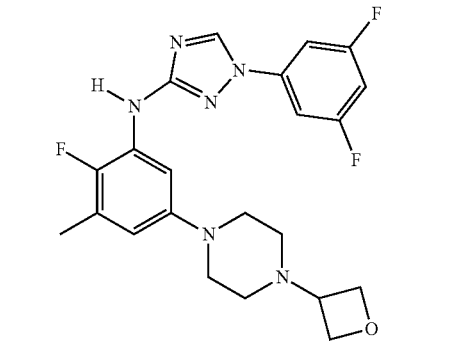 [SMILES: Cc1cc(N2CCN(C3COC3)CC2)cc(Nc2ncn(-c3cc(F)cc(F)c3)n2)c1F]
588 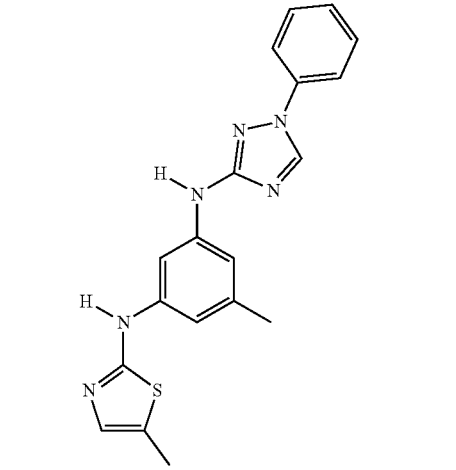
TABLE 1A-continued
Compound Table
589
590
591

TABLE 1A-continued
Compound Table
592 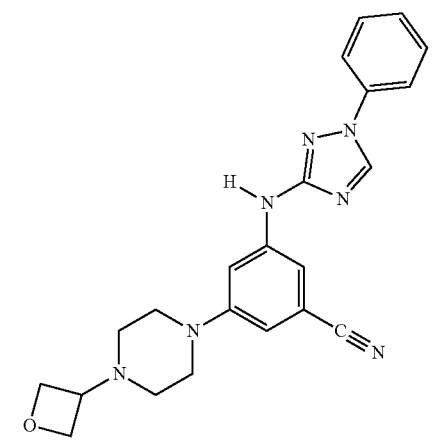 [SMILES: N#Cc1cc(Nc2ncn(-c3ccccc3)n2)cc(N2CCN(C3COC3)CC2)c1]
593 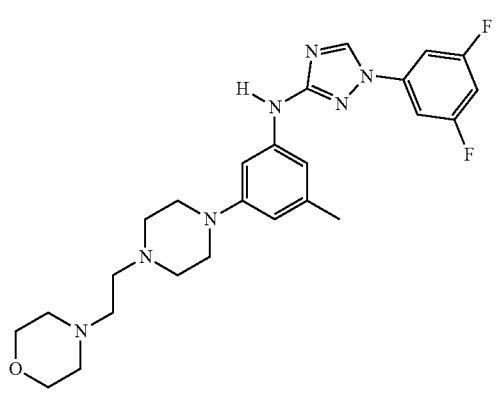 [SMILES: Cc1cc(Nc2ncn(-c3cc(F)cc(F)c3)n2)cc(N2CCN(CCN3CCOCC3)CC2)c1]
594 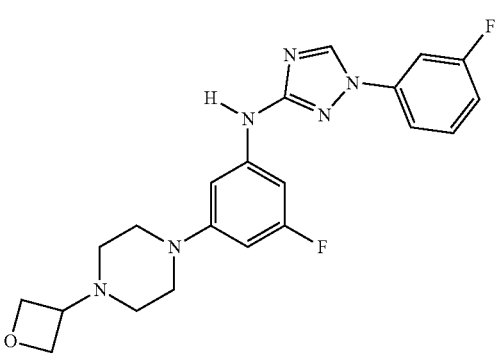 [SMILES: Fc1cc(Nc2ncn(-c3cccc(F)c3)n2)cc(N2CCN(C3COC3)CC2)c1]
TABLE 1A-continued
Compound Table
595 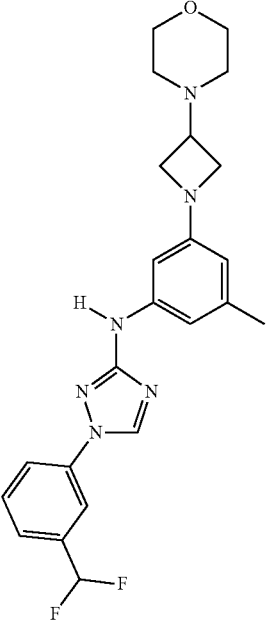 [SMILES: Cc1cc(Nc2ncn(-c3cccc(C(F)F)c3)n2)cc(N2CC(N3CCOCC3)C2)c1]
596 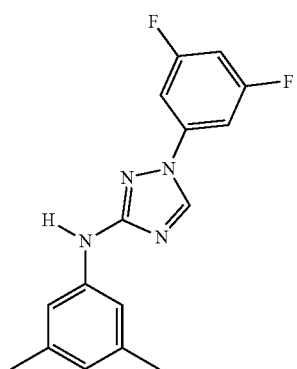
597 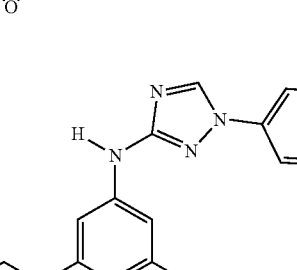

TABLE 1A-continued
Compound Table
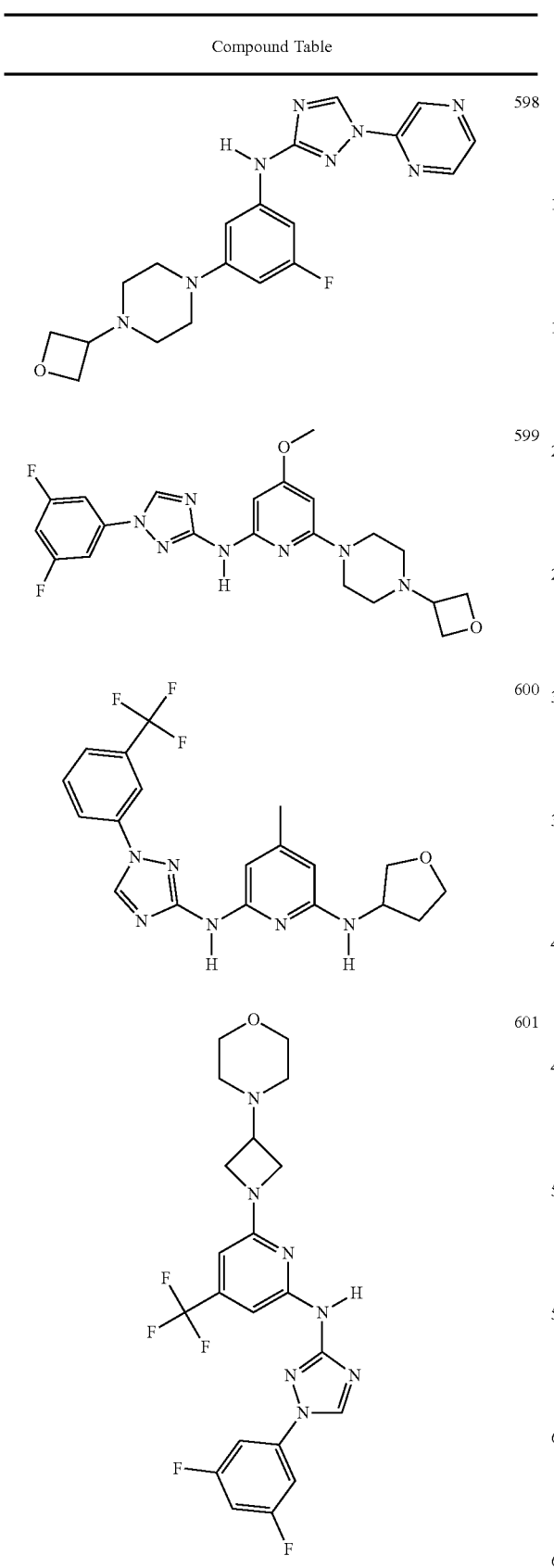
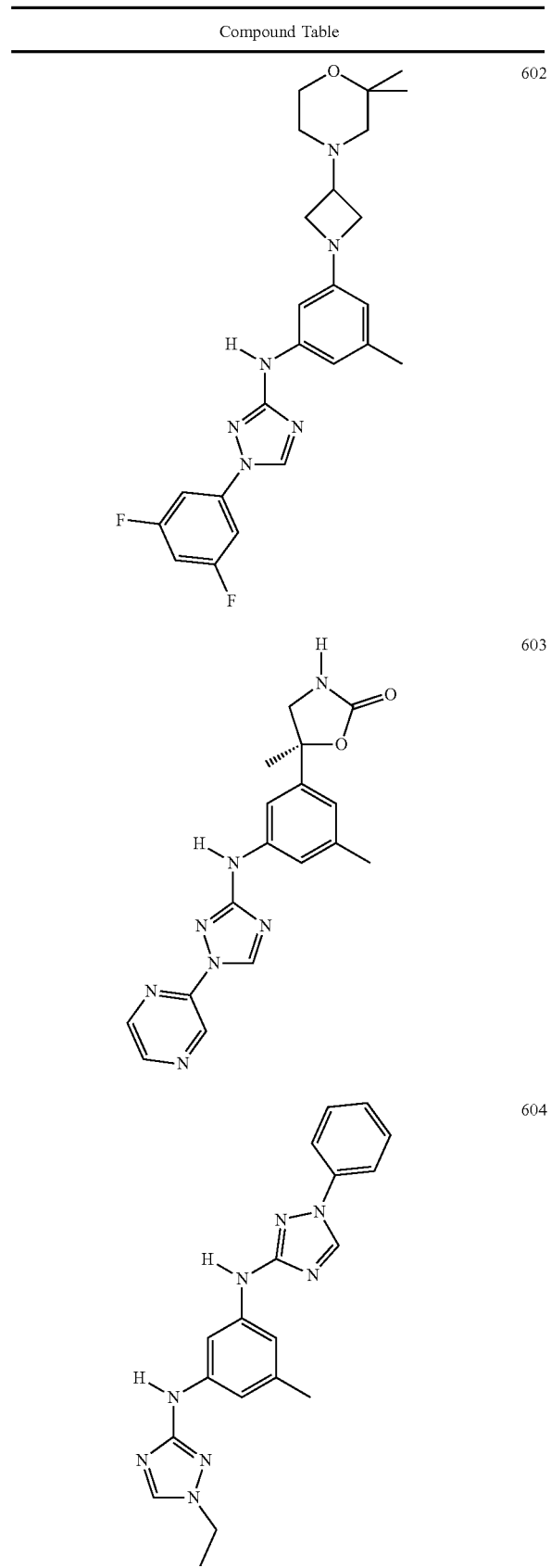

TABLE 1A-continued
Compound Table
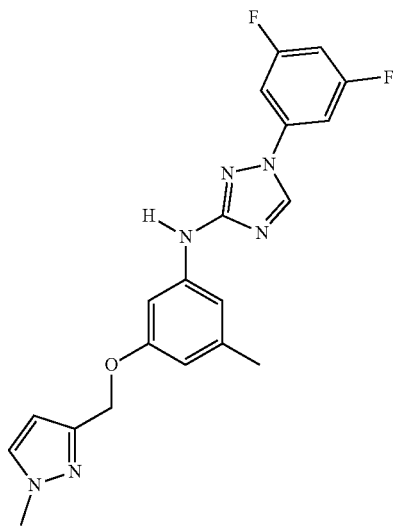 [SMILES: Cc1cc(Nc2ncn(-c3cc(F)cc(F)c3)n2)cc(OCc2ccn(C)n2)c1]
605
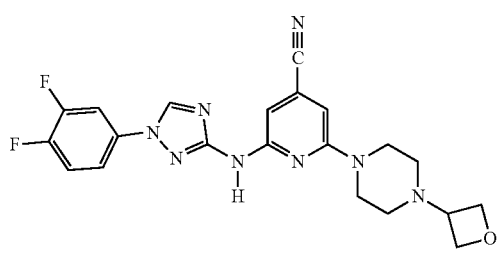 [SMILES: N#Cc1cc(Nc2ncn(-c3ccc(F)c(F)c3)n2)nc(N2CCN(C3COC3)CC2)c1]
606
607
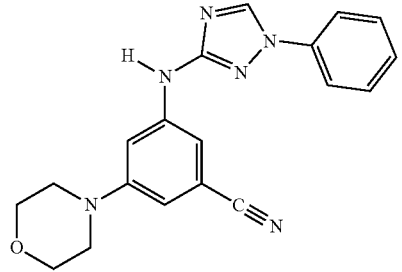 [SMILES: N#Cc1cc(Nc2ncn(-c3ccccc3)n2)cc(N2CCOCC2)c1]
608
609
610
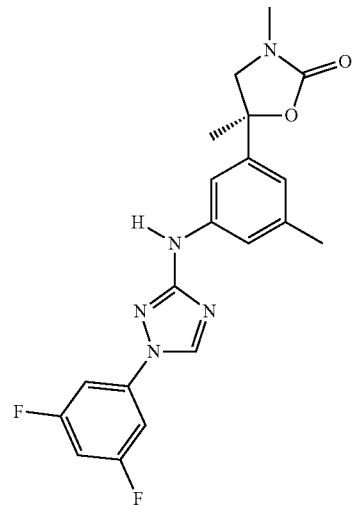 [SMILES: Cc1cc(Nc2ncn(-c3cc(F)cc(F)c3)n2)cc([C@@]2(C)CN(C)C(=O)O2)c1]
611

TABLE 1A-continued
Compound Table
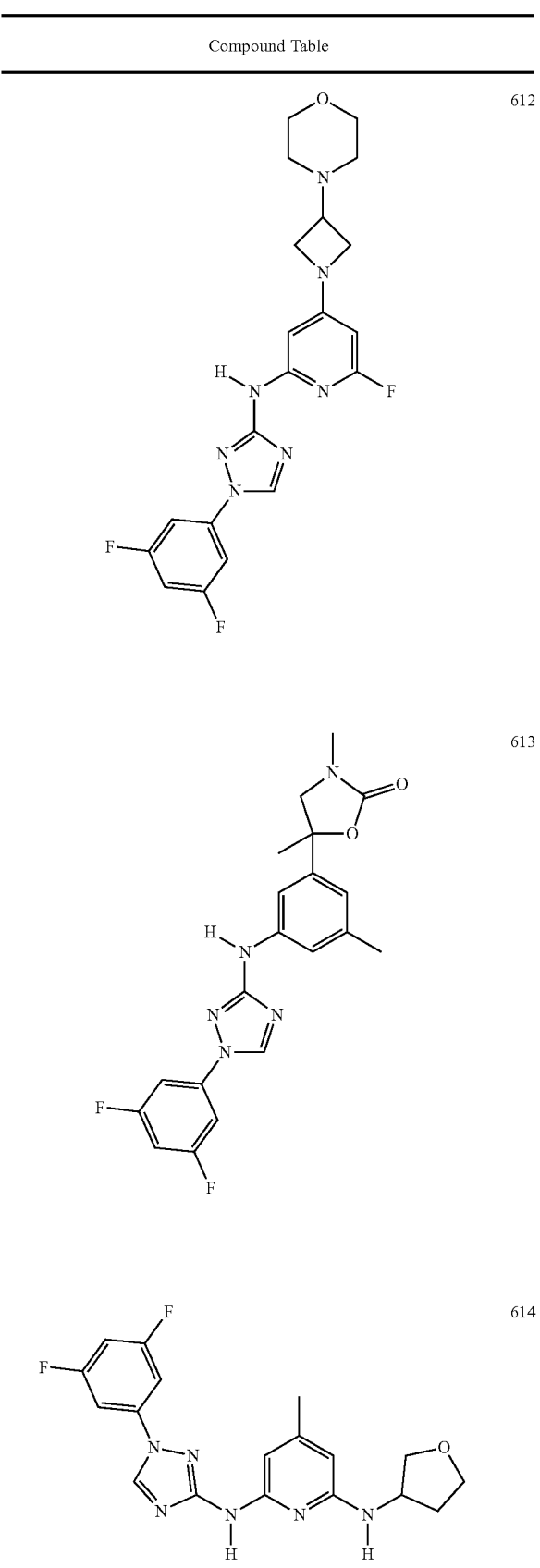
612
613
614
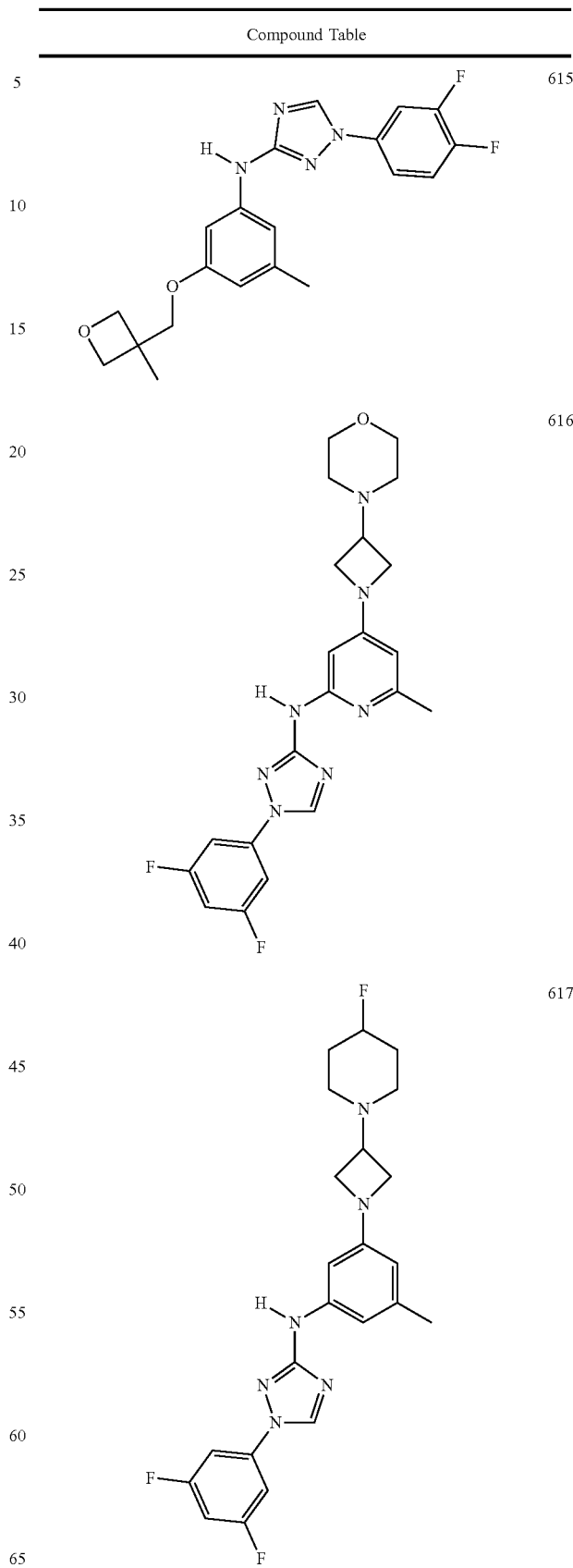
615
616
617

TABLE 1A-continued
Compound Table
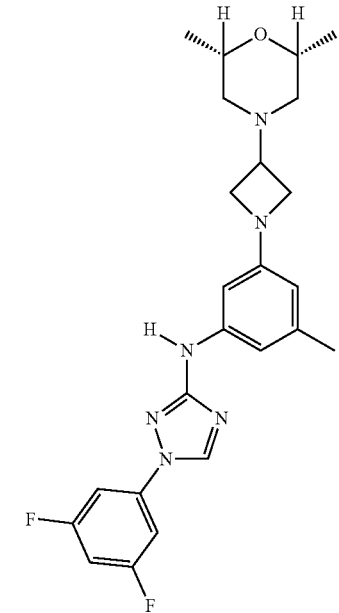 [SMILES: Cc1cc(Nc2ncn(-c3cc(F)cc(F)c3)n2)cc(N2CC(N3C[C@@H](C)O[C@@H](C)C3)C2)c1] 618
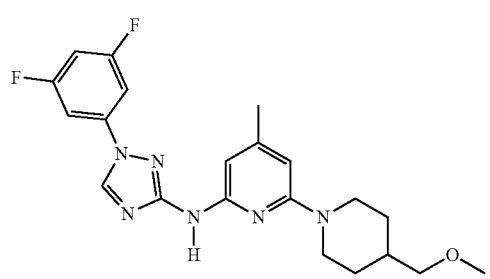 [SMILES: COCC1CCN(c2cc(C)cc(Nc3ncn(-c4cc(F)cc(F)c4)n3)n2)CC1] 619
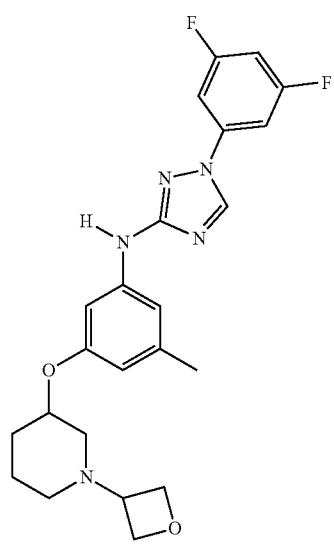 [SMILES: Cc1cc(Nc2ncn(-c3cc(F)cc(F)c3)n2)cc(OC2CCCN(C3COC3)C2)c1] 620
TABLE 1A-continued
Compound Table
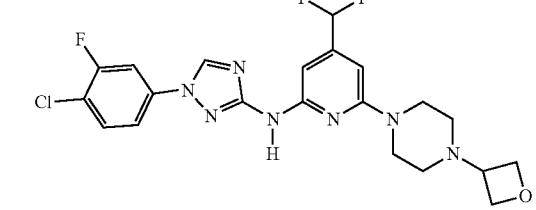 621
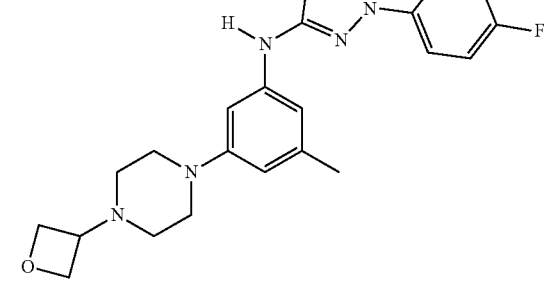 622
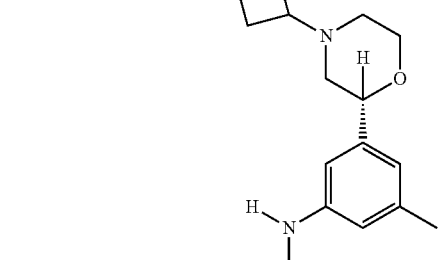 623
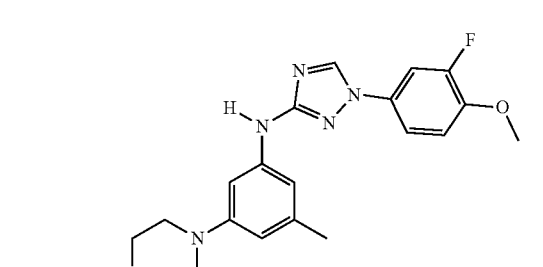 624

TABLE 1A-continued
Compound Table
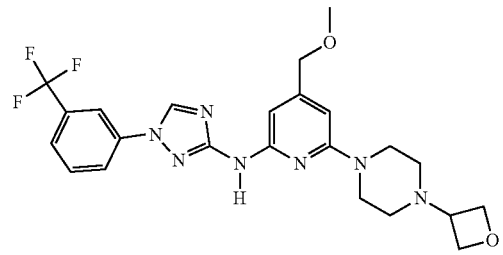 [SMILES: COCc1cc(Nc2ncn(-c3cccc(C(F)(F)F)c3)n2)nc(N2CCN(C3COC3)CC2)c1]
625
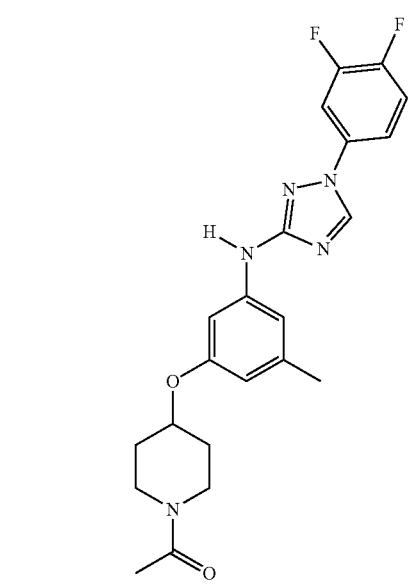 [SMILES: CC(=O)N1CCC(Oc2cc(C)cc(Nc3ncn(-c4ccc(F)c(F)c4)n3)c2)CC1]
626
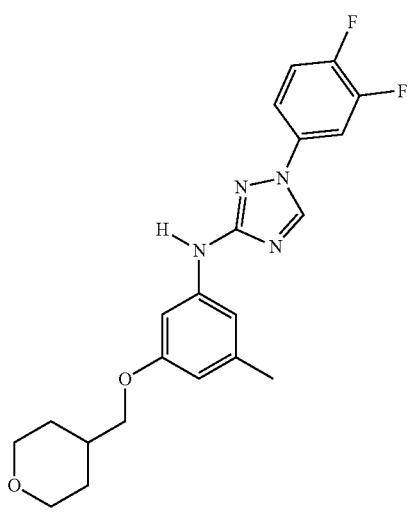 [SMILES: Cc1cc(Nc2ncn(-c3ccc(F)c(F)c3)n2)cc(OCC2CCOCC2)c1]
627
TABLE 1A-continued
Compound Table
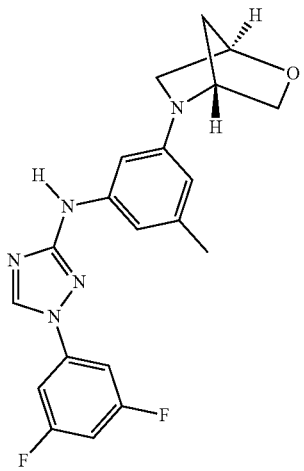 [SMILES: Cc1cc(Nc2ncn(-c3cc(F)cc(F)c3)n2)cc(N2C[C@H]3C[C@@H]2CO3)c1]
628
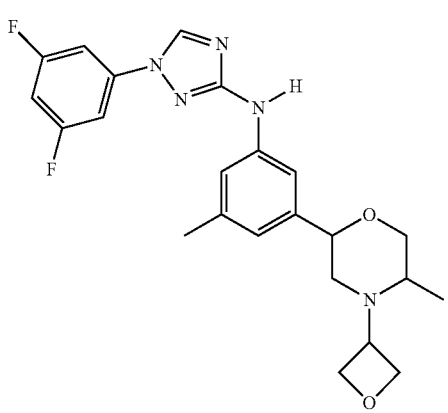 [SMILES: Cc1cc(Nc2ncn(-c3cc(F)cc(F)c3)n2)cc(C2CN(C3COC3)C(C)CO2)c1]
629
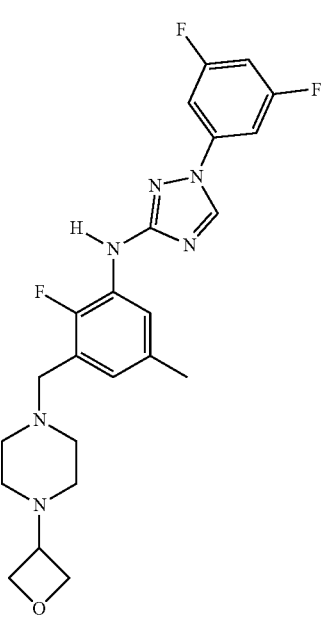 [SMILES: Cc1cc(CN2CCN(C3COC3)CC2)c(F)c(Nc2ncn(-c3cc(F)cc(F)c3)n2)c1]
630

TABLE 1A-continued
Compound Table
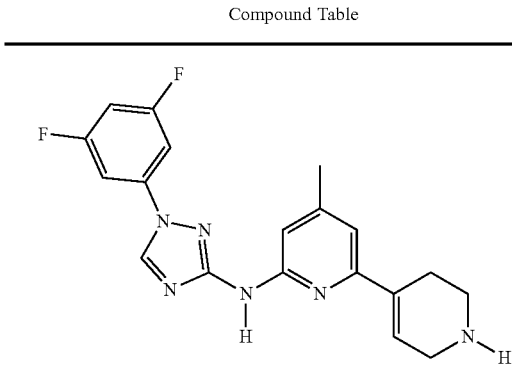
631
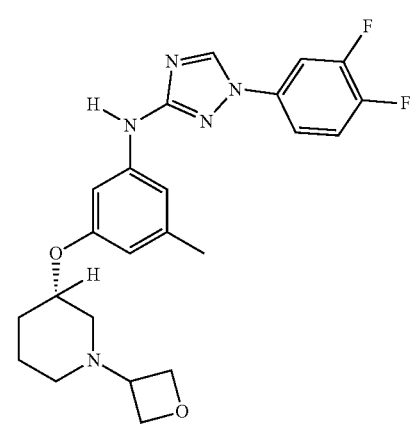 [SMILES: Cc1cc(Nc2ncn(-c3ccc(F)c(F)c3)n2)cc(O[C@H]2CCCN(C3COC3)C2)c1]
632
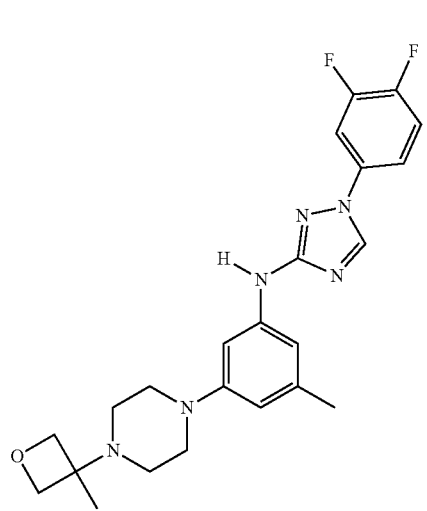 [SMILES: Cc1cc(Nc2ncn(-c3ccc(F)c(F)c3)n2)cc(N2CCN(C3(C)COC3)CC2)c1]
633
TABLE 1A-continued
Compound Table
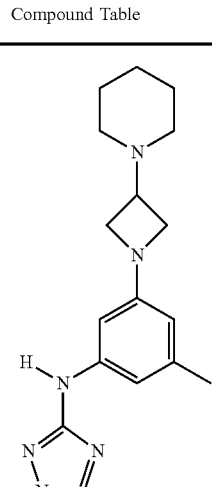
634
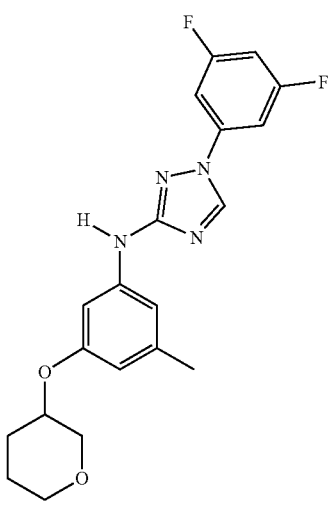 [SMILES: Cc1cc(Nc2ncn(-c3cc(F)cc(F)c3)n2)cc(OC2CCCOC2)c1]
635

TABLE 1A-continued
Compound Table
636 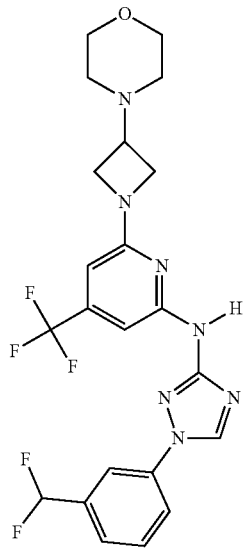 [SMILES: FC(F)c1cccc(-n2cnc(Nc3cc(C(F)(F)F)cc(N4CC(N5CCOCC5)C4)n3)n2)c1]
637 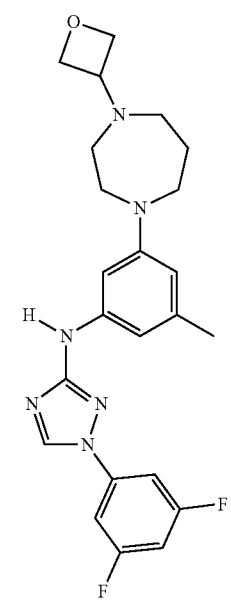 [SMILES: Cc1cc(Nc2ncn(-c3cc(F)cc(F)c3)n2)cc(N2CCCN(C3COC3)CC2)c1]
638 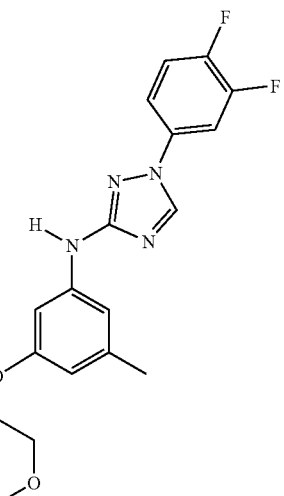
639 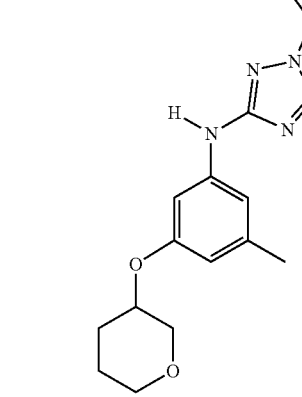
640 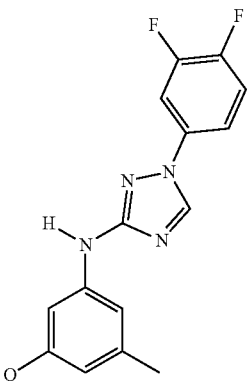
641 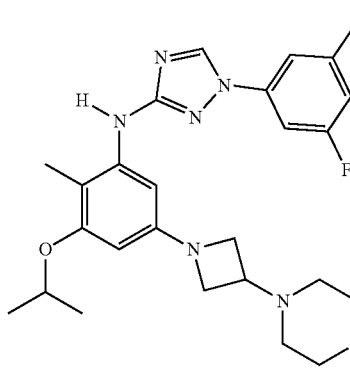

TABLE 1A-continued
Compound Table
642
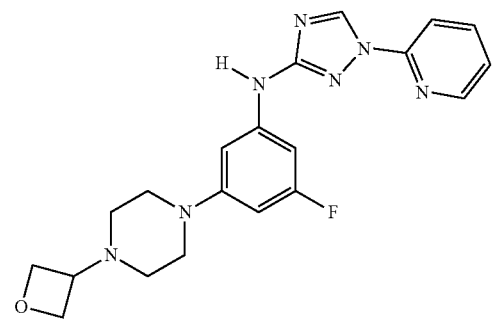
643
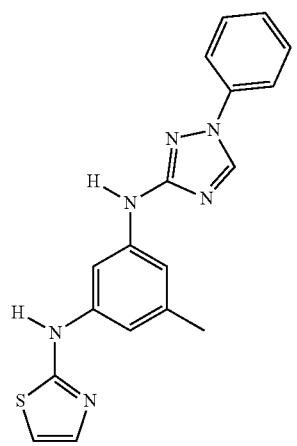
644
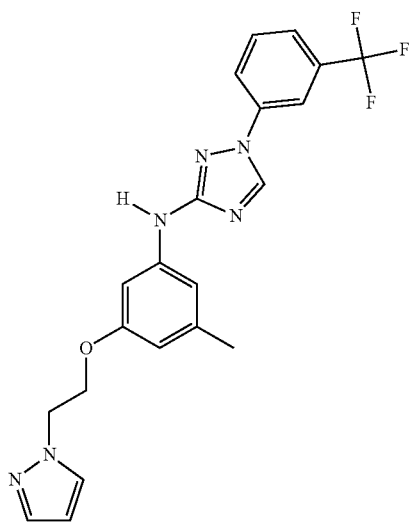 [SMILES: Cc1cc(Nc2ncn(-c3cccc(C(F)(F)F)c3)n2)cc(OCCn2cccn2)c1]
645
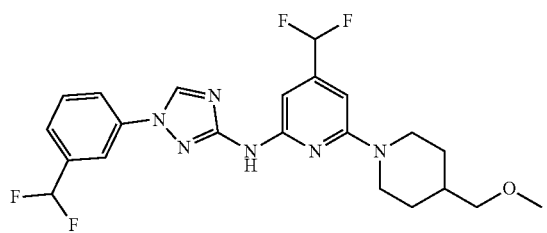 [SMILES: COCC1CCN(c2cc(C(F)F)cc(Nc3ncn(-c4cccc(C(F)F)c4)n3)n2)CC1]
TABLE 1A-continued
Compound Table
646
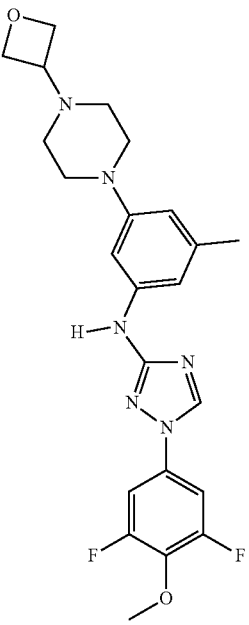 [SMILES: COc1c(F)cc(-n2cnc(Nc3cc(C)cc(N4CCN(C5COC5)CC4)c3)n2)cc1F]
647
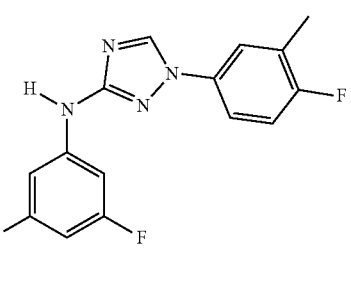
648
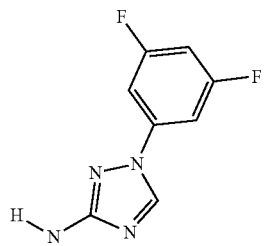
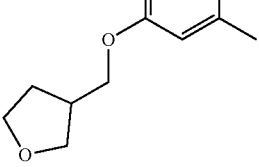

TABLE 1A-continued
Compound Table
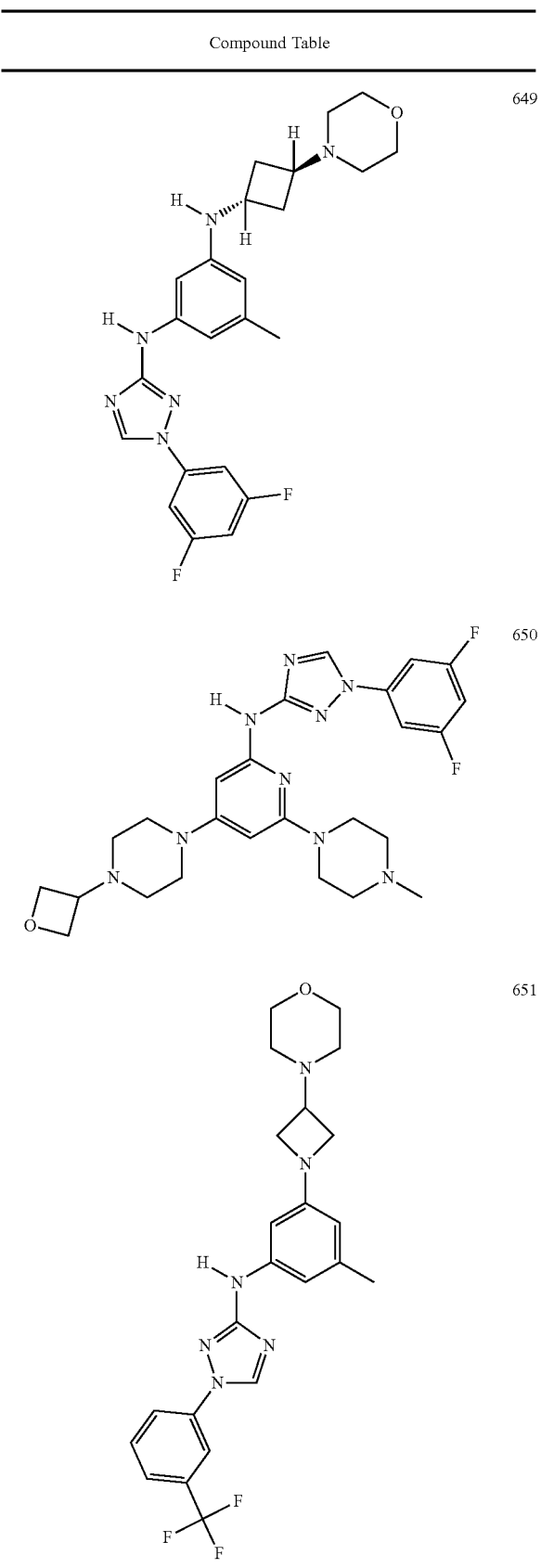
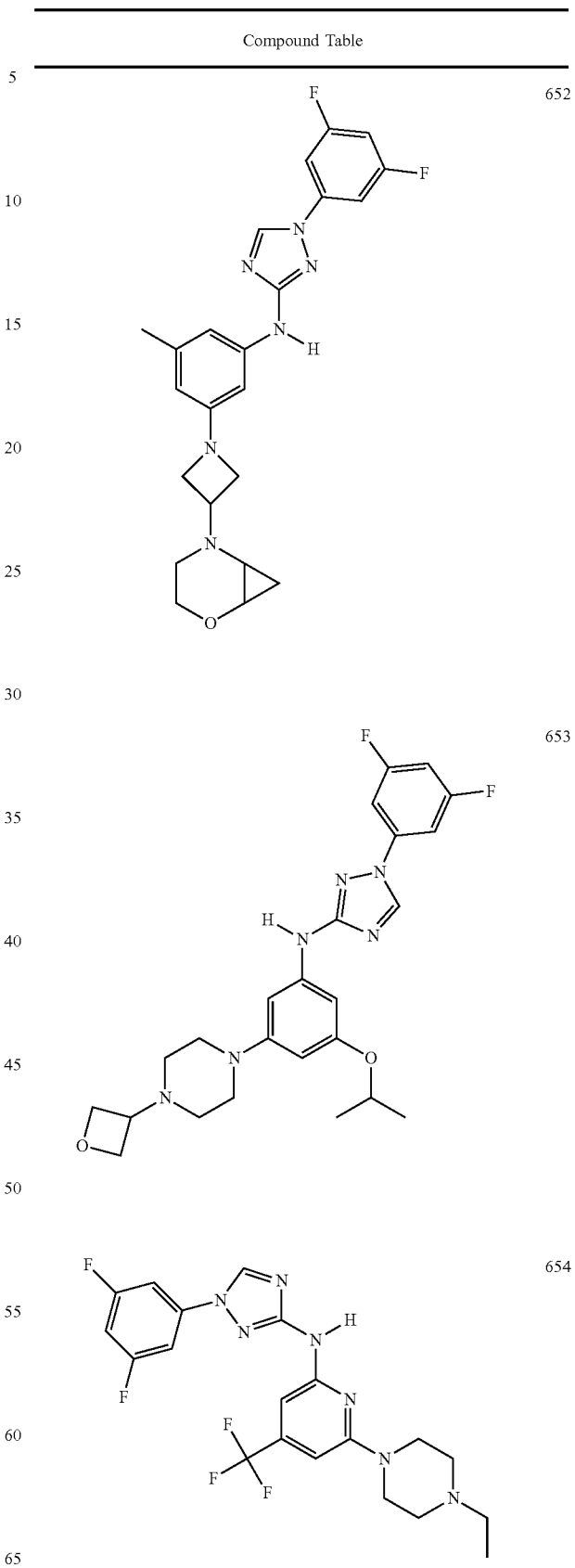

TABLE 1A-continued
Compound Table
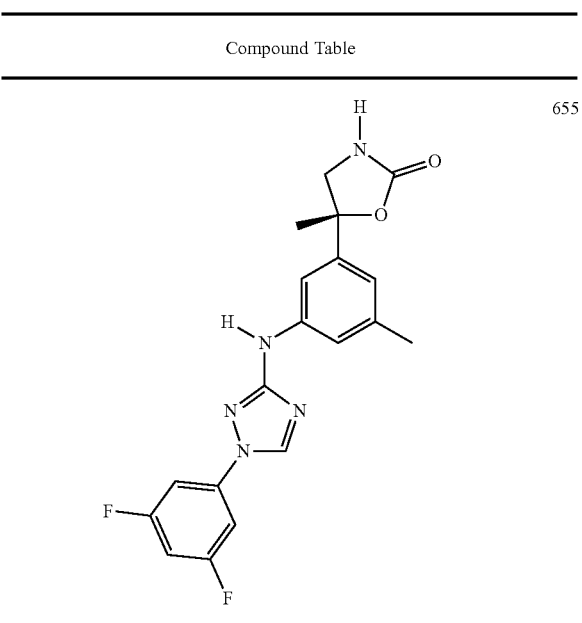
655
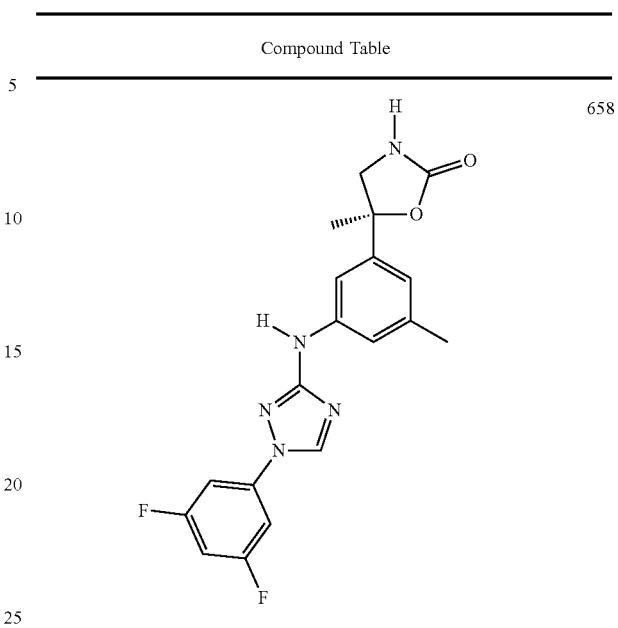
658
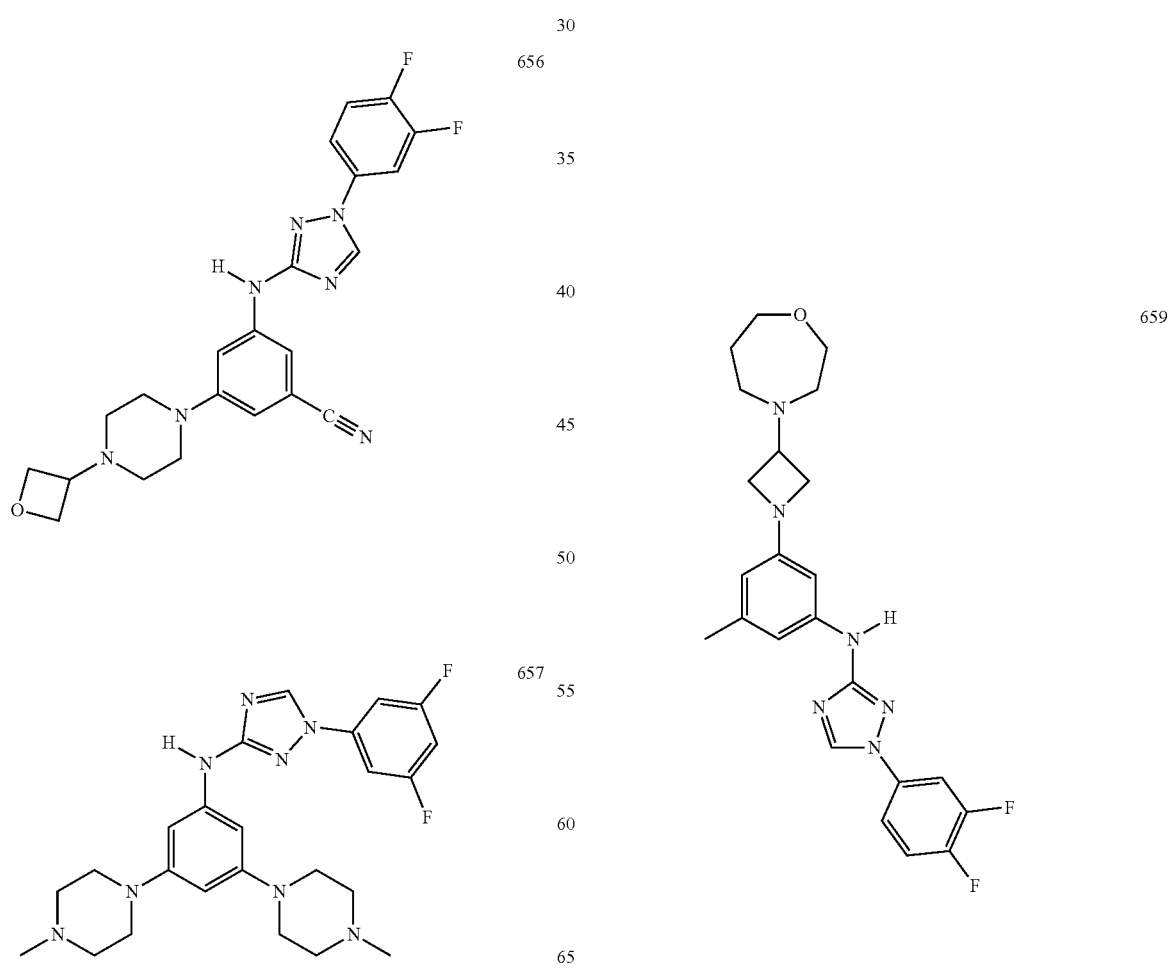
656
659
657

493
TABLE 1A-continued
Compound Table
660
661
494
TABLE 1A-continued
Compound Table
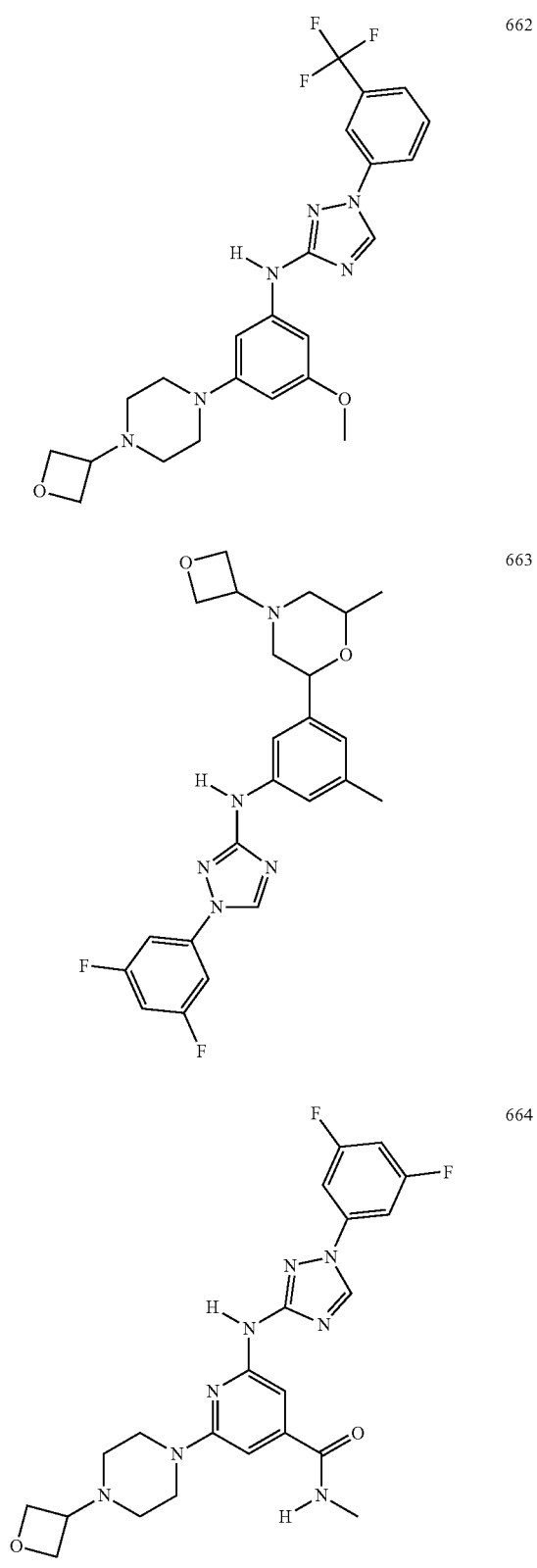
662
663
664

TABLE 1A-continued
Compound Table
665 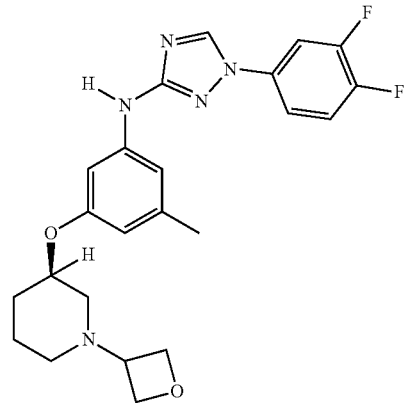 [SMILES: Cc1cc(Nc2ncn(-c3ccc(F)c(F)c3)n2)cc(O[C@@H]2CCCN(C3COC3)C2)c1]
666 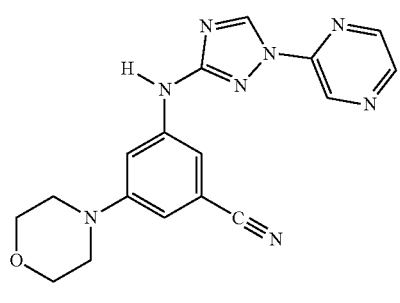 [SMILES: N#Cc1cc(Nc2ncn(-c3cnccn3)n2)cc(N2CCOCC2)c1]
667 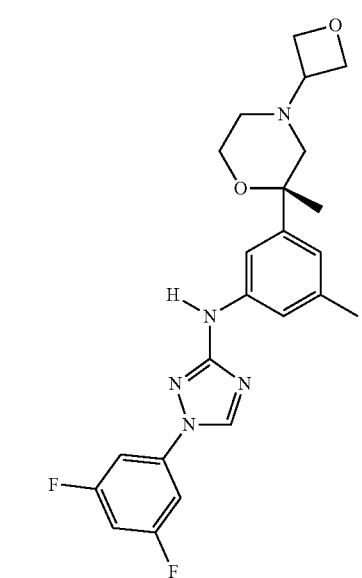 [SMILES: Cc1cc(Nc2ncn(-c3cc(F)cc(F)c3)n2)cc([C@@]2(C)CN(C3COC3)CCO2)c1]
668 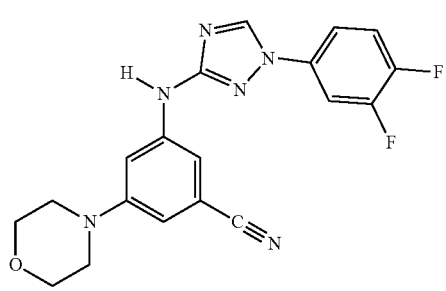 [SMILES: N#Cc1cc(Nc2ncn(-c3ccc(F)c(F)c3)n2)cc(N2CCOCC2)c1]
TABLE 1A-continued
Compound Table
669 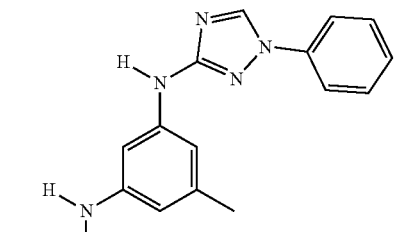
670 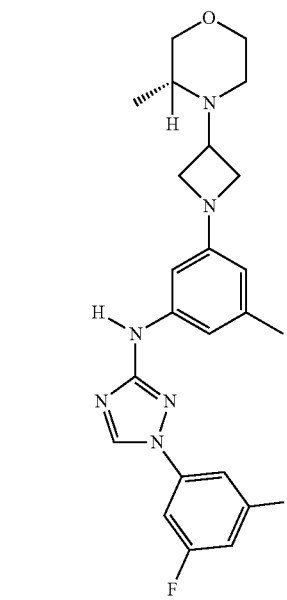
671 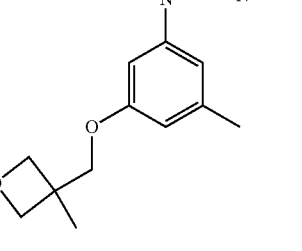

TABLE 1A-continued
Compound Table
672
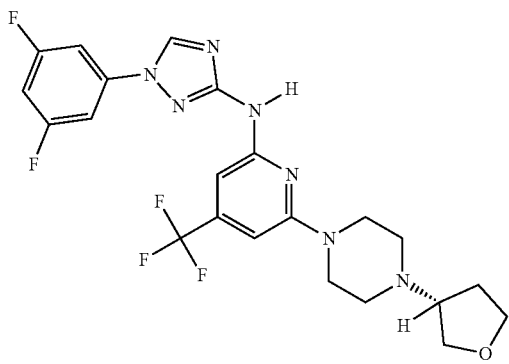 [SMILES: Fc1cc(F)cc(-n2cnc(Nc3cc(C(F)(F)F)cc(N4CCN([C@@H]5CCOC5)CC4)n3)n2)c1]
673
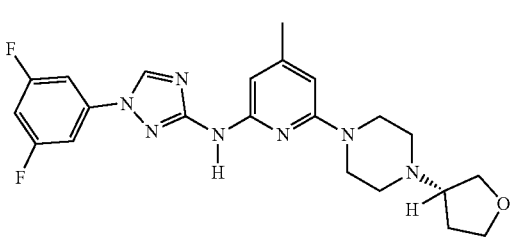 [SMILES: Cc1cc(Nc2ncn(-c3cc(F)cc(F)c3)n2)nc(N2CCN([C@H]3CCOC3)CC2)c1]
674
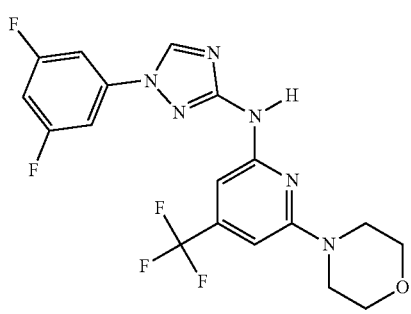
675
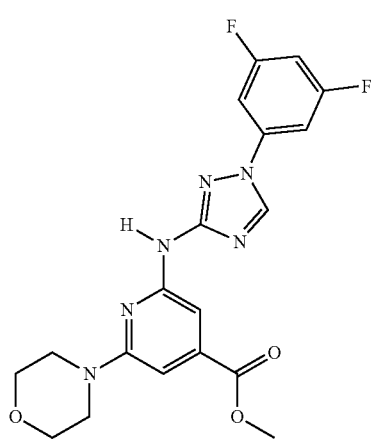 [SMILES: COC(=O)c1cc(Nc2ncn(-c3cc(F)cc(F)c3)n2)nc(N2CCOCC2)c1]
TABLE 1A-continued
Compound Table
676
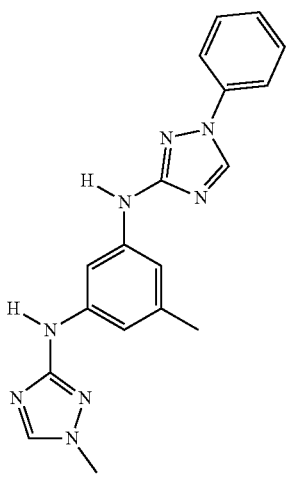
677
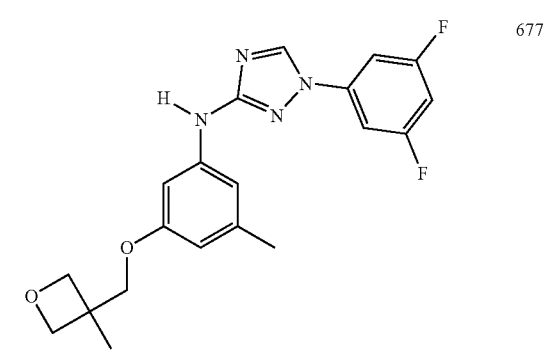
678
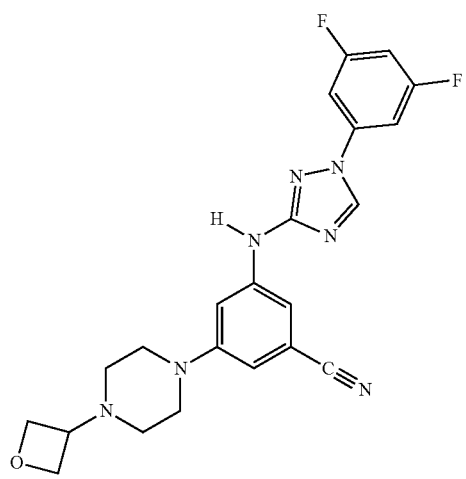 [SMILES: N#Cc1cc(Nc2ncn(-c3cc(F)cc(F)c3)n2)cc(N2CCN(C3COC3)CC2)c1]

TABLE 1A-continued
Compound Table
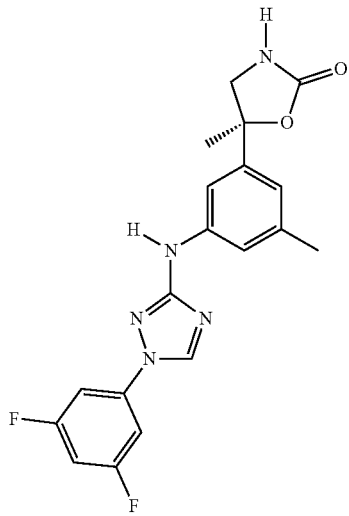 [SMILES: Cc1cc(Nc2ncn(-c3cc(F)cc(F)c3)n2)cc([C@@]2(C)CNC(=O)O2)c1]
679
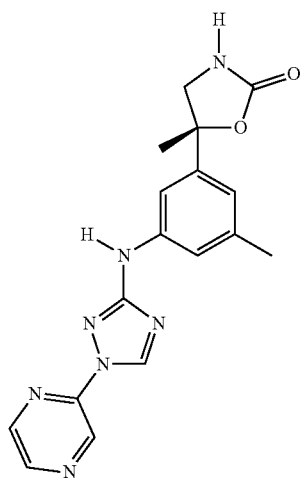
682
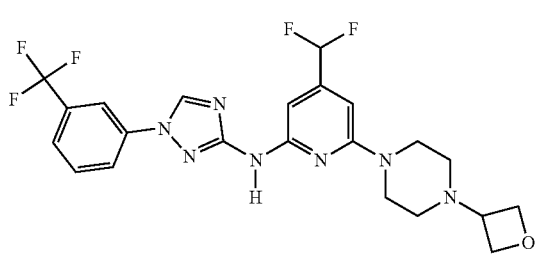 [SMILES: FC(F)c1cc(Nc2ncn(-c3cccc(C(F)(F)F)c3)n2)nc(N2CCN(C3COC3)CC2)c1]
680
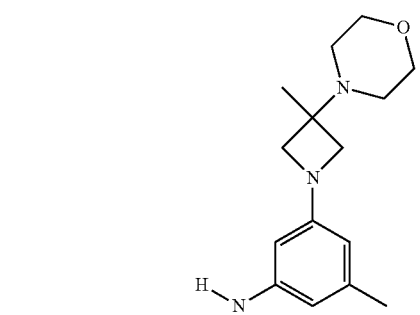
683
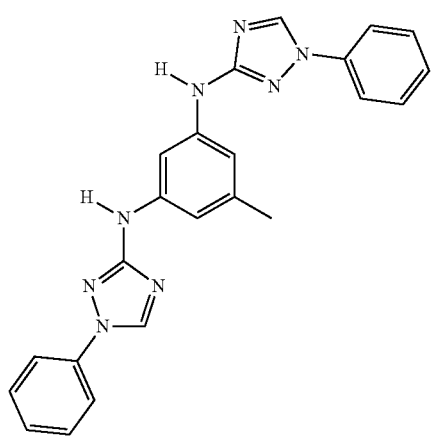 [SMILES: Cc1cc(Nc2ncn(-c3ccccc3)n2)cc(Nc2ncn(-c3ccccc3)n2)c1]
681
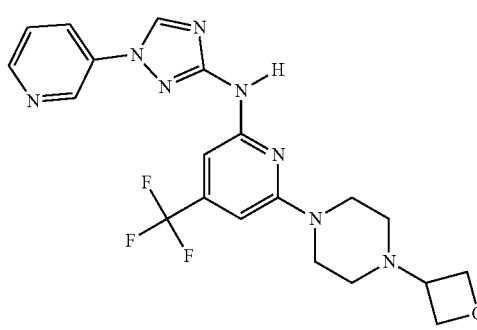
684

TABLE 1A-continued
Compound Table
685
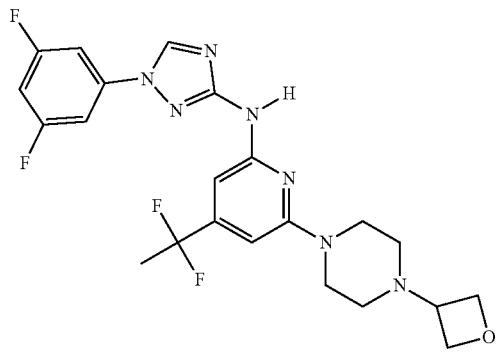 [SMILES: CC(F)(F)c1cc(Nc2ncn(-c3cc(F)cc(F)c3)n2)nc(N2CCN(C3COC3)CC2)c1]
686
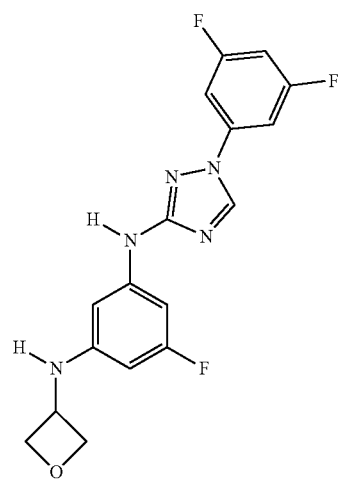
687
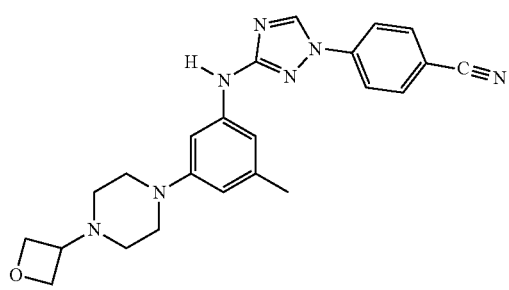 [SMILES: Cc1cc(Nc2ncn(-c3ccc(C#N)cc3)n2)cc(N2CCN(C3COC3)CC2)c1]
TABLE 1A-continued
Compound Table
688
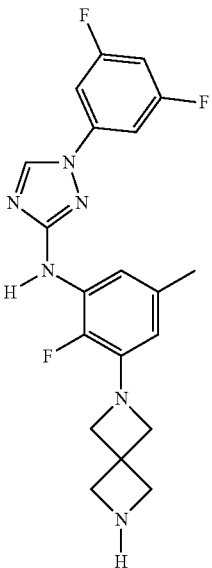 [SMILES: Cc1cc(Nc2ncn(-c3cc(F)cc(F)c3)n2)c(F)c(N2CC3(CNC3)C2)c1]
689
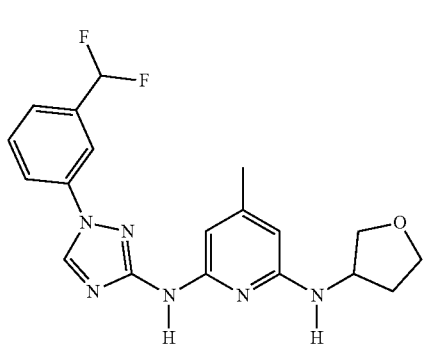 [SMILES: Cc1cc(Nc2ncn(-c3cccc(C(F)F)c3)n2)nc(NC2CCOC2)c1]
690
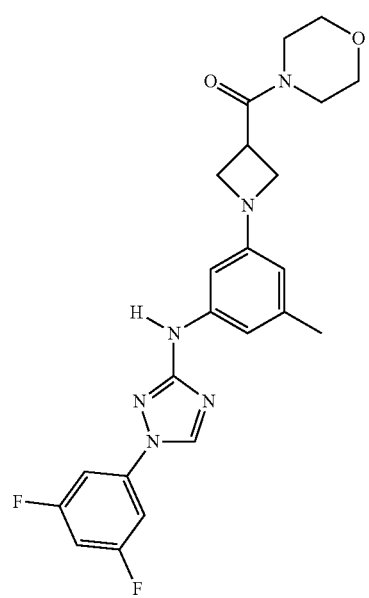 [SMILES: Cc1cc(Nc2ncn(-c3cc(F)cc(F)c3)n2)cc(N2CC(C(=O)N3CCOCC3)C2)c1]

TABLE 1A-continued
Compound Table
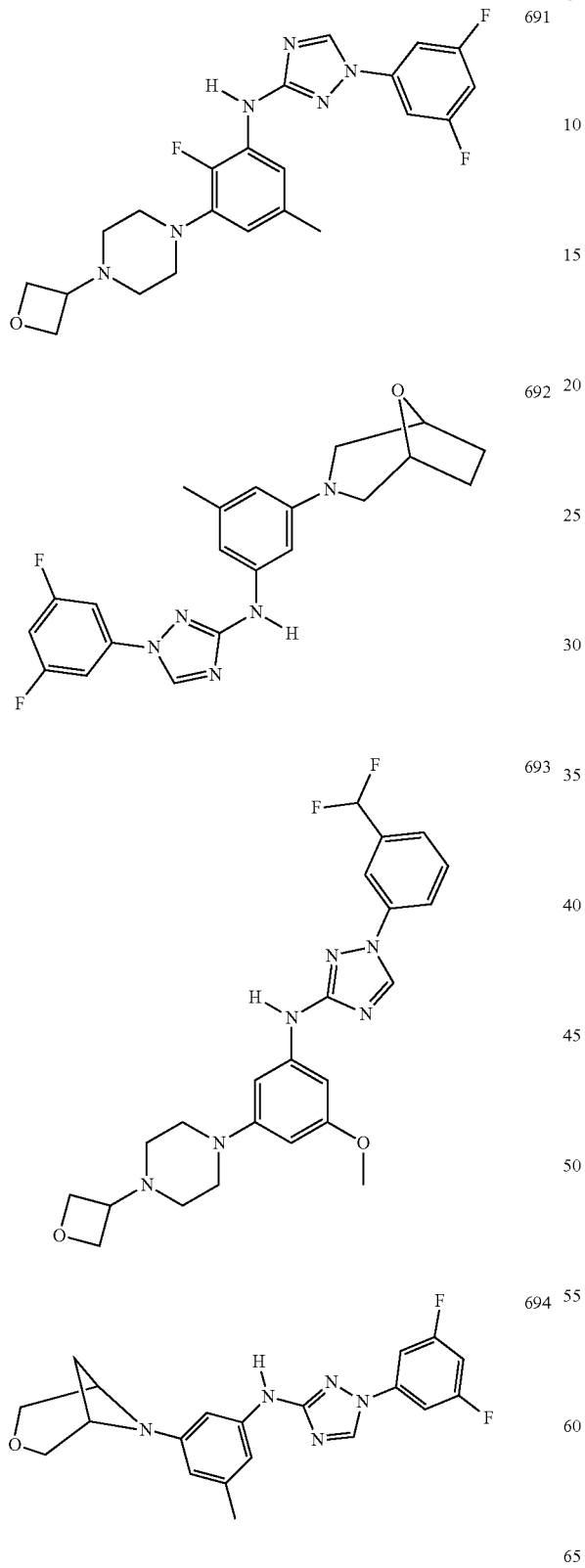
691
692
693
694
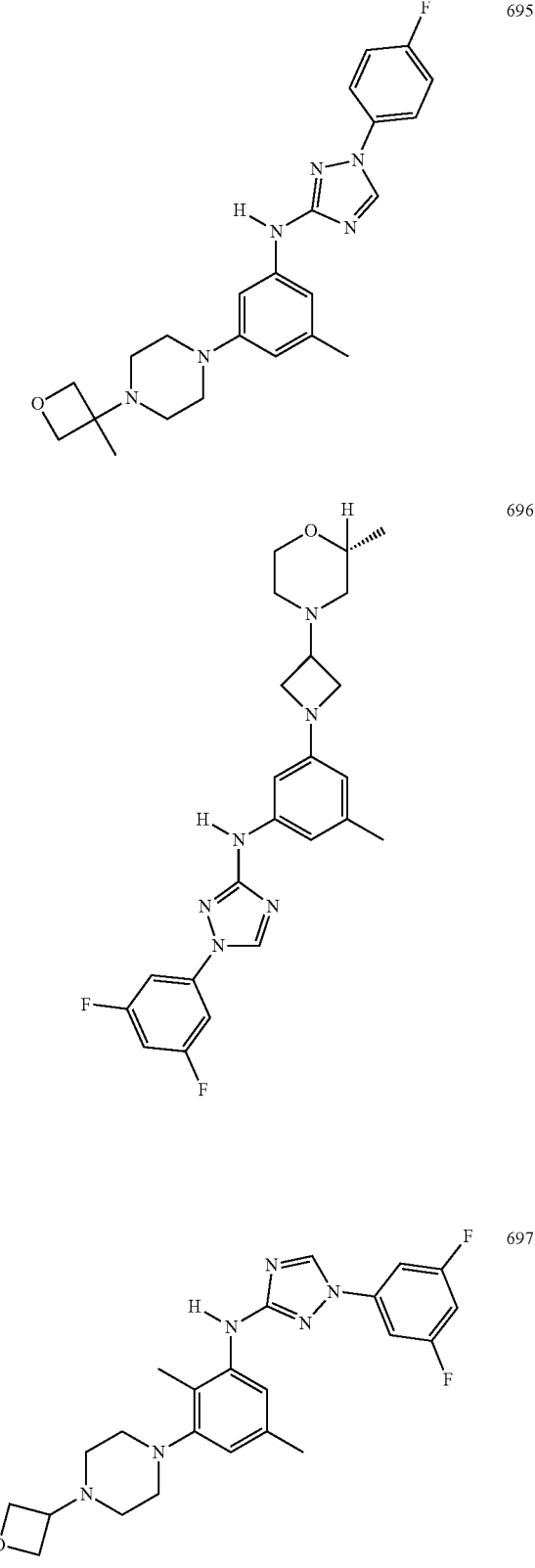
695
696
697

TABLE 1A-continued
Compound Table
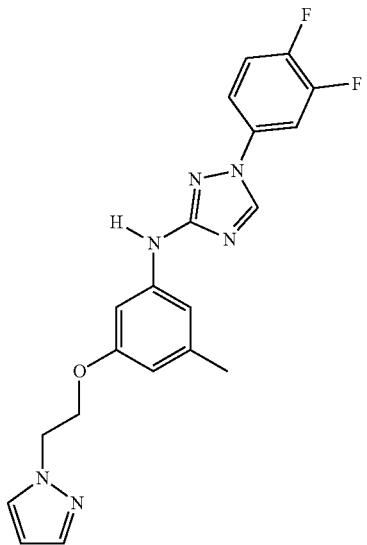 [SMILES: Cc1cc(Nc2ncn(-c3ccc(F)c(F)c3)n2)cc(OCCn2cccn2)c1]
698
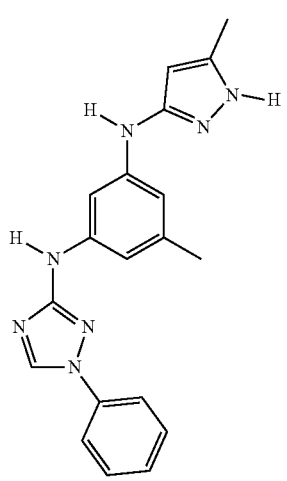 [SMILES: Cc1cc(Nc2cc(C)[nH]n2)cc(Nc2ncn(-c3ccccc3)n2)c1]
699
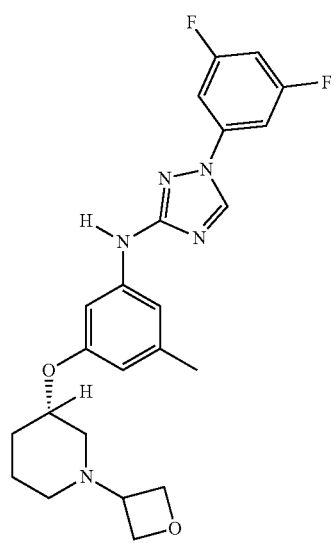 [SMILES: Cc1cc(Nc2ncn(-c3cc(F)cc(F)c3)n2)cc(O[C@H]2CCCN(C3COC3)C2)c1]
700
TABLE 1A-continued
Compound Table
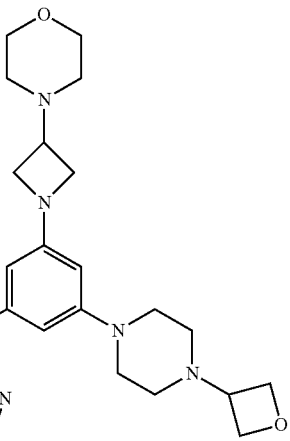
701
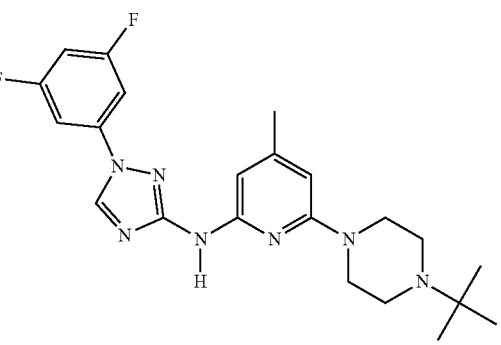
702
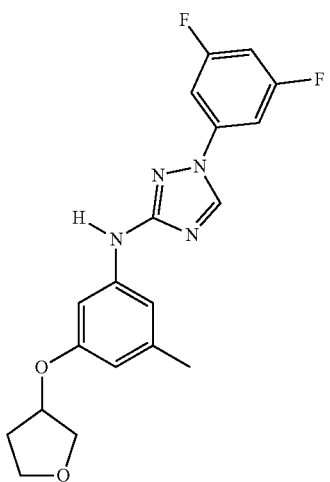 [SMILES: Cc1cc(Nc2ncn(-c3cc(F)cc(F)c3)n2)cc(OC2CCOC2)c1]
703

TABLE 1A-continued
Compound Table
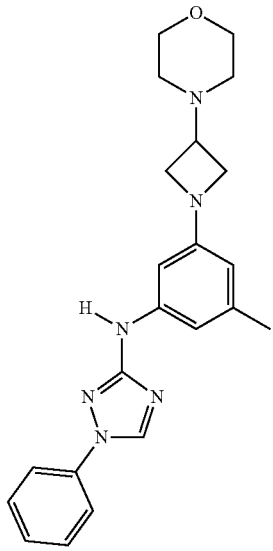 [SMILES: Cc1cc(Nc2ncn(-c3ccccc3)n2)cc(N2CC(N3CCOCC3)C2)c1] 704
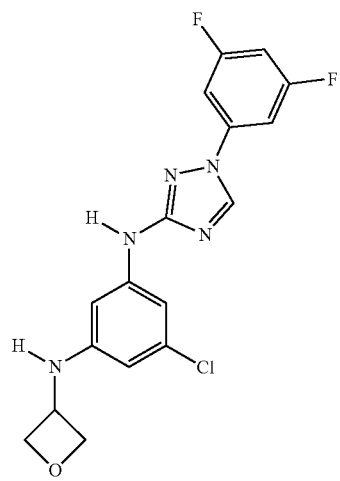 [SMILES: Fc1cc(F)cc(-n2cnc(Nc3cc(Cl)cc(NC4COC4)c3)n2)c1] 705
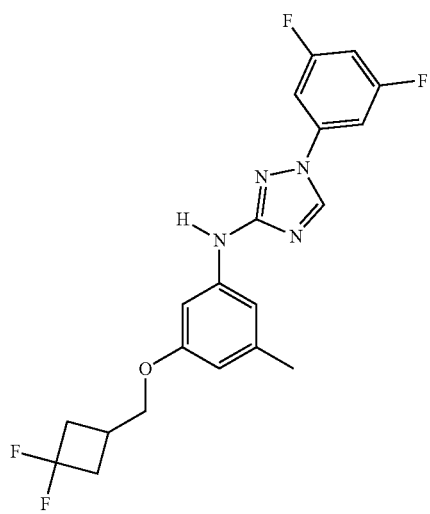 [SMILES: Cc1cc(Nc2ncn(-c3cc(F)cc(F)c3)n2)cc(OCC2CC(F)(F)C2)c1] 706
TABLE 1A-continued
Compound Table
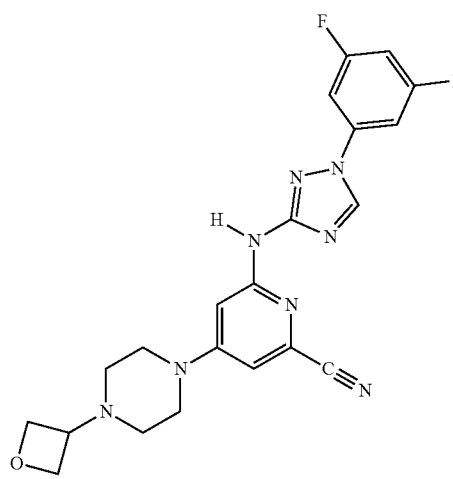 707
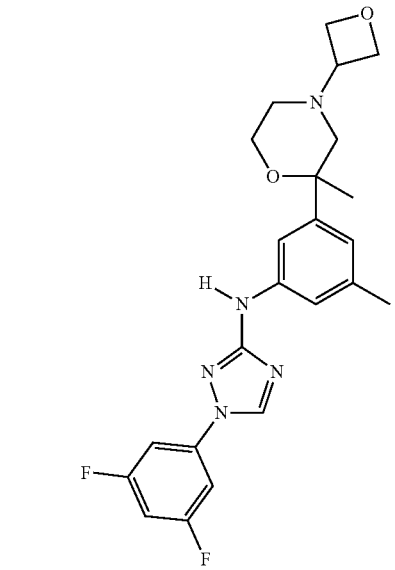 [SMILES: Cc1cc(Nc2ncn(-c3cc(F)cc(F)c3)n2)cc(C2(C)CN(C3COC3)CCO2)c1] 708
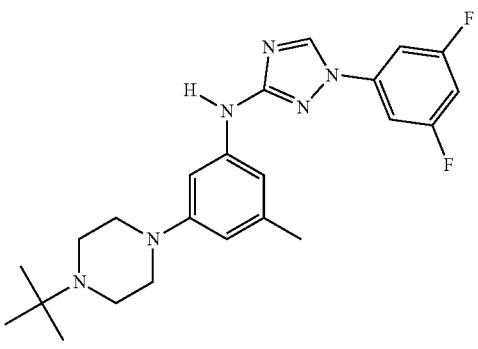 [SMILES: Cc1cc(Nc2ncn(-c3cc(F)cc(F)c3)n2)cc(N2CCN(C(C)(C)C)CC2)c1] 709

TABLE 1A-continued
Compound Table
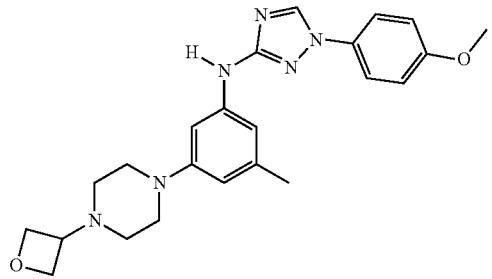 [SMILES: COc1ccc(-n2cnc(Nc3cc(C)cc(N4CCN(C5COC5)CC4)c3)n2)cc1] 710
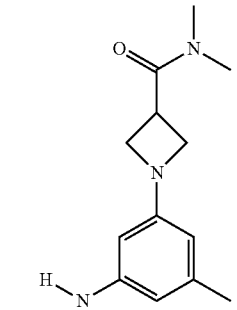 711
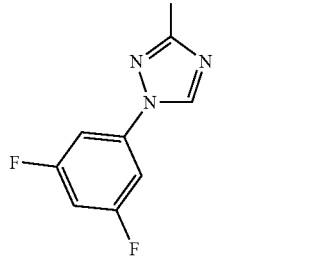 712
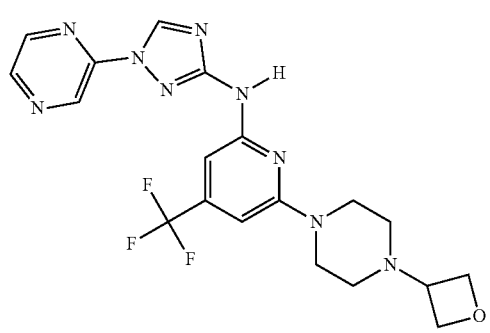 [SMILES: FC(F)(F)c1cc(Nc2ncn(-c3cnccn3)n2)nc(N2CCN(C3COC3)CC2)c1] 713
TABLE 1A-continued
Compound Table
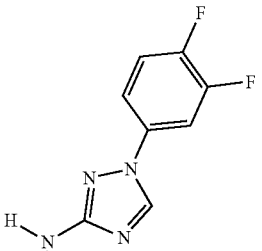 714
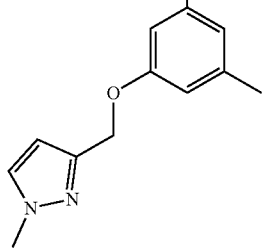 715
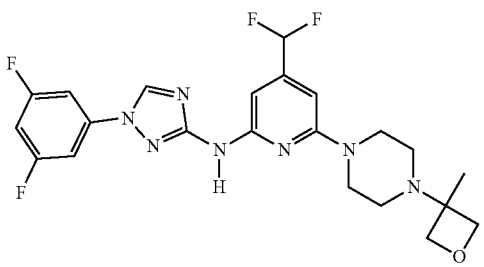 [SMILES: CC1(N2CCN(c3cc(C(F)F)cc(Nc4ncn(-c5cc(F)cc(F)c5)n4)n3)CC2)COC1] 716

TABLE 1A-continued
Compound Table
717
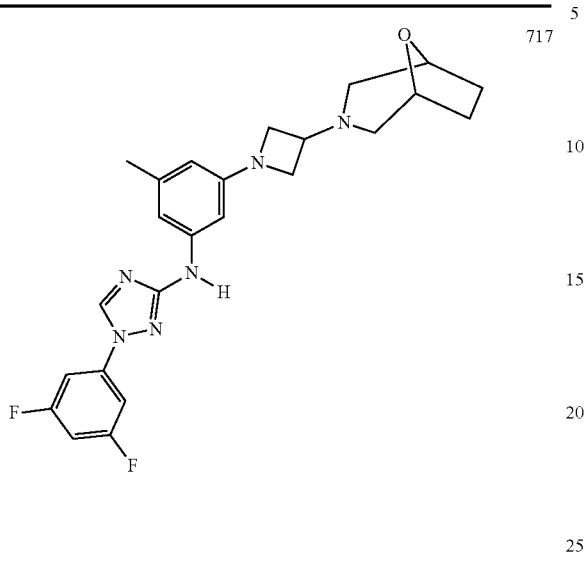
718
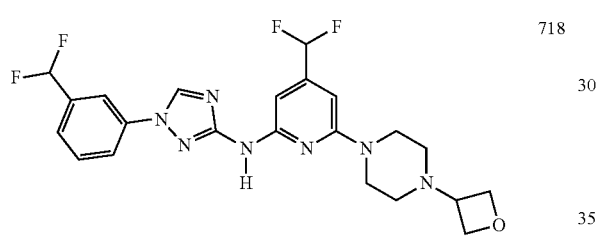
719
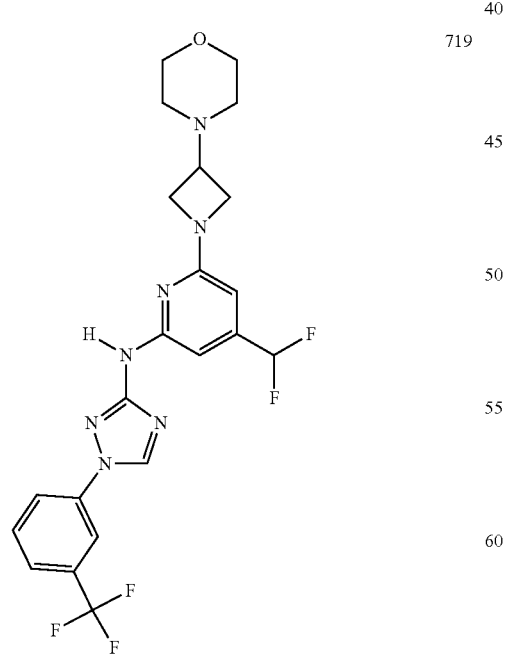
720
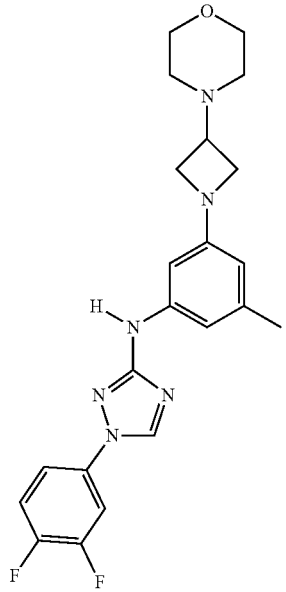 [SMILES: Cc1cc(Nc2ncn(-c3ccc(F)c(F)c3)n2)cc(N2CC(N3CCOCC3)C2)c1]
721
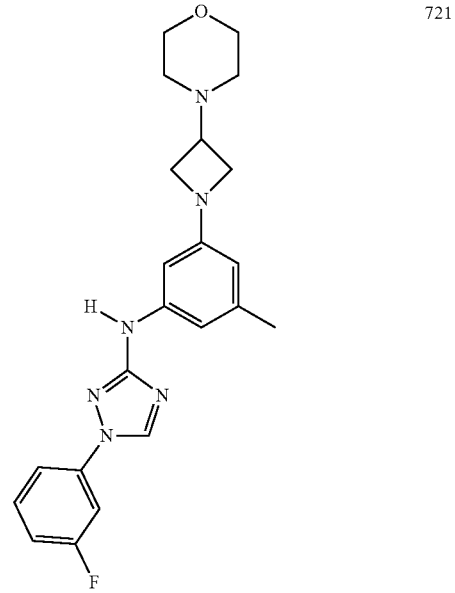
722
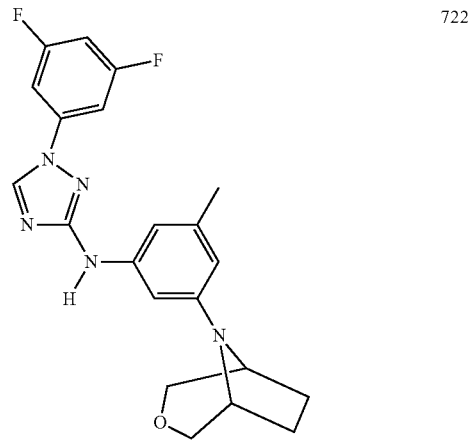

TABLE 1A-continued
Compound Table
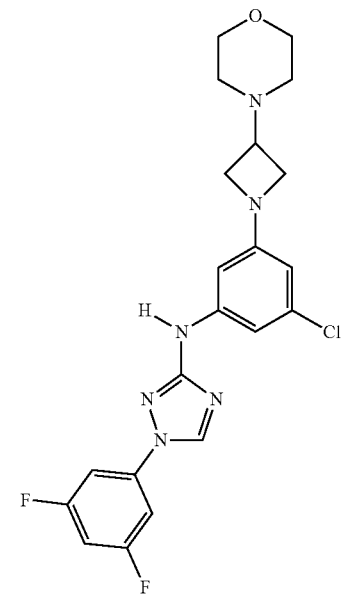 [SMILES: Fc1cc(F)cc(-n2cnc(Nc3cc(Cl)cc(N4CC(N5CCOCC5)C4)c3)n2)c1]
723
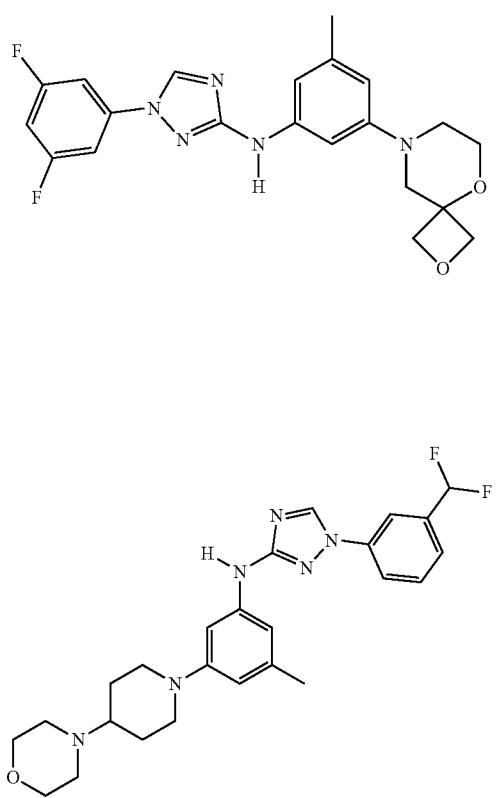
724
725
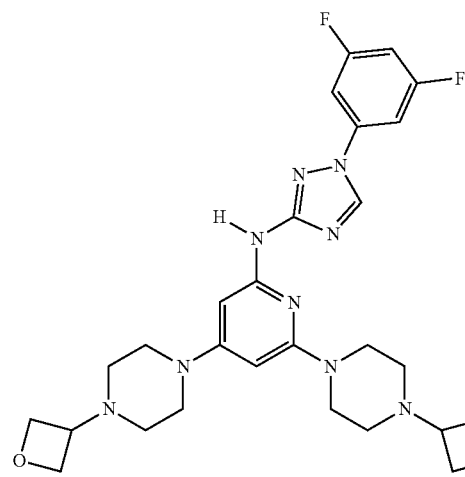
726
727
728
729

TABLE 1A-continued
Compound Table
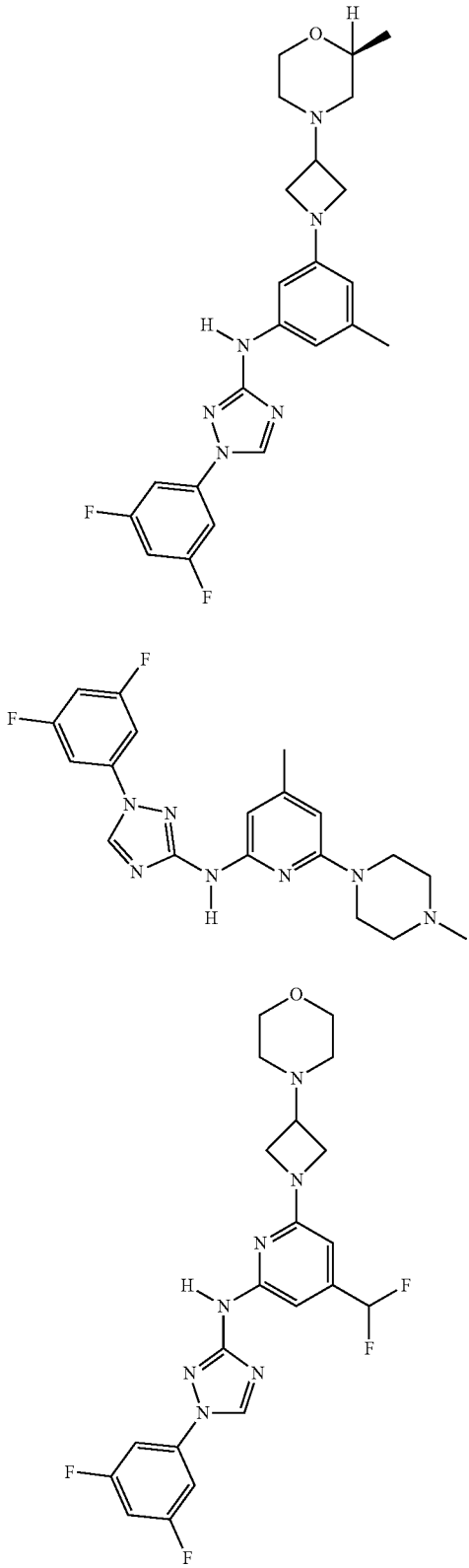
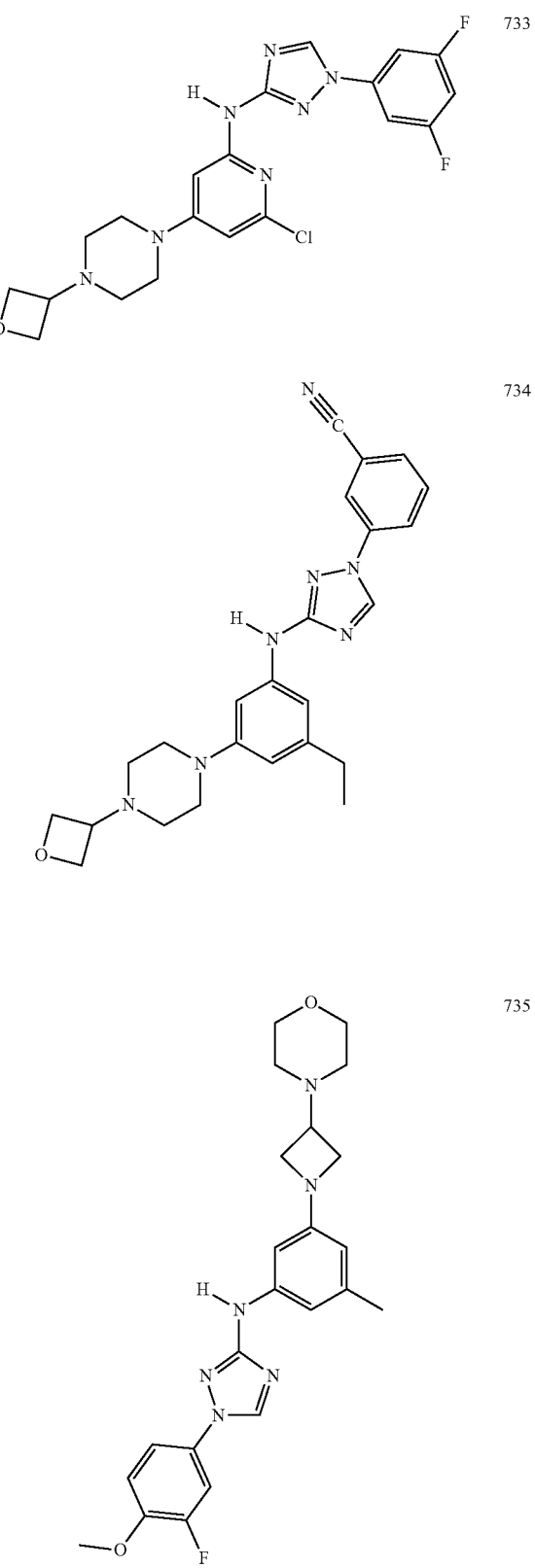

US 10,766,869 B2
517
TABLE 1A-continued
Compound Table
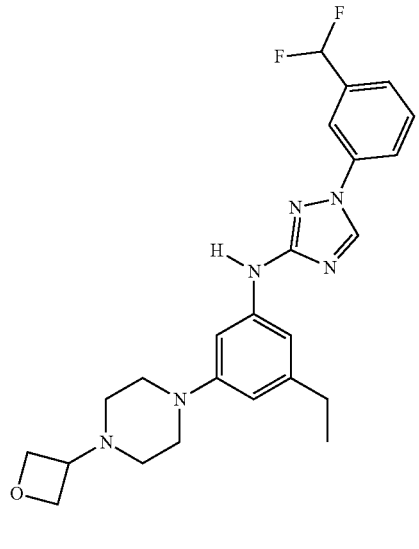 [SMILES: CCc1cc(Nc2ncn(-c3cccc(C(F)F)c3)n2)cc(N2CCN(C3COC3)CC2)c1]
736
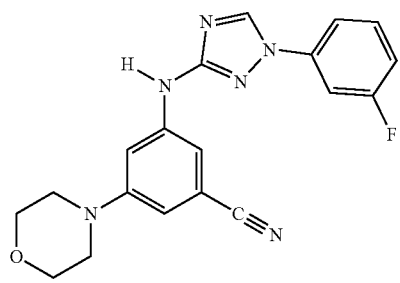 [SMILES: N#Cc1cc(Nc2ncn(-c3cccc(F)c3)n2)cc(N2CCOCC2)c1]
737
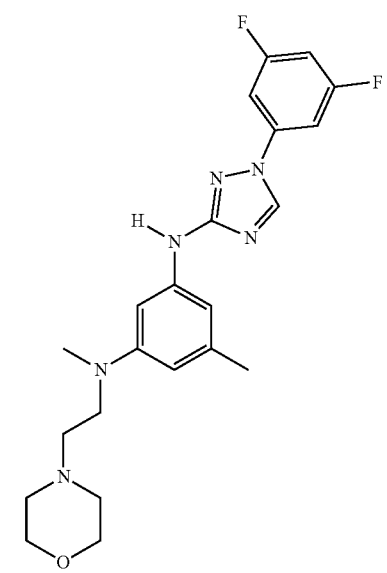 [SMILES: Cc1cc(Nc2ncn(-c3cc(F)cc(F)c3)n2)cc(N(C)CCN2CCOCC2)c1]
738
518
TABLE 1A-continued
Compound Table
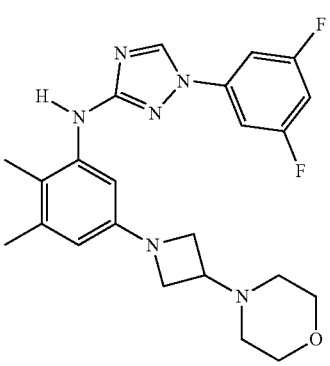 [SMILES: Cc1cc(N2CC(N3CCOCC3)C2)cc(Nc2ncn(-c3cc(F)cc(F)c3)n2)c1C]
739
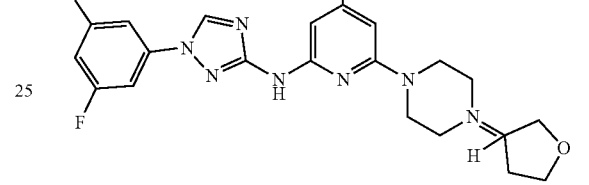
740
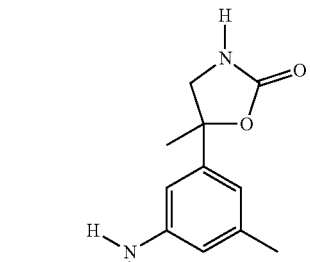
741
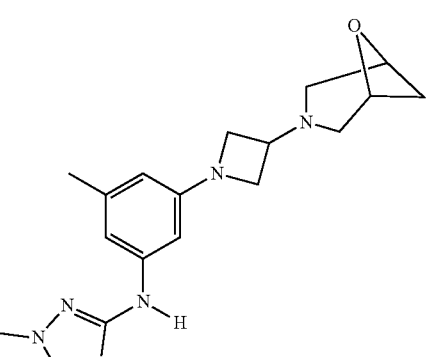
742

TABLE 1A-continued
Compound Table
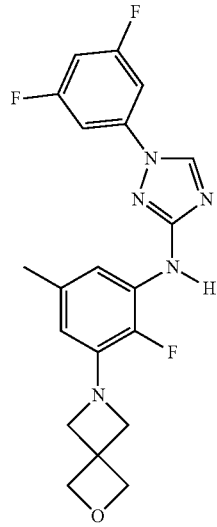 [SMILES: Cc1cc(Nc2ncn(-c3cc(F)cc(F)c3)n2)c(F)c(N2CC3(COC3)C2)c1]
743
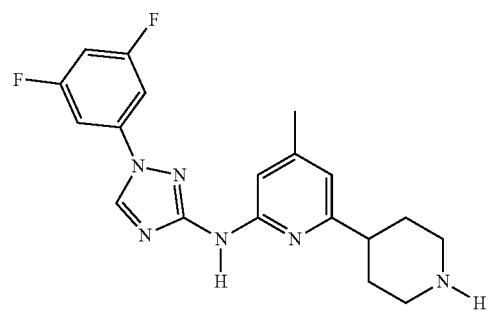 [SMILES: Cc1cc(Nc2ncn(-c3cc(F)cc(F)c3)n2)nc(C2CCNCC2)c1]
744
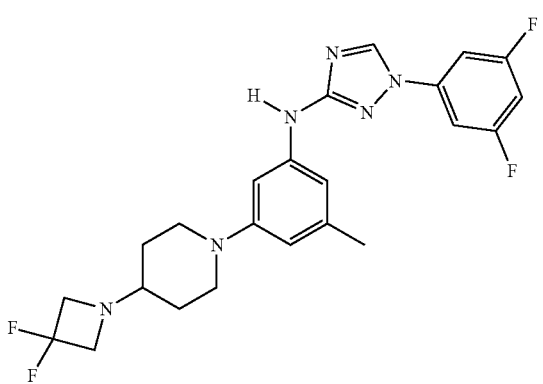 [SMILES: Cc1cc(Nc2ncn(-c3cc(F)cc(F)c3)n2)cc(N2CCC(N3CC(F)(F)C3)CC2)c1]
745
TABLE 1A-continued
Compound Table
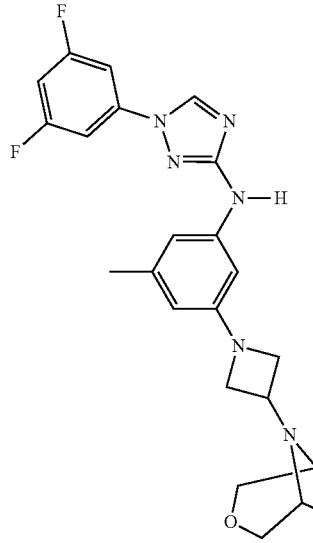
746
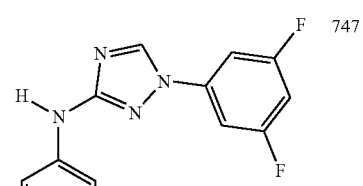
747
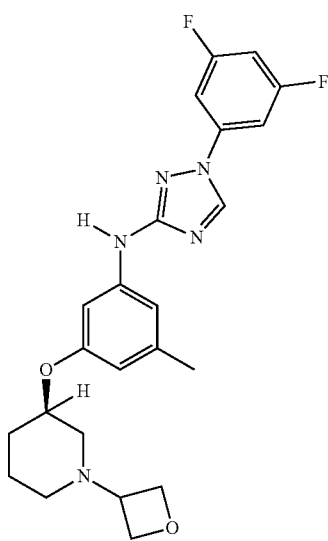 [SMILES: Cc1cc(Nc2ncn(-c3cc(F)cc(F)c3)n2)cc(O[C@@H]2CCCN(C3COC3)C2)c1]
748

TABLE 1A-continued
Compound Table
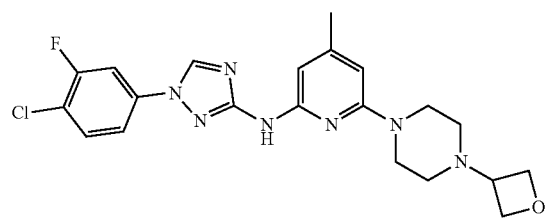 [SMILES: Cc1cc(Nc2ncn(-c3ccc(Cl)c(F)c3)n2)nc(N2CCN(C3COC3)CC2)c1]
749
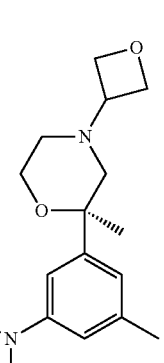
750
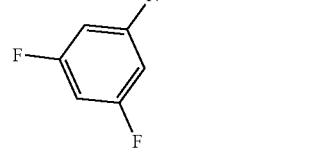
751
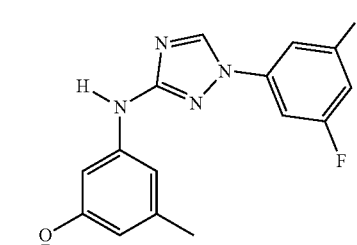
752
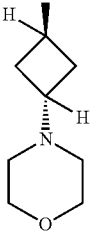
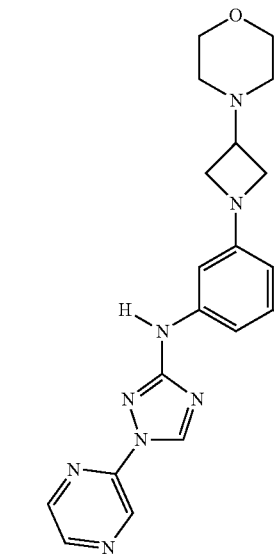
753
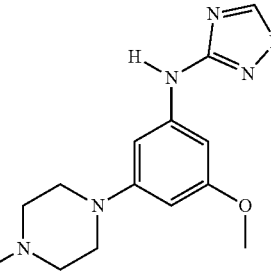
754
755

TABLE 1A-continued
Compound Table
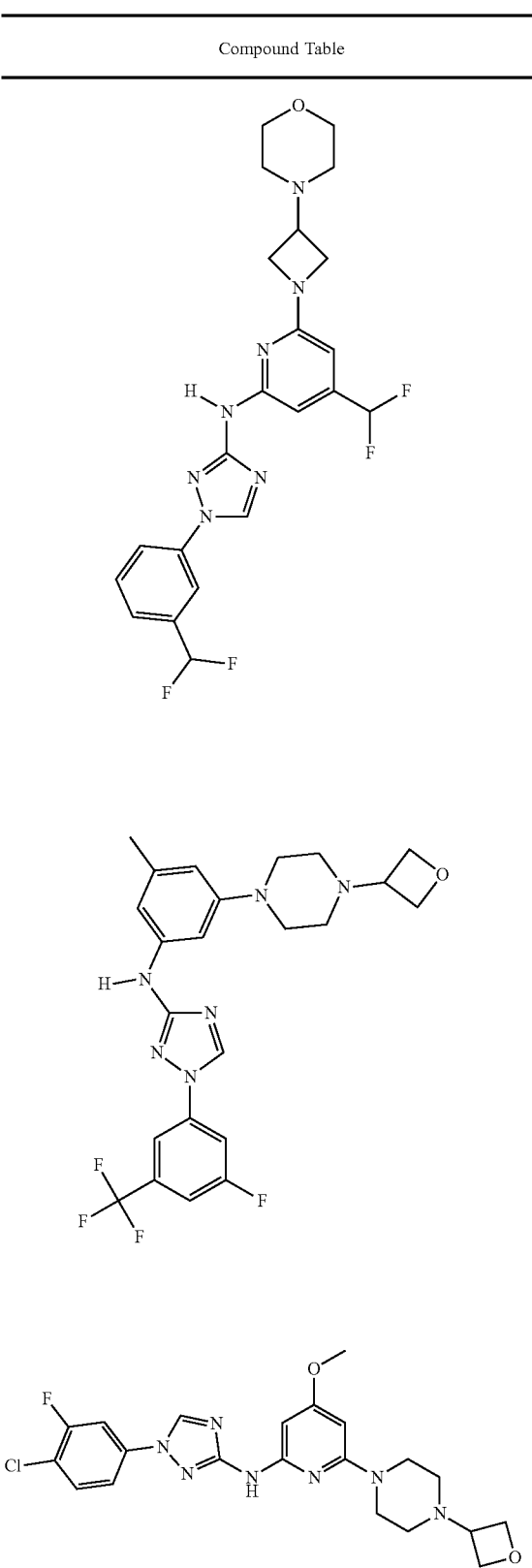
756
757
758
TABLE 1A-continued
Compound Table
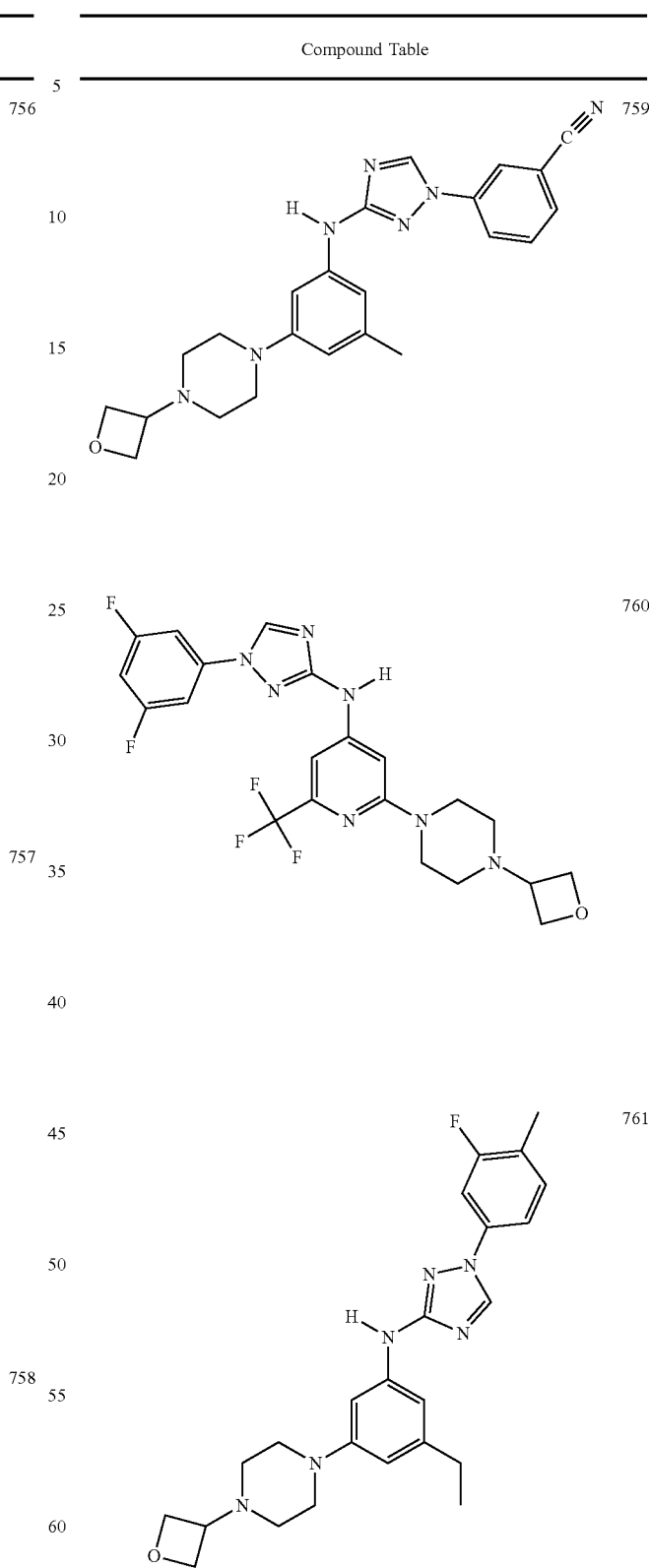
759
760
761

TABLE 1A-continued
Compound Table
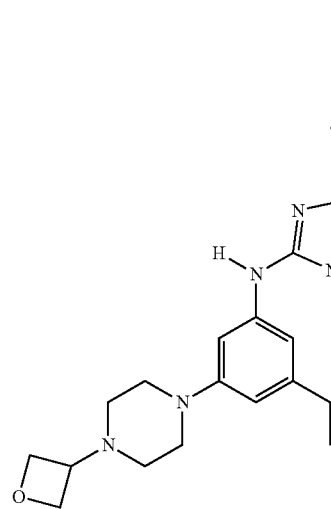
762
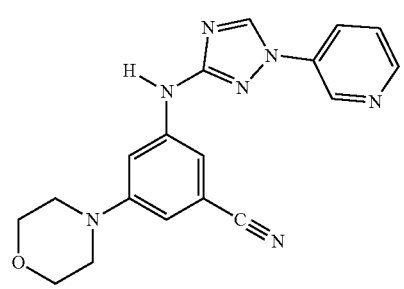 [SMILES: N#Cc1cc(Nc2ncn(-c3cccnc3)n2)cc(N2CCOCC2)c1]
763
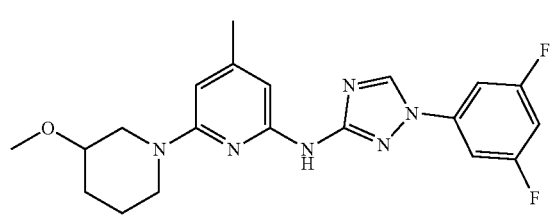 [SMILES: COC1CCCN(c2cc(C)cc(Nc3ncn(-c4cc(F)cc(F)c4)n3)n2)C1]
764
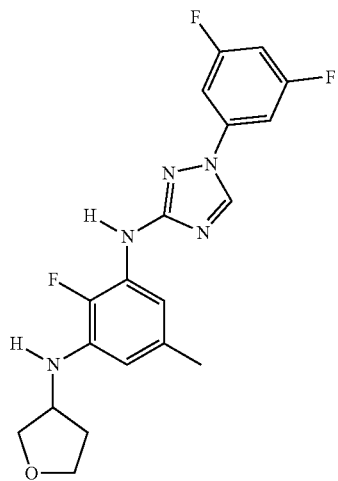 [SMILES: Cc1cc(Nc2ncn(-c3cc(F)cc(F)c3)n2)c(F)c(NC2CCOC2)c1]
765
TABLE 1A-continued
Compound Table
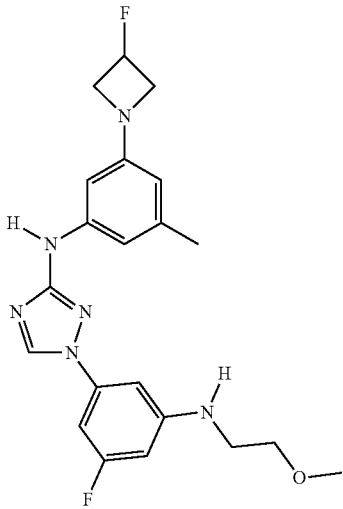 [SMILES: COCCNc1cc(F)cc(-n2cnc(Nc3cc(C)cc(N4CC(F)C4)c3)n2)c1]
766
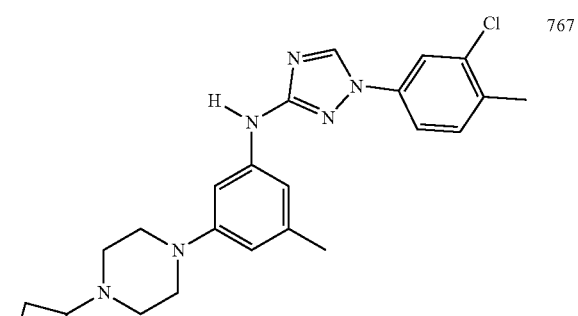
767
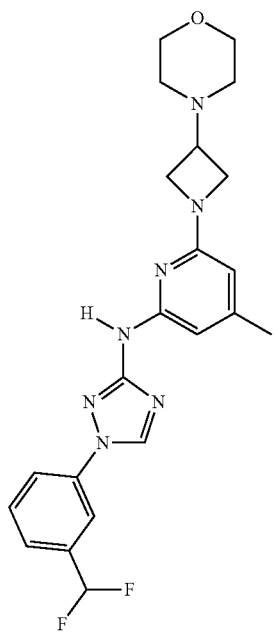 [SMILES: Cc1cc(Nc2ncn(-c3cccc(C(F)F)c3)n2)nc(N2CC(N3CCOCC3)C2)c1]
768

TABLE 1A-continued
Compound Table
769 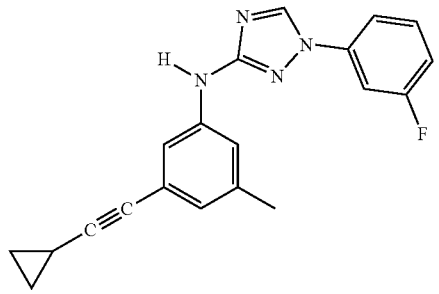 [SMILES: Cc1cc(C#CC2CC2)cc(Nc2ncn(-c3cccc(F)c3)n2)c1]
770 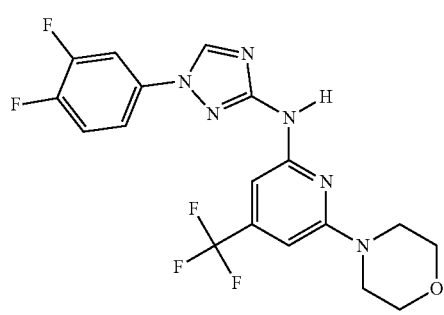 [SMILES: Fc1ccc(-n2cnc(Nc3cc(C(F)(F)F)cc(N4CCOCC4)n3)n2)cc1F]
771 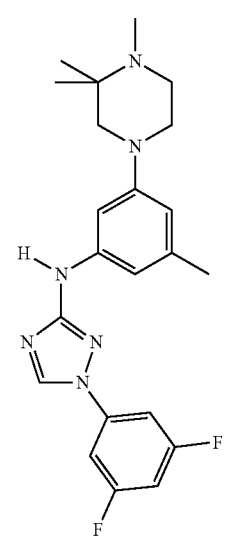 [SMILES: Cc1cc(Nc2ncn(-c3cc(F)cc(F)c3)n2)cc(N2CCN(C)C(C)(C)C2)c1]
772 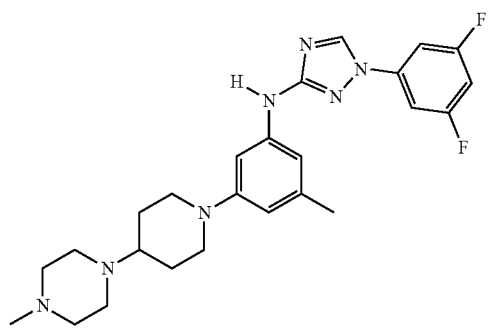 [SMILES: Cc1cc(Nc2ncn(-c3cc(F)cc(F)c3)n2)cc(N2CCC(N3CCN(C)CC3)CC2)c1]
TABLE 1A-continued
Compound Table
773 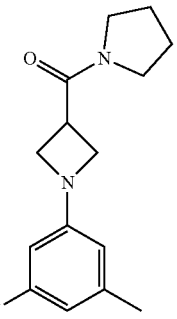
774 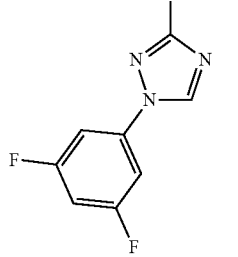
775 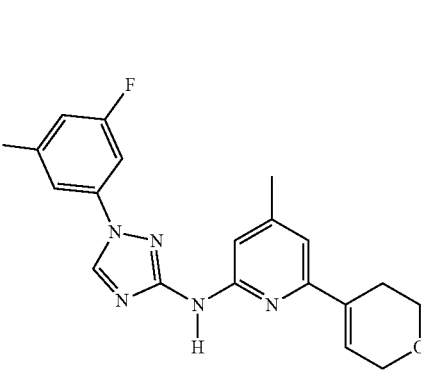
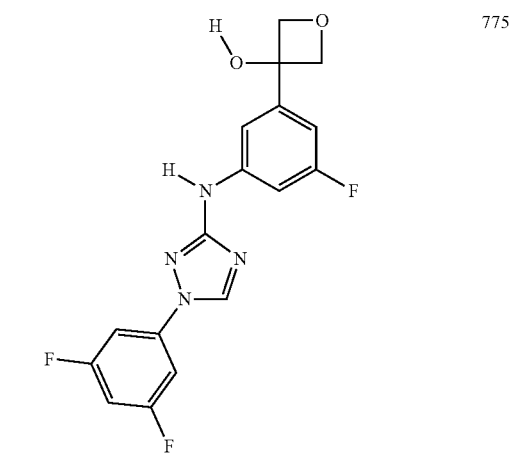

TABLE 1A-continued

Compound Table

| | |
|---|---|
| 776 | 779 |
| 777 | 780 |
| 778 | 781 |

TABLE 1A-continued
Compound Table
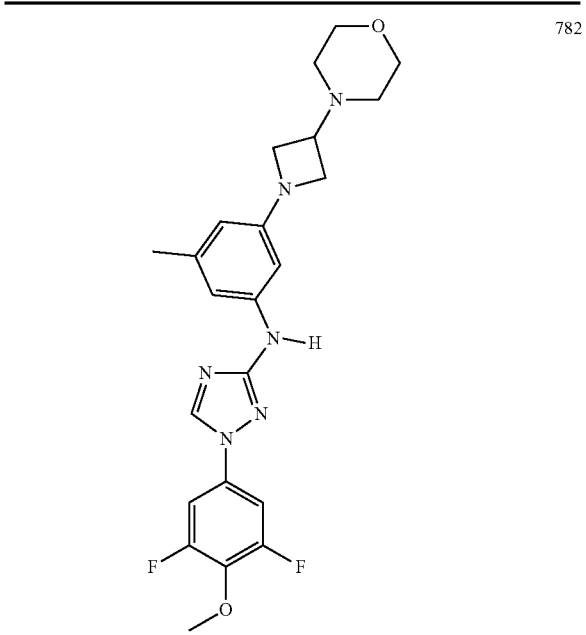
782
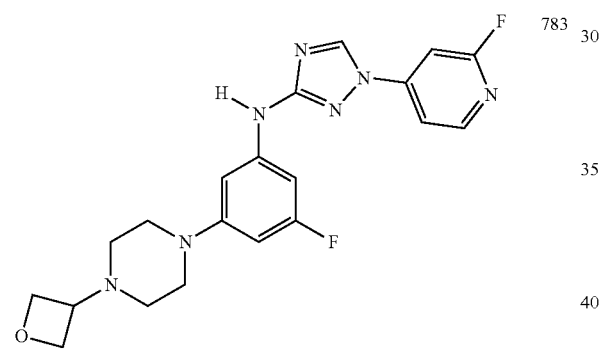
783
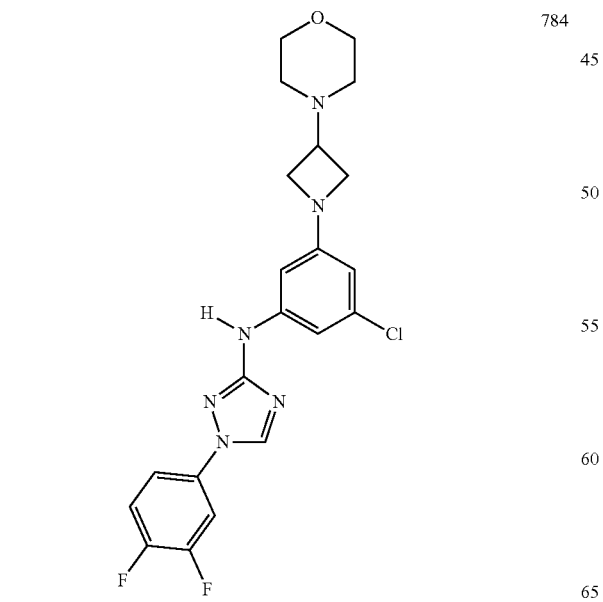
784
TABLE 1A-continued
Compound Table
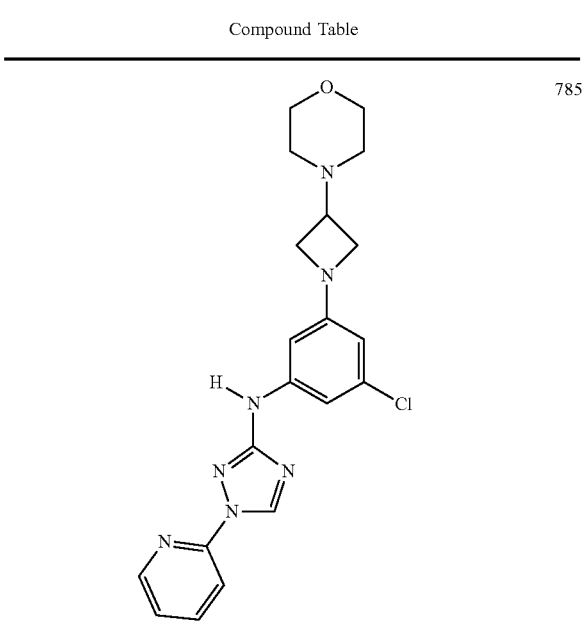
785
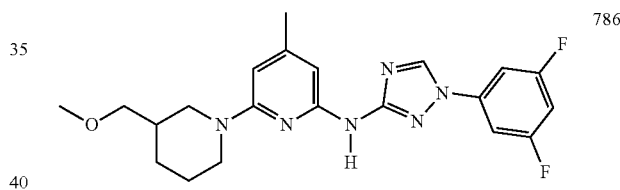
786
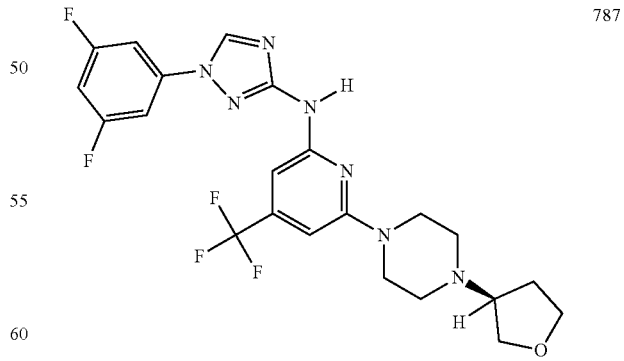
787

TABLE 1A-continued
Compound Table
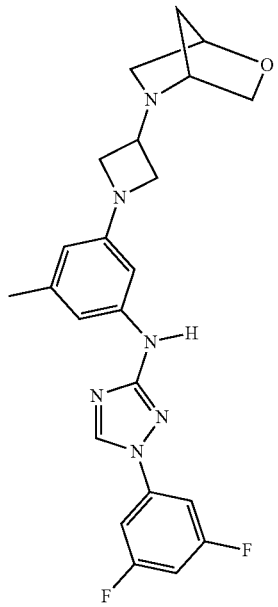 [SMILES: Cc1cc(Nc2ncn(-c3cc(F)cc(F)c3)n2)cc(N2CC(N3CC4CC3CO4)C2)c1]
788
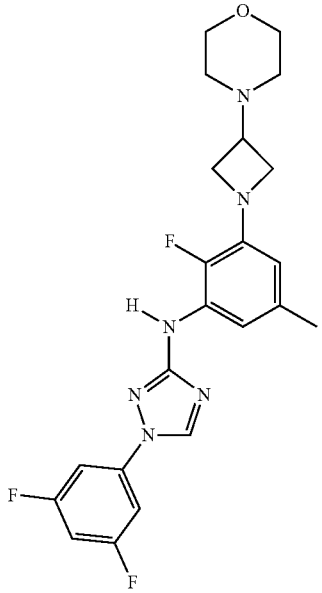
790
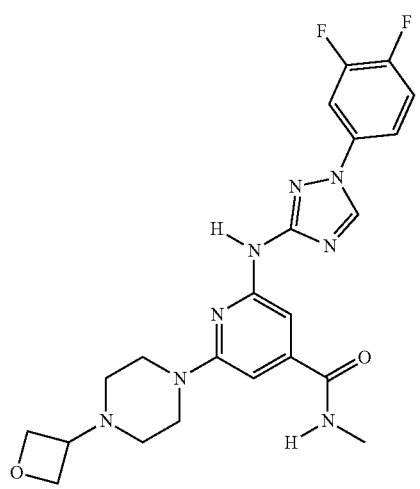 [SMILES: CNC(=O)c1cc(Nc2ncn(-c3ccc(F)c(F)c3)n2)nc(N2CCN(C3COC3)CC2)c1]
789
791

TABLE 1A-continued
Compound Table
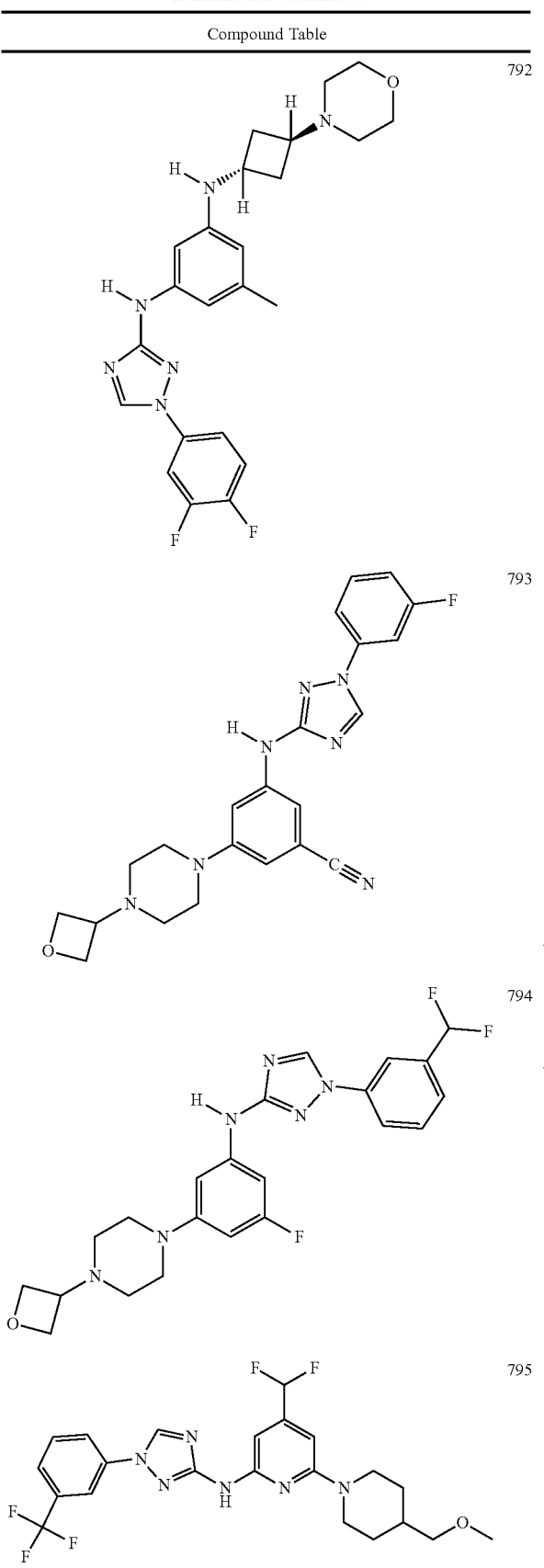
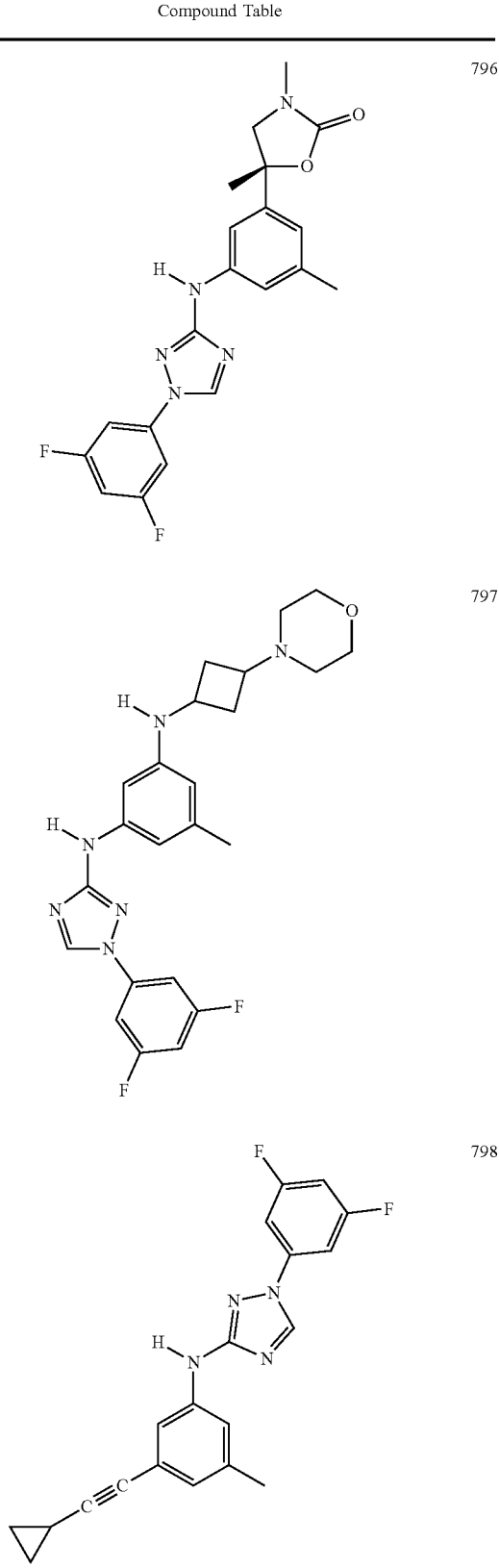

TABLE 1A-continued
Compound Table
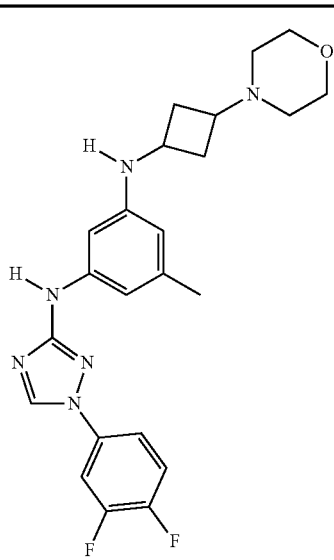
799
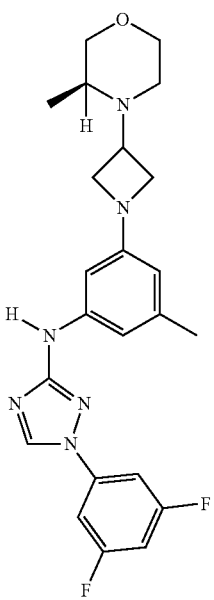
800
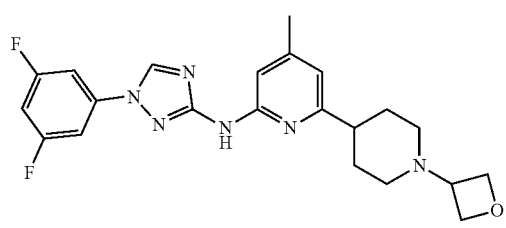 [SMILES: Cc1cc(Nc2ncn(-c3cc(F)cc(F)c3)n2)nc(C2CCN(C3COC3)CC2)c1]
801
TABLE 1A-continued
Compound Table
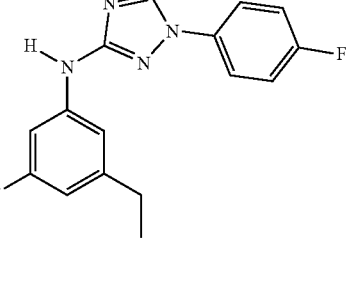
802
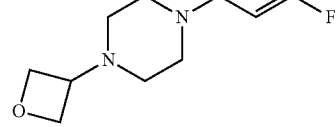
803
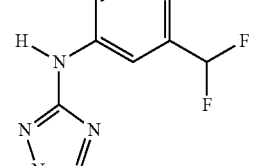
804

TABLE 1A-continued
Compound Table
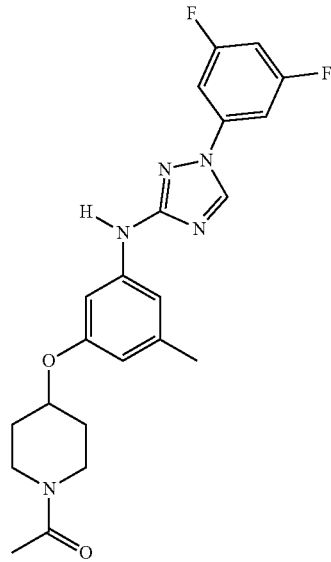 [SMILES: CC(=O)N1CCC(Oc2cc(C)cc(Nc3ncn(-c4cc(F)cc(F)c4)n3)c2)CC1]
805
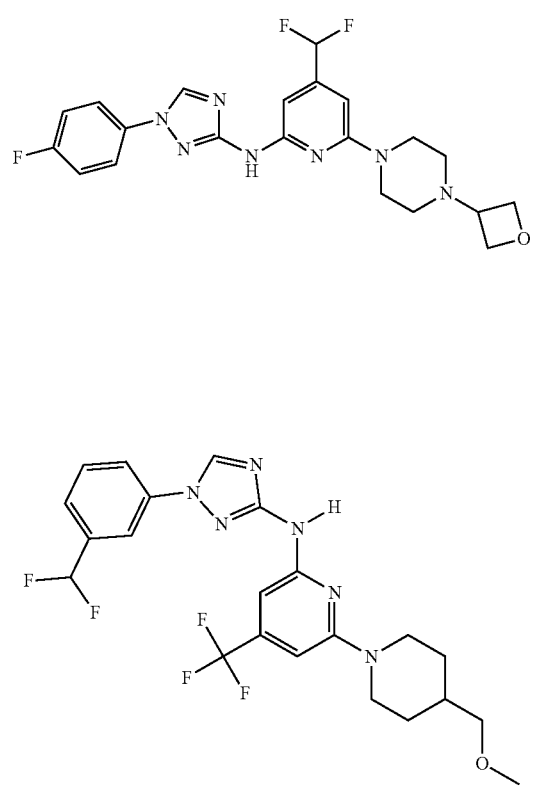
806
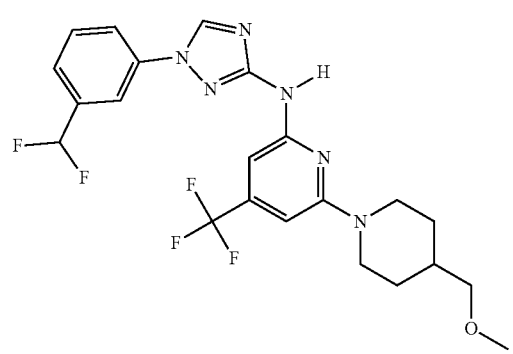 [SMILES: COCC1CCN(c2cc(C(F)(F)F)cc(Nc3ncn(-c4cccc(C(F)F)c4)n3)n2)CC1]
807
TABLE 1A-continued
Compound Table
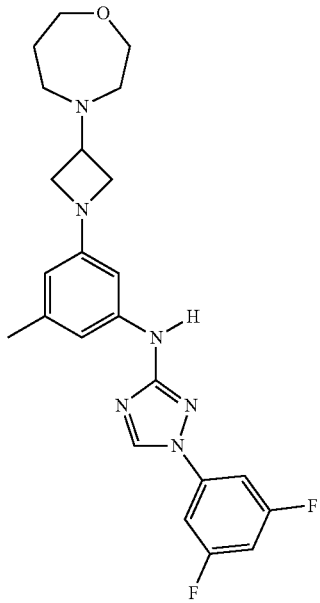 [SMILES: Cc1cc(Nc2ncn(-c3cc(F)cc(F)c3)n2)cc(N2CC(N3CCCOCC3)C2)c1]
808
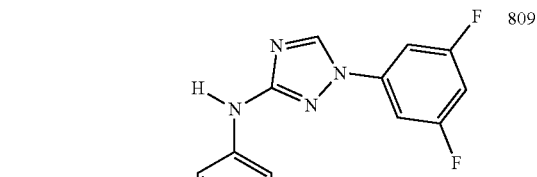
809
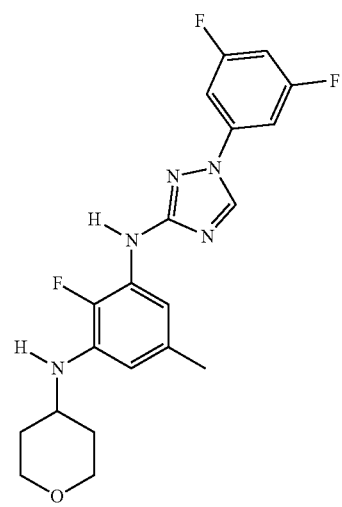 [SMILES: Cc1cc(Nc2ncn(-c3cc(F)cc(F)c3)n2)c(F)c(NC2CCOCC2)c1]
810

TABLE 1A-continued
Compound Table
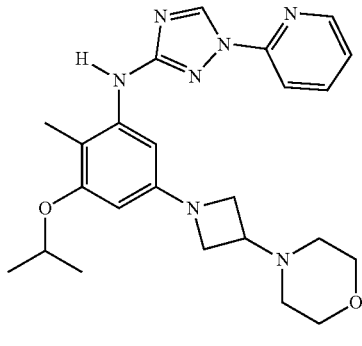 [SMILES: Cc1c(Nc2ncn(-c3ccccn3)n2)cc(N2CC(N3CCOCC3)C2)cc1OC(C)C] 811
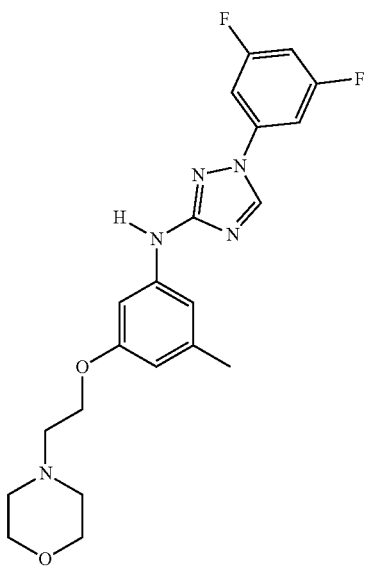 [SMILES: Cc1cc(Nc2ncn(-c3cc(F)cc(F)c3)n2)cc(OCCN2CCOCC2)c1] 812
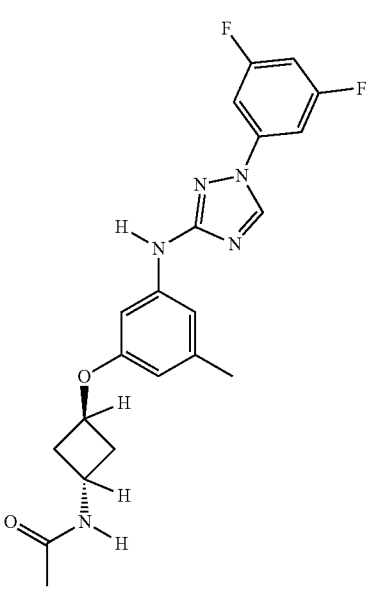 [SMILES: CC(=O)N[C@H]1C[C@H](Oc2cc(C)cc(Nc3ncn(-c4cc(F)cc(F)c4)n3)c2)C1] 813
TABLE 1A-continued
Compound Table
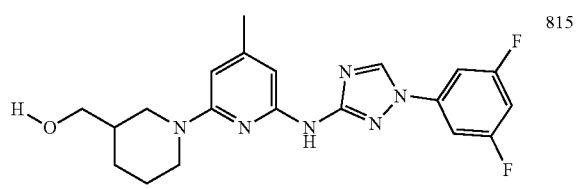 814
815
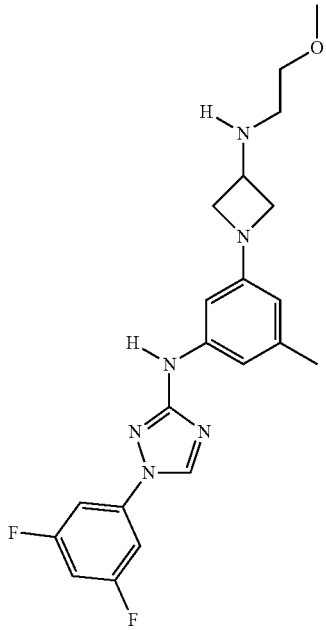 [SMILES: COCCNC1CN(c2cc(C)cc(Nc3ncn(-c4cc(F)cc(F)c4)n3)c2)C1] 816
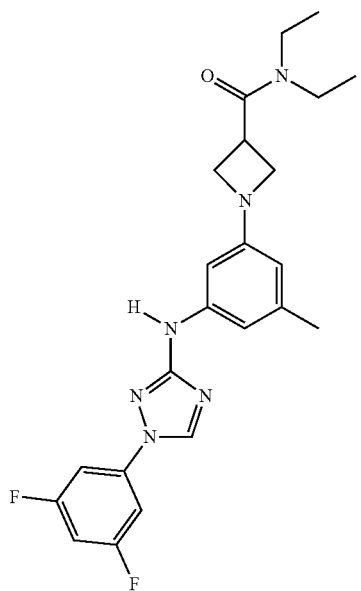 [SMILES: CCN(CC)C(=O)C1CN(c2cc(C)cc(Nc3ncn(-c4cc(F)cc(F)c4)n3)c2)C1] 817

TABLE 1A-continued
Compound Table
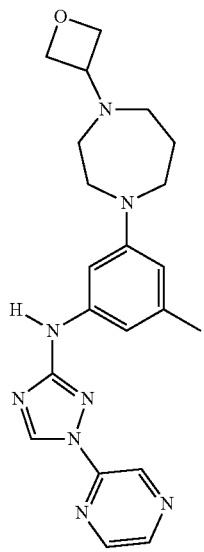 [SMILES: Cc1cc(Nc2ncn(-c3cnccn3)n2)cc(N2CCCN(C3COC3)CC2)c1]
818

819
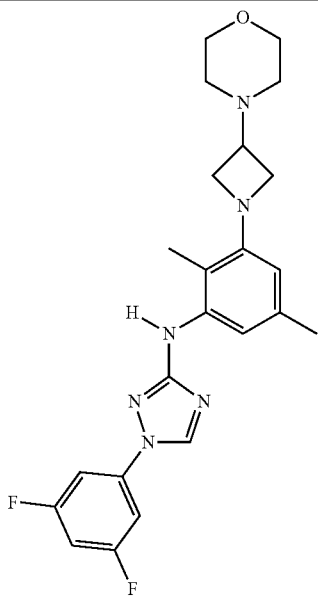
820
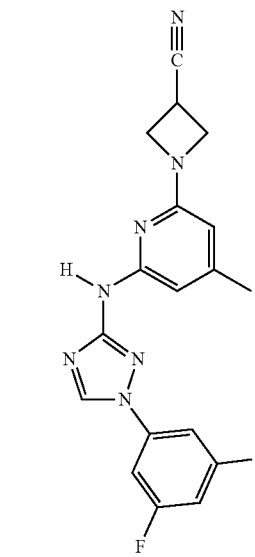
821
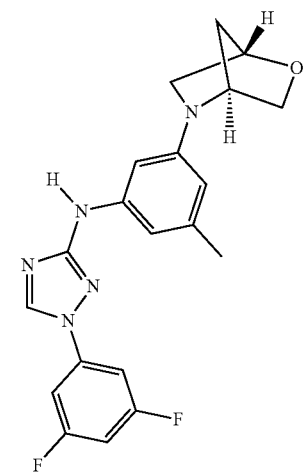 [SMILES: Cc1cc(Nc2ncn(-c3cc(F)cc(F)c3)n2)cc(N2C[C@@H]3C[C@H]2CO3)c1]
822

TABLE 1A-continued
Compound Table
823
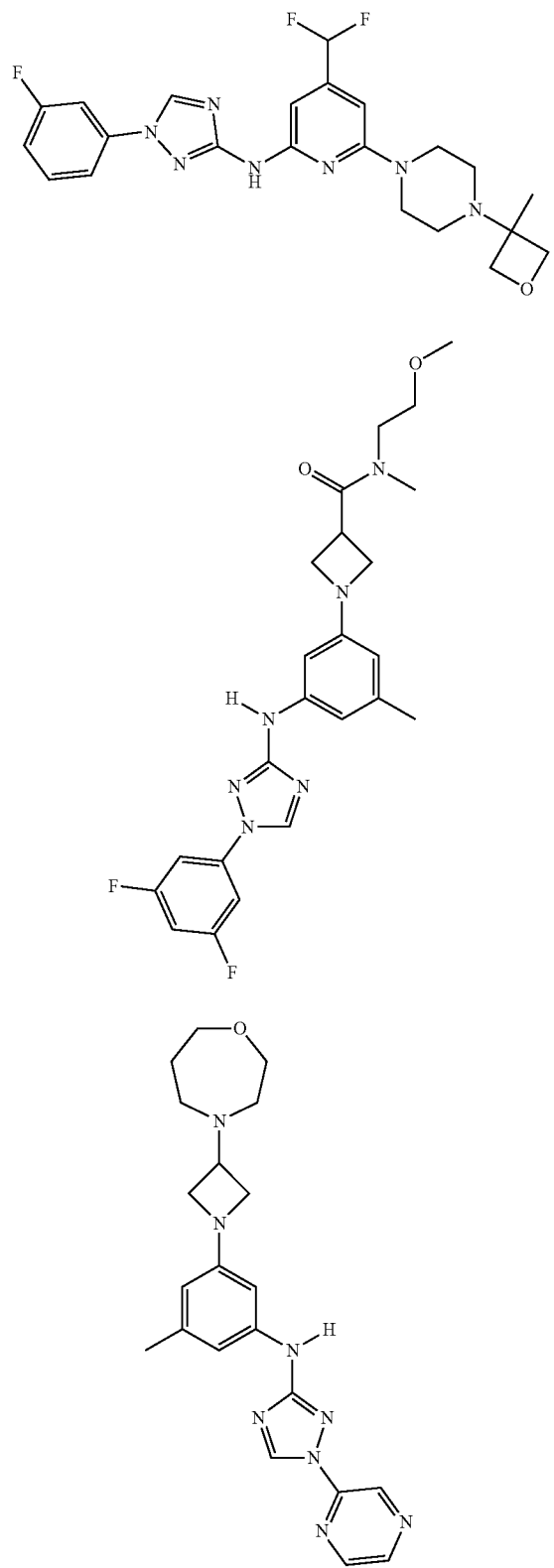
824
825
826
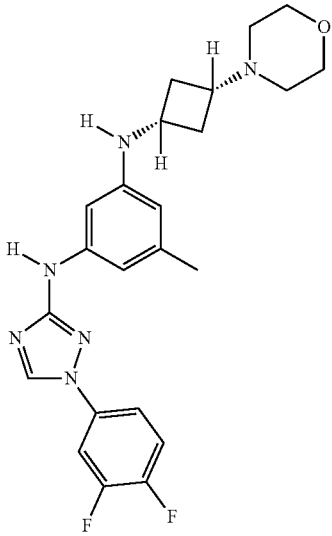 [SMILES: Cc1cc(Nc2ncn(-c3ccc(F)c(F)c3)n2)cc(N[C@H]2C[C@@H](N3CCOCC3)C2)c1]
827
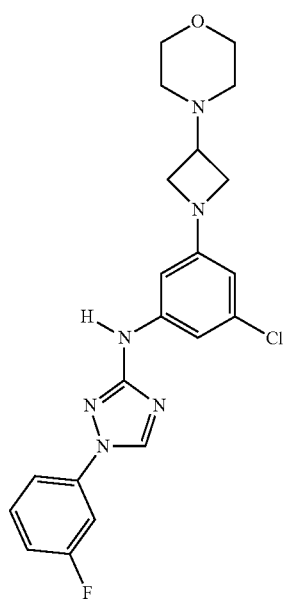 [SMILES: Fc1cccc(-n2cnc(Nc3cc(Cl)cc(N4CC(N5CCOCC5)C4)c3)n2)c1]
828
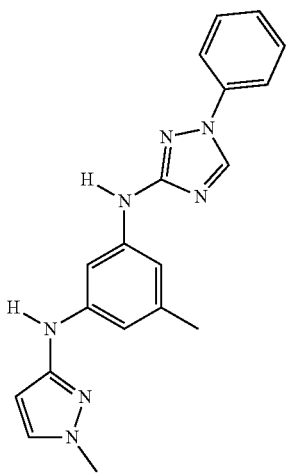 [SMILES: Cc1cc(Nc2ccn(C)n2)cc(Nc2ncn(-c3ccccc3)n2)c1]

TABLE 1A-continued
Compound Table
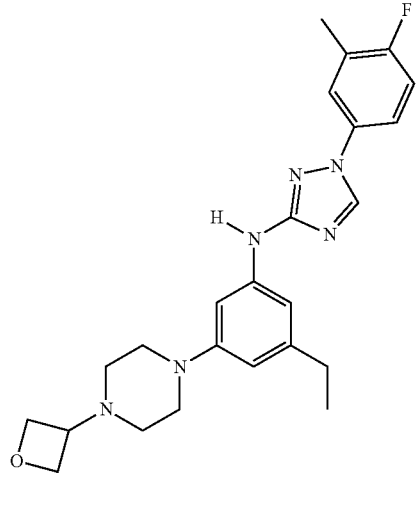 [SMILES: CCc1cc(Nc2ncn(-c3ccc(F)c(C)c3)n2)cc(N2CCN(C3COC3)CC2)c1]
829
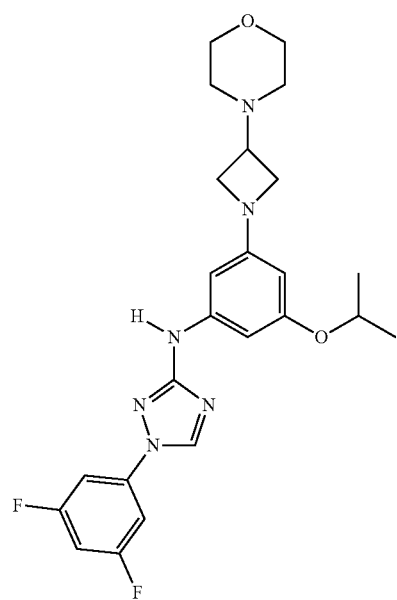 [SMILES: CC(C)Oc1cc(Nc2ncn(-c3cc(F)cc(F)c3)n2)cc(N2CC(N3CCOCC3)C2)c1]
830
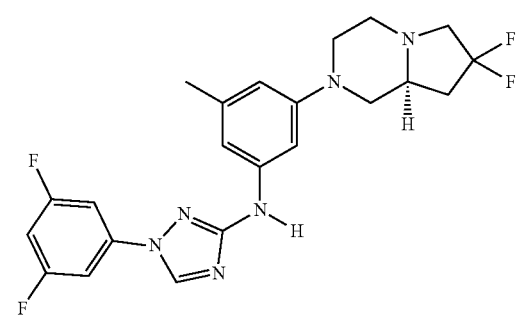 [SMILES: Cc1cc(Nc2ncn(-c3cc(F)cc(F)c3)n2)cc(N2CCN3CC(F)(F)C[C@H]3C2)c1]
831
TABLE 1A-continued
Compound Table
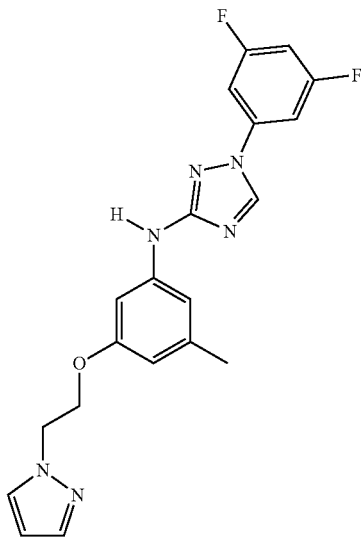 [SMILES: Cc1cc(Nc2ncn(-c3cc(F)cc(F)c3)n2)cc(OCCn2cccn2)c1]
832
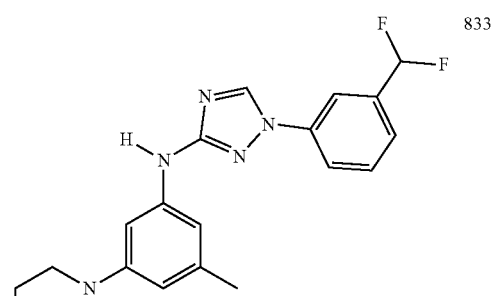
833
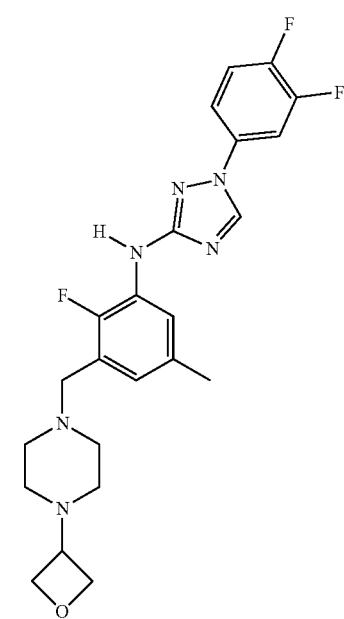 [SMILES: Cc1cc(CN2CCN(C3COC3)CC2)c(F)c(Nc2ncn(-c3ccc(F)c(F)c3)n2)c1]
834

TABLE 1A-continued
Compound Table
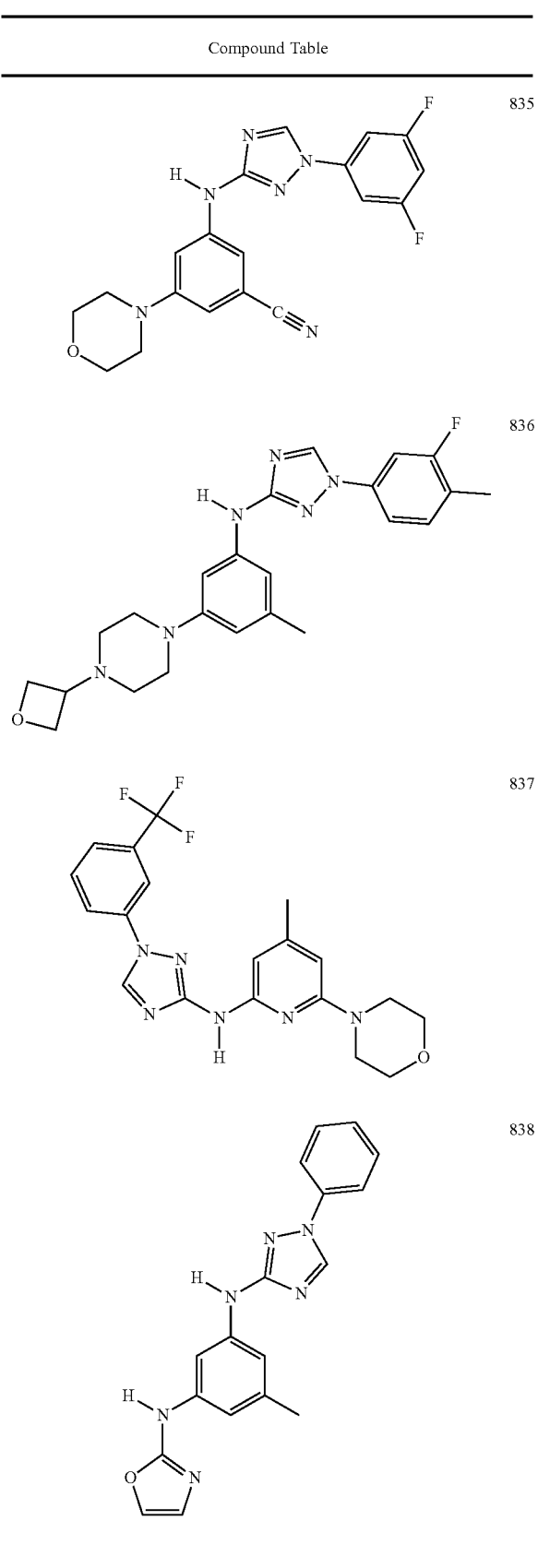
835
836
837
838
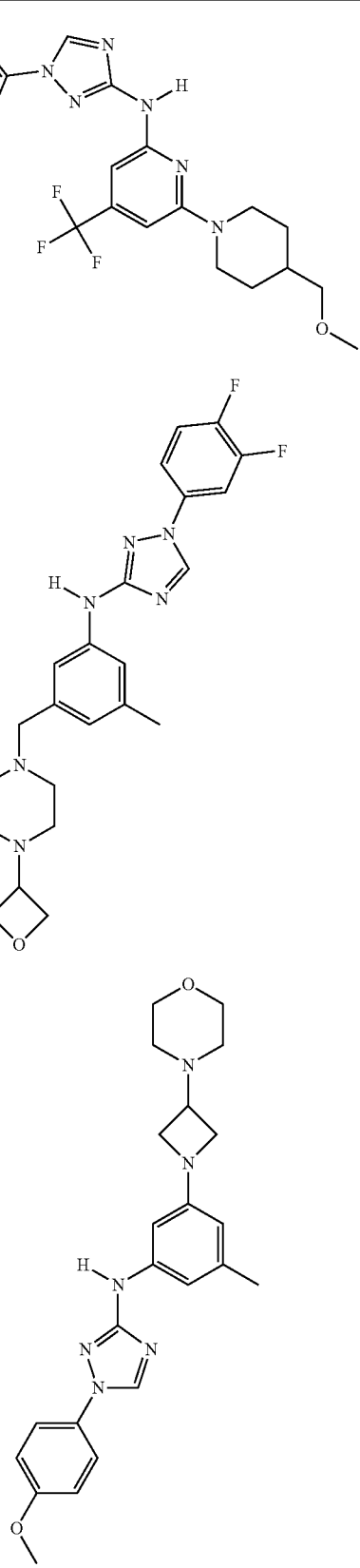
839
840
841

TABLE 1A-continued
Compound Table
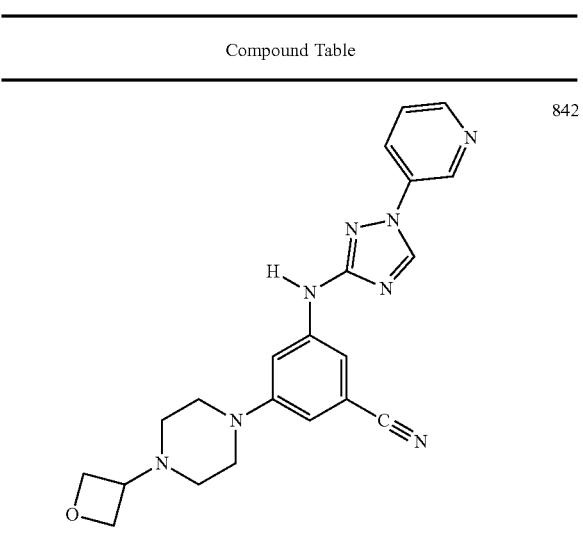 842
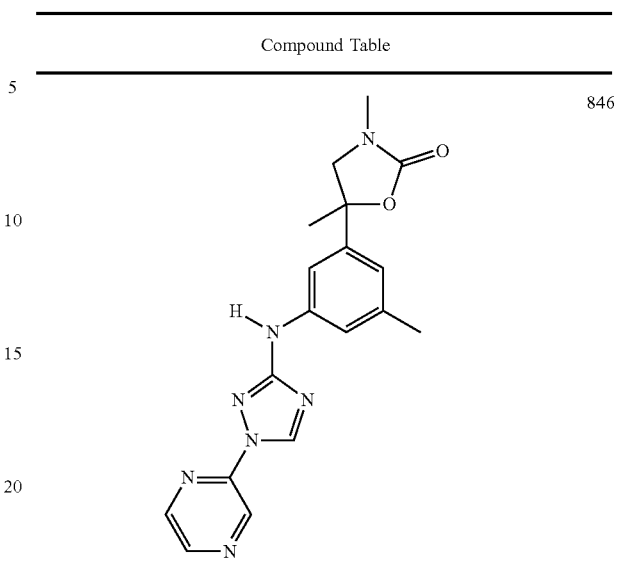 846
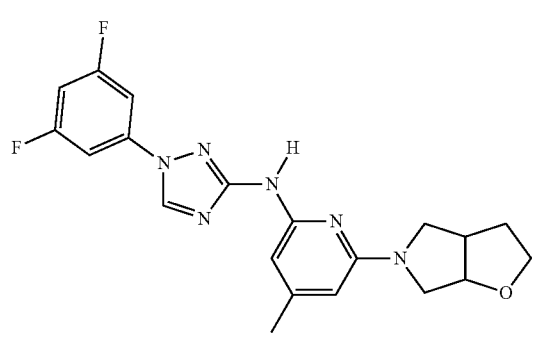 [SMILES: Cc1cc(Nc2ncn(-c3cc(F)cc(F)c3)n2)nc(N2CC3CCOC3C2)c1] 843
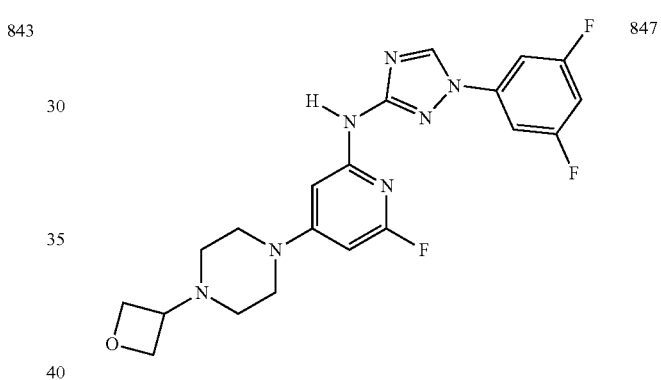 847
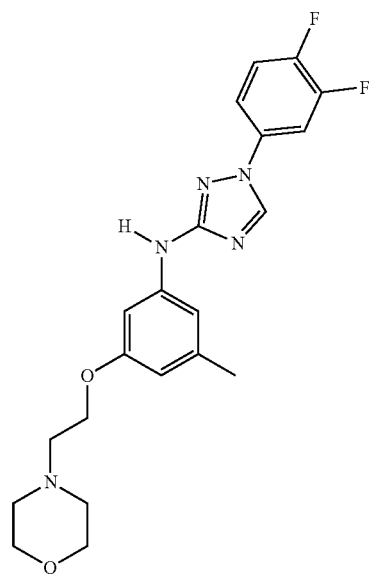 [SMILES: Cc1cc(Nc2ncn(-c3ccc(F)c(F)c3)n2)cc(OCCN2CCOCC2)c1] 845
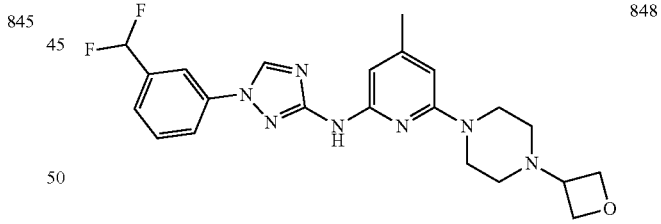 848
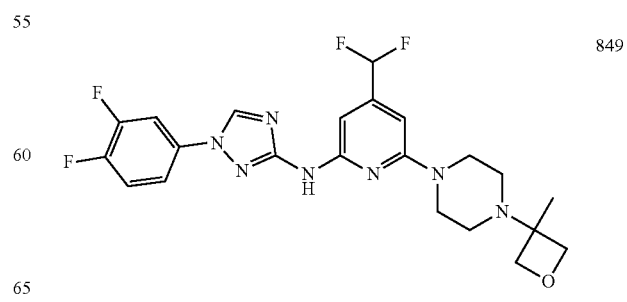 849

TABLE 1A-continued
Compound Table
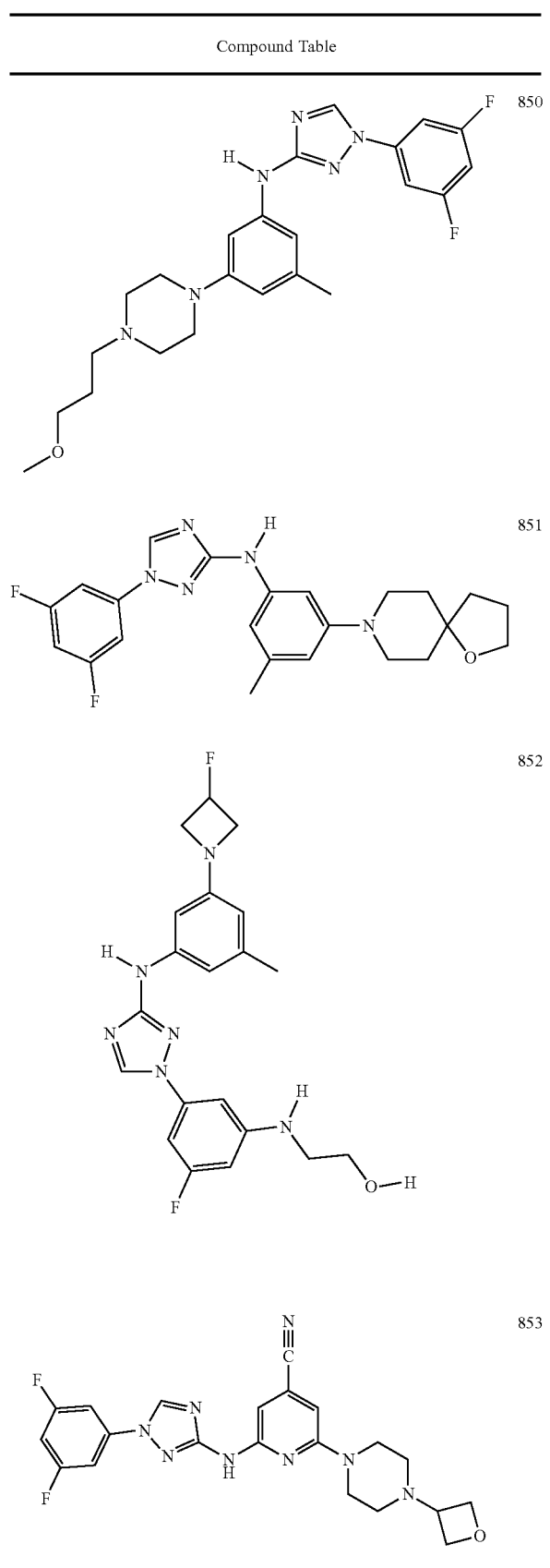
850
851
852
853
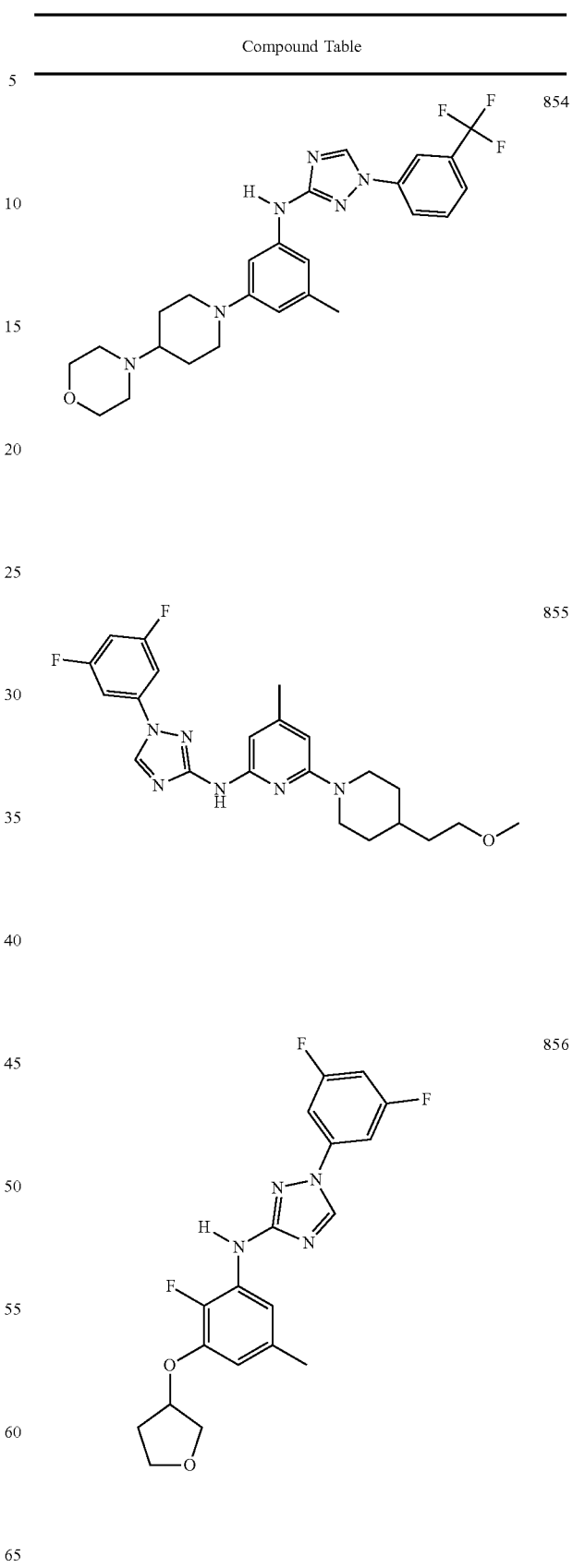
854
855
856

TABLE 1A-continued
Compound Table
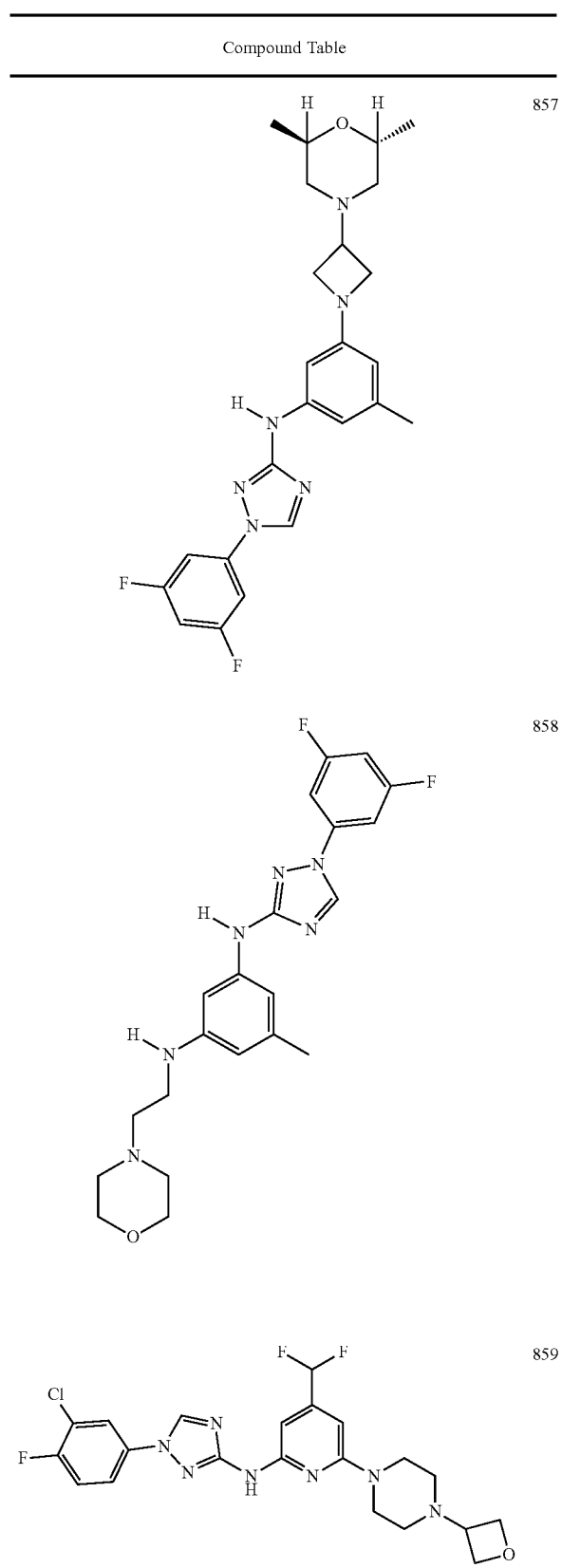
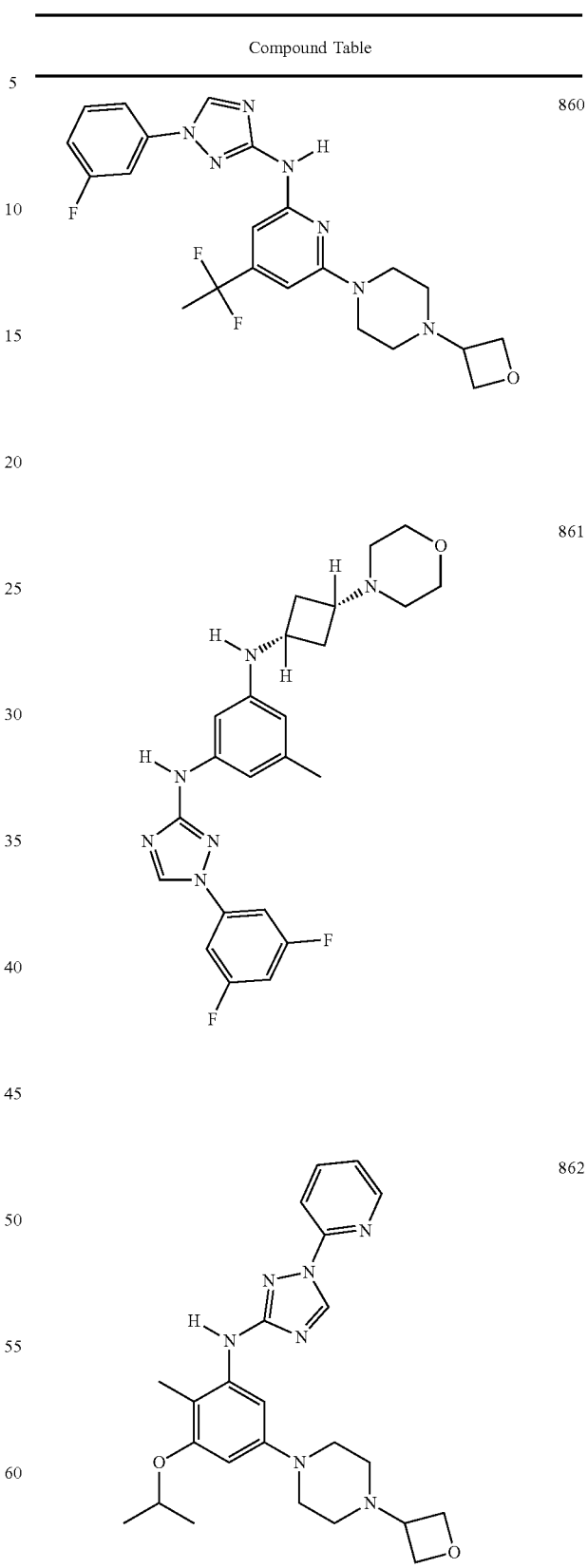

TABLE 1A-continued
Compound Table
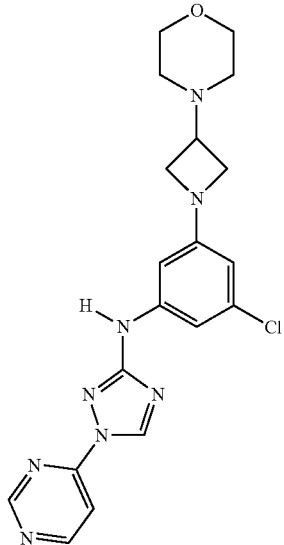 [SMILES: Clc1cc(Nc2ncn(-c3ccncn3)n2)cc(N2CC(N3CCOCC3)C2)c1]
863
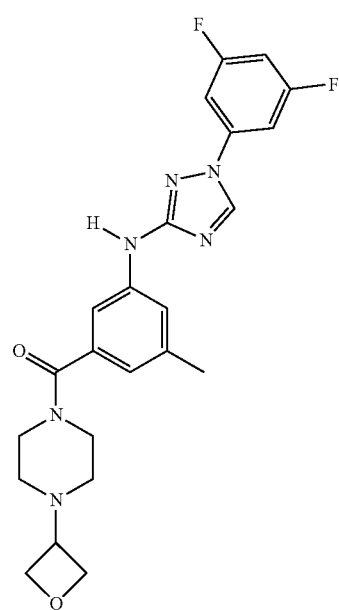 [SMILES: Cc1cc(Nc2ncn(-c3cc(F)cc(F)c3)n2)cc(C(=O)N2CCN(C3COC3)CC2)c1]
864
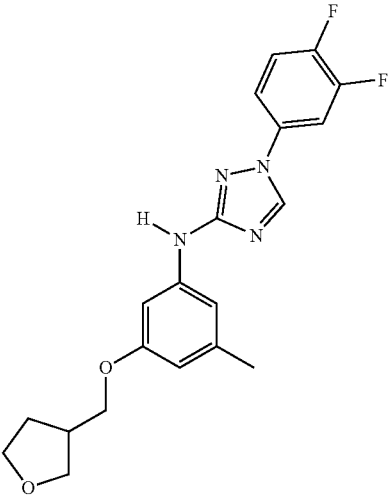 [SMILES: Cc1cc(Nc2ncn(-c3ccc(F)c(F)c3)n2)cc(OCC2CCOC2)c1]
865
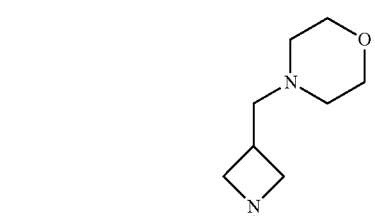
866
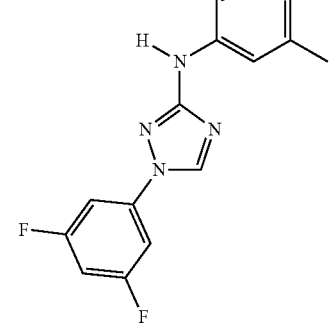
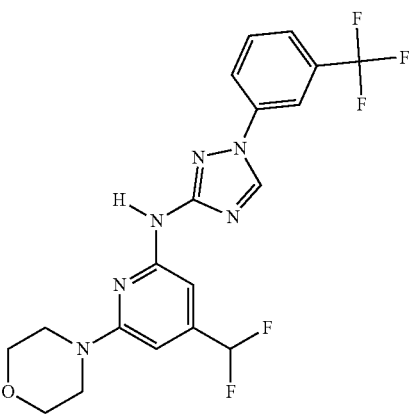 [SMILES: FC(F)c1cc(Nc2ncn(-c3cccc(C(F)(F)F)c3)n2)nc(N2CCOCC2)c1]
867

TABLE 1A-continued

Compound Table

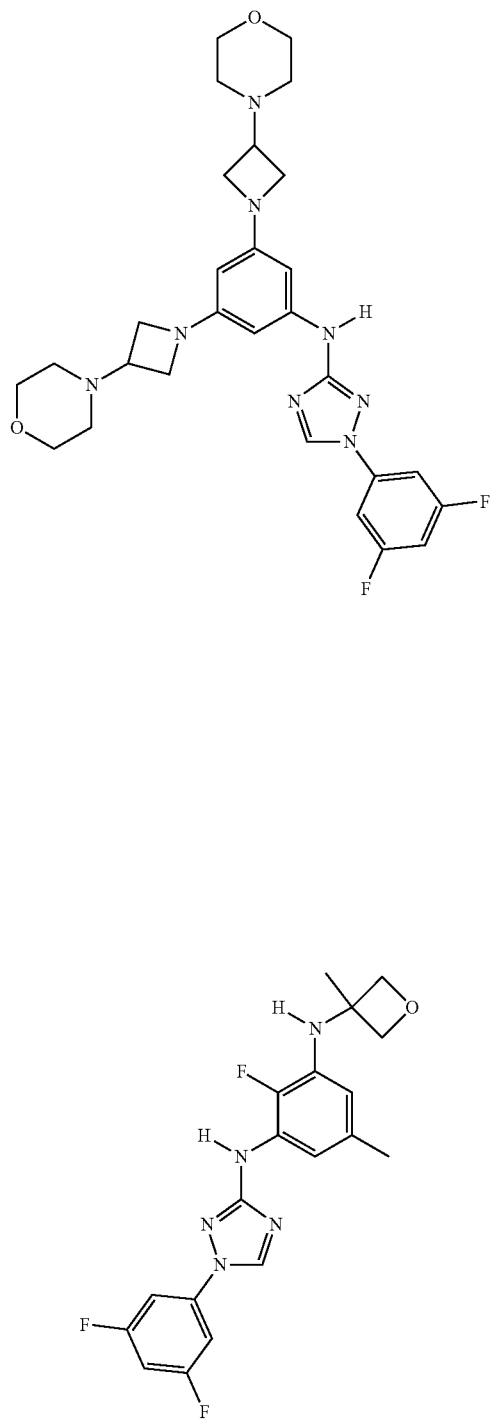

868

869

TABLE 1B

Compound Table

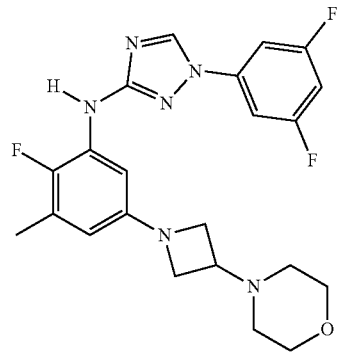 [SMILES: Cc1cc(N2CC(N3CCOCC3)C2)cc(Nc2ncn(-c3cc(F)cc(F)c3)n2)c1F]

870

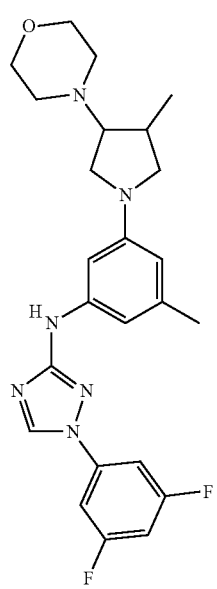

871

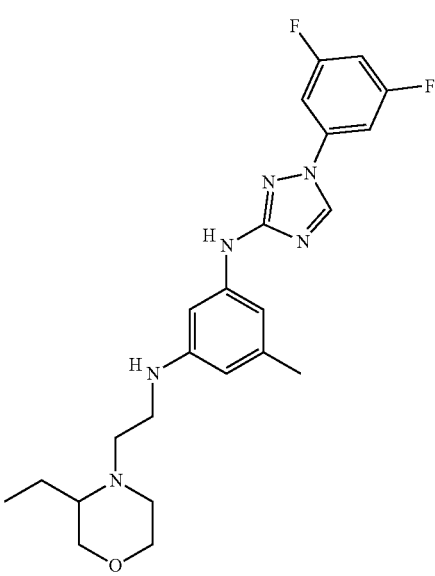

872

In Table 1B below, several compounds have stereocenters with either known (R or S) or unknown absolute configurations and/or known (cis or trans) or unknown configurations. For example, compound 919 is a single enantiomer with the "S" conformation. Compounds 886, 1002, 1009, 1028, 1052, 1053, 1055, and 1061 are each single enantiomers with unknown stereochemistry and are arbitrarily assigned the "S" or "R" conformation.

TABLE 1B-continued
Compound Table
873
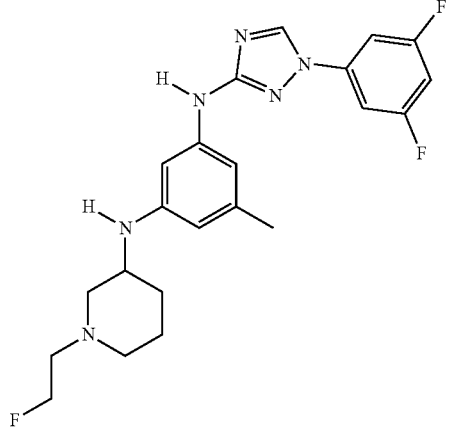 [SMILES: Cc1cc(Nc2ncn(-c3cc(F)cc(F)c3)n2)cc(NC2CCCN(CCF)C2)c1]
874
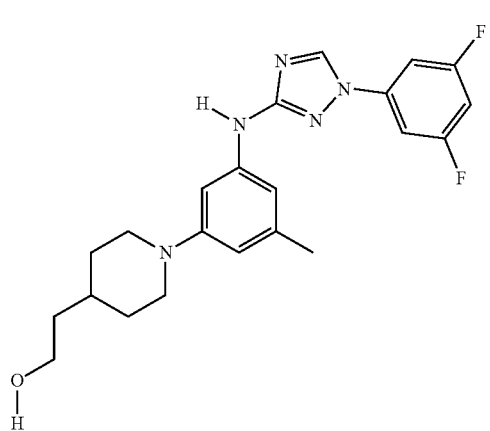 [SMILES: Cc1cc(Nc2ncn(-c3cc(F)cc(F)c3)n2)cc(N2CCC(CCO)CC2)c1]
875
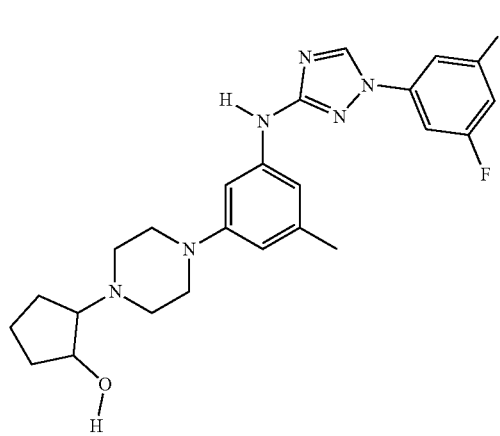
TABLE 1B-continued
Compound Table
876
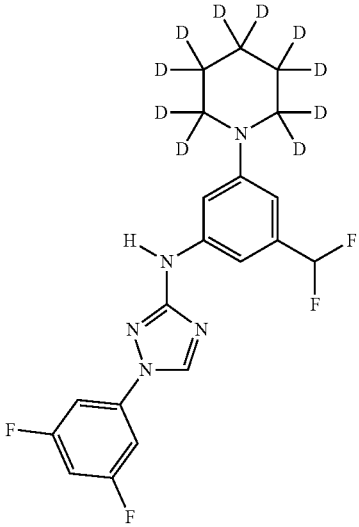 [SMILES: [2H]C1([2H])N(c2cc(Nc3ncn(-c4cc(F)cc(F)c4)n3)cc(C(F)F)c2)C([2H])([2H])C([2H])([2H])C([2H])([2H])C1([2H])[2H]]
877
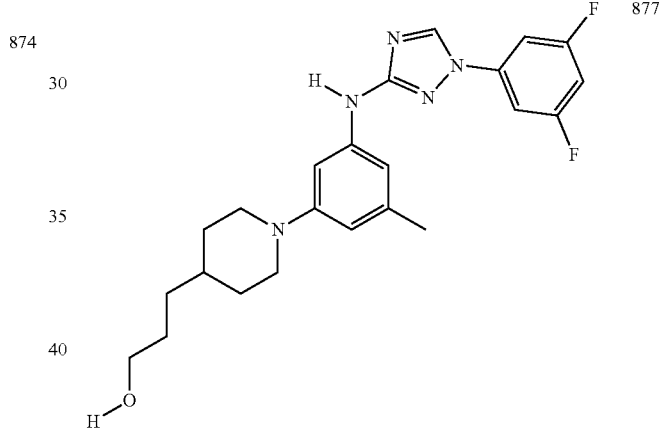
878
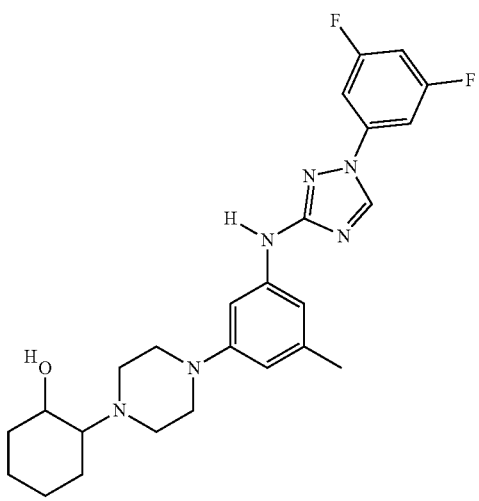

TABLE 1B-continued
Compound Table
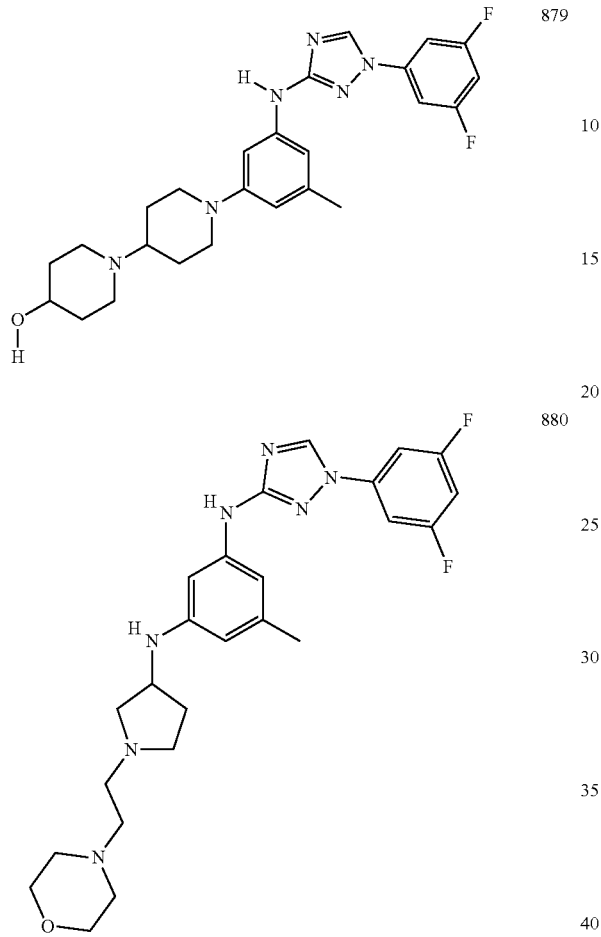
879
880
881
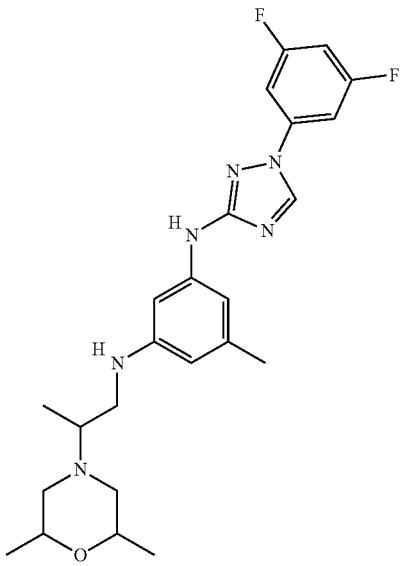
882
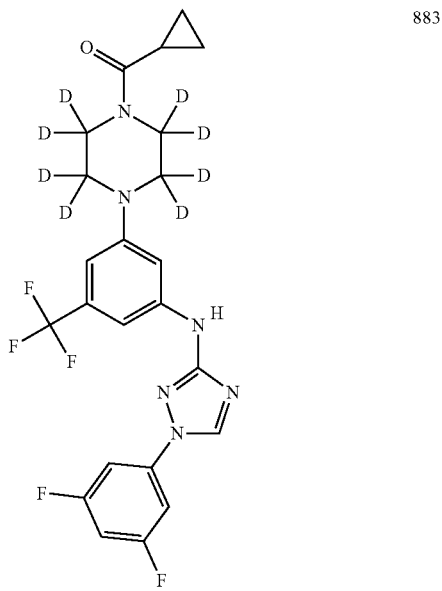
883

TABLE 1B-continued
Compound Table
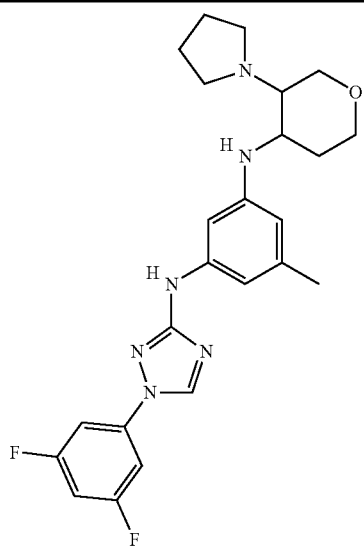
884
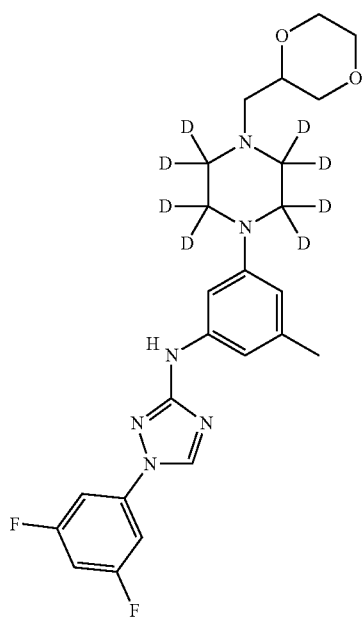
885
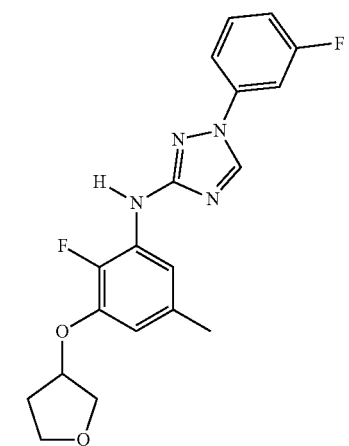 [SMILES: Cc1cc(Nc2ncn(-c3cccc(F)c3)n2)c(F)c(OC2CCOC2)c1]
886
TABLE 1B-continued
Compound Table
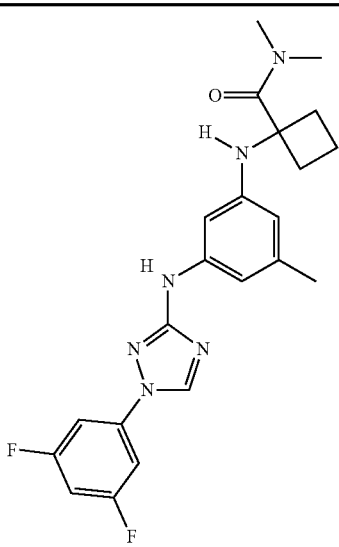
887
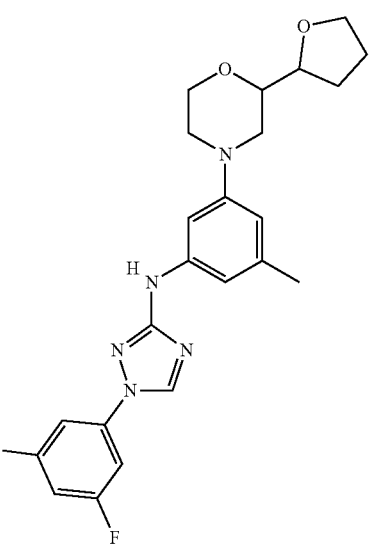
888
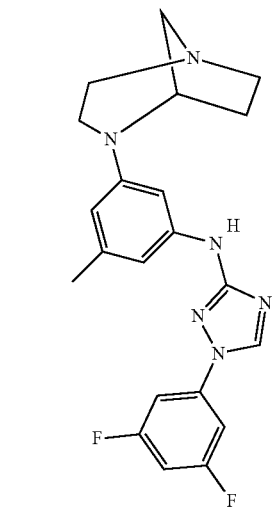
889

TABLE 1B-continued
Compound Table
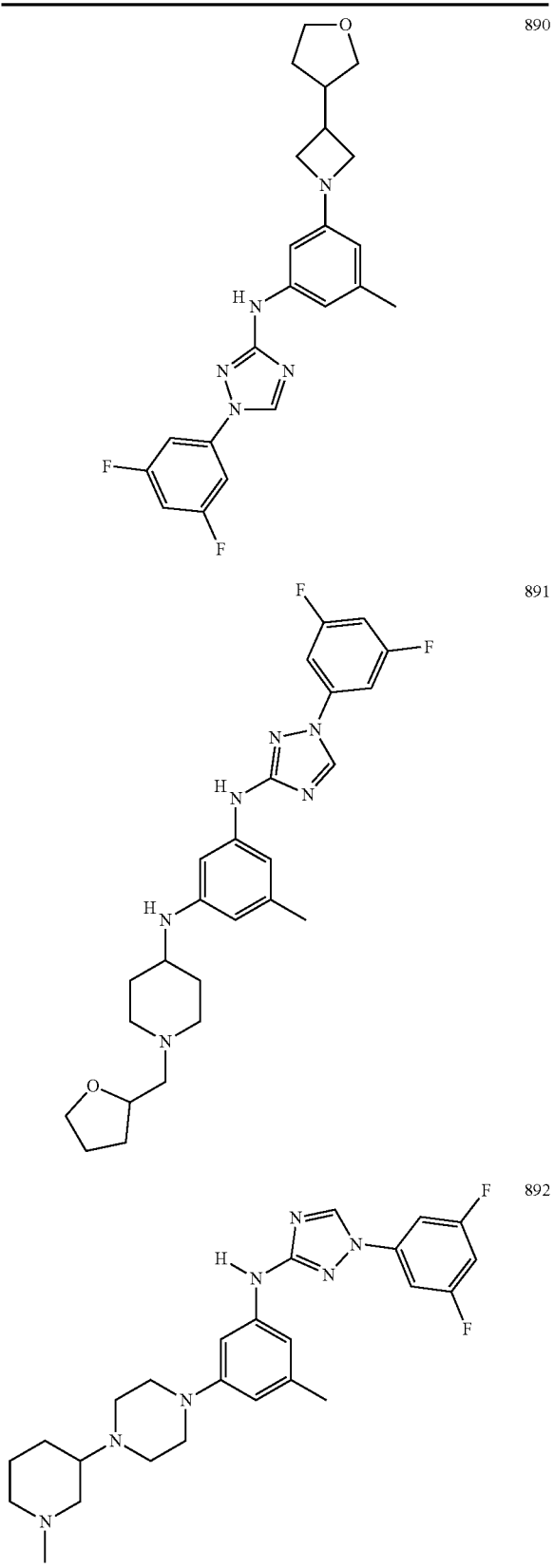
890
891
892
TABLE 1B-continued
Compound Table
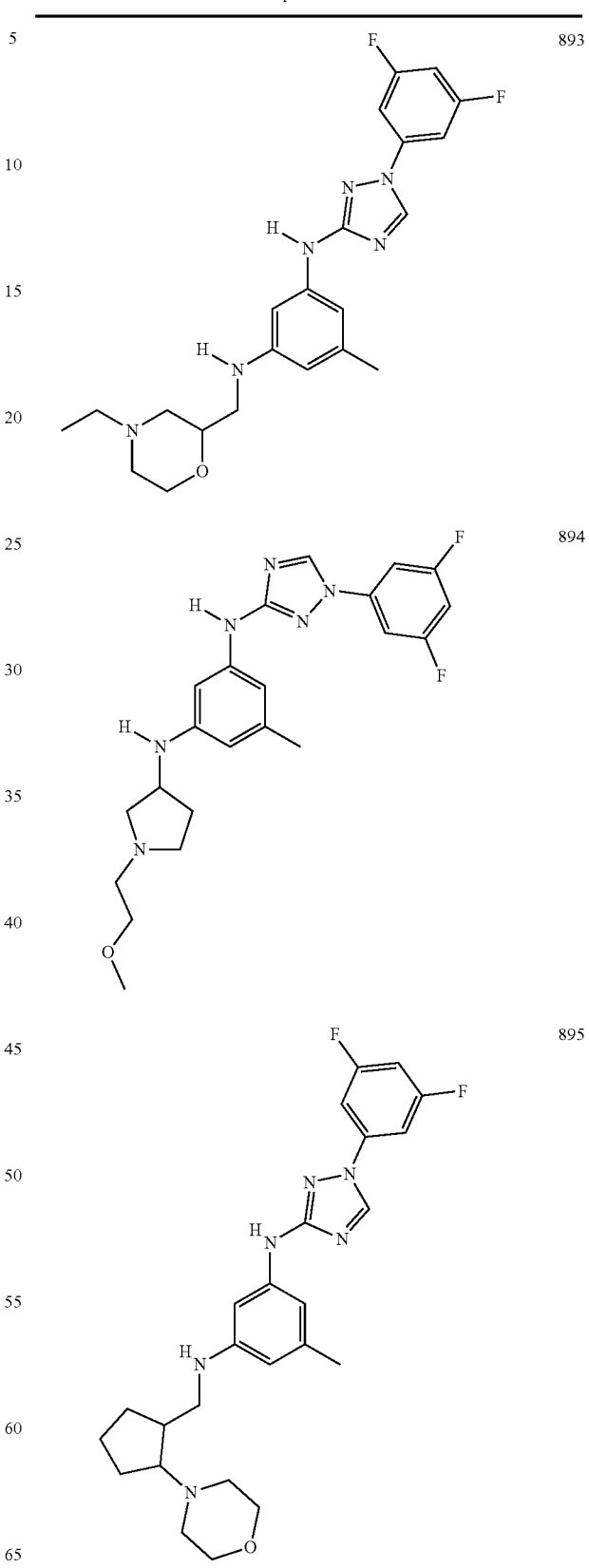
893
894
895

TABLE 1B-continued
Compound Table
896
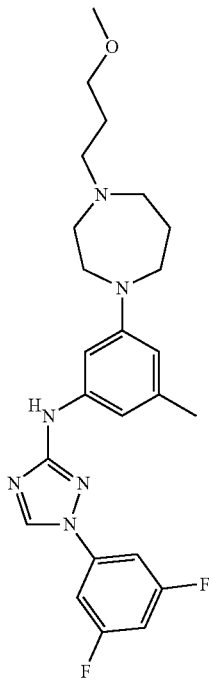
897
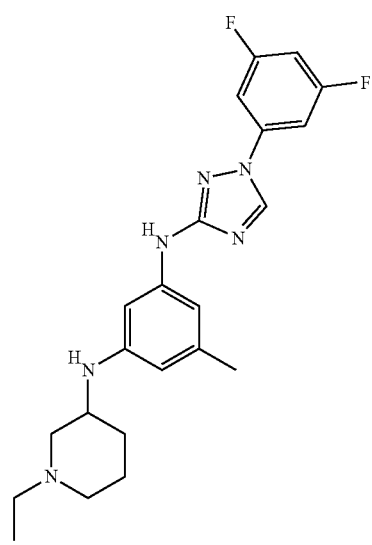
TABLE 1B-continued
Compound Table
898
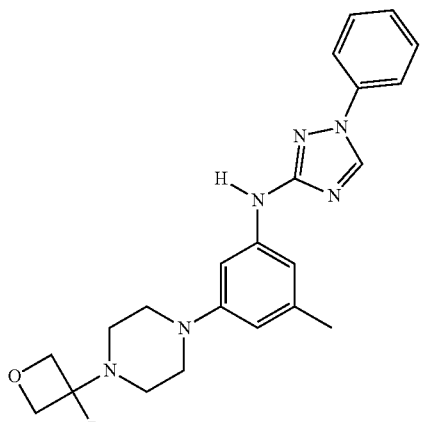
899
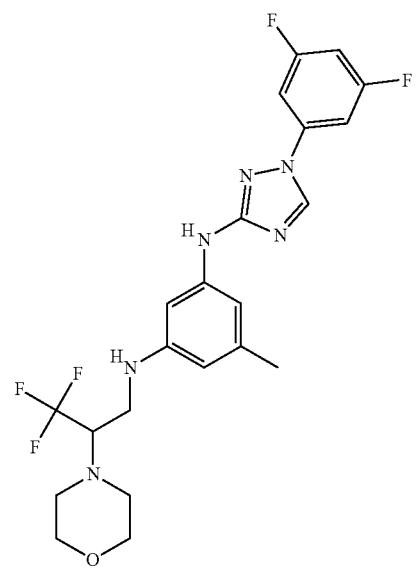
900
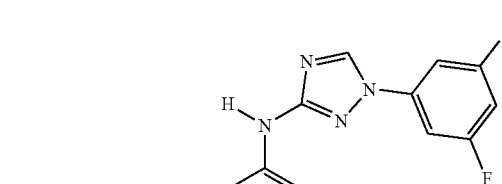

TABLE 1B-continued
Compound Table
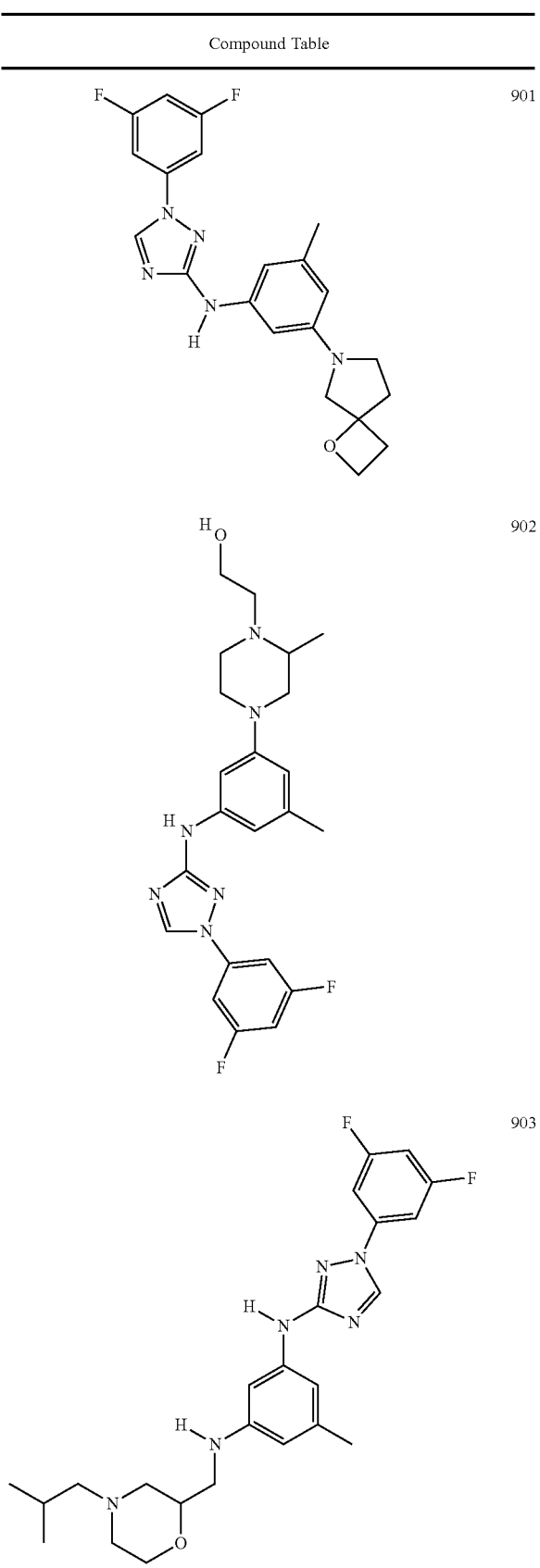
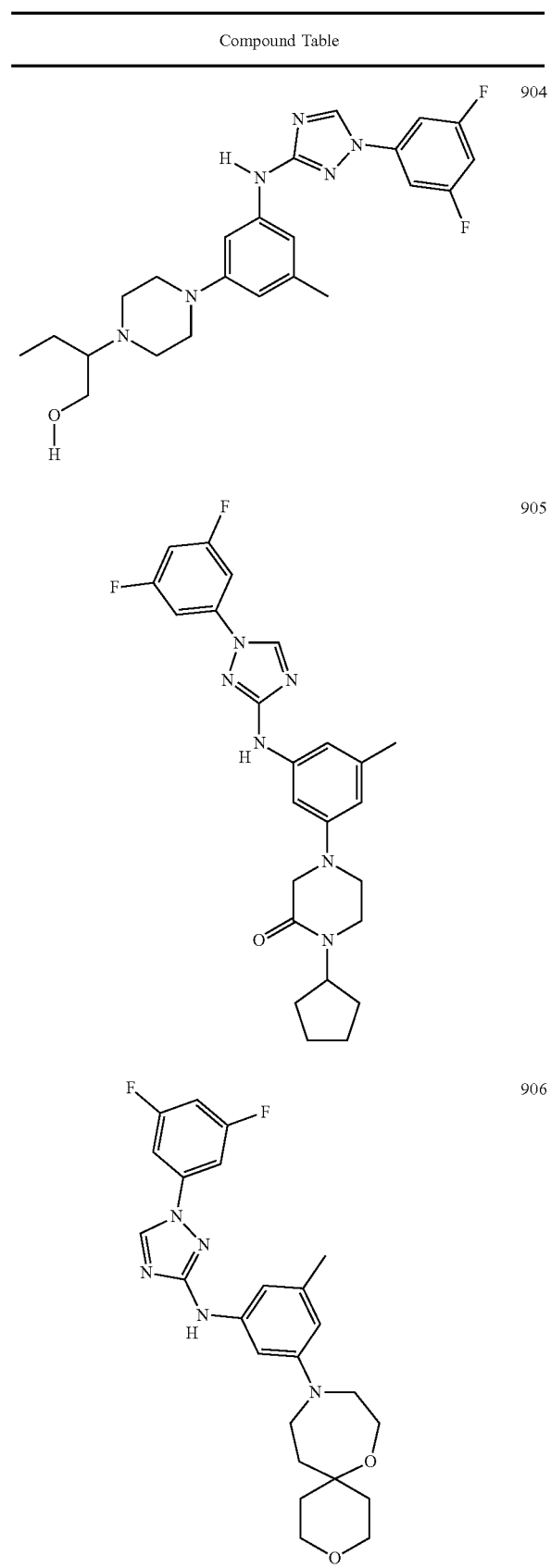

TABLE 1B-continued
Compound Table
907
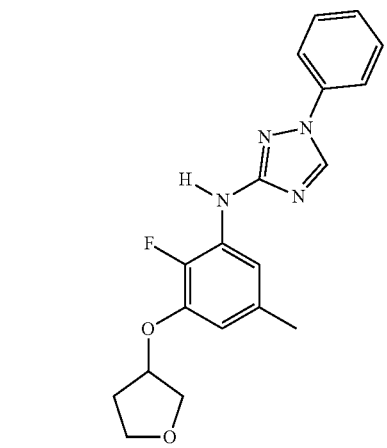 [SMILES: Cc1cc(Nc2ncn(-c3ccccc3)n2)c(F)c(OC2CCOC2)c1]
908
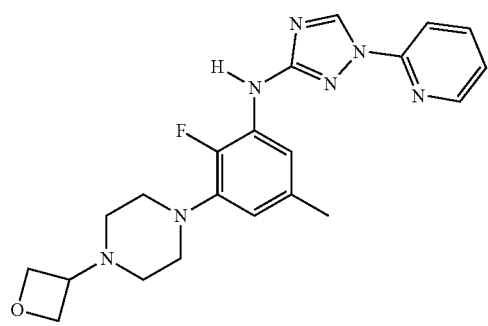 [SMILES: Cc1cc(Nc2ncn(-c3ccccn3)n2)c(F)c(N2CCN(C3COC3)CC2)c1]
909
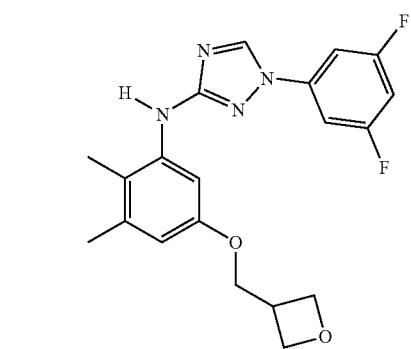 [SMILES: Cc1cc(OCC2COC2)cc(Nc2ncn(-c3cc(F)cc(F)c3)n2)c1C]
910
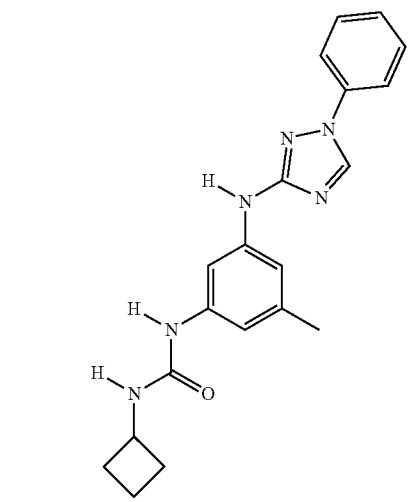 [SMILES: Cc1cc(NC(=O)NC2CCC2)cc(Nc2ncn(-c3ccccc3)n2)c1]
TABLE 1B-continued
Compound Table
911
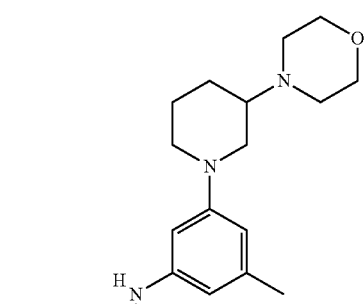
912
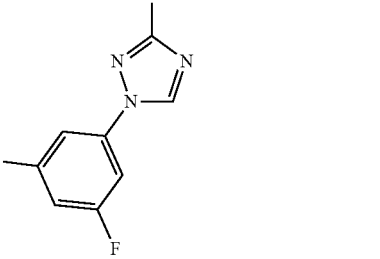
913
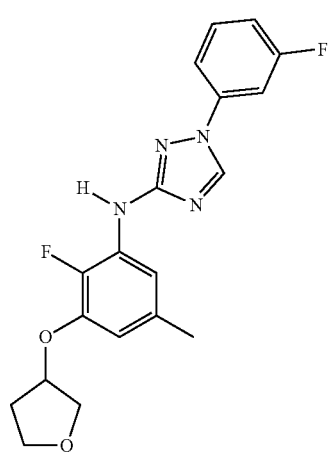 [SMILES: Cc1cc(Nc2ncn(-c3cccc(F)c3)n2)c(F)c(OC2CCOC2)c1]

TABLE 1B-continued
Compound Table
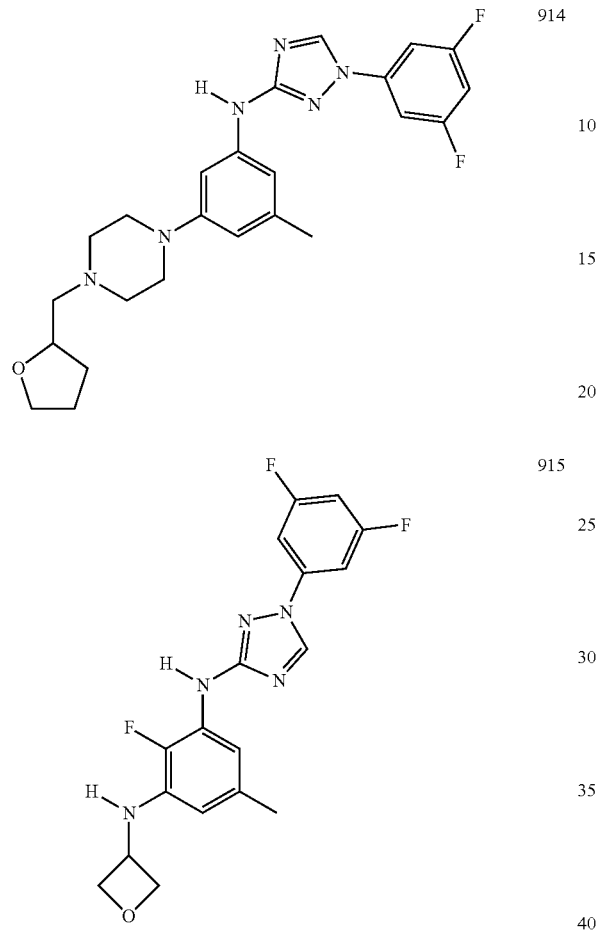
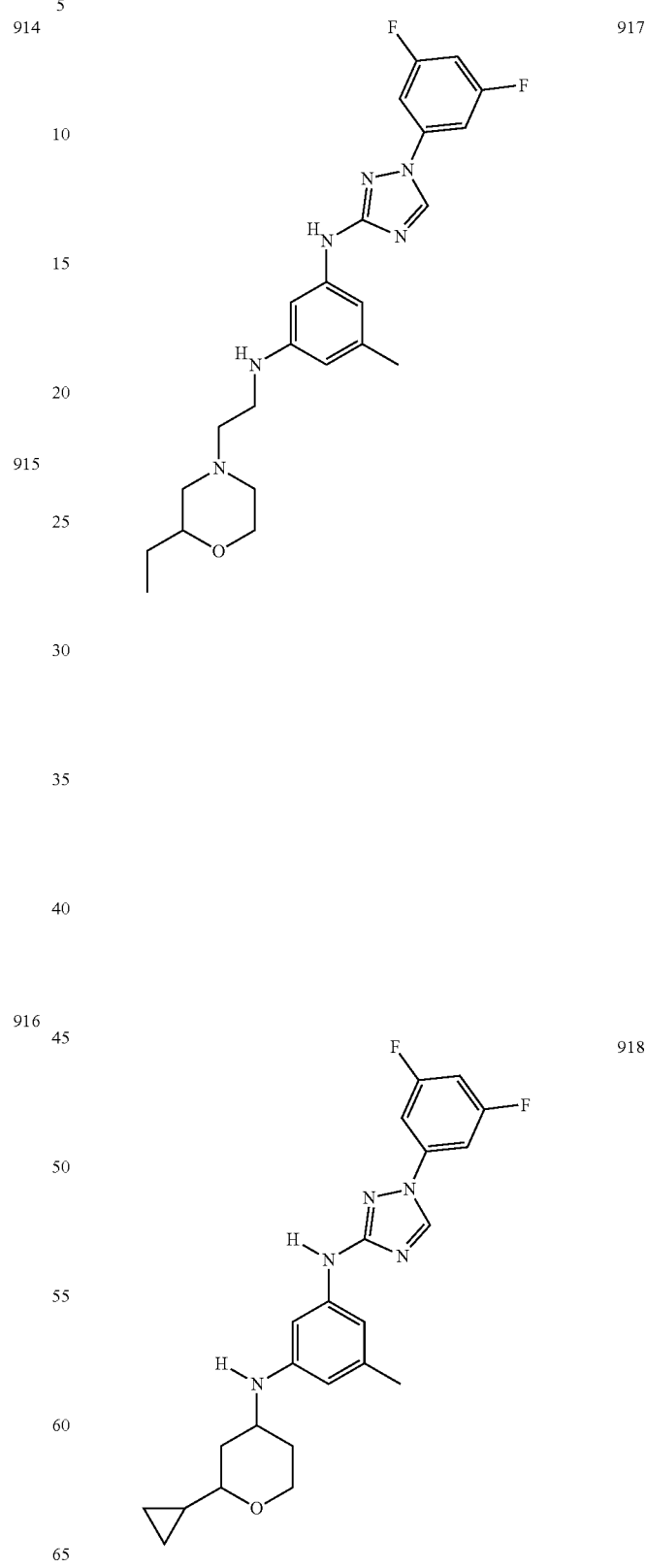

577
TABLE 1B-continued
Compound Table
919
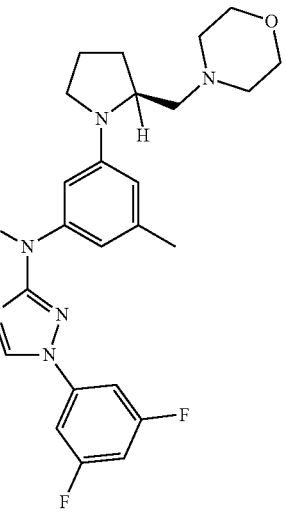
920
578
TABLE 1B-continued
Compound Table
921
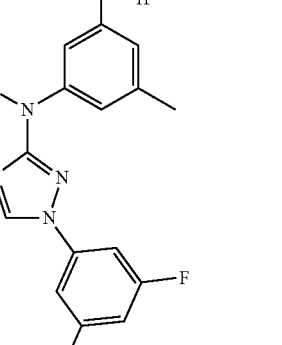
922
923

TABLE 1B-continued
Compound Table
924 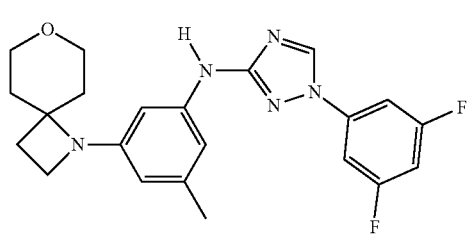 [SMILES: Cc1cc(Nc2ncn(-c3cc(F)cc(F)c3)n2)cc(N2CCC23CCOCC3)c1]
925 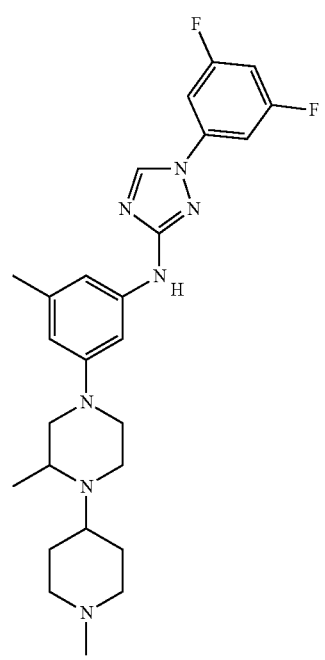
926 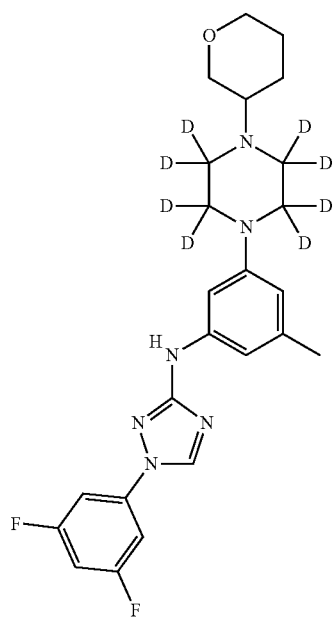
TABLE 1B-continued
Compound Table
927 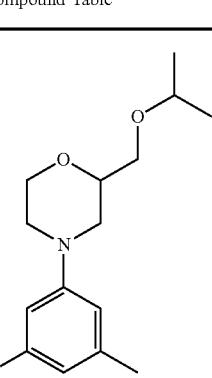
928 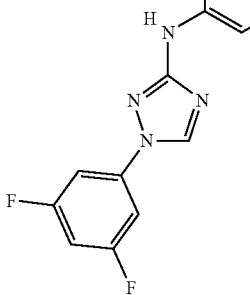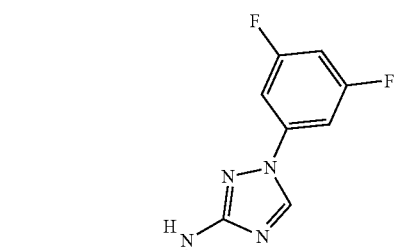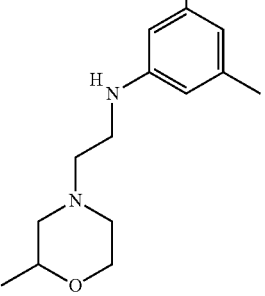
929 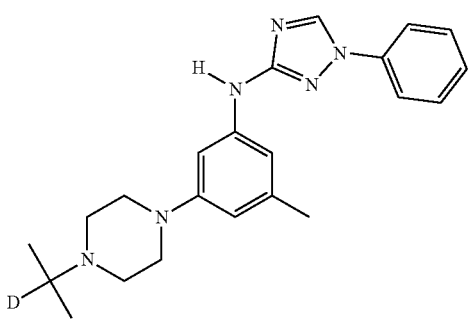 [SMILES: [2H]C(C)(C)N1CCN(c2cc(C)cc(Nc3ncn(-c4ccccc4)n3)c2)CC1]

TABLE 1B-continued
Compound Table
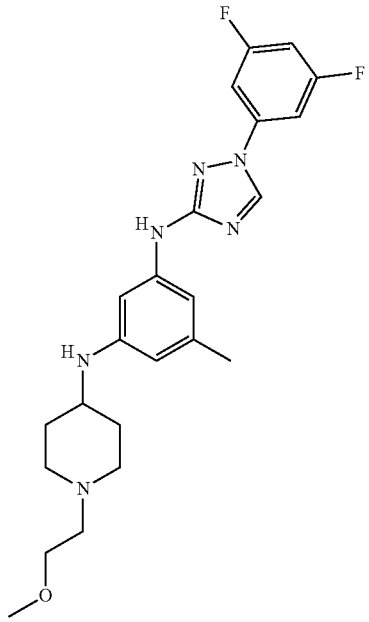
930
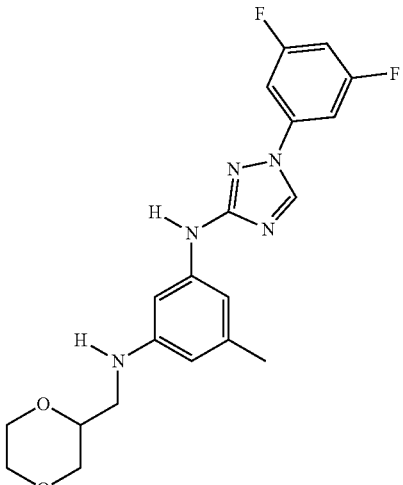
932
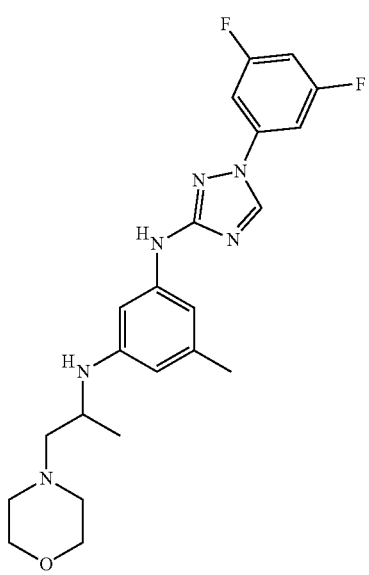
931
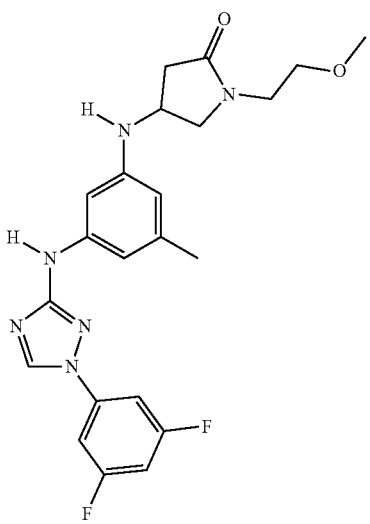 [SMILES: COCCN1CC(Nc2cc(C)cc(Nc3ncn(-c4cc(F)cc(F)c4)n3)c2)CC1=O]
933
934

US 10,766,869 B2
TABLE 1B-continued
Compound Table
935
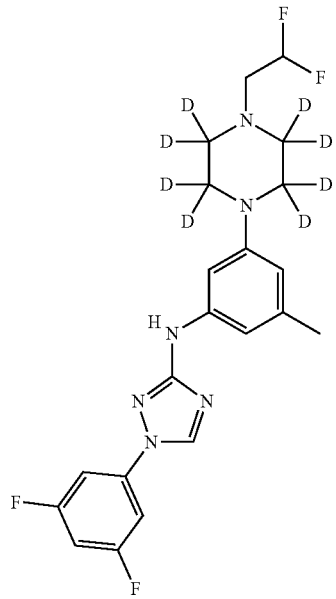
936
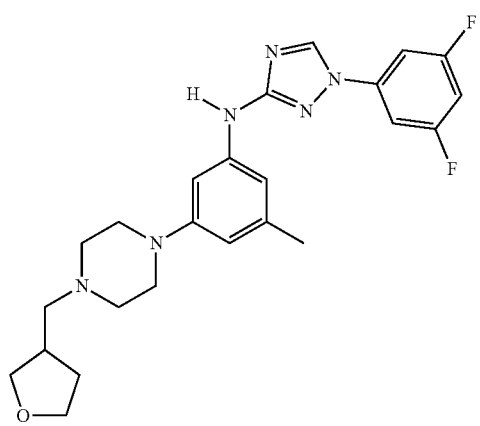
937
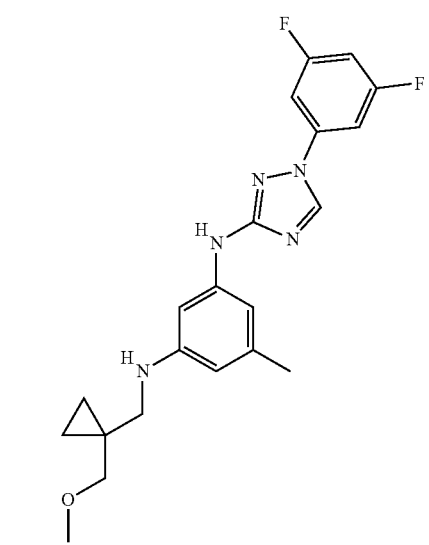
TABLE 1B-continued
Compound Table
938
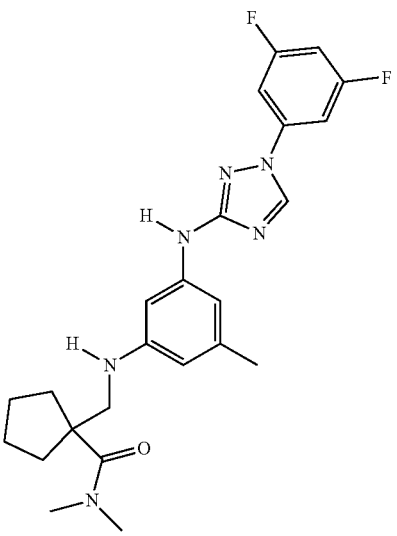 [SMILES: Cc1cc(NCC2(C(=O)N(C)C)CCCC2)cc(Nc2ncn(-c3cc(F)cc(F)c3)n2)c1]
939

585
TABLE 1B-continued
Compound Table
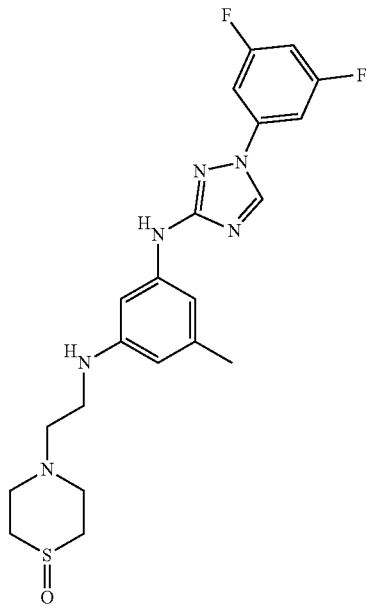
940
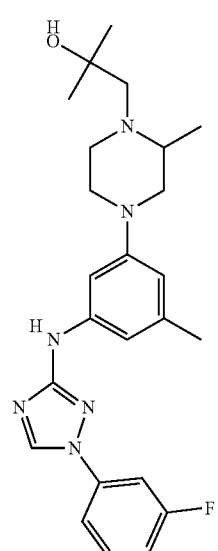
941
586
TABLE 1B-continued
Compound Table
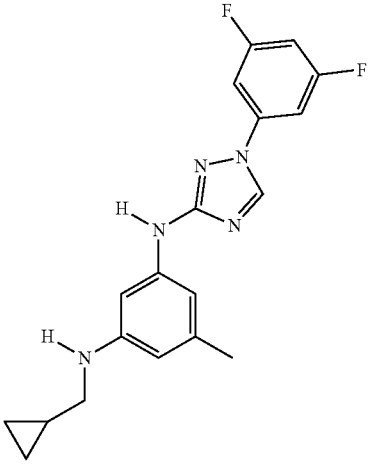 [SMILES: Cc1cc(NCC2CC2)cc(Nc2ncn(-c3cc(F)cc(F)c3)n2)c1]
942
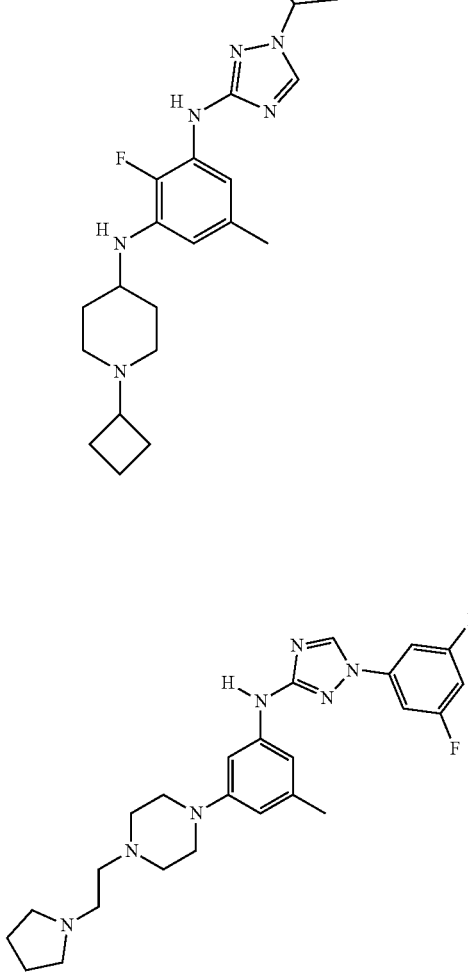
943
944

TABLE 1B-continued
Compound Table
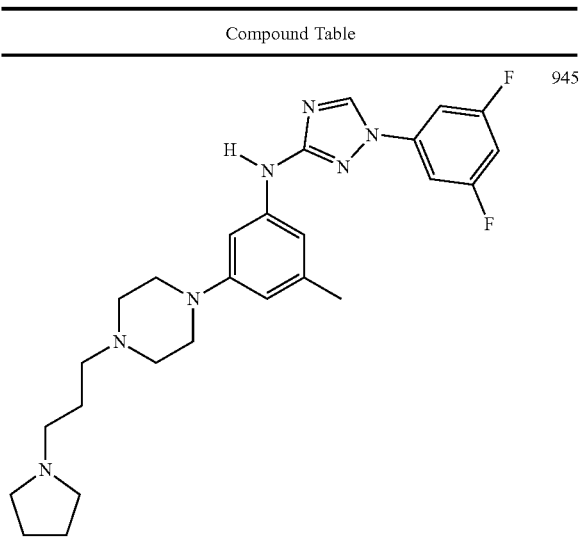
945
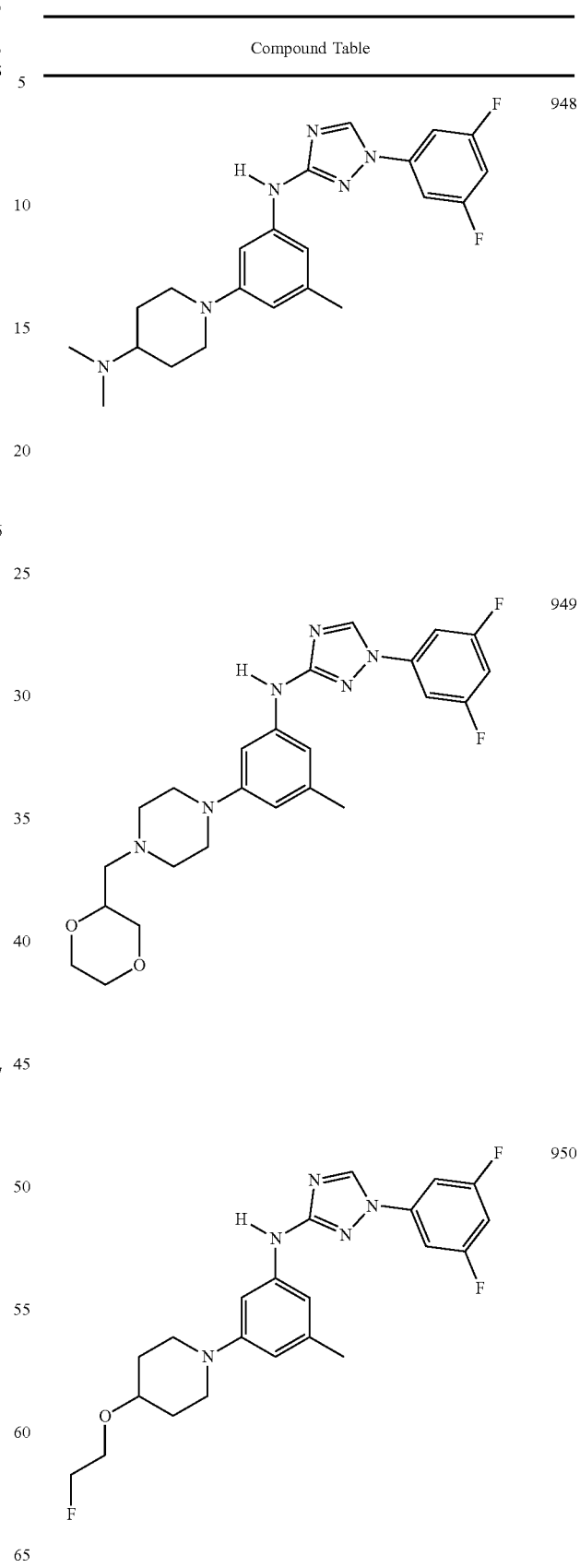
946
947
TABLE 1B-continued
Compound Table
948
949
950

TABLE 1B-continued
Compound Table
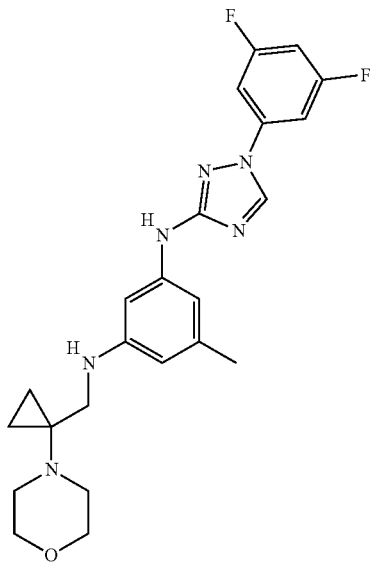
951
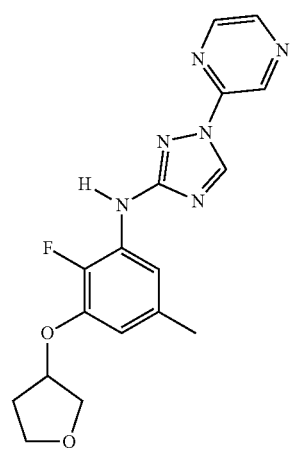 [SMILES: Cc1cc(Nc2ncn(-c3cnccn3)n2)c(F)c(OC2CCOC2)c1]
952
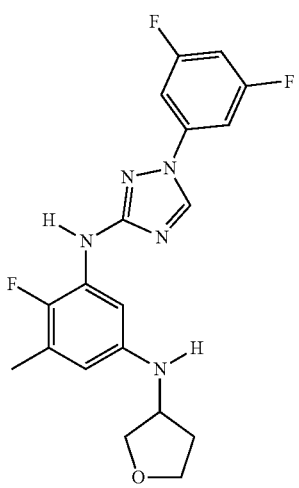 [SMILES: Cc1cc(NC2CCOC2)cc(Nc2ncn(-c3cc(F)cc(F)c3)n2)c1F]
953
TABLE 1B-continued
Compound Table
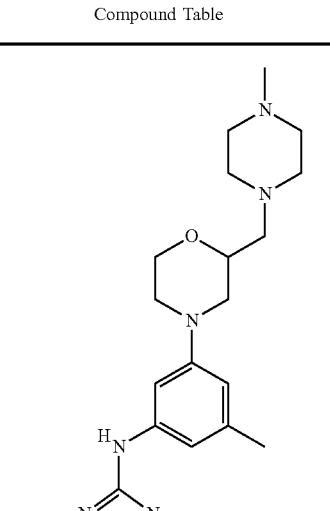
954
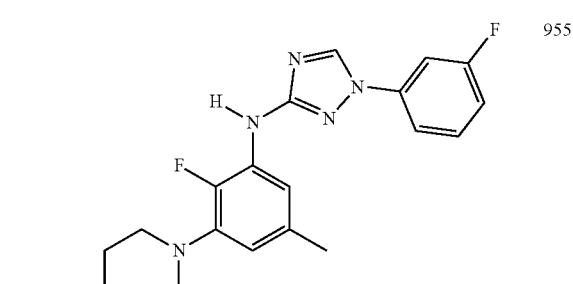
955
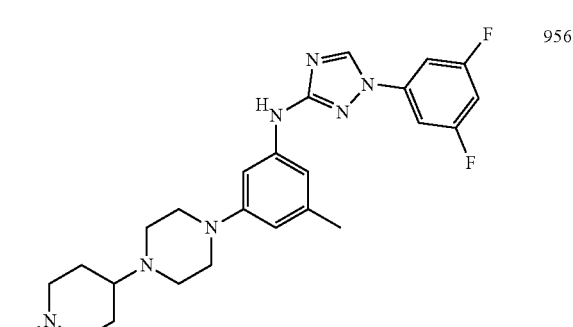
956

TABLE 1B-continued
Compound Table
957
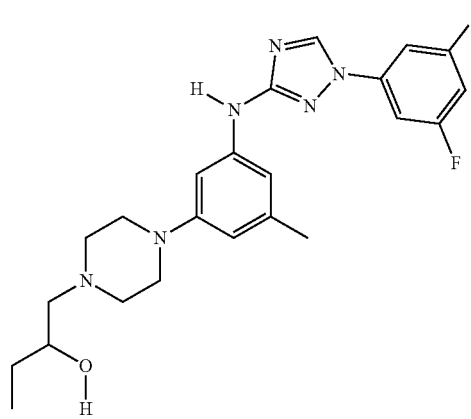
958
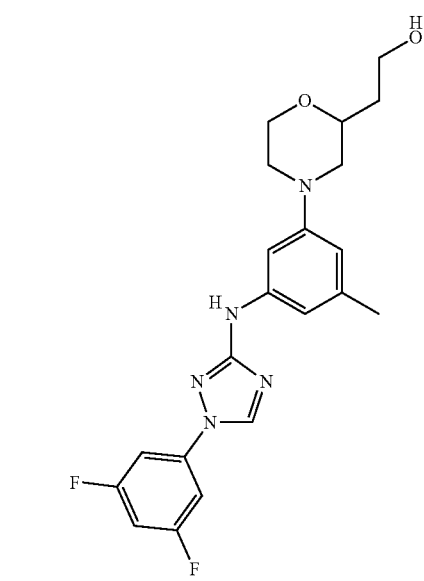
959
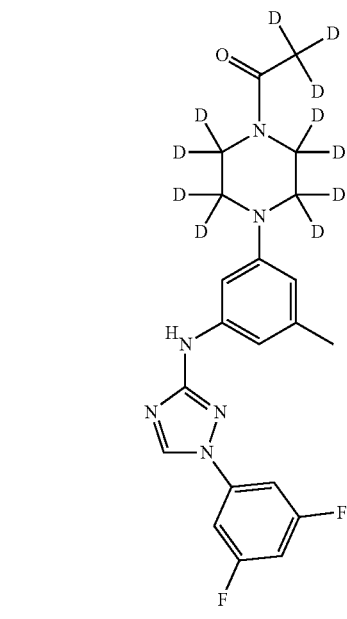
TABLE 1B-continued
Compound Table
960
961
962

TABLE 1B-continued
Compound Table
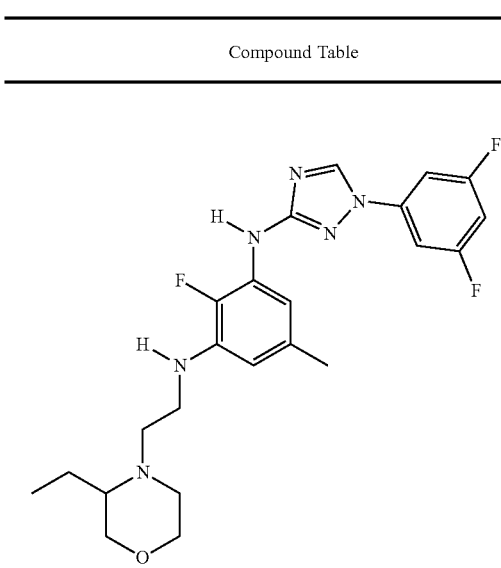
963
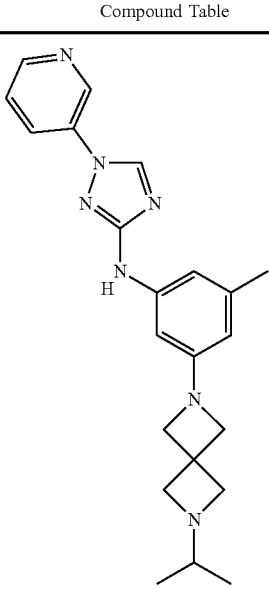
966
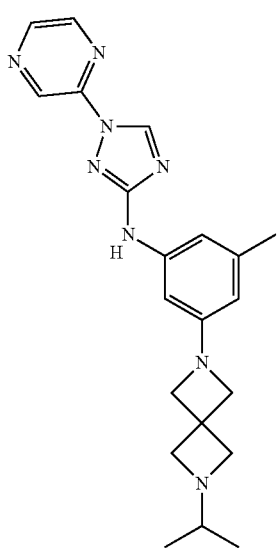
967
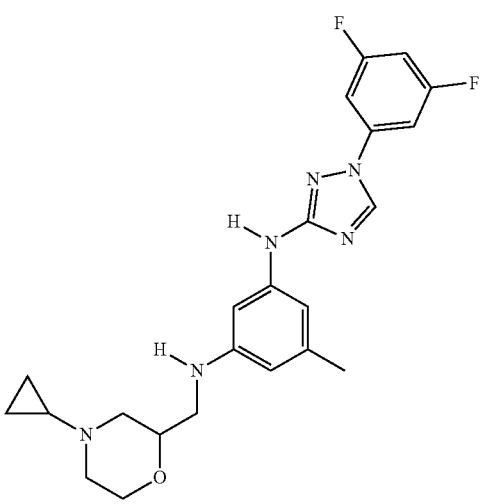 [SMILES: Cc1cc(NCC2CN(C3CC3)CCO2)cc(Nc2ncn(-c3cc(F)cc(F)c3)n2)c1]
968
964
965

TABLE 1B-continued
Compound Table
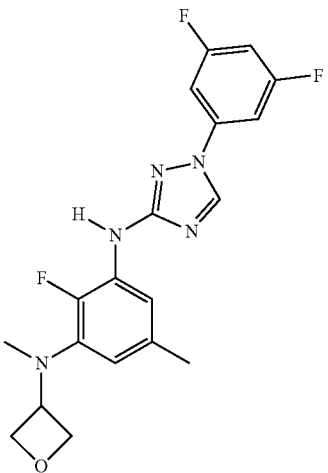 [SMILES: Cc1cc(Nc2ncn(-c3cc(F)cc(F)c3)n2)c(F)c(N(C)C2COC2)c1]
969
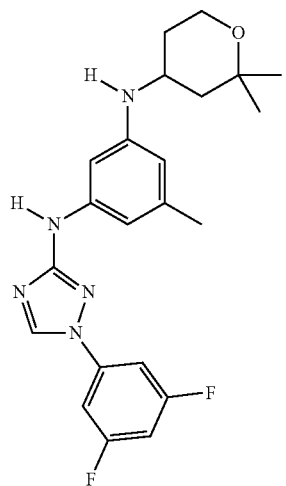 [SMILES: Cc1cc(Nc2ncn(-c3cc(F)cc(F)c3)n2)cc(NC2CCOC(C)(C)C2)c1]
970
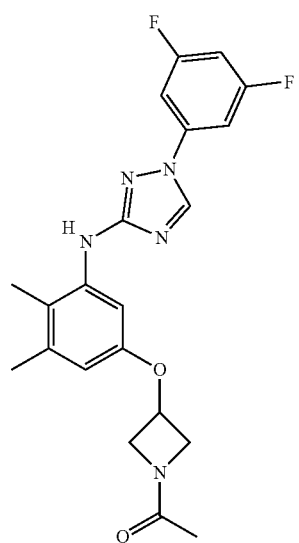
971
TABLE 1B-continued
Compound Table
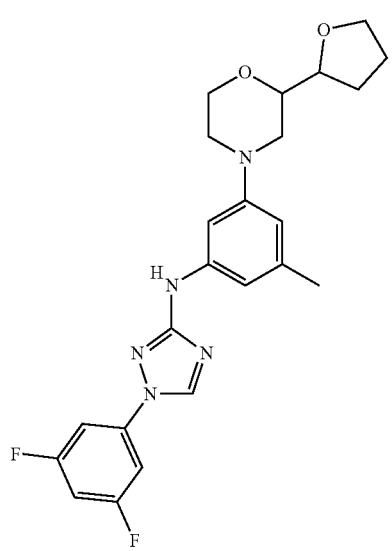
972
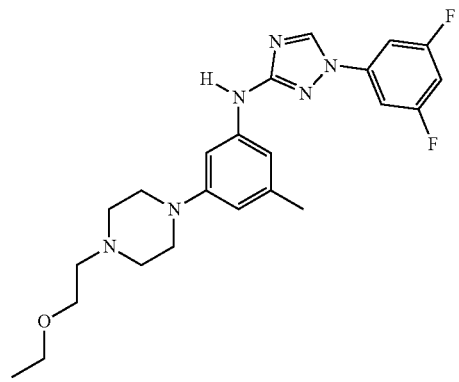 [SMILES: CCOCCN1CCN(c2cc(C)cc(Nc3ncn(-c4cc(F)cc(F)c4)n3)c2)CC1]
973
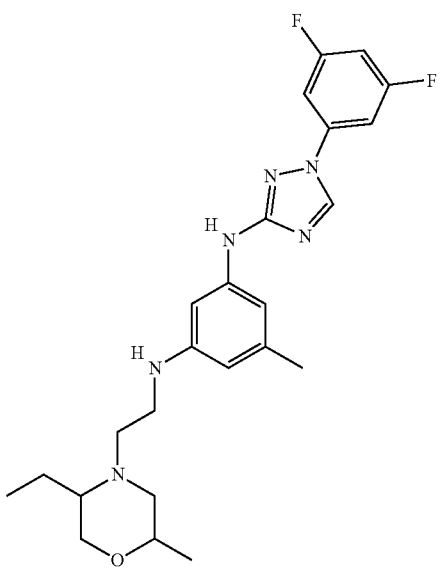
974

TABLE 1B-continued

Compound Table

TABLE 1B-continued
Compound Table
981 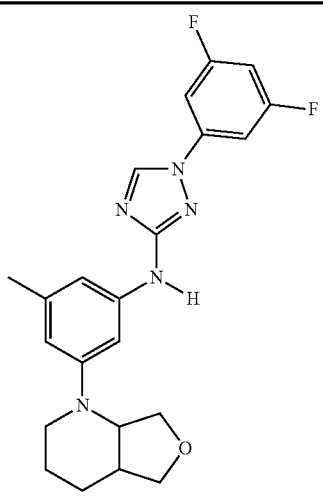
982 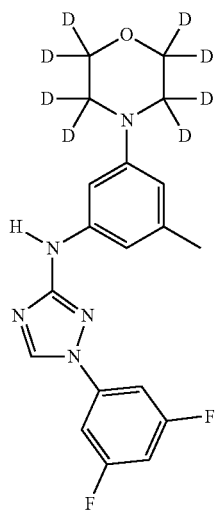 [SMILES: [2H]C1([2H])OC([2H])([2H])C([2H])([2H])N(c2cc(C)cc(Nc3ncn(-c4cc(F)cc(F)c4)n3)c2)C1([2H])[2H]]
983 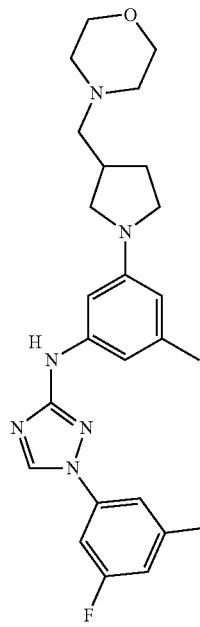
TABLE 1B-continued
Compound Table
984 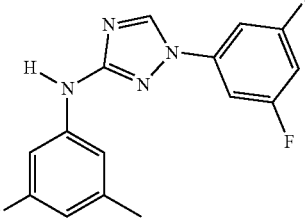
985 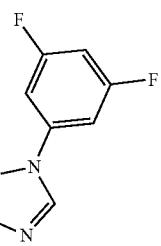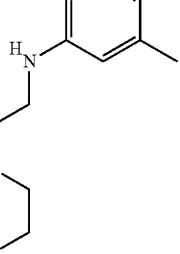
986 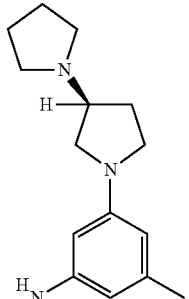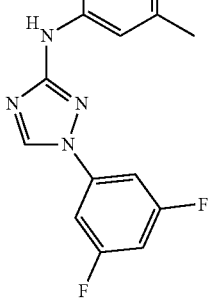

TABLE 1B-continued
Compound Table
987 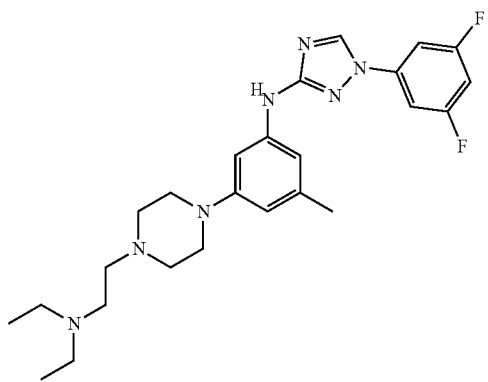
988 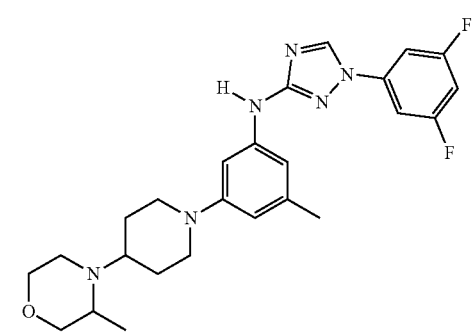 [SMILES: Cc1cc(Nc2ncn(-c3cc(F)cc(F)c3)n2)cc(N2CCC(N3CCOCC3C)CC2)c1]
989 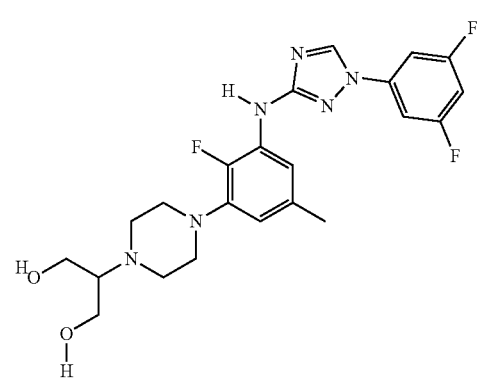
990 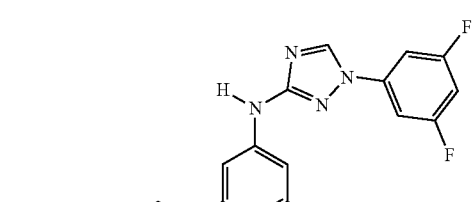
TABLE 1B-continued
Compound Table
991 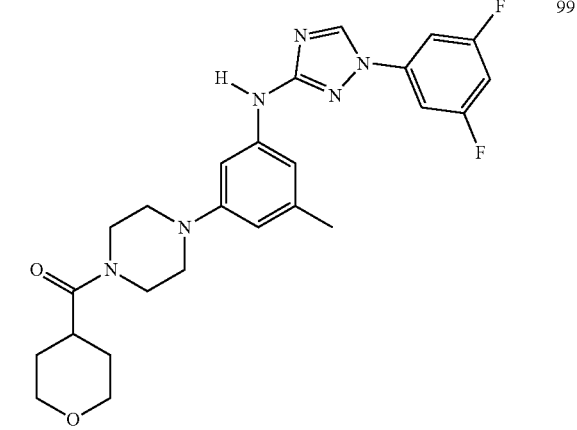
992 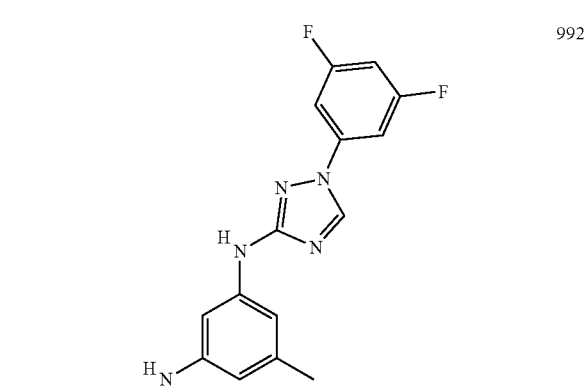
993 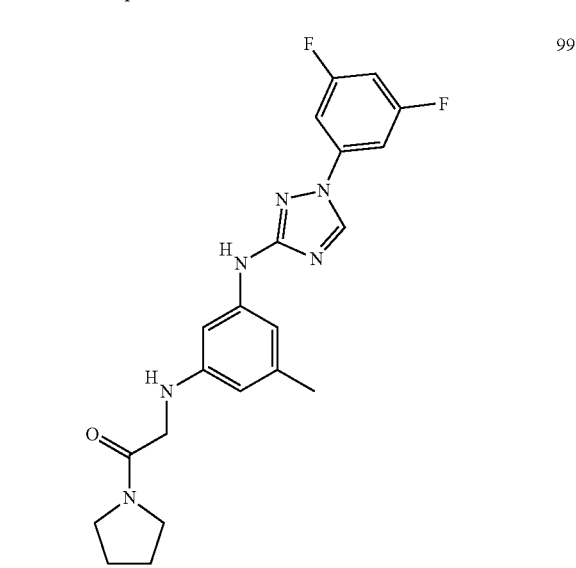

TABLE 1B-continued
Compound Table
994
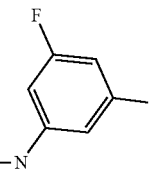
995
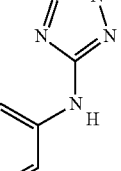
996
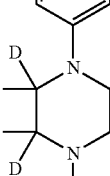
TABLE 1B-continued
Compound Table
997
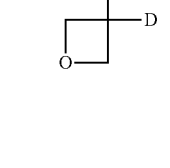
998
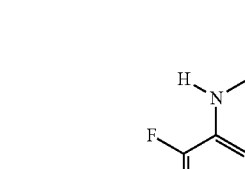
999
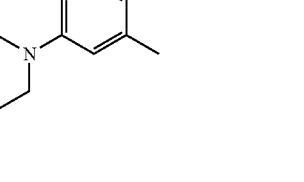

605
TABLE 1B-continued
Compound Table
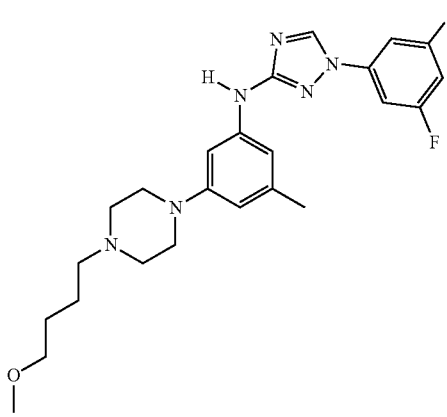
1001
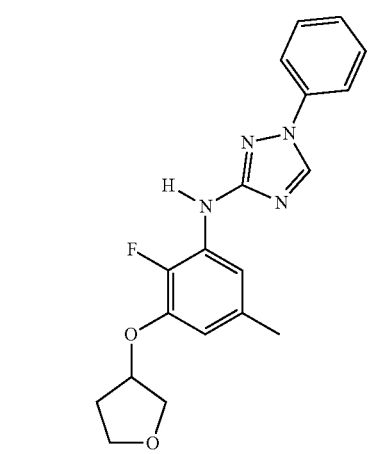 [SMILES: Cc1cc(Nc2ncn(-c3ccccc3)n2)c(F)c(OC2CCOC2)c1]
1002
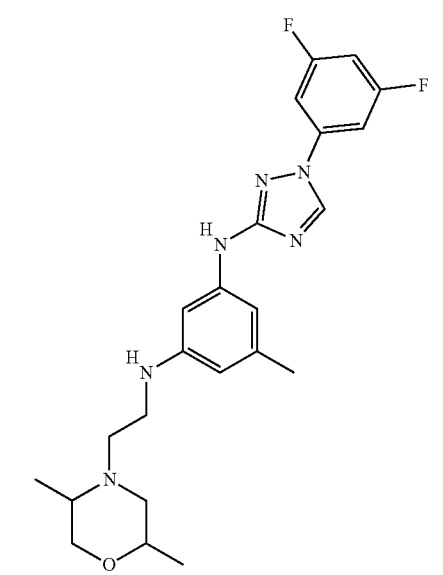
1003
606
TABLE 1B-continued
Compound Table
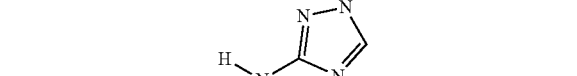
1004
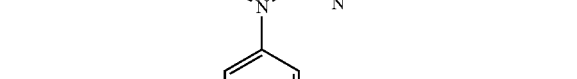
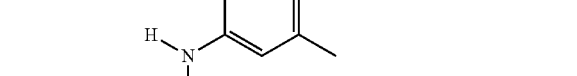
1005
1006

TABLE 1B-continued
Compound Table
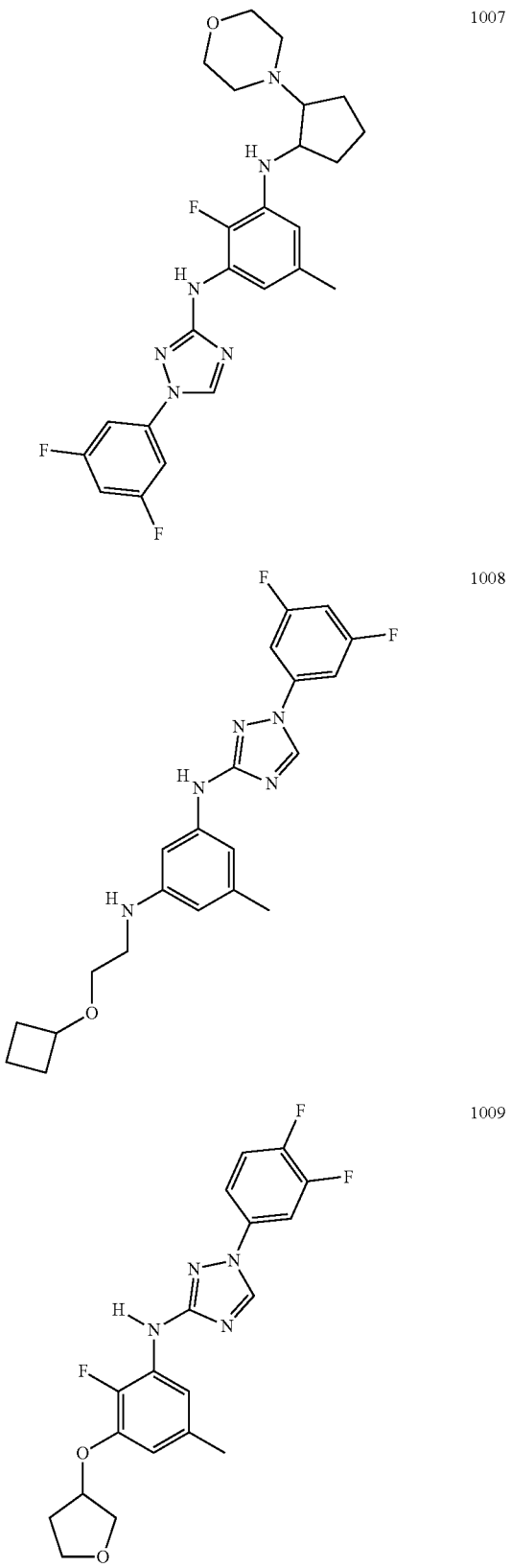
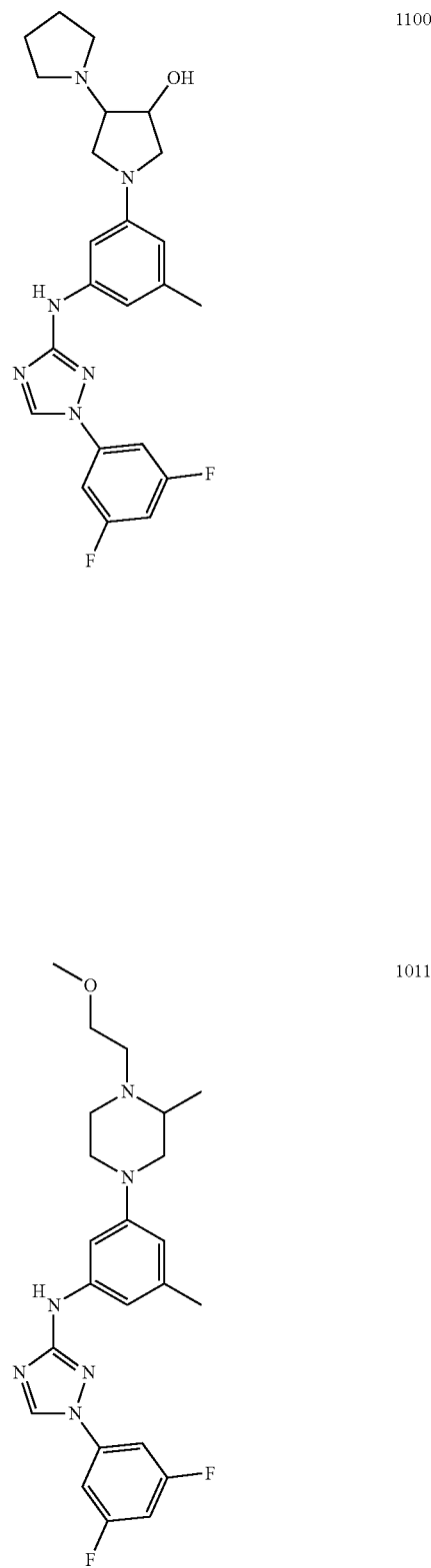

TABLE 1B-continued
Compound Table
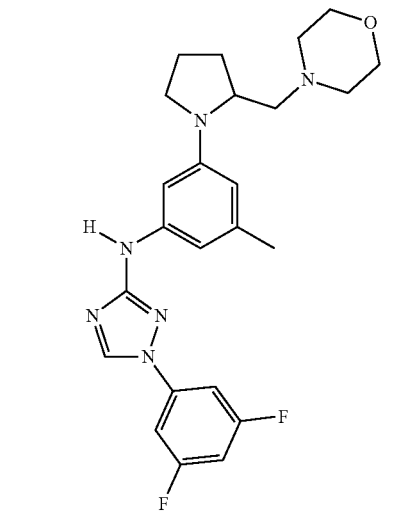 [SMILES: Cc1cc(Nc2ncn(-c3cc(F)cc(F)c3)n2)cc(N2CCCC2CN2CCOCC2)c1]
1012
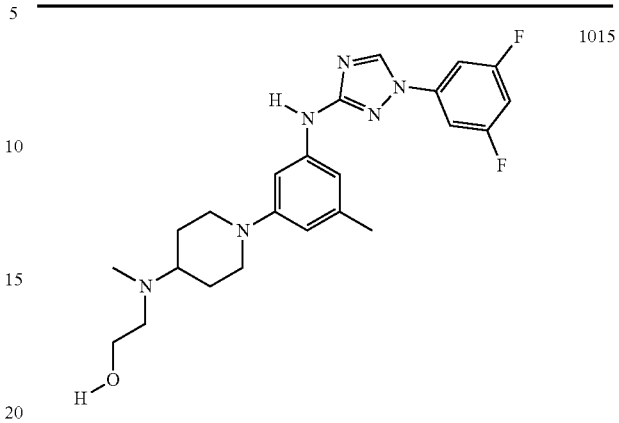
1015
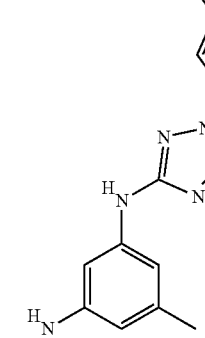
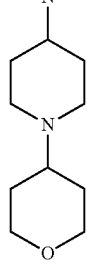
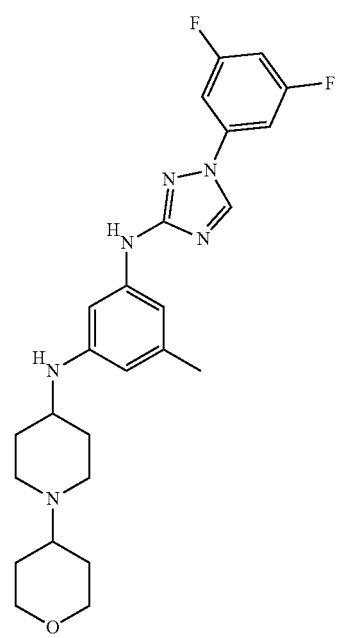
1013
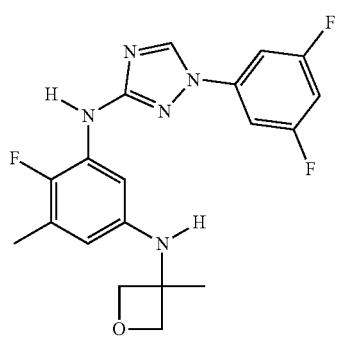 [SMILES: Cc1cc(NC2(C)COC2)cc(Nc2ncn(-c3cc(F)cc(F)c3)n2)c1F]
1016
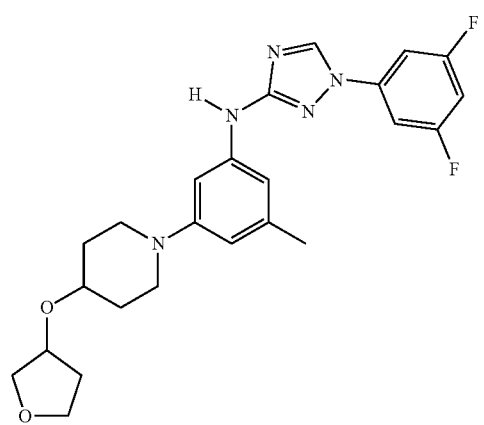
1014
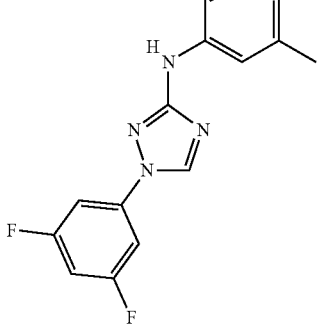
1017

TABLE 1B-continued
Compound Table
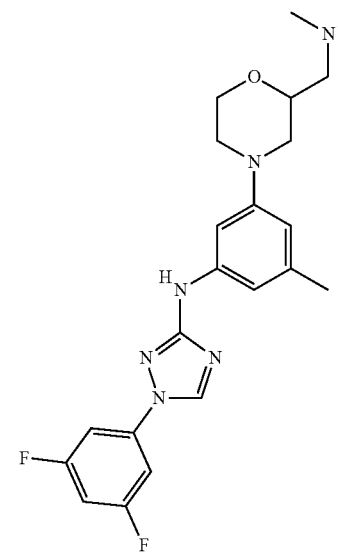
1018
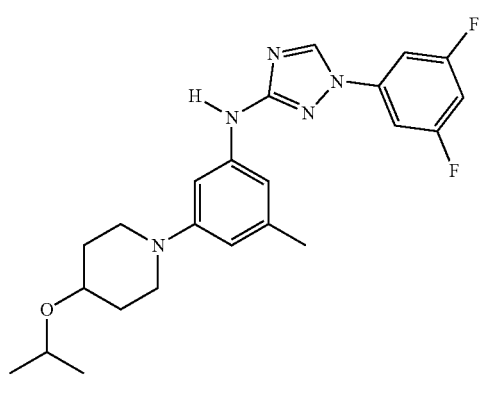 [SMILES: Cc1cc(Nc2ncn(-c3cc(F)cc(F)c3)n2)cc(N2CCC(OC(C)C)CC2)c1]
1019
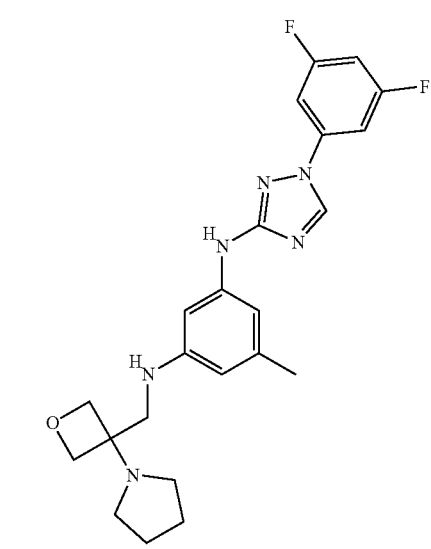
1020
TABLE 1B-continued
Compound Table
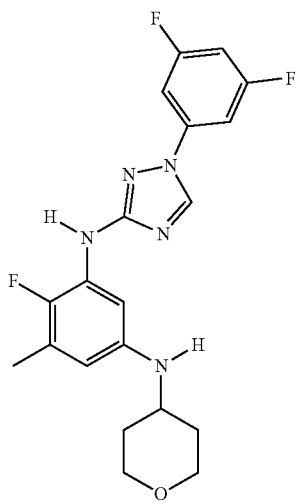 [SMILES: Cc1cc(NC2CCOCC2)cc(Nc2ncn(-c3cc(F)cc(F)c3)n2)c1F]
1021
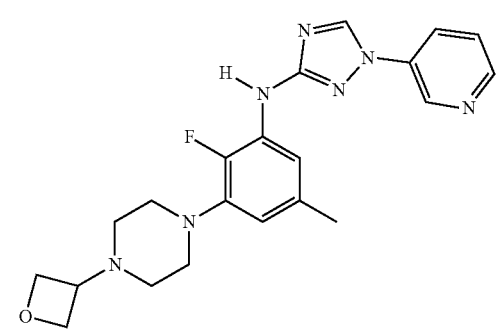 [SMILES: Cc1cc(Nc2ncn(-c3cccnc3)n2)c(F)c(N2CCN(C3COC3)CC2)c1]
1022
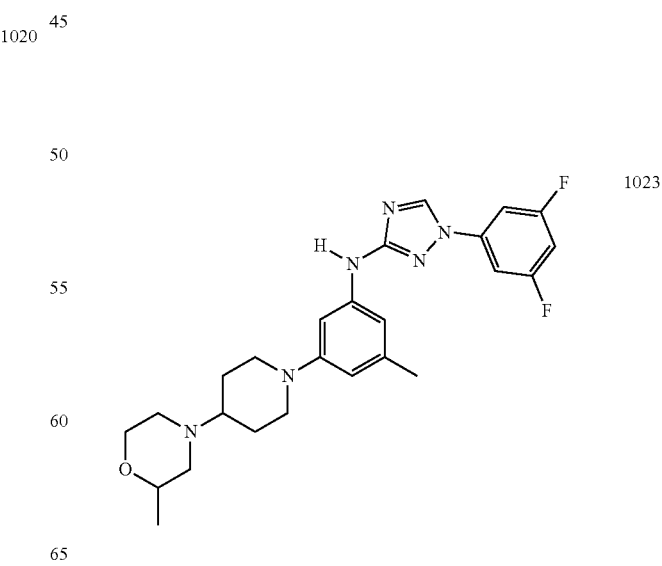
1023

TABLE 1B-continued
Compound Table
1024
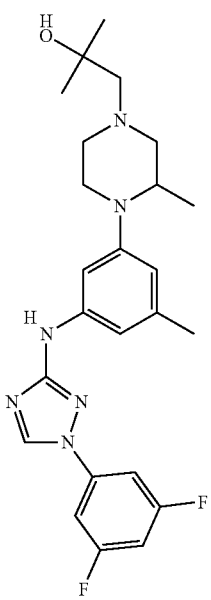
1025
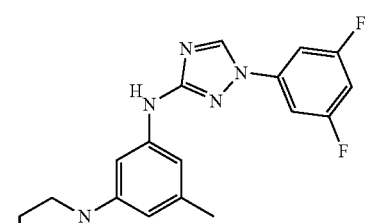
1026
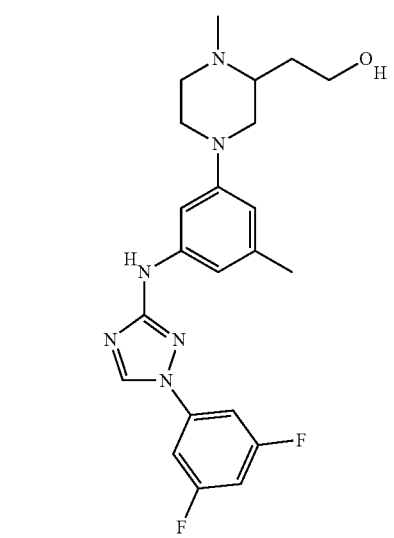
TABLE 1B-continued
Compound Table
1027
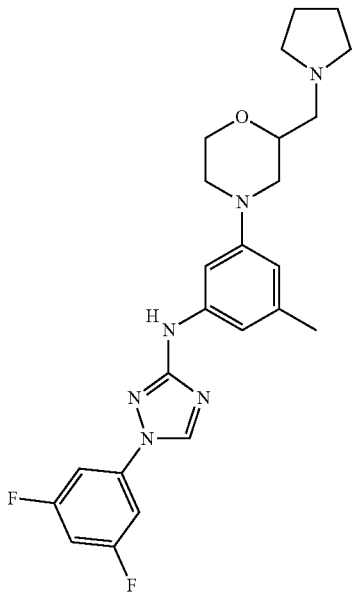
1028
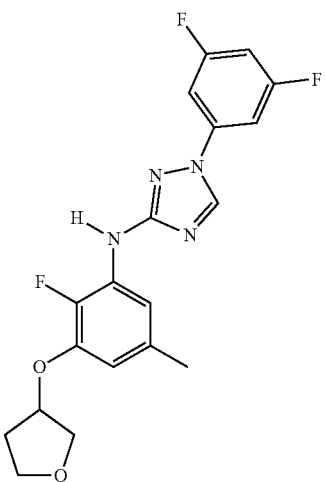 [SMILES: Cc1cc(Nc2ncn(-c3cc(F)cc(F)c3)n2)c(F)c(OC2CCOC2)c1]
1029
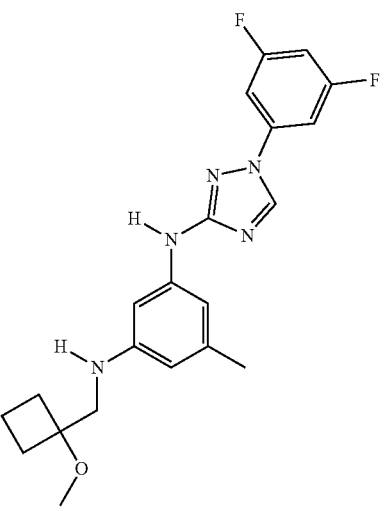 [SMILES: COC1(CNc2cc(C)cc(Nc3ncn(-c4cc(F)cc(F)c4)n3)c2)CCC1]

TABLE 1B-continued
Compound Table
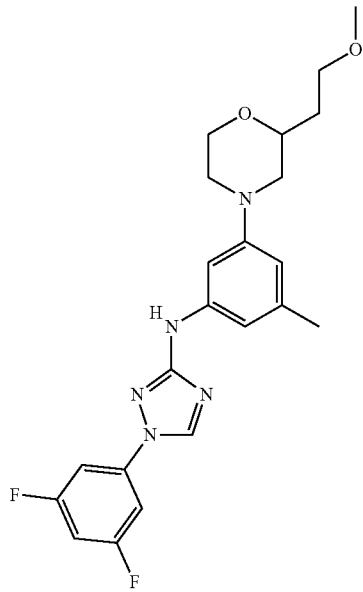
1030
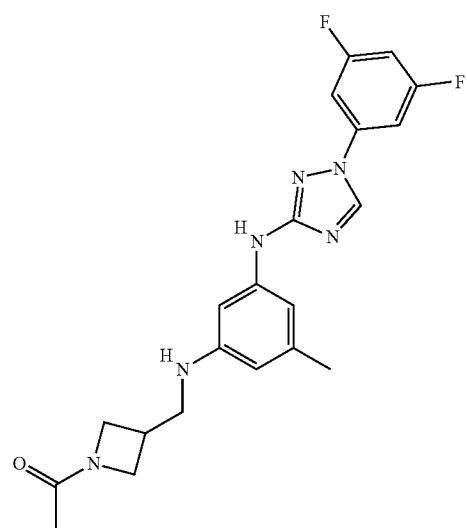
1031
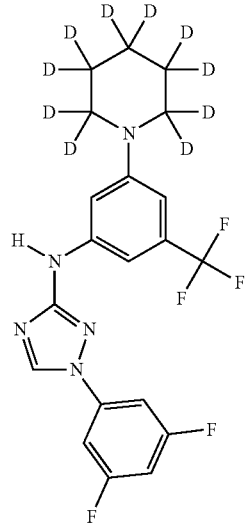
1032
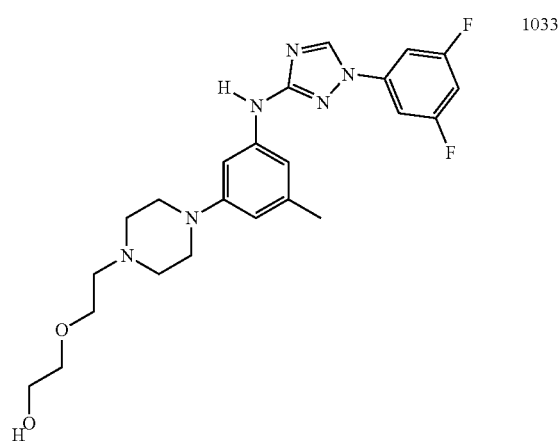
1033
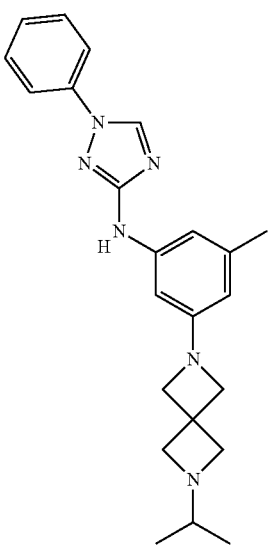
1034

TABLE 1B-continued
Compound Table
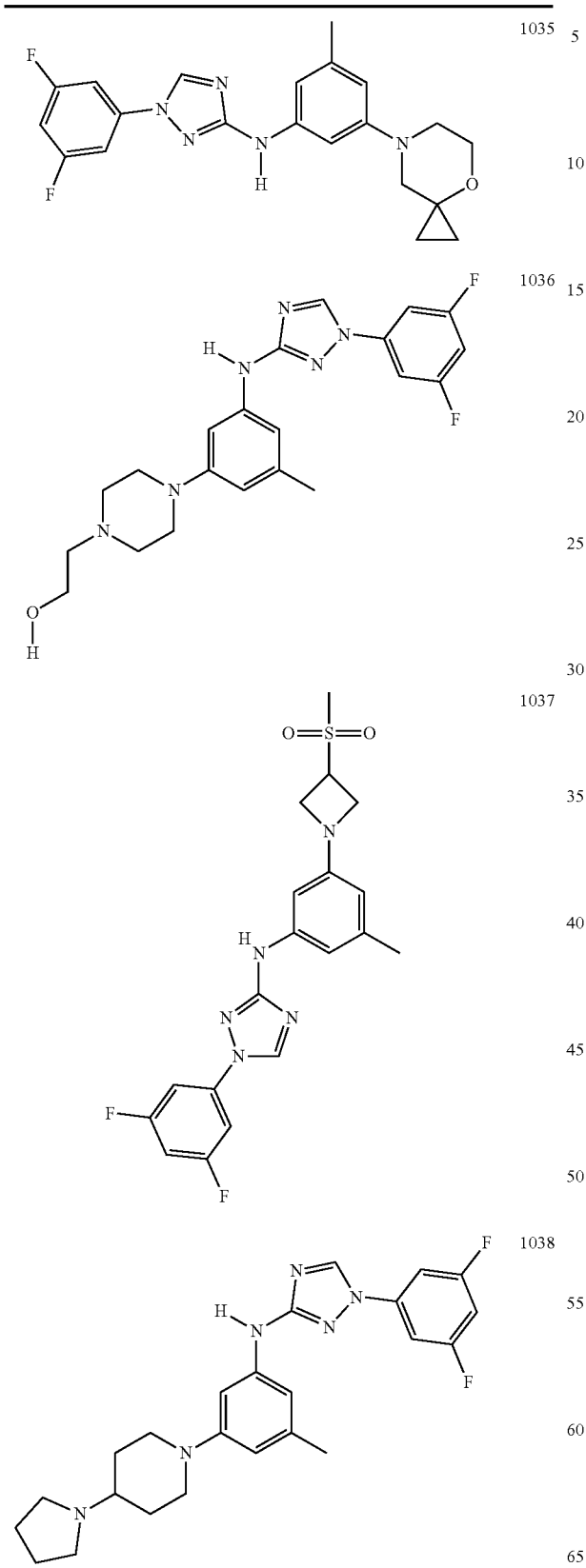
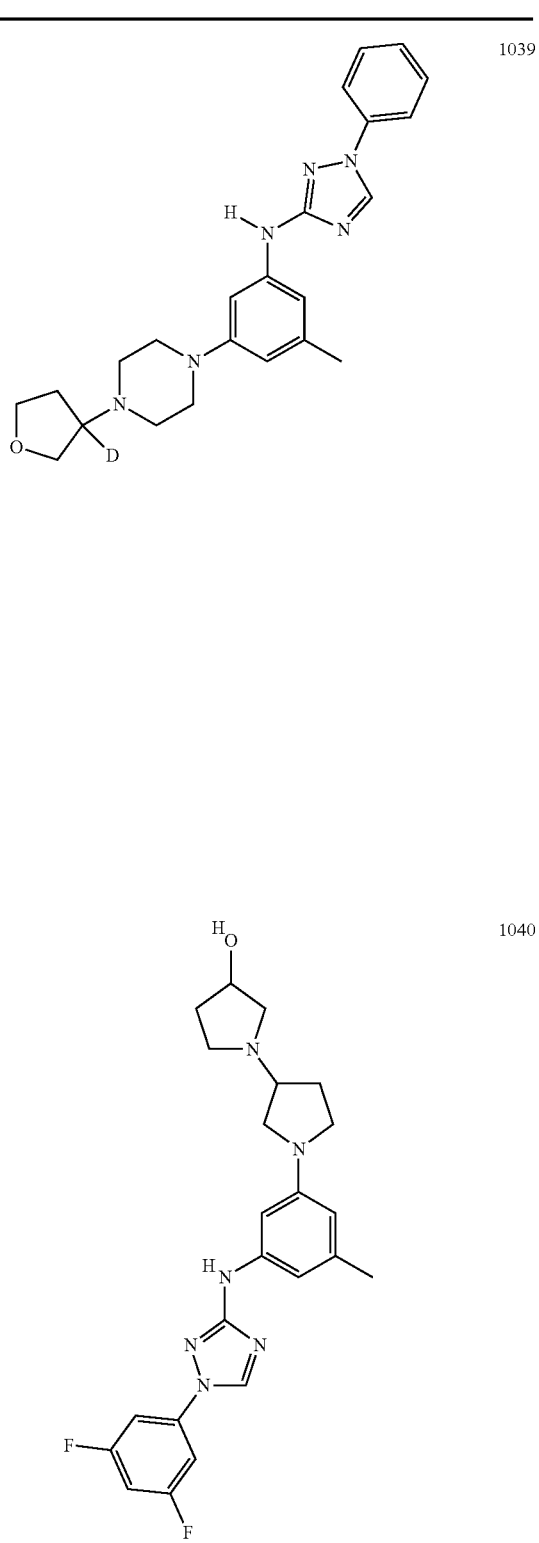

TABLE 1B-continued
Compound Table
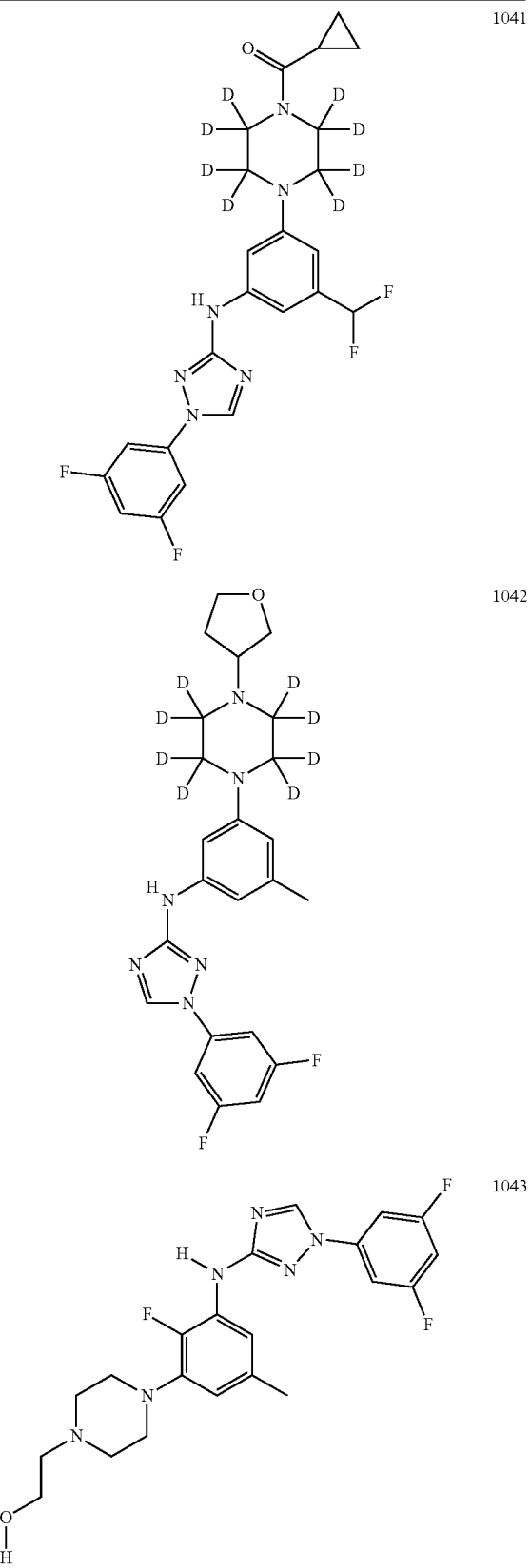
1041
1042
1043
TABLE 1B-continued
Compound Table
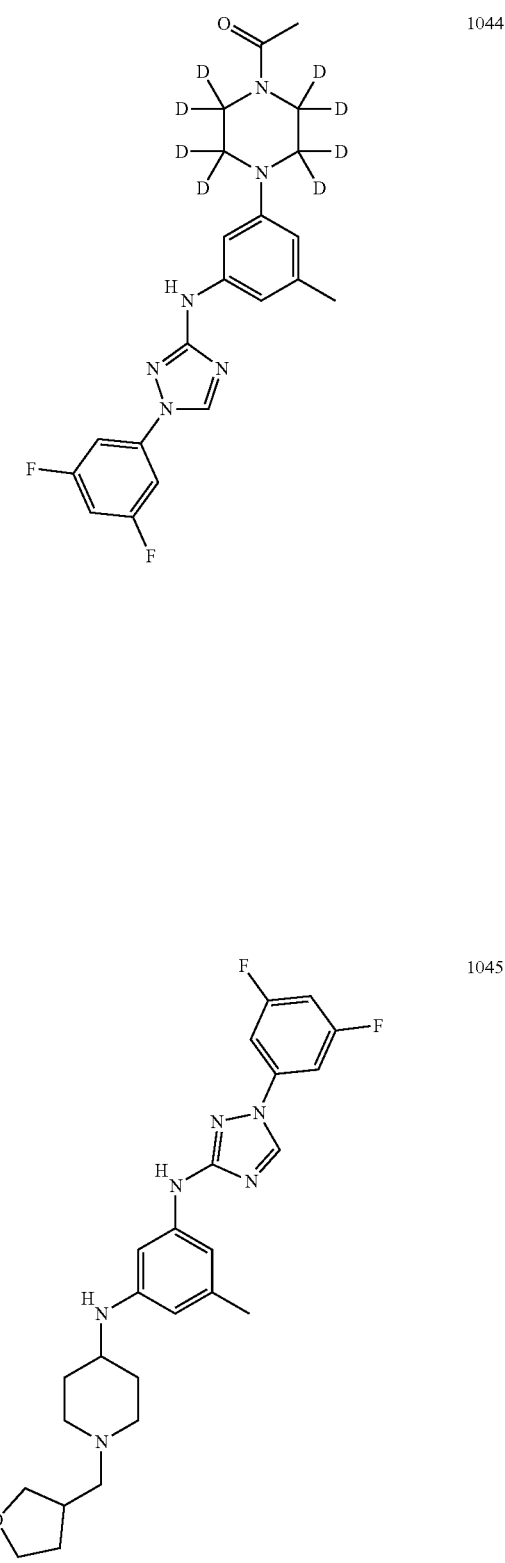
1044
1045

TABLE 1B-continued

Compound Table 1046
1047
1048
1049
1050
1051
1052

TABLE 1B-continued
Compound Table
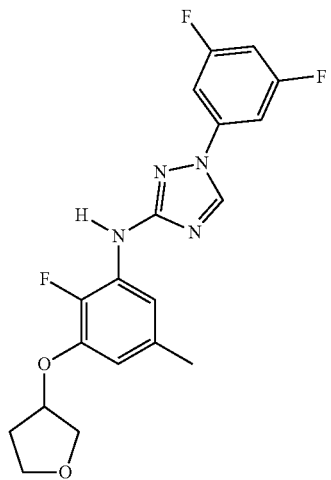 [SMILES: Cc1cc(Nc2ncn(-c3cc(F)cc(F)c3)n2)c(F)c(OC2CCOC2)c1]
1053
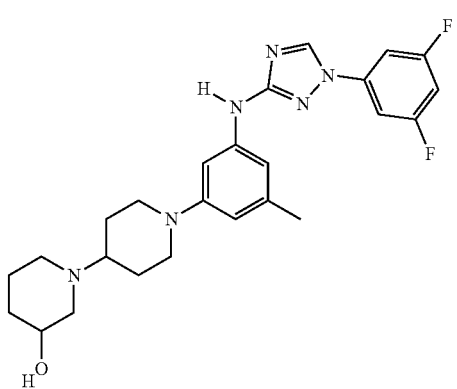
1054
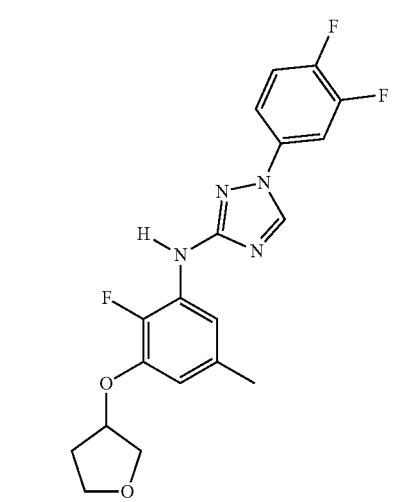 [SMILES: Cc1cc(Nc2ncn(-c3ccc(F)c(F)c3)n2)c(F)c(OC2CCOC2)c1]
1055
TABLE 1B-continued
Compound Table
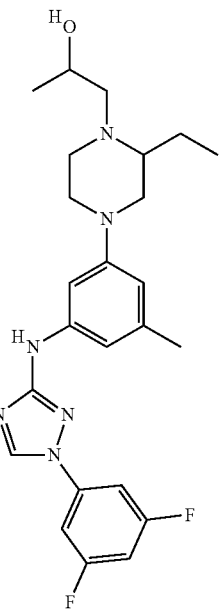
1056
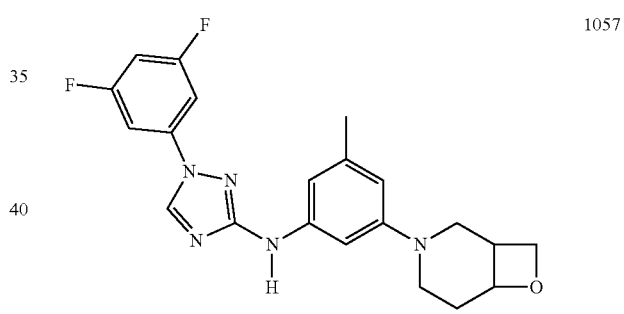
1057
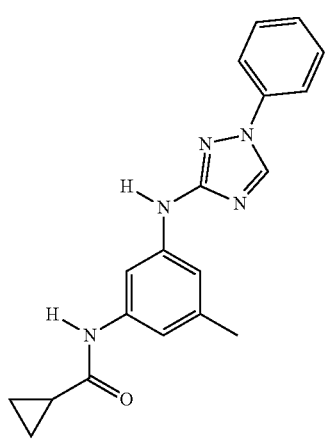 [SMILES: Cc1cc(NC(=O)C2CC2)cc(Nc2ncn(-c3ccccc3)n2)c1]
1058

TABLE 1B-continued
Compound Table
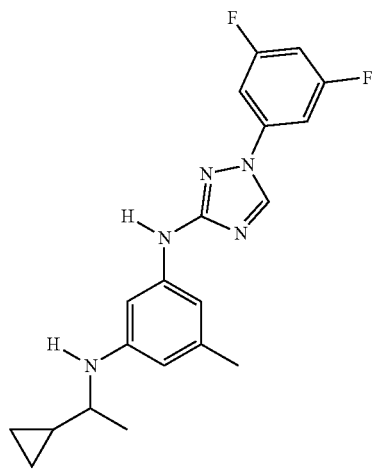 [SMILES: Cc1cc(Nc2ncn(-c3cc(F)cc(F)c3)n2)cc(NC(C)C2CC2)c1]
1059
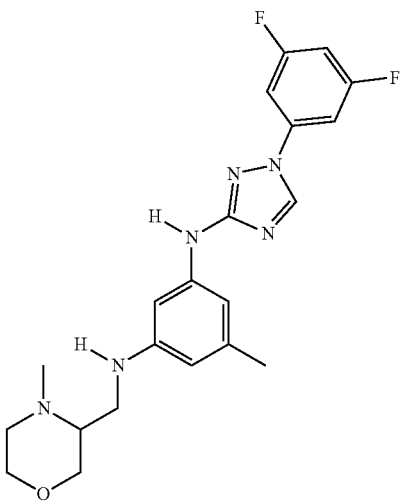 [SMILES: Cc1cc(NCC2COCCN2C)cc(Nc2ncn(-c3cc(F)cc(F)c3)n2)c1]
1062
1060
1063
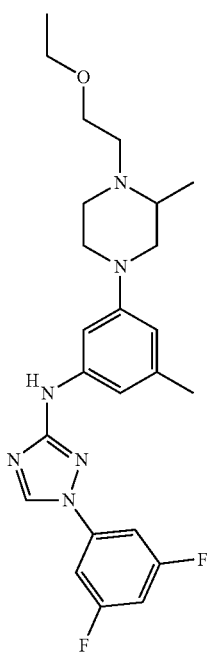
1061

TABLE 1B-continued
Compound Table
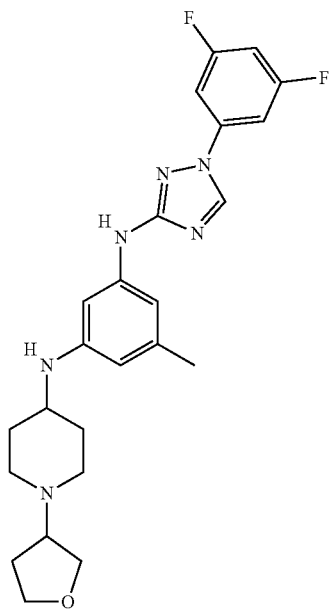
1064
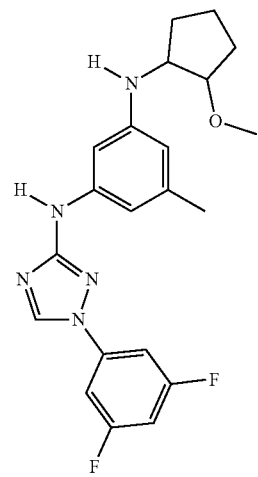 [SMILES: COC1CCCC1Nc1cc(C)cc(Nc2ncn(-c3cc(F)cc(F)c3)n2)c1]
1065
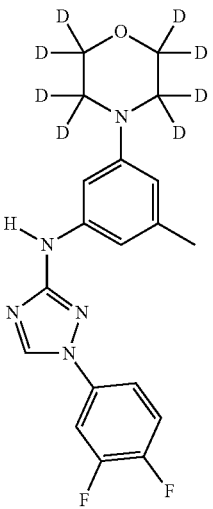 [SMILES: [2H]C1([2H])OC([2H])([2H])C([2H])([2H])N(c2cc(C)cc(Nc3ncn(-c4ccc(F)c(F)c4)n3)c2)C1([2H])[2H]]
1066
TABLE 1B-continued
Compound Table
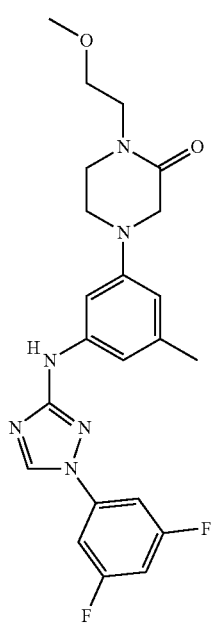
1067
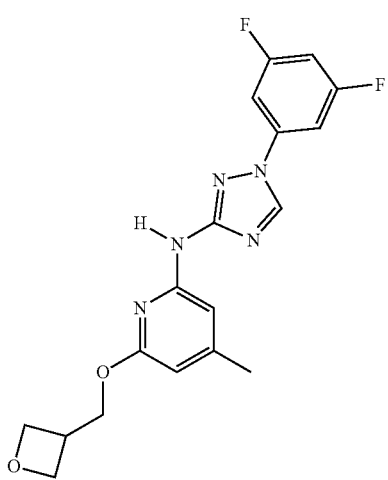 [SMILES: Cc1cc(Nc2ncn(-c3cc(F)cc(F)c3)n2)nc(OCC2COC2)c1]
1068
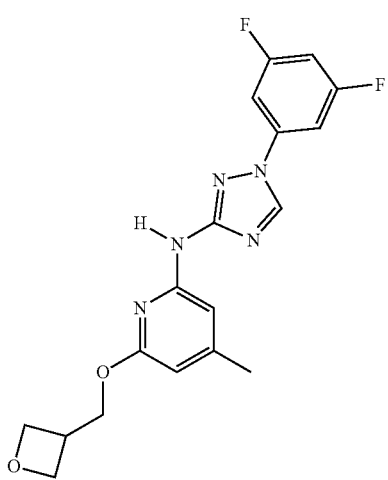 [SMILES: Cc1cc(Nc2ncn(-c3cc(F)cc(F)c3)n2)nc(OCC2COC2)c1]
1069

TABLE 1B-continued
Compound Table
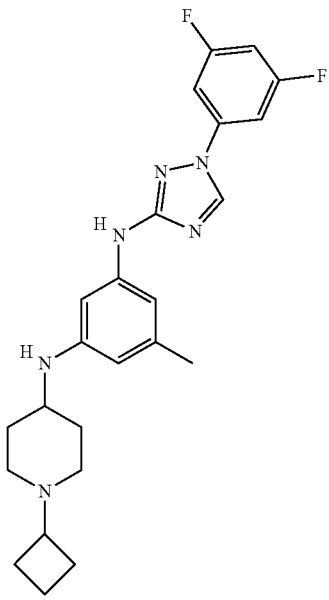
1070
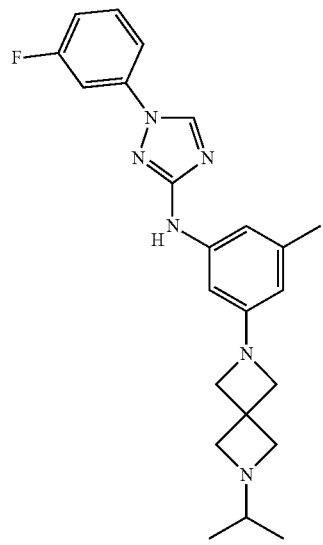
1071
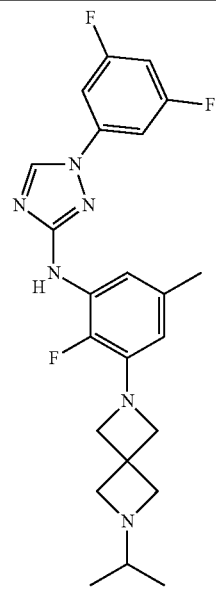
1072
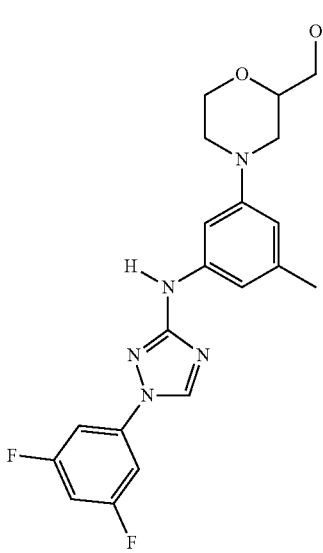
1073
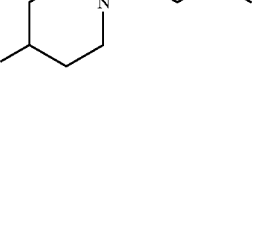
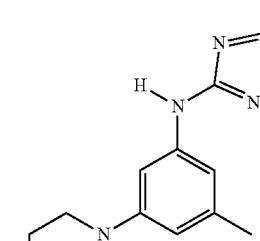
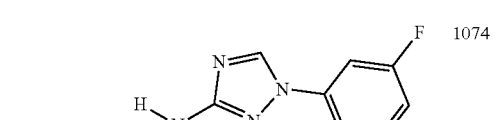
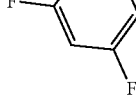
1074

631
TABLE 1B-continued
Compound Table
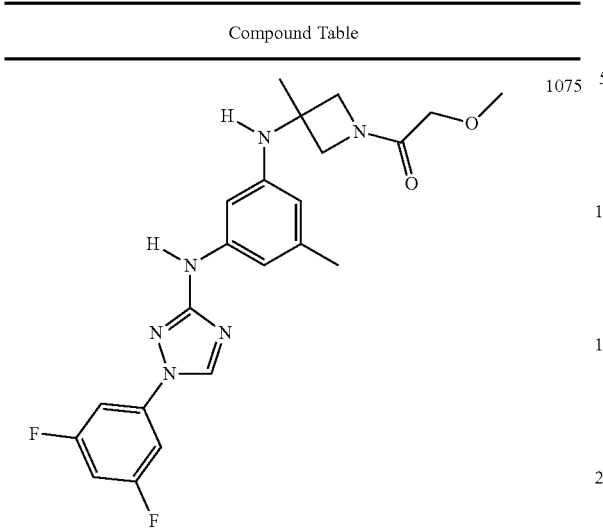
1075
1076
1077
632
TABLE 1B-continued
Compound Table
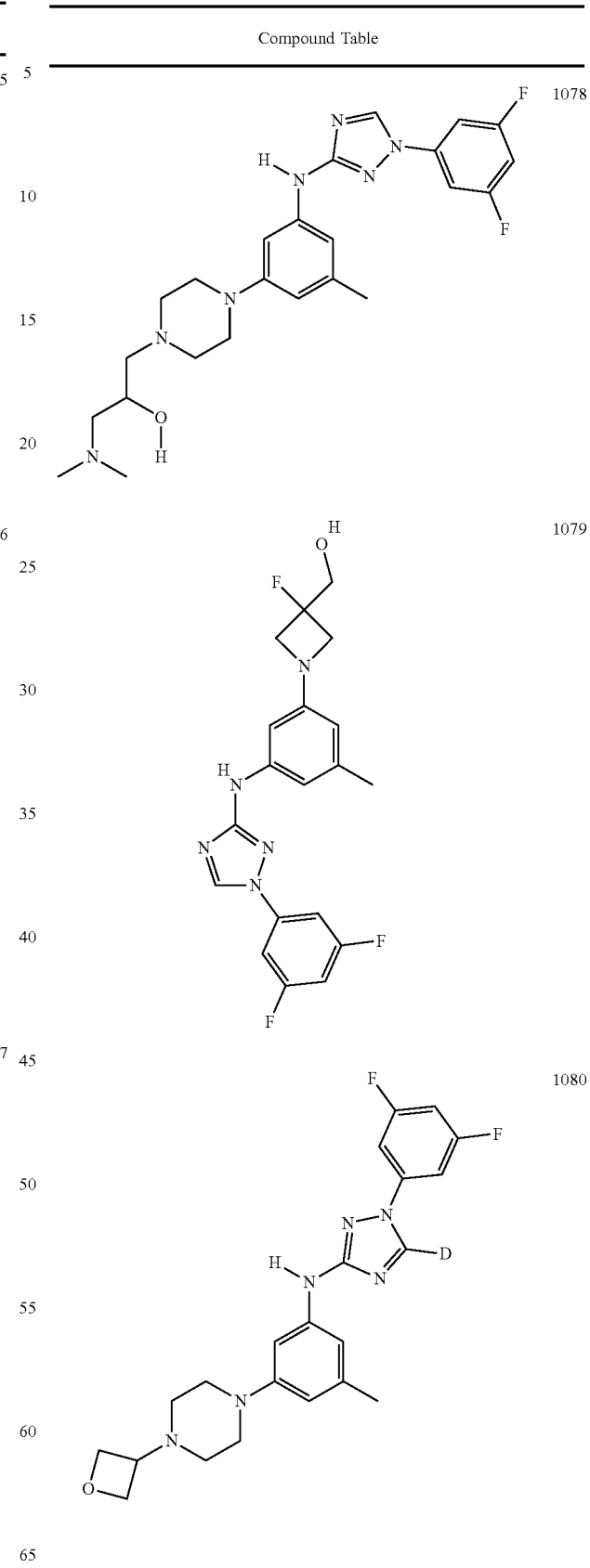
1078
1079
1080

TABLE 1B-continued
Compound Table
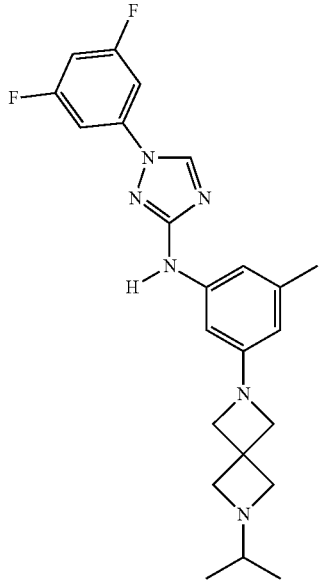 [SMILES: Cc1cc(Nc2ncn(-c3cc(F)cc(F)c3)n2)cc(N2CC3(C2)CN(C(C)C)C3)c1]
1081
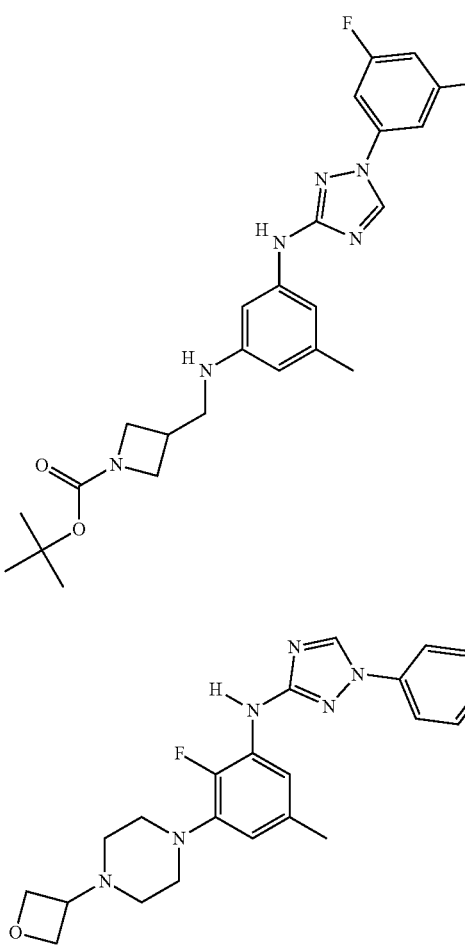
1082
TABLE 1B-continued
Compound Table
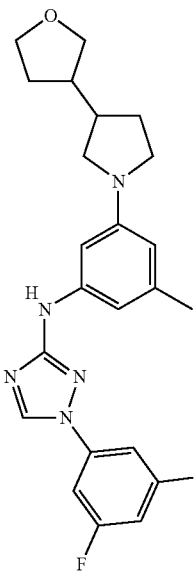
1083
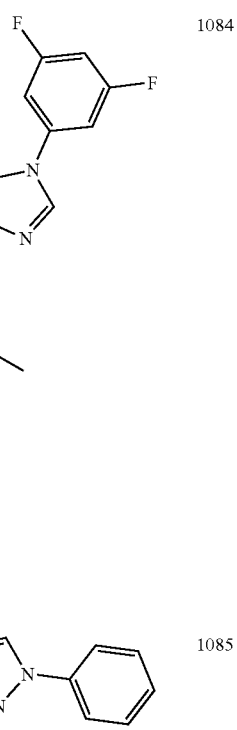
1084
1085

TABLE 1B-continued
Compound Table
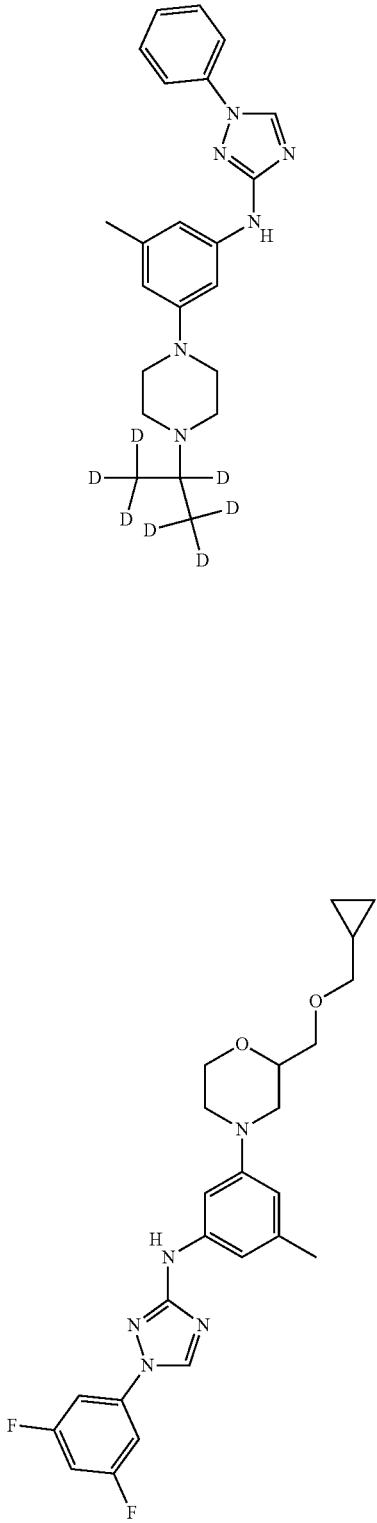
1086
1087
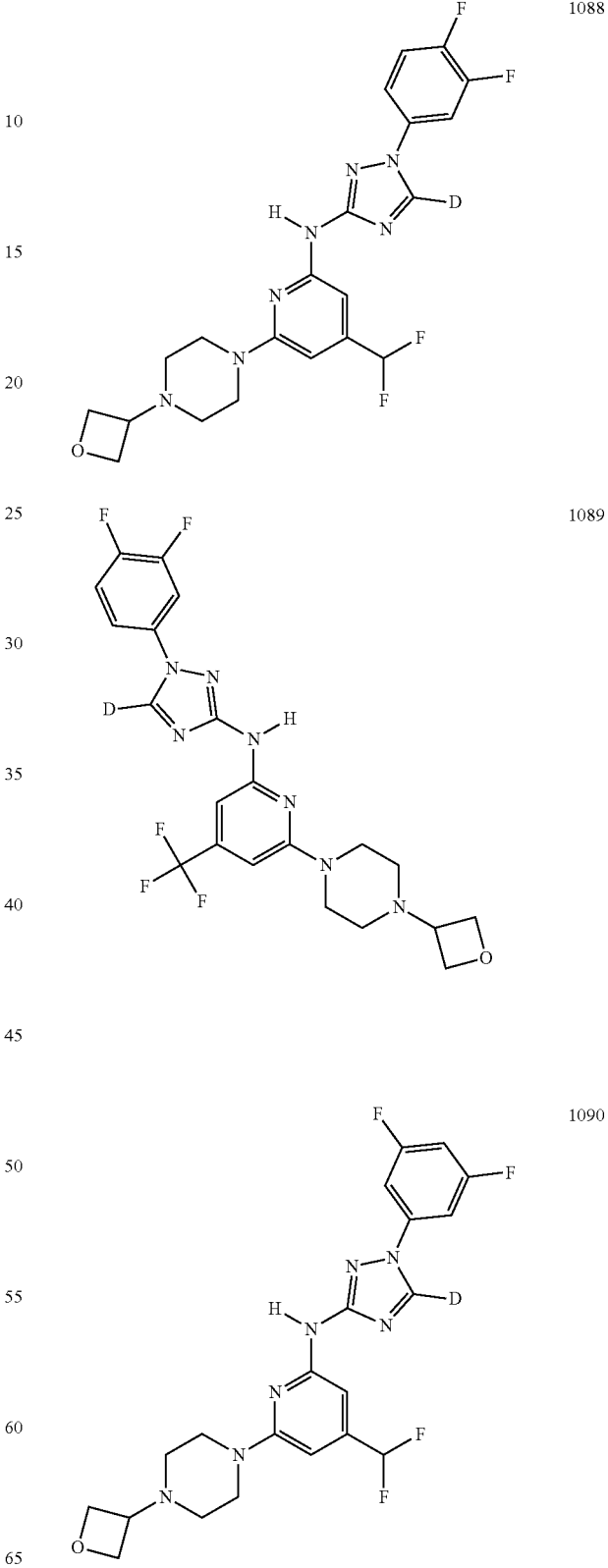
1088
1089
1090

TABLE 1B-continued
Compound Table
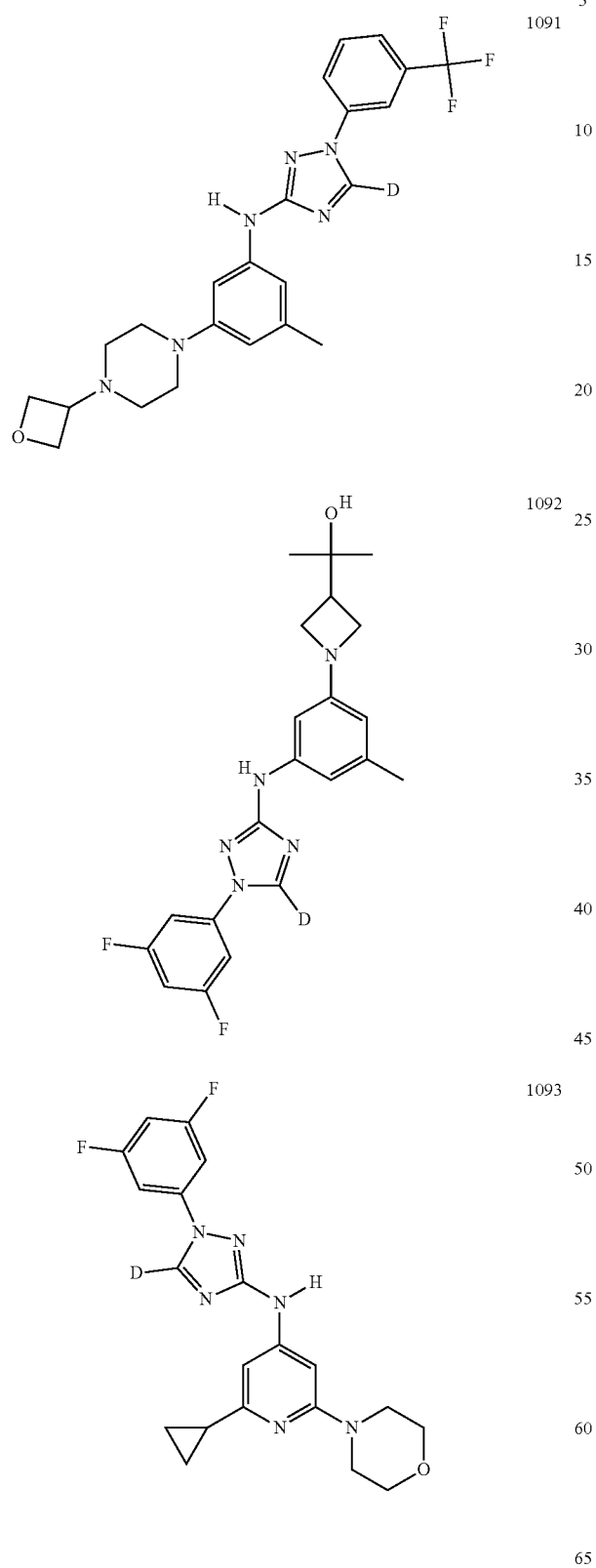
1091
1092
1093
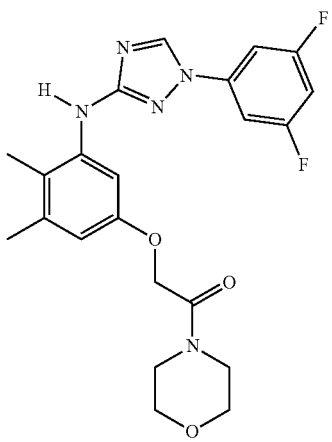 [SMILES: Cc1cc(OCC(=O)N2CCOCC2)cc(Nc2ncn(-c3cc(F)cc(F)c3)n2)c1C]
1094
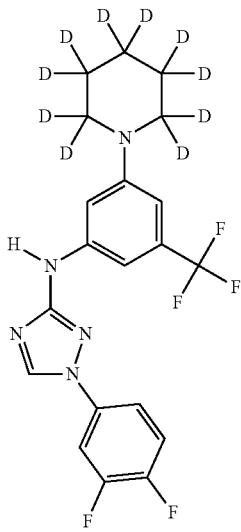 [SMILES: [2H]C1([2H])N(c2cc(Nc3ncn(-c4ccc(F)c(F)c4)n3)cc(C(F)(F)F)c2)C([2H])([2H])C([2H])([2H])C([2H])([2H])C1([2H])[2H]]
1095
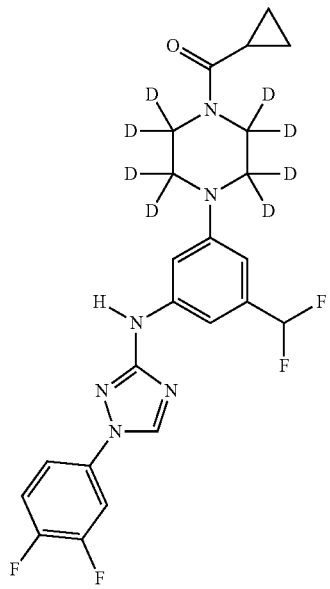 [SMILES: [2H]C1([2H])N(C(=O)C2CC2)C([2H])([2H])C([2H])([2H])N(c2cc(Nc3ncn(-c4ccc(F)c(F)c4)n3)cc(C(F)F)c2)C1([2H])[2H]]
1096

TABLE 1B-continued
Compound Table
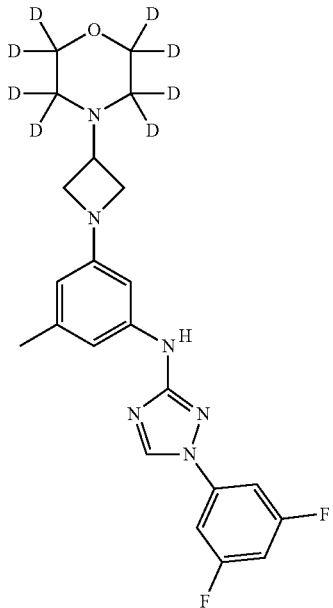
1097
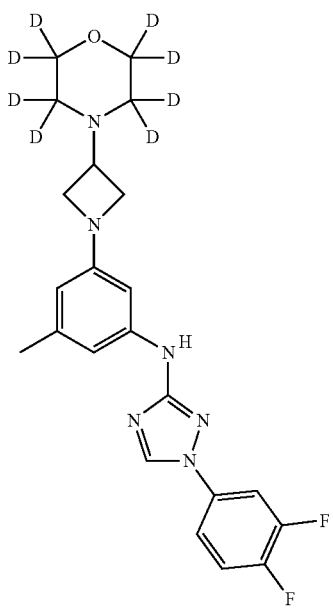
1098
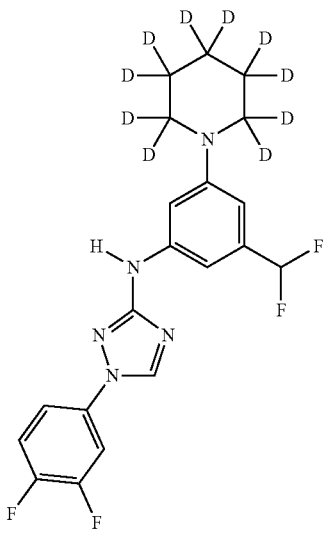 [SMILES: [2H]C1([2H])N(c2cc(Nc3ncn(-c4ccc(F)c(F)c4)n3)cc(C(F)F)c2)C([2H])([2H])C([2H])([2H])C([2H])([2H])C1([2H])[2H]]
1099
1100

TABLE 1B-continued
Compound Table
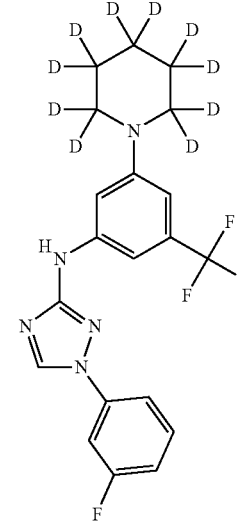 1101
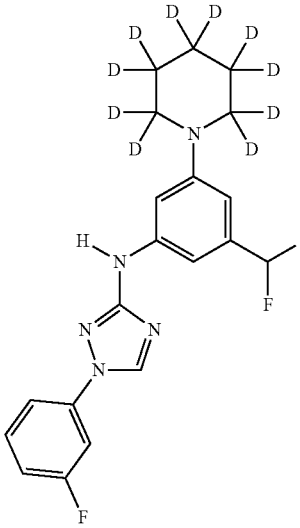 1102
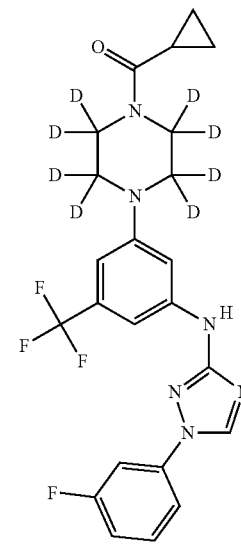 1103
TABLE 1B-continued
Compound Table
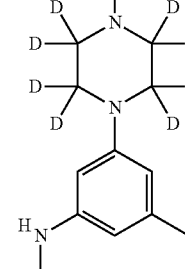 1104
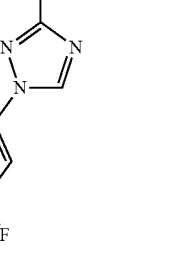 1105
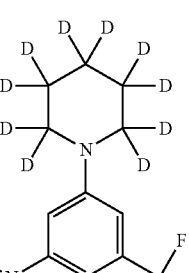 1106

TABLE 1B-continued
Compound Table
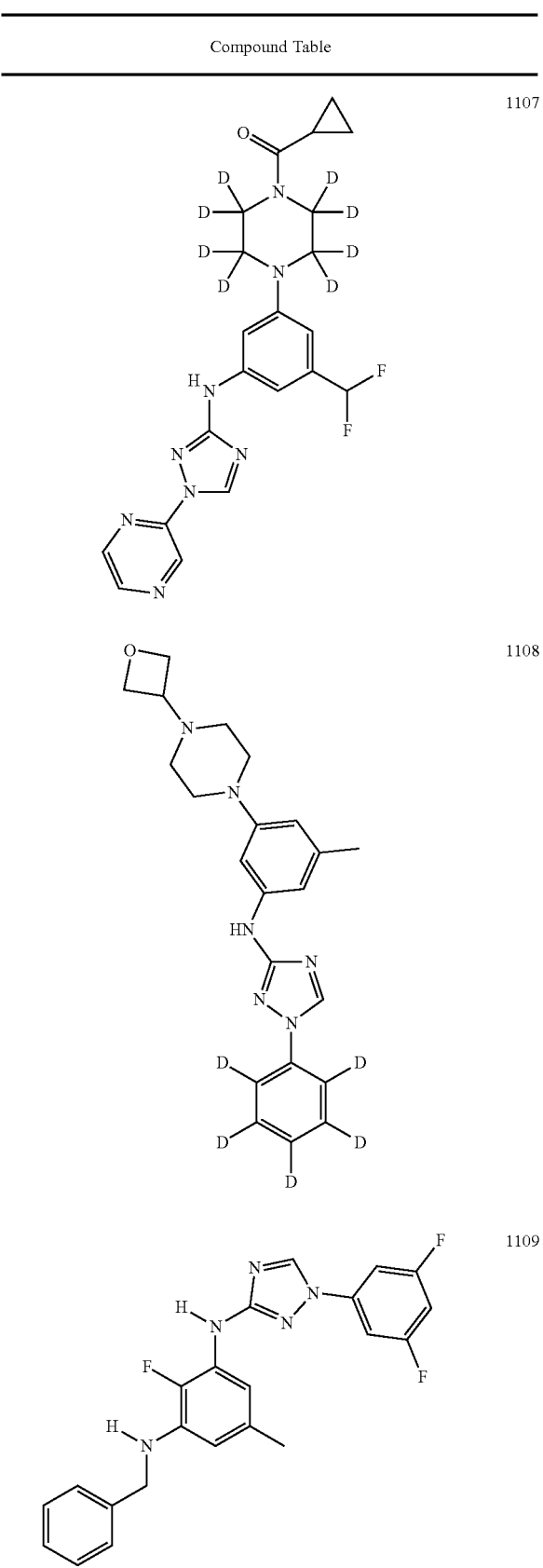
1107
1108
1109
TABLE 1B-continued
Compound Table
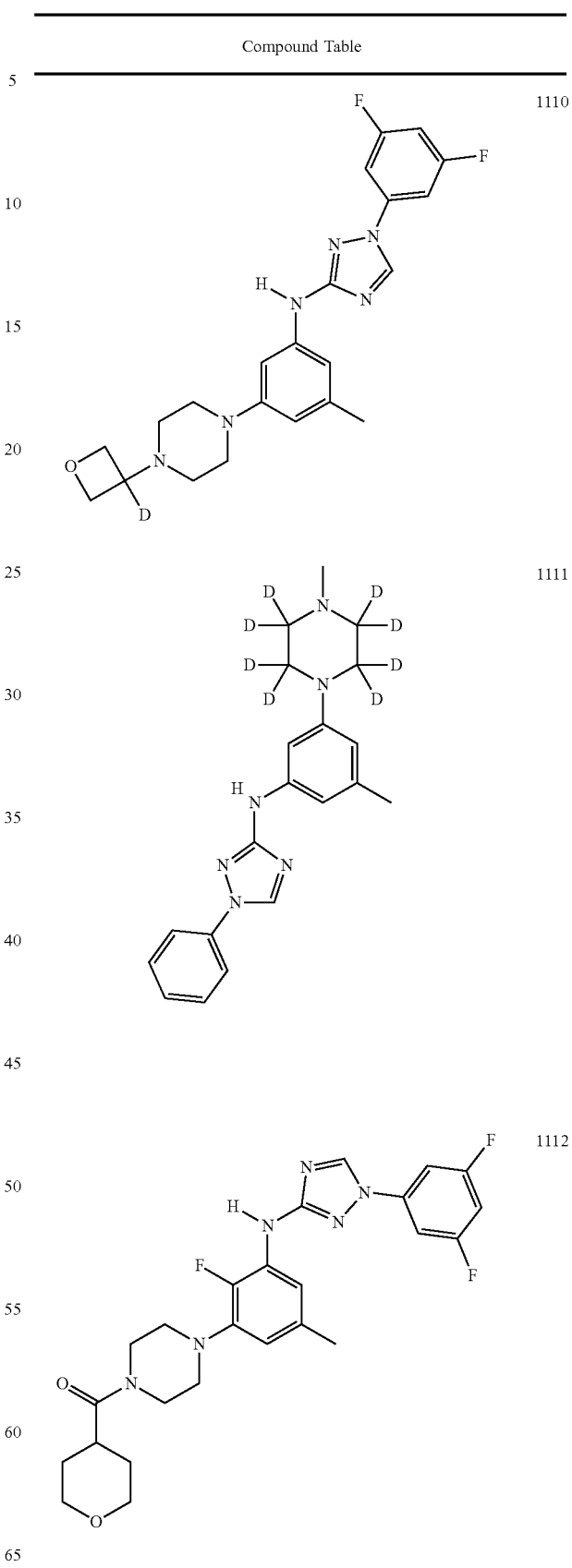
1110
1111
1112

TABLE 1B-continued
Compound Table
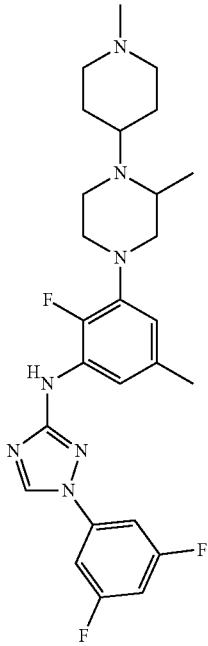
1113
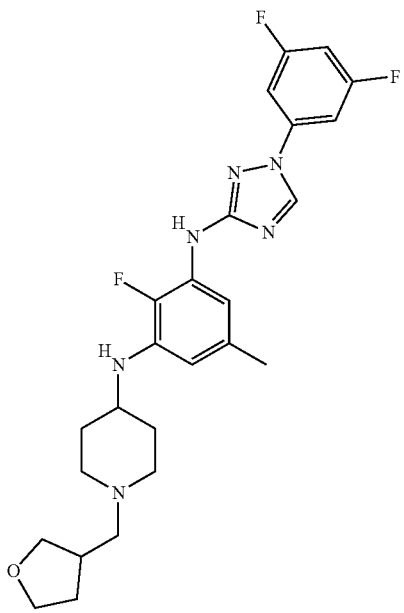
1115
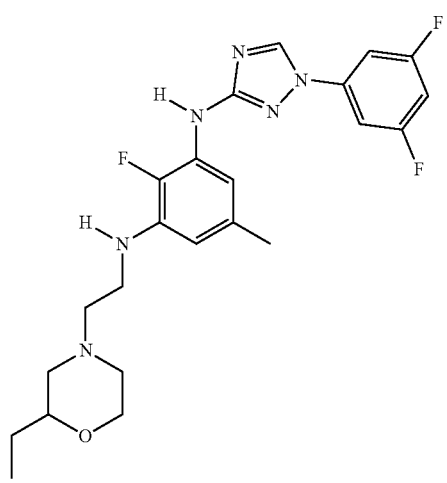 [SMILES: CCC1CN(CCNc2cc(C)cc(Nc3ncn(-c4cc(F)cc(F)c4)n3)c2F)CCO1]
1114
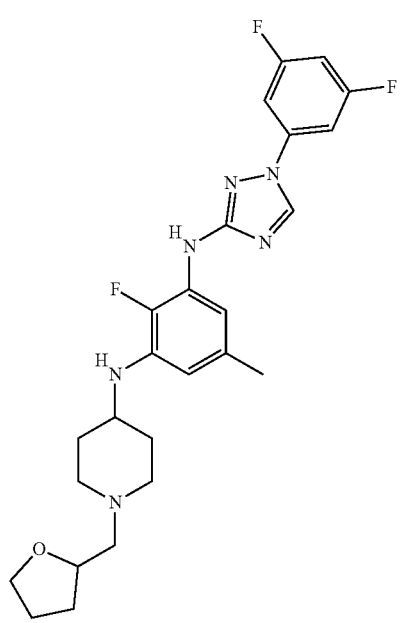
1116

TABLE 1B-continued

Compound Table

| | |
|---|---|
| 1117 | (structure) |
| 1118 | (structure) |
| 1119 | (structure) |
| 1120 | (structure) |
| 1121 | (structure) |
| 1122 | (structure) |

TABLE 1B-continued

Compound Table

1123

TABLE 2

Compound Names (IUPAC Nomenclature)

| Cmpd Number | IUPAC Name |
|---|---|
| 1 | N-[1-(3,5-difluorophenyl)-1,2,4-triazol-3-yl]-2-methyl-6-[4-(oxetan-3-yl)piperazin-1-yl]pyridin-4-amine |
| 2 | 1-(3,5-difluorophenyl)-N-[3-(3-methoxyazetidin-1-yl)-5-methyl-phenyl]-1,2,4-triazol-3-amine |
| 3 | 2-cyclopropyl-N-[1-(3,4-difluorophenyl)-1,2,4-triazol-3-yl]-6-(3,6-dihydro-2H-pyran-4-yl)pyridin-4-amine |
| 4 | 1-[4-[3-[[1-(3,5-difluorophenyl)-1,2,4-triazol-3-yl]amino]-5-(trifluoromethyl)phenyl]piperazin-2-yl]cyclobutanol |
| 5 | N-[3-chloro-5-[4-(oxetan-3-yl)piperazin-1-yl]phenyl]-1-(3,5-difluorophenyl)-1,2,4-triazol-3-amine |
| 6 | 3-methyl-1-[3-methyl-5-[(1-phenyl-1,2,4-triazol-3-yl)amino]phenyl]pyrrolidin-3-ol |
| 7 | N-[3-methyl-5-(6-oxa-2-azaspiro[3.3]heptan-2-yl)phenyl]-1-phenyl-1,2,4-triazol-3-amine |
| 8 | N3-[1-(3,5-difluorophenyl)-1,2,4-triazol-3-yl]-5-methyl-N1-tetrahydrofuran-3-yl-benzene-1,3-diamine |
| 9 | 2-cyclopropyl-6-(1,4-dioxa-8-azaspiro[4.5]decan-8-yl)-N-(1-phenyl-1,2,4-triazol-3-yl)pyridin-4-amine |
| 10 | N-[3,5-di(tetrahydropyran-4-yl)phenyl]-1-phenyl-1,2,4-triazol-3-amine |
| 11 | N-[3-methyl-5-(2-oxa-7-azaspiro[3.5]nonan-7-yl)phenyl]-1-phenyl-1,2,4-triazol-3-amine |
| 12 | methyl 4-[3-methyl-5-[(1-phenyl-1,2,4-triazol-3-yl)amino]phenyl]piperidine-1-carboxylate |
| 13 | N-[3-(4-methylpiperazin-1-yl)-5-(trifluoromethyl)phenyl]-1-(4-pyridyl)-1,2,4-triazol-3-amine |
| 14 | N-[3-ethyl-5-[4-(oxetan-3-yl)piperazin-1-yl]phenyl]-1-(4-fluorophenyl)-1,2,4-triazol-3-amine |
| 15 | N-[3-ethyl-5-(3-morpholinoazetidin-1-yl)phenyl]-1-(3-fluorophenyl)-1,2,4-triazol-3-amine |
| 16 | N-[3-ethyl-5-[4-(oxetan-3-yl)piperazin-1-yl]phenyl]-1-(2-fluoro-4-pyridyl)-1,2,4-triazol-3-amine |
| 17 | N-[3-tert-butyl-5-[4-(oxetan-3-yl)piperazin-1-yl]phenyl]-1-(3,5-difluorophenyl)-1,2,4-triazol-3-amine |
| 18 | N-[3-[3-fluoro-1-(oxetan-3-yl)pyrrolidin-3-yl]-5-methyl-phenyl]-1-phenyl-1,2,4-triazol-3-amine |
| 19 | 1-(3,5-difluorophenyl)-N-[3-(6,8-dihydro-5H-imidazo[1,2-a]pyrazin-7-yl)-5-methyl-phenyl]-1,2,4-triazol-3-amine |
| 20 | N-[3-(4-cyclopropylpiperazin-1-yl)-5-methyl-phenyl]-1-pyrazin-2-yl-1,2,4-triazol-3-amine |

TABLE 2-continued

Compound Names (IUPAC Nomenclature)

| Cmpd Number | IUPAC Name |
|---|---|
| 21 | N-[3-(2,5-dimethylpiperazin-1-yl)-5-methyl-phenyl]-1-phenyl-1,2,4-triazol-3-amine |
| 22 | 2-cyclopropyl-N-[1-(3,4-dimethoxyphenyl)-1,2,4-triazol-3-yl]-6-(4-methyl-1-piperidyl)pyridin-4-amine |
| 23 | 1-(3,5-difluorophenyl)-N-[3-(3-fluoro-1-methyl-pyrrolidin-3-yl)-5-methyl-phenyl]-1,2,4-triazol-3-amine |
| 24 | 1-(5-fluoro-3-pyridyl)-N-[3-methyl-5-[4-(oxetan-3-yl)piperazin-1-yl]phenyl]-1,2,4-triazol-3-amine |
| 25 | 1-(3,5-difluorophenyl)-N-[3-methyl-5-[1-(oxetan-3-yl)pyrrolidin-3-yl]phenyl]-1,2,4-triazol-3-amine |
| 26 | N-[3-(difluoromethyl)-5-[4-(oxetan-3-yl)piperazin-1-yl]phenyl]-1-phenyl-1,2,4-triazol-3-amine |
| 27 | 1-(3-fluorophenyl)-N-(3-methyl-5-morpholino-phenyl)-1,2,4-triazol-3-amine |
| 28 | 1-(2,4-difluorophenyl)-N-[3-fluoro-5-(4-methyl-1,4-diazepan-1-yl)phenyl]-1,2,4-triazol-3-amine |
| 29 | N-[3-[(8aR)-4-isobutyl-3,4,6,7,8,8a-hexahydro-1H-pyrrolo[1,2-a]pyrazin-2-yl]-5-methyl-phenyl]-1-(3,5-difluorophenyl)-1,2,4-triazol-3-amine |
| 30 | 1-(2-methoxypyrimidin-4-yl)-N-[3-methyl-5-[4-(oxetan-3-yl)piperazin-1-yl]phenyl]-1,2,4-triazol-3-amine |
| 31 | N-[3-ethyl-5-[4-(oxetan-3-yl)piperazin-1-yl]phenyl]-1-(p-tolyl)-1,2,4-triazol-3-amine |
| 32 | 1-(3-chloro-5-fluoro-phenyl)-N-[3-methyl-5-[4-(oxetan-3-yl)piperazin-1-yl]phenyl]-1,2,4-triazol-3-amine |
| 33 | 1-(3,5-difluorophenyl)-N-[3-methyl-5-[4-(oxetan-3-yl)piperazin-1-yl]phenyl]-1,2,4-triazol-3-amine |
| 34 | 1-(3,5-difluorophenyl)-N-[3-methyl-5-[(1S,4S)-2-(oxetan-3-yl)-2,5-diazabicyclo[2.2.1]heptan-5-yl]phenyl]-1,2,4-triazol-3-amine |
| 35 | 2-cyclopropyl-N-[1-(3,5-difluorophenyl)-1,2,4-triazol-3-yl]-6-(3,6-dihydro-2H-pyran-4-yl)pyridin-4-amine |
| 36 | 1-(3-fluorophenyl)-N-[3-methyl-5-[1-(oxetan-3-yl)azetidin-3-yl]phenyl]-1,2,4-triazol-3-amine |
| 37 | 1-(3,5-difluorophenyl)-N-[3-methyl-5-(4-methylpiperazin-1-yl)phenyl]-1,2,4-triazol-3-amine |
| 38 | N3-[1-(3,5-difluorophenyl)-1,2,4-triazol-3-yl]-5-methyl-N1-[1-(oxetan-3-yl)-4-piperidyl]benzene-1,3-diamine |
| 39 | N-(3-methyl-5-pyrrolidin-3-yl-phenyl)-1-phenyl-1,2,4-triazol-3-amine |
| 40 | 1-(2-fluoro-4-pyridyl)-N-[3-methyl-5-[4-(oxetan-3-yl)piperazin-1-yl]phenyl]-1,2,4-triazol-3-amine |
| 41 | 1-[3-[2-(ethoxymethyl)pyrrolidin-1-yl]-5-fluoro-phenyl]-N-[3-methyl-5-[4-(oxetan-3-yl)piperazin-1-yl]phenyl]-1,2,4-triazol-3-amine |
| 42 | 1-(2-chloro-4-pyridyl)-N-[3-methyl-5-pyrrolidin-1-yl-phenyl]-1,2,4-triazol-3-amine |
| 43 | 1-(3,4-difluorophenyl)-N-(3-methyl-5-morpholino-phenyl)-1,2,4-triazol-3-amine |
| 44 | 2-cyclopropyl-6-(4-methyl-1-piperidyl)-N-(1-phenyl-1,2,4-triazol-3-yl)pyridin-4-amine |
| 45 | N-(3-methyl-5-morpholino-phenyl)-1-phenyl-1,2,4-triazol-3-amine |
| 46 | 1-(3,4-difluorophenyl)-N-[3-methyl-5-[(3R)-1-(oxetan-3-yl)pyrrolidin-3-yl]oxy-phenyl]-1,2,4-triazol-3-amine |
| 47 | N-[3-cyclopropyl-5-[4-(oxetan-3-yl)piperazin-1-yl]phenyl]-1-phenyl-1,2,4-triazol-3-amine |
| 48 | N-[3-ethyl-5-[4-(oxetan-3-yl)piperazin-1-yl]phenyl]-1-pyrazin-2-yl-1,2,4-triazol-3-amine |
| 49 | N-(3-fluoro-5-morpholino-phenyl)-1-(2-fluorophenyl)-1,2,4-triazol-3-amine |
| 50 | N-[3-ethyl-5-[4-(oxetan-3-yl)piperazin-1-yl]phenyl]-1-(5-fluoropyrimidin-4-yl)-1,2,4-triazol-3-amine |
| 51 | N-[3-[1-[3-(benzenesulfonylmethyl)oxetan-3-yl]-4-piperidyl]-5-methyl-phenyl]-1-phenyl-1,2,4-triazol-3-amine |
| 52 | 1-(3,4-difluorophenyl)-N-[3-methyl-5-[(3S)-1-(oxetan-3-yl)pyrrolidin-3-yl]oxy-phenyl]-1,2,4-triazol-3-amine |
| 53 | [4-[3-[[1-(3,5-difluorophenyl)-1,2,4-triazol-3-yl]amino]-5-methyl-phenyl]-1-methyl-piperazin-2-yl]methanol |
| 54 | N-[3-methyl-5-[4-(oxetan-3-yl)piperazin-1-yl]phenyl]-1-(4-methyl-2-pyridyl)-1,2,4-triazol-3-amine |
| 55 | 1-(3-chlorophenyl)-N-[3-cyclopropyl-5-[4-(oxetan-3-yl)piperazin-1-yl]phenyl]-1,2,4-triazol-3-amine |
| 56 | 1-(3-fluoro-5-methoxy-phenyl)-N-[3-methyl-5-[4-(oxetan-3-yl)piperazin-1-yl]phenyl]-1,2,4-triazol-3-amine |

TABLE 2-continued

Compound Names (IUPAC Nomenclature)

| Cmpd Number | IUPAC Name |
|---|---|
| 57 | (2R)-3-methyl-2-[4-[6-methyl-4-[(1-phenyl-1,2,4-triazol-3-yl)amino]-2-pyridyl]piperazin-2-yl]butan-2-ol |
| 58 | N-[3-ethyl-5-[4-(oxetan-3-yl)piperazin-1-yl]phenyl]-1-(6-methylpyrimidin-4-yl)-1,2,4-triazol-3-amine |
| 59 | [4-[3-methyl-5-[(1-phenyl-1,2,4-triazol-3-yl)amino]phenyl]piperazin-2-yl]methanol |
| 60 | N-[3-methyl-5-(1-methyl-3-piperidyl)phenyl]-1-phenyl-1,2,4-triazol-3-amine |
| 61 | 1-(3,5-difluorophenyl)-N-[3-methyl-5-[1-(oxetan-3-yl)-3,6-dihydro-2H-pyridin-4-yl]phenyl]-1,2,4-triazol-3-amine |
| 62 | N-[3-(difluoromethyl)-5-piperazin-1-yl-phenyl]-1-phenyl-1,2,4-triazol-3-amine |
| 63 | 1-(3,5-difluorophenyl)-N-[3-(4-methylpiperazin-1-yl)-5-(trifluoromethyl)phenyl]-1,2,4-triazol-3-amine |
| 64 | N-[3-methyl-5-[4-(oxetan-3-yl)piperazin-1-yl]phenyl]-1-(2-methylsulfanylpyrimidin-4-yl)-1,2,4-triazol-3-amine |
| 65 | N-[3-methyl-5-[1-(oxetan-3-yl)azetidin-3-yl]phenyl]-1-phenyl-1,2,4-triazol-3-amine |
| 66 | 2,5-difluoro-4-[3-[3-methyl-5-[4-(oxetan-3-yl)piperazin-1-yl]anilino]-1,2,4-triazol-1-yl]benzonitrile |
| 67 | 1-[3-[[1-(3,5-difluorophenyl)-1,2,4-triazol-3-yl]amino]-5-methyl-phenyl]-4-(oxetan-3-yl)piperazin-2-one |
| 68 | N-[3-methyl-5-(4-methylpiperazin-1-yl)phenyl]-1-pyrazin-2-yl-1,2,4-triazol-3-amine |
| 69 | 1-(3,4-difluorophenyl)-N-[3-ethyl-5-[4-(oxetan-3-yl)piperazin-1-yl]phenyl]-1,2,4-triazol-3-amine |
| 70 | N-[3-methyl-5-[4-(oxetan-3-yl)piperazin-1-yl]phenyl]-1-(p-tolyl)-1,2,4-triazol-3-amine |
| 71 | N-[3-methyl-5-[1-(oxetan-3-yl)-4-piperidyl]phenyl]-1-phenyl-1,2,4-triazol-3-amine |
| 72 | ethyl 2-[4-[3-[[1-(3,5-difluorophenyl)-1,2,4-triazol-3-yl]amino]-5-methyl-phenyl]piperazin-1-yl]acetate |
| 73 | N-[3-cyclopropyl-5-[4-(oxetan-3-yl)piperazin-1-yl]phenyl]-1-(3-fluoro-5-methyl-phenyl)-1,2,4-triazol-3-amine |
| 74 | N-[3-methyl-5-[1-(oxetan-3-yl)-3-piperidyl]phenyl]-1-pyrazin-2-yl-1,2,4-triazol-3-amine |
| 75 | N-[3-[4-(3,3-difluorocyclobutyl)piperazin-1-yl]-5-methyl-phenyl]-1-pyrazin-2-yl-1,2,4-triazol-3-amine |
| 76 | 1-methyl-4-[3-methyl-5-[(1-phenyl-1,2,4-triazol-3-yl)amino]phenyl]piperazin-2-one |
| 77 | 1-(3,5-difluorophenyl)-N-(3-methyl-5-piperazin-1-yl-phenyl)-1,2,4-triazol-3-amine |
| 78 | N-[3-[(1S,4S)-2-cyclopropyl-2,5-diazabicyclo[2.2.1]heptan-5-yl]-5-methyl-phenyl]-1-(3,5-difluorophenyl)-1,2,4-triazol-3-amine |
| 79 | 2-[4-[3-[[1-(3,5-difluorophenyl)-1,2,4-triazol-3-yl]amino]-5-methyl-phenyl]piperazin-1-yl]propane-1,3-diol |
| 80 | N-(3-fluoro-5-morpholino-phenyl)-1-phenyl-1,2,4-triazol-3-amine |
| 81 | 4-[3-[3-methyl-5-(4-methylpiperazin-1-yl)anilino]-1,2,4-triazol-1-yl]benzonitrile |
| 82 | N-[3-(difluoromethyl)-5-[4-(oxetan-3-yl)piperazin-1-yl]phenyl]-1-(3,5-difluorophenyl)-1,2,4-triazol-3-amine |
| 83 | 1-(2-fluorophenyl)-N-(3-fluoro-5-pyrrolidin-1-yl-phenyl)-1,2,4-triazol-3-amine |
| 84 | N-(3-methyl-5-morpholino-phenyl)-1-(4-pyridyl)-1,2,4-triazol-3-amine |
| 85 | N-[3-(difluoromethyl)-5-morpholino-phenyl]-1-(2-fluoro-4-pyridyl)-1,2,4-triazol-3-amine |
| 86 | 1-(3-methoxyphenyl)-N-[3-methyl-5-[4-(oxetan-3-yl)piperazin-1-yl]phenyl]-1,2,4-triazol-3-amine |
| 87 | N-[3-(4-cyclopentylpiperazin-1-yl)-5-methyl-phenyl]-1-phenyl-1,2,4-triazol-3-amine |
| 88 | 2-cyclopropyl-N-[1-(3,4-difluorophenyl)-1,2,4-triazol-3-yl]-6-morpholino-pyridin-4-amine |
| 89 | N-[3-(1,1-dioxo-1,4-thiazinan-4-yl)-5-methyl-phenyl]-1-phenyl-1,2,4-triazol-3-amine |
| 90 | 1-[4-[3-[[1-(3,5-difluorophenyl)-1,2,4-triazol-3-yl]amino]-5-methyl-phenyl]-1-piperidyl]ethanone |
| 91 | N-[3-ethyl-5-[4-(oxetan-3-yl)piperazin-1-yl]phenyl]-1-(2-methylpyrimidin-4-yl)-1,2,4-triazol-3-amine |
| 92 | 1-(3,5-difluorophenyl)-N-[3-methyl-5-[(3S)-1-(oxetan-3-yl)pyrrolidin-3-yl]phenyl]-1,2,4-triazol-3-amine |
| 93 | 1-[3-[[1-(3,5-difluorophenyl)-1,2,4-triazol-3-yl]amino]-5-methyl-phenyl]piperazin-2-one |
| 94 | 1-(3-methoxyphenyl)-N-[3-methyl-5-(4-methylpiperazin-1-yl)phenyl]-1,2,4-triazol-3-amine |
| 95 | 1-(3,5-difluorophenyl)-N-[3-methyl-5-[4-(thietan-3-yl)piperazin-1-yl]phenyl]-1,2,4-triazol-3-amine |
| 96 | N-[3-(4-methylpiperazin-1-yl)-5-(trifluoromethyl)phenyl]-1-pyrimidin-4-yl-1,2,4-triazol-3-amine |
| 97 | N-[3-tert-butyl-5-[4-(oxetan-3-yl)piperazin-1-yl]phenyl]-1-(3-fluorophenyl)-1,2,4-triazol-3-amine |
| 98 | N-[3-fluoro-5-(4-methyl-1,4-diazepan-1-yl)phenyl]-1-(3-fluorophenyl)-1,2,4-triazol-3-amine |
| 99 | 1-(3,4-difluorophenyl)-N-(3-fluoro-5-pyrrolidin-1-yl-phenyl)-1,2,4-triazol-3-amine |
| 100 | 2-chloro-N-[1-(3,4-difluorophenyl)-1,2,4-triazol-3-yl]-6-morpholino-pyridin-4-amine |
| 101 | (3S)-3-[3-[[1-(3,5-difluorophenyl)-1,2,4-triazol-3-yl]amino]-5-methyl-phenyl]-1-(oxetan-3-yl)pyrrolidin-3-ol |
| 102 | 1-(4-fluorophenyl)-N-[3-methoxy-5-[4-(oxetan-3-yl)piperazin-1-yl]phenyl]-1,2,4-triazol-3-amine |
| 103 | 1-[3-(2-ethylpyrrolidin-1-yl)-5-fluoro-phenyl]-N-[3-methyl-5-[4-(oxetan-3-yl)piperazin-1-yl]phenyl]-1,2,4-triazol-3-amine |
| 104 | N-[3-methyl-5-[4-(oxetan-3-yl)piperazin-1-yl]phenyl]-1-(2-pyridyl)-1,2,4-triazol-3-amine |
| 105 | 2-cyclopropyl-N-[1-(3,5-difluorophenyl)-1,2,4-triazol-3-yl]-6-[(3R)-3-fluoropyrrolidin-1-yl]pyridin-4-amine |
| 106 | 2-chloro-N-[1-(3-methoxyphenyl)-1,2,4-triazol-3-yl]-6-(1-piperidyl)pyridin-4-amine |
| 107 | 1-(3,5-difluorophenyl)-N-[3-ethyl-5-[4-(oxetan-3-yl)piperazin-1-yl]phenyl]-1,2,4-triazol-3-amine |
| 108 | 1-(3,5-difluorophenyl)-N-[3-methyl-5-(4-piperidyl)phenyl]-1,2,4-triazol-3-amine |
| 109 | N-[3-[3-(dimethylamino)pyrrolidin-1-yl]-5-fluoro-phenyl]-1-(3-fluorophenyl)-1,2,4-triazol-3-amine |
| 110 | N-(3-methyl-5-pyrrolidin-1-yl-phenyl)-1-phenyl-1,2,4-triazol-3-amine |
| 111 | N-[3-methyl-5-[4-(oxetan-3-yl)piperazin-1-yl]phenyl]-1-(6-methylpyrimidin-4-yl)-1,2,4-triazol-3-amine |
| 112 | 1-(3,5-difluorophenyl)-N-[3-fluoro-5-[4-(oxetan-3-yl)piperazin-1-yl]phenyl]-1,2,4-triazol-3-amine |
| 113 | N3-[1-(3,4-difluorophenyl)-1,2,4-triazol-3-yl]-5-methyl-N1-[1-(oxetan-3-yl)pyrrolidin-3-yl]benzene-1,3-diamine |
| 114 | 1-[1-[3-[[1-(3,5-difluorophenyl)-1,2,4-triazol-3-yl]amino]-5-methyl-phenyl]-3-piperidyl]pyrrolidin-2-one |
| 115 | 1-[3-[3-methyl-5-[(1-phenyl-1,2,4-triazol-3-yl)amino]anilino]-1-piperidyl]ethanone |
| 116 | 1-(3,5-difluorophenyl)-N-[3-[3-(methoxymethyl)azetidin-1-yl]-5-methyl-phenyl]-1,2,4-triazol-3-amine |
| 117 | 1-[3-[3-methyl-5-[(1-phenyl-1,2,4-triazol-3-yl)amino]phenyl]-1-piperidyl]ethanone |
| 118 | N-[3-methyl-5-[4-(oxetan-3-yl)piperazin-1-yl]phenyl]-1-phenyl-1,2,4-triazol-3-amine |
| 119 | 1-(3,5-difluorophenyl)-N-[3-(3,4-dimethylpiperazin-1-yl)-5-methyl-phenyl]-1,2,4-triazol-3-amine |
| 120 | N-[3-(1-cyclopropyl-4-piperidyl)-5-methyl-phenyl]-1-phenyl-1,2,4-triazol-3-amine |
| 121 | N-[3-cyclopropyl-5-[4-(oxetan-3-yl)piperazin-1-yl]phenyl]-1-(2,6-difluoro-4-pyridyl)-1,2,4-triazol-3-amine |
| 122 | 1-(2-fluoro-4-pyridyl)-N-[3-[4-(methoxymethyl)-1-piperidyl]-5-methyl-phenyl]-1,2,4-triazol-3-amine |
| 123 | 2-[(2S)-4-[3-[[1-(3,5-difluorophenyl)-1,2,4-triazol-3-yl]amino]-5-(trifluoromethyl)phenyl]piperazin-2-yl]propan-2-ol |
| 124 | N-(3-ethyl-5-piperazin-1-yl-phenyl)-1-pyrazin-2-yl-1,2,4-triazol-3-amine |
| 125 | 2-[4-[3-[[1-(3,5-difluorophenyl)-1,2,4-triazol-3-yl]amino]-5-methyl-phenyl]piperazin-1-yl]acetic acid |
| 127 | N-[3-methyl-5-[4-(2-methyltetrahydrofuran-3-yl)piperazin-1-yl]phenyl]-1-phenyl-1,2,4-triazol-3-amine |
| 128 | N-[3-[(8aR)-3,4,6,7,8,8a-hexahydro-1H-pyrrolo[1,2-a]pyrazin-2-yl]-5-methyl-phenyl]-1-(3,5-difluorophenyl)-1,2,4-triazol-3-amine |
| 129 | N-[3-cyclopropyl-5-[4-(oxetan-3-yl)piperazin-1-yl]phenyl]-1-(2,6-dimethylpyrimidin-4-yl)-1,2,4-triazol-3-amine |
| 130 | 1-(3,5-difluorophenyl)-N-[3-[4-(oxetan-3-yl)piperazin-1-yl]-5-(trifluoromethyl)phenyl]-1,2,4-triazol-3-amine |

TABLE 2-continued

Compound Names (IUPAC Nomenclature)

| Cmpd Number | IUPAC Name |
|---|---|
| 131 | 1-(3,5-difluorophenyl)-N-[3-methyl-5-(oxetan-3-yl)phenyl]-1,2,4-triazol-3-amine |
| 132 | N-[3-ethyl-5-[4-(oxetan-3-yl)piperazin-1-yl]phenyl]-1-(2-methylsulfanylpyrimidin-4-yl)-1,2,4-triazol-3-amine |
| 133 | N-[3-(3,4-dimethylpiperazin-1-yl)-5-methyl-phenyl]-1-phenyl-1,2,4-triazol-3-amine |
| 134 | 1-(5-chloro-3-pyridyl)-N-[3-cyclopropyl-5-[4-(oxetan-3-yl)piperazin-1-yl]phenyl]-1,2,4-triazol-3-amine |
| 135 | 2-chloro-6-morpholino-N-(1-phenyl-1,2,4-triazol-3-yl)pyridin-4-amine |
| 136 | N-[3-methyl-5-[4-(3-methyloxetan-3-yl)piperazin-1-yl]phenyl]-1-pyrazin-2-yl-1,2,4-triazol-3-amine |
| 137 | 1-(3,5-difluorophenyl)-N-[3-methyl-5-(4-tetrahydrofuran-3-ylpiperazin-1-yl)phenyl]-1,2,4-triazol-3-amine |
| 138 | N-[3-methyl-5-(4-methylpiperazin-1-yl)phenyl]-1-(2-pyridyl)-1,2,4-triazol-3-amine |
| 139 | 1-(3,5-difluorophenyl)-N-[3-methyl-5-[4-(oxetan-3-yl)-4-oxido-piperazin-4-ium-1-yl]phenyl]-1,2,4-triazol-3-amine |
| 140 | 2-fluoro-4-[3-[3-methyl-5-[4-(oxetan-3-yl)piperazin-1-yl]anilino]-1,2,4-triazol-1-yl]benzonitrile |
| 141 | 1-(3-chlorophenyl)-N-[3-methyl-5-(4-methylpiperazin-1-yl)phenyl]-1,2,4-triazol-3-amine |
| 142 | 1-[3-methyl-5-[(1-phenyl-1,2,4-triazol-3-yl)amino]phenyl]piperidine-4-carbonitrile |
| 143 | methyl 3-[3-methyl-5-[(1-phenyl-1,2,4-triazol-3-yl)amino]phenyl]piperidine-1-carboxylate |
| 144 | 1-[4-[3-(difluoromethyl)-5-[(1-phenyl-1,2,4-triazol-3-yl)amino]phenyl]piperazin-1-yl]ethanone |
| 145 | 2-chloro-N-[1-(3-methoxyphenyl)-1,2,4-triazol-3-yl]-6-morpholino-pyridin-4-amine |
| 146 | 1-[3-methyl-5-[(1-phenyl-1,2,4-triazol-3-yl)amino]phenyl]piperidine-3-carbonitrile |
| 147 | 1-(3-fluorophenyl)-N-[3-methyl-5-(oxetan-3-yl)phenyl]-1,2,4-triazol-3-amine |
| 148 | N-[3-[4-(2-methoxyethyl)-1-piperidyl]-5-methyl-phenyl]-1-phenyl-1,2,4-triazol-3-amine |
| 149 | N-[3-(4-cyclopropylpiperazin-1-yl)-5-methyl-phenyl]-1-phenyl-1,2,4-triazol-3-amine |
| 150 | 2-cyclopropyl-N-[1-(3,4-difluorophenyl)-1,2,4-triazol-3-yl]-6-tetrahydropyran-4-yl-pyridin-4-amine |
| 151 | 1-(3,5-difluorophenyl)-N-[3-methyl-5-(1-methyl-4-piperidyl)phenyl]-1,2,4-triazol-3-amine |
| 152 | N-[3-[(8aR)-4-isobutyl-3,4,6,7,8,8a-hexahydro-1H-pyrrolo[1,2-a]pyrazin-2-yl]-5-methyl-phenyl]-1-phenyl-1,2,4-triazol-3-amine |
| 153 | N-[3-(4-cyclopropylpiperazin-1-yl)-5-(difluoromethyl)phenyl]-1-(2-fluoro-4-pyridyl)-1,2,4-triazol-3-amine |
| 154 | 1-(6-fluoro-2-pyridyl)-N-[3-methyl-5-[4-(oxetan-3-yl)piperazin-1-yl]phenyl]-1,2,4-triazol-3-amine |
| 155 | 4-[3-(3-methyl-5-morpholino-anilino)-1,2,4-triazol-1-yl]pyridin-2-ol |
| 156 | 2-methyl-6-(4-methylpiperazin-1-yl)-N-(1-phenyl-1,2,4-triazol-3-yl)pyridin-4-amine |
| 157 | N-[3-[(8aR)-3,4,6,7,8,8a-hexahydro-1H-pyrrolo[1,2-a]pyrazin-2-yl]-5-methyl-phenyl]-1-phenyl-1,2,4-triazol-3-amine |
| 158 | N-(3-fluoro-5-morpholino-phenyl)-1-(3-fluorophenyl)-1,2,4-triazol-3-amine |
| 159 | N-(3-methyl-5-piperazin-1-yl-phenyl)-1-phenyl-1,2,4-triazol-3-amine |
| 160 | N-[3-methyl-5-[1-(oxetan-3-yl)-2,5-dihydropyrrol-3-yl]phenyl]-1-phenyl-1,2,4-triazol-3-amine |
| 161 | 1-[1-[3-[[1-(3,5-difluorophenyl)-1,2,4-triazol-3-yl]amino]-5-methyl-phenyl]-4-piperidyl]pyrrolidin-2-one |
| 162 | 1-(3,5-difluorophenyl)-N-[3-[4-(methoxymethyl)-1-piperidyl]-5-methyl-phenyl]-1,2,4-triazol-3-amine |
| 163 | 4-[3-[3-(difluoromethyl)-5-[4-(oxetan-3-yl)piperazin-1-yl]anilino]-1,2,4-triazol-1-yl]-1H-pyridin-2-one |
| 164 | 1-(3,5-difluorophenyl)-N-[3-(3-methoxypyrrolidin-1-yl)-5-methyl-phenyl]-1,2,4-triazol-3-amine |
| 165 | N-(3-morpholino-5-tetrahydrofuran-3-yl-phenyl)-1-phenyl-1,2,4-triazol-3-amine |
| 166 | N-[3-fluoro-5-(1,4-oxazepan-4-yl)phenyl]-1-(3-fluorophenyl)-1,2,4-triazol-3-amine |
| 167 | 1-(4-fluorophenyl)-N-(3-fluoro-5-pyrrolidin-1-yl-phenyl)-1,2,4-triazol-3-amine |
| 168 | N-(3-bromo-5-morpholino-phenyl)-1-phenyl-1,2,4-triazol-3-amine |
| 169 | 1-(3,4-difluorophenyl)-N-[3-methyl-5-[4-(oxetan-3-yl)-1-piperidyl]phenyl]-1,2,4-triazol-3-amine |
| 170 | 2-cyclopropyl-N-[1-(3,5-difluorophenyl)-1,2,4-triazol-3-yl]-6-pyrrolidin-1-yl-pyridin-4-amine |
| 171 | 1-(3,5-difluorophenyl)-N-[3-methyl-5-(6-oxa-2-azaspiro[3.3]heptan-2-yl)phenyl]-1,2,4-triazol-3-amine |
| 172 | N-[3-methyl-5-(4-tetrahydropyran-3-ylpiperazin-1-yl)phenyl]-1-phenyl-1,2,4-triazol-3-amine |
| 173 | 1-(3,5-difluorophenyl)-N-[3-ethyl-5-(3-morpholinoazetidin-1-yl)phenyl]-1,2,4-triazol-3-amine |
| 174 | N-[3-methyl-5-[4-(oxetan-3-yl)piperazin-1-yl]phenyl]-1-pyrimidin-4-yl-1,2,4-triazol-3-amine |
| 175 | 1-(3-fluorophenyl)-N-[3-[4-(oxetan-3-yl)piperazin-1-yl]-5-(trifluoromethyl)phenyl]-1,2,4-triazol-3-amine |
| 176 | N-[3-(4-cyclopropylpiperazin-1-yl)-5-methyl-phenyl]-1-pyrimidin-4-yl-1,2,4-triazol-3-amine |
| 177 | N1-(azetidin-3-yl)-N3-[1-(2,4-difluorophenyl)-1,2,4-triazol-3-yl]-5-fluoro-benzene-1,3-diamine |
| 178 | 1-(3,5-difluorophenyl)-N-[3-methyl-5-[(3R)-1-(oxetan-3-yl)pyrrolidin-3-yl]oxy-phenyl]-1,2,4-triazol-3-amine |
| 179 | N-[3-methyl-5-(4-methyl-1,4-diazepan-1-yl)phenyl]-1-phenyl-1,2,4-triazol-3-amine |
| 180 | N-[3-methyl-5-[1-(oxetan-3-yl)-3-piperidyl]phenyl]-1-pyrimidin-4-yl-1,2,4-triazol-3-amine |
| 181 | N-(3-fluoro-5-morpholino-phenyl)-1-[3-(trifluoromethyl)phenyl]-1,2,4-triazol-3-amine |
| 182 | N1-[1-(3-methoxypropyl)-4-piperidyl]-5-methyl-N3-(1-phenyl-1,2,4-triazol-3-yl)benzene-1,3-diamine |
| 183 | 1-(3,4-difluorophenyl)-N-[3-methoxy-5-[4-(oxetan-3-yl)piperazin-1-yl]phenyl]-1,2,4-triazol-3-amine |
| 184 | N-[3-cyclopropyl-5-[4-(oxetan-3-yl)piperazin-1-yl]phenyl]-1-(2-fluoro-4-pyridyl)-1,2,4-triazol-3-amine |
| 185 | 1-(3,5-difluorophenyl)-N-[3-methyl-5-[(1R,4R)-2-(oxetan-3-yl)-2,5-diazabicyclo[2.2.1]heptan-5-yl]phenyl]-1,2,4-triazol-3-amine |
| 186 | 4-[3-(3-methyl-5-pyrrolidin-1-yl-anilino)-1,2,4-triazol-1-yl]benzonitrile |
| 187 | 1-[3-[[ethyl(methyl)amino]methyl]-5-fluoro-phenyl]-N-[3-methyl-5-[4-(oxetan-3-yl)piperazin-1-yl]phenyl]-1,2,4-triazol-3-amine |
| 188 | N3-[1-(3-fluorophenyl)-1,2,4-triazol-3-yl]-5-methyl-N1-[1-(oxetan-3-yl)pyrrolidin-3-yl]benzene-1,3-diamine |
| 189 | N-[3-(difluoromethyl)-5-[4-(oxetan-3-yl)piperazin-1-yl]phenyl]-1-(2-fluoro-4-pyridyl)-1,2,4-triazol-3-amine |
| 190 | N-(3-methyl-5-pyrrolidin-1-yl-phenyl)-1-[3-(trifluoromethyl)phenyl]-1,2,4-triazol-3-amine |
| 191 | N-[3-methyl-5-[4-(oxetan-3-yl)piperazin-1-yl]phenyl]-1-[4-(trifluoromethyl)phenyl]-1,2,4-triazol-3-amine |
| 192 | N3-[1-(3,5-difluorophenyl)-1,2,4-triazol-3-yl]-5-methyl-N1-[1-(oxetan-3-yl)-4-piperidyl]benzene-1,3-diamine |
| 193 | 1-(3,5-difluorophenyl)-N-[3-[3-fluoro-1-(oxetan-3-yl)pyrrolidin-3-yl]-5-methyl-phenyl]-1,2,4-triazol-3-amine |
| 194 | 1-[4-[3-methyl-5-[(1-phenyl-1,2,4-triazol-3-yl)amino]phenyl]-1-piperidyl]ethanone |
| 195 | N-[3-methyl-5-[4-(oxetan-3-yl)piperazin-1-yl]phenyl]-1-pyrazin-2-yl-1,2,4-triazol-3-amine |
| 196 | ethyl 4-[3-[[1-(3,5-difluorophenyl)-1,2,4-triazol-3-yl]amino]-5-methyl-phenyl]piperazine-1-carboxylate |
| 197 | N3-[1-(3,5-difluorophenyl)-1,2,4-triazol-3-yl]-N1,5-dimethyl-N1-(oxetan-3-yl)benzene-1,3-diamine |
| 198 | 1-(3,4-difluorophenyl)-N-[3-ethyl-5-(3-morpholinoazetidin-1-yl)phenyl]-1,2,4-triazol-3-amine |
| 199 | 1-(3,5-difluorophenyl)-N-[3-methyl-5-(4-tetrahydropyran-3-ylpiperazin-1-yl)phenyl]-1,2,4-triazol-3-amine |
| 200 | 7-[3-[[1-(3,5-difluorophenyl)-1,2,4-triazol-3-yl]amino]-5-methyl-phenyl]-5,6,8,8a-tetrahydro-1H-oxazolo[3,4-a]pyrazin-3-one |
| 201 | 1-(4-fluorophenyl)-N-[3-methyl-5-[[1-(oxetan-3-yl)-4-piperidyl]oxy]phenyl]-1,2,4-triazol-3-amine |
| 202 | 2-cyclopropyl-N-[1-(3,4-difluorophenyl)-1,2,4-triazol-3-yl]-6-(4-methyl-1-piperidyl)pyridin-4-amine |

TABLE 2-continued

Compound Names (IUPAC Nomenclature)

| Cmpd Number | IUPAC Name |
|---|---|
| 203 | N-[3-fluoro-5-(4-methylpiperazin-1-yl)phenyl]-1-(3-fluorophenyl)-1,2,4-triazol-3-amine |
| 204 | 1-(2-ethoxypyrimidin-4-yl)-N-[3-methyl-5-[4-(oxetan-3-yl)piperazin-1-yl]phenyl]-1,2,4-triazol-3-amine |
| 205 | 1-(3-fluoro-5-isopropoxy-phenyl)-N-[3-methyl-5-(4-methylpiperazin-1-yl)phenyl]-1,2,4-triazol-3-amine |
| 206 | 1-(3-ethyl-5-fluoro-phenyl)-N-[3-methyl-5-[4-(oxetan-3-yl)piperazin-1-yl]phenyl]-1,2,4-triazol-3-amine |
| 207 | N-[3-methyl-5-[1-(oxetan-3-yl)-3-piperidyl]phenyl]-1-(2-pyridyl)-1,2,4-triazol-3-amine |
| 208 | 1-(3,5-difluorophenyl)-N-[3-[(3S,4R)-3-fluoro-1-(oxetan-3-yl)-4-piperidyl]-5-methyl-phenyl]-1,2,4-triazol-3-amine; 1-(3,5-difluorophenyl)-N-[3-[(3R,4S)-3-fluoro-1-(oxetan-3-yl)-4-piperidyl]-5-methyl-phenyl]-1,2,4-triazol-3-amine |
| 209 | N-[3-(difluoromethyl)-5-[4-(oxetan-3-yl)piperazin-1-yl]phenyl]-1-(3-pyridyl)-1,2,4-triazol-3-amine |
| 210 | 2-cyclopropyl-N-[1-(3,5-dimethoxyphenyl)-1,2,4-triazol-3-yl]-6-morpholino-pyridin-4-amine |
| 211 | N-[3-[4-(methoxymethyl)-1-piperidyl]-5-methyl-phenyl]-1-(2-pyridyl)-1,2,4-triazol-3-amine |
| 212 | 2-[3-(3-methyl-5-pyrrolidin-1-yl-anilino)-1,2,4-triazol-1-yl]benzonitrile |
| 213 | N-[3-fluoro-5-(4-methylpiperazin-1-yl)phenyl]-1-phenyl-1,2,4-triazol-3-amine |
| 214 | 1-cyclopropyl-4-[3-methyl-5-[(1-phenyl-1,2,4-triazol-3-yl)amino]phenyl]piperazin-2-one |
| 215 | 1-(3,5-difluorophenyl)-N-[3-methyl-5-[4-(3-methyloxetan-3-yl)piperazin-1-yl]phenyl]-1,2,4-triazol-3-amine |
| 216 | 1-(3,5-difluorophenyl)-N-[3-methyl-5-[4-(oxetan-3-yl)-1-piperidyl]phenyl]-1,2,4-triazol-3-amine |
| 217 | 1-(5-chloro-3-pyridyl)-N-[3-methyl-5-[4-(oxetan-3-yl)piperazin-1-yl]phenyl]-1,2,4-triazol-3-amine |
| 218 | N-[3-ethyl-5-[4-(oxetan-3-yl)piperazin-1-yl]phenyl]-1-[3-(trifluoromethyl)phenyl]-1,2,4-triazol-3-amine |
| 219 | N-[3-methyl-5-[(1S,4S)-2-(oxetan-3-yl)-2,5-diazabicyclo[2.2.1]heptan-5-yl]phenyl]-1-phenyl-1,2,4-triazol-3-amine |
| 220 | 1-(3-chloro-5-fluoro-phenyl)-N-[3-methyl-5-(4-methylpiperazin-1-yl)phenyl]-1,2,4-triazol-3-amine |
| 221 | 1-(3,5-difluorophenyl)-N-[3-methyl-5-[1-(oxetan-3-yl)-4-piperidyl]phenyl]-1,2,4-triazol-3-amine |
| 222 | 2-cyclopropyl-6-morpholino-N-(1-phenyl-1,2,4-triazol-3-yl)pyridin-4-amine |
| 223 | 1-(2-fluorophenyl)-N-[3-methyl-5-[4-(oxetan-3-yl)piperazin-1-yl]phenyl]-1,2,4-triazol-3-amine |
| 224 | N-[3-methyl-5-[4-(oxetan-3-yl)piperazin-1-yl]phenyl]-1-(4-pyridyl)-1,2,4-triazol-3-amine |
| 225 | N-[3-cyclopropyl-5-[4-(oxetan-3-yl)piperazin-1-yl]phenyl]-1-(2-fluorophenyl)-1,2,4-triazol-3-amine |
| 226 | 1-(2-fluoro-4-pyridyl)-N-[3-(4-methylpiperazin-1-yl)-5-(trifluoromethyl)phenyl]-1,2,4-triazol-3-amine |
| 227 | 7-[3-methyl-5-[(1-phenyl-1,2,4-triazol-3-yl)amino]phenyl]-5,6,8,8a-tetrahydro-1H-oxazolo[3,4-a]pyrazin-3-one |
| 228 | 1-(3,5-difluorophenyl)-N-[3-[4-(1,1-dioxothietan-3-yl)piperazin-1-yl]-5-methyl-phenyl]-1,2,4-triazol-3-amine |
| 229 | 1-(3,5-difluorophenyl)-N-[3-methyl-5-[1-(oxetan-3-yl)azetidin-3-yl]phenyl]-1,2,4-triazol-3-amine |
| 230 | N-[3-methyl-5-[1-(oxetan-3-yl)pyrrolidin-3-yl]phenyl]-1-(3-fluorophenyl)-1,2,4-triazol-3-amine |
| 231 | 1-(3,4-difluorophenyl)-N-[3-methyl-5-[4-(2,2,2-trifluoroethyl)piperazin-1-yl]phenyl]-1,2,4-triazol-3-amine |
| 232 | 1-(2,6-difluoro-4-pyridyl)-N-[3-methyl-5-[4-(oxetan-3-yl)piperazin-1-yl]phenyl]-1,2,4-triazol-3-amine |
| 233 | 1-[2-(methoxymethyl)phenyl]-N-[3-methyl-5-[4-(oxetan-3-yl)piperazin-1-yl]phenyl]-1,2,4-triazol-3-amine |
| 234 | N-[3,5-bis(2,5-dihydrofuran-3-yl)phenyl]-1-phenyl-1,2,4-triazol-3-amine |
| 235 | N-[3-[3,3-difluoro-1-(oxetan-3-yl)-4-piperidyl]-5-methyl-phenyl]-1-(3,5-difluorophenyl)-1,2,4-triazol-3-amine |
| 236 | N-[3-[4-(oxetan-3-yl)-1-piperidyl]-5-propyl-phenyl]-1-pyrazin-2-yl-1,2,4-triazol-3-amine |
| 237 | N-[2,3-dimethyl-5-[4-(oxetan-3-yl)piperazin-1-yl]phenyl]-1-phenyl-1,2,4-triazol-3-amine |
| 238 | 1-[3-[[1-(3,5-difluorophenyl)-1,2,4-triazol-3-yl]amino]-5-methyl-phenyl]piperidin-4-ol |
| 239 | N-[3-methyl-5-[(3S)-1-(oxetan-3-yl)pyrrolidin-3-yl]oxy-phenyl]-1-phenyl-1,2,4-triazol-3-amine |
| 240 | N3-[1-(3,5-difluorophenyl)-1,2,4-triazol-3-yl]-5-methyl-N1-(oxetan-3-yl)benzene-1,3-diamine |
| 241 | N-(3-fluoro-5-pyrrolidin-1-yl-phenyl)-1-[3-(trifluoromethyl)phenyl]-1,2,4-triazol-3-amine |
| 242 | 3-[3-[[1-(3,5-difluorophenyl)-1,2,4-triazol-3-yl]amino]-5-methyl-phenyl]-1-methyl-pyrrolidin-3-ol |
| 243 | 1-(3,5-difluorophenyl)-N-[3-methyl-5-(4-tetrahydropyran-4-ylpiperazin-1-yl)phenyl]-1,2,4-triazol-3-amine |
| 244 | 2-cyclopropyl-N-[1-(3,5-difluorophenyl)-1,2,4-triazol-3-yl]-6-(4-methyl-1-piperidyl)pyridin-4-amine |
| 245 | 2-cyclopropyl-N-[1-(3,5-dimethoxyphenyl)-1,2,4-triazol-3-yl]-6-[(3R)-3-fluoropyrrolidin-1-yl]pyridin-4-amine |
| 246 | N-[3-chloro-5-[4-(methoxymethyl)-1-piperidyl]phenyl]-1-phenyl-1,2,4-triazol-3-amine |
| 247 | N-[3-methyl-5-(4-methylpiperazin-1-yl)phenyl]-1-phenyl-1,2,4-triazol-3-amine |
| 248 | N-[3-methyl-5-[1-(oxetan-3-yl)-3-piperidyl]phenyl]-1-phenyl-1,2,4-triazol-3-amine |
| 249 | N3-[1-(2-fluoro-4-pyridyl)-1,2,4-triazol-3-yl]-5-methyl-N1-[1-(oxetan-3-yl)pyrrolidin-3-yl]benzene-1,3-diamine |
| 250 | N-[3,5-di(tetrahydropyran-4-yl)phenyl]-1-(3-pyridyl)-1,2,4-triazol-3-amine |
| 251 | N-(3-morpholino-5-tetrahydropyran-4-yl-phenyl)-1-phenyl-1,2,4-triazol-3-amine |
| 252 | N-[3-methyl-5-[4-(oxetan-3-yl)piperazin-1-yl]phenyl]-1-[3-(trifluoromethoxy)phenyl]-1,2,4-triazol-3-amine |
| 253 | N-[3-[4-(2-methoxyethyl)piperazin-1-yl]-5-methyl-phenyl]-1-phenyl-1,2,4-triazol-3-amine |
| 254 | 1-(6-methoxypyrimidin-4-yl)-N-[3-methyl-5-[4-(oxetan-3-yl)piperazin-1-yl]phenyl]-1,2,4-triazol-3-amine |
| 255 | 1-(3-ethyl-5-fluoro-phenyl)-N-[3-methyl-5-(4-methylpiperazin-1-yl)phenyl]-1,2,4-triazol-3-amine |
| 257 | 1-(3-fluorophenyl)-N-[3-(4-methylpiperazin-1-yl)-5-(trifluoromethyl)phenyl]-1,2,4-triazol-3-amine |
| 258 | 1-(3-fluorophenyl)-N-[3-methoxy-5-[4-(oxetan-3-yl)piperazin-1-yl]phenyl]-1,2,4-triazol-3-amine |
| 259 | N-[3-methyl-5-(3-methylpiperazin-1-yl)phenyl]-1-phenyl-1,2,4-triazol-3-amine |
| 260 | N-[3-methyl-5-[1-(oxetan-3-yl)pyrrolidin-3-yl]phenyl]-1-phenyl-1,2,4-triazol-3-amine |
| 261 | N-[3-(1-cyclopropyl-4-piperidyl)-5-methyl-phenyl]-1-(3,5-difluorophenyl)-1,2,4-triazol-3-amine |
| 262 | 1-(5-chloro-3-pyridyl)-N-[3-methyl-5-(4-methylpiperazin-1-yl)phenyl]-1,2,4-triazol-3-amine |
| 263 | N-[1-(3,4-difluorophenyl)-1,2,4-triazol-3-yl]-2-methyl-6-(4-methylpiperazin-1-yl)pyridin-4-amine |
| 264 | 1-(3,5-difluorophenyl)-N-[3-ethyl-5-[4-(3-methyloxetan-3-yl)piperazin-1-yl]phenyl]-1,2,4-triazol-3-amine |
| 265 | N-[1-(3,4-difluorophenyl)-1,2,4-triazol-3-yl]-2-methyl-6-morpholino-pyridin-4-amine |
| 266 | 1-[3-[3-[[1-(3,5-difluorophenyl)-1,2,4-triazol-3-yl]amino]-5-methyl-phenyl]-1-piperidyl]ethanone |
| 267 | 1-(3,5-difluorophenyl)-N-[3-methyl-5-[3-(methylamino)pyrrolidin-1-yl]phenyl]-1,2,4-triazol-3-amine |
| 268 | 1-(3,5-difluorophenyl)-N-[3-fluoro-5-[1-(oxetan-3-yl)pyrrolidin-3-yl]phenyl]-1,2,4-triazol-3-amine |
| 269 | 1-(4-fluorophenyl)-N-(3-methyl-5-pyrrolidin-1-yl-phenyl)-1,2,4-triazol-3-amine |
| 270 | N-[3-methyl-5-(oxetan-3-yl)phenyl]-1-(3-pyridyl)-1,2,4-triazol-3-amine |
| 271 | N-[3-methyl-5-[4-(oxetan-3-yl)piperazin-1-yl]phenyl]-1-(6-methylpyrazin-2-yl)-1,2,4-triazol-3-amine |
| 272 | 1-(3-fluorophenyl)-N-(3-methyl-5-pyrrolidin-1-yl-phenyl)-1,2,4-triazol-3-amine |
| 273 | N-[3-[1-(2,2-difluoroethyl)pyrrolidin-3-yl]-5-methyl-phenyl]-1-phenyl-1,2,4-triazol-3-amine |
| 274 | N-[3-(4-ethylpiperazin-1-yl)-5-methyl-phenyl]-1-phenyl-1,2,4-triazol-3-amine |
| 275 | N-[3-methyl-5-[4-(oxetan-3-yl)piperazin-1-yl]phenyl]-1-(3-pyridyl)-1,2,4-triazol-3-amine |
| 276 | 1-(2,3-difluorophenyl)-N-[3-ethyl-5-[4-(oxetan-3-yl)piperazin-1-yl]phenyl]-1,2,4-triazol-3-amine |

TABLE 2-continued

Compound Names (IUPAC Nomenclature)

| Cmpd Number | IUPAC Name |
|---|---|
| 277 | N-[3-cyclopropyl-5-[4-(oxetan-3-yl)piperazin-1-yl]phenyl]-1-(2-methoxypyrimidin-4-yl)-1,2,4-triazol-3-amine |
| 278 | N3-[1-(3,4-difluorophenyl)-1,2,4-triazol-3-yl]-5-methyl-N1-[1-(oxetan-3-yl)-4-piperidyl]benzene-1,3-diamine |
| 279 | 1-(3,5-difluorophenyl)-N-[3-methyl-5-(2-oxa-7-azaspiro[3.5]nonan-7-yl)phenyl]-1,2,4-triazol-3-amine |
| 280 | 1-[4-[3-methyl-5-[(1-phenyl-1,2,4-triazol-3-yl)amino]phenyl]-1,4-diazepan-1-yl]ethanone |
| 281 | 3-[3-(3-methyl-5-pyrrolidin-1-yl-anilino)-1,2,4-triazol-1-yl]benzonitrile |
| 282 | (3R,4R)-4-[3-[[1-(3,5-difluorophenyl)-1,2,4-triazol-3-yl]amino]-5-methyl-phenyl]-1-(oxetan-3-yl)piperidin-3-ol; (3S,4S)-4-[3-[[1-(3,5-difluorophenyl)-1,2,4-triazol-3-yl]amino]-5-methyl-phenyl]-1-(oxetan-3-yl)piperidin-3-ol |
| 283 | N-[3-(3-aminoazetidin-1-yl)-5-fluoro-phenyl]-1-(2,4-difluorophenyl)-1,2,4-triazol-3-amine |
| 284 | 1-(3,5-difluorophenyl)-N-[3-methyl-5-(3-morpholinopyrrolidin-1-yl)phenyl]-1,2,4-triazol-3-amine |
| 285 | N-[3-cyclopropyl-5-[4-(oxetan-3-yl)piperazin-1-yl]phenyl]-1-(3-fluoro-5-isopropoxy-phenyl)-1,2,4-triazol-3-amine |
| 286 | N-[3-cyclopropyl-5-[4-(oxetan-3-yl)piperazin-1-yl]phenyl]-1-(2-ethoxypyrimidin-4-yl)-1,2,4-triazol-3-amine |
| 287 | N-[3-methyl-5-[4-(oxetan-3-yl)piperazin-1-yl]phenyl]-1-[3-(trifluoromethyl)phenyl]-1,2,4-triazol-3-amine |
| 288 | N-[3-tert-butyl-5-[4-(oxetan-3-yl)piperazin-1-yl]phenyl]-1-pyrazin-2-yl-1,2,4-triazol-3-amine |
| 289 | N-[3-methyl-5-(4-tetrahydropyran-4-ylpiperazin-1-yl)phenyl]-1-phenyl-1,2,4-triazol-3-amine |
| 290 | N-[3-(4-cyclobutylpiperazin-1-yl)-5-methyl-phenyl]-1-phenyl-1,2,4-triazol-3-amine |
| 291 | 1-(5-fluoropyrimidin-4-yl)-N-[3-methyl-5-[4-(oxetan-3-yl)piperazin-1-yl]phenyl]-1,2,4-triazol-3-amine |
| 292 | N-[3-[(1S,4S)-2-cyclopropyl-2,5-diazabicyclo[2.2.1]heptan-5-yl]-5-methyl-phenyl]-1-phenyl-1,2,4-triazol-3-amine |
| 293 | 1-(3,5-difluorophenyl)-N-[3-(3-methoxy-1-piperidyl)-5-methyl-phenyl]-1,2,4-triazol-3-amine |
| 294 | N-[3-methyl-5-[1-(3-methyloxetan-3-yl)-4-piperidyl]phenyl]-1-phenyl-1,2,4-triazol-3-amine |
| 295 | 5-[3-[[1-(3,5-difluorophenyl)-1,2,4-triazol-3-yl]amino]-5-methyl-phenyl]oxazolidin-2-one |
| 296 | 2-cyclopropyl-6-[(3R)-3-fluoropyrrolidin-1-yl]-N-(1-phenyl-1,2,4-triazol-3-yl)pyridin-4-amine |
| 297 | N-[3-methyl-5-(4-methylpiperazin-1-yl)phenyl]-1-(3-pyridyl)-1,2,4-triazol-3-amine |
| 298 | 1-(3,5-difluorophenyl)-N-[3-(2,5-dihydrofuran-3-yl)-5-morpholino-phenyl]-1,2,4-triazol-3-amine |
| 299 | 1-(3,4-difluorophenyl)-N-[3-[4-(methoxymethyl)-1-piperidyl]-5-methyl-phenyl]-1,2,4-triazol-3-amine |
| 300 | 1-[3-[3-methyl-5-[(1-pyrazin-2-yl-1,2,4-triazol-3-yl)amino]phenyl]-1-piperidyl]ethanone |
| 301 | 1-(3,4-difluorophenyl)-N-[3-methyl-5-[1-(oxetan-3-yl)azetidin-3-yl]phenyl]-1,2,4-triazol-3-amine |
| 302 | N-[3-cyclopropyl-5-[4-(oxetan-3-yl)piperazin-1-yl]phenyl]-1-(6-methylpyrimidin-4-yl)-1,2,4-triazol-3-amine |
| 303 | N-[3-ethyl-5-[4-(oxetan-3-yl)piperazin-1-yl]phenyl]-1-[4-(trifluoromethoxy)phenyl]-1,2,4-triazol-3-amine |
| 304 | 1-(3,5-difluorophenyl)-N-[3-methyl-5-[(3S)-1-(oxetan-3-yl)pyrrolidin-3-yl]oxy-phenyl]-1,2,4-triazol-3-amine |
| 305 | N-(3-cyclopropyl-5-morpholino-phenyl)-1-phenyl-1,2,4-triazol-3-amine |
| 306 | N-[3-(2,6-dimethylmorpholin-4-yl)-5-methyl-phenyl]-1-phenyl-1,2,4-triazol-3-amine |
| 307 | N-(2-fluoro-3-methyl-5-morpholino-phenyl)-1-(2-pyridyl)-1,2,4-triazol-3-amine |
| 308 | N-[3-methyl-5-(4-piperidyl)phenyl]-1-phenyl-1,2,4-triazol-3-amine |
| 309 | 5-methyl-N1-[1-(oxetan-3-yl)pyrrolidin-3-yl]-N3-(1-phenyl-1,2,4-triazol-3-yl)benzene-1,3-diamine |
| 310 | 1-(3,5-difluorophenyl)-N-[3-methoxy-5-[4-(oxetan-3-yl)piperazin-1-yl]phenyl]-1,2,4-triazol-3-amine |
| 311 | 2-[4-[3-[[1-(3,5-difluorophenyl)-1,2,4-triazol-3-yl]amino]-5-methyl-phenyl]piperazin-1-yl]-2-methyl-propane-1,3-diol |
| 312 | 1-(2,6-dimethylpyrimidin-4-yl)-N-[3-methyl-5-[4-(oxetan-3-yl)piperazin-1-yl]phenyl]-1,2,4-triazol-3-amine |
| 313 | 1-(3,5-difluorophenyl)-N-[3-(oxetan-3-yl)-5-[4-(oxetan-3-yl)piperazin-1-yl]phenyl]-1,2,4-triazol-3-amine |
| 314 | N-[3-ethyl-5-[4-(oxetan-3-yl)piperazin-1-yl]phenyl]-1-(2-methoxypyrimidin-4-yl)-1,2,4-triazol-3-amine |
| 315 | N-[3,5-bis(3,6-dihydro-2H-pyran-4-yl)phenyl]-1-phenyl-1,2,4-triazol-3-amine |
| 316 | N-[3-methyl-5-(3-piperidyl)phenyl]-1-phenyl-1,2,4-triazol-3-amine |
| 317 | 1-(3,4-difluorophenyl)-N-[3-methyl-5-(4-methylpiperazin-1-yl)phenyl]-1,2,4-triazol-3-amine |
| 318 | 2-[(3R)-1-[3-fluoro-5-[3-[3-methyl-5-[4-(oxetan-3-yl)piperazin-1-yl]anilino]-1,2,4-triazol-1-yl]phenyl]pyrrolidin-3-yl]propan-2-ol |
| 319 | 2,6-dimorpholino-N-(1-phenyl-1,2,4-triazol-3-yl)pyridin-4-amine |
| 320 | 1-(5-fluoro-3-pyridyl)-N-(3-methyl-5-pyrrolidin-1-yl-phenyl)-1,2,4-triazol-3-amine |
| 321 | 1-(2,4-difluorophenyl)-N-(3-fluoro-5-morpholino-phenyl)-1,2,4-triazol-3-amine |
| 322 | N-[3-ethyl-5-[4-(oxetan-3-yl)piperazin-1-yl]phenyl]-1-[4-(trifluoromethyl)phenyl]-1,2,4-triazol-3-amine |
| 323 | 1-(3-fluoro-5-methyl-phenyl)-N-[3-methyl-5-[4-(oxetan-3-yl)piperazin-1-yl]phenyl]-1,2,4-triazol-3-amine |
| 324 | 1-(3,5-difluorophenyl)-N-[3-methyl-5-(4-morpholino-1-piperidyl)phenyl]-1,2,4-triazol-3-amine |
| 325 | 1-(3,5-difluorophenyl)-N-[3-[2-(methoxymethyl)morpholin-4-yl]-5-methyl-phenyl]-1,2,4-triazol-3-amine |
| 326 | N-[3-(4-isopropylpiperazin-1-yl)-5-methyl-phenyl]-1-phenyl-1,2,4-triazol-3-amine |
| 327 | 2-cyclopropyl-N-[1-(3,4-difluorophenyl)-1,2,4-triazol-3-yl]-6-(1-piperidyl)pyridin-4-amine |
| 328 | 1-(3,5-difluorophenyl)-N-[3-methyl-5-(1-methyl-3-piperidyl)phenyl]-1,2,4-triazol-3-amine |
| 329 | 1-(4,6-difluoro-2-pyridyl)-N-[3-methyl-5-[4-(oxetan-3-yl)piperazin-1-yl]phenyl]-1,2,4-triazol-3-amine |
| 330 | N-[3-ethyl-5-[4-(oxetan-3-yl)piperazin-1-yl]phenyl]-1-phenyl-1,2,4-triazol-3-amine |
| 331 | N-[1-(3,5-difluorophenyl)-1,2,4-triazol-3-yl]-4-methyl-6-[4-(oxetan-3-yl)piperazin-1-yl]pyridin-2-amine |
| 332 | 2-cyclopropyl-N-[1-(3,5-difluorophenyl)-1,2,4-triazol-3-yl]-6-[(3S)-3-fluoropyrrolidin-1-yl]pyridin-4-amine |
| 333 | N-[3-methyl-5-(1-methyl-4-piperidyl)phenyl]-1-phenyl-1,2,4-triazol-3-amine |
| 334 | 5-methyl-N1-[1-(oxetan-3-yl)-4-piperidyl]-N3-(1-phenyl-1,2,4-triazol-3-yl)benzene-1,3-diamine |
| 335 | N-(3-chloro-5-morpholino-phenyl)-1-phenyl-1,2,4-triazol-3-amine |
| 336 | N-(3-fluoro-5-pyrrolidin-1-yl-phenyl)-1-phenyl-1,2,4-triazol-3-amine |
| 337 | N-[3-(4-cyclopropyl-1,4-diazepan-1-yl)-5-methyl-phenyl]-1-phenyl-1,2,4-triazol-3-amine |
| 338 | N-[3-ethyl-5-[4-(oxetan-3-yl)piperazin-1-yl]phenyl]-1-(2-fluoro-5-methyl-phenyl)-1,2,4-triazol-3-amine |
| 339 | N-[3-cyclopropyl-5-[4-(oxetan-3-yl)piperazin-1-yl]phenyl]-1-(5-fluoro-3-pyridyl)-1,2,4-triazol-3-amine |
| 340 | N-[3-(1-cyclopropyl-3-piperidyl)-5-methyl-phenyl]-1-phenyl-1,2,4-triazol-3-amine |
| 341 | N-[3-ethyl-5-(3-morpholinoazetidin-1-yl)phenyl]-1-pyrazin-2-yl-1,2,4-triazol-3-amine |
| 342 | 5-methyl-N1-[1-(oxetan-3-yl)-4-piperidyl]-N3-[1-(3-pyridyl)-1,2,4-triazol-3-yl]benzene-1,3-diamine |
| 343 | 1-(2,4-difluorophenyl)-N-[3-fluoro-5-(1,4-oxazepan-4-yl)phenyl]-1,2,4-triazol-3-amine |
| 344 | 1-(3,5-difluorophenyl)-N-[3-methylsulfonyl-5-[4-(oxetan-3-yl)piperazin-1-yl]phenyl]-1,2,4-triazol-3-amine |
| 345 | 2-chloro-N-[1-(3,4-dimethoxyphenyl)-1,2,4-triazol-3-yl]-6-morpholino-pyridin-4-amine |
| 346 | N-(3-bromo-5-morpholino-phenyl)-1-(3,5-difluorophenyl)-1,2,4-triazol-3-amine |
| 347 | 1-(2,4-difluorophenyl)-N-[3-[3-(dimethylamino)pyrrolidin-1-yl]-5-fluoro-phenyl]-1,2,4-triazol-3-amine |
| 348 | N-[3-(4-cyclopropylpiperazin-1-yl)-5-(difluoromethyl)phenyl]-1-phenyl-1,2,4-triazol-3-amine |
| 349 | 1-(3,5-difluorophenyl)-N-[3-methyl-5-(9-methyl-2-oxa-6,9-diazaspiro[3.5]nonan-6-yl)phenyl]-1,2,4-triazol-3-amine |

TABLE 2-continued

Compound Names (IUPAC Nomenclature)

| Cmpd Number | IUPAC Name |
|---|---|
| 350 | 2,2,2-trifluoroethyl 4-[3-[[1-(3,5-difluorophenyl)-1,2,4-triazol-3-yl]amino]-5-methyl-phenyl]piperazine-1-carboxylate |
| 351 | N1-(azetidin-3-yl)-5-fluoro-N3-[1-(3-fluorophenyl)-1,2,4-triazol-3-yl]benzene-1,3-diamine |
| 352 | 1-[4-[3-[[1-(3,5-difluorophenyl)-1,2,4-triazol-3-yl]amino]-5-methyl-phenyl]piperazin-1-yl]-2,2,2-trifluoro-ethanone |
| 353 | N-[3-cyclopropyl-5-[4-(oxetan-3-yl)piperazin-1-yl]phenyl]-1-[6-(methoxymethyl)pyrimidin-4-yl]-1,2,4-triazol-3-amine |
| 354 | 2-cyclopropyl-N-[1-(3,4-dimethoxyphenyl)-1,2,4-triazol-3-yl]-6-morpholino-pyridin-4-amine |
| 355 | 1-[3-[[1-(3,5-difluorophenyl)-1,2,4-triazol-3-yl]amino]-5-methyl-phenyl]azetidin-3-ol |
| 356 | N-(3-methyl-5-pyrrolidin-1-yl-phenyl)-1-[4-(trifluoromethyl)phenyl]-1,2,4-triazol-3-amine |
| 357 | N-[3-morpholino-5-(trifluoromethyl)phenyl]-1-pyrazin-2-yl-1,2,4-triazol-3-amine |
| 358 | N-[3-(3,3a,4,5,7,7a-hexahydro-2H-furo[2,3-c]pyridin-6-yl)-5-methyl-phenyl]-1-phenyl-1,2,4-triazol-3-amine |
| 359 | 1-(3,5-difluorophenyl)-N-[3-isopropyl-5-[4-(oxetan-3-yl)piperazin-1-yl]phenyl]-1,2,4-triazol-3-amine |
| 360 | 4-[3-[[1-(3,5-difluorophenyl)-1,2,4-triazol-3-yl]amino]-5-methyl-phenyl]-1-methyl-piperazin-2-one |
| 361 | 1-(3-fluorophenyl)-N-[3-methylsulfonyl-5-[4-(oxetan-3-yl)piperazin-1-yl]phenyl]-1,2,4-triazol-3-amine |
| 362 | 1-(3,5-difluorophenyl)-N-[3-methyl-5-(3-methylpiperazin-1-yl)phenyl]-1,2,4-triazol-3-amine |
| 363 | N-[3-methyl-5-(oxetan-3-yl)phenyl]-1-phenyl-1,2,4-triazol-3-amine |
| 364 | 1-[6-(methoxymethyl)pyrimidin-4-yl]-N-[3-methyl-5-[4-(oxetan-3-yl)piperazin-1-yl]phenyl]-1,2,4-triazol-3-amine |
| 365 | N-[1-(3,5-difluorophenyl)-1,2,4-triazol-3-yl]-2-methyl-6-(4-methylpiperazin-1-yl)pyridin-4-amine |
| 366 | N-[3-morpholino-5-(trifluoromethyl)phenyl]-1-phenyl-1,2,4-triazol-3-amine |
| 367 | 2-chloro-6-(4-methylpiperazin-1-yl)-N-(1-phenyl-1,2,4-triazol-3-yl)pyridin-4-amine |
| 368 | tert-butyl 4-[3-ethyl-5-[(1-pyrazin-2-yl-1,2,4-triazol-3-yl)amino]phenyl]piperazine-1-carboxylate |
| 369 | N-[3-[(3aR,6aR)-1-methyl-2,3,3a,4,6,6a-hexahydropyrrolo[2,3-c]pyrrol-5-yl]-5-methyl-phenyl]-1-phenyl-1,2,4-triazol-3-amine |
| 370 | 1-[4-[3-[[1-(3,5-difluorophenyl)-1,2,4-triazol-3-yl]amino]-5-methyl-phenyl]piperazin-1-yl]ethanone |
| 371 | N-(3-fluoro-5-morpholino-phenyl)-1-(5-fluoro-3-pyridyl)-1,2,4-triazol-4-amine |
| 372 | N-(3-methyl-5-pyrrolidin-1-yl-phenyl)-1-(p-tolyl)-1,2,4-triazol-3-amine |
| 373 | 1-[3-fluoro-5-[2-methoxyethyl(methyl)amino]phenyl]-N-[3-methyl-5-[4-(oxetan-3-yl)piperazin-1-yl]phenyl]-1,2,4-triazol-3-amine |
| 374 | 1-(3,5-difluorophenyl)-N-(3-methyl-5-morpholino-phenyl)-1,2,4-triazol-3-amine |
| 375 | 1-(3-fluorophenyl)-N-[3-methyl-5-[4-(4-methyloxetan-3-yl)piperazin-1-yl]phenyl]-1,2,4-triazol-3-amine |
| 376 | N-[3-tert-butyl-5-[4-(oxetan-3-yl)piperazin-1-yl]phenyl]-1-phenyl-1,2,4-triazol-3-amine |
| 377 | N-[3-cyclopropyl-5-[4-(oxetan-3-yl)piperazin-1-yl]phenyl]-1-(6-methoxypyrimidin-4-yl)-1,2,4-triazol-3-amine |
| 378 | 2-cyclopropyl-N-[1-(3,5-difluorophenyl)-1,2,4-triazol-3-yl]-6-(1-piperidyl)pyridin-4-amine |
| 379 | 1-(3,5-difluorophenyl)-N-[3-methyl-5-(3-pyrazol-1-ylazetidin-1-yl)phenyl]-1,2,4-triazol-3-amine |
| 380 | N-(3-chloro-5-pyrrolidin-1-yl-phenyl)-1-phenyl-1,2,4-triazol-3-amine |
| 381 | N-[3-methyl-5-(4-methylpiperazin-1-yl)phenyl]-1-pyrimidin-5-yl-1,2,4-triazol-3-amine |
| 382 | 1-(3-fluorophenyl)-N-[3-methyl-5-[1-(oxetan-3-yl)pyrrolidin-3-yl]phenyl]-1,2,4-triazol-3-amine |
| 383 | 1-(2,5-difluorophenyl)-N-[3-methyl-5-[4-(oxetan-3-yl)-1-piperidyl]phenyl]-1,2,4-triazol-3-amine |
| 384 | 1-(3,4-difluorophenyl)-N-[3-methyl-5-[[1-(oxetan-3-yl)-4-piperidyl]oxy]phenyl]-1,2,4-triazol-3-amine |
| 385 | N-[3-[4-(methoxymethyl)-1-piperidyl]-5-methyl-phenyl]-1-(4-pyridyl)-1,2,4-triazol-3-amine |
| 386 | 1-(3,4-difluorophenyl)-N-[3-methyl-5-[4-(oxetan-3-yl)piperazin-1-yl]phenyl]-1,2,4-triazol-3-amine |
| 387 | 1-(5-fluoro-3-pyridyl)-N-[3-methyl-5-(4-methylpiperazin-1-yl)phenyl]-1,2,4-triazol-3-amine |
| 388 | N-[3-cyclopropyl-5-[4-(oxetan-3-yl)piperazin-1-yl]phenyl]-1-(3-fluoro-5-methoxy-phenyl)-1,2,4-triazol-3-amine |
| 389 | N-[3-cyclopropyl-5-[4-(oxetan-3-yl)piperazin-1-yl]phenyl]-1-(3,5-difluorophenyl)-1,2,4-triazol-3-amine |
| 390 | 1-[3-[[ethyl(methyl)amino]methyl]-5-fluoro-phenyl]-N-[3-methyl-5-(4-methylpiperazin-1-yl)phenyl]-1,2,4-triazol-3-amine |
| 391 | N-[3-methyl-5-[(3R)-1-(oxetan-3-yl)pyrrolidin-3-yl]oxy-phenyl]-1-phenyl-1,2,4-triazol-3-amine |
| 392 | N-[3-(difluoromethyl)-5-morpholino-phenyl]-1-phenyl-1,2,4-triazol-3-amine |
| 393 | N-[1-(3,4-difluorophenyl)-1,2,4-triazol-3-yl]-2,6-dimorpholino-pyridin-4-amine |
| 394 | N-(3-fluoro-5-morpholino-phenyl)-1-(4-fluorophenyl)-1,2,4-triazol-3-amine |
| 395 | 1-(3-fluoro-5-methoxy-phenyl)-N-[3-methyl-5-(4-methylpiperazin-1-yl)phenyl]-1,2,4-triazol-3-amine |
| 396 | 1-(3,5-difluorophenyl)-N-[3-[4-(oxetan-3-yl)piperazin-1-yl]-5-propyl-phenyl]-1,2,4-triazol-3-amine |
| 397 | 1-(3-chlorophenyl)-N-[3-methyl-5-[4-(oxetan-3-yl)piperazin-1-yl]phenyl]-1,2,4-triazol-3-amine |
| 398 | N-[3-methyl-5-[4-(2,2,2-trifluoroethyl)piperazin-1-yl]phenyl]-1-phenyl-1,2,4-triazol-3-amine |
| 399 | N-[3-methyl-5-(4-methylpiperazin-1-yl)phenyl]-1-pyridazin-4-yl-1,2,4-triazol-3-amine |
| 400 | 1-(3-chloro-5-fluoro-phenyl)-N-[3-cyclopropyl-5-[4-(oxetan-3-yl)piperazin-1-yl]phenyl]-1,2,4-triazol-3-amine |
| 401 | N-[3-ethyl-5-[4-(oxetan-3-yl)piperazin-1-yl]phenyl]-1-(6-methylpyrazin-2-yl)-1,2,4-triazol-3-amine |
| 402 | 1-[4-[3-methyl-5-[(1-phenyl-1,2,4-triazol-3-yl)amino]anilino]-1-piperidyl]ethanone |
| 403 | 1-(2-fluoro-4-pyridyl)-N-(3-methyl-5-morpholino-phenyl)-1,2,4-triazol-3-amine |
| 404 | N-[3-methyl-5-(oxetan-3-yl)phenyl]-1-(2-pyridyl)-1,2,4-triazol-3-amine |
| 405 | 2-cyclopropyl-N-[1-(3,5-difluorophenyl)-1,2,4-triazol-3-yl]-6-morpholino-pyridin-4-amine |
| 406 | 1-(3-fluorophenyl)-N-[3-methyl-5-[4-(oxetan-3-yl)piperazin-1-yl]phenyl]-1,2,4-triazol-3-amine |
| 407 | 2-cyclopropyl-N-[1-(3,5-difluorophenyl)-1,2,4-triazol-3-yl]-6-tetrahydropyran-4-yl-pyridin-4-amine |
| 408 | 1-(3,5-difluorophenyl)-N-[3-methyl-5-[1-(oxetan-3-yl)-3-piperidyl]phenyl]-1,2,4-triazol-3-amine |
| 409 | 1-(4-fluorophenyl)-N-[3-methyl-5-(oxetan-3-yl)phenyl]-1,2,4-triazol-3-amine |
| 410 | N-[3-methyl-5-[[1-(oxetan-3-yl)-4-piperidyl]oxy]phenyl]-1-phenyl-1,2,4-triazol-3-amine |
| 411 | 1-(3-fluorophenyl)-N-[3-methyl-5-[1-(oxetan-3-yl)-3-piperidyl]phenyl]-1,2,4-triazol-3-amine |
| 412 | 1-(3,4-difluorophenyl)-N-[3-(4-methylpiperazin-1-yl)-5-(trifluoromethyl)phenyl]-1,2,4-triazol-3-amine |
| 413 | N-[3-methyl-5-[4-(oxetan-3-yl)piperazin-1-yl]phenyl]-1-(2,4,5-trifluorophenyl)-1,2,4-triazol-3-amine |
| 414 | N-[3-methyl-5-[4-(oxetan-3-yl)piperazin-1-yl]phenyl]-1-(o-tolyl)-1,2,4-triazol-3-amine |
| 415 | 1-(3-fluoro-5-isopropoxy-phenyl)-N-[3-methyl-5-[4-(oxetan-3-yl)piperazin-1-yl]phenyl]-1,2,4-triazol-3-amine |
| 416 | 3-[3-[[1-(3,5-difluorophenyl)-1,2,4-triazol-3-yl]amino]-5-methyl-phenyl]-1-(oxetan-3-yl)pyrrolidin-3-ol |
| 417 | 1-(2,5-difluorophenyl)-N-[3-ethyl-5-[4-(oxetan-3-yl)piperazin-1-yl]phenyl]-1,2,4-triazol-3-amine |
| 418 | N-[3-methyl-5-[4-(oxetan-3-yl)piperazin-1-yl]phenyl]-1-(2-methylpyrimidin-4-yl)-1,2,4-triazol-3-amine |
| 419 | N-[3-methyl-5-(2,4,5-trimethylpiperazin-1-yl)phenyl]-1-phenyl-1,2,4-triazol-3-amine |
| 420 | N-[3-(4-cyclopropylpiperazin-1-yl)-5-methyl-phenyl]-1-(6-methylpyrazin-2-yl)-1,2,4-triazol-3-amine |
| 421 | 1-(3,5-difluorophenyl)-N-[3-methyl-5-[4-(2,2,2-trifluoroethyl)piperazin-1-yl]phenyl]-1,2,4-triazol-3-amine |
| 422 | methyl 4-[3-[[1-(3,5-difluorophenyl)-1,2,4-triazol-3-yl]amino]-5-methyl-phenyl]piperazine-1-carboxylate |

TABLE 2-continued

Compound Names (IUPAC Nomenclature)

| Cmpd Number | IUPAC Name |
|---|---|
| 423 | N-[3-methyl-5-[(3R,5S)-3,4,5-trimethylpiperazin-1-yl]phenyl]-1-phenyl-1,2,4-triazol-3-amine |
| 424 | 1-(3-fluoro-5-methyl-phenyl)-N-[3-methyl-5-(4-methylpiperazin-1-yl)phenyl]-1,2,4-triazol-3-amine |
| 425 | 1-(3,5-difluorophenyl)-N-[2,3-dimethyl-5-[4-(oxetan-3-yl)piperazin-1-yl]phenyl]-1,2,4-triazol-3-amine |
| 426 | N-(3-chloro-5-morpholino-phenyl)-1-(3,5-difluorophenyl)-1,2,4-triazol-3-amine |
| 427 | 1-(5-fluoro-3-pyridyl)-N-(3-methyl-5-morpholino-phenyl)-1,2,4-triazol-3-amine |
| 428 | 1-(2-chlorophenyl)-N-[3-methyl-5-(4-methylpiperazin-1-yl)phenyl]-1,2,4-triazol-3-amine |
| 429 | 1-(3,5-difluorophenyl)-N-[3-methyl-5-(3-piperidyl)phenyl]-1,2,4-triazol-3-amine |
| 430 | 2-(4-fluoro-1-piperidyl)-6-methyl-N-(1-phenyl-1,2,4-triazol-3-yl)pyridin-4-amine |
| 431 | N-[3-methyl-5-[4-[(3-methyloxetan-3-yl)methyl]piperazin-1-yl]phenyl]-1-phenyl-1,2,4-triazol-3-amine |
| 432 | N-[3-ethyl-5-[4-(oxetan-3-yl)piperazin-1-yl]phenyl]-1-(3-methoxyphenyl)-1,2,4-triazol-3-amine |
| 433 | 1-(3,5-difluorophenyl)-N-[3-methyl-5-[[1-(oxetan-3-yl)-4-piperidyl]oxy]phenyl]-1,2,4-triazol-3-amine |
| 434 | N-[3-methyl-5-(4-tetrahydrofuran-3-ylpiperazin-1-yl)phenyl]-1-phenyl-1,2,4-triazol-3-amine |
| 435 | 1-(3-fluorophenyl)-N-(3-fluoro-5-pyrrolidin-1-yl-phenyl)-1,2,4-triazol-3-amine |
| 436 | N-[3-methyl-5-[4-(3-methyloxetan-3-yl)piperazin-1-yl]phenyl]-1-phenyl-1,2,4-triazol-3-amine |
| 437 | 1-(2,5-difluorophenyl)-N-[3-methyl-5-[4-(oxetan-3-yl)piperazin-1-yl]phenyl]-1,2,4-triazol-3-amine |
| 438 | 4-[3-[[1-(3,5-difluorophenyl)-1,2,4-triazol-3-yl]amino]-5-methyl-phenyl]piperidin-3-ol |
| 439 | N-[3-methyl-5-[4-(oxetan-3-yl)piperazin-1-yl]phenyl]-1-(3-methylsulfanylphenyl)-1,2,4-triazol-3-amine |
| 440 | 1-(3,4-difluorophenyl)-N-(3-fluoro-5-morpholino-phenyl)-1,2,4-triazol-3-amine |
| 441 | N-(3-fluoro-5-pyrrolidin-1-yl-phenyl)-1-[4-(trifluoromethyl)phenyl]-1,2,4-triazol-3-amine |
| 442 | 3-[3-[3-[[1-(3,5-difluorophenyl)-1,2,4-triazol-3-yl]amino]-5-methyl-phenyl]-1-piperidyl]cyclobutanecarboxylic acid |
| 443 | 1-[3-[3-methyl-5-[(1-phenyl-1,2,4-triazol-3-yl)amino]phenyl]pyrrolidin-1-yl]ethanone |
| 444 | 1-(3,5-difluorophenyl)-N-[3-methyl-5-(2-oxa-7-azaspiro[3.4]octan-7-yl)phenyl]-1,2,4-triazol-3-amine |
| 445 | 1-(2,3-difluorophenyl)-N-[3-methyl-5-[4-(oxetan-3-yl)piperazin-1-yl]phenyl]-1,2,4-triazol-3-amine |
| 446 | 1-(2-chlorophenyl)-N-[3-methyl-5-[4-(oxetan-3-yl)piperazin-1-yl]phenyl]-1,2,4-triazol-3-amine |
| 447 | 1-(5-fluoro-3-pyridyl)-N-[3-methyl-5-(oxetan-3-yl)phenyl]-1,2,4-triazol-3-amine |
| 448 | N1-cyclopropyl-N3-[1-(3,5-difluorophenyl)-1,2,4-triazol-3-yl]-5-methyl-benzene-1,3-diamine |
| 449 | 1-[3-[3-methyl-5-[(1-pyrimidin-4-yl-1,2,4-triazol-3-yl)amino]phenyl]-1-piperidyl]ethanone |
| 450 | 1-(2,4-difluorophenyl)-N-[3-fluoro-5-(4-methylpiperazin-1-yl)phenyl]-1,2,4-triazol-3-amine |
| 451 | N-(2-fluoro-3-methyl-5-morpholino-phenyl)-1-(3-pyridyl)-1,2,4-triazol-3-amine |
| 452 | N-(3-fluoro-5-pyrrolidin-1-yl-phenyl)-1-phenyl-1,2,4-triazol-3-amine |
| 453 | N-[3-[4-(3,3-difluorocyclobutyl)piperazin-1-yl]-5-methyl-phenyl]-1-(3,5-difluorophenyl)-1,2,4-triazol-3-amine |
| 454 | N-[3-cyclopropyl-5-[4-(oxetan-3-yl)piperazin-1-yl]phenyl]-1-(2-methylpyrimidin-4-yl)-1,2,4-triazol-3-amine |
| 455 | N-[3-[4-(2-fluorophenyl)piperazin-1-yl]-5-methyl-phenyl]-1-phenyl-1,2,4-triazol-3-amine |
| 456 | 1-(3,5-difluorophenyl)-N-(3-morpholino-5-tetrahydrofuran-3-yl-phenyl)-1,2,4-triazol-3-amine |
| 457 | N-[1-(3,5-difluorophenyl)-1,2,4-triazol-3-yl]-2-(4-fluoro-1-piperidyl)-6-methyl-pyridin-4-amine |
| 458 | cyclopropyl-[4-[3-[[1-(3,5-difluorophenyl)-1,2,4-triazol-3-yl]amino]-5-methyl-phenyl]piperazin-1-yl]methanone |
| 459 | 1-(3,5-difluorophenyl)-N-[3-methyl-5-[(1R,4R)-5-methyl-2,5-diazabicyclo[2.2.1]heptan-2-yl]phenyl]-1,2,4-triazol-3-amine |
| 460 | 2-cyclopropyl-6-[(3S)-3-fluoropyrrolidin-1-yl]-N-(1-phenyl-1,2,4-triazol-3-yl)pyridin-4-amine |
| 461 | 2-methyl-1-[4-[3-methyl-5-[(1-phenyl-1,2,4-triazol-3-yl)amino]phenyl]piperazin-1-yl]propan-2-ol |
| 462 | N-[3-cyclopropyl-5-[4-(oxetan-3-yl)piperazin-1-yl]phenyl]-1-(3-fluorophenyl)-1,2,4-triazol-3-amine |
| 463 | N-[3-ethyl-5-[4-(oxetan-3-yl)piperazin-1-yl]phenyl]-1-(3-methylsulfanylphenyl)-1,2,4-triazol-3-amine |
| 464 | N-[3-[4-(methoxymethyl)-1-piperidyl]-5-methyl-phenyl]-1-pyrimidin-4-yl-1,2,4-triazol-3-amine |
| 465 | N-[3-(2,5-dihydrofuran-3-yl)-5-morpholino-phenyl]-1-phenyl-1,2,4-triazol-3-amine |
| 466 | N-[3-(1-cyclopropyl-3-piperidyl)-5-methyl-phenyl]-1-(3,5-difluorophenyl)-1,2,4-triazol-3-amine |
| 467 | 1-[3-fluoro-5-[(3R)-3-fluoropyrrolidin-1-yl]phenyl]-N-[3-methyl-5-[4-(oxetan-3-yl)piperazin-1-yl]phenyl]-1,2,4-triazol-3-amine |
| 468 | N-[3-ethyl-5-[4-(oxetan-3-yl)piperazin-1-yl]phenyl]-1-(3-fluorophenyl)-1,2,4-triazol-3-amine |
| 469 | 1-(2,5-difluorophenyl)-N-[3-methyl-5-[4-(3-methyloxetan-3-yl)piperazin-1-yl]phenyl]-1,2,4-triazol-3-amine |
| 470 | N-[2,3-dimethyl-5-[4-(oxetan-3-yl)piperazin-1-yl]phenyl]-1-pyrazin-2-yl-1,2,4-triazol-3-amine |
| 471 | N-[2-methoxy-3-methyl-5-[4-(oxetan-3-yl)piperazin-1-yl]phenyl]-1-pyrazin-2-yl-1,2,4-triazol-3-amine |
| 472 | N3-[1-(3,5-difluorophenyl)-1,2,4-triazol-3-yl]-5-methyl-N1-[1-(oxetan-3-yl)pyrrolidin-3-yl]benzene-1,3-diamine |
| 473 | 1-(3,5-difluorophenyl)-N-[3-methyl-5-[(3R)-1-(oxetan-3-yl)pyrrolidin-3-yl]phenyl]-1,2,4-triazol-3-amine |
| 475 | 1-(3,5-difluorophenyl)-N-[3-morpholino-5-(trifluoromethyl)phenyl]-1,2,4-triazol-3-amine |
| 476 | 1-(2-fluoro-5-methyl-phenyl)-N-[3-methyl-5-[4-(oxetan-3-yl)piperazin-1-yl]phenyl]-1,2,4-triazol-3-amine |
| 477 | 2-chloro-N-[1-(3,4-difluorophenyl)-1,2,4-triazol-3-yl]-6-(4-methylpiperazin-1-yl)pyridin-4-amine |
| 478 | N-[3-methyl-5-[4-(oxetan-3-yl)piperazin-1-yl]phenyl]-1-[4-(trifluoromethoxy)phenyl]-1,2,4-triazol-3-amine |
| 479 | N-[3-methyl-5-[(1S,4S)-5-methyl-2,5-diazabicyclo[2.2.1]heptan-2-yl]phenyl]-1-phenyl-1,2,4-triazol-3-amine |
| 480 | [1-[3-fluoro-5-[3-[3-methyl-5-[4-(oxetan-3-yl)piperazin-1-yl]anilino]-1,2,4-triazol-1-yl]phenyl]pyrrolidin-3-yl]methanol |
| 481 | N-[3-[4-(methoxymethyl)-1-piperidyl]-5-methyl-phenyl]-1-phenyl-1,2,4-triazol-3-amine |
| 482 | N-[3-(4-cyclopropylpiperazin-1-yl)-5-methyl-phenyl]-1-(3,5-difluorophenyl)-1,2,4-triazol-3-amine |
| 483 | N-[3-methyl-5-[1-[(3-methyloxetan-3-yl)methyl]-4-piperidyl]phenyl]-1-phenyl-1,2,4-triazol-3-amine |
| 484 | N-[3-methyl-5-[4-(oxetan-3-yl)piperazin-1-yl]phenyl]-1-(2,3,5-trifluorophenyl)-1,2,4-triazol-3-amine |
| 485 | 1-(3,5-difluorophenyl)-N-[3-methyl-5-(3-morpholinoazetidin-1-yl)phenyl]-1,2,4-triazol-3-amine |
| 486 | N-[3-(4-methylpiperazin-1-yl)-5-(trifluoromethyl)phenyl]-1-phenyl-1,2,4-triazol-3-amine |
| 487 | (3R)-3-[3-[[1-(3,5-difluorophenyl)-1,2,4-triazol-3-yl]amino]-5-methyl-phenyl]-1-(oxetan-3-yl)pyrrolidin-3-ol |
| 488 | 1-(6-chloro-2-pyridyl)-N-(3-methyl-5-pyrrolidin-1-yl-phenyl)-1,2,4-triazol-3-amine |
| 489 | N-[3-ethyl-5-[4-(3-methyloxetan-3-yl)piperazin-1-yl]phenyl]-1-pyrazin-2-yl-1,2,4-triazol-3-amine |
| 490 | N1-[1-(3,5-difluorophenyl)-1,2,4-triazol-3-yl]-5-methyl-N3-[(2-methyltetrahydrofuran-2-yl)methyl]benzene-1,3-diamine |
| 491 | 1-[3-fluoro-5-[(2R)-2-(methoxymethyl)pyrrolidin-1-yl]phenyl]-N-[3-methyl-5-[4-(oxetan-3-yl)piperazin-1-yl]phenyl]-1,2,4-triazol-3-amine |
| 492 | 2-cyclopropyl-N-[1-(3,4-difluorophenyl)-1,2,4-triazol-3-yl]-6-[(3S)-3-fluoropyrrolidin-1-yl]pyridin-4-amine |
| 493 | [1-[3-[[1-(3,5-difluorophenyl)-1,2,4-triazol-3-yl]amino]-5-methyl-phenyl]azetidin-3-yl]methanol |
| 494 | N-[3-cyclopropyl-5-[4-(oxetan-3-yl)piperazin-1-yl]phenyl]-1-[3-fluoro-5-(3-methoxyazetidin-1-yl)phenyl]-1,2,4-triazol-3-amine |

TABLE 2-continued

Compound Names (IUPAC Nomenclature)

| Cmpd Number | IUPAC Name |
|---|---|
| 495 | 1-[2-(azepan-1-yl)-4-pyridyl]-N-[3-methyl-5-(4-methylpiperazin-1-yl)phenyl]-1,2,4-triazol-3-amine |
| 496 | N1-[1-(3,5-difluorophenyl)-1,2,4-triazol-3-yl]-5-methyl-N3-(2-tetrahydrofuran-2-ylethyl)benzene-1,3-diamine |
| 497 | 1-(2,4-difluorophenyl)-N-(3-fluoro-5-pyrrolidin-1-yl-phenyl)-1,2,4-triazol-3-amine |
| 498 | 2-cyclopropyl-N-[1-(3,4-difluorophenyl)-1,2,4-triazol-3-yl]-6-[(3R)-3-fluoropyrrolidin-1-yl]pyridin-4-amine |
| 499 | 3-[3-[3-methyl-5-(4-methylpiperazin-1-yl)anilino]-1,2,4-triazol-1-yl]benzonitrile |
| 500 | N-[1-[3-[[1-(3,5-difluorophenyl)-1,2,4-triazol-3-yl]amino]-5-methyl-phenyl]pyrrolidin-3-yl]-N-methyl-acetamide |
| 501 | N-[1-(3,4-difluorophenyl)-1,2,4-triazol-3-yl]-4-methyl-6-(3-morpholinoazetidin-1-yl)pyridin-2-amine |
| 502 | 4-methyl-6-(3-morpholinoazetidin-1-yl)-N-(1-phenyl-1,2,4-triazol-3-yl)pyridin-2-amine |
| 503 | 4-methyl-6-(3-morpholinoazetidin-1-yl)-N-[1-(2-pyridyl)-1,2,4-triazol-3-yl]pyridin-2-amine |
| 504 | N-[1-(2-fluoro-4-pyridyl)-1,2,4-triazol-3-yl]-4-methyl-6-(3-morpholinoazetidin-1-yl)pyridin-2-amine |
| 505 | [3-acetoxy-2-[4-[3-[[1-(3,5-difluorophenyl)-1,2,4-triazol-3-yl]amino]-5-methyl-phenyl]piperazin-1-yl]-2-methyl-propyl] acetate |
| 506 | 1-(3,5-difluorophenyl)-N-[3-methyl-5-[3-(oxetan-3-yl)azetidin-1-yl]phenyl]-1,2,4-triazol-3-amine |
| 507 | N-[3-[4-(oxetan-3-yl)-1-piperidyl]-5-(trifluoromethyl)phenyl]-1-pyrazin-2-yl-1,2,4-triazol-3-amine |
| 508 | 1-(3,5-difluorophenyl)-N-[3-methyl-5-(5-oxa-6-azaspiro[3.3]heptan-6-yl)phenyl]-1,2,4-triazol-3-amine |
| 509 | 2-[4-[3-[[1-(3,5-difluorophenyl)-1,2,4-triazol-3-yl]amino]-5-methyl-phenyl]piperazin-1-yl]-2-methyl-propanoic acid |
| 510 | 1-(3,5-difluorophenyl)-N-[3-methyl-5-(3-pyrrolidin-1-ylazetidin-1-yl)phenyl]-1,2,4-triazol-3-amine |
| 511 | N-[3-isopropyl-5-[4-(oxetan-3-yl)piperazin-1-yl]phenyl]-1-pyrimidin-4-yl-1,2,4-triazol-3-amine |
| 512 | 4-(difluoromethyl)-N-[1-(3,5-difluorophenyl)-1,2,4-triazol-3-yl]-6-[4-(oxetan-3-yl)piperazin-1-yl]pyridin-2-amine |
| 513 | N-[3-(6-oxa-3-azabicyclo[3.1.1]heptan-3-yl)-5-(trifluoromethyl)phenyl]-1-pyrazin-2-yl-1,2,4-triazol-3-amine |
| 514 | N-[3-[4-(oxetan-3-yl)piperazin-1-yl]-5-(trifluoromethyl)phenyl]-1-pyrazin-2-yl-1,2,4-triazol-3-amine |
| 515 | 1-(3,5-difluorophenyl)-N-[3-[4-fluoro-1-(oxetan-3-yl)-4-piperidyl]-5-methyl-phenyl]-1,2,4-triazol-3-amine |
| 516 | 4-[3-[[1-(3,5-difluorophenyl)-1,2,4-triazol-3-yl]amino]-5-methyl-phenyl]-1-(oxetan-3-yl)piperidin-4-ol |
| 517 | 3-[3-[[1-(3,5-difluorophenyl)-1,2,4-triazol-3-yl]amino]-5-methyl-phenyl]oxazolidin-2-one |
| 518 | 1-[3-[[1-(3,5-difluorophenyl)-1,2,4-triazol-3-yl]amino]-5-methyl-phenyl]-3-isopropyl-azetidin-3-ol |
| 519 | 2-[1-[3-[[1-(3,5-difluorophenyl)-1,2,4-triazol-3-yl]amino]-5-methyl-phenyl]azetidin-3-yl]propan-2-ol |
| 520 | N3-[1-(3,5-difluorophenyl)-1,2,4-triazol-3-yl]-N1-(3-methoxycyclobutyl)-5-methyl-benzene-1,3-diamine |
| 521 | N-[3-methyl-5-[4-(oxetan-3-yl)-1-piperidyl]phenyl]-1-pyrazin-2-yl-1,2,4-triazol-3-amine |
| 522 | 1-(3-fluorophenyl)-N-[3-methyl-5-[4-(oxetan-3-yl)-1-piperidyl]phenyl]-1,2,4-triazol-3-amine |
| 523 | 1-(3-fluorophenyl)-N-[3-isopropyl-5-[4-(oxetan-3-yl)piperazin-1-yl]phenyl]-1,2,4-triazol-3-amine |
| 524 | 4-(difluoromethyl)-N-[1-(3,4-difluorophenyl)-1,2,4-triazol-3-yl]-6-[4-(oxetan-3-yl)piperazin-1-yl]pyridin-2-amine |
| 525 | 4-(difluoromethyl)-N-[1-(3-fluorophenyl)-1,2,4-triazol-3-yl]-6-[4-(oxetan-3-yl)piperazin-1-yl]pyridin-2-amine |
| 526 | 4-(difluoromethyl)-6-[4-(oxetan-3-yl)piperazin-1-yl]-N-(1-phenyl-1,2,4-triazol-3-yl)pyridin-2-amine |
| 527 | 1-(3,5-difluorophenyl)-N-[3-methyl-5-(6-oxa-3-azabicyclo[3.1.1]heptan-3-yl)phenyl]-1,2,4-triazol-3-amine |
| 528 | N-[3-(3,3a,4,6,7,7a-hexahydro-2H-furo[3,2-c]pyridin-5-yl)-5-methyl-phenyl]-1-(3,5-difluorophenyl)-1,2,4-triazol-3-amine |
| 529 | N-[1-(3,5-difluorophenyl)-1,2,4-triazol-3-yl]-4-methyl-6-piperazin-1-yl-pyridin-2-amine |
| 530 | 1-(3,5-difluorophenyl)-N-[3-methyl-5-[4-[(3S)-tetrahydrofuran-3-yl]piperazin-1-yl]phenyl]-1,2,4-triazol-3-amine |
| 531 | 1-(3,5-difluorophenyl)-N-[3-methyl-5-[4-[(3R)-tetrahydrofuran-3-yl]piperazin-1-yl]phenyl]-1,2,4-triazol-3-amine |
| 532 | 4-(difluoromethyl)-6-[4-(oxetan-3-yl)piperazin-1-yl]-N-[1-(2-pyridyl)-1,2,4-triazol-3-yl]pyridin-2-amine |
| 533 | tert-butyl 4-[6-[[1-(3,5-difluorophenyl)-1,2,4-triazol-3-yl]amino]-4-methyl-2-pyridyl]piperazine-1-carboxylate |
| 534 | [2-[4-[3-[[1-(3,5-difluorophenyl)-1,2,4-triazol-3-yl]amino]-5-methyl-phenyl]piperazin-1-yl]-3-hydroxy-2-methyl-propyl] acetate |
| 535 | N-[3-methyl-5-[4-(oxetan-3-yl)piperazin-1-yl]phenyl]-1-pyrimidin-5-yl-1,2,4-triazol-3-amine |
| 536 | N-[3-isopropyl-5-[4-(oxetan-3-yl)piperazin-1-yl]phenyl]-1-pyrazin-2-yl-1,2,4-triazol-3-amine |
| 537 | N-[1-(3,5-difluorophenyl)-1,2,4-triazol-3-yl]-4-methyl-6-(3-morpholinoazetidin-1-yl)pyridin-2-amine |
| 538 | N-[1-(3-fluorophenyl)-1,2,4-triazol-3-yl]-4-methyl-6-(3-morpholinoazetidin-1-yl)pyridin-2-amine |
| 539 | N-[3-cyclopropyl-5-(3-morpholinoazetidin-1-yl)phenyl]-1-pyrazin-2-yl-1,2,4-triazol-3-amine |
| 540 | N-[1-(3,5-difluorophenyl)-1,2,4-triazol-3-yl]-6-[4-(oxetan-3-yl)piperazin-1-yl]-4-(trifluoromethyl)pyridin-2-amine |
| 541 | 1-(3,5-difluorophenyl)-N-[3-methyl-5-(2-oxa-8-azaspiro[3.5]nonan-8-yl)phenyl]-1,2,4-triazol-3-amine |
| 542 | 1-[1-[3-[[1-(3,5-difluorophenyl)-1,2,4-triazol-3-yl]amino]-5-methyl-phenyl]azetidin-3-yl]pyrrolidin-2-one |
| 543 | 1-(3,5-difluorophenyl)-N-[3-methyl-5-(9-oxa-6-azaspiro[3.5]nonan-6-yl)phenyl]-1,2,4-triazol-3-amine |
| 544 | N-[3-ethyl-5-(3-morpholinoazetidin-1-yl)phenyl]-1-pyrimidin-5-yl-1,2,4-triazol-3-amine |
| 545 | N-[1-(3-fluorophenyl)-1,2,4-triazol-3-yl]-6-[4-(oxetan-3-yl)piperazin-1-yl]-4-(trifluoromethyl)pyridin-2-amine |
| 546 | N-[1-(3,4-difluorophenyl)-1,2,4-triazol-3-yl]-6-[4-(oxetan-3-yl)piperazin-1-yl]-4-(trifluoromethyl)pyridin-2-amine |
| 547 | 6-[4-(oxetan-3-yl)piperazin-1-yl]-N-(1-phenyl-1,2,4-triazol-3-yl)-4-(trifluoromethyl)pyridin-2-amine |
| 548 | 6-[4-(oxetan-3-yl)piperazin-1-yl]-N-[1-(2-pyridyl)-1,2,4-triazol-3-yl]-4-(trifluoromethyl)pyridin-2-amine |
| 549 | N-[3-ethyl-5-[4-(oxetan-3-yl)piperazin-1-yl]phenyl]-1-pyrimidin-5-yl-1,2,4-triazol-3-amine |
| 550 | N-[3-tert-butyl-5-[4-(oxetan-3-yl)piperazin-1-yl]phenyl]-1-pyrimidin-5-yl-1,2,4-triazol-3-amine |
| 551 | 1-[3-[[1-(3,5-difluorophenyl)-1,2,4-triazol-3-yl]amino]-5-methyl-phenyl]-3-methyl-azetidin-3-ol |
| 552 | 1-(3,5-difluorophenyl)-N-[3-methyl-5-[3-(trifluoromethyl)piperazin-1-yl]phenyl]-1,2,4-triazol-3-amine |
| 553 | 1-[3-[[1-(3,5-difluorophenyl)-1,2,4-triazol-3-yl]amino]-5-methyl-phenyl]-3-ethyl-azetidin-3-ol |
| 554 | 4-[6-[[1-(3,5-difluorophenyl)-1,2,4-triazol-3-yl]amino]-4-(trifluoromethyl)-2-pyridyl]-N-ethyl-piperazine-1-carboxamide |
| 555 | 1-[4-[6-[[1-(3,5-difluorophenyl)-1,2,4-triazol-3-yl]amino]-4-(trifluoromethyl)-2-pyridyl]piperazin-1-yl]ethanone |
| 556 | N-[1-(3,5-difluorophenyl)-1,2,4-triazol-3-yl]-6-piperazin-1-yl-4-(trifluoromethyl)pyridin-2-amine |
| 557 | tert-butyl 4-[6-[[1-(3,5-difluorophenyl)-1,2,4-triazol-3-yl]amino]-4-(trifluoromethyl)-2-pyridyl]piperazine-1-carboxylate |
| 558 | 1-(2,5-difluorophenyl)-N-(3-methyl-5-piperazin-1-yl-phenyl)-1,2,4-triazol-3-amine |
| 559 | 1-(3,4-difluorophenyl)-N-[3-[4-(oxetan-3-yl)piperazin-1-yl]-5-propyl-phenyl]-1,2,4-triazol-3-amine |
| 560 | N-[1-(3,5-difluorophenyl)-1,2,4-triazol-3-yl]-4-methyl-6-morpholino-pyridin-2-amine |
| 561 | 2-[3-[[1-(3,5-difluorophenyl)-1,2,4-triazol-3-yl]amino]-5-methyl-phenyl]-1,3,4,7,8,8a-hexahydropyrrolo[1,2-a]pyrazin-6-one |
| 562 | N-[1-(3,5-difluorophenyl)-1,2,4-triazol-3-yl]-4-methyl-6-(4-tetrahydrofuran-3-ylpiperazin-1-yl)pyridin-2-amine |
| 563 | N-[1-(3,5-difluorophenyl)-1,2,4-triazol-3-yl]-4-methyl-6-[3-(oxetan-3-yl)azetidin-1-yl]pyridin-2-amine |
| 564 | N-[1-(3,5-difluorophenyl)-1,2,4-triazol-3-yl]-6-(4-tetrahydrofuran-3-ylpiperazin-1-yl)-4-(trifluoromethyl)pyridin-2-amine |

TABLE 2-continued

Compound Names (IUPAC Nomenclature)

| Cmpd Number | IUPAC Name |
|---|---|
| 565 | ethyl 1-[6-[[1-(3,5-difluorophenyl)-1,2,4-triazol-3-yl]amino]-4-methyl-2-pyridyl]piperidine-4-carboxylate |
| 566 | N-[3-(3,4,6,7,9,9a-hexahydro-1H-pyrazino[2,1-c][1,4]oxazin-8-yl)-5-methyl-phenyl]-1-(3,5-difluorophenyl)-1,2,4-triazol-3-amine |
| 567 | N-[1-(3,5-difluorophenyl)-1,2,4-triazol-3-yl]-4-[4-(oxetan-3-yl)piperazin-1-yl]-6-(trifluoromethyl)pyridin-2-amine |
| 568 | N-[1-(3,5-difluorophenyl)-1,2,4-triazol-3-yl]-6-(3-fluoro-1-piperidyl)-4-methyl-pyridin-2-amine |
| 569 | 1-[6-[[1-(3,5-difluorophenyl)-1,2,4-triazol-3-yl]amino]-4-methyl-2-pyridyl]-4-methyl-piperidin-4-ol |
| 570 | N-[1-(3,5-difluorophenyl)-1,2,4-triazol-3-yl]-4-methyl-6-(7-oxa-2-azaspiro[3.4]octan-2-yl)pyridin-2-amine |
| 571 | N-[1-(3,5-difluorophenyl)-1,2,4-triazol-3-yl]-4-methyl-6-(3-oxa-6-azaspiro[3.3]heptan-6-yl)pyridin-2-amine |
| 572 | 2-[1-[6-[[1-(3,5-difluorophenyl)-1,2,4-triazol-3-yl]amino]-4-methyl-2-pyridyl]azetidin-3-yl]propan-2-ol |
| 573 | N-[3,5-bis(4-tert-butylpiperazin-1-yl)phenyl]-1-(3,5-difluorophenyl)-1,2,4-triazol-3-amine |
| 574 | N-[3,5-bis[4-(oxetan-3-yl)piperazin-1-yl]phenyl]-1-(3,5-difluorophenyl)-1,2,4-triazol-3-amine |

In Tables 2A and 2B below, several compounds have stereocenters with either known (R or S) or unknown absolute configurations and/or known (cis or trans) or unknown configurations. For example, compounds 603, 611, 623, 632, 655, 665, 667, 672, 673, 679, 682, 696, 700, 740, 748, 750, 751, 787, 796 and 800 in Table 2A are each single enantiomers with unknown stereochemistry and are arbitrarily assigned the "S" or "R" conformation in the compound name. Compounds 649 and 792 in Table 2B are each single enantiomers of unknown cis/trans configuration and are arbitrarily assigned a trans conformation. Compounds 826 and 861 in Table 2B are each single enantiomers of unknown cis/trans configuration and are arbitrarily assigned a cis conformation.

TABLE 2A

| Cmpds No | Single Enantiomer | Absolute Stereochemistry |
|---|---|---|
| 584 | Yes | S |
| 603 | Yes | Unknown |
| 611 | Yes | Unknown |
| 623 | Yes | Unknown |
| 628 | Yes | 1R,4S |
| 632 | Yes | Unknown |
| 655 | Yes | Unknown |
| 665 | Yes | Unknown |
| 667 | Yes | Unknown |
| 670 | Yes | 3R |
| 672 | Yes | Unknown |
| 673 | Yes | Unknown |
| 679 | Yes | Unknown |
| 682 | Yes | Unknown |
| 696 | Yes | Unknown |
| 700 | Yes | Unknown |
| 730 | Yes | S |
| 740 | Yes | Unknown |
| 748 | Yes | Unknown |
| 750 | Yes | Unknown |
| 751 | Yes | Unknown |
| 787 | Yes | Unknown |
| 796 | Yes | Unknown |
| 800 | Yes | Unknown |
| 822 | Yes | 1S,4S |
| 831 | Yes | S |

TABLE 2B

| Cmpds No | Single Enantiomer | cis/trans |
|---|---|---|
| 618 | Yes | cis |
| 649 | Yes | Unknown |
| 752 | Yes | trans |
| 792 | Yes | Unknown |
| 813 | Yes | trans |
| 826 | Yes | Unknown |
| 857 | Yes | trans |
| 861 | Yes | Unknown |

TABLE 2C

Compound Names (IUPAC Nomenclature)

| Cmpd No. | IUPAC Name |
|---|---|
| 575 | N-[3-methyl-5-(2-morpholinoethoxy)phenyl]-1-[3-(trifluoromethyl)phenyl]-1,2,4-triazol-3-amine |
| 576 | 4-(difluoromethyl)-6-[4-(oxetan-3-yl)piperazin-1-yl]-N-(1-pyrazin-2-yl-1,2,4-triazol-3-yl)pyridin-2-amine |
| 577 | 1-(3,4-difluorophenyl)-N-[3-ethyl-5-[4-(3-methyloxetan-3-yl)piperazin-1-yl]phenyl]-1,2,4-triazol-3-amine |
| 578 | 4-methyl-6-[4-(oxetan-3-yl)piperazin-1-yl]-N-[1-[3-(trifluoromethyl)phenyl]-1,2,4-triazol-3-yl]pyridin-2-amine |
| 579 | 4-(1,1-difluoroethyl)-N-[1-(3,4-difluorophenyl)-1,2,4-triazol-3-yl]-6-[4-(oxetan-3-yl)piperazin-1-yl]pyridin-2-amine |
| 580 | N-[1-(3,5-difluorophenyl)-1,2,4-triazol-3-yl]-4-methyl-6-[4-(3-methyloxetan-3-yl)piperazin-1-yl]pyridin-2-amine |
| 581 | 1-(3,5-difluorophenyl)-N-[3-methyl-5-[4-(oxetan-3-yl)morpholin-2-yl]phenyl]-1,2,4-triazol-3-amine |
| 582 | [4-[3-[[1-(3,5-difluorophenyl)-1,2,4-triazol-3-yl]amino]-5-methyl-phenyl]piperazin-1-yl]-morpholino-methanone |
| 583 | N-[3-methyl-5-[[4-(oxetan-3-yl)piperazin-1-yl]methyl]phenyl]-1-pyrazin-2-yl-1,2,4-triazol-3-amine |
| 584 | 1-[3-[[1-(3,5-difluorophenyl)-1,2,4-triazol-3-yl]amino]-5-methyl-phenyl]-N-[(1S)-2-methoxy-1-methyl-ethyl]azetidine-3-carboxamide |
| 585 | N-[3-methyl-5-[4-(3-methyloxetan-3-yl)piperazin-1-yl]phenyl]-1-(3-pyridyl)-1,2,4-triazol-3-amine |
| 586 | 1-(3,5-difluorophenyl)-N-[3-methyl-5-[3-(4-oxa-7-azaspiro[2.5]octan-7-yl)azetidin-1-yl]phenyl]-1,2,4-triazol-3-amine |
| 587 | 1-(3,5-difluorophenyl)-N-[2-fluoro-3-methyl-5-[4-(oxetan-3-yl)piperazin-1-yl]phenyl]-1,2,4-triazol-3-amine |
| 588 | 5-methyl-N1-(5-methylthiazol-2-yl)-N3-(1-phenyl-1,2,4-triazol-3-yl)benzene-1,3-diamine |
| 589 | [1-[3-[[1-(3,5-difluorophenyl)-1,2,4-triazol-3-yl]amino]-5-methyl-phenyl]-4-piperidyl]-morpholino-methanone |
| 590 | 1-(3,4-difluorophenyl)-N-[3-methyl-5-[[1-(oxetan-3-yl)-3-piperidyl]oxy]phenyl]-1,2,4-triazol-3-amine |
| 591 | 1-(3,5-difluorophenyl)-N-[3-isopropoxy-2-methyl-5-[4-(oxetan-3-yl)piperazin-1-yl]phenyl]-1,2,4-triazol-3-amine |
| 592 | 3-[4-(oxetan-3-yl)piperazin-1-yl]-5-[(1-phenyl-1,2,4-triazol-3-yl)amino]benzonitrile |
| 593 | 1-(3,5-difluorophenyl)-N-[3-methyl-5-[4-(2-morpholinoethyl)piperazin-1-yl]phenyl]-1,2,4-triazol-3-amine |
| 594 | N-[3-fluoro-5-[4-(oxetan-3-yl)piperazin-1-yl]phenyl]-1-(3-fluorophenyl)-1,2,4-triazol-3-amine |
| 595 | 1-[3-(difluoromethyl)phenyl]-N-[3-methyl-5-(3-morpholinoazetidin-1-yl)phenyl]-1,2,4-triazol-3-amine |
| 596 | 1-(3,5-difluorophenyl)-N-[3-methyl-5-[[4-(oxetan-3-yl)piperazin-1-yl]methyl]phenyl]-1,2,4-triazol-3-amine |
| 597 | 1-(3-chloro-4-fluoro-phenyl)-N-[3-methyl-5-[4-(oxetan-3-yl)piperazin-1-yl]phenyl]-1,2,4-triazol-3-amine |
| 598 | N-[3-fluoro-5-[4-(oxetan-3-yl)piperazin-1-yl]phenyl]-1-pyrazin-2-yl-1,2,4-triazol-3-amine |
| 599 | N-[1-(3,5-difluorophenyl)-1,2,4-triazol-3-yl]-4-methoxy-6-[4-(oxetan-3-yl)piperazin-1-yl]pyridin-2-amine |
| 600 | 4-methyl-N2-tetrahydrofuran-3-yl-N6-[1-[3-(trifluoromethyl)phenyl]-1,2,4-triazol-3-yl]pyridine-2,6-diamine |

TABLE 2C-continued

Compound Names (IUPAC Nomenclature)

| Cmpd No. | IUPAC Name |
|---|---|
| 601 | N-[1-(3,5-difluorophenyl)-1,2,4-triazol-3-yl]-6-(3-morpholinoazetidin-1-yl)-4-(trifluoromethyl)pyridin-2-amine |
| 602 | 1-(3,5-difluorophenyl)-N-[3-[3-(2,2-dimethylmorpholin-4-yl)azetidin-1-yl]-5-methyl-phenyl]-1,2,4-triazol-3-amine |
| 603 | (5S)-5-methyl-5-[3-methyl-5-[(1-pyrazin-2-yl-1,2,4-triazol-3-yl)amino]phenyl]oxazolidin-2-one |
| 604 | N1-(1-ethyl-1,2,4-triazol-3-yl)-5-methyl-N3-(1-phenyl-1,2,4-triazol-3-yl)benzene-1,3-diamine |
| 605 | 1-(3,5-difluorophenyl)-N-[3-methyl-5-[(1-methylpyrazol-3-yl)methoxy]phenyl]-1,2,4-triazol-3-amine |
| 606 | 1-(4-fluorophenyl)-N-[3-methyl-5-(3-morpholinoazetidin-1-yl)phenyl]-1,2,4-triazol-3-amine |
| 607 | 2-[[1-(3,4-difluorophenyl)-1,2,4-triazol-3-yl]amino]-6-[4-(oxetan-3-yl)piperazin-1-yl]pyridine-4-carbonitrile |
| 608 | 3-morpholino-5-[(1-phenyl-1,2,4-triazol-3-yl)amino]benzonitrile |
| 609 | N-[3-methyl-5-[4-(oxetan-3-yl)-1,4-diazepan-1-yl]phenyl]-1-(2-pyridyl)-1,2,4-triazol-3-amine |
| 610 | 4-methoxy-6-[4-(oxetan-3-yl)piperazin-1-yl]-N-[1-[3-(trifluoromethyl)phenyl]-1,2,4-triazol-3-yl]pyridin-2-amine |
| 611 | (5S)-5-[3-[[1-(3,5-difluorophenyl)-1,2,4-triazol-3-yl]amino]-5-methyl-phenyl]-3,5-dimethyl-oxazolidin-2-one |
| 612 | N-[1-(3,5-difluorophenyl)-1,2,4-triazol-3-yl]-6-fluoro-4-(3-morpholinoazetidin-1-yl)pyridin-2-amine |
| 613 | 5-[3-[[1-(3,5-difluorophenyl)-1,2,4-triazol-3-yl]amino]-5-methyl-phenyl]-3,5-dimethyl-oxazolidin-2-one |
| 614 | N6-[1-(3,5-difluorophenyl)-1,2,4-triazol-3-yl]-4-methyl-N2-tetrahydrofuran-3-yl-pyridine-2,6-diamine |
| 615 | 1-(3,4-difluorophenyl)-N-[3-methyl-5-[(3-methyloxetan-3-yl)methoxy]phenyl]-1,2,4-triazol-3-amine |
| 616 | N-[1-(3,5-difluorophenyl)-1,2,4-triazol-3-yl]-6-methyl-4-(3-morpholinoazetidin-1-yl)pyridin-2-amine |
| 617 | 1-(3,5-difluorophenyl)-N-[3-[3-(4-fluoro-1-piperidyl)azetidin-1-yl]-5-methyl-phenyl]-1,2,4-triazol-3-amine |
| 618 | 1-(3,5-difluorophenyl)-N-[3-[3-[(2R,6S)-2,6-dimethylmorpholin-4-yl]azetidin-1-yl]-5-methyl-phenyl]-1,2,4-triazol-3-amine |
| 619 | N-[1-(3,5-difluorophenyl)-1,2,4-triazol-3-yl]-6-[4-(methoxymethyl)-1-piperidyl]-4-methyl-pyridin-2-amine |
| 620 | 1-(3,5-difluorophenyl)-N-[3-methyl-5-[[1-(oxetan-3-yl)-3-piperidyl]oxy]phenyl]-1,2,4-triazol-3-amine |
| 621 | N-[1-(4-chloro-3-fluoro-phenyl)-1,2,4-triazol-3-yl]-4-(difluoromethyl)-6-[4-(oxetan-3-yl)piperazin-1-yl]pyridin-2-amine |
| 622 | 1-(4-fluorophenyl)-N-[3-methyl-5-[4-(oxetan-3-yl)piperazin-1-yl]phenyl]-1,2,4-triazol-3-amine |
| 623 | 1-(3,5-difluorophenyl)-N-[3-methyl-5-[(2S)-4-(oxetan-3-yl)morpholin-2-yl]phenyl]-1,2,4-triazol-3-amine |
| 624 | 1-(3-fluoro-4-methoxy-phenyl)-N-[3-methyl-5-[4-(oxetan-3-yl)piperazin-1-yl]phenyl]-1,2,4-triazol-3-amine |
| 625 | 4-(methoxymethyl)-6-[4-(oxetan-3-yl)piperazin-1-yl]-N-[1-[3-(trifluoromethyl)phenyl]-1,2,4-triazol-3-yl]pyridin-2-amine |
| 626 | 1-[4-[3-[[1-(3,4-difluorophenyl)-1,2,4-triazol-3-yl]amino]-5-methyl-phenoxy]-1-piperidyl]ethanone |
| 627 | 1-(3,4-difluorophenyl)-N-[3-methyl-5-(tetrahydropyran-4-ylmethoxy)phenyl]-1,2,4-triazol-3-amine |
| 628 | 1-(3,5-difluorophenyl)-N-[3-methyl-5-[(1R,4R)-2-oxa-5-azabicyclo[2.2.1]heptan-5-yl]phenyl]-1,2,4-triazol-3-amine |
| 629 | 1-(3,5-difluorophenyl)-N-[3-methyl-5-[5-methyl-4-(oxetan-3-yl)morpholin-2-yl]phenyl]-1,2,4-triazol-3-amine |
| 630 | 1-(3,5-difluorophenyl)-N-[2-fluoro-5-methyl-3-[[4-(oxetan-3-yl)piperazin-1-yl]methyl]phenyl]-1,2,4-triazol-3-amine |
| 631 | N-[1-(3,5-difluorophenyl)-1,2,4-triazol-3-yl]-4-methyl-6-(1,2,3,6-tetrahydropyridin-4-yl)pyridin-2-amine |
| 632 | 1-(3,4-difluorophenyl)-N-[3-methyl-5-[[(3S)-1-(oxetan-3-yl)-3-piperidyl]oxy]phenyl]-1,2,4-triazol-3-amine |
| 633 | 1-(3,4-difluorophenyl)-N-[3-methyl-5-[4-(3-methyloxetan-3-yl)piperazin-1-yl]phenyl]-1,2,4-triazol-3-amine |
| 634 | 1-(3,5-difluorophenyl)-N-[3-methyl-5-[3-(1-piperidyl)azetidin-1-yl]phenyl]-1,2,4-triazol-3-amine |
| 635 | 1-(3,5-difluorophenyl)-N-(3-methyl-5-tetrahydropyran-3-yloxy-phenyl)-1,2,4-triazol-3-amine |
| 636 | N-[1-[3-(difluoromethyl)phenyl]-1,2,4-triazol-3-yl]-6-(3-morpholinoazetidin-1-yl)-4-(trifluoromethyl)pyridin-2-amine |
| 637 | 1-(3,5-difluorophenyl)-N-[3-methyl-5-[4-(oxetan-3-yl)-1,4-diazepan-1-yl]phenyl]-1,2,4-triazol-3-amine |
| 638 | 1-(3,4-difluorophenyl)-N-(3-methyl-5-tetrahydropyran-3-yloxy-phenyl)-1,2,4-triazol-3-amine |
| 639 | N-[1-[3-(difluoromethyl)phenyl]-1,2,4-triazol-3-yl]-4-methoxy-6-[4-(oxetan-3-yl)piperazin-1-yl]pyridin-2-amine |
| 640 | N-[3-[(3,3-difluorocyclobutyl)methoxy]-5-methyl-phenyl]-1-(3,4-difluorophenyl)-1,2,4-triazol-3-amine |
| 641 | 1-(3,5-difluorophenyl)-N-[3-isopropoxy-2-methyl-5-(3-morpholinoazetidin-1-yl)phenyl]-1,2,4-triazol-3-amine |
| 642 | N-[3-fluoro-5-[4-(oxetan-3-yl)piperazin-1-yl]phenyl]-1-(2-pyridyl)-1,2,4-triazol-3-amine |
| 643 | 5-methyl-N3-(1-phenyl-1,2,4-triazol-3-yl)-N1-thiazol-2-yl-benzene-1,3-diamine |
| 644 | N-[3-methyl-5-(2-pyrazol-1-ylethoxy)phenyl]-1-[3-(trifluoromethyl)phenyl]-1,2,4-triazol-3-amine |
| 645 | 4-(difluoromethyl)-N-[1-[3-(difluoromethyl)phenyl]-1,2,4-triazol-3-yl]-6-[4-(methoxymethyl)-1-piperidyl]pyridin-2-amine |
| 646 | 1-(3,5-difluoro-4-methoxy-phenyl)-N-[3-methyl-5-[4-(oxetan-3-yl)piperazin-1-yl]phenyl]-1,2,4-triazol-3-amine |
| 647 | 1-(4-fluoro-3-methyl-phenyl)-N-[3-fluoro-5-[4-(oxetan-3-yl)piperazin-1-yl]phenyl]-1,2,4-triazol-3-amine |
| 648 | 1-(3,5-difluorophenyl)-N-[3-methyl-5-(tetrahydrofuran-3-ylmethoxy)phenyl]-1,2,4-triazol-3-amine |
| 649 | N1-[1-(3,5-difluorophenyl)-1,2,4-triazol-3-yl]-5-methyl-N3-(3-morpholinocyclobutyl)benzene-1,3-diamine |
| 650 | N-[1-(3,5-difluorophenyl)-1,2,4-triazol-3-yl]-6-(4-methylpiperazin-1-yl)-4-[4-(oxetan-3-yl)piperazin-1-yl]pyridin-2-amine |
| 651 | N-[3-methyl-5-(3-morpholinoazetidin-1-yl)phenyl]-1-[3-(trifluoromethyl)phenyl]-1,2,4-triazol-3-amine |
| 652 | 1-(3,5-difluorophenyl)-N-[3-methyl-5-[3-(5-oxa-2-azabicyclo[4.1.0]heptan-2-yl)azetidin-1-yl]phenyl]-1,2,4-triazol-3-amine |
| 653 | 1-(3,5-difluorophenyl)-N-[3-isopropoxy-5-[4-(oxetan-3-yl)piperazin-1-yl]phenyl]-1,2,4-triazol-3-amine |
| 654 | N-[1-(3,5-difluorophenyl)-1,2,4-triazol-3-yl]-6-(4-ethylpiperazin-1-yl)-4-(trifluoromethyl)pyridin-2-amine |
| 655 | (5R)-5-[3-[[1-(3,5-difluorophenyl)-1,2,4-triazol-3-yl]amino]-5-methyl-phenyl]-5-methyl-oxazolidin-2-one |
| 656 | 3-[[1-(3,4-difluorophenyl)-1,2,4-triazol-3-yl]amino]-5-[4-(oxetan-3-yl)piperazin-1-yl]benzonitrile |
| 657 | N-[3,5-bis(4-methylpiperazin-1-yl)phenyl]-1-(3,5-difluorophenyl)-1,2,4-triazol-3-amine |
| 658 | 5-[3-[[1-(3,5-difluorophenyl)-1,2,4-triazol-3-yl]amino]-5-methyl-phenyl]-5-methyl-oxazolidin-2-one |
| 659 | 1-(3,4-difluorophenyl)-N-[3-methyl-5-[3-(1,4-oxazepan-4-yl)azetidin-1-yl]phenyl]-1,2,4-triazol-3-amine |
| 660 | 6-chloro-N-[1-(3,5-difluorophenyl)-1,2,4-triazol-3-yl]-4-(3-morpholinoazetidin-1-yl)pyridin-2-amine |
| 661 | 1-(3,5-difluorophenyl)-N-[3-[3-(1,1-dioxo-1,4-thiazinan-4-yl)azetidin-1-yl]-5-methyl-phenyl]-1,2,4-triazol-3-amine |
| 662 | N-[3-methoxy-5-[4-(oxetan-3-yl)piperazin-1-yl]phenyl]-1-[3-(trifluoromethyl)phenyl]-1,2,4-triazol-3-amine |
| 663 | 1-(3,5-difluorophenyl)-N-[3-methyl-5-[6-methyl-4-(oxetan-3-yl)piperazin-1-yl]phenyl]-1,2,4-triazol-3-amine |
| 664 | 2-[[1-(3,5-difluorophenyl)-1,2,4-triazol-3-yl]amino]-N-methyl-6-[4-(oxetan-3-yl)piperazin-1-yl]pyridine-4-carboxamide |
| 665 | 1-(3,4-difluorophenyl)-N-[3-methyl-5-[[(3R)-1-(oxetan-3-yl)-3-piperidyl]oxy]phenyl]-1,2,4-triazol-3-amine |
| 666 | 3-morpholino-5-[(1-pyrazin-2-yl-1,2,4-triazol-3-yl)amino]benzonitrile |
| 667 | 1-(3,5-difluorophenyl)-N-[3-methyl-5-[(2S)-2-methyl-4-(oxetan-3-yl)morpholin-2-yl]phenyl]-1,2,4-triazol-3-amine |
| 668 | 3-[[1-(3,4-difluorophenyl)-1,2,4-triazol-3-yl]amino]-5-morpholino-benzonitrile |
| 669 | N3-(1-isopropylpyrazol-3-yl)-5-methyl-N1-(1-phenyl-1,2,4-triazol-3-yl)benzene-1,3-diamine |

TABLE 2C-continued

Compound Names (IUPAC Nomenclature)

| Cmpd No. | IUPAC Name |
|---|---|
| 670 | 1-(3,5-difluorophenyl)-N-[3-methyl-5-[3-[(3R)-3-methylmorpholin-4-yl]azetidin-1-yl]phenyl]-1,2,4-triazol-3-amine |
| 671 | N-[3-methyl-5-[(3-methyloxetan-3-yl)methoxy]phenyl]-1-[3-(trifluoromethyl)phenyl]-1,2,4-triazol-3-amine |
| 672 | N-[1-(3,5-difluorophenyl)-1,2,4-triazol-3-yl]-6-[4-[(3R)-tetrahydrofuran-3-yl]piperazin-1-yl]-4-(trifluoromethyl)pyridine-2-amine |
| 673 | N-[1-(3,5-difluorophenyl)-1,2,4-triazol-3-yl]-4-methyl-6-[4-[(3R)-tetrahydrofuran-3-yl]piperazin-1-yl]pyridin-2-amine |
| 674 | N-[1-(3,5-difluorophenyl)-1,2,4-triazol-3-yl]-6-morpholino-4-(trifluoromethyl)pyridin-2-amine |
| 675 | methyl 2-[[1-(3,5-difluorophenyl)-1,2,4-triazol-3-yl]amino]-6-morpholino-pyridine-4-carboxylate |
| 676 | 5-methyl-N3-(1-methyl-1,2,4-triazol-3-yl)-N1-(1-phenyl-1,2,4-triazol-3-yl)benzene-1,3-diamine |
| 677 | 1-(3,5-difluorophenyl)-N-[3-methyl-5-[(3-methyloxetan-3-yl)methoxy]phenyl]-1,2,4-triazol-3-amine |
| 678 | 3-[[1-(3,5-difluorophenyl)-1,2,4-triazol-3-yl]amino]-5-[4-(oxetan-3-yl)piperazin-1-yl]benzonitrile |
| 679 | (5S)-5-[3-[[1-(3,5-difluorophenyl)-1,2,4-triazol-3-yl]amino]-5-methyl-phenyl]-5-methyl-oxazolidin-2-one |
| 680 | 4-(difluoromethyl)-6-[4-(oxetan-3-yl)piperazin-1-yl]-N-[1-[3-(trifluoromethyl)phenyl]-1,2,4-triazol-3-yl]pyridin-2-amine |
| 681 | 5-methyl-N1,N3-bis(1-phenyl-1,2,4-triazol-3-yl)benzene-1,3-diamine |
| 682 | (5R)-5-methyl-5-[3-methyl-5-[(1-pyrazin-2-yl-1,2,4-triazol-3-yl)amino]phenyl]oxazolidin-2-one |
| 683 | 1-(3,5-difluorophenyl)-N-[3-methyl-5-(3-methyl-3-morpholino-azetidin-1-yl)phenyl]-1,2,4-triazol-3-amine |
| 684 | 6-[4-(oxetan-3-yl)piperazin-1-yl]-N-[1-(3-pyridyl)-1,2,4-triazol-3-yl]-4-(trifluoromethyl)pyridin-2-amine |
| 685 | 4-(1,1-difluoroethyl)-N-[1-(3,5-difluorophenyl)-1,2,4-triazol-3-yl]-6-[4-(oxetan-3-yl)piperazin-1-yl]pyridin-2-amine |
| 686 | N3-[1-(3,5-difluorophenyl)-1,2,4-triazol-3-yl]-5-fluoro-N1-(oxetan-3-yl)benzene-1,3-diamine |
| 687 | 4-[3-[3-methyl-5-[4-(oxetan-3-yl)piperazin-1-yl]anilino]-1,2,4-triazol-1-yl]benzonitrile |
| 688 | N-[3-(2,6-diazaspiro[3.3]heptan-2-yl)-2-fluoro-5-methyl-phenyl]-1-(3,5-difluorophenyl)-1,2,4-triazol-3-amine |
| 689 | N6-[1-[3-(difluoromethyl)phenyl]-1,2,4-triazol-3-yl]-4-methyl-N2-tetrahydrofuran-3-yl-pyridine-2,6-diamine |
| 690 | [1-[3-[[1-(3,5-difluorophenyl)-1,2,4-triazol-3-yl]amino]-5-methyl-phenyl]azetidin-3-yl]-morpholino-methanone |
| 691 | 1-(3,5-difluorophenyl)-N-[2-fluoro-5-methyl-3-[4-(oxetan-3-yl)piperazin-1-yl]phenyl]-1,2,4-triazol-3-amine |
| 692 | 1-(3,5-difluorophenyl)-N-[3-methyl-5-(8-oxa-3-azabicyclo[3.2.1]octan-3-yl)phenyl]-1,2,4-triazol-3-amine |
| 693 | 1-[3-(difluoromethyl)phenyl]-N-[3-methoxy-5-[4-(oxetan-3-yl)piperazin-1-yl]phenyl]-1,2,4-triazol-3-amine |
| 694 | 1-(3,5-difluorophenyl)-N-[3-methyl-5-(3-oxa-6-azabicyclo[3.1.1]heptan-6-yl)phenyl]-1,2,4-triazol-3-amine |
| 695 | 1-(4-fluorophenyl)-N-[3-methyl-5-[4-(3-methyloxetan-3-yl)piperazin-1-yl]phenyl]-1,2,4-triazol-3-amine |
| 696 | 1-(3,5-difluorophenyl)-N-[3-methyl-5-[3-[(2R)-2-methylmorpholin-4-yl]azetidin-1-yl]phenyl]-1,2,4-triazol-3-amine |
| 697 | 1-(3,5-difluorophenyl)-N-[2,5-dimethyl-3-[4-(oxetan-3-yl)piperazin-1-yl]phenyl]-1,2,4-triazol-3-amine |
| 698 | 1-(3,4-difluorophenyl)-N-[3-methyl-5-(2-pyrazol-1-ylethoxy)phenyl]-1,2,4-triazol-3-amine |
| 699 | 5-methyl-N3-(5-methyl-1H-pyrazol-3-yl)-N1-(1-phenyl-1,2,4-triazol-3-yl)benzene-1,3-diamine |
| 700 | 1-(3,5-difluorophenyl)-N-[3-methyl-5-[[(3S)-1-(oxetan-3-yl)-3-piperidyl]oxy]phenyl]-1,2,4-triazol-3-amine |
| 701 | 1-(3,5-difluorophenyl)-N-[3-(3-morpholinoazetidin-1-yl)-5-[4-(oxetan-3-yl)piperazin-1-yl]phenyl]-1,2,4-triazol-3-amine |
| 702 | 6-(4-tert-butylpiperazin-1-yl)-N-[1-(3,5-difluorophenyl)-1,2,4-triazol-3-yl]-4-methyl-pyridin-2-amine |
| 703 | 1-(3,5-difluorophenyl)-N-(3-methyl-5-tetrahydrofuran-3-yloxy-phenyl)-1,2,4-triazol-3-amine |
| 704 | N-[3-methyl-5-(3-morpholinoazetidin-1-yl)phenyl]-1-phenyl-1,2,4-triazol-3-amine |
| 705 | 5-chloro-N3-[1-(3,5-difluorophenyl)-1,2,4-triazol-3-yl]-N1-(oxetan-3-yl)benzene-1,3-diamine |
| 706 | N-[3-[(3,3-difluorocyclobutyl)methoxy]-5-methyl-phenyl]-1-(3,5-difluorophenyl)-1,2,4-triazol-3-amine |
| 707 | 6-[[1-(3,5-difluorophenyl)-1,2,4-triazol-3-yl]amino]-4-[4-(oxetan-3-yl)piperazin-1-yl]pyridine-2-carbonitrile |
| 708 | 1-(3,5-difluorophenyl)-N-[3-methyl-5-[2-methyl-4-(oxetan-3-yl)morpholin-2-yl]phenyl]-1,2,4-triazol-3-amine |
| 709 | N-[3-(4-tert-butylpiperazin-1-yl)-5-methyl-phenyl]-1-(3,5-difluorophenyl)-1,2,4-triazol-3-amine |
| 710 | 1-(4-methoxyphenyl)-N-[3-methyl-5-[4-(oxetan-3-yl)piperazin-1-yl]phenyl]-1,2,4-triazol-3-amine |
| 711 | 1-[3-[[1-(3,5-difluorophenyl)-1,2,4-triazol-3-yl]amino]-5-methyl-phenyl]-N,N-dimethyl-azetidine-3-carboxamide |
| 712 | 6-[4-(oxetan-3-yl)piperazin-1-yl]-N-(1-pyrazin-2-yl-1,2,4-triazol-3-yl)-4-(trifluoromethyl)pyridin-2-amine |
| 713 | [2-[[1-(3,4-difluorophenyl)-1,2,4-triazol-3-yl]amino]-6-[4-(oxetan-3-yl)piperazin-1-yl]-4-pyridyl]methanol |
| 714 | 1-(3,4-difluorophenyl)-N-[3-methyl-5-[(1-methylpyrazol-3-yl)methoxy]phenyl]-1,2,4-triazol-3-amine |
| 715 | 1-(3-chloro-4-methyl-phenyl)-N-[3-ethyl-5-[4-(oxetan-3-yl)piperazin-1-yl]phenyl]-1,2,4-triazol-3-amine |
| 716 | 4-(difluoromethyl)-N-[1-(3,5-difluorophenyl)-1,2,4-triazol-3-yl]-6-[4-(3-methyloxetan-3-yl)piperazin-1-yl]pyridin-2-amine |
| 717 | 1-(3,5-difluorophenyl)-N-[3-methyl-5-[3-(8-oxa-3-azabicyclo[3.2.1]octan-3-yl)azetidin-1-yl]phenyl]-1,2,4-triazol-3-amine |
| 718 | 4-(difluoromethyl)-N-[1-[3-(difluoromethyl)phenyl]-1,2,4-triazol-3-yl]-6-[4-(oxetan-3-yl)piperazin-1-yl]pyridin-2-amine |
| 719 | 4-(difluoromethyl)-6-(3-morpholinoazetidin-1-yl)-N-[1-[3-(trifluoromethyl)phenyl]-1,2,4-triazol-3-yl]pyridin-2-amine |
| 720 | 1-(3,4-difluorophenyl)-N-[3-methyl-5-(3-morpholinoazetidin-1-yl)phenyl]-1,2,4-triazol-3-amine |
| 721 | 1-(3-fluorophenyl)-N-[3-methyl-5-(3-morpholinoazetidin-1-yl)phenyl]-1,2,4-triazol-3-amine |
| 722 | 1-(3,5-difluorophenyl)-N-[3-methyl-5-(3-oxa-8-azabicyclo[3.2.1]octan-8-yl)phenyl]-1,2,4-triazol-3-amine |
| 723 | N-[3-chloro-5-(3-morpholinoazetidin-1-yl)phenyl]-1-(3,5-difluorophenyl)-1,2,4-triazol-3-amine |
| 724 | 1-(3,5-difluorophenyl)-N-[3-(2,5-dioxa-8-azaspiro[3.5]nonan-8-yl)-5-methyl-phenyl]-1,2,4-triazol-3-amine |
| 725 | 1-[3-(difluoromethyl)phenyl]-N-[3-methyl-5-(4-morpholino-1-piperidyl)phenyl]-1,2,4-triazol-3-amine |
| 726 | N-[1-(3,5-difluorophenyl)-1,2,4-triazol-3-yl]-4,6-bis[4-(oxetan-3-yl)piperazin-1-yl]pyridin-2-amine |
| 727 | 1-(3,5-difluorophenyl)-N-[3-methyl-5-(2-oxa-5-azabicyclo[2.2.1]heptan-5-yl)phenyl]-1,2,4-triazol-3-amine |
| 728 | N-[1-(4-fluorophenyl)-1,2,4-triazol-3-yl]-6-[4-(oxetan-3-yl)piperazin-1-yl]-4-(trifluoromethyl)pyridin-2-amine |
| 729 | 4-(difluoromethyl)-N-[1-(3,5-difluorophenyl)-1,2,4-triazol-3-yl]-6-[4-(methoxymethyl)-1-piperidyl]pyridin-2-amine |
| 730 | 1-(3,5-difluorophenyl)-N-[3-methyl-5-[3-[(2S)-2-methylmorpholin-4-yl]azetidin-1-yl]phenyl]-1,2,4-triazol-3-amine |
| 731 | N-[1-(3,5-difluorophenyl)-1,2,4-triazol-3-yl]-4-methyl-6-(4-methylpiperazin-1-yl)pyridin-2-amine |
| 732 | 4-(difluoromethyl)-N-[1-(3,5-difluorophenyl)-1,2,4-triazol-3-yl]-6-(3-morpholinoazetidin-1-yl)pyridin-2-amine |
| 733 | 6-chloro-N-[1-(3,5-difluorophenyl)-1,2,4-triazol-3-yl]-4-[4-(oxetan-3-yl)piperazin-1-yl]pyridin-2-amine |
| 734 | 3-[3-[3-ethyl-5-[4-(oxetan-3-yl)piperazin-1-yl]anilino]-1,2,4-triazol-1-yl]benzonitrile |
| 735 | 1-(3-fluoro-4-methoxy-phenyl)-N-[3-methyl-5-(3-morpholinoazetidin-1-yl)phenyl]-1,2,4-triazol-3-amine |
| 736 | 1-[3-(difluoromethyl)phenyl]-N-[3-ethyl-5-[4-(oxetan-3-yl)piperazin-1-yl]phenyl]-1,2,4-triazol-3-amine |
| 737 | 3-[[1-(3-fluorophenyl)-1,2,4-triazol-3-yl]amino]-5-morpholino-benzonitrile |
| 738 | N3-[1-(3,5-difluorophenyl)-1,2,4-triazol-3-yl]-N1,5-dimethyl-N1-(2-morpholinoethyl)benzene-1,3-diamine |

TABLE 2C-continued

Compound Names (IUPAC Nomenclature)

| Cmpd No. | IUPAC Name |
|---|---|
| 739 | 1-(3,5-difluorophenyl)-N-[2,3-dimethyl-5-(3-morpholinoazetidin-1-yl)phenyl]-1,2,4-triazol-3-amine |
| 740 | N-[1-(3,5-difluorophenyl)-1,2,4-triazol-3-yl]-4-methyl-6-[4-[(3S)-tetrahydrofuran-3-yl]piperazin-1-yl]pyridin-2-amine |
| 741 | 5-methyl-5-[3-methyl-5-[(1-pyrazin-2-yl-1,2,4-triazol-3-yl)amino]phenyl]oxazolidin-2-one |
| 742 | 1-(3,5-difluorophenyl)-N-[3-methyl-5-[3-(6-oxa-3-azabicyclo[3.1.1]heptan-3-yl)azetidin-1-yl]phenyl]-1,2,4-triazol-3-amine |
| 743 | 1-(3,5-difluorophenyl)-N-[2-fluoro-5-methyl-3-(2-oxa-6-azaspiro[3.3]heptan-6-yl)phenyl]-1,2,4-triazol-3-amine |
| 744 | N-[1-(3,5-difluorophenyl)-1,2,4-triazol-3-yl]-4-methyl-6-(4-piperidyl)pyridin-2-amine |
| 745 | N-[3-[4-(3,3-difluoroazetidin-1-yl)-1-piperidyl]-5-methyl-phenyl]-1-(3,5-difluorophenyl)-1,2,4-triazol-3-amine |
| 746 | 1-(3,5-difluorophenyl)-N-[3-methyl-5-[3-(3-oxa-8-azabicyclo[3.2.1]octan-8-yl)azetidin-1-yl]phenyl]-1,2,4-triazol-3-amine |
| 747 | 1-(3,5-difluorophenyl)-N-[3-[4-[3-(dimethylamino)propyl]piperazin-1-yl]-5-methyl-phenyl]-1,2,4-triazol-3-amine |
| 748 | 1-(3,5-difluorophenyl)-N-[3-methyl-5-[[(3R)-1-(oxetan-3-yl)-3-piperidyl]oxy]phenyl]-1,2,4-triazol-3-amine |
| 749 | N-[1-(4-chloro-3-fluoro-phenyl)-1,2,4-triazol-3-yl]-4-methyl-6-[4-(oxetan-3-yl)piperazin-1-yl]pyridin-2-amine |
| 750 | 1-(3,5-difluorophenyl)-N-[3-methyl-5-[(2R)-2-methyl-4-(oxetan-3-yl)morpholin-2-yl]phenyl]-1,2,4-triazol-3-amine |
| 751 | 1-(3,5-difluorophenyl)-N-[3-methyl-5-[(2R)-4-(oxetan-3-yl)morpholin-2-yl]phenyl]-1,2,4-triazol-3-amine |
| 752 | 1-(3,5-difluorophenyl)-N-[3-methyl-5-(3-morpholinocyclobutoxy)phenyl]-1,2,4-triazol-3-amine |
| 753 | N-[3-chloro-5-(3-morpholinoazetidin-1-yl)phenyl]-1-pyrazin-2-yl-1,2,4-triazol-3-amine |
| 754 | 1-[3-fluoro-5-(trifluoromethyl)phenyl]-N-[3-methoxy-5-[4-(oxetan-3-yl)piperazin-1-yl]phenyl]-1,2,4-triazol-3-amine |
| 755 | 1-[6-[[1-(3,5-difluorophenyl)-1,2,4-triazol-3-yl]amino]-4-methyl-2-pyridyl]piperidin-3-ol |
| 756 | 4-(difluoromethyl)-N-[1-[3-(difluoromethyl)phenyl]-1,2,4-triazol-3-yl]-6-(3-morpholinoazetidin-1-yl)pyridin-2-amine |
| 757 | 1-[3-fluoro-5-(trifluoromethyl)phenyl]-N-[3-methyl-5-[4-(oxetan-3-yl)piperazin-1-yl]phenyl]-1,2,4-triazol-3-amine |
| 758 | N-[1-(4-chloro-3-fluoro-phenyl)-1,2,4-triazol-3-yl]-4-methoxy-6-[4-(oxetan-3-yl)piperazin-1-yl]pyridin-2-amine |
| 759 | 3-[3-[3-methyl-5-[4-(oxetan-3-yl)piperazin-1-yl]anilino]-1,2,4-triazol-1-yl]benzonitrile |
| 760 | N-[1-(3,5-difluorophenyl)-1,2,4-triazol-3-yl]-2-[4-(oxetan-3-yl)piperazin-1-yl]-6-(trifluoromethyl)pyridin-4-amine |
| 761 | N-[3-ethyl-5-[4-(oxetan-3-yl)piperazin-1-yl]phenyl]-1-(3-fluoro-4-methyl-phenyl)-1,2,4-triazol-3-amine |
| 762 | 4-[3-[3-ethyl-5-[4-(oxetan-3-yl)piperazin-1-yl]anilino]-1,2,4-triazol-1-yl]benzonitrile |
| 763 | 3-morpholino-5-[[1-(3-pyridyl)-1,2,4-triazol-3-yl]amino]benzonitrile |
| 764 | N-[1-(3,5-difluorophenyl)-1,2,4-triazol-3-yl]-6-(3-methoxy-1-piperidyl)-4-methyl-pyridin-2-amine |
| 765 | N3-[1-(3,5-difluorophenyl)-1,2,4-triazol-3-yl]-2-fluoro-5-methyl-N1-tetrahydrofuran-3-yl-benzene-1,3-diamine |
| 766 | N-[3-(3-fluoroazetidin-1-yl)-5-methyl-phenyl]-1-[3-fluoro-5-(2-methoxyethylamino)phenyl]-1,2,4-triazol-3-amine |
| 767 | 1-(3-chloro-4-methyl-phenyl)-N-[3-methyl-5-[4-(oxetan-3-yl)piperazin-1-yl]phenyl]-1,2,4-triazol-3-amine |
| 768 | N-[1-[3-(difluoromethyl)phenyl]-1,2,4-triazol-3-yl]-4-methyl-6-(3-morpholinoazetidin-1-yl)pyridin-2-amine |
| 769 | N-[3-(2-cyclopropylethynyl)-5-methyl-phenyl]-1-(3-fluorophenyl)-1,2,4-triazol-3-amine |
| 770 | N-[1-(3,4-difluorophenyl)-1,2,4-triazol-3-yl]-6-morpholino-4-(trifluoromethyl)pyridin-2-amine |
| 771 | 1-(3,5-difluorophenyl)-N-[3-methyl-5-(3,3,4-trimethylpiperazin-1-yl)phenyl]-1,2,4-triazol-3-amine |
| 772 | 1-(3,5-difluorophenyl)-N-[3-methyl-5-[4-(4-methylpiperazin-1-yl)-1-piperidyl]phenyl]-1,2,4-triazol-3-amine |
| 773 | [1-[3-[[1-(3,5-difluorophenyl)-1,2,4-triazol-3-yl]amino]-5-methyl-phenyl]azetidin-3-yl]-pyrrolidin-1-yl-methanone |
| 774 | N-[1-(3,5-difluorophenyl)-1,2,4-triazol-3-yl]-6-(3,6-dihydro-2H-pyran-4-yl)-4-methyl-pyridin-2-amine |
| 775 | 3-[3-[[1-(3,5-difluorophenyl)-1,2,4-triazol-3-yl]amino]-5-fluoro-phenyl]oxetan-3-ol |
| 776 | 1-(2-fluoro-4-pyridyl)-N-[3-methyl-5-[4-(oxetan-3-yl)-1,4-diazepan-1-yl]phenyl]-1,2,4-triazol-3-amine |
| 777 | 4-(difluoromethyl)-N-[1-(3,5-difluorophenyl)-1,2,4-triazol-3-yl]-6-(2-oxa-8-azaspiro[3.5]nonan-8-yl)pyridin-2-amine |
| 778 | 1-(3,4-difluorophenyl)-N-(3-methyl-5-tetrahydrofuran-3-yloxy-phenyl)-1,2,4-triazol-3-amine |
| 779 | 1-(3-fluoro-4-methyl-phenyl)-N-[3-fluoro-5-[4-(oxetan-3-yl)piperazin-1-yl]phenyl]-1,2,4-triazol-3-amine |
| 780 | 1-(4-fluoro-3-methyl-phenyl)-N-[3-methyl-5-[4-(oxetan-3-yl)piperazin-1-yl]phenyl]-1,2,4-triazol-3-amine |
| 781 | 1-(3-fluoro-4-methoxy-phenyl)-N-[3-fluoro-5-[4-(oxetan-3-yl)piperazin-1-yl]phenyl]-1,2,4-triazol-3-amine |
| 782 | 1-(3,5-difluoro-4-methoxy-phenyl)-N-[3-methyl-5-(3-morpholinoazetidin-1-yl)phenyl]-1,2,4-triazol-3-amine |
| 783 | N-[3-fluoro-5-[4-(oxetan-3-yl)piperazin-1-yl]phenyl]-1-(2-fluoro-4-pyridyl)-1,2,4-triazol-3-amine |
| 784 | N-[3-chloro-5-(3-morpholinoazetidin-1-yl)phenyl]-1-(3,4-difluorophenyl)-1,2,4-triazol-3-amine |
| 785 | N-[3-chloro-5-(3-morpholinoazetidin-1-yl)phenyl]-1-(2-pyridyl)-1,2,4-triazol-3-amine |
| 786 | N-[1-(3,5-difluorophenyl)-1,2,4-triazol-3-yl]-6-[3-(methoxymethyl)-1-piperidyl]-4-methyl-pyridin-2-amine |
| 787 | N-[1-(3,5-difluorophenyl)-1,2,4-triazol-3-yl]-6-[4-[(3S)-tetrahydrofuran-3-yl]piperazin-1-yl]-4-(trifluoromethyl)pyridin-2-amine |
| 788 | 1-(3,5-difluorophenyl)-N-[3-methyl-5-[3-(2-oxa-5-azabicyclo[2.2.1]heptan-5-yl)azetidin-1-yl]phenyl]-1,2,4-triazol-3-amine |
| 789 | 2-[[1-(3,4-difluorophenyl)-1,2,4-triazol-3-yl]amino]-N-methyl-6-[4-(oxetan-3-yl)piperazin-1-yl]pyridine-4-carboxamide |
| 790 | 1-(3,5-difluorophenyl)-N-[2-fluoro-5-methyl-3-(3-morpholinoazetidin-1-yl)phenyl]-1,2,4-triazol-3-amine |
| 791 | 2-[[1-[3-[[1-(3,5-difluorophenyl)-1,2,4-triazol-3-yl]amino]-5-methyl-phenyl]azetidin-3-yl]amino]ethanol |
| 792 | N1-[1-(3,4-difluorophenyl)-1,2,4-triazol-3-yl]-5-methyl-N3-(3-morpholinocyclobutyl)benzene-1,3-diamine |
| 793 | 3-[[1-(3-fluorophenyl)-1,2,4-triazol-3-yl]amino]-5-[4-(oxetan-3-yl)piperazin-1-yl]benzonitrile |
| 794 | 1-[3-(difluoromethyl)phenyl]-N-[3-fluoro-5-[4-(oxetan-3-yl)piperazin-1-yl]phenyl]-1,2,4-triazol-3-amine |
| 795 | 4-(difluoromethyl)-6-[4-(methoxymethyl)-1-piperidyl]-N-[1-[3-(trifluoromethyl)phenyl]-1,2,4-triazol-3-yl]pyridin-2-amine |
| 796 | (5R)-5-[3-[[1-(3,5-difluorophenyl)-1,2,4-triazol-3-yl]amino]-5-methyl-phenyl]-3,5-dimethyl-oxazolidin-2-one |
| 797 | N3-[1-(3,5-difluorophenyl)-1,2,4-triazol-3-yl]-5-methyl-N1-(3-morpholinocyclobutyl)benzene-1,3-diamine |
| 798 | N-[3-(2-cyclopropylethynyl)-5-methyl-phenyl]-1-(3,5-difluorophenyl)-1,2,4-triazol-3-amine |
| 799 | N3-[1-(3,4-difluorophenyl)-1,2,4-triazol-3-yl]-5-methyl-N1-(3-morpholinocyclobutyl)benzene-1,3-diamine |
| 800 | 1-(3,5-difluorophenyl)-N-[3-methyl-5-[3-[(3S)-3-methylmorpholin-4-yl]azetidin-1-yl]phenyl]-1,2,4-triazol-3-amine |
| 801 | N-[1-(3,5-difluorophenyl)-1,2,4-triazol-3-yl]-4-methyl-6-[1-(oxetan-3-yl)-4-piperidyl]pyridin-2-amine |
| 802 | N-[3-ethyl-5-[4-(3-methyloxetan-3-yl)piperazin-1-yl]phenyl]-1-(4-fluorophenyl)-1,2,4-triazol-3-amine |
| 803 | 1-(3,4-difluorophenyl)-N-[3-fluoro-5-[4-(oxetan-3-yl)piperazin-1-yl]phenyl]-1,2,4-triazol-3-amine |
| 804 | N-[3-(difluoromethyl)]-5-(3-morpholinoazetidin-1-yl)phenyl]-1-(3,5-difluorophenyl)-1,2,4-triazol-3-amine |
| 805 | 1-[4-[3-[[1-(3,5-difluorophenyl)-1,2,4-triazol-3-yl]amino]-5-methyl-phenoxy]-1-piperidyl]ethanone |
| 806 | 4-(difluoromethyl)-N-[1-(4-fluorophenyl)-1,2,4-triazol-3-yl]-6-[4-(oxetan-3-yl)piperazin-1-yl]pyridin-2-amine |
| 807 | N-[1-[3-(difluoromethyl)phenyl]-1,2,4-triazol-3-yl]-6-[4-(methoxymethyl)-1-piperidyl]-4-(trifluoromethyl)pyridin-2-amine |

TABLE 2C-continued

Compound Names (IUPAC Nomenclature)

| Cmpd No. | IUPAC Name |
|---|---|
| 808 | 1-(3,5-difluorophenyl)-N-[3-methyl-5-[3-(1,4-oxazepan-4-yl)azetidin-1-yl]phenyl]-1,2,4-triazol-3-amine |
| 809 | 1-(3,5-difluorophenyl)-N-[3-[4-[2-(dimethylamino)ethyl]piperazin-1-yl]-5-methyl-phenyl]-1,2,4-triazol-3-amine |
| 810 | N3-[1-(3,5-difluorophenyl)-1,2,4-triazol-3-yl]-2-fluoro-5-methyl-N1-tetrahydropyran-4-yl-benzene-1,3-diamine |
| 811 | N-[3-isopropoxy-2-methyl-5-(3-morpholinoazetidin-1-yl)phenyl]-1-(2-pyridyl)-1,2,4-triazol-3-amine |
| 812 | 1-(3,5-difluorophenyl)-N-[3-methyl-5-(2-morpholinoethoxy)phenyl]-1,2,4-triazol-3-amine |
| 813 | N-[3-[3-[[1-(3,5-difluorophenyl)-1,2,4-triazol-3-yl]amino]-5-methyl-phenoxy]cyclobutyl]acetamide |
| 814 | 1-(3,5-difluorophenyl)-N-[3-methyl-5-(2-oxa-8-azaspiro[4.5]decan-8-yl)phenyl]-1,2,4-triazol-3-amine |
| 815 | [1-[6-[[1-(3,5-difluorophenyl)-1,2,4-triazol-3-yl]amino]-4-methyl-2-pyridyl]-3-piperidyl]methanol |
| 816 | 1-(3,5-difluorophenyl)-N-[3-[3-(2-methoxyethylamino)azetidin-1-yl]-5-methyl-phenyl]-1,2,4-triazol-3-amine |
| 817 | 1-[3-[[1-(3,5-difluorophenyl)-1,2,4-triazol-3-yl]amino]-5-methyl-phenyl]-N,N-diethyl-azetidine-3-carboxamide |
| 818 | N-[3-methyl-5-[4-(oxetan-3-yl)-1,4-diazepan-1-yl]phenyl]-1-pyrazin-2-yl-1,2,4-triazol-3-amine |
| 819 | N-[3-chloro-5-(3-morpholinoazetidin-1-yl)phenyl]-1-(2-fluoro-4-pyridyl)-1,2,4-triazol-3-amine |
| 820 | 1-(3,5-difluorophenyl)-N-[2,5-dimethyl-3-(3-morpholinoazetidin-1-yl)phenyl]-1,2,4-triazol-3-amine |
| 821 | 1-[6-[[1-(3,5-difluorophenyl)-1,2,4-triazol-3-yl]amino]-4-methyl-2-pyridyl]azetidine-3-carbonitrile |
| 822 | 1-(3,5-difluorophenyl)-N-[3-methyl-5-[(1S,4S)-2-oxa-5-azabicyclo[2.2.1]heptan-5-yl]phenyl]-1,2,4-triazol-3-amine |
| 823 | 4-(difluoromethyl)-N-[1-(1-fluorophenyl)-1,2,4-triazol-3-yl]-6-[4-(3-methyloxetan-3-yl)piperazin-1-yl]pyridin-2-amine |
| 824 | 1-[3-[[1-(3,5-difluorophenyl)-1,2,4-triazol-3-yl]amino]-5-methyl-phenyl]-N-(2-methoxyethyl)-N-methyl-azetidine-3-carboxamide |
| 825 | N-[3-methyl-5-[3-(1,4-oxazepan-4-yl)azetidin-1-yl]phenyl]-1-pyrazin-2-yl-1,2,4-triazol-3-amine |
| 826 | N1-[1-(3,4-difluorophenyl)-1,2,4-triazol-3-yl]-5-methyl-N3-(3-morpholinocyclobutyl)benzene-1,3-diamine |
| 827 | N-[3-chloro-5-(3-morpholinoazetidin-1-yl)phenyl]-1-(3-fluorophenyl)-1,2,4-triazol-3-amine |
| 828 | 5-methyl-N3-(1-methylpyrazol-3-yl)-N1-(1-phenyl-1,2,4-triazol-3-yl)benzene-1,3-diamine |
| 829 | N-[3-ethyl-5-[4-(oxetan-3-yl)piperazin-1-yl]phenyl]-1-(4-fluoro-3-methyl-phenyl)-1,2,4-triazol-3-amine |
| 830 | 1-(3,5-difluorophenyl)-N-[3-isopropoxy-5-(3-morpholinoazetidin-1-yl)phenyl]-1,2,4-triazol-3-amine |
| 831 | N-[3-[(8aS)-7,7-difluoro-1,3,4,6,8,8a-hexahydropyrrolo[1,2-a]pyrazin-2-yl]-5-methyl-phenyl]-1-(3,5-difluorophenyl)-1,2,4-triazol-3-amine |
| 832 | 1-(3,5-difluorophenyl)-N-[3-methyl-5-(2-pyrazol-1-ylethoxy)phenyl]-1,2,4-triazol-3-amine |
| 833 | 1-[3-(difluoromethyl)phenyl]-N-[3-methyl-5-[4-(oxetan-3-yl)piperazin-1-yl]phenyl]-1,2,4-triazol-3-amine |
| 834 | 1-(3,4-difluorophenyl)-N-[2-fluoro-5-methyl-3-[[4-(oxetan-3-yl)piperazin-1-yl]methyl]phenyl]-1,2,4-triazol-3-amine |
| 835 | 3-[[1-(3,5-difluorophenyl)-1,2,4-triazol-3-yl]amino]-5-morpholino-benzonitrile |
| 836 | 1-(3-fluoro-4-methyl-phenyl)-N-[3-methyl-5-[4-(oxetan-3-yl)piperazin-1-yl]phenyl]-1,2,4-triazol-3-amine |
| 837 | 4-methyl-6-morpholino-N-[1-[3-(trifluoromethyl)phenyl]-1,2,4-triazol-3-yl]pyridin-2-amine |
| 838 | 5-methyl-N1-oxazol-2-yl-N3-(1-phenyl-1,2,4-triazol-3-yl)benzene-1,3-diamine |
| 839 | N-[1-(3,5-difluorophenyl)-1,2,4-triazol-3-yl]-6-[4-(methoxymethyl)-1-piperidyl]-4-(trifluoromethyl)pyridin-2-amine |
| 840 | 1-(3,4-difluorophenyl)-N-[3-methyl-5-[[4-(oxetan-3-yl)piperazin-1-yl]methyl]phenyl]-1,2,4-triazol-3-amine |
| 841 | 1-(4-methoxyphenyl)-N-[3-methyl-5-(3-morpholinoazetidin-1-yl)phenyl]-1,2,4-triazol-3-amine |
| 842 | 3-[4-(oxetan-3-yl)piperazin-1-yl]-5-[[1-(3-pyridyl)-1,2,4-triazol-3-yl]amino]benzonitrile |
| 843 | 6-(2,3,3a,4,6,6a-hexahydrofuro[2,3-c]pyrrol-5-yl)-N-[1-(3,5-difluorophenyl)-1,2,4-triazol-3-yl]-4-methyl-pyridin-2-amine |
| 845 | 1-(3,4-difluorophenyl)-N-[3-methyl-5-(2-morpholinoethoxy)phenyl]-1,2,4-triazol-3-amine |
| 846 | 3,5-dimethyl-5-[3-methyl-5-[(1-pyrazin-2-yl-1,2,4-triazol-3-yl)amino]phenyl]oxazolidin-2-one |
| 847 | N-[1-(3,5-difluorophenyl)-1,2,4-triazol-3-yl]-6-fluoro-4-[4-(oxetan-3-yl)piperazin-1-yl]pyridin-2-amine |
| 848 | N-[1-(3-difluorophenyl)-1,2,4-triazol-3-yl]-4-methyl-6-[4-(oxetan-3-yl)piperazin-1-yl]pyridin-2-amine |
| 849 | 4-(difluoromethyl)-N-[1-(3,4-difluorophenyl)-1,2,4-triazol-3-yl]-6-[4-(3-methyloxetan-3-yl)piperazin-1-yl]pyridin-2-amine |
| 850 | 1-(3,5-difluorophenyl)-N-[3-[4-(3-methoxypropyl)piperazin-1-yl]-5-methyl-phenyl]-1,2,4-triazol-3-amine |
| 851 | 1-(3,5-difluorophenyl)-N-[3-methyl-5-(1-oxa-8-azaspiro[4.5]decan-8-yl)phenyl]-1,2,4-triazol-3-amine |
| 852 | 2-[3-fluoro-5-[3-(3-fluoroazetidin-1-yl)-5-methyl-anilino]-1,2,4-triazol-1-yl]anilino]ethanol |
| 853 | 2-[[1-(3,5-difluorophenyl)-1,2,4-triazol-3-yl]amino]-6-[4-(oxetan-3-yl)piperazin-1-yl]pyridine-4-carbonitrile |
| 854 | N-[3-methyl-5-(4-morpholino-1-piperidyl)phenyl]-1-[3-(trifluoromethyl)phenyl]-1,2,4-triazol-3-amine |
| 855 | N-[1-(3,5-difluorophenyl)-1,2,4-triazol-3-yl]-6-[4-(2-methoxyethyl)-1-piperidyl]-4-methyl-pyridin-2-amine |
| 856 | 1-(3,5-difluorophenyl)-N-(2-fluoro-5-methyl-3-tetrahydrofuran-3-yloxy-phenyl)-1,2,4-triazol-3-amine |
| 857 | 1-(3,5-difluorophenyl)-N-[3-[3-[(2R,6R)-2,6-dimethylmorpholin-4-yl]azetidin-1-yl]-5-methyl-phenyl]-1,2,4-triazol-3-amine |
| 858 | N1-[1-(3,5-difluorophenyl)-1,2,4-triazol-3-yl]-5-methyl-N3-(2-morpholinoethyl)benzene-1,3-diamine |
| 859 | N-[1-(3-chloro-4-fluoro-phenyl)-1,2,4-triazol-3-yl]-4-(difluoromethyl)-6-[4-(oxetan-3-yl)piperazin-1-yl]pyridin-2-amine |
| 860 | 4-(1,1-difluoroethyl)-N-[1-(3-fluorophenyl)-1,2,4-triazol-3-yl]-6-[4-(oxetan-3-yl)piperazin-1-yl]pyridin-2-amine |
| 861 | N1-[1-(3,5-difluorophenyl)-1,2,4-triazol-3-yl]-5-methyl-N3-(3-morpholinocyclobutyl)benzene-1,3-diamine |
| 862 | N-[3-isopropoxy-2-methyl-5-[4-(oxetan-3-yl)piperazin-1-yl]phenyl]-1-(2-pyridyl)-1,2,4-triazol-3-amine |
| 863 | N-[3-chloro-5-(3-morpholinoazetidin-1-yl)phenyl]-1-pyrimidin-4-yl-1,2,4-triazol-3-amine |
| 864 | [3-[[1-(3,5-difluorophenyl)-1,2,4-triazol-3-yl]amino]-5-methyl-phenyl]-[4-(oxetan-3-yl)piperazin-1-yl]methanone |
| 865 | 1-(3,4-difluorophenyl)-N-[3-methyl-5-(tetrahydrofuran-3-ylmethoxy)phenyl]-1,2,4-triazol-3-amine |
| 866 | 1-(3,5-difluorophenyl)-N-[3-methyl-5-[3-(morpholinomethyl)azetidin-1-yl]phenyl]-1,2,4-triazol-3-amine |
| 867 | 4-(difluoromethyl)-6-morpholino-N-[1-[3-(trifluoromethyl)phenyl]-1,2,4-triazol-3-yl]pyridin-2-amine |
| 868 | N-[3,5-bis(3-morpholinoazetidin-1-yl)phenyl]-1-(3,5-difluorophenyl)-1,2,4-triazol-3-amine |
| 869 | N3-[1-(3,5-difluorophenyl)-1,2,4-triazol-3-yl]-2-fluoro-5-methyl-N1-(3-methyloxetan-3-yl)benzene-1,3-diamine |

TABLE 2D

Compound Names (IUPAC Nomenclature)

| Cmpd No. | IUPAC Name |
|---|---|
| 870 | 1-(3,5-difluorophenyl)-N-[2-fluoro-3-methyl-5-(3-morpholinoazetidin-1-yl)phenyl]-1,2,4-triazol-3-amine |
| 871 | 1-(3,5-difluorophenyl)-N-[3-methyl-5-(3-methyl-4-morpholino-pyrrolidin-1-yl)phenyl]-1,2,4-triazol-3-amine |

TABLE 2D-continued

Compound Names (IUPAC Nomenclature)

| Cmpd No. | IUPAC Name |
|---|---|
| 872 | N3-[1-(3,5-difluorophenyl)-1,2,4-triazol-3-yl]-N1-[2-(3-ethylmorpholin-4-yl)ethyl]-5-methyl-benzene-1,3-diamine |
| 873 | N3-[1-(3,5-difluorophenyl)-1,2,4-triazol-3-yl]-N1-[1-(2-fluoroethyl)-3-piperidyl]-5-methyl-benzene-1,3-diamine |
| 874 | 2-[1-[3-[[1-(3,5-difluorophenyl)-1,2,4-triazol-3-yl]amino]-5-methyl-phenyl]-4-piperidyl]ethanol |
| 875 | 2-[4-[3-[[1-(3,5-difluorophenyl)-1,2,4-triazol-3-yl]amino]-5-methyl-phenyl]piperazin-1-yl]cyclopentanol |
| 876 | N-[3-(2,2,3,3,4,4,5,5,6,6-decadeuterio-1-piperidyl)-5-(difluoromethyl)phenyl]-1-(3,5-difluorophenyl)-1,2,4-triazol-3-amine |
| 877 | 3-[1-[3-[[1-(3,5-difluorophenyl)-1,2,4-triazol-3-yl]amino]-5-methyl-phenyl]-4-piperidyl]propan-1-ol |
| 878 | 2-[4-[3-[[1-(3,5-difluorophenyl)-1,2,4-triazol-3-yl]amino]-5-methyl-phenyl]piperazin-1-yl]cyclohexanol |
| 879 | 1-[1-[3-[[1-(3,5-difluorophenyl)-1,2,4-triazol-3-yl]amino]-5-methyl-phenyl]-4-piperidyl]piperidin-4-ol |
| 880 | N3-[1-(3,5-difluorophenyl)-1,2,4-triazol-3-yl]-5-methyl-N1-[1-(2-morpholinoethyl)pyrrolidin-3-yl]benzene-1,3-diamine |
| 881 | N3-[1-(3,5-difluorophenyl)-1,2,4-triazol-3-yl]-5-methyl-N1-[1-(oxetan-3-yl)azetidin-3-yl]benzene-1,3-diamine |
| 882 | N1-[1-(3,5-difluorophenyl)-1,2,4-triazol-3-yl]-N3-[2-(2,6-dimethylmorpholin-4-yl)propyl]-5-methyl-benzene-1,3-diamine |
| 883 | cyclopropyl-[2,2,3,3,5,5,6,6-octadeuterio-4-[3-[[1-(3,5-difluorophenyl)-1,2,4-triazol-3-yl]amino]-5-(trifluoromethyl)phenyl]piperazin-1-yl]methanone |
| 884 | N3-[1-(3,5-difluorophenyl)-1,2,4-triazol-3-yl]-5-methyl-N1-(3-pyrrolidin-1-yltetrahydropyran-4-yl)benzene-1,3-diamine |
| 885 | 1-(3,5-difluorophenyl)-N-[3-methyl-5-[2,2,3,3,5,5,6,6-octadeuterio-4-(1,4-dioxan-2-ylmethyl)piperazin-1-yl]phenyl]-1,2,4-triazol-3-amine |
| 886 | N-(2-fluoro-5-methyl-3-tetrahydrofuran-3-yloxy-phenyl)-1-(3-fluorophenyl)-1,2,4-triazol-3-amine |
| 887 | 1-[3-[[1-(3,5-difluorophenyl)-1,2,4-triazol-3-yl]amino]-5-methyl-anilino]-N,N-dimethyl-cyclobutanecarboxamide |
| 888 | 1-(3,5-difluorophenyl)-N-[3-methyl-5-(2-tetrahydrofuran-2-ylmorpholin-4-yl)phenyl]-1,2,4-triazol-3-amine |
| 889 | N-[3-(1,4-diazabicyclo[3.2.1]octan-4-yl)-5-methyl-phenyl]-1-(3,5-difluorophenyl)-1,2,4-triazol-3-amine |
| 890 | 1-(3,5-difluorophenyl)-N-[3-methyl-5-(3-tetrahydrofuran-3-ylazetidin-1-yl)phenyl]-1,2,4-triazol-3-amine |
| 891 | N3-[1-(3,5-difluorophenyl)-1,2,4-triazol-3-yl]-5-methyl-N1-[1-(tetrahydrofuran-2-ylmethyl)-4-piperidyl]benzene-1,3-diamine |
| 892 | 1-(3,5-difluorophenyl)-N-[3-methyl-5-[4-(1-methyl-3-piperidyl)piperazin-1-yl]phenyl]-1,2,4-triazol-3-amine |
| 893 | N3-[1-(3,5-difluorophenyl)-1,2,4-triazol-3-yl]-N1-[(4-ethylmorpholin-2-yl)methyl]-5-methyl-benzene-1,3-diamine |
| 894 | N3-[1-(3,5-difluorophenyl)-1,2,4-triazol-3-yl]-N1-[1-(2-methoxyethyl)pyrrolidin-3-yl]-5-methyl-benzene-1,3-diamine |
| 895 | N1-[1-(3,5-difluorophenyl)-1,2,4-triazol-3-yl]-5-methyl-N3-[(2-morpholinocyclopentyl)methyl]benzene-1,3-diamine |
| 896 | 1-(3,5-difluorophenyl)-N-[3-[4-(3-methoxypropyl)-1,4-diazepan-1-yl]-5-methyl-phenyl]-1,2,4-triazol-3-amine |
| 897 | N3-[1-(3,5-difluorophenyl)-1,2,4-triazol-3-yl]-N1-(1-ethyl-3-piperidyl)-5-methyl-benzene-1,3-diamine |
| 898 | N-[3-[4-(3-deuteriooxetan-3-yl)piperazin-1-yl]-5-methyl-phenyl]-1-phenyl-1,2,4-triazol-3-amine |
| 899 | N1-[1-(3,5-difluorophenyl)-1,2,4-triazol-3-yl]-5-methyl-N3-(3,3,3-trifluoro-2-morpholino-propyl)benzene-1,3-diamine |
| 900 | 1-[4-[3-[[1-(3,5-difluorophenyl)-1,2,4-triazol-3-yl]amino]-5-methyl-phenyl]piperazin-1-yl]-3-ethoxy-propan-2-ol |
| 901 | 1-(3,5-difluorophenyl)-N-[3-methyl-5-(1-oxa-7-azaspiro[3.4]octan-7-yl)phenyl]-1,2,4-triazol-3-amine |
| 902 | 2-[4-[3-[[1-(3,5-difluorophenyl)-1,2,4-triazol-3-yl]amino]-5-methyl-phenyl]-2-methyl-piperazin-1-yl]ethanol |
| 903 | N1-[1-(3,5-difluorophenyl)-1,2,4-triazol-3-yl]-N3-[(4-isobutylmorpholin-2-yl)methyl]-5-methyl-benzene-1,3-diamine |
| 904 | 2-[4-[3-[[1-(3,5-difluorophenyl)-1,2,4-triazol-3-yl]amino]-5-methyl-phenyl]piperazin-1-yl]butan-1-ol |
| 905 | 1-cyclopentyl-4-[3-[[1-(3,5-difluorophenyl)-1,2,4-triazol-3-yl]amino]-5-methyl-phenyl]piperazin-2-one |
| 906 | 1-(3,5-difluorophenyl)-N-[3-(3,7-dioxa-10-azaspiro[5.6]dodecan-10-yl)-5-methyl-phenyl]-1,2,4-triazol-3-amine |
| 907 | N-(2-fluoro-5-methyl-3-tetrahydrofuran-3-yloxy-phenyl)-1-phenyl-1,2,4-triazol-3-amine |
| 908 | N-[2-fluoro-5-methyl-3-[4-(oxetan-3-yl)piperazin-1-yl]phenyl]-1-(2-pyridyl)-1,2,4-triazol-3-amine |
| 909 | 1-(3,5-difluorophenyl)-N-[2,3-dimethyl-5-(oxetan-3-ylmethoxy)phenyl]-1,2,4-triazol-3-amine |
| 910 | 1-cyclobutyl-3-[3-methyl-5-[(1-phenyl-1,2,4-triazol-3-yl)amino]phenyl]urea |
| 911 | 1-(3,5-difluorophenyl)-N-[3-methyl-5-(3-morpholino-1-piperidyl)phenyl]-1,2,4-triazol-3-amine |
| 912 | N3-[1-(3,5-difluorophenyl)-1,2,4-triazol-3-yl]-5-methyl-N1-(2-morpholinocyclopentyl)benzene-1,3-diamine |
| 913 | N-(2-fluoro-5-methyl-3-tetrahydrofuran-3-yloxy-phenyl)-1-(3-fluorophenyl)-1,2,4-triazol-3-amine |
| 914 | 1-(3,5-difluorophenyl)-N-[3-methyl-5-[4-(tetrahydrofuran-2-ylmethyl)piperazin-1-yl]phenyl]-1,2,4-triazol-3-amine |
| 915 | N3-[1-(3,5-difluorophenyl)-1,2,4-triazol-3-yl]-2-fluoro-5-methyl-N1-(oxetan-3-yl)benzene-1,3-diamine |
| 916 | 1-(3,5-difluorophenyl)-N-[3-methyl-5-(2,2,3,3,5,5,6,6-octadeuteriopiperazin-1-yl)phenyl]-1,2,4-triazol-3-amine |
| 917 | N3-[1-(3,5-difluorophenyl)-1,2,4-triazol-3-yl]-N1-[2-(2-ethylmorpholin-4-yl)ethyl]-5-methyl-benzene-1,3-diamine |
| 918 | N1-(2-cyclopropyltetrahydropyran-4-yl)-N3-[1-(3,5-difluorophenyl)-1,2,4-triazol-3-yl]-5-methyl-benzene-1,3-diamine |
| 919 | 1-(3,5-difluorophenyl)-N-[3-methyl-5-[(2S)-2-(morpholinomethyl)pyrrolidin-1-yl]phenyl]-1,2,4-triazol-3-amine |
| 920 | 1-(3,5-difluorophenyl)-N-[3-methyl-5-(2-methyl-4-morpholino-pyrrolidin-1-yl)phenyl]-1,2,4-triazol-3-amine |
| 921 | 2-[1-[3-[[1-(3,5-difluorophenyl)-1,2,4-triazol-3-yl]amino]-5-methyl-phenyl]azetidin-3-yl]acetonitrile |
| 922 | 2-[2,2,3,3,5,5,6,6-octadeuterio-4-[3-[[1-(3,5-difluorophenyl)-1,2,4-triazol-3-yl]amino]-5-methyl-phenyl]piperazin-1-yl]ethanol |
| 923 | [3-acetoxy-2-[4-[3-[[1-(3,5-difluorophenyl)-1,2,4-triazol-3-yl]amino]-2-fluoro-5-methyl-phenyl]piperazin-1-yl]propyl]acetate |
| 924 | 1-(3,5-difluorophenyl)-N-[3-methyl-5-(7-oxa-1-azaspiro[3.5]nonan-1-yl)phenyl]-1,2,4-triazol-3-amine |
| 925 | 1-(3,5-difluorophenyl)-N-[3-methyl-5-[3-methyl-4-(1-methyl-4-piperidyl)piperazin-1-yl]phenyl]-1,2,4-triazol-3-amine |
| 926 | 1-(3,5-difluorophenyl)-N-[3-methyl-5-(2,2,3,3,5,5,6,6-octadeuterio-4-tetrahydropyran-3-yl-piperazin-1-yl)phenyl]-1,2,4-triazol-3-amine |
| 927 | 1-(3,5-difluorophenyl)-N-[3-[2-(isopropoxymethyl)morpholin-4-yl]-5-methyl-phenyl]-1,2,4-triazol-3-amine |
| 928 | N1-[1-(3,5-difluorophenyl)-1,2,4-triazol-3-yl]-5-methyl-N3-[2-(2-methylmorpholin-4-yl)ethyl]benzene-1,3-diamine |
| 929 | N-[3-[4-(1-deuterio-1-methyl-ethyl)piperazin-1-yl]-5-methyl-phenyl]-1-phenyl-1,2,4-triazol-3-amine |
| 930 | N3-[1-(3,5-difluorophenyl)-1,2,4-triazol-3-yl]-N1-[1-(2-methoxyethyl)-4-piperidyl]-5-methyl-benzene-1,3-diamine |
| 931 | N3-[1-(3,5-difluorophenyl)-1,2,4-triazol-3-yl]-5-methyl-N1-(1-methyl-2-morpholino-ethyl)benzene-1,3-diamine |
| 932 | N1-[1-(3,5-difluorophenyl)-1,2,4-triazol-3-yl]-N3-(1,4-dioxan-2-ylmethyl)-5-methyl-benzene-1,3-diamine |
| 933 | 1-(3,5-difluorophenyl)-N-[3-[4-[2-(dimethylamino)ethoxy]-1-piperidyl]-5-methyl-phenyl]-1,2,4-triazol-3-amine |

TABLE 2D-continued

Compound Names (IUPAC Nomenclature)

| Cmpd No. | IUPAC Name |
|---|---|
| 934 | 4-[3-[[1-(3,5-difluorophenyl)-1,2,4-triazol-3-yl]amino]-5-methyl-anilino]-1-(2-methoxyethyl)pyrrolidin-2-one |
| 935 | 1-(3,5-difluorophenyl)-N-[3-methyl-5-[2,2,3,3,5,5,6,6-octadeuterio-4-(2,2-difluoroethyl)piperazin-1-yl]phenyl]-1,2,4-triazol-3-amine |
| 936 | 1-(3,5-difluorophenyl)-N-[3-methyl-5-[4-(tetrahydrofuran-3-ylmethyl)piperazin-1-yl]phenyl]-1,2,4-triazol-3-amine |
| 937 | N1-[1-(3,5-difluorophenyl)-1,2,4-triazol-3-yl]-N3-[[1-(methoxymethyl)cyclopropyl]methyl]-5-methyl-benzene-1,3-diamine |
| 938 | 1-[[3-[[1-(3,5-difluorophenyl)-1,2,4-triazol-3-yl]amino]-5-methyl-anilino]methyl]-N,N-dimethyl-cyclopentanecarboxamide |
| 939 | N3-[1-(3,5-difluorophenyl)-1,2,4-triazol-3-yl]-5-methyl-N1-(2-morpholinocyclohexyl)benzene-1,3-diamine |
| 940 | N1-[1-(3,5-difluorophenyl)-1,2,4-triazol-3-yl]-5-methyl-N3-[2-(1-oxo-1,4-thiazinan-4-yl)ethyl]benzene-1,3-diamine |
| 941 | 1-[4-[3-[[1-(3,5-difluorophenyl)-1,2,4-triazol-3-yl]amino]-5-methyl-phenyl]-2-methyl-piperazin-1-yl]-2-methyl-propan-2-ol |
| 942 | N3-(cyclopropylmethyl)-N1-[1-(3,5-difluorophenyl)-1,2,4-triazol-3-yl]-5-methyl-benzene-1,3-diamine |
| 943 | N1-(1-cyclobutyl-4-piperidyl)-N3-[1-(3,5-difluorophenyl)-1,2,4-triazol-3-yl]-2-fluoro-5-methyl-benzene-1,3-diamine |
| 944 | 1-(3,5-difluorophenyl)-N-[3-methyl-5-[4-(2-pyrrolidin-1-ylethyl)piperazin-1-yl]phenyl]-1,2,4-triazol-3-amine |
| 945 | 1-(3,5-difluorophenyl)-N-[3-methyl-5-[4-(3-pyrrolidin-1-ylpropyl)piperazin-1-yl]phenyl]-1,2,4-triazol-3-amine |
| 946 | 2-[3-[[3-[[1-(3,5-difluorophenyl)-1,2,4-triazol-3-yl]amino]-5-methyl-anilino]methyl]azetidin-1-yl]propane-1,3-diol |
| 947 | 1-(3,5-difluorophenyl)-N-[3-methyl-5-(2,2,3,3,5,5,6,6-octadeuterio-4-ethyl-piperazin-1-yl)phenyl]-1,2,4-triazol-3-amine |
| 948 | 1-[3-[[1-(3,5-difluorophenyl)-1,2,4-triazol-3-yl]amino]-5-methyl-phenyl]-N,N-dimethyl-piperidin-4-amine |
| 949 | 1-(3,5-difluorophenyl)-N-[3-[4-(1,4-dioxan-2-ylmethyl)piperazin-1-yl]-5-methyl-phenyl]-1,2,4-triazol-3-amine |
| 950 | 1-(3,5-difluorophenyl)-N-[3-[4-(2-fluoroethoxy)-1-piperidyl]-5-methyl-phenyl]-1,2,4-triazol-3-amine |
| 951 | N1-[1-(3,5-difluorophenyl)-1,2,4-triazol-3-yl]-5-methyl-N3-[(1-morpholinocyclopropyl)methyl]benzene-1,3-diamine |
| 952 | N-(2-fluoro-5-methyl-3-tetrahydrofuran-3-yloxy-phenyl)-1-pyrazin-2-yl-1,2,4-triazol-3-amine |
| 953 | N3-[1-(3,5-difluorophenyl)-1,2,4-triazol-3-yl]-4-fluoro-5-methyl-N1-tetrahydrofuran-3-yl-benzene-1,3-diamine |
| 954 | 1-(3,5-difluorophenyl)-N-[3-methyl-5-[2-[(4-methylpiperazin-1-yl)methyl]morpholin-4-yl]phenyl]-1,2,4-triazol-3-amine |
| 955 | N-[2-fluoro-5-methyl-3-[4-(oxetan-3-yl)piperazin-1-yl]phenyl]-1-(3-fluorophenyl)-1,2,4-triazol-3-amine |
| 956 | 1-(3,5-difluorophenyl)-N-[3-methyl-5-[4-(1-methyl-4-piperidyl)piperazin-1-yl]phenyl]-1,2,4-triazol-3-amine |
| 957 | 1-[4-[3-[[1-(3,5-difluorophenyl)-1,2,4-triazol-3-yl]amino]-5-methyl-phenyl]piperazin-1-yl]butan-2-ol |
| 958 | 2-[4-[3-[[1-(3,5-difluorophenyl)-1,2,4-triazol-3-yl]amino]-5-methyl-phenyl]morpholin-2-yl]ethanol |
| 959 | 2,2,2-trideuterio-1-[2,2,3,3,5,5,6,6-octadeuterio-4-[3-[[1-(3,5-difluorophenyl)-1,2,4-triazol-3-yl]amino]-5-methyl-phenyl]piperazin-1-yl]ethanone |
| 960 | N3-[1-(3,5-difluorophenyl)-1,2,4-triazol-3-yl]-5-methyl-N1-[1-(morpholinomethyl)propyl]benzene-1,3-diamine |
| 961 | cyclopropyl-[2,2,3,3,5,5,6,6-octadeuterio-4-[3-[[1-(3,5-difluorophenyl)-1,2,4-triazol-3-yl]amino]-5-methyl-phenyl]piperazin-1-yl]methanone |
| 962 | 1-(3,5-difluorophenyl)-N-[3-[4-(2-ethoxyethoxy)-1-piperidyl]-5-methyl-phenyl]-1,2,4-triazol-3-amine |
| 963 | N3-[1-(3,5-difluorophenyl)-1,2,4-triazol-3-yl]-N1-[2-(3-ethylmorpholin-4-yl)ethyl]-2-fluoro-5-methyl-benzene-1,3-diamine |
| 964 | 2-[4-[3-[[1-(3,5-difluorophenyl)-1,2,4-triazol-3-yl]amino]-5-methyl-phenyl]piperazin-1-yl]propan-1-ol |
| 965 | 2-[3-[[1-(3,5-difluorophenyl)-1,2,4-triazol-3-yl]amino]-4,5-dimethyl-phenoxy]-1-pyrrolidin-1-yl-ethanone |
| 966 | N-[3-(2-isopropyl-2,6-diazaspiro[3.3]heptan-6-yl)-5-methyl-phenyl]-1-(3-pyridyl)-1,2,4-triazol-3-amine |
| 967 | N-[3-(2-isopropyl-2,6-diazaspiro[3.3]heptan-6-yl)-5-methyl-phenyl]-1-pyrazin-2-yl-1,2,4-triazol-3-amine |
| 968 | N3-[(4-cyclopropylmorpholin-2-yl)methyl]-N1-[1-(3,5-difluorophenyl)-1,2,4-triazol-3-yl]-5-methyl-benzene-1,3-diamine |
| 969 | N3-[1-(3,5-difluorophenyl)-1,2,4-triazol-3-yl]-2-fluoro-N1,5-dimethyl-N1-(oxetan-3-yl)benzene-1,3-diamine |
| 970 | N3-[1-(3,5-difluorophenyl)-1,2,4-triazol-3-yl]-N1-(2,2-dimethyltetrahydropyran-4-yl)-5-methyl-benzene-1,3-diamine |
| 971 | 1-[3-[3-[[1-(3,5-difluorophenyl)-1,2,4-triazol-3-yl]amino]-4,5-dimethyl-phenoxy]azetidin-1-yl]ethanone |
| 972 | 1-(3,5-difluorophenyl)-N-[3-methyl-5-(2-tetrahydrofuran-2-ylmorpholin-4-yl)phenyl]-1,2,4-triazol-3-amine |
| 973 | 1-(3,5-difluorophenyl)-N-[3-[4-(2-ethoxyethyl)piperazin-1-yl]-5-methyl-phenyl]-1,2,4-triazol-3-amine |
| 974 | N3-[1-(3,5-difluorophenyl)-1,2,4-triazol-3-yl]-N1-[2-(5-ethyl-2-methyl-morpholin-4-yl)ethyl]-5-methyl-benzene-1,3-diamine |
| 975 | 1-(3,5-difluorophenyl)-N-[3-methyl-5-[3-(4-methylpiperazin-1-yl)azetidin-1-yl]phenyl]-1,2,4-triazol-3-amine |
| 976 | 1-(3,5-difluorophenyl)-N-[3-(4-ethoxy-1-piperidyl)-5-methyl-phenyl]-1,2,4-triazol-3-amine |
| 977 | 1-(3,4-difluorophenyl)-N-[3-(2-isopropyl-2,6-diazaspiro[3.3]heptan-6-yl)-5-methyl-phenyl]-1,2,4-triazol-3-amine |
| 978 | 1-(3,4-difluorophenyl)-N-(2-fluoro-5-methyl-3-tetrahydrofuran-3-yloxy-phenyl)-1,2,4-triazol-3-amine |
| 979 | 1-(3,5-difluorophenyl)-N-[3-methyl-5-[2,2,3,3,5,5,6,6-octadeuterio-4-(oxetan-3-yl)piperazin-1-yl]phenyl]-1,2,4-triazol-3-amine |
| 980 | 6-(cyclopropylmethoxy)-N-[1-(3,5-difluorophenyl)-1,2,4-triazol-3-yl]-4-methyl-pyridin-2-amine |
| 981 | N-[3-(3,4,4a,5,7,7a-hexahydro-2H-furo[3,4-b]pyridin-1-yl)-5-methyl-phenyl]-1-(3,5-difluorophenyl)-1,2,4-triazol-3-amine |
| 982 | 1-(3,5-difluorophenyl)-N-[3-methyl-5-(2,2,3,3,5,5,6,6-octadeuteriomorpholin-4-yl)phenyl]-1,2,4-triazol-3-amine |
| 983 | 1-(3,5-difluorophenyl)-N-[3-methyl-5-[3-(morpholinomethyl)pyrrolidin-1-yl]phenyl]-1,2,4-triazol-3-amine |
| 984 | 1-(3,5-difluorophenyl)-N-[3-methyl-5-[4-(morpholinomethyl)-1-piperidyl]phenyl]-1,2,4-triazol-3-amine |
| 985 | N3-[1-(3,5-difluorophenyl)-1,2,4-triazol-3-yl]-5-methyl-N1-(2-morpholinobutyl)benzene-1,3-diamine |
| 986 | 1-(3,5-difluorophenyl)-N-[3-methyl-5-[(3S)-3-pyrrolidin-1-ylpyrrolidin-1-yl]phenyl]-1,2,4-triazol-3-amine |
| 987 | N-[3-[4-[2-(diethylamino)ethyl]piperazin-1-yl]-5-methyl-phenyl]-1-(3,5-difluorophenyl)-1,2,4-triazol-3-amine |
| 988 | 1-(3,5-difluorophenyl)-N-[3-methyl-5-[4-(3-methylmorpholin-4-yl)-1-piperidyl]phenyl]-1,2,4-triazol-3-amine |
| 989 | 2-[4-[3-[[1-(3,5-difluorophenyl)-1,2,4-triazol-3-yl]amino]-2-fluoro-5-methyl-phenyl]piperazin-1-yl]propane-1,3-diol |
| 990 | 3-[4-[3-[[1-(3,5-difluorophenyl)-1,2,4-triazol-3-yl]amino]-5-methyl-phenyl]piperazin-1-yl]propan-1-ol |
| 991 | [4-[3-[[1-(3,5-difluorophenyl)-1,2,4-triazol-3-yl]amino]-5-methyl-phenyl]piperazin-1-yl]-tetrahydropyran-4-yl-methanone |
| 992 | N1-[1-(2,2-difluoroethyl)-4-piperidyl]-N3-[1-(3,5-difluorophenyl)-1,2,4-triazol-3-yl]-5-methyl-benzene-1,3-diamine |
| 993 | 2-[3-[[1-(3,5-difluorophenyl)-1,2,4-triazol-3-yl]amino]-5-methyl-anilino]-1-pyrrolidin-1-yl-ethanone |
| 994 | N-[3-(4-cyclobutyl-2,2,3,3,5,5,6,6-octadeuterio-piperazin-1-yl)-5-methyl-phenyl]-1-(3,5-difluorophenyl)-1,2,4-triazol-3-amine |
| 995 | 1-[4-[3-[[1-(3,5-difluorophenyl)-1,2,4-triazol-3-yl]amino]-5-methyl-phenyl]piperazin-1-yl]propan-2-ol |

TABLE 2D-continued

Compound Names (IUPAC Nomenclature)

| Cmpd No. | IUPAC Name |
|---|---|
| 996 | 1-(3,5-difluorophenyl)-N-[3-(5-ethyl-2,5-diazabicyclo[2.2.1]heptan-2-yl)-5-methyl-phenyl]-1,2,4-triazol-3-amine |
| 997 | 1-(3,5-difluorophenyl)-N-[3-methyl-5-[2,2,3,3,5,5,6,6-octadeuterio-4-(3-deuteriooxetan-3-yl)piperazin-1-yl]phenyl]-1,2,4-triazol-3-amine |
| 998 | 1-(3,4-difluorophenyl)-N-[2-fluoro-5-methyl-3-[4-(oxetan-3-yl)piperazin-1-yl]phenyl]-1,2,4-triazol-3-amine |
| 999 | N-[1-(3,5-difluorophenyl)-1,2,4-triazol-3-yl]-4-methyl-6-tetrahydropyran-3-yloxy-pyridin-2-amine |
| 1001 | 1-(3,5-difluorophenyl)-N-[3-[4-(4-methoxybutyl)piperazin-1-yl]-5-methyl-phenyl]-1,2,4-triazol-3-amine |
| 1002 | N-(2-fluoro-5-methyl-3-tetrahydrofuran-3-yloxy-phenyl)-1-phenyl-1,2,4-triazol-3-amine |
| 1003 | N1-[1-(3,5-difluorophenyl)-1,2,4-triazol-3-yl]-N3-[2-(2,5-dimethylmorpholin-4-yl)ethyl]-5-methyl-benzene-1,3-diamine |
| 1004 | N1-[1-(3,5-difluorophenyl)-1,2,4-triazol-3-yl]-5-methyl-N3-[(3-methyl-4,5-dihydroisoxazol-5-yl)methyl]benzene-1,3-diamine |
| 1005 | 1-(3,5-difluorophenyl)-N-[3-[4-(2-isopropoxyethyl)piperazin-1-yl]-5-methyl-phenyl]-1,2,4-triazol-3-amine |
| 1006 | 1-(3,5-difluorophenyl)-N-[3-(4-methoxy-1-piperidyl)-5-methyl-phenyl]-1,2,4-triazol-3-amine |
| 1007 | N3-[1-(3,5-difluorophenyl)-1,2,4-triazol-3-yl]-2-fluoro-5-methyl-N1-(2-morpholinocyclopentyl)benzene-1,3-diamine |
| 1008 | N3-[2-(cyclobutoxy)ethyl]-N1-[1-(3,5-difluorophenyl)-1,2,4-triazol-3-yl]-5-methyl-benzene-1,3-diamine |
| 1009 | 1-(3,4-difluorophenyl)-N-(2-fluoro-5-methyl-3-tetrahydrofuran-3-yloxy-phenyl)-1,2,4-triazol-3-amine |
| 1010 | 1-[3-[[1-(3,5-difluorophenyl)-1,2,4-triazol-3-yl]amino]-5-methyl-phenyl]-4-pyrrolidin-1-yl-pyrrolidin-3-ol |
| 1011 | 1-(3,5-difluorophenyl)-N-[3-[4-(2-methoxyethyl)-3-methyl-piperazin-1-yl]-5-methyl-phenyl]-1,2,4-triazol-3-amine |
| 1012 | 1-(3,5-difluorophenyl)-N-[3-methyl-5-[2-(morpholinomethyl)pyrrolidin-1-yl]phenyl]-1,2,4-triazol-3-amine |
| 1013 | N3-[1-(3,5-difluorophenyl)-1,2,4-triazol-3-yl]-5-methyl-N1-(1-tetrahydropyran-4-yl-4-piperidyl)benzene-1,3-diamine |
| 1014 | 1-(3,5-difluorophenyl)-N-[3-methyl-5-(4-tetrahydrofuran-3-yloxy-1-piperidyl)phenyl]-1,2,4-triazol-3-amine |
| 1015 | 2-[[1-[3-[[1-(3,5-difluorophenyl)-1,2,4-triazol-3-yl]amino]-5-methyl-phenyl]-4-piperidyl]-methyl-amino]ethanol |
| 1016 | N3-[1-(3,5-difluorophenyl)-1,2,4-triazol-3-yl]-4-fluoro-5-methyl-N1-(3-methyloxetan-3-yl)benzene-1,3-diamine |
| 1017 | N-[3-[2-(diethylaminomethyl)morpholin-4-yl]-5-methyl-phenyl]-1-(3,5-difluorophenyl)-1,2,4-triazol-3-amine |
| 1018 | 1-(3,5-difluorophenyl)-N-[3-[2-[(dimethylamino)methyl]morpholin-4-yl]-5-methyl-phenyl]-1,2,4-triazol-3-amine |
| 1019 | 1-(3,5-difluorophenyl)-N-[3-(4-isopropoxy-1-piperidyl)-5-methyl-phenyl]-1,2,4-triazol-3-amine |
| 1020 | N1-[1-(3,5-difluorophenyl)-1,2,4-triazol-3-yl]-5-methyl-N3-[(3-pyrrolidin-1-yloxetan-3-yl)methyl]benzene-1,3-diamine |
| 1021 | N3-[1-(3,5-difluorophenyl)-1,2,4-triazol-3-yl]-4-fluoro-5-methyl-N1-tetrahydropyran-4-yl-benzene-1,3-diamine |
| 1022 | N-[2-fluoro-5-methyl-3-[4-(oxetan-3-yl)piperazin-1-yl]phenyl]-1-(3-pyridyl)-1,2,4-triazol-3-amine |
| 1023 | 1-(3,5-difluorophenyl)-N-[3-methyl-5-[4-(2-methylmorpholin-4-yl)-1-piperidyl]phenyl]-1,2,4-triazol-3-amine |
| 1024 | 1-[4-[3-[[1-(3,5-difluorophenyl)-1,2,4-triazol-3-yl]amino]-5-methyl-phenyl]-3-methyl-piperazin-1-yl]-2-methyl-propan-2-ol |
| 1025 | 1-(3,5-difluorophenyl)-N-[3-[4-(4-ethylpiperazin-1-yl)-1-piperidyl]-5-methyl-phenyl]-1,2,4-triazol-3-amine |
| 1026 | 2-[4-[3-[[1-(3,5-difluorophenyl)-1,2,4-triazol-3-yl]amino]-5-methyl-phenyl]-1-methyl-piperazin-2-yl]ethanol |
| 1027 | 1-(3,5-difluorophenyl)-N-[3-methyl-5-[2-(pyrrolidin-1-ylmethyl)morpholin-4-yl]phenyl]-1,2,4-triazol-3-amine |
| 1028 | 1-(3,5-difluorophenyl)-N-(2-fluoro-5-methyl-3-tetrahydrofuran-3-yloxy-phenyl)-1,2,4-triazol-3-amine |
| 1029 | N1-[1-(3,5-difluorophenyl)-1,2,4-triazol-3-yl]-N3-[(1-methoxycyclobutyl)methyl]-5-methyl-benzene-1,3-diamine |
| 1030 | 1-(3,5-difluorophenyl)-N-[3-[2-(2-methoxyethyl)morpholin-4-yl]-5-methyl-phenyl]-1,2,4-triazol-3-amine |
| 1031 | 1-[3-[[1-(3,5-difluorophenyl)-1,2,4-triazol-3-yl]amino]-5-methyl-anilino]methyl]azetidin-1-yl]ethanone |
| 1032 | N-[3-(2,2,3,3,4,4,5,5,6,6-decadeuterio-1-piperidyl)-5-(trifluoromethyl)phenyl]-1-(3,5-difluorophenyl)-1,2,4-triazol-3-amine |
| 1033 | 2-[2-[4-[3-[[1-(3,5-difluorophenyl)-1,2,4-triazol-3-yl]amino]-5-methyl-phenyl]piperazin-1-yl]ethoxy]ethanol |
| 1034 | N-[3-(2-isopropyl-2,6-diazaspiro[3.3]heptan-6-yl)-5-methyl-phenyl]-1-phenyl-1,2,4-triazol-3-amine |
| 1035 | 1-(3,5-difluorophenyl)-N-[3-methyl-5-(4-oxa-7-azaspiro[2.5]octan-7-yl)phenyl]-1,2,4-triazol-3-amine |
| 1036 | 2-[4-[3-[[1-(3,5-difluorophenyl)-1,2,4-triazol-3-yl]amino]-5-methyl-phenyl]piperazin-1-yl]ethanol |
| 1037 | 1-(3,5-difluorophenyl)-N-[3-methyl-5-(3-methylsulfonylazetidin-1-yl)phenyl]-1,2,4-triazol-3-amine |
| 1038 | 1-(3,5-difluorophenyl)-N-[3-methyl-5-(4-pyrrolidin-1-yl-1-piperidyl)phenyl]-1,2,4-triazol-3-amine |
| 1039 | N-[3-[4-(3-deuteriotetrahydrofuran-3-yl)piperazin-1-yl]-5-methyl-phenyl]-1-phenyl-1,2,4-triazol-3-amine |
| 1040 | 1-[1-[3-[[1-(3,5-difluorophenyl)-1,2,4-triazol-3-yl]amino]-5-methyl-phenyl]pyrrolidin-3-yl]pyrrolidin-3-ol |
| 1041 | cyclopropyl-[2,2,3,3,5,5,6,6-octadeuterio-4-[3-(difluoromethyl)-5-[[1-(3,5-difluorophenyl)-1,2,4-triazol-3-yl]amino]phenyl]piperazin-1-yl]methanone |
| 1042 | 1-(3,5-difluorophenyl)-N-[3-methyl-5-(2,2,3,3,5,5,6,6-octadeuterio-4-tetrahydrofuran-3-yl-piperazin-1-yl)phenyl]-1,2,4-triazol-3-amine |
| 1043 | 2-[4-[3-[[1-(3,5-difluorophenyl)-1,2,4-triazol-3-yl]amino]-2-fluoro-5-methyl-phenyl]piperazin-1-yl]ethanol |
| 1044 | 1-[2,2,3,3,5,5,6,6-octadeuterio-4-[3-[[1-(3,5-difluorophenyl)-1,2,4-triazol-3-yl]amino]-5-methyl-phenyl]piperazin-1-yl]ethanone |
| 1045 | N3-[1-(3,5-difluorophenyl)-1,2,4-triazol-3-yl]-5-methyl-N1-[1-(tetrahydrofuran-3-ylmethyl)-4-piperidyl]benzene-1,3-diamine |
| 1046 | N1-[1-(3,5-difluorophenyl)-1,2,4-triazol-3-yl]-N3-[(1-tetrahydropyran-4-yl-4-piperidyl)methyl]benzene-1,3-diamine |
| 1047 | 1-(3,5-difluorophenyl)-N-[3-methyl-5-[4-[(1-methyl-3-piperidyl)methyl]piperazin-1-yl]phenyl]-1,2,4-triazol-3-amine |
| 1048 | N3-[1-(3,5-difluorophenyl)-1,2,4-triazol-3-yl]-N1-(2,6-dioxaspiro[4.5]decan-9-yl)-5-methyl-benzene-1,3-diamine |
| 1049 | 5-methyl-N1-(5-methyloxazol-2-yl)-N3-(1-phenyl-1,2,4-triazol-3-yl)benzene-1,3-diamine |
| 1050 | N3-[1-(3,5-difluorophenyl)-1,2,4-triazol-3-yl]-N1-[1-(2-methoxyethyl)-3-piperidyl]-5-methyl-benzene-1,3-diamine |
| 1051 | 1-(3,5-difluorophenyl)-N-[3-methyl-5-[2-(methylsulfonylmethyl)pyrrolidin-1-yl]phenyl]-1,2,4-triazol-3-amine |
| 1052 | N-(2-fluoro-5-methyl-3-tetrahydrofuran-3-yloxy-phenyl)-1-phenyl-1,2,4-triazol-3-amine |
| 1053 | 1-(3,5-difluorophenyl)-N-(2-fluoro-5-methyl-3-tetrahydrofuran-3-yloxy-phenyl)-1,2,4-triazol-3-amine |
| 1054 | 1-[1-[3-[[1-(3,5-difluorophenyl)-1,2,4-triazol-3-yl]amino]-5-methyl-phenyl]-4-piperidyl]piperidin-3-ol |
| 1055 | 1-(3,4-difluorophenyl)-N-(2-fluoro-5-methyl-3-tetrahydrofuran-3-yloxy-phenyl)-1,2,4-triazol-3-amine |
| 1056 | 1-[4-[3-[[1-(3,5-difluorophenyl)-1,2,4-triazol-3-yl]amino]-5-methyl-phenyl]-2-ethyl-piperazin-1-yl]propan-2-ol |
| 1057 | 1-(3,5-difluorophenyl)-N-[3-methyl-5-(8-oxa-4-azabicyclo[4.2.0]octan-4-yl)phenyl]-1,2,4-triazol-3-amine |
| 1058 | N-[3-methyl-5-[(1-phenyl-1,2,4-triazol-3-yl)amino]phenyl]cyclopropanecarboxamide |

TABLE 2D-continued

Compound Names (IUPAC Nomenclature)

| Cmpd No. | IUPAC Name |
|---|---|
| 1059 | N1-(1-cyclopropylethyl)-N3-[1-(3,5-difluorophenyl)-1,2,4-triazol-3-yl]-5-methyl-benzene-1,3-diamine |
| 1060 | 1-(3,5-difluorophenyl)-N-[3-methyl-5-(3-pyrrolidin-1-ylpyrrolidin-1-yl)phenyl]-1,2,4-triazol-3-amine |
| 1061 | N-(2-fluoro-5-methyl-3-tetrahydrofuran-3-yloxy-phenyl)-1-(3-fluorophenyl)-1,2,4-triazol-3-amine |
| 1062 | N1-[1-(3,5-difluorophenyl)-1,2,4-triazol-3-yl]-5-methyl-N3-[(4-methylmorpholin-3-yl)methyl]benzene-1,3-diamine |
| 1063 | 1-(3,5-difluorophenyl)-N-[3-[4-(2-ethoxyethyl)-3-methyl-piperazin-1-yl]-5-methyl-phenyl]-1,2,4-triazol-3-amine |
| 1064 | N3-[1-(3,5-difluorophenyl)-1,2,4-triazol-3-yl]-5-methyl-N1-(1-tetrahydrofuran-3-yl-4-piperidyl)benzene-1,3-diamine |
| 1065 | N3-[1-(3,5-difluorophenyl)-1,2,4-triazol-3-yl]-N1-(2-methoxycyclopentyl)-5-methyl-benzene-1,3-diamine |
| 1066 | 1-(3,4-difluorophenyl)-N-[3-methyl-5-(2,2,3,3,5,5,6,6-octadeuteriomorpholin-4-yl)phenyl]-1,2,4-triazol-3-amine |
| 1067 | 4-[3-[[1-(3,5-difluorophenyl)-1,2,4-triazol-3-yl]amino]-5-methyl-phenyl]-1-(2-methoxyethyl)piperazin-2-one |
| 1068 | 1-(3,5-difluorophenyl)-N-[3-[4-(4-methoxy-4-piperidyl)-1-piperidyl]-5-methyl-phenyl]-1,2,4-triazol-3-amine |
| 1069 | N-[1-(3,5-difluorophenyl)-1,2,4-triazol-3-yl]-4-methyl-6-(oxetan-3-ylmethoxy)pyridin-2-amine |
| 1070 | N1-(1-cyclobutyl-4-piperidyl)-N3-[1-(3,5-difluorophenyl)-1,2,4-triazol-3-yl]-5-methyl-benzene-1,3-diamine |
| 1071 | 1-(3-fluorophenyl)-N-[3-(2-isopropyl-2,6-diazaspiro[3.3]heptan-6-yl)-5-methyl-phenyl]-1,2,4-triazol-3-amine |
| 1072 | 1-(3,5-difluorophenyl)-N-[2-fluoro-3-(2-isopropyl-2,6-diazaspiro[3.3]heptan-6-yl)-5-methyl-phenyl]-1,2,4-triazol-3-amine |
| 1073 | [4-[3-[[1-(3,5-difluorophenyl)-1,2,4-triazol-3-yl]amino]-5-methyl-phenyl]morpholin-2-yl]methanol |
| 1074 | 1-(3,5-difluorophenyl)-N-[3-methyl-5-[4-(2-pyrrolidin-1-ylethoxy)-1-piperidyl]phenyl]-1,2,4-triazol-3-amine |
| 1075 | 1-[3-[3-[[1-(3,5-difluorophenyl)-1,2,4-triazol-3-yl]amino]-5-methyl-anilino]-3-methyl-azetidin-1-yl]-2-methoxy-ethanone |
| 1076 | 1-[3-[[1-(3,5-difluorophenyl)-1,2,4-triazol-3-yl]amino]-5-methyl-phenyl]-3-methyl-azetidine-3-carbonitrile |
| 1077 | [1-[[1-[3-[[1-(3,5-difluorophenyl)-1,2,4-triazol-3-yl]amino]-5-methyl-phenyl]pyrrolidin-2-yl]methyl]pyrrolidin-2-yl]methanol |
| 1078 | 1-[4-[3-[[1-(3,5-difluorophenyl)-1,2,4-triazol-3-yl]amino]-5-methyl-phenyl]piperazin-1-yl]-3-(dimethylamino)propan-2-ol |
| 1079 | [1-[3-[[1-(3,5-difluorophenyl)-1,2,4-triazol-3-yl]amino]-5-methyl-phenyl]-3-fluoro-azetidin-3-yl]methanol |
| 1080 | 5-deuterio-1-(3,5-difluorophenyl)-N-[3-methyl-5-[4-(oxetan-3-yl)piperazin-1-yl]phenyl]-1,2,4-triazol-3-amine |
| 1081 | 1-(3,5-difluorophenyl)-N-[3-(2-isopropyl-2,6-diazaspiro[3.3]heptan-6-yl)-5-methyl-phenyl]-1,2,4-triazol-3-amine |
| 1082 | N1-[1-(3,5-difluorophenyl)-1,2,4-triazol-3-yl]-5-methyl-N3-[2-(3-methylmorpholin-4-yl)ethyl]benzene-1,3-diamine |
| 1083 | 1-(3,5-difluorophenyl)-N-[3-methyl-5-(tetrahydrofuran-3-ylpyrrolidin-1-yl)phenyl]-1,2,4-triazol-3-amine |
| 1084 | tert-butyl 3-[[3-[[1-(3,5-difluorophenyl)-1,2,4-triazol-3-yl]amino]-5-methyl-anilino]methyl]azetidine-1-carboxylate |
| 1085 | N-[2-fluoro-5-methyl-3-[4-(oxetan-3-yl)piperazin-1-yl]phenyl]-1-phenyl-1,2,4-triazol-3-amine |
| 1086 | N-[3-methyl-5-[4-[1,2,2,2-tetradeuterio-1-(trideuteriomethyl)ethyl]piperazin-1-yl]phenyl]-1-phenyl-1,2,4-triazol-3-amine |
| 1087 | N-[3-[2-(cyclopropylmethoxymethyl)morpholin-4-yl]-5-methyl-phenyl]-1-(3,5-difluorophenyl)-1,2,4-triazol-3-amine |
| 1088 | N-[5-deuterio-1-(3,4-difluorophenyl)-1,2,4-triazol-3-yl]-4-(difluoromethyl)-6-[4-(oxetan-3-yl)piperazin-1-yl]pyridin-2-amine |
| 1089 | N-[5-deuterio-1-(3,4-difluorophenyl)-1,2,4-triazol-3-yl]-6-[4-(oxetan-3-yl)piperazin-1-yl]-4-(trifluoromethyl)pyridin-2-amine |
| 1090 | N-[5-deuterio-1-(3,5-difluorophenyl)-1,2,4-triazol-3-yl]-4-(difluoromethyl)-6-[4-(oxetan-3-yl)piperazin-1-yl]pyridin-2-amine |
| 1091 | 5-deuterio-N-[3-methyl-5-[4-(oxetan-3-yl)piperazin-1-yl]phenyl]-1-[3-(trifluoromethyl)phenyl]-1,2,4-triazol-3-amine |
| 1092 | 2-[1-[3-[[5-deuterio-1-(3,5-difluorophenyl)-1,2,4-triazol-3-yl]amino]-5-methyl-phenyl]azetidin-3-yl]propan-2-ol |
| 1093 | 2-cyclopropyl-N-[5-deuterio-1-(3,5-difluorophenyl)-1,2,4-triazol-3-yl]-6-morpholino-pyridin-4-amine |
| 1094 | 2-[3-[[1-(3,5-difluorophenyl)-1,2,4-triazol-3-yl]amino]-4,5-dimethyl-phenoxy]-1-morpholino-ethanone |
| 1095 | N-[3-(2,2,3,3,4,4,5,5,6,6-decadeuterio-1-piperidyl)-5-(trifluoromethyl)phenyl]-1-(3,4-difluorophenyl)-1,2,4-triazol-3-amine |
| 1096 | cyclopropyl-[2,2,3,3,5,5,6,6-octadeuterio-4-[3-(difluoromethyl)-5-[[1-(3,4-difluorophenyl)-1,2,4-triazol-3-yl]amino]phenyl]piperazin-1-yl]methanone |
| 1097 | 1-(3,5-difluorophenyl)-N-[3-methyl-5-[3-(2,2,3,3,5,5,6,6-octadeuteriomorpholin-4-yl)azetidin-1-yl]phenyl]-1,2,4-triazol-3-amine |
| 1098 | 1-(3,4-difluorophenyl)-N-[3-methyl-5-[3-(2,2,3,3,5,5,6,6-octadeuteriomorpholin-4-yl)azetidin-1-yl]phenyl]-1,2,4-triazol-3-amine |
| 1099 | N-[3-(2,2,3,3,4,4,5,5,6,6-decadeuterio-1-piperidyl)-5-(difluoromethyl)phenyl]-1-(3,4-difluorophenyl)-1,2,4-triazol-3-amine |
| 1100 | cyclopropyl-[2,2,3,3,5,5,6,6-octadeuterio-4-[3-[[1-(3,4-difluorophenyl)-1,2,4-triazol-3-yl]amino]-5-(trifluoromethyl)phenyl]piperazin-1-yl]methanone |
| 1101 | N-[3-(2,2,3,3,4,4,5,5,6,6-decadeuterio-1-piperidyl)-5-(difluoromethyl)phenyl]-1-(3-fluorophenyl)-1,2,4-triazol-3-amine |
| 1102 | N-[3-(2,2,3,3,4,4,5,5,6,6-decadeuterio-1-piperidyl)-5-(difluoromethyl)phenyl]-1-(3-fluorophenyl)-1,2,4-triazol-3-amine |
| 1103 | cyclopropyl-[2,2,3,3,5,5,6,6-octadeuterio-4-[3-[[1-(3-fluorophenyl)-1,2,4-triazol-3-yl]amino]-5-(trifluoromethyl)phenyl]piperazin-1-yl]methanone |
| 1104 | cyclopropyl-[2,2,3,3,5,5,6,6-octadeuterio-4-[3-(difluoromethyl)-5-[[1-(3-fluorophenyl)-1,2,4-triazol-3-yl]amino]phenyl]piperazin-1-yl]methanone |
| 1105 | N-[3-(2,2,3,3,4,4,5,5,6,6-decadeuterio-1-piperidyl)-5-(trifluoromethyl)phenyl]-1-pyrazin-2-yl-1,2,4-triazol-3-amine |
| 1106 | N-[3-(2,2,3,3,4,4,5,5,6,6-decadeuterio-1-piperidyl)-5-(difluoromethyl)phenyl]-1-pyrazin-2-yl-1,2,4-triazol-3-amine |
| 1107 | cyclopropyl-[2,2,3,3,5,5,6,6-octadeuterio-4-[3-(difluoromethyl)-5-[(1-pyrazin-2-yl-1,2,4-triazol-3-yl)amino]phenyl]piperazin-1-yl]methanone |
| 1108 | N-[3-methyl-5-[4-(oxetan-3-yl)piperazin-1-yl]phenyl]-1-(2,3,4,5,6-pentadeuteriophenyl)-1,2,4-triazol-3-amine |
| 1109 | N3-benzyl-N1-[1-(3,5-difluorophenyl)-1,2,4-triazol-3-yl]-2-fluoro-5-methyl-benzene-1,3-diamine |
| 1110 | N-[3-[4-(3-deuteriooxetan-3-yl)piperazin-1-yl]-5-methyl-phenyl]-1-(3,5-difluorophenyl)-1,2,4-triazol-3-amine |
| 1111 | N-[3-methyl-5-(2,2,3,3,5,5,6,6-octadeuterio-4-methyl-piperazin-1-yl)phenyl]-1-phenyl-1,2,4-triazol-3-amine |
| 1112 | [4-[3-[[1-(3,5-difluorophenyl)-1,2,4-triazol-3-yl]amino]-2-fluoro-5-methyl-phenyl]piperazin-1-yl]-tetrahydropyran-4-yl-methanone |
| 1113 | 1-(3,5-difluorophenyl)-N-[2-fluoro-5-methyl-3-[3-methyl-4-(1-methyl-4-piperidyl)piperazin-1-yl]phenyl]-1,2,4-triazol-3-amine |
| 1114 | N3-[1-(3,5-difluorophenyl)-1,2,4-triazol-3-yl]-N1-[2-(2-ethylmorpholin-4-yl)ethyl]-2-fluoro-5-methyl-benzene-1,3-diamine |
| 1115 | N3-[1-(3,5-difluorophenyl)-1,2,4-triazol-3-yl]-2-fluoro-5-methyl-N1-[1-(tetrahydrofuran-3-ylmethyl)-4-piperidyl]benzene-1,3-diamine |
| 1116 | N3-[1-(3,5-difluorophenyl)-1,2,4-triazol-3-yl]-2-fluoro-5-methyl-N1-[1-(tetrahydrofuran-2-ylmethyl)-4-piperidyl]benzene-1,3-diamine |

TABLE 2D-continued

Compound Names (IUPAC Nomenclature)

| Cmpd No. | IUPAC Name |
|---|---|
| 1117 | 1-(3,5-difluorophenyl)-N-[2-fluoro-5-methyl-3-[3-(4-methylpiperazin-1-yl)azetidin-1-yl]phenyl]-1,2,4-triazol-3-amine |
| 1118 | N3-[(4-cyclopropylmorpholin-2-yl)methyl]-N1-[1-(3,5-difluorophenyl)-1,2,4-triazol-3-yl]-2-fluoro-5-methyl-benzene-1,3-diamine |
| 1119 | N3-[1-(3,5-difluorophenyl)-1,2,4-triazol-3-yl]-2-fluoro-5-methyl-N1-(1-methyl-2-morpholino-ethyl)benzene-1,3-diamine |
| 1120 | 1-(3,5-difluorophenyl)-N-[2-fluoro-3-[2-(isopropoxymethyl)morpholin-4-yl]-5-methyl-phenyl]-1,2,4-triazol-3-amine |
| 1121 | N1-[1-(3,5-difluorophenyl)-1,2,4-triazol-3-yl]-2-fluoro-5-methyl-N3-[(1-morpholinocyclopropyl)methyl]benzene-1,3-diamine |
| 1122 | 1-(3,5-difluorophenyl)-N-[2-fluoro-5-methyl-3-(3-tetrahydrofuran-3-ylazetidin-1-yl)phenyl]-1,2,4-triazol-3-amine |
| 1123 | 1-[4-[3-[[1-(3,5-difluorophenyl)-1,2,4-triazol-3-yl]amino]-2-fluoro-5-methyl-phenyl]-2-methyl-piperazin-1-yl]-2-methyl-propan-2-ol |

Salts, Compositions, Uses, Formulation, Administration and Additional Agents
Pharmaceutically Acceptable Salts and Compositions As discussed herein, the compounds of formula I or I' of the present invention and the methods, compositions and kits disclosed herein are useful for the treatment of neurodegenerative or neurological diseases or disorders related to axonal damage, demyelinating diseases, central pontine myelinolysis, nerve injury diseases or disorders, metabolic diseases, mitochondrial diseases, metabolic axonal degeneration, a leukoencephalopathy or a leukodystrophy. In one embodiment, said neurodegenerative or neurological diseases or disorders related to axonal damage, demyelinating diseases, central pontine myelinolysis, nerve injury diseases or disorders, metabolic diseases, mitochondrial diseases, metabolic axonal degeneration, a leukoencephalopathy or a leukodystrophy include, but are not limited to spinal cord injury, stroke, multiple sclerosis, progressive multifocal leukoencephalopathy, congenital hypomyelination, encephalomyelitis, acute disseminated encephalomyelitis, central pontine myelolysis, hypoxic demyelination, ischemic demyelination, neuromyelifis optics, adrenoleukodystrophy, Alexander's disease, Niemann-Pick disease, Pelizaeus Merzbacher disease, periventricular leukomalatia, globoid cell leucodystrophy (Krabbe's disease), Wallerian degeneration, optic neuritis, transverse myelitis, amylotrophic lateral sclerosis (Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy, neuropathy, acute ischemic optic neuropathy, neuromyelitis optica, vitamin B12 deficiency, isolated vitamin E deficiency syndrome, Bassen-Kornzweig syndrome, Leber's hereditary optic atrophy/Leber congenital amaurosis, Marchiafava-Bignami syndrome, metachromatic leukodystrophy, acute hemorrhagic leukoencephalitis, trigeminal neuralgia, Bell's palsy, schizophrenia, cerebral ischemia, multiple system atrophy, traumatic glaucoma, tropical spastic paraparesis/human T-lymphotropic virus 1 (HTLV-1) associated myelopathy, essential tremor or osmotic hyponatremia.

In another embodiment, the compounds of formula I or I' of the present invention and the methods, compositions and kits disclosed herein are useful for treating, preventing or ameliorating one or more symptoms of multiple sclerosis or another neurodegenerative disease selected from auditory impairment, optic neuritis, decreased visual acuity, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, motor dysfunction, walking impairment, muscle atrophy, spasms, cramps, hypotonia, clonus, myoclonus, myokymia, restless leg syndrome, gait disturbances, footdrop, dysfunctional reflexes, paraesthesia, anaesthesia, neuralgia, neuropathic and neurogenic pain, L'hermitte's, proprioceptive dysfunction, trigeminal neuralgia, ataxia, intention tremor, dysmetria, vestibular ataxia, vertigo, speech ataxia, dystonia, disability progression, dysdiadochokinesia, frequent micturation, bladder spasticity, flaccid bladder, detrusor-sphincter dyssynergia, erectile dysfunction or anorgasmy.

Accordingly, in another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents. In one embodiment, the pharmaceutical composition comprises a therapeutically effective amount of a compound of the present invention or a pharmaceutically acceptable salt thereof and one or more pharmaceutically acceptable carriers or vehicles.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also useful for treating or lessening the severity of, in a subject, a disease or disorder selected from neurodegenerative or neurological diseases or disorders related to axonal damage, demyelinating diseases, central pontine myelinolysis, nerve injury diseases or disorders, metabolic diseases, mitochondrial diseases, metabolic axonal degeneration, a leukoencephalopathy or a leukodystrophy.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising the compound of the invention and a pharmaceutically acceptable carrier.

In another aspect, the invention features a pharmaceutical composition comprising a therapeutically effective amount of the compound or a pharmaceutically acceptable salt thereof of the compounds of formula I or I' and one or more pharmaceutically acceptable carriers or vehicles.

Uses of Compounds and Pharmaceutically Acceptable Salts and Compositions

In one embodiment, the methods described herein also provide a method of promoting oligodendrocyte proliferation, differentiation or survival comprising contacting oligodendrocytes with a compound of formula I or I' or a composition thereof.

In another embodiment, a method of the present invention comprises promoting oligodendrocyte proliferation, differentiation or survival. In another embodiment, a method of the present invention comprises promoting oligodendrocyte proliferation, differentiation or survival with a compound of formula I or I' or a composition thereof. In another embodiment, a method of the present invention is useful for treating or lessening the severity of a disease or disorder selected from a disease or disorder associated with a lack of oligodendrocyte proliferation, differentiation or survival comprising administering a therapeutically effective amount of the compounds of formula I or I' or compositions thereof to a subject in need thereof.

In another embodiment, a method of the present invention comprises promoting myelination by contacting neuronal cells, oligodendrocyte cells or oligodendrocyte precursor cells. In one embodiment, a method of the present invention comprises promoting myelination by contacting neuronal cells, oligodendrocyte cells or oligodendrocyte precursor cells with a compound of formula I or I' or a composition thereof.

In another embodiment, a method of the present invention comprises promoting survival of cells of the nervous system. In another embodiment, a method of the present invention comprises promoting survival of cells of the nervous system comprising contacting the cells with a compound or composition of formula I or I'. In one embodiment, the cells of the nervous system comprise brain cells, cortical neurons, oligodendrocytes or oligodendrocyte precursor cells.

In another embodiment, a method of the present invention is useful for treating or lessening the severity of a disease or disorder selected from a disease or condition associated with demyelination comprising administering a therapeutically effective amount of the compounds of formula I or I' or compositions thereof to a subject in need thereof. In one embodiment, the disease or condition associated with demyelination is a CNS disorder or a CNS demyelinating disease as described herein. In one embodiment, the disease is multiple sclerosis.

In another embodiment, the subject has, or is at risk of having, multiple sclerosis. The subject with multiple sclerosis can be at any stage of treatment or disease. In one embodiment, the subject with multiple sclerosis has one or more of: benign multiple sclerosis, relapsing remitting multiple sclerosis, quiescent relapsing remitting multiple sclerosis, active relapsing remitting multiple sclerosis, primary progressive multiple sclerosis, or secondary progressive multiple sclerosis, clinically isolated syndrome, or clinically defined multiple sclerosis. In one embodiment, the type of multiple sclerosis is primary progressive multiple sclerosis. In another embodiment, the type of multiple sclerosis is relapsing-remitting multiple sclerosis. In yet another embodiment, the type of multiple sclerosis is secondary progressive multiple sclerosis. In still a further embodiment, the type of multiple sclerosis is progressive relapsing multiple sclerosis. In another embodiment, the subject is asymptomatic. In another embodiment, the subject has one or more multiple sclerosis-like symptoms, such as those having clinically isolated syndrome or clinically defined multiple sclerosis. In yet other embodiments, the subject has one or more multiple sclerosis relapses.

In another embodiment, the subject has a relapsing form of multiple sclerosis such as relapsing remitting multiple sclerosis or relapsing secondary progressive multiple sclerosis. In one embodiment, the subject has relapsing remitting multiple sclerosis and has one or more ongoing clinical exacerbations. In another embodiment, the subject has relapsing remitting multiple sclerosis and one or more subclinical activities. In one embodiment, the clinical exacerbation or subclinical activity is shown by gadolinium enhancement of white matter lesions using T1/T2 magnetic resonance imaging. In another embodiment, the clinical exacerbation or subclinical activity is shown by development of new or enlarged white matter lesions on magnetic resonance imaging of the brain or spinal cord. In one embodiment, the development of new or enlarged white matter lesions is monitored by T1/T2 magnetic resonance imaging. In another embodiment, the development of new or enlarged white matter lesions is monitored by Proton Density magnetic resonance imaging. In yet another embodiment, the development of new or enlarged white matter lesions is monitored by MTR magnetic resonance imaging. See also, Gaitán, M. I. and Reich, D. S. (2014) MRI in Diagnosis and Disease Monitoring, in Multiple Sclerosis and CNS Inflammatory Disorders (eds L. M. Samkoff and A. D. Goodman), John Wiley & Sons, Ltd., Chichester, UK. doi: 10.1002/9781118298633.ch4 which is incorporated herein in its entirety by reference.

In another embodiment, the clinical exacerbations or subclinical activities are monitored by a functional readout such as ambulatory changes (gait changes, sway changes, etc.), T25W changes and/or EDSS changes. In another embodiment, the clinical exacerbations or subclinical activities are monitored by a visual evoked potential assay, a visual acuity assay or a measurement of optic nerve thickness. In another embodiment, the clinical exacerbations or subclinical activities are monitored by a myelin labelling assay.

In another embodiment, the subject with multiple sclerosis can be at any stage of treatment or disease and treatment with compounds of formula I or I' of the present invention result in improvement of the disease or symptoms. In one embodiment, improvement in the disease or symptoms is evidenced by a reduction or disappearance of one or more white matter lesions in the brain. In another embodiment, improvement in the disease or symptoms is evidenced by improved function such as improved ambulation, improved gait, reduced sway, improved T25W scores or improved EDSS scores. In another embodiment, improvement in the disease or symptoms is evidenced by improvements in the visual acuity assay or a visual evoked potential assay. In another embodiment, improvement in the disease or symptoms is evidenced by enhanced optic nerve thickness. In another embodiment, improvement in the disease or symptoms is evidenced by increased myelination in a myelin labelling assay.

In another embodiment, the compounds of formula I or I' of the present invention and the methods, compositions and kits disclosed herein are useful for promoting myelin regeneration in progressive demyelinating diseases. In one embodiment, the compounds of formula I or I' of the present invention and the methods, compositions and kits disclosed herein are useful for promoting myelin regeneration in primary progressive multiple sclerosis. In another embodiment, the compounds of formula I or I' of the present invention and the methods, compositions and kits disclosed herein are useful for promoting myelin regeneration in secondary progressive multiple sclerosis. In another embodiment, the compounds of formula I or I' of the present invention and the methods, compositions and kits disclosed herein are useful for promoting myelin regeneration in relapsing-remitting multiple sclerosis. In another embodiment, the compounds of formula I or I' of the present invention and the methods, compositions and kits disclosed herein are useful for promoting myelin regeneration in progressive relapsing multiple sclerosis.

In yet another embodiment, the compounds of formula I or I' of the present invention and the methods, compositions and kits disclosed herein are useful for promoting remyelination at the cellular level wherein oligodendrocyte cells are stimulated to regenerate or differentiate. In another embodiment, the compounds of formula I or I' of the present invention and the methods, compositions and kits disclosed herein are useful for promoting remyelination at the cellular level wherein oligodendrocyte cells are stimulated to remyelinate axons.

In another embodiment, the compounds of formula I or I' of the present invention and the methods, compositions and kits disclosed herein are useful for promoting remyelination at the cellular level whereby oligodendrocyte cells are stimulated to regenerate or differentiate thereby treating demyelinating diseases or disorders. In yet another embodiment, the compounds of formula I or I' of the present invention and the methods, compositions and kits disclosed herein are useful for promoting remyelination at the cellular level whereby axons are remyelinated by oligodendrocyte cells thereby treating demyelinating diseases or disorders.

In another embodiment, the compounds of formula I or I' of the present invention and the methods, compositions and kits disclosed herein are useful for inducing endogenous oligodendrocytes or oligodendrocyte precursor cells to contact an axon and produce myelin.

In another aspect, the present invention provides a method of treating or lessening the severity of, in a subject, a disease or disorder selected from a demyelinating disease, central pontine myelinolysis, a nerve injury disease or disorder, a leukoencephalopathy or a leukodystrophy comprising administering an effective amount of a compound, a pharmaceutically acceptable salt thereof or a pharmaceutical composition of the compounds of formula I or I'.

In one aspect, the present invention provides a method of treating or lessening the severity of, in a subject, a disease or disorder selected from spinal cord injury, stroke, multiple sclerosis, progressive multifocal leukoencephalopathy, congenital hypomyelination, encephalomyelitis, acute disseminated encephalomyelitis, central pontine myelolysis, hypoxic demyelination, ischemic demyelination, neuromyelitis optics, adrenoleukodystrophy, Alexander's disease, Niemann-Pick disease, Pelizaeus Merzbacher disease, periventricular leukomalatia, globoid cell leucodystrophy (Krabbe's disease), Wallerian degeneration, optic neuritis, transverse myelitis, amylotrophic lateral sclerosis (Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy, neuropathy, acute ischemic optic neuropathy, neuromyelitis optica, vitamin B12 deficiency, isolated vitamin E deficiency syndrome, Bassen-Kornzweig syndrome, Leber's hereditary optic atrophy/Leber congenital amaurosis, Marchiafava-Bignami syndrome, metachromatic leukodystrophy, acute hemorrhagic leukoencephalitis, trigeminal neuralgia, Bell's palsy, schizophrenia, cerebral ischemia, multiple system atrophy, traumatic glaucoma, tropical spastic paraparesis/human T-lymphotropic virus 1 (HTLV-1) associated myelopathy, essential tremor or osmotic hyponatremia comprising administering an effective amount of a compound, a pharmaceutically acceptable salt thereof or a pharmaceutical composition of the compounds of formula I or I'.

In another aspect, the present invention provides a method of treating, preventing or ameliorating one or more symptoms of multiple sclerosis or another neurodegenerative disease selected from auditory impairment, optic neuritis, decreased visual acuity, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, motor dysfunction, walking impairment, muscle atrophy, spasms, cramps, hypotonia, clonus, myoclonus, myokymia, restless leg syndrome, gait disturbances, footdrop, dysfunctional reflexes, paraesthesia, anaesthesia, neuralgia, neuropathic and neurogenic pain, L'hermitte's, proprioceptive dysfunction, trigeminal neuralgia, ataxia, intention tremor, dysmetria, vestibular ataxia, vertigo, speech ataxia, dystonia, disability progression, dysdiadochokinesia, frequent micturation, bladder spasticity, flaccid bladder, detrusor-sphincter dyssynergia, erectile dysfunction or anorgasmy comprising administering an effective amount of a compound, a pharmaceutically acceptable salt thereof or a pharmaceutical composition of the compounds of formula I or I'.

In yet another aspect, the present invention provides a method of treating or lessening the severity of, in a subject, a disease or disorder selected from a demyelinating disease, central pontine myelinolysis, a nerve injury disease or disorder, a leukoencephalopathy or a leukodystrophy comprising administering an effective amount of a compound, a pharmaceutically acceptable salt thereof or a pharmaceutical composition of the compounds of formula I or I' with one or more additional therapeutic agents administered concurrently with, prior to, or subsequent to treatment with the compound or pharmaceutical composition.

In another aspect, the present invention provides a method of treating or lessening the severity of, in a subject, a disease or disorder selected from spinal cord injury, stroke, multiple sclerosis, progressive multifocal leukoencephalopathy, congenital hypomyelination, encephalomyelitis, acute disseminated encephalomyelitis, central pontine myelolysis, hypoxic demyelination, ischemic demyelination, neuromyelitis optics, adrenoleukodystrophy, Alexander's disease, Niemann-Pick disease, Pelizaeus Merzbacher disease, periventricular leukomalatia, globoid cell leucodystrophy (Krabbe's disease), Wallerian degeneration, optic neuritis, transverse myelitis, amylotrophic lateral sclerosis (Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy, neuropathy, acute ischemic optic neuropathy, neuromyelitis optica, vitamin B12 deficiency, isolated vitamin E deficiency syndrome, Bassen-Kornzweig syndrome, Leber's hereditary optic atrophy/Leber congenital amaurosis, Marchiafava-Bignami syndrome, metachromatic leukodystrophy, acute hemorrhagic leukoencephalitis, trigeminal neuralgia, Bell's palsy, schizophrenia, cerebral ischemia, multiple system atrophy, traumatic glaucoma, tropical spastic paraparesis/human T-lymphotropic virus 1 (HTLV-1) associated myelopathy, essential tremor or osmotic hyponatremia comprising administering an effective amount of a compound, a pharmaceutically acceptable salt thereof or a pharmaceutical composition of the compounds of formula I or I' with one or more additional therapeutic agents administered concurrently with, prior to, or subsequent to treatment with the compound or pharmaceutical composition.

In another aspect, the present invention provides a method of treating or lessening the severity of, in a subject, a type of multiple sclerosis selected from primary progressive multiple sclerosis, relapsing-remitting multiple sclerosis, secondary progressive multiple sclerosis or progressive relapsing multiple sclerosis. In one aspect, the type of multiple sclerosis is primary progressive multiple sclerosis. In another aspect, the type of multiple sclerosis is relapsing-remitting multiple sclerosis. In yet another aspect, the type of multiple sclerosis is secondary progressive multiple sclerosis. In still a further aspect, the type of multiple sclerosis is progressive relapsing multiple sclerosis.

In another aspect, the present invention provides a method for treating, preventing or ameliorating one or more symptoms of multiple sclerosis or another neurodegenerative disease selected from auditory impairment, optic neuritis, decreased visual acuity, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, motor dysfunction, walking impairment, muscle atrophy, spasms, cramps, hypotonia, clonus, myoclonus, myokymia, restless leg syndrome, gait disturbances, footdrop, dysfunctional reflexes, paraesthesia, anaesthesia, neuralgia, neuropathic and neurogenic pain, L'hermitte's, proprioceptive dysfunction, trigeminal neuralgia, ataxia, intention tremor, dysmetria, vestibular ataxia, vertigo, speech ataxia, dystonia, disability progression, dysdiadochokinesia, frequent micturation, bladder spasticity, flaccid bladder, detrusor-sphincter dyssynergia, erectile dysfunction or anorgasmy comprising administering an effective amount of a compound, a pharmaceutically acceptable salt thereof or a pharmaceutical composition of the compounds of formula I or I' with one or more additional therapeutic agents administered concurrently with, prior to, or subsequent to treatment with the compound or pharmaceutical composition.

Manufacture of Medicaments

In one aspect, the present invention provides the use of a compound or pharmaceutical composition described herein for the manufacture of a medicament for use in treating or lessening the severity of, in a subject, a disease or disorder selected from a demyelinating disease, central pontine myelinolysis, a nerve injury disease or disorder or a leukoencephalopathy.

In another aspect, the present invention provides the use of a compound or pharmaceutical composition described herein for the manufacture of a medicament for use in treating or lessening the severity of, in a subject, a disease or disorder selected from spinal cord injury, stroke, multiple sclerosis, progressive multifocal leukoencephalopathy, congenital hypomyelination, encephalomyelitis, acute disseminated encephalomyelitis, central pontine myelolysis, hypoxic demyelination, ischemic demyelination, neuromyelitis optics, adrenoleukodystrophy, Alexander's disease, Niemann-Pick disease, Pelizaeus Merzbacher disease, periventricular leukomalatia, globoid cell leucodystrophy (Krabbe's disease), Wallerian degeneration, optic neuritis, transverse myelitis, amylotrophic lateral sclerosis (Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy, neuropathy, acute ischemic optic neuropathy, neuromyelitis optica, vitamin B12 deficiency, isolated vitamin E deficiency syndrome, Bassen-Kornzweig syndrome, Leber's hereditary optic atrophy/Leber congenital amaurosis, Marchiafava-Bignami syndrome, metachromatic leukodystrophy, acute hemorrhagic leukoencephalitis, trigeminal neuralgia, Bell's palsy, schizophrenia, cerebral ischemia, multiple system atrophy, traumatic glaucoma, tropical spastic paraparesis/human T-lymphotropic virus 1 (HTLV-1) associated myelopathy, essential tremor or osmotic hyponatremia.

In another aspect, the present invention provides the use of a compound or pharmaceutical composition described herein for the manufacture of a medicament for use in treating, preventing or ameliorating one or more symptoms of multiple sclerosis or another neurodegenerative disease selected from auditory impairment, optic neuritis, decreased visual acuity, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, motor dysfunction, walking impairment, muscle atrophy, spasms, cramps, hypotonia, clonus, myoclonus, myokymia, restless leg syndrome, gait disturbances, footdrop, dysfunctional reflexes, paraesthesia, anaesthesia, neuralgia, neuropathic and neurogenic pain, L'hermitte's, proprioceptive dysfunction, trigeminal neuralgia, ataxia, intention tremor, dysmetria, vestibular ataxia, vertigo, speech ataxia, dystonia, disability progression, dysdiadochokinesia, frequent micturation, bladder spasticity, flaccid bladder, detrusor-sphincter dyssynergia, erectile dysfunction or anorgasmy.

In yet another aspect, the present invention provides the use of a compound or pharmaceutical composition described herein for the manufacture of a medicament in combination with one or more additional therapeutic agents administered concurrently with, prior to, or subsequent to treatment with the compound or pharmaceutical composition.

In one aspect, the present invention provides the use of a compound or pharmaceutical composition described herein for the manufacture of a medicament for use in treating or lessening the severity of, in a subject, a disease or disorder selected from a demyelinating disease, central pontine myelinolysis, a nerve injury disease or disorder or a leukoencephalopathy with one or more additional therapeutic agents administered concurrently with, prior to, or subsequent to treatment with the compound or pharmaceutical composition.

In another aspect, the present invention provides the use of a compound or pharmaceutical composition described herein for the manufacture of a medicament for use in treating or lessening the severity of, in a subject, a disease or disorder selected from spinal cord injury, stroke, multiple sclerosis, progressive multifocal leukoencephalopathy, congenital hypomyelination, encephalomyelitis, acute disseminated encephalomyelitis, central pontine myelolysis, hypoxic demyelination, ischemic demyelination, neuromyelitis optics, adrenoleukodystrophy, Alexander's disease, Niemann-Pick disease, Pelizaeus Merzbacher disease, periventricular leukomalatia, globoid cell leucodystrophy (Krabbe's disease), Wallerian degeneration, optic neuritis, transverse myelitis, amylotrophic lateral sclerosis (Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy, neuropathy, acute ischemic optic neuropathy, neuromyelitis optica, vitamin B12 deficiency, isolated vitamin E deficiency syndrome, Bassen-Kornzweig syndrome, Leber's hereditary optic atrophy/Leber congenital amaurosis, Marchiafava-Bignami syndrome, metachromatic leukodystrophy, acute hemorrhagic leukoencephalitis, trigeminal neuralgia, Bell's palsy, schizophrenia, cerebral ischemia, multiple system atrophy, traumatic glaucoma, tropical spastic paraparesis/human T-lymphotropic virus 1 (HTLV-1) associated myelopathy, essential tremor or osmotic hyponatremia in combination with one or more additional therapeutic agents administered concurrently with, prior to, or subsequent to treatment with the compound or pharmaceutical composition.

In another aspect, the present invention provides the use of a compound or pharmaceutical composition described herein for the manufacture of a medicament for use in treating or lessening the severity of, in a subject, a type of multiple sclerosis selected from primary progressive multiple sclerosis, relapsing-remitting multiple sclerosis, secondary progressive multiple sclerosis or progressive relapsing multiple sclerosis. In one aspect, the type of multiple sclerosis is primary progressive multiple sclerosis. In another aspect, the type of multiple sclerosis is relapsing-remitting multiple sclerosis. In yet another aspect, the type of multiple sclerosis is secondary progressive multiple sclerosis. In still a further aspect, the type of multiple sclerosis is progressive relapsing multiple sclerosis.

In yet another aspect, the present the present invention provides the use of a compound or pharmaceutical composition described herein for the manufacture of a medicament for use in treating, preventing or ameliorating one or more symptoms of multiple sclerosis or another neurodegenerative disease selected from auditory impairment, optic neuritis, decreased visual acuity, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, motor dysfunction, walking impairment, muscle atrophy, spasms, cramps, hypotonia, clonus, myoclonus, myokymia, restless leg syndrome, gait disturbances, footdrop, dysfunctional reflexes, paraesthesia, anaesthesia, neuralgia, neuropathic and neurogenic pain, L'hermitte's, proprioceptive dysfunction, trigeminal neuralgia, ataxia, intention tremor, dysmetria, vestibular ataxia, vertigo, speech ataxia, dystonia, disability progression, dysdiadochokinesia, frequent micturation, bladder spasticity, flaccid bladder, detrusor-sphincter dyssynergia, erectile dysfunction or anorgasmy in combination with one or more additional therapeutic agents administered concurrently with, prior to, or subsequent to treatment with the compound or pharmaceutical composition.

Administration of Pharmaceutically Acceptable Salts and Compositions

In certain embodiments of the invention an "effective amount" of the compound, a pharmaceutically acceptable salt thereof or pharmaceutically acceptable composition is that amount effective for treating or lessening the severity of, in a subject, a disease or disorder selected from one or more of a demyelinating disease, central pontine myelinolysis, a nerve injury disease or disorder or a leukoencephalopathy.

The exact amount required will vary from subject to subject, depending on the species, age, and general condition of the subject, the severity of the disease, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Additional Therapeutic Agents

It will also be appreciated that the compounds of formula I or I' of the present invention and the methods, compositions and kits disclosed herein can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." Additional appropriate therapeutic agents or approaches are described generally in The Merck Manual, Nineteenth Edition, Ed. Robert S. Porter and Justin L. Kaplan, Merck Sharp & Dohme Corp., a subsidiary of Merck & Co., Inc., 2011, and the Food and Drug Administration website, www.fda.gov, the entire contents of which are hereby incorporated by reference.

In one embodiment, the additional therapeutic agents is an immunomodulatory agent, such as an IFN-β 1 molecule including but not limited to an interferon beta 1a (Avonex®, Rebif®) or an interferon beta 1b (Betaseron®, Betaferon®, Extavia®). Immunomodulatory agents also include other interferons and fragments, analogues, homologues, derivatives, and natural variants thereof with substantially similar biological activity to interferon beta 1a molecules.

In another embodiment, the additional therapeutic agent is a polymer of glutamic acid, lysine, alanine and tyrosine such as glatiramer acetate (Copaxone®).

In another embodiment, the additional therapeutic agent is an antibody or fragment thereof against alpha-4 integrin (e.g., natalizumab (Tysabri®)).

In another embodiment, the additional therapeutic agent is an anthracenedione molecule such as mitoxantrone (Novantrone®).

In another embodiment, the additional therapeutic agent is a sphingosine 1-phosphate receptor modulator such as fingolimod (Gilenya®) and those described in WO 2012/109108 the entire contents of which is hereby incorporated by reference.

In another embodiment, the additional therapeutic agent is a dimethyl fumarate such as an oral dimethyl fumarate (Tecfidera®).

In another embodiment, the additional therapeutic agent is an antibody to the alpha subunit of the IL-2 receptor of T cells such as daclizumab (Zenapax®).

In another embodiment, the additional therapeutic agent is an antibody against CD52 such as alemtuzumab (Lemtrada®).

In another embodiment, the additional therapeutic agent is an inhibitor of a dihydroorotate dehydrogenase such as teriflunomide (Aubagio®).

In another embodiment, the additional therapeutic agent is an antibody to CD20 such as ocrelizumab, rituximab or ofatumumab.

In another embodiment, the additional therapeutic agent is a corticosteroid such as, but not limited to methylprednisolone, Depo-Medrol®, Solu-Medrol®, Deltasone®, Delta-Cortef®, Medrol®, Decadron® or Acthar®.

In another embodiment, the additional therapeutic agent is an anti-VLA4 antibody, such as Natalizumab (Tysabri®) or a related VLA-4 antibodies such as those described in U.S. Pat. Nos. 5,840,299, 6,602,503, Sanchez-Madrid et al, (1986) Eur. J. Immunol 16: 1343-1349; Hemler et al, (1987) J Biol. Chem. 2: 11478-11485; Issekutz et al. (1991) J Immunol 147: 109 (TA-2 mab); Pulido et al. (1991) J Biol. Chem. 266: 10241-10245; and U.S. Pat. No. 5,888,507 the entire contents of each patent or publication hereby incorporated by reference in their entirety.

In another embodiment, the additional therapeutic agent is a LINGO-1 antagonist (e.g., an antibody against LINGO (e.g., LINGO-1, LINGO-2, LINGO-3, LINGO-4) or a Nogo receptor-1 (NgR1) modulator and compositions thereof such as those disclosed in WO2004/085648, WO2006/002437, WO2007/008547, WO2007/025219, WO2007/064882, WO2007/056161, WO2007/133746, WO2007/098283, WO2008/086006, WO2009/061500, WO2010/005570, WO2010/062904, WO 2013/173364, WO2014/058875, each of which is hereby incorporated by reference in its entirety.

In another embodiment, the additional therapeutic agent is a TAJ modulator, such as those disclosed in WO2006/017673, which is hereby incorporated by reference in its entirety.

In another embodiment, the additional therapeutic agent is a TrkA antagonist such as those disclosed in WO2008/013782 or a TrkB antagonist such as those disclosed in WO2009/048605, each of which is hereby incorporated by reference in its entirety.

In another embodiment, the additional therapeutic agent is a sclerostin modulator such as those disclosed in WO2013/063095, which is hereby incorporated by reference in its entirety.

In another embodiment, the additional therapeutic agent is an autotaxin (ATX) inhibitor or LPA receptor antagonist, such as those described in WO2015048301, WO2015042053, WO2015042052, WO2015008230, WO2015008229, WO2014202458, WO2014139882, WO2014133112, WO2014097151, WO2014110000, WO2014/081756, WO2014/081752, WO2014/048865, WO2014168824, WO2014143583, WO2014139978, WO2013/186159, WO2012/024620, WO2012/166415, WO2012078593, WO2012078805, WO2012024620, WO2013070879, WO2013/061297, WO2013/054185, WO2014/018881, WO2014/018887, WO2014/018891, WO2014/025708, WO2104/025709, WO2014/152725, WO2012028243, WO2012005227, WO2011/159635, WO2011/159550, WO2011116867, WO2011053948, WO2011041729, WO2011041694, WO2011041462, WO2011041461, WO2011017561, WO2011017350, WO2010115491, WO2011006569, WO20110141761, WO2010112124, WO2010112116, WO2010077883, WO2010077882, WO2010068775, WO2010063352, WO2010051031, WO2010051030, WO2009046841, WO2009046842, WO2009046804, WO2009023854, WO2009/135590, WO2008/014286, WO 2010/141768, US2006/194850, US 2003/114505, US 2004/122236, US 2006/194850, U.S. Pat. No. 6,964,945, US2005/0256160, US 2006/148830, US 2008/0293764, US2010/0249157, the disclosure of each patent application and patent hereby incorporated by reference in its entirety.

In another embodiment, the additional therapeutic agent is a Nox4 modulator such as those described in WO2013/037499, which is hereby incorporated by reference in its entirety.

In another embodiment, the additional therapeutic agent is a remyelinating antibody such as rHIgM22.

In another embodiment, the additional therapeutic agent is dalfampridine (Ampyra®)

In another embodiment, the additional therapeutic agent is a death receptor 6 (DR6) antagonist, a p75 antagonist or a combination thereof such as those disclosed in U.S. Pat. No. 8,894,999 and WO2014106104 each of which is incorporated herein by reference in its entirety.

In another embodiment, the additional therapeutic agent is Cethrin™.

In another embodiment, the additional therapeutic agent is an activin receptor modulator such as those described in WO2015/001352, which is hereby incorporated by reference in its entirety.

In another embodiment, the additional therapeutic agent is a GLP-1 like peptide or a derivative of GLP-1 like peptides such as those disclosed in WO2015/000942, WO2014/202727, WO2012/140117, WO2012/062803, WO 2012/062804, WO2011/080102 and WO2009/030771, each of which is incorporated herein by reference in its entirety. In another embodiment, the GLP-1 derivative is Liraglutide or Semaglutide.

In another embodiment, the additional therapeutic agent is a RXR modulator such as those disclosed in US2015/0038585 and WO2013056232 each of which is incorporated herein by reference in its entirety. In another embodiment, the RXR modulator is HX630.

In another embodiment, the additional therapeutic agent is an activator of the NRF2/KEAP1/ARE pathway such as those disclosed in WO2014/197818 which is hereby incorporated by reference in its entirety.

In another embodiment, the additional therapeutic agent is a PPAR agonist such as those disclosed in WO2014/165827 which is hereby incorporated by reference in its entirety.

In another embodiment, the additional therapeutic agent is an inhibitor of HDAC4 such as those disclosed in WO2013/080120 which is hereby incorporated by reference in its entirety.

In another embodiment, the additional therapeutic agent is a gamma secretase inhibitor such as DAPT.

In another embodiment, the additional therapeutic agent is an antipsychotic medication such as quetiapine.

In another embodiment, the additional therapeutic agent is a thyroid hormone.

In another embodiment, the additional therapeutic agent is a thyroid translocator protein (TSPO) such as etifoxine.

In another embodiment, the additional therapeutic agent is insulin-like growth factor 1 (IGF-1).

In another embodiment, the additional therapeutic agent is an anticholinergic such as benzatropine.

In another embodiment, the additional therapeutic agent is an antihistamine/anticholinergic such as clemastine or clemastine fumarate.

In another embodiment, the additional therapeutic agent is one that removes antiaquaporin by plasmapheresis.

In another embodiment, the additional therapeutic agent is a hyaluronan inhibitor or antagonist such as those described in WO2015023691, which is hereby incorporated by reference in its entirety.

In another embodiment, the additional therapeutic agent is a hyaluronidase inhibitor such as a PH20 inhibitor or those described in WO2013/102144, WO2011/133862, and WO2010/007729 each of which is hereby incorporated by reference in its entirety.

In another embodiment, the additional therapeutic agent is a Toll-Like Receptor-2 (TLR-2) inhibitor.

In another embodiment, the additional therapeutic agent is a Semaphorin 3A antagonist or antibody such as those disclosed in WO2014123186, which is hereby incorporated by reference in its entirety.

In another embodiment, the additional therapeutic agent is a CXCR2 inhibitor or antagonist.

In another embodiment, the additional therapeutic agent is a Semaphorin 3F agonist.

In another embodiment, the additional therapeutic agent is a Wnt polypeptide or Wnt inhibitor such as those disclosed in WO 2013/040309 and WO 2012/097093, each of which is hereby incorporated by reference in its entirety.

In another embodiment, the additional therapeutic agent is a mitochondrial pore modulator such as Olesoxime.

In another embodiment, the additional therapeutic agent is a PSA NCAM antagonist, a CXCR2 inhibitor or antagonist, a MRF agonist, a GM-98 agonist, a Tcf4 inhibitor, a retinoid, a neuregulin 1-erbB signaling modulator, a zpf191 activator, an miR219 activator, an miR338 activator or an miR138 activator.

In certain embodiments, the additional agent is an immunomodulatory agent such as an IFN-β 1 molecule which is administered intravenously, subcutaneously or intramuscularly. In one embodiment, the IFN-β 1 molecule is administered at 20-45 microgram once a week by intramuscular injection. In another embodiment, the IFN-β 1 molecule is administered at 20-30 microgram three times a week by intramuscular injection. In another embodiment, the IFN-β 1 molecule is administered at 40-50 micrograms once a week, by subcutaneous injection.

In another embodiment, the IFN-β 1 molecule is administered in an amount of between 10 and 50 µg intramuscularly three times a week.

In another embodiment, the IFN-β 1 molecule is administered in an amount of between 10 and 50 µg intramuscularly every five to ten days.

In another embodiment, the IFN-β 1 molecule is administered in an amount between 200 and 600 µg every other day by subcutaneous injection. In one embodiment, the IFN-β 1 molecule is an interferon β-1b (Betaseron®, Betaferon®, or Extavia®).

These combinations are useful for treating or lessening the severity of, in a subject, the diseases described herein including neurodegenerative diseases such as multiple sclerosis. These combinations are also useful in the kits described herein.

It will also be appreciated that the compounds of formula I or I' of the present invention and the methods, compositions and kits disclosed herein can be employed in combination therapies to not only treat or lessen the severity of, in a subject, the diseases described herein but may also be used in symptom management. Those additional agents include those useful for treating symptoms such as bladder problems (e.g., Botox®, DDAVP Nasal Spray®, Detrol®, Ditropan®, Ditropan XL®, Enablex®, Flomax®, Hytrin®, Minipress®, Oxytrol®, Pro-Banthine®, Sanctura®, Tofranil®, Vesicare®); infections (Bactrim®, Septra®, Cipro®, Macrodantin®, Hiprex®, Pyridium®); bowel dysfunction (Colace®, Dulcolax®, Enemeez®, Fleet enema, Mineral oil, Metamucil®, Milk of Magnesi®a, glycerin suppositories); depression (Cymbalta®, Effexor®, Paxil®, Prozac®, Wellbutrin®, Zoloft®); dizziness and vertigo (Antivert®); emotional changes (Nuedexta®), Fatigue (Amantadine®, Provigil®, Prozac®), itching (Atarax®); pain (Dilantin®, Elavil®, Klonipin®, Neurontin®, Pamelor®, Aventyl®, Tegetrol®); sexual problems (Cialis®, Levitra®, Papaverine®, MUSE®, Prostin VR®, Viagra®); spasticity (Dantrium®, Gablofen®, Klonipin®, Lioresal®, Valium®, Zanaflex®); tremors (Laniazid®, Nydrazid®, Klonopin®, Rivotril®); and walking or gait difficulties (Ampyra®).

The amount of additional therapeutic agent present in or with the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In another aspect, the present invention features a kit comprising a compound and/or pharmaceutical composition of formula I or I' of the present invention and instructions for use thereof.

In another embodiment, the kits of the present invention further comprise one or more additional therapeutic agent(s). In another embodiment, the additional therapeutic agent is selected from an immunomodulatory agent, such as an IFN-β 1 molecule including but not limited to an interferon beta 1a (Avonex®, Rebif®) or an interferon beta 1b (Betaseron®, Betaferon®, Extavia®).

In another embodiment, the additional therapeutic agent is a polymer of glutamic acid, lysine, alanine and tyrosine such as glatiramer acetate (Copaxone®).

In another embodiment, the additional therapeutic agent is an antibody or fragment thereof against alpha-4 integrin (e.g., natalizumab (Tysabri®)).

In another embodiment, the additional therapeutic agent is an anthracenedione molecule such as mitoxantrone (Novantrone®).

In another embodiment, the additional therapeutic agent is a sphingosine 1-phosphate receptor modulator such as fingolimod (Gilenya®) and those described in WO 2012/109108 the entire contents of which is hereby incorporated by reference.

In another embodiment, the additional therapeutic agent is a dimethyl fumarate such as an oral dimethyl fumarate (Tecfidera®).

In another embodiment, the additional therapeutic agent is an antibody to the alpha subunit of the IL-2 receptor of T cells such as daclizumab (Zenapax®).

In another embodiment, the additional therapeutic agent is an antibody against CD52 such as alemtuzumab (Lemtrada®).

In another embodiment, the additional therapeutic agent is an inhibitor of a dihydroorotate dehydrogenase such as teriflunomide (Aubagio®).

In another embodiment, the additional therapeutic agent is an antibody to CD20 such as ocrelizumab, rituximab or ofatumumab.

In another embodiment, the additional therapeutic agent is a corticosteroid such as, but not limited to methylprednisolone, Depo-Medrol®, Solu-Medrol®, Deltasone®, Delta-Cortef®, Medrol®, Decadron® or Acthar®.

In another embodiment, the additional therapeutic agent is one or more compounds useful for treating symptoms of the disease such as bladder problems (e.g., Botox®, DDAVP Nasal Spray®, Detrol®, Ditropan®, Ditropan XL®, Enablex®, Flomax®, Hytrin®, Minipress®, Oxytrol®, Pro-Banthine®, Sanctura®, Tofranil®, Vesicare®); infections (Bactrim®, Septra®, Cipro®, Macrodantin®, Hiprex®, Pyridium®); bowel dysfunction (Colace®, Dulcolax®, Enemeez®, Fleet enema, Mineral oil, Metamucil®, Milk of Magnesia®, glycerin suppositories); depression (Cymbalta®, Effexor®, Paxil®, Prozac®, Wellbutrin®, Zoloft®); dizziness and vertigo (Antivert®); emotional changes (Nuedexta®), Fatigue (Amantadine®, Provigil®, Prozac®), itching (Atarax®); pain (Dilantin®, Elavil®, Klonipin®, Neurontin®, Pamelor®, Aventyl®, Tegetrol®); sexual problems (Cialis®, Levitra®, Papaverine®, MUSE®, Prostin VR®, Viagra®); spasticity (Dantrium®, Gablofen®, Klonipin®, Lioresal®, Valium®, Zanaflex®); tremors (Laniazid®, Nydrazid®, Klonopin®, Rivotril®); or walking or gait difficulties (Ampyra®).

In another embodiment, the kits of the present invention are drawn to kits wherein the compounds or the pharmaceutical compositions of the present invention and the one or more additional therapeutic agent(s) are in separate containers.

In another embodiment, the kits of the present invention are drawn to kits wherein the compounds or the pharmaceutical compositions of the present invention and the one or more additional therapeutic agent(s) are in the same container.

In another embodiment, the container is a bottle, vial, or blister pack, or combination thereof.

SCHEMES AND EXAMPLES

The compounds of the invention may be readily prepared by known methods and by using the following methods, schemes and examples. Illustrated below in Scheme A through Scheme Q are general methods for preparing the compounds of the present invention. Compounds were named using either IUPAC nomenclature or the nomenclature used in ChemBioDraw Ultra (Version 12.0.2.1076, CambridgeSoft®). Anywhere in the present application where a name of a compound may not correctly describe the structure of the compound, the structure supersedes the name and governs.

EXAMPLES

General Methods.

$^1$H NMR (obtained on a Bruker 400 MHz Advance III QNP probe 1H/13C/19F/31P or a Bruker 300 MHz Advance I QNP probe 1H/13C/19F/31P) spectra were obtained as solutions in an appropriate deuterated solvent such as dimethyl sulfoxide-d6 (DMSO-D6 or DMSO-d6). Mass spectra (MS) were obtained using either Method 1 or Method 2 as follows. Method 1: Mass spectra (MS) were obtained using a Waters Acquity UPLC-MS system equipped with a Waters 3100 mass detector. Compound purity and retention times were determined by reversed phase HPLC using an Acquity CSH C18 column (50×2.1 mm, 1.7 µm particle) from Waters (pn: 186005296), and a dual gradient run from 5-95% mobile phase B over 0.60 minutes. Mobile phase A=H$_2$O (0.1% CF$_3$CO$_2$H). Mobile phase B=CH$_3$CN (0.1% CF$_3$CO$_2$H). Flow rate=0.6 mL/min, injection volume=2 µL, and column temperature=25° C. Method 2: Mass spectra (MS) were obtained using a Waters Acquity UPLC-MS system equipped with a Waters 3100 mass detector. Compound purity and retention times were determined by reversed phase HPLC using an Acquity CSH Fluoro Phenyl column (50×2.1 mm, 1.7 µm particle) from Waters (pn: 186005351), and a dual gradient run from 5-95% mobile phase B over 0.60 minutes. Mobile phase A=H$_2$O (0.1% CF$_3$CO$_2$H). Mobile phase B=CH$_3$CN (0.1% CF$_3$CO$_2$H). Flow rate=0.6 mL/min, injection volume=2 µL, and column temperature=25° C. Normal phase flash chromatography was performed using pre-packed Isco RediSepRf high performance columns. Pyridine, dichloromethane (CH$_2$Cl$_2$ or DCM), tetrahydrofuran (THF), dimethylformamide (DMF), acetonitrile (ACN), methanol (MeOH), and 1,4-dioxane were from Baker or Aldrich and in some cases the reagents were Aldrich Sure-Seal bottles kept under dry nitrogen. All reactions were stirred magnetically unless otherwise noted.

The following definitions describe terms and abbreviations used herein:
DCM dichloromethane
DMA diemethylacetamide
EtOAc/EA ethyl acetate
Hex hexanes
HEP heptanes
HPLC high-performance liquid chromatography
LCMS liquid chromatography-mass spectrometry
ESI-MS electrospray ionization mass spectrometry
TLC thin layer chromatography
DMF N,N-dimethylformamide
DMSO dimethylsulfoxide
THF tetrahydrofuran
Et$_3$N triethylamine
NMP N-methylpyrrolidone
HOAc acetic acid
TFA trifluoroacetic acid
ACN acetonitrile
DCM dichloromethane
DCE dichloroethane
DMA dimethylacetamide
N2 nitrogen
R.T./RT/rt room temperature
AT ambient temperature
MeOH methanol
EtOH ethanol
t-BuOH t-butanol
t-BuONa sodium t-butoxide
Pd/C palladium on carbon
SnAr nucleophilic aromatic substitution mechanism
t-BuXPhos Palladacycle chloro(2-di-t-butylphosphino-2',4', 6'-tri-i-propyl-1,1'-biphenyl) [2-(2-aminoethyl)phenyl] palladium(II)
Pd$_2$(dba)$_3$ tris(dibenzylideneacetone)dipalladium
ISCO flash chromatography system
SiO$_2$ silica gel
MP-TMT macroporous polystyrene-bound trimecaptotriazine
PL-HCO$_3$ MP SPE polymer supported bicarbonate resin
RBF round-bottom flask
Cmpd Compound Scheme A: General Route A to Compounds of Formula I or I'

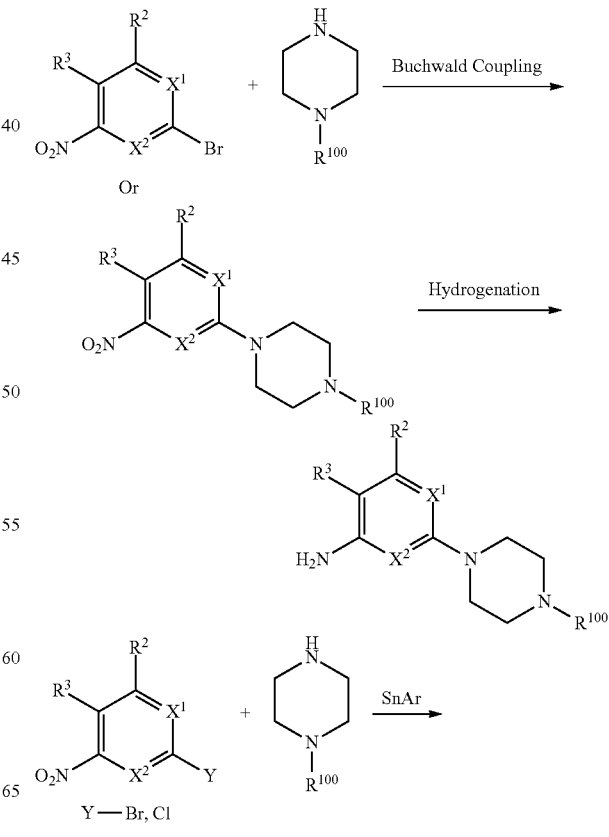

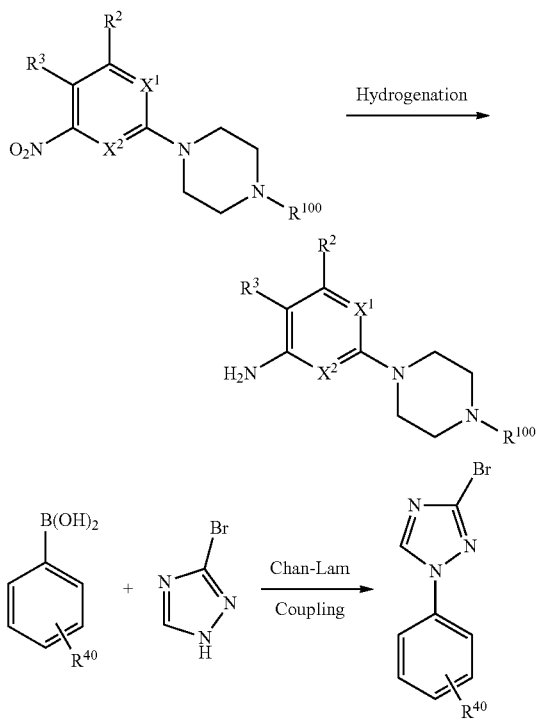

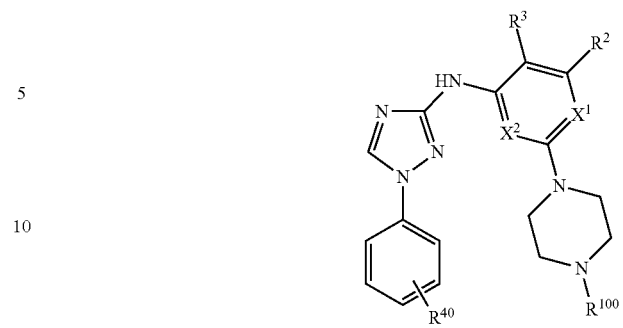

Compounds of the invention may be prepared as generally outlined in Scheme A, which shows representative structures wherein $L^1$ is a bond, the piperazinyl may represent $G^1$ or $G^2$, $R^{100}$ may represent $-L^2-R^6$, $-L^2-R^7$, or optional $G^2$ substituents, $R^{40}$ may represent optional $R^4$ substituents, and $R^2$, $R^3$, $X^1$, and $X^2$ are as defined herein. The methods of Scheme A may also be applied to other variations of $L^1$ with $G^1$ to $G^5$ that bond to the parent molecular moiety through a nitrogen atom.

Example 1

Preparation of 1-(3,5-difluorophenyl)-N-[3-methyl-5-[4-(oxetan-3-yl)piperazin-1-yl]phenyl]-1,2,4-triazol-3-amine (Compound 33)

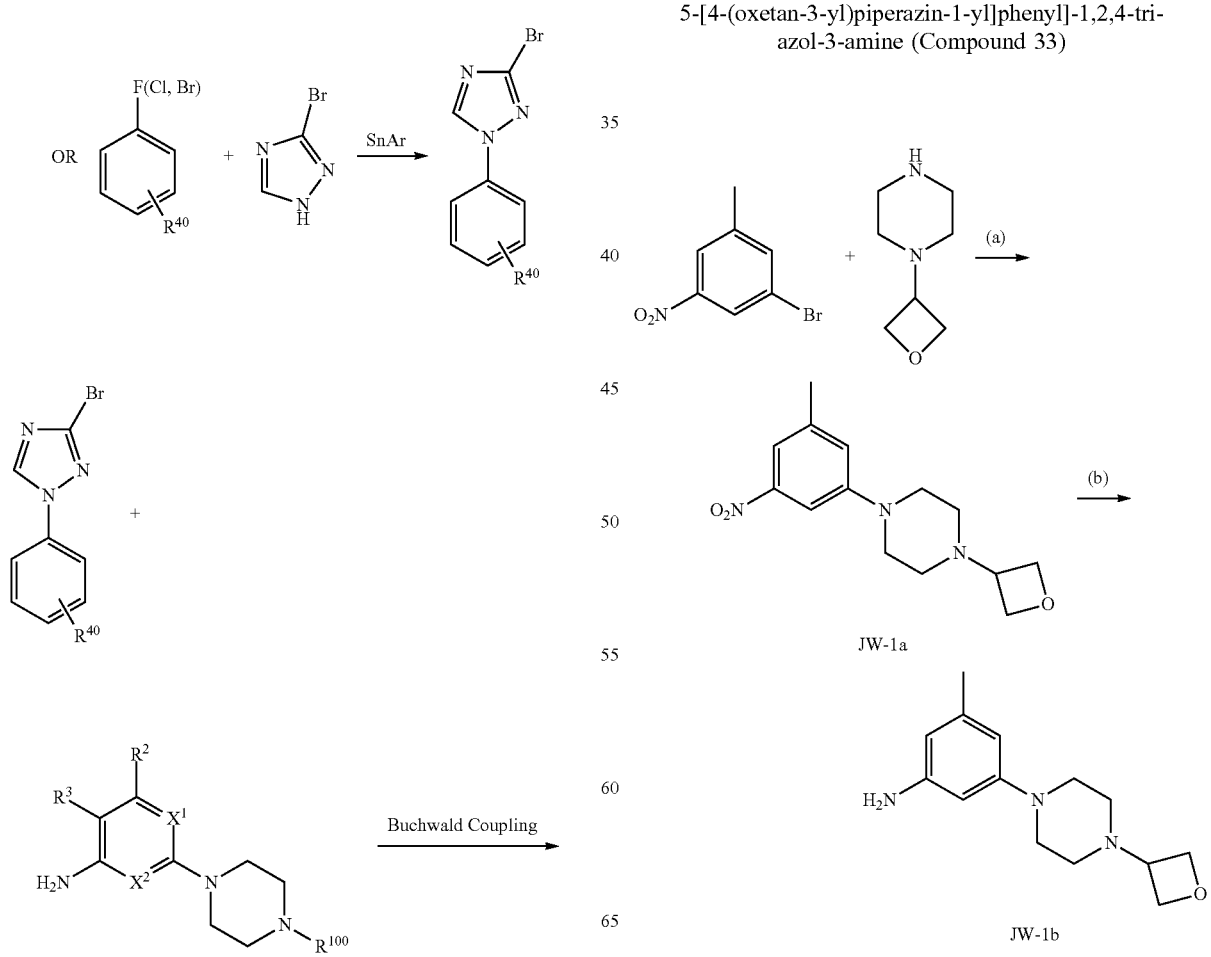

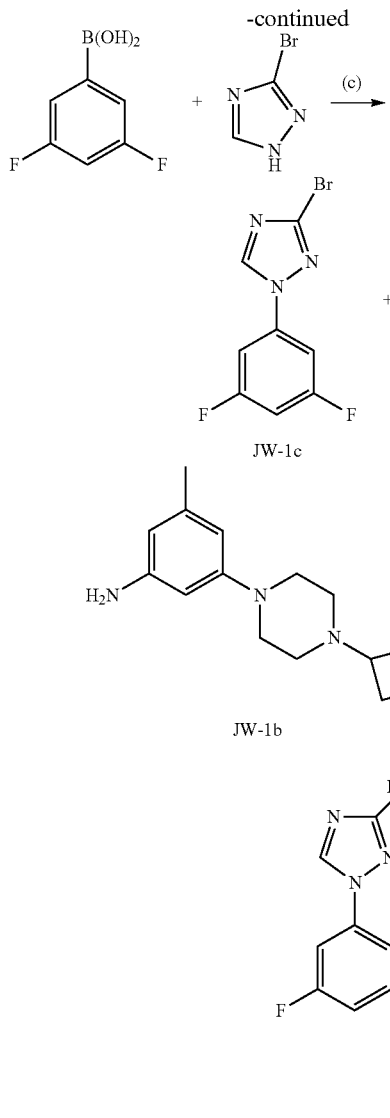

(a) t-BuXPhos Palladacycle, t-BuOH, t-BuONa, 60° C.; (b) Pd on Carbon, 10% WT Degussa, H₂; (c) Cu(OAc)₂/Pyridine/CH₂Cl₂/room temp; (d) t-BuXPhos Palladacycle, t-BuOH Preparation of 1-(3-methyl-5-nitro-phenyl)-4-(oxetan-3-yl)piperazine (JW-1a)

Sodium 2-methylpropan-2-olate (10.5 g, 109.4 mmol), 1-(oxetan-3-yl)piperazine (6.28 g, 44.2 mmol), t-BuXPhos Palladacycle (93 mg, 0.88 mmol) and 1-bromo-3-methyl-5-nitro-benzene (9.54 g, 44.1 mmol) were mixed in 2-methylpropan-2-ol (50 mL) and the reaction was degassed with $N_2$ for 10 seconds. The reaction was stirred at 60 degrees for 3 hours and LCMS indicated that the reaction was complete. The reaction was quenched with 1 ml water and the mixture was extracted with DCM (3×3 ml). The combined DCM layers were dried over $Na_2SO_4$, concentrated and purified on silica gel (120 grams column, 10-90% ethyl acetate: hexanes) to afford 5.9 g (31%) of desired product JW-1a. ¹H NMR (300 MHz, CDCl3) δ 7.61-7.42 (m, 2H), 7.00 (s, 1H), 4.68 (dt, J=12.4, 6.4 Hz, 4H), 3.67-3.46 (m, 1H), 3.41-3.17 (m, 4H), 2.59-2.44 (m, 4H), 2.40 (s, 3H) ppm. ESI-MS m/z calc. 277.14264, found 278.45 (M+1)+; Retention time: 0.57 minutes.

Preparation of 3-methyl-5-[4-(oxetan-3-yl)piperazin-1-yl]aniline (JW-1b)

To a 250 ml RBF was added Pd on carbon 10% WT, Degussa (250 mg, 2.3 mmol) under N2 and EtOH (60 mL) was added into the reaction under N2. 1-(3-Methyl-5-nitrophenyl)-4-(oxetan-3-yl)piperazine JW-1a (6.5 g, 23.4 mmol) was added and the reaction was stirred at R.T. under a hydrogen balloon. The reaction was stirred overnight and LCMS showed that the reaction was complete. The catalyst was filtered off and the filtrated was concentrated to afford 5.34 g (92%) of desired product JW-1b. ¹H NMR (300 MHz, CDCl3) δ 6.19 (s, 1H), 6.08 (d, J=1.5 Hz, 2H), 4.80-4.48 (m, 4H), 3.73-3.39 (m, 3H), 3.31-3.08 (m, 4H), 2.66-2.38 (m, 4H), 2.22 (s, 3H) ppm. ESI-MS m/z calc. 247.16846, found 248.48 (M+1)+; Retention time: 0.25 minutes.

Preparation of 3-bromo-1-(3,5-difluorophenyl)-1,2,4-triazole (JW-1c)

3-bromo-1-(3,5-difluorophenyl)-1,2,4-triazole was prepared by either Method 1 or Method 2 as follows.

Method 1: Diacetoxycopper (2.30 g, 12.7 mmol), 3,5-difluorophenyl-boronic acid (1.60 g, 10.1 mmol), 3-bromo-1H-1,2,4-triazole (1.25 g, 8.4 mmol) and 4A molecular sieve (150 mg) were mixed in DCM (50 mL), and pyridine (1.3 mL, 16.90 mmol) was added. The mixture was stirred at RT under air for 3 days. LCMS showed that no starting material remained and desired product was formed. The reaction was filtered through a plug of Celite via suction and the solid was washed with additional DCM (200 ml). The combined organic layer was washed with 0.1 N aqueous HCl three times (50 ml×3) and brine (200 ml). The organic layer was concentrated and purified on silica gel (120 g column, dry loading method on Celite) using 10-90% EtOAc:Hexanes to afford 1.23 g (50%) of desired product JW-1c. ¹H NMR (400 MHz, DMSO-d6) δ 9.40 (s, 1H), 7.78-7.61 (m, 2H), 7.41 (tt, J=9.3, 2.3 Hz, 1H) ppm. ESI-MS m/z calc. 258.95566, found 260.05 (M+1)+; Retention time: 0.8 minutes.

Method 2: A DMSO (100 mL) mixture of 3-bromo-1H-1,2,4-triazole (2.95 g, 20 mmol), 1,3,5-trifluorobenzene (10.57 g, 80.0 mmol) and $K_2CO_3$ (6.63 g, 48.0 mmol) was stirred at 109° C. overnight. Both TLC and LCMS indicated the major peak to be the desired product. To the reaction mixture was added brine and EtOAc, the organic phase was dried over $MgSO_4$, filtered, concentrated in vacuo and purified on an ISCO system using 80 g silica gel column eluting with 75% heptanes and 25% EtOAc to give (1.3 g, 25%) of the desired product, 3-bromo-1-(3,5-difluorophenyl)-1,2,4-triazole (1.3 g, 4.99 mmol, 25%). ¹H NMR (400 MHz, CDCl₃) δ 8.46 (s, 1H), 7.28 (td, J=4.1, 2.2 Hz, 2H), 6.90 (tt, J=8.6, 2.3 Hz, 1H) ppm. ESI-MS m/z calc. 258.95566, found 262.01 (M+1)⁺; Retention time: 0.79 minutes.

Preparation of 1-(3,5-difluorophenyl)-N-[3-methyl-5-[4-(oxetan-3-yl)piperazin-1-yl]phenyl]-1,2,4-triazol-3-amine (Compound 33)

Sodium t-butoxide (669 mg, 6.96 mmol), 3-methyl-5-[4-(oxetan-3-yl)piperazin-1-yl]aniline JW-1b (852 mg, 3.44 mmol), 3-bromo-1-(3,5-difluorophenyl)-1,2,4-triazole JW-1c (902 mg, 3.46 mmol) and t-BuXPhos Palladacycle (83 mg, 0.12 mmol) were mixed in t-BuOH (12 mL) and the reaction was degassed with $N_2$ for 30 seconds. The reaction was stirred and heated at 60 degrees for 3 hours and the LCMS indicated that the reaction was complete. The reaction was quenched with 1 ml water and brine was added into the solution. The reaction was extracted with DCM (3×30 ml) and the combined organic layer was washed with water and brine. The organic layer was dried over $Na_2SO_4$, concentrated in vacuo and the crude was purified on silica gel (12 gram column, 10-100% EtOAc:Hexanes) to afford 768 mg (51%) of desired cmpd 33. $^1$H NMR (300 MHz, $CDCl_3$) δ 8.32 (s, 1H), 7.28-7.21 (m, 2H), 7.12 (t, J=1.9 Hz, 1H), 6.88-6.68 (m, 3H), 6.46 (d, J=14.4 Hz, 1H), 4.81-4.70 (m, 4H), 3.67-3.48 (m, 1H), 3.33 (dd, J=13.0, 8.2 Hz, 4H), 2.61-2.51 (m, 4H), 2.35 (s, 3H) ppm. ESI-MS m/z calc. 426.19797, found 427.36 (M+1)+; Retention time: 0.65 minutes.

Example 2

Preparation of 1-(3-fluorophenyl)-N-[3-methyl-5-[4-(oxetan-3-yl)piperazin-1-yl]phenyl]-1,2,4-triazol-3-amine (Compound 406)

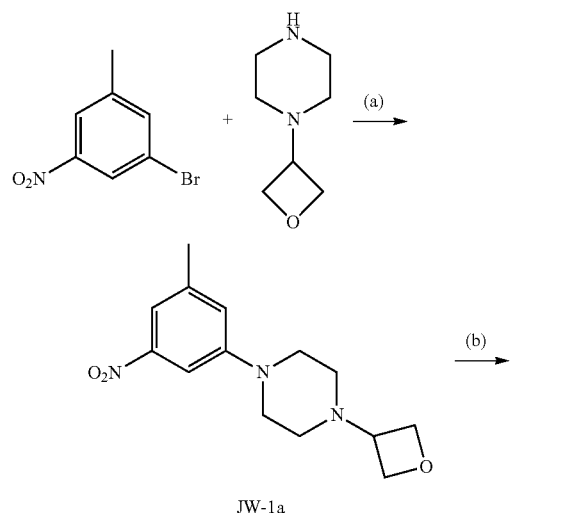

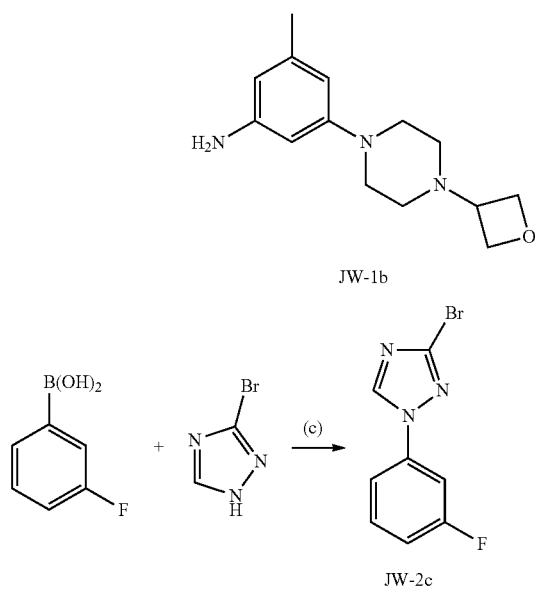

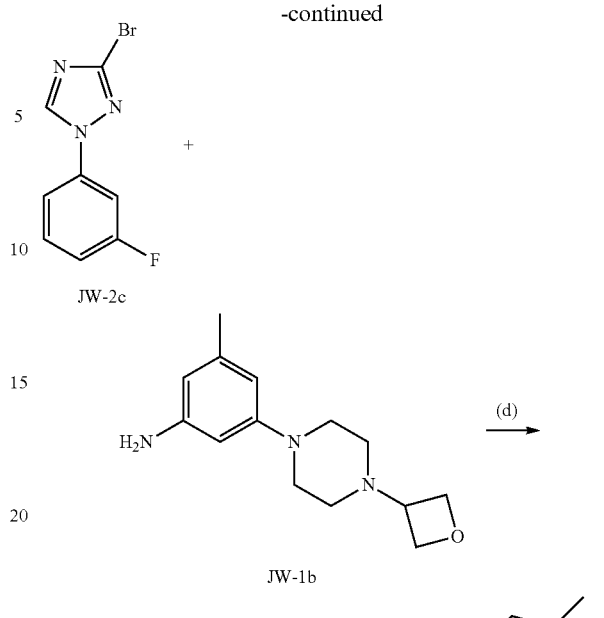

(a) t-BuXPhos Palladacycle, t-BuOH, t-BuONa, 60° C.; (b) Pd on Carbon, 10% WT., Degussa, H2; (c) Cu(OAc)$_2$/Pyridine/DCM/R.T.; (d) t-BuXPhos Palladacycle, t-BuOH Preparation of 3-bromo-1-(3-fluorophenyl)-1,2,4-triazole (JW-2c)

3-bromo-1H-1,2,4-triazole (9.6 g, 64.9 mmol), pyridine (10.5 mL, 129.8 mmol), copper (II) acetate (17.7 g, 97.3 mmol) and (3-fluorophenyl) boronic acid (11.4 g, 81.1 mmol) were mixed in DCM (200 mL) and the reaction was stirred at room temperature for 3 days. The solid was filtered off and the filtrate was washed with water several times. The organic layer was dried, concentrated and purified on silica gel to afford 6.3 g of desired product JW-2c in 38% yield. $^1$H NMR (400 MHz, CDCl3) δ 8.45 (s, 1H), 7.54-7.47 (m, 1H), 7.45 (t, J=7.5 Hz, 2H), 7.20-7.04 (m, 1H) ppm. ESI-MS m/z calc. 240.96509, found 242.27 (M+1)+; Retention time: 0.75 minutes.

Preparation of (1-(3-fluorophenyl)-N-[3-methyl-5-[4-(oxetan-3-yl)piperazin-1-yl]phenyl]-1,2,4-triazol-3-amine) (Compound 406)

Sodium t-butoxide (95 mg, 0.99 mmol), t-BuXPhos Palladacycle (13 mg, 0.019 mmol), 3-bromo-1-(3-fluorophenyl)-1,2,4-triazole JW-2c (120 mg, 0.49 mmol) and 3-methyl-5-[4-(oxetan-3-yl)piperazin-1-yl]aniline JW-1b (122 mg, 0.49 mmol) were mixed in t-BuOH (2 mL) and the reaction was degassed for 20 seconds. The reaction was stirred at 60 degrees for 1 hr. The reaction was cooled to room temperature and diluted with 2 ml water. The reaction was extracted with DCM and purified on normal phase (4 gram column, Hex:EtOAc, 10-100%) to afford 83.2 mg (37%) of desired product. $^1$H NMR (300 MHz, DMSO-d6) δ 9.25 (s, 1H), 9.11 (s, 1H), 7.79-7.66 (m, 2H), 7.62-7.52 (m, 1H), 7.24-7.04 (m, 2H), 6.88 (s, 1H), 6.31 (s, 1H), 4.57 (t, J=6.5 Hz, 2H), 3.45 (p, J=6.3 Hz, 1H), 3.27-3.12 (m, 4H), 2.47-2.38 (m, 4H), 2.23 (s, 3H) ppm. ESI-MS m/z calc. 408.2074, found 409.45 (M+1)+; Retention time: 0.65 minutes.

Example 3

Preparation of 1-(3,4-difluorophenyl)-N-[3-methyl-5-[4-(oxetan-3-yl)piperazin-1-yl]phenyl]-1,2,4-triazol-3-amine (Compound 386)

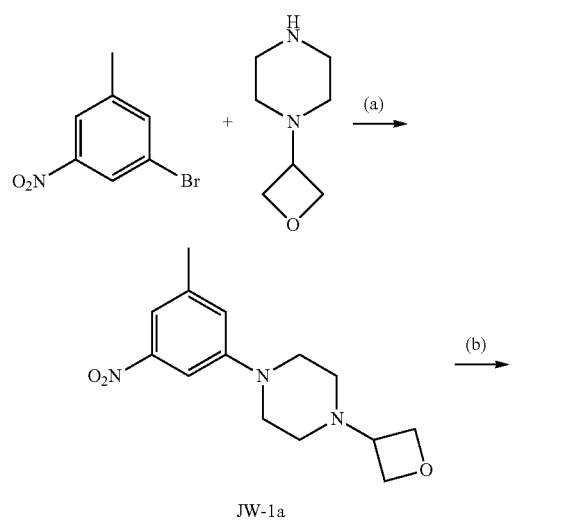

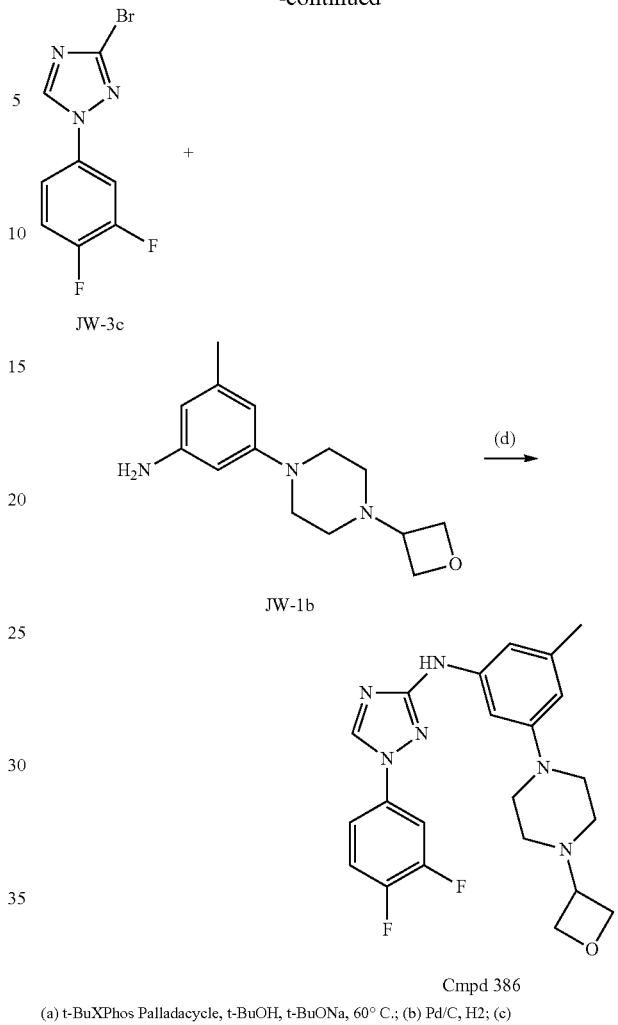

(a) t-BuXPhos Palladacycle, t-BuOH, t-BuONa, 60° C.; (b) Pd/C, H2; (c) Cu(OAc)2/Pyridine/DCM/R.T.; (d) t-BuXPhos Palladacycle, t-BuOH Preparation of 3-bromo-1-(3,4-difluorophenyl)-1,2,4-triazole (JW-3c)

Diacetoxycopper (18.4 g, 101.4 mmol), bromo-triazole (10 g, 67.6 mmol), and 4A molecular sieves (250 mg, 0.33 mmol) were mixed in DCM, to which 4-difluorophenyl) boronic acid (14.9 g, 94.6 mmol), pyridine (10.9 mL, 135.2 mmol) was added. The mixture was stirred at RT under air for 3 days. LCMS showed that no starting material remaining and desired product was formed. The reaction was filtered and the solid was washed with additional DCM (200 ml). The combined organic layer was concentrated with silica gel and dry-loaded to purify on silica gel (240 grams column, 10-90% ethyl acetate:hexanes) to afford 10.5 g (60%) of desired product JW3-c. $^1$H NMR (400 MHz, DMSO-D6) δ 9.30 (s, 1H), 8.08-7.96 (m, 1H), 7.77-7.62 (m, 2H) ppm. ESI-MS m/z calc. 258.95566, found 260.32 (M+1)+; Retention time: 0.96 minutes.

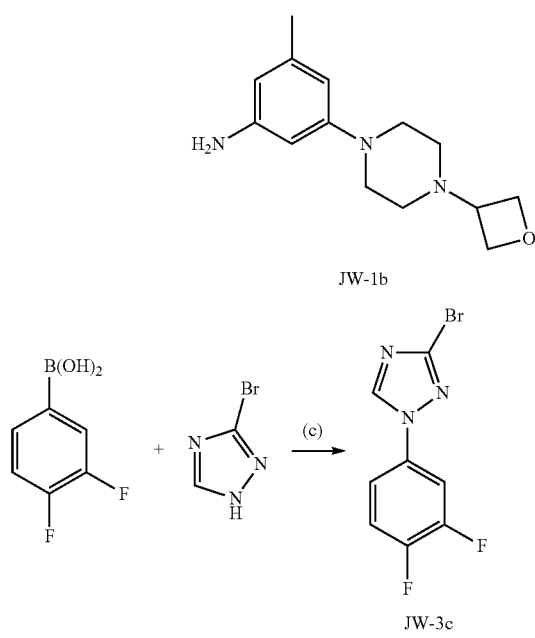

Preparation of (1-(3,4-difluorophenyl)-N-[3-methyl-5-[4-(oxetan-3-yl)piperazin-1-yl]phenyl]-1,2,4-triazol-3-amine) (Compound 386)

Sodium t-butoxide (69 mg, 0.72 mmol), t-BuXphos Palladacycle (12 mg, 0.02 mmol), 3-bromo-1-(3,4-difluorophenyl)-1,2,4-triazole JW-3c (120 mg, 0.46 mmol) and 3-methyl-5-[4-(oxetan-3-yl)piperazin-1-yl]aniline JW-1b (114 mg, 0.46 mmol) were mixed in t-BuOH (2 mL) and the reaction was degassed for 20 seconds. The reaction was stirred at 60 degrees for 1 hour. The reaction was cooled to room temperature and diluted with 2 ml water. The reaction was extracted with DCM (10 ml) and purified on normal phase (4 grams column, Hex:EtOAc, 10-100%) to afford 73 mg (35%) of desired product cmpd 386. $^1$H NMR (300 MHz, DMSO-d6) δ 9.24 (s, 1H), 9.05 (s, 1H), 8.18-7.81 (m, 1H), 7.81-7.53 (m, 2H), 7.13 (s, 1H), 6.88 (s, 1H), 6.31 (s, 1H), 4.57 (t, J=6.5 Hz, 2H), 4.53-4.39 (m, 2H), 3.45 (p, J=6.2 Hz, 1H), 3.24-3.10 (m, 4H), 2.46-2.37 (m, 4H), 2.23 (s, 3H) ppm. ESI-MS m/z calc. 426.19797, found 427.41 (M+1)+; Retention time: 0.66 minutes.

Example 4

Preparation of 1-(2,5-difluorophenyl)-N-[3-methyl-5-[4-(oxetan-3-yl)piperazin-1-yl]phenyl]-1,2,4-triazol-3-amine (Compound 437)

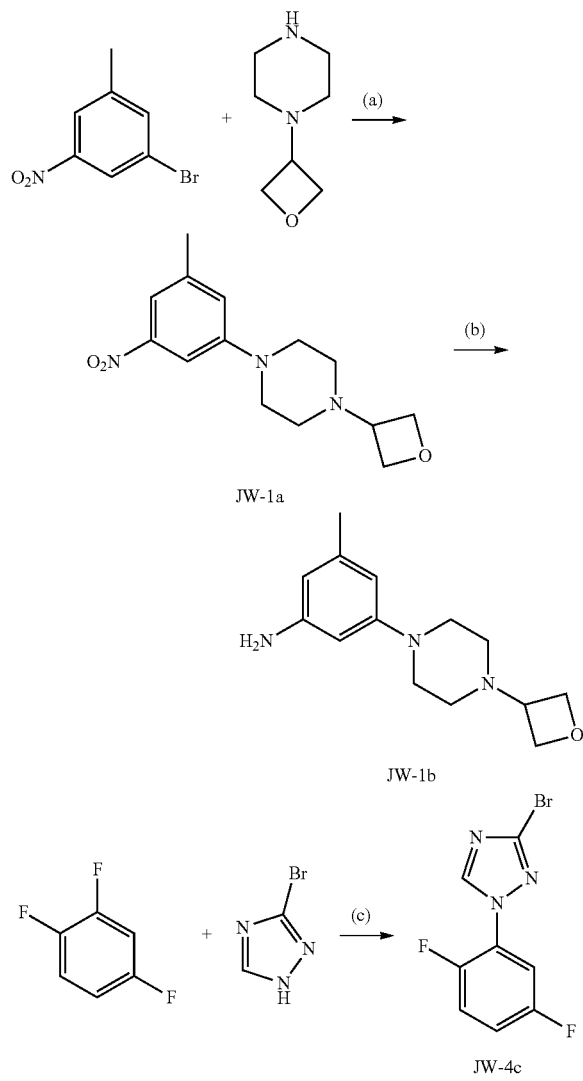

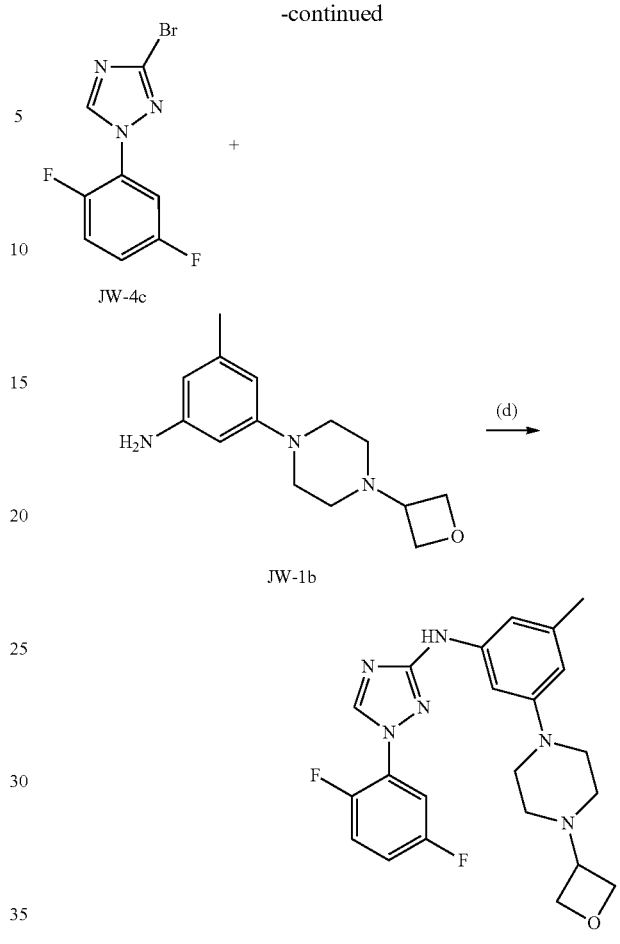

(a) t-BuXPhos Palladacycle, t-BuOH, t-BuONa, 60° C.; (b) Pd on carbon, 10% WT., Degussa, H$_2$; (c) K$_2$CO$_3$/DMF/100° C.; (d) t-BuXPhos Palladacycle, t-BuOH/t-BuONa.

Preparation of 3-bromo-1-(2,5-difluorophenyl)-1,2,4-triazole (JW-4c)

Combined 3-bromo-1H-1,2,4-triazole (29.6 g, 200 mmol), 1,2,4-trifluorobenzene (79.3 g, 62.70 mL, 600.0 mmol) and potassium carbonate (27.6 g, 200.0 mmol) in 500 mL of DMF and heated to 100°-110° for 22 hours. The mixture was cooled and DMF removed under vacuum to dryness. 250 mL of water was added and the organics extracted with EtOAc. The organic layer was dried over sodium sulfate, filtered and evaporated. The crude mixture was purified on silica gel (220 grams column, 10-50% Ethyl acetate:Hexanes) to afford 13 g (25%) of product JW-4c as off white solid. $^1$H NMR (300 MHz, DMSO-d6) δ 9.10 (d, J=2.0 Hz, 1H), 7.77 (ddd, J=8.9, 5.9, 3.2 Hz, 1H), 7.65 (ddd, J=10.4, 9.3, 4.8 Hz, 1H), 7.52-7.41 (m, 1H) ppm. ESI-MS m/z calc. 258.95566, found 260.01 (M+1)+; Retention time: 0.79 minutes.

Preparation of 1-(2,5-difluorophenyl)-N-[3-methyl-5-[4-(oxetan-3-yl)piperazin-1-yl]phenyl]-1,2,4-triazol-3-amine (Compound 437)

Sodium t-butoxide (86 mg, 0.90 mmol), t-BuXphos Palladacycle (12 mg, 0.02 mmol), 3-bromo-1-(2,5-difluorophenyl)-1,2,4-triazole JW-4c (164 mg, 0.60 mmol) and 3-methyl-5-[4-(oxetan-3-yl)piperazin-1-yl]aniline (JW-1b) (154 mg, 0.62 mmol) were mixed in t-BuOH (2.0 mL) and the reaction was degassed with $N_2$ for 30 seconds. The reaction was heated at 60 degrees for 3 hours and the LCMS indicated that the reaction was complete. The reaction was cooled to room temperature and water was added to quench the reaction. Brine was added, the reaction was extracted with DCM and the organic layer was dried and concentrated in vacuo. The crude product was purified on reverse phase (12 grams, 10-90% water:acetonitrile) and the desired fractions were collected, neutralized with aq. NaHCO3 and extracted with EtOAc to afford 85 mg (32%) of free base desired product cmpd 437. $^1$H NMR (300 MHz, DMSO-d6) δ 9.30 (s, 1H), 8.80 (d, J=2.4 Hz, 1H), 7.69 (ddd, J=9.2, 6.0, 3.2 Hz, 1H), 7.67-7.48 (m, 1H), 7.40-7.23 (m, 1H), 7.14 (s, 1H), 6.86 (s, 1H), 6.31 (s, 1H), 4.57 (t, J=6.5 Hz, 2H), 4.47 (t, J=6.0 Hz, 2H), 3.58-3.40 (m, 1H), 3.23-3.00 (m, 4H), 2.45-2.31 (m, 4H), 2.22 (s, 3H) ppm. ESI-MS m/z calc. 426.19797, found 427.45 (M+1)+; Retention time: 0.64 minutes.

Example 5

Preparation of N-[3-methyl-5-(4-methylpiperazin-1-yl)phenyl]-1-phenyl-1,2,4-triazol-3-amine (Compound 247)

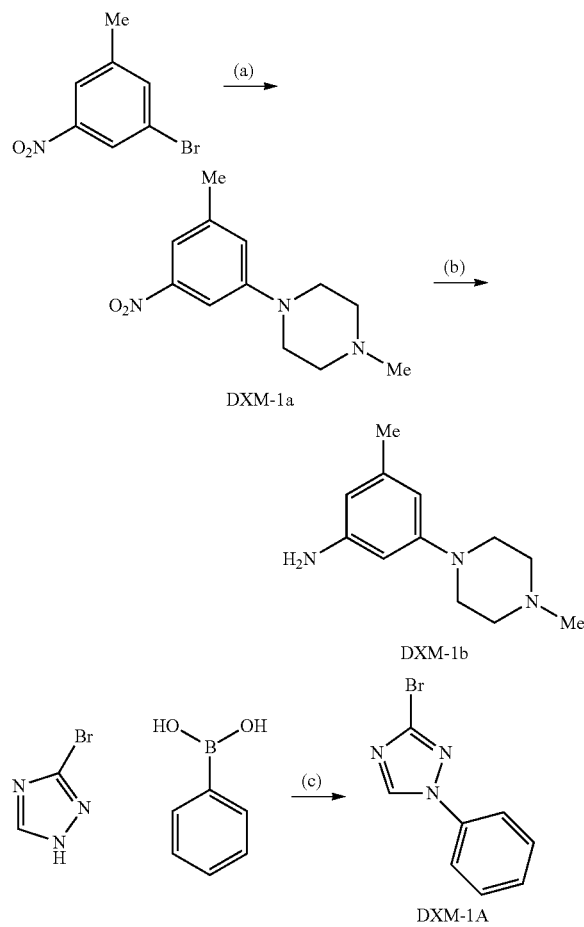

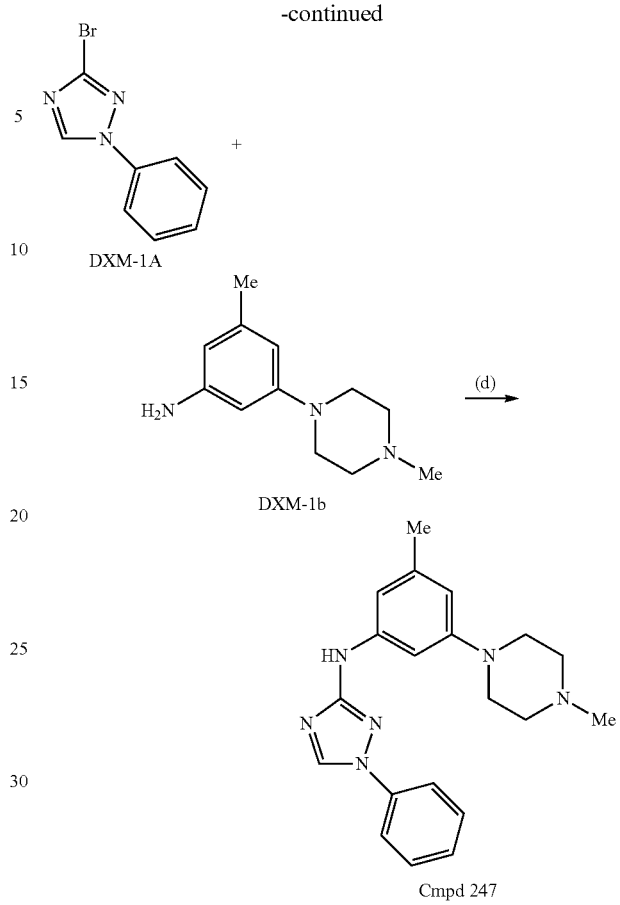

Cmpd 247

(a) t-BuONa, 1-Me-piperazine, t-BuXPhosPd, 40° C., t-BuOH; (b) 10% Pd/C, H$_2$, 50 psi, RT, MeOH; (c) pyridine, Cu(II) acetate, RT, 4 days (d) t-BuONa, t-BuXPhosPd, 40° C., t-BuOH.

Preparation of 3-bromo-1-phenyl-1H-1,2,4-triazole (DXM-1A)

To a suspension of 3-bromo-1H-1,2,4-triazole (10 g, 67.6 mM) and phenylboronic acid (16.5 g, 135.2 mM) in 500 mL of DCM, was added the following: pyridine; (10.9 mL, 10.7 g, 135.2 mM), copper (II) acetate; (18.4 g, 101.5 mM) and powdered 4A molecular sieves (45 g). The resulting blue colored suspension was stirred at room temperature for 10 days open to the air. Additional DCM (500 mL) was added to the reaction and the mixture filtered through a pad of diatomaceous earth, washing the cake with DCM, 10% MeOH/DCM, and finally DCM. The filtrates were collected and concentrated under reduced pressure to provide a viscous residue, which was partitioned between ethyl acetate and 1N HCl. The organic phase was washed with water (2×), brine (1×) then dried over anhydrous sodium sulphate. Suction filtered the organic layer to remove particulates and evaporated under reduced pressure to give the crude product which was purified on CombiFlash (240 g column) SiO$_2$ eluting with 25% ethyl acetate/heptanes. Combined clean fractions and reduced the volume of the fractions under reduced pressure until crystals formed. Isolated crystals via suction filtration, washed with additional heptanes and air dried to yield 3-bromo-1-phenyl-1H-1,2,4-triazole as a white crystalline solid (5.1 g, 34% yield). $^1$H NMR (400 MHz, DMSO-d6) δ 9.32 (s, 1H), 7.92-7.79 (m, 2H), 7.58

(dd, J=11.3, 4.5 Hz, 2H), 7.51-7.41 (m, 1H) ppm. ESI-MS m/z calc. 222.9745, found 224.0 (M+1)+; Retention time: 0.75 minutes.

Preparation of 1-methyl-3-nitro-5-(4-N-methylpiperazin-1-yl)benzene (DXM-1a)

3-Bromo-5-nitro-toluene, (20.0 g, 93 mM) and 1-methylpiperazine, (11.5 mL, 10.2 g, 102 mM) were placed into a 500 mL round bottom flask and dissolved in 250 mL of dry tert-butanol and purged with $N_2$ for 10 minutes. The solution was warmed with a heat gun several times to prevent solidification during the nitrogen purge. During the N2 purge, added chloro(2-di-t-butylphosphino-2',4',6'-tri-i-propyl-1,1'-biphenyl) [2-(2-aminoethyl)phenyl]palladium(II), min. 98% [t-BuXPhos Palladacycle] (1.5 g, 2.32 mM) followed by sodium tert-butoxide; (13.4 g, 139.0 mM) and the reaction was allowed to stir at 40° C. under nitrogen for one hour. Upon addition of the base, the reaction turned dark and the solution became homogeneous, with subsequent precipitation of a white solid. The solvent was partially removed under reduced pressure and the residue partitioned between ethyl acetate and water; the organic phase washed with brine, dried over anhydrous sodium sulphate and concentrated to dryness under reduced pressure. Material was purified on SiO2 with a 0-100% gradient of ethyl acetate to 10% methanol/ethyl acetate as eluent. Material was recrystallized in methyl t-butyl ether to give a medium yellow powder. The mother liquor was evaporated under pressure and re-purified on SiO2 with a 0-100% gradient of dichloromethane to 10% methanol/dichloromethane as the eluent. This material was combined with the first crop and recrystallized from boiling methyl t-butyl ether giving 12 g (52%) of DXM-1a as a medium yellow powder. $^1$H NMR (400 MHz, CDCl3) δ 7.53 (d, J=1.8 Hz, 1H), 7.48 (s, 1H), 7.00 (s, 1H), 3.38-3.19 (m, 4H), 2.66-2.49 (m, 4H), 2.39 (s, 3H), 2.36 (d, J=2.0 Hz, 3H) ppm. ESI-MS m/z calc. 235.13, found 236.0 (M+1)+; Retention time: 0.55 minutes.

Preparation of 3-methyl-5-(4-N-methylpiperazin-1-yl)aniline (DXM-1b)

1-Methyl-4-(3-methyl-5-nitro-phenyl) piperazine (DXM-1a, 25 g, 106 mM) was dissolved/suspended in 500 mL of methanol and placed under carbon dioxide before adding 6 g of 10% palladium on carbon (Degussa type, 50% water) to the vessel. Reaction was placed under a hydrogen atmosphere at 50 psi for 14 hours. Note: the initial dark yellow color changes to a light tan solution. The reaction mixture was pulled through a pad of diatomaceous earth, washed with methanol and the solvent was removed under reduced pressure to afford 22 g (70%) of DXM-1b as a tan oil. $^1$H NMR (400 MHz, CDCl3) δ 7.48-7.17 (m, 1H), 6.20 (s, 1H), 6.14-5.97 (m, 2H), 3.27-3.07 (m, 4H), 2.69-2.52 (m, 4H), 2.36 (s, 3H), 2.22 (s, 3H) ppm. ESI-MS m/z calc. 205.1579, found 206.0 (M+1)+; Retention time: 0.26 minutes.

Preparation of N-[3-methyl-5-(4-methylpiperazin-1-yl)phenyl]-1-N-phenyl-1,2,4-triazol-3-amine (Compound 247)

3-bromo-1-N-phenyl-1,2,4-triazole (DXM-1A) (18 g, 80.4 mM, and 3-methyl-5-(4-methylpiperazin-1-yl)aniline; (18.2 g, 88.4 mM) were dissolved into dry tert-butanol (500 mL) and purged with $N_2$ for several minutes. Near the end of the purge, chloro(2-di-t-butylphosphino-2',4',6'-tri-i-propyl-1,1'-biphenyl) [2-(2-aminoethyl)phenyl]palladium(II), min. 98% [t-BuXPhos Palladacycle], (1.5 g, 2.01 mM) and sodium tert-butoxide; (12 g, 121 mM) were added sequentially. The reaction was placed under N2, stirred and heated at 40° C. for 60 min. Note: a gradual colour change from initial light tan solution to pale yellow suspension was observed and the reaction becomes quite viscous. The reaction was deemed complete by HPLC. Approximately 200 mL of solvent was removed under reduced pressure and the mixture was poured into 2 L of water with stirring. The precipitate was collected via suction filtration and washed with water containing a small amount of sodium carbonate. The wet cake was transferred to a round bottom with methanol and solvents were evaporated under reduced pressure. Dissolved this crude material into dichloromethane and added brine and some saturated sodium carbonate solution (pH 10) and split the layers. The organic phase was dried with anhydrous sodium sulphate and the solvent was removed under reduced pressure to give a light tan solid which was recrystallized from boiling CH3CN (100 mL) and let stand overnight under a nitrogen atmosphere. Isolated crystals via suction filtration and washed with cold CH3CN. A second crop was obtained and kept separate. Main material was recrystallized again from 100 mL of boiling CH3CN, isolated via suction filtration and washed with cold CH3CN. Material was dissolved into DCM and pulled through a 100 uM filter then treated with 2M hydrogen chloride in Et2O (32 mL, 1.1 equiv). The solvents were partially removed under reduced pressure, diluted with hexanes and the resulting precipitate was isolated via suction filtration. Washed with more hexanes and dried under high vacuum to constant weight to yield 20.7 g (64%) of cmpd 247 as the HCl salt and as a white powder. $^1$H NMR (400 MHz, CDCl3) δ 10.81 (s, 1H), 9.31 (s, 1H), 9.08 (s, 1H), 7.84 (dd, J=8.6, 1.0 Hz, 2H), 7.55 (dd, J=8.4, 7.6 Hz, 2H), 7.35 (t, J=7.4 Hz, 1H), 7.20 (s, 1H), 6.95 (s, 1H), 6.37 (s, 1H), 3.73 (d, J=11.3 Hz, 2H), 3.50 (d, J=10.8 Hz, 2H), 3.29-3.00 (m, 4H), 2.81 (d, J=4.7 Hz, 3H), 2.24 (s, 3H) ppm. ESI-MS m/z calc. 348.20624, found 349.0 (M+1)+; Retention time: 0.59 minutes.

Example 6

Preparation of 1-(3-fluoro-5-methyl-phenyl)-N-[3-methyl-5-[4-(oxetan-3-yl)piperazin-1-yl]phenyl]-1,2,4-triazol-3-amine (Compound 323)

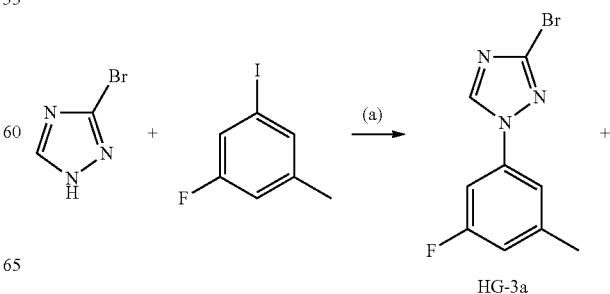

HG-3a

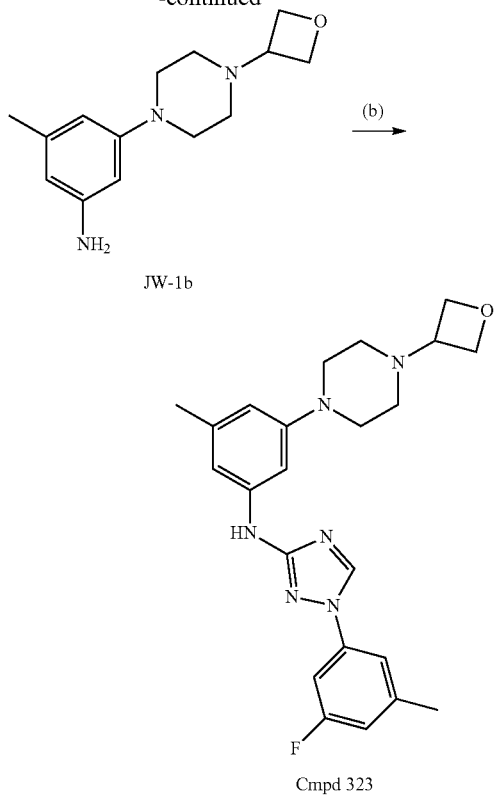

Cmpd 323

(a) CuI/Cs2CO3/DMSO (b) t-BuXPHOS Palladacycle/t-BuOK/t-BuOH

Preparation of 3-bromo-1-(3-fluoro-5-methylphenyl)-1H-1,2,4-triazole (HG-3a)

To a 100 ml flask was added 3-bromo-1H-1,2,4-triazole (739.8 mg, 5 mmol), CuI (95.2 mg, 0.50 mmol) and $Cs_2CO_3$ (1.629 g, 5.0 mmol) and the flask was evacuated then backfilled with $N_2$ before adding DMSO (5 mL) and 1-fluoro-3-iodo-5-methyl-benzene (590.1 mg, 2.50 mmol). The reaction mixture was heated at 100° C. for 20 h at which time LCMS indicated the major peak was desired product. To the reaction mixture was added EtOAc, the mixture was filtered through celite and to the filtrate was added brine. The organic phase was dried over MgSO4, filtered, evaporated to dryness and purified on an Isco 40 g silica gel column eluting with heptanes and ethyl acetate to afford 3-bromo-1-(3-fluoro-5-methyl-phenyl)-1,2,4-triazole HG-3a (170 mg, 26.6%). $^1$H NMR (300 MHz, CDCl3) δ 8.43 (s, 1H), 7.29 (d, J=2.7 Hz, 1H), 7.23 (dt, J=9.0, 2.0 Hz, 1H), 6.97 (d, J=9.1 Hz, 1H), 2.46 (s, 3H) ppm. ESI-MS m/z calc. 254.98074, found 257.97 (M+1)$^+$; Retention time: 0.81 minutes.

Preparation of 1-(3-fluoro-5-methylphenyl)-N-(3-methyl-5-(4-(oxetan-3-yl)piperazin-1-yl)phenyl)-1H-1,2,4-triazol-3-amine (Compound 323)

To a t-BuOH (1.69 mL) solution of 3-bromo-1-(3-fluoro-5-methyl-phenyl)-1,2,4-triazole HG-3a (110 mg, 0.43 mmol) and 3-methyl-5-[4-(oxetan-3-yl)piperazin-1-yl]aniline JW-1b (117 mg, 0.473 mmol) was added t-BuXPhos Palladacycle (14 mg, 0.022 mmol) and t-BuOK (145 mg, 1.29 mmol), the reaction mixture stirred at 85° C. for 1 h before LCMS indicated the major peak was desired product. To the reaction mixture was added EtOAc and brine, the organic phase was dried over MgSO4, filtered, concentrated down and purified by an Isco 150 g Gold C18 column eluting with H2O/CH3CN/TFA. The product fractions were extracted with EtOAc, the organic phase dried over MgSO4, filtered and concentrated to dryness to afford 1-(3-fluoro-5-methylphenyl)-N-(3-methyl-5-(4-(oxetan-3-yl)piperazin-1-yl)phenyl)-1H-1,2,4-triazol-3-amine, cmpd 323 (89 mg 48% yield). $^1$H NMR (300 MHz, CDCl3) δ 8.30 (s, 1H), 7.24 (s, 1H), 7.15 (s, 1H), 6.88 (d, J=8.6 Hz, 1H), 6.79 (s, 1H), 6.60 (s, 1H), 6.42 (s, 1H), 4.80-4.62 (m, 4H), 3.67-3.47 (m, 1H), 3.39-3.22 (m, 4H), 2.61-2.49 (m, 4H), 2.45 (s, 3H), 2.35 (s, 3H) ppm. ESI-MS m/z calc. 422.22305, found 423.3 (M+1)$^+$; Retention time: 0.62 minutes.

Example 7

Preparation of 1-(3,5-difluorophenyl)-N-[3-ethyl-5-[4-(oxetan-3-yl)piperazin-1-yl]phenyl]-1,2,4-triazol-3-amine (Compound 107)

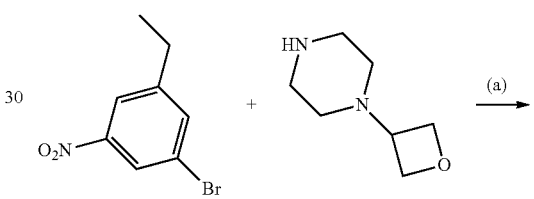

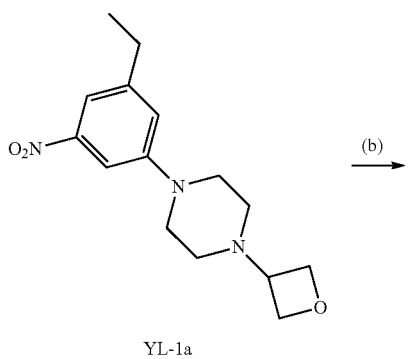

YL-1a

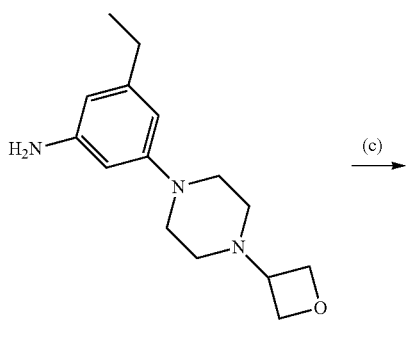

YL-1b

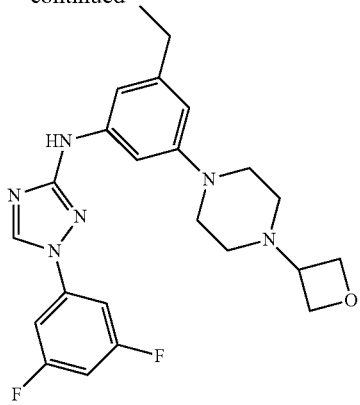

Cmpd 107

Reagents and conditions: (a) Pd₂(dba)₃, X—PHOS, dioxane, 105° C.; (b) H₂, Pd/C, EtOAc; c) 1-(3,5-difluorophenyl)-1,2,4-triazol-3-amine, t-BuXPhos Palladacycle, NaOtBu, dioxane, 120° C.

Preparation of 1-(3-ethyl-5-nitro-phenyl)-4-(oxetan-3-yl)piperazine (YL-1a)

To a 250 mL round bottom flask with stirrer and reflux condenser was added 1-bromo-3-ethyl-5-nitro-benzene (10 g, 42.2 mmol), 1-(oxetan-3-yl)piperazine (Pharmablock, 6.96 g, 48.5 mmol) and cesium carbonate (27.47 g, 84.3 mmol) in 1,4-dioxane (116 mL). The reaction mixture was purged with $N_2$ for 5 min. To the mixture was added Pd₂(dba)₃ (772 mg, 0.84 mmol) and t-BuXPhos Palladacycle (804 mg, 1.69 mmol) and the resultant mixture was again purged with nitrogen for 5 minutes. The mixture was warmed to 105° C. and refluxed at this temperature for 18 h. The reaction mixture was cooled to ambient temperature, diluted with ethyl acetate:DCM (1:1, 500 mL), filtered through a florisil-bed and the bed washed with ethyl acetate:DCM (1:1, 4×500 ml). The combined filtrates were concentrated under reduced pressure to dryness. ISCO purification (80 g silica; 20% to 50% to 90% of EtOAc in hex) gave 1-(3-ethyl-5-nitro-phenyl)-4-(oxetan-3-yl)piperazine YL-1a (5.76 g, 47%). ¹H NMR (300 MHz, CDCl₃) δ 7.60-7.49 (m, 2H), 7.04 (s, 1H), 4.70 (dt, J=12.3, 6.4 Hz, 4H), 3.67-3.51 (m, 1H), 3.42-3.22 (m, 4H), 2.71 (q, J=7.6 Hz, 2H), 2.60-2.43 (m, 4H), 1.28 (t, J=7.6 Hz, 3H) ppm. ESI-MS m/z calc. 291.16, found 292.13 (M+1)+; Retention time: 0.63 minutes.

Preparation of 3-ethyl-5-[4-(oxetan-3-yl)piperazin-1-yl]aniline (YL-1b)

To Pd on C, wet, Degussa (631 mg, 0.59 mmol) under N2 was added a solution of 1-(3-ethyl-5-nitro-phenyl)-4-(oxetan-3-yl)piperazine YL-1a (5.76 g, 19.8 mmol) in EtOAc (80 mL) and MeOH (20 mL) under N2. The mixture was shaken under H2 (50 psi) for 2 hr on a Parr apparatus. The reaction mixture was filtered through celite and evaporated to dryness to give 3-ethyl-5-[4-(oxetan-3-yl)piperazin-1-yl]aniline YL-1b (4.7 g, 91%). ¹H NMR (300 MHz, CDCl₃) δ 6.25 (s, 1H), 6.11 (dd, J=3.9, 1.7 Hz, 2H), 4.83-4.57 (m, 4H), 3.58 (dd, J=12.9, 6.3 Hz, 3H), 3.32-3.11 (m, 4H), 2.52 (dt, J=10.0, 6.3 Hz, 6H), 1.22 (t, J=7.6 Hz, 3H) ppm. ESI-MS m/z calc. 261.18, found 262.48 (M+1)+; Retention time: 0.52 minutes.

Preparation of 1-(3,5-difluorophenyl)-N-[3-ethyl-5-[4-(oxetan-3-yl)piperazin-1-yl]phenyl]-1,2,4-triazol-3-amine (Compound 107)

A mixture of 3-bromo-1-(3,5-difluorophenyl)-1,2,4-triazole JW-1c (5.55 g, 21.4 mmol), 3-ethyl-5-[4-(oxetan-3-yl)piperazin-1-yl]aniline YL-1b (4.65 g, 17.79 mmol) and sodium t-butoxide (2.22 g, 23.13 mmol) in t-butyl alcohol (100 mL) and dioxane (15 mL) was purged with $N_2$ for 30 min. [2-(2-Aminoethyl)phenyl]-chloro-palladium; ditert-butyl-[2-(2,4,6-triisopropylphenyl)phenyl]phosphane (366 mg, 0.53 mmol) was added and the resultant mixture was heated at 55 C° for 8 h. LCMS showed the desired product with 10% of starting materials remaining. Additional [2-(2-aminoethyl)phenyl]-chloro-palladium; ditert-butyl-[2-(2,4,6-triisopropylphenyl)phenyl]phosphane (122 mg, 0.18 mmol) was added and the reaction mixture was heated at 70° C. for another 2 h. The reaction mixture was cooled to RT and diluted with water (300 mL). The slurry was stirred for 2 h, filtered, the solid collected, washed with water (250 mL) and triturated with ether, then MeOH and dried in vacuo to afford 6 g of product. The product was dissolved in MeOH/DCM (1:9) and filtered through Florisil (50 g) columns. The filtrate was evaporated in vacuo to give 5.2 g of desired product. The desired product was dissolved in MeOH/DCM (1:9; 100 mL) then macroporous polystyrene-bound trimecaptotriazine (MP-TMT) (0.64 mmol/g; 5.5 g, 5 equivalents, Biotage #801472) was added and the suspension rotated at 45~50° C. for 4 h. After filtration, the solvent was evaporated to dryness to afford 1-(3,5-difluorophenyl)-N-[3-ethyl-5-[4-(oxetan-3-yl)piperazin-1-yl]phenyl]-1,2,4-triazol-3-amine, cmpd 107 (4.7 g, 59%). ¹H NMR (300 MHz, CDCl₃) δ 8.31 (s, 1H), 7.25 (d, J=5.9 Hz, 2H), 7.14 (s, 1H), 6.88-6.74 (m, 2H), 6.69 (s, 1H), 6.46 (s, 1H), 4.89-4.51 (m, 4H), 3.59 (p, J=6.4 Hz, 1H), 3.42-3.22 (m, 4H), 2.65 (q, J=7.6 Hz, 2H), 2.59-2.41 (m, 4H), 1.28 (t, J=7.6 Hz, 3H) ppm. ESI-MS m/z calc. 440.21, found 441.49 (M+1)+; Retention time: 0.69 minutes.

Example 8

Preparation of N-[3-ethyl-5-[4-(oxetan-3-yl)piperazin-1-yl]phenyl]-1-pyrazin-2-yl-1,2,4-triazol-3-amine (Compound 48)

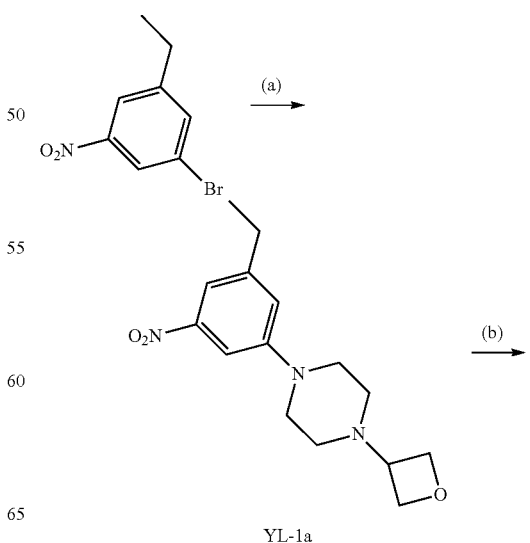

YL-1a

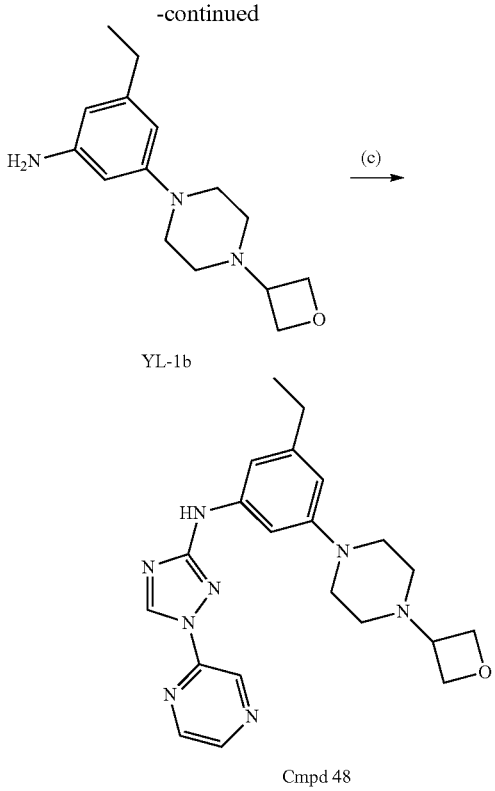

Cmpd 48

Reagents and conditions: (a) Pd₂(dba)₃, X—PHOS, dioxane, 105° C.; (b) H₂, Pd/C, EtOAc; (c) 2-(3-bromo-1,2,4-triazol-1-yl)pyrazine, t-BuXPhos Palladacycle, NaOtBu, dioxane, 120° C.

Preparation of
2-(3-bromo-1,2,4-triazol-1-yl)pyrazine

A mixture of $K_2CO_3$ (29.19 g, 211.2 mmol), 3-bromo-1H-1,2,4-triazole (25 g, 169.0 mmol) and 2-chloropyrazine (19.36 g, 169.0 mmol) in NMP (130 mL) was heated at 125° C. for 6 hrs. The reaction was quenched with water (300 mL) and stirred for 1 h. The solids were collected, washed with water, ether and dried to give 2-(3-bromo-1,2,4-triazol-1-yl)pyrazine (32 g, 83.8%). $^1$H NMR (300 MHz, $CD_3OD$+ $CDCl_3$) δ 9.40-9.05 (m, 2H), 8.70 (d, J=2.5 Hz, 1H), 8.56 (dd, J=2.5, 1.5 Hz, 1H) ppm. ESI-MS m/z calc. 224.97, found 226.29 (M+1)+; Retention time: 0.75 minutes.

Preparation of 1-(3-ethyl-5-nitro-phenyl)-4-(oxetan-3-yl)piperazine (YL-1a)

To a 250 mL RB flask with stirrer and reflux condenser was added 1-bromo-3-ethyl-5-nitro-benzene (10 g, 42.16 mmol), 1-(oxetan-3-yl)piperazine (6.96 g, 48.48 mmol) and cesium carbonate (27.47 g, 84.32 mmol) in 1,4-dioxane (116 mL). The reaction mixture was purged with $N_2$ for 5 min. To above mixture was added $Pd_2(dba)_3$ (772 mg, 0.84 mmol) and X-PHOS (804 mg, 1.69 mmol) and the resultant mixture was degassed by bubbling in a stream of nitrogen for 5 minutes. The resulting reaction mixture was heated to 105° C. and refluxed at this temperature for 18 h. The reaction mixture was cooled to ambient temperature, diluted with ethyl acetate:DCM (1:1, 500 mL), filtered through a florisil-bed and the bed washed with ethyl acetate:DCM (1:1, 4×500 ml). The combined filtrates were concentrated under reduced pressure to dryness and then purified on an ISCO column (80 g silica) eluting with 20% to 50% to 90% of EtOAc in hex) to give 1-(3-ethyl-5-nitro-phenyl)-4-(oxetan-3-yl)piperazine, YL-1a (5.76 g, 47%). $^1$H NMR (300 MHz, $CDCl_3$) δ 7.60-7.49 (m, 2H), 7.04 (s, 1H), 4.70 (dt, J=12.3, 6.4 Hz, 4H), 3.67-3.51 (m, 1H), 3.42-3.22 (m, 4H), 2.71 (q, J=7.6 Hz, 2H), 2.60-2.43 (m, 4H), 1.28 (t, J=7.6 Hz, 3H) ppm. ESI-MS m/z calc. 291.16, found 292.13 (M+1)+; Retention time: 0.63 minutes.

Preparation of 3-ethyl-5-[4-(oxetan-3-yl)piperazin-1-yl]aniline (YL-1b)

To Pd on C, wet, Degussa (631.2 mg, 0.59 mmol) under N2 was added a solution of 1-(3-ethyl-5-nitro-phenyl)-4-(oxetan-3-yl)piperazine (5.76 g, 19.77 mmol) in EtOAc (80 mL) and MeOH (20 mL) under N2. The mixture was shaken on a Parr apparatus under H2 (50 psi) for 2 h. The reaction mixture was filtered through celite and evaporated in vacuo to give 3-ethyl-5-[4-(oxetan-3-yl)piperazin-1-yl]aniline YL-1b (4.7 g, 91.0%). $^1$H NMR (300 MHz, $CDCl_3$) δ 6.25 (s, 1H), 6.11 (dd, J=3.9, 1.7 Hz, 2H), 4.83-4.57 (m, 4H), 3.58 (dd, J=12.9, 6.3 Hz, 3H), 3.32-3.11 (m, 4H), 2.52 (dt, J=10.0, 6.3 Hz, 6H), 1.22 (t, J=7.6 Hz, 3H) ppm. ESI-MS m/z calc. 261.18, found 262.48 (M+1)+; Retention time: 0.52 minutes.

Preparation of N-[3-ethyl-5-[4-(oxetan-3-yl)piperazin-1-yl]phenyl]-1-pyrazin-2-yl-1,2,4-triazol-3-amine (Compound 48)

A mixture of 2-(3-bromo-1,2,4-triazol-1-yl)pyrazine (1.30 g, 5.74 mmol), 3-ethyl-5-[4-(oxetan-3-yl)piperazin-1-yl]aniline YL-1b (1.25 g, 4.78 mmol) and sodium t-butoxide (598 mg, 6.22 mmol) in butan-1-ol (30 mL) and dioxane (10 mL) was purged with $N_2$ for 30 min. t-BuXPhos Palladacycle (131 mg, 0.19 mmol) was added and the resultant mixture was heated at 55° C. for 8 h, then at 70° C. for another 2 h. The reaction mixture was cooled to RT and diluted with water (300 mL). The slurry was stirred for 2 h. The solids were collected, washed with water (250 mL) and triturated with ether, then MeOH and dried in vacuo to afford 3 g of pure product. The above product in MeOH/DCM (1:9) was filtered through a Florisil (20 g) column and the combined solvents were evaporated in vacuo to give 2 g of desired product. The above product was dissolved in MeOH/DCM (1:9; 100 mL) and treated with 5 equivalents of MP-TMT (0.64 mmol/g) and rotated at 45~50° C. for 4 h. After filtration, the excess solvent was pumped down to afford N-[3-ethyl-5-[4-(oxetan-3-yl)piperazin-1-yl]phenyl]-1-pyrazin-2-yl-1,2,4-triazol-3-amine, cmpd 48 (2.12 g, 52%). $^1$H NMR (300 MHz, $CDCl_3$) δ 9.18 (d, J=1.3 Hz, 1H), 8.93 (s, 1H), 8.57 (d, J=2.5 Hz, 1H), 8.41 (dd, J=2.5, 1.5 Hz, 1H), 7.19 (t, J=2.0 Hz, 1H), 6.83 (d, J=10.4 Hz, 2H), 6.48 (s, 1H), 4.82-4.63 (m, 4H), 3.68-3.53 (m, 1H), 3.40-3.25 (m, 4H), 2.65 (q, J=7.6 Hz, 2H), 2.61-2.42 (m, 4H), 1.29 (t, J=7.6 Hz, 3H) ppm. ESI-MS m/z calc. 406.22, found 407.47 (M+1)+; Retention time: 0.67 minutes.

Using the general synthetic scheme outlined in Scheme A and the experimental procedures listed above in Examples 1-8, the following compounds were prepared:

| Cmpd No. | IUPAC name |
|---|---|
| 38 | N3-[1-(3,5-difluorophenyl)-1,2,4-triazol-3-yl]-5-methyl-N1-[1-(oxetan-3-yl)-4-piperidyl]benzene-1,3-diamine |

| Cmpd No. | IUPAC name |
|---|---|
| 334 | 5-methyl-N1-[1-(oxetan-3-yl)-4-piperidyl]-N3-(1-phenyl-1,2,4-triazol-3-yl)benzene-1,3-diamine |
| 278 | N3-[1-(3,4-difluorophenyl)-1,2,4-triazol-3-yl]-5-methyl-N1-[1-(oxetan-3-yl)-4-piperidyl]benzene-1,3-diamine |
| 192 | N3-[1-(3-fluorophenyl)-1,2,4-triazol-3-yl]-5-methyl-N1-[1-(oxetan-3-yl)-4-piperidyl]benzene-1,3-diamine |
| 472 | N3-[1-(3,5-difluorophenyl)-1,2,4-triazol-3-yl]-5-methyl-N1-[1-(oxetan-3-yl)pyrrolidin-3-yl]benzene-1,3-diamine |
| 309 | 5-methyl-N1-[1-(oxetan-3-yl)pyrrolidin-3-yl]-N3-(1-phenyl-1,2,4-triazol-3-yl)benzene-1,3-diamine |
| 188 | N3-[1-(3-fluorophenyl)-1,2,4-triazol-3-yl]-5-methyl-N1-[1-(oxetan-3-yl)pyrrolidin-3-yl]benzene-1,3-diamine |
| 113 | N3-[1-(3,4-difluorophenyl)-1,2,4-triazol-3-yl]-5-methyl-N1-[1-(oxetan-3-yl)pyrrolidin-3-yl]benzene-1,3-diamine |
| 421 | 1-(3,5-difluorophenyl)-N-[3-methyl-5-[4-(2,2,2-trifluoroethyl)piperazin-1-yl]phenyl]-1,2,4-triazol-3-amine |
| 231 | 1-(3,4-difluorophenyl)-N-[3-methyl-5-[4-(2,2,2-trifluoroethyl)piperazin-1-yl]phenyl]-1,2,4-triazol-3-amine |
| 482 | N-[3-(4-cyclopropylpiperazin-1-yl)-5-methyl-phenyl]-1-(3,5-difluorophenyl)-1,2,4-triazol-3-amine |
| 17 | N-[3-tert-butyl-5-[4-(oxetan-3-yl)piperazin-1-yl]phenyl]-1-(3,5-difluorophenyl)-1,2,4-triazol-3-amine |
| 97 | N-[3-tert-butyl-5-[4-(oxetan-3-yl)piperazin-1-yl]phenyl]-1-(3-fluorophenyl)-1,2,4-triazol-3-amine |
| 376 | N-[3-tert-butyl-5-[4-(oxetan-3-yl)piperazin-1-yl]phenyl]-1-phenyl-1,2,4-triazol-3-amine |
| 69 | 1-(3,4-difluorophenyl)-N-[3-ethyl-5-[4-(oxetan-3-yl)piperazin-1-yl]phenyl]-1,2,4-triazol-3-amine |
| 14 | N-[3-ethyl-5-[4-(oxetan-3-yl)piperazin-1-yl]phenyl]-1-(4-fluorophenyl)-1,2,4-triazol-3-amine |
| 102 | 1-(4-fluorophenyl)-N-[3-methoxy-5-[4-(oxetan-3-yl)piperazin-1-yl]phenyl]-1,2,4-triazol-3-amine |
| 258 | 1-(3-fluorophenyl)-N-[3-methoxy-5-[4-(oxetan-3-yl)piperazin-1-yl]phenyl]-1,2,4-triazol-3-amine |
| 183 | 1-(3,4-difluorophenyl)-N-[3-methoxy-5-[4-(oxetan-3-yl)piperazin-1-yl]phenyl]-1,2,4-triazol-3-amine |
| 37 | 1-(3,5-difluorophenyl)-N-[3-methyl-5-(4-methylpiperazin-1-yl)phenyl]-1,2,4-triazol-3-amine |
| 54 | N-[3-methyl-5-[4-(oxetan-3-yl)piperazin-1-yl]phenyl]-1-(4-methyl-2-pyridyl)-1,2,4-triazol-3-amine |
| 453 | N-[3-[4-(3,3-difluorocyclobutyl)piperazin-1-yl]-5-methyl-phenyl]-1-(3,5-difluorophenyl)-1,2,4-triazol-3-amine |
| 237 | N-[2,3-dimethyl-5-[4-(oxetan-3-yl)piperazin-1-yl]phenyl]-1-phenyl-1,2,4-triazol-3-amine |
| 425 | 1-(3,5-difluorophenyl)-N-[2,3-dimethyl-5-[4-(oxetan-3-yl)piperazin-1-yl]phenyl]-1,2,4-triazol-3-amine |
| 216 | 1-(3,5-difluorophenyl)-N-[3-methyl-5-[4-(oxetan-3-yl)-1-piperidyl]phenyl]-1,2,4-triazol-3-amine |
| 484 | N-[3-methyl-5-[4-(oxetan-3-yl)piperazin-1-yl]phenyl]-1-(2,3,5-trifluorophenyl)-1,2,4-triazol-3-amine |
| 66 | 2,5-difluoro-4-[3-[3-methyl-5-[4-(oxetan-3-yl)piperazin-1-yl]anilino]-1,2,4-triazol-1-yl]benzonitrile |
| 413 | N-[3-methyl-5-[4-(oxetan-3-yl)piperazin-1-yl]phenyl]-1-(2,4,5-trifluorophenyl)-1,2,4-triazol-3-amine |
| 140 | 2-fluoro-4-[3-[3-methyl-5-[4-(oxetan-3-yl)piperazin-1-yl]anilino]-1,2,4-triazol-1-yl]benzonitrile |
| 86 | 1-(3-methoxyphenyl)-N-[3-methyl-5-[4-(oxetan-3-yl)piperazin-1-yl]phenyl]-1,2,4-triazol-3-amine |
| 94 | 1-(3-methoxyphenyl)-N-[3-methyl-5-(4-methylpiperazin-1-yl)phenyl]-1,2,4-triazol-3-amine |
| 56 | 1-(3-fluoro-5-methoxy-phenyl)-N-[3-methyl-5-[4-(oxetan-3-yl)piperazin-1-yl]phenyl]-1,2,4-triazol-3-amine |
| 395 | 1-(3-fluoro-5-methoxy-phenyl)-N-[3-methyl-5-(4-methylpiperazin-1-yl)phenyl]-1,2,4-triazol-3-amine |
| 397 | 1-(3-chlorophenyl)-N-[3-methyl-5-[4-(oxetan-3-yl)piperazin-1-yl]phenyl]-1,2,4-triazol-3-amine |
| 141 | 1-(3-chlorophenyl)-N-[3-methyl-5-(4-methylpiperazin-1-yl)phenyl]-1,2,4-triazol-3-amine |
| 187 | 1-[3-[[ethyl(methyl)amino]methyl]-5-fluoro-phenyl]-N-[3-methyl-5-[4-(oxetan-3-yl)piperazin-1-yl]phenyl]-1,2,4-triazol-3-amine |
| 390 | 1-[3-[[ethyl(methyl)amino]methyl]-5-fluoro-phenyl]-N-[3-methyl-5-(4-methylpiperazin-1-yl)phenyl]-1,2,4-triazol-3-amine |
| 255 | 1-(3-ethyl-5-fluoro-phenyl)-N-[3-methyl-5-(4-methylpiperazin-1-yl)phenyl]-1,2,4-triazol-3-amine |
| 206 | 1-(3-ethyl-5-fluoro-phenyl)-N-[3-methyl-5-[4-(oxetan-3-yl)piperazin-1-yl]phenyl]-1,2,4-triazol-3-amine |
| 415 | 1-(3-fluoro-5-isopropoxy-phenyl)-N-[3-methyl-5-[4-(oxetan-3-yl)piperazin-1-yl]phenyl]-1,2,4-triazol-3-amine |
| 223 | 1-(2-fluorophenyl)-N-[3-methyl-5-[4-(oxetan-3-yl)piperazin-1-yl]phenyl]-1,2,4-triazol-3-amine |
| 373 | 1-[3-fluoro-5-[2-methoxyethyl(methyl)amino]phenyl]-N-[3-methyl-5-[4-(oxetan-3-yl)piperazin-1-yl]phenyl]-1,2,4-triazol-3-amine |
| 103 | 1-[3-(2-ethylpyrrolidin-1-yl)-5-fluoro-phenyl]-N-[3-methyl-5-[4-(oxetan-3-yl)piperazin-1-yl]phenyl]-1,2,4-triazol-3-amine |
| 41 | 1-[3-[2-(ethoxymethyl)pyrrolidin-1-yl]-5-fluoro-phenyl]-N-[3-methyl-5-[4-(oxetan-3-yl)piperazin-1-yl]phenyl]-1,2,4-triazol-3-amine |
| 480 | [1-[3-fluoro-5-[3-[3-methyl-5-[4-(oxetan-3-yl)piperazin-1-yl]anilino]-1,2,4-triazol-1-yl]phenyl]pyrrolidin-3-yl]methanol |
| 467 | 1-[3-fluoro-5-[(3R)-3-fluoropyrrolidin-1-yl]phenyl]-N-[3-methyl-5-[4-(oxetan-3-yl)piperazin-1-yl]phenyl]-1,2,4-triazol-3-amine |
| 318 | 2-[(3R)-1-[3-fluoro-5-[3-[3-methyl-5-[4-(oxetan-3-yl)piperazin-1-yl]anilino]-1,2,4-triazol-1-yl]phenyl]pyrrolidin-3-yl]propan-2-ol |
| 491 | 1-[3-fluoro-5-[(2R)-2-(methoxymethyl)pyrrolidin-1-yl]phenyl]-N-[3-methyl-5-[4-(oxetan-3-yl)piperazin-1-yl]phenyl]-1,2,4-triazol-3-amine |
| 287 | N-[3-methyl-5-[4-(oxetan-3-yl)piperazin-1-yl]phenyl]-1-[3-(trifluoromethyl)phenyl]-1,2,4-triazol-3-amine |
| 218 | N-[3-ethyl-5-[4-(oxetan-3-yl)piperazin-1-yl]phenyl]-1-[3-(trifluoromethyl)phenyl]-1,2,4-triazol-3-amine |
| 252 | N-[3-methyl-5-[4-(oxetan-3-yl)piperazin-1-yl]phenyl]-1-[3-(trifluoromethoxy)phenyl]-1,2,4-triazol-3-amine |
| 432 | N-[3-ethyl-5-[4-(oxetan-3-yl)piperazin-1-yl]phenyl]-1-(3-methoxyphenyl)-1,2,4-triazol-3-amine |
| 70 | N-[3-methyl-5-[4-(oxetan-3-yl)piperazin-1-yl]phenyl]-1-(p-tolyl)-1,2,4-triazol-3-amine |
| 31 | N-[3-ethyl-5-[4-(oxetan-3-yl)piperazin-1-yl]phenyl]-1-(p-tolyl)-1,2,4-triazol-3-amine |
| 476 | 1-(2-fluoro-5-methyl-phenyl)-N-[3-methyl-5-[4-(oxetan-3-yl)piperazin-1-yl]phenyl]-1,2,4-triazol-3-amine |
| 338 | N-[3-ethyl-5-[4-(oxetan-3-yl)piperazin-1-yl]phenyl]-1-(2-fluoro-5-methyl-phenyl)-1,2,4-triazol-3-amine |
| 213 | N-[3-fluoro-5-(4-methylpiperazin-1-yl)phenyl]-1-phenyl-1,2,4-triazol-3-amine |
| 98 | N-[3-fluoro-5-(4-methyl-1,4-diazepan-1-yl)phenyl]-1-(3-fluorophenyl)-1,2,4-triazol-3-amine |
| 203 | N-[3-fluoro-5-(4-methylpiperazin-1-yl)phenyl]-1-(3-fluorophenyl)-1,2,4-triazol-3-amine |
| 109 | N-[3-[3-(dimethylamino)pyrrolidin-1-yl]-5-fluoro-phenyl]-1-(3-fluorophenyl)-1,2,4-triazol-3-amine |
| 166 | N-[3-fluoro-5-(1,4-oxazepan-4-yl)phenyl]-1-(3-fluorophenyl)-1,2,4-triazol-3-amine |
| 351 | N1-(azetidin-3-yl)-5-fluoro-N3-[1-(3-fluorophenyl)-1,2,4-triazol-3-yl]benzene-1,3-diamine |
| 177 | N1-(azetidin-3-yl)-N3-[1-(2,4-difluorophenyl)-1,2,4-triazol-3-yl]-5-fluoro-benzene-1,3-diamine |
| 343 | 1-(2,4-difluorophenyl)-N-[3-fluoro-5-(1,4-oxazepan-4-yl)phenyl]-1,2,4-triazol-3-amine |
| 28 | 1-(2,4-difluorophenyl)-N-[3-fluoro-5-(4-methyl-1,4-diazepan-1-yl)phenyl]-1,2,4-triazol-3-amine |
| 450 | 1-(2,4-difluorophenyl)-N-[3-fluoro-5-(4-methylpiperazin-1-yl)phenyl]-1,2,4-triazol-3-amine |
| 347 | 1-(2,4-difluorophenyl)-N-[3-[3-(dimethylamino)pyrrolidin-1-yl]-5-fluoro-phenyl]-1,2,4-triazol-3-amine |
| 283 | N-[3-(3-aminoazetidin-1-yl)-5-fluoro-phenyl]-1-(2,4-difluorophenyl)-1,2,4-triazol-3-amine |
| 149 | N-[3-(4-cyclopropylpiperazin-1-yl)-5-methyl-phenyl]-1-phenyl-1,2,4-triazol-3-amine |
| 306 | N-[3-(2,6-dimethylmorpholin-4-yl)-5-methyl-phenyl]-1-phenyl-1,2,4-triazol-3-amine |
| 179 | N-[3-methyl-5-(4-methyl-1,4-diazepan-1-yl)phenyl]-1-phenyl-1,2,4-triazol-3-amine |
| 337 | N-[3-(4-cyclopropyl-1,4-diazepan-1-yl)-5-methyl-phenyl]-1-phenyl-1,2,4-triazol-3-amine |
| 280 | 1-[4-[3-methyl-5-[(1-phenyl-1,2,4-triazol-3-yl)amino]phenyl]-1,4-diazepan-1-yl]ethanone |

| Cmpd No. | IUPAC name |
|---|---|
| 76 | 1-methyl-4-[3-methyl-5-[(1-phenyl-1,2,4-triazol-3-yl)amino]phenyl]piperazin-2-one |
| 157 | N-[3-[(8aR)-3,4,6,7,8,8a-hexahydro-1H-pyrrolo[1,2-a]pyrazin-2-yl]-5-methyl-phenyl]-1-phenyl-1,2,4-triazol-3-amine |
| 128 | N-[3-[(8aR)-3,4,6,7,8,8a-hexahydro-1H-pyrrolo[1,2-a]pyrazin-2-yl]-5-methyl-phenyl]-1-(3,5-difluorophenyl)-1,2,4-triazol-3-amine |
| 152 | N-[3-[(8aR)-4-isobutyl-3,4,6,7,8,8a-hexahydro-1H-pyrrolo[1,2-a]pyrazin-2-yl]-5-methyl-phenyl]-1-phenyl-1,2,4-triazol-3-amine |
| 29 | N-[3-[(8aR)-4-isobutyl-3,4,6,7,8,8a-hexahydro-1H-pyrrolo[1,2-a]pyrazin-2-yl]-5-methyl-phenyl]-1-(3,5-difluorophenyl)-1,2,4-triazol-3-amine |
| 481 | N-[3-[4-(methoxymethyl)-1-piperidyl]-5-methyl-phenyl]-1-phenyl-1,2,4-triazol-3-amine |
| 162 | 1-(3,5-difluorophenyl)-N-[3-[4-(methoxymethyl)-1-piperidyl]-5-methyl-phenyl]-1,2,4-triazol-3-amine |
| 200 | 7-[3-[[1-(3,5-difluorophenyl)-1,2,4-triazol-3-yl]amino]-5-methyl-phenyl]-5,6,8,8a-tetrahydro-1H-oxazolo[3,4-a]pyrazin-3-one |
| 227 | 7-[3-methyl-5-[(1-phenyl-1,2,4-triazol-3-yl)amino]phenyl]-5,6,8,8a-tetrahydro-1H-oxazolo[3,4-a]pyrazin-3-one |
| 59 | [4-[3-methyl-5-[(1-phenyl-1,2,4-triazol-3-yl)amino]phenyl]piperazin-2-yl]methanol |
| 81 | 4-[3-methyl-5-(4-methylpiperazin-1-yl)anilino]-1,2,4-triazol-1-yl]benzonitrile |
| 499 | 3-[3-[3-methyl-5-(4-methylpiperazin-1-yl)anilino]-1,2,4-triazol-1-yl]benzonitrile |
| 428 | 1-(2-chlorophenyl)-N-[3-methyl-5-(4-methylpiperazin-1-yl)phenyl]-1,2,4-triazol-3-amine |
| 317 | 1-(3,4-difluorophenyl)-N-[3-methyl-5-(4-methylpiperazin-1-yl)phenyl]-1,2,4-triazol-3-amine |
| 299 | 1-(3,4-difluorophenyl)-N-[3-[4-(methoxymethyl)-1-piperidyl]-5-methyl-phenyl]-1,2,4-triazol-3-amine |
| 412 | 1-(3,4-difluorophenyl)-N-[3-methyl-5-(4-methylpiperazin-1-yl)-5-(trifluoromethyl)phenyl]-1,2,4-triazol-3-amine |
| 182 | N1-[1-(3-methoxypropyl)-4-piperidyl]-5-methyl-N3-(1-phenyl-1,2,4-triazol-3-yl)benzene-1,3-diamine |
| 142 | 1-[3-methyl-5-[(1-phenyl-1,2,4-triazol-3-yl)amino]phenyl]piperidine-4-carbonitrile |
| 146 | 1-[3-methyl-5-[(1-phenyl-1,2,4-triazol-3-yl)amino]phenyl]piperidine-3-carbonitrile |
| 115 | 1-[3-[3-methyl-5-[(1-phenyl-1,2,4-triazol-3-yl)amino]anilino]-1-piperidyl]ethanone |
| 479 | N-[3-methyl-5-[(1S,4S)-5-methyl-2,5-diazabicyclo[2.2.1]heptan-2-yl]phenyl]-1-phenyl-1,2,4-triazol-3-amine |
| 5 | N-[3-chloro-5-[4-(oxetan-3-yl)piperazin-1-yl]phenyl]-1-(3,5-difluorophenyl)-1,2,4-triazol-3-amine |
| 310 | 1-(3,5-difluorophenyl)-N-[3-methoxy-5-[4-(oxetan-3-yl)piperazin-1-yl]phenyl]-1,2,4-triazol-3-amine |
| 169 | 1-(3,4-difluorophenyl)-N-[3-methyl-5-[4-(oxetan-3-yl)-1-piperidyl]phenyl]-1,2,4-triazol-3-amine |
| 383 | 1-(2,5-difluorophenyl)-N-[3-methyl-5-[4-(oxetan-3-yl)-1-piperidyl]phenyl]-1,2,4-triazol-3-amine |
| 207 | N-[3-methyl-5-[1-(oxetan-3-yl)-3-piperidyl]phenyl]-1-(2-pyridyl)-1,2,4-triazol-3-amine |
| 411 | 1-(3-fluorophenyl)-N-[3-methyl-5-[1-(oxetan-3-yl)-3-piperidyl]phenyl]-1,2,4-triazol-3-amine |
| 439 | N-[3-methyl-5-[4-(oxetan-3-yl)piperazin-1-yl]phenyl]-1-(3-methylsulfanylphenyl)-1,2,4-triazol-3-amine |
| 463 | N-[3-ethyl-5-[4-(oxetan-3-yl)piperazin-1-yl]phenyl]-1-(3-methylsulfanylphenyl)-1,2,4-triazol-3-amine |
| 478 | N-[3-methyl-5-[4-(oxetan-3-yl)piperazin-1-yl]phenyl]-1-[4-(trifluoromethoxy)phenyl]-1,2,4-triazol-3-amine |
| 303 | N-[3-ethyl-5-[4-(oxetan-3-yl)piperazin-1-yl]phenyl]-1-[4-(trifluoromethoxy)phenyl]-1,2,4-triazol-3-amine |
| 191 | [4-(oxetan-3-yl)piperazin-1-yl]phenyl]-1-[4-(trifluoromethyl)phenyl]-1,2,4-triazol-3-amine |
| 322 | N-[3-ethyl-5-[4-(oxetan-3-yl)piperazin-1-yl]phenyl]-1-[4-(trifluoromethyl)phenyl]-1,2,4-triazol-3-amine |
| 522 | 1-(3-fluorophenyl)-N-[3-methyl-5-[4-(oxetan-3-yl)-1-piperidyl]phenyl]-1,2,4-triazol-3-amine |
| 523 | 1-(3-fluorophenyl)-N-[3-isopropyl-5-[4-(oxetan-3-yl)piperazin-1-yl]phenyl]-1,2,4-triazol-3-amine |
| 574 | N-[3,5-bis[4-(oxetan-3-yl)piperazin-1-yl]phenyl]-1-(3,5-difluorophenyl)-1,2,4-triazol-3-amine |
| 559 | 1-(3,4-difluorophenyl)-N-[3-[4-(oxetan-3-yl)piperazin-1-yl]-5-propyl-phenyl]-1,2,4-triazol-3-amine |
| 558 | 1-(2,5-difluorophenyl)-N-(3-methyl-5-piperazin-1-yl-phenyl)-1,2,4-triazol-3-amine |
| 573 | N-[3,5-bis(4-tert-butylpiperazin-1-yl)phenyl]-1-(3,5-difluorophenyl)-1,2,4-triazol-3-amine |
| 657 | N-[3,5-bis(4-methylpiperazin-1-yl)phenyl]-1-(3,5-difluorophenyl)-1,2,4-triazol-3-amine |
| 709 | N-[3-(4-tert-butylpiperazin-1-yl)-5-methyl-phenyl]-1-(3,5-difluorophenyl)-1,2,4-triazol-3-amine |
| 723 | N-[3-chloro-5-(3-morpholinoazetidin-1-yl)phenyl]-1-(3,5-difluorophenyl)-1,2,4-triazol-3-amine |
| 753 | N-[3-chloro-5-(3-morpholinoazetidin-1-yl)phenyl]-1-pyrazin-2-yl-1,2,4-triazol-3-amine |
| 854 | N-[3-methyl-5-(4-morpholino-1-piperidyl)phenyl]-1-[3-(trifluoromethyl)phenyl]-1,2,4-triazol-3-amine |
| 651 | N-[3-methyl-5-(3-morpholinoazetidin-1-yl)phenyl]-1-[3-(trifluoromethyl)phenyl]-1,2,4-triazol-3-amine |
| 833 | 1-[3-(difluoromethyl)phenyl]-N-[3-methyl-5-[4-(oxetan-3-yl)piperazin-1-yl]phenyl]-1,2,4-triazol-3-amine |
| 736 | 1-[3-(difluoromethyl)phenyl]-N-[3-ethyl-5-[4-(oxetan-3-yl)piperazin-1-yl]phenyl]-1,2,4-triazol-3-amine |
| 595 | 1-[3-(difluoromethyl)phenyl]-N-[3-methyl-5-(3-morpholinoazetidin-1-yl)phenyl]-1,2,4-triazol-3-amine |
| 725 | 1-[3-(difluoromethyl)phenyl]-N-[3-methyl-5-(4-morpholino-1-piperidyl)phenyl]-1,2,4-triazol-3-amine |
| 693 | 1-[3-(difluoromethyl)phenyl]-N-[3-methoxy-5-[4-(oxetan-3-yl)piperazin-1-yl]phenyl]-1,2,4-triazol-3-amine |
| 662 | N-[3-methoxy-5-[4-(oxetan-3-yl)piperazin-1-yl]phenyl]-1-[3-(trifluoromethyl)phenyl]-1,2,4-triazol-3-amine |
| 609 | N-[3-methyl-5-[4-(oxetan-3-yl)-1,4-diazepan-1-yl]phenyl]-1-(2-pyridyl)-1,2,4-triazol-3-amine |
| 776 | 1-(2-fluoro-4-pyridyl)-N-[3-methyl-5-[4-(oxetan-3-yl)-1,4-diazepan-1-yl]phenyl]-1,2,4-triazol-3-amine |
| 818 | N-[3-methyl-5-[4-(oxetan-3-yl)-1,4-diazepan-1-yl]phenyl]-1-pyrazin-2-yl-1,2,4-triazol-3-amine |
| 637 | 1-(3,5-difluorophenyl)-N-[3-methyl-5-[4-(oxetan-3-yl)-1,4-diazepan-1-yl]phenyl]-1,2,4-triazol-3-amine |
| 697 | 1-(3,5-difluorophenyl)-N-[2,5-dimethyl-3-[4-(oxetan-3-yl)piperazin-1-yl]phenyl]-1,2,4-triazol-3-amine |
| 739 | 1-(3,5-difluorophenyl)-N-[2,3-dimethyl-5-(3-morpholinoazetidin-1-yl)phenyl]-1,2,4-triazol-3-amine |
| 785 | N-[3-chloro-5-(3-morpholinoazetidin-1-yl)phenyl]-1-(2-pyridyl)-1,2,4-triazol-3-amine |
| 863 | N-[3-chloro-5-(3-morpholinoazetidin-1-yl)phenyl]-1-pyrimidin-4-yl-1,2,4-triazol-3-amine |
| 827 | N-[3-chloro-5-(3-morpholinoazetidin-1-yl)phenyl]-1-(3-fluorophenyl)-1,2,4-triazol-3-amine |
| 819 | N-[3-chloro-5-(3-morpholinoazetidin-1-yl)phenyl]-1-(2-fluoro-4-pyridyl)-1,2,4-triazol-3-amine |
| 784 | N-[3-chloro-5-(3-morpholinoazetidin-1-yl)phenyl]-1-(3,4-difluorophenyl)-1,2,4-triazol-3-amine |
| 587 | 1-(3,5-difluorophenyl)-N-[2-fluoro-3-methyl-5-[4-(oxetan-3-yl)piperazin-1-yl]phenyl]-1,2,4-triazol-3-amine |
| 808 | 1-(3,5-difluorophenyl)-N-[3-methyl-5-[3-(1,4-oxazepan-4-yl)azetidin-1-yl]phenyl]-1,2,4-triazol-3-amine |
| 659 | 1-(3,4-difluorophenyl)-N-[3-methyl-5-[3-(1,4-oxazepan-4-yl)azetidin-1-yl]phenyl]-1,2,4-triazol-3-amine |
| 825 | N-[3-methyl-5-[3-(1,4-oxazepan-4-yl)azetidin-1-yl]phenyl]-1-pyrazin-2-yl-1,2,4-triazol-3-amine |
| 701 | 1-(3,5-difluorophenyl)-N-[3-(3-morpholinoazetidin-1-yl)-5-[4-(oxetan-3-yl)piperazin-1-yl]phenyl]-1,2,4-triazol-3-amine |
| 642 | N-[3-fluoro-5-[4-(oxetan-3-yl)piperazin-1-yl]phenyl]-1-(2-pyridyl)-1,2,4-triazol-3-amine |
| 594 | N-[3-fluoro-5-[4-(oxetan-3-yl)piperazin-1-yl]phenyl]-1-(3-fluorophenyl)-1,2,4-triazol-3-amine |
| 783 | N-[3-fluoro-5-[4-(oxetan-3-yl)piperazin-1-yl]phenyl]-1-(2-fluoro-4-pyridyl)-1,2,4-triazol-3-amine |
| 803 | 1-(3,4-difluorophenyl)-N-[3-fluoro-5-[4-(oxetan-3-yl)piperazin-1-yl]phenyl]-1,2,4-triazol-3-amine |
| 868 | N-[3,5-bis(3-morpholinoazetidin-1-yl)phenyl]-1-(3,5-difluorophenyl)-1,2,4-triazol-3-amine |
| 759 | 3-[3-[3-methyl-5-[4-(oxetan-3-yl)piperazin-1-yl]anilino]-1,2,4-triazol-1-yl]benzonitrile |

| Cmpd No. | IUPAC name |
|---|---|
| 734 | 3-[3-[3-ethyl-5-[4-(oxetan-3-yl)piperazin-1-yl]anilino]-1,2,4-triazol-1-yl]benzonitrile |
| 767 | 1-(3-chloro-4-methyl-phenyl)-N-[3-methyl-5-[4-(oxetan-3-yl)piperazin-1-yl]phenyl]-1,2,4-triazol-3-amine |
| 836 | 1-(3-fluoro-4-methyl-phenyl)-N-[3-methyl-5-[4-(oxetan-3-yl)piperazin-1-yl]phenyl]-1,2,4-triazol-3-amine |
| 715 | 1-(3-chloro-4-methyl-phenyl)-N-[3-ethyl-5-[4-(oxetan-3-yl)piperazin-1-yl]phenyl]-1,2,4-triazol-3-amine |
| 761 | N-[3-ethyl-5-[4-(oxetan-3-yl)piperazin-1-yl]phenyl]-1-(3-fluoro-4-methyl-phenyl)-1,2,4-triazol-3-amine |
| 762 | 4-[3-[3-ethyl-5-[4-(oxetan-3-yl)piperazin-1-yl]anilino]-1,2,4-triazol-1-yl]benzonitrile |
| 687 | 4-[3-[3-methyl-5-[4-(oxetan-3-yl)piperazin-1-yl]anilino]-1,2,4-triazol-1-yl]benzonitrile |
| 829 | N-[3-ethyl-5-[4-(oxetan-3-yl)piperazin-1-yl]phenyl]-1-(4-fluoro-3-methyl-phenyl)-1,2,4-triazol-3-amine |
| 780 | 1-(4-fluoro-3-methyl-phenyl)-N-[3-methyl-5-[4-(oxetan-3-yl)piperazin-1-yl]phenyl]-1,2,4-triazol-3-amine |
| 597 | 1-(3-chloro-4-fluoro-phenyl)-N-[3-methyl-5-[4-(oxetan-3-yl)piperazin-1-yl]phenyl]-1,2,4-triazol-3-amine |
| 721 | 1-(3-fluorophenyl)-N-[3-methyl-5-(3-morpholinoazetidin-1-yl)phenyl]-1,2,4-triazol-3-amine |
| 606 | 1-(4-fluorophenyl)-N-[3-methyl-5-(3-morpholinoazetidin-1-yl)phenyl]-1,2,4-triazol-3-amine |
| 794 | 1-[3-(difluoromethyl)phenyl]-N-[3-fluoro-5-[4-(oxetan-3-yl)piperazin-1-yl]phenyl]-1,2,4-triazol-3-amine |
| 647 | 1-(4-fluoro-3-methyl-phenyl)-N-[3-fluoro-5-[4-(oxetan-3-yl)piperazin-1-yl]phenyl]-1,2,4-triazol-3-amine |
| 779 | 1-(3-fluoro-4-methyl-phenyl)-N-[3-fluoro-5-[4-(oxetan-3-yl)piperazin-1-yl]phenyl]-1,2,4-triazol-3-amine |
| 622 | 1-(4-fluorophenyl)-N-[3-methyl-5-[4-(oxetan-3-yl)piperazin-1-yl]phenyl]-1,2,4-triazol-3-amine |
| 641 | 1-(3,5-difluorophenyl)-N-[3-isopropoxy-2-methyl-5-(3-morpholinoazetidin-1-yl)phenyl]-1,2,4-triazol-3-amine |
| 591 | 1-(3,5-difluorophenyl)-N-[3-isopropoxy-2-methyl-5-[4-(oxetan-3-yl)piperazin-1-yl]phenyl]-1,2,4-triazol-3-amine |
| 757 | 1-[3-fluoro-5-(trifluoromethyl)phenyl]-N-[3-methyl-5-[4-(oxetan-3-yl)piperazin-1-yl]phenyl]-1,2,4-triazol-3-amine |
| 754 | 1-[3-fluoro-5-(trifluoromethyl)phenyl]-N-[3-methoxy-5-[4-(oxetan-3-yl)piperazin-1-yl]phenyl]-1,2,4-triazol-3-amine |
| 624 | 1-(3-fluoro-4-methoxy-phenyl)-N-[3-methyl-5-[4-(oxetan-3-yl)piperazin-1-yl]phenyl]-1,2,4-triazol-3-amine |
| 781 | 1-(3-fluoro-4-methoxy-phenyl)-N-[3-fluoro-5-[4-(oxetan-3-yl)piperazin-1-yl]phenyl]-1,2,4-triazol-3-amine |
| 646 | 1-(3,5-difluoro-4-methoxy-phenyl)-N-[3-methyl-5-[4-(oxetan-3-yl)piperazin-1-yl]phenyl]-1,2,4-triazol-3-amine |
| 710 | 1-(4-methoxyphenyl)-N-[3-methyl-5-[4-(oxetan-3-yl)piperazin-1-yl]phenyl]-1,2,4-triazol-3-amine |
| 782 | 1-(3,5-difluoro-4-methoxy-phenyl)-N-[3-methyl-5-(3-morpholinoazetidin-1-yl)phenyl]-1,2,4-triazol-3-amine |
| 841 | 1-(4-methoxyphenyl)-N-[3-methyl-5-(3-morpholinoazetidin-1-yl)phenyl]-1,2,4-triazol-3-amine |
| 735 | 1-(3-fluoro-4-methoxy-phenyl)-N-[3-methyl-5-(3-morpholinoazetidin-1-yl)phenyl]-1,2,4-triazol-3-amine |
| 1080 | 5-deuterio-1-(3,5-difluorophenyl)-N-[3-methyl-5-[4-(oxetan-3-yl)piperazin-1-yl]phenyl]-1,2,4-triazol-3-amine |
| 966 | N-[3-(2-isopropyl-2,6-diazaspiro[3.3]heptan-6-yl)-5-methyl-phenyl]-1-(3-pyridyl)-1,2,4-triazol-3-amine |
| 1071 | 1-(3-fluorophenyl)-N-[3-(2-isopropyl-2,6-diazaspiro[3.3]heptan-6-yl)-5-methyl-phenyl]-1,2,4-triazol-3-amine |
| 977 | 1-(3,4-difluorophenyl)-N-[3-(2-isopropyl-2,6-diazaspiro[3.3]heptan-6-yl)-5-methyl-phenyl]-1,2,4-triazol-3-amine |
| 1034 | N-[3-(2-isopropyl-2,6-diazaspiro[3.3]heptan-6-yl)-5-methyl-phenyl]-1-phenyl-1,2,4-triazol-3-amine |
| 967 | N-[3-(2-isopropyl-2,6-diazaspiro[3.3]heptan-6-yl)-5-methyl-phenyl]-1-pyrazin-2-yl-1,2,4-triazol-3-amine |
| 965 | 2-[3-[[1-(3,5-difluorophenyl)-1,2,4-triazol-3-yl]amino]-4,5-dimethyl-phenoxy]-1-pyrrolidin-1-yl-ethanone |
| 909 | 1-(3,5-difluorophenyl)-N-[2,3-dimethyl-5-(oxetan-3-ylmethoxy)phenyl]-1,2,4-triazol-3-amine |
| 971 | 1-[3-[3-[[1-(3,5-difluorophenyl)-1,2,4-triazol-3-yl]amino]-4,5-dimethyl-phenoxy]azetidin-1-yl]ethanone |
| 1108 | N-[3-methyl-5-[4-(oxetan-3-yl)piperazin-1-yl]phenyl]-1-(2,3,4,5,6-pentadeuteriophenyl)-1,2,4-triazol-3-amine |

Scheme B: General Route B for Preparation of Compounds of Formula I or I'

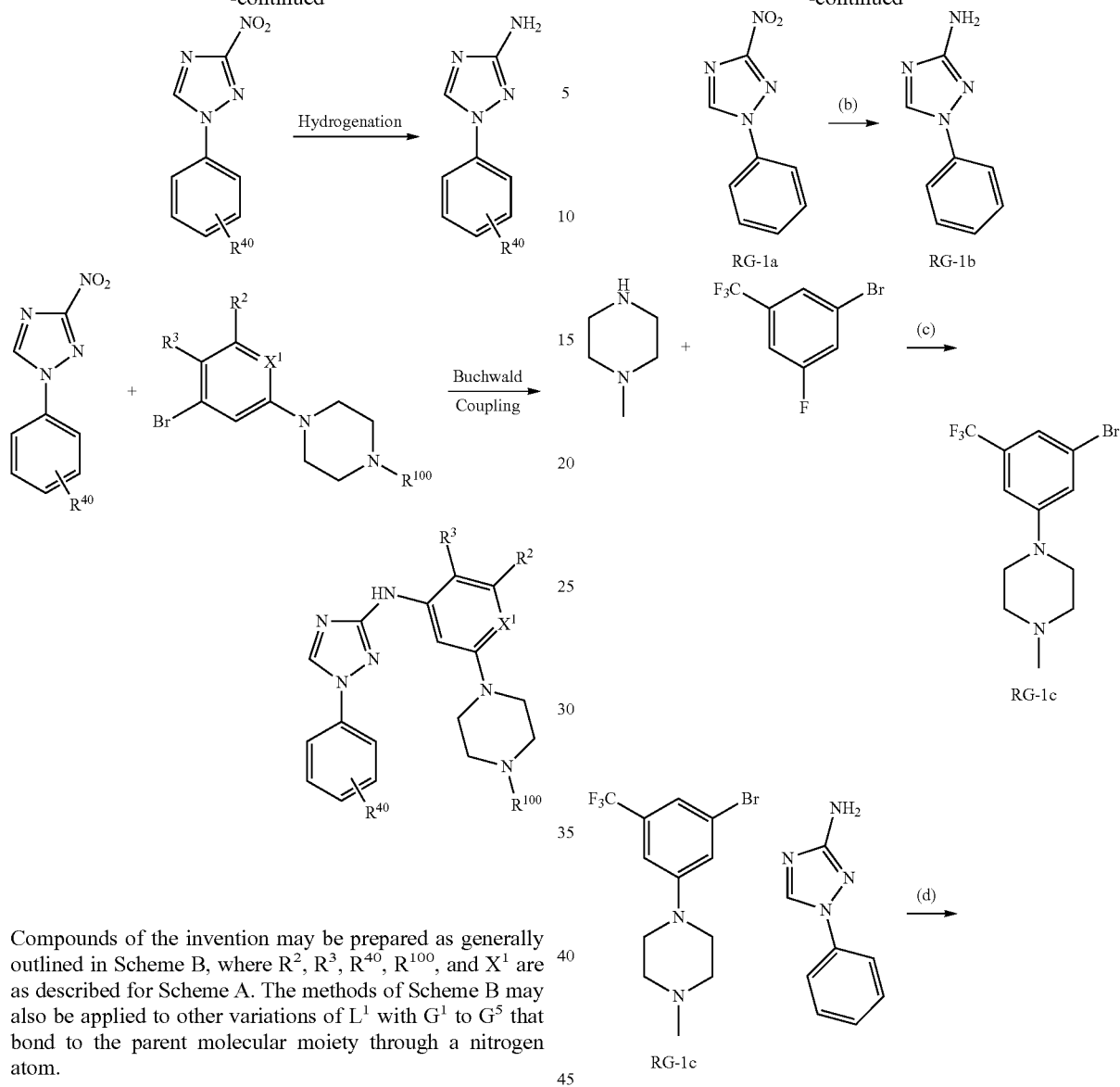

Compounds of the invention may be prepared as generally outlined in Scheme B, where $R^2$, $R^3$, $R^{40}$, $R^{100}$, and $X^1$ are as described for Scheme A. The methods of Scheme B may also be applied to other variations of $L^1$ with $G^1$ to $G^5$ that bond to the parent molecular moiety through a nitrogen atom.

Example 9A

Preparation of N-[3-(4-methylpiperazin-1-yl)-5-(trifluoromethyl)phenyl]-1-phenyl-1,2,4-triazol-3-amine (Compound 486)

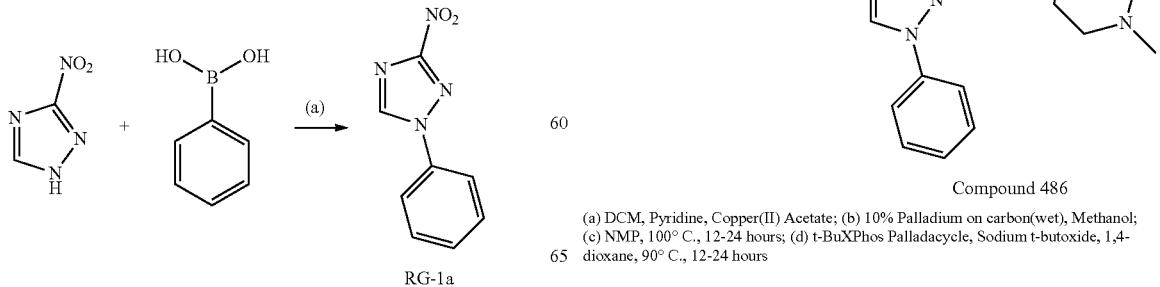

(a) DCM, Pyridine, Copper(II) Acetate; (b) 10% Palladium on carbon(wet), Methanol; (c) NMP, 100° C., 12-24 hours; (d) t-BuXPhos Palladacycle, Sodium t-butoxide, 1,4-dioxane, 90° C., 12-24 hours

Preparation of 3-nitro-1-phenyl-1,2,4-triazole (RG-1a)

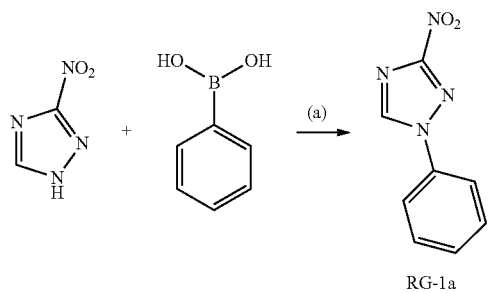

a) DCM, Pyridine, Copper(II) Acetate 3-nitro-1H-1,2,4-triazole (20 g, 175 mmol) and phenylboronic acid (43 g, 350 mmol) were suspended in 2.4 L of DCM and pyridine (28.4 mL, 27.8 g, 35 mmol) was added followed by copper (II) acetate (32 g, 175 mmol). The blue coloured suspension was stirred at room temperature for 10 days open to the air. The reaction was pulled through a pad of diatomaceous earth and the filter cake washed with DCM, MeOH, and finally DCM. The filtrates were combined and concentrated to a viscous residue which was partitioned between EtOAc and 1N HCl. The organic phase was washed with water and brine, dried over Na2SO4 and the solvent removed under reduced pressure. The crude material was purified on 800 grams of SiO2 eluting with 0-25% Ethyl Acetate in DCM. The combined pure fractions were concentrated to dryness to yield 3-nitro-1-phenyl-1,2,4-triazole, RG-1a (16 g, 24%). $^1$H NMR (300 MHz, Acetone-d6) δ 9.31 (s, 1H), 7.96 (d, J=7.9 Hz, 2H), 7.67 (dd, J=10.3, 5.0 Hz, 2H), 7.61-7.46 (m, 1H) ppm. ESI-MS m/z calc. 190.05, found 191.0 (M+1)+; Retention time: 0.73 minutes.

Preparation of 1-phenyl-1,2,4-triazol-3-amine (RG-1b)

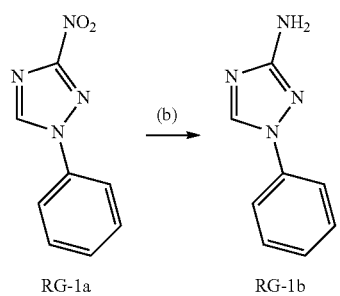

b) 10% Palladium on carbon(wet), Methanol, H$_2$ 3-nitro-1-phenyl-1,2,4-triazole (16 g, 84.14 mmoles) was dissolved into 250 mL of methanol and placed under an atmosphere of CO2 before adding 10% Palladium on carbon (wet) Degussa type. The reaction was placed under 50 psi of H2 for 3.0 hours in a Parr apparatus. The reaction was pulled through a pad of diatomaceous earth and washed with more MeOH. The solvent was removed under reduced pressure and yielded 1-phenyl-1,2,4-triazol-3-amine, RG-1b (13.3 grams, 89%). $^1$H NMR (300 MHz, Acetone-d6) δ 8.58 (s, 1H), 7.78-7.71 (m, 2H), 7.52-7.41 (m, 2H), 7.30 (dt, J=9.0, 4.3 Hz, 1H), 5.10 (s, 2H) ppm. ESI-MS m/z calc. 160.07489, found 160.95 (M+1)+; Retention time: 0.55 minutes.

Preparation of 1-[3-bromo-5-(trifluoromethyl)phenyl]-4-methyl-piperazine (RG-1c)

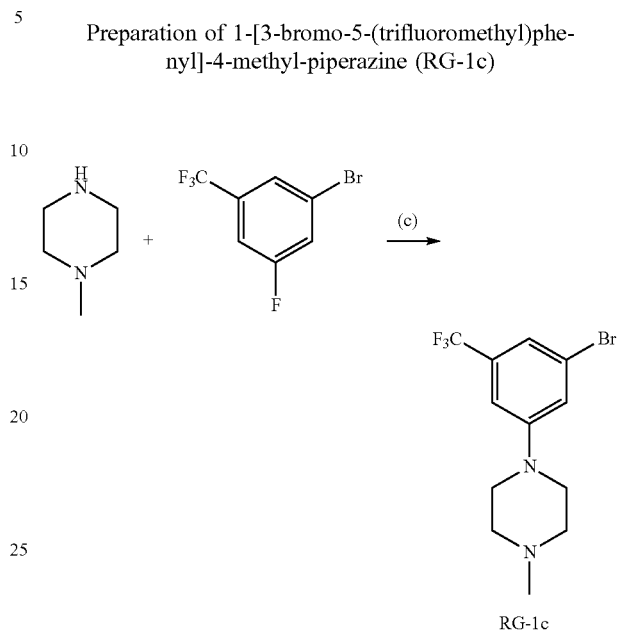

c) NMP, 100° C., 12-24 hours

1-Bromo-3-fluoro-5-(trifluoromethyl)benzene (1.52 g, 6.255 mmol) was dissolved in NMP (2.0 mL). Methylpiperazine (1.88 g, 2.08 mL, 18.8 mmol) was added and the vial was sealed. The reaction mixture was stirred overnight at 100° C. then concentrated to an oil. The oil was diluted with DCM (20 mL), washed with 50% saturated sodium bicarbonate, passed through a phase separator, and the organic layer concentrated to dryness to yield 1-[3-bromo-5-(trifluoromethyl)phenyl]-4-methyl-piperazine RG-1c (1.731 g, 83%). $^1$H NMR (300 MHz, DMSO-d6) δ 7.36 (s, 1H), 7.18 (s, 2H), 3.30-3.16 (m, 4H), 2.46-2.33 (m, 4H), 2.21 (s, 3H) ppm. ESI-MS m/z calc. 322.02924, found 323.03 (M+1)+; Retention time: 0.62 minutes.

Preparation of N-[3-(4-methylpiperazin-1-yl)-5-(trifluoromethyl)phenyl]-1-phenyl-1,2,4-triazol-3-amine (Compound 486)

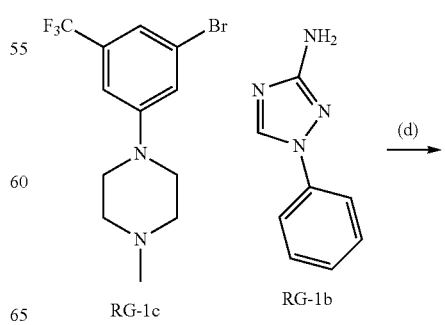

-continued

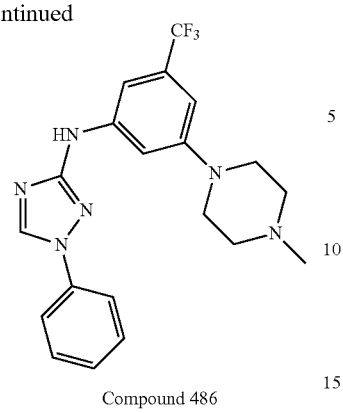

Compound 486 d) t-BuXPhos Palladacycle, Sodium t-butoxide, 1,4- dioxane, 90° C., 12-24 hours

1-Phenyl-1,2,4-triazol-3-amine, RG-1b (64 mg, 0.4 mmol), sodium tert-butoxide (57.6 mg, 0.6 mmol), t-BuXPhos Palladacycle (29.5 mg, 0.04 mmol), and 1-[3-bromo-5-(trifluoromethyl)phenyl]-4-methyl-piperazine RG-1c (129 mg, 0.4 mmol) were weighed into a 20 ml vial. Vacuum was applied to the vial and then flushed with nitrogen three times. Dioxane (2 mL) was added and the mixture stirred in a sealed vial at 90° C. overnight. The crude reaction mixture was diluted with dichloromethane (20 mL), then washed with 50% saturated sodium bicarbonate. The organic layer was passed through a phase separator and concentrated to dryness. The residue was diluted with DMSO (2 mL) and purified by reverse phase HPLC using a gradient of acetonitrile in water (10-99%) and TFA as a modifier to yield the product as the TFA salt. The pooled desired pure fractions were concentrated to dryness. The combined fractions with diluted DCM and washed with saturated sodium bicarbonate. The organics were passed through a phase separator, acidified with 2M HCl in diethyl ether, and concentrated to dryness to yield the HCl salt of N-[3-(4-methylpiperazin-1-yl)-5-(trifluoromethyl)phenyl]-1-phenyl-1,2,4-triazol-3-amine, cmpd 486 (99 mg, 56%). $^1$H NMR (300 MHz, DMSO-d6) δ 9.13 (s, 1H), 7.89-7.79 (d, 2H), 7.56 (m, 4H), 7.38 (t, J=7.4 Hz, 1H), 6.84 (s, 1H), 3.88 (d, J=9.7 Hz, 2H), 3.51 (m, 2H), 3.19 (m, 4H), 2.85 (s, 3H) ppm. ESI-MS m/z calc. 402.17798, found 403.28 (M+1)+; Retention time: 3.08 minutes.

Example 9B

Preparation of 1-(3,5-Difluorophenyl)-N-(2-fluoro-5-methyl-3-(4-(oxetan-3-yl)piperazin-1-yl)phenyl)-1H-1,2,4-triazol-3-amine (Compound 691)

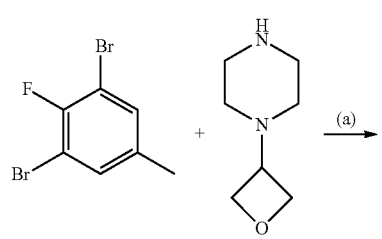

-continued

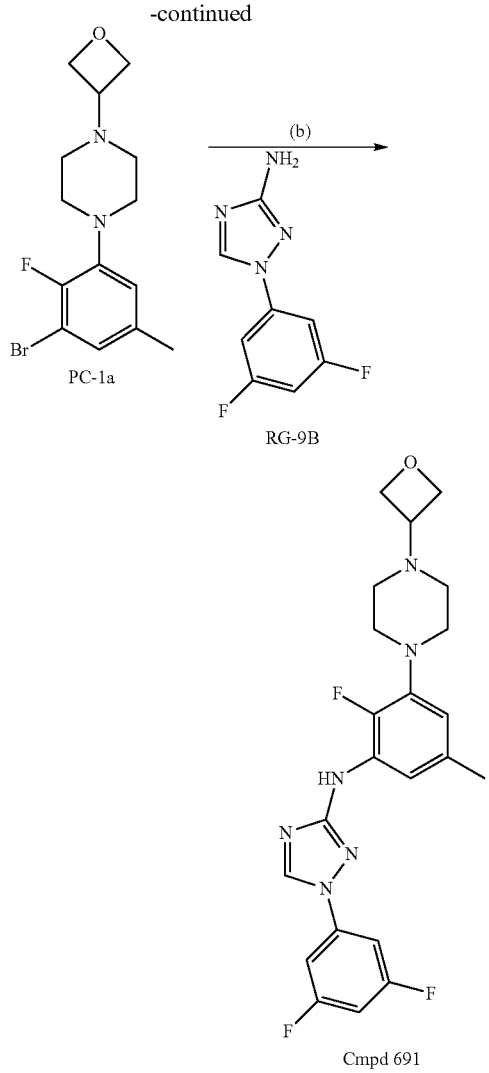

Preparation of 1-(3-bromo-2-fluoro-5-methylphenyl)-4-(oxetan-3-yl)piperazine (PC-1a)

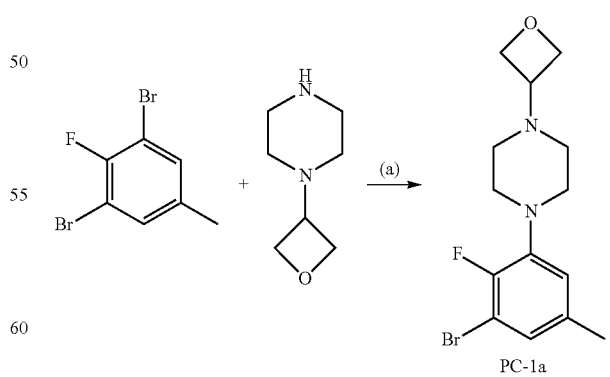

A 50 ml round-bottomed two-necked flask was charged with: 1,3-dibromo-2-fluoro-5-methyl-benzene (1.81 g, 6.76 mmol), 1-(oxetan-3-yl)piperazine (970 mg, 6.75 mmol), BINAP (168 mg, 0.270 mmol), cesium carbonate (4.40 g, 13.5 mmol), Pd₂(dba)₃ (124 mg, 0.135 mmol) and 1,4-dioxane (11 mL) under nitrogen and then heated at reflux overnight. The reaction mixture was filtered through Celite with the aid of EtOAc and then concentrated. Purification by column chromatography (80 g column; 40-100% EtOAc in heptane) gave product PC-1a (1.2 g, 54%) as an off-white solid. $^1$H NMR (400 MHz, DMSO-d6) δ 7.06 (dd, J=5.8, 1.3 Hz, 1H), 6.84 (dd, J=7.8, 1.6 Hz, 1H), 4.56 (t, J=6.6 Hz, 2H), 4.46 (t, J=6.1 Hz, 2H), 3.52-3.40 (m, 1H), 3.11-2.93 (m, 4H), 2.47-2.35 (m, 4H), 2.25 (s, 3H) ppm. ESI-MS m/z calc. 328.05865, (M+1) found 329.11.

Preparation of 1-(3,5-Difluorophenyl)-N-(2-fluoro-5-methyl-3-(4-(oxetan-3-yl)piperazin-1-yl)phenyl)-1H-1,2,4-triazol-3-amine (Compound 691)

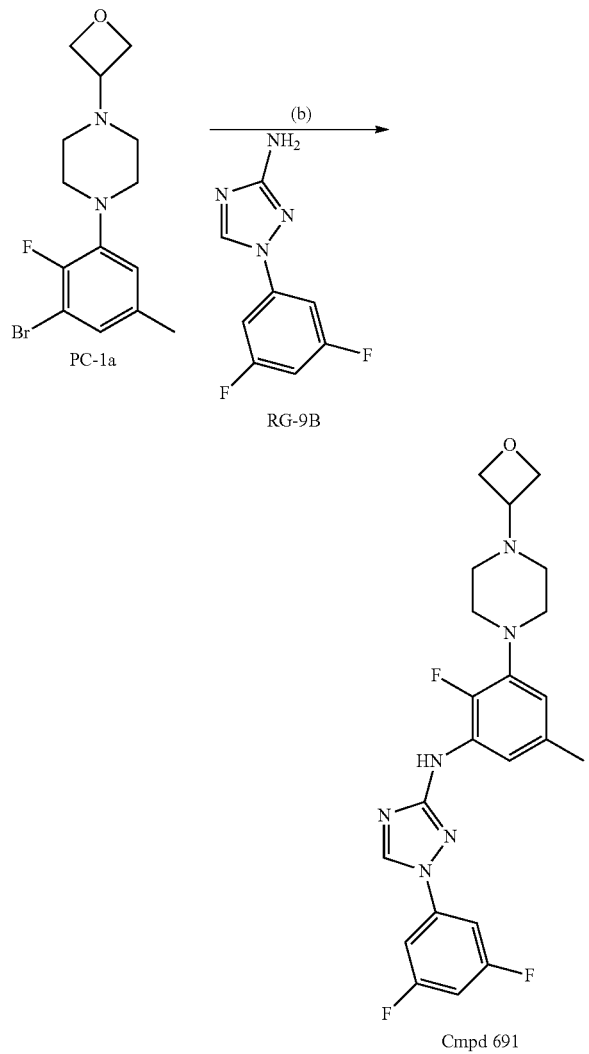 [SMILES: Cc1cc(Br)c(F)c(N2CCN(C3COC3)CC2)c1 ; Nc1ncn(-c2cc(F)cc(F)c2)n1 ; Cc1cc(Nc2ncn(-c3cc(F)cc(F)c3)n2)c(F)c(N2CCN(C3COC3)CC2)c1]

A 20 mL scintillation vial was charged with 1-(3,5-difluorophenyl)-1,2,4-triazol-3-amine RG-9B (281 mg, 1.43 mmol), 1-(3-bromo-2-fluoro-5-methyl-phenyl)-4-(oxetan-3-yl)piperazine PC-1a (471 mg, 1.43 mmol), Xphos palladacycle (Strem 46-0268) (53 mg, 0.0717 mmol), sodium tert-butoxide (275 mg, 2.86 mmol) and tBuOH (12 mL) under nitrogen and stirred on a heating block set to 100° C. for 2 h. Brine and EtOAc were added and the layers separated. The organics were concentrated, the crude residue was purified by column chromatography (80 g column; 50-100% EtOAc in heptane) and the relevant fractions concentrated. The impure material was sonicated in the presence of EtOAc and filtered off. The solid was collected and sonicated in the presence of MeOH to give product (185 mg, 29%) as a white solid after filtration. $^1$H NMR (400 MHz, DMSO-d6) δ 9.16 (s, 1H), 8.81 (d, J=1.7 Hz, 1H), 7.65-7.55 (m, 2H), 7.50 (d, J=5.8 Hz, 1H), 7.25 (tt, J=9.3, 2.3 Hz, 1H), 6.44 (d, J=5.9 Hz, 1H), 4.56 (t, J=6.5 Hz, 2H), 4.47 (t, J=6.1 Hz, 2H), 3.52-3.44 (m, 1H), 3.06-2.97 (m, 4H), 2.43 (s, 4H), 2.27 (s, 3H) ppm. ESI-MS m/z calc. 444.18854, found 445.33 (M+1).

Using the general synthetic scheme outlined in Scheme B and the experimental procedures listed above in Example 9A or 9B, the following compounds were prepared:

| Cmpd No. | IUPAC Name |
|---|---|
| 269 | 1-(4-fluorophenyl)-N-(3-methyl-5-pyrrolidin-1-yl-phenyl)-1,2,4-triazol-3-amine |
| 272 | 1-(3-fluorophenyl)-N-(3-methyl-5-pyrrolidin-1-yl-phenyl)-1,2,4-triazol-3-amine |
| 167 | 1-(4-fluorophenyl)-N-(3-fluoro-5-pyrrolidin-1-yl-phenyl)-1,2,4-triazol-3-amine |
| 158 | N-(3-fluoro-5-morpholino-phenyl)-1-(3-fluorophenyl)-1,2,4-triazol-3-amine |
| 435 | 1-(3-fluorophenyl)-N-(3-fluoro-5-pyrrolidin-1-yl-phenyl)-1,2,4-triazol-3-amine |
| 394 | N-(3-fluoro-5-morpholino-phenyl)-1-(4-fluorophenyl)-1,2,4-triazol-3-amine |
| 441 | N-(3-fluoro-5-pyrrolidin-1-yl-phenyl)-1-[4-(trifluoromethyl)phenyl]-1,2,4-triazol-3-amine |
| 356 | N-(3-methyl-5-pyrrolidin-1-yl-phenyl)-1-[4-(trifluoromethyl)phenyl]-1,2,4-triazol-3-amine |
| 241 | N-(3-fluoro-5-pyrrolidin-1-yl-phenyl)-1-[3-(trifluoromethyl)phenyl]-1,2,4-triazol-3-amine |
| 181 | N-(3-fluoro-5-morpholino-phenyl)-1-[3-(trifluoromethyl)phenyl]-1,2,4-triazol-3-amine |
| 497 | 1-(2,4-difluorophenyl)-N-(3-fluoro-5-pyrrolidin-1-yl-phenyl)-1,2,4-triazol-3-amine |
| 321 | 1-(2,4-difluorophenyl)-N-(3-fluoro-5-morpholino-phenyl)-1,2,4-triazol-3-amine |
| 190 | N-(3-methyl-5-pyrrolidin-1-yl-phenyl)-1-[3-(trifluoromethyl)phenyl]-1,2,4-triazol-3-amine |
| 99 | 1-(3,4-difluorophenyl)-N-(3-fluoro-5-pyrrolidin-1-yl-phenyl)-1,2,4-triazol-3-amine |
| 440 | 1-(3,4-difluorophenyl)-N-(3-fluoro-5-morpholino-phenyl)-1,2,4-triazol-3-amine |
| 49 | N-(3-fluoro-5-morpholino-phenyl)-1-(2-fluorophenyl)-1,2,4-triazol-3-amine |
| 83 | 1-(2-fluorophenyl)-N-(3-fluoro-5-pyrrolidin-1-yl-phenyl)-1,2,4-triazol-3-amine |
| 43 | 1-(3,4-difluorophenyl)-N-(3-methyl-5-morpholino-phenyl)-1,2,4-triazol-3-amine |
| 27 | 1-(3-fluorophenyl)-N-(3-methyl-5-morpholino-phenyl)-1,2,4-triazol-3-amine |
| 374 | 1-(3,5-difluorophenyl)-N-(3-methyl-5-morpholino-phenyl)-1,2,4-triazol-3-amine |
| 186 | 4-[3-(3-methyl-5-pyrrolidin-1-yl-anilino)-1,2,4-triazol-1-yl]benzonitrile |
| 372 | N-(3-methyl-5-pyrrolidin-1-yl-phenyl)-1-(p-tolyl)-1,2,4-triazol-3-amine |
| 281 | 3-[3-(3-methyl-5-pyrrolidin-1-yl-anilino)-1,2,4-triazol-1-yl]benzonitrile |
| 212 | 2-[3-(3-methyl-5-pyrrolidin-1-yl-anilino)-1,2,4-triazol-1-yl]benzonitrile |
| 335 | N-(3-chloro-5-morpholino-phenyl)-1-phenyl-1,2,4-triazol-3-amine |
| 426 | N-(3-chloro-5-morpholino-phenyl)-1-(3,5-difluorophenyl)-1,2,4-triazol-3-amine |
| 168 | N-(3-bromo-5-morpholino-phenyl)-1-phenyl-1,2,4-triazol-3-amine |
| 346 | N-(3-bromo-5-morpholino-phenyl)-1-(3,5-difluorophenyl)-1,2,4-triazol-3-amine |

| Cmpd No. | IUPAC Name |
| --- | --- |
| 392 | N-[3-(difluoromethyl)-5-morpholino-phenyl]-1-phenyl-1,2,4-triazol-3-amine |
| 246 | N-[3-chloro-5-[4-(methoxymethyl)-1-piperidyl]phenyl]-1-phenyl-1,2,4-triazol-3-amine |
| 85 | N-[3-(difluoromethyl)-5-morpholino-phenyl]-1-(2-fluoro-4-pyridyl)-1,2,4-triazol-3-amine |
| 431 | N-[3-methyl-5-[4-[(3-methyloxetan-3-yl)methyl]piperazin-1-yl]phenyl]-1-phenyl-1,2,4-triazol-3-amine |
| 330 | N-[3-ethyl-5-[4-(oxetan-3-yl)piperazin-1-yl]phenyl]-1-phenyl-1,2,4-triazol-3-amine |
| 468 | N-[3-ethyl-5-[4-(oxetan-3-yl)piperazin-1-yl]phenyl]-1-(3-fluorophenyl)-1,2,4-triazol-3-amine |
| 344 | 1-(3,5-difluorophenyl)-N-[3-methylsulfonyl-5-[4-(oxetan-3-yl)piperazin-1-yl]phenyl]-1,2,4-triazol-3-amine |
| 16 | N-[3-ethyl-5-[4-(oxetan-3-yl)piperazin-1-yl]phenyl]-1-(2-fluoro-4-pyridyl)-1,2,4-triazol-3-amine |
| 361 | 1-(3-fluorophenyl)-N-[3-methylsulfonyl-5-[4-(oxetan-3-yl)piperazin-1-yl]phenyl]-1,2,4-triazol-3-amine |
| 417 | 1-(2,5-difluorophenyl)-N-[3-ethyl-5-[4-(oxetan-3-yl)piperazin-1-yl]phenyl]-1,2,4-triazol-3-amine |
| 110 | N-(3-methyl-5-pyrrolidin-1-yl-phenyl)-1-phenyl-1,2,4-triazol-3-amine |
| 380 | N-(3-chloro-5-pyrrolidin-1-yl-phenyl)-1-phenyl-1,2,4-triazol-3-amine |
| 45 | N-(3-methyl-5-morpholino-phenyl)-1-phenyl-1,2,4-triazol-3-amine |
| 336 | N-(3-fluoro-5-pyrrolidin-1-yl-phenyl)-1-phenyl-1,2,4-triazol-3-amine |
| 175 | 1-(3-fluorophenyl)-N-[3-[4-(oxetan-3-yl)piperazin-1-yl]-5-(trifluoromethyl)phenyl]-1,2,4-triazol-3-amine |
| 130 | 1-(3,5-difluorophenyl)-N-[3-[4-(oxetan-3-yl)piperazin-1-yl]-5-(trifluoromethyl)phenyl]-1,2,4-triazol-3-amine |
| 1 | N-[1-(3,5-difluorophenyl)-1,2,4-triazol-3-yl]-2-methyl-6-[4-(oxetan-3-yl)piperazin-1-yl]pyridin-4-amine |
| 295 | 5-[3-[[1-(3,5-difluorophenyl)-1,2,4-triazol-3-yl]amino]-5-methyl-phenyl]oxazolidin-2-one |
| 501 | N-[1-(3,4-difluorophenyl)-1,2,4-triazol-3-yl]-4-methyl-6-(3-morpholinoazetidin-1-yl)pyridin-2-amine |
| 502 | 4-methyl-6-(3-morpholinoazetidin-1-yl)-N-(1-phenyl-1,2,4-triazol-3-yl)pyridin-2-amine |
| 512 | 4-(difluoromethyl)-N-[1-(3,5-difluorophenyl)-1,2,4-triazol-3-yl]-6-[4-(oxetan-3-yl)piperazin-1-yl]pyridin-2-amine |
| 517 | 3-[3-[[1-(3,5-difluorophenyl)-1,2,4-triazol-3-yl]amino]-5-methyl-phenyl]oxazolidin-2-one |
| 524 | 4-(difluoromethyl)-N-[1-(3,4-difluorophenyl)-1,2,4-triazol-3-yl]-6-[4-(oxetan-3-yl)piperazin-1-yl]pyridin-2-amine |
| 525 | 4-(difluoromethyl)-N-[1-(3-fluorophenyl)-1,2,4-triazol-3-yl]-6-[4-(oxetan-3-yl)piperazin-1-yl]pyridin-2-amine |
| 526 | 4-(difluoromethyl)-6-[4-(oxetan-3-yl)piperazin-1-yl]-N-(1-phenyl-1,2,4-triazol-3-yl)pyridin-2-amine |
| 843 | 6-(2,3,3a,4,6,6a-hexahydrofuro[2,3-c]pyrrol-5-yl)-N-[1-(3,5-difluorophenyl)-1,2,4-triazol-3-yl]-4-methyl-pyridin-2-amine |
| 581 | 1-(3,5-difluorophenyl)-N-[3-methyl-5-[4-(oxetan-3-yl)morpholin-2-yl]phenyl]-1,2,4-triazol-3-amine |
| 751 | 1-(3,5-difluorophenyl)-N-[3-methyl-5-[(2R)-4-(oxetan-3-yl)morpholin-2-yl]phenyl]-1,2,4-triazol-3-amine |
| 623 | 1-(3,5-difluorophenyl)-N-[3-methyl-5-[(2S)-4-(oxetan-3-yl)morpholin-2-yl]phenyl]-1,2,4-triazol-3-amine |
| 577 | 1-(3,4-difluorophenyl)-N-[3-ethyl-5-[4-(3-methyloxetan-3-yl)piperazin-1-yl]phenyl]-1,2,4-triazol-3-amine |
| 820 | 1-(3,5-difluorophenyl)-N-[2,5-dimethyl-3-(3-morpholinoazetidin-1-yl)phenyl]-1,2,4-triazol-3-amine |
| 691 | 1-(3,5-difluorophenyl)-N-[2-fluoro-5-methyl-3-[4-(oxetan-3-yl)piperazin-1-yl]phenyl]-1,2,4-triazol-3-amine |
| 835 | 3-[[1-(3,5-difluorophenyl)-1,2,4-triazol-3-yl]amino]-5-morpholino-benzonitrile |
| 678 | 3-[[1-(3,5-difluorophenyl)-1,2,4-triazol-3-yl]amino]-5-[4-(oxetan-3-yl)piperazin-1-yl]benzonitrile |
| 656 | 3-[[1-(3,4-difluorophenyl)-1,2,4-triazol-3-yl]amino]-5-[4-(oxetan-3-yl)piperazin-1-yl]benzonitrile |
| 668 | 3-[[1-(3,4-difluorophenyl)-1,2,4-triazol-3-yl]amino]-5-morpholino-benzonitrile |
| 737 | 3-[[1-(3-fluorophenyl)-1,2,4-triazol-3-yl]amino]-5-morpholino-benzonitrile |
| 793 | 3-[[1-(3-fluorophenyl)-1,2,4-triazol-3-yl]amino]-5-[4-(oxetan-3-yl)piperazin-1-yl]benzonitrile |
| 608 | 3-morpholino-5-[(1-phenyl-1,2,4-triazol-3-yl)amino]benzonitrile |
| 804 | N-[3-(difluoromethyl)-5-(3-morpholinoazetidin-1-yl)phenyl]-1-(3,5-difluorophenyl)-1,2,4-triazol-3-amine |
| 592 | 3-[4-(oxetan-3-yl)piperazin-1-yl]-5-[(1-phenyl-1,2,4-triazol-3-yl)amino]benzonitrile |
| 681 | 5-methyl-N1,N3-bis(1-phenyl-1,2,4-triazol-3-yl)benzene-1,3-diamine |
| 813 | N-[3-[3-[[1-(3,5-difluorophenyl)-1,2,4-triazol-3-yl]amino]-5-methyl-phenoxy]cyclobutyl]acetamide |
| 752 | 1-(3,5-difluorophenyl)-N-[3-methyl-5-(3-morpholinocyclobutoxy)phenyl]-1,2,4-triazol-3-amine |
| 663 | 1-(3,5-difluorophenyl)-N-[3-methyl-5-[6-methyl-4-(oxetan-3-yl)morpholin-2-yl]phenyl]-1,2,4-triazol-3-amine |
| 629 | 1-(3,5-difluorophenyl)-N-[3-methyl-5-[5-methyl-4-(oxetan-3-yl)morpholin-2-yl]phenyl]-1,2,4-triazol-3-amine |
| 708 | 1-(3,5-difluorophenyl)-N-[3-methyl-5-[2-methyl-4-(oxetan-3-yl)morpholin-2-yl]phenyl]-1,2,4-triazol-3-amine |
| 750 | 1-(3,5-difluorophenyl)-N-[3-methyl-5-[(2R)-2-methyl-4-(oxetan-3-yl)morpholin-2-yl]phenyl]-1,2,4-triazol-3-amine |
| 667 | 1-(3,5-difluorophenyl)-N-[3-methyl-5-[(2S)-2-methyl-4-(oxetan-3-yl)morpholin-2-yl]phenyl]-1,2,4-triazol-3-amine |
| 1058 | N-[3-methyl-5-[(1-phenyl-1,2,4-triazol-3-yl)amino]phenyl]cyclopropanecarboxamide |
| 910 | 1-cyclobutyl-3-[3-methyl-5-[(1-phenyl-1,2,4-triazol-3-yl)amino]phenyl]urea |
| 908 | N-[2-fluoro-5-methyl-3-[4-(oxetan-3-yl)piperazin-1-yl]phenyl]-1-(2-pyridyl)-1,2,4-triazol-3-amine |
| 1085 | N-[2-fluoro-5-methyl-3-[4-(oxetan-3-yl)piperazin-1-yl]phenyl]-1-phenyl-1,2,4-triazol-3-amine |
| 923 | [3-acetoxy-2-[4-[3-[[1-(3,5-difluorophenyl)-1,2,4-triazol-3-yl]amino]-2-fluoro-5-methyl-phenyl]piperazin-1-yl]propyl]acetate |
| 989 | 2-[4-[3-[[1-(3,5-difluorophenyl)-1,2,4-triazol-3-yl]amino]-2-fluoro-5-methyl-phenyl]piperazin-1-yl]propane-1,3-diol |
| 999 | N-[1-(3,5-difluorophenyl)-1,2,4-triazol-3-yl]-4-methyl-6-tetrahydropyran-3-yloxy-pyridin-2-amine |
| 980 | 6-(cyclopropylmethoxy)-N-[1-(3,5-difluorophenyl)-1,2,4-triazol-3-yl]-4-methyl-pyridin-2-amine |
| 1069 | N-[1-(3,5-difluorophenyl)-1,2,4-triazol-3-yl]-4-methyl-6-(oxetan-3-ylmethoxy)pyridin-2-amine |
| 998 | 1-(3,4-difluorophenyl)-N-[2-fluoro-5-methyl-3-[4-(oxetan-3-yl)piperazin-1-yl]phenyl]-1,2,4-triazol-3-amine |
| 1022 | N-[2-fluoro-5-methyl-3-[4-(oxetan-3-yl)piperazin-1-yl]phenyl]-1-(3-pyridyl)-1,2,4-triazol-3-amine |
| 1100 | cyclopropyl-[2,2,3,3,5,5,6,6-octadeuterio-4-[3-[[1-(3,4-difluorophenyl)-1,2,4-triazol-3-yl]amino]-5-(trifluoromethyl)phenyl]piperazin-1-yl]methanone |
| 1101 | N-[3-(2,2,3,3,4,4,5,5,6,6-decadeuterio-1-piperidyl)-5-(trifluoromethyl)phenyl]-1-(3-fluorophenyl)-1,2,4-triazol-3-amine |
| 1102 | N-[3-(2,2,3,3,4,4,5,5,6,6-decadeuterio-1-piperidyl)-5-(difluoromethyl)phenyl]-1-(3-fluorophenyl)-1,2,4-triazol-3-amine |
| 1103 | cyclopropyl-[2,2,3,3,5,5,6,6-octadeuterio-4-[3-[[1-(3-fluorophenyl)-1,2,4-triazol-3-yl]amino]-5-(trifluoromethyl)phenyl]piperazin-1-yl]methanone |
| 1104 | cyclopropyl-[2,2,3,3,5,5,6,6-octadeuterio-4-[3-(difluoromethyl)-5-[[1-(3-fluorophenyl)-1,2,4-triazol-3-yl]amino]phenyl]piperazin-1-yl]methanone |
| 1105 | N-[3-(2,2,3,3,4,4,5,5,6,6-decadeuterio-1-piperidyl)-5-(trifluoromethyl)phenyl]-1-pyrazin-2-yl-1,2,4-triazol-3-amine |
| 1106 | N-[3-(2,2,3,3,4,4,5,5,6,6-decadeuterio-1-piperidyl)-5-(difluoromethyl)phenyl]-1-pyrazin-2-yl-1,2,4-triazol-3-amine |
| 1107 | cyclopropyl-[2,2,3,3,5,5,6,6-octadeuterio-4-[3-(difluoromethyl)-5-[(1-pyrazin-2-yl-1,2,4-triazol-3-yl)amino]phenyl]piperazin-1-yl]methanone |

Scheme C: General Route C for Preparation of Compounds of Formula I or I'

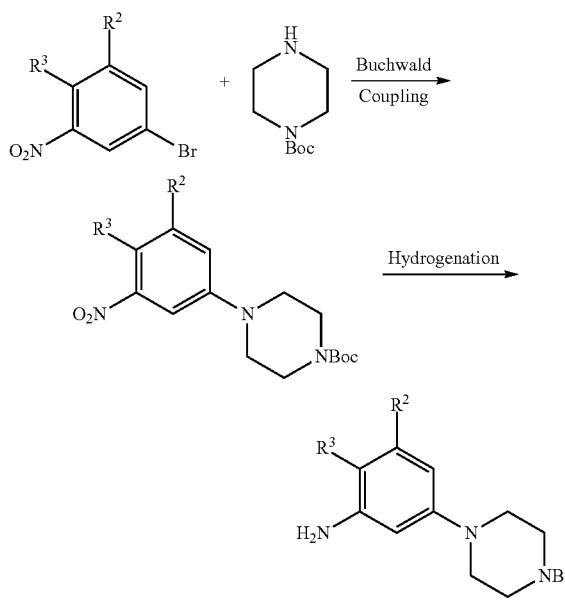

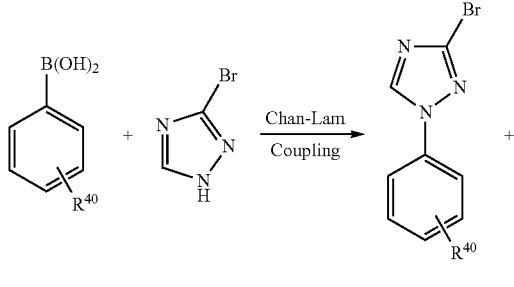

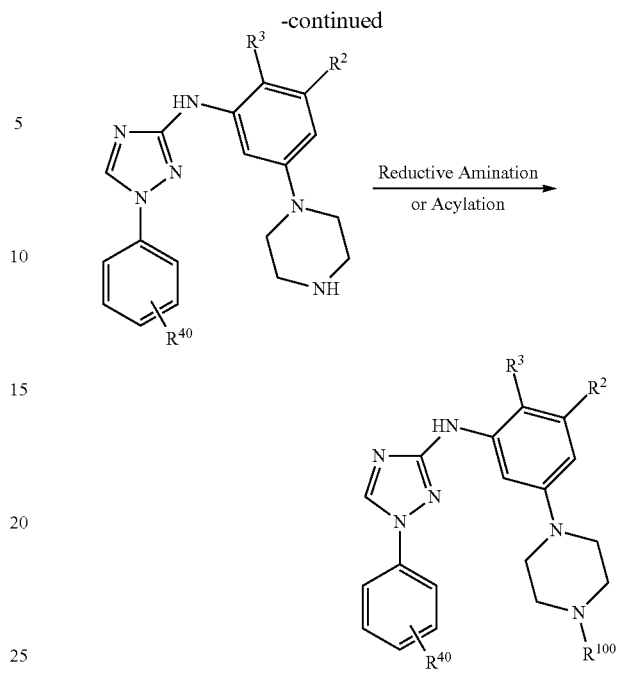

Compounds of the invention may be prepared as generally outlined in Scheme C, where $R^2$, $R^3$, $R^{40}$, and $R^{100}$ are as described for Scheme A. The methods of Scheme C may also be applied to other variations of $L^1$ with $G^1$ to $G^5$ that bond to the parent molecular moiety through a nitrogen atom and the $G^1$ to $G^5$ group contains an available nitrogen for reductive amination or acylation.

Example 10

Preparation of 1-(3,5-difluorophenyl)-N-[3-methyl-5-[4-(oxetan-3-yl)piperazin-1-yl]phenyl]-1,2,4-triazol-3-amine (Compound 33)

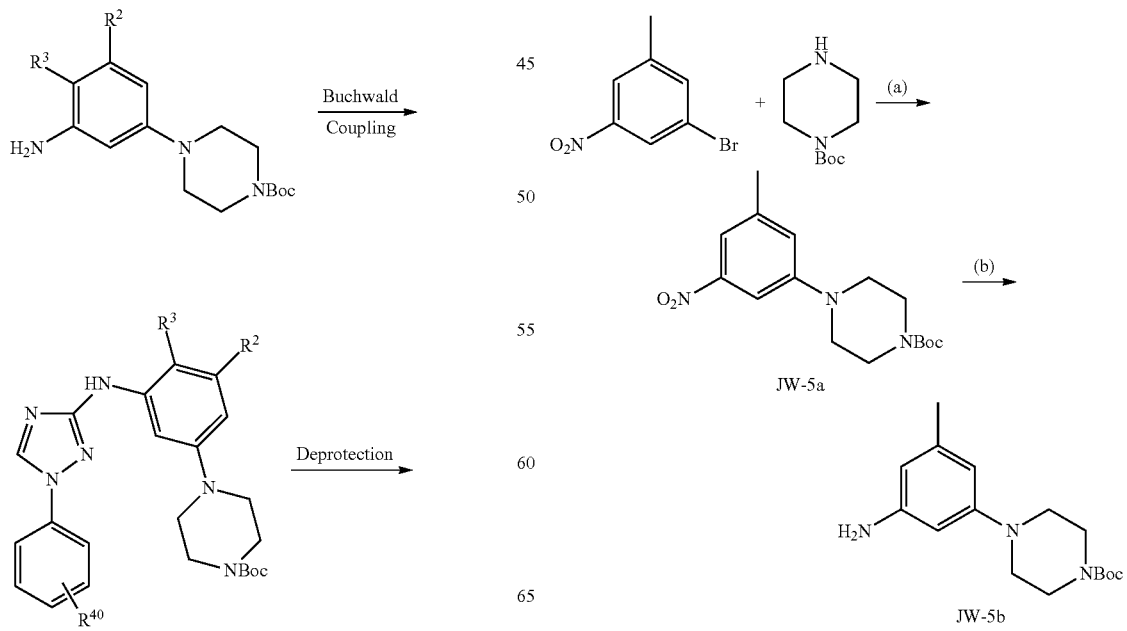

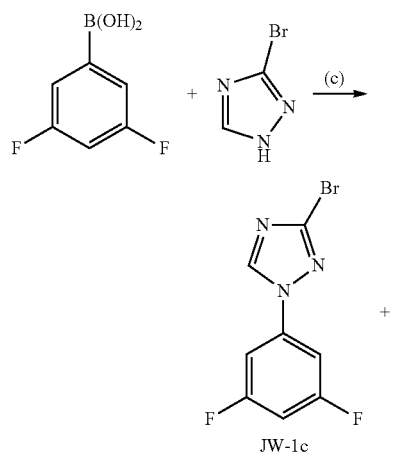

JW-1c

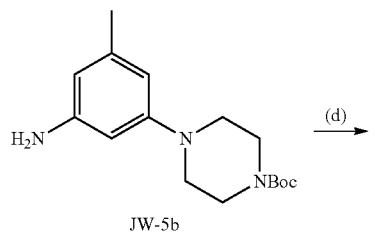

JW-5b

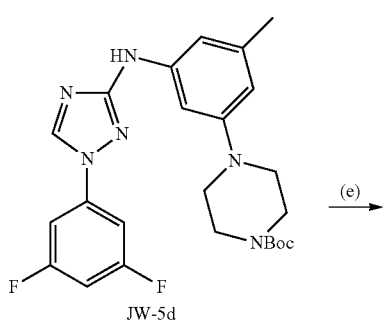

JW-5d

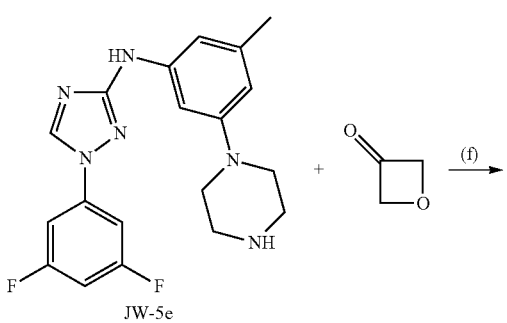

JW-5e

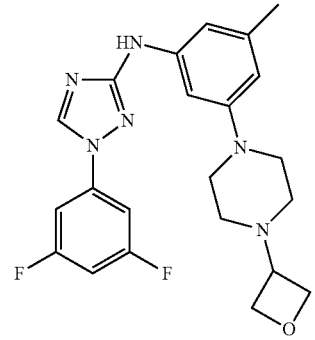

Cmpd 33

(a) t-BuXPhos Palladacycle, t-BuOH, t-BuONa, 60° C.; (b) Pd on Carbon, 10% WT., Degussa,, H₂; (c) Cu(OAc)₂/Pyridine/DCM/R.T.; (d) t-BuXPhos Palladacycle/t-BuOH/t-BuONa; (e) TFA/DCM/R.T.; (f) Na(OAc)₃BH.

Preparation of tert-butyl 4-(3-methyl-5-nitro-phenyl)piperazine-1-carboxylate (JW-5a)

To a 250 ml RBF was added 1-bromo-3-methyl-5-nitrobenzene (7.6 g, 35.2 mmol) and tert-butyl piperazine-1-carboxylate (6.68 g, 35.8 mmol) into 2-methylpropan-2-ol (50 mL). To this mixture was added sodium 2-methylpropan-2-olate (8.4 g, 87.4 mmol) and chloro[2-(di-tert-butylphosphino)-2',4',6'-triisopropyl-1,1'-biphenyl][2-(2-aminoethyl)phenyl)]palladium(II) (231 mg, 2.171 mmol). The mixture was degassed under nitrogen for 1 minute. The reaction was stirred and heated at 75° C. overnight. The reaction was then diluted with EtOAc (100 ml) and 10 ml of water was added slowly. This mixture was washed with water (100 ml) and brine (200 ml). The organic layer was dried over Na₂SO₄ and concentrated in vacuo. The crude material was purified on a short plug of silica gel (50 g) using 1:1 EtOAc:Hexanes to afford 6.1 g (48%) of desired product JW-5a as an off-white solid. $^1$H NMR (400 MHz, CDCl₃) δ 7.55 (d, J=2.5 Hz, 2H), 7.02 (s, 1H), 3.68-3.55 (m, 4H), 3.31-3.14 (m, 4H), 2.42 (s, 3H), 1.51 (s, 9H) ppm. ESI-MS m/z calc. 321.16885, found 322.1 (M+1)+; Retention time: 0.84 minutes.

Preparation of tert-butyl 4-(3-amino-5-methyl-phenyl)piperazine-1-carboxylate (JW-5b)

Catalyst palladium on carbon (10% WT, Degussa, 120 mg, 1.1 mmol) was added to a 250 ml RBF under N2 and EtOH (50 mL) was added. tert-Butyl 4-(3-methyl-5-nitro-phenyl)piperazine-1-carboxylate JW-5a (2.9 g, 9.1 mmol) was added and the reaction was stirred under H2 overnight. The catalyst was filtered and the solvent was removed in vacuo to give 2.45 g of desired product JW-5b. $^1$H NMR (400 MHz, CDCl3) δ 6.19 (s, 1H), 6.13-6.03 (m, 2H), 3.55 (dd, J=10.7, 5.6 Hz, 6H), 3.16-3.02 (m, 4H), 2.22 (s, 3H), 1.48 (s, 9H) ppm. ESI-MS m/z calc. 291.19467, found 292.45 (M+1)+; Retention time: 0.6 minutes.

Preparation of tert-butyl 4-[3-[[1-(3,5-difluorophenyl)-1,2,4-triazol-3-yl]amino]-5-methyl-phenyl]piperazine-1-carboxylate (JW-5d)

3-bromo-1-(3,5-difluorophenyl)-1,2,4-triazole JW-1c (850 mg, 3.3 mmol), sodium 2-methylpropan-2-olate (630 mg, 6.6 mmol) and chloro[2-(di-tert-butylphosphino)-2',4',6'-triisopropyl-1,1'-biphenyl][2-(2-aminoethyl)phenyl)]palladium(II) (52 mg, 0.49 mmol) and tert-butyl 4-(3-amino-5-methyl-phenyl)piperazine-1-carboxylate JW-5b (1.2 g, 3.5 mmol) were mixed in 2-methylpropan-2-ol (10 ml) and the reaction was degassed under nitrogen for 20 seconds. The reaction was capped in a reaction tube (5 ml) and the reaction heated at 75 degrees overnight. The reaction was cooled to room temperature and to the mixture was added 1 ml of MeOH. The solvent was removed in vacuo and the crude was adsorbed onto 5 grams of silica gel and purified on silica gel (12 gram column, Hexanes:EtOAc 30-100%) to afford 732 mg (50%) of desired product JW-5d. $^1$H NMR (300 MHz, Acetone-d6) δ 8.92 (s, 1H), 8.34 (s, 1H), 7.57 (dd, J=8.7, 2.3 Hz, 2H), 7.33 (s, 1H), 7.09-6.88 (m, 2H), 6.43 (s, 1H), 3.63-3.49 (m, 4H), 3.25-3.07 (m, 4H), 2.29 (s, 3H), 1.47 (s, 9H) ppm. ESI-MS m/z calc. 470.22418, found 471.0 (M+1)+; Retention time: 0.81 minutes.

Preparation of 1-(3,5-difluorophenyl)-N-(3-methyl-5-piperazin-1-yl-phenyl)-1,2,4-triazol-3-amine (JW-5e)

tert-Butyl 4-[3-[[1-(3,5-difluorophenyl)-1,2,4-triazol-3-yl]amino]-5-methyl-phenyl]piperazine-1-carboxylate JW-5d (600 mg, 1.1 mmol) was dissolved in a mixture of DCM (6 mL) and TFA (3.0 ml). The reaction was stirred at room temperature for 2 hours and the LCMS indicated that the reaction was complete. The solvent was removed and the crude was dissolved in DCM (10 mL) and the solution was washed with NaHCO3 (sat. aq., 20 ml) and brine (20 ml). The combined aqueous phase was extracted with DCM (5 ml×5) and the combined organic layers were dried over Na2SO4 and concentrated in vacuo to afford 321 mg of desired product JW-5e. $^1$H NMR (400 MHz, DMSO-d6) δ 9.45 (s, 1H), 9.26 (s, 2H), 9.19 (s, 1H), 7.63 (dd, J=8.5, 2.1 Hz, 2H), 7.26 (d, J=2.3 Hz, 1H), 7.19 (s, 1H), 6.97 (s, 1H), 6.40 (s, 1H), 3.46-3.31 (m, 4H), 3.24 (s, 4H), 2.25 (s, 3H) ppm. ESI-MS m/z calc. 370.17175, found 371.0 (M+1)+; Retention time: 0.64 minutes.

Preparation of 1-(3,5-difluorophenyl)-N-[3-methyl-5-[4-(oxetan-3-yl)piperazin-1-yl]phenyl]-1,2,4-triazol-3-amine (Compound 33)

1-(3,5-Difluorophenyl)-N-(3-methyl-5-piperazin-1-yl-phenyl)-1,2,4-triazol-3-amine (52 mg, 0.14 mmol) was dissolved in DCE (2 mL). Oxetan-3-one (25 mg, 0.35 mmol) and Na(OAc)3BH (123 mg, 0.58 mmol) were added to the reaction. The reaction was stirred at room temperature overnight. 1N NaOH (aq., 1 mL) was added and the organic layer was separated and the aqueous layer was extracted with DCM (2 ml). The combined organic layer was dried over Na2SO4 and concentrated in vacuo. The crude material was purified on silica gel using DCM:MeOH (0-4%) to afford desired product cmpd 33. $^1$H NMR (300 MHz, CDCl3) δ 8.32 (s, 1H), 7.28-7.21 (m, 2H), 7.12 (t, J=1.9 Hz, 1H), 6.88-6.68 (m, 3H), 6.46 (d, J=14.4 Hz, 1H), 4.81-4.70 (m, 4H), 3.67-3.48 (m, 1H), 3.33 (dd, J=13.0, 8.2 Hz, 4H), 2.61-2.51 (m, 4H), 2.35 (s, 3H) ppm. ESI-MS m/z calc. 426.19797, found 427.36 (M+1)+; Retention time: 0.65 minutes.

Example 11

Preparation of N-[3-methyl-5-[4-(oxetan-3-yl)piperazin-1-yl]phenyl]-1-phenyl-1,2,4-triazol-3-amine (Compound 118)

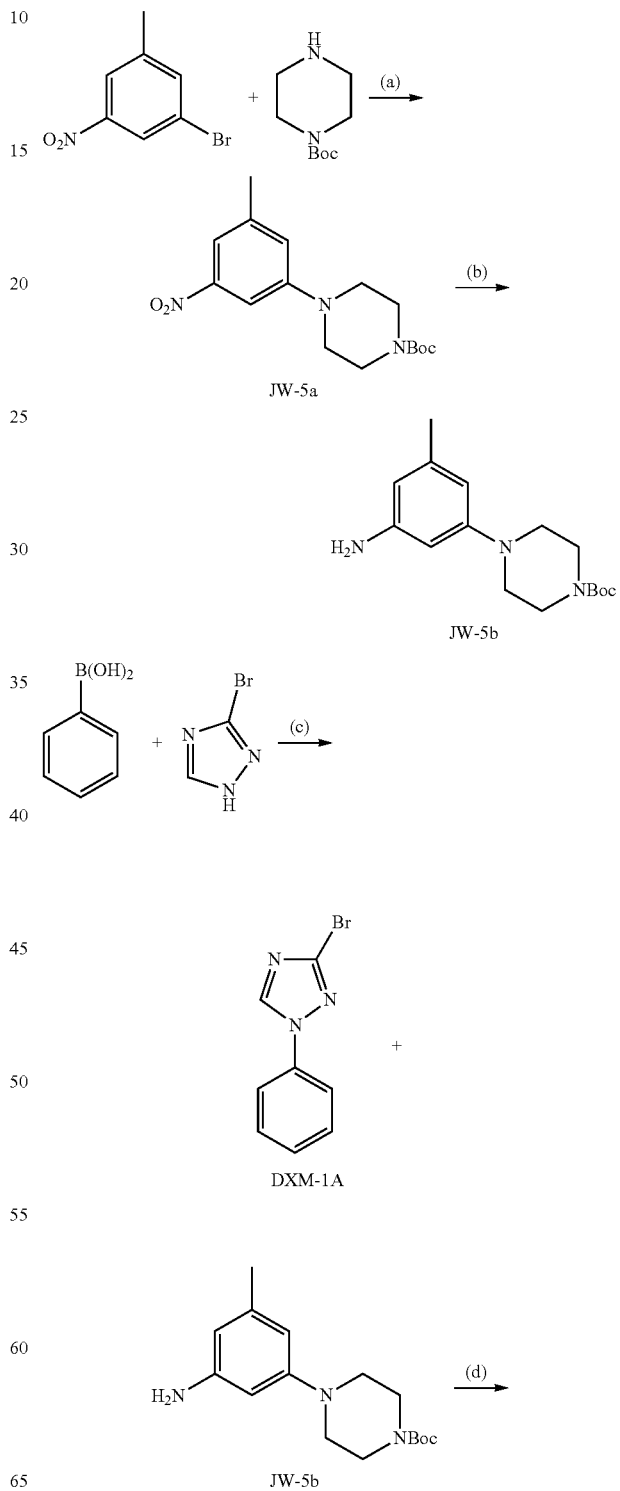

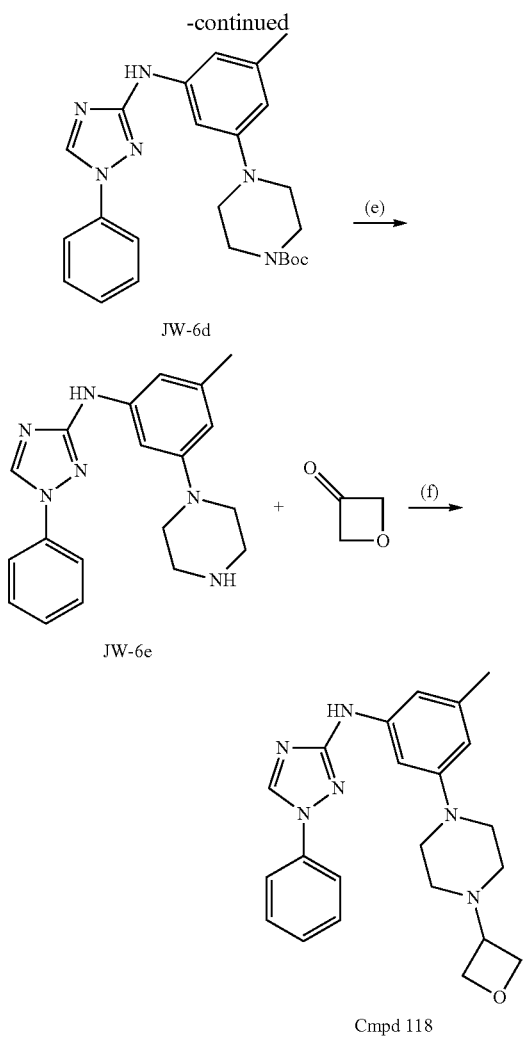

(a) t-BuXPhos Palladacycle, t-BuOH, t-BuONa, 60° C.; (b) Pd /C, H2;
(c) Cu(OAc)2/Pyridine/DCM/R.T.; (d) t-BuXPhos Palladacycle/
t-BuOH/t-BuONa; (e) TFA/DCM/R.T.; (f) Na(OAc)3BH.

Preparation of tert-butyl 4-[3-methyl-5-[(1-phenyl-1,2,4-triazol-3-yl)amino]phenyl]piperazine-1-carboxylate (JW-6d)

tert-Butyl 4-(3-amino-5-methyl-phenyl)piperazine-1-carboxylate JW-5b (1.9 g, 6.5 mmol), 3-bromo-1-phenyl-1,2,4-triazole (DXM-1A) (1.0 g, 4.49 mmol) were added to t-BuOH (15.0 mL). t-BuXPhos Palladacycle (82 mg, 0.12 mmol) and sodium t-butoxide (631 mg, 6.6 mmol) were added to the reaction mixture. The reaction was degassed with nitrogen for 1 min and heated at 60° C. overnight. The reaction was diluted with EtOAc (100 mL) and washed with water (100 mL) and brine (100 mL). The solvent was removed under reduced pressure and purified on silica gel (40 g column, 10-90% Hex:EtOAc) to afford 1.21 g (55%) of desired product JW-6d. $^1$H NMR (400 MHz, DMSO-d6) δ 9.22 (s, 1H), 9.05 (s, 1H), 7.83 (dd, J=8.6, 1.0 Hz, 2H), 7.62-7.45 (m, 2H), 7.35 (t, J=7.4 Hz, 1H), 7.16 (s, 1H), 6.93 (s, 1H), 6.31 (s, 1H), 3.60-3.37 (m, 4H), 3.20-2.93 (m, 4H), 2.23 (s, 3H), 1.43 (s, 9H) ppm. ESI-MS m/z calc. 434.243, found 435.0 (M+1)+; Retention time: 0.78 minutes.

Preparation of N-(3-methyl-5-piperazin-1-yl-phenyl)-1-phenyl-1,2,4-triazol-3-amine (JW-6e)

tert-Butyl 4-[3-methyl-5-[(1-phenyl-1,2,4-triazol-3-yl)amino]phenyl]piperazine-1-carboxylate JW-6d (1.88 g, 4.3 mmol) was dissolved in DCM (20 mL) and HCl (12 mL of a 2M soln in diethyl ether, 24.0 mmol) was added into the reaction. The reaction was stirred at 50 degrees overnight and a solid was generated. The solid was collected by filtration and washed with diethyl ether (20 mL) and dried in vacuo to afford 1.582 g (92%) of desired product JW-6e. $^1$HNMR (400 MHz, DMSO-d6) δ 9.31 (s, 1H), 9.08 (s, 1H), 7.84 (d, J=7.6 Hz, 1H), 7.55 (t, J=8.0 Hz, 1H), 7.35 (t, J=7.4 Hz, 1H), 7.23 (s, 1H), 6.98 (s, 1H), 6.39 (s, 1H), 3.48-3.30 (m, 4H), 3.25 (s, 4H), 2.25 (s, 3H) ppm. ESI-MS m/z calc. 334.19058, found 335.47 (M+1)+; Retention time: 0.64 minutes.

Preparation of N-[3-methyl-5-[4-(oxetan-3-yl)piperazin-1-yl]phenyl]-1-phenyl-1,2,4-triazol-3-amine (Compound 118)

N-(3-Methyl-5-piperazin-1-yl-phenyl)-1-phenyl-1,2,4-triazol-3-amine JW-6e (1.42 g, 4.2 mmol) and oxetan-3-one (612 mg, 8.5 mmol) were stirred in DCE (25 mL) at room temperature for 15 mins and Na(OAc)3BH (2.7 g, 12.7 mmol) was added into the reaction. The reaction was stirred at room temperature for 5 hours and the LCMS indicated that the reaction was completed. 1N NaOH aq. solution (10 ml) was added into the reaction and the reaction was washed with water and extracted with DCM (100 ml×3). The organic layers were combined and dried over Na2SO4 and purified on CombiFlash (40 g column, 10-90% EtOAc:Hexane) to afford 1.02 g (61%) of desired product, cmpd 118. $^1$H NMR (300 MHz, DMSO-d6) δ 9.18 (s, 1H), 9.05 (s, 1H), 7.89-7.75 (m, 2H), 7.55 (t, J=8.0 Hz, 2H), 7.34 (t, J=7.4 Hz, 1H), 7.16 (s, 1H), 6.88 (s, 1H), 6.29 (s, 1H), 4.57 (t, J=6.5 Hz, 2H), 4.49 (t, J=6.0 Hz, 2H), 3.56-3.38 (m, 1H), 3.22-3.09 (m, 3H), 2.47-2.37 (m, 4H), 2.22 (s, 3H) ppm. ESI-MS m/z calc. 390.2168, found 391.5 (M+1)+; Retention time: 0.62 minutes.

Example 12

Preparation of N-[3-(difluoromethyl)-5-[4-(oxetan-3-yl)piperazin-1-yl]phenyl]-1-phenyl-1,2,4-triazol-3-amine (Compound 26)

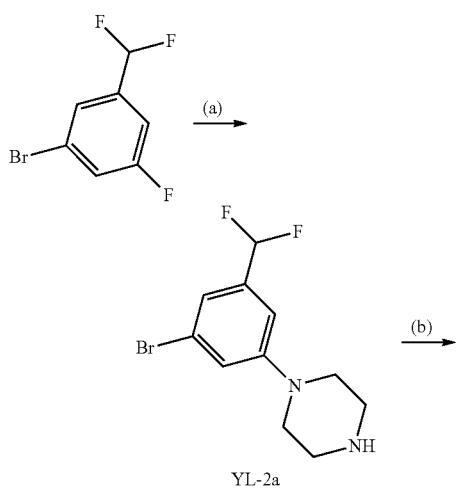

-continued

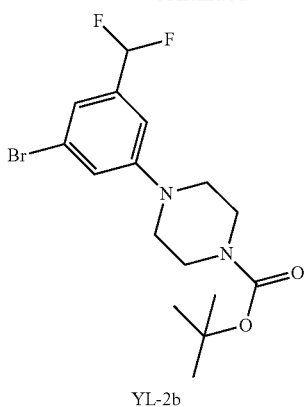

YL-2b

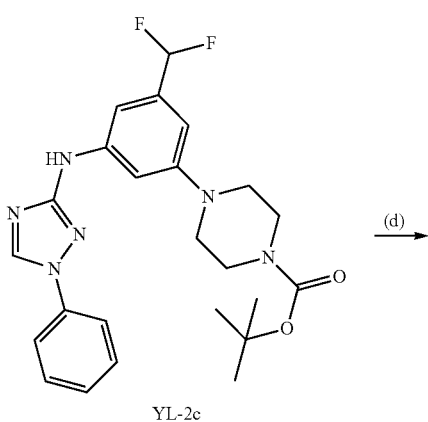

YL-2c

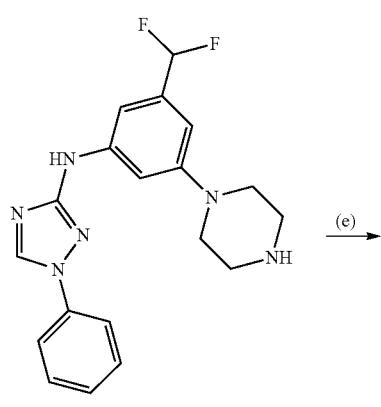

YL-2d

-continued

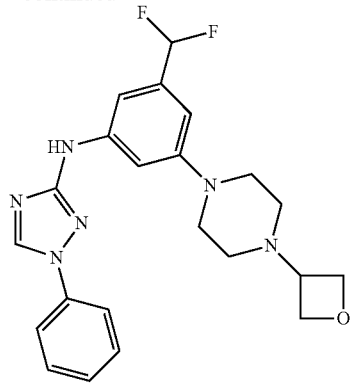

Cmpd 26

Reagents and conditions: (a) 1-cyclopropylpiperazine, 200° C.; (b) (tBuO)₂CO, DCM; (c) 1-phenyl-1,2,4-triazol-3-amine, t-BuXPhos Palladacycle, NaOtBu, dioxane, 120° C.; (d) TFA, DCM; (e) oxetan-3-one, NaBH(OAc)₃, HOAc, DCM.

Preparation of 1-bromo[3-(difluoromethyl)phenyl]piperazine (YL-2a)

A mixture of 1-bromo-3-(difluoromethyl)-5-fluoro-benzene (1 g, 4.44 mmol) and 1-cyclopropylpiperazine (2.80 g, 22.22 mmol) was microwaved at 200° C. for 1 h. Pumped down solvent and purified the crude mixture by ISCO purification (40 g silica; 0% to 5% to 30% of MeOH in DCM) to provide 1-[3-bromo-5-(difluoromethyl)phenyl]piperazine (920 mg, 89%). ¹H NMR (300 MHz, CD3OD) δ 7.20 (s, 1H), 7.09 (s, 1H), 7.05 (d, J=1.0 Hz, 1H), 6.66 (t, J=56.1 Hz, 1H), 3.20 (dd, J=6.2, 4.0 Hz, 4H), 2.98 (dd, J=6.2, 4.1 Hz, 4H) ppm. ESI-MS m/z calc. 290.02, found 291.19 (M+1)+; Retention time: 0.63 minutes.

Preparation of t-Butyl 4-[3-bromo-5-(difluoromethyl)phenyl]piperazine-1-carboxylate (YL-2b)

A mixture of 1-[3-bromo-5-(difluoromethyl)phenyl]piperazine (920 mg, 3.16 mmol) and (tBuO)₂CO (1.03 g, 4.74 mmol) in dichloromethane (15 mL) was stirred at RT for 30 min. The reaction was quenched with MeOH (300 uL), diluted with DCM (15 mL) and washed with water (2×3 mL). The organic layer was filtered through florisil (5 g) and pumped down to dryness. The crude material was purified by ISCO purification (12 g silica; 10% to 100% of EtOAc in hex) to give t-butyl 4-[3-bromo-5-(difluoromethyl)phenyl]piperazine-1-carboxylate YL-2b (830 mg, 67%). ¹H NMR (300 MHz, CDCl₃) δ 7.11 (d, J=0.8 Hz, 2H), 6.94 (s, 1H), 6.55 (t, J=56.3 Hz, 1H), 3.70-3.50 (m, 4H), 3.28-3.12 (m, 4H), 1.50 (s, 9H) ppm. ESI-MS m/z calc. 390.08, found 391.18 (M+1)+; Retention time: 1.01 minutes.

Preparation of t-butyl 4-[3-(difluoromethyl)-5-[(1-phenyl-1,2,4-triazol-3-yl)amino]phenyl]piperazine-1-carboxylate (YL-2c)

t-Butyl 4-[3-bromo-5-(difluoromethyl)phenyl]piperazine-1-carboxylate YL-2b (160 mg, 0.41 mmol), 1-phenyl-1,2,4-triazol-3-amine RG-1b (79 mg, 0.49 mmol) and sodium t-butoxide (79 mg, 0.82 mmol) were suspended in dioxane (6 mL) and purged with N₂ for several minutes before addition of t-BuXPhos Palladacycle (13 mg, 0.02 mmol). The vial was capped and microwaved at 120° C. for 35 minutes. The reaction was quenched with MeOH (0.5 mL), 1N HCl (800 uL) and diluted with DCM. After filtration through Florisil (5 g), the excess solvent was pumped down in vacuo. ISCO purification (12 g silica; 0% to 10% of MeOH in DCM) gave t-butyl 4-[3-(difluoromethyl)-5-[(1-phenyl-1,2,4-triazol-3-yl)amino]phenyl]piperazine-1-carboxylate YL-2c (100 mg, 52%). $^1$H NMR (300 MHz, CDCl$_3$) δ 8.37 (s, 1H), 7.72-7.66 (m, 2H), 7.53 (ddd, J=8.3, 5.3, 1.8 Hz, 2H), 7.43-7.35 (m, 2H), 7.30 (s, 1H), 7.15 (s, 1H), 6.80-6.41 (m, 2H), 3.68-3.56 (m, 4H), 3.30-3.19 (m, 4H), 1.52 (s, 9H) ppm. ESI-MS m/z calc. 470.22, found 471.28 (M+1)+; Retention time: 0.93 minutes.

Preparation of N-[3-(difluoromethyl)-5-piperazin-1-yl-phenyl]-1-phenyl-1,2,4-triazol-3-amine (YL-2d)

A mixture of tert-butyl 4-[3-(difluoromethyl)-5-[(1-phenyl-1,2,4-triazol-3-yl)amino]phenyl]piperazine-1-carboxylate YL-2c (100 mg, 0.21 mmol) and TFA (818 μL, 10.6 mmol) in DCM was stirred at RT for 1 h. LCMS showed the desired product. Pumped down the solvent to dryness. The crude product was dissolved in DCM and filtered through PL-HCO$_3$ MP SPE (500 mg). The filtrate was evaporated in vacuo to give N-[3-(difluoromethyl)-5-piperazin-1-yl-phenyl]-1-phenyl-1,2,4-triazol-3-amine YL-2d (64 mg, 77%). $^1$H NMR (300 MHz, CD3OD) δ 8.80 (s, 1H), 7.85-7.75 (m, 2H), 7.51 (dd, J=16.5, 8.1 Hz, 3H), 7.36 (dd, J=13.5, 6.0 Hz, 2H), 6.68 (dd, J=64.3, 48.6 Hz, 2H), 3.39 (dd, J=6.5, 3.7 Hz, 4H), 3.26 (dd, J=6.5, 3.6 Hz, 4H) ppm. ESI-MS m/z calc. 370.17, found 371.29 (M+1)+; Retention time: 0.64 minutes.

Preparation of N-[3-(difluoromethyl)-5-[4-(oxetan-3-yl)piperazin-1-yl]phenyl]-1-phenyl-1,2,4-triazol-3-amine (Compound 26)

To a solution of N-[3-(difluoromethyl)-5-piperazin-1-yl-phenyl]-1-phenyl-1,2,4-triazol-3-amine YL-2d (120 mg, 0.32 mmol), oxetan-3-one (234 mg, 3.24 mmol) and acetic acid (117 mg, 1.94 mmol) in dichloromethane (6.0 mL) was added NaBH(OAc)$_3$ (412 mg, 1.94 mmol) and the mixture was stirred for 18 h. The reaction was diluted with DCM and slowly quenched with MeOH and saturated NaHCO$_3$. After separation, the organic layer was washed with water, saturated NaCl and dried then evaporated in vacuo. The crude material was subjected to ISCO purification (12 g silica; 0% to 5% to 10% of MeOH in DCM) to give N-[3-(difluoromethyl)-5-[4-(oxetan-3-yl)piperazin-1-yl]phenyl]-1-phenyl-1,2,4-triazol-3-amine, cmpd 26 (107 mg, 74%). $^1$H NMR (300 MHz, CDCl$_3$) δ 8.35 (s, 1H), 7.73-7.65 (m, 2H), 7.53 (ddd, J=8.3, 5.3, 1.8 Hz, 2H), 7.38 (ddd, J=8.7, 4.6, 1.2 Hz, 2H), 7.17 (s, 1H), 6.86 (s, 1H), 6.63 (dd, J=67.7, 45.7 Hz, 2H), 4.72 (p, J=6.4 Hz, 4H), 3.59 (p, J=6.4 Hz, 1H), 3.41-3.24 (m, 4H), 2.61-2.48 (m, 4H) ppm. ESI-MS m/z calc. 426.20, found 427.41 (M+1)+; Retention time: 0.65 minutes.

Example 13

Preparation of 1-(2-fluoro-4-pyridyl)-N-[3-methyl-5-[4-(oxetan-3-yl)piperazin-1-yl]phenyl]-1,2,4-triazol-3-amine (Compound 40)

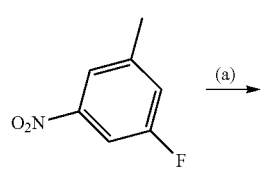

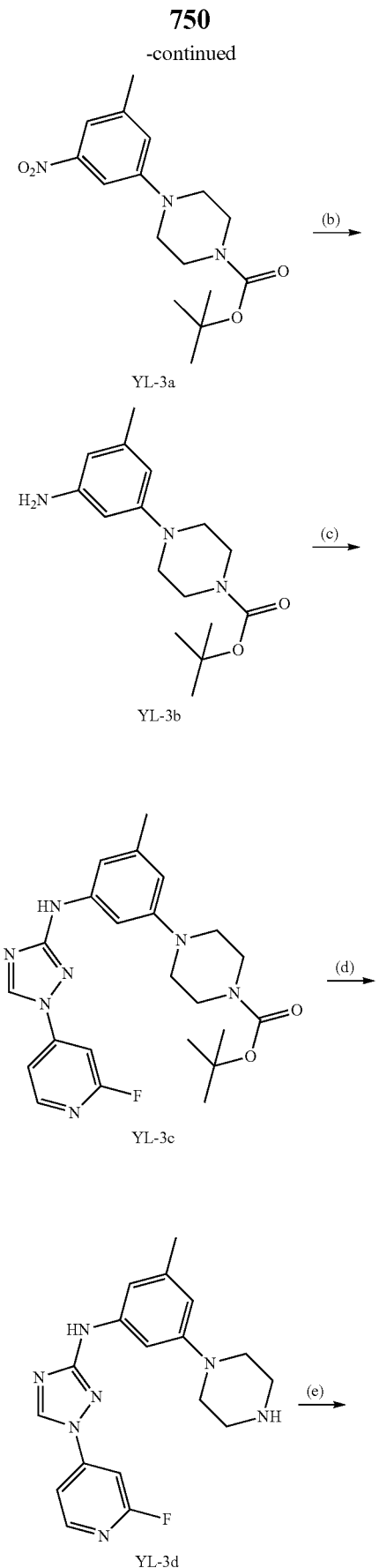

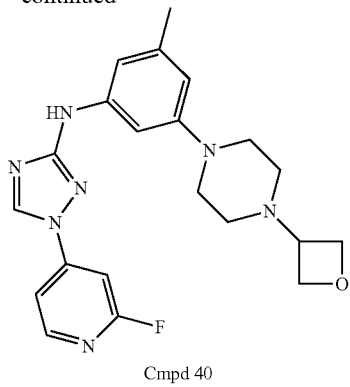

Cmpd 40

Reagents and conditions: (a) t-butyl piperazine-1-carboxylate, t-BuXPhos Palladacycle, NaOtBu, tBuOH, 40° C.; (b) H₂, Pd/C, EtOAc; (c) 4-(3-bromo-1,2,4-triazol-1-yl)-2-fluoro-pyridine, t-BuXPhos Palladacycle, NaOtBu, dioxane, 120° C.; (d) TFA, DCM; (e) oxetan-3-one, NaBH(OAc)₃, HOAc, DCM.

Preparation of t-butyl 4-(3-methyl-5-nitro-phenyl)piperazine-1-carboxylate (YL-3a)

A mixture of 1-bromo-3-methyl-5-nitro-benzene (50 g, 231 mmol), sodium t-butoxide (33.36 g, 347 mmol) and tert-butyl piperazine-1-carboxylate (47.40 g, 255 mmol) in dry t-BuOH (500 mL) was purged with N₂ for 40 min. After the purge, t-BuXPhos Palladacycle (7.54 g, 11.57 mmol) was added and the mixture was heated at 40° C. for 60 min. The reaction was then quenched with MeOH and solvents removed under reduced pressure. The residue was partitioned between EtOAc and water, the organic phase washed with more water, then brine, dried (Na₂SO₄) and removed solvent under reduced pressure. The crude product was purified on SiO2 column (330 g) eluting with a DCM/EtOAc (0-50%) gradient to afford t-butyl 4-(3-methyl-5-nitro-phenyl)piperazine-1-carboxylate YL-3a (40 g, 54%). ¹H NMR (400 MHz, DMSO-d6) δ 7.49 (s, 1H), 7.45 (s, 1H), 7.25 (s, 1H), 3.54-3.37 (m, 4H), 3.28-3.17 (m, 4H), 2.37 (s, 3H), 1.42 (s, 9H) ppm.

Preparation of t-butyl 4-(3-amino-5-methyl-phenyl)piperazine-1-carboxylate (YL-3b)

To 10% Pd on C, wet, Degussa (139 mg, 0.13 mmol) under N₂ was added a solution of t-butyl 4-(3-methyl-5-nitro-phenyl)piperazine-1-carboxylate YL-3a (1.4 g, 4.36 mmol) in EtOAc (20 mL) and MeOH (5 mL) and the mixture was shaken under H2 (50 psi) for 2 hr. The reaction mixture was filtered through Celite and the filtrate pumped down to give t-butyl 4-(3-amino-5-methyl-phenyl)piperazine-1-carboxylate YL-3b (1.25 g, 99%). ¹H NMR (300 MHz, CDCl₃) δ 6.21 (s, 1H), 6.13-6.07 (m, 2H), 3.62-3.50 (m, 4H), 3.18-3.03 (m, 4H), 2.24 (s, 3H), 1.50 (s, 9H) ppm. ESI-MS m/z calc. 291.19, found 292.12 (M+1)⁺; Retention time: 0.64 minutes.

Preparation of t-butyl 4-[3-[[1-(2-fluoro-4-pyridyl)-1,2,4-triazol-3-yl]amino]-5-methyl-phenyl]piperazine-1-carboxylate (YL-3c)

t-Butyl 4-(3-amino-5-methyl-phenyl)piperazine-1-carboxylate YL-3b (180 mg, 0.62 mmol), 4-(3-bromo-1,2,4-triazol-1-yl)-2-fluoro-pyridine (180 mg, 0.74 mmol) and sodium t-butoxide (119 mg, 1.24 mmol) were suspended in dioxane (4.8 mL) and purged with N₂ for several minutes before addition of the t-BuXPhos Palladacycle (20 mg, 0.03 mmol). The vial was capped and microwaved at 120° C. for 35 minutes. LC/MS showed desired product so the reaction was quenched with MeOH (0.5 mL), 1N HCl (800 uL) and diluted with DCM. After filtration through Florisil (5 g), the excess solvent was removed under reduced pressure then the crude product subjected to ISCO purification (12 g silica; 10% to 50% to 100% of EtOAc in hex) to give t-butyl 4-[3-[[1-(2-fluoro-4-pyridyl)-1,2,4-triazol-3-yl]amino]-5-methyl-phenyl]piperazine-1-carboxylate YL-3c (73 mg, 26%). ¹H NMR (300 MHz, CD₃OD+CDCl₃) δ 8.84 (s, 1H), 8.24 (d, J=5.7 Hz, 1H), 7.63 (d, J=5.7 Hz, 1H), 7.41 (s, 1H), 7.13 (s, 1H), 6.91 (s, 1H), 6.41 (s, 1H), 3.67-3.49 (m, 4H), 3.26-3.05 (m, 4H), 2.31 (s, 3H), 1.46 (s, 9H) ppm. ESI-MS m/z calc. 453.23, found 454.21 (M+1)⁺; Retention time: 0.81 minutes.

Preparation of 1-(2-fluoro-4-pyridyl)-N-(3-methyl-5-piperazin-1-yl-phenyl)-1,2,4-triazol-3-amine (YL-3d)

To a solution of t-butyl 4-[3-[[1-(2-fluoro-4-pyridyl)-1,2,4-triazol-3-yl]amino]-5-methyl-phenyl]piperazine-1-carboxylate YL-3c (73 mg, 0.16 mmol) in DCM (3 mL) was added TFA (620 µL, 8.05 mmol) and the reaction mixture stirred for 2 hr. Pumped down solvent to 1-(2-fluoro-4-pyridyl)-N-(3-methyl-5-piperazin-1-yl-phenyl)-1,2,4-triazol-3-amine YL-3d (50 mg, 88%). ¹H NMR (300 MHz, CDCl₃) δ 8.45 (s, 1H), 8.30 (d, J=5.2 Hz, 1H), 7.45 (d, J=4.6 Hz, 1H), 7.06 (s, 1H), 6.79 (s, 1H), 6.69 (s, 1H), 6.44 (s, 1H), 3.19 (s, 4H), 3.06 (s, 4H), 2.34 (s, 3H) ppm. ESI-MS m/z calc. 353.18, found 354.41 (M+1)⁺; Retention time: 0.62 minutes.

Preparation of 1-(2-fluoro-4-pyridyl)-N-[3-methyl-5-[4-(oxetan-3-yl)piperazin-1-yl]phenyl]-1,2,4-triazol-3-amine (Compound 40)

To a solution of 1-(2-fluoro-4-pyridyl)-N-(3-methyl-5-piperazin-1-yl-phenyl)-1,2,4-triazol-3-amine YL-3d (50 mg, 0.14 mmol), oxetan-3-one (102 mg, 1.42 mmol) and acetic acid (48 µL, 0.85 mmol) in dichloromethane (2.5 mL) was added NaBH(OAc)₃ (180 mg, 0.85 mmol) carefully and the mixture was stirred for 2 h. LCMS showed desired product so the reaction was diluted with DCM and slowly quenched with MeOH and sat. NaHCO₃ (3 mL). After separation, the organic layer was washed with water, sat NaCl and dried. The organics were concentrated to dryness and the crude material was subjected to ISCO purification (12 g silica; 0% to 5% to 10% of MeOH in DCM) to give 1-(2-fluoro-4-pyridyl)-N-[3-methyl-5-[4-(oxetan-3-yl)piperazin-1-yl]phenyl]-1,2,4-triazol-3-amine, cmpd 40 (50 mg, 82%). ¹H NMR (300 MHz, CDCl₃) δ 8.46 (d, J=6.7 Hz, 1H), 8.32 (d, J=5.6 Hz, 1H), 7.52-7.44 (m, 1H), 7.27 (d, J=1.5 Hz, 1H), 7.08 (s, 1H), 6.82 (s, 1H), 6.71 (s, 1H), 6.46 (s, 1H), 4.80-4.65 (m, 4H), 3.68-3.54 (m, 1H), 3.38-3.25 (m, 4H), 2.63-2.50 (m, 4H), 2.37 (s, 3H) ppm. ESI-MS m/z calc. 409.20, found 410.28 (M+1)+; Retention time: 0.59 minutes.

Using the general synthetic scheme outlined in Scheme C and the experimental procedures listed above in Examples 10-13, the following compounds were prepared:

| Cmpd No. | IUPAC Name |
|---|---|
| 458 | cyclopropyl-[4-[3-[[1-(3,5-difluorophenyl)-1,2,4-triazol-3-yl]amino]-5-methyl-phenyl]piperazin-1-yl]methanone |
| 196 | ethyl 4-[3-[[1-(3,5-difluorophenyl)-1,2,4-triazol-3-yl]amino]-5-methyl-phenyl]piperazine-1-carboxylate |
| 350 | 2,2,2-trifluoroethyl 4-[3-[[1-(3,5-difluorophenyl)-1,2,4-triazol-3-yl]amino]-5-methyl-phenyl]piperazine-1-carboxylate |
| 137 | 1-(3,5-difluorophenyl)-N-[3-methyl-5-(4-tetrahydrofuran-3-ylpiperazin-1-yl)phenyl]-1,2,4-triazol-3-amine |
| 199 | 1-(3,5-difluorophenyl)-N-[3-methyl-5-(4-tetrahydropyran-3-ylpiperazin-1-yl)phenyl]-1,2,4-triazol-3-amine |
| 243 | 1-(3,5-difluorophenyl)-N-[3-methyl-5-(4-tetrahydropyran-4-ylpiperazin-1-yl)phenyl]-1,2,4-triazol-3-amine |
| 352 | 1-[4-[3-[[1-(3,5-difluorophenyl)-1,2,4-triazol-3-yl]amino]-5-methyl-phenyl]piperazin-1-yl]-2,2,2-trifluoro-ethanone |
| 290 | N-[3-(4-cyclobutylpiperazin-1-yl)-5-methyl-phenyl]-1-phenyl-1,2,4-triazol-3-amine |
| 434 | N-[3-methyl-5-(4-tetrahydrofuran-3-ylpiperazin-1-yl)phenyl]-1-phenyl-1,2,4-triazol-3-amine |
| 127 | N-[3-methyl-5-[4-(2-methyltetrahydrofuran-3-yl)piperazin-1-yl]phenyl]-1-phenyl-1,2,4-triazol-3-amine |
| 172 | N-[3-methyl-5-(4-tetrahydropyran-3-ylpiperazin-1-yl)phenyl]-1-phenyl-1,2,4-triazol-3-amine |
| 87 | N-[3-(4-cyclopentylpiperazin-1-yl)-5-methyl-phenyl]-1-phenyl-1,2,4-triazol-3-amine |
| 370 | 1-[4-[3-[[1-(3,5-difluorophenyl)-1,2,4-triazol-3-yl]amino]-5-methyl-phenyl]piperazin-1-yl]ethanone |
| 422 | methyl 4-[3-[[1-(3,5-difluorophenyl)-1,2,4-triazol-3-yl]amino]-5-methyl-phenyl]piperazine-1-carboxylate |
| 233 | 1-[2-(methoxymethyl)phenyl]-N-[3-methyl-5-[4-(oxetan-3-yl)piperazin-1-yl]phenyl]-1,2,4-triazol-3-amine |
| 414 | N-[3-methyl-5-[4-(oxetan-3-yl)piperazin-1-yl]phenyl]-1-(o-tolyl)-1,2,4-triazol-3-amine |
| 95 | 1-(3,5-difluorophenyl)-N-[3-methyl-5-[4-(thietan-3-yl)piperazin-1-yl]phenyl]-1,2,4-triazol-3-amine |
| 228 | 1-(3,5-difluorophenyl)-N-[3-[4-(1,1-dioxothietan-3-yl)piperazin-1-yl]-5-methyl-phenyl]-1,2,4-triazol-3-amine |
| 159 | N-(3-methyl-5-piperazin-1-yl-phenyl)-1-phenyl-1,2,4-triazol-3-amine |
| 77 | 1-(3,5-difluorophenyl)-N-(3-methyl-5-piperazin-1-yl-phenyl)-1,2,4-triazol-3-amine |
| 259 | N-[3-methyl-5-(3-methylpiperazin-1-yl)phenyl]-1-phenyl-1,2,4-triazol-3-amine |
| 362 | 1-(3,5-difluorophenyl)-N-[3-methyl-5-(3-methylpiperazin-1-yl)phenyl]-1,2,4-triazol-3-amine |
| 21 | N-[3-(2,5-dimethylpiperazin-1-yl)-5-methyl-phenyl]-1-phenyl-1,2,4-triazol-3-amine |
| 133 | N-[3-(3,4-dimethylpiperazin-1-yl)-5-methyl-phenyl]-1-phenyl-1,2,4-triazol-3-amine |
| 119 | 1-(3,5-difluorophenyl)-N-[3-(3,4-dimethylpiperazin-1-yl)-5-methyl-phenyl]-1,2,4-triazol-3-amine |
| 419 | N-[3-methyl-5-(2,4,5-trimethylpiperazin-1-yl)phenyl]-1-phenyl-1,2,4-triazol-3-amine |
| 292 | N-[3-[(1S,4S)-2-cyclopropyl-2,5-diazabicyclo[2.2.1]heptan-5-yl]-5-methyl-phenyl]-1-phenyl-1,2,4-triazol-3-amine |
| 78 | N-[3-[(1S,4S)-2-cyclopropyl-2,5-diazabicyclo[2.2.1]heptan-5-yl]-5-methyl-phenyl]-1-(3,5-difluorophenyl)-1,2,4-triazol-3-amine |
| 219 | N-[3-methyl-5-[(1S,4S)-2-(oxetan-3-yl)-2,5-diazabicyclo[2.2.1]heptan-5-yl]phenyl]-1-phenyl-1,2,4-triazol-3-amine |
| 34 | 1-(3,5-difluorophenyl)-N-[3-methyl-5-[(1S,4S)-2-(oxetan-3-yl)-2,5-diazabicyclo[2.2.1]heptan-5-yl]phenyl]-1,2,4-triazol-3-amine |
| 459 | 1-(3,5-difluorophenyl)-N-[3-methyl-5-[(1R,4R)-5-methyl-2,5-diazabicyclo[2.2.1]heptan-2-yl]phenyl]-1,2,4-triazol-3-amine |
| 185 | 1-(3,5-difluorophenyl)-N-[3-methyl-5-[(1R,4R)-2-(oxetan-3-yl)-2,5-diazabicyclo[2.2.1]heptan-5-yl]phenyl]-1,2,4-triazol-3-amine |
| 93 | 1-[3-[[1-(3,5-difluorophenyl)-1,2,4-triazol-3-yl]amino]-5-methyl-phenyl]piperazin-2-one |
| 67 | 1-[3-[[1-(3,5-difluorophenyl)-1,2,4-triazol-3-yl]amino]-5-methyl-phenyl]-4-(oxetan-3-yl)piperazin-2-one |
| 392 | N-[3-(difluoromethyl)-5-morpholino-phenyl]-1-phenyl-1,2,4-triazol-3-amine |
| 85 | N-[3-(difluoromethyl)-5-morpholino-phenyl]-1-(2-fluoro-4-pyridyl)-1,2,4-triazol-3-amine |
| 125 | 2-[4-[3-[[1-(3,5-difluorophenyl)-1,2,4-triazol-3-yl]amino]-5-methyl-phenyl]piperazin-1-yl]acetic acid |

-continued

| Cmpd No. | IUPAC Name |
|---|---|
| 438 | 4-[3-[[1-(3,5-difluorophenyl)-1,2,4-triazol-3-yl]amino]-5-methyl-phenyl]piperidin-3-ol |
| 282 | (3R,4R)-4-[3-[[1-(3,5-difluorophenyl)-1,2,4-triazol-3-yl]amino]-5-methyl-phenyl]-1-(oxetan-3-yl)piperidin-3-ol; (3S,4S)-4-[3-[[1-(3,5-difluorophenyl)-1,2,4-triazol-3-yl]amino]-5-methyl-phenyl]-1-(oxetan-3-yl)piperidin-3-ol |
| 72 | ethyl 2-[4-[3-[[1-(3,5-difluorophenyl)-1,2,4-triazol-3-yl]amino]-5-methyl-phenyl]piperazin-1-yl]acetate |
| 509 | 2-[4-[3-[[1-(3,5-difluorophenyl)-1,2,4-triazol-3-yl]amino]-5-methyl-phenyl]piperazin-1-yl]-2-methyl-propanoic acid |
| 530 | 1-(3,5-difluorophenyl)-N-[3-methyl-5-[4-[(3S)-tetrahydrofuran-3-yl]piperazin-1-yl]phenyl]-1,2,4-triazol-3-amine |
| 531 | 1-(3,5-difluorophenyl)-N-[3-methyl-5-[4-[(3R)-tetrahydrofuran-3-yl]piperazin-1-yl]phenyl]-1,2,4-triazol-3-amine |
| 898 | N-[3-[4-(3-deuteriooxetan-3-yl)piperazin-1-yl]-5-methyl-phenyl]-1-phenyl-1,2,4-triazol-3-amine |
| 997 | 1-(3,5-difluorophenyl)-N-[3-methyl-5-[2,2,3,3,5,5,6,6-octadeuterio-4-(3-deuteriooxetan-3-yl)piperazin-1-yl]phenyl]-1,2,4-triazol-3-amine |

Scheme D: General Route D for Preparation of Compounds of Formula I or I'

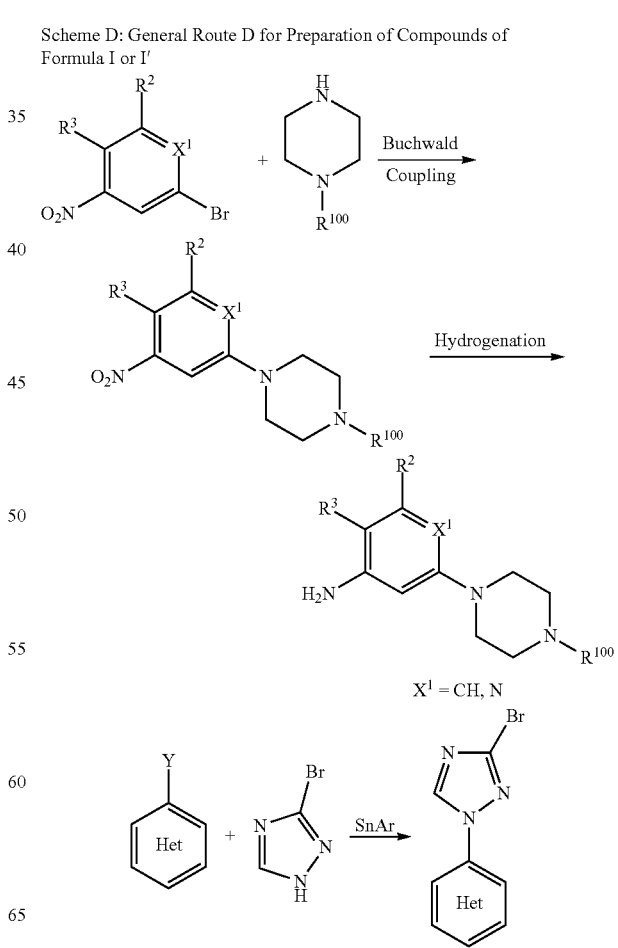

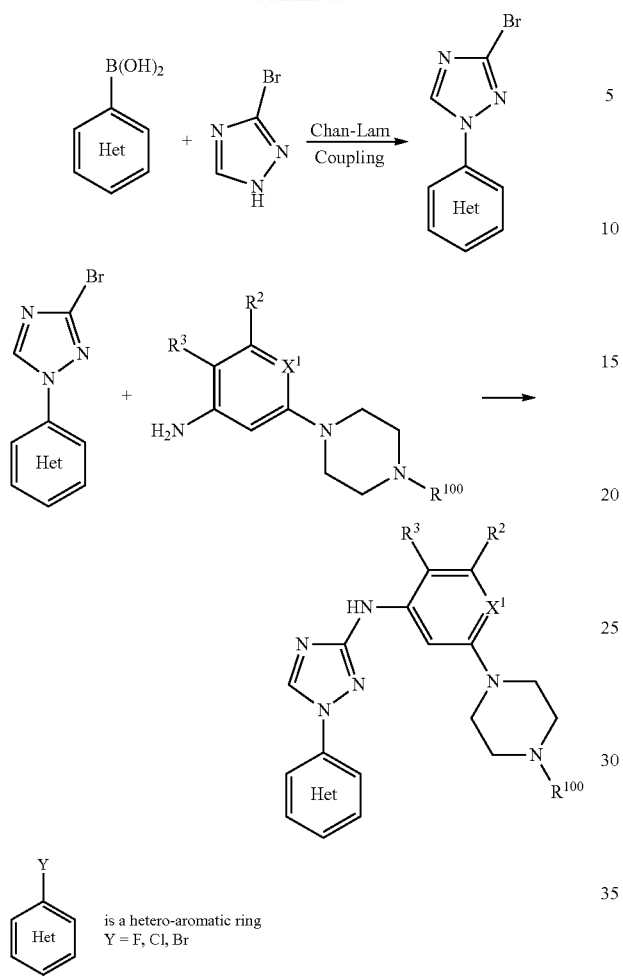

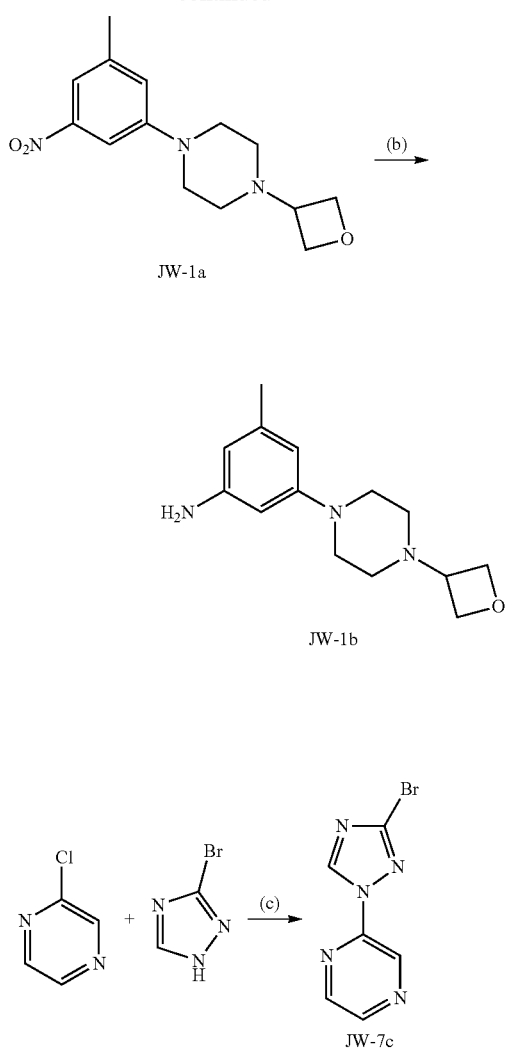

Compounds of the invention may be prepared as generally outlined in Scheme D, where R², R³, R¹⁰⁰, and X¹ are as described for Scheme A. The methods of Scheme D may also be applied to other variations of L¹ with G¹ to G⁵ that bond to the parent molecular moiety through a nitrogen atom.

Example 14

Preparation of (N-[3-methyl-5-[4-(oxetan-3-yl)piperazin-1-yl]phenyl]-1-pyrazin-2-yl-1,2,4-triazol-3-amine) (Compound 195)

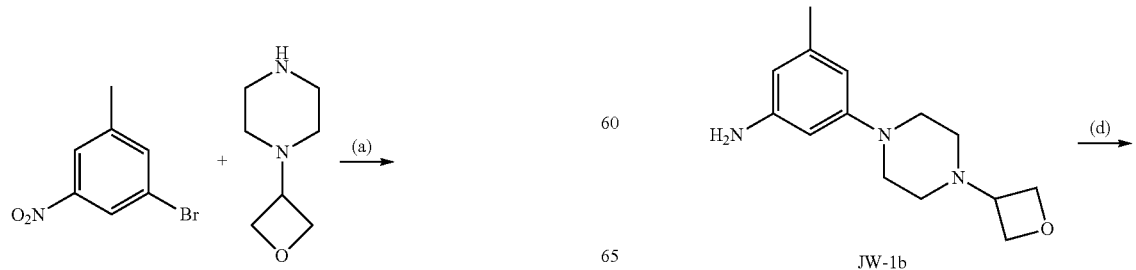

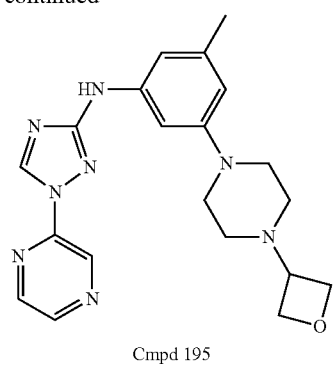

Cmpd 195

(a) t-BuXPhos Palladacycle, t-BuOH/t-BuONa, 60° C.; (b) Pd/C, H₂; (c) K₂CO₃/NMP; (d) t-BuXPhos Palladacycle/t-BuOH/t-BuONA Preparation of 2-(3-bromo-1,2,4-triazol-1-yl)pyrazine (JW-7c)

K₂CO₃ (19.1 g, 138.4 mmol), 3-bromo-4H-1,2,4-triazole (17.06 g, 115.3 mmol) and 2-chloropyrazine (13.2 g, 115.3 mmol) were mixed in NMP (100 mL) and the reaction was heated at 120° C. for 6 hrs. LCMS showed that the reaction was almost completed. The solid was filtered off when the reaction was still hot and the filtrate was left standing overnight. A solid precipitated out during this course and the solid was filtered and washed with cold diethyl ether to afford 13.4 g (46%) of desired product JW-7c. ¹H NMR (300 MHz, DMSO-d6) δ 9.47 (s, 1H), 9.15 (d, J=1.2 Hz, 1H), 8.81 (t, J=3.9 Hz, 1H), 8.66 (dd, J=2.5, 1.4 Hz, 1H) ppm. ESI-MS m/z calc. 224.96501, found 226.25 (M+1)+; Retention time: 0.66 minutes.

Preparation of N-[3-methyl-5-[4-(oxetan-3-yl)piperazin-1-yl]phenyl]-1-pyrazin-2-yl-1,2,4-triazol-3-amine (Compound 195)

2-(3-Bromo-1,2,4-triazol-1-yl)pyrazine JW-7c (120 mg, 0.53 mmol), sodium 2-methylpropan-2-olate (98 mg, 1.02 mmol), chloro[2-(di-tert-butylphosphino)-2',4',6'-triisopropyl-1,1'-biphenyl][2-(2-aminoethyl)phenyl)]palladium(II) (31 mg, 0.29 mmol) and 3-methyl-5-[4-(oxetan-3-yl)piperazin-1-yl]aniline JW-1b (131 mg) were mixed in 2-methylpropan-2-ol (1.8 mL) and the reaction was degassed with nitrogen for 30 seconds then heated at 60° C. for 2 hours. The reaction was cooled to R.T. and water (1 mL) was added. The reaction was extracted with DCM and organic layer was dried and concentrated in vacuo. The crude was purified on silica gel (12 gram column, using 1-4% DCM:MeOH) to afford 148 mg (58%) of desired product cmpd 195. ¹H NMR (300 MHz, DMSO-d6) δ 9.44 (s, 1H), 9.20 (s, 1H), 9.05 (d, J=1.4 Hz, 1H), 8.66 (d, J=2.5 Hz, 1H), 8.58 (dd, J=2.6, 1.4 Hz, 1H), 7.16 (s, 1H), 6.93 (s, 1H), 6.34 (s, 1H), 4.57 (t, J=6.5 Hz, 2H), 4.52-4.41 (m, 2H), 3.46 (dt, J=11.1, 5.6 Hz, 1H), 3.16 (dd, J=5.1, 3.7 Hz, 4H), 2.47-2.38 (m, 4H), 2.26 (d, J=8.1 Hz, 3H) ppm. ESI-MS m/z calc. 392.2073, found 393.48 (M+1)+; Retention time: 0.59 minutes.

Example 15

Preparation of N-[3-(4-cyclopropylpiperazin-1-yl)-5-methyl-phenyl]-1-pyrazin-2-yl-1,2,4-triazol-3-amine (Compound 20)

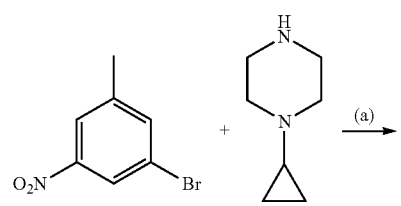

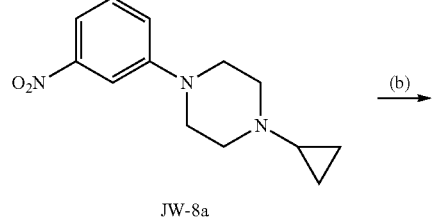

JW-8a

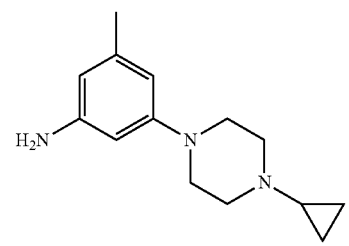

JW-8b

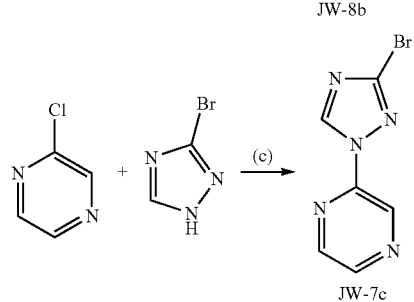

JW-7c

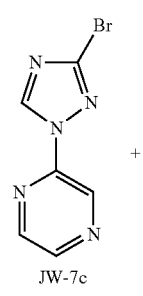

JW-7c

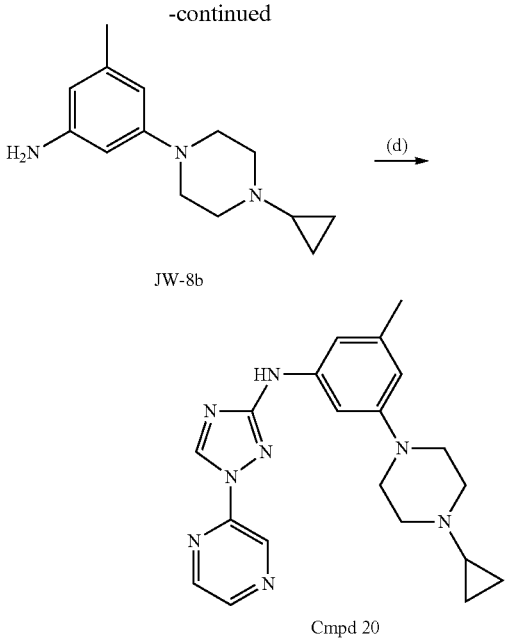

Cmpd 20

(a) t-BuXPhos Palladacycle, t-BuOH/t-BuONa, 60° C.; (b) Pd on Carbon, 10% WT Degussa H₂; (c) K₂CO₃/NMP; (d) t-BuXPhos Palladacycle/t-BuOH/t-BuONa Preparation of 1-cyclopropyl-4-(3-methyl-5-nitro-phenyl)piperazine (JW-8a)

3-Bromo-5-nitro-toluene, (7.78 g, 36.0 mmol) and 1-cyclopropylpiperazine (5.0 g, 39.6 mmol) were dissolved in 100 mL of dry t-BuOH and purged with N₂ for 10 minutes. During the purge added t-BuXphos Palladacycle (620 mg, 0.90 mmol) followed by sodium t-butoxide, (5.20 g, 54.0 mmol) and reaction was allowed to stir at 30° C. under N2 for two hours. Solvent was removed under reduced pressure and the residue partitioned between EtOAc and water, then the organic phase washed with brine, dried (Na₂SO₄) and solvent removed under reduced pressure. The crude material was Isco purified on SiO2 with DCM changing to isocratic 10%/EtOAc/DCM as eluent to afford 6.75 g (64%) of JW-8a as a dark yellow, waxy solid. ¹H NMR (400 MHz, Acetone-d6) δ 7.51 (t, J=2.1 Hz, 1H), 7.43 (d, J=0.6 Hz, 1H), 7.21 (s, 1H), 3.35-3.18 (m, 4H), 2.83-2.67 (m, 4H), 2.40 (s, 3H), 1.75-1.59 (m, 1H), 0.57-0.41 (m, 2H), 0.38 (dt, J=3.8, 2.5 Hz, 2H) ppm. ESI-MS m/z calc. 261.14774, found 262.0 (M+1)+; Retention time: 0.58 minutes.

Preparation of 3-(4-cyclopropylpiperazin-1-yl)-5-methyl-aniline (JW-8b)

1-cyclopropyl-4-(3-methyl-5-nitro-phenyl)piperazine JW-8a (6.75 g, 25.4 mmol) was dissolved in 200 mL of MeOH and placed under a CO2 atmosphere before adding 10% Pd/C Degussa type 50% water (700 mg; 0.65 mmol). Reaction placed under 50 psi H2 for 24 hours. Reaction was pulled through a pad of diatomaceous earth and washed the cake with more MeOH. Solvent was removed under reduced pressure to afford 6.1 g (90%) of JW-8b as a tan, partially solidified oil. ¹H NMR (400 MHz, Acetone-d6) δ 6.07 (t, J=2.0 Hz, 1H), 6.05 (d, J=0.5 Hz, 1H), 6.01-5.93 (m, 1H), 3.02 (dd, J=5.9, 4.2 Hz, 4H), 2.74-2.60 (m, 4H), 2.12 (d, J=0.4 Hz, 3H), 1.70-1.54 (m, 1H), 0.50-0.37 (m, 2H), 0.38-0.26 (m, 2H) ppm. ESI-MS m/z calc. 231.17355, found 232.0 (M+1)+; Retention time: 0.27 minutes.

Preparation of N-[3-(4-cyclopropylpiperazin-1-yl)-5-methyl-phenyl]-1-pyrazin-2-yl-1,2,4-triazol-3-amine (Compound 20)

3-(4-Cyclopropylpiperazin-1-yl)-5-methyl-aniline JW-8b (122.7 mg, 0.53 mmol), sodium t-butoxide (154.3 mg, 1.606 mmol), t-BuXPhos Palladacycle (15 mg, 0.02 mmol) and 2-(3-bromo-1,2,4-triazol-1-yl)pyrazine JW-7c (119 mg, 0.53 mmol) were mixed in t-BuOH (1.5 mL) and the reaction was degassed with nitrogen for 20 seconds, then heated at 60 degrees for 2 hours. The reaction was cooled to R.T. and water was added. The reaction was extracted with DCM and organic layer dried and concentrated in vacuo. The crude was purified on silica gel eluting with 1-4% DCM:MeOH to afford 91 mg (37%) of desired product cmpd 20. ¹H NMR (300 MHz, DMSO-d6) δ 9.42 (s, 1H), 9.19 (s, 1H), 9.05 (d, J=1.2 Hz, 1H), 8.66 (d, J=2.4 Hz, 1H), 8.58 (dd, J=2.6, 1.4 Hz, 1H), 7.15 (s, 1H), 6.92 (s, 1H), 6.33 (s, 1H), 3.16-3.03 (m, 4H), 2.79-2.66 (m, 4H), 2.24 (s, 3H), 1.75-1.56 (m, 1H), 0.52-0.41 (m, 2H), 0.37-0.30 (m, 2H) ppm. ESI-MS m/z calc. 376.2124, found 377.46 (M+1)+; Retention time: 0.61 minutes.

Using the general synthetic scheme outlined in Scheme D and the experimental procedures listed above in Examples 14 and 15, the following compounds were prepared:

| Cmpd No. | IUPAC Name |
|---|---|
| 381 | N-[3-methyl-5-(4-methylpiperazin-1-yl)phenyl]-1-pyrimidin-5-yl-1,2,4-triazol-3-amine |
| 399 | N-[3-methyl-5-(4-methylpiperazin-1-yl)phenyl]-1-pyridazin-4-yl-1,2,4-triazol-3-amine |
| 275 | N-[3-methyl-5-[4-(oxetan-3-yl)piperazin-1-yl]phenyl]-1-(3-pyridyl)-1,2,4-triazol-3-amine |
| 104 | N-[3-methyl-5-[4-(oxetan-3-yl)piperazin-1-yl]phenyl]-1-(2-pyridyl)-1,2,4-triazol-3-amine |
| 224 | N-[3-methyl-5-[4-(oxetan-3-yl)piperazin-1-yl]phenyl]-1-(4-pyridyl)-1,2,4-triazol-3-amine |
| 68 | N-[3-methyl-5-(4-methylpiperazin-1-yl)phenyl]-1-pyrazin-2-yl-1,2,4-triazol-3-amine |
| 342 | 5-methyl-N1-[1-(oxetan-3-yl)-4-piperidyl]-N3-[1-(3-pyridyl)-1,2,4-triazol-3-yl]benzene-1,3-diamine |
| 249 | N3-[1-(2-fluoro-4-pyridyl)-1,2,4-triazol-3-yl]-5-methyl-N1-[1-(oxetan-3-yl)pyrrolidin-3-yl]benzene-1,3-diamine |
| 329 | 1-(4,6-difluoro-2-pyridyl)-N-[3-methyl-5-[4-(oxetan-3-yl)piperazin-1-yl]phenyl]-1,2,4-triazol-3-amine |

| Cmpd No. | IUPAC Name |
|---|---|
| 174 | N-[3-methyl-5-[4-(oxetan-3-yl)piperazin-1-yl]phenyl]-1-pyrimidin-4-yl-1,2,4-triazol-3-amine |
| 176 | N-[3-(4-cyclopropylpiperazin-1-yl)-5-methyl-phenyl]-1-pyrimidin-4-yl-1,2,4-triazol-3-amine |
| 288 | N-[3-tert-butyl-5-[4-(oxetan-3-yl)piperazin-1-yl]phenyl]-1-pyrazin-2-yl-1,2,4-triazol-3-amine |
| 271 | N-[3-methyl-5-[4-(oxetan-3-yl)piperazin-1-yl]phenyl]-1-(6-methylpyrazin-2-yl)-1,2,4-triazol-3-amine |
| 401 | N-[3-ethyl-5-[4-(oxetan-3-yl)piperazin-1-yl]phenyl]-1-(6-methylpyrazin-2-yl)-1,2,4-triazol-3-amine |
| 420 | N-[3-(4-cyclopropylpiperazin-1-yl)-5-methyl-phenyl]-1-(6-methylpyrazin-2-yl)-1,2,4-triazol-3-amine |
| 154 | 1-(6-fluoro-2-pyridyl)-N-[3-methyl-5-[4-(oxetan-3-yl)piperazin-1-yl]phenyl]-1,2,4-triazol-3-amine |
| 75 | N-[3-[4-(3,3-difluorocyclobutyl)piperazin-1-yl]-5-methyl-phenyl]-1-pyrazin-2-yl-1,2,4-triazol-3-amine |
| 124 | N-(3-ethyl-5-piperazin-1-yl-phenyl)-1-pyrazin-2-yl-1,2,4-triazol-3-amine |
| 368 | tert-butyl 4-[3-ethyl-5-[(1-pyrazin-2-yl-1,2,4-triazol-3-yl)amino]phenyl]piperazine-1-carboxylate |
| 470 | N-[2,3-dimethyl-5-[4-(oxetan-3-yl)piperazin-1-yl]phenyl]-1-pyrazin-2-yl-1,2,4-triazol-3-amine |
| 471 | N-[2-methoxy-3-methyl-5-[4-(oxetan-3-yl)piperazin-1-yl]phenyl]-1-pyrazin-2-yl-1,2,4-triazol-3-amine |
| 451 | N-(2-fluoro-3-methyl-5-morpholino-phenyl)-1-(3-pyridyl)-1,2,4-triazol-3-amine |
| 307 | N-(2-fluoro-3-methyl-5-morpholino-phenyl)-1-(2-pyridyl)-1,2,4-triazol-3-amine |
| 387 | 1-(5-fluoro-3-pyridyl)-N-[3-methyl-5-(4-methylpiperazin-1-yl)phenyl]-1,2,4-triazol-3-amine |
| 262 | 1-(5-chloro-3-pyridyl)-N-[3-methyl-5-(4-methylpiperazin-1-yl)phenyl]-1,2,4-triazol-3-amine |
| 217 | 1-(5-chloro-3-pyridyl)-N-[3-methyl-5-[4-(oxetan-3-yl)piperazin-1-yl]phenyl]-1,2,4-triazol-3-amine |
| 232 | 1-(2,6-difluoro-4-pyridyl)-N-[3-methyl-5-[4-(oxetan-3-yl)piperazin-1-yl]phenyl]-1,2,4-triazol-3-amine |
| 111 | N-[3-methyl-5-[4-(oxetan-3-yl)piperazin-1-yl]phenyl]-1-(6-methylpyrimidin-4-yl)-1,2,4-triazol-3-amine |
| 254 | 1-(6-methoxypyrimidin-4-yl)-N-[3-methyl-5-[4-(oxetan-3-yl)piperazin-1-yl]phenyl]-1,2,4-triazol-3-amine |
| 312 | 1-(2,6-dimethylpyrimidin-4-yl)-N-[3-methyl-5-[4-(oxetan-3-yl)piperazin-1-yl]phenyl]-1,2,4-triazol-3-amine |
| 418 | N-[3-methyl-5-[4-(oxetan-3-yl)piperazin-1-yl]phenyl]-1-(2-methylpyrimidin-4-yl)-1,2,4-triazol-3-amine |
| 204 | 1-(2-ethoxypyrimidin-4-yl)-N-[3-methyl-5-[4-(oxetan-3-yl)piperazin-1-yl]phenyl]-1,2,4-triazol-3-amine |
| 30 | 1-(2-methoxypyrimidin-4-yl)-N-[3-methyl-5-[4-(oxetan-3-yl)piperazin-1-yl]phenyl]-1,2,4-triazol-3-amine |
| 364 | 1-[6-(methoxymethyl)pyrimidin-4-yl]-N-[3-methyl-5-[4-(oxetan-3-yl)piperazin-1-yl]phenyl]-1,2,4-triazol-3-amine |
| 314 | N-[3-ethyl-5-[4-(oxetan-3-yl)piperazin-1-yl]phenyl]-1-(2-methoxypyrimidin-4-yl)-1,2,4-triazol-3-amine |
| 58 | N-[3-ethyl-5-[4-(oxetan-3-yl)piperazin-1-yl]phenyl]-1-(6-methylpyrimidin-4-yl)-1,2,4-triazol-3-amine |
| 91 | N-[3-ethyl-5-[4-(oxetan-3-yl)piperazin-1-yl]phenyl]-1-(2-methylpyrimidin-4-yl)-1,2,4-triazol-3-amine |
| 64 | N-[3-methyl-5-[4-(oxetan-3-yl)piperazin-1-yl]phenyl]-1-(2-methylsulfanylpyrimidin-4-yl)-1,2,4-triazol-3-amine |
| 132 | N-[3-ethyl-5-[4-(oxetan-3-yl)piperazin-1-yl]phenyl]-1-(2-methylsulfanylpyrimidin-4-yl)-1,2,4-triazol-3-amine |
| 291 | 1-(5-fluoropyrimidin-4-yl)-N-[3-methyl-5-[4-(oxetan-3-yl)piperazin-1-yl]phenyl]-1,2,4-triazol-3-amine |
| 50 | N-[3-ethyl-5-[4-(oxetan-3-yl)piperazin-1-yl]phenyl]-1-(5-fluoropyrimidin-4-yl)-1,2,4-triazol-3-amine |
| 495 | 1-[2-(azepan-1-yl)-4-pyridyl]-N-[3-methyl-5-(4-methylpiperazin-1-yl)phenyl]-1,2,4-triazol-3-amine |
| 138 | N-[3-methyl-5-(4-methylpiperazin-1-yl)phenyl]-1-(2-pyridyl)-1,2,4-triazol-3-amine |
| 297 | N-[3-methyl-5-(4-methylpiperazin-1-yl)phenyl]-1-(3-pyridyl)-1,2,4-triazol-3-amine |
| 211 | N-[3-[4-(methoxymethyl)-1-piperidyl]-5-methyl-phenyl]-1-(2-pyridyl)-1,2,4-triazol-3-amine |
| 122 | 1-(2-fluoro-4-pyridyl)-N-[3-[4-(methoxymethyl)-1-piperidyl]-5-methyl-phenyl]-1,2,4-triazol-3-amine |
| 464 | N-[3-[4-(methoxymethyl)-1-piperidyl]-5-methyl-phenyl]-1-pyrimidin-4-yl-1,2,4-triazol-3-amine |

-continued

| Cmpd No. | IUPAC Name |
|---|---|
| 385 | N-[3-[4-(methoxymethyl)-1-piperidyl]-5-methyl-phenyl]-1-(4-pyridyl)-1,2,4-triazol-3-amine |
| 226 | 1-(2-fluoro-4-pyridyl)-N-[3-(4-methylpiperazin-1-yl)-5-(trifluoromethyl)phenyl]-1,2,4-triazol-3-amine |
| 96 | N-[3-(4-methylpiperazin-1-yl)-5-(trifluoromethyl)phenyl]-1-pyrimidin-4-yl-1,2,4-triazol-3-amine |
| 13 | N-[3-(4-methylpiperazin-1-yl)-5-(trifluoromethyl)phenyl]-1-(4-pyridyl)-1,2,4-triazol-3-amine |
| 48 | N-[3-ethyl-5-[4-(oxetan-3-yl)piperazin-1-yl]phenyl]-1-pyrazin-2-yl-1,2,4-triazol-3-amine |
| 300 | 1-[3-[3-methyl-5-[(1-pyrazin-2-yl-1,2,4-triazol-3-yl)amino]phenyl]-1-piperidyl]ethanone |
| 236 | N-[3-[4-(oxetan-3-yl)piperazin-1-yl]-5-propyl-phenyl]-1-pyrazin-2-yl-1,2,4-triazol-3-amine |
| 511 | N-[3-isopropyl-5-[4-(oxetan-3-yl)piperazin-1-yl]phenyl]-1-pyrimidin-4-yl-1,2,4-triazol-3-amine |
| 521 | N-[3-methyl-5-[4-(oxetan-3-yl)-1-piperidyl]phenyl]-1-pyrazin-2-yl-1,2,4-triazol-3-amine |
| 535 | N-[3-methyl-5-[4-(oxetan-3-yl)piperazin-1-yl]phenyl]-1-pyrimidin-5-yl-1,2,4-triazol-3-amine |
| 536 | N-[3-isopropyl-5-[4-(oxetan-3-yl)piperazin-1-yl]phenyl]-1-pyrazin-2-yl-1,2,4-triazol-3-amine |
| 550 | N-[3-tert-butyl-5-[4-(oxetan-3-yl)piperazin-1-yl]phenyl]-1-pyrimidin-5-yl-1,2,4-triazol-3-amine |
| 549 | N-[3-ethyl-5-[4-(oxetan-3-yl)piperazin-1-yl]phenyl]-1-pyrimidin-5-yl-1,2,4-triazol-3-amine |
| 539 | N-[3-cyclopropyl-5-(3-morpholinoazetidin-1-yl)phenyl]-1-pyrazin-2-yl-1,2,4-triazol-3-amine |
| 544 | N-[3-ethyl-5-(3-morpholinoazetidin-1-yl)phenyl]-1-pyrimidin-5-yl-1,2,4-triazol-3-amine |
| 598 | N-[3-fluoro-5-[4-(oxetan-3-yl)piperazin-1-yl]phenyl]-1-pyrazin-2-yl-1,2,4-triazol-3-amine |
| 811 | N-[3-isopropoxy-2-methyl-5-(3-morpholinoazetidin-1-yl)phenyl]-1-(2-pyridyl)-1,2,4-triazol-3-amine |
| 862 | N-[3-isopropoxy-2-methyl-5-[4-(oxetan-3-yl)piperazin-1-yl]phenyl]-1-(2-pyridyl)-1,2,4-triazol-3-amine |

Scheme E: General Route E for Preparation of Compound of Formula I or I'

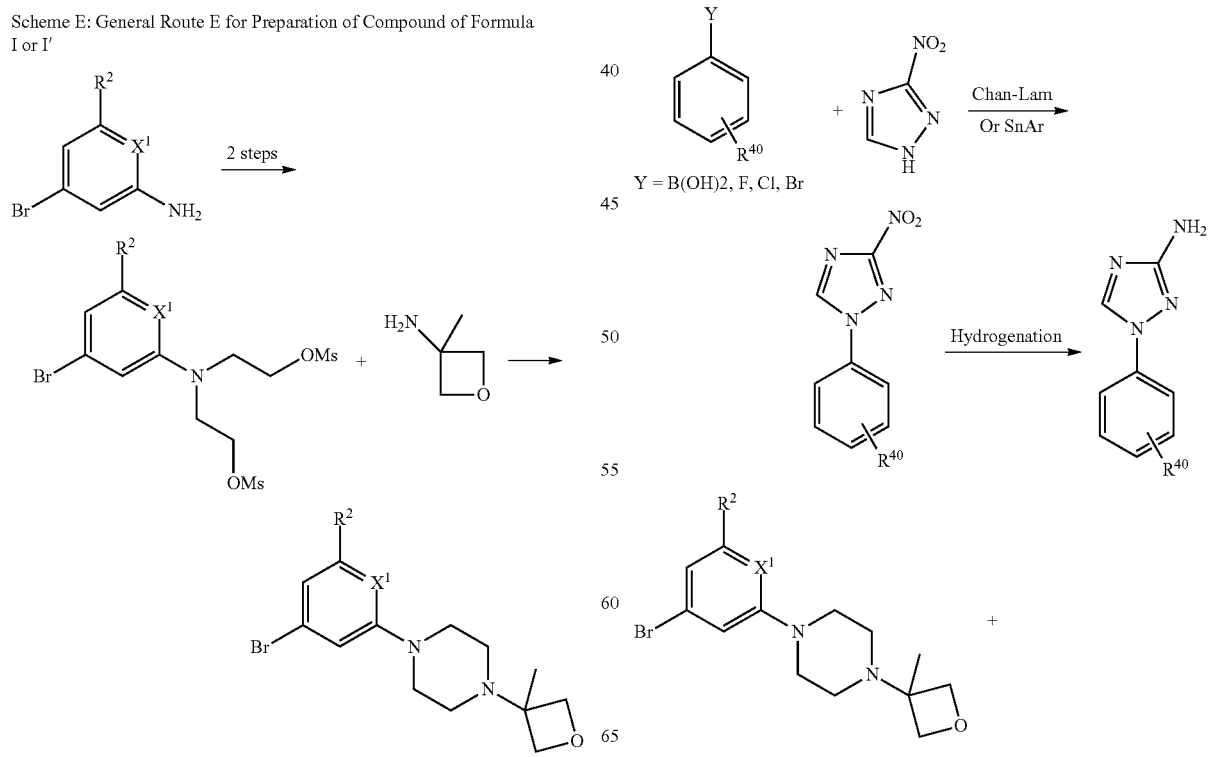

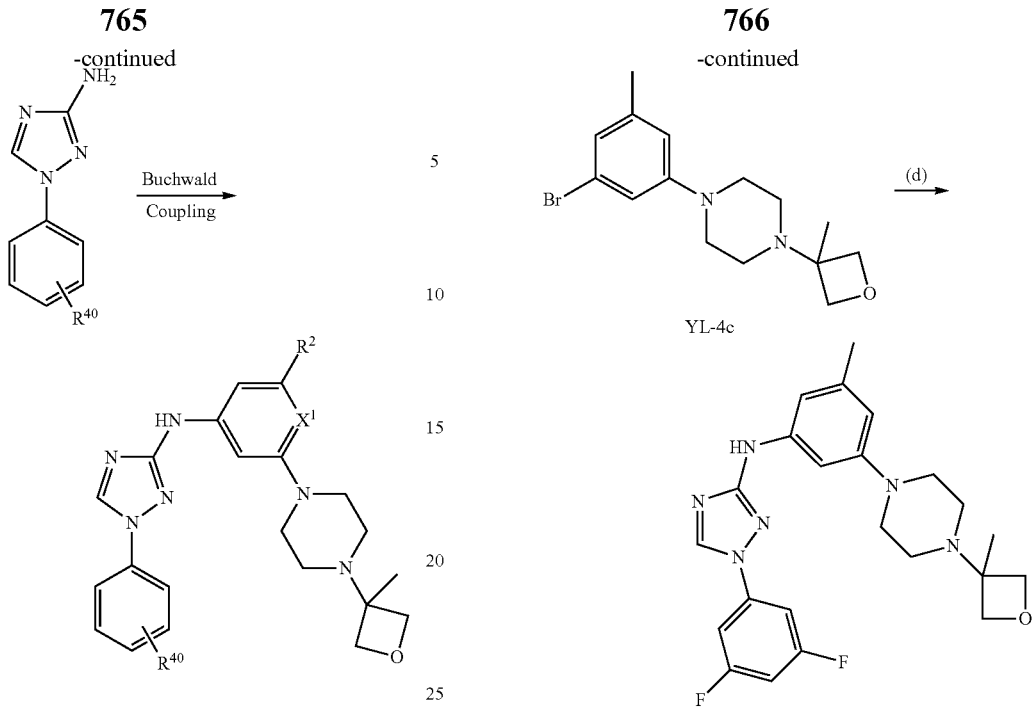

Compounds of the invention may be prepared as generally outlined in Scheme E, where $R^2$, $R^{40}$, and $X^1$ are as described for Scheme A. The methods of Scheme E may also be applied to other variations of $L^1$ with $G^1$ to $G^2$ that bond to $-L^2-R^6$, $-L^2-R^7$, or optional $G^2$ substituent through a nitrogen atom in $G^1$ or $G^2$.

Example 16

Preparation of 1-(3,5-difluorophenyl)-N-[3-methyl-5-[4-(3-methyloxetan-3-yl)piperazin-1-yl]phenyl]-1,2,4-triazol-3-amine (Compound 215)

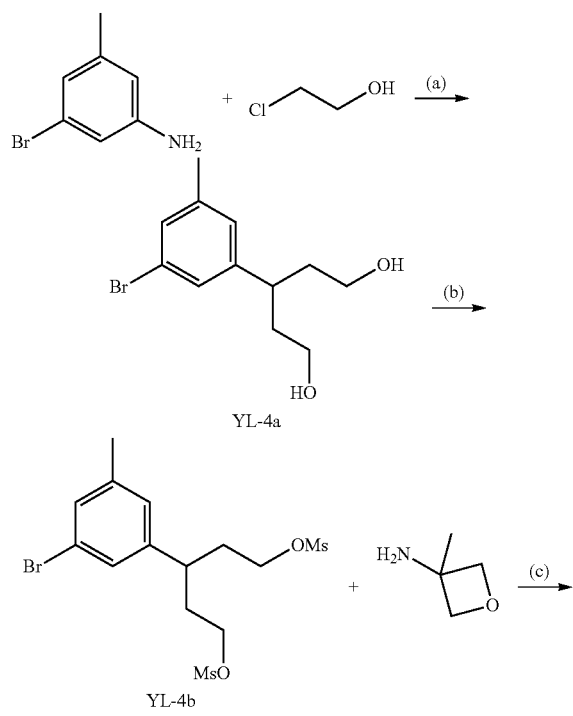

Reagents and conditions: (a) 2-chloroethanol, KI, CaCO₃, MeOH, water 100° C.; (b) methanesulfonyl chloride, Et₃N, EtOAc; (c) K₂CO₃, dioxane, 160° C.; (d) 1-(3,5-difluorophenyl)-1,2,4-triazol-3-amine, t-BuXPhos Palladacycle, NaOtBu, dioxane, 120° C..

Preparation of 2-[3-bromo-N-(2-hydroxyethyl)-5-methyl-anilino]ethanol (YL-4a)

A mixture of 3-bromo-5-methyl-aniline (1.86 g, 10 mmol), 2-chloroethanol (3.22 g, 40.00 mmol), KI (166 mg, 1.00 mmol) and CaCO₃ (2.00 g, 20.00 mmol) in water (6 mL) and EtOH (6 mL) was heated at 100° C. for 36 h, then at 120° C. for 20 h. The reaction mixture was cooled to RT, diluted with EtOAc, washed with H₂O, sat. NaCl and dried then evaporated under reduced pressure. The crude material was subjected to ISCO purification (40 g silica; 0% to 10% of MeOH in DCM) to give 2-[3-bromo-N-(2-hydroxyethyl)-5-methyl-anilino]ethanol YL-4a (1.4 g, 51%). ¹HNMR (300 MHz, CDCl₃) δ 6.71 (d, J=22.0 Hz, 2H), 6.47 (s, 1H), 3.87 (t, J=4.9 Hz, 4H), 3.61-3.53 (m, 4H), 3.41 (s, 2H), 2.29 (s, 3H) ppm. ESI-MS m/z calc. 273.04, found 274.31 (M+1)+; Retention time: 0.68 minutes.

Preparation of 2-[3-bromo-5-methyl-N-(2-methyl-sulfonyloxyethyl)anilino]ethyl methanesulfonate (YL-4b)

To 2-[3-bromo-N-(2-hydroxyethyl)-5-methyl-anilino] ethanol YL-4a (720 mg, 2.63 mmol) in EtOAc (15 mL) was added methanesulfonyl chloride (902 mg, 7.88 mmol) and Et₃N (930 mg, 9.19 mmol). The reaction mixture was stirred at RT for 1 h. The reaction mixture was diluted with EtOAc, washed with water, sat. NaHCO₃, sat. NaCl and dried then evaporated under reduced pressure. The crude material was subjected to ISCO purification (40 g silica; 10% to 100% of EtOAc in hex) to give 2-[3-bromo-5-methyl-N-(2-methyl-sulfonyloxyethyl)anilino]ethyl methanesulfonate YL-4b (950 mg, 84%). ¹H NMR (300 MHz, CDCl₃) δ 6.79 (s, 1H), 6.67 (d, J=1.8 Hz, 1H), 6.47 (s, 1H), 4.37 (t, J=5.8 Hz, 4H), 3.76 (t, J=5.8 Hz, 4H), 3.02 (s, 6H), 2.30 (s, 3H) ppm. ESI-MS m/z calc. 428.99, found 430.24 (M+1)+; Retention time: 0.85 minutes.

Preparation of 1-(3-bromo-5-methyl-phenyl)-4-(3-methyloxetan-3-yl)piperazine (YL-4c)

A mixture of 2-[3-bromo-5-methyl-N-(2-methylsulfonyloxyethyl)anilino]ethyl methanesulfonate YL-4b (220 mg, 0.51 mmol), 3-methyloxetan-3-amine (54 mg, 0.62 mmol) and K₂CO₃ (212 mg, 1.53 mmol) in dioxane (15 mL) was microwaved at 160° C. for 16 h. ISCO purification of the crude material (12 g silica; 10% to 50% to 100% of EtOAc in hex) gave 1-(3-bromo-5-methyl-phenyl)-4-(3-methyloxetan-3-yl)piperazine YL-4c (85 mg, 51%). $^1$H NMR (300 MHz, CDCl₃) δ 6.86 (d, J=1.8 Hz, 1H), 6.83 (s, 1H), 6.65 (s, 1H), 4.64 (d, J=5.4 Hz, 2H), 4.29 (d, J=5.8 Hz, 2H), 3.29-3.13 (m, 4H), 2.61-2.44 (m, 4H), 2.35-2.22 (m, 3H), 1.42 (s, 3H) ppm. ESI-MS m/z calc. 324.08, found 325.39 (M+1)+; Retention time: 0.64 minutes.

Preparation of 1-(3,5-difluorophenyl)-N-[3-methyl-5-[4-(3-methyloxetan-3-yl)piperazin-1-yl]phenyl]-1,2,4-triazol-3-amine (Compound 215)

1-(3-Bromo-5-methyl-phenyl)-4-(3-methyloxetan-3-yl)piperazine (440 mg, 1.35 mmol), 1-(3,5-difluorophenyl)-1,2,4-triazol-3-amine (319 mg, 1.62 mmol) and sodium t-butoxide (325 mg, 3.38 mmol) were suspended in dioxane (20 mL) and purged with N₂ for several minutes before addition of t-BuXPhos Palladacycle (88 mg, 0.14 mmol). The mixture was microwaved at 120° C. for 40 minutes. LC/MS showed desired product. The reaction was quenched with MeOH (2 mL) and diluted with DCM, then solvent was removed by evaporation under reduced pressure. The solids were triturated with water, then were collected and dissolved in 20% MeOH in DCM. After filtration through Florisil (10 g), the excess solvent was pumped down. The solids were triturated with EtOAC, ether and dried. The above product was dissolved in MeOH/DCM (1:9; 100 mL) 3 equivalents of MP-TMT (F15118/Biotage/0.64 mmol/g; 3 g) were added and rotated at 45~50° C. for 4 h. After filtration, the excess solvent was pumped down to afford 1-(3,5-difluorophenyl)-N-[3-methyl-5-[4-(3-methyloxetan-3-yl)piperazin-1-yl]phenyl]-1,2,4-triazol-3-amine, cmpd 215 (1750 mg, 72%). $^1$H NMR (300 MHz, CD3OD) δ 8.60 (s, 1H), 7.33 (d, J=6.6 Hz, 2H), 7.15 (s, 1H), 6.79 (d, J=14.4 Hz, 2H), 6.37 (s, 1H), 4.63 (d, J=5.1 Hz, 2H), 4.26 (d, J=5.3 Hz, 2H), 3.24 (s, 4H), 2.53 (s, 4H), 2.28 (s, 3H), 1.40 (s, 3H) ppm. ESI-MS m/z calc. 440.21, found 441.45 (M+1)+; Retention time: 0.69 minutes.

Example 17

Preparation of N-[3-methyl-5-[4-(3-methyloxetan-3-yl)piperazin-1-yl]phenyl]-1-phenyl-1,2,4-triazol-3-amine (Compound 436)

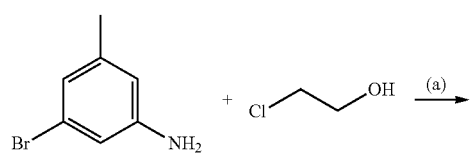

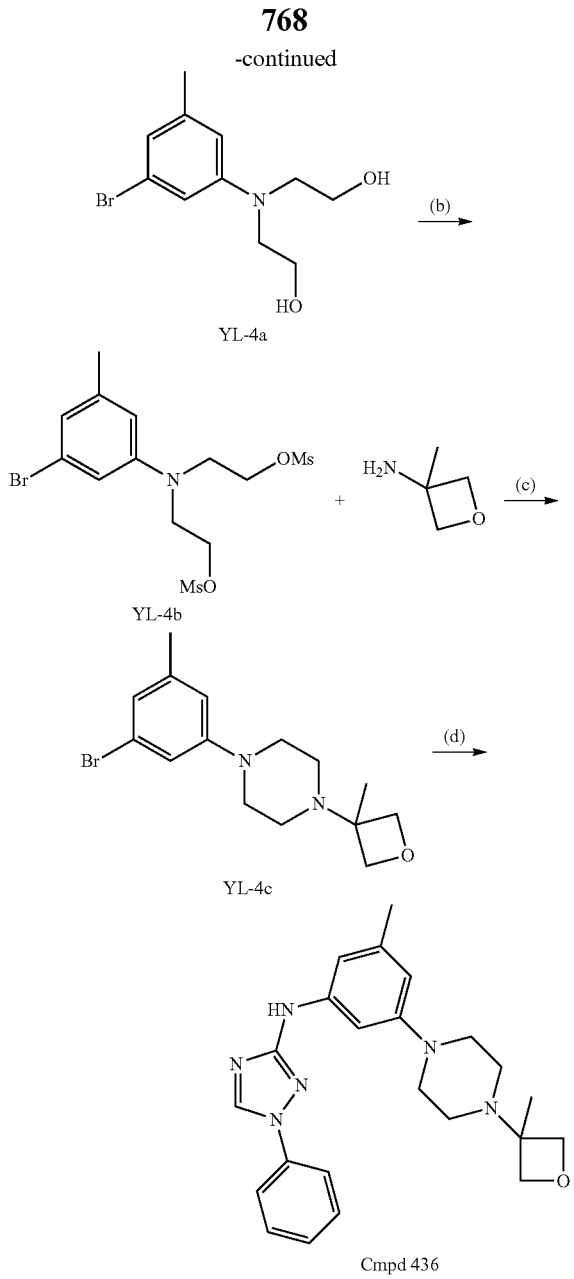

Reagents and conditions: (a) 2-chloroethanol, KI, CaCO₃, MeOH, water 100° C.; (b) methanesulfonyl chloride, Et₃N, EtOAc; (c) K₂CO₃, dioxane, 160° C.; (d) 1-phenyl-1,2,4-triazol-3-amine, t-BuXPhos Palladacycle, NaOtBu, dioxane, 120° C..

Preparation of N-[3-methyl-5-[4-(3-methyloxetan-3-yl)piperazin-1-yl]phenyl]-1-phenyl-1,2,4-triazol-3-amine (Compound 436)

1-(3-bromo-5-methyl-phenyl)-4-(3-methyloxetan-3-yl)piperazine YL-4c (180 mg, 0.55 mmol), 1-phenyl-1,2,4-triazol-3-amine (106 mg, 0.66 mmol) and sodium t-butoxide (133 mg, 1.38 mmol) were suspended in dioxane (10 mL) and purged with N₂ for several minutes before addition of the t-BuXPhos Palladacycle (36 mg, 0.055 mmol). The mixture was microwaved at 120° C. for 40 minutes. LC/MS showed desired product. The reaction was quenched with MeOH (2 mL), then diluted with DCM and filtered (Florisil/5 g). The filtrate was evaporated in vacuo then subjected to ISCO purification (12 g silica; 10% to 50% to 100% of EtOAc in hex) to give N-[3-methyl-5-[4-(3-methyloxetan-3-yl)piperazin-1-yl]phenyl]-1-phenyl-1,2,4-triazol-3-amine, cmpd 436 (153 mg, 65%). $^1$H NMR (300 MHz, CDCl3) δ 8.32 (s, 1H), 7.74-7.65 (m, 2H), 7.56-7.46 (m, 2H), 7.41-7.32 (m, 1H), 7.12 (d, J=1.9 Hz, 1H), 6.83 (s, 1H), 6.65 (s, 1H), 6.41 (s, 1H), 4.67 (d, J=5.5 Hz, 2H), 4.30 (d, J=5.8 Hz, 2H), 3.37-3.22 (m, 4H), 2.64-2.48 (m, 4H), 2.35 (s, 3H), 1.44 (s, 3H) ppm. ESI-MS m/z calc. 404.23, found 405.45 (M+1)+; Retention time: 0.66 minutes.

Using the general synthetic scheme outlined in Scheme E and the experimental procedures listed above in Examples 16 and 17, the following compounds were prepared:

| Cmpd No. | IUPAC Name |
|---|---|
| 375 | 1-(3-fluorophenyl)-N-[3-methyl-5-[4-(3-methyloxetan-3-yl)piperazin-1-yl]phenyl]-1,2,4-triazol-3-amine |
| 469 | 1-(2,5-difluorophenyl)-N-[3-methyl-5-[4-(3-methyloxetan-3-yl)piperazin-1-yl]phenyl]-1,2,4-triazol-3-amine |
| 264 | 1-(3,5-difluorophenyl)-N-[3-ethyl-5-[4-(3-methyloxetan-3-yl)piperazin-1-yl]phenyl]-1,2,4-triazol-3-amine |
| 489 | N-[3-ethyl-5-[4-(3-methyloxetan-3-yl)piperazin-1-yl]phenyl]-1-pyrazin-2-yl-1,2,4-triazol-3-amine |
| 505 | [3-acetoxy-2-[4-[3-[[1-(3,5-difluorophenyl)-1,2,4-triazol-3-yl]amino]-5-methyl-phenyl]piperazin-1-yl]-2-methyl-propyl] acetate |
| 534 | [2-[4-[3-[[1-(3,5-difluorophenyl)-1,2,4-triazol-3-yl]amino]-5-methyl-phenyl]piperazin-1-yl]-3-hydroxy-2-methyl-propyl] acetate |
| 215 | 1-(3,5-difluorophenyl)-N-[3-methyl-5-[4-(3-methyloxetan-3-yl)piperazin-1-yl]phenyl]-1,2,4-triazol-3-amine |

Scheme F: General Route F for Preparation of Compounds of Formula I or I'

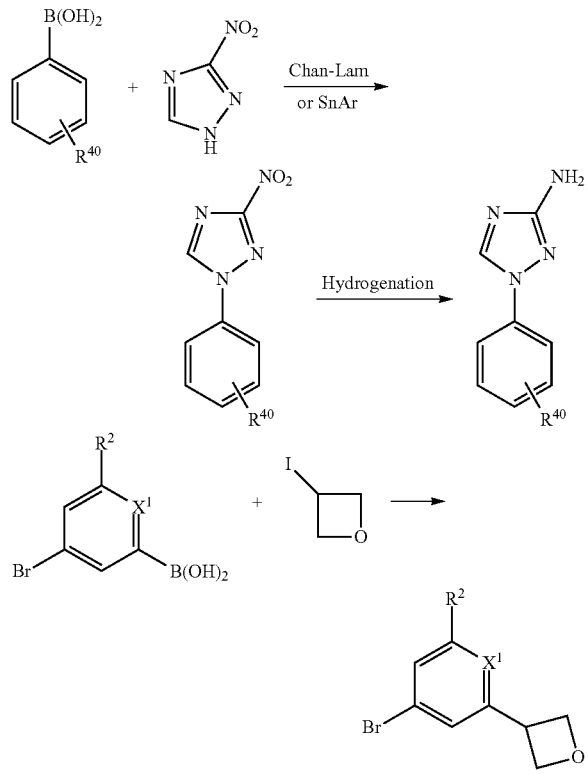

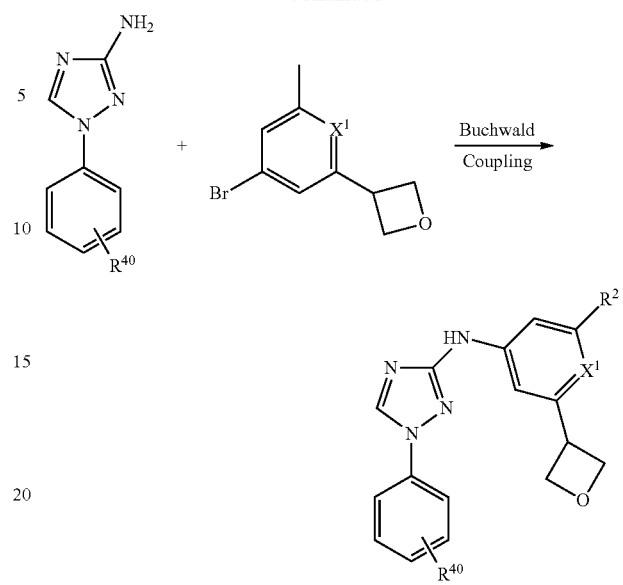

Compounds of the invention may be prepared as generally outlined in Scheme F, where $R^2$, $R^{40}$, and $X^1$ are as described for Scheme A. The methods of Scheme F may also be applied to other variations of $G^1$ to $G^5$ that bond to the parent molecular moiety through a carbon atom.

Example 18

Preparation of N-[3-methyl-5-(oxetan-3-yl)phenyl]-1-phenyl-1,2,4-triazol-3-amine (Compound 363)

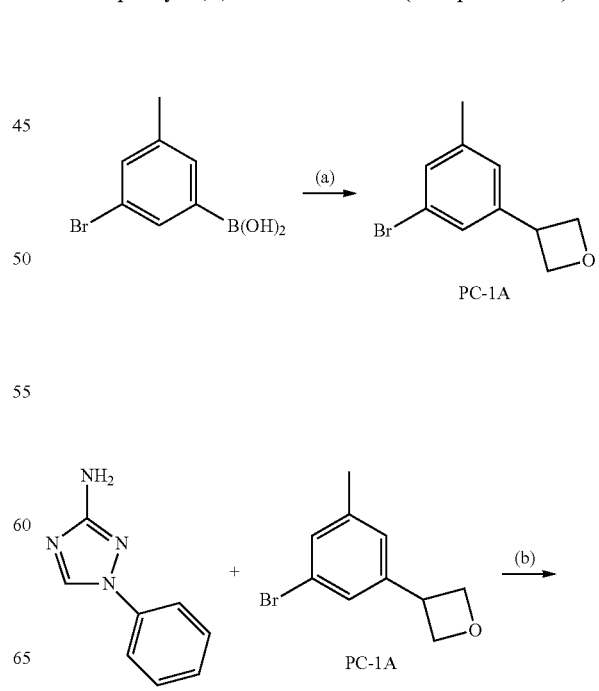

-continued

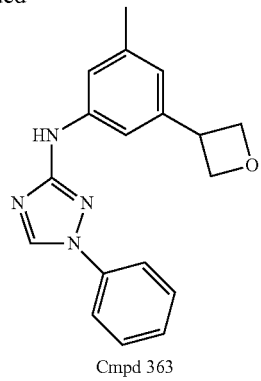

Cmpd 363

(a) 3-Iodooxetane, NiI₂, (1R,2R)-2-aminocyclohexan-1-ol hydrochloride, NaHMDS, i-PrOH, 80° C., microwave; (b) X-phos palladacycle, NaOt-Bu, dioxane, 70° C..

Preparation of (3-(3-bromo-5-methyl-phenyl)oxetane) PC-1a

A microwave 20 ml vial was charged with (3-bromo-5-methyl-phenyl)boronic acid (2.34 g, 10.9 mmol), (1R,2R)-2-aminocyclohexan-1-ol hydrochloride (82 mg, 0.544 mmol), NiI₂ (170 mg, 0.544 mmol) and (bis(trimethylsilyl)amino)sodium (1.99 g, 10.9 mmol). The mixture was capped and then placed under a nitrogen atmosphere. iPrOH (8.5 mL) and 3-iodooxetane (1 g, 5.44 mmol) were added and the mixture microwaved for 30 min at 120° C. The mixture was filtered through Florisil with the aid of EtOAc and concentrated to dryness. Purification by column chromatography (80 g column; 25-100% EtOAc in hexane over 8 min) gave 3-(3-bromo-5-methyl-phenyl)oxetane PC-1a (420 mg, 34%) as a colorless oil. $^1$H NMR (400 MHz, CDCl3) δ 7.34 (s, 1H), 7.25 (s, 1H), 7.14 (s, 1H), 5.06 (dd, J=8.3, 6.1 Hz, 2H), 4.73 (t, J=6.3 Hz, 2H), 4.19-4.11 (m, 1H), 2.35 (s, 3H) ppm.

Preparation of (N-[3-methyl-5-(oxetan-3-yl)phenyl]-1-phenyl-1,2,4-triazol-3-amine) (Compound 363)

A Schlenk tube was charged with 3-(3-bromo-5-methyl-phenyl)oxetane PC-1a (143 mg, 0.630 mmol), 1-phenyl-1,2,4-triazol-3-amine RG-1b (101 mg, 0.567 mmol), X-phos palladacycle (Strem 46-0268, 19 mg, 0.025 mmol) and sodium tert-butoxide (121 mg, 1.26 mmol) then dioxane (2 mL) and vacuum/nitrogen cycled two times. The tube was immersed in a bead bath set to 70° C. for 3 h at which point DCM and water were added. The layers were separated through a phase separator and the organics were concentrated to dryness. After purification by column chromatography (C18 AQ 40 g column; aq. TFA/MeCN) the pure fractions were passed through a SPE bicarbonate cartridge (Agilent Stratospheres 5 g/60 mL) and concentrated to dryness. Trituration with MeOH gave N-[3-methyl-5-(oxetan-3-yl)phenyl]-1-phenyl-1,2,4-triazol-3-amine, cmpd 363 (60 mg, 31%) as a white solid. $^1$H NMR (300 MHz, DMSO-d6) δ 9.41 (s, 1H), 9.08 (s, 1H), 7.85 (dd, J=8.6, 1.1 Hz, 2H), 7.56 (dd, J=10.7, 5.3 Hz, 3H), 7.40-7.29 (m, 2H), 6.71 (s, 1H), 4.95 (dd, J=8.4, 5.8 Hz, 2H), 4.62 (dd, J=6.7, 5.8 Hz, 2H), 4.23-4.11 (m, 1H), 2.28 (d, J=6.4 Hz, 3H) ppm. ESI-MS m/z calc. 306.1481, found 307.18 (M+1)⁺; Retention time: 0.77 minutes.

Using the general synthetic scheme outlined in Scheme F and the experimental procedures listed above in Example 18, the following compounds were prepared:

| Cmpd No. | IUPAC Name |
|---|---|
| 229 | 1-(3,5-difluorophenyl)-N-[3-methyl-5-[1-(oxetan-3-yl)azetidin-3-yl]phenyl]-1,2,4-triazol-3-amine |
| 65 | N-[3-methyl-5-[1-(oxetan-3-yl)azetidin-3-yl]phenyl]-1-phenyl-1,2,4-triazol-3-amine |
| 36 | 1-(3-fluorophenyl)-N-[3-methyl-5-[1-(oxetan-3-yl)azetidin-3-yl]phenyl]-1,2,4-triazol-3-amine |
| 301 | 1-(3,4-difluorophenyl)-N-[3-methyl-5-[1-(oxetan-3-yl)azetidin-3-yl]phenyl]-1,2,4-triazol-3-amine |
| 313 | 1-(3,5-difluorophenyl)-N-[3-(oxetan-3-yl)-5-[4-(oxetan-3-yl)piperazin-1-yl]phenyl]-1,2,4-triazol-3-amine |
| 147 | 1-(3-fluorophenyl)-N-[3-methyl-5-(oxetan-3-yl)phenyl]-1,2,4-triazol-3-amine |
| 404 | N-[3-methyl-5-(oxetan-3-yl)phenyl]-1-(2-pyridyl)-1,2,4-triazol-3-amine |
| 270 | N-[3-methyl-5-(oxetan-3-yl)phenyl]-1-(3-pyridyl)-1,2,4-triazol-3-amine |
| 131 | 1-(3,5-difluorophenyl)-N-[3-methyl-5-(oxetan-3-yl)phenyl]-1,2,4-triazol-3-amine |
| 409 | 1-(4-fluorophenyl)-N-[3-methyl-5-(oxetan-3-yl)phenyl]-1,2,4-triazol-3-amine |
| 447 | 1-(5-fluoro-3-pyridyl)-N-[3-methyl-5-(oxetan-3-yl)phenyl]-1,2,4-triazol-3-amine |

Scheme G: General Route G for Preparation of Compound of Formula I or I'

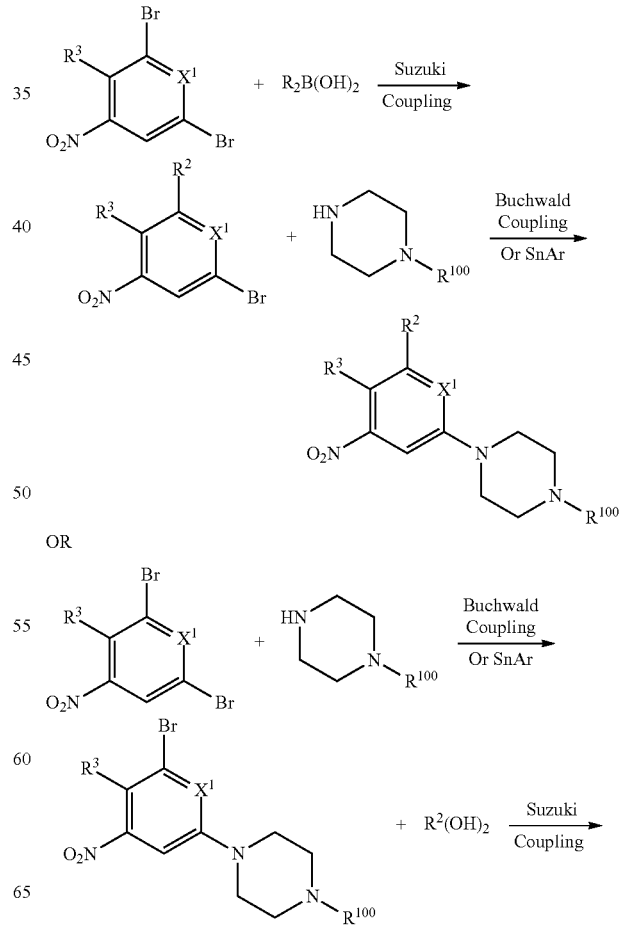

773
-continued

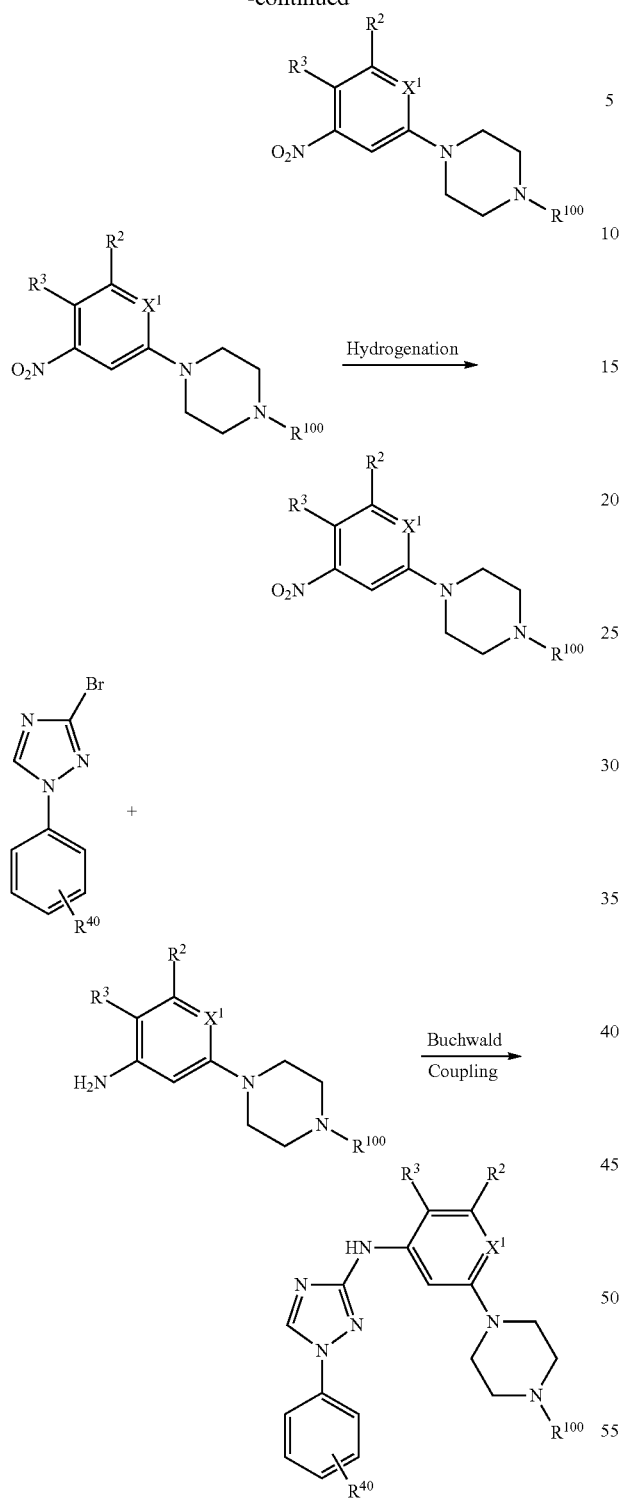

$X^1$ = CH, N

Compounds of the invention may be prepared as generally outlined in Scheme G, where $R^2$, $R^3$, $R^{40}$, $R^{100}$, and $X^1$ are as described for Scheme A. The methods of Scheme G may also be applied to other variations of $L^1$ with $G^1$ to $G^5$ that bond to the parent molecular moiety through a nitrogen atom.

774

Example 19

Preparation of N-(3-cyclopropyl-5-(4-(oxetan-3-yl)piperazin-1-yl)phenyl)-1-(3,5-difluorophenyl)-1H-1,2,4-triazol-3-amine (Compound 389)

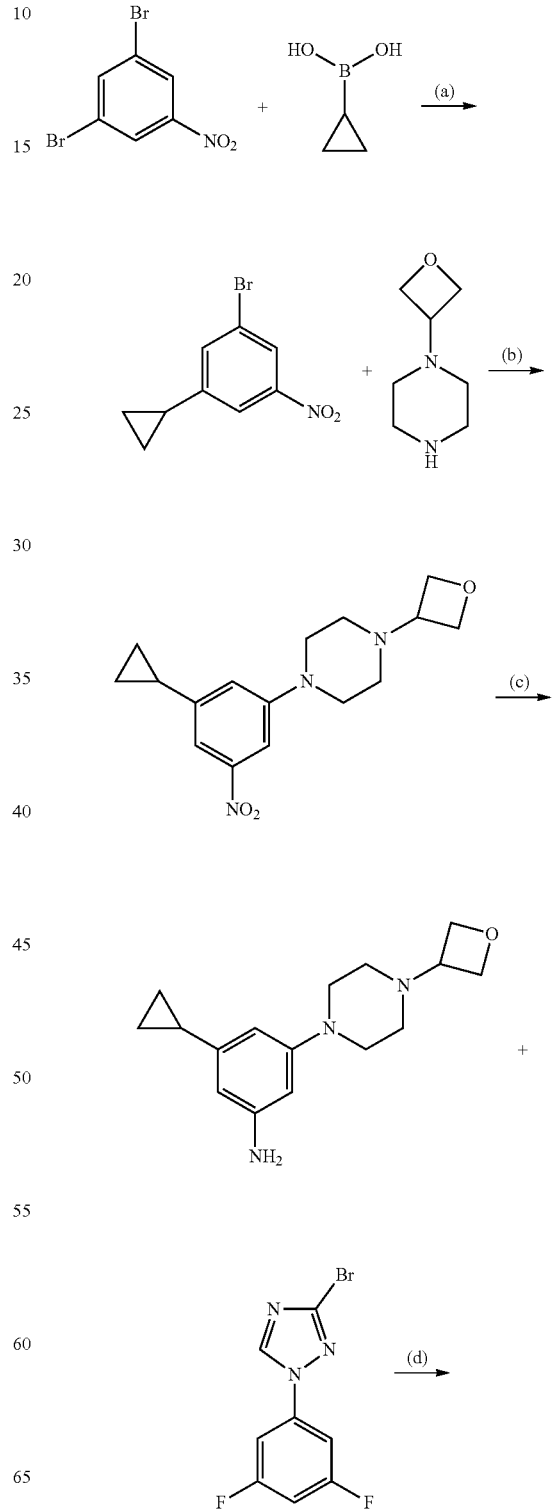

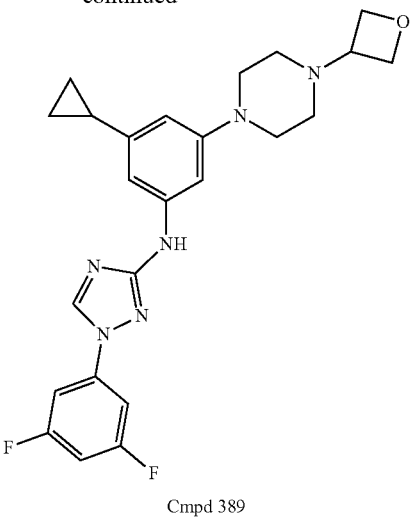

Cmpd 389

(a) Dichloro[1,1'-bis(diphenylphosphino)ferrocene]palladium(II) dichloromethane adduct, K₃PO₄, dioxane, 90° C.; (b) t-BuXPhos Palladacycle, t-BuOK, t-BuOH, 80° C. (c) Fe, NH₄Cl(2M) THF, EtOH, H₂O, reflux (d) t-BuXPhos Palladacycle, t-BuOK, t-BuOH, 80° C.

Preparation of 1-bromo-3-cyclopropyl-5-nitrobenzene (HG-2a)

A dioxane (313 mL) mixture of 1,3-dibromo-5-nitrobenzene (8.8 g, 31.3 mmol), cyclopropylboronic acid (2.96 g, 34.5 mmol), dichloro[1,1'-bis(diphenylphosphino)ferrocene]palladium(II) dichloromethane (2.292 g, 3.13 mmol) and K₃PO₄ (33.24 g, 156.6 mmol) was stirred at 90° C. for 4 h. LCMS indicated a new peak. To the reaction mixture was added EA and brine, the organic phase was dried over MgSO₄, filtered, concentrated down and purified on an Isco 220 g column with heptanes and EA, the product and side product were eluted with 3% EA and 97% heptanes. NMR indicated the desired product and side product in a 2.5 to 1 ratio. The side product was carried on and removed in the next step. (3.52 g, 10.18 mmol, 33%) ¹HNMR (300 MHz, CDCl₃) δ 8.15 (t, J=1.9 Hz, 1H), 7.85 (t, J=1.8 Hz, 1H), 7.54 (t, J=1.6 Hz, 1H), 2.07-1.89 (m, 2H), 1.18-1.10 (m, 2H), 0.85-0.79 (m, 2H) ppm. Note: NMR spectrum is a mixture of 1-bromo-3-cyclopropyl-5-nitrobenzene and 1,3-dicyclopropyl-5-nitro-benzene.

Preparation of 1-(3-cyclopropyl-5-nitrophenyl)-4-(oxetan-3-yl)piperazine (HG-2b)

To a t-BuOH (57.68 mL) solution of 1-bromo-3-cyclopropyl-5-nitro-benzene HG-2a (5 g, 14.5 mmol) and 1-(oxetan-3-yl)piperazine (2.467 g, 17.4 mmol) was added t-BuXPhos Palladacycle (471 mg, 0.723 mmol) and t-BuOK (4.868 g, 43.4 mmol) and the reaction mixture was stirred at 80° C. for 1 h. LCMS indicated the major peak was desired product. Work up: To the reaction mixture was added EA and brine, organic phase was dried over MgSO₄, filtered, concentrated to dryness and purified by Isco 80 g silica gel column eluting with heptanes and EA. The product was eluted with 100% EA to give 1-(3-cyclopropyl-5-nitrophenyl)-4-(oxetan-3-yl)piperazine HG-2b (2.4 g, 55%) ¹H NMR (400 MHz, CDCl₃) δ 7.52 (t, J=2.2 Hz, 1H), 7.36 (t, J=1.6 Hz, 1H), 6.98 (dd, J=11.3, 9.5 Hz, 1H), 4.70 (dt, J=12.3, 6.4 Hz, 4H), 3.58 (p, J=6.4 Hz, 1H), 3.38-3.27 (m, 4H), 2.60-2.45 (m, 4H), 2.04-1.88 (m, 1H), 1.11-0.97 (m, 2H), 0.80-0.71 (m, 2H) ppm. ESI-MS m/z calc. 303.1583, found 304.16 (M+1)⁺; Retention time: 0.58 minutes.

Preparation of 3-cyclopropyl-5-(4-(oxetan-3-yl)piperazin-1-yl)aniline (HG-2c)

To a THF (23 mL) and EtOH (23 mL) solution of 1-(3-cyclopropyl-5-nitro-phenyl)-4-(oxetan-3-yl)piperazine HG-2b (2.3 g, 7.582 mmol) was added NH₄Cl (37.91 mL of 2 M, 75.82 mmol) and Fe (1.27 g, 22.8 mmol) and the reaction mixture was refluxed for 1 h. LCMS indicated the reaction was completed. Work up: The reaction mixture was cooled to RT and filtered through celite. To the filtrate was added EA and brine, the organic phase was dried over MgSO₄, filtered, and concentrated to dryness. The crude product was purified by Isco 150 g Gold amine column eluting with heptanes and EA. The product was eluted with 50% heptanes and 50% EA to give 3-cyclopropyl-5-(4-(oxetan-3-yl)piperazin-1-yl)aniline HG-2c (1.6 g, 77%). ¹H NMR (400 MHz, CDCl₃) δ 6.22-6.13 (m, 1H), 6.08 (t, J=2.1 Hz, 1H), 5.96 (t, J=1.6 Hz, 1H), 4.78-4.61 (m, 4H), 3.56 (s, 2H), 3.27-3.12 (m, 4H), 2.50 (dd, J=15.6, 10.6 Hz, 4H), 1.79 (tt, J=8.4, 5.1 Hz, 1H), 0.95-0.82 (m, 2H), 0.74-0.58 (m, 2H) ppm. ESI-MS m/z calc. 273.1841, found 274.18 (M+1)⁺; Retention time: 0.2 minutes.

Preparation of N-(3-cyclopropyl-5-(4-(oxetan-3-yl)piperazin-1-yl)phenyl)-1-(3,5-difluorophenyl)-1H-1,2,4-triazol-3-amine (Compound 389)

To a t-BuOH (1.6 mL) solution of 3-bromo-1-(3,5-difluorophenyl)-1,2,4-triazole (104 mg, 0.4 mmol) and 3-cyclopropyl-5-[4-(oxetan-3-yl)piperazin-1-yl]aniline HG-2c (115 mg, 0.42 mmol) was added t-BuXPhos Palladacycle (13 mg, 0.02 mmol) and t-BuOK (135 mg, 1.2 mmol) and the reaction mixture was stirred at 85° C. for 1 h. LCMS indicated the major peak was desired product. Work up: To the reaction mixture was added EA and brine, the organic phase was concentrated down and purified by Isco Gold 150 g C18 column eluting with H2O/CH3CN/TFA. The product fractions were extracted with EA, the organic phase was dried over MgSO₄, filtered and concentrated down to afford N-(3-cyclopropyl-5-(4-(oxetan-3-yl)piperazin-1-yl)phenyl)-1-(3,5-difluorophenyl)-1H-1,2,4-triazol-3-amine, cmpd 389 (69 mg, 37% yield). ¹H NMR (400 MHz, CDCl3) δ 8.30 (s, 1H), 7.24 (dd, J=7.7, 2.0 Hz, 2H), 7.07 (t, J=2.0 Hz, 1H), 6.85-6.76 (m, 1H), 6.71 (s, 1H), 6.62 (s, 1H), 6.36 (s, 1H), 4.71 (p, J=6.3 Hz, 4H), 3.64-3.53 (m, 1H), 3.37-3.25 (m, 4H), 2.58-2.48 (m, 4H), 1.90 (ddd, J=13.4, 8.4, 5.0 Hz, 1H), 1.01-0.89 (m, 2H), 0.81-0.69 (m, 2H) ppm. ESI-MS m/z calc. 452.21362, found 453.28 (M+1)⁺; Retention time: 0.63 minutes.

Using the general synthetic scheme outlined in Scheme G and the experimental procedures listed above in Example 19, the following compounds were prepared:

| Cmpd No. | IUPAC Name |
|---|---|
| 359 | 1-(3,5-difluorophenyl)-N-[3-isopropyl-5-[4-(oxetan-3-yl)piperazin-1-yl]phenyl]-1,2,4-triazol-3-amine |
| 222 | 2-cyclopropyl-6-morpholino-N-(1-phenyl-1,2,4-triazol-3-yl)pyridin-4-amine |
| 405 | 2-cyclopropyl-N-[1-(3,5-difluorophenyl)-1,2,4-triazol-3-yl]-6-morpholino-pyridin-4-amine |
| 305 | N-(3-cyclopropyl-5-morpholino-phenyl)-1-phenyl-1,2,4-triazol-3-amine |
| 339 | N-[3-cyclopropyl-5-[4-(oxetan-3-yl)piperazin-1-yl]phenyl]-1-(5-fluoro-3-pyridyl)-1,2,4-triazol-3-amine |
| 55 | 1-(3-chlorophenyl)-N-[3-cyclopropyl-5-[4-(oxetan-3-yl)piperazin-1-yl]phenyl]-1,2,4-triazol-3-amine |
| 494 | N-[3-cyclopropyl-5-[4-(oxetan-3-yl)piperazin-1-yl]phenyl]-1-[3-fluoro-5-(3-methoxyazetidin-1-yl)phenyl]-1,2,4-triazol-3-amine |
| 134 | 1-(5-chloro-3-pyridyl)-N-[3-cyclopropyl-5-[4-(oxetan-3-yl)piperazin-1-yl]phenyl]-1,2,4-triazol-3-amine |
| 184 | N-[3-cyclopropyl-5-[4-(oxetan-3-yl)piperazin-1-yl]phenyl]-1-(2-fluoro-4-pyridyl)-1,2,4-triazol-3-amine |
| 47 | N-[3-cyclopropyl-5-[4-(oxetan-3-yl)piperazin-1-yl]phenyl]-1-phenyl-1,2,4-triazol-3-amine |
| 32 | 1-(3-chloro-5-fluoro-phenyl)-N-[3-methyl-5-[4-(oxetan-3-yl)piperazin-1-yl]phenyl]-1,2,4-triazol-3-amine |
| 220 | 1-(3-chloro-5-fluoro-phenyl)-N-[3-methyl-5-(4-methylpiperazin-1-yl)phenyl]-1,2,4-triazol-3-amine |
| 424 | 1-(3-fluoro-5-methyl-phenyl)-N-[3-methyl-5-(4-methylpiperazin-1-yl)phenyl]-1,2,4-triazol-3-amine |
| 400 | 1-(3-chloro-5-fluoro-phenyl)-N-[3-cyclopropyl-5-[4-(oxetan-3-yl)piperazin-1-yl]phenyl]-1,2,4-triazol-3-amine |
| 73 | N-[3-cyclopropyl-5-[4-(oxetan-3-yl)piperazin-1-yl]phenyl]-1-(3-fluoro-5-methyl-phenyl)-1,2,4-triazol-3-amine |
| 388 | N-[3-cyclopropyl-5-[4-(oxetan-3-yl)piperazin-1-yl]phenyl]-1-(3-fluoro-5-methoxy-phenyl)-1,2,4-triazol-3-amine |
| 205 | 1-(3-fluoro-5-isopropoxy-phenyl)-N-[3-methyl-5-(4-methylpiperazin-1-yl)phenyl]-1,2,4-triazol-3-amine |
| 462 | N-[3-cyclopropyl-5-[4-(oxetan-3-yl)piperazin-1-yl]phenyl]-1-(3-fluorophenyl)-1,2,4-triazol-3-amine |
| 285 | N-[3-cyclopropyl-5-[4-(oxetan-3-yl)piperazin-1-yl]phenyl]-1-(3-fluoro-5-isopropoxy-phenyl)-1,2,4-triazol-3-amine |
| 121 | N-[3-cyclopropyl-5-[4-(oxetan-3-yl)piperazin-1-yl]phenyl]-1-(2,6-difluoro-4-pyridyl)-1,2,4-triazol-3-amine |
| 302 | N-[3-cyclopropyl-5-[4-(oxetan-3-yl)piperazin-1-yl]phenyl]-1-(6-methylpyrimidin-4-yl)-1,2,4-triazol-3-amine |
| 377 | N-[3-cyclopropyl-5-[4-(oxetan-3-yl)piperazin-1-yl]phenyl]-1-(6-methoxypyrimidin-4-yl)-1,2,4-triazol-3-amine |
| 129 | N-[3-cyclopropyl-5-[4-(oxetan-3-yl)piperazin-1-yl]phenyl]-1-(2,6-dimethylpyrimidin-4-yl)-1,2,4-triazol-3-amine |
| 454 | N-[3-cyclopropyl-5-[4-(oxetan-3-yl)piperazin-1-yl]phenyl]-1-(2-methylpyrimidin-4-yl)-1,2,4-triazol-3-amine |
| 286 | N-[3-cyclopropyl-5-[4-(oxetan-3-yl)piperazin-1-yl]phenyl]-1-(2-ethoxypyrimidin-4-yl)-1,2,4-triazol-3-amine |
| 277 | N-[3-cyclopropyl-5-[4-(oxetan-3-yl)piperazin-1-yl]phenyl]-1-(2-methoxypyrimidin-4-yl)-1,2,4-triazol-3-amine |
| 353 | N-[3-cyclopropyl-5-[4-(oxetan-3-yl)piperazin-1-yl]phenyl]-1-[6-(methoxymethyl)pyrimidin-4-yl]-1,2,4-triazol-3-amine |
| 225 | N-[3-cyclopropyl-5-[4-(oxetan-3-yl)piperazin-1-yl]phenyl]-1-(2-fluorophenyl)-1,2,4-triazol-3-amine |
| 378 | 2-cyclopropyl-N-[1-(3,5-difluorophenyl)-1,2,4-triazol-3-yl]-6-(1-piperidyl)pyridin-4-amine |
| 170 | 2-cyclopropyl-N-[1-(3,5-difluorophenyl)-1,2,4-triazol-3-yl]-6-pyrrolidin-1-yl-pyridin-4-amine |
| 327 | 2-cyclopropyl-N-[1-(3,4-difluorophenyl)-1,2,4-triazol-3-yl]-6-(1-piperidyl)pyridin-4-amine |
| 88 | 2-cyclopropyl-N-[1-(3,4-difluorophenyl)-1,2,4-triazol-3-yl]-6-morpholino-pyridin-4-amine |
| 202 | 2-cyclopropyl-N-[1-(3,4-difluorophenyl)-1,2,4-triazol-3-yl]-6-(4-methyl-1-piperidyl)pyridin-4-amine |
| 244 | 2-cyclopropyl-N-[1-(3,5-difluorophenyl)-1,2,4-triazol-3-yl]-6-(4-methyl-1-piperidyl)pyridin-4-amine |
| 22 | 2-cyclopropyl-N-[1-(3,4-dimethoxyphenyl)-1,2,4-triazol-3-yl]-6-(4-methyl-1-piperidyl)pyridin-4-amine |
| 354 | 2-cyclopropyl-N-[1-(3,4-dimethoxyphenyl)-1,2,4-triazol-3-yl]-6-morpholino-pyridin-4-amine |
| 498 | 2-cyclopropyl-N-[1-(3,4-difluorophenyl)-1,2,4-triazol-3-yl]-6-[(3R)-3-fluoropyrrolidin-1-yl]pyridin-4-amine |
| 492 | 2-cyclopropyl-N-[1-(3,4-difluorophenyl)-1,2,4-triazol-3-yl]-6-[(3S)-3-fluoropyrrolidin-1-yl]pyridin-4-amine |
| 332 | 2-cyclopropyl-N-[1-(3,5-difluorophenyl)-1,2,4-triazol-3-yl]-6-[(3S)-3-fluoropyrrolidin-1-yl]pyridin-4-amine |

-continued

| Cmpd No. | IUPAC Name |
|---|---|
| 460 | 2-cyclopropyl-6-[(3S)-3-fluoropyrrolidin-1-yl]-N-(1-phenyl-1,2,4-triazol-3-yl)pyridin-4-amine |
| 44 | 2-cyclopropyl-6-(4-methyl-1-piperidyl)-N-(1-phenyl-1,2,4-triazol-3-yl)pyridin-4-amine |
| 245 | 2-cyclopropyl-N-[1-(3,5-dimethoxyphenyl)-1,2,4-triazol-3-yl]-6-[(3R)-3-fluoropyrrolidin-1-yl]pyridin-4-amine |
| 210 | 2-cyclopropyl-N-[1-(3,5-dimethoxyphenyl)-1,2,4-triazol-3-yl]-6-morpholino-pyridin-4-amine |
| 296 | 2-cyclopropyl-6-[(3R)-3-fluoropyrrolidin-1-yl]-N-(1-phenyl-1,2,4-triazol-3-yl)pyridin-4-amine |
| 9 | 2-cyclopropyl-6-(1,4-dioxa-8-azaspiro[4.5]decan-8-yl)-N-(1-phenyl-1,2,4-triazol-3-yl)pyridin-4-amine |
| 105 | 2-cyclopropyl-N-[1-(3,5-difluorophenyl)-1,2,4-triazol-3-yl]-6-[(3R)-3-fluoropyrrolidin-1-yl]pyridin-4-amine |

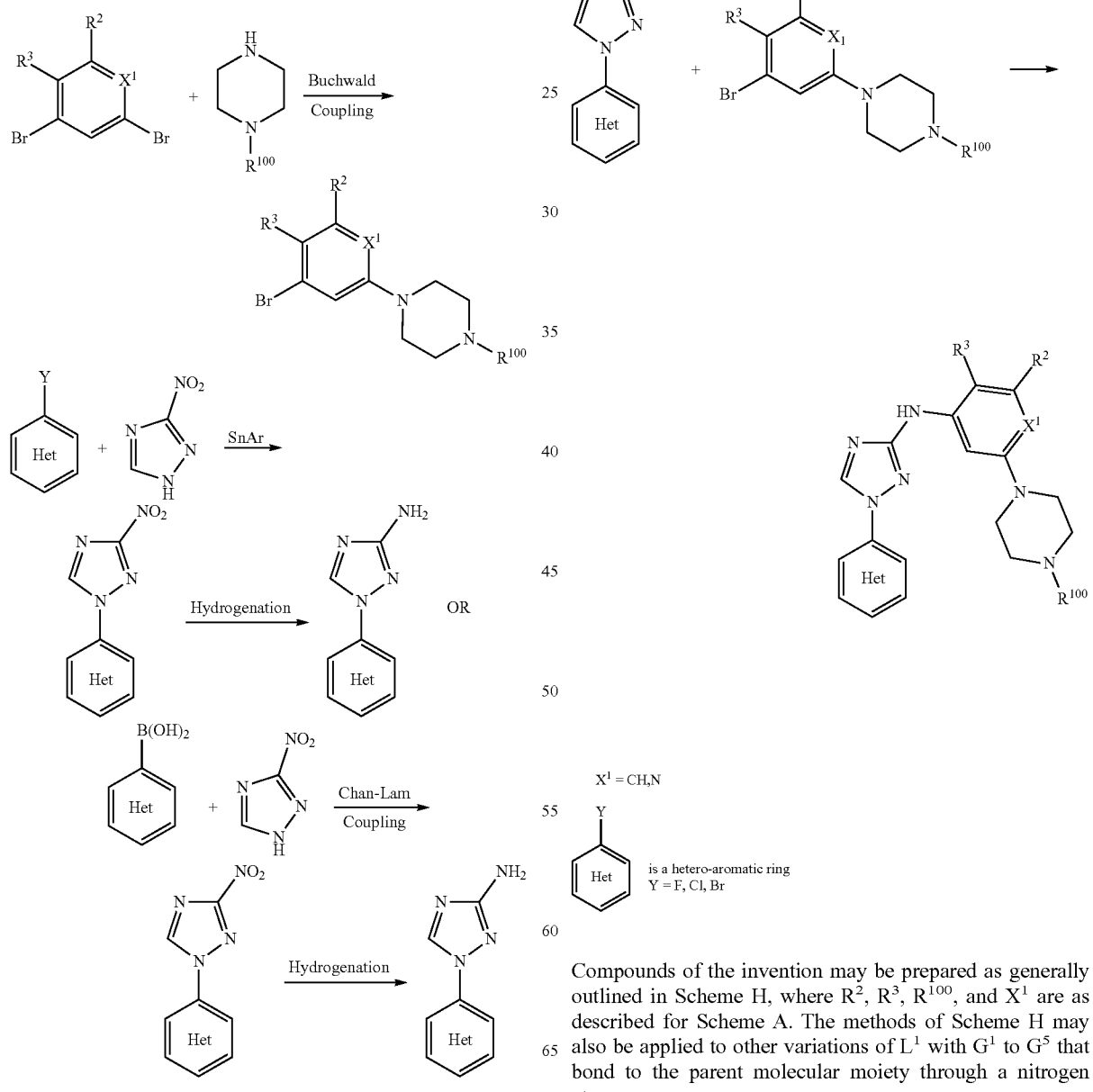

Compounds of the invention may be prepared as generally outlined in Scheme H, where $R^2$, $R^3$, $R^{100}$, and $X^1$ are as described for Scheme A. The methods of Scheme H may also be applied to other variations of $L^1$ with $G^1$ to $G^5$ that bond to the parent molecular moiety through a nitrogen atom.

Example 20

Preparation of (1-(5-fluoro-3-pyridyl)-N-(3-methyl-5-pyrrolidin-1-yl-phenyl)-1,2,4-triazol-3-amine) (Compound 320)

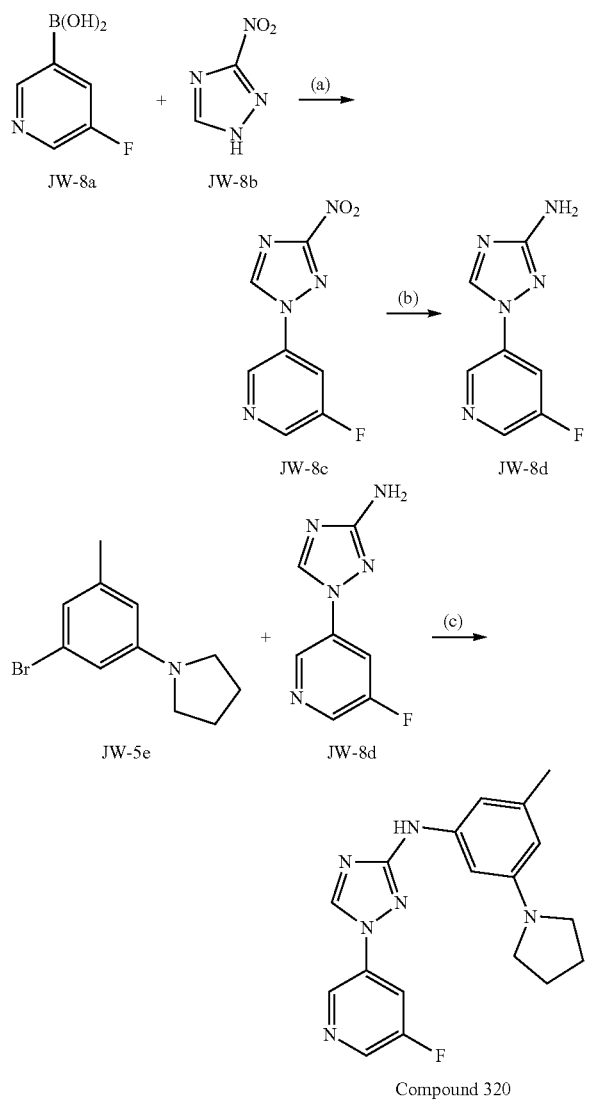

(a)Cu(OAc)₂/Pyridine/DCM/R.T. (b)H2/Pd on Carbon (c)t-Bu-XPhos Palladacycle/t-BuOH/t-BuONa/Microwave/120° C./15 mins

Preparation of 3-fluoro-5-(3-nitro-1,2,4-triazol-1-yl) pyridine (JW-8c)

3-nitro-4H-1,2,4-triazole (JW-8b, 4.8 g, 42.1 mmol), (5-fluoro-3-pyridyl)boronic acid (5.93 g, 42.1 mmol), diacetoxycopper (JW-8a, 11.5 g, 63.1 mmol) and pyridine (6.66 g, 6.8 mL, 84.2 mmol) were mixed in DCM (200 mL) and the reaction was stirred at room temperature for 7 days. The solvent was evaporated and the material was re-dissolved in MeOH and DCM, then adsorbed onto 15 grams of silica gel. The material was dry-loaded and purified on silica gel (eluting with 10-70% EtoAc:Hexanes) to afford 1.2 g desired product JW-8c. $^1$H NMR (400 MHz, DMSO-d6) δ 9.68 (d, J=3.3 Hz, 1H), 9.08 (dd, J=1.2, 0.5 Hz, 1H), 8.93-8.76 (m, 1H), 8.54-8.39 (m, 1H) ppm. ESI-MS m/z calc. 209.0349, found 210.41 (M+1)+; Retention time: 0.7 minutes.

Preparation of 1-(5-fluoro-3-pyridyl)-1,2,4-triazol-3-amine (JW-8d)

3-fluoro-5-(3-nitro-1,2,4-triazol-1-yl)pyridine (JW-5c, 170 mg, 0.82 mM) was dissolved into 10 mL of MeOH and placed under an atmosphere of $CO_2$. 85 mg of 10% Pd/C Degussa type 50% water catalyst was added into the reaction. The reaction was stirred at room temperature under a hydrogen atmosphere with an attached hydrogen-filled balloon overnight. The catalyst was removed by filtration and the filtrate was concentrated to afford 144 mg of desired product as a white solid (JW-8d) in 89% yield. $^1$H NMR (400 MHz, DMSO-d6) δ 8.95 (s, 1H), 8.88 (s, 1H), 8.45 (d, J=2.5 Hz, 1H), 8.06 (dt, J=10.2, 2.3 Hz, 1H) ppm. ESI-MS m/z calc. 179.06073, found 180.0 (M+1)+; Retention time: 0.51 minutes.

Preparation of 1-(5-fluoro-3-pyridyl)-N-(3-methyl-5-pyrrolidin-1-yl-phenyl)-1,2,4-triazol-3-amine (Compound 320)

1-(3-bromo-5-methyl-phenyl)pyrrolidine (JW-5e, 80 mg, 0.33 mmol), 1-(5-fluoro-3-pyridyl)-1,2,4-triazol-3-amine (JW-8d, 60 mg, 0.33 mmol), sodium 2-methylpropan-2-olate (32 mg, 0.33 mmol) and t-BuXPhos Palladacycle (24 mg, 0.03 mmol) were dissolved in dioxane (2 mL) and the reaction was degassed with nitrogen for 10 seconds. The reaction was capped in a microwave tube and heated at 128 degrees in a microwave for 20 minutes. The reaction was quenched with 1 ml MeOH. The reaction was diluted with water and extracted with DCM. The organic phase was concentrated and the crude sample was purified on reverse phase. The fraction was free based with aq. $NaHCO_3$ and extracted with DCM. The organic layer was dried and concentrated. This material was dissolved in DCM and treated with HCl in ether to obtain 76 mg of white solid as the HCl salt of desired product cmpd 320 in 58% yield. $^1$H NMR (400 MHz, DMSO-d6) δ 9.75 (s, 1H), 9.30-9.24 (m, 1H), 9.11 (s, 1H), 8.45 (d, J=10.5 Hz, 1H), 7.76 (s, 1H), 7.10 (s, 1H), 6.64 (d, J=72.9 Hz, 1H), 3.52 (s, 3H), 2.46 (s, 1H), 2.30 (s, 2H), 2.09 (d, J=13.7 Hz, 4H) ppm. ESI-MS m/z calc. 338.16553, found 339.47 (M+1)+; Retention time: 0.71 minutes.

Using the general synthetic scheme outlined in Scheme H and the experimental procedures listed above in Example 20, the following compounds were prepared:

| Cmpd No. | IUPAC Name |
| --- | --- |
| 403 | 1-(2-fluoro-4-pyridyl)-N-(3-methyl-5-morpholino-phenyl)-1,2,4-triazol-3-amine |
| 155 | 4-[3-(3-methyl-5-morpholino-anilino)-1,2,4-triazol-1-yl]pyridin-2-ol |

-continued

| Cmpd No. | IUPAC Name |
|---|---|
| 427 | 1-(5-fluoro-3-pyridyl)-N-(3-methyl-5-morpholino-phenyl)-1,2,4-triazol-3-amine |
| 320 | 1-(5-fluoro-3-pyridyl)-N-(3-methyl-5-pyrrolidin-1-yl-phenyl)-1,2,4-triazol-3-amine |
| 371 | N-(3-fluoro-5-morpholino-phenyl)-1-(5-fluoro-3-pyridyl)-1,2,4-triazol-3-amine |
| 84 | N-(3-methyl-5-morpholino-phenyl)-1-(4-pyridyl)-1,2,4-triazol-3-amine |
| 42 | 1-(2-chloro-4-pyridyl)-N-(3-methyl-5-pyrrolidin-1-yl-phenyl)-1,2,4-triazol-3-amine |
| 488 | 1-(6-chloro-2-pyridyl)-N-(3-methyl-5-pyrrolidin-1-yl-phenyl)-1,2,4-triazol-3-amine |
| 503 | 4-methyl-6-(3-morpholinoazetidin-1-yl)-N-[1-(2-pyridyl)-1,2,4-triazol-3-yl]pyridin-2-amine |
| 504 | N-[1-(2-fluoro-4-pyridyl)-1,2,4-triazol-3-yl]-4-methyl-6-(3-morpholinoazetidin-1-yl)pyridin-2-amine |
| 507 | N-[3-[4-(oxetan-3-yl)-1-piperidyl]-5-(trifluoromethyl)phenyl]-1-pyrazin-2-yl-1,2,4-triazol-3-amine |
| 513 | N-[3-(6-oxa-3-azabicyclo[3.1.1]heptan-3-yl)-5-(trifluoromethyl)phenyl]-1-pyrazin-2-yl-1,2,4-triazol-3-amine |
| 514 | N-[3-[4-(oxetan-3-yl)piperazin-1-yl]-5-(trifluoromethyl)phenyl]-1-pyrazin-2-yl-1,2,4-triazol-3-amine |
| 529 | N-[1-(3,5-difluorophenyl)-1,2,4-triazol-3-yl]-4-methyl-6-piperazin-1-yl-pyridin-2-amine |
| 532 | 4-(difluoromethyl)-6-[4-(oxetan-3-yl)piperazin-1-yl]-N-[1-(2-pyridyl)-1,2,4-triazol-3-yl]pyridin-2-amine |
| 533 | tert-butyl 4-[6-[[1-(3,5-difluorophenyl)-1,2,4-triazol-3-yl]amino]-4-methyl-2-pyridyl]piperazine-1-carboxylate |
| 684 | 6-[4-(oxetan-3-yl)piperazin-1-yl]-N-[1-(3-pyridyl)-1,2,4-triazol-3-yl]-4-(trifluoromethyl)pyridin-2-amine |
| 763 | 3-morpholino-5-[[1-(3-pyridyl)-1,2,4-triazol-3-yl]amino]benzonitrile |
| 666 | 3-morpholino-5-[(1-pyrazin-2-yl-1,2,4-triazol-3-yl)amino]benzonitrile |
| 842 | 3-[4-(oxetan-3-yl)piperazin-1-yl]-5-[[1-(3-pyridyl)-1,2,4-triazol-3-yl]amino]benzonitrile |

Scheme I: General Route I for Preparation of Compounds of Formula I or I'

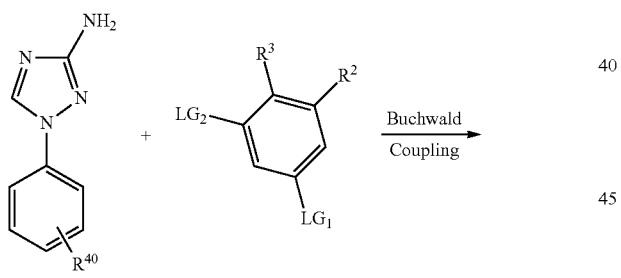

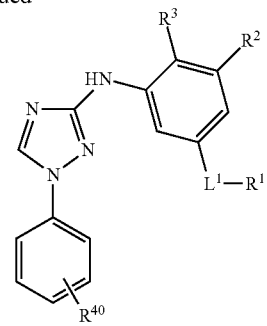

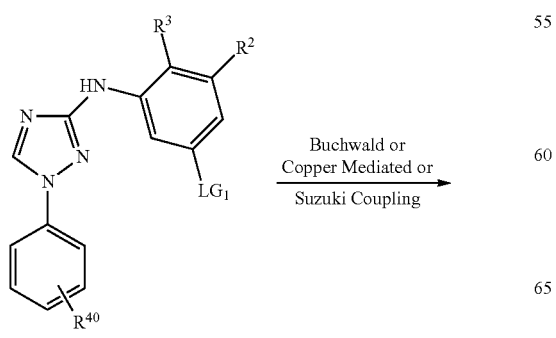

Compounds of the invention may be prepared as generally outlined in Scheme I, where $LG_1$ and $LG_2$ are leaving groups such as Br or Cl, $R^2$, $R^3$, and $R^{40}$ are as described for Scheme A, and -$L^1$-$R^1$ is bonded to the parent molecular moiety through a nitrogen or carbon atom.

Example 20A

Preparation of 1-(3,5-difluorophenyl)-N-[3-methyl-5-(3-morpholinoazetidin-1-yl)phenyl]-1,2,4-triazol-3-amine (Compound 485)

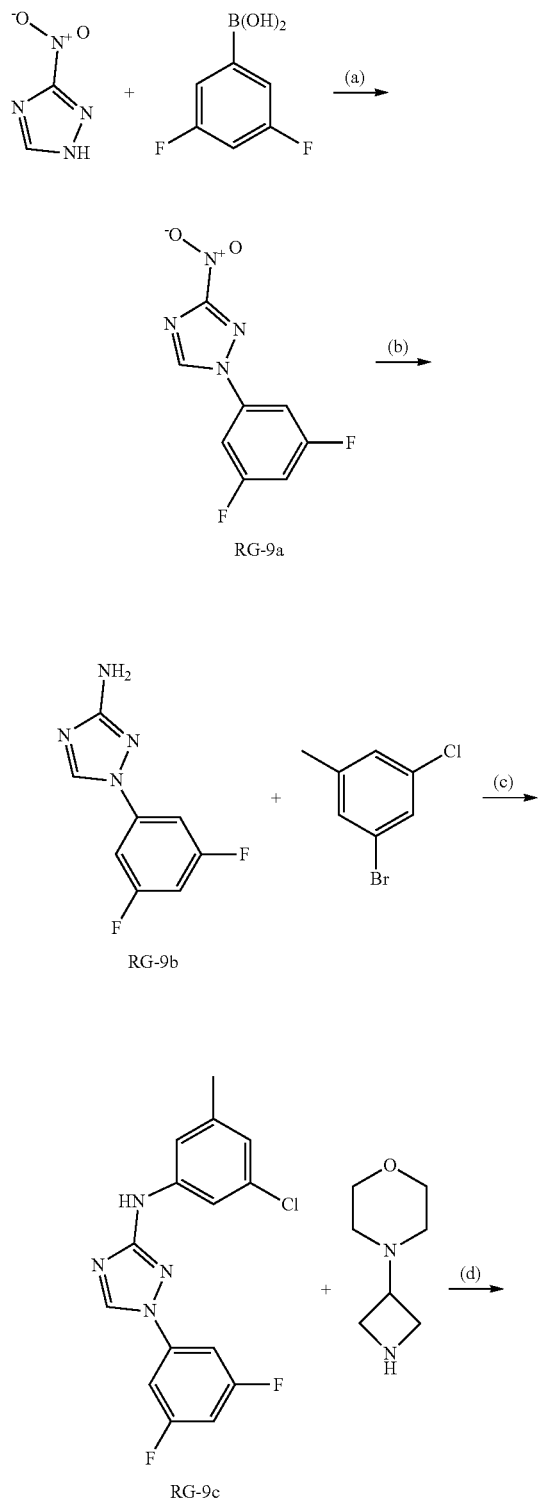

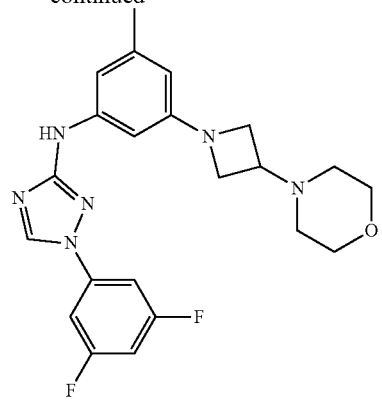

Cmpd 485 a) Cu(OAc)2, Pyridine, 4Å sieves, DCM, R.T.; (b) Pd/C, H2; (c) t-BuXPhos Palladacycle/t-BuOH, 1,4-dioxane, t-BuONa; (d) t-BuXPhos Palladacycle, t-BuOH, 1,4-dioxane, t-BuONa.

Preparation of 1-(3,5-difluorophenyl)-3-nitro-1H-1,2,4-triazole (RG-9a)

3-Nitro-1H-1,2,4-triazole (5.10 g, 44.71 mmol), diacetoxycopper (12.18 g, 67.06 mmol), (3,5-difluorophenyl)boronic acid (10.59 g, 67.06 mmol), 4A sieves (717.3 mg, 44.71 mmol) were mixed in DCE (200 mL) and pyridine (7.07 g, 7.23 mL, 89.42 mmol) was added. The reaction was stirred at room temperature for 2 days. The solvent was removed under reduced pressure and the crude material was purified on silica gel (10-60% Hex:EtOAc) to afford 1-(3,5-difluorophenyl)-3-nitro-1H-1,2,4-triazole RG-9a (5.2 g, 20.2 mmol, 45%) 1H NMR (400 MHz, DMSO-d6) δ 9.65 (s, 1H), 7.89-7.71 (m, 2H), 7.53 (tt, J=9.3, 2.3 Hz, 1H) ppm. ESI-MS m/z calc. 226.03023, found 227.03 (M+1)+; 227.03 (M−1)+; Retention time: 2.72 minutes.

Preparation of 1-(3,5-difluorophenyl)-1,2,4-triazol-3-amine (RG-9b)

1-(3,5-difluorophenyl)-3-nitro-1,2,4-triazole RG-9a (16.6 g, 73.4 mM) was dissolved/suspended in 250 mL of MeOH and placed under a CO2 atmosphere before adding 10% Pd/C Degussa type 50% H2O; (2.5 g, 0.03 mM). Reaction was placed under an atmosphere of H2 (50 psi) for 2.0 hours with agitation, then suctioned filtered the reaction through a pad of diatomaceous earth and washed with MeOH. Important note: much of the product resides on the pad due to it's insolubility. Washed everything back into the Parr bottle and diluted with 250 ml 3:7 MeOH/THF with fresh catalyst and replaced under 50 psi H2 for another 1.0 hours. note: no appreciable amounts of H2 taken up upon retreatment—hydroxyl amine is still present. Material was pulled through a pad of diatomaceous earth and washed with 7:3 THF/MeOH, until only the carbon remained and the solvents were removed under reduced pressure. Crude material was stirred in THF for one hour at ambient temperature, and isolated a light gray powder after suction filtration and washing with Et2O-filtrates retained. Note: most of the colour remains in filtrates and the precipitate has minimal amounts of the hydroxyl amine. Precipitate (8 g) was suspended in 16 mL of TFE and 25 mL of THF and heated to reflux, stirred until cool and isolated precipitate via suction filtration. Filtrates from the previous trituration were evaporated to dryness in vacuo and re-suspended in 25 mL of THF, heated to reflux and likewise stirred until cool. The precipitate from this THF trituration was added to the TFE/THF filtrates retained from the 1st batch, boiled, cooled, and isolated via suction filtration and combined with the 1st material. Yielded 1-(3,5-difluorophenyl)-1,2,4-triazol-3-amine RG-9b (10 g, 45.9 mmol, 63%). 1H NMR (400 MHz, Acetone-d6) δ 8.73 (s, 1H), 7.63-7.34 (m, 2H), 6.95 (tt, J=9.1, 2.3 Hz, 1H), 5.30 (brd s, 2H) ppm. ESI-MS m/z calc. 196.05605, found 197.0 (M+1)+; Retention time: 0.66 minutes.

Preparation of N-(3-chloro-5-methyl-phenyl)-1-(3,5-difluorophenyl)-1,2,4-triazol-3-amine (RG-9c)

1-(3,5-difluorophenyl)-1,2,4-triazol-3-amine RG-9b (1.8 g, 9.176 mmol), 1-bromo-3-chloro-5-methyl-benzene (3.76 g, 18.30 mmol), sodium t-butoxide (1.9 g, 19.77 mmol) and t-BuXphos Palladacyle (365 mg, 0.495 mmol) were dissolved into dry t-BuOH (21 mL) and dry dioxane (7 mL) and purged with N2 for ~10 minutes. Stirred mixture at 90° C. for 1 h. LC/MS showed no remaining starting material so poured the reaction mixture into 250 mls of water and filtered. Washed the filter cake with additional water, then with methanol. Dried the filter cake in the high vac at 50° C. overnight. Yielded N-(3-chloro-5-methyl-phenyl)-1-(3,5-difluorophenyl)-1,2,4-triazol-3-amine RG-9c (2.4 g, 7.260 mmol, 79%) 1H NMR (300 MHz, DMSO-d6) δ 9.78 (s, 1H), 9.20 (s, 1H), 7.63 (dd, J=8.6, 2.2 Hz, 2H), 7.55 (t, J=1.8 Hz, 1H), 7.34 (s, 1H), 7.28 (m, 1H), 6.76 (s, 1H), 2.29 (s, 3H) ppm. ESI-MS m/z calc. 320.06403, found 321.07 (M+1)+; Retention time: 1.03 minutes.

Preparation of 1-(3,5-difluorophenyl)-N-[3-methyl-5-(3-morpholinoazetidin-1-yl)phenyl]-1,2,4-triazol-3-amine (Compound 485)

Sodium t-butoxide (230 mg, 2.393 mmol), N-(3-chloro-5-methyl-phenyl)-1-(3,5-difluorophenyl)-1,2,4-triazol-3-amine RG-9c (200 mg, 0.5833 mmol), 4-(azetidin-3-yl)morpholine (125 mg, 0.8791 mmol), and t-BuXphos palladacycle (21 mg, 0.031 mmol) was added to a one dram vial. Diluted the solids with t-BuOH (3 mL) and dioxane (1 mL). Added a stir bar, flushed the reaction with nitrogen for 5 minutes, and sealed the vials. Heated to 50° C. LCMS showed after 30 minutes, very little desired product. Continued to stir for 6 h. Little change. Added additional t-Bu Xphos palladacycle (21 mg, 0.031 mmol) from a different bottle of catalyst and heated for another 30 minutes. The reaction is now complete. Diluted with DCM (10 mls) and washed organics with 50% saturated sodium bicarbonate. Combined organics from a previous run to purify in one batch. Passed the organics through a phase separator and concentrated to dryness. Diluted with 2 mls of DMSO and purified on a 275 gram C-18 AQ reverse phase column with a TFA modifier (0-100% ACN in water). Pooled desired pure tubes and diluted with DCM (10 mls) and washed with 50% saturated sodium bicarbonate. Passed the organics through a phase separator containing a plug of florisil, and concentrated to dryness to yield the desired product 1-(3,5-difluorophenyl)-N-[3-methyl-5-(3-morpholinoazetidin-1-yl)phenyl]-1,2,4-triazol-3-amine 485 (174 mg, 0.396 mmol, 68%) 1H NMR (300 MHz, DMSO-d6) δ 9.33 (s, 1H), 9.15 (s, 1H), 7.60 (d, J=6.3 Hz, 2H), 7.24 (t, J=9.2 Hz, 1H), 6.72 (d, J=14.7 Hz, 2H), 5.82 (s, 1H), 3.89 (t, J=7.2 Hz, 2H), 3.58 (m, 6H), 3.25 (m, 1H), 2.34 (m, 4H), 2.19 (s, 3H) ppm. ESI-MS m/z calc. 426.19797, found 427.25 (M+1)+; Retention time: 0.66 minutes.

Using the general synthetic scheme outlined in Scheme I and the experimental procedures listed above in Example 20A, the following compounds were prepared:

| Cmpd No. | IUPAC Name |
| --- | --- |
| 2 | 1-(3,5-difluorophenyl)-N-[3-(3-methoxyazetidin-1-yl)-5-methyl-phenyl]-1,2,4-triazol-3-amine |
| 293 | 1-(3,5-difluorophenyl)-N-[3-(3-methoxy-1-piperidyl)-5-methyl-phenyl]-1,2,4-triazol-3-amine |
| 116 | 1-(3,5-difluorophenyl)-N-[3-[3-(methoxymethyl)azetidin-1-yl]-5-methyl-phenyl]-1,2,4-triazol-3-amine |
| 279 | 1-(3,5-difluorophenyl)-N-[3-methyl-5-(2-oxa-7-azaspiro[3.5]nonan-7-yl)phenyl]-1,2,4-triazol-3-amine |
| 11 | N-[3-methyl-5-(2-oxa-7-azaspiro[3.5]nonan-7-yl)phenyl]-1-phenyl-1,2,4-triazol-3-amine |
| 326 | N-[3-(4-isopropylpiperazin-1-yl)-5-methyl-phenyl]-1-phenyl-1,2,4-triazol-3-amine |
| 253 | N-[3-[4-(2-methoxyethyl)piperazin-1-yl]-5-methyl-phenyl]-1-phenyl-1,2,4-triazol-3-amine |
| 274 | N-[3-(4-ethylpiperazin-1-yl)-5-methyl-phenyl]-1-phenyl-1,2,4-triazol-3-amine |
| 214 | 1-cyclopropyl-4-[3-methyl-5-[(1-phenyl-1,2,4-triazol-3-yl)amino]phenyl]piperazin-2-one |
| 6 | 3-methyl-1-[3-methyl-5-[(1-phenyl-1,2,4-triazol-3-yl)amino]phenyl]pyrrolidin-3-ol |
| 369 | N-[3-[(3aR,6aR)-1-methyl-2,3,3a,4,6,6a-hexahydropyrrolo[2,3-c]pyrrol-5-yl]-5-methyl-phenyl]-1-phenyl-1,2,4-triazol-3-amine |
| 423 | N-[3-methyl-5-[(3R,5S)-3,4,5-trimethylpiperazin-1-yl]phenyl]-1-phenyl-1,2,4-triazol-3-amine |
| 455 | N-[3-[4-(2-fluorophenyl)piperazin-1-yl]-5-methyl-phenyl]-1-phenyl-1,2,4-triazol-3-amine |
| 289 | N-[3-methyl-5-(4-tetrahydropyran-4-ylpiperazin-1-yl)phenyl]-1-phenyl-1,2,4-triazol-3-amine |
| 461 | 2-methyl-1-[4-[3-methyl-5-[(1-phenyl-1,2,4-triazol-3-yl)amino]phenyl]piperazin-1-yl]propan-2-ol |
| 398 | N-[3-methyl-5-[4-(2,2,2-trifluoroethyl)piperazin-1-yl]phenyl]-1-phenyl-1,2,4-triazol-3-amine |
| 465 | N-[3-(2,5-dihydrofuran-3-yl)-5-morpholino-phenyl]-1-phenyl-1,2,4-triazol-3-amine |

-continued

| Cmpd No. | IUPAC Name |
|---|---|
| 298 | 1-(3,5-difluorophenyl)-N-[3-(2,5-dihydrofuran-3-yl)-5-morpholino-phenyl]-1,2,4-triazol-3-amine |
| 165 | N-(3-morpholino-5-tetrahydrofuran-3-yl-phenyl)-1-phenyl-1,2,4-triazol-3-amine |
| 456 | 1-(3,5-difluorophenyl)-N-(3-morpholino-5-tetrahydrofuran-3-yl-phenyl)-1,2,4-triazol-3-amine |
| 89 | N-[3-(1,1-dioxo-1,4-thiazinan-4-yl)-5-methyl-phenyl]-1-phenyl-1,2,4-triazol-3-amine |
| 7 | N-[3-methyl-5-(6-oxa-2-azaspiro[3.3]heptan-2-yl)phenyl]-1-phenyl-1,2,4-triazol-3-amine |
| 148 | N-[3-[4-(2-methoxyethyl)-1-piperidyl]-5-methyl-phenyl]-1-phenyl-1,2,4-triazol-3-amine |
| 40 | 1-[4-[3-methyl-5-[(1-phenyl-1,2,4-triazol-3-yl)amino]anilino]-1-piperidyl]ethanone |
| 112 | 1-(3,5-difluorophenyl)-N-[3-fluoro-5-[4-(oxetan-3-yl)piperazin-1-yl]phenyl]-1,2,4-triazol-3-amine |
| 485 | 1-(3,5-difluorophenyl)-N-[3-methyl-5-(3-morpholinoazetidin-1-yl)phenyl]-1,2,4-triazol-3-amine |
| 506 | 1-(3,5-difluorophenyl)-N-[3-methyl-5-[3-(oxetan-3-yl)azetidin-1-yl]phenyl]-1,2,4-triazol-3-amine |
| 508 | 1-(3,5-difluorophenyl)-N-[3-methyl-5-(3-oxa-6-azaspiro[3.3]heptan-6-yl)phenyl]-1,2,4-triazol-3-amine |
| 510 | 1-(3,5-difluorophenyl)-N-[3-methyl-5-(3-pyrrolidin-1-ylazetidin-1-yl)phenyl]-1,2,4-triazol-3-amine |
| 518 | 1-[3-[[1-(3,5-difluorophenyl)-1,2,4-triazol-3-yl]amino]-5-methyl-phenyl]-3-isopropyl-azetidin-3-ol |
| 519 | 2-[1-[3-[[1-(3,5-difluorophenyl)-1,2,4-triazol-3-yl]amino]-5-methyl-phenyl]azetidin-3-yl]propan-2-ol |
| 520 | N3-[1-(3,5-difluorophenyl)-1,2,4-triazol-3-yl]-N1-(3-methoxycyclobutyl)-5-methyl-benzene-1,3-diamine |
| 527 | 1-(3,5-difluorophenyl)-N-[3-methyl-5-(6-oxa-3-azabicyclo[3.1.1]heptan-3-yl)phenyl]-1,2,4-triazol-3-amine |
| 528 | N-[3-(3,3a,4,6,7,7a-hexahydro-2H-furo[3,2-c]pyridin-5-yl)-5-methyl-phenyl]-1-(3,5-difluorophenyl)-1,2,4-triazol-3-amine |
| 197 | N3-[1-(3,5-difluorophenyl)-1,2,4-triazol-3-yl]-N1,5-dimethyl-N1-(oxetan-3-yl)benzene-1,3-diamine |
| 240 | N3-[1-(3,5-difluorophenyl)-1,2,4-triazol-3-yl]-5-methyl-N1-(oxetan-3-yl)benzene-1,3-diamine |
| 325 | 1-(3,5-difluorophenyl)-N-[3-[2-(methoxymethyl)morpholin-4-yl]-5-methyl-phenyl]-1,2,4-triazol-3-amine |
| 349 | 1-(3,5-difluorophenyl)-N-[3-methyl-5-(9-methyl-2-oxa-6,9-diazaspiro[3.5]nonan-6-yl)phenyl]-1,2,4-triazol-3-amine |
| 551 | 1-[3-[[1-(3,5-difluorophenyl)-1,2,4-triazol-3-yl]amino]-5-methyl-phenyl]-3-methyl-azetidin-3-ol |
| 561 | 2-[3-[[1-(3,5-difluorophenyl)-1,2,4-triazol-3-yl]amino]-5-methyl-phenyl]-1,3,4,7,8,8a-hexahydropyrrolo[1,2-a]pyrazin-6-one |
| 553 | 1-[3-[[1-(3,5-difluorophenyl)-1,2,4-triazol-3-yl]amino]-5-methyl-phenyl]-3-ethyl-azetidin-3-ol |
| 161 | 1-[1-[3-[[1-(3,5-difluorophenyl)-1,2,4-triazol-3-yl]amino]-5-methyl-phenyl]-4-piperidyl]pyrrolidin-2-one |
| 8 | N3-[1-(3,5-difluorophenyl)-1,2,4-triazol-3-yl]-5-methyl-N1-tetrahydrofuran-3-yl-benzene-1,3-diamine |
| 542 | 1-[1-[3-[[1-(3,5-difluorophenyl)-1,2,4-triazol-3-yl]amino]-5-methyl-phenyl]azetidin-3-yl]pyrrolidin-2-one |
| 566 | N-[3-(3,4,6,7,9,9a-hexahydro-1H-pyrazino[2,1-c][1,4]oxazin-8-yl)-5-methyl-phenyl]-1-(3,5-difluorophenyl)-1,2,4-triazol-3-amine |
| 164 | 1-(3,5-difluorophenyl)-N-[3-(3-methoxypyrrolidin-1-yl)-5-methyl-phenyl]-1,2,4-triazol-3-amine |
| 541 | 1-(3,5-difluorophenyl)-N-[3-methyl-5-(2-oxa-8-azaspiro[3.5]nonan-8-yl)phenyl]-1,2,4-triazol-3-amine |
| 552 | 1-(3,5-difluorophenyl)-N-[3-methyl-5-[3-(trifluoromethyl)piperazin-1-yl]phenyl]-1,2,4-triazol-3-amine |
| 355 | 1-[3-[[1-(3,5-difluorophenyl)-1,2,4-triazol-3-yl]amino]-5-methyl-phenyl]azetidin-3-ol |
| 543 | 1-(3,5-difluorophenyl)-N-[3-methyl-5-(9-oxa-6-azaspiro[3.5]nonan-6-yl)phenyl]-1,2,4-triazol-3-amine |
| 855 | N-[1-(3,5-difluorophenyl)-1,2,4-triazol-3-yl]-6-[4-(2-methoxyethyl)-1-piperidyl]4-methyl-pyridin-2-amine |
| 683 | 1-(3,5-difluorophenyl)-N-[3-methyl-5-(3-methyl-3-morpholino-azetidin-1-yl)phenyl]-1,2,4-triazol-3-amine |
| 602 | 1-(3,5-difluorophenyl)-N-[3-[3-(2,2-dimethylmorpholin-4-yl)azetidin-1-yl]-5-methyl-phenyl]-1,2,4-triazol-3-amine |
| 857 | 1-(3,5-difluorophenyl)-N-[3-[3-[(2R,6R)-2,6-dimethylmorpholin-4-yl]azetidin-1-yl]-5-methyl-phenyl]-1,2,4-triazol-3-amine |
| 617 | 1-(3,5-difluorophenyl)-N-[3-[3-(4-fluoro-1-piperidyl)azetidin-1-yl]-5-methyl-phenyl]-1,2,4-triazol-3-amine |

-continued

| Cmpd No. | IUPAC Name |
|---|---|
| 731 | N-[1-(3,5-difluorophenyl)-1,2,4-triazol-3-yl]-4-methyl-6-(4-methylpiperazin-1-yl)pyridin-2-amine |
| 702 | 6-(4-tert-butylpiperazin-1-yl)-N-[1-(3,5-difluorophenyl)-1,2,4-triazol-3-yl]-4-methyl-pyridin-2-amine |
| 631 | N-[1-(3,5-difluorophenyl)-1,2,4-triazol-3-yl]-4-methyl-6-(1,2,3,6-tetrahydropyridin-4-yl)pyridin-2-amine |
| 744 | N-[1-(3,5-difluorophenyl)-1,2,4-triazol-3-yl]-4-methyl-6-(4-piperidyl)pyridin-2-amine |
| 707 | 6-[[1-(3,5-difluorophenyl)-1,2,4-triazol-3-yl]amino]-4-[4-(oxetan-3-yl)piperazin-1-yl]pyridine-2-carbonitrile |
| 774 | N-[1-(3,5-difluorophenyl)-1,2,4-triazol-3-yl]-6-(3,6-dihydro-2H-pyran-4-yl)-4-methyl-pyridin-2-amine |
| 801 | N-[1-(3,5-difluorophenyl)-1,2,4-triazol-3-yl]-4-methyl-6-[1-(oxetan-3-yl)-4-piperidyl]pyridin-2-amine |
| 724 | 1-(3,5-difluorophenyl)-N-[3-(2,5-dioxa-8-azaspiro[3.5]nonan-8-yl)-5-methyl-phenyl]-1,2,4-triazol-3-amine |
| 831 | N-[3-[(8aS)-7,7-difluoro-13,4,6,8,8a-hexahydropyrrolo[1,2-a]pyrazin-2-yl]-5-methyl-phenyl]-1-(3,5-difluorophenyl)-1,2,4-triazol-3-amine |
| 634 | 1-(3,5-difluorophenyl)-N-[3-methyl-5-[3-(1-piperidyl)azetidin-1-yl]phenyl]-1,2,4-triazol-3-amine |
| 690 | [1-[3-[[1-(3,5-difluorophenyl)-1,2,4-triazol-3-yl]amino]-5-methyl-phenyl]azetidin-3-yl]-morpholino-methanone |
| 742 | 1-(3,5-difluorophenyl)-N-[3-methyl-5-[3-(6-oxa-3-azabicyclo[3.1.1]heptan-3-yl)azetidin-1-yl]phenyl]-1,2,4-triazol-3-amine |
| 730 | 1-(3,5-difluorophenyl)-N-[3-methyl-5-[3-[(2S)-2-methylmorpholin-4-yl]azetidin-1-yl]phenyl]-1,2,4-triazol-3-amine |
| 618 | 1-(3,5-difluorophenyl)-N-[3-[3-[(2R,6S)-2,6-dimethylmorpholin-4-yl]azetidin-1-yl]-5-methyl-phenyl]-1,2,4-triazol-3-amine |
| 696 | 1-(3,5-difluorophenyl)-N-[3-methyl-5-[3-[(2R)-2-methylmorpholin-4-yl]azetidin-1-yl]phenyl]-1,2,4-triazol-3-amine |
| 800 | 1-(3,5-difluorophenyl)-N-[3-methyl-5-[3-[(3S)-3-methylmorpholin-4-yl]azetidin-1-yl]phenyl]-1,2,4-triazol-3-amine |
| 670 | 1-(3,5-difluorophenyl)-N-[3-methyl-5-[3-[(3R)-3-methylmorpholin-4-yl]azetidin-1-yl]phenyl]-1,2,4-triazol-3-amine |
| 711 | 1-[3-[[1-(3,5-difluorophenyl)-1,2,4-triazol-3-yl]amino]-5-methyl-phenyl]-N,N-dimethyl-azetidine-3-carboxamide |
| 773 | [1-[3-[[1-(3,5-difluorophenyl)-1,2,4-triazol-3-yl]amino]-5-methyl-phenyl]azetidin-3-yl]-pyrrolidin-1-yl-methanone |
| 817 | 1-[3-[[1-(3,5-difluorophenyl)-1,2,4-triazol-3-yl]amino]-5-methyl-phenyl]-N,N-diethyl-azetidine-3-carboxamide |
| 824 | 1-[3-[[1-(3,5-difluorophenyl)-1,2,4-triazol-3-yl]amino]-5-methyl-phenyl]-N-(2-methoxyethyl)-N-methyl-azetidine-3-carboxamide |
| 584 | 1-[3-[[1-(3,5-difluorophenyl)-1,2,4-triazol-3-yl]amino]-5-methyl-phenyl]-N-[(1S)-2-methoxy-1-methyl-ethyl]azetidine-3-carboxamide |
| 722 | 1-(3,5-difluorophenyl)-N-[3-methyl-5-(3-oxa-8-azabicyclo[3.2.1]octan-8-yl)phenyl]-1,2,4-triazol-3-amine |
| 727 | 1-(3,5-difluorophenyl)-N-[3-methyl-5-(2-oxa-5-azabicyclo[2.2.1]heptan-5-yl)phenyl]-1,2,4-triazol-3-amine |
| 694 | 1-(3,5-difluorophenyl)-N-[3-methyl-5-(3-oxa-6-azabicyclo[3.1.1]heptan-6-yl)phenyl]-1,2,4-triazol-3-amine |
| 692 | 1-(3,5-difluorophenyl)-N-[3-methyl-5-(8-oxa-3-azabicyclo[3.2.1]octan-3-yl)phenyl]-1,2,4-triazol-3-amine |
| 746 | 1-(3,5-difluorophenyl)-N-[3-methyl-5-[3-(3-oxa-8-azabicyclo[3.2.1]octan-8-yl)azetidin-1-yl]phenyl]-1,2,4-triazol-3-amine |
| 661 | 1-(3,5-difluorophenyl)-N-[3-[3-(1,1-dioxo-1,4-thiazinan-4-yl)azetidin-1-yl]-5-methyl-phenyl]-1,2,4-triazol-3-amine |
| 717 | 1-(3,5-difluorophenyl)-N-[3-methyl-5-[3-(8-oxa-3-azabicyclo[3.2.1]octan-3-yl)azetidin-1-yl]phenyl]-1,2,4-triazol-3-amine |
| 586 | 1-(3,5-difluorophenyl)-N-[3-methyl-5-[3-(4-oxa-7-azaspiro[2.5]octan-7-yl)azetidin-1-yl]phenyl]-1,2,4-triazol-3-amine |
| 788 | 1-(3,5-difluorophenyl)-N-[3-methyl-5-[3-(2-oxa-5-azabicyclo[2.2.1]heptan-5-yl)azetidin-1-yl]phenyl]-1,2,4-triazol-3-amine |
| 720 | 1-(3,4-difluorophenyl)-N-[3-methyl-5-(3-morpholinoazetidin-1-yl)phenyl]-1,2,4-triazol-3-amine |
| 866 | 1-(3,5-difluorophenyl)-N-[3-methyl-5-[3-(morpholinomethyl)azetidin-1-yl]phenyl]-1,2,4-triazol-3-amine |

-continued

| Cmpd No. | IUPAC Name |
|---|---|
| 652 | 1-(3,5-difluorophenyl)-N-[3-methyl-5-[3-(5-oxa-2-azabicyclo[4.1.0]heptan-2-yl)azetidin-1-yl]phenyl]-1,2,4-triazol-3-amine |
| 852 | 2-[3-fluoro-5-[3-[3-(3-fluoroazetidin-1-yl)-5-methyl-anilino]-1,2,4-triazol-1-yl]anilino]ethanol |
| 766 | N-[3-(3-fluoroazetidin-1-yl)-5-methyl-phenyl]-1-[3-fluoro-5-(2-methoxyethylamino)phenyl]-1,2,4-triazol-3-amine |
| 791 | 2-[[1-[3-[[1-(3,5-difluorophenyl)-1,2,4-triazol-3-yl]amino]-5-methyl-phenyl]azetidin-3-yl]amino]ethanol |
| 816 | 1-(3,5-difluorophenyl)-N-[3-[3-(2-methoxyethylamino)azetidin-1-yl]-5-methyl-phenyl]-1,2,4-triazol-3-amine |
| 704 | N-[3-methyl-5-(3-morpholinoazetidin-1-yl)phenyl]-1-phenyl-1,2,4-triazol-3-amine |
| 828 | 5-methyl-N3-(1-methylpyrazol-3-yl)-N1-(1-phenyl-1,2,4-triazol-3-yl)benzene-1,3-diamine |
| 604 | N1-(1-ethyl-1,2,4-triazol-3-yl)-5-methyl-N3-(1-phenyl-1,2,4-triazol-3-yl)benzene-1,3-diamine |
| 830 | 1-(3,5-difluorophenyl)-N-[3-isopropoxy-5-(3-morpholinoazetidin-1-yl)phenyl]-1,2,4-triazol-3-amine |
| 653 | 1-(3,5-difluorophenyl)-N-[3-isopropoxy-5-[4-(oxetan-3-yl)piperazin-1-yl]phenyl]-1,2,4-triazol-3-amine |
| 797 | N3-[1-(3,5-difluorophenyl)-1,2,4-triazol-3-yl]-5-methyl-N1-(3-morpholinocyclobutyl)benzene-1,3-diamine |
| 799 | N3-[1-(3,4-difluorophenyl)-1,2,4-triazol-3-yl]-5-methyl-N1-(3-morpholinocyclobutyl)benzene-1,3-diamine |
| 822 | 1-(3,5-difluorophenyl)-N-[3-methyl-5-[(1S,4S)-2-oxa-5-azabicyclo[2.2.1]heptan-5-yl]phenyl]-1,2,4-triazol-3-amine |
| 628 | 1-(3,5-difluorophenyl)-N-[3-methyl-5-[(1R,4R)-2-oxa-5-azabicyclo[2.2.1]heptan-5-yl]phenyl]-1,2,4-triazol-3-amine |
| 669 | N3-(1-isopropylpyrazol-3-yl)-5-methyl-N1-(1-phenyl-1,2,4-triazol-3-yl)benzene-1,3-diamine |
| 802 | N-[3-ethyl-5-[4-(3-methyloxetan-3-yl)piperazin-1-yl]phenyl]-1-(4-fluorophenyl)-1,2,4-triazol-3-amine |
| 649 | N1-[1-(3,5-difluorophenyl)-1,2,4-triazol-3-yl]-5-methyl-N3-(3-morpholinocyclobutyl)benzene-1,3-diamine |
| 861 | N1-[1-(3,5-difluorophenyl)-1,2,4-triazol-3-yl]-5-methyl-N3-(3-morpholinocyclobutyl)benzene-1,3-diamine |
| 792 | N1-[1-(3,4-difluorophenyl)-1,2,4-triazol-3-yl]-5-methyl-N3-(3-morpholinocyclobutyl)benzene-1,3-diamine |
| 826 | N1-[1-(3,4-difluorophenyl)-1,2,4-triazol-3-yl]-5-methyl-N3-(3-morpholinocyclobutyl)benzene-1,3-diamine |
| 643 | 5-methyl-N3-(1-phenyl-1,2,4-triazol-3-yl)-N1-thiazol-2-yl-benzene-1,3-diamine |
| 588 | 5-methyl-N1-(5-methylthiazol-2-yl)-N3-(1-phenyl-1,2,4-triazol-3-yl)benzene-1,3-diamine |
| 676 | 5-methyl-N3-(1-methyl-1,2,4-triazol-3-yl)-N1-(1-phenyl-1,2,4-triazol-3-yl)benzene-1,3-diamine |
| 838 | 5-methyl-N1-oxazol-2-yl-N3-(1-phenyl-1,2,4-triazol-3-yl)benzene-1,3-diamine |
| 790 | 1-(3,5-difluorophenyl)-N-[2-fluoro-5-methyl-3-(3-morpholinoazetidin-1-yl)phenyl]-1,2,4-triazol-3-amine |
| 743 | 1-(3,5-difluorophenyl)-N-[2-fluoro-5-methyl-3-(2-oxa-6-azaspiro[3.3]heptan-6-yl)phenyl]-1,2,4-triazol-3-amine |
| 810 | N3-[1-(3,5-difluorophenyl)-1,2,4-triazol-3-yl]-2-fluoro-5-methyl-N1-tetrahydropyran-4-yl-benzene-1,3-diamine |
| 765 | N3-[1-(3,5-difluorophenyl)-1,2,4-triazol-3-yl]-2-fluoro-5-methyl-N1-tetrahydrofuran-3-yl-benzene-1,3-diamine |
| 699 | 5-methyl-N3-(5-methyl-1H-pyrazol-3-yl)-N1-(1-phenyl-1,2,4-triazol-3-yl)benzene-1,3-diamine |
| 593 | 1-(3,5-difluorophenyl)-N-[3-methyl-5-[4-(2-morpholinoethyl)piperazin-1-yl]phenyl]-1,2,4-triazol-3-amine |
| 850 | 1-(3,5-difluorophenyl)-N-[3-[4-(3-methoxypropyl)piperazin-1-yl]-5-methyl-phenyl]-1,2,4-triazol-3-amine |
| 771 | 1-(3,5-difluorophenyl)-N-[3-methyl-5-(3,3,4-trimethylpiperazin-1-yl)phenyl]-1,2,4-triazol-3-amine |
| 738 | N3-[1-(3,5-difluorophenyl)-1,2,4-triazol-3-yl]-N1,5-dimethyl-N1-(2-morpholinoethyl)benzene-1,3-diamine |
| 814 | 1-(3,5-difluorophenyl)-N-[3-methyl-5-(2-oxa-8-azaspiro[4.5]decan-8-yl)phenyl]-1,2,4-triazol-3-amine |
| 582 | [4-[3-[[1-(3,5-difluorophenyl)-1,2,4-triazol-3-yl]amino]-5-methyl-phenyl]piperazin-1-yl]-morpholino-methanone |
| 858 | N1-[1-(3,5-difluorophenyl)-1,2,4-triazol-3-yl]-5-methyl-N3-(2-morpholinoethyl)benzene-1,3-diamine |
| 589 | [1-[3-[[1-(3,5-difluorophenyl)-1,2,4-triazol-3-yl]amino]-5-methyl-phenyl]-4-piperidyl]-morpholino-methanone |

-continued

| Cmpd No. | IUPAC Name |
|---|---|
| 747 | 1-(3,5-difluorophenyl)-N-[3-[4-[3-(dimethylamino)propyl]piperazin-1-yl]-5-methyl-phenyl]-1,2,4-triazol-3-amine |
| 772 | 1-(3,5-difluorophenyl)-N-[3-methyl-5-[4-(4-methylpiperazin-1-yl)-1-piperidyl]phenyl]-1,2,4-triazol-3-amine |
| 809 | 1-(3,5-difluorophenyl)-N-[3-[4-[2-(dimethylamino)ethyl]piperazin-1-yl]-5-methyl-phenyl]-1,2,4-triazol-3-amine |
| 745 | N-[3-[4-(3,3-difluoroazetidin-1-yl)-1-piperidyl]-5-methyl-phenyl]-1-(3,5-difluorophenyl)-1,2,4-triazol-3-amine |
| 948 | 1-[3-[[1-(3,5-difluorophenyl)-1,2,4-triazol-3-yl]amino]-5-methyl-phenyl]-N,N-dimethyl-piperidin-4-amine |
| 1054 | 1-[1-[3-[[1-(3,5-difluorophenyl)-1,2,4-triazol-3-yl]amino]-5-methyl-phenyl]-4-piperidyl]piperidin-3-ol |
| 1035 | 1-(3,5-difluorophenyl)-N-[3-methyl-5-(4-oxa-7-azaspiro[2.5]octan-7-yl)phenyl]-1,2,4-triazol-3-amine |
| 1026 | 2-[4-[3-[[1-(3,5-difluorophenyl)-1,2,4-triazol-3-yl]amino]-5-methyl-phenyl]-1-methyl-piperazin-2-yl]ethanol |
| 875 | 2-[4-[3-[[1-(3,5-difluorophenyl)-1,2,4-triazol-3-yl]amino]-5-methyl-phenyl]piperazin-1-yl]cyclopentanol |
| 1049 | 5-methyl-N1-(5-methyloxazol-2-yl)-N3-(1-phenyl-1,2,4-triazol-3-yl)benzene-1,3-diamine |
| 1045 | N3-[1-(3,5-difluorophenyl)-1,2,4-triazol-3-yl]-5-methyl-N1-[1-(tetrahydrofuran-3-ylmethyl)-4-piperidyl]benzene-1,3-diamine |
| 917 | N3-[1-(3,5-difluorophenyl)-1,2,4-triazol-3-yl]-N1-[2-(2-ethylmorpholin-4-yl)ethyl]-5-methyl-benzene-1,3-diamine |
| 951 | N1-[1-(3,5-difluorophenyl)-1,2,4-triazol-3-yl]-5-methyl-N3-[(1-morpholinocyclopropyl)methyl]benzene-1,3-diamine |
| 896 | 1-(3,5-difluorophenyl)-N-[3-[4-(3-methoxypropyl)-1,4-diazepan-1-yl]-5-methyl-phenyl]-1,2,4-triazol-3-amine |
| 911 | 1-(3,5-difluorophenyl)-N-[3-methyl-5-(3-morpholino-1-piperidyl)phenyl]-1,2,4-triazol-3-amine |
| 895 | N1-[1-(3,5-difluorophenyl)-1,2,4-triazol-3-yl]-5-methyl-N3-[(2-morpholinocyclopentyl)methyl]benzene-1,3-diamine |
| 1023 | 1-(3,5-difluorophenyl)-N-[3-methyl-5-[4-(2-methylmorpholin-4-yl)-1-piperidyl]phenyl]-1,2,4-triazol-3-amine |
| 1003 | N1-[1-(3,5-difluorophenyl)-1,2,4-triazol-3-yl]-N3-[2-(2,5-dimethylmorpholin-4-yl)ethyl]-5-methyl-benzene-1,3-diamine |
| 968 | N3-[(4-cyclopropylmorpholin-2-yl)methyl]-N1-[1-(3,5-difluorophenyl)-1,2,4-triazol-3-yl]-5-methyl-benzene-1,3-diamine |
| 905 | 1-cyclopentyl-4-[3-[[1-(3,5-difluorophenyl)-1,2,4-triazol-3-yl]amino]-5-methyl-phenyl]piperazin-2-one |
| 1027 | 1-(3,5-difluorophenyl)-N-[3-methyl-5-[2-(pyrrolidin-1-ylmethyl)morpholin-4-yl]phenyl]-1,2,4-triazol-3-amine |
| 1017 | N-[3-[2-(diethylaminomethyl)morpholin-4-yl]-5-methyl-phenyl]-1-(3,5-difluorophenyl)-1,2,4-triazol-3-amine |
| 1047 | 1-(3,5-difluorophenyl)-N-[3-methyl-5-[4-[(1-methyl-3-piperidyl)methyl]piperazin-1-yl]phenyl]-1,2,4-triazol-3-amine |
| 945 | 1-(3,5-difluorophenyl)-N-[3-methyl-5-[4-(3-pyrrolidin-1-ylpropyl)piperazin-1-yl]phenyl]-1,2,4-triazol-3-amine |
| 944 | 1-(3,5-difluorophenyl)-N-[3-methyl-5-[4-(2-pyrrolidin-1-ylethyl)piperazin-1-yl]phenyl]-1,2,4-triazol-3-amine |
| 1025 | 1-(3,5-difluorophenyl)-N-[3-[4-(4-ethylpiperazin-1-yl)-1-piperidyl]-5-methyl-phenyl]-1,2,4-triazol-3-amine |
| 996 | 1-(3,5-difluorophenyl)-N-[3-(5-ethyl-2,5-diazabicyclo[2.2.1]heptan-2-yl)-5-methyl-phenyl]-1,2,4-triazol-3-amine |
| 1020 | N1-[1-(3,5-difluorophenyl)-1,2,4-triazol-3-yl]-5-methyl-N3-[(3-pyrrolidin-1-yloxetan-3-yl)methyl]benzene-1,3-diamine |
| 897 | N3-[1-(3,5-difluorophenyl)-1,2,4-triazol-3-yl]-N1-(1-ethyl-3-piperidyl)-5-methyl-benzene-1,3-diamine |
| 976 | 1-(3,5-difluorophenyl)-N-[3-(4-ethoxy-1-piperidyl)-5-methyl-phenyl]-1,2,4-triazol-3-amine |
| 925 | 1-(3,5-difluorophenyl)-N-[3-methyl-5-[3-methyl-4-(1-methyl-4-piperidyl)piperazin-1-yl]phenyl]-1,2,4-triazol-3-amine |
| 1038 | 1-(3,5-difluorophenyl)-N-[3-methyl-5-(4-pyrrolidin-1-yl-1-piperidyl)phenyl]-1,2,4-triazol-3-amine |
| 1030 | 1-(3,5-difluorophenyl)-N-[3-[2-(2-methoxyethyl)morpholin-4-yl]-5-methyl-phenyl]-1,2,4-triazol-3-amine |
| 889 | N-[3-(1,4-diazabicyclo[3.2.1]octan-4-yl)-5-methyl-phenyl]-1-(3,5-difluorophenyl)-1,2,4-triazol-3-amine |
| 1019 | 1-(3,5-difluorophenyl)-N-[3-(4-isopropoxy-1-piperidyl)-5-methyl-phenyl]-1,2,4-triazol-3-amine |
| 1001 | 1-(3,5-difluorophenyl)-N-[3-[4-(4-methoxybutyl)piperazin-1-yl]-5-methyl-phenyl]-1,2,4-triazol-3-amine |
| 987 | N-[3-[4-[2-(diethylamino)ethyl]piperazin-1-yl]-5-methyl-phenyl]-1-(3,5-difluorophenyl)-1,2,4-triazol-3-amine |

-continued

| Cmpd No. | IUPAC Name |
| --- | --- |
| 1068 | 1-(3,5-difluorophenyl)-N-[3-[4-(4-methoxy-1-piperidyl)-1-piperidyl]-5-methyl-phenyl]-1,2,4-triazol-3-amine |
| 1006 | 1-(3,5-difluorophenyl)-N-[3-(4-methoxy-1-piperidyl)-5-methyl-phenyl]-1,2,4-triazol-3-amine |
| 927 | 1-(3,5-difluorophenyl)-N-[3-[2-(isopropoxymethyl)morpholin-4-yl]-5-methyl-phenyl]-1,2,4-triazol-3-amine |
| 973 | 1-(3,5-difluorophenyl)-N-[3-[4-(2-ethoxyethyl)piperazin-1-yl]-5-methyl-phenyl]-1,2,4-triazol-3-amine |
| 956 | 1-(3,5-difluorophenyl)-N-[3-methyl-5-[4-(1-methyl-4-piperidyl)piperazin-1-yl]phenyl]-1,2,4-triazol-3-amine |
| 949 | 1-(3,5-difluorophenyl)-N-[3-[4-(1,4-dioxan-2-ylmethyl)piperazin-1-yl]-5-methyl-phenyl]-1,2,4-triazol-3-amine |
| 1018 | 1-(3,5-difluorophenyl)-N-[3-[2-[(dimethylamino)methyl]morpholin-4-yl]-5-methyl-phenyl]-1,2,4-triazol-3-amine |
| 871 | 1-(3,5-difluorophenyl)-N-[3-methyl-5-(3-methyl-4-morpholino-pyrrolidin-1-yl)phenyl]-1,2,4-triazol-3-amine |
| 903 | N1-[1-(3,5-difluorophenyl)-1,2,4-triazol-3-yl]-N3-[(4-isobutylmorpholin-2-yl)methyl]-5-methyl-benzene-1,3-diamine |
| 1070 | N1-(1-cyclobutyl-4-piperidyl)-N3-[1-(3,5-difluorophenyl)-1,2,4-triazol-3-yl]-5-methyl-benzene-1,3-diamine |
| 931 | N3-[1-(3,5-difluorophenyl)-1,2,4-triazol-3-yl]-5-methyl-N1-(1-methyl-2-morpholino-ethyl)benzene-1,3-diamine |
| 928 | N1-[1-(3,5-difluorophenyl)-1,2,4-triazol-3-yl]-5-methyl-N3-[2-(2-methylmorpholin-4-yl)ethyl]benzene-1,3-diamine |
| 1064 | N3-[1-(3,5-difluorophenyl)-1,2,4-triazol-3-yl]-5-methyl-N1-(1-tetrahydrofuran-3-yl-4-piperidyl)benzene-1,3-diamine |
| 890 | 1-(3,5-difluorophenyl)-N-[3-methyl-5-(3-tetrahydrofuran-3-ylazetidin-1-yl)phenyl]-1,2,4-triazol-3-amine |
| 974 | N3-[1-(3,5-difluorophenyl)-1,2,4-triazol-3-yl]-N1-[2-(5-ethyl-2-methyl-morpholin-4-yl)ethyl]-5-methyl-benzene-1,3-diamine |
| 1013 | N3-[1-(3,5-difluorophenyl)-1,2,4-triazol-3-yl]-5-methyl-N1-(1-tetrahydropyran-4-yl-4-piperidyl)benzene-1,3-diamine |
| 872 | N3-[1-(3,5-difluorophenyl)-1,2,4-triazol-3-yl]-N1-[2-(3-ethylmorpholin-4-yl)ethyl]-5-methyl-benzene-1,3-diamine |
| 991 | [4-[3-[[1-(3,5-difluorophenyl)-1,2,4-triazol-3-yl]amino]-5-methyl-phenyl]piperazin-1-yl]-tetrahydropyran-4-yl-methanone |
| 870 | 1-(3,5-difluorophenyl)-N-[2-fluoro-3-methyl-5-(3-morpholinoazetidin-1-yl)phenyl]-1,2,4-triazol-3-amine |
| 984 | 1-(3,5-difluorophenyl)-N-[3-methyl-5-[4-(morpholinomethyl)-1-piperidyl]phenyl]-1,2,4-triazol-3-amine |
| 1036 | 2-[4-[3-[[1-(3,5-difluorophenyl)-1,2,4-triazol-3-yl]amino]-5-methyl-phenyl]piperazin-1-yl]ethanol |
| 1024 | 1-[4-[3-[[1-(3,5-difluorophenyl)-1,2,4-triazol-3-yl]amino]-5-methyl-phenyl]-3-methyl-piperazin-1-yl]-2-methyl-propan-2-ol |
| 912 | N3-[1-(3,5-difluorophenyl)-1,2,4-triazol-3-yl]-5-methyl-N1-(2-morpholinocyclopentyl)benzene-1,3-diamine |
| 1033 | 2-[2-[4-[3-[[1-(3,5-difluorophenyl)-1,2,4-triazol-3-yl]amino]-5-methyl-phenyl]piperazin-1-yl]ethoxy]ethanol |
| 879 | 1-[1-[3-[[1-(3,5-difluorophenyl)-1,2,4-triazol-3-yl]amino]-5-methyl-phenyl]-4-piperidyl]piperidin-4-ol |
| 1079 | [1-[3-[[1-(3,5-difluorophenyl)-1,2,4-triazol-3-yl]amino]-5-methyl-phenyl]-3-fluoro-azetidin-3-yl]methanol |
| 1078 | 1-[4-[3-[[1-(3,5-difluorophenyl)-1,2,4-triazol-3-yl]amino]-5-methyl-phenyl]piperazin-1-yl]-3-(dimethylamino)propan-2-ol |
| 990 | 3-[4-[3-[[1-(3,5-difluorophenyl)-1,2,4-triazol-3-yl]amino]-5-methyl-phenyl]piperazin-1-yl]propan-1-ol |
| 964 | 3-[4-[3-[[1-(3,5-difluorophenyl)-1,2,4-triazol-3-yl]amino]-5-methyl-phenyl]piperazin-1-yl]propan-1-ol |
| 881 | N3-[1-(3,5-difluorophenyl)-1,2,4-triazol-3-yl]-5-methyl-N1-[1-(oxetan-3-yl)azetidin-3-yl]benzene-1,3-diamine |
| 985 | N3-[1-(3,5-difluorophenyl)-1,2,4-triazol-3-yl]-5-methyl-N1-(2-morpholinobutyl)benzene-1,3-diamine |
| 901 | 1-(3,5-difluorophenyl)-N-[3-methyl-5-(1-oxa-7-azaspiro[3.4]octan-7-yl)phenyl]-1,2,4-triazol-3-amine |
| 1005 | 1-(3,5-difluorophenyl)-N-[3-[4-(2-isopropoxyethyl)piperazin-1-yl]-5-methyl-phenyl]-1,2,4-triazol-3-amine |
| 1067 | 4-[3-[[1-(3,5-difluorophenyl)-1,2,4-triazol-3-yl]amino]-5-methyl-phenyl]-1-(2-methoxyethyl)piperazin-2-one |
| 878 | 2-[4-[3-[[1-(3,5-difluorophenyl)-1,2,4-triazol-3-yl]amino]-5-methyl-phenyl]piperazin-1-yl]cyclohexanol |
| 953 | N3-[1-(3,5-difluorophenyl)-1,2,4-triazol-3-yl]-4-fluoro-5-methyl-N1-tetrahydrofuran-3-yl-benzene-1,3-diamine |
| 1062 | N1-[1-(3,5-difluorophenyl)-1,2,4-triazol-3-yl]-5-methyl-N3-[(4-methylmorpholin-3-yl)methyl]benzene-1,3-diamine |
| 958 | 2-[4-[3-[[1-(3,5-difluorophenyl)-1,2,4-triazol-3-yl]amino]-5-methyl-phenyl]morpholin-2-yl]ethanol |

-continued

| Cmpd No. | IUPAC Name |
|---|---|
| 1016 | N3-[1-(3,5-difluorophenyl)-1,2,4-triazol-3-yl]-4-fluoro-5-methyl-N1-(3-methyloxetan-3-yl)benzene-1,3-diamine |
| 1021 | N3-[1-(3,5-difluorophenyl)-1,2,4-triazol-3-yl]-4-fluoro-5-methyl-N1-tetrahydropyran-4-yl-benzene-1,3-diamine |
| 988 | 1-(3,5-difluorophenyl)-N-[3-methyl-5-[4-(3-methylmorpholin-4-yl)-1-piperidyl]phenyl]-1,2,4-triazol-3-amine |
| 877 | 3-[1-[3-[[1-(3,5-difluorophenyl)-1,2,4-triazol-3-yl]amino]-5-methyl-phenyl]-4-piperidyl]propan-1-ol |
| 986 | 1-(3,5-difluorophenyl)-N-[3-methyl-5-[(3S)-3-pyrrolidin-1-ylpyrrolidin-1-yl]phenyl]-1,2,4-triazol-3-amine |
| 995 | 1-[4-[3-[[1-(3,5-difluorophenyl)-1,2,4-triazol-3-yl]amino]-5-methyl-phenyl]piperazin-1-yl]propan-2-ol |
| 1040 | 1-[1-[3-[[1-(3,5-difluorophenyl)-1,2,4-triazol-3-yl]amino]-5-methyl-phenyl]pyrrolidin-3-yl]pyrrolidin-3-ol |
| 1011 | 1-(3,5-difluorophenyl)-N-[3-[4-(2-methoxyethyl)-3-methyl-piperazin-1-yl]-5-methyl-phenyl]-1,2,4-triazol-3-amine |
| 880 | N3-[1-(3,5-difluorophenyl)-1,2,4-triazol-3-yl]-5-methyl-N1-[1-(2-morpholinoethyl)pyrrolidin-3-yl]benzene-1,3-diamine |
| 1082 | N1-[1-(3,5-difluorophenyl)-1,2,4-triazol-3-yl]-5-methyl-N3-[2-(3-methylmorpholin-4-yl)ethyl]benzene-1,3-diamine |
| 874 | 2-[1-[3-[[1-(3,5-difluorophenyl)-1,2,4-triazol-3-yl]amino]-5-methyl-phenyl]-4-piperidyl]ethanol |
| 1050 | N3-[1-(3,5-difluorophenyl)-1,2,4-triazol-3-yl]-N1-[1-(2-methoxyethyl)-3-piperidyl]-5-methyl-benzene-1,3-diamine |
| 1012 | 1-(3,5-difluorophenyl)-N-[3-methyl-5-[2-(morpholinomethyl)pyrrolidin-1-yl]phenyl]-1,2,4-triazol-3-amine |
| 930 | N3-[1-(3,5-difluorophenyl)-1,2,4-triazol-3-yl]-N1-[1-(2-methoxyethyl)-4-piperidyl]-5-methyl-benzene-1,3-diamine |
| 1010 | 1-[3-[[1-(3,5-difluorophenyl)-1,2,4-triazol-3-yl]amino]-5-methyl-phenyl]-4-pyrrolidin-1-yl-pyrrolidin-3-ol |
| 1014 | 1-(3,5-difluorophenyl)-N-[3-methyl-5-(4-tetrahydrofuran-3-yloxy-1-piperidyl)phenyl]-1,2,4-triazol-3-amine |
| 983 | 1-(3,5-difluorophenyl)-N-[3-methyl-5-[3-(morpholinomethyl)pyrrolidin-1-yl]phenyl]-1,2,4-triazol-3-amine |
| 894 | N3-[1-(3,5-difluorophenyl)-1,2,4-triazol-3-yl]-N1-[1-(2-methoxyethyl)pyrrolidin-3-yl]-5-methyl-benzene-1,3-diamine |
| 939 | N3-[1-(3,5-difluorophenyl)-1,2,4-triazol-3-yl]-5-methyl-N1-(2-morpholinocyclohexyl)benzene-1,3-diamine |
| 972 | 1-(3,5-difluorophenyl)-N-[3-methyl-5-(2-tetrahydrofuran-2-ylmorpholin-4-yl)phenyl]-1,2,4-triazol-3-amine |
| 1063 | 1-(3,5-difluorophenyl)-N-[3-[4-(2-ethoxyethyl)-3-methyl-piperazin-1-yl]-5-methyl-phenyl]-1,2,4-triazol-3-amine |
| 936 | 1-(3,5-difluorophenyl)-N-[3-methyl-5-[4-(tetrahydrofuran-3-ylmethyl)piperazin-1-yl]phenyl]-1,2,4-triazol-3-amine |
| 888 | 1-(3,5-difluorophenyl)-N-[3-methyl-5-(2-tetrahydrofuran-2-ylmorpholin-4-yl)phenyl]-1,2,4-triazol-3-amine |
| 1077 | [1-[[1-[3-[[1-(3,5-difluorophenyl)-1,2,4-triazol-3-yl]amino]-5-methyl-phenyl]pyrrolidin-2-yl]methyl]pyrrolidin-2-yl]methanol |
| 933 | 1-(3,5-difluorophenyl)-N-[3-[4-[2-(dimethylamino)ethoxy]-1-piperidyl]-5-methyl-phenyl]-1,2,4-triazol-3-amine |
| 904 | 2-[4-[3-[[1-(3,5-difluorophenyl)-1,2,4-triazol-3-yl]amino]-5-methyl-phenyl]piperazin-1-yl]butan-1-ol |
| 893 | N3-[1-(3,5-difluorophenyl)-1,2,4-triazol-3-yl]-N1-[(4-ethylmorpholin-2-yl)methyl]-5-methyl-benzene-1,3-diamine |
| 892 | 1-(3,5-difluorophenyl)-N-[3-methyl-5-[4-(1-methyl-3-piperidyl)piperazin-1-yl]phenyl]-1,2,4-triazol-3-amine |
| 950 | 1-(3,5-difluorophenyl)-N-[3-[4-(2-fluoroethoxy)-1-piperidyl]-5-methyl-phenyl]-1,2,4-triazol-3-amine |
| 906 | 1-(3,5-difluorophenyl)-N-[3-(3,7-dioxa-10-azaspiro[5.6]dodecan-10-yl)-5-methyl-phenyl]-1,2,4-triazol-3-amine |
| 954 | 1-(3,5-difluorophenyl)-N-[3-methyl-5-[2-[(4-methylpiperazin-1-yl)methyl]morpholin-4-yl]phenyl]-1,2,4-triazol-3-amine |
| 962 | 1-(3,5-difluorophenyl)-N-[3-[4-(2-ethoxyethoxy)-1-piperidyl]-5-methyl-phenyl]-1,2,4-triazol-3-amine |
| 1057 | 1-(3,5-difluorophenyl)-N-[3-methyl-5-(8-oxa-4-azabicyclo[4.2.0]octan-4-yl)phenyl]-1,2,4-triazol-3-amine |
| 1031 | 1-[3-[[3-[[1-(3,5-difluorophenyl)-1,2,4-triazol-3-yl]amino]-5-methyl-anilino]methyl]azetidin-1-yl]ethanone |
| 946 | 2-[3-[[3-[[1-(3,5-difluorophenyl)-1,2,4-triazol-3-yl]amino]-5-methyl-anilino]methyl]azetidin-1-yl]propane-1,3-diol |
| 1087 | N-[3-[2-(cyclopropylmethoxymethyl)morpholin-4-yl]-5-methyl-phenyl]-1-(3,5-difluorophenyl)-1,2,4-triazol-3-amine |
| 902 | 2-[4-[3-[[1-(3,5-difluorophenyl)-1,2,4-triazol-3-yl]amino]-5-methyl-phenyl]-2-methyl-piperazin-1-yl]ethanol |

-continued

| Cmpd No. | IUPAC Name |
|---|---|
| 960 | N3-[1-(3,5-difluorophenyl)-1,2,4-triazol-3-yl]-5-methyl-N1-[1-(morpholinomethyl)propyl]benzene-1,3-diamine |
| 924 | 1-(3,5-difluorophenyl)-N-[3-methyl-5-(7-oxa-1-azaspiro[3.5]nonan-1-yl)phenyl]-1,2,4-triazol-3-amine |
| 1060 | 1-(3,5-difluorophenyl)-N-[3-methyl-5-(3-pyrrolidin-1-ylpyrrolidin-1-yl)phenyl]-1,2,4-triazol-3-amine |
| 919 | 1-(3,5-difluorophenyl)-N-[3-methyl-5-[(2S)-2-(morpholinomethyl)pyrrolidin-1-yl]phenyl]-1,2,4-triazol-3-amine |
| 1056 | 1-[4-[3-[[1-(3,5-difluorophenyl)-1,2,4-triazol-3-yl]amino]-5-methyl-phenyl]-2-ethyl-piperazin-1-yl]propan-2-ol |
| 981 | N-[3-(3,4,4a,5,7,7a-hexahydro-2H-furo[3,4-b]pyridin-1-yl)-5-methyl-phenyl]-1-(3,5-difluorophenyl)-1,2,4-triazol-3-amine |
| 1074 | 1-(3,5-difluorophenyl)-N-[3-methyl-5-[4-(2-pyrrolidin-1-ylethoxy)-1-piperidyl]phenyl]-1,2,4-triazol-3-amine |
| 891 | N3-[1-(3,5-difluorophenyl)-1,2,4-triazol-3-yl]-5-methyl-N1-[1-(tetrahydrofuran-2-ylmethyl)-4-piperidyl]benzene-1,3-diamine |
| 1083 | 1-(3,5-difluorophenyl)-N-[3-methyl-5-(3-tetrahydrofuran-3-ylpyrrolidin-1-yl)phenyl]-1,2,4-triazol-3-amine |
| 975 | 1-(3,5-difluorophenyl)-N-[3-methyl-5-[3-(4-methylpiperazin-1-yl)azetidin-1-yl]phenyl]-1,2,4-triazol-3-amine |
| 957 | 1-[4-[3-[[1-(3,5-difluorophenyl)-1,2,4-triazol-3-yl]amino]-5-methyl-phenyl]piperazin-1-yl]butan-2-ol |
| 915 | N3-[1-(3,5-difluorophenyl)-1,2,4-triazol-3-yl]-2-fluoro-5-methyl-N1-(oxetan-3-yl)benzene-1,3-diamine |
| 1043 | 2-[4-[3-[[1-(3,5-difluorophenyl)-1,2,4-triazol-3-yl]amino]-2-fluoro-5-methyl-phenyl]piperazin-1-yl]ethanol |
| 969 | N3-[1-(3,5-difluorophenyl)-1,2,4-triazol-3-yl]-2-fluoro-N1,5-dimethyl-N1-(oxetan-3-yl)benzene-1,3-diamine |
| 1015 | 2-[[1-[3-[[1-(3,5-difluorophenyl)-1,2,4-triazol-3-yl]amino]-5-methyl-phenyl]-4-piperidyl]-methyl-amino]ethanol |
| 900 | 1-[4-[3-[[1-(3,5-difluorophenyl)-1,2,4-triazol-3-yl]amino]-5-methyl-phenyl]piperazin-1-yl]-3-ethoxy-propan-2-ol |
| 941 | 1-[4-[3-[[1-(3,5-difluorophenyl)-1,2,4-triazol-3-yl]amino]-5-methyl-phenyl]-2-methyl-piperazin-1-yl]-2-methyl-propan-2-ol |
| 1073 | [4-[3-[[1-(3,5-difluorophenyl)-1,2,4-triazol-3-yl]amino]-5-methyl-phenyl]morpholin-2-yl]methanol |
| 873 | N3-[1-(3,5-difluorophenyl)-1,2,4-triazol-3-yl]-N1-[1-(2-fluoroethyl)-3-piperidyl]-5-methyl-benzene-1,3-diamine |
| 885 | 1-(3,5-difluorophenyl)-N-[3-methyl-5-[2,2,3,3,5,5,6,6-octadeuterio-4-(1,4-dioxan-2-ylmethyl)piperazin-1-yl]phenyl]-1,2,4-triazol-3-amine |
| 935 | 1-(3,5-difluorophenyl)-N-[3-methyl-5-[2,2,3,3,5,5,6,6-octadeuterio-4-(2,2-difluoroethyl)piperazin-1-yl]phenyl]-1,2,4-triazol-3-amine |
| 922 | 2-[2,2,3,3,5,5,6,6-octadeuterio-4-[3-[[1-(3,5-difluorophenyl)-1,2,4-triazol-3-yl]amino]-5-methyl-phenyl]piperazin-1-yl]ethanol |
| 961 | cyclopropyl-[2,2,3,3,5,5,6,6-octadeuterio-4-[3-[[1-(3,5-difluorophenyl)-1,2,4-triazol-3-yl]amino]-5-methyl-phenyl]piperazin-1-yl]methanone |
| 1044 | 1-[2,2,3,3,5,5,6,6-octadeuterio-4-[3-[[1-(3,5-difluorophenyl)-1,2,4-triazol-3-yl]amino]-5-methyl-phenyl]piperazin-1-yl]ethanone |
| 959 | 2,2,2-trideuterio-1-[2,2,3,3,5,5,6,6-octadeuterio-4-[3-[[1-(3,5-difluorophenyl)-1,2,4-triazol-3-yl]amino]-5-methyl-phenyl]piperazin-1-yl]ethanone |
| 926 | 1-(3,5-difluorophenyl)-N-[3-methyl-5-(2,2,3,3,5,5,6,6-octadeuterio-4-tetrahydropyran-3-yl-piperazin-1-yl)phenyl]-1,2,4-triazol-3-amine |
| 1042 | 1-(3,5-difluorophenyl)-N-[3-methyl-5-(2,2,3,3,5,5,6,6-octadeuterio-4-tetrahydrofuran-3-yl-piperazin-1-yl)phenyl]-1,2,4-triazol-3-amine |
| 994 | N-[3-(4-cyclobutyl-2,2,3,3,5,5,6,6-octadeuterio-piperazin-1-yl)-5-methyl-phenyl]-1-(3,5-difluorophenyl)-1,2,4-triazol-3-amine |
| 947 | 1-(3,5-difluorophenyl)-N-[3-methyl-5-(2,2,3,3,5,5,6,6-octadeuterio-4-ethyl-piperazin-1-yl)phenyl]-1,2,4-triazol-3-amine |
| 884 | N3-[1-(3,5-difluorophenyl)-1,2,4-triazol-3-yl]-5-methyl-N1-(3-pyrrolidin-1-yltetrahydropyran-4-yl)benzene-1,3-diamine |
| 914 | 1-(3,5-difluorophenyl)-N-[3-methyl-5-[4-(tetrahydrofuran-2-ylmethyl)piperazin-1-yl]phenyl]-1,2,4-triazol-3-amine |
| 1046 | N1-[1-(3,5-difluorophenyl)-1,2,4-triazol-3-yl]-5-methyl-N3-[(1-tetrahydropyran-4-yl-4-piperidyl)methyl]benzene-1,3-diamine |
| 920 | 1-(3,5-difluorophenyl)-N-[3-methyl-5-(2-methyl-4-morpholino-pyrrolidin-1-yl)phenyl]-1,2,4-triazol-3-amine |
| 1007 | N3-[1-(3,5-difluorophenyl)-1,2,4-triazol-3-yl]-2-fluoro-5-methyl-N1-(2-morpholinocyclopentyl)benzene-1,3-diamine |

-continued

| Cmpd No. | IUPAC Name |
|---|---|
| 1072 | 1-(3,5-difluorophenyl)-N-[2-fluoro-3-(2-isopropyl-2,6-diazaspiro[3.3]heptan-6-yl)-5-methyl-phenyl]-1,2,4-triazol-3-amine |
| 979 | 1-(3,5-difluorophenyl)-N-[3-methyl-5-[2,2,3,3,5,5,6,6-octadeuterio-4-(oxetan-3-yl)piperazin-1-yl]phenyl]-1,2,4-triazol-3-amine |
| 916 | 1-(3,5-difluorophenyl)-N-[3-methyl-5-(2,2,3,3,5,5,6,6-octadeuteriopiperazin-1-yl)phenyl]-1,2,4-triazol-3-amine |
| 963 | N3-[1-(3,5-difluorophenyl)-1,2,4-triazol-3-yl]-N1-[2-(3-ethylmorpholin-4-yl)ethyl]-2-fluoro-5-methyl-benzene-1,3-diamine |
| 943 | N1-(1-cyclobutyl-4-piperidyl)-N3-[1-(3,5-difluorophenyl)-1,2,4-triazol-3-yl]-2-fluoro-5-methyl-benzene-1,3-diamine |
| 1086 | N-[3-methyl-5-[4-[1,2,2,2-tetradeuterio-1-(trideuteriomethyl)ethyl]piperazin-1-yl]phenyl]-1-phenyl-1,2,4-triazol-3-amine |
| 929 | N-[3-[4-(1-deuterio-1-methyl-ethyl)piperazin-1-yl]-5-methyl-phenyl]-1-phenyl-1,2,4-triazol-3-amine |
| 932 | N1-[1-(3,5-difluorophenyl)-1,2,4-triazol-3-yl]-N3-(1,4-dioxan-2-ylmethyl)-5-methyl-benzene-1,3-diamine |
| 934 | 4-[3-[[1-(3,5-difluorophenyl)-1,2,4-triazol-3-yl]amino]-5-methyl-anilino]-1-(2-methoxyethyl)pyrrolidin-2-one |
| 937 | N1-[1-(3,5-difluorophenyl)-1,2,4-triazol-3-yl]-N3-[[1-(methoxymethyl)cyclopropyl]methyl]-5-methyl-benzene-1,3-diamine |
| 882 | N1-[1-(3,5-difluorophenyl)-1,2,4-triazol-3-yl]-N3-[2-(2,6-dimethylmorpholin-4-yl)propyl]-5-methyl-benzene-1,3-diamine |
| 970 | N3-[1-(3,5-difluorophenyl)-1,2,4-triazol-3-yl]-N1-(2,2-dimethyltetrahydropyran-4-yl)-5-methyl-benzene-1,3-diamine |
| 992 | N1-[1-(2,2-difluoroethyl)-4-piperidyl]-N3-[1-(3,5-difluorophenyl)-1,2,4-triazol-3-yl]-5-methyl-benzene-1,3-diamine |
| 938 | 1-[[3-[[1-(3,5-difluorophenyl)-1,2,4-triazol-3-yl]amino]-5-methyl-anilino]methyl]-N,N-dimethyl-cyclopentanecarboxamide |
| 899 | N1-[1-(3,5-difluorophenyl)-1,2,4-triazol-3-yl]-5-methyl-N3-(3,3,3-trifluoro-2-morpholino-propyl)benzene-1,3-diamine |
| 1008 | N3-[2-(cyclobutoxy)ethyl]-N1-[1-(3,5-difluorophenyl)-1,2,4-triazol-3-yl]-5-methyl-benzene-1,3-diamine |
| 1051 | 1-(3,5-difluorophenyl)-N-[3-methyl-5-[2-(methylsulfonylmethyl)pyrrolidin-1-yl]phenyl]-1,2,4-triazol-3-amine |
| 1048 | N3-[1-(3,5-difluorophenyl)-1,2,4-triazol-3-yl]-N1-(2,6-dioxaspiro[4.5]decan-9-yl)-5-methyl-benzene-1,3-diamine |
| 942 | N3-(cyclopropylmethyl)-N1-[1-(3,5-difluorophenyl)-1,2,4-triazol-3-yl]-5-methyl-benzene-1,3-diamine |
| 918 | N1-(2-cyclopropyltetrahydropyran-4-yl)-N3-[1-(3,5-difluorophenyl)-1,2,4-triazol-3-yl]-5-methyl-benzene-1,3-diamine |
| 1075 | 1-[3-[3-[[1-(3,5-difluorophenyl)-1,2,4-triazol-3-yl]amino]-5-methyl-anilino]-3-methyl-azetidin-1-yl]-2-methoxy-ethanone |
| 1084 | tert-butyl 3-[[3-[[1-(3,5-difluorophenyl)-1,2,4-triazol-3-yl]amino]-5-methyl-anilino]methyl]azetidine-1-carboxylate |
| 1037 | 1-(3,5-difluorophenyl)-N-[3-methyl-5-(3-methylsulfonylazetidin-1-yl)phenyl]-1,2,4-triazol-3-amine |
| 1059 | N1-(1-cyclopropylethyl)-N3-[1-(3,5-difluorophenyl)-1,2,4-triazol-3-yl]-5-methyl-benzene-1,3-diamine |
| 993 | 2-[3-[[1-(3,5-difluorophenyl)-1,2,4-triazol-3-yl]amino]-5-methyl-anilino]-1-pyrrolidin-1-yl-ethanone |
| 940 | N1-[1-(3,5-difluorophenyl)-1,2,4-triazol-3-yl]-5-methyl-N3-[2-(1-oxo-1,4-thiazinan-4-yl)ethyl]benzene-1,3-diamine |
| 1004 | N1-[1-(3,5-difluorophenyl)-1,2,4-triazol-3-yl]-5-methyl-N3-[(3-methyl-4,5-dihydroisoxazol-5-yl)methyl]benzene-1,3-diamine |
| 1076 | 1-[3-[[1-(3,5-difluorophenyl)-1,2,4-triazol-3-yl]amino]-5-methyl-phenyl]-3-methyl-azetidine-3-carbonitrile |
| 1029 | N1-[1-(3,5-difluorophenyl)-1,2,4-triazol-3-yl]-N3-[(1-methoxycyclobutyl)methyl]-5-methyl-benzene-1,3-diamine |
| 921 | 2-[1-[3-[[1-(3,5-difluorophenyl)-1,2,4-triazol-3-yl]amino]-5-methyl-phenyl]azetidin-3-yl]acetonitrile |
| 887 | 1-[3-[[1-(3,5-difluorophenyl)-1,2,4-triazol-3-yl]amino]-5-methyl-anilino]-N,N-dimethyl-cyclobutanecarboxamide |
| 1065 | N3-[1-(3,5-difluorophenyl)-1,2,4-triazol-3-yl]-N1-(2-methoxycyclopentyl)-5-methyl-benzene-1,3-diamine |
| 1032 | N-[3-(2,2,3,3,4,4,5,5,6,6-decadeuterio-1-piperidyl)-5-(trifluoromethyl)phenyl]-1-(3,5-difluorophenyl)-1,2,4-triazol-3-amine |
| 876 | N-[3-(2,2,3,3,4,4,5,5,6,6-decadeuterio-1-piperidyl)-5-(difluoromethyl)phenyl]-1-(3,5-difluorophenyl)-1,2,4-triazol-3-amine |

-continued

| Cmpd No. | IUPAC Name |
|---|---|
| 883 | cyclopropyl-[2,2,3,3,5,5,6,6-octadeuterio-4-[3-[[1-(3,5-difluorophenyl)-1,2,4-triazol-3-yl]amino]-5-(trifluoromethyl)phenyl]piperazin-1-yl]methanone |
| 1041 | cyclopropyl-[2,2,3,3,5,5,6,6-octadeuterio-4-[3-(difluoromethyl)-5-[[1-(3,5-difluorophenyl)-1,2,4-triazol-3-yl]amino]phenyl]piperazin-1-yl]methanone |
| 1066 | 1-(3,4-difluorophenyl)-N-[3-methyl-5-(2,2,3,3,5,5,6,6-octadeuteriomorpholin-4-yl)phenyl]-1,2,4-triazol-3-amine |
| 982 | 1-(3,5-difluorophenyl)-N-[3-methyl-5-(2,2,3,3,5,5,6,6-octadeuteriomorpholin-4-yl)phenyl]-1,2,4-triazol-3-amine |
| 1039 | N-[3-[4-(3-deuteriotetrahydrofuran-3-yl)piperazin-1-yl]-5-methyl-phenyl]-1-phenyl-1,2,4-triazol-3-amine |
| 1091 | 5-deuterio-N-[3-methyl-5-[4-(oxetan-3-yl)piperazin-1-yl]phenyl]-1-[3-(trifluoromethyl)phenyl]-1,2,4-triazol-3-amine |
| 1092 | 2-[1-[3-[[5-deuterio-1-(3,5-difluorophenyl)-1,2,4-triazol-3-yl]amino]-5-methyl-phenyl]azetidin-3-yl]propan-2-ol |
| 1095 | N-[3-(2,2,3,3,4,4,5,5,6,6-decadeuterio-1-piperidyl)-5-(trifluoromethyl)phenyl]-1-(3,4-difluorophenyl)-1,2,4-triazol-3-amine |
| 1096 | cyclopropyl-[2,2,3,3,5,5,6,6-octadeuterio-4-[3-(difluoromethyl)-5-[[1-(3,4-difluorophenyl)-1,2,4-triazol-3-yl]amino]phenyl]piperazin-1-yl]methanone |
| 1097 | 1-(3,5-difluorophenyl)-N-[3-methyl-5-[3-(2,2,3,3,5,5,6,6-octadeuteriomorpholin-4-yl)azetidin-1-yl]phenyl]-1,2,4-triazol-3-amine |
| 1098 | 1-(3,4-difluorophenyl)-N-[3-methyl-5-[3-(2,2,3,3,5,5,6,6-octadeuteriomorpholin-4-yl)azetidin-1-yl]phenyl]-1,2,4-triazol-3-amine |
| 1099 | N-[3-(2,2,3,3,4,4,5,5,6,6-decadeuterio-1-piperidyl)-5-(difluoromethyl)phenyl]-1-(3,4-difluorophenyl)-1,2,4-triazol-3-amine |
| 1109 | N3-benzyl-N1-[1-(3,5-difluorophenyl)-1,2,4-triazol-3-yl]-2-fluoro-5-methyl-benzene-1,3-diamine |
| 1112 | [4-[3-[[1-(3,5-difluorophenyl)-1,2,4-triazol-3-yl]amino]-2-fluoro-5-methyl-phenyl]piperazin-1-yl]-tetrahydropyran-4-yl-methanone |
| 1113 | 1-(3,5-difluorophenyl)-N-[2-fluoro-5-methyl-3-[3-methyl-4-(1-methyl-4-piperidyl)piperazin-1-yl]phenyl]-1,2,4-triazol-3-amine |
| 1114 | N3-[1-(3,5-difluorophenyl)-1,2,4-triazol-3-yl]-N1-[2-(2-ethylmorpholin-4-yl)ethyl]-2-fluoro-5-methyl-benzene-1,3-diamine |
| 1115 | N3-[1-(3,5-difluorophenyl)-1,2,4-triazol-3-yl]-2-fluoro-5-methyl-N1-[1-(tetrahydrofuran-3-ylmethyl)-4-piperidyl]benzene-1,3-diamine |
| 1116 | N3-[1-(3,5-difluorophenyl)-1,2,4-triazol-3-yl]-2-fluoro-5-methyl-N1-[1-(tetrahydrofuran-2-ylmethyl)-4-piperidyl]benzene-1,3-diamine |
| 1117 | 1-(3,5-difluorophenyl)-N-[2-fluoro-5-methyl-3-[3-(4-methylpiperazin-1-yl)azetidin-1-yl]phenyl]-1,2,4-triazol-3-amine |
| 1118 | N3-[(4-cyclopropylmorpholin-2-yl)methyl]-N1-[1-(3,5-difluorophenyl)-1,2,4-triazol-3-yl]-2-fluoro-5-methyl-benzene-1,3-diamine |
| 1119 | N3-[1-(3,5-difluorophenyl)-1,2,4-triazol-3-yl]-2-fluoro-5-methyl-N1-(1-methyl-2-morpholino-ethyl)benzene-1,3-diamine |
| 1120 | 1-(3,5-difluorophenyl)-N-[2-fluoro-3-[2-(isopropoxymethyl)morpholin-4-yl]-5-methyl-phenyl]-1,2,4-triazol-3-amine |
| 1121 | N1-[1-(3,5-difluorophenyl)-1,2,4-triazol-3-yl]-2-fluoro-5-methyl-N3-[(1-morpholinocyclopropyl)methyl]benzene-1,3-diamine |
| 1122 | 1-(3,5-difluorophenyl)-N-[2-fluoro-5-methyl-3-(3-tetrahydrofuran-3-ylazetidin-1-yl)phenyl]-1,2,4-triazol-3-amine |
| 1123 | 1-[4-[3-[[1-(3,5-difluorophenyl)-1,2,4-triazol-3-yl]amino]-2-fluoro-5-methyl-phenyl]-2-methyl-piperazin-1-yl]-2-methyl-propan-2-ol |

807

Scheme J: General Route J for Preparation of Compounds of Formula I or I′

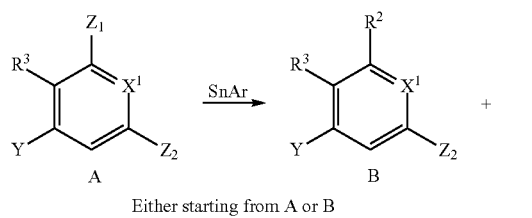

Either starting from A or B

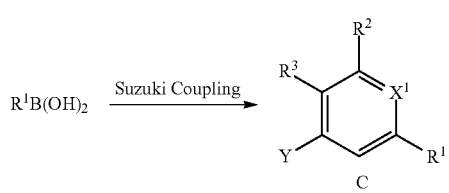

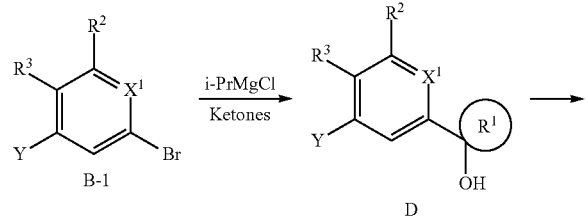

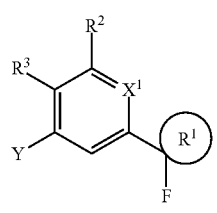

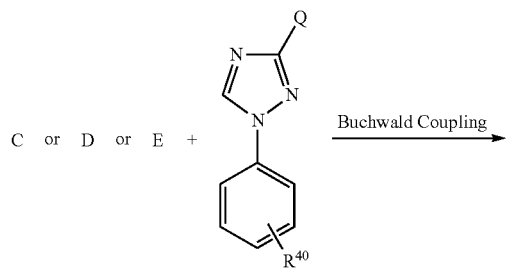

808
-continued a) Deprotection
b) Reductive amination or Acylation

Or a) Reduction
a) Deprotection
b) Reductive amination or Acylation $R^{60}$ is $R^1$, or $X^1$ = CH, N
Y = NH$_2$, Cl, Br
$Z_1, Z_2$ = Cl, Br
Q = NH$_2$, Br Compounds of the invention may be prepared as generally outlined in Scheme J, where $R^2$, $R^3$, $R^{40}$, and $X^1$ are as described for Scheme A. The group represents an $R^1$ group, or protected derivative thereof, attached to the parent molecule by a carbon atom. The methods of Scheme J are useful for preparing compounds where $L^1$ is a bond and $R^1$ is bonded to the parent molecular moiety by a carbon atom in $R^1$, including those having a hydroxyl or halo at the point of attachment on $R^1$ (e.g., D or E in Scheme J). Functional groups present in $R^1$ (e.g., amine) may be subject to further manipulation such as the steps of deprotection, reductive amination, and/or acylation to arrive at further compounds of the invention.

Example 21

Preparation of 1-(3,5-difluorophenyl)-N-[3-methyl-5-[1-(oxetan-3-yl)-4-piperidyl]phenyl]-1,2,4-triazol-3-amine (Compound 221)

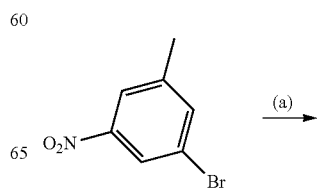

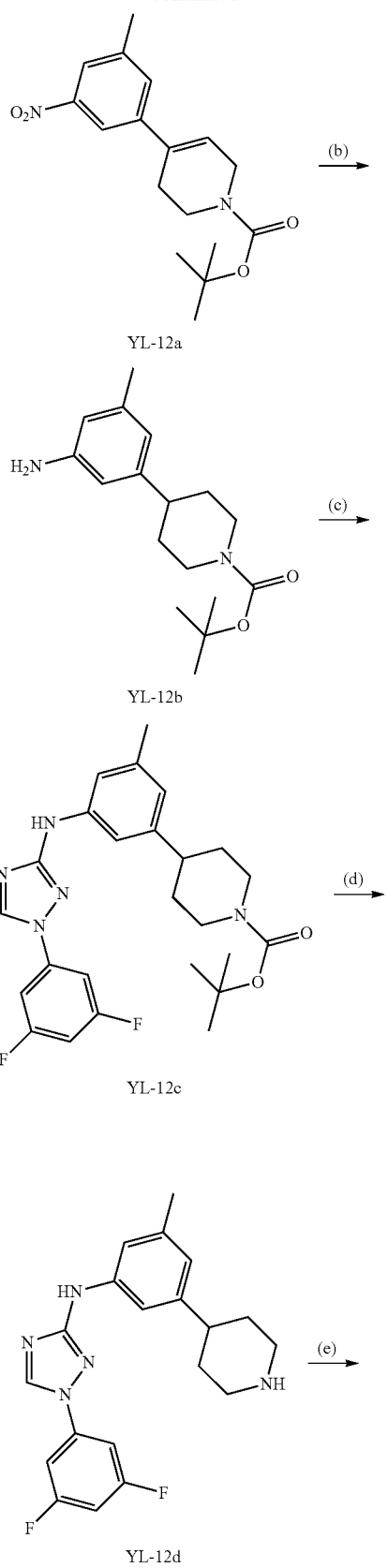

YL-12a

YL-12b

YL-12c

YL-12d

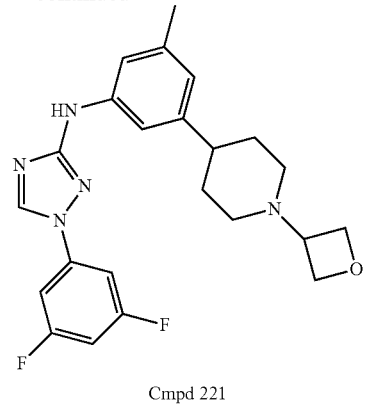

Cmpd 221

Reagents and conditions: (a) t-butyl 4-(4,4,5,5-tetramethyl-1,3,2-dioxaborolan-2-yl)-3,6-dihydro-2H-pyridine-1-carboxylate, Pd(dppf)Cl₂•DCM, 130° C.; (b) H₂, Pd/C, EtOAc; (c) 1-(3,5-difluorophenyl)-1,2,4-triazol-3-amine, t-BuXPhos Palladacycle, NaOtBu, dioxane, 45° C.; (d) TFA, DCM; (e) oxetan-3-one, NaBH(OAc)₃, HOAc, DCM.

Preparation of t-butyl 4-(3-methyl-5-nitro-phenyl)-3,6-dihydro-2H-pyridine-1-carboxylate (YL-12a)

A mixture of 1-bromo-3-methyl-5-nitro-benzene; (3.18 g, 14.7 mM) and t-butyl 4-(4,4,5,5-tetramethyl-1,3,2-dioxaborolan-2-yl)-3,6-dihydro-2H-pyridine-1-carboxylate, (5 g, 16.17 mM) in dry dioxane (80 mL) was purged with $N_2$ for several minutes. $Na_2CO_3$ (20 mL; 2M) and Pd(dppf)Cl₂.DCM (1.08 g, 1.47 mM) was added and the reaction was heated at 70° C. for 3 hours. Pumped down solvent and the residue was partitioned between EtOAc and water. Organic phase was washed with water, brine, dried ($Na_2SO_4$) and solvent was removed under reduced pressure. Crude product was purified on SiO2 with DCM=>EtOAc 0-50% to give t-butyl 4-(3-methyl-5-nitro-phenyl)-3,6-dihydro-2H-pyridine-1-carboxylate, YL-12a (2.7 g, 46.7%)$^1$H NMR (400 MHz, CDCl₃) δ 8.02 (s, 1H), 7.92 (s, 1H), 7.49 (s, 1H), 6.16 (s, 1H), 4.11 (t, J=7.1 Hz, 3H), 3.66 (t, J=5.6 Hz, 2H), 2.54 (s, 2H), 2.46 (s, 3H), 1.50 (s, 9H) ppm. ESI-MS m/z calc. 318.16, found 320.0 (M+1)+; Retention time: 0.93 minutes.

Preparation of t-butyl 4-(3-amino-5-methyl-phenyl)piperidine-1-carboxylate (YL-12b)

To t-butyl 4-(3-methyl-5-nitro-phenyl)-3,6-dihydro-2H-pyridine-1-carboxylate (2.25 g, 7.07 mM) in MeOH (100 mL) under N2, was added Pd on C, wet, Degussa (500 mg) and the reaction mixture was shaken under H2 (50 psi) for 2 h. After filtration, the solvent was removed under reduced pressure to give t-butyl 4-(3-amino-5-methyl-phenyl)piperidine-1-carboxylate YL-12b (1.93 g, 84.7%). $^1$H NMR (400 MHz, CDCl₃) δ 6.43 (s, 1H), 6.37 (s, 1H), 6.34 (s, 1H), 4.22 (s, 2H), 3.58 (s, 2H), 2.76 (s, 2H), 2.58-2.39 (m, 1H), 2.24 (s, 3H), 1.77 (d, J=12.8 Hz, 2H), 1.67-1.50 (m, 2H), 1.48 (s, 9H) ppm. ESI-MS m/z calc. 290.20, found 291.0 (M+1)+; Retention time: 0.64 minutes.

Preparation of t-butyl 4-[3-[[1-(3,5-difluorophenyl)-1,2,4-triazol-3-yl]amino]-5-methyl-phenyl]piperidine-1-carboxylate (YL-12c)

A mixture of 3-bromo-1-(3,5-difluorophenyl)-1,2,4-triazole (407 mg, 1.56 mmol) and t-butyl 4-(3-amino-5-methyl-phenyl)piperidine-1-carboxylate (500 mg, 1.72 mmol) in 10 mL of dry t-BuOH was purged with N₂ for several minutes. t-BuXPhos Palladacycle (100 mg, 0.16 mM) and sodium t-butoxide (225 mg, 2.35 mM) were added and the reaction mixture was heated at 30° C. under N2 for 1 h. Reaction was quenched with MeOH and the solvent was pumped down. The residue was partitioned between EtOAc and water. The organic phase was washed with water, brine and dried (Na₂SO₄). Pumped down solvent. Crude materials were suspended in Et₂O and heated to reflux and cooled to RT. The solid was isolated, washed with Et₂O, hexanes and dried to give t-butyl 4-[3-[[1-(3,5-difluorophenyl)-1,2,4-triazol-3-yl]amino]-5-methyl-phenyl]piperidine-1-carboxylate YL-12c (476 mg, 52.5%). ¹H NMR (400 MHz, CDCl₃) δ 8.34 (s, 1H), 7.24 (d, J=2.0 Hz, 1H), 7.21 (s, 1H), 7.17 (s, 1H), 6.83-6.76 (m, 1H), 6.67 (s, 1H), 4.25 (d, J=12.2 Hz, 2H), 2.81 (t, J=11.9 Hz, 2H), 2.72-2.50 (m, 1H), 2.36 (s, 2H), 1.85 (d, J=12.9 Hz, 2H), 1.66 (ddd, J=21.1, 15.7, 11.5 Hz, 4H), 1.49 (s, 9H) ppm. ESI-MS m/z calc. 469.23, found 470.0 (M+1)+; Retention time: 1.01 minutes.

Preparation of 1-(3,5-difluorophenyl-[3-methyl-5-(4-piperidyl)phenyl]-1,2,4-triazol-3-amine (YL-12d)

To a solution of tert-butyl 4-[3-[[1-(3,5-difluoro phenyl)-1,2,4-triazol-3-yl]amino]-5-methyl-phenyl]piperidine-1-carboxylate (476 m g, 1.1 mmol) in DCM (10 mL) was added TFA (2 mL). The resultant mixture was stirred under N2 for 2 h. Pumped down solvent. The residue was partitioned between EtOAc and sat'd Na₂CO₃. The organic layer was washed with brine and dried with Na₂SO₄. Pumped down solvent. Crude product were then triturated with hexanes/DCM (3:1) to give 1-(3,5-difluorophenyl-[3-methyl-5-(4-piperidyl)phenyl]-1,2,4-triazol-3-amine YL-12d (300 mg, 60%). ¹H NMR (400 MHz, Acetone-d6) δ 8.92 (s, 1H), 8.37 (s, 1H), 7.63-7.53 (m, 2H), 7.45 (s, 1H), 7.41 (s, 1H), 7.00 (tt, J=9.1, 2.3 Hz, 1H), 6.65 (s, 1H), 3.11 (d, J=11.9 Hz, 2H), 2.78-2.63 (m, 8H), 2.57 (tt, J=11.9, 3.7 Hz, 1H), 2.32 (s, 3H), 1.82-1.73 (m, 2H), 1.63 (qd, J=12.4, 4.0 Hz, 2H) ppm. ESI-MS m/z calc. 369.18, found 370.0 (M+1)+; Retention time: 0.62 minutes.

Preparation of 1-(3,5-difluorophenyl)-N-[3-methyl-5-[1-(oxetan-3-yl)-4-piperidyl]phenyl]-1,2,4-triazol-3-amine (Compound 221)

To a solution of 1-(3,5-difluorophenyl)-N-[3-methyl-5-(4-piperidyl)phenyl]-1,2,4-triazol-3-amine (129 mg, 0.31 mmol), oxetan-3-one YL-12d (226 mg, 3.14 mmol) and acetic acid (107 μL, 1.89 mmol) in dichloromethane (5.5 mL) was added NaBH(OAc)₃ (400 mg, 1.89 mmol). The mixture was stirred for 4 h. Reaction was diluted with DCM and quenched with MeOH and sat. NaHCO₃ (3 mL). After separation, the organic layer was washed with water, sat NaCl and dried. Pumped down solvent. ISCO purifications (12 g silica; 0% to 5% to 10% of MeOH in DCM) gave 1-(3,5-difluorophenyl)-N-[3-methyl-5-[1-(oxetan-3-yl)-4-piperidyl]phenyl]-1,2,4-triazol-3-amine, cmpd 221 (123 mg, 87%)¹H NMR (300 MHz, DMSO-d6) δ 9.41 (s, 1H), 9.16 (s, 1H), 7.62 (dd, J=8.7, 2.2 Hz, 2H), 7.35 (s, 1H), 7.30-7.18 (m, 2H), 6.59 (s, 1H), 4.55 (t, J=6.5 Hz, 2H), 4.45 (t, J=6.1 Hz, 2H), 3.48-3.35 (m, 1H), 2.79 (d, J=11.1 Hz, 2H), 2.47-2.34 (m, 1H), 2.27 (s, 3H), 1.93-1.55 (m, 6H) ppm. ESI-MS m/z calc. 425.20, found 426.46 (M+1)+; Retention time: 0.67 minutes.

Using the general synthetic scheme outlined in Scheme J and the experimental procedures in Example 21 the following compounds were prepared:

| Cmpd No. | IUPAC Name |
|---|---|
| 61 | 1-(3,5-difluorophenyl)-N-[3-methyl-5-[1-(oxetan-3-yl)-3,6-dihydro-2H-pyridin-4-yl]phenyl]-1,2,4-triazol-3-amine |
| 315 | N-[3,5-bis(3,6-dihydro-2H-pyran-4-yl)phenyl]-1-phenyl-1,2,4-triazol-3-amine |
| 250 | N-[3,5-di(tetrahydropyran-4-yl)phenyl]-1-(3-pyridyl)-1,2,4-triazol-3-amine |
| 10 | N-[3,5-di(tetrahydropyran-4-yl)phenyl]-1-phenyl-1,2,4-triazol-3-amine |
| 234 | N-[3,5-bis(2,5-dihydrofuran-3-yl)phenyl]-1-phenyl-1,2,4-triazol-3-amine |
| 71 | N-[3-methyl-5-[1-(oxetan-3-yl)-4-piperidyl]phenyl]-1-phenyl-1,2,4-triazol-3-amine |
| 221 | 1-(3,5-difluorophenyl)-N-[3-methyl-5-[1-(oxetan-3-yl)-4-piperidyl]phenyl]-1,2,4-triazol-3-amine |
| 294 | N-[3-methyl-5-[1-(3-methyloxetan-3-yl)-4-piperidyl]phenyl]-1-phenyl-1,2,4-triazol-3-amine |
| 51 | N-[3-[1-[3-(benzenesulfonylmethyl)oxetan-3-yl]-4-piperidyl]-5-methyl-phenyl]-1-phenyl-1,2,4-triazol-3-amine |
| 483 | N-[3-methyl-5-[1-[(3-methyloxetan-3-yl)methyl]-4-piperidyl]phenyl]-1-phenyl-1,2,4-triazol-3-amine |
| 39 | N-(3-methyl-5-pyrrolidin-3-yl-phenyl)-1-phenyl-1,2,4-triazol-3-amine |
| 443 | 1-[3-[3-methyl-5-[(1-phenyl-1,2,4-triazol-3-yl)amino]phenyl]pyrrolidin-1-yl]ethanone |
| 273 | N-[3-[1-(2,2-difluoroethyl)pyrrolidin-3-yl]-5-methyl-phenyl]-1-phenyl-1,2,4-triazol-3-amine |
| 452 | N-(3-fluoro-5-pyrrolidin-3-yl-phenyl)-1-phenyl-1,2,4-triazol-3-amine |
| 308 | N-[3-methyl-5-(4-piperidyl)phenyl]-1-phenyl-1,2,4-triazol-3-amine |
| 108 | 1-(3,5-difluorophenyl)-N-[3-methyl-5-(4-piperidyl)phenyl]-1,2,4-triazol-3-amine |
| 333 | N-[3-methyl-5-(1-methyl-4-piperidyl)phenyl]-1-phenyl-1,2,4-triazol-3-amine |
| 151 | 1-(3,5-difluorophenyl)-N-[3-methyl-5-(1-methyl-4-piperidyl)phenyl]-1,2,4-triazol-3-amine |
| 316 | N-[3-methyl-5-(3-piperidyl)phenyl]-1-phenyl-1,2,4-triazol-3-amine |
| 429 | 1-(3,5-difluorophenyl)-N-[3-methyl-5-(3-piperidyl)phenyl]-1,2,4-triazol-3-amine |
| 60 | N-[3-methyl-5-(1-methyl-3-piperidyl)phenyl]-1-phenyl-1,2,4-triazol-3-amine |
| 328 | 1-(3,5-difluorophenyl)-N-[3-methyl-5-(1-methyl-3-piperidyl)phenyl]-1,2,4-triazol-3-amine |
| 117 | 1-[3-[3-methyl-5-[(1-phenyl-1,2,4-triazol-3-yl)amino]phenyl]-1-piperidyl]ethanone |
| 266 | 1-[3-[3-[[1-(3,5-difluorophenyl)-1,2,4-triazol-3-yl]amino]-5-methyl-phenyl]-1-piperidyl]ethanone |
| 194 | 1-[4-[3-methyl-5-[(1-phenyl-1,2,4-triazol-3-yl)amino]phenyl]-1-piperidyl]ethanone |
| 90 | 1-[4-[3-[[1-(3,5-difluorophenyl)-1,2,4-triazol-3-yl]amino]-5-methyl-phenyl]-1-piperidyl]ethanone |
| 340 | N-[3-(1-cyclopropyl-3-piperidyl)-5-methyl-phenyl]-1-phenyl-1,2,4-triazol-3-amine |
| 120 | N-[3-(1-cyclopropyl-4-piperidyl)-5-methyl-phenyl]-1-phenyl-1,2,4-triazol-3-amine |
| 466 | N-[3-(1-cyclopropyl-3-piperidyl)-5-methyl-phenyl]-1-(3,5-difluorophenyl)-1,2,4-triazol-3-amine |
| 261 | N-[3-(1-cyclopropyl-4-piperidyl)-5-methyl-phenyl]-1-(3,5-difluorophenyl)-1,2,4-triazol-3-amine |
| 143 | methyl 3-[3-methyl-5-[(1-phenyl-1,2,4-triazol-3-yl)amino]phenyl]piperidine-1-carboxylate |
| 12 | methyl 4-[3-methyl-5-[(1-phenyl-1,2,4-triazol-3-yl)amino]phenyl]piperidine-1-carboxylate |
| 25 | 1-(3,5-difluorophenyl)-N-[3-methyl-5-[1-(oxetan-3-yl)pyrrolidin-3-yl]phenyl]-1,2,4-triazol-3-amine |
| 473 | 1-(3,5-difluorophenyl)-N-[3-methyl-5-[(3R)-1-(oxetan-3-yl)pyrrolidin-3-yl]phenyl]-1,2,4-triazol-3-amine |
| 92 | 1-(3,5-difluorophenyl)-N-[3-methyl-5-[(3S)-1-(oxetan-3-yl)pyrrolidin-3-yl]phenyl]-1,2,4-triazol-3-amine |
| 230 | N-[3-fluoro-5-[1-(oxetan-3-yl)pyrrolidin-3-yl]phenyl]-1-(3-fluorophenyl)-1,2,4-triazol-3-amine |
| 268 | 1-(3,5-difluorophenyl)-N-[3-fluoro-5-[1-(oxetan-3-yl)pyrrolidin-3-yl]phenyl]-1,2,4-triazol-3-amine |
| 382 | 1-(3-fluorophenyl)-N-[3-methyl-5-[1-(oxetan-3-yl)pyrrolidin-3-yl]phenyl]-1,2,4-triazol-3-amine |
| 260 | N-[3-methyl-5-[1-(oxetan-3-yl)pyrrolidin-3-yl]phenyl]-1,2,4-triazol-3-amine |

| Cmpd No. | IUPAC Name |
|---|---|
| 416 | 3-[3-[[1-(3,5-difluorophenyl)-1,2,4-triazol-3-yl]amino]-5-methyl-phenyl]-1-(oxetan-3-yl)pyrrolidin-3-ol |
| 160 | N-[3-methyl-5-[1-(oxetan-3-yl)-2,5-dihydropyrrol-3-yl]phenyl]-1-phenyl-1,2,4-triazol-3-amine |
| 18 | N-[3-[3-fluoro-1-(oxetan-3-yl)pyrrolidin-3-yl]-5-methyl-phenyl]-1-phenyl-1,2,4-triazol-3-amine |
| 193 | 1-(3,5-difluorophenyl)-N-[3-[3-fluoro-1-(oxetan-3-yl)pyrrolidin-3-yl]-5-methyl-phenyl]-1,2,4-triazol-3-amine |
| 242 | 3-[3-[[1-(3,5-difluorophenyl)-1,2,4-triazol-3-yl]amino]-5-methyl-phenyl]-1-methyl-pyrrolidin-3-ol |
| 23 | 1-(3,5-difluorophenyl)-N-[3-(3-fluoro-1-methyl-pyrrolidin-3-yl)-5-methyl-phenyl]-1,2,4-triazol-3-amine |
| 101 | (3S)-3-[3-[[1-(3,5-difluorophenyl)-1,2,4-triazol-3-yl]amino]-5-methyl-phenyl]-1-(oxetan-3-yl)pyrrolidin-3-ol |
| 487 | (3R)-3-[3-[[1-(3,5-difluorophenyl)-1,2,4-triazol-3-yl]amino]-5-methyl-phenyl]-1-(oxetan-3-yl)pyrrolidin-3-ol |
| 248 | N-[3-methyl-5-[1-(oxetan-3-yl)-3-piperidyl]phenyl]-1-phenyl-1,2,4-triazol-3-amine |
| 408 | 1-(3,5-difluorophenyl)-N-[3-methyl-5-[1-(oxetan-3-yl)-3-piperidyl]phenyl]-1,2,4-triazol-3-amine |
| 180 | N-[3-methyl-5-[1-(oxetan-3-yl)-3-piperidyl]phenyl]-1-pyrimidin-4-yl-1,2,4-triazol-3-amine |
| 74 | N-[3-methyl-5-[1-(oxetan-3-yl)-3-piperidyl]phenyl]-1-pyrazin-2-yl-1,2,4-triazol-3-amine |
| 449 | 1-[3-[3-methyl-5-[(1-pyrimidin-4-yl-1,2,4-triazol-3-yl)amino]phenyl]-1-piperidyl]ethanone |
| 515 | 1-(3,5-difluorophenyl)-N-[3-[4-fluoro-1-(oxetan-3-yl)-4-piperidyl]-5-methyl-phenyl]-1,2,4-triazol-3-amine |
| 516 | 4-[3-[[1-(3,5-difluorophenyl)-1,2,4-triazol-3-yl]amino]-5-methyl-phenyl]-1-(oxetan-3-yl)piperidin-4-ol |
| 613 | 5-[3-[[1-(3,5-difluorophenyl)-1,2,4-triazol-3-yl]amino]-5-methyl-phenyl]-3,5-dimethyl-oxazolidin-2-one |
| 846 | 3,5-dimethyl-5-[3-methyl-5-[(1-pyrazin-2-yl-1,2,4-triazol-3-yl)amino]phenyl]oxazolidin-2-one |
| 658 | 5-[3-[[1-(3,5-difluorophenyl)-1,2,4-triazol-3-yl]amino]-5-methyl-phenyl]-5-methyl-oxazolidin-2-one |
| 741 | 5-methyl-5-[3-methyl-5-[(1-pyrazin-2-yl-1,2,4-triazol-3-yl)amino]phenyl]oxazolidin-2-one |
| 611 | (5S)-5-[3-[[1-(3,5-difluorophenyl)-1,2,4-triazol-3-yl]amino]-5-methyl-phenyl]-3,5-dimethyl-oxazolidin-2-one |
| 796 | (5R)-5-[3-[[1-(3,5-difluorophenyl)-1,2,4-triazol-3-yl]amino]-5-methyl-phenyl]-3,5-dimethyl-oxazolidin-2-one |
| 603 | (5S)-5-methyl-5-[3-methyl-5-[(1-pyrazin-2-yl-1,2,4-triazol-3-yl)amino]phenyl]oxazolidin-2-one |
| 682 | (5R)-5-methyl-5-[3-methyl-5-[(1-pyrazin-2-yl-1,2,4-triazol-3-yl)amino]phenyl]oxazolidin-2-one |
| 679 | (5S)-5-[3-[[1-(3,5-difluorophenyl)-1,2,4-triazol-3-yl]amino]-5-methyl-phenyl]-5-methyl-oxazolidin-2-one |
| 655 | (5R)-5-[3-[[1-(3,5-difluorophenyl)-1,2,4-triazol-3-yl]amino]-5-methyl-phenyl]-5-methyl-oxazolidin-2-one |
| 755 | 1-[6-[[1-(3,5-difluorophenyl)-1,2,4-triazol-3-yl]amino]-4-methyl-2-pyridyl]piperidin-3-ol |

Scheme K: General Route K for Preparation of Compounds of Formula I or I'

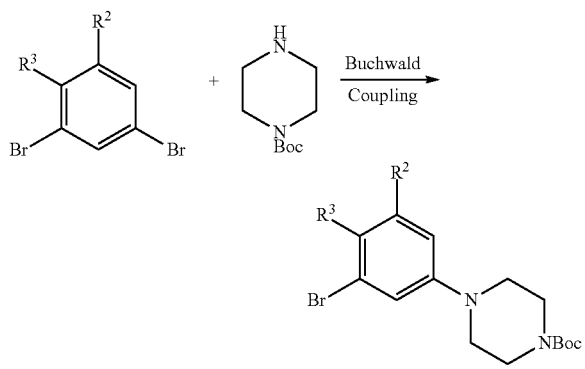

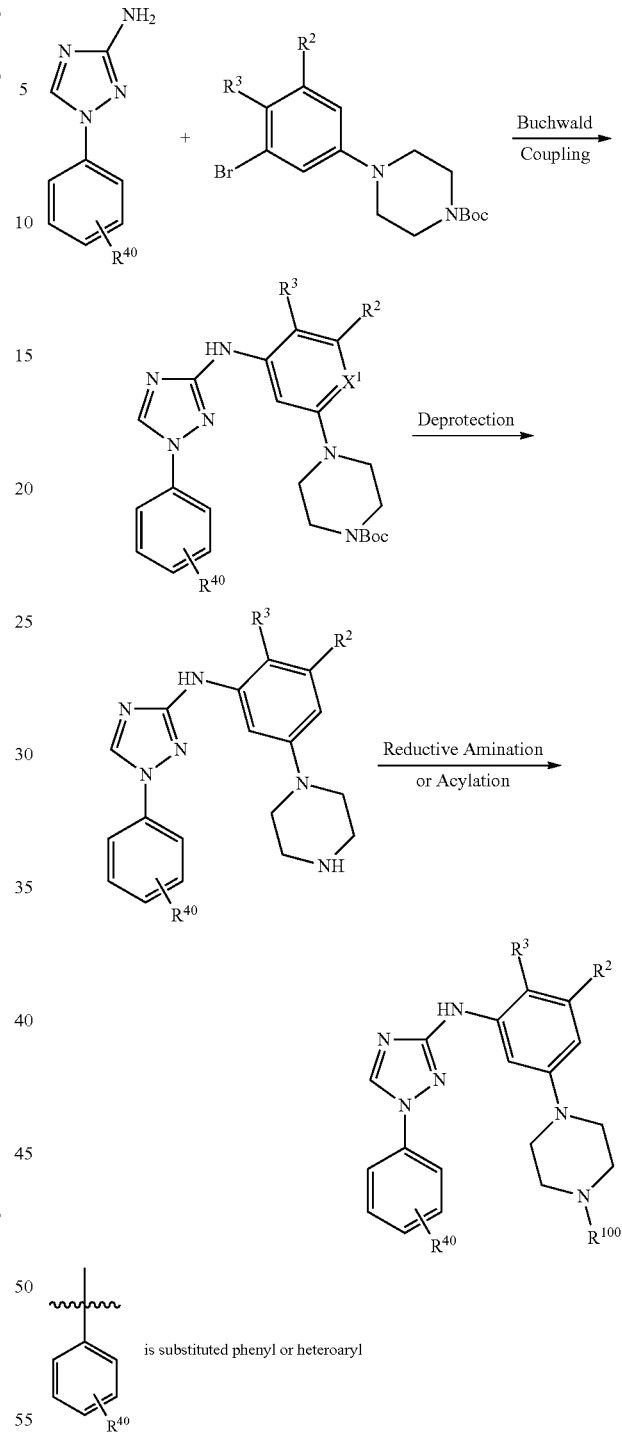

Compounds of the invention may be prepared as generally outlined in Scheme K, where $R^2$, $R^3$, $R^{40}$, and $R^{100}$ are as described for Scheme A. The methods of Scheme K are useful for preparing compounds where $R^{100}$ is attached by reduction amination or acylation of an amine group. The methods of Scheme K may also be applied to other variations of $L^1$ with $G^1$ to $G^5$ that bond to the parent molecular moiety through a nitrogen atom.

Example 22

Preparation of N-[3-(difluoromethyl)-5-[4-(oxetan-3-yl)piperazin-1-yl]phenyl]-1-phenyl-1,2,4-triazol-3-amine (Compound 26)

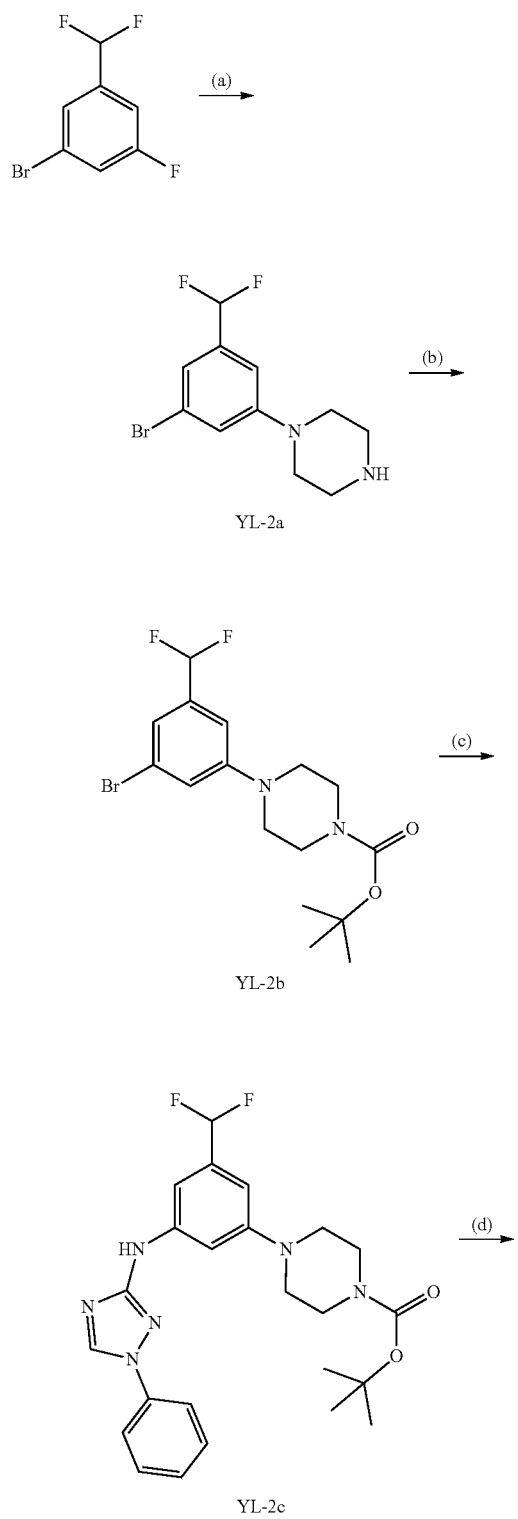

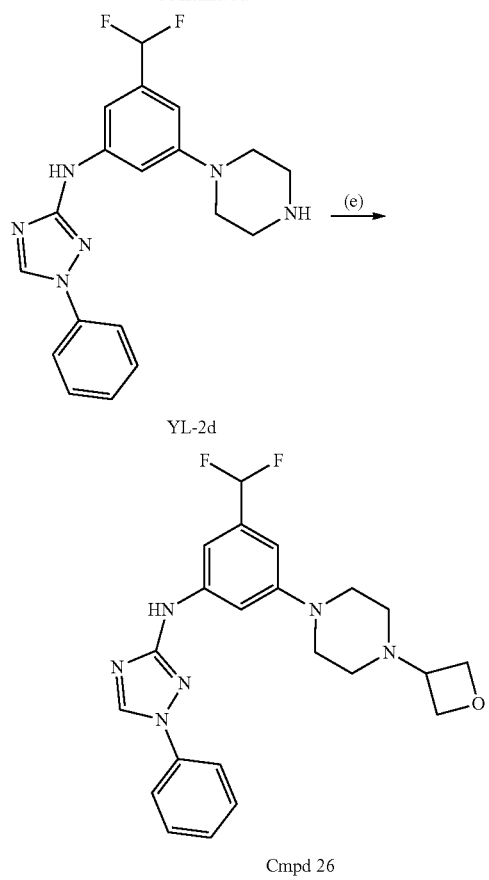

Reagents and conditions: (a) 1-cyclopropylpiperazine, 200° C.; (b) (tBuO)₂CO, DCM; (c) 1-phenyl-1,2,4-triazol-3-amine, t-BuXPhos Palladacycle, NaOtBu, dioxane, 120° C.; (d) TFA, DCM; (e) oxetan-3-one, NaBH(OAc)₃, HOAc, DCM.

Using the general synthetic scheme outlined in Scheme K and the experimental procedures listed above in Example 22, the following compounds were prepared:

| Cmpd No. | IUPAC Name |
|---|---|
| 144 | 1-[4-[3-(difluoromethyl)-5-[(1-phenyl-1,2,4-triazol-3-yl)amino]phenyl]piperazin-1-yl]ethanone |
| 62 | N-[3-(difluoromethyl)-5-piperazin-1-yl-phenyl]-1-phenyl-1,2,4-triazol-3-amine |
| 446 | 1-(2-chlorophenyl)-N-[3-methyl-5-[4-(oxetan-3-yl)piperazin-1-yl]phenyl]-1,2,4-triazol-3-amine |

Scheme L: General Route L for Preparation of Compounds of Formula I or I'

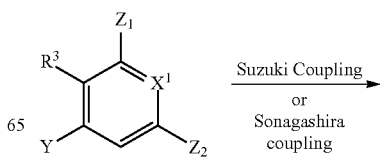

817

-continued

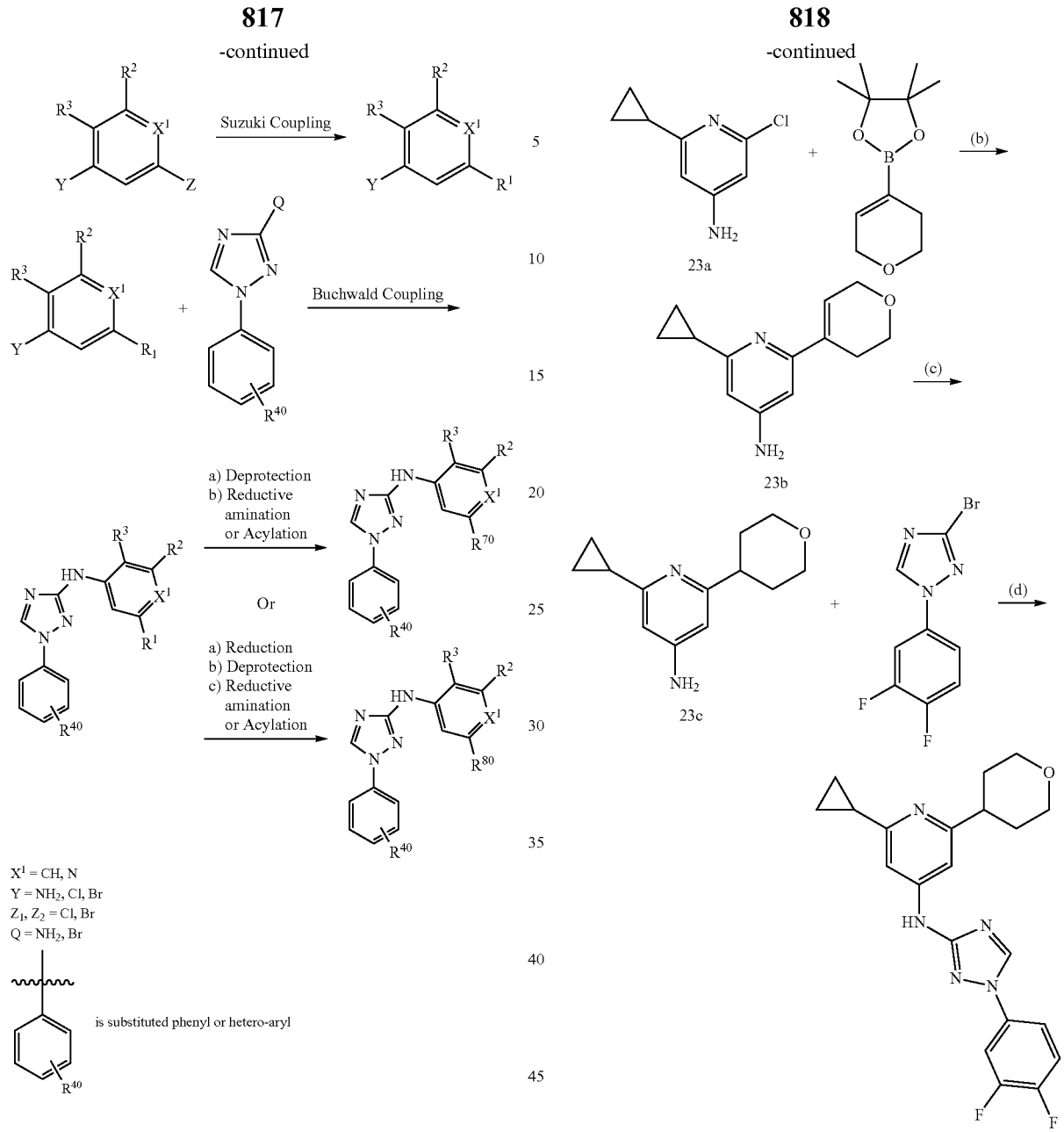

$X^1$ = CH, N
Y = $NH_2$, Cl, Br
$Z_1$, $Z_2$ = Cl, Br
Q = $NH_2$, Br is substituted phenyl or hetero-aryl Compounds of the invention may be prepared as generally outlined in Scheme L, where $R^1$, $R^2$, $R^3$, $R^{40}$, and $X^1$ are as described in Scheme A. $R^{70}$ and $R^{80}$ represent various substituted $R^1$ groups arrived at by the indicated synthetic manipulations.

Example 23

Preparation of 2-cyclopropyl-N-(1-(3,4-difluorophenyl)-1H-1,2,4-triazol-3-yl)-6-(tetrahydro-2H-pyran-4-yl)pyridin-4-amine (Compound 150)

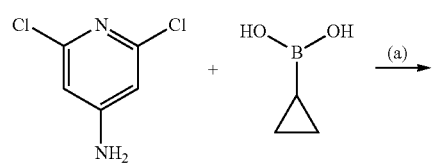

818

-continued (a) tricyclohexylphosphane/Pd(OAc)2/K3PO4/toluene/H2O; (b) 4-di-tert-butyl-phosphanyl-N,N-dimethylaniline; (c) Pd/C/H2/THF/HOAc; (d) t-BuXPHOS Palladacycle/t-BuOK/t-BuOH Preparation of 2-cyclopropyl-N-(1-(3,4-difluorophenyl)-1H-1,2,4-triazol-3-yl)-6-(tetrahydro-2H-pyran-4-yl)pyridin-4-amine (Compound 150)

A t-BuOH (5 mL) mixture of 2-cyclopropyl-6-tetrahydro-pyran-4-yl-pyridin-4-amine 23b, (130 mg, 0.56 mmol), 3-bromo-1-(3,5-difluorophenyl)-1,2,4-triazole (287 mg, 1.11 mmol), t-BuXPhos Palladacycle (72 mg, 0.111 mmol) and t-BuOK (93 mg, 0.83 mmol) was stirred at 45° C. for 1 h. LCMS indicated the reaction was 90% completed so the reaction mixture was stirred at 45° C. for one more hour. LCMS was the same as before. Work up: the reaction mixture was filtered through Celite, to the filtrate was added EA and brine, the organic phase was dried over $MgSO_4$, filtered, concentrated down and purified by Isco (40 g Gold) silica gel column with HEP and EA, the product was eluted with 30% HEP and 70% EA and give 76 mg (32%) of 2-cyclopropyl-N-(1-(3,4-difluorophenyl)-1H-1,2,4-triazol-3-yl)-6-(tetrahydro-2H-pyran-4-yl)pyridin-4-amine, cmpd 150. $^1$H NMR (300 MHz, CDCl3) δ 8.36 (s, 1H), 7.26 (d, J=2.2 Hz, 2H), 7.17 (d, J=2.0 Hz, 1H), 7.05 (d, J=1.9 Hz, 1H), 6.95-6.78 (m, 2H), 4.11 (d, J=10.9 Hz, 2H), 3.58 (td, J=11.3, 3.5 Hz, 2H), 2.97-2.79 (m, 1H), 2.03 (td, J=8.0, 4.0 Hz, 1H), 1.96-1.80 (m, 4H), 1.11-1.02 (m, 2H), 0.97 (ddd, J=10.3, 6.4, 3.9 Hz, 2H) ppm. ESI-MS m/z calc. 397.17142, found 398.21 (M+1)$^+$; Retention time: 0.61 minutes.

Using the general synthetic scheme outlined in Scheme L and the experimental procedures listed above in Example 23, the following compounds were prepared:

| Cmpd No. | IUPAC Name |
|---|---|
| 150 | 2-cyclopropyl-N-[1-(3,4-difluorophenyl)-1,2,4-triazol-3-yl]-6-tetrahydropyran-4-yl-pyridin-4-amine |
| 407 | 2-cyclopropyl-N-[1-(3,5-difluorophenyl)-1,2,4-triazol-3-yl]-6-tetrahydropyran-4-yl-pyridin-4-amine |
| 3 | 2-cyclopropyl-N-[1-(3,4-difluorophenyl)-1,2,4-triazol-3-yl]-6-(3,6-dihydro-2H-pyran-4-yl)pyridin-4-amine |
| 35 | 2-cyclopropyl-N-[1-(3,5-difluorophenyl)-1,2,4-triazol-3-yl]-6-(3,6-dihydro-2H-pyran-4-yl)pyridin-4-amine |
| 798 | N-[3-(2-cyclopropylethynyl)-5-methyl-phenyl]-1-(3,5-difluorophenyl)-1,2,4-triazol-3-amine |
| 769 | N-[3-(2-cyclopropylethynyl)-5-methyl-phenyl]-1-(3-fluorophenyl)-1,2,4-triazol-3-amine |

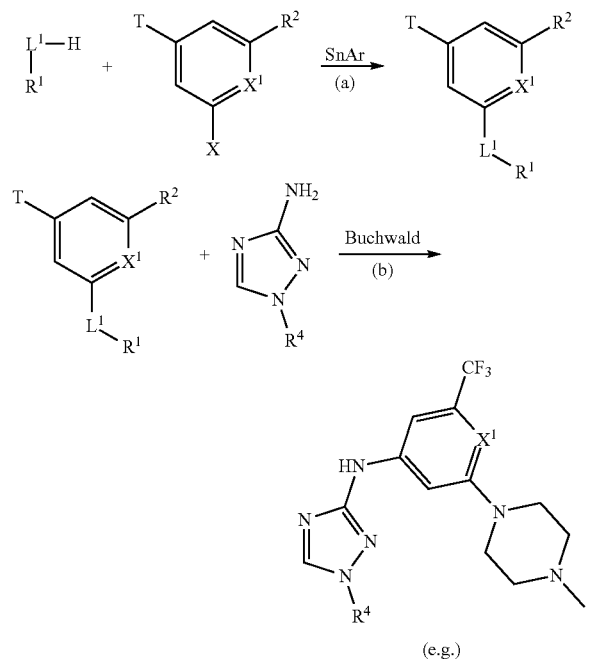

Scheme M: General Route M for Preparation of Compounds of Formula I or I'

R2 = H, CH3, CF3, Cl, Ethyl, amines
Q = C, N
X = Cl, Br, F
T = Cl, Br

Compounds of the invention may be prepared as generally outlined in Scheme M, where R$^2$, R$^4$, and X$^1$ are as described herein, and HL$^1$-R$^1$ is an amine such that -L$^1$-R, as defined herein, is bonded to the parent molecular moiety through a nitrogen atom. In the indicated example, an N-methyl piperazine moiety serves as L$^1$-R$^1$.

(a) NMP, 100° C., 12-24 hours; (b) t-BuXPhos Palladacycle, Sodium t-butoxide, 1,4-dioxane, 90° C., 12-24 hours Example 23A Preparation of N-[3-(4-methylpiperazin-1-yl)-5-(trifluoromethyl)phenyl]-1-phenyl-1,2,4-triazol-3-amine (Compound 486)

Preparation of 1-[3-bromo-5-(trifluoromethyl)phenyl]-4-methyl-piperazine

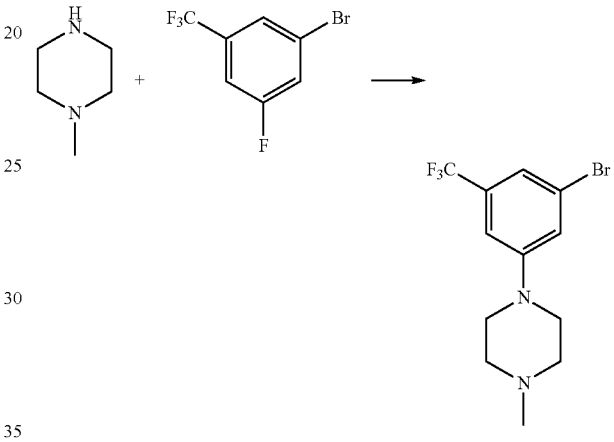

1-Bromo-3-fluoro-5-(trifluoromethyl)benzene (1.52 g, 6.26 mmol) was dissolved in NMP (2.0 mL). Methylpiperazine (1.88 g, 2.08 mL, 18.8 mmol) was added and the vial was sealed. Stirred the reaction mixture overnight at 100° C. The reaction mixture was concentrated to an oil. The oil was diluted with DCM (20 ml), the organic phase washed with 50% saturated sodium bicarbonate, passed through a phase separator, and concentrated to dryness to yield 1-[3-bromo-5-(trifluoromethyl)phenyl]-4-methyl-piperazine (1.73 g, 83%). $^1$H NMR (300 MHz, DMSO-d6) δ 7.36 (s, 1H), 7.18 (s, 2H), 3.30-3.16 (m, 4H), 2.46-2.33 (m, 4H), 2.21 (s, 3H) ppm. ESI-MS m/z calc. 322.02924, found 323.03 (M+1)+; Retention time: 0.62 minutes.

Preparation of N-[3-(4-methylpiperazin-1-yl)-5-(trifluoromethyl)phenyl]-1-phenyl-1,2,4-triazol-3-amine (Compound 486)

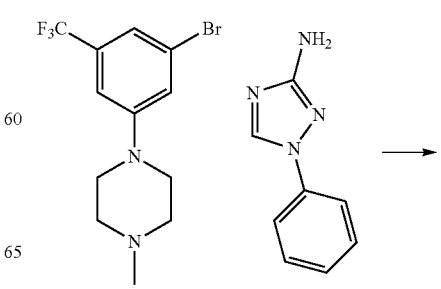

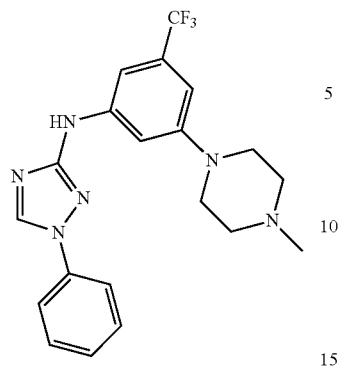

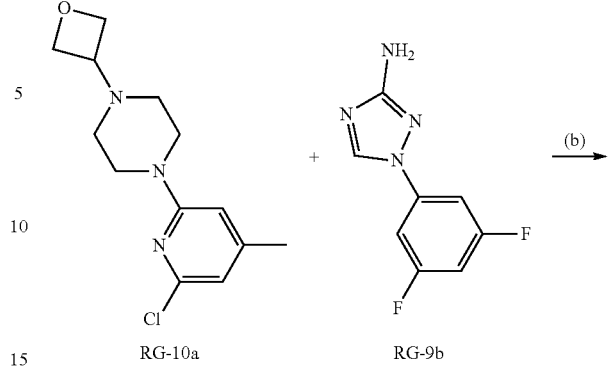

RG-10a      RG-9b

1-Phenyl-1,2,4-triazol-3-amine (64 mg, 0.4 mmol), sodium tert-butoxide (57.60 mg, 0.5994 mmol), t-BuXPhos Palladacycle (30 mg, 0.4 mmol), and 1-[3-bromo-5-(trifluoromethyl)phenyl]-4-methyl-piperazine (129 mg, 0.4 mmol) were weighed into a 20 ml vial. Vacuum was applied to the vial and flushed with nitrogen three times. Dioxane (2 mL) was added and stirred the mixture in a sealed vial at 90° C. overnight. The crude reaction mixture was diluted with dichloromethane (20 ml), and washed with 50% saturated sodium bicarbonate. The organic layer was passed through a phase separator and concentrated to dryness. The residue was diluted with DMSO (2 ml) and purified by reverse phase HPLC using a gradient of acetonitrile in water (10-99%) and TFA as a modifier to yield the product as the TFA salt. The pooled desired pure fractions were concentrated to dryness. Diluted combined fractions with DCM and washed with saturated sodium bicarbonate. The organics were passed through a phase separator, acidified with 2M HCl in diethyl ether, and concentrated to dryness to yield the HCl salt of N-[3-(4-methylpiperazin-1-yl)-5-(trifluoromethyl)phenyl]-1-phenyl-1,2,4-triazol-3-amine, cmpd 486 (99 mg, 565). $^1$H NMR (300 MHz, DMSO-d6) δ 9.13 (s, 1H), 7.89-7.79 (d, 2H), 7.56 (m, 4H), 7.38 (t, J=7.4 Hz, 1H), 6.84 (s, 1H), 3.88 (d, J=9.7 Hz, 2H), 3.51 (m, 2H), 3.19 (m, 4H), 2.85 (s, 3H) ppm. ESI-MS m/z calc. 402.17798, found 403.28 (M+1)+; Retention time: 3.08 minutes.

Example 23B

Preparation of N-r 1-(3,5-difluorophenyl)-1,2,4-triazol-3-yl-4-methyl-6-[4-(oxetan-3-yl)piperazin-1-yl]pyridin-2-amine (Compound 331)

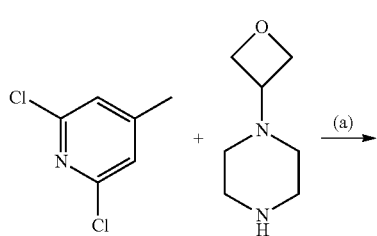

Cmpd 331 a) DIEA, NMP, 100° C., 20 h; (b) t-BuXPhos Palladacycle, t-BuOH, 1,4-dioxane, t-BuONa, 90° C., 1 h.

Preparation of 1-(6-chloro-4-methyl-2-pyridyl)-4-(oxetan-3-yl)piperazine (RG-10a)

2,6-dichloro-4-methyl-pyridine (653 mg, 4.030 mmol), DIEA (625.0 mg, 842 μL, 4.84 mmol), and 1-(oxetan-3-yl)piperazine (704 mg, 4.95 mmol) were combined in a 20 ml vial. Added a stir bar and NMP (4.0 mL) before sealing the vial and heating overnight at 100° C. After 20 h, the reaction was complete. Diluted with DMSO (5 mls), and injected on a C-18 Aq 275 g column and eluted with 0-41% ACN in water with a TFA modifier over 18 minutes. Pooled desired product fractions and concentrated to dryness, then diluted with DCM and minimal methanol to dissolve. Washed with 50% saturated sodium bicarbonate. Passed through a phase separator and concentrated to dryness to yield 1-(6-chloro-4-methyl-2-pyridyl)-4-(oxetan-3-yl)piperazine RG-10a (661 mg, 2.46 mmol, 61%). 1H NMR (300 MHz, DMSO-d6) δ 6.63 (s, 1H), 6.54 (s, 1H), 4.56 (t, J=6.5 Hz, 2H), 4.46 (t, J=6.1 Hz, 2H), 3.54-3.45 (m, 4H), 3.41 (m, 1H), 2.38-2.26 (m, 4H), 2.21 (s, 3H) ppm. ESI-MS m/z calc. 267.11383, found 268.14 (M+1)+; Retention time: 0.59 minutes.

Preparation of N-[1-(3,5-difluorophenyl)-1,2,4-triazol-3-yl]-4-methyl-6-[4-(oxetan-3-yl)piperazin-1-yl]pyridin-2-amine (Compound 331)

1-(3,5-difluorophenyl)-1,2,4-triazol-3-amine (123 mg, 0.6270 mmol), t-BuXPhos palladacycle (25 mg, 0.03384 mmol), sodium t-butoxide (100 mg, 1.041 mmol) and 1-(6-chloro-4-methyl-2-pyridyl)-4-(oxetan-3-yl)piperazine RG-10a (171 mg, 0.6351 mmol) were dissolved into dry t-BuOH (1.75 mL) and dry dioxane (600 μL). Purged with $N_2$ for ~10 minutes. Stirred at 50° C. for 1 h. LC/MS showed no remaining starting material so concentrated to dryness and diluted with 20 ml of DCM. Washed with 10 ml of 50% sat. sodium bicarbonate, passed through a phase separator, and concentrated to dryness. Diluted with DCM (10 ml, poor solubility) and passed through a plug of florisil then concentrated to dryness. Diluted with 8 mls of DMSO and injected on the C18 50 g Aq column eluting with 0-60% ACN in water over 17 minutes with a TFA modifier. Combined desired fractions, concentrated to dryness and diluted with DCM. Washed with 50% sat. sodium bicarbonate, passed through a phase separator, and concentrated to dryness. Diluted with 5 mls of DCM and injected on a 40 g Si gold column eluting with 0-100% (ethyl acetate (10% methanol)) in heptane over 22 minutes. Combined desired fractions and concentrated to dryness to give N-[1-(3,5-difluorophenyl)-1,2,4-triazol-3-yl]-4-methyl-6-[4-(oxetan-3-yl)piperazin-1-yl]pyridin-2-amine 331 (125 mg, 0.289 mmol, 46%) 1H NMR (300 MHz, DMSO-d6) δ 9.40 (s, 1H), 9.18 (s, 1H), 7.64 (dd, J=8.6, 2.2 Hz, 2H), 7.32-7.20 (m, 1H), 6.97 (s, 1H), 6.17 (s, 1H), 4.57 (t, J=6.5 Hz, 2H), 4.48 (t, J=6.1 Hz, 2H), 3.52 (m, 4H), 3.47-3.37 (m, 1H), 2.33 (m, 4H), 2.23 (s, 3H) ppm. ESI-MS m/z calc. 427.1932, found 428.29 (M+1)+; Retention time: 0.62 minutes.

Using the general synthetic scheme outlined in Scheme M and the experimental procedures for Example 23A and 23B, the following compounds were prepared:

| Cmpd No. | IUPAC Name |
|---|---|
| 393 | N-[1-(3,4-difluorophenyl)-1,2,4-triazol-3-yl]-2,6-dimorpholino-pyridin-4-amine |
| 319 | 2,6-dimorpholino-N-(1-phenyl-1,2,4-triazol-3-yl)pyridin-4-amine |
| 265 | N-[1-(3,4-difluorophenyl)-1,2,4-triazol-3-yl]-2-methyl-6-morpholino-pyridin-4-amine |
| 153 | N-[3-(4-cyclopropylpiperazin-1-yl)-5-(difluoromethyl)phenyl]-1-(2-fluoro-4-pyridyl)-1,2,4-triazol-3-amine |
| 348 | N-[3-(4-cyclopropylpiperazin-1-yl)-5-(difluoromethyl)phenyl]-1-phenyl-1,2,4-triazol-3-amine |
| 209 | N-[3-(difluoromethyl)-5-[4-(oxetan-3-yl)piperazin-1-yl]phenyl]-1-(3-pyridyl)-1,2,4-triazol-3-amine |
| 82 | N-[3-(difluoromethyl)-5-[4-(oxetan-3-yl)piperazin-1-yl]phenyl]-1-(3,5-difluorophenyl)-1,2,4-triazol-3-amine |
| 189 | N-[3-(difluoromethyl)-5-[4-(oxetan-3-yl)piperazin-1-yl]phenyl]-1-(2-fluoro-4-pyridyl)-1,2,4-triazol-3-amine |
| 163 | 4-[3-[3-(difluoromethyl)-5-[4-(oxetan-3-yl)piperazin-1-yl]anilino]-1,2,4-triazol-1-yl]-1H-pyridin-2-one |
| 475 | 1-(3,5-difluorophenyl)-N-[3-morpholino-5-(trifluoromethyl)phenyl]-1,2,4-triazol-3-amine |
| 63 | 1-(3,5-difluorophenyl)-N-[3-(4-methylpiperazin-1-yl)-5-(trifluoromethyl)phenyl]-1,2,4-triazol-3-amine |
| 366 | N-[3-morpholino-5-(trifluoromethyl)phenyl]-1-phenyl-1,2,4-triazol-3-amine |
| 257 | 1-(3-fluorophenyl)-N-[3-(4-methylpiperazin-1-yl)-5-(trifluoromethyl)phenyl]-1,2,4-triazol-3-amine |
| 4 | 1-[4-[3-[[1-(3,5-difluorophenyl)-1,2,4-triazol-3-yl]amino]-5-(trifluoromethyl)phenyl]piperazin-2-yl]cyclobutanol |
| 123 | 2-[(2S)-4-[3-[[1-(3,5-difluorophenyl)-1,2,4-triazol-3-yl]amino]-5-(trifluoromethyl)phenyl]piperazin-2-yl]propan-2-ol |
| 331 | N-[1-(3,5-difluorophenyl)-1,2,4-triazol-3-yl]-4-methyl-6-[4-(oxetan-3-yl)piperazin-1-yl]pyridin-2-amine |
| 547 | 6-[4-(oxetan-3-yl)piperazin-1-yl]-N-(1-phenyl-1,2,4-triazol-3-yl)-4-(trifluoromethyl)pyridin-2-amine |
| 545 | N-[1-(3-fluorophenyl)-1,2,4-triazol-3-yl]-6-[4-(oxetan-3-yl)piperazin-1-yl]-4-(trifluoromethyl)pyridin-2-amine |
| 546 | N-[1-(3,4-difluorophenyl)-1,2,4-triazol-3-yl]-6-[4-(oxetan-3-yl)piperazin-1-yl]-4-(trifluoromethyl)pyridin-2-amine |
| 540 | N-[1-(3,5-difluorophenyl)-1,2,4-triazol-3-yl]-6-[4-(oxetan-3-yl)piperazin-1-yl]-4-(trifluoromethyl)pyridin-2-amine |
| 560 | N-[1-(3,5-difluorophenyl)-1,2,4-triazol-3-yl]-4-methyl-6-morpholino-pyridin-2-amine |
| 554 | 4-[6-[[1-(3,5-difluorophenyl)-1,2,4-triazol-3-yl]amino]-4-(trifluoromethyl)-2-pyridyl]-N-ethyl-piperazine-1-carboxamide |
| 562 | N-[1-(3,5-difluorophenyl)-1,2,4-triazol-3-yl]-4-methyl-6-(4-tetrahydrofuran-3-ylpiperazin-1-yl)pyridin-2-amine |
| 564 | N-[1-(3,5-difluorophenyl)-1,2,4-triazol-3-yl]-6-(4-tetrahydrofuran-3-ylpiperazin-1-yl)-4-(trifluoromethyl)pyridin-2-amine |
| 555 | 1-[4-[6-[[1-(3,5-difluorophenyl)-1,2,4-triazol-3-yl]amino]-4-(trifluoromethyl)-2-pyridyl]piperazin-1-yl]ethanone |
| 569 | 1-[6-[[1-(3,5-difluorophenyl)-1,2,4-triazol-3-yl]amino]-4-methyl-2-pyridyl]-4-methyl-piperidin-4-ol |
| 571 | N-[1-(3,5-difluorophenyl)-1,2,4-triazol-3-yl]-4-methyl-6-(3-oxa-6-azaspiro[3.3]heptan-6-yl)pyridin-2-amine |
| 570 | N-[1-(3,5-difluorophenyl)-1,2,4-triazol-3-yl]-4-methyl-6-(7-oxa-2-azaspiro[3.4]octan-2-yl)pyridin-2-amine |
| 537 | N-[1-(3,5-difluorophenyl)-1,2,4-triazol-3-yl]-4-methyl-6-(3-morpholinoazetidin-1-yl)pyridin-2-amine |
| 556 | N-[1-(3,5-difluorophenyl)-1,2,4-triazol-3-yl]-6-piperazin-1-yl-4-(trifluoromethyl)pyridin-2-amine |
| 567 | N-[1-(3,5-difluorophenyl)-1,2,4-triazol-3-yl]-4-[4-(oxetan-3-yl)piperazin-1-yl]-6-(trifluoromethyl)pyridin-2-amine |
| 568 | N-[1-(3,5-difluorophenyl)-1,2,4-triazol-3-yl]-6-(3-fluoro-1-piperidyl)-4-methyl-pyridin-2-amine |
| 572 | 2-[1-[6-[[1-(3,5-difluorophenyl)-1,2,4-triazol-3-yl]amino]-4-methyl-2-pyridyl]azetidin-3-yl]propan-2-ol |
| 565 | ethyl 1-[6-[[1-(3,5-difluorophenyl)-1,2,4-triazol-3-yl]amino]-4-methyl-2-pyridyl]piperidine-4-carboxylate |
| 563 | N-[1-(3,5-difluorophenyl)-1,2,4-triazol-3-yl]-4-methyl-6-[3-(oxetan-3-yl)azetidin-1-yl]pyridin-2-amine |
| 548 | 6-[4-(oxetan-3-yl)piperazin-1-yl]-N-[1-(2-pyridyl)-1,2,4-triazol-3-yl]-4-(trifluoromethyl)pyridin-2-amine |
| 538 | N-[1-(3-fluorophenyl)-1,2,4-triazol-3-yl]-4-methyl-6-(3-morpholinoazetidin-1-yl)pyridin-2-amine |
| 557 | tert-butyl 4-[6-[[1-(3,5-difluorophenyl)-1,2,4-triazol-3-yl]amino]-4-(trifluoromethyl)-2-pyridyl]piperazine-1-carboxylate |
| 821 | 1-[6-[[1-(3,5-difluorophenyl)-1,2,4-triazol-3-yl]amino]-4-methyl-2-pyridyl]azetidine-3-carbonitrile |
| 619 | N-[1-(3,5-difluorophenyl)-1,2,4-triazol-3-yl]-6-[4-(methoxymethyl)-1-piperidyl]-4-methyl-pyridin-2-amine |
| 654 | N-[1-(3,5-difluorophenyl)-1,2,4-triazol-3-yl]-6-(4-ethylpiperazin-1-yl)-4-(trifluoromethyl)pyridin-2-amine |
| 760 | N-[1-(3,5-difluorophenyl)-1,2,4-triazol-3-yl]-2-[4-(oxetan-3-yl)piperazin-1-yl]-6-(trifluoromethyl)pyridin-4-amine |
| 732 | 4-(difluoromethyl)-N-[1-(3,5-difluorophenyl)-1,2,4-triazol-3-yl]-6-(3-morpholinoazetidin-1-yl)pyridin-2-amine |
| 847 | N-[1-(3,5-difluorophenyl)-1,2,4-triazol-3-yl]-6-fluoro-4-[4-(oxetan-3-yl)piperazin-1-yl]pyridin-2-amine |
| 815 | [1-[6-[[1-(3,5-difluorophenyl)-1,2,4-triazol-3-yl]amino]-4-methyl-2-pyridyl]-3-piperidyl]methanol |
| 755 | 1-[6-[[1-(3,5-difluorophenyl)-1,2,4-triazol-3-yl]amino]-4-methyl-2-pyridyl]piperidin-3-ol |
| 764 | N-[1-(3,5-difluorophenyl)-1,2,4-triazol-3-yl]-6-(3-methoxy-1-piperidyl)-4-methyl-pyridin-2-amine |
| 616 | N-[1-(3,5-difluorophenyl)-1,2,4-triazol-3-yl]-6-methyl-4-(3-morpholinoazetidin-1-yl)pyridin-2-amine |
| 786 | N-[1-(3,5-difluorophenyl)-1,2,4-triazol-3-yl]-6-[3-(methoxymethyl)-1-piperidyl]-4-methyl-pyridin-2-amine |
| 787 | N-[1-(3,5-difluorophenyl)-1,2,4-triazol-3-yl]-6-[4-[(3S)-tetrahydrofuran-3-yl]piperazin-1-yl]-4-(trifluoromethyl)pyridin-2-amine |
| 672 | N-[1-(3,5-difluorophenyl)-1,2,4-triazol-3-yl]-6-[4-[(3R)-tetrahydrofuran-3-yl]piperazin-1-yl]-4-(trifluoromethyl)pyridin-2-amine |

-continued

| Cmpd No. | IUPAC Name |
|---|---|
| 777 | 4-(difluoromethyl)-N-[1-(3,5-difluorophenyl)-1,2,4-triazol-3-yl]-6-(2-oxa-8-azaspiro[3.5]nonan-8-yl)pyridin-2-amine |
| 740 | N-[1-(3,5-difluorophenyl)-1,2,4-triazol-3-yl]-4-methyl-6-[4-[(3S)-tetrahydrofuran-3-yl]piperazin-1-yl]pyridin-2-amine |
| 673 | N-[1-(3,5-difluorophenyl)-1,2,4-triazol-3-yl]-4-methyl-6-[4-[(3R)-tetrahydrofuran-3-yl]piperazin-1-yl]pyridin-2-amine |
| 601 | N-[1-(3,5-difluorophenyl)-1,2,4-triazol-3-yl]-6-(3-morpholinoazetidin-1-yl)-4-(trifluoromethyl)pyridin-2-amine |
| 729 | 4-(difluoromethyl)-N-[1-(3,5-difluorophenyl)-1,2,4-triazol-3-yl]-6-[4-(methoxymethyl)-1-piperidyl]pyridin-2-amine |
| 839 | N-[1-(3,5-difluorophenyl)-1,2,4-triazol-3-yl]-6-[4-(methoxymethyl)-1-piperidyl]-4-(trifluoromethyl)pyridin-2-amine |
| 674 | N-[1-(3,5-difluorophenyl)-1,2,4-triazol-3-yl]-6-morpholino-4-(trifluoromethyl)pyridin-2-amine |
| 733 | 6-chloro-N-[1-(3,5-difluorophenyl)-1,2,4-triazol-3-yl]-4-[4-(oxetan-3-yl)piperazin-1-yl]pyridin-2-amine |
| 650 | N-[1-(3,5-difluorophenyl)-1,2,4-triazol-3-yl]-6-(4-methylpiperazin-1-yl)-4-[4-(oxetan-3-yl)piperazin-1-yl]pyridin-2-amine |
| 726 | N-[1-(3,5-difluorophenyl)-1,2,4-triazol-3-yl]-4,6-bis[4-(oxetan-3-yl)piperazin-1-yl]pyridin-2-amine |
| 712 | 6-[4-(oxetan-3-yl)piperazin-1-yl]-N-(1-pyrazin-2-yl-1,2,4-triazol-3-yl)-4-(trifluoromethyl)pyridin-2-amine |
| 770 | N-[1-(3,4-difluorophenyl)-1,2,4-triazol-3-yl]-6-morpholino-4-(trifluoromethyl)pyridin-2-amine |
| 680 | 4-(difluoromethyl)-6-[4-(oxetan-3-yl)piperazin-1-yl]-N-[1-[3-(trifluoromethyl)phenyl]-1,2,4-triazol-3-yl]pyridin-2-amine |
| 719 | 4-(difluoromethyl)-6-(3-morpholinoazetidin-1-yl)-N-[1-[3-(trifluoromethyl)phenyl]-1,2,4-triazol-3-yl]pyridin-2-amine |
| 578 | 4-methyl-6-[4-(oxetan-3-yl)piperazin-1-yl]-N-[1-[3-(trifluoromethyl)phenyl]-1,2,4-triazol-3-yl]pyridin-2-amine |
| 576 | 4-(difluoromethyl)-6-[4-(oxetan-3-yl)piperazin-1-yl]-N-(1-pyrazin-2-yl-1,2,4-triazol-3-yl)pyridin-2-amine |
| 867 | 4-(difluoromethyl)-6-morpholino-N-[1-[3-(trifluoromethyl)phenyl]-1,2,4-triazol-3-yl]pyridin-2-amine |
| 837 | 4-methyl-6-morpholino-N-[1-[3-(trifluoromethyl)phenyl]-1,2,4-triazol-3-yl]pyridin-2-amine |
| 853 | 2-[[1-(3,5-difluorophenyl)-1,2,4-triazol-3-yl]amino]-6-[4-(oxetan-3-yl)piperazin-1-yl]pyridine-4-carbonitrile |
| 607 | 2-[[1-(3,4-difluorophenyl)-1,2,4-triazol-3-yl]amino]-6-[4-(oxetan-3-yl)piperazin-1-yl]pyridine-4-carbonitrile |
| 848 | N-[1-[3-(difluoromethyl)phenyl]-1,2,4-triazol-3-yl]-4-methyl-6-[4-(oxetan-3-yl)piperazin-1-yl]pyridin-2-amine |
| 768 | N-[1-[3-(difluoromethyl)phenyl]-1,2,4-triazol-3-yl]-4-methyl-6-(3-morpholinoazetidin-1-yl)pyridin-2-amine |
| 664 | 2-[[1-(3,5-difluorophenyl)-1,2,4-triazol-3-yl]amino]-N-methyl-6-[4-(oxetan-3-yl)piperazin-1-yl]pyridine-4-carboxamide |
| 580 | N-[1-(3,5-difluorophenyl)-1,2,4-triazol-3-yl]-4-methyl-6-[4-(3-methyloxetan-3-yl)piperazin-1-yl]pyridin-2-amine |
| 756 | 4-(difluoromethyl)-N-[1-[3-(difluoromethyl)phenyl]-1,2,4-triazol-3-yl]-6-(3-morpholinoazetidin-1-yl)pyridin-2-amine |
| 718 | 4-(difluoromethyl)-N-[1-[3-(difluoromethyl)phenyl]-1,2,4-triazol-3-yl]-6-[4-(oxetan-3-yl)piperazin-1-yl]pyridin-2-amine |
| 636 | N-[1-[3-(difluoromethyl)phenyl]-1,2,4-triazol-3-yl]-6-(3-morpholinoazetidin-1-yl)-4-(trifluoromethyl)pyridin-2-amine |
| 716 | 4-(difluoromethyl)-N-[1-(3,5-difluorophenyl)-1,2,4-triazol-3-yl]-6-[4-(3-methyloxetan-3-yl)piperazin-1-yl]pyridin-2-amine |
| 689 | N6-[1-[3-(difluoromethyl)phenyl]-1,2,4-triazol-3-yl]-4-methyl-N2-tetrahydrofuran-3-yl-pyridine-2,6-diamine |
| 600 | 4-methyl-N2-tetrahydrofuran-3-yl-N6-[1-[3-(trifluoromethyl)phenyl]-1,2,4-triazol-3-yl]pyridine-2,6-diamine |
| 614 | N6-[1-(3,5-difluorophenyl)-1,2,4-triazol-3-yl]-4-methyl-N2-tetrahydrofuran-3-yl-pyridine-2,6-diamine |
| 807 | N-[1-[3-(difluoromethyl)phenyl]-1,2,4-triazol-3-yl]-6-[4-(methoxymethyl)-1-piperidyl]-4-(trifluoromethyl)pyridin-2-amine |
| 645 | 4-(difluoromethyl)-N-[1-[3-(difluoromethyl)phenyl]-1,2,4-triazol-3-yl]-6-[4-(methoxymethyl)-1-piperidyl]pyridin-2-amine |
| 795 | 4-(difluoromethyl)-6-[4-(methoxymethyl)-1-piperidyl]-N-[1-[3-(trifluoromethyl)phenyl]-1,2,4-triazol-3-yl]pyridin-2-amine |
| 849 | 4-(difluoromethyl)-N-[1-(3,4-difluorophenyl)-1,2,4-triazol-3-yl]-6-[4-(3-methyloxetan-3-yl)piperazin-1-yl]pyridin-2-amine |
| 639 | N-[1-[3-(difluoromethyl)phenyl]-1,2,4-triazol-3-yl]-4-methoxy-6-[4-(oxetan-3-yl)piperazin-1-yl]pyridin-2-amine |
| 610 | 4-methoxy-6-[4-(oxetan-3-yl)piperazin-1-yl]-N-[1-[3-(trifluoromethyl)phenyl]-1,2,4-triazol-3-yl]pyridin-2-amine |
| 599 | N-[1-(3,5-difluorophenyl)-1,2,4-triazol-3-yl]-4-methoxy-6-[4-(oxetan-3-yl)piperazin-1-yl]pyridin-2-amine |
| 612 | N-[1-(3,5-difluorophenyl)-1,2,4-triazol-3-yl]-6-fluoro-4-(3-morpholinoazetidin-1-yl)pyridin-2-amine |
| 660 | 6-chloro-N-[1-(3,5-difluorophenyl)-1,2,4-triazol-3-yl]-4-(3-morpholinoazetidin-1-yl)pyridin-2-amine |
| 625 | 4-(methoxymethyl)-6-[4-(oxetan-3-yl)piperazin-1-yl]-N-[1-[3-(trifluoromethyl)phenyl]-1,2,4-triazol-3-yl]pyridin-2-amine |
| 823 | 4-(difluoromethyl)-N-[1-(3-fluorophenyl)-1,2,4-triazol-3-yl]-6-[4-(3-methyloxetan-3-yl)piperazin-1-yl]pyridin-2-amine |
| 789 | 2-[[1-(3,4-difluorophenyl)-1,2,4-triazol-3-yl]amino]-N-methyl-6-[4-(oxetan-3-yl)piperazin-1-yl]pyridine-4-carboxamide |
| 758 | N-[1-(4-chloro-3-fluoro-phenyl)-1,2,4-triazol-3-yl]-4-methoxy-6-[4-(oxetan-3-yl)piperazin-1-yl]pyridin-2-amine |
| 621 | N-[1-(4-chloro-3-fluoro-phenyl)-1,2,4-triazol-3-yl]-4-(difluoromethyl)-6-[4-(oxetan-3-yl)piperazin-1-yl]pyridin-2-amine |
| 749 | N-[1-(4-chloro-3-fluoro-phenyl)-1,2,4-triazol-3-yl]-4-methyl-6-[4-(oxetan-3-yl)piperazin-1-yl]pyridin-2-amine |
| 728 | N-[1-(4-fluorophenyl)-1,2,4-triazol-3-yl]-6-[4-(oxetan-3-yl)piperazin-1-yl]-4-(trifluoromethyl)pyridin-2-amine |
| 675 | methyl 2-[[1-(3,5-difluorophenyl)-1,2,4-triazol-3-yl]amino]-6-morpholino-pyridine-4-carboxylate |
| 859 | N-[1-(3-chloro-4-fluoro-phenyl)-1,2,4-triazol-3-yl]-4-(difluoromethyl)-6-[4-(oxetan-3-yl)piperazin-1-yl]pyridin-2-amine |
| 579 | 4-(1,1-difluoroethyl)-N-[1-(3,4-difluorophenyl)-1,2,4-triazol-3-yl]-6-[4-(oxetan-3-yl)piperazin-1-yl]pyridin-2-amine |
| 806 | 4-(difluoromethyl)-N-[1-(4-fluorophenyl)-1,2,4-triazol-3-yl]-6-[4-(oxetan-3-yl)piperazin-1-yl]pyridin-2-amine |
| 685 | 4-(1,1-difluoroethyl)-N-[1-(3,5-difluorophenyl)-1,2,4-triazol-3-yl]-6-[4-(oxetan-3-yl)piperazin-1-yl]pyridin-2-amine |
| 860 | 4-(1,1-difluoroethyl)-N-[1-(3-fluorophenyl)-1,2,4-triazol-3-yl]-6-[4-(oxetan-3-yl)piperazin-1-yl]pyridin-2-amine |
| 713 | [2-[[1-(3,4-difluorophenyl)-1,2,4-triazol-3-yl]amino]-6-[4-(oxetan-3-yl)piperazin-1-yl]-4-pyridyl]methanol |

Scheme N: General Route N for Preparation of Compounds of Formula I or I'

-continued

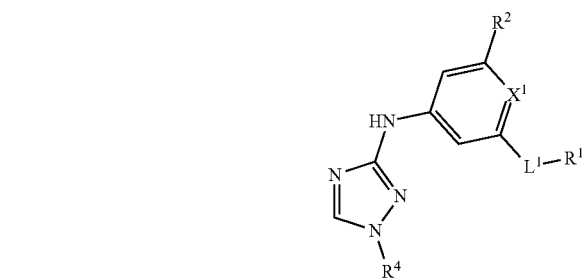

X = Cl, Br, F

Compounds of the invention may be prepared as generally outlined in Scheme N, where $R^2$, $R^4$, and $X^1$ are as described herein, and $HL^1-R^1$ is an amine such that $-L^1-R$, as defined herein, is bonded to the parent molecular moiety through a nitrogen atom.

Example 24

Preparation of N-[1-(3,5-difluorophenyl)-1,2,4-triazol-3-yl]-2-methyl-6-(4-methylpiperazin-1-yl)pyridin-4-amine (Compound 365)

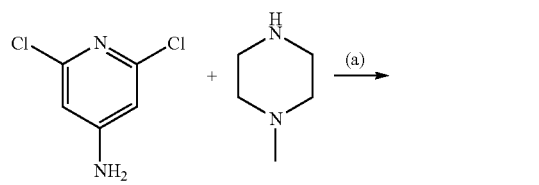

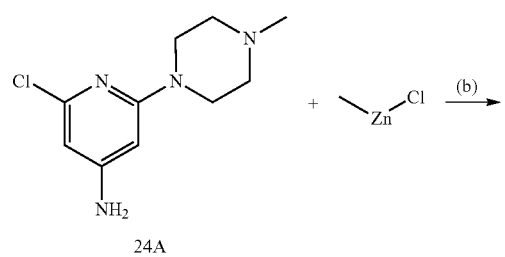

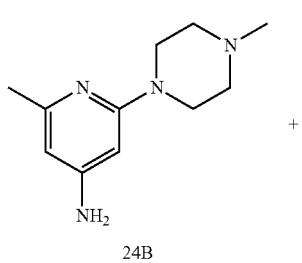

-continued

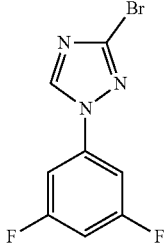

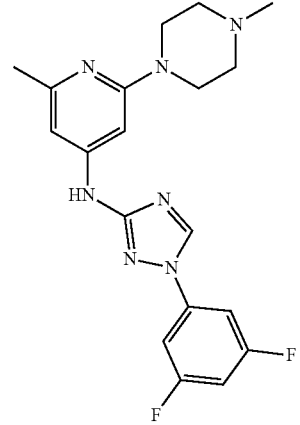

Cmpd 365

(a) DIEA/dioxane; (b) palladium; triphenylphosphane/THF; (c) t-BuXPHOS Palladacycle/t-BuOK/t-BuOH Preparation of 2-chloro-6-(4-methylpiperazin-1-yl)pyridin-4-amine (24A)

A mixture of dioxane (100 mL), 2,6-dichloropyridin-4-amine (4.89 g, 30 mmol), 1-methylpiperazine (15 g, 150 mmol) and DIEA (11.6 g, 15.7 mL, 90 mmol) was stirred at 130° C. in a Qian cap pressure bottle for 4 days. LCMS indicated that the reaction was 80% complete so the reaction was worked up. Work up: the reaction mixture was cooled to RT, EtOAc was added and brine, the organic phase was dried over MgSO$_4$, filtered, concentrated down and the crude product was purified by Isco (275 g Gold amine column) eluting with EA and heptanes. The product was eluted with 70% EA and 30% heptanes to give 2-chloro-6-(4-methylpiperazin-1-yl)pyridin-4-amine, 24A (2.42 g, 35%). $^1$H NMR (400 MHz, CDCl3) δ 6.02 (d, J=1.6 Hz, 1H), 5.72 (d, J=1.6 Hz, 1H), 4.05 (s, 2H), 3.54-3.44 (m, 4H), 2.54-2.45 (m, 4H), 2.34 (s, 3H) ppm. ESI-MS m/z calc. 226.09853, found 227.14 (M+1)$^+$; Retention time: 0.45 minutes.

Preparation of 2-methyl-6-(4-methylpiperazin-1-yl)pyridin-4-amine (24B)

To a degassed THF (30 mL) solution of 2-chloro-6-(4-methylpiperazin-1-yl)pyridin-4-amine (1) (1.16 g, 5 mmol) was added palladiumtriphenylphosphane (231 mg, 0.20 mmol) and chloro(methyl)zinc (15 mL of 2 M soln, 30 mmol) and the reaction mixture was refluxed in a pressure bottle for 2 days. LCMS indicated the reaction was completed. Work up: the reaction mixture was cooled to RT, filtered through Celite and concentrated down. To the crude mixture was added 200 ml water, the mixture was stirred for 3 h until all catalyst had precipitated out. Catalyst was filtered off, the aq phase was extracted with EA (70 ml×2), the organic phase was dried over MgSO$_4$, filtered and concentrated down and used as it is. It gave crude 2-methyl-6-(4-methylpiperazin-1-yl)pyridin-4-amine (24B) (500 mg, 35%. $^1$H NMR (400 MHz, CD3OD) δ 6.00-5.91 (m, 1H), 5.80 (dd, J=7.6, 1.5 Hz, 1H), 3.42-3.31 (m, 4H), 2.58-2.48 (m, 4H), 2.31 (d, J=3.8 Hz, 3H), 2.20 (s, 3H) ppm. ESI-MS m/z calc. 206.15315, found 207.15 (M+1)$^+$; Retention time: 0.27 minutes.

Preparation of N-(1-(3,5-difluorophenyl)-1H-1,2,4-triazol-3-yl)-2-methyl-6-(4-methylpiperazin-1-yl)pyridin-4-amine (Compound 365)

To a t-BuOH (5 mL) mixture of 2-methyl-6-(4-methylpiperazin-1-yl)pyridin-4-amine 24B (100 mg, 0.485 mmol), 3-bromo-1-(3,5-difluorophenyl)-1,2,4-triazole 24C (189 mg, 0.727 mmol) and t-BuXPhos Palladacycle (63 mg, 0.097 mmol) was added t-BuOK (163 mg, 1.45 mmol) at 45° C., and the reaction mixture was stirred at 45° C. for 1 h. LCMS indicated desired product only. Work up: to the reaction mixture was added EA and brine, the organic phase was dried with MgSO$_4$, filtered, concentrated down and purified by Isco 40 g Gold silica gel column with DCM and MeOH. The product was eluted with 15% MeOH and 85% DCM and gave N-(1-(3,5-difluorophenyl)-1H-1,2,4-triazol-3-yl)-2-methyl-6-(4-methylpiperazin-1-yl)pyridin-4-amine, cmpd 365 (94 mg, 47%). $^1$H NMR (400 MHz, DMSO-d6) δ 9.78 (s, 1H), 9.21 (s, 1H), 7.70-7.53 (m, 2H), 7.28 (tt, J=9.3, 2.3 Hz, 1H), 6.94 (s, 1H), 6.72 (s, 1H), 3.50-3.37 (m, 4H), 2.44-2.33 (m, 4H), 2.25 (s, 3H), 2.22 (s, 3H) ppm. ESI-MS m/z calc. 385.18265, found 386.19 (M+1)$^+$; Retention time: 0.52 minutes.

Using the general synthetic scheme outlined in Scheme N and the experimental procedures listed above in Example 24, the following compounds were prepared:

| Cmpd No. | IUPAC Name |
|---|---|
| 367 | 2-chloro-6-(4-methylpiperazin-1-yl)-N-(1-phenyl-1,2,4-triazol-3-yl)pyridin-4-amine |
| 477 | 2-chloro-N-[1-(3,4-difluorophenyl)-1,2,4-triazol-3-yl]-6-(4-methylpiperazin-1-yl)pyridin-4-amine |
| 135 | 2-chloro-6-morpholino-N-(1-phenyl-1,2,4-triazol-3-yl)pyridin-4-amine |
| 100 | 2-chloro-N-[1-(3,4-difluorophenyl)-1,2,4-triazol-3-yl]-6-morpholino-pyridin-4-amine |
| 251 | N-(3-morpholino-5-tetrahydropyran-4-yl-phenyl)-1-phenyl-1,2,4-triazol-3-amine |
| 57 | (2R)-3-methyl-2-[4-[6-methyl-4-[(1-phenyl-1,2,4-triazol-3-yl)amino]-2-pyridyl]piperazin-2-yl]butan-2-ol |
| 345 | 2-chloro-N-[1-(3,4-dimethoxyphenyl)-1,2,4-triazol-3-yl]-6-morpholino-pyridin-4-amine |
| 106 | 2-chloro-N-[1-(3-methoxyphenyl)-1,2,4-triazol-3-yl]-6-(1-piperidyl)pyridin-4-amine |
| 145 | 2-chloro-N-[1-(3-methoxyphenyl)-1,2,4-triazol-3-yl]-6-morpholino-pyridin-4-amine |
| 365 | N-[1-(3,5-difluorophenyl)-1,2,4-triazol-3-yl]-2-methyl-6-(4-methylpiperazin-1-yl)pyridin-4-amine |
| 263 | N-[1-(3,4-difluorophenyl)-1,2,4-triazol-3-yl]-2-methyl-6-(4-methylpiperazin-1-yl)pyridin-4-amine |
| 156 | 2-methyl-6-(4-methylpiperazin-1-yl)-N-(1-phenyl-1,2,4-triazol-3-yl)pyridin-4-amine |
| 430 | 2-(4-fluoro-1-piperidyl)-6-methyl-N-(1-phenyl-1,2,4-triazol-3-yl)pyridin-4-amine |
| 457 | N-[1-(3,5-difluorophenyl)-1,2,4-triazol-3-yl]-2-(4-fluoro-1-piperidyl)-6-methyl-pyridin-4-amine |

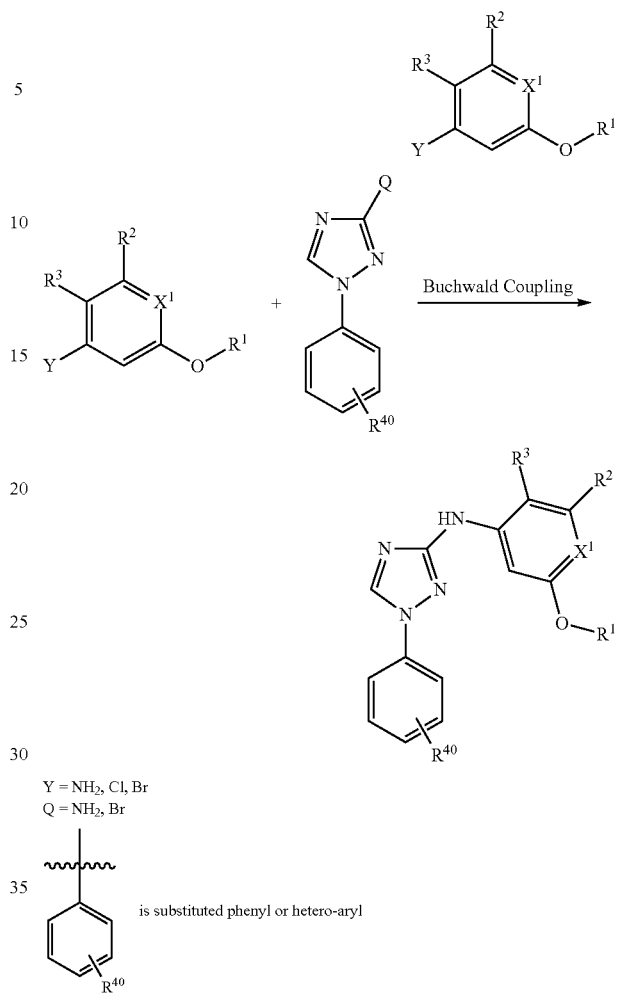

Y = NH$_2$, Cl, Br
Q = NH$_2$, Br is substituted phenyl or hetero-aryl

Compounds of the invention may be prepared as generally outlined in Scheme O, where R$^1$, R$^2$, R$^3$, R$^{40}$, and X$^1$ are as described herein. The methods of Scheme O are useful for the preparation of compounds where L$^1$ is an oxygen atom. R$^1$ groups, or protected derivatives thereof, may be subjected to further synthetic manipulation (e.g., deprotection, reductive amination, acylation, etc.) to arrive at additional compounds of the invention.

Example 25

Preparation of 1-(3,5-difluorophenyl)-N-[3-methyl-5-[[1-(oxetan-3-yl)-4-piperidyl]oxy]phenyl]-1,2,4-triazol-3-amine (Compound 433)

Scheme O: General Route O for Preparation of Compounds of Formula I or I'

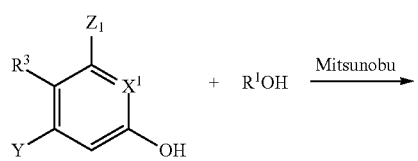

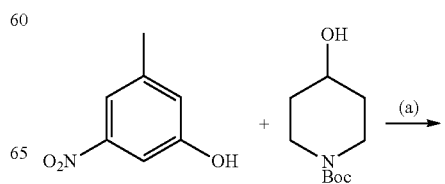

831
-continued

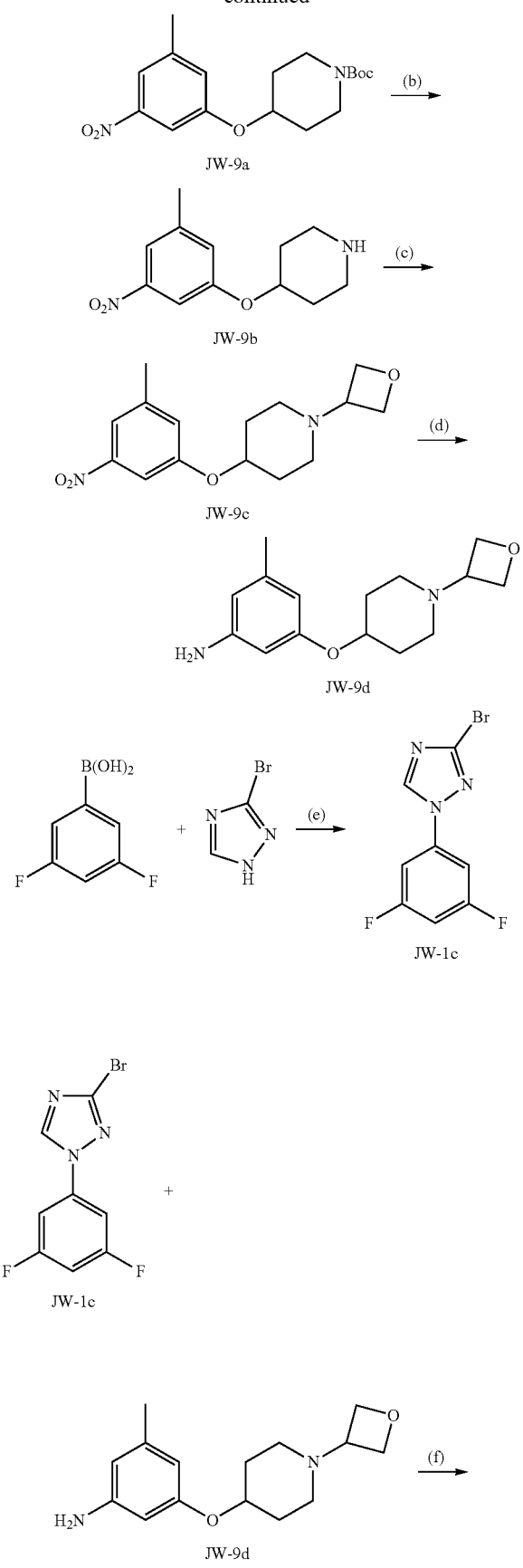

832
-continued

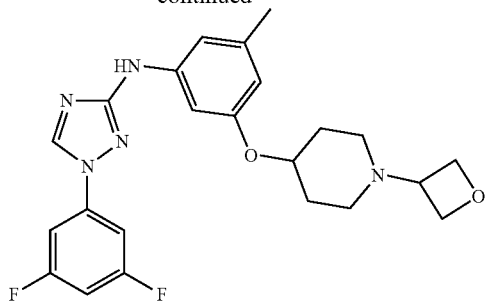

Compound 433

(a)DIAD/PPh3.THF.R.T.; (b)TFA/DCM/R.T.; (c)Na(OAc)₃BH/oxetan-3-one; (d)H2/Pd on Carbon, 10% weight; (e)Cu(OAc)₂/Pyridine/DCM/R.T.; (f) t-BuXPhos Palladacycle/t-BuOH/t-BuONa Preparation of (tert-butyl 4-(3-methyl-5-nitro-phenoxy)piperidine-1-carboxylate (JW-9a)

3-methyl-5-nitro-phenol (4.0 g, 26.1 mmol), tert-butyl 4-hydroxypiperidine-1-carboxylate (5.3 g, 26.1 mmol) and triphenylphosphane (6.9 g, 6.1 mL, 26 mmol) were mixed in THF (40 mL) and isopropyl (NE)-N-isopropoxycarbonyliminocarbamate (5.3 g, 26 mmol) was added into the reaction. The mixture was stirred at RT overnight, then diluted with water and extracted with DCM (100 ml×2). The combined organic layer was dried and concentrated. The crude product was purified on silica gel eluting with EtOAc:Hexanes (10-30%) to afford 5.98 g (68%) of JW-9a, (tert-butyl 4-(3-methyl-5-nitro-phenoxy)piperidine-1-carboxylate.

Preparation of 4-(3-methyl-5-nitro-phenoxy)piperidine (JW-9b)

tert-Butyl 4-(3-methyl-5-nitro-phenoxy)piperidine-1-carboxylate (JW-9a) (5.1 g, 15.2 mmol) was dissolved in DCM (20 mL) and TFA (10 mL) was added into the solution. The reaction was stirred at room temperature for 30 minutes and LCMS showed that the reaction was complete. The solvent was removed and the crude was dissolved in DCM (50 ml) and washed with NaHCO₃ (aq.) and brine. The organic layer was dried and concentrated to afford 2.65 g (53%) of JW-9b, 4-(3-methyl-5-nitro-phenoxy)piperidine in 53% yield. ESI-MS m/z calc. 236.12, found 237.45 (M+1)⁺; Retention time: 0.60 minutes.

Preparation of 4-(3-methyl-5-nitro-phenoxy)-1-(oxetan-3-yl)piperidine (JW-9c)

4-(3-methyl-5-nitro-phenoxy)piperidine (JW-9b) (2.5 g, 10.6 mmol) and oxetan-3-one (1.52 g, 21.1 mmol) were mixed in DCE (25 mL) and the reaction was stirred at room temperature for 20 minutes. Sodium triacetoxyborohydride (4.5 g, 21.2 mmol) was added into the reaction and the reaction was stirred at room temperature overnight. LCMS showed that the reaction was complete. The reaction was quenched with 1N NaOH (aq.) and extracted with DCM. The organic layer was dried and concentrated. The crude was purified on silica gel using 10-90% EtOAc:Hexanes to afford 1.82 g (405) of JW-9c, 4-(3-methyl-5-nitro-phenoxy)-1-(oxetan-3-yl)piperidine. ESI-MS m/z calc. 292.14, found 293.39 (M+1)⁺; Retention time: 0.60 minutes.

Preparation of 3-methyl-5-[[1-(oxetan-3-yl)-4-piperidyl]oxy]aniline (JW-9d)

To a 250 ml RBF was added Pd on carbon (10% by weight, 62 mg) under N2 and EtOH (20 mL) was added. 4-(3-Methyl-5-nitro-phenoxy)-1-(oxetan-3-yl)piperidine (JW-9c) (1.72 g, 5.88 mmol) was added into the reaction and the reaction was stirred at room temperature under H2 with an attached balloon overnight. LCMS showed that the reaction was complete. The catalyst was filtered off and the filtrate was concentrated to afford 1.28 g (83%) of JW-9d, of 3-methyl-5-[[1-(oxetan-3-yl)-4-piperidyl]oxy]aniline. ESI-MS m/z calc. 262.17, found 263.47 (M+1)$^+$; Retention time: 0.26 minutes.

Preparation of 3-bromo-1-(3,5-difluorophenyl)-1,2,4-triazole (JW-1c)

Diacetoxycopper (2.30 g, 12.7 mmol), 3,5-difluorophenyl-boronic acid (1.60 g, 10.1 mmol), 3-bromo-1H-1,2,4-triazole (1.25 g, 8.4 mmol) and 4A molecular sieves (150 mg) were mixed in DCM (50 mL) and pyridine (1.3 mL, 16.9 mmol) was added. The mixture was stirred at RT under air for 3 days. LCMS showed that no starting material remaining and desired product was formed. The reaction was filtered through a plug of Celite via suction and the solid cake was washed with an additional 200 ml DCM. The combined organic layer was washed with 0.1 N aqueous HCl (50 ml×3) and brine (200 ml). The organic layer was concentrated and crude product purified on silica gel (120 g column, dry loading method on celite) using 10-90% EtOAc:Hexanes to afford 1.23 g (50%) of desired product JW-1c, 3-bromo-1-(3,5-difluorophenyl)-1,2,4-triazole. $^1$H NMR (400 MHz, DMSO-d6) δ 9.40 (s, 1H), 7.78-7.61 (m, 2H), 7.41 (tt, J=9.3, 2.3 Hz, 1H) ppm. ESI-MS m/z calc. 258.96, found 260.05 (M+1)+; Retention time: 0.8 minutes.

Preparation of 1-(3,5-difluorophenyl)-N-[3-methyl-5-[[1-(oxetan-3-yl)-4-piperidyl]oxy]phenyl]-1,2,4-triazol-3-amine (Compound 433)

Sodium t-butoxide (148.6 mg, 1.546 mmol), t-BuXPhos Palladacycle (21 mg, 0.03 mmol), 3-methyl-5-[[1-(oxetan-3-yl)-4-piperidyl]oxy]aniline (JW-9d) (200 mg, 0.77 mmol) and 3-bromo-1-(3,5-difluorophenyl)-1,2,4-triazole (JW-1c) (199 mg, 0.76 mmol) were mixed in t-BuOH (2.5 mL) and the reaction was degassed with N$_2$ for 30 seconds. The reaction was heated at 60 degrees for 3 hours and LCMS indicated that the reaction was complete. The reaction was cooled to room temperature and water was added to quench the reaction. Brine was added, the mixture was extracted with DCM and the organic layer was dried and concentrated. The crude was purified on reverse phase using 10-90% acetonitrile:water (0.1% TFA) and the desired fraction was converted into free base to afford 15.3 mg (11%) of cmpd 433, 1-(3,5-difluorophenyl)-N-[3-methyl-5-[[1-(oxetan-3-yl)-4-piperidyl]oxy]phenyl]-1,2,4-triazol-3-amine. 1H NMR (300 MHz, DMSO-d6) δ 9.48 (s, 1H), 9.16 (s, 1H), 7.60 (d, J=6.4 Hz, 2H), 7.42-7.20 (m, 2H), 6.83 (s, 1H), 6.28 (s, 1H), 4.53 (t, J=6.5 Hz, 2H), 4.43 (t, J=6.1 Hz, 2H), 4.32 (s, 1H), 3.41 (dd, J=12.6, 6.3 Hz, 1H), 2.58 (s, 2H), 2.22 (s, 3H), 2.15-1.94 (m, 4H), 1.77-1.55 (m, 2H) ppm. ESI-MS m/z calc. 441.19763, found 442.44 (M+1)+; Retention time: 0.65 minutes.

Using the general synthetic scheme outlined in Scheme O and the experimental procedures in Example 25, the following compounds were prepared:

| Cmpd No. | IUPAC Name |
|---|---|
| 304 | 1-(3,5-difluorophenyl)-N-[3-methyl-5-[(3S)-1-(oxetan-3-yl)pyrrolidin-3-yl]oxy-phenyl]-1,2,4-triazol-3-amine |
| 433 | 1-(3,5-difluorophenyl)-N-[3-methyl-5-[[1-(oxetan-3-yl)-4-piperidyl]oxy]phenyl]-1,2,4-triazol-3-amine |
| 384 | 1-(3,4-difluorophenyl)-N-[3-methyl-5-[[1-(oxetan-3-yl)-4-piperidyl]oxy]phenyl]-1,2,4-triazol-3-amine |
| 410 | N-[3-methyl-5-[[1-(oxetan-3-yl)-4-piperidyl]oxy]phenyl]-1-phenyl-1,2,4-triazol-3-amine |
| 201 | 1-(4-fluorophenyl)-N-[3-methyl-5-[[1-(oxetan-3-yl)-4-piperidyl]oxy]phenyl]-1,2,4-triazol-3-amine |
| 52 | 1-(3,4-difluorophenyl)-N-[3-methyl-5-[(3S)-1-(oxetan-3-yl)pyrrolidin-3-yl]oxy-phenyl]-1,2,4-triazol-3-amine |
| 239 | N-[3-methyl-5-[(3S)-1-(oxetan-3-yl)pyrrolidin-3-yl]oxy-phenyl]-1-phenyl-1,2,4-triazol-3-amine |
| 178 | 1-(3,5-difluorophenyl)-N-[3-methyl-5-[(3R)-1-(oxetan-3-yl)pyrrolidin-3-yl]oxy-phenyl]-1,2,4-triazol-3-amine |
| 391 | N-[3-methyl-5-[(3R)-1-(oxetan-3-yl)pyrrolidin-3-yl]oxy-phenyl]-1-phenyl-1,2,4-triazol-3-amine |
| 46 | 1-(3,4-difluorophenyl)-N-[3-methyl-5-[(3R)-1-(oxetan-3-yl)pyrrolidin-3-yl]oxy-phenyl]-1,2,4-triazol-3-amine |
| 703 | 1-(3,5-difluorophenyl)-N-(3-methyl-5-tetrahydrofuran-3-yloxy-phenyl)-1,2,4-triazol-3-amine |
| 778 | 1-(3,4-difluorophenyl)-N-(3-methyl-5-tetrahydrofuran-3-yloxy-phenyl)-1,2,4-triazol-3-amine |
| 805 | 1-[4-[3-[[1-(3,5-difluorophenyl)-1,2,4-triazol-3-yl]amino]-5-methyl-phenoxy]-1-piperidyl]ethanone |
| 626 | 1-[4-[3-[[1-(3,4-difluorophenyl)-1,2,4-triazol-3-yl]amino]-5-methyl-phenoxy]-1-piperidyl]ethanone |
| 620 | 1-(3,5-difluorophenyl)-N-[3-methyl-5-[[1-(oxetan-3-yl)-3-piperidyl]oxy]phenyl]-1,2,4-triazol-3-amine |
| 590 | 1-(3,4-difluorophenyl)-N-[3-methyl-5-[[1-(oxetan-3-yl)-3-piperidyl]oxy]phenyl]-1,2,4-triazol-3-amine |
| 700 | 1-(3,5-difluorophenyl)-N-[3-methyl-5-[[(3S)-1-(oxetan-3-yl)-3-piperidyl]oxy]phenyl]-1,2,4-triazol-3-amine |
| 748 | 1-(3,5-difluorophenyl)-N-[3-methyl-5-[[(3R)-1-(oxetan-3-yl)-3-piperidyl]oxy]phenyl]-1,2,4-triazol-3-amine |
| 632 | 1-(3,4-difluorophenyl)-N-[3-methyl-5-[[(3S)-1-(oxetan-3-yl)-3-piperidyl]oxy]phenyl]-1,2,4-triazol-3-amine |
| 665 | 1-(3,4-difluorophenyl)-N-[3-methyl-5-[[(3R)-1-(oxetan-3-yl)-3-piperidyl]oxy]phenyl]-1,2,4-triazol-3-amine |
| 677 | 1-(3,5-difluorophenyl)-N-[3-methyl-5-[(3-methyloxetan-3-yl)methoxy]phenyl]-1,2,4-triazol-3-amine |
| 615 | 1-(3,4-difluorophenyl)-N-[3-methyl-5-[(3-methyloxetan-3-yl)methoxy]phenyl]-1,2,4-triazol-3-amine |
| 671 | N-[3-methyl-5-[(3-methyloxetan-3-yl)methoxy]phenyl]-1-[3-(trifluoromethyl)phenyl]-1,2,4-triazol-3-amine |
| 812 | 1-(3,5-difluorophenyl)-N-[3-methyl-5-(2-morpholinoethoxy)phenyl]-1,2,4-triazol-3-amine |
| 845 | 1-(3,4-difluorophenyl)-N-[3-methyl-5-(2-morpholinoethoxy)phenyl]-1,2,4-triazol-3-amine |
| 575 | N-[3-methyl-5-(2-morpholinoethoxy)phenyl]-1-[3-(trifluoromethyl)phenyl]-1,2,4-triazol-3-amine |
| 635 | 1-(3,5-difluorophenyl)-N-(3-methyl-5-tetrahydropyran-3-yloxy-phenyl)-1,2,4-triazol-3-amine |
| 638 | 1-(3,4-difluorophenyl)-N-(3-methyl-5-tetrahydropyran-3-yloxy-phenyl)-1,2,4-triazol-3-amine |
| 706 | N-[3-[(3,3-difluorocyclobutyl)methoxy]-5-methyl-phenyl]-1-(3,5-difluorophenyl)-1,2,4-triazol-3-amine |
| 640 | N-[3-[(3,3-difluorocyclobutyl)methoxy]-5-methyl-phenyl]-1-(3,4-difluorophenyl)-1,2,4-triazol-3-amine |
| 832 | 1-(3,5-difluorophenyl)-N-[3-methyl-5-(2-pyrazol-1-ylethoxy)phenyl]-1,2,4-triazol-3-amine |
| 698 | 1-(3,4-difluorophenyl)-N-[3-methyl-5-(2-pyrazol-1-ylethoxy)phenyl]-1,2,4-triazol-3-amine |
| 644 | N-[3-methyl-5-(2-pyrazol-1-ylethoxy)phenyl]-1-[3-(trifluoromethyl)phenyl]-1,2,4-triazol-3-amine |
| 605 | 1-(3,5-difluorophenyl)-N-[3-methyl-5-[(1-methylpyrazol-3-yl)methoxy]phenyl]-1,2,4-triazol-3-amine |
| 714 | 1-(3,4-difluorophenyl)-N-[3-methyl-5-[(1-methylpyrazol-3-yl)methoxy]phenyl]-1,2,4-triazol-3-amine |
| 648 | 1-(3,5-difluorophenyl)-N-[3-methyl-5-(tetrahydrofuran-3-ylmethoxy)phenyl]-1,2,4-triazol-3-amine |
| 865 | 1-(3,4-difluorophenyl)-N-[3-methyl-5-(tetrahydrofuran-3-ylmethoxy)phenyl]-1,2,4-triazol-3-amine |
| 627 | 1-(3,4-difluorophenyl)-N-[3-methyl-5-(tetrahydropyran-4-ylmethoxy)phenyl]-1,2,4-triazol-3-amine |
| 978 | 1-(3,4-difluorophenyl)-N-(2-fluoro-5-methyl-3-tetrahydrofuran-3-yloxy-phenyl)-1,2,4-triazol-3-amine |

-continued

| Cmpd No. | IUPAC Name |
|---|---|
| 913 | N-(2-fluoro-5-methyl-3-tetrahydrofuran-3-yloxy-phenyl)-1-(3-fluorophenyl)-1,2,4-triazol-3-amine |
| 907 | N-(2-fluoro-5-methyl-3-tetrahydrofuran-3-yloxy-phenyl)-1-phenyl-1,2,4-triazol-3-amine |
| 952 | N-(2-fluoro-5-methyl-3-tetrahydrofuran-3-yloxy-phenyl)-1-pyrazin-2-yl-1,2,4-triazol-3-amine |
| 1053 | 1-(3,5-difluorophenyl)-N-(2-fluoro-5-methyl-3-tetrahydrofuran-3-yloxy-phenyl)-1,2,4-triazol-3-amine |
| 1028 | 1-(3,5-difluorophenyl)-N-(2-fluoro-5-methyl-3-tetrahydrofuran-3-yloxy-phenyl)-1,2,4-triazol-3-amine |
| 886 | N-(2-fluoro-5-methyl-3-tetrahydrofuran-3-yloxy-phenyl)-1-(3-fluorophenyl)-1,2,4-triazol-3-amine |
| 1061 | N-(2-fluoro-5-methyl-3-tetrahydrofuran-3-yloxy-phenyl)-1-(3-fluorophenyl)-1,2,4-triazol-3-amine |
| 1009 | 1-(3,4-difluorophenyl)-N-(2-fluoro-5-methyl-3-tetrahydrofuran-3-yloxy-phenyl)-1,2,4-triazol-3-amine |
| 1055 | 1-(3,4-difluorophenyl)-N-(2-fluoro-5-methyl-3-tetrahydrofuran-3-yloxy-phenyl)-1,2,4-triazol-3-amine |
| 1002 | N-(2-fluoro-5-methyl-3-tetrahydrofuran-3-yloxy-phenyl)-1-phenyl-1,2,4-triazol-3-amine |
| 1052 | N-(2-fluoro-5-methyl-3-tetrahydrofuran-3-yloxy-phenyl)-1-phenyl-1,2,4-triazol-3-amine |
| 1094 | 2-[3-[[1-(3,5-difluorophenyl)-1,2,4-triazol-3-yl]amino]-4,5-dimethyl-phenoxy]-1-morpholino-ethanone |

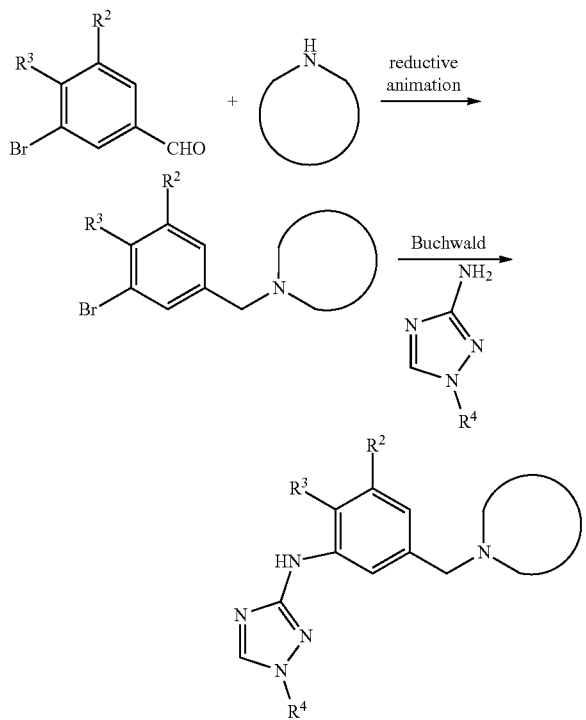

Scheme P: General Route P for Preparation of Compounds of Formula I or I'

Compounds of the invention may be prepared as generally outlined in Scheme P, where R² and R⁴ are as described herein.

Example 26

Preparation of 1-(3,5-difluorophenyl)-N-[3-methyl-5-[[4-(oxetan-3-yl)piperazin-1-yl]methyl]phenyl]-1,2,4-triazol-3-amine (Compound 596)

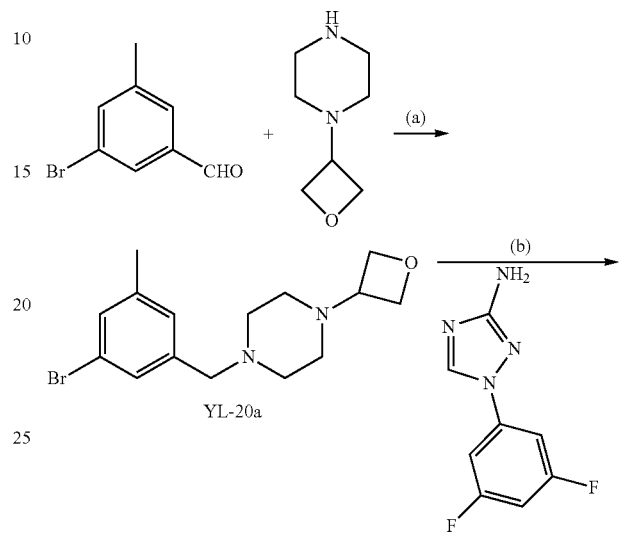

Cmpd 596

Reagents and conditions: (a) NaBH(OAc)$_3$, HOAc, DCM; (b) 1-(3,5-difluorophenyl)-1,2,4-triazol-3-amine, t-BuXPhos Palladacycle, NaOtBu, dioxane, 120° C.

Preparation of 1-(3-bromo-5-methylbenzyl)-4-(oxetan-3-yl)piperazine (YL-20a)

To a solution of 3-bromo-5-methyl-benzaldehyde (7.50 g, 37.68 mmol), 1-(oxetan-3-yl)piperazine (4 g, 28.13 mmol) and acetic acid (3 mL, 52.75 mmol) in dichloromethane (150 mL) was added NaBH(OAc)$_3$ (11.98 g, 56.52 mmol) carefully. The mixture was stirred for 4 h. LCMS showed desired product. The reaction was diluted with DCM and slowly quenched with MeOH and sat. NaHCO$_3$ (50 mL). After separation, the organic layer was washed with water, sat NaCl and dried over sodium sulfate, filtered and concentrated to give 1-[(3-bromo-5-methyl-phenyl)methyl]-4-(oxetan-3-yl)piperazine YL-20a (7.3 g, 59.6%) $^1$H NMR (300 MHz, CDCl$_3$) δ 7.29 (s, 1H), 7.23 (s, 1H), 7.05 (s, 1H), 4.82-4.50 (m, 4H), 3.61-3.48 (m, 1H), 3.47 (d, J=5.7 Hz, 2H), 2.51 (m, 4H), 2.39 (m, 4H), 2.33 (s, 3H) ppm. ESI-MS m/z calc 324.08, found 325.48 (M+1)+; Retention time: 0.66 minutes.

Preparation of 1-(3,5-difluorophenyl)-N-[3-methyl-5-[[4-(oxetan-3-yl)piperazin-1-yl]methyl]phenyl]-1,2,4-triazol-3-amine (Compound 596)

1-[(3-bromo-5-methyl-phenyl)methyl]-4-(oxetan-3-yl)piperazine YL-20a (290 mg, 0.89 mmol), 1-(3,5-difluorophenyl)-1,2,4-triazol-3-amine (JW-1c) (216 mg, 0.99 mmol), and sodium t-butoxide (174 mg, 1.81 mmol) were suspended in dioxane (13 mL) and purged with $N_2$ for several minutes before addition of t-BuXPhos Palladacycle (52 mg, 0.076 mmol). The mixture was microwaved at 125° C. for 45 minutes. The reaction was quenched with MeOH (2 mL) and diluted with DCM. After filtration (Florisil/10 g), the excess solvent was pumped down. ISCO purification (40 g silica; 0% to 10% of MeOH in DCM) followed by DCM/MeOH trituation gave cmpd 596 1-(3,5-difluorophenyl)-N-[3-methyl-5-[[4-(oxetan-3-yl)piperazin-1-yl]methyl]phenyl]-1,2,4-triazol-3-amine (180 mg, 43.5%). $^1$H NMR (300 MHz, CDCl$_3$) δ 8.33 (s, 1H), 7.39 (s, 1H), 7.30 (d, J=2.2 Hz, 1H), 7.27 (s, 1H), 7.23 (s, 1H), 6.89-6.75 (m, 2H), 6.70 (s, 1H), 4.75-4.53 (m, 4H), 3.62-3.44 (m, 3H), 2.59 (m, 4H), 2.40 (m, 7H) ppm. ESI-MS m/z calc. 440.21, found 441.67 (M+1)+; Retention time: 0.68 minutes.

Example 27

Preparation of N-[3-[4-(3-deuteriooxetan-3-yl)piperazin-1-yl]-5-methyl-phenyl]-1-(3,5-difluorophenyl)-1,2,4-triazol-3-amine (Compound 1100)

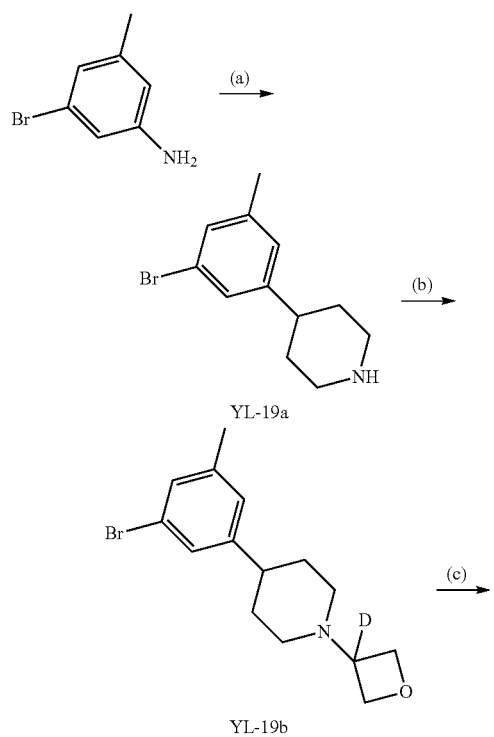

YL-19a

YL-19b

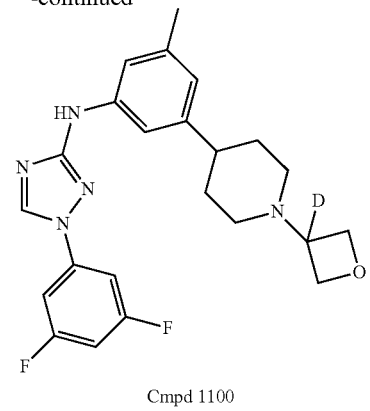

Cmpd 1100

Reagents and conditions: (a) 2-chloro-N-(2-chloroethyl)ethanamine (Hydrochloric Acid (1)), 160° C.; (b) oxetan-3-one, NaBD(OAc)3, DOAc, DCM; (c) 1-phenyl-1,2,4-triazol-3-amine, t-BuXPhos Palladacycle, NaOtBu, dioxane, 120° C.

Preparation of 1-(3-bromo-5-methyl-phenyl)piperazine (YL-19a)

A mixture of 3-bromo-5-methyl-aniline (5 g, 26.87 mmol) and 2-chloro-N-(2-chloroethyl)ethanamine (Hydrochloric Acid (1)) (5.28 g, 29.56 mmol) in butan-1-ol (100 mL) was refluxed at 125° C. for 16 h. After filtration, the solids were collected, washed with n-butanol and dried. The solid was dissolved in EtOAc (200 mL) and treated with sat. Na$_2$CO$_3$ (40 mL). The organic layer was collected, then excess solvent was removed in vacuo. ISCO purification (40 g silica; 0% to 10% to 30% of MeOH in DCM) gave 1-(3-bromo-5-methyl-phenyl)piperazine YL-19a (2.7 g, 39.4%). $^1$H NMR (300 MHz, CDCl$_3$) δ 6.86 (d, J=1.9 Hz, 1H), 6.83 (s, 1H), 6.66 (s, 1H), 3.50 (s, 1H), 3.14 (dd, J=6.3, 3.6 Hz, 4H), 3.02 (dd, J=6.2, 3.6 Hz, 4H), 2.29 (d, J=0.4 Hz, 3H) ppm. ESI-MS m/z calc. 254.04, found 255.32 (M+1)+; Retention time: 0.64 minutes.

Preparation of 1-(3-bromo-5-methyl-phenyl)-4-(3-deuteriooxetan-3-yl)piperazine (YL-19b)

To a solution of 1-(3-bromo-5-methyl-phenyl)piperazine, YL-19a (640 mg, 2.38 mmol), oxetan-3-one (1.37 g, 19.02 mmol) and acetic acid (676 μL, 11.89 mmol) in dichloromethane (21 mL) was added NaBD(OAc)$_3$ (2.52 g, 11.89 mmol) carefully. CD3OD (2 mL) was added to the above mixture. The reaction mixture was stirred at RT for 18 h. Reaction was diluted with DCM and slowly quenched with MeOH and sat. NaHCO$_3$ (50 mL). After separation, the organic layer was washed with water, sat NaCl and dried. The excess solvent was removed in vacuo and the crude product purified by ISCO purification (12 g silica; 0% to 5% to 10% of MeOH in DCM) to give 1-(3-bromo-5-methyl-phenyl)-4-(3-deuteriooxetan-3-yl)piperazine YL-19b (300 mg, 58.4%). $^1$H NMR (300 MHz, CDCl$_3$) δ 6.90-6.79 (m, 2H), 6.65 (s, 1H), 4.69 (q, J=6.3 Hz, 4H), 3.29-3.16 (m, 4H), 2.57-2.44 (m, 4H), 2.30 (s, 3H) ppm. ESI-MS m/z calc. 311.07, found 312.38 (M+1)+; Retention time: 0.67 minutes.

Preparation of N-[3-[4-(3-deuteriooxetan-3-yl)piperazin-1-yl]-5-methyl-phenyl]-1-(3,5-difluorophenyl)-1,2,4-triazol-3-amine (Compound 1100)

A mixture of 1-(3-bromo-5-methyl-phenyl)-4-(3-deuteriooxetan-3-yl)piperazine YL-19b (150 mg, 0.48 mmol), 1-(3,5-difluorophenyl)-1,2,4-triazol-3-amine (113 mg, 0.58 mmol) and sodium t-butoxide (115 mg, 1.20 mmol) in dioxane (6.0 mL) was purged with $N_2$ for several minutes. t-BuXPhos Palladacycle (31 mg, 0.048 mmol) was added. The mixture was microwaved at 120° C. for 35 minutes. The reaction was quenched with MeOH (2 mL) and diluted with DCM. After filtration (Florisil/5 g), the excess solvent was pumped down. ISCO purification (12 g silica; 0% to 5% to 10% of MeOH in DCM) followed by ether trituration gave N-[3-[4-(3-deuteriooxetan-3-yl)piperazin-1-yl]-5-methyl-phenyl]-1-(3,5-difluorophenyl)-1,2,4-triazol-3-amine, Cmpd 1110 (120 mg, 55.5%). $^1$H NMR (300 MHz, CDCl$_3$) δ 8.31 (s, 1H), 7.25 (dd, J=7.8, 2.0 Hz, 2H), 7.12 (s, 1H), 6.87-6.73 (m, 2H), 6.66 (s, 1H), 6.43 (s, 1H), 4.80-4.61 (m, 4H), 3.40-3.21 (m, 4H), 2.64-2.48 (m, 4H), 2.35 (s, 3H) ppm. ESI-MS m/z calc. 427.20, found 428.49 (M+1)+; Retention time: 0.7 minutes.

| Cmpd No. | IUPAC Name |
|---|---|
| 1088 | N-[5-deuterio-1-(3,4-difluorophenyl)-1,2,4-triazol-3-yl]-4-(difluoromethyl)-6-[4-(oxetan-3-yl)piperazin-1-yl]pyridin-2-amine |
| 1089 | N-[5-deuterio-1-(3,4-difluorophenyl)-1,2,4-triazol-3-yl]-6-[4-(oxetan-3-yl)piperazin-1-yl]-4-(trifluoromethyl)pyridin-2-amine |
| 1090 | N-[5-deuterio-1-(3,5-difluorophenyl)-1,2,4-triazol-3-yl]-4-(difluoromethyl)-6-[4-(oxetan-3-yl)piperazin-1-yl]pyridin-2-amine |
| 1093 | 2-cyclopropyl-N-[5-deuterio-1-(3,5-difluorophenyl)-1,2,4-triazol-3-yl]-6-morpholino-pyridin-4-amine |

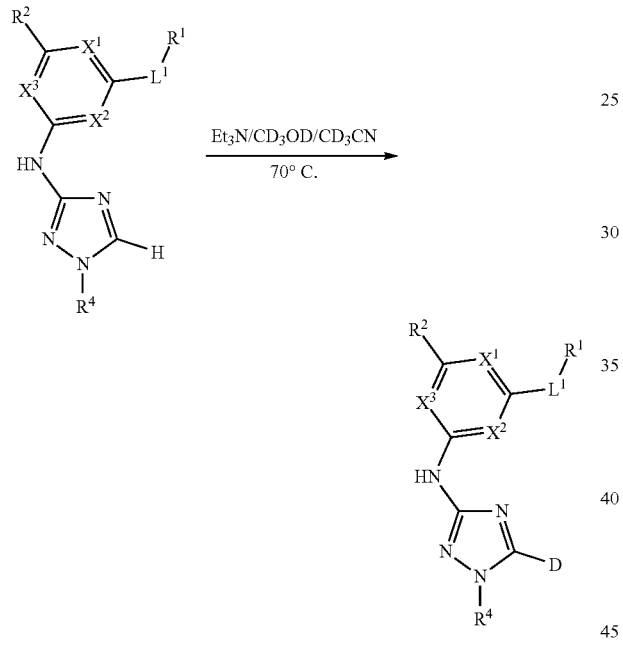

Scheme Q: General Route Q for Preparation of Compounds of Formula I or I'

Deuterium compounds of the present invention may also be prepared as generally outlined in Scheme Q above, where $X^1$, $X^2$, $X^3$, $L^1$, $R^1$ $R^2$, and $R^4$ are as described herein.

Using the general synthetic scheme outlined in Scheme Q the following compounds were prepared:

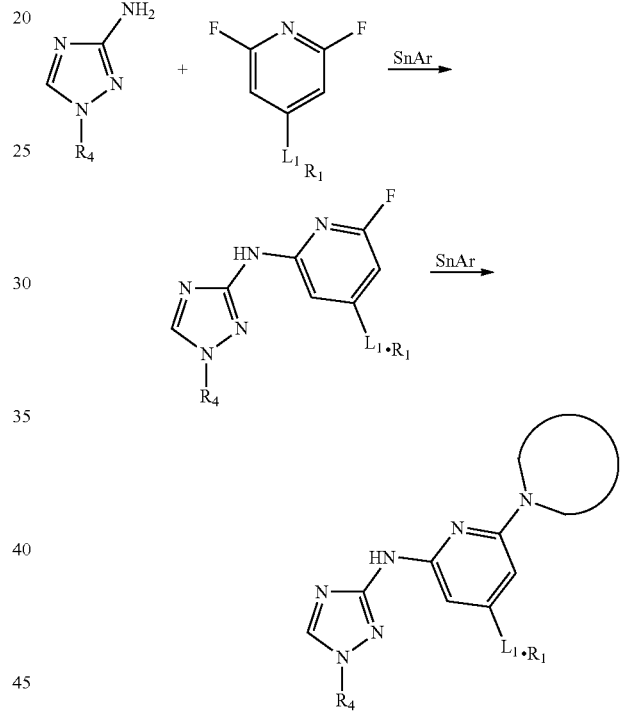

Scheme R: General Route R for Preparation of Compounds of Formula I or I'

Compounds of the invention may be prepared as generally outlined in Scheme R, where $L^1$, $R^1$, $R^2$ and $R^4$ are as described herein.

TABLE 3

Analytical Data

| Cmpd No. | LC/MS (M + H) | LC/MS Ret. Time (min) | $^1$H-NMR |
|---|---|---|---|
| 1 | 428.19 | 0.51 | 1H NMR (400 MHz, DMSO-d6) δ 9.80 (s, 1H), 9.21 (s, 1H), 7.63 (dd, J = 8.3, 2.0 Hz, 2H), 7.29 (dd, J = 10.3, 8.1 Hz, 1H), 6.92 (s, 1H), 6.74 (s, 1H), 4.57 (t, J = 6.5 Hz, 2H), 4.48 (t, J = 6.0 Hz, 2H), 3.44 (dd, J = 11.3, 5.5 Hz, 5H), 2.40-2.31 (m, 4H), 2.26 (s, 3H) ppm. |
| 2 | 372.19 | 0.76 | 1H NMR (400 MHz, CDCl3) δ 8.31 (s, 1H), 7.26 (dd, J = 7.7, 2.0 Hz, 2H), 6.83-6.59 (m, 4H), 5.97 (d, J = 8.7 Hz, 1H), 4.37 (dt, J = 10.7, |

TABLE 3-continued

Analytical Data

| Cmpd No. | LC/MS (M + H) | LC/MS Ret. Time (min) | ¹H-NMR |
|---|---|---|---|
| | | | 5.2 Hz, 1H), 4.17-4.11 (m, 2H), 3.75 (dt, J = 28.4, 14.3 Hz, 2H), 3.39-3.35 (m, 3H), 2.32 (d, J = 6.4 Hz, 3H) ppm. |
| 3 | 396.18 | 0.62 | 1H NMR (300 MHz, DMSO-d6) δ 9.97 (s, 1H), 9.15 (s, 1H), 8.01 (d, J = 11.3 Hz, 1H), 7.80-7.62 (m, 2H), 7.42 (d, J = 4.1 Hz, 2H), 6.65 (s, 1H), 4.26 (s, 2H), 3.81 (t, J = 5.4 Hz, 2H), 2.47-2.37 (m, 2H), 2.05 (d, J = 16.4 Hz, 1H), 0.96-0.80 (m, 4H) ppm. |
| 4 | 495.18 | 0.65 | 1H NMR (400 MHz, DMSO-d6) δ 9.21 (s, 1H), 7.61 (dd, J = 8.2, 2.0 Hz, 2H), 7.56 (s, 1H), 7.46 (s, 1H), 7.29 (td, J = 9.2, 2.2 Hz, 1H), 6.87 (s, 1H), 3.90 (t, J = 12.9 Hz, 2H), 3.58-3.53 (m, 1H), 3.33-3.16 (m, 2H), 3.11-2.94 (m, 2H), 2.48-2.33 (m, 2H), 2.08 (m, 2H), 1.73 (m, 1H), 1.66-1.54 (m, 1H) ppm. |
| 5 | 447.19 | 0.64 | 1H NMR (300 MHz, DMSO-d6) δ 9.64 (s, 1H), 9.18 (s, 1H), 7.59 (dd, J = 8.5, 2.1 Hz, 2H), 7.32-7.22 (m, 1H), 7.16 (d, J = 21.6 Hz, 2H), 6.52 (s, 1H), 4.57 (t, J = 6.5 Hz, 2H), 4.48 (t, J = 6.1 Hz, 2H), 3.45 (dt, J = 12.7, 6.2 Hz, 2H), 3.19 (dd, J = 10.5, 5.4 Hz, 4H), 2.45-2.36 (m, 4H) ppm. |
| 6 | 350.36 | 0.68 | 1H NMR (300 MHz, DMSO-d6) δ 9.13-9.03 (m, 1H), 7.87 (d, J = 8.0 Hz, 2H), 7.54 (t, J = 8.0 Hz, 2H), 7.34 (t, J = 7.4 Hz, 1H), 7.13 (s, 1H), 6.84 (d, J = 18.2 Hz, 1H), 6.15 (s, 1H), 3.46 (dd, J = 18.0, 9.8 Hz, 2H), 3.35-3.17 (m, 2H), 2.31-2.17 (m, 3H), 1.95 (dd, J = 18.0, 9.6 Hz, 2H), 1.44-1.32 (m, 3H) ppm. |
| 7 | 348 | 0.27 | 1H NMR (400 MHz, CDCl3) δ 8.33 (s, 1H), 7.78-7.61 (m, 2H), 7.53 (t, J = 8.0 Hz, 2H), 7.37 (t, J = 7.4 Hz, 1H), 6.75 (s, 1H), 6.65 (d, J = 5.8 Hz, 2H), 5.94 (s, 1H), 4.87 (s, 4H), 4.07 (s, 4H), 2.32 (s, 3H) ppm. |
| 8 | 372.51 | 0.7 | 1H NMR (300 MHz, DMSO-d6) δ 9.23 (s, 1H), 9.15 (s, 1H), 7.70-7.60 (m, 2H), 7.24 (t, J = 9.3 Hz, 1H), 6.95 (s, 1H), 6.51 (s, 1H), 5.95 (s, 1H), 5.78-5.66 (m, 1H), 3.97-3.86 (m, 2H), 3.82 (t, J = 7.7 Hz, 1H), 3.73 (m, 1H), 3.55 (m, 1H), 2.22 (m, 1H), 2.15 (s, 3H), 1.81 (m, 1H) ppm. |
| 9 | 419.16 | 0.61 | 1H NMR (400 MHz, CDCl3) δ 8.33 (s, 1H), 7.67 (d, J = 8.0 Hz, 2H), 7.51 (t, J = 7.9 Hz, 2H), 7.38 (d, J = 7.2 Hz, 1H), 6.87 (s, 1H), 6.76 (s, 1H), 6.61 (s, 1H), 3.99 (d, J = 7.6 Hz, 4H), 3.69 (s, 4H), 1.89 (s, 1H), 1.82-1.69 (m, 4H), 1.02 (s, 2H), 0.85 (s, 2H) ppm. |
| 10 | 405.4 | 0.86 | 1H NMR (300 MHz, CDCl3) δ 8.34 (s, 1H), 7.75-7.66 (m, 2H), 7.59-7.49 (m, 2H), 7.42-7.34 (m, 1H), 7.31 (d, J = 1.5 Hz, 2H), 6.74 (s, 1H), 6.69 (s, 1H), 4.19-4.05 (m, 4H), 3.57 (td, J = 11.4, 3.1 Hz, 4H), 2.79 (ddd, J = 15.7, 10.4, 4.9 Hz, 2H), 1.98-1.78 (m, 8H) ppm. |
| 11 | 376.38 | 0.62 | 1H NMR (300 MHz, CDCl3) δ 8.24 (s, 1H), 7.66-7.55 (m, 2H), 7.49-7.36 (m, 2H), 7.31-7.24 (m, 1H), 7.12-6.99 (m, 2H), 6.71 (s, 1H), 6.32 (s, 1H), 4.41 (s, 4H), 3.08 (dd, J = 6.6, 4.6 Hz, 4H), 2.24 (s, 3H), 1.94 (dd, J = 6.6, 4.6 Hz, 4H) ppm. |
| 12 | 392 | 0.88 | 1H NMR (400 MHz, CDCl3) δ 8.31 (s, 1H), 7.77-7.60 (m, 2H), 7.50 (t, J = 8.0 Hz, 2H), 7.35 (t, J = 7.4 Hz, 1H), 7.21 (s, 2H), 6.68 (s, 1H), 6.63 (s, 1H), 4.29 (s, 2H), 3.72 (s, 3H), 2.87 (s, 2H), 2.74-2.55 (m, 1H), 2.35 (s, 3H), 1.87 (d, J = 12.8 Hz, 2H), 1.66 (d, J = 14.7 Hz, 3H) ppm. |
| 13 | 404 | 0.52 | 1H NMR (300 MHz, Acetone-d6) δ 9.10 (s, 1H), 8.85 (s, 1H), 8.71 (dd, J = 4.7, 1.6 Hz, 2H), 7.84 (dd, J = 4.7, 1.6 Hz, 2H), 7.66 (s, 1H), 7.54 (s, 1H), 6.82 (s, 1H), 3.41-3.23 (m, 4H), 2.64-2.49 (m, 4H), 2.29 (s, 3H) ppm. |
| 14 | 423.24 | 0.65 | 1H NMR (300 MHz, DMSO-d6) δ 9.21 (s, 1H), 9.02 (s, 1H), 7.93-7.75 (m, 2H), 7.43 (dd, J = 12.1, |

TABLE 3-continued

Analytical Data

| Cmpd No. | LC/MS (M + H) | LC/MS Ret. Time (min) | ¹H-NMR |
|---|---|---|---|
| | | | 5.5 Hz, 2H), 7.15 (s, 1H), 6.93 (s, 1H), 6.33 (s, 1H), 4.71-4.52 (m, 2H), 4.49 (t, J = 6.0 Hz, 2H), 3.54-3.38 (m, 1H), 3.15 (s, 4H), 2.53 (d, J = 9.7 Hz, 2H), 2.35 (d, J = 41.2 Hz, 4H), 1.26-1.11 (m, 3H) ppm. |
| 15 | 423 | 0.67 | 1H NMR (400 MHz, CDCl3) δ 8.31 (s, 1H), 7.44 (dd, J = 12.5, 6.1 Hz, 3H), 7.02 (ddd, J = 8.2, 5.1, 2.2 Hz, 2H), 6.76-6.60 (m, 2H), 5.97 (s, 1H), 4.00 (t, J = 6.9 Hz, 2H), 3.75 (dd, J = 10.1, 5.1 Hz, 6H), 3.43-3.22 (m, 1H), 2.59 (q, J = 7.6 Hz, 2H), 2.45 (s, 4H), 1.24 (t, J = 7.6 Hz, 4H) ppm. |
| 16 | 424.48 | 0.65 | 1H NMR (300 MHz, CDCl3) δ 8.47 (s, 1H), 8.32 (d, J = 5.6 Hz, 1H), 7.47 (d, J = 5.6 Hz, 1H), 7.27 (s, 1H), 7.10 (s, 1H), 6.86 (s, 1H), 6.71 (s, 1H), 6.49 (s, 1H), 4.77-4.65 (m, 4H), 3.67-3.55 (m, 1H), 2.66 (q, J = 7.6 Hz, 2H), 2.60-2.49 (m, 4H), 1.29 (t, J = 7.6 Hz, 3H) ppm. |
| 17 | 469.44 | 0.72 | 1H NMR (300 MHz, DMSO-d6) δ 9.34 (s, 1H), 9.17 (s, 1H), 7.69-7.51 (m, 2H), 7.38-7.16 (m, 2H), 7.07 (s, 1H), 6.53 (d, J = 10.5 Hz, 1H), 4.58 (t, J = 6.5 Hz, 2H), 4.48 (t, J = 6.0 Hz, 2H), 3.67-3.39 (m, 1H), 3.24-3.08 (m, 4H), 2.39 (dd, J = 26.2, 21.4 Hz, 4H), 1.28 (s, 9H) ppm. |
| 18 | 394.23 | 0.59 | 1H NMR (300 MHz, DMSO-d6) δ 9.48 (s, 1H), 9.09 (s, 1H), 7.85 (dd, J = 8.6, 1.0 Hz, 2H), 7.68 (s, 1H), 7.56 (t, J = 8.0 Hz, 2H), 7.35 (dd, J = 9.0, 5.7 Hz, 2H), 6.75 (s, 1H), 4.61 (td, J = 6.5, 1.6 Hz, 2H), 4.52 (dd, J = 10.4, 5.9 Hz, 2H), 3.83-3.72 (m, 1H), 3.19-2.86 (m, 3H), 2.81-2.71 (m, 1H), 2.40-2.22 (m, 5H) ppm. |
| 19 | 408.25 | 0.68 | 1H NMR (300 MHz, DMSO-d6) δ 9.41 (s, 1H), 9.17 (s, 1H), 7.65 (dd, J = 8.6, 2.1 Hz, 2H), 7.30-7.20 (m, 2H), 7.10 (m, 1H), 6.92-6.86 (m, 2H), 6.47 (s, 1H), 4.37 (s, 2H), 4.09 (t, J = 5.3 Hz, 2H), 3.71 (t, J = 5.3 Hz, 2H), 2.26 (s, 3H) ppm. |
| 20 | 377.46 | 0.61 | 1H NMR (300 MHz, DMSO-d6) δ 9.42 (s, 1H), 9.19 (s, 1H), 9.05 (d, J = 1.2 Hz, 1H), 8.66 (d, J = 2.4 Hz, 1H), 8.58 (dd, J = 2.6, 1.4 Hz, 1H), 7.15 (s, 1H), 6.92 (s, 1H), 6.33 (s, 1H), 3.16-3.03 (m, 4H), 2.79-2.66 (m, 4H), 2.24 (s, 3H), 1.75-1.56 (m, 1H), 0.52-0.41 (m, 2H), 0.37-0.30 (m, 2H) ppm. |
| 21 | 363 | 0.58 | 1H NMR (400 MHz, CDCl3) δ 8.31 (s, 1H), 7.68 (d, J = 7.7 Hz, 2H), 7.49 (t, J = 7.9 Hz, 2H), 7.35 (d, J = 7.4 Hz, 1H), 7.19 (s, 1H), 7.06 (s, 1H), 6.68 (s, 1H), 6.56 (s, 1H), 3.24-2.96 (m, 4H), 2.72 (dd, J = 12.0, 9.4 Hz, 1H), 2.53 (dd, J = 11.4, 9.6 Hz, 1H), 2.34 (s, 3H), 1.95 (s, 2H), 1.10 (d, J = 6.3 Hz, 3H), 1.00 (d, J = 6.1 Hz, 3H) ppm. |
| 22 | 435.3 | 0.65 | 1H NMR (400 MHz, DMSO-d6) δ 9.56 (s, 1H), 9.03 (s, 1H), 7.42 (d, J = 2.5 Hz, 1H), 7.34 (dd, J = 8.6, 2.5 Hz, 1H), 7.11 (d, J = 8.8 Hz, 1H), 7.02 (s, 1H), 6.65 (d, J = 1.3 Hz, 1H), 4.18 (d, J = 12.5 Hz, 2H), 3.85 (s, 3H), 3.79 (s, 3H), 2.70 (t, J = 11.4 Hz, 2H), 1.79 (td, J = 8.0, 4.0 Hz, 2H), 1.63 (d, J = 13.0 Hz, 2H), 1.55 (m, 1H), 1.23 (dd, J = 18.5, 10.4 Hz, 1H), 1.09 (dd, J = 22.1, 10.1 Hz, 1H), 0.91 (d, J = 6.4 Hz, 3H), 0.80 (ddt, J = 12.4, 9.6, 3.3 Hz, 4H) ppm. |
| 23 | 388.26 | 0.62 | 1H NMR (300 MHz, DMSO-d6) δ 9.60 (s, 1H), 9.19 (s, 1H), 7.74 (s, 1H), 7.63 (m, 2H), 7.32-7.19 (m, 2H), 6.75 (s, 1H), 3.08-2.79 (m, 3H), 2.67 (dd, J = 14.3, 7.1 Hz, 1H), 2.36 (s, 3H), 2.40-2.32 (m, 1H), 2.30 (s, 3H), 2.28-2.22 (m, 1H) ppm. |

TABLE 3-continued

Analytical Data

| Cmpd No. | LC/MS (M + H) | LC/MS Ret. Time (min) | ¹H-NMR |
|---|---|---|---|
| 24 | 410.25 | 0.55 | 1H NMR (400 MHz, CDCl3) δ 8.84 (d, J = 1.6 Hz, 1H), 8.48 (d, J = 2.5 Hz, 1H), 8.39 (s, 1H), 7.80 (dt, J = 9.0, 2.3 Hz, 1H), 7.09 (s, 1H), 6.80 (s, 1H), 6.66 (s, 1H), 6.44 (s, 1H), 4.71 (p, J = 6.3 Hz, 4H), 3.67-3.52 (m, 1H), 3.37-3.21 (m, 4H), 2.61-2.46 (m, 4H), 2.36 (s, 3H) ppm. |
| 25 | 412.3 | 0.61 | 1H NMR (400 MHz, DMSO-d6) δ 9.42 (s, 1H), 9.16 (s, 1H), 7.62 (dd, J = 8.6, 2.1 Hz, 2H), 7.52 (s, 1H), 7.29-7.19 (m, 1H), 7.18 (s, 1H), 6.62 (s, 1H), 4.58 (td, J = 6.5, 1.9 Hz, 2H), 4.50 (td, J = 6.0, 1.2 Hz, 2H), 3.69-3.60 (m, 1H), 3.29-3.21 (m, 1H), 2.97 (t, J = 8.4 Hz, 1H), 2.73 (dd, J = 14.9, 7.8 Hz, 1H), 2.59 (td, J = 8.7, 5.6 Hz, 1H), 2.44-2.38 (m, 1H), 2.26 (s, 3H), 1.79 (dt, J = 13.8, 8.3 Hz, 1H) ppm. |
| 26 | 427.41 | 0.65 | 1H NMR (300 MHz, CDCl3) δ 8.35 (s, 1H), 7.73-7.65 (m, 2H), 7.53 (ddd, J = 8.3, 5.3, 1.8 Hz, 2H), 7.38 (ddd, J = 8.7, 4.6, 1.2 Hz, 2H), 7.17 (s, 1H), 6.86 (s, 1H), 6.63 (dd, J = 67.7, 45.7 Hz, 2H), 4.72 (p, J = 6.4 Hz, 4H), 3.59 (p, J = 6.4 Hz, 1H), 3.41-3.24 (m, 4H), 2.61-2.48 (m, 4H) ppm. |
| 27 | 354.03 | 0.68 | 1H NMR (400 MHz, DMSO-d6) δ 9.38 (s, 1H), 9.04 (s, 1H), 7.89 (s, 2H), 7.40 (t, J = 8.8 Hz, 3H), 6.99 (d, J = 39.5 Hz, 1H), 6.54 (s, 1H), 3.84 (s, 4H), 3.22 (s, 4H), 2.26 (s, 3H) ppm. |
| 28 | 403 | 0.66 | 1H NMR (400 MHz, DMSO-d6) δ 10.69 (s, 1H), 9.56 (s, 1H), 8.77 (d, J = 2.2 Hz, 1H), 7.88 (dd, J = 14.9, 9.0 Hz, 1H), 7.65 (t, J = 8.8 Hz, 1H), 7.35 (t, J = 7.5 Hz, 1H), 6.83 (d, J = 16.8 Hz, 2H), 6.15 (d, J = 12.6 Hz, 1H), 3.86-3.60 (m, 2H), 3.44 (s, 4H), 3.31-2.97 (m, 2H), 2.80 (d, J = 4.8 Hz, 3H), 2.29 (s, 1H), 2.19 (s, 1H), 2.19 (s, 1H) ppm. |
| 29 | 467 | 0.7 | 1H NMR (400 MHz, DMSO-d6) δ 9.32 (s, 1H), 9.16 (s, 1H), 7.60 (dd, J = 8.5, 2.1 Hz, 2H), 7.29 (s, 1H), 7.24 (ddd, J = 9.2, 5.8, 2.2 Hz, 1H), 6.64 (s, 1H), 6.23 (s, 1H), 3.93 (d, J = 8.7 Hz, 1H), 3.53 (dd, J = 11.5, 2.9 Hz, 1H), 3.38 (dt, J = 9.8, 4.9 Hz, 1H), 3.00 (dd, J = 17.7, 9.5 Hz, 2H), 2.71 (t, J = 10.9 Hz, 1H), 2.30-2.13 (m, 4H), 2.08-1.87 (m, 2H), 1.76 (dtd, J = 22.3, 17.5, 10.4 Hz, 4H), 1.60-1.29 (m, 2H), 1.09 (dd, J = 8.4, 5.7 Hz, 2H), 0.83 (dd, J = 6.5, 4.7 Hz, 6H) ppm. |
| 30 | 423.26 | 0.54 | 1H NMR (400 MHz, CDCl3) δ 9.00 (s, 1H), 8.64 (d, J = 5.4 Hz, 1H), 7.35 (t, J = 12.8 Hz, 1H), 7.04 (d, J = 22.0 Hz, 1H), 6.83 (s, 2H), 6.45 (s, 1H), 4.72 (dq, J = 12.6, 6.4 Hz, 4H), 4.11 (d, J = 5.8 Hz, 3H), 3.60 (p, J = 6.4 Hz, 1H), 3.36-3.24 (m, 4H), 2.59-2.49 (m, 4H), 2.36 (s, 3H) ppm. |
| 31 | 419.23 | 0.63 | 1H NMR (400 MHz, CDCl3) δ 8.27 (s, 1H), 7.56 (d, J = 8.4 Hz, 2H), 7.32-7.28 (m, 2H), 7.17 (s, 1H), 6.83 (s, 1H), 6.60 (s, 1H), 6.43 (s, 1H), 4.72 (p, J = 6.3 Hz, 3H), 3.64-3.54 (m, 1H), 3.37-3.26 (m, 3H), 2.63 (q, J = 7.6 Hz, 2H), 2.57-2.50 (m, 3H), 2.43 (s, 3H), 1.27 (t, J = 7.6 Hz, 3H) ppm. |
| 32 | 443.24 | 0.63 | 1H NMR (300 MHz, CDCl3) δ 8.32 (s, 1H), 7.59-7.47 (m, 1H), 7.36 (dt, J = 9.3, 2.1 Hz, 1H), 7.16 (s, 1H), 7.13-7.02 (m, 1H), 6.77 (s, 1H), 6.63 (s, 1H), 6.43 (s, 1H), 4.80-4.64 (m, 4H), 3.68-3.51 (m, 1H), 3.38-3.24 (m, 4H), 2.62-2.49 (m, 4H), 2.35 (s, 3H) ppm. |
| 33 | 427.36 | 0.65 | 1H NMR (300 MHz, CDCl3) δ 8.32 (s, 1H), 7.28-7.21 (m, 2H), 7.12 (t, J = 1.9 Hz, 1H), 6.88-6.68 (m, 3H), 6.46 (d, J = 14.4 Hz, 1H), 4.81-4.70 (m, 4H), 3.67-3.48 (m, 1H), 3.33 (dd, J = 13.0, 8.2 Hz, 4H), 2.61-2.51 (m, 4H), 2.35 (s, 3H) ppm. |
| 34 | 439 | 0.68 | 1H NMR (400 MHz, CDCl3) δ 8.29 (s, 1H), 7.26 (d, J = 2.1 Hz, 2H), 7.22 (d, J = 7.8 Hz, 2H), 6.80 (s, 1H), 6.78-6.73 (m, 1H), 6.59 (s, |

TABLE 3-continued

Analytical Data

| Cmpd No. | LC/MS (M + H) | LC/MS Ret. Time (min) | ¹H-NMR |
|---|---|---|---|
| | | | 1H), 6.54 (s, 1H), 6.02 (s, 1H), 4.69 (t, J = 6.7 Hz, 1H), 4.63 (t, J = 6.5 Hz, 1H), 4.57 (s, 1H), 4.50 (d, J = 5.8 Hz, 1H), 4.32 (s, 1H), 4.05-3.95 (m, 1H), 3.60 (s, 1H), 3.45 (d, J = 9.2 Hz, 1H), 3.12 (d, J = 9.1 Hz, 1H), 3.06 (s, 1H), 2.95 (d, J = 9.2 Hz, 1H), 2.30 (s, 2H), 1.97 (d, J = 8.6 Hz, 1H) ppm. |
| 35 | 396.23 | 0.62 | 1H NMR (300 MHz, DMSO-d6) δ 10.01 (s, 1H), 9.23 (s, 1H), 7.66 (d, J = 7.9 Hz, 2H), 7.43 (s, 1H), 7.41 (s, 1H), 7.27 (t, J = 9.3 Hz, 1H), 6.65 (s, 1H), 4.25 (s, 2H), 3.81 (t, J = 5.0 Hz, 2H), 2.46 (s, 2H), 2.03 (s, 1H), 1.00-0.76 (m, 4H) ppm. |
| 36 | 380.25 | 0.73 | 1H NMR (300 MHz, DMSO-d6) δ 9.42 (s, 1H), 9.13 (s, 1H), 7.73 (dd, J = 10.1, 1.9 Hz, 2H), 7.59 (dd, J = 12.6, 6.0 Hz, 2H), 7.25-7.14 (m, 3H), 6.64 (s, 1H), 4.59 (t, J = 6.6 Hz, 2H), 4.45-4.40 (m, 2H), 3.81-3.53 (m, 4H), 3.20 (t, J = 6.0 Hz, 2H), 2.27 (s, 3H) ppm. |
| 37 | 385.05 | 0.77 | 1H NMR (400 MHz, DMSO-d6) δ 10.77 (s, 1H), 9.40 (s, 1H), 9.17 (s, 1H), 7.68-7.52 (m, 2H), 7.25 (t, J = 9.2 Hz, 1H), 7.16 (s, 1H), 3.53-3.39 (m, 2H), 6.95 (s, 1H), 6.39 (s, 1H), 3.74 (d, J = 11.5 Hz, 2H), 3.13 (p, J = 11.5 Hz, 4H), 2.82 (d, J = 4.6 Hz, 3H), 2.25 (s, 3H) ppm. |
| 38 | 441.45 | 0.59 | 1H NMR (400 MHz, DMSO-d6) δ 9.17 (s, 1H), 9.13 (s, 1H), 7.62 (dd, J = 8.5, 2.2 Hz, 2H), 7.29-7.16 (m, 1H), 7.05 (s, 1H), 6.38 (s, 1H), 5.96 (s, 1H), 5.33 (d, J = 7.7 Hz, 1H), 4.52 (t, J = 6.5 Hz, 2H), 4.43 (t, J = 6.1 Hz, 2H), 3.51-3.34 (m, 1H), 3.20 (s, 1H), 2.70 (t, J = 12.7 Hz, 2H), 2.12 (s, 3H), 1.98 (d, J = 10.9 Hz, 2H), 1.89 (t, J = 11.3 Hz, 2H), 1.41 (dd, J = 20.3, 11.2 Hz, 2H) ppm. |
| 39 | 320 | 0.73 | 1H NMR (400 MHz, DMSO-d6) δ 9.43 (s, 1H), 9.10 (s, 1H), 7.85 (d, J = 7.7 Hz, 1H), 7.56 (t, J = 8.0 Hz, 1H), 7.43 (s, 1H), 7.40-7.26 (m, 1H), 6.67 (s, 1H), 3.58 (d, J = 8.1 Hz, 1H), 3.50-3.30 (m, 1H), 3.24 (s, 1H), 3.03 (d, J = 11.4 Hz, 1H), 2.31 (d, J = 22.3 Hz, 1H), 2.29 (s, 3H), 2.02-1.78 (m, 1H) ppm. |
| 40 | 410.28 | 0.59 | 1H NMR (300 MHz, CDCl3) δ 8.46 (d, J = 6.7 Hz, 1H), 8.32 (d, J = 5.6 Hz, 1H), 7.52-7.44 (m, 1H), 7.27 (d, J = 1.5 Hz, 1H), 7.08 (s, 1H), 6.82 (s, 1H), 6.71 (s, 1H), 6.46 (s, 1H), 4.80-4.65 (m, 4H), 3.68-3.54 (m, 1H), 3.38-3.25 (m, 4H), 2.63-2.50 (m, 4H), 2.37 (s, 3H) ppm. |
| 41 | 536.32 | 0.67 | 1H NMR (300 MHz, CDCl3) δ 8.28 (s, 1H), 7.23 (s, 1H), 6.75 (d, J = 12.9 Hz, 2H), 6.66 (dd, J = 7.2, 2.0 Hz, 2H), 6.40 (s, 1H), 6.33 (d, J = 12.0 Hz, 1H), 4.79-4.64 (m, 4H), 3.92 (s, 1H), 3.65-3.41 (m, 6H), 3.31 (dd, J = 9.6, 5.7 Hz, 5H), 3.21 (d, J = 7.1 Hz, 1H), 2.58-2.49 (m, 4H), 2.34 (s, 3H), 2.16-1.97 (m, 5H), 1.22 (t, J = 7.0 Hz, 3H) ppm. |
| 42 | 354.79 | 0.69 | 1H NMR (300 MHz, CDCl3) δ 8.69 (s, 1H), 8.52 (d, J = 5.6 Hz, 1H), 7.84-7.70 (m, 1H), 7.65 (dd, J = 5.6, 1.9 Hz, 1H), 7.34 (s, 1H), 7.06 (s, 1H), 6.52 (s, 1H), 3.61 (t, J = 6.7 Hz, 2H), 3.06 (s, 1H), 3.00 (d, J = 2.9 Hz, 1H), 2.40 (s, 3H), 2.28-2.11 (m, 4H) ppm. |
| 43 | 372.08 | 2.38 | 1H NMR (400 MHz, DMSO-d6) δ 9.44 (s, 1H), 9.08 (s, 1H), 8.16-7.90 (m, 1H), 7.85-7.58 (m, 1H), 7.40 (s, 1H), 7.04 (s, 1H), 6.56 (s, 1H), 3.85 (s, 1H), 3.23 (s, 1H), 2.27 (s, 1H) ppm. |
| 44 | 375.25 | 0.67 | 1H NMR (300 MHz, DMSO-d6) δ 9.56 (s, 1H), 9.10 (s, 1H), 7.83 (dd, J = 8.6, 1.1 Hz, 2H), 7.56 (t, J = 8.0 Hz, 2H), 7.36 (t, J = 7.4 Hz, 1H), 6.91 (s, 1H), 6.77 (d, J = 1.4 Hz, 1H), 4.16 (d, J = 13.1 Hz, 2H), 2.72 (t, J = 11.7 Hz, 2H), 1.82 (td, J = 7.9, 3.9 Hz, 1H), 1.64 (d, J = 12.5 Hz, 2H), 1.56 (s, 1H), 1.19-0.97 (m, 2H), 0.91 (d, J = 6.4 Hz, 3H), 0.87-0.69 (m, 4H) ppm. |

TABLE 3-continued

Analytical Data

| Cmpd No. | LC/MS (M + H) | LC/MS Ret. Time (min) | ¹H-NMR |
|---|---|---|---|
| 45 | 336 | 2.28 | 1H NMR (400 MHz, CDCl3) δ 8.31 (s, 1H), 7.78-7.61 (m, 2H), 7.49 (t, J = 8.0 Hz, 2H), 7.35 (t, J = 7.4 Hz, 1H), 7.14 (s, 1H), 6.81 (s, 1H), 6.66 (s, 1H), 6.39 (s, 1H), 3.89 (d, J = 4.1 Hz, 4H), 3.30-3.13 (m, 4H), 2.33 (s, 3H) ppm. |
| 46 | 428.44 | 0.65 | 1H NMR (300 MHz, DMSO-d6) δ 9.41 (s, 1H), 9.06 (s, 1H), 8.12-7.89 (m, 1H), 7.81-7.52 (m, 2H), 7.11 (s, 1H), 6.95 (s, 1H), 6.24 (s, 1H), 4.87 (s, 1H), 4.59 (t, J = 5.9 Hz, 2H), 4.48 (dd, J = 9.6, 5.6 Hz, 2H), 3.73 (s, 1H), 2.94 (s, 1H), 2.73 (s, 2H), 2.53 (s, 1H), 2.41-2.13 (m, 4H), 1.90 (s, 1H) ppm. |
| 47 | 417.32 | 0.61 | 1H NMR (400 MHz, CDCl3) δ 8.22 (s, 1H), 7.59 (d, J = 7.8 Hz, 2H), 7.41 (t, J = 7.9 Hz, 2H), 7.26 (t, J = 7.4 Hz, 1H), 7.00 (t, J = 2.0 Hz, 1H), 6.65 (s, 1H), 6.55 (s, 1H), 6.25 (s, 1H), 4.68-4.54 (m, 4H), 3.49 (p, J = 6.4 Hz, 1H), 3.25-3.13 (m, 4H), 2.52-2.38 (m, 4H), 1.85-1.71 (m, 1H), 0.90-0.79 (m, 2H), 0.70-0.59 (m, 2H) ppm. |
| 48 | 407.53 | 0.6 | 1H NMR (300 MHz, CDCl3) δ 9.09 (d, J = 1.3 Hz, 1H), 8.83 (s, 1H), 8.47 (d, J = 2.5 Hz, 1H), 8.31 (dd, J = 2.5, 1.5 Hz, 1H), 7.10 (t, J = 2.0 Hz, 1H), 6.75 (d, J = 5.0 Hz, 2H), 6.39 (s, 1H), 4.63 (dd, J = 6.4, 2.2 Hz, 4H), 3.59-3.43 (m, 1H), 3.31-3.18 (m, 4H), 2.56 (q, J = 7.6 Hz, 2H), 2.48 (dd, J = 14.3, 9.3 Hz, 4H), 1.20 (t, J = 7.6 Hz, 3H) ppm. |
| 49 | 358.08 | 2.93 | 1H NMR (400 MHz, DMSO-d6) δ 9.64 (s, 1H), 8.81 (s, 1H), 7.86 (d, J = 6.9 Hz, 1H), 7.63-7.27 (m, 4H), 7.02 (d, J = 12.4 Hz, 2H), 3.75 (s, 4H), 3.12 (s, 4H) ppm. |
| 50 | 425.2 | 0.54 | 1H NMR (400 MHz, CDCl3) δ 9.02 (s, 1H), 8.86 (d, J = 2.1 Hz, 1H), 8.77 (d, J = 3.7 Hz, 1H), 7.37 (t, J = 2.1 Hz, 1H), 6.84 (s, 1H), 6.74 (s, 1H), 6.46 (s, 1H), 4.73 (p, J = 6.4 Hz, 4H), 3.60 (p, J = 6.4 Hz, 1H), 3.40-3.24 (m, 4H), 2.63 (q, J = 7.6 Hz, 2H), 2.58-2.46 (m, 4H), 1.27 (t, J = 7.6 Hz, 3H) ppm. |
| 51 | 544.41 | 0.73 | 1H NMR (300 MHz, CDCl3) δ 8.34 (s, 1H), 8.06-7.98 (m, 2H), 7.75-7.59 (m, 5H), 7.57-7.48 (m, 2H), 7.40-7.33 (m, 1H), 7.24 (d, J = 5.9 Hz, 2H), 6.67 (s, 2H), 4.84 (dd, J = 71.0, 21.8 Hz, 4H), 4.25-4.05 (m, 1H), 3.73 (s, 2H), 2.95 (s, 2H), 2.54 (s, 2H), 2.38 (s, 3H), 1.88 (s, 2H), 1.63 (d, J = 19.5 Hz, 2H) ppm. |
| 52 | 428.4 | 0.65 | 1H NMR (300 MHz, DMSO-d6) δ 9.41 (s, 1H), 9.06 (s, 1H), 8.11-7.84 (m, 1H), 7.78-7.55 (m, 2H), 7.11 (s, 1H), 6.94 (s, 1H), 6.23 (s, 1H), 4.85 (s, 1H), 4.58 (dd, J = 6.5, 5.1 Hz, 2H), 4.47 (dd, J = 10.6, 5.7 Hz, 2H), 3.66 (s, 1H), 3.31 (s, 1H), 2.89 (s, 1H), 2.69 (s, 2H), 2.38-2.17 (m, 4H), 1.86 (s, 1H) ppm. |
| 53 | 415.28 | 0.66 | 1H NMR (300 MHz, DMSO-d6) δ 9.35 (s, 1H), 9.16 (s, 1H), 7.61 (dd, J = 8.6, 2.1 Hz, 2H), 7.24 (m, 2H), 6.81 (s, 1H), 6.30 (s, 1H), 4.57 (m, 1H), 4.11 (dd, J = 10.5, 5.2 Hz, 1H), 3.67 (d, J = 10.6 Hz, 2H), 3.48 (d, J = 10.5 Hz, 1H), 3.41-3.35 (m, 1H), 3.17 (d, J = 5.3 Hz, 1H), 2.76 (m, 2H), 2.24 (m, 6H) ppm. |
| 54 | 406.53 | 0.67 | 1H NMR (300 MHz, CDCl3) δ 8.93 (s, 1H), 8.28 (d, J = 5.0 Hz, 1H), 7.64 (s, 1H), 7.14 (s, 1H), 7.07 (d, J = 5.0 Hz, 1H), 6.85 (s, 1H), 6.78 (s, 1H), 6.43 (s, 1H), 4.84-4.60 (m, 4H), 3.72-3.51 (m, 1H), 3.42-3.26 (m, 4H), 2.64-2.50 (m, 4H), 2.47 (s, 3H), 2.36 (s, 3H) ppm. |

TABLE 3-continued

Analytical Data

| Cmpd No. | LC/MS (M + H) | LC/MS Ret. Time (min) | ¹H-NMR |
|---|---|---|---|
| 55 | 451.25 | 0.64 | 1H NMR (400 MHz, CDCl3) δ 8.32 (s, 1H), 7.74 (d, J = 1.9 Hz, 1H), 7.60-7.50 (m, 1H), 7.43 (t, J = 8.1 Hz, 1H), 7.38-7.30 (m, 1H), 7.14 (s, 1H), 6.70 (s, 1H), 6.61 (s, 1H), 6.35 (s, 1H), 4.71 (p, J = 6.3 Hz, 4H), 3.65-3.53 (m, 1H), 3.38-3.24 (m, 4H), 2.60-2.48 (m, 4H), 1.90 (ddd, J = 13.5, 8.5, 5.1 Hz, 1H), 1.01-0.88 (m, 2H), 0.82-0.64 (m, 2H) ppm. |
| 56 | 439.28 | 0.61 | 1H NMR (400 MHz, DMSO-d6) δ 9.25 (s, 1H), 9.11 (s, 1H), 7.36-7.12 (m, 3H), 6.81 (dt, J = 11.2, 2.3 Hz, 2H), 6.31 (s, 1H), 4.57 (t, J = 6.5 Hz, 2H), 4.48 (t, J = 6.1 Hz, 2H), 3.86 (s, 3H), 3.53-3.38 (m, 1H), 3.25-3.05 (m, 4H), 2.46-2.34 (m, 3H), 2.22 (s, 3H) ppm. |
| 57 | 422.41 | 2.48 | 1H NMR (400 MHz, DMSO-d6) δ 9.25 (s, 1H), 7.88 (d, J = 7.7 Hz, 2H), 7.63-7.55 (m, 2H), 7.46 (t, J = 7.4 Hz, 2H), 6.89 (s, 1H), 4.36 (t, J = 18.6 Hz, 1H), 4.14 (d, J = 13.0 Hz, 1H), 3.52-3.25 (m, 5H), 2.52 (s, 3H), 1.91 (dd, J = 13.5, 6.7 Hz, 1H), 1.78 (s, 1H), 1.20 (s, 1H), 1.12 (s, 2H), 0.88 (d, J = 6.5 Hz, 3H), 0.84 (d, J = 6.8 Hz, 1H), 0.77 (d, J = 6.8 Hz, 2H) ppm. mixture of diastereomers |
| 58 | 421.28 | 0.54 | 1H NMR (400 MHz, CDCl3) δ 9.01 (s, 1H), 8.90 (d, J = 0.9 Hz, 1H), 7.59 (d, J = 9.2 Hz, 1H), 7.07 (t, J = 2.0 Hz, 1H), 6.91 (s, 1H), 6.89 (s, 1H), 4.72 (dt, J = 16.1, 6.4 Hz, 4H), 3.60 (p, J = 6.4 Hz, 1H), 3.37-3.28 (m, 4H), 2.66 (dd, J = 13.3, 5.6 Hz, 2H), 2.64 (s, 3H), 2.59-2.50 (m, 4H), 1.29 (t, J = 7.6 Hz, 3H) ppm. |
| 59 | 365 | 0.58 | |
| 60 | 348 | 0.61 | 1H NMR (400 MHz, Acetone-d6) δ 8.79 (s, 1H), 8.25 (s, 1H), 7.93-7.82 (m, 2H), 7.59-7.49 (m, 3H), 7.40 (s, 1H), 7.38-7.30 (m, 1H), 6.64 (s, 1H), 2.95-2.65 (m, 5H), 2.31 (s, 3H), 2.23 (s, 3H), 1.97 (t, J = 10.9 Hz, 1H), 1.89 (td, J = 11.4, 3.1 Hz, 2H), 1.79-1.61 (m, 2H), 1.44 (ddd, J = 24.6, 12.3, 4.4 Hz, 1H) ppm. |
| 61 | 424.19 | 0.76 | 1H NMR (300 MHz, CDCl3) δ 8.33 (s, 1H), 7.44 (s, 1H), 7.32-7.13 (m, 3H), 6.90 (d, J = 20.4 Hz, 2H), 6.80 (ddd, J = 8.7, 6.6, 2.2 Hz, 1H), 6.20 (s, 1H), 4.75 (d, J = 6.5 Hz, 3H), 3.84-3.32 (m, 1H), 3.13 (dd, J = 12.6, 6.8 Hz, 2H), 2.63 (d, J = 2.8 Hz, 4H), 2.39 (s, 3H) ppm. |
| 62 | 371.29 | 0.64 | 1H NMR (300 MHz, CD3OD) δ 8.80 (s, 1H), 7.85-7.75 (m, 2H), 7.51 (dd, J = 16.5, 8.1 Hz, 3H), 7.36 (dd, J = 13.5, 6.0 Hz, 2H), 6.68 (dd, J = 64.3, 48.6 Hz, 2H), 3.39 (dd, J = 6.5, 3.7 Hz, 4H), 3.26 (dd, J = 6.5, 3.6 Hz, 4H) ppm. |
| 63 | 439.34 | 3.24 | 1H NMR (300 MHz, DMSO-d6) δ 9.22 (s, 1H), 7.66-7.55 (m, 2H), 7.53 (s, 1H), 7.49 (s, 1H), 7.28 (td, J = 9.2, 2.2 Hz, 1H), 6.87 (s, 1H), 3.90 (m, 2H), 3.53 (m, 2H), 3.21 (m, 4H), 2.85 (s, 3H) ppm. |
| 64 | 439.15 | 0.58 | 1H NMR (400 MHz, CDCl3) δ 9.00 (s, 1H), 8.61 (dd, J = 20.2, 5.4 Hz, 1H), 7.37 (d, J = 5.4 Hz, 1H), 7.06 (s, 1H), 6.84 (s, 2H), 6.45 (s, 1H), 4.72 (dq, J = 12.6, 6.4 Hz, 4H), 3.59 (p, J = 6.4 Hz, 1H), 3.36-3.24 (m, 4H), 2.62 (s, 3H), 2.54 (dd, J = 11.2, 6.3 Hz, 4H), 2.36 (s, 3H) ppm. |
| 65 | 362.24 | 0.57 | 1H NMR (300 MHz, DMSO-d6) δ 9.35 (s, 1H), 9.07 (s, 1H), 7.89-7.82 (m, 2H), 7.62 (s, 1H), 7.55 (t, J = 7.9 Hz, 2H), 7.35 (t, J = 7.4 Hz, 1H), 7.23 (s, 1H), 6.63 (s, 1H), 4.59 (t, J = 6.6 Hz, 2H), 4.46-4.40 (m, 2H), 3.82-3.71 (m, 1H), 3.70-3.52 (m, 3H), 3.24-3.14 (m, 2H), 2.27 (s, 3H) ppm. |

TABLE 3-continued

Analytical Data

| Cmpd No. | LC/MS (M + H) | LC/MS Ret. Time (min) | ¹H-NMR |
|---|---|---|---|
| 66 | 452.29 | 0.66 | 1H NMR (300 MHz, DMSO-d6) δ 9.51 (s, 1H), 8.96 (d, J = 2.3 Hz, 1H), 8.33 (dd, J = 11.3, 5.7 Hz, 1H), 7.96 (dd, J = 10.0, 6.1 Hz, 1H), 7.14 (s, 1H), 6.88 (s, 1H), 6.34 (s, 1H), 4.57 (t, J = 6.5 Hz, 2H), 4.48 (t, J = 6.1 Hz, 2H), 3.50-3.39 (m, 1H), 3.21-3.10 (m, 4H), 2.45-2.36 (m, 4H), 2.23 (s, 3H) ppm. |
| 67 | 441 | 0.64 | 1H NMR (400 MHz, DMSO-d6) δ 9.62 (s, 1H), 9.19 (s, 1H), 7.63 (dd, J = 8.4, 2.1 Hz, 2H), 7.37 (d, J = 12.2 Hz, 2H), 7.27 (dd, J = 10.3, 8.1 Hz, 1H), 6.66 (s, 1H), 4.60 (t, J = 6.6 Hz, 2H), 4.51 (t, J = 6.1 Hz, 2H), 3.73-3.52 (m, 3H), 3.12 (s, 2H), 2.79-2.65 (m, 2H), 2.30 (s, 3H) ppm. |
| 68 | 351.44 | 0.6 | 1H NMR (300 MHz, DMSO-d6) δ 9.43 (s, 1H), 9.20 (s, 1H), 9.05 (d, J = 1.3 Hz, 1H), 8.66 (d, J = 2.5 Hz, 1H), 8.58 (dd, J = 2.6, 1.4 Hz, 1H), 7.16 (s, 1H), 6.92 (s, 1H), 6.33 (s, 1H), 3.20-3.00 (m, 4H), 2.46 (d, J = 4.8 Hz, 3H), 2.32-2.18 (m, 6H) ppm. |
| 69 | 441.24 | 0.65 | 1H NMR (300 MHz, DMSO-d6) δ 9.29 (d, J = 13.3 Hz, 1H), 9.06 (s, 1H), 7.95 (dd, J = 12.9, 7.8 Hz, 1H), 7.68 (dd, J = 8.7, 5.1 Hz, 2H), 7.13 (s, 1H), 6.93 (s, 1H), 6.34 (s, 1H), 4.58 (t, J = 6.5 Hz, 2H), 4.48 (t, J = 6.1 Hz, 2H), 3.61-3.41 (m, 1H), 3.15 (s, 4H), 2.54 (d, J = 8.0 Hz, 2H), 2.34 (d, J = 43.4 Hz, 4H), 1.32-1.12 (m, 3H) ppm. |
| 70 | 405.23 | 0.61 | 1H NMR (400 MHz, CDCl3) δ 8.27 (s, 1H), 7.56 (d, J = 8.4 Hz, 2H), 7.32-7.28 (m, 2H), 7.15 (s, 1H), 6.80 (s, 1H), 6.67 (s, 1H), 6.40 (s, 1H), 4.72 (p, J = 6.4 Hz, 4H), 3.58 (p, J = 6.5 Hz, 1H), 3.35-3.23 (m, 4H), 2.58-2.49 (m, 4H), 2.42 (s, 3H), 2.35 (d, J = 7.5 Hz, 3H) ppm. |
| 71 | 390.46 | 0.65 | 1H NMR (300 MHz, CDCl3) δ 8.33 (s, 1H), 7.76-7.66 (m, 2H), 7.57-7.47 (m, 2H), 7.42-7.32 (m, 1H), 7.27 (s, 1H), 7.22 (s, 1H), 6.67 (d, J = 18.2 Hz, 2H), 4.70 (d, J = 6.6 Hz, 4H), 3.54 (p, J = 6.6 Hz, 1H), 2.90 (d, J = 9.9 Hz, 2H), 2.62-2.43 (m, 1H), 2.37 (s, 3H), 2.06-1.76 (m, 6H) ppm. |
| 72 | 457.18 | 0.82 | 1H NMR (400 MHz, DMSO-d6) δ 9.45 (s, 1H), 9.19 (s, 1H), 7.63 (d, J = 6.4 Hz, 2H), 7.26 (t, J = 9.5 Hz, 1H), 7.18 (s, 1H), 6.93 (s, 1H), 6.40 (s, 1H), 4.34 (s, 2H), 4.26 (dd, J = 14.3, 7.2 Hz, 2H), 3.75 (s, 2H), 3.61 (s, 2H), 3.31 (s, 2H), 3.17 (s, 2H), 2.25 (s, 3H), 1.26 (dd, J = 13.9, 6.8 Hz, 3H) ppm. |
| 73 | 449.35 | 0.85 | H NMR (300 MHz, CDCl3) δ 8.30 (s, 1H), 7.24 (d, J = 9.4 Hz, 1H), 7.10 (t, J = 2.0 Hz, 1H), 6.87 (d, J = 9.2 Hz, 1H), 6.72 (s, 1H), 6.61 (s, 1H), 6.35 (s, 1H), 4.79-4.60 (m, 4H), 3.59 (p, J = 6.3 Hz, 1H), 3.39-3.24 (m, 4H), 2.61-2.49 (m, 4H), 2.45 (s, 3H), 1.96-1.78 (m, 1H), 1.05-0.89 (m, 2H), 0.75 (dt, J = 6.7, 4.6 Hz, 2H) ppm. |
| 74 | 392 | 0.6 | 1H NMR (400 MHz, CDCl3) δ 9.20 (d, J = 1.2 Hz, 1H), 8.91 (s, 1H), 8.57 (d, J = 2.5 Hz, 1H), 8.49-8.30 (m, 1H), 7.31 (s, 1H), 7.22 (s, 1H), 6.82 (s, 1H), 6.70 (s, 1H), 4.76-4.56 (m, 4H), 3.59-3.45 (m, 1H), 2.94-2.76 (m, 3H), 2.37 (s, 3H), 2.01 (d, J = 12.5 Hz, 1H), 1.85 (dt, J = 38.3, 11.5 Hz, 3H), 1.55 (dd, J = 28.9, 16.5 Hz, 2H) ppm. |
| 75 | 427.2 | 0.62 | 1H NMR (300 MHz, CDCl3) δ 9.19 (d, J = 1.3 Hz, 1H), 8.92 (s, 1H), 8.57 (d, J = 2.5 Hz, 1H), 8.41 (dd, J = 2.5, 1.5 Hz, 1H), 7.19 (s, 1H), 6.77 (d, J = 8.0 Hz, 2H), 6.45 (s, 1H), 3.37-3.20 (m, 4H), 2.88-2.64 (m, 3H), 2.63-2.41 (m, 6H), 2.36 (s, 3H) ppm. |
| 76 | 363 | 0.75 | 1H NMR (400 MHz, DMSO-d6) δ 9.28 (s, 1H), 9.08 (s, 1H), 7.85 (d, J = 7.6 Hz, 2H), 7.54 (t, J = 8.0 Hz, 2H), 7.35 (t, J = 7.4 Hz, 1H), 7.19 (s, 1H), 6.90 (s, 1H), 6.34 (s, 1H), 3.75 (s, 2H), 3.60-3.35 (m, 3H), 2.90 (s, 3H), 2.24 (s, 3H) ppm. |

TABLE 3-continued

Analytical Data

| Cmpd No. | LC/MS (M + H) | LC/MS Ret. Time (min) | ¹H-NMR |
|---|---|---|---|
| 77 | 371 | 0.64 | 1H NMR (400 MHz, DMSO-d6) δ 9.45 (s, 1H), 9.26 (s, 2H), 9.19 (s, 1H), 7.63 (dd, J = 8.5, 2.1 Hz, 2H), 7.26 (d, J = 2.3 Hz, 1H), 7.19 (s, 1H), 6.97 (s, 1H), 6.40 (s, 1H), 3.46-3.31 (m, 4H), 3.24 (s, 4H), 2.25 (s, 3H) ppm. |
| 78 | 423 | 0.64 | 1H NMR (400 MHz, CDCl3) δ 8.28 (s, 1H), 7.23 (d, J = 5.9 Hz, 2H), 6.80 (d, J = 7.6 Hz, 1H), 6.76 (t, J = 8.7 Hz, 1H), 6.63 (s, 1H), 6.54 (s, 1H), 6.06 (s, 1H), 4.25 (s, 1H), 3.65 (s, 1H), 3.48 (q, J = 8.8 Hz, 2H), 3.13 (d, J = 9.4 Hz, 1H), 2.90 (d, J = 9.7 Hz, 1H), 2.31 (s, 3H), 1.94 (t, J = 10.3 Hz, 3H), 1.27 (s, 1H), 0.55-0.30 (m, 4H) ppm. |
| 79 | 445.41 | 0.64 | 1H NMR (300 MHz, CDCl3) δ 8.31 (s, 1H), 7.27 (d, J = 2.3 Hz, 1H), 7.24 (d, J = 2.1 Hz, 1H), 7.10 (s, 1H), 6.88-6.73 (m, 2H), 6.65 (s, 1H), 6.43 (s, 1H), 3.77 (dd, J = 9.4, 8.4 Hz, 4H), 3.35-3.23 (m, 4H), 3.05-2.88 (m, 4H), 2.84 (dd, J = 12.3, 6.3 Hz, 1H), 2.35 (s, 3H) ppm. |
| 80 | 340 | 0.36 | 1H NMR (400 MHz, DMSO-d6) δ 9.56 (s, 1H), 9.09 (s, 1H), 7.83 (d, J = 7.7 Hz, 2H), 7.55 (t, J = 7.9 Hz, 2H), 7.36 (t, J = 7.4 Hz, 1H), 7.03 (s, 1H), 7.00 (s, 2H), 6.29 (d, J = 12.4 Hz, 1H), 3.90-3.60 (m, 4H), 3.20-2.96 (m, 4H) ppm. |
| 81 | 374 | 0.58 | 1H NMR (300 MHz, Acetone-d6) δ 8.76 (s, 1H), 8.15-7.87 (m, 3H), 7.64 (s, 1H), 7.23 (s, 1H), 7.00 (s, 1H), 6.53 (s, 1H), 3.42-3.20 (m, 3H), 2.75-2.55 (m, 3H), 2.42 (s, 3H), 2.40 (s, 3H) ppm. |
| 82 | 463.36 | 0.69 | 1H NMR (300 MHz, CD3OD + CDCl3) δ 8.72 (s, 1H), 7.46 (s, 1H), 7.40 (dd, J = 8.1, 2.2 Hz, 2H), 7.24 (s, 1H), 6.78 (ddt, J = 110.8, 76.2, 29.5 Hz, 3H), 4.75 (dt, J = 12.5, 6.5 Hz, 4H), 3.65 (s, 1H), 3.36 (s, 4H), 2.61 (s, 4H) ppm. |
| 83 | 342.09 | 3.33 | 1H NMR (400 MHz, DMSO-d6) δ 9.49 (s, 1H), 8.78 (d, J = 2.4 Hz, 1H), 7.84 (td, J = 7.8, 2.1 Hz, 1H), 7.63-7.35 (m, 3H), 6.76 (d, J = 11.8 Hz, 1H), 6.67 (s, 1H), 5.86 (d, J = 12.1 Hz, 1H), 3.21 (t, J = 6.4 Hz, 4H), 1.95 (t, J = 6.5 Hz, 4H) ppm. |
| 84 | 337.11 | 0.51 | 1H NMR (400 MHz, CD3OD) δ 9.38 (s, 1H), 8.90 (d, J = 6.9 Hz, 2H), 8.63 (d, J = 6.0 Hz, 2H), 8.15 (d, J = 26.7 Hz, 1H), 7.36 (d, J = 22.6 Hz, 1H), 7.12 (d, J = 24.4 Hz, 1H), 4.19 (s, 4H), 3.73 (s, 4H), 2.45 (s, 3H) ppm. |
| 85 | 391.27 | 0.78 | 1H NMR (300 MHz, DMSO-d6) δ 9.82 (s, 1H), 9.38 (s, 1H), 8.39 (d, J = 5.6 Hz, 1H), 7.85-7.76 (m, 1H), 7.61 (s, 1H), 7.37 (d, J = 4.7 Hz, 2H), 6.94 (t, J = 56.1 Hz, 1H), 6.70 (s, 1H), 3.85-3.71 (m, 4H), 3.21-3.09 (m, 4H) ppm. |
| 86 | 421.28 | 0.59 | 1H NMR (400 MHz, CDCl3) δ 8.31 (s, 1H), 7.39 (t, J = 8.1 Hz, 1H), 7.28 (d, J = 1.7 Hz, 1H), 7.23 (dd, J = 8.0, 0.8 Hz, 1H), 7.18 (s, 1H), 6.95-6.84 (m, 1H), 6.78 (s, 1H), 6.70 (s, 1H), 6.40 (s, 1H), 4.71 (p, J = 6.1 Hz, 4H), 3.89 (s, 3H), 3.58 (p, J = 6.3 Hz, 1H), 3.36-3.26 (m, 4H), 2.58-2.47 (m, 4H), 2.34 (s, 3H) ppm. |
| 87 | 403.42 | 0.66 | 1H NMR (300 MHz, DMSO-d6) δ 9.17 (s, 1H), 9.04 (s, 1H), 7.82 (dd, J = 8.6, 1.0 Hz, 2H), 7.55 (dd, J = 10.7, 5.2 Hz, 2H), 7.34 (t, J = 7.4 Hz, 1H), 7.13 (s, 1H), 6.88 (s, 1H), 6.27 (s, 1H), 3.20-3.01 (m, 4H), 2.54 (dd, J = 9.5, 4.7 Hz, 4H), 2.44 (d, J = 8.1 Hz, 1H), 2.22 (s, 3H), 1.90-1.75 (m, 2H), 1.72-1.45 (m, 4H), 1.36 (dt, J = 16.2, 7.3 Hz, 2H) ppm. |
| 88 | 399.29 | 0.62 | 1H NMR (400 MHz, DMSO-d6) δ 9.70 (s, 1H), 9.14 (d, J = 22.9 Hz, 1H), 7.98 (ddd, J = 11.7, 7.0, 2.3 Hz, 1H), 7.73-7.58 (m, 2H), 6.87 (t, J = 9.6 Hz, 1H), 6.82 (s, 1H), 3.75-3.63 (m, 4H), 3.39-3.32 (m, 4H), 1.87 (ddd, J = 12.8, 8.0, 4.8 Hz, 1H), 0.92-0.82 (m, 2H), 0.82-0.74 (m, 2H) ppm. |

TABLE 3-continued

Analytical Data

| Cmpd No. | LC/MS (M + H) | LC/MS Ret. Time (min) | ¹H-NMR |
|---|---|---|---|
| 89 | 384.33 | 3.63 | 1H NMR (300 MHz, CDCl3) δ 8.76 (s, 1H), 8.27 (s, 1H), 7.77 (d, J = 7.9 Hz, 2H), 7.60 (dd, J = 13.0, 5.7 Hz, 3H), 7.48 (t, J = 7.4 Hz, 1H), 7.00 (s, 1H), 6.66 (s, 1H), 4.03-3.92 (m, 4H), 3.41 (s, 4H), 2.39 (s, 3H) ppm. |
| 90 | 412 | 0.81 | 1H NMR (300 MHz, Acetone-d6) δ 8.89 (s, 1H), 8.33 (s, 1H), 7.65-7.48 (m, 2H), 7.42 (d, J = 16.4 Hz, 2H), 6.94 (tt, J = 9.0, 2.3 Hz, 1H), 6.66 (s, 1H), 4.71 (d, J = 13.2 Hz, 1H), 4.12-3.96 (m, 1H), 3.22 (td, J = 13.6, 2.7 Hz, 1H), 2.77 (ddd, J = 12.2, 8.4, 3.5 Hz, 1H), 2.63 (dd, J = 12.8, 9.9 Hz, 1H), 2.33 (s, 3H), 2.10 (s, 3H), 2.00-1.82 (m, 2H), 1.81-1.49 (m, 2H) ppm. |
| 91 | 421.28 | 0.53 | 1H NMR (400 MHz, CDCl3) δ 9.04 (s, 1H), 8.75 (d, J = 5.5 Hz, 1H), 7.53 (t, J = 5.4 Hz, 1H), 7.09 (t, J = 2.0 Hz, 1H), 6.88 (s, 1H), 6.74 (s, 1H), 6.49 (s, 1H), 4.73 (dq, J = 12.6, 6.4 Hz, 4H), 3.69-3.53 (m, 1H), 3.37-3.24 (m, 3H), 2.76 (s, 3H), 2.72-2.58 (m, 2H), 2.59-2.48 (m, 3H), 1.29 (dd, J = 9.5, 5.7 Hz, 3H) ppm. |
| 92 | | | 1H NMR (400 MHz, DMSO-d6) δ 9.42 (s, 1H), 9.16 (s, 1H), 7.62 (dd, J = 8.6, 2.1 Hz, 2H), 7.52 (s, 1H), 7.29-7.19 (m, 1H), 7.18 (s, 1H), 6.62 (s, 1H), 4.58 (td, J = 6.5, 1.9 Hz, 2H), 4.50 (td, J = 6.0, 1.2 Hz, 2H), 3.69-3.60 (m, 1H), 3.29-3.21 (m, 1H), 2.97 (t, J = 8.4 Hz, 1H), 2.73 (dd, J = 14.9, 7.8 Hz, 1H), 2.59 (td, J = 8.7, 5.6 Hz, 1H), 2.44-2.38 (m, 1H), 2.26 (s, 3H), 1.79 (dt, J = 13.8, 8.3 Hz, 1H) ppm. |
| 93 | 385 | 0.6 | 1H NMR (400 MHz, DMSO-d6) δ 9.60 (d, J = 7.5 Hz, 1H), 9.18 (s, 1H), 7.63 (d, J = 6.4 Hz, 2H), 7.36 (t, J = 10.2 Hz, 2H), 7.26 (t, J = 9.3 Hz, 1H), 6.63 (s, 1H), 3.98 (s, 2H), 3.56 (dd, J = 15.0, 4.8 Hz, 4H), 2.29 (s, 3H) ppm. |
| 94 | 379.24 | 0.59 | 1H NMR (400 MHz, CDCl3) δ 8.31 (s, 1H), 7.38 (t, J = 8.2 Hz, 1H), 7.29 (t, J = 2.2 Hz, 1H), 7.26-7.13 (m, 2H), 6.88 (ddd, J = 16.8, 8.4, 7.7 Hz, 1H), 6.78 (d, J = 10.8 Hz, 2H), 6.40 (s, 1H), 3.89 (s, 3H), 3.35-3.26 (m, 4H), 2.68-2.58 (m, 4H), 2.40 (s, 3H), 2.35 (d, J = 12.3 Hz, 3H) ppm. |
| 95 | 443.11 | 0.63 | 1H NMR (400 MHz, CDCl3) δ 8.31 (s, 1H), 7.25 (dd, J = 7.8, 2.1 Hz, 2H), 7.10 (s, 1H), 6.83-6.73 (m, 2H), 6.66 (s, 1H), 6.42 (s, 1H), 3.84-3.71 (m, 1H), 3.49 (t, J = 8.9 Hz, 2H), 3.33-3.21 (m, 4H), 3.07 (dd, J = 9.0, 7.7 Hz, 2H), 2.54 (dd, J = 14.9, 10.0 Hz, 4H), 2.35 (s, 3H) ppm. |
| 96 | 405 | 0.59 | 1H NMR (300 MHz, Acetone-d6) δ 9.17 (s, 1H), 9.05 (d, J = 1.1 Hz, 1H), 8.97 (d, J = 5.5 Hz, 2H), 7.80 (dd, J = 5.5, 1.2 Hz, 1H), 7.64 (d, J = 2.0 Hz, 1H), 7.54 (s, 1H), 6.84 (s, 1H), 3.41-3.21 (m, 4H) note: water peak under the CH2s, 2.61-2.49 (m, 4H), 2.29 (s, 3H) ppm. |
| 97 | 451.44 | 0.71 | 1H NMR (300 MHz, DMSO-d6) δ 9.26 (s, 1H), 9.13 (s, 1H), 7.71 (dd, J = 5.0, 2.8 Hz, 1H), 7.68 (s, 1H), 7.60 (td, J = 8.4, 6.5 Hz, 1H), 7.26 (s, 1H), 7.23-7.13 (m, 1H), 7.10 (s, 1H), 6.50 (s, 1H), 4.58 (t, J = 6.5 Hz, 2H), 4.49 (t, J = 6.0 Hz, 2H), 3.56-3.38 (m, 1H), 3.25-3.09 (m, 4H), 2.47-2.30 (m, 4H), 1.26 (d, J = 9.4 Hz, 9H) ppm. |
| 98 | 385 | 0.65 | 1H NMR (400 MHz, DMSO-d6) δ 9.49 (s, 1H), 9.15 (s, 1H), 7.70 (dd, J = 8.3, 5.6 Hz, 2H), 7.60 (dd, J = 14.7, 8.3 Hz, 1H), 7.20 (t, J = 8.2 Hz, 1H), 6.98 (s, 1H), 6.66 (d, J = 11.4 Hz, 1H), 6.03 (d, J = 13.1 Hz, 1H), 3.51 (d, J = 4.2 Hz, 2H), 3.43 (t, J = 6.1 Hz, 2H), 3.34 (s, 3H), 2.64 (d, J = 4.6 Hz, 2H), 2.48-2.40 (m, 2H), 2.27 (s, 3H), 1.92 (d, J = 4.9 Hz, 2H) ppm. |
| 99 | 360.09 | 3.41 | 1H NMR (400 MHz, DMSO-d6) δ 9.50 (s, 1H), 9.09 (s, 1H), 8.07-7.92 (m, 1H), 7.76-7.57 (m, 2H), 6.76 (d, J = 11.8 Hz, 1H), 6.69 (s, 1H), 5.88 (d, J = 12.3 Hz, 1H), 3.22 (t, J = 6.3 Hz, 4H), 1.96 (t, J = 6.5 Hz, 4H) ppm. |

TABLE 3-continued

Analytical Data

| Cmpd No. | LC/MS (M + H) | LC/MS Ret. Time (min) | ¹H-NMR |
|---|---|---|---|
| 100 | 393.12 | 1.08 | 1H NMR (300 MHz, CD3OD) δ 9.83 (s, 1H), 8.80 (ddd, J = 11.4, 6.9, 2.7 Hz, 1H), 8.64 (ddt, J = 8.2, 4.2, 2.1 Hz, 1H), 8.46 (dt, J = 10.1, 8.7 Hz, 1H), 7.93 (dd, J = 12.8, 1.5 Hz, 2H), 4.88-4.71 (m, 4H), 4.54-4.37 (m, 4H) ppm. |
| 101 |  |  | 1H NMR (300 MHz, DMSO-d6) δ 9.46 (s, 1H), 9.17 (s, 1H), 7.74 (s, 1H), 7.69-7.58 (m, 2H), 7.25 (m, 2H), 6.85 (s, 1H), 5.18 (s, 1H), 4.57 (dd, J = 9.9, 4.3 Hz, 2H), 4.51 (dd, J = 13.1, 6.0 Hz, 2H), 3.82-3.71 (m, 1H), 2.92-2.70 (m, 4H), 2.29 (s, 3H), 2.21-1.97 (m, 2H) ppm. |
| 102 | 425.22 | 0.63 | 1H NMR (300 MHz, DMSO-d6) δ 9.27 (s, 1H), 9.03 (s, 1H), 7.96-7.70 (m, 2H), 7.42 (dd, J = 12.1, 5.5 Hz, 2H), 6.94-6.75 (m, 2H), 6.04 (s, 1H), 4.57 (t, J = 6.5 Hz, 2H), 4.48 (t, J = 6.0 Hz, 2H), 3.71 (s, 3H), 3.44 (dt, J = 15.2, 7.7 Hz, 1H), 3.25-3.07 (m, 4H), 2.37 (t, J = 22.6 Hz, 4H) ppm. |
| 103 | 506.25 | 0.69 | 1H NMR (300 MHz, CDCl3) δ 8.26 (s, 1H), 7.20 (s, 1H), 6.77 (s, 1H), 6.70-6.54 (m, 3H), 6.40 (s, 1H), 6.20 (d, J = 12.1 Hz, 1H), 4.79-4.65 (m, 44H), 3.60 (dd, J = 13.0, 6.6 Hz, 2H), 3.52-3.40 (m, 1H), 3.36-3.29 (m, 4H), 3.28-3.14 (m, 1H), 2.53 (s, 4H), 2.36 (d, J = 11.7 Hz, 3H), 2.06-1.99 (m, 1H), 1.82-1.48 (m, 5H), 1.32-1.21 (m, 3H) ppm. |
| 104 | 392.4 | 0.61 | 1H NMR (300 MHz, DMSO-d6) δ 9.31 (s, 1H), 9.12 (s, 1H), 8.49 (ddd, J = 4.8, 1.8, 0.8 Hz, 1H), 8.08 (ddd, J = 8.2, 7.5, 1.8 Hz, 1H), 7.74 (d, J = 8.2 Hz, 1H), 7.40 (ddd, J = 7.5, 4.9, 1.0 Hz, 1H), 7.15 (s, 1H), 6.92 (s, 1H), 6.32 (s, 1H), 4.56 (q, J = 6.6 Hz, 3H), 4.54-4.36 (m, 3H), 3.55-3.38 (m, 1H), 3.16 (dd, J = 7.4, 3.7 Hz, 4H), 2.46-2.40 (m, 4H), 2.24 (s, 3H) ppm. |
| 105 | 401.27 | 0.64 | 1H NMR (400 MHz, CDCl3) δ 8.34-8.25 (m, 1H), 7.26-7.12 (m, 3H), 6.83-6.72 (m, 1H), 6.54-6.45 (m, 2H), 5.45-5.20 (m, 1H), 3.83 (dd, J = 26.4, 13.0 Hz, 1H), 3.72-3.48 (m, 3H), 2.34 (dd, J = 22.0, 10.3 Hz, 1H), 2.22-1.98 (m, 1H), 1.92-1.80 (m, 1H), 1.03 (s, 2H), 0.84 (d, J = 3.0 Hz, 2H) ppm. |
| 106 | 385.15 | 0.86 | 1H NMR (400 MHz, CDCl3) δ 8.34 (d, J = 12.0 Hz, 1H), 7.41 (t, J = 8.2 Hz, 1H), 7.22 (dd, J = 7.7, 1.6 Hz, 1H), 7.00 (s, 1H), 6.94 (d, J = 1.5 Hz, 1H), 6.94-6.91 (m, 1H), 6.68 (d, J = 1.5 Hz, 1H), 3.90 (s, 3H), 3.57 (s, 4H), 1.67 (s, 6H) ppm. |
| 107 | 441.4 | 0.65 | 1H NMR (300 MHz, CDCl3) δ 8.32 (s, 1H), 7.25 (dd, J = 7.9, 2.2 Hz, 2H), 7.14 (t, J = 2.1 Hz, 1H), 6.80 (ddd, J = 10.9, 3.3, 1.9 Hz, 3H), 6.46 (s, 1H), 4.79-4.65 (m, 4H), 3.59 (p, J = 6.4 Hz, 1H), 2.64 (q, J = 7.6 Hz, 2H), 2.58-2.45 (m, 4H), 1.28 (t, J = 7.6 Hz, 3H) ppm. |
| 108 | 370 | 0.62 | 1H NMR (400 MHz, Acetone-d6) δ 8.92 (s, 1H), 8.37 (s, 1H), 7.63-7.53 (m, 2H), 7.45 (s, 1H), 7.41 (s, 1H), 7.00 (tt, J = 9.1, 2.3 Hz, 1H), 6.65 (s, 1H), 3.11 (d, J = 11.9 Hz, 2H), 2.78-2.63 (m, 8H), 2.57 (tt, J = 11.9, 3.7 Hz, 1H), 2.32 (s, 3H), 1.82-1.73 (m, 2H), 1.63 (qd, J = 12.4, 4.0 Hz, 2H) ppm. |
| 109 | 385 | 0.66 | 1H NMR (400 MHz, DMSO-d6) δ 9.52 (s, 1H), 9.15 (s, 1H), 7.80-7.66 (m, 2H), 7.65-7.52 (m, 1H), 7.19 (t, J = 7.4 Hz, 1H), 6.82 (s, 1H), 6.68 (d, J = 11.8 Hz, 1H), 5.88 (d, J = 12.1 Hz, 1H), 3.46 (t, J = 8.1 Hz, 1H), 3.35 (d, J = 11.0 Hz, 4H), 3.30-3.15 (m, 1H), 3.05 (t, J = 8.5 Hz, 1H), 2.83-2.68 (m, 1H), 2.22 (s, 6H), 1.91-1.71 (m, 1H) ppm. |
| 110 | 320 | 2.3 | 1H NMR (400 MHz, CDCl3) δ 8.31 (s, 1H), 7.79-7.60 (m, 2H), 7.60-7.38 (m, 2H), 7.40-7.28 (m, 1H), 6.79 (s, 1H), 6.62 (s, 2H), 6.06 (s, 1H), 3.34 (m, 4H), 2.32 (s, 3H), 2.03 (m, 4H) ppm. |

TABLE 3-continued

Analytical Data

| Cmpd No. | LC/MS (M + H) | LC/MS Ret. Time (min) | ¹H-NMR |
|---|---|---|---|
| 111 | 407.33 | 0.56 | 1H NMR (400 MHz, CDCl3) δ 9.02 (s, 1H), 8.90 (d, J = 0.8 Hz, 1H), 7.59 (s, 1H), 7.03 (d, J = 11.4 Hz, 1H), 6.90 (s, 1H), 6.88 (s, 1H), 6.45 (s, 1H), 4.72 (dt, J = 16.0, 6.4 Hz, 4H), 3.59 (p, J = 6.4 Hz, 1H), 3.36-3.25 (m, 4H), 2.64 (s, 3H), 2.59-2.49 (m, 4H), 2.37 (s, 3H) ppm. |
| 112 | 431.25 | 0.63 | 1H NMR (300 MHz, DMSO-d6) δ 9.63 (s, 1H), 9.18 (s, 1H), 7.67-7.55 (m, 2H), 7.31-7.20 (m, 1H), 7.02-6.92 (m, 2H), 6.31 (d, J = 12.7 Hz, 1H), 4.57 (t, J = 6.5 Hz, 2H), 4.48 (t, J = 6.0 Hz, 2H), 3.51-3.39 (m, 1H), 3.23-3.14 (m, 4H), 2.44-2.34 (m, 4H) ppm. |
| 113 | 427.45 | 0.65 | 1H NMR (300 MHz, DMSO-d6) δ 9.13 (s, 1H), 9.05 (s, 1H), 8.09-7.95 (m, 1H), 7.70 (ddt, J = 19.2, 17.6, 5.8 Hz, 2H), 6.89 (s, 1H), 6.52 (s, 1H), 5.92 (s, 1H), 5.62 (d, J = 6.5 Hz, 1H), 4.56 (td, J = 6.5, 3.6 Hz, 2H), 4.45 (dd, J = 12.6, 6.1 Hz, 2H), 3.85 (s, 1H), 3.67-3.50 (m, 1H), 2.78 (dt, J = 17.5, 8.8 Hz, 1H), 2.60 (dd, J = 13.9, 8.1 Hz, 1H), 2.47-2.34 (m, 2H), 2.33-2.17 (m, 1H), 2.14 (s, 3H), 1.66 (td, J = 12.8, 7.4 Hz, 1H) ppm. |
| 114 | 453.28 | 0.66 | 1H NMR (300 MHz, DMSO-d6) δ 9.29 (s, 1H), 9.14 (s, 1H), 7.59 (m, 2H), 7.23 (m, 2H), 6.80 (s, 1H), 6.31 (s, 1H), 3.93 (m, 1H), 3.63 (d, J = 11.8 Hz, 1H), 3.52 (d, J = 12.0 Hz, 1H), 3.40 (t, J = 7.0 Hz, 2H), 2.83-2.72 (m, 1H), 2.63 (m, 1H), 2.26-2.18 (m, 5H), 1.93 (m, 2H), 1.71 (m, 4H) ppm. |
| 115 | 391 | 0.62 | |
| 116 | 386.19 | 0.72 | |
| 117 | 376 | 0.8 | 1H NMR (400 MHz, Acetone-d6) δ 8.81 (d, J = 4.5 Hz, 1H), 8.35 (d, J = 3.8 Hz, 1H), 7.95-7.84 (m, 2H), 7.62-7.51 (m, 3H), 7.44 (s, 1H), 7.36 (td, J = 7.4, 3.1 Hz, 1H), 6.68 (d, J = 15.5 Hz, 1H), 4.78-4.50 (m, 1H), 4.01-3.86 (m, 1H), 3.19-3.05 (m, 1H), 2.70 (ddd, J = 11.6, 7.9, 4.0 Hz, 1H), 2.54 (dd, J = 14.8, 8.0 Hz, 2H), 2.32 (s, 3H), 1.91-1.71 (m, 3H), 1.71-1.42 (m, 2H) ppm. |
| 118 | 391.36 | 0.63 | 1H NMR (300 MHz, DMSO-d6) δ 9.19 (s, 1H), 9.05 (s, 1H), 7.82 (dd, J = 8.6, 1.0 Hz, 2H), 7.55 (dd, J = 10.8, 5.2 Hz, 2H), 7.34 (t, J = 7.4 Hz, 1H), 7.16 (s, 1H), 6.88 (s, 1H), 6.29 (s, 1H), 4.57 (t, J = 6.5 Hz, 2H), 4.49 (t, J = 6.1 Hz, 2H), 3.45 (p, J = 6.2 Hz, 1H), 3.23-3.03 (m, 4H), 2.45-2.35 (m, 4H), 2.22 (s, 3H) ppm. |
| 119 | 399 | 0.63 | 1H NMR (400 MHz, CDCl3) δ 8.29 (s, 1H), 7.25 (d, J = 4.5 Hz, 2H), 7.23 (d, J = 2.1 Hz, 1H), 7.19 (s, 1H), 6.77 (tt, J = 8.7, 2.2 Hz, 1H), 6.69 (s, 1H), 6.62 (s, 1H), 6.40 (s, 1H), 3.66-3.52 (m, 2H), 3.48 (dt, J = 11.9, 5.4 Hz, 1H), 3.14-2.91 (m, 2H), 2.68 (s, 1H), 2.51 (d, J = 11.5 Hz, 1H), 2.40 (s, 2H), 2.33 (s, 2H), 1.21 (dd, J = 9.1, 4.8 Hz, 3H) ppm. |
| 120 | 374 | 0.64 | 1H NMR (300 MHz, CDCl3) δ 8.30 (s, 1H), 7.79-7.60 (m, 2H), 7.58-7.43 (m, 2H), 7.42-7.28 (m, 1H), 7.17 (s, 1H), 6.68 (s, 1H), 6.62 (s, 1H), 3.17 (d, J = 11.5 Hz, 2H), 2.50 (tt, J = 11.7, 3.8 Hz, 1H), 2.40-2.22 (m, 5H), 2.04 (s, 1H), 1.94-1.55 (m, 6H), 0.47 (d, J = 6.8 Hz, 4H) ppm. |
| 121 | 454.32 | 0.61 | 1H NMR (400 MHz, CDCl3) δ 8.44 (s, 1H), 7.12 (d, J = 12.2 Hz, 2H), 7.11 (s, 2H), 7.00 (t, J = 1.8 Hz, 1H), 6.84 (s, 1H), 6.70 (d, J = 20.8 Hz, 1H), 6.39 (s, 1H), 4.80-4.60 (m, 4H), 3.69-3.47 (m, 1H), 3.29 (dd, J = 14.1, 9.1 Hz, 4H), 2.53 (dd, J = 12.9, 8.1 Hz, 4H), 1.96-1.84 (m, 1H), 1.07-0.89 (m, 2H), 0.84-0.65 (m, 2H) ppm. |
| 122 | 397 | 0.59 | 1H NMR (300 MHz, Acetone-d6) δ 9.08 (s, 1H), 8.44 (s, 1H), 8.33 (d, J = 5.6 Hz, 1H), 7.88-7.76 (m, 1H), 7.56-7.49 (m, 1H), 7.31 (t, J = 2.0 Hz, |

TABLE 3-continued

Analytical Data

| Cmpd No. | LC/MS (M + H) | LC/MS Ret. Time (min) | ¹H-NMR |
|---|---|---|---|
| | | | 1H), 6.97 (s, 1H), 6.41 (s, 1H), 3.78 (d, J = 12.4 Hz, 2H), 3.29 (s, 3H), 3.25 (d, J = 6.1 Hz, 2H), 2.83 (d, J = 9.2 Hz, 4H), 2.74 (td, J = 12.3, 2.4 Hz, 2H), 2.28 (s, 3H), 1.89-1.65 (m, 3H— methine proton contained within the multiplet), 1.49-1.25 (m, 2H) ppm. |
| 123 | 483.2 | 0.67 | 1H NMR (400 MHz, DMSO-d6) δ 9.22 (s, 1H), 7.62 (m, 3H), 7.43 (s, 1H), 7.28 (tt, J = 9.3, 2.3 Hz, 1H), 6.85 (s, 1H), 3.95-3.84 (m, 2H), 3.34 (d, J = 11.8 Hz, 1H), 3.24 (dd, J = 11.4, 2.7 Hz, 1H), 3.21-3.04 (m, 2H), 2.99-2.88 (m, 1H), 1.31 (s, 3H), 1.28 (s, 3H) ppm. |
| 124 | 351.16 | 0.6 | 1H NMR (300 MHz, CD3OD) δ 9.17-9.02 (m, 2H), 8.58 (d, J = 2.6 Hz, 1H), 8.51 (dd, J = 2.6, 1.4 Hz, 1H), 7.32 (t, J = 2.1 Hz, 1H), 7.00 (s, 1H), 6.50 (s, 1H), 3.43 (dd, J = 12.3, 6.2 Hz, 8H), 2.63 (q, J = 7.6 Hz, 2H), 1.26 (t, J = 7.6 Hz, 3H) ppm. |
| 125 | 429.14 | 0.78 | 1H NMR (400 MHz, DMSO-d6) δ 9.44 (s, 2H), 9.19 (s, 1H), 7.63 (d, J = 6.9 Hz, 3H), 7.26 (t, J = 8.9 Hz, 1H), 7.18 (s, 1H), 6.95 (s, 1H), 6.40 (s, 1H), 4.24 (s, 2H), 3.76-3.57 (m, 4H), 3.48 (dd, J = 11.8, 4.4 Hz, 4H), 2.25 (s, 3H) ppm. |
| 127 | 419.44 | 0.63 | 1H NMR (300 MHz, DMSO-d6) δ 9.17 (s, 1H), 9.05 (s, 1H), 7.91-7.76 (m, 2H), 7.55 (t, J = 7.9 Hz, 2H), 7.34 (t, J = 7.4 Hz, 1H), 7.14 (d, J = 7.1 Hz, 1H), 6.88 (d, J = 5.7 Hz, 1H), 6.28 (s, 1H), 4.18-3.55 (m, 2H), 3.11 (d, J = 3.4 Hz, 4H), 2.75 (dd, J = 15.6, 6.5 Hz, 1H), 2.63-2.51 (m, 4H), 2.37 (q, J = 7.1 Hz, 1H), 2.25 (d, J = 15.2 Hz, 3H), 1.97 (ddt, J = 31.7, 21.1, 12.4 Hz, 2H), 1.17-0.94 (m, 3H) ppm. |
| 128 | 411 | 0.63 | 1H NMR (400 MHz, DMSO-d6) δ 9.34 (s, 1H), 9.16 (s, 1H), 7.60 (dd, J = 8.5, 2.0 Hz, 2H), 7.31 (s, 1H), 7.28-7.12 (m, 1H), 6.75 (s, 1H), 6.33 (s, 1H), 3.77 (d, J = 9.6 Hz, 1H), 3.61 (d, J = 11.6 Hz, 1H), 3.10-2.97 (m, 2H), 2.75 (td, J = 11.6, 3.1 Hz, 1H), 2.43 (t, J = 10.6 Hz, 1H), 2.29-2.16 (m, 3H), 2.14-1.98 (m, 2H), 1.93-1.76 (m, 1H), 1.77-1.60 (m, 2H), 1.39 (tt, J = 17.7, 8.7 Hz, 1H) ppm. |
| 129 | 447.34 | 0.6 | 1H NMR (400 MHz, CDCl3) δ 9.01 (s, 1H), 7.38 (s, 1H), 7.01 (t, J = 2.0 Hz, 1H), 6.89 (s, 1H), 6.80 (s, 1H), 6.38 (s, 1H), 4.71 (dt, J = 16.0, 6.4 Hz, 4H), 3.59 (p, J = 6.4 Hz, 1H), 3.37-3.25 (m, 4H), 2.71 (s, 3H), 2.59 (s, 3H), 2.56-2.47 (m, 4H), 1.97-1.84 (m, 1H), 1.05-0.92 (m, 2H), 0.82-0.68 (m, 2H) ppm. |
| 130 | 481.27 | 0.64 | 1H NMR (300 MHz, DMSO-d6) δ 9.82 (s, 1H), 9.22 (s, 1H), 7.60 (dd, J = 8.5, 2.2 Hz, 2H), 7.50 (s, 1H), 7.42 (s, 1H), 7.27 (ddd, J = 11.5, 6.8, 2.2 Hz, 1H), 6.75 (s, 1H), 4.58 (t, J = 6.5 Hz, 2H), 4.48 (t, J = 6.1 Hz, 2H), 3.52-3.41 (m, 1H), 3.29-3.21 (m, 4H), 2.46-2.38 (m, 4H) ppm. |
| 131 | 343.15 | 0.85 | 1H NMR (300 MHz, DMSO-d6) δ 9.51 (s, 1H), 9.17 (s, 1H), 7.69-7.55 (m, 3H), 7.24 (ddd, J = 9.4, 8.3, 3.6 Hz, 2H), 6.73 (s, 1H), 4.96 (dd, J = 8.3, 5.7 Hz, 2H), 4.65-4.57 (m, 2H), 4.25-4.11 (m, 1H), 2.30 (s, 3H) ppm. |
| 132 | 453.15 | 0.6 | 1H NMR (400 MHz, CDCl3) δ 9.00 (d, J = 4.0 Hz, 1H), 8.64 (t, J = 4.7 Hz, 1H), 7.36 (d, J = 5.4 Hz, 1H), 7.07 (t, J = 2.0 Hz, 1H), 6.88 (s, 1H), 6.83 (s, 1H), 6.49 (s, 1H), 4.72 (dq, J = 12.6, 6.4 Hz, 4H), 3.60 (p, J = 6.4 Hz, 1H), 3.37-3.25 (m, 4H), 2.66 (dd, J = 12.9, 5.2 Hz, 2H), 2.63 (s, 3H), 2.60-2.47 (m, 4H), 1.29 (t, J = 7.6 Hz, 3H) ppm. |

TABLE 3-continued

Analytical Data

| Cmpd No. | LC/MS (M + H) | LC/MS Ret. Time (min) | $^1$H-NMR |
|---|---|---|---|
| 133 | 363 | 0.59 | 1H NMR (400 MHz, CDCl3) δ 8.30 (s, 1H), 7.67 (d, J = 7.7 Hz, 2H), 7.48 (t, J = 7.9 Hz, 2H), 7.33 (t, J = 7.4 Hz, 1H), 7.20 (s, 1H), 6.74 (s, 1H), 6.60 (s, 1H), 6.38 (s, 1H), 3.69-3.51 (m, 2H), 3.14-2.90 (m, 2H), 2.68 (d, J = 18.9 Hz, 1H), 2.60-2.26 (m, 7H), 1.21 (d, J = 5.6 Hz, 3H) ppm. |
| 134 | 452.29 | 0.59 | 1H NMR (400 MHz, CDCl3) δ 8.89 (d, J = 2.2 Hz, 1H), 8.56 (d, J = 2.0 Hz, 1H), 8.38 (s, 1H), 8.04 (d, J = 2.2 Hz, 1H), 7.09 (s, 1H), 6.70 (s, 1H), 6.67 (s, 1H), 6.37 (s, 1H), 4.71 (p, J = 6.2 Hz, 4H), 3.73-3.48 (m, 1H), 3.40-3.16 (m, 4H), 2.64-2.45 (m, 4H), 2.01-1.75 (m, 1H), 1.04-0.87 (m, 2H), 0.85-0.63 (m, 2H) ppm. |
| 135 | 357.11 | 1.06 | 1H NMR (300 MHz, CD3OD) δ 8.83 (s, 1H), 7.90-7.74 (m, 2H), 7.54 (dd, J = 8.7, 7.2 Hz, 2H), 7.47-7.32 (m, 1H), 6.96 (s, 2H), 3.91-3.71 (m, 4H), 3.57-3.43 (m, 4H) ppm. |
| 136 | 407.52 | 0.58 | 1H NMR (300 MHz, CDCl3) δ 9.19 (d, J = 1.4 Hz, 1H), 8.93 (s, 1H), 8.57 (d, J = 2.5 Hz, 1H), 8.40 (dd, J = 2.5, 1.5 Hz, 1H), 7.18 (s, 1H), 6.82 (d, J = 14.8 Hz, 2H), 6.44 (s, 1H), 4.68 (d, J = 5.6 Hz, 2H), 4.30 (d, J = 5.7 Hz, 2H), 3.37-3.25 (m, 4H), 2.64-2.52 (m, 4H), 2.36 (s, 3H), 1.44 (s, 3H) ppm. |
| 137 | 441.36 | 0.64 | 1H NMR (300 MHz, DMSO-d6) δ 11.13 (s, 1H), 9.43 (s, 1H), 9.18 (s, 1H), 7.71-7.55 (m, 2H), 7.27 (ddd, J = 9.3, 5.7, 2.3 Hz, 1H), 7.11 (s, 1H), 6.99 (s, 1H), 6.39 (s, 1H), 4.15 (dd, J = 10.2, 4.2 Hz, 1H), 4.10-3.90 (m, 2H), 3.89-3.61 (m, 4H), 3.51 (dd, J = 22.4, 10.8 Hz, 2H), 3.34-3.01 (m, 4H), 2.37-2.14 (m, 5H) ppm. |
| 138 | 350 | 0.56 | 1H NMR (400 MHz, Acetone-d6) δ 8.95 (s, 1H), 8.46 (ddd, J = 4.8, 1.8, 0.8 Hz, 1H), 8.27 (s, 1H), 8.03 (ddd, J = 8.2, 7.5, 1.8 Hz, 1H), 7.85 (d, J = 8.2 Hz, 1H), 7.36 (ddd, J = 7.4, 4.8, 1.0 Hz, 1H), 7.31 (t, J = 1.9 Hz, 1H), 7.01 (s, 1H), 6.38 (s, 1H), 3.28-3.13 (m, 4H), 2.58-2.42 (m, 4H), 2.28 (s, 3H), 2.26 (s, 3H) ppm. |
| 139 | 443 | 0.63 | 1H NMR (400 MHz, CDCl3) δ 8.30 (s, 1H), 7.22 (d, J = 5.6 Hz, 2H), 7.16 (s, 1H), 7.12 (s, 1H), 6.88 (s, 1H), 6.78 (t, J = 8.7 Hz, 1H), 6.41 (s, 1H), 5.40-5.24 (m, 2H), 4.77 (t, J = 7.2 Hz, 2H), 4.53-4.43 (m, 1H), 3.90 (t, J = 11.5 Hz, 2H), 3.54 (d, J = 13.1 Hz, 2H), 3.30 (t, J = 9.7 Hz, 2H), 3.16 (d, J = 10.3 Hz, 2H), 2.34 (s, 3H) ppm. |
| 140 | 434.28 | 0.63 | 1H NMR (400 MHz, DMSO-d6) δ 9.45 (s, 1H), 9.27 (s, 1H), 8.14 (dd, J = 8.5, 7.4 Hz, 1H), 7.99 (dd, J = 11.0, 1.9 Hz, 1H), 7.85 (dd, J = 8.6, 1.9 Hz, 1H), 7.14 (s, 1H), 6.89 (s, 1H), 6.34 (s, 1H), 4.58 (t, J = 6.5 Hz, 2H), 4.49 (t, J = 6.0 Hz, 2H), 3.46 (m, 1H), 3.15 (m, 4H), 2.45-2.38 (m, 4H), 2.24 (s, 3H) ppm. |
| 141 | 383.24 | 0.62 | 1H NMR (400 MHz, DMSO-d6) δ 9.24 (s, 1H), 9.12 (s, 1H), 7.93 (t, J = 2.0 Hz, 1H), 7.81 (dd, J = 8.2, 1.2 Hz, 1H), 7.57 (t, J = 8.1 Hz, 1H), 7.40 (dd, J = 8.0, 1.2 Hz, 1H), 7.22 (s, 1H), 6.82 (s, 1H), 6.30 (s, 1H), 3.19-3.06 (m, 4H), 2.48-2.42 (m, 4H), 2.22 (d, J = 2.5 Hz, 6H) ppm. |
| 142 | 359 | 0.62 | 1H NMR (300 MHz, CDCl3) δ 8.31 (s, 1H), 7.67 (dd, J = 8.6, 1.1 Hz, 2H), 7.49 (t, J = 7.9 Hz, 2H), 7.35 (t, J = 7.4 Hz, 1H), 7.15 (s, 1H), 6.78 (s, 1H), 6.63 (s, 1H), 6.38 (s, 1H), 3.61-3.42 (m, 2H), 3.25-3.05 (m, 2H), 2.91-2.70 (m, 1H), 2.32 (s, 3H), 2.17-1.91 (m, 4H) ppm. |
| 143 | 392 | 0.9 | 1H NMR (400 MHz, CDCl3) δ 8.33 (s, 1H), 7.69 (d, J = 8.3 Hz, 2H), 7.51 (t, J = 7.9 Hz, 2H), 7.35 (t, J = 7.4 Hz, 1H), 7.23 (s, 1H), 6.73 (s, 1H), 6.66 (s, 1H), 4.25 (s, 2H), 3.71 (s, 3H), 2.78 (s, 2H), 2.66 (s, 1H), 2.36 (s, 3H), 2.07 (d, J = 11.6 Hz, 1H), 1.79 (d, J = 11.8 Hz, 1H), 1.72-1.53 (m, 3H) ppm. |

TABLE 3-continued

Analytical Data

| Cmpd No. | LC/MS (M + H) | LC/MS Ret. Time (min) | $^1$H-NMR |
|---|---|---|---|
| 144 | 413.37 | 0.77 | 1H NMR (300 MHz, CDCl3) δ 8.35 (s, 1H), 7.73-7.65 (m, 2H), 7.59-7.49 (m, 2H), 7.44-7.36 (m, 2H), 7.16 (s, 1H), 6.93 (s, 1H), 6.63 (dd, J = 66.1, 47.2 Hz, 2H), 3.88-3.78 (m, 2H), 3.70-3.64 (m, 2H), 3.35-3.25 (m, 4H), 2.18 (s, 3H) ppm. |
| 145 | 387.14 | 0.82 | 1H NMR (400 MHz, CDCl3) δ 8.23 (s, 1H), 7.30 (t, J = 8.1 Hz, 1H), 7.13 (s, 1H), 7.10 (d, J = 8.4 Hz, 1H), 6.83 (dd, J = 20.8, 14.6 Hz, 3H), 6.65 (s, 1H), 3.78 (s, 3H), 3.74-3.65 (m, 4H), 3.50-3.35 (m, 4H) ppm. |
| 146 | 359 | 0.78 | 1H NMR (300 MHz, CDCl3) δ 8.32 (s, 1H), 7.77-7.60 (m, 2H), 7.50 (dd, J = 11.2, 4.6 Hz, 2H), 7.41-7.29 (m, 1H), 6.73 (s, 1H), 6.70 (s, 1H), 6.37 (s, 1H), 3.69 (dd, J = 12.4, 3.4 Hz, 1H), 3.45 (dd, J = 9.7, 6.1 Hz, 1H), 3.26 (dd, J = 12.4, 8.7 Hz, 1H), 3.14-3.00 (m, 1H), 2.91 (ddd, J = 12.4, 8.6, 3.7 Hz, 1H), 2.32 (s, 3H), 2.15-2.01 (m, 1H), 1.96-1.68 (m, 3H) ppm. |
| 147 | 325.19 | 0.81 | 1H NMR (300 MHz, DMSO-d6) δ 9.47 (s, 1H), 9.14 (s, 1H), 7.77-7.69 (m, 2H), 7.60 (dt, J = 8.4, 5.6 Hz, 2H), 7.31 (s, 1H), 7.19 (td, J = 8.3, 1.5 Hz, 1H), 6.72 (s, 1H), 4.95 (dd, J = 8.4, 5.8 Hz, 2H), 4.62 (dd, J = 6.7, 5.8 Hz, 2H), 4.24-4.11 (m, 1H), 2.30 (s, 3H) ppm. |
| 148 | 392 | 0.63 | 1H NMR (300 MHz, CDCl3) δ 8.30 (s, 1H), 7.67 (d, J = 7.5 Hz, 2H), 7.49 (t, J = 7.9 Hz, 2H), 7.33 (t, J = 7.4 Hz, 1H), 7.11 (s, 1H), 6.78 (s, 1H), 6.56 (s, 1H), 6.41 (s, 1H), 3.72 (d, J = 12.6 Hz, 2H), 3.47 (dd, J = 11.0, 4.7 Hz, 2H), 3.35 (s, 3H), 2.75 (t, J = 11.4 Hz, 2H), 2.32 (s, 3H), 1.80 (d, J = 13.0 Hz, 2H), 1.58 (s, 3H), 1.40 (d, J = 7.9 Hz, 2H) ppm. |
| 149 | 375 | 0.61 | 1H NMR (400 MHz, DMSO-d6) δ 9.16 (s, 1H), 9.04 (s, 1H), 7.82 (d, J = 7.8 Hz, 2H), 7.55 (t, J = 7.9 Hz, 2H), 7.34 (t, J = 7.4 Hz, 1H), 7.15 (s, 1H), 6.87 (s, 1H), 6.28 (s, 1H), 3.14-3.01 (m, 4H), 2.80-2.59 (m, 4H), 2.22 (s, 3H), 1.72-1.58 (m, 1H), 0.43 (dd, J = 6.1, 4.0 Hz, 2H), 0.36 (d, J = 3.1 Hz, 2H) ppm. |
| 150 | 398.26 | 0.61 | 1H NMR (300 MHz, CDCl3) δ 8.30 (s, 1H), 7.65-7.53 (m, 1H), 7.49-7.30 (m, 2H), 7.15 (d, J = 2.0 Hz, 1H), 7.05 (d, J = 2.0 Hz, 1H), 6.84 (s, 1H), 4.10 (d, J = 10.7 Hz, 2H), 3.64-3.50 (m, 2H), 2.94-2.79 (m, 1H), 2.08-1.97 (m, 1H), 1.97-1.78 (m, 4H), 1.09-1.00 (m, 2H), 0.96 (ddd, J = 18.9, 10.7, 8.2 Hz, 2H) ppm. |
| 151 | 384 | 0.63 | 1H NMR (400 MHz, CDCl3) δ 8.30 (s, 1H), 7.25-7.20 (m, 2H), 7.16 (s, 1H), 6.78 (tt, J = 8.7, 2.2 Hz, 1H), 6.70 (s, 1H), 6.66 (s, 1H), 3.05 (d, J = 11.2 Hz, 2H), 2.47 (d, J = 15.7 Hz, 1H), 2.38 (s, 3H), 2.36 (s, 3H), 2.16 (s, 2H), 1.90 (s, 4H) ppm. |
| 152 | 431 | 0.66 | 1H NMR (400 MHz, DMSO-d6) δ 9.18 (s, 1H), 9.06 (s, 1H), 7.83 (d, J = 7.6 Hz, 2H), 7.53 (t, J = 8.0 Hz, 2H), 7.34 (t, J = 7.4 Hz, 1H), 7.24 (s, 1H), 6.71 (s, 1H), 6.21 (s, 1H), 3.96-3.85 (m, 1H), 3.51 (dd, J = 11.5, 2.8 Hz, 1H), 3.00 (dd, J = 18.9, 9.7 Hz, 2H), 2.70 (t, J = 10.9 Hz, 1H), 2.34-2.14 (m, 4H), 2.10-1.88 (m, 2H), 1.87-1.59 (m, 4H), 1.46 (ddt, J = 21.4, 14.9, 5.5 Hz, 2H), 1.18-1.05 (m, 1H), 0.83 (dd, J = 6.5, 4.2 Hz, 6H) ppm. |
| 153 | 430.33 | 0.64 | 1H NMR (300 MHz, CD3OD + CDCl3) δ 8.59 (s, 1H), 7.91 (d, J = 5.7 Hz, 1H), 7.33 (d, J = 5.7 Hz, 1H), 7.07 (d, J = 14.0 Hz, 2H), 6.91 (s, 1H), 6.28 (dd, J = 67.1, 46.2 Hz, 2H), 2.94-2.87 (m, 4H), 2.56-2.39 (m, 4H), 1.44-1.32 (m, 1H), 0.26-0.06 (m, 4H) ppm. |
| 154 | 410.44 | 0.65 | 1H NMR (300 MHz, CDCl3) δ 8.87 (s, 1H), 7.98 (q, J = 7.9 Hz, 1H), 7.68 (dd, J = 7.8, 1.1 Hz, 1H), 7.10 (s, 1H), 6.92-6.82 (m, 2H), 6.74 (s, 1H), 6.44 (s, 1H), 4.74 (d, J = 6.4 Hz, 4H), |

TABLE 3-continued

Analytical Data

| Cmpd No. | LC/MS (M + H) | LC/MS Ret. Time (min) | ¹H-NMR |
|---|---|---|---|
| | | | 3.73-3.56 (m, 1H), 3.34 (s, 4H), 2.59 (s, 4H), 2.36 (s, 3H) ppm. |
| 155 | 353.47 | 0.67 | 1H NMR (400 MHz, DMSO-d6) δ 9.62 (d, J = 12.8 Hz, 1H), 9.23 (s, 1H), 7.60 (d, J = 7.2 Hz, 1H), 7.39 (s, 1H), 7.26 (s, 1H), 7.13 (s, 1H), 7.09 (s, 1H), 6.87 (dd, J = 7.2, 2.2 Hz, 1H), 6.76 (d, J = 2.1 Hz, 1H), 6.64 (s, 1H), 3.87 (s, 3H), 3.26 (s, 3H) ppm. |
| 156 | 350.22 | 0.5 | 1H NMR (300 MHz, DMSO-d6) δ 9.64 (s, 1H), 9.11 (s, 1H), 7.83 (dd, J = 8.6, 1.1 Hz, 2H), 7.56 (dd, J = 10.7, 5.2 Hz, 2H), 7.37 (t, J = 7.4 Hz, 1H), 6.96 (s, 1H), 6.72 (s, 1H), 3.49-3.35 (m, 4H), 2.46-2.31 (m, 4H), 2.24 (s, 3H), 2.22 (s, 3H) ppm. |
| 157 | 375 | 0.6 | 1H NMR (400 MHz, DMSO-d6) δ 9.20 (s, 1H), 9.06 (s, 1H), 7.83 (d, J = 7.6 Hz, 2H), 7.54 (t, J = 8.0 Hz, 2H), 7.34 (t, J = 7.4 Hz, 1H), 7.26 (s, 1H), 6.82 (s, 1H), 6.30 (s, 1H), 3.75 (d, J = 9.8 Hz, 1H), 3.60 (d, J = 11.7 Hz, 1H), 3.34 (s, 1H), 3.12-2.93 (m, 2H), 2.75 (td, J = 11.6, 3.1 Hz, 1H), 2.42 (t, J = 10.6 Hz, 1H), 2.24 (d, J = 15.1 Hz, 4H), 2.07 (dd, J = 17.1, 8.3 Hz, 2H), 1.96-1.78 (m, 1H), 1.78-1.60 (m, 2H), 1.39 (tt, J = 17.7, 8.8 Hz, 1H) ppm. |
| 158 | 358.15 | 2.9 | 1H NMR (400 MHz, DMSO-d6) δ 9.58 (d, J = 42.0 Hz, 1H), 9.08 (s, 1H), 7.88 (dd, J = 8.9, 4.6 Hz, 2H), 7.42 (t, J = 8.7 Hz, 2H), 7.06 (d, J = 10.5 Hz, 2H), 6.32 (t, J = 42.3 Hz, 1H), 3.74 (d, J = 29.6 Hz, 4H), 3.15 (s, 4H) ppm. |
| 159 | 335 | 0.58 | 1H NMR (400 MHz, DMSO-d6) δ 9.31 (s, 1H), 9.08 (s, 1H), 7.84 (d, J = 7.6 Hz, 1H), 7.55 (t, J = 8.0 Hz, 1H), 7.35 (t, J = 7.4 Hz, 1H), 7.23 (s, 1H), 6.98 (s, 1H), 6.39 (s, 1H), 3.48-3.30 (m, 4H), 3.25 (s, 4H), 2.25 (s, 3H) ppm. |
| 160 | 374.24 | 0.59 | 1H NMR (300 MHz, DMSO-d6) δ 9.41 (s, 1H), 9.09 (s, 1H), 7.88-7.81 (m, 2H), 7.66 (s, 1H), 7.55 (t, J = 8.0 Hz, 2H), 7.35 (t, J = 7.4 Hz, 1H), 7.29 (s, 1H), 6.80 (s, 1H), 6.23 (s, 1H), 4.66 (t, J = 6.5 Hz, 2H), 4.56 (t, J = 5.9 Hz, 2H), 4.05-3.93 (m, 1H), 3.85 (s, 2H), 3.63 (s, 2H), 2.28 (s, 3H) ppm. |
| 161 | 453.28 | 0.65 | 1H NMR (300 MHz, DMSO-d6) δ 9.34 (s, 1H), 9.16 (s, 1H), 7.66-7.52 (m, 2H), 7.31-7.17 (m, 2H), 6.81 (s, 1H), 6.33 (s, 1H), 3.91 (m, 1H), 3.76 (d, J = 12.0 Hz, 2H), 3.29 (m, 2H), 2.77 (t, J = 11.5 Hz, 2H), 2.27-2.18 (m, 5H), 1.91 (m, 2H), 1.80-1.73 (m, 2H), 1.61 (d, J = 9.6 Hz, 2H) ppm. |
| 162 | 414 | 0.63 | 1H NMR (400 MHz, Acetone-d6) δ 8.91 (s, 1H), 8.28 (s, 1H), 7.56 (dd, J = 8.6, 2.2 Hz, 2H), 7.32 (t, J = 1.9 Hz, 1H), 7.00 (ddd, J = 9.1, 5.7, 2.3 Hz, 1H), 6.93 (s, 1H), 6.39 (s, 1H), 3.78 (d, J = 12.4 Hz, 2H), 3.29 (s, 3H), 3.25 (d, J = 6.2 Hz, 2H), 2.77-2.67 (m, 2H), 2.27 (s, 3H), 1.80 (d, J = 13.1 Hz, 2H), 1.74 (dd, J = 10.7, 4.4 Hz, 1H), 1.38 (ddd, J = 15.4, 12.4, 3.9 Hz, 2H) ppm. |
| 163 | 444.42 | 0.55 | 1H NMR (300 MHz, DMSO-d6) δ 9.69 (s, 1H), 9.22 (s, 1H), 7.59 (d, J = 7.2 Hz, 1H), 7.37 (s, 1H), 7.30 (s, 1H), 7.09-6.66 (m, 5H), 4.58 (t, J = 6.5 Hz, 2H), 4.49 (t, J = 6.1 Hz, 2H), 3.48 (dd, J = 12.5, 6.3 Hz, 1H), 3.25-3.17 (m, 4H), 2.46-2.38 (m, 4H) ppm. |
| 164 | 386.28 | 0.85 | 1H NMR (300 MHz, DMSO-d6) δ 9.28 (s, 1H), 9.15 (s, 1H), 7.68-7.53 (m, 2H), 7.32-7.16 (m, 1H), 6.89 (s, 1H), 6.63 (s, 1H), 5.93 (s, 1H), 4.08 (d, J = 2.5 Hz, 1H), 3.44 (dd, J = 10.4, 5.0 Hz, 1H), 3.32-3.18 (m, 6H), 2.21 (s, 3H), 2.08 (m, 2H) ppm. |
| 165 | 392.31 | 0.67 | 1H NMR (300 MHz, CDCl3) δ 8.25 (s, 1H), 7.65-7.55 (m, 2H), 7.42 (t, J = 7.9 Hz, 2H), 7.29 (d, J = 7.4 Hz, 1H), 7.07 (t, J = 2.1 Hz, 1H), 6.87 (s, 1H), 6.64 (s, 1H), 6.38 (s, 1H), 4.15-3.96 (m, 2H), 3.91-3.83 (m, 1H), |

TABLE 3-continued

Analytical Data

| Cmpd No. | LC/MS (M + H) | LC/MS Ret. Time (min) | ¹H-NMR |
|---|---|---|---|
| | | | 3.82-3.77 (m, 4H), 3.72 (dd, J = 8.4, 7.3 Hz, 1H), 3.32 (dd, J = 15.4, 7.7 Hz, 1H), 3.19-3.09 (m, 4H), 2.36-2.24 (m, 1H), 1.98 (ddd, J = 15.9, 12.3, 7.9 Hz, 1H) ppm. |
| 166 | 372 | 0.87 | 1H NMR (400 MHz, DMSO-d6) δ 9.50 (s, 1H), 9.14 (s, 1H), 7.81-7.65 (m, 2H), 7.65-7.49 (m, 1H), 7.20 (t, J = 8.4 Hz, 1H), 6.98 (s, 1H), 6.70 (d, J = 11.4 Hz, 1H), 6.11 (d, J = 12.9 Hz, 1H), 3.74 (t, J = 4.6 Hz, 2H), 3.57 (dd, J = 11.2, 5.7 Hz, 6H), 2.01-1.84 (m, 2H) ppm. |
| 167 | 342.13 | 3.36 | 1H NMR (400 MHz, DMSO-d6) δ 9.48 (d, J = 29.2 Hz, 1H), 9.09 (d, J = 45.6 Hz, 1H), 7.71 (t, J = 8.1 Hz, 2H), 7.56 (d, J = 22.2 Hz, 1H), 6.85-6.58 (m, 2H), 5.83 (t, J = 29.4 Hz, 1H), 3.10 (d, J = 104.7 Hz, 4H), 1.96 (s, 4H) ppm. |
| 168 | 400.23 | 0.89 | 1H NMR (300 MHz, CD3OD) δ 8.53 (s, 1H), 7.74 (d, J = 1.3 Hz, 2H), 7.55 (s, 1H), 7.50 (d, J = 1.7 Hz, 1H), 7.42-7.34 (m, 1H), 7.32 (t, J = 1.8 Hz, 1H), 7.21 (t, J = 2.1 Hz, 1H), 6.71-6.62 (m, 1H), 3.97-3.82 (m, 4H), 3.29-3.13 (m, 4H) ppm. |
| 169 | 426.51 | 0.64 | H NMR (300 MHz, DMSO-d6) δ 9.24 (s, 1H), 9.06 (s, 1H), 8.03-7.82 (m, 1H), 7.78-7.54 (m, 2H), 7.15 (s, 1H), 6.82 (s, 1H), 6.29 (s, 1H), 4.62 (dd, J = 7.9, 5.9 Hz, 2H), 4.38 (t, J = 6.1 Hz, 2H), 3.67 (d, J = 12.5 Hz, 2H), 2.85-2.56 (m, 3H), 2.21 (s, 3H), 1.88-1.53 (m, 3H), 1.14 (dt, J = 12.1, 8.7 Hz, 2H) ppm. |
| 170 | 383.31 | 0.65 | 1H NMR (400 MHz, DMSO-d6) δ 9.64 (s, 1H), 9.19 (s, 1H), 7.26 (tt, J = 9.3, 2.3 Hz, 1H), 6.67 (d, J = 1.5 Hz, 1H), 6.60 (d, J = 1.3 Hz, 1H), 3.33 (dd, J = 11.6, 5.1 Hz, 4H), 1.91 (t, J = 6.6 Hz, 4H), 1.82 (ddd, J = 12.8, 8.2, 4.7 Hz, 1H), 0.92-0.83 (m, 2H), 0.77 (ddd, J = 9.5, 6.1, 3.3 Hz, 2H) ppm. |
| 171 | 384.12 | 0.79 | 1H NMR (300 MHz, DMSO-d6) δ 9.29 (s, 1H), 9.14 (s, 1H), 7.60 (dd, J = 8.7, 2.2 Hz, 2H), 7.24 (tt, J = 10.5, 8.2 Hz, 1H), 6.71 (d, J = 10.8 Hz, 2H), 5.81 (s, 1H), 4.72 (s, 4H), 3.94 (s, 4H), 2.19 (s, 3H) ppm. |
| 172 | 419.4 | 0.64 | 1H NMR (300 MHz, DMSO-d6) δ 9.17 (s, 1H), 9.05 (s, 1H), 7.93-7.73 (m, 2H), 7.55 (t, J = 8.0 Hz, 2H), 7.34 (t, J = 7.4 Hz, 1H), 7.14 (s, 1H), 6.87 (s, 1H), 6.27 (s, 1H), 3.94 (d, J = 12.8 Hz, 1H), 3.74 (d, J = 11.2 Hz, 1H), 3.20 (t, J = 10.4 Hz, 2H), 3.15-2.94 (m, 4H), 2.69 (d, J = 23.0 Hz, 4H), 2.33 (ddd, J = 19.6, 12.8, 6.6 Hz, 1H), 2.22 (s, 3H), 1.97 (d, J = 11.1 Hz, 1H), 1.66 (d, J = 13.1 Hz, 1H), 1.58-1.26 (m, 2H) ppm. |
| 173 | 441 | 0.68 | 1H NMR (400 MHz, CDCl3) δ 8.29 (s, 1H), 7.35-7.14 (m, 3H), 6.77 (ddd, J = 8.7, 5.5, 2.3 Hz, 1H), 6.71-6.51 (m, 3H), 5.98 (s, 1H), 4.01 (t, J = 7.0 Hz, 2H), 3.75 (dd, J = 10.1, 5.2 Hz, 6H), 3.50-3.23 (m, 1H), 2.60 (q, J = 7.6 Hz, 2H), 2.46 (s, 4H), 1.25 (t, J = 7.6 Hz, 4H—water peak) ppm. |
| 174 | 393.48 | 0.59 | 1H NMR (300 MHz, DMSO-d6) δ 9.46 (d, J = 13.0 Hz, 1H), 9.29 (s, 1H), 9.11 (t, J = 10.6 Hz, 1H), 8.96 (d, J = 5.6 Hz, 1H), 7.72 (dd, J = 5.6, 1.2 Hz, 1H), 7.13 (s, 1H), 6.93 (s, 1H), 6.35 (s, 1H), 4.58 (t, J = 6.5 Hz, 2H), 4.49 (t, J = 6.0 Hz, 2H), 3.57-3.39 (m, 1H), 3.25-3.07 (m, 4H), 2.46-2.34 (m, 4H), 2.25 (s, 3H) ppm. |
| 175 | | | 1H NMR (300 MHz, DMSO-d6) δ 9.76 (s, 1H), 9.18 (s, 1H), 7.75-7.56 (m, 3H), 7.51 (s, 1H), 7.43 (s, 1H), 7.21 (t, J = 8.3 Hz, 1H), 6.74 (s, 1H), 4.58 (t, J = 6.5 Hz, 2H), 4.49 (t, J = 6.1 Hz, 2H), 3.52-3.41 (m, 1H), 3.29-3.20 (m, 4H), 2.47-2.38 (m, 4H) ppm. |
| 176 | 377.5 | 0.62 | 1H NMR (300 MHz, DMSO-d6) δ 9.47 (s, 1H), 9.29 (s, 1H), 9.08 (d, J = 0.9 Hz, 1H), 8.97 (d, J = 5.6 Hz, 1H), 7.71 (dd, J = 5.6, 1.1 Hz, 1H), 7.12 (s, 1H), 6.92 (s, 1H), 6.34 (s, 1H), |

TABLE 3-continued

Analytical Data

| Cmpd No. | LC/MS (M + H) | LC/MS Ret. Time (min) | ¹H-NMR |
|---|---|---|---|
| | | | 3.21-2.98 (m, 4H), 2.78-2.64 (m, 4H), 2.24 (s, 3H), 1.74-1.55 (m, 1H), 0.59-0.42 (m, 2H), 0.37 (dd, J = 7.9, 4.5 Hz, 2H) ppm. |
| 177 | 361 | 0.64 | 1H NMR (400 MHz, DMSO-d6) δ 9.56 (s, 1H), 9.42 (s, 1H), 9.24 (s, 1H), 8.76 (d, J = 2.2 Hz, 1H), 7.92 (td, J = 8.9, 6.1 Hz, 1H), 7.78-7.54 (m, 1H), 7.38 (t, J = 7.9 Hz, 1H), 6.76 (d, J = 11.8 Hz, 1H), 6.64 (s, 1H), 5.86 (d, J = 11.4 Hz, 1H), 4.29 (dd, J = 13.9, 6.7 Hz, 1H), 4.22 (s, 2H), 3.85 (d, J = 7.7 Hz, 2H) ppm. |
| 178 | 428.44 | 0.64 | 1H NMR (300 MHz, DMSO-d6) δ 9.47 (s, 1H), 9.16 (s, 1H), 7.75-7.53 (m, 2H), 7.25 (tt, J = 9.2, 2.2 Hz, 1H), 7.13 (s, 1H), 6.93 (s, 1H), 6.24 (s, 1H), 4.84 (t, J = 6.7 Hz, 1H), 4.56 (td, J = 6.5, 1.8 Hz, 2H), 4.46 (q, J = 6.0 Hz, 2H), 3.71-3.52 (m, 1H), 2.87 (dd, J = 10.3, 6.1 Hz, 1H), 2.76-2.57 (m, 2H), 2.48-2.39 (m, 1H), 2.36-2.14 (m, 4H), 1.94-1.70 (m, 1H) ppm. |
| 179 | 363 | 0.6 | 1H NMR (300 MHz, DMSO-d6) δ 11.05 (s, 1H), 9.25 (s, 1H), 9.09 (s, 1H), 7.84 (d, J = 7.7 Hz, 2H), 7.55 (t, J = 7.9 Hz, 2H), 7.35 (t, J = 7.4 Hz, 1H), 7.14 (s, 1H), 6.77 (s, 1H), 6.18 (s, 1H), 3.76 (d, J = 10.6 Hz, 2H), 3.46 (dd, J = 27.4, 6.9 Hz, 4H), 3.17 (dd, J = 29.4, 20.5 Hz, 2H), 2.80 (d, J = 4.7 Hz, 3H), 2.44-2.28 (m, 1H), 2.23 (s, 4H) ppm. |
| 180 | 392 | 0.59 | 1H NMR (400 MHz, CDCl3) δ 9.03 (s, 2H), 8.87 (d, J = 5.5 Hz, 1H), 7.77 (dd, J = 5.5, 1.1 Hz, 1H), 7.32 (s, 1H), 7.16 (s, 1H), 6.79 (s, 1H), 6.70 (s, 1H), 4.79-4.53 (m, 4H), 3.60-3.42 (m, 1H), 2.88 (d, J = 9.2 Hz, 3H), 2.37 (s, 3H), 2.01 (d, J = 12.6 Hz, 1H), 1.96-1.38 (m, 6H) ppm. |
| 181 | 408.15 | 3.2 | 1H NMR (400 MHz, DMSO-d6) δ 9.65 (d, J = 19.1 Hz, 1H), 9.27 (s, 1H), 8.17 (d, J = 7.8 Hz, 2H), 7.79 (dd, J = 22.6, 14.9 Hz, 1H), 7.72 (d, J = 8.2 Hz, 1H), 7.16 (s, 1H), 6.87 (t, J = 24.8 Hz, 1H), 6.27 (t, J = 41.6 Hz, 1H), 3.79-3.73 (m, 4H), 3.17-3.10 (m, 4H) ppm. |
| 182 | 421 | 0.61 | 1H NMR (400 MHz, CDCl3) δ 8.30 (s, 1H), 7.68 (dd, J = 8.6, 1.1 Hz, 2H), 7.49 (t, J = 8.0 Hz, 2H), 7.34 (t, J = 7.4 Hz, 1H), 6.98 (s, 1H), 6.56 (s, 1H), 6.46 (s, 1H), 6.06 (s, 1H), 3.56 (s, 1H), 3.44 (t, J = 6.4 Hz, 2H), 3.34 (s, 3H), 2.91 (d, J = 11.5 Hz, 2H), 2.49-2.39 (m, 2H), 2.26 (s, 3H), 2.12 (d, J = 10.4 Hz, 3H), 1.85-1.73 (m, 2H), 1.57-1.44 (m, 2H) ppm. |
| 183 | 443.22 | 0.64 | 1H NMR (300 MHz, DMSO-d6) δ 9.33 (s, 1H), 9.07 (s, 1H), 8.02-7.81 (m, 1H), 7.80-7.50 (m, 2H), 6.82 (s, 2H), 6.05 (s, 1H), 4.57 (t, J = 6.5 Hz, 2H), 4.48 (t, J = 6.0 Hz, 2H), 3.72 (s, 3H), 3.56-3.38 (m, 1H), 3.23-3.00 (m, 4H), 2.41 (d, J = 4.3 Hz, 4H) ppm. |
| 184 | 436.27 | 0.58 | 1H NMR (400 MHz, CDCl3) δ 8.46 (s, 1H), 8.32 (d, J = 5.6 Hz, 1H), 7.46 (d, J = 5.6 Hz, 1H), 7.26 (s, 1H), 7.03 (t, J = 2.1 Hz, 1H), 6.75 (s, 1H), 6.67 (s, 1H), 6.39 (s, 1H), 4.72 (dq, J = 12.6, 6.4 Hz, 4H), 3.66-3.51 (m, 1H), 3.36-3.25 (m, 4H), 2.60-2.48 (m, 4H), 1.96-1.83 (m, 1H), 1.05-0.90 (m, 2H), 0.79-0.67 (m, 2H) ppm. |
| 185 | 439 | 0.68 | 1H NMR (300 MHz, CDCl3) δ 8.30 (s, 1H), 7.23 (dd, J = 7.9, 2.2 Hz, 2H), 6.80 (s, 1H), 6.76 (dt, J = 8.7, 2.3 Hz, 1H), 6.71 (s, 1H), 6.54 (s, 1H), 6.02 (s, 1H), 4.69 (t, J = 6.7 Hz, 1H), 4.63 (t, J = 6.4 Hz, 1H), 4.56 (t, J = 6.2 Hz, 1H), 4.48 (t, J = 6.0 Hz, 1H), 4.31 (s, 1H), 4.05-3.92 (m, 1H), 3.58 (s, 1H), 3.45 (dd, J = 9.2, 2.0 Hz, 1H), 3.08 (dd, J = 19.0, 8.6 Hz, 2H), 2.93 (d, J = 9.3 Hz, 1H), 2.31 (s, 3H), 1.99 (dd, J = 18.2, 9.5 Hz, 2H) ppm. |

TABLE 3-continued

Analytical Data

| Cmpd No. | LC/MS (M + H) | LC/MS Ret. Time (min) | $^1$H-NMR |
|---|---|---|---|
| 186 | 345.41 | 0.67 | 1H NMR (300 MHz, CDCl3) δ 8.44 (d, J = 8.2 Hz, 1H), 7.95-7.70 (m, 4H), 6.82-6.52 (m, 3H), 6.10 (s, 1H), 3.35 (t, J = 5.6 Hz, 4H), 2.35 (s, 3H), 2.16-1.86 (m, 4H) ppm. |
| 187 | 480.33 | 0.51 | 1H NMR (400 MHz, CDCl3) δ 8.34 (s, 1H), 7.45 (s, 1H), 7.34 (d, J = 9.5 Hz, 1H), 7.17 (s, 1H), 7.04 (t, J = 8.5 Hz, 1H), 6.78 (s, 1H), 6.60 (s, 1H), 6.41 (s, 1H), 4.71 (p, J = 6.2 Hz, 4H), 3.59 (dt, J = 12.0, 6.0 Hz, 2H), 3.55 (s, 2H), 3.37-3.27 (m, 4H), 2.51 (dt, J = 14.4, 6.1 Hz, 5H), 2.35 (s, 3H), 2.2 (s, 3H), 1.14 (t, J = 7.1 Hz, 3H) ppm. |
| 188 | 409.5 | 0.64 | 1H NMR (300 MHz, DMSO-d6) δ 9.14 (s, 1H), 9.10 (s, 1H), 7.84-7.64 (m, 2H), 7.58 (td, J = 8.4, 6.5 Hz, 1H), 7.18 (td, J = 8.3, 1.6 Hz, 1H), 6.91 (s, 1H), 6.52 (s, 1H), 5.93 (s, 1H), 5.62 (d, J = 6.4 Hz, 1H), 4.56 (td, J = 6.4, 3.9 Hz, 2H), 4.45 (dd, J = 13.4, 6.0 Hz, 2H), 3.86 (s, 1H), 3.66-3.48 (m, 1H), 2.78 (dd, J = 17.4, 10.5 Hz, 1H), 2.61 (dd, J = 13.8, 8.2 Hz, 1H), 2.48-2.32 (m, 2H), 2.33-2.19 (m, 1H), 2.14 (s, 3H), 1.77-1.55 (m, 1H) ppm. |
| 189 | 446.4 | 0.62 | 1H NMR (300 MHz, CD3OD + CDCl3) δ 8.95 (s, 1H), 8.30 (d, J = 5.7 Hz, 1H), 7.73-7.67 (m, 1H), 7.47 (s, 1H), 7.42 (s, 1H), 7.32 (s, 1H), 6.62 (t, J = 39.5 Hz, 2H), 4.77 (dt, J = 12.5, 6.5 Hz, 4H), 3.65 (dd, J = 14.1, 7.0 Hz, 1H), 3.39 (d, J = 4.0 Hz, 4H), 2.66 (s, 4H) ppm. |
| 190 | 388.14 | 2.66 | |
| 191 | 459.13 | 0.62 | 1H NMR (300 MHz, CDCl3) δ 8.40 (s, 1H), 7.88-7.68 (m, 4H), 7.11 (s, 1H), 6.82 (s, 1H), 6.72 (s, 1H), 6.43 (s, 1H), 4.79-4.63 (m, 4H), 3.67-3.51 (m, 1H), 3.36-3.23 (m, 4H), 2.60-2.47 (m, 4H), 2.35 (s, 3H) ppm. |
| 192 | 423.49 | 0.59 | 1H NMR (300 MHz, CDCl3) δ 8.33 (s, 1H), 7.62-7.38 (m, 3H), 7.14-6.97 (m, 2H), 6.64 (s, 1H), 6.44 (s, 1H), 6.09 (s, 1H), 4.82-4.50 (m, 4H), 3.57 (s, 1H), 3.40 (s, 1H), 2.77 (d, J = 11.5 Hz, 2H), 2.37-2.22 (m, 3H), 2.19 (d, J = 11.4 Hz, 2H), 2.04 (dd, J = 13.4, 7.9 Hz, 2H), 1.61-1.49 (m, 2H) ppm. |
| 193 | 430.31 | 0.61 | 1H NMR (300 MHz, DMSO-d6) δ 9.61 (s, 1H), 9.19 (s, 1H), 7.71-7.57 (m, 3H), 7.26 (ddd, J = 9.4, 8.7, 4.0 Hz, 2H), 6.78 (s, 1H), 4.60 (t, J = 6.4 Hz, 2H), 4.52 (q, J = 5.9 Hz, 2H), 3.83-3.72 (m, 1H), 3.12 (dd, J = 24.3, 11.3 Hz, 1H), 3.00-2.82 (m, 2H), 2.74 (dd, J = 13.5, 8.8 Hz, 1H), 2.42-2.23 (m, 5H) ppm. |
| 194 | 376 | 0.79 | 1H NMR (400 MHz, CDCl3) δ 8.32 (s, 1H), 7.68 (dd, J = 8.5, 0.9 Hz, 2H), 7.51 (t, J = 8.0 Hz, 2H), 7.35 (t, J = 7.4 Hz, 1H), 7.25 (s, 1H), 7.21 (s, 1H), 6.71 (s, 1H), 6.63 (s, 1H), 4.79 (d, J = 13.4 Hz, 1H), 3.94 (d, J = 13.6 Hz, 1H), 3.18 (td, J = 13.1, 2.4 Hz, 1H), 2.79-2.56 (m, 2H), 2.35 (s, 3H), 2.14 (s, 3H), 1.93 (t, J = 12.8 Hz, 2H), 1.76-1.57 (m, 3H) ppm. |
| 195 | 393.48 | 0.59 | 1H NMR (300 MHz, DMSO-d6) δ 9.44 (s, 1H), 9.20 (s, 1H), 9.05 (d, J = 1.4 Hz, 1H), 8.66 (d, J = 2.5 Hz, 1H), 8.58 (dd, J = 2.6, 1.4 Hz, 1H), 7.16 (s, 1H), 6.93 (s, 1H), 6.34 (s, 1H), 4.57 (t, J = 6.5 Hz, 2H), 4.52-4.41 (m, 2H), 3.46 (dt, J = 11.1, 5.6 Hz, 1H), 3.16 (dd, J = 5.1, 3.7 Hz, 4H), 2.47-2.38 (m, 4H), 2.26 (d, J = 8.1 Hz, 3H) ppm. |
| 196 | 443.27 | 0.34 | |
| 197 | 372.18 | 0.75 | 1H NMR (300 MHz, DMSO-d6) δ 9.36 (s, 1H), 9.16 (s, 1H), 7.61 (dd, J = 8.6, 2.2 Hz, 2H), 7.32-7.20 (m, 1H), 6.86-6.75 (m, 2H), 6.08 (s, 1H), 4.78 (m, 2H), 4.61-4.49 (m, 3H), 2.80 (m, 3H), 2.22 (s, 3H) ppm. |
| 198 | 441 | 0.69 | 1H NMR (400 MHz, CDCl3) δ 8.24 (s, 1H), 7.57 (ddd, J = 10.9, 6.8, 2.6 Hz, 1H), 7.37 (ddd, J = 6.3, 4.6, 3.2 Hz, 1H), 7.33-7.18 (m, 3H), |

TABLE 3-continued

Analytical Data

| Cmpd No. | LC/MS (M + H) | LC/MS Ret. Time (min) | ¹H-NMR |
|---|---|---|---|
| | | | 6.74-6.51 (m, 3H), 5.97 (s, 1H), 4.00 (t, J = 7.0 Hz, 2H), 3.87-3.65 (m, 5H), 3.35 (dd, J = 12.2, 5.5 Hz, 1H), 2.59 (q, J = 7.6 Hz, 2H), 2.46 (s, 3H), 1.24 (t, J = 7.6 Hz, 3H) ppm. |
| 199 | 455.35 | 0.66 | 1H NMR (300 MHz, DMSO-d6) δ 10.52 (s, 1H), 9.43 (s, 1H), 9.17 (s, 1H), 7.74-7.48 (m, 2H), 7.26 (tt, J = 9.3, 2.3 Hz, 1H), 7.04 (d, J = 33.2 Hz, 1H), 6.39 (s, 1H), 4.15 (d, J = 10.8 Hz, 1H), 3.91-3.48 (m, 6H), 3.45-3.07 (m, 6H), 2.22 (d, J = 20.2 Hz, 4H), 1.83 (dd, J = 18.9, 10.7 Hz, 2H), 1.70-1.45 (m, 1H) ppm. |
| 200 | 427 | 0.77 | 1H NMR (400 MHz, DMSO-d6) δ 9.37 (s, 1H), 9.16 (s, 1H), 7.61 (dd, J = 8.5, 2.1 Hz, 2H), 7.23 (dt, J = 9.3, 5.8 Hz, 2H), 6.88 (s, 1H), 6.37 (s, 1H), 4.43 (t, J = 8.1 Hz, 1H), 4.08-3.93 (m, 2H), 3.85-3.74 (m, 1H), 3.66 (dt, J = 15.8, 7.9 Hz, 2H), 3.45 (dd, J = 7.0, 5.1 Hz, 1H), 3.17 (dd, J = 13.1, 8.3 Hz, 1H), 2.78-2.55 (m, 2H), 2.78-2.55 (m, 2H), 2.24 (s, 3H) ppm. |
| 201 | 424.44 | 0.64 | 1H NMR (300 MHz, DMSO-d6) δ 9.33 (s, 1H), 9.04 (d, J = 13.4 Hz, 1H), 7.96-7.76 (m, 2H), 7.53-7.36 (m, 2H), 7.22 (s, 1H), 6.90 (s, 1H), 6.27 (s, 1H), 4.54 (t, J = 6.5 Hz, 2H), 4.43 (t, J = 6.1 Hz, 2H), 4.39-4.25 (m, 1H), 3.51-3.37 (m, 1H), 2.56 (d, J = 5.8 Hz, 2H), 2.28-2.18 (m, 3H), 2.14-1.89 (m, 4H), 1.73-1.55 (m, 2H) ppm. |
| 202 | 411.27 | 0.67 | 1H NMR (300 MHz, DMSO-d6) δ 9.64 (s, 1H), 9.12 (s, 1H), 8.03-7.86 (m, 1H), 7.75-7.58 (m, 2H), 6.87 (s, 1H), 6.78 (s, 1H), 4.16 (d, J = 12.6 Hz, 2H), 2.71 (t, J = 11.7 Hz, 2H), 1.83 (d, J = 4.7 Hz, 1H), 1.64 (d, J = 12.7 Hz, 3H), 1.13 (dd, J = 21.0, 9.5 Hz, 2H), 0.91 (d, J = 6.2 Hz, 3H), 0.86-0.75 (m, 4H) ppm. |
| 203 | 371 | 0.65 | 1H NMR (400 MHz, DMSO-d6) δ 9.59 (s, 1H), 9.15 (s, 1H), 7.71 (t, J = 8.7 Hz, 2H), 7.66-7.52 (m, 1H), 7.21 (t, J = 8.7 Hz, 1H), 7.01 (s, 1H), 6.95 (d, J = 11.3 Hz, 1H), 6.29 (d, J = 12.5 Hz, 1H), 3.16 (d, J = 4.4 Hz, 4H), 2.46 (m, 4H) ppm |
| 204 | 437.35 | 0.58 | 1H NMR (400 MHz, CDCl3) δ 8.95 (s, 1H), 8.59 (d, J = 0.6 Hz, 1H), 7.13-6.99 (m, 2H), 6.86 (d, J = 7.8 Hz, 2H), 6.44 (s, 1H), 4.82-4.61 (m, 4H), 4.51 (q, J = 7.1 Hz, 2H), 3.59 (p, J = 6.4 Hz, 1H), 3.38-3.26 (m, 4H), 2.62-2.47 (m, 4H), 2.36 (s, 3H), 1.46 (t, J = 7.1 Hz, 3H) ppm. |
| 205 | 425.36 | 0.91 | 1H NMR (300 MHz, CDCl3) δ 8.28 (s, 1H), 7.17 (s, 1H), 7.04 (s, 1H), 6.98 (dt, J = 9.3, 2.1 Hz, 1H), 6.76 (s, 1H), 6.62-6.50 (m, 2H), 6.42 (s, 1H), 4.60 (dt, J = 12.1, 6.0 Hz, 1H), 3.34-3.23 (m, 4H), 2.69-2.57 (m, 4H), 2.39 (s, 3H), 2.34 (s, 3H), 1.40 (d, J = 6.1 Hz, 6H) ppm. |
| 206 | 437.3 | 0.64 | 1H NMR (400 MHz, CDCl3) δ 8.31 (s, 1H), 7.31 (s, 1H), 7.25 (dt, J = 9.4, 2.1 Hz, 1H), 7.19 (s, 1H), 6.90 (d, J = 9.3 Hz, 1H), 6.76 (s, 1H), 6.62 (s, 1H), 6.41 (s, 1H), 4.71 (p, J = 6.4 Hz, 4H), 3.59 (p, J = 6.4 Hz, 1H), 3.36-3.27 (m, 4H), 2.74 (q, J = 7.6 Hz, 2H), 2.57-2.48 (m, 4H), 2.34 (s, 3H), 1.35-1.25 (m, 3H) ppm. |
| 207 | 391 | 0.62 | 1H NMR (400 MHz, DMSO-d6) δ 9.43 (s, 1H), 9.14 (s, 1H), 8.59-8.38 (m, 1H), 8.08 (td, J = 8.0, 1.8 Hz, 1H), 7.77 (d, J = 8.2 Hz, 1H), 7.41 (dd, J = 7.2, 5.4 Hz, 2H), 7.31 (s, 1H), 6.59 (s, 1H), 4.63-4.33 (m, 4H), 3.52-3.35 (m, 1H), 2.85-2.57 (m, 3H), 2.27 (s, 3H), 1.97-1.69 (m, 4H), 1.61 (dd, J = 25.1, 12.6 Hz, 1H), 1.42 (tt, J = 12.3, 6.2 Hz, 1H) ppm. |

TABLE 3-continued

Analytical Data

| Cmpd No. | LC/MS (M + H) | LC/MS Ret. Time (min) | ¹H-NMR |
|---|---|---|---|
| 208 | 444.17 | 0.81 | 1H NMR (400 MHz, CD3OD) δ 8.87 (s, 1H), 8.16 (s, 1H), 7.59-7.46 (m, 2H), 7.36 (s, 1H), 7.31 (s, 1H), 6.95 (tt, J = 9.0, 2.2 Hz, 1H), 6.69 (s, 1H), 4.76 (dtd, J = 48.0, 10.0, 4.9 Hz, 1H), 4.19 (dt, J = 15.0, 7.3 Hz, 1H), 3.48 (dddd, J = 30.0, 24.1, 15.3, 6.7 Hz, 1H), 3.26-2.99 (m, 3H), 2.89-2.36 (m, 5H), 2.34 (s, 3H), 2.06-1.79 (m, 2H) ppm. |
| 209 | 428.44 | 0.54 | 1H NMR (300 MHz, CDCl3) δ 9.03 (d, J = 2.2 Hz, 1H), 8.64 (dd, J = 4.8, 1.4 Hz, 1H), 8.40 (s, 1H), 8.01 (ddd, J = 8.3, 2.6, 1.5 Hz, 1H), 7.49 (ddd, J = 8.3, 4.8, 0.7 Hz, 1H), 7.34 (s, 1H), 7.15 (s, 1H), 6.91 (s, 1H), 6.64 (dd, J = 69.9, 43.5 Hz, 2H), 4.81-4.65 (m, 4H), 3.68-3.51 (m, 1H), 3.46-3.26 (m, 4H), 2.55 (d, J = 4.3 Hz, 4H) ppm. |
| 210 | 423.12 | 0.61 | 1H NMR (300 MHz, DMSO-d6) δ 9.73 (s, 1H), 9.17 (s, 1H), 7.05 (d, J = 2.2 Hz, 2H), 7.01 (d, J = 1.3 Hz, 1H), 6.76 (d, J = 1.3 Hz, 1H), 6.49 (t, J = 2.2 Hz, 1H), 3.82 (s, 6H), 3.74-3.60 (m, 4H), 3.38-3.34 (m, 4H), 1.89-1.76 (m, 1H), 0.94-0.71 (m, 4H) ppm. |
| 211 | 379 | 0.58 | 1H NMR (300 MHz, CDCl3) δ 8.94 (s, 1H), 8.41 (ddd, J = 4.8, 1.7, 0.8 Hz, 1H), 7.94-7.83 (m, 1H), 7.80 (d, J = 8.1 Hz, 1H), 7.23 (ddd, J = 7.1, 4.9, 1.3 Hz, 1H), 7.14 (s, 1H), 6.79 (d, J = 7.1 Hz, 2H), 6.43 (s, 1H), 3.76 (d, J = 12.3 Hz, 2H), 3.37 (s, 3H), 3.28 (d, J = 6.4 Hz, 2H), 2.77 (td, J = 12.2, 2.2 Hz, 2H), 2.33 (s, 3H), 1.85 (d, J = 12.7 Hz, 2H), 1.42 (dd, J = 11.7, 3.2 Hz, 2H) ppm. |
| 212 | 345.16 | 0.66 | 1H NMR (300 MHz, CDCl3) δ 8.65 (s, 1H), 8.05-7.73 (m, 3H), 7.71-7.39 (m, 3H), 7.11-6.97 (m, 1H), 6.63 (s, 1H), 3.63 (t, J = 6.4 Hz, 4H), 2.48-2.32 (s, 3H), 2.29-2.14 (m, 4H) ppm. |
| 213 | 353 | 0.62 | 1H NMR (400 MHz, CDCl3) δ 8.32 (s, 1H), 7.83-7.61 (m, 2H), 7.50 (dd, J = 10.7, 5.3 Hz, 2H), 7.45-7.30 (m, 1H), 7.06-6.86 (m, 1H), 6.81 (s, 1H), 6.73 (s, 1H), 6.25 (dd, J = 12.0, 2.1 Hz, 1H), 3.29 (s, 4H), 2.63 (s, 4H), 2.40 (s, 3H) ppm. |
| 214 | 389.38 | 0.79 | 1H NMR (300 MHz, DMSO-d6) δ 9.24 (s, 1H), 9.07 (s, 1H), 7.84 (dd, J = 8.6, 1.1 Hz, 2H), 7.65-7.49 (m, 2H), 7.35 (t, J = 7.4 Hz, 1H), 7.15 (s, 1H), 6.89 (s, 1H), 6.29 (s, 1H), 3.73 (s, 2H), 3.51-3.30 (m, 4H), 2.89-2.70 (m, 1H), 2.34-2.17 (m, 3H), 0.82-0.61 (m, 4H) ppm. |
| 215 | 441.49 | 0.68 | 1H NMR (300 MHz, CD3OD + CDCl3) δ 8.63 (s, 1H), 7.46-7.31 (m, 2H), 7.18 (d, J = 12.5 Hz, 1H), 6.95-6.74 (m, 2H), 6.43 (s, 1H), 4.68 (t, J = 8.0 Hz, 2H), 4.33 (d, J = 5.9 Hz, 2H), 4.01 (d, J = 47.0 Hz, 1H), 3.34-3.22 (m, 4H), 2.70-2.51 (m, 4H), 2.34 (s, 3H), 1.46 (s, 3H) ppm. |
| 216 | 426.51 | 0.65 | 1H NMR (300 MHz, DMSO-d6) δ 9.28 (d, J = 18.8 Hz, 1H), 9.15 (s, 1H), 7.72-7.53 (m, 2H), 7.34-7.15 (m, 2H), 6.79 (s, 1H), 6.31 (s, 1H), 4.62 (dd, J = 7.8, 5.9 Hz, 2H), 4.37 (t, J = 6.2 Hz, 2H), 3.69 (d, J = 12.5 Hz, 2H), 2.83-2.61 (m, 3H), 2.24 (d, J = 17.0 Hz, 3H), 1.86-1.70 (m, 1H), 1.65 (d, J = 12.7 Hz, 2H), 1.15 (dt, J = 11.9, 8.7 Hz, 2H) ppm. |
| 217 | 426.23 | 0.57 | 1H NMR (400 MHz, CDCl3) δ 8.89 (d, J = 2.3 Hz, 1H), 8.56 (d, J = 2.1 Hz, 1H), 8.38 (s, 1H), 8.05 (t, J = 2.2 Hz, 1H), 7.13 (d, J = 1.9 Hz, 1H), 6.78 (s, 1H), 6.70 (s, 1H), 6.43 (s, 1H), 4.71 (p, J = 6.4 Hz, 4H), 3.59 (p, J = 6.4 Hz, 1H), 3.40-3.24 (m, 4H), 2.59-2.46 (m, 4H), 2.35 (s, 3H) ppm. |
| 218 | 473.13 | 0.64 | 1H NMR (400 MHz, CDCl3) δ 8.40 (s, 1H), 8.05 (s, 1H), 7.84 (d, J = 7.8 Hz, 1H), 7.68-7.57 (m, 2H), 7.31 (dd, J = 6.9, 4.8 Hz, 1H), 6.76 (s, 1H), 6.68 (s, 1H), 6.46 (s, 1H), 4.72 (dq, J = 12.5, |

TABLE 3-continued

Analytical Data

| Cmpd No. | LC/MS (M + H) | LC/MS Ret. Time (min) | ¹H-NMR |
|---|---|---|---|
| | | | 6.4 Hz, 4H), 3.66-3.52 (m, 1H), 3.38-3.29 (m, 3H), 2.64 (q, J = 7.6 Hz, 2H), 2.57-2.49 (m, 3H), 1.28 (t, J = 7.6 Hz, 3H) ppm. |
| 219 | 403 | 0.6 | 1H NMR (400 MHz, CDCl3) δ 8.30 (s, 1H), 7.64 (d, J = 8.5 Hz, 2H), 7.50 (t, J = 7.7 Hz, 2H), 7.35 (t, J = 7.0 Hz, 1H), 6.90 (s, 1H), 6.61 (s, 1H), 6.58 (s, 1H), 5.99 (s, 1H), 4.74 (d, J = 6.9 Hz, 2H), 4.66 (s, 2H), 4.41 (s, 1H), 4.12 (dd, J = 14.3, 7.1 Hz, 2H), 3.91 (s, 1H), 3.78-3.66 (m, 1H), 3.57-3.45 (m, 1H), 3.15 (d, J = 30.9 Hz, 2H), 2.31 (s, 3H), 2.13 (s, 1H) ppm. |
| 220 | 401.25 | 0.64 | 1H NMR (300 MHz, CDCl3) δ 8.32 (s, 1H), 7.57-7.48 (m, 1H), 7.36 (dt, J = 9.3, 2.1 Hz, 1H), 7.17 (s, 1H), 7.14-7.02 (m, 1H), 6.75 (s, 1H), 6.62 (s, 1H), 6.44 (s, 1H), 3.40-3.24 (m, 4H), 2.66 (s, 4H), 2.42 (s, 3H), 2.35 (s, 3H) ppm. |
| 221 | 426.46 | 0.67 | 1H NMR (300 MHz, DMSO-d6) δ 9.41 (s, 1H), 9.16 (s, 1H), 7.62 (dd, J = 8.7, 2.2 Hz, 2H), 7.35 (s, 1H), 7.30-7.18 (m, 2H), 6.59 (s, 1H), 4.55 (t, J = 6.5 Hz, 2H), 4.45 (t, J = 6.1 Hz, 2H), 3.48-3.35 (m, 1H), 2.79 (d, J = 11.1 Hz, 2H), 2.47-2.34 (m, 1H), 2.27 (s, 3H), 1.93-1.55 (m, 6H) ppm. |
| 222 | 363.19 | 0.64 | 1H NMR (300 MHz, CD3OD) δ 8.93 (s, 1H), 7.88-7.75 (m, 2H), 7.63-7.50 (m, 2H), 7.51-7.29 (m, 2H), 6.65 (s, 1H), 3.88 (dd, J = 6.0, 3.7 Hz, 4H), 3.57 (dd, J = 5.9, 3.8 Hz, 4H), 2.16 (tt, J = 8.3, 4.9 Hz, 1H), 1.33-1.20 (m, 2H), 0.98 (dt, J = 7.2, 4.8 Hz, 2H) ppm. |
| 223 | 409.27 | 0.58 | 1H NMR (400 MHz, CDCl3) δ 8.48 (d, J = 2.5 Hz, 1H), 8.01-7.87 (m, 1H), 7.35-7.28 (m, 3H), 7.12 (d, J = 1.9 Hz, 1H), 6.83 (s, 1H), 6.77 (s, 1H), 6.42 (s, 1H), 4.72 (p, J = 6.4 Hz, 4H), 3.58 (p, J = 6.4 Hz, 1H), 3.33-3.24 (m, 4H), 2.58-2.48 (m, 4H), 2.35 (s, 3H) ppm. |
| 224 | 392.44 | 0.53 | 1H NMR (300 MHz, DMSO-d6) δ 9.37 (s, 1H), 9.29 (s, 1H), 8.69 (dd, J = 4.7, 1.5 Hz, 2H), 7.81 (dd, J = 4.7, 1.6 Hz, 2H), 7.14 (s, 1H), 6.91 (s, 1H), 6.33 (s, 1H), 4.58 (t, J = 6.5 Hz, 2H), 4.49 (t, J = 6.1 Hz, 2H), 3.45 (p, J = 6.3 Hz, 1H), 3.20-3.01 (m, 4H), 2.47-2.35 (m, 4H), 2.24 (s, 3H) ppm. |
| 225 | 435.28 | 0.6 | 1H NMR (400 MHz, CDCl3) δ 8.48 (d, J = 2.5 Hz, 1H), 7.97 (ddd, J = 7.3, 4.0, 1.4 Hz, 1H), 7.35-7.28 (m, 3H), 7.08 (t, J = 2.0 Hz, 1H), 6.89 (d, J = 8.7 Hz, 1H), 6.76 (s, 1H), 6.35 (s, 1H), 4.78-4.63 (m, 4H), 3.58 (p, J = 6.4 Hz, 1H), 3.33-3.22 (m, 4H), 2.54 (dd, J = 14.0, 9.0 Hz, 4H), 1.96-1.82 (m, 1H), 1.00-0.91 (m, 2H), 0.79-0.70 (m, 2H) ppm. |
| 226 | | | 1H NMR (300 MHz, Acetone-d6) δ 9.16 (s, 1H), 8.91 (s, 1H), 8.37 (d, J = 5.6 Hz, 1H), 7.91-7.75 (m, 1H), 7.64 (d, J = 2.0 Hz, 1H), 7.52 (d, J = 1.4 Hz, 2H), 6.83 (s, 1H), 3.41-3.23 (m, 4H), 2.87 (s, 2H), 2.60-2.45 (m, 4H), 2.29 (s, 3H) ppm. |
| 227 | 391 | 0.71 | 1H NMR (400 MHz, DMSO-d6) δ 9.23 (s, 1H), 9.05 (s, 1H), 7.83 (d, J = 7.7 Hz, 2H), 7.55 (t, J = 8.0 Hz, 2H), 7.35 (t, J = 7.4 Hz, 1H), 7.22 (s, 1H), 6.91 (s, 1H), 6.34 (s, 1H), 4.43 (t, J = 8.1 Hz, 1H), 4.11-3.91 (m, 2H), 3.84-3.71 (m, 1H), 3.71-3.50 (m, 2H), 3.16 (td, J = 12.7, 3.6 Hz, 1H), 2.65 (ddd, J = 28.7, 17.4, 7.7 Hz, 2H), 2.23 (s, 3H) ppm. |
| 228 | 475.02 | 0.73 | 1H NMR (300 MHz, CDCl3) δ 8.39 (s, 1H), 7.26 (dd, J = 7.6, 1.8 Hz, 2H), 7.15 (s, 1H), 6.87 (s, 1H), 6.81 (tt, J = 8.7, 2.2 Hz, 1H), 6.40 (s, 1H), 5.33 (dd, J = 4.8, 2.8 Hz, 2H), 4.48-4.40 (m, 2H), 3.42-3.22 (m, 8H), 2.06 (d, J = 3.8 Hz, 3H) ppm. |
| 229 | 398.26 | 0.26 | 1H NMR (400 MHz, DMSO-d6) δ 9.46 (s, 1H), 9.17 (s, 1H), 7.69-7.58 (m, 3H), 7.29-7.19 (m, 2H), 6.65 (s, 1H), 4.58 (t, J = 6.5 Hz, 2H), 4.45-4.38 (m, 2H), 3.81-3.73 (m, 1H), 3.67 (t, J = 7.1 Hz, |

TABLE 3-continued

Analytical Data

| Cmpd No. | LC/MS (M + H) | LC/MS Ret. Time (min) | ¹H-NMR |
|---|---|---|---|
| | | | 2H), 3.64-3.56 (m, 1H), 3.19 (t, J = 6.6 Hz, 2H), 2.27 (s, 3H) ppm. |
| 230 | 398.26 | 0.6 | 1H NMR (400 MHz, DMSO-d6) δ 9.72 (s, 1H), 9.15 (s, 1H), 7.77-7.68 (m, 2H), 7.60 (td, J = 8.4, 6.4 Hz, 1H), 7.41-7.31 (m, 2H), 7.21 (td, J = 8.2, 1.6 Hz, 1H), 6.62 (d, J = 9.6 Hz, 1H), 4.59 (td, J = 6.5, 2.0 Hz, 2H), 4.51 (td, J = 6.0, 1.6 Hz, 2H), 3.69-3.60 (m, 1H), 2.95-2.87 (m, 1H), 2.69-2.61 (m, 2H), 2.49-2.43 (m, 2H), 2.34-2.21 (m, 1H), 1.78 (td, J = 14.9, 7.4 Hz, 1H) ppm. |
| 231 | 453.42 | 0.7 | 1H NMR (300 MHz, DMSO-d6) δ 9.24 (s, 1H), 9.05 (s, 1H), 8.02-7.84 (m, 1H), 7.76-7.51 (m, 2H), 7.12 (s, 1H), 6.88 (s, 1H), 6.30 (s, 1H), 3.30-3.16 (m, 2H), 3.17-2.98 (m, 4H), 2.85-2.68 (m, 4H), 2.22 (s, 3H) ppm. |
| 232 | 428.3 | 0.59 | 1H NMR (400 MHz, CDCl3) δ 8.45 (s, 1H), 7.13 (s, 2H), 7.04 (d, J = 15.7 Hz, 1H), 6.81 (s, 1H), 6.71 (s, 1H), 6.47 (s, 1H), 4.81-4.64 (m, 4H), 3.66-3.50 (m, 1H), 3.38-3.26 (m, 4H), 2.53 (dd, J = 13.3, 8.4 Hz, 4H), 2.35 (d, J = 10.7 Hz, 3H) ppm. |
| 233 | 435.51 | 0.63 | 1H NMR (300 MHz, CDCl3) δ 8.26 (s, 1H), 7.61 (dt, J = 7.1, 3.2 Hz, 1H), 7.54 (dt, J = 5.7, 3.2 Hz, 1H), 7.50-7.42 (m, 2H), 7.07 (s, 1H), 6.82 (s, 1H), 6.77 (s, 1H), 6.39 (s, 1H), 4.80-4.61 (m, 4H), 4.49 (s, 2H), 3.57 (p, J = 6.4 Hz, 1H), 3.43 (s, 3H), 3.33-3.21 (m, 4H), 2.59-2.44 (m, 4H), 2.33 (s, 3H) ppm. |
| 234 | 373.36 | 0.84 | 1H NMR (300 MHz, CDCl3) δ 8.35 (s, 1H), 7.75-7.66 (m, 2H), 7.53 (ddd, J = 6.8, 4.9, 2.4 Hz, 3H), 7.46-7.35 (m, 2H), 7.21 (d, J = 8.4 Hz, 1H), 6.88 (s, 1H), 6.08-6.02 (m, 1H), 6.00-5.94 (m, 1H), 4.96-4.80 (m, 8H) ppm. |
| 235 | 462.13 | 0.86 | 1H NMR (400 MHz, CD3OD) δ 8.88 (s, 1H), 7.70-7.42 (m, 3H), 7.34 (s, 1H), 6.95 (tt, J = 9.0, 2.3 Hz, 1H), 6.73 (s, 1H), 4.68 (ddt, J = 19.4, 12.5, 4.8 Hz, 3H), 4.16-3.66 (m, 3H), 3.19-2.86 (m, 3H), 2.46-2.10 (m, 5H), 1.24-1.14 (m, 2H) ppm. |
| 236 | 421.51 | 0.58 | 1H NMR (300 MHz, CDCl3) δ 11.33 (d, J = 12.2 Hz, 1H), 9.26 (d, J = 1.6 Hz, 1H), 8.13 (dd, J = 4.7, 1.7 Hz, 1H), 8.02 (d, J = 12.0 Hz, 1H), 7.88 (d, J = 4.7 Hz, 1H), 6.60 (dd, J = 8.6, 1.9 Hz, 3H), 4.83-4.62 (m, 4H), 3.68-3.50 (m, 1H), 3.38-3.20 (m, 4H), 2.67-2.45 (m, 6H), 1.68 (dq, J = 14.7, 7.4 Hz, 3H), 0.99 (t, J = 7.3 Hz, 3H) ppm. |
| 237 | 405.33 | 0.62 | 1H NMR (300 MHz, CDCl3) δ 8.33 (s, 1H), 7.77-7.65 (m, 2H), 7.53 (dd, J = 10.7, 5.1 Hz, 2H), 7.42-7.29 (m, 2H), 7.03 (d, J = 2.0 Hz, 1H), 6.62 (s, 1H), 4.74 (t, J = 6.4 Hz, 4H), 3.63 (p, J = 6.5 Hz, 1H), 3.03 (t, J = 4.7 Hz, 4H), 2.56 (s, 4H), 2.30 (s, 3H), 2.21 (d, J = 16.5 Hz, 3H) ppm. |
| 238 | 386.19 | 0.61 | 1H NMR (300 MHz, DMSO-d6) δ 9.32 (s, 1H), 9.16 (s, 1H), 7.60 (dd, J = 8.6, 2.1 Hz, 2H), 7.31-7.17 (m, 2H), 6.77 (s, 1H), 6.31 (s, 1H), 4.68 (d, J = 4.3 Hz, 1H), 3.63 (m, 1H), 3.53 (d, J = 12.9 Hz, 2H), 2.85 (t, J = 10.1 Hz, 2H), 2.21 (s, 3H), 1.81 (d, J = 11.1 Hz, 2H), 1.47 (m, 2H) ppm. |
| 239 | 392.44 | 0.63 | 1H NMR (300 MHz, DMSO-d6) δ 9.35 (s, 1H), 9.06 (s, 1H), 7.95-7.82 (m, 1H), 7.55 (t, J = 8.0 Hz, 2H), 7.36 (t, J = 7.4 Hz, 1H), 7.15 (s, 1H), 6.94 (s, 1H), 6.21 (s, 1H), 4.83 (s, 1H), 4.57 (td, J = 6.5, 1.8 Hz, 2H), 4.47 (dd, J = 10.4, 5.9 Hz, 2H), 3.64 (s, 1H), 2.99-2.83 (m, 1H), 2.63 (d, J = 9.9 Hz, 2H), 2.48-2.41 (m, 1H), 2.40-2.16 (m, 4H), 1.86 (d, J = 5.1 Hz, 1H) ppm. |
| 240 | 358.13 | 0.81 | 1H NMR (300 MHz, DMSO-d6) δ 9.26 (s, 1H), 9.15 (s, 1H), 7.66 (dd, J = 8.7, 2.2 Hz, 2H), 7.32-7.15 (m, 1H), 6.83 (s, 1H), 6.57 (s, 1H), |

TABLE 3-continued

Analytical Data

| Cmpd No. | LC/MS (M + H) | LC/MS Ret. Time (min) | ¹H-NMR |
|---|---|---|---|
| | | | 6.28 (d, J = 5.6 Hz, 1H), 5.82 (s, 1H), 4.84 (t, J = 5.9 Hz, 2H), 4.47 (m, 3H), 2.15 (s, 3H) ppm. |
| 241 | 392.13 | 3.61 | 1H NMR (400 MHz, DMSO-d6) δ 9.56 (s, 1H), 9.26 (s, 1H), 8.26-8.04 (m, 2H), 7.80 (t, J = 8.0 Hz, 1H), 7.71 (d, J = 7.8 Hz, 1H), 6.88 (s, 1H), 6.67 (d, J = 11.7 Hz, 1H), 5.86 (t, J = 16.9 Hz, 1H), 3.25 (s, 4H), 1.97 (t, J = 6.5 Hz, 4H) ppm. |
| 242 | 386.24 | 0.7 | 1H NMR (400 MHz, DMSO-d6) δ 9.42 (s, 1H), 9.16 (s, 1H), 7.84 (s, 1H), 7.65 (dd, J = 8.5, 2.1 Hz, 2H), 7.28-7.18 (m, 1H), 7.12 (s, 1H), 6.86 (s, 1H), 5.15 (s, 1H), 2.89 (d, J = 9.6 Hz, 1H), 2.83-2.65 (m, 3H), 2.34 (s, 3H), 2.28 (s, 3H), 2.20-2.10 (m, 1H), 2.07-1.99 (m, 1H) ppm. |
| 243 | 455.4 | 0.64 | 1H NMR (300 MHz, DMSO-d6) δ 10.81 (s, 1H), 9.43 (s, 1H), 9.18 (s, 1H), 7.72-7.55 (m, 2H), 7.26 (tt, J = 9.3, 2.3 Hz, 1H), 7.12 (s, 1H), 6.99 (s, 1H), 6.40 (s, 1H), 4.00 (dd, J = 11.4, 3.8 Hz, 2H), 3.76 (d, J = 9.6 Hz, 2H), 3.61 (d, J = 8.0 Hz, 2H), 3.46 (s, 1H), 3.31 (t, J = 11.3 Hz, 2H), 3.24-3.08 (m, 4H), 2.28 (d, J = 12.6 Hz, 3H), 2.04 (t, J = 14.2 Hz, 2H), 1.92-1.62 (m, 2H) ppm. |
| 244 | 411.27 | 0.69 | 1H NMR (300 MHz, DMSO-d6) δ 9.70 (s, 1H), 9.21 (s, 1H), 7.70-7.55 (m, 2H), 7.28 (dd, J = 10.5, 8.3 Hz, 1H), 6.90 (s, 1H), 6.76 (s, 1H), 4.17 (d, J = 13.2 Hz, 2H), 2.73 (t, J = 11.4 Hz, 2H), 1.85 (d, J = 4.7 Hz, 1H), 1.64 (d, J = 12.1 Hz, 3H), 1.10 (d, J = 11.1 Hz, 2H), 0.91 (d, J = 6.2 Hz, 3H), 0.88-0.69 (m, 4H) ppm. |
| 245 | 425.27 | 0.64 | 1H NMR (300 MHz, DMSO-d6) δ 9.62 (d, J = 24.0 Hz, 1H), 9.16 (s, 1H), 7.06 (d, J = 2.2 Hz, 2H), 6.79 (s, 1H), 6.63 (s, 1H), 6.49 (t, J = 2.2 Hz, 1H), 5.40 (d, J = 53.9 Hz, 1H), 3.83 (s, 6H), 3.73-3.46 (m, 3H), 3.43-3.34 (m, 1H), 2.23 (s, 2H), 1.80 (s, 1H), 0.88 (d, J = 4.7 Hz, 2H), 0.79 (d, J = 7.7 Hz, 2H) ppm. |
| 246 | 398.29 | 0.96 | 1H NMR (300 MHz, CDCl3) δ 8.25 (s, 1H), 7.66-7.55 (m, 2H), 7.43 (ddd, J = 8.3, 5.4, 1.8 Hz, 2H), 7.28 (ddd, J = 7.4, 3.9, 1.2 Hz, 1H), 6.98 (dt, J = 14.2, 1.9 Hz, 2H), 6.78 (s, 1H), 6.45 (t, J = 1.9 Hz, 1H), 3.67 (d, J = 12.4 Hz, 2H), 3.29 (s, 3H), 3.20 (d, J = 6.3 Hz, 2H), 2.71 (td, J = 12.4, 2.4 Hz, 2H), 1.85-1.61 (m, 3H), 1.42-1.21 (m, 2H) ppm. |
| 247 | 349 | 2.12 | 1H NMR (400 MHz, CDCl3) δ 8.30 (s, 1H), 7.75-7.60 (m, 2H), 7.49 (dd, J = 10.7, 5.2 Hz, 2H), 7.34 (d, J = 7.4 Hz, 2H), 7.13 (s, 1H), 6.78 (s, 1H), 6.61 (s, 1H), 6.39 (s, 1H), 3.36-3.15 (m, 4H), 2.68-2.50 (m, 4H), 2.37 (s, 3H), 2.32 (s, 3H) ppm. |
| 248 | 390 | 0.61 | 1H NMR (400 MHz, CDCl3) δ 8.32 (s, 1H), 7.69 (d, J = 7.8 Hz, 2H), 7.51 (t, J = 7.9 Hz, 2H), 7.36 (d, J = 8.3 Hz, 2H), 7.15 (s, 1H), 6.76 (s, 1H), 6.65 (s, 1H), 4.75-4.55 (m, 4H), 3.50 (p, J = 6.4 Hz, 1H), 2.84 (dd, J = 18.4, 7.1 Hz, 3H), 2.35 (s, 3H), 2.00 (d, J = 12.5 Hz, 1H), 1.95-1.63 (m, 5H), 1.50 (dd, J = 22.9, 10.4 Hz, 1H) ppm. |
| 249 | 410.49 | 0.61 | 1H NMR (300 MHz, DMSO-d6) δ 9.34 (s, 1H), 9.32 (s, 1H), 8.36 (d, J = 5.7 Hz, 1H), 7.84 (d, J = 5.8 Hz, 1H), 7.63 (s, 1H), 6.93 (s, 1H), 6.53 (s, 1H), 5.95 (s, 1H), 5.68 (d, J = 6.5 Hz, 1H), 4.68-4.52 (m, 2H), 4.44 (dt, J = 19.2, 9.6 Hz, 2H), 3.87 (s, 1H), 3.72-3.50 (m, 1H), 2.78 (dd, J = 18.4, 10.3 Hz, 1H), 2.62 (d, J = 5.9 Hz, 1H), 2.41 (dd, J = 13.7, 8.3 Hz, 2H), 2.32-2.20 (m, 1H), 2.16 (s, 3H), 1.67 (dd, J = 12.0, 5.4 Hz, 1H) ppm. |
| 250 | 406.39 | 0.66 | 1H NMR (300 MHz, CDCl3) δ 9.04 (d, J = 2.2 Hz, 1H), 8.64 (dd, J = 4.8, 1.4 Hz, 1H), 8.40 (s, 1H), 8.03 (ddd, J = 8.3, 2.6, 1.5 Hz, 1H), 7.50 (ddd, J = 8.3, 4.8, 0.7 Hz, 1H), 7.30 (d, J = 1.4 Hz, 2H), 6.80 (s, 1H), 6.76 (s, 1H), 4.12 (dd, J = 10.3, |

TABLE 3-continued

Analytical Data

| Cmpd No. | LC/MS (M + H) | LC/MS Ret. Time (min) | ¹H-NMR |
|---|---|---|---|
| | | | 3.0 Hz, 4H), 3.57 (td, J = 11.3, 3.2 Hz, 4H), 2.79 (ddd, J = 15.6, 10.5, 5.0 Hz, 2H), 1.96-1.77 (m, 8H) ppm. |
| 251 | 406.44 | 0.69 | 1H NMR (300 MHz, CDCl3) δ 8.34 (s, 1H), 7.73-7.65 (m, 3H), 7.52 (ddd, J = 8.3, 5.3, 1.8 Hz, 3H), 7.42-7.33 (m, 1H), 7.19 (t, J = 2.1 Hz, 1H), 6.89 (t, J = 1.5 Hz, 1H), 6.74 (s, 1H), 6.46 (d, J = 1.6 Hz, 1H), 4.11 (dd, J = 10.3, 3.1 Hz, 2H), 3.92-3.88 (m, 4H), 3.55 (td, J = 11.4, 2.9 Hz, 3H), 3.26-3.22 (m, 4H), 2.81-2.68 (m, 1H), 1.91-1.80 (m, 4H) ppm. |
| 252 | 475.11 | 0.63 | 1H NMR (400 MHz, CDCl3) δ 8.36 (s, 1H), 7.67 (s, 1H), 7.56 (ddd, J = 23.0, 11.6, 5.0 Hz, 2H), 7.27 (s, 1H), 7.19 (dt, J = 21.6, 7.9 Hz, 1H), 6.73 (d, J = 10.2 Hz, 2H), 6.42 (s, 1H), 4.79-4.60 (m, 4H), 3.58 (p, J = 6.4 Hz, 1H), 3.38-3.21 (m, 4H), 2.61-2.44 (m, 4H), 2.34 (s, 3H) ppm. |
| 253 | 393.39 | 0.64 | 1H NMR (300 MHz, CDCl3) δ 8.35 (s, 1H), 7.67 (dt, J = 12.4, 6.4 Hz, 2H), 7.52 (dd, J = 10.6, 5.1 Hz, 2H), 7.45-7.33 (m, 1H), 7.13 (s, 1H), 6.82 (s, 1H), 6.73 (s, 1H), 6.40 (s, 1H), 3.29 (s, 4H), 2.87 (s, 4H), 2.59-2.37 (m, 2H), 2.36 (d, J = 8.9 Hz, 3H), 1.24 (s, 5H) ppm. |
| 254 | 423.31 | 0.59 | 1H NMR (400 MHz, CDCl3) δ 8.96 (s, 1H), 8.62 (d, J = 0.6 Hz, 1H), 7.08 (dd, J = 3.5, 1.3 Hz, 2H), 6.92 (s, 1H), 6.84 (s, 1H), 6.44 (s, 1H), 4.72 (p, J = 6.4 Hz, 4H), 4.07 (s, 3H), 3.59 (p, J = 6.4 Hz, 1H), 3.36-3.26 (m, 4H), 2.54 (dd, J = 11.2, 6.3 Hz, 4H), 2.36 (s, 3H) ppm. |
| 255 | 395.26 | 0.64 | 1H NMR (400 MHz, CDCl3) δ 8.21 (s, 1H), 7.23 (s, 1H), 7.15 (d, J = 9.4 Hz, 1H), 7.11 (s, 1H), 6.80 (d, J = 9.1 Hz, 1H), 6.62 (d, J = 21.7 Hz, 1H), 6.57 (s, 1H), 6.32 (s, 1H), 3.26-3.16 (m, 4H), 2.65 (q, J = 7.6 Hz, 2H), 2.56-2.48 (m, 4H), 2.29 (s, 3H), 2.25 (s, 3H), 1.28-1.17 (m, 3H) ppm. |
| 257 | 421.31 | 3.17 | 1H NMR (300 MHz, DMSO-d6) δ 9.19 (s, 1H), 7.72 (m, 2H), 7.67-7.56 (m, 1H), 7.53 (d, J = 12.3 Hz, 2H), 7.24 (td, J = 11.8, 5.1 Hz, 1H), 6.86 (s, 1H), 3.88 (m, 2H), 3.55 (m, 2H), 3.28-3.12 (m, 4H), 2.86 (s, 3H) ppm. |
| 258 | 425.22 | 0.63 | 1H NMR (300 MHz, DMSO-d6) δ 9.35 (d, J = 7.3 Hz, 1H), 9.13 (s, 1H), 7.84-7.65 (m, 2H), 7.60 (td, J = 8.3, 6.4 Hz, 1H), 7.19 (td, J = 8.3, 1.4 Hz, 1H), 6.84 (d, J = 2.0 Hz, 2H), 6.05 (d, J = 1.9 Hz, 1H), 4.57 (t, J = 6.5 Hz, 2H), 4.48 (t, J = 6.0 Hz, 2H), 3.72 (s, 3H), 3.55-3.40 (m, 1H), 3.24-2.97 (m, 4H), 2.37 (dd, J = 24.8, 20.2 Hz, 4H) ppm. |
| 259 | 349 | 0.59 | 1H NMR (400 MHz, CDCl3) δ 8.32 (s, 1H), 7.68 (d, J = 7.6 Hz, 2H), 7.48 (t, J = 7.9 Hz, 2H), 7.34 (t, J = 7.4 Hz, 1H), 7.19 (s, 1H), 6.76 (s, 1H), 6.67 (s, 1H), 6.40 (s, 1H), 3.60 (t, J = 9.6 Hz, 2H), 3.22-2.93 (m, 3H), 2.75 (td, J = 11.5, 3.5 Hz, 1H), 2.54-2.36 (m, 1H), 2.33 (s, 3H), 1.57 (s, 1H), 1.15 (d, J = 6.3 Hz, 3H) ppm. |
| 260 | 376.29 | 0.6 | 1H NMR (400 MHz, DMSO-d6) δ 9.28 (s, 1H), 9.06 (s, 1H), 7.85 (dd, J = 8.6, 1.0 Hz, 2H), 7.58-7.52 (m, 2H), 7.50 (s, 1H), 7.35 (t, J = 7.4 Hz, 1H), 7.21 (s, 1H), 6.60 (s, 1H), 4.59 (t, J = 6.5 Hz, 2H), 4.51 (td, J = 6.0, 2.0 Hz, 2H), 3.65 (dt, J = 12.4, 6.2 Hz, 1H), 3.29-3.20 (m, 1H), 2.95 (t, J = 8.4 Hz, 1H), 2.70 (dd, J = 14.8, 8.0 Hz, 1H), 2.61 (td, J = 8.6, 5.4 Hz, 1H), 2.47-2.41 (m, 1H), 2.30-2.21 (m, 4H), 1.79 (dt, J = 14.4, 8.1 Hz, 1H) ppm. |
| 261 | 410 | 0.67 | 1H NMR (300 MHz, CDCl3) δ 8.29 (s, 1H), 7.30-7.22 (m, 3H), 7.21 (s, 1H), 7.16 (s, 1H), 6.78 (tt, J = 8.7, 2.3 Hz, 1H), 6.71 (s, 1H), 6.66 (s, 1H), 3.17 (d, J = 11.5 Hz, 2H), 2.50 (tt, J = 12.0, 4.1 Hz, 1H), 2.35 (s, 3H), 2.28 (dd, J = 11.7, 2.6 Hz, 2H), 1.83 (dd, J = 14.0, 7.0 Hz, |

TABLE 3-continued

Analytical Data

| Cmpd No. | LC/MS (M + H) | LC/MS Ret. Time (min) | ¹H-NMR |
|---|---|---|---|
| | | | 2H), 1.75 (dd, J = 12.5, 3.3 Hz, 1H), 1.69-1.57 (m, 1H), 0.47 (d, J = 6.5 Hz, 4H) ppm. |
| 262 | 384.23 | 0.57 | 1H NMR (400 MHz, CDCl3) δ 8.89 (d, J = 2.2 Hz, 1H), 8.56 (d, J = 2.1 Hz, 1H), 8.38 (s, 1H), 8.06 (t, J = 2.2 Hz, 1H), 7.13 (s, 1H), 6.77 (s, 1H), 6.72 (s, 1H), 6.44 (s, 1H), 3.34-3.21 (m, 4H), 2.60 (dd, J = 18.9, 13.9 Hz, 4H), 2.38 (s, 3H), 2.35 (s, 3H) ppm. |
| 263 | 386.15 | 0.52 | 1H NMR (400 MHz, DMSO-d6) δ 9.72 (s, 1H), 9.12 (s, 1H), 8.07-7.90 (m, 1H), 7.78-7.58 (m, 2H), 6.93 (s, 1H), 6.72 (s, 1H), 3.51-3.36 (m, 4H), 2.39 (dd, J = 19.5, 14.6 Hz, 4H), 2.25 (s, 3H), 2.22 (s, 3H) ppm. |
| 264 | 455.15 | 0.68 | 1H NMR (300 MHz, CDCl3) δ 8.32 (s, 1H), 7.26 (dd, J = 8.0, 2.2 Hz, 2H), 7.13 (t, J = 2.0 Hz, 1H), 6.83 (d, J = 1.8 Hz, 1H), 6.78 (dt, J = 8.7, 2.3 Hz, 1H), 6.66 (s, 1H), 6.47 (s, 1H), 4.67 (d, J = 5.5 Hz, 2H), 4.30 (d, J = 5.7 Hz, 2H), 3.38-3.18 (m, 4H), 2.65 (q, J = 7.6 Hz, 2H), 2.61-2.48 (m, 4H), 1.44 (s, 3H), 1.28 (t, J = 7.6 Hz, 4H) ppm. |
| 265 | 373.14 | 0.62 | 1H NMR (300 MHz, CD3OD) δ 8.95 (s, 1H), 7.86 (ddd, J = 11.3, 6.9, 2.6 Hz, 1H), 7.68 (ddt, J = 8.3, 4.2, 2.2 Hz, 1H), 7.61-7.34 (m, 2H), 6.90 (s, 1H), 3.87 (dd, J = 6.0, 3.8 Hz, 4H), 3.66 (s, 1H), 3.57 (dd, J = 6.1, 3.7 Hz, 4H), 2.51 (s, 3H) ppm. |
| 266 | 412 | 0.84 | 1H NMR (400 MHz, DMSO-d6) δ 9.47 (s, 1H), 9.17 (s, 1H), 7.63 (d, J = 8.1 Hz, 2H), 7.46 (s, 1H), 7.33 (d, J = 15.0 Hz, 1H), 7.25 (t, J = 8.4 Hz, 1H), 6.63 (d, J = 21.7 Hz, 1H), 4.47 (t, J = 10.7 Hz, 1H), 3.85 (t, J = 11.0 Hz, 1H), 3.05 (dd, J = 23.7, 10.5 Hz, 1H), 2.70-2.59 (m, 1H), 2.28 (s, 3H), 2.03 (s, 3H), 1.95 (d, J = 11.3 Hz, 1H), 1.82-1.61 (m, 3H), 1.61-1.35 (m, 2H) ppm. |
| 267 | 385.29 | 0.66 | 1H NMR (300 MHz, DMSO-d6) δ 9.27 (s, 1H), 9.15 (s, 1H), 7.60 (dd, J = 8.7, 2.2 Hz, 2H), 7.24 (tt, J = 10.4, 8.1 Hz, 1H), 6.90 (m, 1H), 6.60 (m, 1H), 5.90 (m, 1H), 3.43 (dd, J = 9.0, 6.1 Hz, 1H), 3.32-3.16 (m, 3H), 3.01 (dd, J = 9.1, 4.7 Hz, 1H), 2.33 (s, 3H), 2.20 (s, 3H), 2.14-2.01 (m, 1H), 1.79 (m, 1H) ppm. |
| 268 | 416.26 | 0.6 | 1H NMR (300 MHz, DMSO-d6) δ 9.81 (s, 1H), 9.20 (s, 1H), 7.70-7.58 (m, 2H), 7.40 (s, 1H), 7.29 (ddt, J = 18.7, 9.3, 2.2 Hz, 2H), 6.64 (d, J = 9.9 Hz, 1H), 4.58 (td, J = 6.5, 1.9 Hz, 2H), 4.50 (t, J = 5.7 Hz, 2H), 3.69-3.58 (m, 1H), 2.97-2.88 (m, 1H), 2.69-2.61 (m, 2H), 2.44 (dd, J = 8.9, 7.3 Hz, 2H), 2.35-2.19 (m, 1H), 1.78 (dt, J = 15.1, 7.2 Hz, 1H) ppm. |
| 269 | 338.1 | 2.33 | 1H NMR (400 MHz, DMSO-d6) δ 9.10 (s, 1H), 9.00 (s, 1H), 7.94-7.76 (m, 2H), 7.47-7.33 (m, 2H), 6.84 (s, 1H), 6.66 (s, 1H), 5.91 (s, 1H), 3.41-3.27 (m, 4H), 2.20 (s, 3H), 2.08-1.85 (m, 4H) ppm. |
| 270 | 308 | 0.61 | 1H NMR (400 MHz, CDCl3) δ 9.02 (d, J = 2.5 Hz, 1H), 8.62 (dd, J = 4.8, 1.3 Hz, 1H), 8.40 (s, 1H), 8.04 (ddd, J = 8.3, 2.6, 1.5 Hz, 1H), 7.56-7.42 (m, 2H), 6.88 (d, J = 5.9 Hz, 2H), 5.09 (dd, J = 8.3, 6.0 Hz, 2H), 4.82 (t, J = 6.3 Hz, 2H), 4.30-4.12 (m, 1H), 2.40 (s, 3H) ppm. |
| 271 | 407.25 | 0.61 | 1H NMR (300 MHz, DMSO-d6) δ 9.42 (s, 1H), 9.15 (s, 1H), 8.84 (s, 1H), 8.56 (s, 1H), 7.16 (s, 1H), 6.92 (s, 1H), 6.34 (s, 1H), 4.58 (t, J = 6.5 Hz, 2H), 4.49 (t, J = 6.1 Hz, 2H), 3.45 (dt, J = 12.7, 6.5 Hz, 1H), 3.25-3.03 (m, 4H), 2.56 (s, 3H), 2.40 (dd, J = 15.5, 10.8 Hz, 4H), 2.26 (d, J = 9.5 Hz, 3H) ppm. |
| 272 | 338.13 | 2.38 | 1H NMR (400 MHz, DMSO-d6) δ 9.34 (d, J = 41.3 Hz, 1H), 9.14 (s, 1H), 7.73 (s, 2H), 7.59 (dt, J = 14.9, 7.4 Hz, 1H), 7.19 (t, J = 7.7 Hz, 1H), 6.85 (s, 1H), 5.98 (s, 1H), 3.36 (s, 3H), 2.24 (s, 3H), 1.95 (d, J = 51.8 Hz, 3H) ppm. |

TABLE 3-continued

Analytical Data

| Cmpd No. | LC/MS (M + H) | LC/MS Ret. Time (min) | ¹H-NMR |
|---|---|---|---|
| 273 | 384 | 0.26 | |
| 274 | 363.42 | 0.62 | 1H NMR (300 MHz, DMSO-d6) δ 10.75 (s, 1H), 9.33 (s, 1H), 9.09 (s, 1H), 7.98-7.75 (m, 2H), 7.65-7.45 (m, 2H), 7.46-7.33 (m, 1H), 7.21 (s, 1H), 6.99 (d, J = 15.5 Hz, 1H), 6.38 (s, 1H), 3.74 (d, J = 10.6 Hz, 2H), 3.57 (d, J = 8.9 Hz, 2H), 3.14 (dt, J = 19.6, 9.9 Hz, 6H), 2.26 (d, J = 7.7 Hz, 3H), 1.29 (t, J = 7.3 Hz, 3H) ppm. |
| 275 | 392.44 | 0.54 | 1H NMR (300 MHz, DMSO-d6) δ 9.29 (s, 1H), 9.19-9.05 (m, 2H), 8.55 (dd, J = 4.7, 1.4 Hz, 1H), 8.20 (ddd, J = 8.3, 2.6, 1.4 Hz, 1H), 7.60 (ddd, J = 8.4, 4.8, 0.6 Hz, 1H), 7.15 (s, 1H), 6.89 (s, 1H), 6.31 (s, 1H), 4.57 (t, J = 6.5 Hz, 2H), 4.49 (t, J = 6.1 Hz, 2H), 3.45 (p, J = 6.3 Hz, 1H), 3.16 (dd, J = 8.5, 5.1 Hz, 4H), 2.45-2.32 (m, 4H), 2.23 (s, 3H) ppm. |
| 276 | 441.17 | 0.61 | 1H NMR (400 MHz, CDCl3) δ 8.49 (d, J = 2.6 Hz, 1H), 7.25 (ddd, J = 8.3, 5.3, 2.6 Hz, 1H), 7.20-7.12 (m, 1H), 7.11 (t, J = 2.1 Hz, 1H), 6.86 (s, 1H), 6.80 (s, 1H), 6.46 (s, 1H), 4.80-4.61 (m, 4H), 3.59 (p, J = 6.4 Hz, 1H), 3.36-3.24 (m, 4H), 2.64 (q, J = 7.6 Hz, 2H), 2.58-2.47 (m, 4H), 1.28 (t, J = 7.6 Hz, 3H) ppm. |
| 277 | 449.32 | 0.56 | 1H NMR (400 MHz, CDCl3) δ 9.00 (s, 1H), 8.63 (t, J = 6.0 Hz, 1H), 7.35 (d, J = 5.4 Hz, 1H), 7.01 (t, J = 2.0 Hz, 1H), 6.83 (s, 1H), 6.77 (s, 1H), 6.39 (s, 1H), 4.72 (dt, J = 14.5, 6.4 Hz, 4H), 4.10 (d, J = 6.2 Hz, 3H), 3.59 (p, J = 6.4 Hz, 1H), 3.36-3.23 (m, 4H), 2.62-2.48 (m, 4H), 1.97-1.81 (m, 1H), 1.03-0.92 (m, 2H), 0.81-0.66 (m, 2H) ppm. |
| 278 | 441.45 | 0.6 | 1H NMR (300 MHz, CDCl3) δ 8.30 (d, J = 18.3 Hz, 1H), 7.69-7.55 (m, 1H), 7.47-7.29 (m, 2H), 6.95 (d, J = 11.2 Hz, 1H), 6.59 (s, 1H), 6.50 (s, 1H), 6.10 (s, 1H), 4.96 (s, 2H), 4.76 (t, J = 7.3 Hz, 2H), 3.96 (s, 2H), 3.68-3.45 (m, 2H), 3.24 (s, 2H), 2.57 (d, J = 40.5 Hz, 2H), 2.11 (dd, J = 36.1, 13.1 Hz, 2H) ppm. |
| 279 | 412.33 | 0.64 | 1H NMR (300 MHz, CDCl3) δ 8.22 (d, J = 13.2 Hz, 1H), 7.16 (s, 1H), 7.08 (s, 1H), 6.71 (dd, J = 10.6, 8.6 Hz, 3H), 6.35 (s, 1H), 4.42 (s, 5H), 3.12 (dd, J = 14.7, 9.2 Hz, 4H), 2.21 (d, J = 22.0 Hz, 3H), 2.07-1.87 (m, 5H) ppm. |
| 280 | 391 | 66 | |
| 281 | 344.8 | 0.69 | 1H NMR (300 MHz, CDCl3) δ 8.38 (s, 1H), 8.03 (dt, J = 2.2, 0.9 Hz, 1H), 7.93 (s, 1H), 7.72-7.56 (m, 2H), 6.77 (s, 1H), 6.62 (s, 2H), 6.10 (s, 1H), 3.37 (d, J = 6.1 Hz, 4H), 2.35 (s, 3H), 2.05 (t, J = 5.1 Hz, 4H) ppm. |
| 282 | 442.15 | 0.73 | 1H NMR (400 MHz, DMSO-d6) δ 9.42 (s, 1H), 9.17 (s, 1H), 7.77-7.53 (m, 2H), 7.34 (s, 1H), 7.30-7.19 (m, 2H), 6.59 (s, 1H), 4.55 (dd, J = 12.7, 6.3 Hz, 3H), 4.44 (td, J = 6.0, 2.3 Hz, 2H), 3.65 (d, J = 4.4 Hz, 1H), 3.64-3.23 (m, 6H), 2.86 (dd, J = 10.2, 3.5 Hz, 1H), 2.70 (d, J = 10.8 Hz, 1H), 2.27 (s, 3H), 2.21 (d, J = 4.5 Hz, 1H), 1.80 (dd, J = 11.2, 8.8 Hz, 1H), 1.73-1.49 (m, 3H) ppm. |
| 283 | 361 | 68 | 1H NMR (400 MHz, DMSO-d6) δ 9.53 (s, 1H), 8.75 (d, J = 2.2 Hz, 1H), 7.87 (td, J = 8.9, 6.0 Hz, 1H), 7.64 (ddd, J = 11.6, 9.0, 2.7 Hz, 1H), 7.33 (t, J = 7.9 Hz, 1H), 6.78 (d, J = 11.9 Hz, 1H), 6.49 (d, J = 7.2 Hz, 1H), 5.80-5.63 (m, 1H), 3.99 (dd, J = 14.9, 7.8 Hz, 2H), 3.83-3.69 (m, 1H), 3.35 (dd, J = 14.9, 7.8 Hz, 2H—partially obscured by MeOH) ppm. |

TABLE 3-continued

Analytical Data

| Cmpd No. | LC/MS (M + H) | LC/MS Ret. Time (min) | ¹H-NMR |
|---|---|---|---|
| 284 | 441 | 0.68 | 1H NMR (400 MHz, CDCl3) δ 8.30 (s, 1H), 7.33-7.16 (m, 5H), 6.93 (s, 1H), 6.81-6.69 (m, 1H), 6.60 (s, 1H), 6.47 (s, 1H), 6.03 (s, 1H), 3.78 (t, J = 4.7 Hz, 3H), 3.69-3.55 (m, 1H), 3.50 (t, J = 8.4 Hz, 1H), 3.37 (dt, J = 16.4, 8.1 Hz, 1H), 3.26 (t, J = 8.5 Hz, 1H), 3.04-2.87 (m, 1H), 2.58 (d, J = 20.4 Hz, 4H), 2.32 (s, 2H), 2.30-2.17 (m, 1H), 1.95 (dd, J = 19.9, 10.7 Hz, 1H). |
| 285 | 493.38 | 0.94 | H NMR (300 MHz, CDCl3) δ 8.28 (s, 1H), 7.10 (s, 1H), 7.04 (s, 1H), 7.00-6.92 (m, 1H), 6.71 (s, 1H), 6.57 (d, J = 10.7 Hz, 2H), 6.36 (s, 1H), 4.79-4.67 (m, 4H), 4.68-4.53 (m, 1H), 3.68-3.50 (m, 1H), 3.41-3.23 (m, 4H), 2.61-2.44 (m, 4H), 1.97-1.82 (m, 1H), 1.40 (d, J = 6.0 Hz, 6H), 0.96 (dt, J = 6.2, 4.3 Hz, 2H) 0.84-0.67 (m, 2H) ppm. |
| 286 | 463.32 | 0.6 | 1H NMR (400 MHz, CDCl3) δ 8.95 (s, 1H), 8.59 (d, J = 0.8 Hz, 1H), 7.06 (t, J = 2.0 Hz, 1H), 7.03 (d, J = 0.8 Hz, 1H), 6.87 (s, 1H), 6.77 (s, 1H), 6.37 (s, 1H), 4.72 (dq, J = 12.7, 6.4 Hz, 4H), 4.51 (q, J = 7.1 Hz, 2H), 3.66-3.48 (m, 1H), 3.36-3.25 (m, 4H), 2.61-2.46 (m, 4H), 1.98-1.84 (m, 1H), 1.46 (t, J = 7.1 Hz, 3H), 1.06-0.90 (m, 2H), 0.79-0.68 (m, 2H) ppm. |
| 287 | 459.13 | 0.62 | 1H NMR (400 MHz, CDCl3) δ 8.40 (s, 1H), 8.04 (s, 1H), 7.84 (d, J = 7.8 Hz, 1H), 7.69-7.53 (m, 2H), 7.31 (s, 1H), 6.70 (s, 2H), 6.43 (s, 1H), 4.72 (dq, J = 12.5, 6.4 Hz, 4H), 3.59 (p, J = 6.4 Hz, 1H), 3.37-3.25 (m, 4H), 2.60-2.47 (m, 4H), 2.35 (s, 3H) ppm. |
| 288 | 435.42 | 0.68 | 1H NMR (300 MHz, DMSO-d6) δ 9.45 (s, 1H), 9.21 (s, 1H), 9.01 (d, J = 1.2 Hz, 1H), 8.66 (d, J = 2.5 Hz, 1H), 8.58 (dd, J = 2.5, 1.4 Hz, 1H), 7.29 (s, 1H), 7.12 (s, 1H), 6.53 (s, 1H), 4.58 (t, J = 6.4 Hz, 2H), 4.55-4.36 (m, 3H), 3.56-3.40 (m, 1H), 3.16 (d, J = 4.7 Hz, 4H), 2.42 (t, J = 9.0 Hz, 4H), 1.29 (s, 9H) ppm. |
| 289 | 419.4 | 0.63 | 1H NMR (300 MHz, CDCl3) δ 8.33 (s, 1H), 7.69 (dd, J = 8.5, 1.1 Hz, 2H), 7.52 (dd, J = 10.6, 5.1 Hz, 2H), 7.37 (dt, J = 9.1, 4.2 Hz, 1H), 7.13 (s, 1H), 6.82 (s, 1H), 6.65 (s, 1H), 6.42 (s, 1H), 4.08 (dd, J = 11.0, 4.0 Hz, 2H), 3.43 (td, J = 11.8, 1.8 Hz, 2H), 3.34-3.19 (m, 4H), 2.81-2.69 (m, 4H), 2.59-2.42 (m, 1H), 1.85 (dd, J = 12.4, 1.8 Hz, 2H), 1.65 (qd, J = 12.4, 4.5 Hz, 3H) ppm. |
| 290 | 389.38 | 0.65 | 1H NMR (300 MHz, DMSO-d6) δ 9.17 (s, 1H), 9.04 (s, 1H), 7.82 (dd, J = 8.6, 1.1 Hz, 2H), 7.55 (dd, J = 10.7, 5.2 Hz, 2H), 7.34 (t, J = 7.4 Hz, 1H), 7.14 (s, 1H), 6.88 (s, 1H), 6.28 (s, 1H), 3.20-3.02 (m, 4H), 2.74 (p, J = 8.0 Hz, 1H), 2.48-2.32 (m, 4H), 2.24 (d, J = 15.9 Hz, 3H), 2.07-1.91 (m, 2H), 1.91-1.74 (m, 2H), 1.74-1.51 (m, 2H) ppm. |
| 291 | 411.16 | 0.51 | 1H NMR (400 MHz, CDCl3) δ 9.02 (s, 1H), 8.87 (d, J = 2.1 Hz, 1H), 8.77 (d, J = 3.7 Hz, 1H), 7.40 (s, 1H), 6.77 (s, 1H), 6.66 (s, 1H), 6.43 (s, 1H), 4.80-4.66 (m, 3H), 3.60 (dd, J = 12.6, 6.1 Hz, 1H), 3.39-3.25 (m, 3H), 2.60-2.46 (m, 3H), 2.34 (s, 3H) ppm. |
| 292 | 387 | 0.63 | 1H NMR (400 MHz, CDCl3) δ 8.30 (s, 1H), 7.67 (d, J = 7.7 Hz, 2H), 7.48 (t, J = 7.9 Hz, 2H), 7.33 (t, J = 7.4 Hz, 1H), 6.84 (s, 1H), 6.60 (s, 1H), 6.57 (s, 1H), 6.04 (s, 1H), 4.25 (s, 1H), 3.64 (s, 1H), 3.56-3.41 (m, 2H), 3.12 (d, J = 9.5 Hz, 1H), 2.90 (d, J = 9.6 Hz, 1H), 2.30 (s, 3H), 2.01-1.87 (m, 3H), 0.41 (dd, J = 13.4, 6.3 Hz, 4H) ppm. |
| 293 | 400.24 | 0.64 | 1H NMR (400 MHz, CDCl3) δ 8.24 (s, 1H), 7.18-7.15 (m, 1H), 7.10 (s, 1H), 6.70 (ddt, J = 8.6, 4.5, 2.2 Hz, 2H), 6.63 (s, 1H), 6.35 (s, 1H), 3.68 (dd, J = 11.8, 3.8 Hz, 1H), 3.41-3.35 (m, 4H), 2.84-2.68 (m, 2H), 2.25 (s, 3H), |

TABLE 3-continued

Analytical Data

| Cmpd No. | LC/MS (M + H) | LC/MS Ret. Time (min) | ¹H-NMR |
|---|---|---|---|
| | | | 2.05-1.96 (m, 1H), 1.81 (ddd, J = 17.2, 8.3, 4.3 Hz, 1H), 1.70-1.51 (m, 3H), 1.45-1.33 (m, 1H) ppm. |
| 294 | 404.5 | 0.66 | 1H NMR (300 MHz, CDCl3) δ 8.33 (s, 1H), 7.71 (dd, J = 8.6, 1.1 Hz, 2H), 7.57-7.48 (m, 2H), 7.38 (dt, J = 8.0, 3.7 Hz, 1H), 7.28-7.25 (m, 1H), 7.23 (s, 1H), 6.72 (s, 1H), 6.67 (s, 1H), 4.68 (s, 2H), 4.27 (d, J = 5.7 Hz, 2H), 2.71 (s, 2H), 2.51 (s, 1H), 2.27 (d, J = 63.5 Hz, 5H), 1.91 (s, 4H), 1.47 (s, 3H) ppm. |
| 295 | 372.1 | 0.75 | 1H NMR (300 MHz, DMSO-d6) δ 9.63 (s, 1H), 9.19 (s, 1H), 7.74-7.54 (m, 4H), 7.34 (s, 1H), 7.30-7.18 (m, 1H), 6.70 (s, 1H), 5.60-5.50 (m, 1H), 3.90 (t, J = 8.6 Hz, 1H), 3.28 (m, 1H), 2.31 (s, 3H) ppm. |
| 296 | 365.17 | 0.62 | 1H NMR (400 MHz, CDCl3) δ 8.35 (s, 1H), 7.65 (d, J = 7.7 Hz, 2H), 7.50 (t, J = 7.9 Hz, 2H), 7.35 (dd, J = 18.9, 11.5 Hz, 1H), 6.68 (d, J = 1.5 Hz, 1H), 6.48 (t, J = 3.5 Hz, 1H), 5.35 (d, J = 53.2 Hz, 1H), 3.96-3.65 (m, 3H), 3.59 (td, J = 10.2, 6.6 Hz, 1H), 2.48-2.26 (m, 2H), 2.08-2.03 (m, 1H), 1.02-0.95 (m, 2H), 0.91 (ddd, J = 10.3, 6.3, 3.9 Hz, 2H) ppm. |
| 297 | 350 | 0.49 | 1H NMR (400 MHz, Acetone-d6) δ 9.14 (d, J = 2.6 Hz, 1H), 8.90 (s, 1H), 8.56 (dd, J = 4.7, 1.2 Hz, 1H), 8.31 (s, 1H), 8.27-8.15 (m, 1H), 7.56 (dd, J = 8.3, 4.7 Hz, 1H), 7.31 (s, 1H), 7.00 (s, 1H), 6.38 (s, 1H), 3.30-3.09 (m, 4H), 2.62-2.41 (m, 4H), 2.27 (d, J = 5.6 Hz, 6H) ppm. |
| 298 | 426.28 | 0.82 | 1H NMR (300 MHz, DMSO-d6) δ 9.45 (s, 1H), 9.17 (s, 1H), 7.60 (dd, J = 8.7, 2.2 Hz, 2H), 7.31-7.15 (m, 3H), 6.60 (s, 1H), 6.44-6.34 (m, 1H), 4.89 (d, J = 3.0 Hz, 2H), 4.74 (d, J = 3.5 Hz, 2H), 3.82-3.70 (m, 4H), 3.20-3.08 (m, 4H) ppm. |
| 299 | 414 | 0.65 | 1H NMR (300 MHz, Acetone-d6) δ 8.82 (s, 1H), 8.25 (s, 1H), 7.87 (ddd, J = 11.8, 7.0, 2.6 Hz, 1H), 7.79-7.63 (m, 1H), 7.53 (dt, J = 10.2, 8.8 Hz, 1H), 7.31 (t, J = 2.0 Hz, 1H), 6.95 (s, 1H), 6.38 (s, 1H), 3.77 (d, J = 12.4 Hz, 2H), 3.29 (s, 3H), 3.25 (d, J = 6.1 Hz, 2H), 2.72 (td, J = 12.3, 2.4 Hz, 2H), 2.27 (s, 3H), 1.87-1.68 (m, 3H), 1.37 (ddd, J = 14.9, 12.0, 3.8 Hz, 2H) ppm. |
| 300 | 378 | 0.77 | 1H NMR (400 MHz, CDCl3) δ 9.21 (d, J = 11.6 Hz, 1H), 8.92 (d, J = 5.0 Hz, 1H), 8.66-8.50 (m, 1H), 8.39 (s, 1H), 7.27 (dd, J = 21.0, 9.5 Hz, 3H), 6.93 (d, J = 21.7 Hz, 1H), 6.71 (d, J = 7.0 Hz, 1H), 4.77 (dd, J = 37.1, 12.4 Hz, 1H), 3.90 (t, J = 12.6 Hz, 1H), 3.12 (dd, J = 26.0, 13.6 Hz, 1H), 2.80-2.62 (m, 1H), 2.58 (t, J = 11.9 Hz, 1H), 2.38 (d, J = 9.0 Hz, 3H), 2.14 (d, J = 10.4 Hz, 4H), 2.00-1.49 (m, 4H) ppm. |
| 301 | 398.26 | 0.6 | 1H NMR (400 MHz, DMSO-d6) δ 9.39 (s, 1H), 9.07 (s, 1H), 7.97 (ddd, J = 11.8, 7.0, 2.5 Hz, 1H), 7.72 (d, J = 9.1 Hz, 1H), 7.69-7.60 (m, 1H), 7.59 (s, 1H), 7.23 (s, 1H), 7.23 (s, 1H), 6.64 (s, 1H), 4.59 (t, J = 6.6 Hz, 2H), 4.45-4.40 (m, 2H), 3.81-3.73 (m, 1H), 3.68-3.54 (m, 3H), 3.25-3.13 (m, 2H), 2.27 (s, 3H) ppm. |
| 302 | 433.39 | 0.58 | 1H NMR (400 MHz, CDCl3) δ 9.01 (s, 1H), 8.90 (d, J = 0.9 Hz, 1H), 7.57 (s, 1H), 7.05-6.94 (m, 2H), 6.81 (s, 1H), 6.38 (s, 1H), 4.71 (dt, J = 16.5, 6.4 Hz, 4H), 3.59 (p, J = 6.4 Hz, 1H), 3.38-3.24 (m, 4H), 2.64 (s, 3H), 2.59-2.49 (m, 4H), 1.96-1.85 (m, 1H), 1.08-0.91 (m, 2H), 0.82-0.71 (m, 2H) ppm. |
| 303 | 489.1 | 0.64 | 1H NMR (300 MHz, CDCl3) δ 8.31 (s, 1H), 7.77-7.66 (m, 2H), 7.43-7.32 (m, 2H), 7.11 (t, J = 2.0 Hz, 1H), 6.86 (s, 1H), 6.77 (s, 1H), 6.46 (s, 1H), 4.79-4.63 (m, 4H), 3.59 (p, J = 6.4 Hz, 1H), 3.37-3.24 (m, 4H), 2.72-2.57 (m, 2H), 2.56-2.46 (m, 4H), 1.28 (t, J = 7.6 Hz, 3H) ppm. |

TABLE 3-continued

Analytical Data

| Cmpd No. | LC/MS (M + H) | LC/MS Ret. Time (min) | ¹H-NMR |
|---|---|---|---|
| 304 | 428.44 | 0.67 | 1H NMR (300 MHz, DMSO-d6) δ 9.56 (s, 1H), 9.20 (s, 1H), 7.63 (d, J = 6.7 Hz, 2H), 7.27 (td, J = 9.3, 2.2 Hz, 1H), 7.14 (s, 1H), 7.03 (s, 1H), 6.33 (s, 2H), 5.09 (d, J = 19.2 Hz, 1H), 4.67 (d, J = 49.7 Hz, 3H), 4.16-3.92 (m, 2H), 3.90-3.59 (m, 3H), 3.35 (ddd, J = 46.7, 32.3, 22.1 Hz, 2H), 2.30 (d, J = 14.1 Hz, 4H) ppm. |
| 305 | 362.38 | 0.75 | 1H NMR (300 MHz, CDCl3) δ 8.33 (s, 1H), 7.73-7.65 (m, 2H), 7.51 (t, J = 7.9 Hz, 2H), 7.40-7.33 (m, 1H), 7.11 (t, J = 2.1 Hz, 1H), 6.73 (dd, J = 9.9, 8.3 Hz, 2H), 6.33 (d, J = 1.5 Hz, 1H), 3.97-3.81 (m, 4H), 3.27-3.17 (m, 4H), 1.90 (ddd, J = 16.9, 8.5, 5.1 Hz, 1H), 1.01-0.90 (m, 2H), 0.75 (dt, J = 6.7, 4.6 Hz, 2H) ppm. |
| 306 | 364 | 0.7 | 1H NMR (400 MHz, DMSO-d6) δ 9.20 (s, 1H), 9.06 (s, 1H), 7.84 (dd, J = 5.4, 3.3 Hz, 2H), 7.61-7.46 (m, 2H), 7.33 (dd, J = 19.9, 13.5 Hz, 2H), 6.81 (d, J = 5.3 Hz, 1H), 6.29 (d, J = 16.5 Hz, 1H), 4.07 (dd, J = 6.2, 2.8 Hz, 1H), 3.81-3.65 (m, 1H), 3.54 (d, J = 11.8 Hz, 1H), 3.16 (dd, J = 11.9, 2.8 Hz, 1H), 2.85 (dd, J = 11.7, 6.0 Hz, 1H), 2.25 (d, J = 23.1 Hz, 4H), 1.20 (dd, J = 22.3, 6.3 Hz, 6H) ppm. |
| 307 | 355.17 | 0.66 | 1H NMR (400 MHz, DMSO-d6) δ 9.22 (s, 1H), 8.51 (d, J = 3.4 Hz, 1H), 8.40 (d, J = 4.8 Hz, 1H), 8.16 (d, J = 8.2 Hz, 1H), 8.05 (td, J = 7.9, 1.8 Hz, 1H), 7.43 (dd, J = 7.0, 5.2 Hz, 1H), 7.13 (s, 1H), 4.05 (dd, J = 8.2, 3.8 Hz, 4H), 3.52-3.44 (m, 4H), 2.29 (d, J = 1.8 Hz, 3H) ppm. |
| 308 | 334 | 0.59 | 1H NMR (400 MHz, Acetone-d6) δ 8.78 (s, 1H), 8.24 (s, 1H), 7.87 (dd, J = 8.6, 1.1 Hz, 2H), 7.54 (dd, J = 8.4, 7.6 Hz, 2H), 7.47 (s, 1H), 7.43 (s, 1H), 7.35 (t, J = 7.4 Hz, 1H), 3.19 (d, J = 12.0 Hz, 2H), 2.77 (dd, J = 12.0, 9.9 Hz, 2H), 2.61 (t, J = 11.9 Hz, 1H), 2.31 (s, 3H), 1.82 (d, J = 12.5 Hz, 2H), 1.70 (ddd, J = 25.1, 12.5, 3.9 Hz, 2H) ppm. |
| 309 | 391.45 | 0.63 | 1H NMR (300 MHz, DMSO-d6) δ 9.06 (d, J = 10.2 Hz, 2H), 7.97-7.76 (m, 2H), 7.54 (t, J = 8.0 Hz, 2H), 7.34 (t, J = 7.4 Hz, 1H), 6.90 (s, 1H), 6.55 (s, 1H), 5.92 (s, 1H), 5.59 (d, J = 6.4 Hz, 1H), 4.68-4.52 (m, 2H), 4.46 (dd, J = 12.2, 6.2 Hz, 2H), 3.88 (s, 1H), 3.59 (s, 1H), 2.83 (s, 1H), 2.59 (s, 1H), 2.38 (s, 2H), 2.32-2.17 (m, 1H), 2.14 (s, 3H), 1.67 (d, J = 6.3 Hz, 1H) ppm. |
| 310 | 443.32 | 0.61 | 1H NMR (400 MHz, DMSO-d6) δ 9.41 (s, 1H), 9.16 (s, 1H), 7.59 (dd, J = 8.5, 2.1 Hz, 2H), 7.26 (dd, J = 10.4, 8.2 Hz, 1H), 6.83 (d, J = 2.0 Hz, 2H), 6.06 (s, 1H), 4.57 (t, J = 6.5 Hz, 2H), 4.48 (t, J = 6.1 Hz, 2H), 3.72 (s, 3H), 3.50-3.39 (m, 1H), 3.20-3.11 (m, 4H), 2.44-2.37 (m, 4H) ppm. |
| 311 | 459.54 | 0.64 | 1H NMR (300 MHz, CDCl3) δ 8.31 (s, 1H), 7.25 (dd, J = 7.7, 2.0 Hz, 2H), 7.07 (s, 1H), 6.79 (dd, J = 9.0, 5.5 Hz, 3H), 6.41 (s, 1H), 3.72 (d, J = 11.1 Hz, 1H), 3.52 (d, J = 10.6 Hz, 1H), 3.26 (t, J = 4.8 Hz, 4H), 3.02 (dd, J = 11.0, 5.0 Hz, 2H), 2.83-2.68 (m, 2H), 2.64 (d, J = 3.0 Hz, 2H), 2.35 (s, 3H), 1.14 (s, 3H) ppm. |
| 312 | 421.28 | 0.57 | 1H NMR (400 MHz, CDCl3) δ 9.02 (s, 1H), 7.39 (s, 1H), 7.06 (s, 1H), 6.93 (s, 1H), 6.87 (s, 1H), 6.44 (s, 1H), 4.72 (dt, J = 15.5, 6.4 Hz, 4H), 3.59 (p, J = 6.4 Hz, 1H), 3.37-3.25 (m, 4H), 2.71 (s, 3H), 2.59 (s, 3H), 2.57-2.48 (m, 4H), 2.36 (s, 3H) ppm. |
| 313 | 469.34 | 0.58 | 19F NMR (282 MHz, DMSO-d6) δ −107.59 (s) ppm. |

TABLE 3-continued

Analytical Data

| Cmpd No. | LC/MS (M + H) | LC/MS Ret. Time (min) | ¹H-NMR |
|---|---|---|---|
| 314 | 437.3 | 0.56 | 1H NMR (400 MHz, CDCl3) δ 9.00 (s, 1H), 8.64 (d, J = 5.4 Hz, 1H), 7.36 (d, J = 5.4 Hz, 1H), 7.08 (t, J = 2.0 Hz, 1H), 6.88 (s, 1H), 6.81 (s, 1H), 6.49 (s, 1H), 4.72 (dq, J = 12.5, 6.4 Hz, 4H), 4.11 (s, 3H), 3.60 (p, J = 6.4 Hz, 1H), 3.38-3.23 (m, 4H), 2.65 (q, J = 7.6 Hz, 2H), 2.61-2.48 (m, 4H), 1.28 (t, J = 7.4, Hz, 3H) ppm. |
| 315 | 401.35 | 0.89 | 1H NMR (300 MHz, CDCl3) δ 8.35 (s, 1H), 7.74-7.66 (m, 2H), 7.58-7.48 (m, 4H), 7.42-7.34 (m, 1H), 7.06 (t, J = 1.5 Hz, 1H), 6.79 (s, 1H), 6.20 (tt, J = 2.9, 1.5 Hz, 2H), 4.37 (q, J = 2.8 Hz, 4H), 3.98 (t, J = 5.5 Hz, 4H), 2.65-2.52 (m, 4H) ppm. |
| 316 | 334 | 0.6 | 1H NMR (300 MHz, Acetone-d6) δ 8.79 (s, 1H), 7.89 (t, J = 1.6 Hz, 1H), 7.88-7.83 (m, 1H), 7.61-7.50 (m, 2H), 7.48 (s, 1H), 7.41 (s, 1H), 7.39-7.31 (m, 1H), 6.62 (s, 1H), 3.05 (dd, J = 20.8, 10.4 Hz, 2H), 2.78-2.51 (m, 6H), 2.31 (s, 3H), 1.96 (d, J = 12.5 Hz, 1H), 1.76-1.50 (m, 3H) ppm. |
| 317 | 385 | 0.61 | 1H NMR (400 MHz, Acetone-d6) δ 8.82 (s, 1H), 8.27 (s, 1H), 7.87 (ddd, J = 11.7, 7.0, 2.6 Hz, 1H), 7.79-7.66 (m, 1H), 7.53 (dt, J = 10.2, 8.8 Hz, 1H), 7.29 (t, J = 1.9 Hz, 1H), 6.98 (s, 1H), 6.38 (s, 1H), 3.24-3.12 (m, 4H), 2.58-2.41 (m, 4H), 2.27 (d, J = 3.5 Hz, 6H) ppm. |
| 318 | 536.22 | 0.62 | 1H NMR (300 MHz, CDCl3) δ 8.28 (s, 1H), 6.70 (s, 2H), 6.63 (t, J = 4.7 Hz, 2H), 6.41 (s, 1H), 6.20 (d, J = 11.7 Hz, 1H), 4.79-4.66 (m, 4H), 3.59 (dt, J = 12.6, 6.3 Hz, 1H), 3.53-3.35 (m, 3H), 3.35-3.23 (m, 4H), 2.60-2.51 (m, 4H), 2.49-2.38 (m, 1H), 2.33 (s, 3H), 2.17-1.92 (m, 2H), 1.33 (d, J = 8.0 Hz, 6H) ppm. |
| 319 | 408.2 | 0.63 | 1H NMR (300 MHz, CD3OD) δ 8.92 (s, 1H), 7.92-7.71 (m, 3H), 7.69-7.50 (m, 3H), 7.42 (t, J = 7.5 Hz, 1H), 3.85 (t, J = 4.8 Hz, 8H), 3.43 (t, J = 4.8 Hz, 8H) ppm. |
| 320 | 339.47 | 0.71 | 1H NMR (400 MHz, DMSO-d6) δ 9.75 (s, 1H), 9.30-9.24 (m, 1H), 9.11 (s, 1H), 8.45 (d, J = 10.5 Hz, 1H), 7.76 (s, 1H), 7.10 (s, 1H), 6.64 (d, J = 72.9 Hz, 1H), 3.52 (s, 3H), 2.46 (s, 1H), 2.30 (s, 2H), 2.09 (d, J = 13.7 Hz, 4H) ppm. |
| 321 | 376.08 | 2.96 | 1H NMR (400 MHz, DMSO-d6) δ 9.65 (s, 1H), 8.78 (d, J = 2.3 Hz, 1H), 7.90 (td, J = 8.9, 5.9 Hz, 1H), 7.64 (ddd, J = 11.6, 8.9, 2.8 Hz, 1H), 7.33 (t, J = 8.6 Hz, 1H), 7.01 (d, J = 1.9 Hz, 2H), 6.33 (t, J = 19.4 Hz, 1H), 3.91-3.71 (m, 4H), 3.15-3.07 (m, 4H) ppm. |
| 322 | 473.13 | 0.64 | 1H NMR (300 MHz, CDCl3) δ 8.41 (s, 1H), 7.88-7.71 (m, 4H), 7.13 (d, J = 1.9 Hz, 1H), 6.87 (s, 1H), 6.79 (s, 1H), 6.47 (s, 1H), 4.81-4.62 (m, 4H), 3.69-3.51 (m, 1H), 3.39-3.25 (m, 4H), 2.65 (q, J = 7.6 Hz, 2H), 2.57-2.48 (m, 4H), 1.28 (t, J = 7.6 Hz, 3H) ppm. |
| 323 | 423.3 | 0.62 | 1H NMR (300 MHz, CDCl3) δ 8.30 (s, 1H), 7.24 (s, 1H), 7.15 (s, 1H), 6.88 (d, J = 8.6 Hz, 1H), 6.79 (s, 1H), 6.60 (s, 1H), 6.42 (s, 1H), 4.80-4.62 (m, 4H), 3.67-3.47 (m, 1H), 3.39-3.22 (m, 4H), 2.61-2.49 (m, 4H), 2.45 (s, 3H), 2.35 (s, 3H) ppm. |
| 324 | 455 | 0.62 | 1H NMR (400 MHz, CDCl3) δ 8.30 (s, 1H), 7.33-7.20 (m, 4H), 7.12 (s, 1H), 6.78 (tt, J = 8.7, 2.3 Hz, 1H), 6.73 (s, 1H), 6.65 (s, 1H), 6.42 (s, 1H), 3.81 (d, J = 12.5 Hz, 2H), 3.77-3.67 (m, 4H), 2.78 (dd, J = 12.2, 10.2 Hz, 2H), 2.67-2.55 (m, 4H), 2.37 (t, J = 7.4 Hz, 1H), 2.32 (s, 3H), 1.95 (d, J = 12.6 Hz, 2H), 1.75-1.61 (m, 2H) ppm. |
| 325 | 416.27 | 0.79 | 1H NMR (300 MHz, DMSO-d6) δ 9.39 (s, 1H), 9.17 (s, 1H), 7.66-7.55 (m, 2H), 7.30-7.20 (m, 2H), 6.82 (s, 1H), 6.33 (s, 1H), 3.94 (d, J = 11.5 Hz, 1H), 3.77-3.38 (m, 7H), 3.29 (s, 3H), 2.68 (td, J = 11.7, 3.3 Hz, 1H), 2.23 (s, 3H) ppm. |

TABLE 3-continued

Analytical Data

| Cmpd No. | LC/MS (M + H) | LC/MS Ret. Time (min) | ¹H-NMR |
|---|---|---|---|
| 326 | 377.37 | 0.63 | 1H NMR (300 MHz, CDCl3) δ 8.32 (s, 1H), 7.68 (ddd, J = 17.3, 9.2, 7.1 Hz, 2H), 7.59-7.46 (m, 2H), 7.43-7.32 (m, 1H), 7.12 (d, J = 1.9 Hz, 1H), 6.82 (s, 1H), 6.60 (s, 1H), 6.42 (s, 1H), 3.35-3.22 (m, 4H), 2.82-2.61 (m, 5H), 2.35 (s, 3H), 1.13 (d, J = 6.5 Hz, 6H) ppm. |
| 327 | 397.26 | 0.66 | 1H NMR (300 MHz, CDCl3) δ 8.29 (s, 1H), 7.58 (ddd, J = 10.8, 6.8, 2.5 Hz, 1H), 7.37 (dddd, J = 20.3, 12.3, 7.4, 2.2 Hz, 2H), 6.92 (s, 1H), 6.76 (d, J = 1.6 Hz, 1H), 6.61 (d, J = 1.6 Hz, 1H), 3.54 (s, 4H), 1.90 (ddd, J = 12.9, 8.1, 4.8 Hz, 1H), 1.65 (s, 6H), 1.09-0.99 (m, 2H), 0.86 (ddd, J = 10.1, 6.4, 3.7 Hz, 2H) ppm. |
| 328 | 384 | 0.64 | 1H NMR (300 MHz, Acetone-d6) δ 8.94 (s, 1H), 7.61 (d, J = 2.2 Hz, 1H), 7.57 (d, J = 7.0 Hz, 2H), 7.37 (s, 1H), 7.02 (dd, J = 10.2, 8.0 Hz, 1H), 6.67 (s, 1H), 2.97-2.64 (m, 5H), 2.32 (s, 3H), 2.23 (s, 3H), 1.92 (ddd, J = 16.2, 13.9, 6.8 Hz, 4H), 1.72 (ddd, J = 16.6, 12.4, 8.4 Hz, 2H), 1.44 (ddd, J = 24.4, 12.3, 5.0 Hz, 1H) ppm. |
| 329 | 428.49 | 0.64 | 1H NMR (300 MHz, DMSO-d6) δ 9.43 (s, 1H), 9.11 (s, 1H), 7.44 (dd, J = 8.8, 1.8 Hz, 1H), 7.27 (d, J = 8.5 Hz, 1H), 7.09 (s, 1H), 6.94 (s, 1H), 6.34 (s, 1H), 4.57 (t, J = 6.5 Hz, 2H), 4.48 (t, J = 6.1 Hz, 2H), 3.55-3.40 (m, 1H), 3.25-3.03 (m, 3H), 2.49-2.36 (m, 7H), 2.24 (s, 3H) ppm. |
| 330 | 405.54 | 0.65 | 1H NMR (300 MHz, CDCl3) δ 8.33 (s, 1H), 7.74-7.66 (m, 2H), 7.55-7.47 (m, 2H), 7.39-7.32 (m, 1H), 7.16 (t, J = 2.1 Hz, 1H), 6.85 (s, 1H), 6.67 (s, 1H), 6.44 (s, 1H), 4.78-4.65 (m, 4H), 3.59 (p, J = 6.4 Hz, 1H), 3.38-3.26 (m, 4H), 2.64 (q, J = 7.6 Hz, 2H), 2.58-2.41 (m, 4H), 1.64 (s, 6H), 1.28 (t, J = 7.6 Hz, 3H) ppm. |
| 331 | 428.29 | 0.62 | 1H NMR (300 MHz, DMSO-d6) δ 9.40 (s, 1H), 9.18 (s, 1H), 7.64 (dd, J = 8.6, 2.2 Hz, 2H), 7.32-7.20 (m, 1H), 6.97 (s, 1H), 6.17 (s, 1H), 4.57 (t, J = 6.5 Hz, 2H), 4.48 (t, J = 6.1 Hz, 2H), 3.52 (m, 4H), 3.47-3.37 (m, 1H), 2.33 (m, 4H), 2.23 (s, 3H) ppm. |
| 332 | 401.18 | 0.64 | 1H NMR (300 MHz, DMSO-d6) δ 9.66 (d, J = 18.6 Hz, 1H), 9.20 (s, 1H), 7.69-7.55 (m, 2H), 7.26 (dd, J = 10.5, 8.2 Hz, 1H), 6.74 (d, J = 1.6 Hz, 1H), 6.61 (d, J = 1.6 Hz, 1H), 5.38 (dd, J = 49.3, 17.3 Hz, 1H), 3.74-3.45 (m, 3H), 3.37 (d, J = 7.8 Hz, 1H), 2.25 (s, 2H), 1.85 (s, 1H), 0.89 (d, J = 4.7 Hz, 2H), 0.79 (d, J = 8.1 Hz, 2H) ppm. |
| 333 | 348 | 0.6 | 1H NMR (400 MHz, CDCl3) δ 8.30 (s, 1H), 7.68 (dd, J = 8.6, 1.0 Hz, 2H), 7.50 (dd, J = 10.7, 5.2 Hz, 2H), 7.34 (t, J = 7.4 Hz, 1H), 7.24 (s, 1H), 7.19 (s, 1H), 6.68 (s, 1H), 6.62 (s, 1H), 3.05 (d, J = 10.2 Hz, 2H), 2.48 (s, 1H), 2.38 (s, 3H), 2.35 (s, 3H), 2.16 (s, 2H), 1.90 (s, 3H) ppm. |
| 334 | 405.49 | 0.58 | 1H NMR (400 MHz, DMSO-d6) δ 9.02 (s, 2H), 7.91-7.76 (m, 2H), 7.52 (t, J = 8.0 Hz, 2H), 7.35 (t, J = 7.4 Hz, 1H), 7.00 (s, 1H), 6.45 (s, 1H), 5.94 (s, 1H), 5.27 (d, J = 7.6 Hz, 1H), 4.54 (t, J = 6.5 Hz, 2H), 4.43 (t, J = 6.1 Hz, 2H), 3.47-3.35 (m, 1H), 3.19 (s, 1H), 2.70 (t, J = 11.4 Hz, 2H), 2.13 (s, 3H), 2.03-1.77 (m, 4H), 1.41 (dd, J = 20.6, 10.7 Hz, 2H) ppm. |
| 335 | 356.3 | 0.89 | 1H NMR (300 MHz, CDCl3) δ 8.34 (s, 1H), 7.74-7.64 (m, 2H), 7.59-7.47 (m, 2H), 7.39 (dt, J = 9.2, 4.3 Hz, 1H), 7.10 (d, J = 1.8 Hz, 2H), 6.72 (s, 1H), 6.53 (t, J = 1.9 Hz, 1H), 3.94-3.82 (m, 4H), 3.28-3.17 (m, 4H) ppm. |
| 336 | 324 | 0.51 | 1H NMR (400 MHz, DMSO-d6) δ 9.44 (s, 1H), 9.08 (s, 1H), 7.83 (d, J = 7.6 Hz, 2H), 7.55 (t, J = 8.0 Hz, 2H), 7.35 (t, J = 7.4 Hz, 1H), 6.77 (d, J = 11.7 Hz, 1H), 6.70 (s, 1H), 5.86 (d, J = 12.3 Hz, 1H), 3.22 (t, J = 6.4 Hz, 4H), 1.96 (t, J = 6.5 Hz, 4H) ppm. |

TABLE 3-continued

Analytical Data

| Cmpd No. | LC/MS (M + H) | LC/MS Ret. Time (min) | ¹H-NMR |
|---|---|---|---|
| 337 | 389 | 0.61 | 1H NMR (400 MHz, DMSO-d6) δ 10.72 (s, 1H), 9.19 (s, 1H), 9.06 (s, 1H), 7.84 (d, J = 7.6 Hz, 2H), 7.55 (t, J = 8.0 Hz, 2H), 7.35 (t, J = 7.4 Hz, 1H), 7.13 (s, 1H), 6.74 (s, 1H), 6.16 (s, 1H), 3.89-3.67 (m, 2H), 3.62-3.37 (m, 4H), 3.36-3.18 (m, 1H), 2.96 (d, J = 4.0 Hz, 1H), 2.23 (s, 3H), 1.29-1.05 (m, 2H), 0.83 (t, J = 11.5 Hz, 2H) ppm. |
| 338 | 437.12 | 0.62 | 1H NMR (400 MHz, CDCl3) δ 8.46 (d, J = 2.4 Hz, 1H), 7.78 (dd, J = 7.4, 1.7 Hz, 1H), 7.21 (t, J = 2.0 Hz, 1H), 7.15 (dd, J = 11.6, 8.4 Hz, 1H), 7.11-7.06 (m, 1H), 6.83 (s, 1H), 6.77 (s, 1H), 6.45 (s, 1H), 4.71 (dt, J = 14.4, 6.4 Hz, 4H), 3.59 (p, J = 6.4 Hz, 1H), 3.37-3.26 (m, 4H), 2.64 (q, J = 7.6 Hz, 2H), 2.57-2.48 (m, 4H), 2.41 (s, 3H), 1.29 (t, J = 10.7, 4.5 Hz, 3H) ppm. |
| 339 | 436.31 | 0.57 | 1H NMR (400 MHz, CDCl3) δ 8.84 (s, 1H), 8.48 (d, J = 2.4 Hz, 1H), 8.39 (s, 1H), 7.78 (d, J = 8.9 Hz, 1H), 7.03 (d, J = 13.9 Hz, 1H), 6.73 (s, 1H), 6.65 (s, 1H), 6.37 (s, 1H), 4.71 (p, J = 6.3 Hz, 4H), 3.65-3.51 (m, 1H), 3.39-3.22 (m, 4H), 2.61-2.47 (m, 4H), 1.90 (dd, J = 8.9, 4.2 Hz, 1H), 0.97 (dd, J = 12.7, 6.4 Hz, 2H), 0.80-0.65 (m, 2H) ppm. |
| 340 | 374 | 0.64 | 1H NMR (300 MHz, CDCl3) δ 8.31 (s, 1H), 7.79-7.60 (m, 2H), 7.50 (t, J = 7.9 Hz, 2H), 7.34 (t, J = 7.4 Hz, 2H), 7.16 (s, 1H), 6.67 (s, 2H), 3.16 (dd, J = 29.4, 10.9 Hz, 2H), 2.75 (ddd, J = 11.7, 8.2, 3.8 Hz, 1H), 2.35 (s, 3H), 2.31-2.07 (m, 2H), 1.95 (d, J = 12.3 Hz, 1H), 1.87-1.38 (m, 5H) ppm. |
| 341 | 407 | 0.61 | 1H NMR (400 MHz, CDCl3) δ 9.17 (d, J = 1.3 Hz, 1H), 8.90 (s, 1H), 8.54 (d, J = 2.5 Hz, 1H), 8.38 (dd, J = 2.5, 1.5 Hz, 1H), 6.86 (s, 1H), 6.72 (t, J = 2.0 Hz, 1H), 6.68 (s, 1H), 5.99 (s, 1H), 4.02 (t, J = 7.0 Hz, 2H), 3.85-3.67 (m, 6H), 3.36 (dd, J = 11.6, 6.0 Hz, 1H), 2.60 (q, J = 7.6 Hz, 2H), 2.47 (s, 4H), 1.26 (t, J = 7.6 Hz, 4H) ppm. |
| 342 | 406.53 | 0.53 | 1H NMR (300 MHz, CDCl3) δ 8.94 (d, J = 2.2 Hz, 1H), 8.66-8.48 (m, 1H), 8.28 (s, 1H), 8.05-7.89 (m, 1H), 7.48-7.29 (m, 1H), 6.83 (dt, J = 3.8, 2.1 Hz, 1H), 6.55 (s, 1H), 6.45 (s, 1H), 6.04 (d, J = 19.5 Hz, 1H), 4.58 (p, J = 6.4 Hz, 4H), 3.50-3.41 (m, 1H), 3.36-3.23 (m, 1H), 2.66 (d, J = 11.7 Hz, 2H), 2.20 (s, 3H), 2.09 (dd, J = 14.0, 11.3 Hz, 2H), 2.01-1.88 (m, 2H), 1.49-1.38 (m, 2H) ppm. |
| 343 | 390 | 3.07 | 1H NMR (400 MHz, DMSO-d6) δ 9.49 (s, 1H), 8.76 (d, J = 2.2 Hz, 1H), 7.87 (dt, J = 8.9, 4.5 Hz, 1H), 7.64 (td, J = 8.9, 4.5 Hz, 1H), 7.35 (d, J = 7.9 Hz, 1H), 6.90 (s, 1H), 6.73 (d, J = 11.3 Hz, 1H), 6.11 (d, J = 13.0 Hz, 1H), 3.72 (t, J = 4.7 Hz, 2H), 3.56 (dd, J = 11.0, 5.4 Hz, 6H), 2.00-1.83 (m, 2H) ppm. |
| 344 | 490.53 | 0.64 | 1H NMR (300 MHz, CDCl3) δ 8.42 (s, 1H), 7.60 (t, J = 2.0 Hz, 1H), 7.45 (t, J = 1.6 Hz, 1H), 7.39 (s, 1H), 7.28-7.21 (m, 2H), 7.10-7.03 (m, 1H), 6.83 (tt, J = 8.6, 2.2 Hz, 1H), 4.72 (dt, J = 12.4, 6.4 Hz, 4H), 3.68-3.54 (m, 1H), 3.48-3.33 (m, 4H), 3.10 (s, 3H), 2.62-2.47 (m, 4H) ppm. |
| 345 | 417.09 | 0.76 | 1H NMR (400 MHz, DMSO-d6) δ 10.07 (s, 1H), 9.15-9.01 (m, 1H), 7.42 (d, J = 2.5 Hz, 1H), 7.34 (dd, J = 8.6, 2.5 Hz, 1H), 7.12 (t, J = 6.0 Hz, 2H), 6.85 (s, 1H), 3.85 (s, 3H), 3.81 (s, 3H), 3.72-3.67 (m, 4H), 3.43-3.36 (m, 4H) ppm. |
| 346 | 436.18 | 0.95 | 1H NMR (300 MHz, CD3OD) δ 8.61 (s, 1H), 7.42-7.31 (m, 2H), 7.25 (dd, J = 17.5, 1.8 Hz, 2H), 6.89-6.75 (m, 1H), 6.68 (s, 1H), 3.97-3.80 (m, 4H), 3.29-3.12 (m, 4H) ppm. |
| 347 | 403 | 223 | 1H NMR (400 MHz, DMSO-d6) δ 11.19 (s, 1H), 9.58 (s, 1H), 8.77 (d, J = 2.3 Hz, 1H), 7.90 (td, J = 8.9, |

TABLE 3-continued

Analytical Data

| Cmpd No. | LC/MS (M + H) | LC/MS Ret. Time (min) | ¹H-NMR |
|---|---|---|---|
| | | | 5.9 Hz, 1H), 7.64 (ddd, J = 11.7, 9.0, 2.8 Hz, 1H), 7.34 (t, J = 8.5 Hz, 1H), 6.81 (d, J = 11.8 Hz, 1H), 6.74 (s, 1H), 5.98 (d, J = 11.9 Hz, 1H), 3.98 (d, J = 7.3 Hz, 1H), 3.61 (t, J = 9.0 Hz, 1H), 3.57-3.49 (m, 1H), 3.45 (d, J = 5.9 Hz, 1H), 3.25 (dd, J = 16.9, 8.2 Hz, 1H), 2.80 (t, J = 4.3 Hz, 6H), 2.41 (s, 1H), 2.35-2.25 (m, 1H) ppm. |
| 348 | 411.39 | 0.66 | 1H NMR (300 MHz, CDCl3) δ 8.36 (s, 1H), 7.75-7.66 (m, 2H), 7.58-7.47 (m, 2H), 7.38 (ddd, J = 8.7, 4.6, 1.2 Hz, 2H), 7.12 (d, J = 22.4 Hz, 2H), 6.81-6.40 (m, 2H), 3.35-3.20 (m, 4H), 2.89-2.75 (m, 4H), 1.77-1.67 (m, 1H), 0.62-0.41 (m, 4H) ppm. |
| 349 | 427.21 | 0.67 | 1H NMR (300 MHz, DMSO-d6) δ 9.40 (s, 1H), 9.18 (s, 1H), 7.62 (dd, J = 8.6, 2.1 Hz, 2H), 7.34 (s, 1H), 7.31-7.17 (m, 1H), 6.82 (s, 1H), 6.38 (s, 1H), 4.77 (d, J = 6.7 Hz, 2H), 4.21 (d, J = 6.8 Hz, 2H), 3.05 (m, 2H), 2.63-2.52 (m, 4H), 2.49 (s, 3H), 2.24 (s, 3H) ppm. |
| 350 | 497.2 | 0.44 | 1H NMR (400 MHz, CD3OD) δ 9.01 (s, 1H), 7.96-7.73 (m, 1H), 7.63 (d, J = 6.3 Hz, 2H), 7.35 (s, 1H), 7.00 (t, J = 9.2 Hz, 2H), 4.30-4.13 (m, 2H), 4.00 (s, 4H), 3.74 (dd, J = 13.9, 8.8 Hz, 4H), 2.43 (s, 3H), 1.31 (t, J = 7.1 Hz, 4H) ppm. |
| 351 | 343 | 0.63 | 1H NMR (400 MHz, DMSO-d6) δ 9.58 (s, 1H), 9.52 (s, 1H), 9.35 (s, 1H), 9.17 (s, 1H), 7.76 (dd, J = 14.8, 5.0 Hz, 2H), 7.63 (dd, J = 14.5, 8.1 Hz, 1H), 7.27-7.13 (m, 1H), 6.79 (d, J = 11.8 Hz, 1H), 6.69 (s, 1H), 5.87 (d, J = 11.4 Hz, 1H), 4.31 (dd, J = 14.1, 6.7 Hz, 1H), 4.23 (d, J = 7.0 Hz, 2H), 3.84 (dd, J = 16.4, 7.2 Hz, 2H) ppm. |
| 352 | 467.28 | 0.82 | 1H NMR (300 MHz, CDCl3) δ 8.34 (s, 1H), 7.25 (dd, J = 7.8, 2.2 Hz, 2H), 7.19-6.97 (m, 1H), 6.91-6.72 (m, 3H), 6.42 (s, 1H), 4.01-3.85 (m, 2H), 3.85-3.70 (m, 2H), 3.43-3.19 (m, 4H), 2.36 (s, 3H) ppm. |
| 353 | 463.32 | 0.55 | 1H NMR (400 MHz, CDCl3) δ 9.02 (s, 1H), 8.92 (d, J = 1.1 Hz, 1H), 7.90 (d, J = 0.9 Hz, 1H), 7.18 (t, J = 2.1 Hz, 1H), 6.87 (s, 1H), 6.71 (s, 1H), 6.41 (s, 1H), 4.72 (dq, J = 12.6, 6.4 Hz, 4H), 4.63 (s, 2H), 4.14 (q, J = 7.1 Hz, 1H), 3.58 (s, 3H), 3.39-3.25 (m, 4H), 2.61-2.48 (m, 4H), 1.90 (tt, J = 8.4, 5.1 Hz, 1H), 1.05-0.89 (m, 2H), 0.87-0.70 (m, 2H) ppm. |
| 354 | 423.28 | 0.58 | 1H NMR (400 MHz, DMSO-d6) δ 9.67 (s, 1H), 9.04 (s, 1H), 7.43 (d, J = 2.4 Hz, 1H), 7.35 (dd, J = 8.6, 2.4 Hz, 1H), 7.10 (d, J = 8.7 Hz, 1H), 7.00 (s, 1H), 6.76 (s, 1H), 3.85 (s, 3H), 3.80 (s, 3H), 3.73-3.62 (m, 4H), 3.37-3.33 (m, 4H), 1.83 (ddd, J = 13.2, 8.3, 5.1 Hz, 1H), 0.85 (dd, J = 7.2, 4.8 Hz, 2H), 0.82-0.73 (m, 2H) ppm. |
| 355 | 358.22 | 0.69 | 1H NMR (300 MHz, DMSO-d6) δ 9.33 (s, 1H), 9.16 (s, 1H), 7.67-7.52 (m, 2H), 7.30-7.17 (m, 1H), 6.76 (s, 1H), 6.67 (s, 1H), 5.81 (s, 1H), 5.60 (d, J = 6.7 Hz, 1H), 4.56 (dd, J = 11.6, 5.3 Hz, 1H), 4.05 (t, J = 7.0 Hz, 2H), 3.48 (dd, J = 7.5, 5.2 Hz, 2H), 2.19 (s, 3H) ppm. |
| 356 | 388.17 | 2.65 | |
| 357 | 392.18 | 0.85 | 1H NMR (300 MHz, DMSO-d6) δ 9.91 (s, 1H), 9.26 (s, 1H), 9.03 (d, J = 1.3 Hz, 1H), 8.69 (d, J = 2.5 Hz, 1H), 8.60 (dd, J = 2.5, 1.4 Hz, 1H), 7.52 (s, 1H), 7.48 (s, 1H), 6.77 (s, 1H), 3.82-3.72 (m, 4H), 3.23-3.15 (m, 4H) ppm. |
| 358 | 376.38 | 0.59 | 1H NMR (300 MHz, CDCl3) δ 8.24 (s, 1H), 7.69-7.56 (m, 2H), 7.42 (dd, J = 10.7, 5.1 Hz, 2H), 7.34-7.23 (m, 1H), 7.11 (d, J = 8.4 Hz, 1H), 6.64 (d, J = 19.1 Hz, 1H), 6.57 (s, 1H), 6.31 (d, J = 18.5 Hz, 1H), 4.02-3.68 (m, 4H), 3.18-2.98 (m, 1H), 2.85-2.68 (m, 1H), 2.67-2.52 (m, 1H), 2.25 (s, 3H), 2.18-1.88 (m, 2H), 1.84-1.53 (m, 3H) ppm. |

TABLE 3-continued

Analytical Data

| Cmpd No. | LC/MS (M + H) | LC/MS Ret. Time (min) | 1H-NMR |
|---|---|---|---|
| 359 | 455.29 | 0.67 | 1H NMR (300 MHz, DMSO-d6) δ 9.33 (s, 1H), 9.16 (s, 1H), 7.72-7.49 (m, 2H), 7.25 (dd, J = 10.4, 8.2 Hz, 1H), 7.10 (s, 1H), 7.03 (s, 1H), 6.38 (s, 1H), 4.58 (t, J = 6.5 Hz, 2H), 4.48 (t, J = 6.0 Hz, 2H), 3.56-3.39 (m, 1H), 3.16 (s, 4H), 2.79 (dt, J = 14.2, 7.0 Hz, 1H), 2.42 (d, J = 4.6 Hz, 4H), 1.21 (t, J = 6.7 Hz, 6H) ppm. |
| 360 | 399.25 | 0.79 | 1H NMR (300 MHz, DMSO-d6) δ 9.34 (s, 1H), 9.15 (s, 1H), 7.62 (dd, J = 8.7, 2.2 Hz, 2H), 7.28-7.17 (m, 1H), 7.13 (s, 1H), 6.88 (s, 1H), 6.34 (s, 1H), 3.74 (s, 2H), 3.52-3.39 (m, 4H), 2.90 (s, 3H), 2.24 (s, 3H) ppm. |
| 361 | 473.37 | 0.66 | 1H NMR (300 MHz, CDCl3) δ 8.43 (s, 1H), 7.61 (t, J = 2.0 Hz, 1H), 7.57-7.34 (m, 5H), 7.14-7.00 (m, 2H), 4.72 (dq, J = 12.4, 6.4 Hz, 4H), 3.68-3.52 (m, 1H), 3.50-3.26 (m, 4H), 3.10 (s, 3H), 2.64-2.43 (m, 4H) ppm. |
| 362 | 385 | 0.62 | 1H NMR (300 MHz, Acetone-d6) δ 8.93 (s, 1H), 8.36 (s, 1H), 7.58 (dd, J = 8.7, 2.3 Hz, 2H), 7.40 (s, 1H), 7.02 (ddd, J = 9.1, 5.7, 2.3 Hz, 1H), 6.90 (s, 1H), 6.39 (s, 1H), 3.59 (t, J = 10.4 Hz, 2H), 3.12-2.52 (m, 4H-water peak), 2.37-2.22 (m, 4H), 1.11 (d, J = 6.3 Hz, 3H) ppm. |
| 363 | 307.18 | 0.77 | 1H NMR (300 MHz, DMSO-d6) δ 9.41 (s, 1H), 9.08 (s, 1H), 7.85 (dd, J = 8.6, 1.1 Hz, 2H), 7.56 (dd, J = 10.7, 5.3 Hz, 3H), 7.40-7.29 (m, 2H), 6.71 (s, 1H), 4.95 (dd, J = 8.4, 5.8 Hz, 2H), 4.62 (dd, J = 6.7, 5.8 Hz, 2H), 4.23-4.11 (m, 1H), 2.28 (d, J = 6.4 Hz, 3H) ppm. |
| 364 | 437.3 | 0.53 | 1H NMR (400 MHz, CDCl3) δ 9.03 (s, 1H), 8.93 (d, J = 1.1 Hz, 1H), 7.89 (d, J = 0.9 Hz, 1H), 7.33 (s, 1H), 6.79 (s, 1H), 6.71 (s, 1H), 6.45 (s, 1H), 4.72 (p, J = 6.4 Hz, 4H), 4.64 (d, J = 8.4 Hz, 2H), 3.57 (s, 3H), 3.36 (dd, J = 13.1, 8.2 Hz, 4H), 2.61-2.49 (m, 4H) ppm. |
| 365 | 386.19 | 0.52 | 1H NMR (400 MHz, DMSO-d6) δ 9.78 (s, 1H), 9.21 (s, 1H), 7.70-7.53 (m, 2H), 7.28 (tt, J = 9.3, 2.3 Hz, 1H), 6.94 (s, 1H), 6.72 (s, 1H), 3.50-3.37 (m, 4H), 2.44-2.33 (m, 4H), 2.25 (s, 3H), 2.22 (s, 3H). |
| 366 | 390.24 | 4.33 | 1H NMR (300 MHz, DMSO-d6) δ 9.13 (s, 1H), 7.88-7.79 (m, 2H), 7.56 (m, 4H), 7.38 (t, J = 7.4 Hz, 1H), 6.81 (s, 1H), 3.80 (m, 4H), 3.28-3.18 (m, 4H) ppm. |
| 367 | 370.17 | 0.76 | 1H NMR (300 MHz, CD3OD) δ 8.83 (s, 1H), 7.90-7.72 (m, 2H), 7.66-7.48 (m, 2H), 7.46-7.33 (m, 1H), 7.13-6.89 (m, 2H), 4.41 (d, J = 11.5 Hz, 2H), 3.73-3.48 (m, 2H), 3.21 (q, J = 10.7, 9.0 Hz, 4H), 2.96 (s, 3H) ppm. |
| 368 | 451.28 | 0.81 | 1H NMR (300 MHz, CDCl3) δ 9.19 (d, J = 1.3 Hz, 1H), 8.93 (s, 1H), 8.57 (d, J = 2.5 Hz, 1H), 8.41 (dd, J = 2.5, 1.5 Hz, 1H), 7.11 (s, 1H), 6.92 (s, 1H), 6.80 (s, 1H), 6.48 (s, 1H), 3.70-3.52 (m, 4H), 3.32-3.15 (m, 4H), 2.66 (q, J = 7.6 Hz, 2H), 1.52 (s, 9H), 1.29 (t, J = 7.6 Hz, 3H) ppm. |
| 369 | 375.43 | 0.64 | 1H NMR (300 MHz, DMSO-d6) δ 10.60 (s, 1H), 9.22 (d, J = 16.0 Hz, 1H), 9.15-9.00 (m, 1H), 7.96-7.81 (m, 2H), 7.65-7.47 (m, 2H), 7.36 (q, J = 7.4 Hz, 1H), 7.04 (s, 1H), 6.82 (d, J = 8.9 Hz, 1H), 6.20-6.11 (m, 1H), 4.12 (d, J = 6.1 Hz, 1H), 3.89 (d, J = 11.9 Hz, 1H), 3.67-3.49 (m, 1H), 3.43-3.08 (m, 5H), 2.85 (dd, J = 18.9, 4.9 Hz, 3H), 2.43 (d, J = 7.1 Hz, 1H), 2.23 (s, 3H), 2.23 (s, 3H), 1.78 (dd, J = 14.9, 7.9 Hz, 1H) ppm. |
| 370 | 413.25 | 0.28 | 1H NMR (400 MHz, CD3OD) δ 8.95 (s, 1H), 8.00 (s, 1H), 7.61 (d, J = 7.9 Hz, 2H), 7.36 (s, 1H), 7.10-6.91 (m, 2H), 4.04 (s, 4H), 3.76 (d, J = 24.8 Hz, 4H), 2.22 (s, 3H) ppm. |

TABLE 3-continued

Analytical Data

| Cmpd No. | LC/MS (M + H) | LC/MS Ret. Time (min) | ¹H-NMR |
|---|---|---|---|
| 371 | 359.41 | 0.9 | 1H NMR (400 MHz, DMSO-d6) δ 9.77 (s, 1H), 9.26 (s, 1H), 9.04 (s, 1H), 8.61 (s, 1H), 8.32 (s, 1H), 7.15 (s, 1H), 7.06 (d, J = 11.4 Hz, 1H), 6.45 (d, J = 11.8 Hz, 1H), 3.80 (s, 4H), 3.18 (s, 4H) ppm. |
| 372 | 334.12 | 0.68 | 1H NMR (300 MHz, CDCl3) δ 8.27 (s, 1H), 7.68-7.48 (m, 2H), 7.36-7.28 (m, 2H), 6.81 (s, 1H), 6.62 (s, 2H), 6.07 (s, 1H), 3.51-3.27 (m, 4H), 2.42 (s, 3H), 2.40-2.27 (m, 3H), 2.12-1.93 (m, 4H) ppm. |
| 373 | 496.22 | 0.61 | 1H NMR (400 MHz, CDCl3) δ 8.27 (s, 1H), 7.17 (s, 1H), 6.83 (s, 1H), 6.78 (s, 2H), 6.67 (dt, J = 9.2, 1.9 Hz, 1H), 6.44-6.31 (m, 2H), 4.71 (dt, J = 14.8, 6.4 Hz, 4H), 3.64-3.51 (m, 5H), 3.38 (s, 3H), 3.34-3.26 (m, 4H), 3.06 (s, 3H), 2.57-2.46 (m, 4H), 2.33 (s, 3H) ppm. |
| 374 | 372.08 | 2.5 | 1H NMR (400 MHz, DMSO-d6) δ 9.51 (s, 1H), 9.18 (s, 1H), 7.67 (d, J = 6.9 Hz, 2H), 7.42 (s, 1H), 7.34-7.15 (m, 1H), 7.04 (s, 1H), 6.58 (s, 1H), 3.77 (d, J = 61.3 Hz, 4H), 3.20 (d, J = 28.0 Hz, 4H), 2.30 (d, J = 23.2 Hz, 3H) ppm. |
| 375 | 423.45 | 0.66 | 1H NMR (300 MHz, CDCl3) δ 8.33 (s, 1H), 7.54-7.40 (m, 3H), 7.12 (s, 1H), 7.10-6.99 (m, 1H), 6.81 (s, 1H), 6.65 (s, 1H), 6.42 (s, 1H), 4.67 (d, J = 5.5 Hz, 2H), 4.30 (d, J = 5.7 Hz, 2H), 3.42-3.14 (m, 4H), 2.68-2.46 (m, 4H), 2.35 (s, 3H), 1.44 (s, 3H) ppm. |
| 376 | 433.44 | 0.7 | 1H NMR (300 MHz, DMSO-d6) δ 9.20 (s, 1H), 9.07 (s, 1H), 7.96-7.74 (m, 2H), 7.55 (t, J = 8.0 Hz, 2H), 7.34 (t, J = 7.4 Hz, 1H), 7.24 (s, 1H), 7.13 (s, 1H), 6.48 (s, 1H), 4.57 (q, J = 6.2 Hz, 2H), 4.47 (dt, J = 9.0, 6.1 Hz, 2H), 3.56-3.39 (m, 1H), 3.25-3.07 (m, 4H), 2.47-2.41 (m, 3H), 1.28 (s, 8H) ppm. |
| 377 | 449.32 | 0.61 | 1H NMR (400 MHz, CDCl3) δ 8.95 (s, 1H), 8.62 (d, J = 0.6 Hz, 1H), 7.05 (d, J = 0.6 Hz, 1H), 7.03 (t, J = 2.0 Hz, 1H), 6.85 (d, J = 17.5 Hz, 1H), 6.77 (s, 1H), 6.37 (s, 1H), 4.79-4.65 (m, 4H), 4.07 (s, 3H), 3.59 (p, J = 6.4 Hz, 1H), 3.36-3.24 (m, 4H), 2.59-2.47 (m, 4H), 1.97-1.85 (m, 1H), 1.05-0.91 (m, 2H), 0.81-0.69 (m, 2H) ppm. |
| 378 | 397.31 | 0.67 | 1H NMR (400 MHz, DMSO-d6) δ 9.67 (s, 1H), 9.20 (s, 1H), 7.70-7.54 (m, 2H), 7.33-7.14 (m, 1H), 6.89 (d, J = 1.4 Hz, 1H), 6.76 (d, J = 1.4 Hz, 1H), 3.49-3.36 (m, 4H), 1.85 (ddd, J = 12.9, 8.1, 4.9 Hz, 1H), 1.55 (dd, J = 15.1, 4.4 Hz, 6H), 0.91-0.73 (m, 4H) ppm. |
| 379 | 408.25 | 0.89 | 1H NMR (300 MHz, DMSO-d6) δ 9.33 (s, 1H), 9.14 (s, 1H), 7.91 (d, J = 2.3 Hz, 1H), 7.64-7.54 (m, 2H), 7.53 (d, J = 1.5 Hz, 1H), 7.22 (tt, J = 10.4, 8.2 Hz, 1H), 6.78 (d, J = 10.2 Hz, 2H), 6.31-6.27 (m, 1H), 5.90 (s, 1H), 5.39 (m, 1H), 4.30 (t, J = 7.4 Hz, 2H), 4.11-4.02 (m, 2H), 2.22 (s, 3H) ppm. |
| 380 | 340 | 3.45 | 1H NMR (400 MHz, Acetone-d6) δ 8.80 (s, 1H), 8.40 (s, 1H), 7.86 (dd, J = 8.6, 1.0 Hz, 2H), 7.55 (t, J = 8.0 Hz, 2H), 7.37 (d, J = 7.4 Hz, 1H), 7.10 (t, J = 1.8 Hz, 1H), 7.02 (t, J = 2.0 Hz, 1H), 6.13 (t, J = 2.0 Hz, 1H), 3.31 (t, J = 6.6 Hz, 4H). 2.02, (t, J = 6.6.Hz, 4H—under the acetone peak) ppm. |
| 381 | 351.35 | 0.56 | 1H NMR (300 MHz, DMSO-d6) δ 10.85 (s, 1H), 9.51 (s, 1H), 9.31 (s, 2H), 9.24 (s, 1H), 9.17 (s, 1H), 7.20 (s, 1H), 6.93 (d, J = 17.4 Hz, 1H), 6.40 (s, 1H), 3.75 (d, J = 10.7 Hz, 2H), 3.50 (d, J = 9.7 Hz, 2H), 3.19-3.10 (m, 4H), 2.79 (t, J = 13.4 Hz, 3H), 2.27 (d, J = 11.9 Hz, 3H) ppm. |
| 382 | 394.29 | 0.6 | 1H NMR (300 MHz, DMSO-d6) δ 9.35 (s, 1H), 9.12 (s, 1H), 7.73 (s, 1H), 7.70 (d, J = 1.6 Hz, 1H), 7.65-7.54 (m, 1H), 7.52 (s, 1H), 7.18 (dd, J = 13.0, 4.5 Hz, 2H), 6.61 (s, 1H), 4.59 (t, J = 6.5 Hz, 2H), 4.51 (td, J = 6.0, 1.4 Hz, 2H), 3.66 (dd, J = 12.3, 6.2 Hz, 1H), 3.29-3.19 (m, 1H), |

TABLE 3-continued

Analytical Data

| Cmpd No. | LC/MS (M + H) | LC/MS Ret. Time (min) | ¹H-NMR |
|---|---|---|---|
| | | | 2.96 (t, J = 8.4 Hz, 1H), 2.72 (dd, J = 14.9, 8.2 Hz, 1H), 2.61 (dd, J = 14.3, 8.6 Hz, 1H), 2.47-2.38 (m, 1H), 2.32-2.17 (m, 4H), 1.79 (dt, J = 14.5, 8.0 Hz, 1H) ppm. |
| 383 | 426.51 | 0.64 | 1H NMR (300 MHz, DMSO-d6) δ 9.30 (s, 1H), 8.81 (d, J = 2.4 Hz, 1H), 7.69 (ddd, J = 9.2, 6.0, 3.2 Hz, 1H), 7.64-7.48 (m, 1H), 7.41-7.23 (m, 1H), 7.18 (s, 1H), 6.79 (s, 1H), 6.30 (s, 1H), 4.62 (dd, J = 7.8, 5.9 Hz, 2H), 4.37 (t, J = 6.1 Hz, 2H), 3.67 (d, J = 12.3 Hz, 2H), 2.81-2.58 (m, 3H), 2.21 (s, 3H), 1.77 (d, J = 10.1 Hz, 1H), 1.65 (d, J = 13.1 Hz, 2H), 1.14 (dt, J = 11.9, 8.6 Hz, 2H) ppm. |
| 384 | 442.44 | 0.65 | 1H NMR (300 MHz, DMSO-d6) δ 9.40 (s, 1H), 9.07 (s, 1H), 7.92 (ddd, J = 15.9, 9.5, 7.4 Hz, 1H), 7.77-7.63 (m, 2H), 7.25 (s, 1H), 6.88 (s, 1H), 6.28 (s, 1H), 4.54 (t, J = 6.5 Hz, 2H), 4.43 (t, J = 6.1 Hz, 2H), 4.37-4.18 (m, 1H), 3.53-3.36 (m, 1H), 2.60 (dd, J = 17.1, 11.7 Hz, 2H), 2.21 (d, J = 9.7 Hz, 3H), 2.15-1.90 (m, 4H), 1.78-1.54 (m, 2H) ppm. |
| 385 | 379 | 0.49 | 1H NMR (300 MHz, DMSO-d6) δ 9.36 (s, 1H), 9.30 (s, 1H), 8.78-8.64 (m, 2H), 7.81 (dd, J = 4.7, 1.6 Hz, 2H), 7.16 (s, 1H), 6.86 (s, 1H), 6.32 (s, 1H), 3.68 (d, J = 12.4 Hz, 2H), 3.34 (s, 1H), 3.25 (s, 3H), 3.19 (dd, J = 11.9, 5.6 Hz, 3H), 2.77-2.59 (m, 2H), 2.23 (s, 3H), 1.74 (d, J = 10.1 Hz, 3H), 1.41-1.20 (m, 2H) ppm. |
| 386 | 427.41 | 0.66 | 1H NMR (300 MHz, DMSO-d6) δ 9.24 (s, 1H), 9.05 (s, 1H), 8.18-7.81 (m, 1H), 7.81-7.53 (m, 2H), 7.13 (s, 1H), 6.88 (s, 1H), 6.31 (s, 1H), 4.57 (t, J = 6.5 Hz, 2H), 4.53-4.39 (m, 2H), 3.45 (p, J = 6.2 Hz, 1H), 3.24-3.10 (m, 4H), 2.46-2.37 (m, 4H), 2.23 (s, 3H) ppm. |
| 387 | 368.21 | 0.55 | 1H NMR (400 MHz, CDCl3) δ 8.74 (s, 1H), 8.38 (d, J = 2.5 Hz, 1H), 8.30 (s, 1H), 7.71 (dt, J = 9.1, 2.3 Hz, 1H), 7.00 (s, 1H), 6.71 (s, 1H), 6.57 (s, 1H), 6.35 (s, 1H), 3.30-3.16 (m, 3H), 2.64-2.47 (m, 3H), 2.31 (s, 2H), 2.26 (s, 3H) ppm. |
| 388 | 465.38 | 0.86 | 1H NMR (300 MHz, CDCl3) δ 8.29 (s, 1H), 7.13-7.05 (m, 2H), 7.00 (dt, J = 9.3, 2.1 Hz, 1H), 6.74 (s, 1H), 6.60 (dt, J = 11.3, 2.3 Hz, 2H), 6.37 (s, 1H), 4.83-4.62 (m, 4H), 3.89 (s, 3H), 3.68-3.48 (m, 1H), 3.40-3.21 (m, 4H), 2.61-2.43 (m, 4H), 1.89 (ddd, J = 13.4, 8.4, 5.1 Hz, 1H), 1.02-0.88 (m, 2H), 0.82-0.64 (m, 2H) ppm. |
| 389 | 453.28 | 0.63 | 1H NMR (400 MHz, CDCl3) δ 8.30 (s, 1H), 7.24 (dd, J = 7.7, 2.0 Hz, 2H), 7.07 (t, J = 2.0 Hz, 1H), 6.85-6.76 (m, 1H), 6.71 (s, 1H), 6.62 (s, 1H), 6.36 (s, 1H), 4.71 (p, J = 6.3 Hz, 4H), 3.64-3.53 (m, 1H), 3.37-3.25 (m, 4H), 2.58-2.48 (m, 4H), 1.90 (ddd, J = 13.4, 8.4, 5.0 Hz, 1H), 1.01-0.89 (m, 2H), 0.81-0.69 (m, 2H) ppm. |
| 390 | 438.38 | 0.5 | 1H NMR (400 MHz, CDCl3) δ 8.34 (s, 1H), 7.45 (s, 1H), 7.34 (d, J = 9.4 Hz, 1H), 7.17 (s, 1H), 7.05 (d, J = 9.0 Hz, 1H), 6.77 (s, 1H), 6.61 (s, 1H), 6.42 (s, 1H), 3.54 (s, 2H), 3.37-3.22 (m, 4H), 2.67-2.56 (m, 4H), 2.50 (q, J = 7.1 Hz, 2H), 2.38 (s, 3H), 2.34 (s, 3H), 2.25 (s, 3H), 1.13 (t, J = 7.0 Hz, 3H) ppm. |
| 391 | 392.49 | 0.62 | 1H NMR (300 MHz, DMSO-d6) δ 9.36 (s, 1H), 9.06 (s, 1H), 7.93-7.69 (m, 2H), 7.55 (t, J = 8.0 Hz, 2H), 7.36 (t, J = 7.4 Hz, 1H), 7.15 (s, 1H), 6.94 (s, 1H), 6.22 (s, 1H), 4.87 (s, 1H), 4.59 (t, J = 5.7 Hz, 2H), 4.49 (dd, J = 9.3, 5.9 Hz, 2H), 3.73 (s, 1H), 2.95 (s, 1H), 2.73 (s, 2H), 2.52 (s, 1H), 2.39-2.16 (m, 4H), 1.90 (s, 1H) ppm. |
| 392 | 372.28 | 0.83 | 1H NMR (300 MHz, CD3OD + CDCl3) δ 8.51 (s, 1H), 7.77-7.69 (m, 2H), 7.57-7.49 (m, 2H), 7.44-7.33 (m, 2H), 7.27 (s, 1H), 6.63 (dd, J = 64.1, |

TABLE 3-continued

Analytical Data

| Cmpd No. | LC/MS (M + H) | LC/MS Ret. Time (min) | ¹H-NMR |
|---|---|---|---|
| | | | 49.2 Hz, 2H), 3.98-3.83 (m, 4H), 3.31-3.20 (m, 4H) ppm. |
| 393 | 444.21 | 0.64 | |
| 394 | 358.15 | 2.96 | 1H NMR (400 MHz, DMSO-d6) δ 9.58 (d, J = 40.8 Hz, 1H), 9.13 (d, J = 19.3 Hz, 1H), 7.71 (t, J = 9.6 Hz, 2H), 7.57 (d, J = 37.5 Hz, 1H), 7.18 (d, J = 24.8 Hz, 1H), 7.00 (s, 2H), 6.30 (t, J = 16.7 Hz, 1H), 3.72 (d, J = 25.2 Hz, 4H), 3.12 (s, 4H) ppm. |
| 395 | 397.24 | 0.62 | 1H NMR (400 MHz, CDCl3) δ 8.29 (s, 1H), 7.17 (s, 1H), 7.07 (s, 1H), 7.01 (dt, J = 9.3, 2.0 Hz, 1H), 6.75 (s, 1H), 6.66 (s, 1H), 6.60 (dt, J = 10.4, 2.2 Hz, 1H), 6.42 (s, 1H), 3.88 (s, 3H), 3.36-3.22 (m, 4H), 2.67-2.55 (m, 4H), 2.38 (s, 3H), 2.34 (s, 3H) ppm. |
| 396 | 455.53 | 0.7 | 1H NMR (300 MHz, CDCl3) δ 8.32 (d, J = 3.8 Hz, 1H), 7.25 (dd, J = 7.9, 2.2 Hz, 2H), 7.15 (t, J = 2.0 Hz, 1H), 6.86-6.75 (m, 2H), 6.71 (s, 1H), 6.45 (s, 1H), 4.83-4.62 (m, 4H), 3.59 (p, J = 6.4 Hz, 1H), 3.40-3.21 (m, 4H), 2.66-2.46 (m, 6H), 1.69 (dd, J = 15.1, 7.4 Hz, 2H), 0.99 (t, J = 7.3 Hz, 3H) ppm. |
| 397 | 425.19 | 0.62 | 1H NMR (400 MHz, DMSO-d6) δ 9.25 (s, 1H), 9.12 (s, 1H), 7.93 (t, J = 2.0 Hz, 1H), 7.81 (dd, J = 8.2, 1.3 Hz, 1H), 7.58 (t, J = 8.1 Hz, 1H), 7.40 (dd, J = 8.0, 1.2 Hz, 1H), 7.21 (s, 1H), 6.84 (s, 1H), 6.31 (s, 1H), 4.57 (t, J = 6.5 Hz, 2H), 4.48 (t, J = 6.0 Hz, 2H), 3.46 (dd, J = 12.4, 6.3 Hz, 1H), 3.22-3.12 (m, 4H), 2.45-2.36 (m, 4H), 2.22 (s, 3H) ppm. |
| 398 | 417.37 | 0.68 | 1H NMR (300 MHz, CDCl3) δ 8.24 (s, 1H), 7.59 (ddd, J = 16.1, 8.6, 6.5 Hz, 2H), 7.48-7.34 (m, 2H), 7.34-7.23 (m, 1H), 7.04 (s, 1H), 6.73 (s, 1H), 6.54 (s, 1H), 6.31 (s, 1H), 3.26-3.11 (m, 4H), 2.97 (q, J = 9.6 Hz, 2H), 2.86-2.68 (m, 4H), 2.25 (s, 3H) ppm. |
| 399 | 351.31 | 0.56 | 1H NMR (300 MHz, DMSO-d6) δ 10.97 (s, 1H), 9.87 (dd, J = 2.8, 0.9 Hz, 1H), 9.69 (d, J = 8.1 Hz, 1H), 9.51 (s, 1H), 9.47-9.24 (m, 1H), 8.14 (dd, J = 6.0, 2.8 Hz, 1H), 7.19 (s, 1H), 7.00 (s, 1H), 6.45 (s, 1H), 3.76 (d, J = 9.3 Hz, 2H), 3.51 (d, J = 8.1 Hz, 2H), 3.31-3.04 (m, 4H), 2.79 (t, J = 13.9 Hz, 3H), 2.27 (s, 3H) ppm. |
| 400 | 469.34 | 0.84 | 1H NMR (300 MHz, CDCl3) δ 8.32 (s, 1H), 7.52 (d, J = 1.0 Hz, 1H), 7.39-7.31 (m, 1H), 7.16-7.02 (m, 2H), 6.70 (s, 1H), 6.61 (s, 1H), 6.36 (s, 1H), 4.80-4.62 (m, 4H), 3.67-3.51 (m, 1H), 3.38-3.27 (m, 4H), 2.61-2.50 (m, 4H), 1.97-1.82 (m, 1H), 1.03-0.89 (m, 2H), 0.75 (dt, J = 6.6, 4.6 Hz, 2H) ppm. |
| 401 | 421.26 | 0.63 | 1H NMR (300 MHz, DMSO-d6) δ 9.43 (s, 1H), 9.15 (s, 1H), 8.83 (s, 1H), 8.56 (s, 1H), 7.16 (s, 1H), 6.98 (s, 1H), 6.37 (s, 1H), 4.58 (t, J = 6.5 Hz, 2H), 4.49 (t, J = 6.0 Hz, 2H), 3.54-3.38 (m, 1H), 3.16 (d, J = 4.7 Hz, 4H), 2.70-2.52 (m, 5H), 2.40 (t, J = 13.3 Hz, 4H), 1.19 (t, J = 7.6 Hz, 3H) ppm. |
| 402 | 391 | 0.59 | 1H NMR (400 MHz, CDCl3) δ 8.30 (s, 1H), 7.66 (d, J = 8.2 Hz, 2H), 7.49 (t, J = 7.9 Hz, 2H), 7.35 (t, J = 7.4 Hz, 1H), 7.00 (s, 1H), 6.61 (s, 1H), 6.49 (s, 1H), 6.07 (s, 1H), 4.52 (d, J = 13.6 Hz, 1H), 3.82 (d, J = 13.9 Hz, 1H), 3.63-3.50 (m, 2H), 3.31-3.12 (m, 1H), 2.96-2.76 (m, 1H), 2.27 (s, 3H), 2.19 (d, J = 16.2 Hz, 1H), 2.12 (s, 3H), 1.39 (d, J = 4.9 Hz, 2H) ppm. |
| 403 | 355.45 | 0.73 | 1H NMR (400 MHz, DMSO-d6) δ 9.84 (s, 1H), 9.37 (d, J = 21.6 Hz, 1H), 8.31 (dd, J = 24.3, 5.5 Hz, 1H), 8.00 (d, J = 5.3 Hz, 1H), 7.85 (d, J = 23.0 Hz, 2H), 7.20 (s, 1H), 6.89 (d, J = 29.4 Hz, 1H), 4.03 (s, 4H), 3.37 (d, J = 40.0 Hz, 4H), 2.32 (s, 3H) ppm. |
| 404 | 308 | 0.79 | 1H NMR (400 MHz, CDCl3) δ 8.96 (s, 1H), 8.42 (d, J = 4.2 Hz, 1H), 7.87 (dt, J = 15.3, 4.8 Hz, |

TABLE 3-continued

Analytical Data

| Cmpd No. | LC/MS (M + H) | LC/MS Ret. Time (min) | ¹H-NMR |
|---|---|---|---|
| | | | 2H), 7.53 (s, 1H), 7.24 (d, J = 9.3 Hz, 2H), 6.93 (s, 1H), 6.86 (s, 1H), 5.10 (dd, J = 8.4, 6.0 Hz, 2H), 4.84 (t, J = 6.4 Hz, 2H), 4.36-4.12 (m, 1H), 2.40 (s, 3H) ppm. |
| 405 | 399.15 | 0.65 | 1H NMR (300 MHz, CD3OD) δ 9.03 (s, 1H), 7.67-7.45 (m, 2H), 7.36 (s, 1H), 7.05 (tt, J = 9.0, 2.3 Hz, 1H), 6.64 (s, 1H), 3.88 (dd, J = 6.0, 3.7 Hz, 4H), 3.59 (dd, J = 6.0, 3.7 Hz, 4H), 2.17 (tt, J = 8.3, 5.0 Hz, 1H), 1.36-1.18 (m, 2H), 0.99 (dt, J = 7.2, 4.8 Hz, 2H) ppm. |
| 406 | 409.45 | 0.65 | 1H NMR (300 MHz, DMSO-d6) δ 9.25 (s, 1H), 9.11 (s, 1H), 7.79-7.66 (m, 2H), 7.62-7.52 (m, 1H), 7.24-7.04 (m, 2H), 6.88 (s, 1H), 6.31 (s, 1H), 4.57 (t, J = 6.5 Hz, 2H), 3.45 (p, J = 6.3 Hz, 1H), 3.27-3.12 (m, 4H), 2.47-2.38 (m, 4H), 2.23 (s, 3H) ppm. |
| 407 | 398.21 | 0.61 | 1H NMR (300 MHz, CDCl3) δ 8.36 (s, 1H), 7.26 (d, J = 2.2 Hz, 2H), 7.17 (d, J = 2.0 Hz, 1H), 7.05 (d, J = 1.9 Hz, 1H), 6.95-6.78 (m, 2H), 4.11 (d, J = 10.9 Hz, 2H), 3.58 (td, J = 11.3, 3.5 Hz, 2H), 2.97-2.79 (m, 1H), 2.03 (td, J = 8.0, 4.0 Hz, 1H), 1.96-1.80 (m, 4H), 1.11-1.02 (m, 2H), 0.97 (ddd, J = 10.3, 6.4, 3.9 Hz, 2H) ppm. |
| 408 | 426 | 0.64 | 1H NMR (400 MHz, CDCl3) δ 8.31 (s, 1H), 7.31 (s, 1H), 7.26 (d, J = 5.6 Hz, 3H), 7.14 (s, 1H), 6.87-6.74 (m, 2H), 6.68 (s, 1H), 4.76-4.58 (m, 4H), 3.50 (p, J = 6.6 Hz, 1H), 2.84 (dd, J = 16.7, 9.1 Hz, 3H), 2.36 (s, 3H), 2.00 (d, J = 12.6 Hz, 1H), 1.95-1.68 (m, 4H), 1.58-1.43 (m, 1H) ppm. |
| 409 | 325.19 | 0.82 | 1H NMR (300 MHz, DMSO-d6) δ 9.45 (s, 1H), 9.13 (s, 1H), 7.77-7.68 (m, 2H), 7.59 (dt, J = 8.4, 5.5 Hz, 2H), 7.31 (s, 1H), 7.19 (td, J = 8.2, 2.0 Hz, 1H), 6.72 (s, 1H), 4.95 (dd, J = 8.3, 5.8 Hz, 2H), 4.62 (dd, J = 6.6, 5.9 Hz, 2H), 4.26-4.09 (m, 1H), 2.30 (s, 3H) ppm. |
| 410 | 406.48 | 0.63 | 1H NMR (300 MHz, DMSO-d6) δ 9.34 (s, 1H), 9.06 (s, 1H), 7.82 (d, J = 7.6 Hz, 2H), 7.54 (t, J = 7.9 Hz, 2H), 7.36 (t, J = 7.4 Hz, 1H), 7.28 (s, 1H), 6.88 (s, 1H), 6.27 (s, 1H), 4.54 (t, J = 6.4 Hz, 2H), 4.44 (t, J = 6.1 Hz, 2H), 4.31 (s, 1H), 3.41 (dd, J = 13.4, 6.3 Hz, 1H), 2.57 (s, 2H), 2.25 (d, J = 14.3 Hz, 3H), 2.14-1.94 (m, 4H), 1.65 (d, J = 8.8 Hz, 2H) ppm. |
| 411 | 408 | 0.66 | 1H NMR (400 MHz, CDCl3) δ 8.32 (s, 1H), 7.46 (dd, J = 5.8, 4.1 Hz, 3H), 7.33 (s, 1H), 7.14 (s, 1H), 7.05 (ddd, J = 10.4, 7.0, 3.4 Hz, 1H), 6.67 (d, J = 5.5 Hz, 2H), 4.75-4.53 (m, 4H), 3.60-3.39 (m, 1H), 2.96-2.73 (m, 3H), 2.36 (s, 3H), 2.00 (d, J = 12.1 Hz, 1H), 1.94-1.60 (m, 5H), 1.50 (dt, J = 12.3, 10.4 Hz, 1H) ppm. |
| 412 | 439 | 0.67 | 1H NMR (300 MHz, Acetone-d6) δ 8.89 (s, 1H), 8.74 (s, 1H), 7.87 (ddd, J = 11.7, 7.0, 2.6 Hz, 1H), 7.79-7.70 (m, 1H), 7.63 (d, J = 2.0 Hz, 1H), 7.61-7.50 (m, 2H), 6.80 (s, 1H), 3.37-3.24 (m, 4H), 2.62-2.46 (m, 4H), 2.29 (s, 3H) ppm. |
| 413 | 445.18 | 0.65 | 1H NMR (300 MHz, DMSO-d6) δ 9.30 (s, 1H), 8.77 (d, J = 2.3 Hz, 1H), 7.96 (tt, J = 14.8, 5.6 Hz, 2H), 7.11 (s, 1H), 6.86 (s, 1H), 6.30 (s, 1H), 4.57 (t, J = 6.4 Hz, 2H), 4.47 (t, J = 6.0 Hz, 2H), 3.49-3.39 (m, 1H), 3.13 (s, 4H), 2.40 (s, 4H), 2.21 (s, 3H) ppm. |
| 414 | 405.3 | 2.82 | 1H NMR (300 MHz, CDCl3) δ 8.72 (s, 1H), 8.24 (s, 1H), 7.55-7.33 (m, 4H), 7.16 (s, 1H), 6.92 (s, 1H), 6.42 (s, 1H), 5.13-5.00 (m, 2H), 4.82 (t, J = 7.6 Hz, 2H), 4.27-4.12 (m, 1H), 3.56 (d, J = 4.6 Hz, 4H), 3.25 (s, 4H), 2.36 (d, J = 11.2 Hz, 6H) ppm. |
| 415 | 467.32 | 0.65 | 1H NMR (400 MHz, CDCl3) δ 8.27 (s, 1H), 7.17 (s, 1H), 7.03 (s, 1H), 6.98 (dt, J = 9.3, 2.1 Hz, 1H), 6.76 (s, 1H), 6.61 (s, 1H), 6.57 (dt, J = 10.6, |

TABLE 3-continued

Analytical Data

| Cmpd No. | LC/MS (M + H) | LC/MS Ret. Time (min) | ¹H-NMR |
|---|---|---|---|
| | | | 2.2 Hz, 1H), 6.41 (s, 1H), 4.71 (p, J = 6.3 Hz, 4H), 4.59 (dt, J = 12.1, 6.1 Hz, 1H), 3.65-3.51 (m, 1H), 3.37-3.26 (m, 4H), 2.60-2.46 (m, 4H), 2.34 (s, 3H), 1.40 (d, J = 6.1 Hz, 6H) ppm. |
| 416 | 428.28 | 0.6 | 1H NMR (300 MHz, DMSO-d6) δ 9.46 (s, 1H), 9.17 (s, 1H), 7.74 (s, 1H), 7.69-7.58 (m, 2H), 7.25 (m, 2H), 6.85 (s, 1H), 5.18 (s, 1H), 4.57 (dd, J = 9.9, 4.3 Hz, 2H), 4.51 (dd, J = 13.1, 6.0 Hz, 2H), 3.82-3.71 (m, 1H), 2.92-2.70 (m, 4H), 2.29 (s, 3H), 2.21-1.97 (m, 2H) ppm. |
| 417 | 441.24 | 0.66 | 1H NMR (300 MHz, CDCl3) δ 8.53 (d, J = 2.4 Hz, 1H), 7.74 (ddd, J = 9.2, 6.1, 3.1 Hz, 1H), 7.28-7.20 (m, 1H), 7.17 (t, J = 2.0 Hz, 1H), 6.98 (ddt, J = 9.2, 6.9, 3.4 Hz, 1H), 6.83 (s, 1H), 6.73 (s, 1H), 6.47 (s, 1H), 4.85-4.60 (m, 4H), 3.70-3.52 (m, 1H), 3.44-3.21 (m, 4H), 2.65 (q, J = 7.6 Hz, 2H), 2.60-2.38 (m, 4H), 1.28 (t, J = 7.6 Hz, 3H) ppm. |
| 418 | 407.29 | 0.61 | 1H NMR (400 MHz, CDCl3) δ 9.04 (s, 1H), 8.74 (d, J = 5.5 Hz, 1H), 7.52 (d, J = 5.5 Hz, 1H), 7.13 (s, 1H), 7.08 (t, J = 1.9 Hz, 1H), 6.84 (s, 1H), 6.44 (s, 1H), 4.72 (dq, J = 12.6, 6.4 Hz, 4H), 3.59 (p, J = 6.4 Hz, 1H), 3.36-3.24 (m, 4H), 2.75 (s, 3H), 2.61-2.46 (m, 4H), 2.35 (s, 3H) ppm. |
| 419 | 377 | 0.6 | 1H NMR (400 MHz, CDCl3) δ 8.31 (s, 1H), 7.67 (d, J = 7.8 Hz, 2H), 7.49 (t, J = 7.8 Hz, 2H), 7.33 (t, J = 7.4 Hz, 1H), 7.20 (s, 1H), 7.05 (s, 1H), 6.75 (s, 1H), 6.56 (s, 1H), 3.38-3.19 (m, 1H), 3.12 (dd, J = 11.7, 2.6 Hz, 1H), 2.89 (dd, J = 11.9, 3.0 Hz, 1H), 2.79-2.60 (m, 1H), 2.36 (d, J = 18.0 Hz, 7H), 2.24-2.09 (m, 1H), 1.06 (d, J = 6.2 Hz, 3H), 1.02 (d, J = 6.1 Hz, 3H) ppm. |
| 420 | 391.23 | 0.63 | 1H NMR (300 MHz, DMSO-d6) δ 9.41 (s, 1H), 9.14 (s, 1H), 8.84 (s, 1H), 8.56 (s, 1H), 7.15 (s, 1H), 6.90 (s, 1H), 6.18 (d, J = 83.2 Hz, 1H), 3.19-3.01 (m, 4H), 2.78-2.61 (m, 4H), 2.56 (s, 3H), 2.23 (s, 3H), 1.75-1.56 (m, 1H), 0.56-0.40 (m, 2H), 0.39-0.27 (m, 2H) ppm. |
| 421 | 453.42 | 0.71 | 1H NMR (300 MHz, DMSO-d6) δ 9.32 (s, 1H), 9.15 (s, 1H), 7.72-7.45 (m, 2H), 7.24 (tt, J = 9.3, 2.2 Hz, 1H), 7.21-7.12 (m, 1H), 6.86 (s, 1H), 6.32 (s, 1H), 3.24 (dd, J = 20.4, 10.2 Hz, 2H), 3.18-3.06 (m, 4H), 2.84-2.69 (m, 4H), 2.23 (s, 3H) ppm. |
| 422 | 429.23 | 0.32 | |
| 423 | 377.41 | 0.59 | |
| 424 | 381.26 | 0.62 | 1H NMR (300 MHz, CDCl3) δ 8.30 (s, 1H), 7.24 (d, J = 2.0 Hz, 1H), 7.17 (s, 1H), 6.87 (d, J = 9.2 Hz, 1H), 6.77 (s, 1H), 6.60 (s, 1H), 6.42 (s, 1H), 3.39-3.25 (m, 4H), 2.65 (s, 4H), 2.44 (d, J = 6.3 Hz, 3H), 2.41 (s, 3H), 2.35 (s, 3H) ppm. |
| 425 | 441.45 | 0.68 | 1H NMR (300 MHz, CDCl3) δ 8.33 (s, 1H), 7.77 (d, J = 2.3 Hz, 1H), 7.24 (dd, J = 8.0, 2.2 Hz, 2H), 6.79 (tt, J = 8.7, 2.3 Hz, 1H), 6.56 (s, 1H), 6.51 (d, J = 2.2 Hz, 1H), 4.83-4.64 (m, 4H), 3.61 (p, J = 6.3 Hz, 1H), 3.41-3.26 (m, 4H), 2.57 (d, J = 4.3 Hz, 4H), 2.32 (s, 3H), 2.18 (s, 3H) ppm. |
| 426 | 392.22 | 0.93 | 1H NMR (300 MHz, CDCl3) δ 8.33 (s, 1H), 7.25 (dd, J = 7.9, 2.2 Hz, 2H), 7.11-7.04 (m, 2H), 6.82 (tt, J = 8.7, 2.3 Hz, 1H), 6.69 (s, 1H), 6.55 (t, J = 1.9 Hz, 1H), 3.97-3.81 (m, 4H), 3.23 (dd, J = 5.7, 4.1 Hz, 4H) ppm. |
| 427 | 355.45 | 0.68 | 1H NMR (400 MHz, DMSO-d6) δ 9.58 (s, 1H), 9.22 (s, 1H), 9.05 (s, 1H), 8.58 (d, J = 2.5 Hz, 1H), 8.32 (d, J = 8.7 Hz, 1H), 7.48 (s, 1H), 7.03 (d, J = 29.9 Hz, 1H), 6.54 (d, J = 67.9 Hz, 1H), 3.88 (s, 3H), 3.27 (s, 3H), 2.30 (d, J = 19.3 Hz, 2H) ppm. |
| 428 | 383 | 0.6 | 1H NMR (400 MHz, Acetone-d6) δ 8.53 (s, 1H), 8.22 (s, 1H), 7.76 (dd, J = 7.9, 1.6 Hz, 1H), |

TABLE 3-continued

Analytical Data

| Cmpd No. | LC/MS (M + H) | LC/MS Ret. Time (min) | ¹H-NMR |
|---|---|---|---|
| | | | 7.68 (dd, J = 7.8, 1.5 Hz, 1H), 7.53 (dtd, J = 17.0, 7.5, 1.5 Hz, 2H), 7.26 (s, 1H), 6.97 (s, 1H), 6.34 (s, 1H), 3.24-3.07 (m, 4H), 2.91 (s, 2H), 2.60-2.36 (m, 4H), 2.24 (s, 6H) ppm. |
| 429 | 370 | 0.63 | 1H NMR (300 MHz, Acetone-d6) δ 8.93 (s, 1H), 7.65-7.52 (m, 2H), 7.48 (s, 1H), 7.40 (s, 1H), 7.01 (tt, J = 9.1, 2.3 Hz, 1H), 6.65 (s, 1H), 3.09 (dd, J = 19.9, 10.3 Hz, 2H), 2.82 (s, 2H), 2.73-2.55 (m, 3H), 2.32 (s, 3H), 2.01-1.93 (m, 1H), 1.79-1.53 (m, 3H) ppm. |
| 430 | 353.09 | 0.6 | 1H NMR (400 MHz, CDCl3) δ 8.27 (s, 1H), 7.59 (d, J = 8.3 Hz, 2H), 7.44 (dd, J = 10.8, 5.1 Hz, 2H), 7.35-7.24 (m, 1H), 7.09 (s, 1H), 6.88 (s, 1H), 6.46 (s, 1H), 4.77 (dtt, J = 48.8, 6.7, 3.4 Hz, 1H), 3.70 (dd, J = 14.2, 5.8 Hz, 2H), 3.56-3.41 (m, 2H), 2.31 (s, 3H), 2.01-1.91 (m, 1H), 1.90-1.74 (m, 3H) ppm. |
| 431 | 419.49 | 0.65 | 1H NMR (300 MHz, CDCl3) δ 8.33 (s, 1H), 7.69 (dd, J = 8.6, 1.1 Hz, 2H), 7.56-7.46 (m, 3H), 7.40-7.32 (m, 1H), 7.11 (s, 1H), 6.84 (s, 1H), 6.70 (s, 1H), 6.39 (s, 1H), 4.55 (d, J = 5.7 Hz, 2H), 4.40 (d, J = 5.5 Hz, 2H), 3.26 (s, 4H), 2.60 (d, J = 32.4 Hz, 6H), 2.34 (s, 3H), 1.49 (s, 3H) ppm. |
| 432 | 435.19 | 0.6 | 1H NMR (400 MHz, CDCl3) δ 8.32 (s, 1H), 7.46-7.34 (m, 1H), 7.30 (t, J = 2.2 Hz, 1H), 7.23 (ddd, J = 8.0, 2.0, 0.8 Hz, 1H), 7.18 (t, J = 2.0 Hz, 1H), 6.89 (ddd, J = 8.3, 2.5, 0.7 Hz, 1H), 6.85 (s, 1H), 6.79 (s, 1H), 6.44 (s, 1H), 4.71 (dq, J = 12.5, 6.4 Hz, 4H), 3.90 (d, J = 4.4 Hz, 3H), 3.58 (p, J = 6.4 Hz, 1H), 3.40-3.25 (m, 4H), 2.71-2.56 (m, 2H), 2.56-2.45 (m, 4H), 1.27 (t, J = 7.6 Hz, 3H) ppm. |
| 433 | 442.44 | 0.65 | 1H NMR (300 MHz, DMSO-d6) δ 9.48 (s, 1H), 9.16 (s, 1H), 7.60 (d, J = 6.4 Hz, 2H), 7.42-7.20 (m, 2H), 6.83 (s, 1H), 6.28 (s, 1H), 4.53 (t, J = 6.5 Hz, 2H), 4.43 (t, J = 6.1 Hz, 2H), 4.32 (s, 1H), 3.41 (dd, J = 12.6, 6.3 Hz, 1H), 2.58 (s, 2H), 2.22 (s, 3H), 2.15-1.94 (m, 4H), 1.77-1.55 (m, 2H) ppm. |
| 434 | 405.4 | 0.63 | 1H NMR (300 MHz, DMSO-d6) δ 9.18 (s, 1H), 9.04 (s, 1H), 7.82 (dd, J = 8.6, 1.0 Hz, 2H), 7.55 (dd, J = 10.7, 5.2 Hz, 2H), 7.34 (t, J = 7.4 Hz, 1H), 7.14 (s, 1H), 6.88 (s, 1H), 6.28 (s, 1H), 3.91-3.73 (m, 2H), 3.66 (dd, J = 15.6, 8.0 Hz, 1H), 3.53 (dd, J = 8.5, 6.6 Hz, 1H), 3.11 (t, J = 4.9 Hz, 4H), 2.92 (p, J = 6.8 Hz, 1H), 2.66-2.53 (m, 2H), 2.49-2.44 (m, 2H), 2.22 (s, 3H), 2.09-1.91 (m, 1H), 1.78 (ddd, J = 15.6, 12.3, 8.2 Hz, 1H) ppm. |
| 435 | 342.13 | 3.3 | 1H NMR (400 MHz, DMSO-d6) δ 9.41 (d, J = 60.2 Hz, 1H), 9.06 (s, 1H), 7.87 (dd, J = 8.9, 4.7 Hz, 3H), 7.42 (t, J = 8.7 Hz, 2H), 6.92-6.57 (m, 2H), 5.92 (d, J = 12.4 Hz, 1H), 3.24 (s, 4H), 1.97 (s, 4H) ppm. |
| 436 | 405.49 | 0.64 | 1H NMR (300 MHz, CDCl3) δ 8.24 (s, 1H), 8.24 (s, 1H), 7.63-7.56 (m, 2H), 7.47-7.39 (m, 2H), 7.28 (ddd, J = 7.4, 3.9, 1.1 Hz, 1H), 7.05 (s, 1H), 6.75 (s, 1H), 6.62 (s, 1H), 6.32 (s, 1H), 4.63 (s, 2H), 4.21 (d, J = 5.9 Hz, 2H), 3.26 (s, 4H), 2.54 (s, 4H), 2.26 (s, 3H), 1.39 (s, 3H) ppm. |
| 437 | 427.45 | 0.64 | 1H NMR (300 MHz, DMSO-d6) δ 9.30 (s, 1H), 8.80 (d, J = 2.4 Hz, 1H), 7.69 (ddd, J = 9.2, 6.0, 3.2 Hz, 1H), 7.67-7.48 (m, 1H), 7.40-7.23 (m, 1H), 7.14 (s, 1H), 6.86 (s, 1H), 6.31 (s, 1H), 4.57 (t, J = 6.5 Hz, 2H), 4.47 (t, J = 6.0 Hz, 2H), 3.58-3.40 (m, 1H), 3.23-3.00 (m, 4H), 2.45-2.31 (m, 4H), 2.22 (s, 3H) ppm. |

TABLE 3-continued

Analytical Data

| Cmpd No. | LC/MS (M + H) | LC/MS Ret. Time (min) | ¹H-NMR |
|---|---|---|---|
| 438 | 386.15 | 0.73 | 1H NMR (400 MHz, DMSO-d6) δ 9.49 (s, 1H), 9.29 (s, 1H), 9.20 (s, 1H), 7.65 (d, J = 6.9 Hz, 2H), 7.28 (t, J = 23.5 Hz, 3H), 6.56 (s, 1H), 3.91 (s, 1H), 3.57 (s, 1H), 3.38 (q, J = 7.0 Hz, 1H), 3.34-3.11 (m, 2H), 2.94 (s, 1H), 2.74-2.53 (m, 2H), 2.29 (s, 3H), 1.87 (s, 2H) ppm. |
| 439 | 437.17 | 0.61 | 1H NMR (400 MHz, CDCl3) δ 8.32 (s, 1H), 7.61 (s, 1H), 7.46-7.36 (m, 2H), 7.24-7.14 (m, 2H), 6.77 (s, 1H), 6.61 (s, 1H), 6.41 (s, 1H), 4.78-4.62 (m, 4H), 3.66-3.53 (m, 1H), 3.37-3.25 (m, 4H), 2.57 (s, 3H), 2.55-2.51 (m, 4H), 2.34 (s, 3H) ppm. |
| 440 | 376.11 | 3.02 | 1H NMR (400 MHz, DMSO-d6) δ 9.57 (d, J = 39.5 Hz, 1H), 9.10 (s, 1H), 7.94 (dd, J = 37.4, 25.7 Hz, 1H), 7.84-7.55 (m, 2H), 7.11-6.86 (m, 2H), 6.28 (t, J = 29.1 Hz, 1H), 3.85-3.68 (m, 4H), 3.23-3.00 (m, 4H) ppm. |
| 441 | 392.13 | 3.58 | 1H NMR (400 MHz, DMSO-d6) δ 9.58 (s, 1H), 9.26 (s, 1H), 8.06 (d, J = 8.3 Hz, 2H), 7.94 (d, J = 8.4 Hz, 2H), 6.90-6.72 (m, 2H), 5.91 (d, J = 11.4 Hz, 1H), 3.24 (s, 4H), 1.97 (s, 4H) ppm. |
| 442 | 468.17 | 0.81 | 1H NMR (400 MHz, DMSO-d6) δ 9.56 (s, 1H), 9.19 (s, 1H), 7.65 (d, J = 6.3 Hz, 2H), 7.42 (s, 1H), 7.28 (d, J = 14.4 Hz, 2H), 6.65 (s, 1H), 3.84 (s, 1H), 3.39 (d, J = 10.0 Hz, 2H), 3.34-3.22 (m, 1H), 2.95 (d, J = 20.8 Hz, 3H), 2.85-2.73 (m, 2H), 2.66-2.39 (m, 2H), 2.29 (s, 3H), 1.97 (s, 2H), 1.85-1.63 (m, 2H) ppm. |
| 443 | 362 | 0.93 | 1H NMR (400 MHz, CDCl3) δ 8.34 (s, 1H), 7.68 (d, J = 7.7 Hz, 2H), 7.51 (t, J = 7.9 Hz, 2H), 7.44-7.28 (m, 2H), 7.19 (d, J = 16.6 Hz, 1H), 6.75 (s, 1H), 6.67 (s, 1H), 4.04 (dd, J = 11.5, 7.3 Hz, 1H), 3.96-3.79 (m, 1H), 3.67 (d, J = 8.1 Hz, 1H), 3.61-3.27 (m, 3H), 2.46-2.26 (m, 4H) note: contains singlet for methyl\, 2.18-2.01 (m, 4H) ppm. note: contains singlet for methyl |
| 444 | 398.21 | 0.85 | 1H NMR (300 MHz, DMSO-d6) δ 9.30 (s, 1H), 9.16 (s, 1H), 7.67-7.55 (m, 2H), 7.25 (tt, J = 10.3, 8.1 Hz, 1H), 6.90 (s, 1H), 6.65 (s, 1H), 5.93 (s, 1H), 4.56 (dd, J = 15.6, 6.0 Hz, 4H), 3.50 (s, 2H), 3.25 (t, J = 6.9 Hz, 2H), 2.26 (t, J = 6.8 Hz, 2H), 2.21 (s, 3H) ppm. |
| 445 | 427.18 | 0.59 | 1H NMR (400 MHz, CDCl3) δ 8.48 (d, J = 2.6 Hz, 1H), 7.75 (ddt, J = 8.3, 6.6, 1.7 Hz, 1H), 7.25 (ddd, J = 8.3, 5.2, 2.5 Hz, 1H), 7.16 (ddd, J = 15.6, 8.0, 1.6 Hz, 1H), 7.09 (s, 1H), 6.82 (s, 1H), 6.71 (s, 1H), 6.43 (s, 1H), 4.71 (dt, J = 13.0, 6.4 Hz, 4H), 3.66-3.49 (m, 1H), 3.36-3.24 (m, 4H), 2.59-2.46 (m, 4H), 2.35 (s, 3H) ppm. |
| 446 | 425.38 | 0.64 | 1H NMR (300 MHz, CDCl3) δ 8.37 (s, 1H), 7.70 (dd, J = 7.9, 1.7 Hz, 1H), 7.57 (dd, J = 7.9, 1.6 Hz, 1H), 7.41 (dtd, J = 20.3, 7.5, 1.7 Hz, 2H), 7.10 (s, 1H), 6.80 (s, 1H), 6.75 (s, 1H), 6.39 (s, 1H), 4.77-4.63 (m, 4H), 3.58 (p, J = 6.4 Hz, 1H), 3.36-3.19 (m, 4H), 2.60-2.44 (m, 4H), 2.33 (s, 3H) ppm. |
| 447 | 326 | 0.74 | 1H NMR (400 MHz, DMSO-d6) δ 9.58 (s, 1H), 9.22 (s, 1H), 9.03 (s, 1H), 8.59 (d, J = 2.5 Hz, 1H), 8.24 (dt, J = 10.1, 2.3 Hz, 1H), 7.60 (s, 1H), 7.31 (s, 1H), 6.74 (s, 1H), 4.96 (dd, J = 8.3, 5.8 Hz, 2H), 4.74-4.53 (m, 2H), 4.29-4.07 (m, 1H), 2.30 (s, 3H) ppm. |
| 448 | 342.19 | 0.8 | 1H NMR (300 MHz, DMSO-d6) δ 9.23 (s, 1H), 9.15 (s, 2H), 7.72-7.59 (m, 2H), 7.16 (d, J = 2.0 Hz, 1H), 6.51 (d, J = 12.4 Hz, 1H), 6.11 (d, J = 10.8 Hz, 1H), 5.99 (d, J = 0.8 Hz, 1H), 2.16 (s, 3H), 0.74-0.59 (m, 2H), 0.44-0.35 (m, 2H) ppm. |
| 449 | 378 | 0.75 | 1H NMR (400 MHz, CDCl3) δ 9.12-8.95 (m, 2H), 8.93-8.81 (m, 1H), 7.79 (dd, J = 37.6, 5.3 Hz, 1H), 7.26 (q, J = 19.8 Hz, 2H), 6.89 (d, J = 18.4 Hz, 1H), 6.71 (d, J = 5.8 Hz, 1H), 4.79 (dd, J = 50.4, 12.6 Hz, 1H), 3.90 (s, 1H), 3.11 (dd, J = 26.1, |

TABLE 3-continued

Analytical Data

| Cmpd No. | LC/MS (M + H) | LC/MS Ret. Time (min) | ¹H-NMR |
|---|---|---|---|
| | | | 14.1 Hz, 1H), 2.68 (t, J = 11.3 Hz, 1H), 2.58 (dd, J = 22.1, 10.0 Hz, 2H), 2.38 (d, J = 8.5 Hz, 3H), 2.14 (d, J = 12.6 Hz, 4H-methine buried under the doublet), 1.87 (t, J = 14.9 Hz, 1H), 1.81-1.53 (m, 3H) ppm. |
| 450 | 389 | 0.65 | 1H NMR (400 MHz, DMSO-d6) δ 11.05 (s, 1H), 9.68 (s, 1H), 8.79 (d, J = 2.2 Hz, 1H), 7.89 (td, J = 8.9, 5.9 Hz, 1H), 7.64 (ddd, J = 11.6, 9.0, 2.7 Hz, 1H), 7.41-7.27 (m, 2H), 7.11 (d, J = 12.2 Hz, 1H), 6.90 (s, 1H), 6.40 (d, J = 12.2 Hz, 1H), 3.76 (d, J = 10.6 Hz, 2H), 3.48 (d, J = 9.1 Hz, 2H), 3.26-3.02 (m, 4H), 2.79 (d, J = 4.7 Hz, 3H) ppm. |
| 451 | 355.13 | 0.53 | 1H NMR (400 MHz, DMSO-d6) δ 9.75 (d, J = 2.3 Hz, 1H), 9.44 (s, 1H), 9.18 (d, J = 8.5 Hz, 1H), 8.77 (dd, J = 5.4, 1.1 Hz, 1H), 8.73 (d, J = 5.1 Hz, 1H), 8.05 (dd, J = 8.6, 5.4 Hz, 1H), 7.33 (d, J = 2.2 Hz, 1H), 4.14 (m, 4H), 3.57 (m, 4H), 2.31 (d, J = 1.7 Hz, 3H) ppm. |
| 452 | 324 | 0.73 | 1H NMR (400 MHz, DMSO-d6) δ 9.83 (s, 1H), 9.66 (d, J = 23.4 Hz, 2H), 9.15 (s, 1H), 7.87 (d, J = 7.8 Hz, 2H), 7.57 (t, J = 7.4 Hz, 2H), 7.51 (d, J = 11.5 Hz, 1H), 7.38 (t, J = 7.4 Hz, 1H), 7.32 (s, 1H), 6.75 (d, J = 9.5 Hz, 1H), 3.60 (s, 1H), 3.42 (s, 2H), 3.20 (d, J = 24.0 Hz, 1H), 3.05 (s, 1H), 2.37 (s, 1H), 2.04-1.79 (m, 1H) ppm. |
| 453 | 461.23 | 0.7 | 1H NMR (300 MHz, CDCl3) δ 8.31 (s, 1H), 7.26 (dd, J = 7.8, 2.1 Hz, 2H), 7.11 (s, 1H), 6.88-6.74 (m, 2H), 6.68 (s, 1H), 6.43 (s, 1H), 3.37-3.20 (m, 4H), 2.84-2.65 (m, 3H), 2.62-2.44 (m, 6H), 2.35 (s, 3H) ppm. |
| 454 | 433.3 | 0.63 | 1H NMR (400 MHz, CDCl3) δ 9.06 (d, J = 15.6 Hz, 1H), 8.75 (d, J = 5.5 Hz, 1H), 7.52 (t, J = 8.0 Hz, 1H), 7.01 (t, J = 2.1 Hz, 1H), 6.81 (s, 1H), 6.78 (s, 1H), 6.39 (s, 1H), 4.72 (dt, J = 14.5, 6.4 Hz, 4H), 3.59 (p, J = 6.4 Hz, 1H), 3.37-3.22 (m, 4H), 2.75 (s, 3H), 2.56 (dd, J = 14.3, 9.3 Hz, 4H), 1.90 (tt, J = 8.4, 5.1 Hz, 1H), 1.03-0.90 (m, 2H), 0.84-0.70 (m, 2H) ppm. |
| 455 | 429.39 | 0.72 | 1H NMR (300 MHz, DMSO-d6) δ 9.22 (s, 1H), 9.06 (s, 1H), 7.83 (dd, J = 8.6, 1.0 Hz, 2H), 7.64-7.49 (m, 2H), 7.34 (t, J = 7.4 Hz, 1H), 7.26-7.07 (m, 4H), 7.01 (dt, J = 8.0, 5.7 Hz, 1H), 6.92 (s, 1H), 6.36 (s, 1H), 3.28 (d, J = 5.8 Hz, 4H), 3.18 (d, J = 5.3 Hz, 4H), 2.26 (d, J = 7.8 Hz, 3H) ppm. |
| 456 | 428.35 | 0.73 | 1H NMR (300 MHz, CDCl3) δ 8.26 (s, 1H), 7.19-7.14 (m, 2H), 7.05 (t, J = 2.1 Hz, 1H), 6.85 (d, J = 4.0 Hz, 1H), 6.77-6.65 (m, 2H), 6.40 (s, 1H), 4.11-3.98 (m, 2H), 3.91-3.78 (m, 5H), 3.73 (dd, J = 8.4, 7.0 Hz, 1H), 3.37-3.25 (m, 1H), 3.22-3.09 (m, 4H), 2.38-2.24 (m, 1H), 1.98 (ddd, J = 15.7, 12.4, 7.8 Hz, 1H) ppm. |
| 457 | 389.1 | 0.62 | 1H NMR (400 MHz, CDCl3) δ 8.22 (s, 1H), 7.13-7.05 (m, 2H), 6.79 (s, 2H), 6.69 (tt, J = 8.7, 2.3 Hz, 1H), 6.40 (s, 1H), 4.74 (dtt, J = 48.8, 6.8, 3.5 Hz, 1H), 3.65 (dd, J = 12.7, 7.2 Hz, 2H), 3.55-3.39 (m, 2H), 1.89 (d, J = 5.8 Hz, 3H), 1.86-1.69 (m, 4H) ppm. |
| 458 | 439.22 | 0.31 | 1H NMR (400 MHz, CD3OD) δ 8.94 (s, 1H), 7.98 (s, 1H), 7.73-7.50 (m, 2H), 7.21 (d, J = 111.2 Hz, 1H), 6.99 (tt, J = 9.0, 2.2 Hz, 1H), 4.18 (d, J = 67.2 Hz, 4H), 3.71 (d, J = 44.6 Hz, 4H), 2.42 (s, 3H), 2.06 (ddd, J = 12.7, 7.8, 4.7 Hz, 1H), 1.00-0.84 (m, 5H) ppm. |
| 459 | 397 | 0.68 | 1H NMR (300 MHz, CDCl3) δ 8.29 (s, 1H), 7.35-7.12 (m, 3H), 6.89-6.64 (m, 3H), 6.55 (s, 1H), 6.05 (s, 1H), 4.24 (s, 1H), 3.54 (s, 1H), 3.42 (s, 2H), 3.05 (dd, J = 9.5, 1.8 Hz, 1H), 2.71 (d, J = 9.4 Hz, 1H), 2.41 (s, 3H), 2.31 (s, 3H), 2.01 (s, 1H), 1.93 (d, J = 9.5 Hz, 1H) ppm. |
| 460 | 365.17 | 0.62 | 1H NMR (300 MHz, DMSO-d6) δ 9.59 (s, 1H), 9.10 (s, 1H), 7.92-7.78 (m, 2H), 7.56 (t, J = 8.0 Hz, |

TABLE 3-continued

Analytical Data

| Cmpd No. | LC/MS (M + H) | LC/MS Ret. Time (min) | ¹H-NMR |
|---|---|---|---|
| | | | 2H), 7.37 (t, J = 7.4 Hz, 1H), 6.73 (d, J = 1.4 Hz, 1H), 6.66 (s, 1H), 5.41 (d, J = 54.5 Hz, 1H), 3.74-3.45 (m, 3H), 3.43-3.33 (m, 1H), 2.24 (s, 2H), 1.81 (d, J = 8.1 Hz, 1H), 0.88 (dd, J = 4.9, 2.3 Hz, 2H), 0.79 (d, J = 8.1 Hz, 2H) ppm. |
| 461 | 407.43 | 0.63 | 1H NMR (300 MHz, CDCl3) δ 8.33 (s, 1H), 7.75-7.63 (m, 2H), 7.52 (dd, J = 10.6, 5.1 Hz, 2H), 7.37 (t, J = 7.4 Hz, 1H), 7.13 (d, J = 16.5 Hz, 1H), 6.81 (s, 1H), 6.68 (s, 1H), 6.39 (s, 1H), 3.71 (d, J = 12.6 Hz, 2H), 3.40 (s, 8H), 3.04 (d, J = 70.0 Hz, 6H), 2.36 (d, J = 9.2 Hz, 3H) ppm. |
| 462 | 435.35 | 0.9 | 1H NMR (300 MHz, CDCl3) δ 8.33 (s, 1H), 7.53-7.39 (m, 3H), 7.15-6.97 (m, 2H), 6.73 (s, 1H), 6.65 (s, 1H), 6.36 (s, 1H), 4.79-4.65 (m, 4H), 3.66-3.50 (m, 1H), 3.39-3.21 (m, 4H), 2.60-2.45 (m, 4H), 1.95-1.81 (m, 1H), 1.03-0.86 (m, 2H), 0.82-0.68 (m, 2H) ppm. |
| 463 | 451.08 | 0.62 | 1H NMR (400 MHz, CDCl3) δ 8.32 (s, 1H), 7.62 (s, 1H), 7.43-7.36 (m, 2H), 7.21 (dt, J = 7.4, 1.9 Hz, 2H), 6.82 (s, 1H), 6.63 (s, 1H), 6.45 (s, 1H), 4.78-4.65 (m, 4H), 3.66-3.50 (m, 1H), 3.38-3.28 (m, 4H), 2.64 (q, J = 7.6 Hz, 2H), 2.57 (s, 3H), 2.56-2.51 (m, 4H), 1.32-1.21 (m, 3H) ppm. |
| 464 | 380 | 0.63 | 1H NMR (400 MHz, Acetone-d6) δ 9.09 (s, 1H), 9.01 (d, J = 1.1 Hz, 1H), 8.92 (d, J = 5.5 Hz, 1H), 8.44 (s, 1H), 7.81 (dd, J = 5.5, 1.3 Hz, 1H), 7.29 (d, J = 1.9 Hz, 1H), 6.99 (s, 1H), 6.42 (s, 1H), 3.78 (d, J = 12.4 Hz, 2H), 3.30 (s, 3H), 3.25 (d, J = 6.2 Hz, 2H), 2.87-2.62 (m, 2H), 2.28 (s, 3H), 1.88-1.70 (m, 3H—methine contained in this muliplet), 1.38 (ddd, J = 15.6, 12.4, 4.1 Hz, 2H) ppm. |
| 465 | 390.37 | 0.72 | 1H NMR (300 MHz, CDCl3) δ 8.34 (s, 1H), 7.74-7.64 (m, 2H), 7.58-7.47 (m, 2H), 7.42-7.34 (m, 1H), 7.18 (t, J = 2.0 Hz, 1H), 7.14-7.08 (m, 1H), 6.82 (s, 1H), 6.59-6.52 (m, 1H), 6.24 (dd, J = 4.0, 2.0 Hz, 1H), 5.05 (td, J = 4.8, 2.2 Hz, 2H), 4.88 (td, J = 4.9, 1.8 Hz, 2H), 3.97-3.84 (m, 4H), 3.32-3.16 (m, 4H) ppm. |
| 466 | 410 | 0.67 | 1H NMR (300 MHz, CDCl3) δ 8.30 (s, 1H), 7.30 (s, 1H), 7.29-7.23 (m, 3H), 7.14 (s, 1H), 6.78 (tt, J = 8.7, 2.3 Hz, 1H), 6.70 (d, J = 1.7 Hz, 2H), 3.26-3.15 (m, 1H), 3.11 (d, J = 11.2 Hz, 1H), 2.74 (ddd, J = 11.6, 7.5, 3.5 Hz, 1H), 2.36 (s, 3H), 2.32-2.11 (m, 2H), 1.96 (d, J = 12.4 Hz, 1H), 1.88-1.57 (m, 3H), 1.51 (td, J = 12.2, 4.0 Hz, 1H), 0.53-0.37 (m, 4H) ppm. |
| 467 | 496.22 | 0.63 | 1H NMR (300 MHz, CDCl3) δ 8.29 (s, 1H), 7.23 (s, 1H), 6.78-6.65 (m, 3H), 6.61 (s, 1H), 6.39 (s, 1H), 6.23 (d, J = 11.5 Hz, 1H), 5.43 (d, J = 52.9 Hz, 1H), 3.96-3.63 (m, 4H), 3.63-3.44 (m, 4H), 3.39 (d, J = 10.2 Hz, 1H), 3.06-2.70 (m, 4H), 2.48 (d, J = 7.9 Hz, 4H), 2.34 (s, 3H), 2.17 (s, 1H), 0.89 (d, J = 7.8 Hz, 2H) ppm. |
| 468 | 423.49 | 0.67 | 1H NMR (300 MHz, CDCl3) δ 8.33 (s, 1H), 7.57-7.40 (m, 3H), 7.16 (t, J = 2.1 Hz, 1H), 7.10-6.98 (m, 1H), 6.84 (s, 1H), 6.70 (s, 1H), 6.45 (s, 1H), 4.85-4.57 (m, 4H), 3.59 (p, J = 6.4 Hz, 1H), 3.43-3.18 (m, 4H), 2.64 (q, J = 7.6 Hz, 2H), 2.60-2.40 (m, 4H), 1.28 (t, J = 7.6 Hz, 3H) ppm. |
| 469 | 441.24 | 0.66 | 1H NMR (300 MHz, CDCl3) δ 8.53 (d, J = 2.4 Hz, 1H), 7.75 (ddd, J = 9.2, 6.1, 3.1 Hz, 1H), 7.27-7.19 (m, 1H), 7.14 (s, 1H), 6.99 (ddd, J = 12.4, 7.0, 3.3 Hz, 1H), 6.80 (s, 1H), 6.73 (s, 1H), 6.43 (s, 1H), 4.67 (d, J = 5.6 Hz, 2H), 4.30 (d, J = 5.7 Hz, 2H), 3.46-3.15 (m, 4H), 2.67-2.47 (m, 4H), 2.36 (s, 3H), 1.44 (s, 3H) ppm. |
| 470 | 407.47 | 0.65 | 1H NMR (300 MHz, CDCl3) δ 9.21 (d, J = 1.4 Hz, 1H), 9.21 (d, J = 1.4 Hz, 1H), 8.93 (s, 1H), 8.57 (d, J = 2.5 Hz, 1H), 8.40 (dd, J = 2.5, 1.5 Hz, 1H), 7.34 (d, J = 2.2 Hz, 1H), 7.03 (d, J = 2.1 Hz, |

TABLE 3-continued

Analytical Data

| Cmpd No. | LC/MS (M + H) | LC/MS Ret. Time (min) | ¹H-NMR |
|---|---|---|---|
| | | | 1H), 6.79 (s, 1H), 4.88-4.58 (m, 4H), 3.64 (p, J = 6.5 Hz, 1H), 3.04 (t, J = 4.6 Hz, 4H), 2.32 (s, 3H), 2.20 (s, 3H) ppm. |
| 471 | 423.19 | 0.59 | 1H NMR (300 MHz, CDCl3) δ 9.16 (d, J = 1.3 Hz, 1H), 8.95 (s, 1H), 8.56 (d, J = 2.5 Hz, 1H), 8.41 (dd, J = 2.5, 1.5 Hz, 1H), 7.90 (d, J = 2.8 Hz, 1H), 7.47 (s, 1H), 6.39 (d, J = 2.7 Hz, 1H), 4.81-4.63 (m, 4H), 3.78 (s, 3H), 3.59 (p, J = 6.5 Hz, 1H), 3.37-3.24 (m, 4H), 2.62-2.50 (m, 4H), 2.33 (s, 3H) ppm. |
| 472 | 427.45 | 0.66 | H NMR (300 MHz, DMSO-d6) δ 9.21 (s, 1H), 9.14 (s, 1H), 7.77-7.53 (m, 2H), 7.23 (tt, J = 9.3, 2.2 Hz, 1H), 6.94 (s, 1H), 6.49 (s, 1H), 5.94 (s, 1H), 5.66 (d, J = 6.5 Hz, 1H), 4.56 (td, J = 6.4, 4.0 Hz, 2H), 4.45 (dt, J = 8.6, 5.9 Hz, 2H), 3.88 (d, J = 5.9 Hz, 1H), 3.74-3.51 (m, 1H), 2.89-2.69 (m, 1H), 2.62 (dd, J = 13.7, 8.2 Hz, 1H), 2.41 (dt, J = 8.9, 5.9 Hz, 2H), 2.31-2.19 (m, 1H), 2.15 (s, 3H), 1.67 (td, J = 12.6, 7.2 Hz, 1H) ppm. |
| 473 | | | 1H NMR (400 MHz, DMSO-d6) δ 9.42 (s, 1H), 9.16 (s, 1H), 7.62 (dd, J = 8.6, 2.1 Hz, 2H), 7.52 (s, 1H), 7.29-7.19 (m, 1H), 7.18 (s, 1H), 6.62 (s, 1H), 4.58 (td, J = 6.5, 1.9 Hz, 2H), 4.50 (td, J = 6.0, 1.2 Hz, 2H), 3.69-3.60 (m, 1H), 3.29-3.21 (m, 1H), 2.97 (t, J = 8.4 Hz, 1H), 2.73 (dd, J = 14.9, 7.8 Hz, 1H), 2.59 (td, J = 8.7, 5.6 Hz, 1H), 2.44-2.38 (m, 1H), 2.26 (s, 3H), 1.79 (dt, J = 13.8, 8.3 Hz, 1H) ppm. |
| 475 | 426.3 | 4.59 | 1H NMR (300 MHz, DMSO-d6) δ 9.21 (s, 1H), 7.56 (m, 4H), 7.26 (t, J = 9.3 Hz, 1H), 6.81 (s, 1H), 3.84-3.75 (m, 4H), 3.28-3.15 (m, 4H) ppm. |
| 476 | 423.17 | 0.6 | 1H NMR (400 MHz, CDCl3) δ 8.46 (d, J = 2.4 Hz, 1H), 7.77 (dd, J = 7.4, 1.9 Hz, 1H), 7.19 (s, 1H), 7.16 (dd, J = 11.5, 8.4 Hz, 1H), 7.12-7.06 (m, 1H), 6.78 (s, 1H), 6.67 (s, 1H), 6.41 (s, 1H), 4.71 (dt, J = 14.3, 6.4 Hz, 4H), 3.65-3.52 (m, 1H), 3.38-3.26 (m, 4H), 2.59-2.49 (m, 4H), 2.41 (s, 3H), 2.35 (s, 3H) ppm. |
| 477 | 406.18 | 0.8 | 1H NMR (300 MHz, CD3OD) δ 8.84 (s, 1H), 7.81 (ddd, J = 11.4, 6.9, 2.6 Hz, 1H), 7.64 (dddd, J = 9.0, 4.1, 2.6, 1.6 Hz, 1H), 7.45 (dt, J = 10.2, 8.7 Hz, 1H), 7.02 (q, J = 1.5 Hz, 2H), 4.43 (d, J = 11.0 Hz, 2H), 3.60 (d, J = 9.1 Hz, 2H), 3.20 (s, 4H), 2.96 (s, 3H) ppm. |
| 478 | 475.11 | 0.63 | 1H NMR (300 MHz, CDCl3) δ 8.31 (s, 1H), 7.76-7.67 (m, 2H), 7.37 (d, J = 8.4 Hz, 2H), 7.08 (s, 1H), 6.83 (s, 1H), 6.67 (s, 1H), 6.42 (s, 1H), 4.79-4.63 (m, 4H), 3.59 (p, J = 6.4 Hz, 1H), 3.36-3.24 (m, 4H), 2.59-2.46 (m, 4H), 2.35 (s, 3H) ppm. |
| 479 | 361 | 0.61 | 1H NMR (400 MHz, CDCl3) δ 8.30 (s, 1H), 7.66 (dd, J = 8.6, 1.0 Hz, 2H), 7.49 (t, J = 8.0 Hz, 2H), 7.33 (t, J = 7.4 Hz, 1H), 6.83 (s, 1H exch), 6.58 (d, J = 5.0 Hz, 2H), 6.03 (s, 1H), 4.25 (s, 1H), 3.56 (s, 1H), 3.42 (s, 2H), 3.08 (d, J = 9.4 Hz, 1H), 2.72 (d, J = 9.5 Hz, 1H), 2.42 (s, 3H), 2.30 (s, 3H), 2.04 (d, J = 9.6 Hz, 2H—heavy due to a broad peak underneath), 1.94 (d, J = 9.5 Hz, 1H) ppm. |
| 480 | 508.23 | 0.58 | 1H NMR (300 MHz, CDCl3) δ 8.28 (s, 1H), 7.40 (s, 1H), 6.84 (s, 1H), 6.77 (s, 1H), 6.65-6.51 (m, 2H), 6.41 (s, 1H), 6.18 (dt, J = 11.8, 2.1 Hz, 1H), 4.73 (dt, J = 14.6, 6.3 Hz, 4H), 3.79 (dd, J = 10.5, 6.1 Hz, 1H), 3.71-3.50 (m, 3H), 3.48-3.37 (m, 2H), 3.36-3.28 (m, 4H), 3.22 (dd, J = 9.5, 6.6 Hz, 1H), 2.82 (m, 1H), 2.70-2.57 (m, 2H), 2.58-2.49 (m, 4H), 2.32 (s, 3H), 2.18 (tt, J = 16.0, 6.7 Hz, 1H), 1.86 (ddd, J = 15.8, 12.7, 7.9 Hz, 1H), 1.75 (s, 1H) ppm. |
| 481 | 378 | 0.6 | 1H NMR (400 MHz, Acetone-d6) δ 8.77 (s, 1H), 8.15 (s, 1H), 7.86 (dd, J = 8.6, 1.0 Hz, 2H), |

TABLE 3-continued

Analytical Data

| Cmpd No. | LC/MS (M + H) | LC/MS Ret. Time (min) | ¹H-NMR |
|---|---|---|---|
| | | | 7.54 (dd, J = 8.4, 7.6 Hz, 2H), 7.39-7.30 (m, 2H), 6.96 (s, 1H), 6.36 (s, 1H), 3.77 (d, J = 12.4 Hz, 2H), 3.29 (s, 3H), 3.25 (d, J = 6.2 Hz, 2H), 2.72 (td, J = 12.3, 2.4 Hz, 2H), 2.26 (s, 3H), 1.80 (d, J = 12.9 Hz, 2H), 1.76-1.67 (m, 1H), 1.37 (qd, J = 12.4, 4.0 Hz, 2H) ppm. |
| 482 | 411.48 | 0.67 | 1H NMR (300 MHz, DMSO-d6) δ 9.29 (s, 1H), 9.14 (s, 1H), 7.71-7.50 (m, 2H), 7.23 (tt, J = 9.3, 2.2 Hz, 1H), 7.16 (s, 1H), 6.84 (s, 1H), 6.30 (s, 1H), 3.17-2.99 (m, 4H), 2.80-2.60 (m, 4H), 2.25 (d, J = 14.5 Hz, 3H), 1.77-1.56 (m, 1H), 0.58-0.40 (m, 2H), 0.41-0.23 (m, 2H) ppm. |
| 483 | 418.5 | 0.65 | 1H NMR (300 MHz, CDCl3) δ 8.33 (s, 1H), 7.74-7.67 (m, 2H), 7.56-7.47 (m, 2H), 7.41-7.33 (m, 1H), 7.24 (s, 2H), 6.68 (d, J = 5.5 Hz, 2H), 4.54 (d, J = 5.6 Hz, 2H), 4.37 (d, J = 5.7 Hz, 2H), 2.75 (d, J = 11.5 Hz, 2H), 2.60 (s, 2H), 2.54-2.41 (m, 1H), 2.37 (s, 3H), 2.21-2.08 (m, 2H), 1.89-1.75 (m, 4H), 1.46 (s, 3H) ppm. |
| 484 | 445.31 | 0.66 | 1H NMR (300 MHz, DMSO-d6) δ 9.38 (s, 1H), 8.87 (d, J = 2.3 Hz, 1H), 7.69-7.52 (m, 2H), 7.13 (s, 1H), 6.86 (s, 1H), 6.32 (s, 1H), 4.57 (t, J = 6.5 Hz, 2H), 4.47 (t, J = 6.0 Hz, 2H), 3.50-3.39 (m, 1H), 3.19-3.09 (m, 4H), 2.45-2.35 (m, 4H), 2.22 (s, 3H) ppm. |
| 485 | 427.16 | 2.9 | 1H NMR (300 MHz, DMSO-d6) δ 9.33 (s, 1H), 9.15 (s, 1H), 7.60 (d, J = 6.5 Hz, 2H), 7.24 (t, J = 9.3 Hz, 1H), 6.74 (s, 1H), 6.69 (s, 1H), 5.82 (s, 1H), 3.89 (t, J = 6.9 Hz, 2H), 3.63-3.53 (m, 6H), 3.29-3.22 (m, 1H), 2.34 (m, 4H), 2.19 (s, 3H) ppm. |
| 486 | 403.28 | 3.08 | 1H NMR (300 MHz, DMSO-d6) δ 9.13 (s, 1H), 7.89-7.79 (d, 2H), 7.56 (m, 4H), 7.38 (t, J = 7.4 Hz, 1H), 6.84 (s, 1H), 3.88 (d, J = 9.7 Hz, 2H), 3.51 (m, 2H), 3.19 (m, 4H), 2.85 (s, 3H) ppm. |
| 487 | | | 1H NMR (300 MHz, DMSO-d6) δ 9.46 (s, 1H), 9.17 (s, 1H), 7.74 (s, 1H), 7.69-7.58 (m, 2H), 7.25 (m, 2H), 6.85 (s, 1H), 5.18 (s, 1H), 4.57 (dd, J = 9.9, 4.3 Hz, 2H), 4.51 (dd, J = 13.1, 6.0 Hz, 2H), 3.82-3.71 (m, 1H), 2.92-2.70 (m, 4H), 2.29 (s, 3H), 2.21-1.97 (m, 2H) ppm. |
| 488 | 354.83 | 0.73 | 1H NMR (300 MHz, CDCl3) δ 8.92 (s, 1H), 7.83 (t, J = 7.8 Hz, 1H), 7.74 (dd, J = 8.0, 0.9 Hz, 1H), 7.25 (dd, J = 7.7, 0.9 Hz, 1H), 6.76 (s, 2H), 6.64 (d, J = 1.6 Hz, 1H), 6.09 (s, 1H), 3.45-3.26 (m, 4H), 2.40-2.31 (s, 3H), 2.04 (td, J = 6.3, 3.1 Hz, 4H) ppm. |
| 489 | 421.51 | 0.61 | 1H NMR (300 MHz, CDCl3) δ 9.19 (d, J = 1.4 Hz, 1H), 8.92 (s, 1H), 8.57 (d, J = 2.5 Hz, 1H), 8.41 (dd, J = 2.5, 1.5 Hz, 1H), 7.18 (t, J = 2.0 Hz, 1H), 6.84 (s, 1H), 6.76 (s, 1H), 6.48 (s, 1H), 4.68 (d, J = 5.5 Hz, 2H), 4.30 (d, J = 5.7 Hz, 2H), 3.39-3.23 (m, 4H), 2.65 (q, J = 7.6 Hz, 2H), 2.61-2.46 (m, 4H), 1.45 (s, 3H), 1.29 (t, J = 7.6 Hz, 3H) ppm. |
| 490 | 400.24 | 0.8 | 1H NMR (300 MHz, DMSO-d6) δ 9.20 (s, 1H), 9.15 (s, 1H), 7.72-7.60 (m, 2H), 7.28-7.17 (m, 1H), 7.04 (s, 1H), 6.46 (s, 1H), 6.04 (s, 1H), 5.31 (t, J = 6.2 Hz, 1H), 3.75 (t, J = 6.4 Hz, 2H), 3.06 (d, J = 6.0 Hz, 2H), 2.14 (s, 3H), 1.95-1.83 (m, 3H), 1.65-1.56 (m, 1H), 1.20 (s, 3H) ppm. |
| 491 | 522.23 | 0.65 | 1H NMR (300 MHz, CDCl3) δ 8.27 (s, 1H), 7.22 (s, 1H), 6.76 (d, J = 10.3 Hz, 2H), 6.71-6.58 (m, 2H), 6.40 (s, 2H), 6.32 (dd, J = 12.0, 2.1 Hz, 1H), 4.77-4.60 (m, 4H), 3.92 (s, 1H), 3.59 (dd, J = 12.9, 6.4 Hz, 1H), 3.54-3.43 (m, 2H), 3.40 (s, 3H), 3.30 (dd, J = 11.0, 6.3 Hz, 5H), 3.24-3.15 (m, 1H), 2.59-2.46 (m, 4H), 2.34 (s, 3H), 2.07 (m, 2H) ppm. |
| 492 | 401.18 | 0.64 | 1H NMR (300 MHz, DMSO-d6) δ 9.63 (s, 1H), 9.10 (s, 1H), 8.04-7.91 (m, 1H), 7.75-7.58 (m, 2H), 6.73 (d, J = 1.6 Hz, 1H), 6.61 (d, J = 1.6 Hz, 1H), 5.41 (d, J = 53.7 Hz, 1H), |

TABLE 3-continued

Analytical Data

| Cmpd No. | LC/MS (M + H) | LC/MS Ret. Time (min) | ¹H-NMR |
|---|---|---|---|
| | | | 3.73-3.46 (m, 3H), 3.42-3.32 (m, 1H), 2.25 (d, J = 8.9 Hz, 2H), 1.82 (dd, J = 8.7, 4.0 Hz, 1H), 0.96-0.83 (m, 2H), 0.78 (dd, J = 8.2, 2.8 Hz, 2H) ppm. |
| 493 | 372.42 | 0.66 | 1H NMR (300 MHz, DMSO-d6) δ 9.32 (s, 1H), 9.15 (s, 1H), 7.59 (dd, J = 8.6, 2.1 Hz, 2H), 7.25 (dd, J = 10.4, 8.1 Hz, 1H), 6.68 (d, J = 8.9 Hz, 2H), 5.78 (s, 1H), 4.76 (t, J = 5.3 Hz, 1H), 3.80 (t, J = 7.4 Hz, 2H), 3.55 (dt, J = 18.8, 6.3 Hz, 4H), 2.75 (d, J = 7.7 Hz, 1H), 2.19 (s, 3H) ppm. |
| 494 | 520.39 | 0.64 | 1H NMR (400 MHz, CDCl3) δ 8.26 (s, 1H), 7.08 (t, J = 1.8 Hz, 1H), 6.73-6.67 (m, 3H), 6.57 (s, 1H), 6.37 (s, 1H), 6.08 (dt, J = 10.5, 1.9 Hz, 1H), 4.70 (p, J = 6.2 Hz, 4H), 4.45-4.31 (m, 1H), 4.22-4.15 (m, 2H), 3.81 (dd, J = 8.0, 4.3 Hz, 2H), 3.64-3.51 (m, 1H), 3.37 (s, 3H), 3.34-3.25 (m, 4H), 2.57-2.48 (m, 4H), 1.94-1.82 (m, 1H), 1.01-0.87 (m, 2H), 0.81-0.68 (m, 2H) ppm. |
| 495 | 447 | 0.52 | 1H NMR (400 MHz, CDCl3) δ 8.36 (s, 1H), 8.18 (d, J = 5.5 Hz, 1H), 7.19 (s, 1H), 6.86 (d, J = 1.6 Hz, 1H), 6.72 (s, 1H), 6.68 (dd, J = 5.6, 1.7 Hz, 1H), 6.65 (s, 1H), 3.80-3.60 (m, 4H), 3.33 (s, 4H), 2.66 (s, 4H), 2.42 (s, 3H), 2.31 (s, 3H), 1.84 (s, 4H), 1.59 (dd, J = 6.2, 2.8 Hz, 4H) ppm. |
| 496 | 400.24 | 0.69 | 1H NMR (300 MHz, DMSO-d6) δ 9.21 (s, 1H), 9.14 (s, 1H), 7.65 (dd, J = 8.7, 2.1 Hz, 2H), 7.29-7.18 (m, 1H), 6.95 (s, 1H), 6.47 (s, 1H), 5.93 (s, 1H), 5.51 (s, 1H), 3.91-3.72 (m, 2H), 3.59 (dd, J = 14.5, 7.9 Hz, 1H), 3.08 (s, 2H), 2.14 (s, 3H), 1.97 (m, 1H), 1.86-1.71 (m, 4H), 1.49-1.39 (m, 1H) ppm. |
| 497 | 360.09 | 3.36 | |
| 498 | 401.18 | 0.64 | 1H NMR (400 MHz, DMSO-d6) δ 9.67 (s, 1H), 9.12 (s, 1H), 8.05-7.90 (m, 1H), 7.68 (dt, J = 17.4, 5.7 Hz, 2H), 6.73 (d, J = 1.6 Hz, 1H), 6.62 (d, J = 1.5 Hz, 1H), 5.41 (d, J = 54.0 Hz, 1H), 3.72-3.44 (m, 3H), 3.37 (dd, J = 16.5, 9.3 Hz, 1H), 2.22 (d, J = 14.5 Hz, 2H), 1.83 (td, J = 8.0, 4.1 Hz, 1H), 0.87 (dd, J = 15.2, 5.6 Hz, 2H), 0.78 (dd, J = 8.1, 3.0 Hz, 2H) ppm. |
| 499 | 374 | 0.59 | 1H NMR (300 MHz, DMSO-d6) δ 9.29 (s, 1H), 9.16 (s, 1H), 8.31 (s, 1H), 8.24-8.09 (m, 1H), 7.78 (t, J = 7.2 Hz, 2H), 7.21 (s, 1H), 6.86 (s, 1H), 6.32 (s, 1H), 3.15 (d, J = 4.4 Hz, 3H), 2.56-2.40 (m, 4H—CH2s under solvent peak, 2.23 (s, 6H both CH3s co-incident) ppm. |
| 500 | 427.21 | 0.81 | 1H NMR (300 MHz, DMSO-d6) δ 9.31 (s, 1H), 9.16 (s, 1H), 7.60 (d, J = 6.9 Hz, 2H), 7.25 (dd, J = 10.3, 8.0 Hz, 1H), 6.94 (d, J = 10.3 Hz, 1H), 6.67-6.61 (m, 1H), 5.97 (s, 1H), 5.18 (m, 1H), 4.67 (m, 1H), 3.51-3.37 (m, 2H), 3.28-3.12 (m, 3H), 2.90 (s, 2H), 2.75 (s, 1H), 2.21 (s, 3H), 2.12 (s, 1H), 2.02 (s, 2H) ppm. |
| 501 | 428.49 | 0.58 | 1H NMR (300 MHz, CDCl3) δ 8.28 (s, 1H), 7.60 (ddd, J = 10.8, 6.8, 2.5 Hz, 1H), 7.47-7.38 (m, 1H), 7.37-7.28 (m, 2H), 7.20 (d, J = 4.0 Hz, 2H), 5.80 (s, 1H), 4.06 (t, J = 7.5 Hz, 2H), 3.87 (dd, J = 8.1, 5.4 Hz, 2H), 3.82-3.66 (m, 4H), 3.41-3.23 (m, 1H), 2.47 (d, J = 4.3 Hz, 4H), 2.33 (s, 3H) ppm. |
| 502 | 392.49 | 0.56 | 1H NMR (300 MHz, CDCl3) δ 8.34 (s, 1H), 7.70 (d, J = 7.7 Hz, 2H), 7.52 (t, J = 7.9 Hz, 2H), 7.37 (t, J = 7.4 Hz, 1H), 7.28 (s, 1H), 7.20 (s, 1H), 5.79 (s, 1H), 4.06 (t, J = 7.5 Hz, 2H), 4.25-3.69 (m, 9H), 3.87 (dd, J = 8.0, 5.4 Hz, 2H), 3.83-3.66 (m, 4H), 3.39-3.24 (m, 1H), 3.47-3.24 (m, 1H), 2.47 (d, J = 4.2 Hz, 4H), 2.58-2.17 (m, 8H), 2.32 (s, 3H) ppm. |

TABLE 3-continued

Analytical Data

| Cmpd No. | LC/MS (M + H) | LC/MS Ret. Time (min) | ¹H-NMR |
|---|---|---|---|
| 503 | 393.48 | 0.54 | 1H NMR (300 MHz, CDCl3) δ 8.97 (s, 1H), 8.44 (dd, J = 4.1, 1.0 Hz, 1H), 7.97-7.81 (m, 2H), 7.28-7.22 (m, 3H), 5.81 (s, 1H), 4.06 (t, J = 7.5 Hz, 2H), 3.87 (dd, J = 8.0, 5.4 Hz, 2H), 3.82-3.66 (m, 4H), 3.40-3.26 (m, 1H), 2.47 (d, J = 4.2 Hz, 4H), 2.34 (s, 3H) ppm. |
| 504 | 411.52 | 0.54 | 1H NMR (300 MHz, CDCl3) δ 8.49 (s, 1H), 8.33 (d, J = 5.6 Hz, 1H), 7.57-7.47 (m, 1H), 7.31 (s, 1H), 7.28-7.25 (m, 1H), 7.21 (s, 1H), 5.83 (s, 1H), 4.07 (t, J = 7.5 Hz, 2H), 3.87 (dd, J = 8.1, 5.4 Hz, 2H), 3.83-3.69 (m, 4H), 3.39-3.25 (m, 1H), 2.47 (s, 4H), 2.35 (s, 3H) ppm. |
| 505 | 543.56 | 0.68 | 1H NMR (300 MHz, CDCl3) δ 8.33 (s, 1H), 7.27 (dd, J = 7.7, 2.4 Hz, 2H), 7.23-7.12 (m, 2H), 6.80 (tt, J = 8.7, 2.2 Hz, 1H), 6.73 (s, 1H), 6.38 (s, 1H), 4.37-3.98 (m, 4H), 3.33 (d, J = 11.9 Hz, 2H), 3.18-3.06 (m, 1H), 3.04-2.81 (m, 4H), 2.78-2.60 (m, 1H), 2.34 (s, 3H), 2.08 (d, J = 10.3 Hz, 6H) ppm. |
| 506 | 398.21 | 0.76 | 1H NMR (300 MHz, DMSO-d6) δ 9.28 (s, 1H), 9.13 (s, 1H), 7.59 (dd, J = 8.7, 2.2 Hz, 2H), 7.23 (m, 1H), 6.70 (d, J = 4.5 Hz, 2H), 5.80 (s, 1H), 4.71 (dd, J = 7.8, 6.0 Hz, 2H), 4.32 (t, J = 6.0 Hz, 2H), 3.92 (t, J = 7.5 Hz, 2H), 3.52 (dd, J = 7.1, 5.4 Hz, 2H), 3.29-3.21 (m, 1H), 3.04 (m, 1H), 2.19 (s, 3H) ppm. |
| 507 | 446.3 | 0.69 | 1H NMR (300 MHz, DMSO-d6) δ 9.86 (s, 1H), 9.25 (s, 1H), 9.00 (d, J = 1.4 Hz, 1H), 8.68 (d, J = 2.5 Hz, 1H), 8.60 (dd, J = 2.5, 1.4 Hz, 1H), 7.56 (s, 1H), 7.38 (s, 1H), 6.73 (s, 1H), 4.63 (dd, J = 7.8, 5.9 Hz, 1H), 4.39 (t, J = 6.2 Hz, 1H), 3.79 (d, J = 12.4 Hz, 2H), 2.77 (m, 3H), 1.91-1.63 (m, 4H), 1.45 (s, 1H), 1.16 (m, 2H) ppm. |
| 508 | 384.21 | 0.81 | 1H NMR (300 MHz, DMSO-d6) δ 9.29 (s, 1H), 9.14 (s, 1H), 7.67-7.52 (m, 2H), 7.23 (tt, J = 9.3, 2.3 Hz, 1H), 6.73 (s, 1H), 6.70 (s, 1H), 5.82 (s, 1H), 4.45 (t, J = 7.5 Hz, 2H), 4.06 (d, J = 9.4 Hz, 2H), 3.81 (d, J = 9.3 Hz, 2H), 2.88 (t, J = 7.5 Hz, 2H), 2.19 (s, 3H) ppm. |
| 509 | 457.18 | 0.82 | 1H NMR (400 MHz, DMSO-d6) δ 9.32 (s, 1H), 9.15 (s, 1H), 7.60 (dd, J = 8.5, 2.1 Hz, 2H), 7.24 (tt, J = 9.3, 2.2 Hz, 1H), 7.13 (s, 1H), 6.87 (s, 1H), 6.31 (s, 1H), 3.17 (d, J = 5.0 Hz, 4H), 2.86-2.71 (m, 4H), 2.23 (s, 3H), 1.26 (s, 6H) ppm. |
| 510 | 411.22 | 0.67 | 1H NMR (300 MHz, DMSO-d6) δ 9.27 (s, 1H), 9.14 (s, 1H), 7.59 (m, 2H), 7.28-7.17 (m, 1H), 6.73 (s, 1H), 6.68 (s, 1H), 5.80 (s, 1H), 3.89 (t, J = 7.0 Hz, 2H), 3.65-3.56 (m, 2H), 3.47-3.35 (m, 1H), 2.46 (m, 2H), 2.19 (s, 3H), 1.71 (m, 4H) ppm. |
| 511 | 421.56 | 0.62 | 1H NMR (300 MHz, DMSO-d6) δ 9.48 (s, 1H), 9.30 (d, J = 5.3 Hz, 1H), 9.08 (d, J = 1.0 Hz, 1H), 8.98 (d, J = 5.6 Hz, 1H), 7.68 (dd, J = 5.6, 1.3 Hz, 1H), 7.11 (s, 1H), 7.05 (s, 1H), 6.41 (s, 1H), 4.58 (t, J = 6.5 Hz, 3H), 4.53-4.36 (m, 3H), 3.48 (dd, J = 12.4, 6.1 Hz, 3H), 3.20-3.12 (m, 4H), 2.81 (dt, J = 13.4, 6.6 Hz, 1H), 2.42 (dd, J = 13.0, 8.4 Hz, 4H), 1.19 (dd, J = 14.7, 7.0 Hz, 6H) ppm. |
| 512 | 464.44 | 0.66 | 1H NMR (300 MHz, CDCl3) δ 8.35 (s, 1H), 7.48 (s, 1H), 7.33 (s, 1H), 7.25 (d, J = 2.2 Hz, 2H), 6.89-6.77 (m, 1H), 6.64-6.33 (m, 2H), 4.79-4.64 (m, 4H), 3.73-3.61 (m, 4H), 3.62-3.48 (m, 1H), 2.58-2.38 (m, 4H) ppm. |
| 513 | 404.24 | 0.84 | 1H NMR (300 MHz, DMSO-d6) δ 9.88 (s, 1H), 9.26 (s, 1H), 9.04 (d, J = 1.3 Hz, 1H), 8.68 (d, J = 2.5 Hz, 1H), 8.59 (dd, J = 2.5, 1.4 Hz, 1H), 7.42 (s, 1H), 7.36 (s, 1H), 6.53 (s, 1H), 4.75 (d, J = 6.3 Hz, 2H), 3.61 (d, J = 11.3 Hz, 2H), 3.49 (d, J = 11.3 Hz, 2H), 3.15 (m, 1H), 1.95 (d, J = 8.7 Hz, 1H) ppm. |
| 514 | 447.34 | 0.61 | 1H NMR (300 MHz, DMSO-d6) δ 9.90 (s, 1H), 9.26 (s, 1H), 9.02 (d, J = 1.3 Hz, 1H), 8.68 (d, J = 2.5 Hz, |

TABLE 3-continued

Analytical Data

| Cmpd No. | LC/MS (M + H) | LC/MS Ret. Time (min) | ¹H-NMR |
|---|---|---|---|
| | | | 1H), 8.60 (dd, J = 2.5, 1.4 Hz, 1H), 7.53 (s, 1H), 7.45 (s, 1H), 6.77 (s, 1H), 4.59 (t, J = 6.5 Hz, 2H), 4.51 (t, J = 5.8 Hz, 2H), 3.51 (m, 1H), 3.30-3.15 (m, 4H), 2.49 (m, 4H) ppm. |
| 515 | 444.17 | 0.82 | 1H NMR (400 MHz, DMSO-d6) δ 9.19 (s, 1H), 7.77-7.49 (m, 3H), 7.44 (s, 1H), 7.35-7.15 (m, 1H), 6.70 (s, 1H), 4.80 (d, J = 6.1 Hz, 4H), 4.56 (s, 1H), 3.49 (d, J = 9.3 Hz, 2H), 3.30-3.06 (m, 2H), 2.67-2.47 (m, 5H), 2.45-2.17 (m, 6H) ppm. |
| 516 | 442.19 | 0.78 | 1H NMR (400 MHz, DMSO-d6) δ 9.43 (s, 1H), 9.18 (s, 1H), 7.75-7.57 (m, 3H), 7.24 (dd, J = 12.7, 5.6 Hz, 2H), 6.84 (s, 1H), 4.74 (s, 2H), 4.50 (d, J = 40.8 Hz, 3H), 3.44 (s, 1H), 2.30 (s, 3H), 2.24 (s, 2H), 1.92 (d, J = 12.4 Hz, 3H), 1.62 (d, J = 11.3 Hz, 2H) ppm. |
| 517 | 372.14 | 0.78 | 1H NMR (400 MHz, DMSO-d6) δ 9.58 (s, 1H), 9.18 (s, 1H), 8.21 (s, 1H), 7.70 (d, J = 6.5 Hz, 2H), 7.23 (dd, J = 10.4, 8.1 Hz, 1H), 7.04 (s, 1H), 6.78 (s, 1H), 4.48-4.40 (m, 2H), 4.09-4.03 (m, 2H), 2.29 (s, 3H) ppm. |
| 518 | 400.28 | 0.81 | 1H NMR (300 MHz, DMSO-d6) δ 9.27 (s, 1H), 9.14 (s, 1H), 7.65-7.53 (m, 2H), 7.30-7.13 (m, 1H), 6.76 (s, 1H), 6.66 (s, 1H), 5.81 (s, 1H), 5.33 (s, 1H), 3.78 (d, J = 7.6 Hz, 2H), 3.55 (d, J = 7.6 Hz, 2H), 2.19 (s, 3H), 1.84 (m, 1H), 0.91 (d, J = 6.8 Hz, 6H) ppm. |
| 519 | 400.28 | 0.69 | 1H NMR (300 MHz, DMSO-d6) δ 9.25 (s, 1H), 9.14 (s, 1H), 7.60 (dd, J = 8.7, 2.2 Hz, 2H), 7.30-7.15 (m, 1H), 6.75 (s, 1H), 6.64 (s, 1H), 5.79 (s, 1H), 4.36 (s, 1H), 3.75 (t, J = 7.5 Hz, 2H), 3.67 (t, J = 6.8 Hz, 2H), 2.80-2.64 (m, 1H), 2.19 (s, 3H), 1.06 (s, 6H) ppm. |
| 520 | 386.23 | 0.71 | 1H NMR (300 MHz, DMSO-d6) δ 9.17 (d, J = 2.8 Hz, 1H), 9.13 (d, J = 1.3 Hz, 1H), 7.71-7.56 (m, 2H), 7.22 (t, J = 9.3 Hz, 1H), 6.94 (s, 0.5H), 6.85 (s, 0.5H), 6.51 (s, 0.5H), 6.48 (s, 0.5H), 5.90 (s, 0.5H), 5.87 (s, 0.5H), 5.80-5.66 (m, 1H), 4.06-3.95 (m, 0.5H), 3.91-3.79 (m, 0.5H), 3.65 (m, 0.5H), 3.41 (m, 0.5H), 3.15 (d, J = 2.7 Hz, 3H), 2.79-2.67 (m, 1H), 2.28 (m, 1H), 2.18-2.06 (m, 4H), 1.70 (m, 1H) ppm. mixture of cis and trans |
| 521 | 392.58 | 0.58 | 1H NMR (300 MHz, DMSO-d6) δ 9.38 (s, 1H), 9.18 (s, 1H), 9.02 (dd, J = 7.7, 1.3 Hz, 1H), 8.64 (dd, J = 8.2, 2.0 Hz, 1H), 8.57 (dd, J = 2.5, 1.4 Hz, 1H), 7.18 (s, 1H), 6.87 (s, 1H), 6.32 (s, 1H), 4.61 (dt, J = 12.3, 6.2 Hz, 2H), 4.37 (dd, J = 14.4, 8.2 Hz, 2H), 3.69 (d, J = 12.3 Hz, 2H), 2.81-2.63 (m, 3H), 2.23 (s, 3H), 1.78 (dd, J = 21.3, 11.5 Hz, 1H), 1.67 (d, J = 12.8 Hz, 2H), 1.16 (qd, J = 12.4, 3.7 Hz, 2H) ppm. |
| 522 | 408.6 | 0.64 | 1H NMR (300 MHz, DMSO-d6) δ 9.20 (s, 1H), 9.10 (s, 1H), 7.84-7.64 (m, 2H), 7.64-7.45 (m, 1H), 7.28-7.05 (m, 2H), 6.82 (s, 1H), 6.29 (s, 1H), 4.62 (d, J = 7.9, 5.9 Hz, 2H), 4.46-4.25 (m, 2H), 3.68 (d, J = 12.3 Hz, 2H), 2.87-2.60 (m, 3H), 2.22 (s, 3H), 1.89-1.73 (m, 1H), 1.66 (d, J = 12.3 Hz, 2H), 1.15 (qd, J = 12.1, 3.6 Hz, 2H) ppm. |
| 523 | 437.58 | 0.66 | |
| 524 | 464.49 | 0.66 | 1H NMR (300 MHz, CDCl3) δ 8.30 (s, 1H), 7.58 (ddd, J = 10.7, 6.8, 2.5 Hz, 1H), 7.48 (s, 1H), 7.45-7.39 (m, 1H), 7.34 (dd, J = 9.0, 7.8 Hz, 2H), 6.54 (dd, J = 87.5, 31.4 Hz, 2H), 4.80-4.63 (m, 4H), 3.72-3.49 (m, 5H), 2.53-2.36 (m, 4H) ppm. |
| 525 | 446.44 | 0.64 | 1H NMR (300 MHz, CDCl3) δ 8.37 (s, 1H), 7.56-7.43 (m, 4H), 7.40 (s, 1H), 7.08 (tdd, J = 7.4, 4.9, 2.6 Hz, 1H), 6.54 (dd, J = 88.5, 32.4 Hz, 2H), 4.79-4.60 (m, 4H), 3.71-3.49 (m, 5H), 2.52-2.37 (m, 4H) ppm. |

TABLE 3-continued

Analytical Data

| Cmpd No. | LC/MS (M + H) | LC/MS Ret. Time (min) | ¹H-NMR |
|---|---|---|---|
| 526 | 428.58 | 0.64 | 1H NMR (300 MHz, CDCl3) δ 8.36 (s, 1H), 7.74-7.65 (m, 2H), 7.53 (dd, J = 11.3, 5.8 Hz, 3H), 7.39 (ddd, J = 9.1, 8.7, 4.9 Hz, 2H), 6.53 (dd, J = 89.5, 33.3 Hz, 2H), 4.80-4.62 (m, 4H), 3.70-3.50 (m, 5H), 2.51-2.39 (m, 4H) ppm. |
| 527 | 384.25 | 0.9 | 1H NMR (300 MHz, DMSO-d6) δ 9.29 (s, 1H), 9.15 (s, 1H), 7.60 (m, 2H), 7.23 (m, 1H), 7.03 (m, 1H), 6.78 (s, 1H), 6.13 (s, 1H), 4.71 (d, J = 6.4 Hz, 2H), 3.54 (d, J = 11.2 Hz, 2H), 3.41 (d, J = 11.0 Hz, 2H), 3.12 (m, 1H), 2.25 (s, 3H), 1.93 (d, J = 8.6 Hz, 1H) ppm. |
| 528 | 412.35 | 0.68 | 1H NMR (300 MHz, DMSO-d6) δ 9.32 (s, 1H), 9.16 (s, 1H), 7.68-7.52 (m, 2H), 7.31 (s, 1H), 7.29-7.18 (m, 1H), 6.75 (s, 1H), 6.35 (s, 1H), 3.97 (d, J = 11.4 Hz, 1H), 3.83 (m, 3H), 3.10 (td, J = 11.1, 3.9 Hz, 1H), 2.79-2.68 (m, 1H), 2.68-2.57 (m, 1H), 2.22 (s, 3H), 2.09-1.94 (m, 2H), 1.61 (m, 3H) ppm. |
| 529 | 372.51 | 0.6 | 1H NMR (300 MHz, CD3OD + CDCl3) δ 8.62 (s, 1H), 7.39 (dd, J = 8.0, 2.2 Hz, 2H), 7.23 (s, 1H), 6.85 (tt, J = 8.8, 2.3 Hz, 1H), 6.19 (s, 1H), 3.77-3.61 (m, 4H), 3.20-3.08 (m, 4H), 2.37 (s, 3H) ppm. |
| 530 | 441.54 | 0.66 | 1H NMR (300 MHz, CD3OD + CDCl3) δ 8.39 (s, 1H), 7.08 (dd, J = 8.0, 2.0 Hz, 2H), 6.82 (s, 1H), 6.65 (s, 1H), 6.52 (ddd, J = 8.8, 5.5, 2.2 Hz, 1H), 6.10 (s, 1H), 3.77 (td, J = 8.4, 4.4 Hz, 2H), 3.61 (dd, J = 10.1, 6.4 Hz, 1H), 3.47 (dt, J = 28.4, 14.3 Hz, 2H), 3.17 (s, 4H), 2.87 (d, J = 13.9 Hz, 4H), 2.02 (s, 4H), 1.89 (dd, J = 27.7, 16.6 Hz, 1H) ppm. |
| 531 | 441.49 | 0.66 | 1H NMR (300 MHz, CD3OD + CDCl3) δ 8.70 (s, 1H), 7.41 (dd, J = 7.8, 1.9 Hz, 2H), 7.21 (s, 1H), 6.97-6.74 (m, 2H), 6.42 (s, 1H), 3.99 (ddd, J = 15.4, 8.6, 5.7 Hz, 2H), 3.90-3.60 (m, 2H), 3.28 (t, J = 5.0 Hz, 4H), 3.16-3.00 (m, 1H), 2.86-2.56 (m, 4H), 2.33 (s, 3H), 2.25-2.08 (m, 1H), 1.99-1.88 (m, 1H) ppm. |
| 532 | 429.48 | 0.62 | 1H NMR (300 MHz, CDCl3) δ 9.00 (s, 1H), 8.45 (d, J = 4.3 Hz, 1H), 7.90 (ddd, J = 17.5, 12.1, 4.8 Hz, 3H), 7.57 (s, 1H), 7.40 (s, 1H), 6.61 (t, J = 56.2 Hz, 1H), 6.38 (s, 1H), 4.79-4.63 (m, 4H), 3.70-3.61 (m, 4H), 3.55 (dd, J = 12.8, 6.5 Hz, 1H), 2.51-2.38 (m, 4H) ppm. |
| 533 | 472.5 | 0.73 | 1H NMR (300 MHz, CDCl3) δ 8.34 (s, 1H), 7.29 (d, J = 2.3 Hz, 1H), 7.27 (d, J = 2.2 Hz, 1H), 7.22 (s, 1H), 7.17 (s, 1H), 6.81 (tt, J = 8.7, 2.3 Hz, 1H), 6.14 (s, 1H), 3.53 (t, J = 5.1 Hz, 8H), 2.36 (s, 3H), 1.51 (s, 9H) ppm. |
| 534 | 501.53 | 0.66 | 1H NMR (300 MHz, CDCl3) δ 8.32 (s, 1H), 7.25 (dd, J = 7.9, 2.2 Hz, 2H), 7.10 (d, J = 1.9 Hz, 1H), 6.87-6.69 (m, 3H), 6.41 (s, 1H), 4.01 (s, 2H), 3.36-3.18 (m, 4H), 2.82 (dd, J = 5.7, 2.9 Hz, 4H), 2.61 (d, J = 13.9 Hz, 1H), 2.42 (d, J = 13.9 Hz, 1H), 2.35 (s, 3H), 2.13 (s, 3H), 1.23 (s, 3H) ppm. |
| 535 | 393.52 | 0.56 | 1H NMR (300 MHz, DMSO-d6) δ 9.37 (s, 1H), 9.28 (s, 2H), 9.20 (s, 1H), 9.16 (s, 1H), 7.14 (s, 1H), 6.89 (s, 1H), 6.32 (s, 1H), 4.57 (t, J = 6.5 Hz, 2H), 4.48 (t, J = 6.1 Hz, 2H), 3.54-3.39 (m, 1H), 3.23-3.12 (m, 3H), 2.47-2.32 (m, 4H), 2.23 (s, 3H) ppm. |
| 536 | 421.21 | 0.62 | 1H NMR (300 MHz, DMSO-d6) δ 9.45 (s, 1H), 9.21 (s, 1H), 9.02 (d, J = 1.2 Hz, 1H), 8.66 (d, J = 2.5 Hz, 1H), 8.58 (dd, J = 2.5, 1.4 Hz, 1H), 7.13 (s, 1H), 7.06 (s, 1H), 6.40 (s, 1H), 4.58 (t, J = 6.5 Hz, 2H), 4.49 (t, J = 6.0 Hz, 2H), 3.50-3.41 (m, 1H), 3.16 (d, J = 4.7 Hz, 4H), 2.92-2.70 (m, 1H), 2.35 (d, J = 44.0 Hz, 4H), 1.21 (d, J = 6.9 Hz, 6H) ppm. |
| 537 | 428.18 | 2.22 | 1H NMR (300 MHz, CDCl3) δ 8.48 (s, 1H), 7.48 (s, 1H), 7.34-7.21 (m, 4H), 6.84 (tt, J = 8.7, 2.2 Hz, 1H), 4.57 (d, J = 6.2 Hz, 4H), |

TABLE 3-continued

Analytical Data

| Cmpd No. | LC/MS (M + H) | LC/MS Ret. Time (min) | ¹H-NMR |
|---|---|---|---|
| | | | 3.97 (t, J = 4.4 Hz, 4H), 3.91-3.79 (m, 1H), 3.02 (s, 4H), 2.40 (s, 3H) ppm. |
| 538 | 410.21 | 2.13 | 1H NMR (300 MHz, CDCl3) δ 8.48 (s, 1H), 7.48 (s, 1H), 7.34-7.21 (m, 4H), 6.84 (tt, J = 8.7, 2.2 Hz, 1H), 4.57 (d, J = 6.2 Hz, 4H), 3.97 (t, J = 4.4 Hz, 4H), 3.91-3.79 (m, 1H), 3.02 (s, 4H), 2.40 (s, 3H) ppm. |
| 539 | 419 | 0.61 | 1H NMR (400 MHz, Acetone-d6) δ 9.11 (d, J = 1.3 Hz, 1H), 8.94 (s, 1H), 8.60 (d, J = 2.5 Hz, 1H), 8.48 (dd, J = 2.5, 1.5 Hz, 1H), 8.30 (s, 1H), 7.93 (s, 2H), 6.90-6.63 (m, 2H), 4.00 (t, J = 7.0 Hz, 2H), 3.74-3.57 (m, 5H), 3.40-3.23 (m, 2H), 1.94-1.75 (m, 1H), 0.91 (ddd, J = 8.4, 6.4, 4.2 Hz, 2H), 0.69 (dt, J = 6.5, 4.3 Hz, 2H) ppm. |
| 540 | 482.54 | 0.68 | 1H NMR (300 MHz, CDCl3) δ 8.37 (s, 1H), 7.60 (s, 1H), 7.43 (s, 1H), 7.27 (s, 1H), 7.25 (d, J = 2.2 Hz, 1H), 6.83 (tt, J = 8.7, 2.2 Hz, 1H), 6.45 (s, 1H), 4.71 (p, J = 6.4 Hz, 4H), 3.75-3.62 (m, 4H), 3.61-3.51 (m, 1H), 2.54-2.34 (m, 4H) ppm. |
| 541 | 412.21 | 0.64 | 1H NMR (300 MHz, DMSO-d6) δ 9.34 (s, 1H), 9.16 (s, 1H), 7.62 (dd, J = 8.7, 2.2 Hz, 2H), 7.35 (s, 1H), 7.23 (tt, J = 9.3, 4.6 Hz, 1H), 6.80 (s, 1H), 6.37 (s, 1H), 4.32 (s, 4H), 3.05-2.96 (m, 2H), 2.23 (s, 3H), 1.83-1.71 (m, 2H), 1.58 (m, 2H) ppm. |
| 542 | 425.18 | 0.74 | 1H NMR (300 MHz, DMSO-d6) δ 9.32 (s, 1H), 9.14 (s, 1H), 7.65-7.54 (m, 2H), 7.28-7.18 (m, 1H), 6.74 (s, 2H), 5.84 (s, 1H), 4.99-4.88 (m, 1H), 4.00 (t, J = 7.7 Hz, 2H), 3.88-3.80 (m, 2H), 3.53 (t, J = 6.9 Hz, 2H), 2.27 (t, J = 8.0 Hz, 2H), 2.20 (s, 3H), 2.02-1.90 (m, 2H) ppm. |
| 543 | 412.56 | 0.9 | 1H NMR (300 MHz, DMSO-d6) δ 9.36 (s, 1H), 9.16 (s, 1H), 7.61 (dd, J = 8.6, 2.1 Hz, 2H), 7.35 (s, 1H), 7.27-7.18 (m, 1H), 6.77 (s, 1H), 6.34 (s, 1H), 3.70-3.60 (m, 2H), 3.07 (s, 2H), 3.04-2.96 (m, 2H), 2.23 (s, 3H), 1.99 (m, 4H), 1.86-1.65 (m, 2H) ppm. |
| 544 | 407 | 0.48 | 1H NMR (400 MHz, CDCl3) δ 9.19 (s, 1H), 9.12 (s, 2H), 8.39 (s, 1H), 6.68 (s, 1H), 6.67-6.57 (m, 2H), 5.98 (s, 1H), 4.00 (t, J = 7.0 Hz, 2H), 3.75 (dd, J = 10.5, 5.0 Hz, 6H), 3.40-3.26 (m, 1H), 2.59 (q, J = 7.6 Hz, 2H), 2.46 (s, 4H), 1.24 (t, J = 7.6 Hz, 3H) ppm. |
| 545 | 464.53 | 0.66 | 1H NMR (300 MHz, CDCl3) δ 8.38 (s, 1H), 7.64 (s, 1H), 7.57-7.43 (m, 3H), 7.39 (s, 1H), 7.15-7.03 (m, 1H), 6.44 (s, 1H), 4.71 (p, J = 6.4 Hz, 4H), 3.74-3.62 (m, 4H), 3.61-3.49 (m, 1H), 2.54-2.38 (m, 4H) ppm. |
| 546 | 482.45 | 0.68 | 1H NMR (300 MHz, CDCl3) δ 8.31 (s, 1H), 7.64-7.52 (m, 2H), 7.49-7.30 (m, 3H), 6.44 (s, 1H), 4.71 (p, J = 6.4 Hz, 4H), 3.75-3.60 (m, 4H), 3.60-3.50 (m, 1H), 2.55-2.36 (m, 4H) ppm. |
| 547 | 446.53 | 0.66 | 1H NMR (300 MHz, CDCl3) δ 8.37 (s, 1H), 7.73-7.66 (m, 3H), 7.54 (dd, J = 10.6, 5.1 Hz, 2H), 7.44-7.35 (m, 2H), 6.43 (s, 1H), 4.77-4.63 (m, 4H), 3.76-3.61 (m, 4H), 3.60-3.51 (m, 1H), 2.53-2.39 (m, 4H) ppm. |
| 548 | 447.52 | 0.65 | 1H NMR (300 MHz, CDCl3) δ 9.00 (s, 1H), 8.45 (dd, J = 4.8, 0.9 Hz, 1H), 7.98-7.88 (m, 1H), 7.84 (d, J = 8.1 Hz, 1H), 7.70 (s, 1H), 7.42 (s, 1H), 7.27 (d, J = 1.2 Hz, 1H), 6.44 (s, 1H), 4.79-4.64 (m, 4H), 3.74-3.62 (m, 4H), 3.52 (s, 1H), 2.54-2.39 (m, 4H) ppm. |
| 549 | 407.56 | 0.58 | 1H NMR (300 MHz, DMSO-d6) δ 9.37 (s, 1H), 9.27 (s, 2H), 9.20 (s, 1H), 9.15 (s, 1H), 7.14 (s, 1H), 6.96 (s, 1H), 6.35 (s, 1H), 4.57 (t, J = 6.5 Hz, 2H), 4.48 (t, J = 6.1 Hz, 2H), 3.55-3.39 (m, 1H), 3.24-3.03 (m, 4H), 2.59-2.51 (m, 2H), 2.38 (dd, J = 26.7, 22.1 Hz, 4H), 1.19 (q, J = 7.8 Hz, 3H) ppm. |

TABLE 3-continued

Analytical Data

| Cmpd No. | LC/MS (M + H) | LC/MS Ret. Time (min) | ¹H-NMR |
|---|---|---|---|
| 550 | 435.55 | 0.61 | 1H NMR (300 MHz, DMSO-d6) δ 9.36 (s, 1H), 9.26 (s, 2H), 9.21 (s, 1H), 9.15 (s, 1H), 7.25 (s, 1H), 7.09 (s, 1H), 6.51 (s, 1H), 4.58 (t, J = 6.5 Hz, 2H), 4.49 (t, J = 6.1 Hz, 2H), 3.54-3.38 (m, 1H), 3.22-3.04 (m, 4H), 2.47-2.33 (m, 4H), 1.28 (s, 9H) ppm. |
| 551 | 372.27 | 0.72 | 1H NMR (300 MHz, DMSO-d6) δ 9.29 (s, 1H), 9.14 (s, 1H), 7.67-7.52 (m, 2H), 7.23 (tt, J = 9.3, 2.3 Hz, 1H), 6.73 (s, 1H), 6.69 (s, 1H), 5.81 (s, 1H), 5.48 (s, 1H), 3.72 (d, J = 7.2 Hz, 2H), 3.59 (d, J = 7.1 Hz, 2H), 2.19 (s, 3H), 1.46 (s, 3H) ppm. |
| 552 | 439.56 | 0.68 | 1H NMR (300 MHz, DMSO-d6) δ 9.38 (s, 1H), 9.16 (s, 1H), 7.64-7.52 (m, 2H), 7.33 (s, 1H), 7.29-7.16 (m, 1H), 6.79 (s, 1H), 6.35 (s, 1H), 3.63 (d, J = 11.2 Hz, 1H), 3.57-3.42 (m, 2H), 3.02 (m, 1H), 2.94-2.66 (m, 4H), 2.23 (s, 3H) ppm. |
| 553 | 386.59 | 0.76 | 1H NMR (300 MHz, DMSO-d6) δ 9.29 (s, 1H), 9.14 (s, 1H), 7.67-7.54 (m, 2H), 7.23 (tt, J = 9.3, 2.2 Hz, 1H), 6.75 (s, 1H), 6.68 (s, 1H), 5.82 (s, 1H), 5.40 (s, 1H), 3.74 (d, J = 7.4 Hz, 2H), 3.56 (d, J = 7.4 Hz, 2H), 2.20 (s, 3H), 1.72 (q, J = 7.2 Hz, 2H), 0.93 (t, J = 7.3 Hz, 3H) ppm. |
| 554 | 497.52 | 0.89 | 1H NMR (300 MHz, CDCl3) δ 8.37 (s, 1H), 7.62 (s, 1H), 7.40 (s, 1H), 7.28 (s, 1H), 7.27-7.23 (m, 1H), 6.83 (tt, J = 8.7, 2.2 Hz, 1H), 6.43 (s, 1H), 4.44 (s, 1H), 3.73-3.61 (m, 4H), 3.59-3.50 (m, 4H), 3.41-3.27 (m, 2H), 2.98 (d, J = 7.3 Hz, 1H), 1.23-1.11 (m, 3H) ppm. |
| 555 | 468.49 | 0.88 | 1H NMR (300 MHz, CDCl3) δ 8.38 (s, 1H), 7.64 (s, 1H), 7.41 (s, 1H), 7.28 (s, 1H), 7.25 (d, J = 2.2 Hz, 1H), 6.84 (ddd, J = 8.7, 5.5, 2.3 Hz, 1H), 6.45 (s, 1H), 3.82-3.74 (m, 2H), 3.74-3.66 (m, 2H), 3.61 (dd, J = 10.6, 5.3 Hz, 4H), 2.21 (d, J = 19.0 Hz, 3H) ppm. |
| 556 | 426.55 | 0.67 | 1H NMR (300 MHz, CDCl3) δ 8.36 (s, 1H), 7.58 (s, 1H), 7.40 (s, 1H), 7.27 (s, 1H), 7.25 (d, J = 2.1 Hz, 1H), 6.83 (tt, J = 8.7, 2.2 Hz, 1H), 6.45 (s, 1H), 3.64-3.54 (m, 4H), 3.08-2.92 (m, 4H) ppm. |
| 557 | 526.23 | 1.09 | 1H NMR (300 MHz, CDCl3) δ 8.37 (s, 1H), 7.61 (s, 1H), 7.38 (s, 1H), 7.27 (s, 1H), 7.25 (d, J = 2.2 Hz, 1H), 6.83 (tt, J = 8.7, 2.3 Hz, 1H), 6.45 (s, 1H), 3.70-3.45 (m, 8H), 1.52 (s, 9H) ppm. |
| 558 | 371 | 0.64 | freebase—1H NMR (400 MHz, DMSO-d6) δ 9.30 (s, 1H), 8.81 (d, J = 2.3 Hz, 1H), 7.69 (ddd, J = 9.2, 6.0, 3.2 Hz, 1H), 7.59 (ddd, J = 11.1, 9.2, 4.8 Hz, 1H), 7.37-7.25 (m, 1H), 7.15 (s, 1H), 6.83 (s, 1H), 6.28 (s, 1H), 3.31 (s, 2H), 3.13-2.95 (m, 4H), 2.93-2.76 (m, 4H), 2.21 (s, 3H) ppm. bis HCl salt—1H NMR (400 MHz, DMSO-d6) δ 9.64 (s, 1H), 9.51 (s, 1H), 8.84 (d, J = 2.4 Hz, 1H), 7.79 (ddd, J = 9.1, 6.0, 3.2 Hz, 1H), 7.60 (ddd, J = 11.0, 9.3, 4.8 Hz, 1H), 7.43-7.19 (m, 1H), 7.04 (s, 1H), 6.49 (s, 1H), 3.59-3.38 (m, 4H), 3.29 (s, 4H), 2.26 (s, 3H) ppm. |
| 559 | 455.32 | 3.05 | 1H NMR (300 MHz, CDCl3) δ 8.26 (s, 1H), 7.57 (ddd, J = 10.9, 6.8, 2.5 Hz, 1H), 7.45-7.35 (m, 1H), 7.32 (dd, J = 9.3, 8.1 Hz, 1H), 7.13 (t, J = 2.0 Hz, 1H), 6.80 (s, 1H), 6.71 (s, 1H), 6.44 (s, 1H), 4.83-4.61 (m, 4H), 3.69-3.50 (m, 1H), 3.43-3.21 (m, 4H), 2.63-2.40 (m, 6H), 1.67 (dt, J = 14.7, 7.4 Hz, 2H), 0.99 (t, J = 7.3 Hz, 3H) ppm. |
| 560 | 373.5 | 0.63 | 1H NMR (300 MHz, CDCl3) δ 8.35 (s, 1H), 7.26 (dd, J = 7.8, 2.2 Hz, 2H), 6.92-6.76 (m, 3H), 6.60 (d, J = 1.3 Hz, 1H), 3.95-3.76 (m, 4H), 3.63-3.46 (m, 4H), 2.43 (s, 3H) ppm. |
| 561 | 425 | 0.76 | 1H NMR (400 MHz, CDCl3) δ 8.31 (s, 1H), 7.25-7.19 (m, 3H), 6.79 (tt, J = 8.7, 2.3 Hz, 1H), 6.73 (s, 1H), 6.68 (s, 1H), 6.41 (s, 1H), 4.19-4.08 (m, 1H), 3.87-3.75 (m, 2H), |

TABLE 3-continued

Analytical Data

| Cmpd No. | LC/MS (M + H) | LC/MS Ret. Time (min) | ¹H-NMR |
|---|---|---|---|
| | | | 3.73-3.65 (m, 1H), 3.06 (td, J = 12.7, 3.8 Hz, 1H), 2.76 (td, J = 12.2, 3.5 Hz, 1H), 2.53 (dd, J = 12.4, 11.3 Hz, 1H), 2.46 (dd, J = 9.6, 6.3 Hz, 2H), 2.33 (s, 3H), 2.27 (td, J = 13.1, 7.6 Hz, 1H), 1.80-1.65 (m, 1H) ppm. |
| 562 | 442.62 | 0.62 | 1H NMR (300 MHz, CDCl3) δ 8.34 (s, 1H), 7.29 (d, J = 2.3 Hz, 1H), 7.27 (d, J = 2.2 Hz, 1H), 7.21 (s, 2H), 6.81 (tt, J = 8.7, 2.3 Hz, 1H), 6.13 (s, 1H), 4.05-3.91 (m, 2H), 3.83 (dd, J = 15.9, 8.2 Hz, 1H), 3.72 (dd, J = 8.5, 7.0 Hz, 1H), 3.56 (t, J = 5.1 Hz, 4H), 3.03 (p, J = 7.1 Hz, 1H), 2.66 (dt, J = 10.4, 5.0 Hz, 2H), 2.60-2.47 (m, 2H), 2.36 (s, 3H), 2.11 (ddt, J = 7.6, 4.3, 3.7 Hz, 1H), 1.93 (ddd, J = 15.9, 12.2, 8.2 Hz, 1H) ppm. |
| 563 | 399.52 | 0.89 | 1H NMR (300 MHz, DMSO) δ 9.33 (s, 1H), 9.17 (s, 1H), 7.64 (m, 2H), 7.26 (m, 1H), 7.08 (s, 1H), 5.77 (s, 1H), 4.71 (dd, J = 7.8, 6.1 Hz, 2H), 4.31 (t, J = 6.0 Hz, 2H), 4.02 (t, J = 8.0 Hz, 2H), 3.63 (dd, J = 8.0, 5.3 Hz, 2H), 3.26 (m, 1H), 3.01 (m, 1H), 2.22 (s, 3H) ppm. |
| 564 | 496.53 | 0.68 | 1H NMR (300 MHz, CDCl3) δ 8.37 (s, 1H), 7.59 (s, 1H), 7.42 (s, 1H), 7.27 (s, 1H), 7.25 (d, J = 2.1 Hz, 1H), 6.83 (tt, J = 8.7, 2.2 Hz, 1H), 6.44 (s, 1H), 4.07-3.90 (m, 2H), 3.83 (dd, J = 15.9, 8.1 Hz, 1H), 3.72 (dd, J = 8.5, 6.8 Hz, 1H), 3.62 (t, J = 5.1 Hz, 4H), 3.11-2.98 (m, 1H), 2.74-2.61 (m, 2H), 2.60-2.43 (m, 2H), 2.17-2.05 (m, 1H), 1.93 (ddd, J = 15.6, 12.3, 8.2 Hz, 1H) ppm. |
| 565 | 443.25 | 0.65 | 1H NMR (400 MHz, CDCl3) δ 8.33 (s, 1H), 7.30-7.26 (m, 2H), 7.19 (s, 1H), 7.17 (s, 1H), 6.80 (tt, J = 8.7, 2.3 Hz, 1H), 6.16 (s, 1H), 4.24 (ddd, J = 12.3, 7.9, 4.4 Hz, 2H), 4.21-4.15 (m, 2H), 3.00-2.88 (m, 2H), 2.53 (tt, J = 11.1, 3.9 Hz, 1H), 2.35 (s, 3H), 2.00 (dd, J = 13.6, 3.3 Hz, 2H), 1.85-1.70 (m, 2H), 1.31-1.26 (m, 3H) ppm. |
| 566 | 427 | 0.65 | 1H NMR (400 MHz, CDCl3) δ 8.29 (s, 1H), 7.23 (dd, J = 7.9, 2.2 Hz, 2H), 7.17 (s, 1H), 6.77 (tt, J = 8.7, 2.3 Hz, 1H), 6.71 (s, 1H), 6.63 (s, 1H), 6.40 (s, 1H), 3.90 (dd, J = 11.3, 3.2 Hz, 1H), 3.77 (dtd, J = 13.8, 11.3, 2.5 Hz, 2H), 3.66 (d, J = 10.8 Hz, 1H), 3.46 (d, J = 10.3 Hz, 1H), 3.41-3.33 (m, 1H), 2.99 (td, J = 11.8, 3.0 Hz, 1H), 2.93-2.86 (m, 1H), 2.74 (d, J = 11.4 Hz, 1H), 2.60-2.39 (m, 4H), 2.33 (s, 3H) ppm. |
| 567 | 482.49 | 0.66 | 1H NMR (300 MHz, CDCl3) δ 8.39 (s, 1H), 7.95 (s, 1H), 7.72 (d, J = 2.0 Hz, 1H), 7.24 (dd, J = 7.8, 2.2 Hz, 2H), 6.84 (tt, J = 8.7, 2.2 Hz, 1H), 6.75 (d, J = 2.1 Hz, 1H), 4.72 (dt, J = 12.4, 6.4 Hz, 4H), 3.64-3.46 (m, 5H), 2.63-2.47 (m, 4H) ppm. |
| 568 | 389.15 | 0.62 | 1H NMR (400 MHz, CDCl3) δ 8.34 (s, 1H), 7.30-7.27 (m, 3H), 7.24 (s, 1H), 7.18 (s, 1H), 6.81 (tt, J = 8.7, 2.3 Hz, 1H), 6.16 (s, 1H), 4.72 (dtt, J = 47.8, 7.3, 3.7 Hz, 1H), 4.03-3.88 (m, 1H), 3.67-3.51 (m, 2H), 3.45-3.35 (m, 1H), 2.35 (s, 3H), 2.12-1.97 (m, 1H), 1.97-1.79 (m, 2H), 1.70-1.59 (m, 1H) ppm. |
| 569 | 401.17 | 0.59 | 1H NMR (400 MHz, CDCl3) δ 8.33 (s, 1H), 7.31-7.25 (m, 2H), 7.17 (d, J = 8.0 Hz, 2H), 6.81 (tt, J = 8.7, 2.3 Hz, 1H), 6.17 (s, 1H), 3.88 (dt, J = 13.3, 4.3 Hz, 2H), 3.40 (ddd, J = 13.4, 10.0, 3.8 Hz, 2H), 2.35 (s, 3H), 1.78-1.62 (m, 4H), 1.31 (d, J = 4.9 Hz, 3H) ppm. |
| 570 | 399.19 | 0.6 | 1H NMR (400 MHz, CDCl3) δ 8.33 (s, 1H), 7.30-7.26 (m, 2H), 7.23 (s, 1H), 7.20 (s, 1H), 6.81 (ddt, J = 7.9, 5.6, 2.8 Hz, 1H), 5.82 (s, 1H), 3.98 (s, 3H), 3.94 (s, 2H), 3.90 (dt, J = 7.0, 4.4 Hz, 3H), 2.34 (s, 3H), 2.22 (t, J = 7.0 Hz, 2H) ppm. |
| 571 | 385.19 | 0.6 | 1H NMR (400 MHz, CDCl3) δ 8.33 (s, 1H), 7.27 (d, J = 2.2 Hz, 1H), 7.22 (s, 2H), 7.20 (s, |

TABLE 3-continued

Analytical Data

| Cmpd No. | LC/MS (M + H) | LC/MS Ret. Time (min) | ¹H-NMR |
|---|---|---|---|
| | | | 1H), 6.81 (ddd, J = 8.7, 5.5, 2.3 Hz, 1H), 5.81 (s, 1H), 4.60 (t, J = 7.5 Hz, 2H), 4.18 (dd, J = 10.6, 5.5 Hz, 4H), 2.93 (t, J = 7.5 Hz, 2H), 2.34 (s, 3H) ppm. |
| 572 | 401.17 | 0.6 | 1H NMR (400 MHz, CDCl3) δ 8.33 (s, 1H), 7.29-7.25 (m, 3H), 7.18 (d, J = 5.8 Hz, 1H), 6.80 (ddt, J = 7.8, 3.3, 2.3 Hz, 1H), 5.81 (s, 1H), 4.05-3.84 (m, 4H), 2.77 (tt, J = 8.4, 6.0 Hz, 1H), 2.33 (s, 3H), 1.27 (s, 6H) ppm. |
| 573 | 553.38 | 0.54 | 1H NMR (400 MHz, DMSO-d6) δ 9.22 (s, 1H), 9.14 (s, 1H), 7.58 (d, J = 6.4 Hz, 2H), 7.23 (t, J = 9.2 Hz, 1H), 6.78 (d, J = 1.6 Hz, 2H), 6.02 (s, 1H), 3.08 (d, 8H), 2.67-2.59 (m, 8H), 1.04 (s, 18H) ppm. |
| 574 | 553.33 | 0.5 | 1H NMR (400 MHz, DMSO-d6) δ 9.24 (s, 1H), 9.14 (s, 1H), 7.58 (d, J = 6.5 Hz, 2H), 7.23 (t, J = 9.3 Hz, 1H), 6.80 (d, J = 1.6 Hz, 2H), 6.07 (s, 1H), 4.57 (t, J = 6.5 Hz, 4H), 4.47 (t, J = 6.0 Hz, 4H), 3.49-3.40 (m, 2H), 3.19-3.09 (m, 8H), 2.45-2.36 (m, 8H) ppm. |

TABLE 3A

Analytical Data

| Cmpd No. in PRV2 | LCMS (M + H) | LC/MS Ret. Time (min) | ¹H-NMR |
|---|---|---|---|
| 575 | 448.22 | 0.63 | 1H NMR (400 MHz, CDCl3) δ 8.40 (s, 1H), 8.00 (d, J = 2.1 Hz, 1H), 7.89 (dt, J = 7.7, 1.9 Hz, 1H), 7.74-7.58 (m, 2H), 7.21 (t, J = 2.2 Hz, 1H), 6.83 (t, J = 1.8 Hz, 1H), 6.73 (s, 1H), 6.41 (t, J = 1.7 Hz, 1H), 4.19 (d, J = 12.2 Hz, 2H), 3.77 (d, J = 5.5 Hz, 4H), 2.87 (s, 2H), 2.65 (s, 4H), 2.36 (s, 3H) ppm. |
| 576 | 430.65 | 0.62 | 1H NMR (300 MHz, MeOD + CDCl3) δ 9.16 (d, J = 13.5 Hz, 1H), 8.99 (d, J = 12.8 Hz, 1H), 8.59 (s, 1H), 8.47 (s, 1H), 7.49 (s, 1H), 6.57 (dd, J = 87.9, 31.7 Hz, 2H), 4.96-4.55 (m, 4H), 3.93-3.46 (m, 5H), 2.48 (s, 4H) ppm. |
| 577 | 455.71 | 0.71 | 1H NMR (300 MHz, CDCl3) δ 8.26 (s, 1H), 7.58 (ddd, J = 10.9, 6.8, 2.5 Hz, 1H), 7.39 (tdd, J = 4.0, 3.2, 1.4 Hz, 1H), 7.32 (dd, J = 9.3, 8.1 Hz, 1H), 7.09 (t, J = 2.0 Hz, 1H), 6.84 (s, 1H), 6.70 (s, 1H), 6.46 (s, 1H), 4.67 (d, J = 5.5 Hz, 2H), 4.30 (d, J = 5.7 Hz, 2H), 3.40-3.16 (m, 4H), 2.64 (q, J = 7.6 Hz, 2H), 2.57 (dd, J = 10.9, 5.9 Hz, 4H), 1.44 (s, 3H), 1.28 (t, J = 7.6 Hz, 3H) ppm. |
| 578 | 460.29 | 0.6 | 1H NMR (400 MHz, CDCl3) δ 8.42 (d, J = 6.6 Hz, 1H), 7.98 (s, 1H), 7.90 (d, J = 7.7 Hz, 1H), 7.72-7.58 (m, 2H), 7.23 (d, J = 4.5 Hz, 2H), 6.14 (s, 1H), 4.81-4.62 (m, 4H), 3.62-3.57 (m, 4H), 3.55 (dd, J = 12.9, 6.5 Hz, 1H), 2.47 (dd, J = 15.4, 10.4 Hz, 4H), 2.35 (s, 3H) ppm. |
| 579 | 478.2 | 0.69 | 1H NMR (300 MHz, CDCl3) δ 8.31 (s, 1H), 7.57 (ddd, J = 10.7, 6.8, 2.5 Hz, 1H), 7.50 (s, 1H), 7.42 (ddd, J = 6.3, 4.6, 3.2 Hz, 1H), 7.38-7.30 (m, 2H), 6.37 (s, 1H), 4.71 (p, J = 6.4 Hz, 4H), 3.73-3.60 (m, 4H), 3.54 (dd, J = 12.8, 6.4 Hz, 1H), 2.55-2.33 (m, 4H), 1.95 (t, J = 18.3 Hz, 3H) ppm. |

TABLE 3A-continued

Analytical Data

| Cmpd No. in PRV2 | LCMS (M + H) | LC/MS Ret. Time (min) | ¹H-NMR |
|---|---|---|---|
| 580 | 442.66 | 0.63 | 1H NMR (300 MHz, CDCl3) δ 8.33 (s, 1H), 7.29 (d, J = 2.3 Hz, 1H), 7.27 (d, J = 2.2 Hz, 1H), 7.20 (d, J = 4.7 Hz, 2H), 6.81 (tt, J = 8.7, 2.2 Hz, 1H), 6.13 (s, 1H), 4.67 (d, J = 5.5 Hz, 2H), 4.29 (d, J = 5.7 Hz, 2H), 3.78-3.41 (m, 4H), 2.63-2.42 (m, 4H), 2.35 (s, 3H), 1.40 (s, 3H) ppm. |
| 581 | 428.24 | 0.75 | 1H NMR (300 MHz, MeOD) δ 8.84 (s, 1H), 8.12 (s, 1H), 7.58-7.42 (m, 3H), 7.24 (s, 1H), 6.92 (tt, J = 9.0, 2.2 Hz, 1H), 6.75 (s, 1H), 4.76-4.61 (m, 4H), 4.54 (dd, J = 10.3, 1.8 Hz, 1H), 4.06 (dd, J = 11.6, 2.1 Hz, 1H), 3.85 (td, J = 11.6, 2.2 Hz, 1H), 3.64-3.52 (m, 1H), 2.84 (dd, J = 34.1, 11.5 Hz, 2H), 2.32 (s, 3H), 2.21 (td, J = 11.5, 3.4 Hz, 1H), 2.06 (t, J = 10.9 Hz, 1H) ppm. |
| 582 | 483.84 | 2.82 | 1H NMR (300 MHz, DMSO-D6) δ 9.63 (s, 1H), 9.20 (s, 1H), 7.71 (d, J = 7.3 Hz, 2H), 7.59 (s, 1H), 7.26 (tt, J = 9.3, 2.3 Hz, 1H), 7.06 (s, 1H), 6.69 (s, 1H), 3.59 (t, J = 4.6 Hz, 4H), 3.53-3.39 (m, 4H), 3.39-3.26 (m, 4H), 3.21 (t, J = 4.7 Hz, 4H), 2.28 (s, 3H) ppm. |
| 583 | 407.61 | 0.57 | 1H NMR (300 MHz, CDCl3) δ 9.25 (d, J = 1.3 Hz, 1H), 8.93 (s, 1H), 8.58 (d, J = 2.5 Hz, 1H), 8.40 (dd, J = 2.5, 1.5 Hz, 1H), 7.36 (d, J = 23.3 Hz, 2H), 6.83 (d, J = 13.5 Hz, 2H), 4.75-4.56 (m, 4H), 3.63-3.44 (m, 3H), 2.59 (s, 4H), 2.41 (d, J = 8.5 Hz, 7H) ppm. |
| 584 | 457.38 | 0.74 | 1H NMR (300 MHz, DMSO-D6) δ 9.30 (s, 1H), 9.14 (s, 1H), 7.87 (d, J = 8.0 Hz, 1H), 7.63-7.54 (m, 2H), 7.22 (tt, J = 9.3, 2.2 Hz, 1H), 6.78-6.66 (m, 2H), 5.83 (s, 1H), 3.94 (t, J = 6.7 Hz, 3H), 3.78 (td, J = 6.6, 2.6 Hz, 2H), 3.47 (m, 5H), 3.29 (m, 2H), 3.23-3.14 (m, 2H), 2.20 (s, 3H), 1.04 (m, 3H) ppm. |
| 585 | 406.66 | 0.67 | 1H NMR (300 MHz, CDCl3) δ 9.04 (d, J = 2.3 Hz, 1H), 8.62 (dd, J = 4.8, 1.4 Hz, 1H), 8.38 (s, 1H), 8.01 (ddd, J = 8.3, 2.6, 1.5 Hz, 1H), 7.47 (ddd, J = 8.3, 4.8, 0.6 Hz, 1H), 7.12 (s, 1H), 6.80 (d, J = 5.5 Hz, 2H), 6.42 (s, 1H), 4.67 (d, J = 5.5 Hz, 2H), 4.29 (d, J = 5.7 Hz, 2H), 3.37-3.16 (m, 4H), 2.65-2.47 (m, 4H), 2.35 (s, 3H), 1.43 (s, 3H) ppm. |
| 586 | 453.41 | 0.68 | 1H NMR (300 MHz, DMSO-D6) δ 9.29 (s, 1H), 9.14 (s, 1H), 7.66-7.53 (m, 2H), 7.22 (tt, J = 9.3, 2.3 Hz, 1H), 6.78 (s, 1H), 6.67 (s, 1H), 5.83 (s, 1H), 4.92 (s, 2H), 4.20 (s, 2H), 3.94 (t, J = 6.6 Hz, 2H), 3.59 (m, 3H), 3.54-3.44 (m, 2H), 3.22 (s, 2H), 2.60 (m, 2H), 2.19 (s, 3H) ppm. |
| 587 | 445.3 | 0.6 | 1H NMR (400 MHz, DMSO-D6) δ 9.18 (s, 1H), 8.96 (d, J = 1.3 Hz, 1H), 7.68-7.53 (m, 3H), 7.26 (tt, J = 9.2, 2.2 Hz, 1H), 6.41 (dd, J = 5.5, 2.8 Hz, 1H), 4.57 (t, J = 6.5 Hz, 2H), 4.47 (t, J = 6.1 Hz, 2H), 3.49-3.41 (m, 1H), 3.17-3.06 (m, 4H), 2.44-2.37 (m, 4H), 2.19 (d, J = 1.8 Hz, 3H) ppm. |
| 588 | 363.27 | 0.69 | 1H NMR (300 MHz, MeOD) δ 8.57 (s, 1H), 7.80 (d, J = 7.7 Hz, 3H), 7.52 (dd, J = 10.6, 5.1 Hz, 2H), 7.43-7.32 (m, 1H), 6.93-6.84 (m, 2H), 6.73 (s, 1H), 2.41-2.26 (m, 6H) ppm. |
| 589 | 482.87 | 2.57 | 1H NMR (300 MHz, DMSO-D6) δ 9.9 (s, 1H), 9.24 (s, 1H), 7.90 (s, 1H), 7.77 (d, J = 7.8 Hz, 2H), 7.41-7.20 (m, 2H), 6.98 (s, 1H), 3.72-3.35 (m, 10H), 3.15-2.98 (m, 1H), 2.34 (s, 3H), 2.02 (d, J = 51.9 Hz, 4H) ppm. |

TABLE 3A-continued

Analytical Data

| Cmpd No. in PRV2 | LCMS (M + H) | LC/MS Ret. Time (min) | ¹H-NMR |
|---|---|---|---|
| 590 | 442.28 | 0.61 | 1H NMR (400 MHz, CDCl3) δ 8.29 (s, 1H), 7.66 (ddd, J = 10.9, 6.8, 2.6 Hz, 1H), 7.47-7.40 (m, 1H), 7.35-7.27 (m, 2H), 6.86 (s, 1H), 6.75 (d, J = 1.6 Hz, 1H), 6.41 (t, J = 1.7 Hz, 1H), 4.70-4.58 (m, 4H), 4.46 (tt, J = 8.9, 4.1 Hz, 1H), 3.55 (p, J = 6.5 Hz, 1H), 3.09-2.97 (m, 1H), 2.66 (dt, J = 10.5, 4.0 Hz, 1H), 2.34 (s, 3H), 2.22 (dp, J = 13.4, 4.6 Hz, 1H), 2.04-1.85 (m, 3H), 1.74 (ddt, J = 11.0, 7.0, 3.8 Hz, 1H), 1.53 (tdd, J = 12.1, 9.7, 4.3 Hz, 1H) ppm. |
| 591 | 485 | 0.7 | 1H NMR (400 MHz, CDCl3) δ 8.30 (s, 1H), 7.59 (d, J = 2.3 Hz, 1H), 7.22 (dd, J = 7.9, 2.2 Hz, 2H), 6.87-6.72 (m, 1H), 6.55 (s, 1H), 6.24 (d, J = 2.2 Hz, 1H), 4.70 (p, J = 6.4 Hz, 4H), 4.47 (dt, J = 12.1, 6.0 Hz, 1H), 3.68-3.50 (m, 1H), 3.35-3.20 (m, 4H), 2.65-2.46 (m, 4H), 2.13 (s, 3H), 1.34 (d, J = 6.1 Hz, 6H) ppm. |
| 592 | 402.25 | 0.64 | 1H NMR (300 MHz, CDCl3) δ 8.35 (s, 1H), 7.74-7.65 (m, 2H), 7.63-7.45 (m, 3H), 7.40 (d, J = 1.2 Hz, 1H), 7.32 (t, J = 2.1 Hz, 1H), 6.88 (s, 1H), 6.78 (d, J = 0.9 Hz, 1H), 4.71 (dt, J = 14.5, 6.4 Hz, 4H), 3.64-3.52 (m, 1H), 3.37-3.25 (m, 4H), 2.61-2.44 (m, 4H) ppm. |
| 593 | 483.91 | 2.39 | 1H NMR (300 MHz, DMSO-D6) δ 10.99 (s, 1H), 9.45 (s, 1H), 9.18 (s, 1H), 7.68-7.58 (m, 2H), 7.34-7.20 (m, 1H), 7.15 (s, 1H), 6.98 (s, 1H), 6.43 (s, 1H), 5.06 (s, 8H), 4.03 (s, 1H), 3.80 (s, 3H), 3.67 (s, 4H), 3.18 (s, 2H), 2.26 (s, 3H) ppm. |
| 594 | 413 | 0.66 | 1H NMR (400 MHz, Acetone-D6) δ 8.90 (s, 1H), 8.61 (s, 1H), 7.74 (dd, J = 8.2, 1.2 Hz, 1H), 7.68 (dt, J = 10.3, 2.3 Hz, 1H), 7.59 (td, J = 8.2, 6.3 Hz, 1H), 7.19-7.07 (m, 3H), 6.29 (dt, J = 12.5, 2.2 Hz, 1H), 4.61 (t, J = 6.5 Hz, 2H), 4.54 (t, J = 6.1 Hz, 2H), 3.59-3.42 (m, 1H), 3.38-3.14 (m, 4H), 2.59-2.37 (m, 4H) ppm. |
| 595 | 441.31 | 0.6 | 1H NMR (400 MHz, CDCl3) δ 8.38 (s, 1H), 7.92 (s, 1H), 7.78 (ddd, J = 8.1, 2.1, 1.0 Hz, 1H), 7.66-7.53 (m, 1H), 7.47 (d, J = 7.7 Hz, 1H), 6.73 (ddd, J = 56.2, 32.2, 18.0 Hz, 4H), 5.96 (s, 1H), 4.02 (t, J = 7.0 Hz, 2H), 3.77 (dd, J = 10.9, 5.8 Hz, 6H), 3.45-3.29 (m, 1H), 2.47 (s, 4H), 2.32 (s, 3H) ppm. |
| 596 | 441.67 | 0.68 | 1H NMR (300 MHz, CDCl3) δ 8.33 (s, 1H), 7.39 (s, 1H), 7.30 (d, J = 2.2 Hz, 1H), 7.27 (s, 1H), 7.23 (s, 1H), 6.89-6.75 (m, 2H), 6.70 (s, 1H), 4.75-4.53 (m, 4H), 3.62-3.44 (m, 3H), 2.59 (s, 4H), 2.40 (d, J = 10.4 Hz, 7H) ppm. |
| 597 | 443.34 | 0.63 | 1H NMR (300 MHz, CDCl3) δ 8.26 (s, 1H), 7.79 (dd, J = 6.3, 2.7 Hz, 1H), 7.62-7.48 (m, 1H), 7.35-7.23 (m, 1H), 7.12 (m, 1H), 6.79 (s, 1H), 6.68 (s, 1H), 6.42 (s, 1H), 4.72 (p, J = 6.3 Hz, 4H), 3.59 (p, J = 6.4 Hz, 1H), 3.39-3.24 (m, 4H), 2.59-2.47 (m, 4H), 2.35 (s, 3H) ppm. |
| 598 | 397 | 0.59 | 1H NMR (400 MHz, CDCl3) δ 9.18 (d, J = 1.2 Hz, 1H), 8.92 (s, 1H), 8.57 (d, J = 2.5 Hz, 1H), 8.47-8.31 (m, 1H), 7.26 (s, 1H), 6.90 (dd, J = 14.6, 12.5 Hz, 3H), 6.28 (d, J = 11.9 Hz, 1H), 4.70 (dt, J = 15.4, 6.4 Hz, 4H), 3.67-3.51 (m, 1H), 3.41-3.23 (m, 3H), 2.67-2.40 (m, 4H) ppm. |
| 599 | 444.28 | 0.56 | 1H NMR (400 MHz, CDCl3) δ 8.34 (s, 1H), 7.28-7.25 (m, 2H), 7.12 (d, J = 1.7 Hz, 1H), 6.80 (dddd, J = 8.6, 6.4, 4.4, 2.3 Hz, 1H), 5.82 (d, J = 1.7 Hz, 1H), 4.80-4.59 (m, 4H), 3.92 (s, 3H), 3.65-3.49 (m, 5H), 2.51-2.40 (m, 4H) ppm. |
| 600 | 405.26 | 0.63 | 1H NMR (400 MHz, CDCl3) δ 8.44 (s, 1H), 7.98 (s, 1H), 7.92 (dd, J = 7.4, 5.5 Hz, 2H), 7.71-7.56 (m, 2H), 7.25 (s, 1H), 5.90 (s, 1H), 5.08 (d, J = 7.1 Hz, 1H), 4.36 (dtt, J = 10.5, 7.0, 3.4 Hz, 1H), 4.10-3.95 (m, 2H), 3.88 (td, J = 8.4, 5.4 Hz, 1H), 3.75 (dd, J = 9.1, 3.2 Hz, 1H), |

TABLE 3A-continued

Analytical Data

| Cmpd No. in PRV2 | LCMS (M + H) | LC/MS Ret. Time (min) | ¹H-NMR |
|---|---|---|---|
| | | | 2.34 (d, J = 6.1 Hz, 3H), 2.29 (dt, J = 12.8, 4.9 Hz, 1H), 1.91 (dddd, J = 12.7, 7.6, 5.4, 3.6 Hz, 1H) ppm. |
| 601 | 482.22 | 0.66 | 1H NMR (400 MHz, CDCl3) δ 8.37 (s, 1H), 7.61 (s, 1H), 7.42 (s, 1H), 7.27 (dd, J = 7.7, 2.2 Hz, 2H), 6.84 (ddd, J = 8.7, 5.4, 2.2 Hz, 1H), 6.12 (s, 1H), 4.16-4.06 (m, 2H), 3.93 (dd, J = 8.4, 5.3 Hz, 2H), 3.82-3.73 (m, 4H), 3.36 (dt, J = 12.2, 6.1 Hz, 1H), 2.47 (s, 4H) ppm. |
| 602 | 455.4 | 0.69 | 1H NMR (300 MHz, DMSO-D6) δ 9.29 (s, 1H), 9.14 (s, 1H), 7.65-7.53 (m, 2H), 7.23 (ttt, J = 9.3, 5.8, 2.3 Hz, 1H), 6.75 (s, 1H), 6.68 (s, 1H), 5.82 (s, 1H), 3.90 (t, J = 7.0 Hz, 2H), 3.66-3.57 (m, 2H), 3.57-3.48 (m, 2H), 3.21 (m, 1H), 2.27 (m, 2H), 2.19 (s, 3H), 2.13 (s, 2H), 1.16 (s, 6H) ppm. |
| 603 | | | 1H NMR (400 MHz, DMSO-D6) δ 9.72 (s, 1H), 9.23 (s, 1H), 9.14 (d, J = 1.3 Hz, 1H), 8.68 (d, J = 2.5 Hz, 1H), 8.58 (dd, J = 2.5, 1.4 Hz, 1H), 7.70 (s, 1H), 7.63 (s, 1H), 7.35 (s, 1H), 6.74 (s, 1H), 3.65 (d, J = 8.5 Hz, 1H), 3.51 (d, J = 8.5 Hz, 1H), 2.32 (s, 3H), 1.68 (s, 3H) ppm. |
| 604 | 361.12 | 0.72 | 1H NMR (300 MHz, CDCl3) δ 8.37 (s, 1H), 7.83 (s, 1H), 7.75-7.65 (m, 3H), 7.50 (dd, J = 10.7, 5.1 Hz, 2H), 7.34 (t, J = 7.4 Hz, 1H), 7.06 (d, J = 13.6 Hz, 2H), 6.93 (d, J = 8.7 Hz, 2H), 4.09 (t, J = 7.3 Hz, 2H), 2.38 (s, 3H), 1.52 (t, J = 7.3 Hz, 3H) ppm. |
| 605 | 397.17 | 0.82 | 1H NMR (400 MHz, CDCl3) δ 8.33 (s, 1H), 7.37 (d, J = 2.2 Hz, 1H), 7.30 (d, J = 2.2 Hz, 1H), 7.17 (t, J = 2.2 Hz, 1H), 6.89 (d, J = 1.7 Hz, 1H), 6.80 (tt, J = 8.7, 2.3 Hz, 1H), 6.51 (t, J = 1.7 Hz, 1H), 6.39 (d, J = 2.3 Hz, 1H), 5.13 (s, 2H), 3.94 (s, 3H), 2.37 (s, 3H) ppm. |
| 606 | 409 | 0.65 | 1H NMR (300 MHz, CDCl3) δ 8.23 (s, 1H), 7.74-7.53 (m, 2H), 7.24-7.09 (m, 2H), 6.67 (s, 1H), 6.64-6.48 (m, 2H), 5.93 (s, 1H), 3.97 (t, J = 7.0 Hz, 2H), 3.74 (t, J = 4.8 Hz, 6H), 3.45-3.25 (m, 1H), 2.46 (d, J = 4.3 Hz, 4H), 2.30 (s, 3H) ppm. |
| 607 | 439.65 | 0.65 | 1H NMR (300 MHz, CDCl3) δ 8.31 (s, 1H), 7.66-7.52 (m, 2H), 7.49-7.41 (m, 1H), 7.40-7.29 (m, 2H), 6.46 (d, J = 0.8 Hz, 1H), 4.70 (dt, J = 13.2, 6.4 Hz, 4H), 3.69-3.50 (m, 5H), 2.55-2.35 (m, 4H) ppm. |
| 608 | 347.17 | 0.84 | 1H NMR (300 MHz, MeOD) δ 8.58 (s, 1H), 7.74 (d, J = 7.6 Hz, 2H), 7.56 (s, 1H), 7.54 (s, 1H), 7.51 (d, J = 1.9 Hz, 1H), 7.47 (t, J = 2.1 Hz, 1H), 7.39 (t, J = 7.4 Hz, 1H), 6.78 (d, J = 1.2 Hz, 1H), 3.97-3.81 (m, 4H), 3.31-3.15 (m, 4H) ppm. |
| 609 | 406 | 0.63 | 1H NMR (400 MHz, CDCl3) δ 8.93 (s, 1H), 8.41 (ddd, J = 4.8, 1.8, 0.8 Hz, 1H), 7.93-7.81 (m, 1H), 7.77 (d, J = 8.2 Hz, 1H), 7.23 (ddd, J = 7.3, 4.9, 1.1 Hz, 1H), 7.00 (t, J = 1.9 Hz, 1H), 6.71 (s, 1H), 6.56 (s, 1H), 6.16 (s, 1H), 4.65 (t, J = 6.5 Hz, 2H), 4.58 (t, J = 6.2 Hz, 2H), 3.76-3.65 (m, 1H), 3.61 (dt, J = 12.9, 5.6 Hz, 4H), 2.70-2.55 (m, 2H), 2.53-2.35 (m, 2H), 2.31 (s, 3H), 2.14-1.96 (m, 2H) ppm. |
| 610 | 476.32 | 0.58 | 1H NMR (400 MHz, CDCl3) δ 8.33 (s, 1H), 7.90 (s, 1H), 7.84-7.74 (m, 1H), 7.61-7.49 (m, 2H), 7.08 (d, J = 1.7 Hz, 1H), 5.73 (d, J = 1.7 Hz, 1H), 4.62 (p, J = 6.4 Hz, 4H), 3.83 (s, 3H), 3.54-3.37 (m, 5H), 2.37 (dd, J = 14.3, 9.2 Hz, 4H) ppm. |
| 611 | | | 1H NMR (400 MHz, DMSO-D6) δ 9.61 (s, 1H), 9.19 (s, 1H), 7.71-7.60 (m, 3H), 7.29-7.20 (m, 2H), 6.73 (s, 1H), 3.69 (d, J = 8.8 Hz, 1H), 3.60 (d, J = 8.8 Hz, 1H), 2.77 (s, 3H), 2.31 (s, 3H), 1.68 (s, 3H) ppm. |
| 612 | 432.33 | 0.57 | 1H NMR (300 MHz, DMSO-D6) δ 9.93 (s, 1H), 9.21 (s, 1H), 7.69-7.53 (m, 2H), 7.35-7.21 (m, |

TABLE 3A-continued

Analytical Data

| Cmpd No. in PRV2 | LCMS (M + H) | LC/MS Ret. Time (min) | ¹H-NMR |
|---|---|---|---|
| | | | 1H), 6.92 (s, 1H), 5.59 (d, J = 1.4 Hz, 1H), 4.03 (t, J = 7.6 Hz, 2H), 3.81 (dd, J = 8.2, 5.0 Hz, 2H), 3.61 (s, 4H), 3.33-3.26 (m, 1H), 2.37 (s, 4H) ppm. |
| 613 | 400.19 | 0.8 | 1H NMR (300 MHz, DMSO-D6) δ 9.61 (s, 1H), 9.19 (s, 1H), 7.67 (dd, J = 6.7, 4.4 Hz, 3H), 7.25 (dd, J = 10.5, 8.2 Hz, 2H), 6.73 (s, 1H), 3.70 (d, J = 8.8 Hz, 1H), 3.59 (d, J = 8.8 Hz, 1H), 2.77 (s, 3H), 2.31 (s, 3H), 1.68 (s, 3H) ppm. |
| 614 | 373.22 | 0.6 | 1H NMR (400 MHz, CDCl3) δ 8.37 (s, 1H), 7.92 (s, 1H), 7.37-7.25 (m, 3H), 6.81 (tt, J = 8.7, 2.3 Hz, 1H), 5.90 (s, 1H), 5.08 (s, 1H), 4.41-4.28 (m, 1H), 4.00 (ddd, J = 14.7, 11.1, 6.5 Hz, 2H), 3.88 (td, J = 8.4, 5.4 Hz, 1H), 3.74 (dd, J = 9.1, 3.2 Hz, 1H), 2.34 (s, 3H), 2.33-2.20 (m, 1H), 1.91 (dddd, J = 12.7, 7.5, 5.4, 3.6 Hz, 1H) ppm. |
| 615 | 387.18 | 0.86 | 1H NMR (400 MHz, CDCl3) δ 8.14 (s, 1H), 7.45 (ddd, J = 10.8, 6.8, 2.6 Hz, 1H), 7.32-7.23 (m, 1H), 7.18 (dd, J = 9.4, 8.2 Hz, 1H), 6.99 (s, 1H), 6.72 (s, 1H), 6.62 (s, 1H), 6.29 (d, J = 2.2 Hz, 1H), 4.52 (d, J = 5.9 Hz, 2H), 4.34 (d, J = 5.9 Hz, 2H), 3.94 (s, 2H), 2.22 (s, 3H), 1.33 (s, 3H) ppm. |
| 616 | 428.62 | 0.57 | 1H NMR (300 MHz, CDCl3) δ 8.35 (s, 1H), 7.27 (d, J = 2.2 Hz, 1H), 7.24 (d, J = 2.2 Hz, 1H), 6.83 (tt, J = 8.8, 2.3 Hz, 2H), 6.54 (s, 1H), 6.49 (s, 1H), 4.15 (t, J = 7.4 Hz, 2H), 3.99-3.90 (m, 2H), 3.82-3.72 (m, 4H), 3.41-3.30 (m, 1H), 2.48 (s, 4H), 2.42 (s, 3H) ppm. |
| 617 | 443.42 | 0.69 | 1H NMR (300 MHz, DMSO-D6) δ 9.28 (s, 1H), 9.14 (s, 1H), 7.60 (m, 2H), 7.23 (ttt, J = 9.2, 5.8, 2.3 Hz, 1H), 6.74 (s, 1H), 6.69 (s, 1H), 5.82 (s, 1H), 4.78 (m, 0.5H), 4.62 (m, 0.5H), 3.91 (t, J = 6.9 Hz, 2H), 3.58-3.48 (m, 2H), 3.28-3.18 (m, 1H), 2.45 (m, 2H), 2.26 (m, 2H), 2.19 (s, 3H), 1.81 (m, 4H) ppm. |
| 618 | 455.4 | 0.7 | 1H NMR (300 MHz, DMSO-D6) δ 9.34 (s, 1H), 9.15 (s, 1H), 7.66-7.54 (m, 2H), 7.25 (tt, J = 9.2, 2.2 Hz, 1H), 6.76 (s, 1H), 6.68 (s, 1H), 5.81 (s, 1H), 3.89 (t, J = 7.0 Hz, 2H), 3.62-3.47 (m, 4H), 3.29-3.16 (m, 1H), 2.71 (d, J = 10.6 Hz, 2H), 2.19 (s, 3H), 1.58 (t, J = 10.6 Hz, 2H), 1.06 (d, J = 6.2 Hz, 6H) ppm. |
| 619 | 415.25 | 0.63 | 1H NMR (400 MHz, CDCl3) δ 8.33 (s, 1H), 7.28 (dd, J = 7.4, 2.6 Hz, 2H), 7.24 (s, 1H), 7.15 (s, 1H), 6.80 (tt, J = 8.7, 2.3 Hz, 1H), 6.15 (s, 1H), 4.32 (d, J = 13.0 Hz, 2H), 3.37 (s, 3H), 3.27 (d, J = 6.2 Hz, 2H), 2.81 (td, J = 12.7, 2.3 Hz, 2H), 2.34 (s, 3H), 1.85 (ddd, J = 17.3, 9.8, 2.4 Hz, 3H), 1.38-1.21 (m, 2H) ppm. |
| 620 | 442.37 | 0.62 | 1H NMR (400 MHz, CDCl3) δ 8.34 (s, 1H), 7.33-7.30 (m, 3H), 6.81 (tt, J = 8.7, 2.3 Hz, 1H), 6.75 (dd, J = 4.5, 2.7 Hz, 2H), 6.42 (t, J = 1.7 Hz, 1H), 4.63 (q, J = 6.4 Hz, 4H), 4.47 (tt, J = 8.9, 4.1 Hz, 1H), 3.56 (p, J = 6.5 Hz, 1H), 3.10-2.99 (m, 1H), 2.66 (dd, J = 11.1, 4.1 Hz, 1H), 2.34 (s, 3H), 2.22 (td, J = 11.3, 10.1, 5.1 Hz, 1H), 2.06-1.86 (m, 3H), 1.79-1.66 (m, 1H), 1.54 (tdd, J = 12.1, 9.7, 4.2 Hz, 1H) ppm. |
| 621 | 480.24 | 0.65 | 1H NMR (300 MHz, CDCl3) δ 8.35 (s, 1H), 7.61-7.50 (m, 2H), 7.48 (s, 1H), 7.44 (dd, J = 9.0, 2.4 Hz, 1H), 7.35 (s, 1H), 6.60 (t, J = 56.1 Hz, 1H), 6.39 (s, 1H), 4.71 (p, J = 6.4 Hz, 4H), 3.67-3.60 (m, 4H), 3.55 (p, J = 6.4 Hz, 1H), 2.45 (t, J = 5.1 Hz, 4H), 2.03 (s, 3H) ppm. |
| 622 | 408 | 0.65 | 1H NMR (300 MHz, CDCl3) δ 8.23 (s, 1H), 7.72-7.58 (m, 2H), 7.19 (t, J = 8.6 Hz, 2H), 7.07 (s, 1H), 6.80 (s, 1H), 6.64 (s, 1H), 6.39 (s, 1H), 4.82-4.60 (m, 4H), 3.56 (p, J = 6.3 Hz, 1H), 3.37-3.16 (m, 4H), 2.62-2.40 (m, 4H), 2.33 (s, 3H) ppm. |

TABLE 3A-continued

Analytical Data

| Cmpd No. in PRV2 | LCMS (M + H) | LC/MS Ret. Time (min) | ¹H-NMR |
|---|---|---|---|
| 623 | 428.28 | 0.76 | 1H NMR (300 MHz, MeOD) δ 8.85 (s, 1H), 7.62-7.40 (m, 3H), 7.26 (s, 1H), 6.93 (tt, J = 9.0, 2.2 Hz, 1H), 6.76 (s, 1H), 4.77-4.64 (m, 3H), 4.54 (dd, J = 10.3, 2.1 Hz, 1H), 4.04 (dd, J = 11.5, 2.0 Hz, 1H), 3.85 (td, J = 11.5, 2.3 Hz, 1H), 3.55 (dd, J = 12.7, 6.2 Hz, 1H), 2.86 (d, J = 11.4 Hz, 1H), 2.75 (d, J = 11.4 Hz, 1H), 2.33 (s, 3H), 2.22-1.93 (m, 2H), 1.20 (dd, J = 23.1, 9.8 Hz, 1H) ppm. |
| 624 | 439.25 | 0.6 | 1H NMR (400 MHz, DMSO-D6) δ 9.17 (s, 1H), 8.97 (s, 1H), 7.74 (dd, J = 12.4, 2.6 Hz, 1H), 7.64-7.56 (m, 1H), 7.35 (t, J = 9.1 Hz, 1H), 7.14 (d, J = 2.1 Hz, 1H), 6.86 (s, 1H), 6.29 (s, 1H), 4.57 (t, J = 6.5 Hz, 2H), 4.48 (t, J = 6.0 Hz, 2H), 3.89 (s, 3H), 3.45 (p, J = 6.3 Hz, 1H), 3.14 (t, J = 4.9 Hz, 4H), 2.41 (d, J = 9.8 Hz, 1H), 2.41 (s, 3H), 2.22 (s, 3H) ppm. |
| 625 | 490.37 | 0.6 | 1H NMR (300 MHz, CDCl3) δ 8.32 (s, 1H), 7.91 (s, 1H), 7.80 (dd, J = 5.4, 3.4 Hz, 1H), 7.62-7.47 (m, 2H), 7.26 (s, 1H), 6.22 (s, 1H), 4.71-4.55 (m, 4H), 4.39 (s, 2H), 3.61-3.50 (m, 4H), 3.48-3.41 (m, 1H), 3.39 (s, 3H), 2.45-2.29 (m, 4H) ppm. |
| 626 | 428.28 | 0.78 | 1H NMR (400 MHz, CDCl3) δ 8.29 (s, 1H), 7.58 (ddd, J = 10.9, 6.8, 2.6 Hz, 1H), 7.44-7.37 (m, 1H), 7.32 (dd, J = 9.4, 8.2 Hz, 1H), 7.19 (t, J = 2.2 Hz, 1H), 7.05 (s, 1H), 6.81 (d, J = 1.7 Hz, 1H), 6.40 (t, J = 1.7 Hz, 1H), 4.58 (tt, J = 6.8, 3.5 Hz, 1H), 3.84 (ddd, J = 12.5, 8.1, 3.8 Hz, 1H), 3.74 (ddd, J = 13.6, 8.1, 3.7 Hz, 1H), 3.64 (ddd, J = 13.4, 7.1, 4.0 Hz, 1H), 3.42 (ddd, J = 13.6, 7.2, 3.9 Hz, 1H), 2.34 (s, 3H), 2.15 (s, 3H), 2.05-1.80 (m, 4H) ppm. |
| 627 | 401.3 | 0.9 | 1H NMR (400 MHz, CDCl3) δ 8.27 (d, J = 5.2 Hz, 1H), 7.60 (ddd, J = 10.9, 6.8, 2.6 Hz, 1H), 7.47-7.39 (m, 1H), 7.36-7.31 (m, 1H), 7.15-7.02 (m, 1H), 6.83 (d, J = 2.0 Hz, 1H), 6.73-6.59 (m, 1H), 6.39 (d, J = 1.9 Hz, 1H), 4.03 (td, J = 11.4, 4.5 Hz, 2H), 3.87 (d, J = 6.4 Hz, 2H), 3.48 (td, J = 11.9, 2.3 Hz, 2H), 2.36 (d, J = 0.6 Hz, 3H), 1.80 (dd, J = 13.0, 3.7 Hz, 2H), 1.49 (qd, J = 12.2, 4.7 Hz, 2H) ppm. |
| 628 | 384.3 | 0.86 | 1H NMR (300 MHz, DMSO-D6) δ 9.24 (s, 1H), 9.14 (s, 1H), 7.65-7.52 (m, 2H), 7.23 (tt, J = 9.3, 2.3 Hz, 1H), 6.90-6.82 (m, 1H), 6.69 (s, 1H), 6.02 (s, 1H), 4.61 (s, 1H), 4.43 (s, 1H), 3.81-3.68 (m, 2H), 3.50 (dd, J = 9.1, 1.6 Hz, 1H), 2.98 (d, J = 9.2 Hz, 1H), 2.21 (s, 3H), 1.97-1.78 (m, 2H) ppm. |
| 629 | 442.33 | 0.75 | 1H NMR (300 MHz, DMSO-D6) δ 9.51 (s, 1H), 9.18 (s, 1H), 8.15 (s, 1H), 7.68-7.60 (m, 2H), 7.56 (d, J = 1.8 Hz, 1H), 7.35-7.18 (m, 2H), 6.70 (d, J = 1.7 Hz, 1H), 4.67-4.50 (m, 3H), 4.50-4.34 (m, 2H), 3.75 (dd, J = 11.2, 3.1 Hz, 1H), 3.64 (t, J = 7.1 Hz, 1H), 3.32 (t, J = 10.8 Hz, 1H), 2.73 (d, J = 2.2 Hz, 1H), 2.29 (s, 4H), 1.90 (t, J = 10.8 Hz, 1H), 0.79 (d, J = 6.4 Hz, 3H) ppm. |
| 630 | 459.26 | 0.64 | 1H NMR (300 MHz, CDCl3) δ 8.34 (s, 1H), 8.00 (dd, J = 7.7, 1.8 Hz, 1H), 7.30 (s, 1H), 7.27 (d, J = 2.2 Hz, 1H), 6.97 (d, J = 3.8 Hz, 1H), 6.82 (tt, J = 8.7, 2.3 Hz, 1H), 6.75 (d, J = 4.6 Hz, 1H), 4.74-4.56 (m, 4H), 3.62 (d, J = 1.2 Hz, 2H), 3.59-3.46 (m, 1H), 2.60 (s, 4H), 2.40 (s, 7H) ppm. |
| 631 | 369.22 | 0.62 | 1H NMR (400 MHz, DMSO-D6) δ 9.69 (s, 1H), 9.21 (s, 1H), 7.67 (dd, J = 8.6, 2.2 Hz, 2H), 7.55 (s, 1H), 7.32-7.20 (m, 1H), 6.84 (s, 1H), 6.76 (s, 1H), 3.44-3.40 (m, 1H), 3.37-3.30 (m, 2H), 2.92 (t, J = 5.7 Hz, 1H), 2.45-2.41 (m, 2H), 2.33 (s, 3H) ppm. |
| 632 | 442.32 | 0.62 | 1H NMR (400 MHz, CDCl3) δ 8.29 (s, 1H), 7.65 (ddd, J = 10.9, 6.8, 2.6 Hz, 1H), |

TABLE 3A-continued

Analytical Data

| Cmpd No. in PRV2 | LCMS (M + H) | LC/MS Ret. Time (min) | $^1$H-NMR |
|---|---|---|---|
| | | | 7.50-7.37 (m, 1H), 7.34-7.29 (m, 1H), 7.28 (d, J = 2.0 Hz, 1H), 6.88 (s, 1H), 6.76 (d, J = 1.8 Hz, 1H), 6.41 (t, J = 1.7 Hz, 1H), 4.70-4.58 (m, 4H), 4.46 (tt, J = 8.9, 4.1 Hz, 1H), 3.61-3.49 (m, 1H), 3.09-3.00 (m, 1H), 2.66 (dt, J = 10.8, 4.0 Hz, 1H), 2.34 (s, 3H), 2.21 (dp, J = 12.2, 3.9 Hz, 1H), 2.06-1.84 (m, 3H), 1.71 (tdd, J = 14.7, 7.7, 3.9 Hz, 1H), 1.53 (tdd, J = 12.5, 9.5, 4.2 Hz, 1H) ppm. |
| 633 | 441.67 | 0.68 | 1H NMR (300 MHz, CDCl3) δ 8.26 (s, 1H), 7.58 (ddd, J = 10.9, 6.8, 2.5 Hz, 1H), 7.45-7.37 (m, 1H), 7.32 (dd, J = 9.3, 8.1 Hz, 1H), 7.07 (s, 1H), 6.81 (s, 1H), 6.65 (s, 1H), 6.43 (s, 1H), 4.67 (d, J = 5.5 Hz, 2H), 4.30 (d, J = 5.7 Hz, 2H), 3.37-3.17 (m, 4H), 2.66-2.47 (m, 4H), 2.35 (s, 3H), 1.44 (s, 3H) ppm. |
| 634 | 425.36 | 0.69 | 1H NMR (300 MHz, DMSO-D6) δ 9.33 (s, 1H), 9.15 (s, 1H), 7.66-7.54 (m, 2H), 7.30-7.18 (m, 1H), 6.75 (s, 1H), 6.68 (s, 1H), 5.82 (s, 1H), 3.90 (t, J = 6.8 Hz, 2H), 3.51 (t, J = 6.3 Hz, 2H), 3.24-3.10 (m, 1H), 2.26 (m, 4H), 2.19 (s, 3H), 1.45 (m, 6H) ppm. |
| 635 | 387.18 | 0.9 | 1H NMR (400 MHz, CDCl3) δ 8.19 (s, 1H), 7.15-7.12 (m, 2H), 7.09 (t, J = 2.3 Hz, 1H), 6.65 (dddd, J = 8.6, 6.8, 4.8, 2.3 Hz, 3H), 6.28 (t, J = 1.6 Hz, 1H), 4.23 (tt, J = 7.7, 3.8 Hz, 1H), 3.93 (ddd, J = 11.4, 3.8, 1.7 Hz, 1H), 3.68 (dt, J = 11.3, 4.4 Hz, 1H), 3.49-3.36 (m, 2H), 2.20 (s, 3H), 2.05 (ddd, J = 9.7, 7.2, 4.6 Hz, 1H), 1.83-1.72 (m, 1H), 1.68 (ddd, J = 12.6, 8.6, 3.9 Hz, 1H), 1.56 (dtd, J = 13.6, 9.0, 4.7 Hz, 1H) ppm. |
| 636 | 496.26 | 0.64 | 1H NMR (400 MHz, CDCl3) δ 8.43 (s, 1H), 7.83 (dd, J = 5.4, 4.4 Hz, 2H), 7.70-7.57 (m, 2H), 7.53 (d, J = 7.7 Hz, 1H), 7.44 (s, 1H), 6.75 (t, J = 56.2 Hz, 1H), 6.11 (s, 1H), 4.16-4.05 (m, 2H), 3.93 (dd, J = 8.4, 5.3 Hz, 2H), 3.84-3.70 (m, 4H), 3.43-3.29 (m, 1H), 2.47 (s, 4H) ppm. |
| 637 | 441 | 0.66 | 1H NMR (400 MHz, CDCl3) δ 8.29 (s, 1H), 7.23 (dd, J = 7.9, 2.2 Hz, 2H), 7.08 (s, 1H), 6.77 (tt, J = 8.7, 2.3 Hz, 1H), 6.61 (s, 1H), 6.44 (s, 1H), 6.16 (s, 1H), 4.65 (t, J = 6.5 Hz, 2H), 4.58 (t, J = 6.2 Hz, 2H), 3.75-3.53 (m, 5H), 2.67-2.56 (m, 2H), 2.45-2.36 (m, 2H), 2.30 (s, 3H), 2.11-1.98 (m, 2H) ppm. |
| 638 | 387.23 | 0.88 | 1H NMR (400 MHz, CDCl3) δ 8.31 (s, 1H), 7.61 (ddd, J = 10.9, 6.8, 2.7 Hz, 1H), 7.42 (dp, J = 8.3, 1.9 Hz, 1H), 7.34-7.26 (m, 1H), 7.22 (t, J = 2.2 Hz, 1H), 6.96 (s, 1H), 6.80 (s, 1H), 6.41 (t, J = 1.6 Hz, 1H), 4.36 (tt, J = 7.7, 3.8 Hz, 1H), 4.08 (ddd, J = 11.3, 3.8, 1.6 Hz, 1H), 3.83 (dt, J = 11.3, 4.4 Hz, 1H), 3.63-3.49 (m, 2H), 2.34 (s, 3H), 2.19 (dq, J = 11.4, 4.5 Hz, 1H), 1.97-1.87 (m, 1H), 1.82 (ddt, J = 12.5, 8.3, 4.3 Hz, 1H), 1.76-1.63 (m, 1H) ppm. |
| 639 | 458.32 | 0.55 | 1H NMR (400 MHz, CDCl3) δ 8.40 (s, 1H), 7.88 (s, 1H), 7.83-7.77 (m, 1H), 7.61 (t, J = 7.9 Hz, 1H), 7.50 (d, J = 7.7 Hz, 1H), 7.26 (s, 1H), 7.19 (dd, J = 7.5, 1.7 Hz, 1H), 6.74 (t, J = 56.2 Hz, 1H), 5.81 (d, J = 1.7 Hz, 1H), 4.71 (p, J = 6.4 Hz, 4H), 3.92 (s, 3H), 3.63-3.49 (m, 5H), 2.52-2.39 (m, 4H) ppm. |
| 640 | 407.21 | 0.93 | 1H NMR (400 MHz, CDCl3) δ 8.28 (s, 1H), 7.60 (ddd, J = 10.9, 6.8, 2.6 Hz, 1H), 7.45-7.39 (m, 1H), 7.33 (dd, J = 9.4, 8.2 Hz, 1H), 7.14 (t, J = 2.2 Hz, 1H), 6.84 (t, J = 1.8 Hz, 1H), 6.68 (s, 1H), 6.39 (t, J = 1.7 Hz, 1H), 4.12-3.92 (m, 2H), 2.87-2.61 (m, 3H), 2.61-2.45 (m, 2H), 2.36 (s, 3H) ppm. |
| 641 | 485 | 0.71 | 1H NMR (400 MHz, CDCl3) δ 8.30 (s, 1H), 7.31-7.17 (m, 3H), 7.12 (d, J = 2.1 Hz, 1H), 6.76 (tt, J = 8.7, 2.3 Hz, 1H), 6.54 (s, 1H), 5.77 (d, J = 2.1 Hz, 1H), 4.46 (dt, J = 12.1, 6.1 Hz, 1H), 4.00 (t, J = 6.9 Hz, 2H), 3.74 (dd, J = 8.2, |

TABLE 3A-continued

Analytical Data

| Cmpd No. in PRV2 | LCMS (M + H) | LC/MS Ret. Time (min) | ¹H-NMR |
|---|---|---|---|
| | | | 4.1 Hz, 6H), 3.42-3.24 (m, 1H), 2.53-2.37 (m, 4H), 2.11 (s, 3H), 1.33 (d, J = 6.1 Hz, 6H) ppm. |
| 642 | 396 | 0.62 | 1H NMR (400 MHz, Acetone-D6) δ 8.99 (s, 1H), 8.66 (s, 1H), 8.48 (ddd, J = 4.8, 1.8, 0.8 Hz, 1H), 8.05 (ddd, J = 8.2, 7.5, 1.8 Hz, 1H), 7.86 (dt, J = 8.2, 0.9 Hz, 1H), 7.39 (ddd, J = 7.4, 4.8, 1.0 Hz, 1H), 7.13 (tt, J = 4.1, 2.0 Hz, 2H), 6.30 (dt, J = 12.5, 2.2 Hz, 1H), 4.61 (t, J = 6.5 Hz, 2H), 4.55 (t, J = 6.1 Hz, 2H), 3.59-3.42 (m, 1H), 3.39-3.15 (m, 4H), 2.58-2.38 (m, 4H) ppm. |
| 643 | 349.26 | 0.68 | 1H NMR (300 MHz, CDCl3) δ 8.38 (s, 1H), 7.84 (s, 1H), 7.70 (dd, J = 8.5, 1.1 Hz, 2H), 7.55-7.44 (m, 2H), 7.40-7.31 (m, 2H), 7.25 (s, 1H), 6.86 (s, 1H), 6.76 (s, 1H), 6.64 (d, J = 3.7 Hz, 1H), 2.38 (s, 3H) ppm. |
| 644 | 429.27 | 0.84 | 1H NMR (400 MHz, CDCl3) δ 7.84 (s, 1H), 7.75 (d, J = 7.6 Hz, 1H), 7.56-7.36 (m, 4H), 7.02 (s, 1H), 6.68 (s, 1H), 6.20 (d, J = 1.9 Hz, 1H), 6.13 (t, J = 2.0 Hz, 1H), 4.42 (t, J = 5.2 Hz, 2H), 4.24 (t, J = 5.2 Hz, 2H), 2.19 (s, 3H) ppm. |
| 645 | 465.3 | 0.7 | 1H NMR (400 MHz, CDCl3) δ 8.41 (s, 1H), 7.90-7.78 (m, 2H), 7.64 (dd, J = 8.5, 7.7 Hz, 1H), 7.53 (t, J = 6.4 Hz, 1H), 7.46 (s, 1H), 7.33 (s, 1H), 6.67 (dt, J = 66.6, 56.2 Hz, 3H), 6.40 (s, 1H), 4.37 (d, J = 13.2 Hz, 2H), 3.38 (s, 3H), 3.30 (t, J = 10.6 Hz, 2H), 2.88 (td, J = 12.8, 2.4 Hz, 2H), 1.86 (t, J = 10.9 Hz, 3H), 1.36-1.22 (m, 2H) ppm. |
| 646 | 457.23 | 2.86 | 1H NMR (400 MHz, CDCl3) δ 8.13 (s, 1H), 7.17 (d, J = 1.4 Hz, 1H), 7.01 (s, 1H), 6.69 (s, 1H), 6.51 (s, 1H), 6.33 (s, 1H), 4.62 (p, J = 6.4 Hz, 4H), 3.96 (t, J = 1.0 Hz, 3H), 3.50 (p, J = 6.4 Hz, 1H), 3.26-3.18 (m, 4H), 2.45 (dd, J = 6.0, 4.0 Hz, 4H), 2.26 (s, 3H) ppm. |
| 647 | 427.31 | 0.62 | 1H NMR (300 MHz, CDCl3) δ 8.25 (s, 1H), 7.58-7.50 (m, 1H), 7.45 (dt, J = 7.3, 3.6 Hz, 1H), 7.14 (t, J = 8.8 Hz, 1H), 6.99 (dt, J = 10.7, 2.1 Hz, 1H), 6.78 (dd, J = 5.7, 3.5 Hz, 2H), 6.26 (dt, J = 11.9, 2.2 Hz, 1H), 4.71 (dt, J = 13.1, 6.3 Hz, 4H), 3.58 (p, J = 6.5 Hz, 1H), 3.38-3.22 (m, 4H), 2.63-2.46 (m, 5H), 2.38 (d, J = 2.0 Hz, 3H) ppm. |
| 648 | 387.14 | 0.88 | 1H NMR (400 MHz, CDCl3) δ 8.21 (s, 1H), 7.12 (d, J = 2.3 Hz, 1H), 7.01 (t, J = 2.2 Hz, 1H), 6.73-6.49 (m, 3H), 6.26 (t, J = 1.6 Hz, 1H), 3.90-3.73 (m, 4H), 3.71-3.62 (m, 1H), 3.60 (dd, J = 8.9, 5.3 Hz, 1H), 2.72-2.57 (m, 1H), 2.21 (s, 3H), 2.00 (dtd, J = 12.7, 8.1, 5.6 Hz, 1H), 1.63 (dtd, J = 12.8, 7.5, 5.9 Hz, 1H) ppm. |
| 649 | 441.35 | 0.65 | 1H NMR (300 MHz, DMSO-D6) δ 9.20 (s, 1H), 9.14 (s, 1H), 7.64 (dd, J = 8.6, 2.2 Hz, 2H), 7.32-7.18 (m, 1H), 6.84 (t, J = 2.0 Hz, 1H), 6.47 (s, 1H), 5.91-5.76 (m, 2H), 3.83-3.70 (m, 1H), 3.58 (t, J = 4.6 Hz, 4H), 2.95-2.78 (m, 1H), 2.35-2.18 (m, 6H), 2.14 (s, 3H), 2.02-1.94 (m, 1H) ppm. |
| 650 | 512.37 | 0.51 | 1H NMR (400 MHz, DMSO-D6) δ 9.16 (s, 2H), 7.59 (dd, J = 8.6, 2.2 Hz, 2H), 7.28-7.20 (m, 1H), 6.84 (d, J = 1.4 Hz, 1H), 5.77 (s, 1H), 4.57 (t, J = 6.5 Hz, 2H), 4.48 (t, J = 6.1 Hz, 2H), 3.48-3.42 (m, 4H), 3.35-3.25 (m, 3H), 2.37 (m, 8H), 2.21 (s, 3H) ppm. |
| 651 | 459.31 | 0.71 | 1H NMR (400 MHz, DMSO-D6) δ 9.32 (s, 1H), 9.23 (s, 1H), 8.17 (s, 1H), 7.79 (t, J = 7.8 Hz, 1H), 7.69 (d, J = 7.9 Hz, 1H), 6.89 (s, 1H), 6.63 (s, 1H), 5.81 (s, 1H), 3.90 (t, J = 7.0 Hz, 2H), 3.66-3.55 (m, 6H), 3.29-3.19 (m, 1H), 2.35 (s, 4H), 2.19 (s, 3H) ppm. |
| 652 | 439.37 | 0.69 | 1H NMR (300 MHz, DMSO-D6) δ 9.30 (s, 1H), 9.14 (s, 1H), 7.60 (dd, J = 11.3, 4.8 Hz, 2H), 7.27-7.16 (m, 1H), 6.76 (s, 1H), 6.70 (s, 1H), 5.84 (s, 1H), 3.92 (m, 2H), 3.79-3.71 (m, 1H), |

TABLE 3A-continued

Analytical Data

| Cmpd No. in PRV2 | LCMS (M + H) | LC/MS Ret. Time (min) | ¹H-NMR |
|---|---|---|---|
| | | | 3.70-3.62 (m, 1H), 3.61-3.46 (m, 4H), 2.60 (d, J = 11.7 Hz, 2H), 2.38 (dd, J = 13.1, 7.2 Hz, 1H), 2.20 (s, 3H), 0.67 (m, 1H), 0.32 (dd, J = 13.2, 6.2 Hz, 1H) ppm. |
| 653 | 471 | 0.69 | 1H NMR (400 MHz, CDCl3) δ 8.30 (s, 1H), 7.31-7.15 (m, 2H), 6.95 (s, 1H), 6.87-6.72 (m, 2H), 6.69 (s, 1H), 6.13 (t, J = 1.9 Hz, 1H), 4.69 (p, J = 6.3 Hz, 4H), 4.57 (dt, J = 12.1, 6.0 Hz, 1H), 3.55 (p, J = 6.4 Hz, 1H), 3.35-3.20 (m, 4H), 2.55-2.41 (m, 4H), 1.38 (d, J = 6.1 Hz, 6H) ppm. |
| 654 | 454.54 | 0.7 | 1H NMR (300 MHz, CDCl3) δ 8.37 (s, 1H), 7.60 (d, J = 14.3 Hz, 1H), 7.47 (s, 1H), 7.28 (d, J = 2.8 Hz, 1H), 7.25 (d, J = 2.2 Hz, 1H), 6.83 (tt, J = 8.7, 2.3 Hz, 1H), 6.45 (s, 1H), 3.78-3.46 (m, 4H), 2.69-2.55 (m, 4H), 2.50 (q, J = 7.2 Hz, 2H), 1.16 (t, J = 7.2 Hz, 3H) ppm. |
| 655 | | | 1H NMR (400 MHz, DMSO-D6) δ 9.59 (s, 1H), 9.18 (s, 1H), 7.71-7.61 (m, 3H), 7.60 (s, 1H), 7.30 (s, 1H), 7.24 (ddd, J = 9.3, 5.8, 2.3 Hz, 1H), 6.72 (s, 1H), 3.63 (d, J = 8.5 Hz, 1H), 3.50 (d, J = 8.5 Hz, 1H), 2.31 (s, 2H), 1.67 (s, 2H) ppm. |
| 656 | 438.61 | 0.66 | 1H NMR (300 MHz, CDCl3) δ 8.29 (s, 1H), 7.56 (ddd, J = 10.6, 6.7, 2.5 Hz, 1H), 7.42 (ddd, J = 6.4, 4.6, 3.1 Hz, 1H), 7.39-7.36 (m, 1H), 7.35-7.31 (m, 1H), 7.29 (s, 1H), 6.86 (s, 1H), 6.79 (dd, J = 2.1, 1.2 Hz, 1H), 4.71 (dt, J = 12.4, 6.4 Hz, 4H), 3.65-3.53 (m, 1H), 3.39-3.26 (m, 4H), 2.62-2.45 (m, 4H) ppm. |
| 657 | 469.29 | 0.53 | 1H NMR (400 MHz, DMSO-D6) δ 9.25 (s, 1H), 9.15 (s, 1H), 7.58 (dd, J = 8.6, 2.2 Hz, 2H), 7.29-7.19 (m, 1H), 6.79 (d, J = 1.9 Hz, 2H), 6.06 (s, 1H), 3.18-3.04 (m, 8H), 2.47-2.40 (m, 8H), 2.22 (s, 6H) ppm. |
| 658 | 386.13 | 0.75 | 1H NMR (400 MHz, DMSO-D6) δ 9.60 (s, 1H), 9.19 (s, 1H), 7.65 (s, 3H), 7.61 (s, 1H), 7.30 (s, 1H), 7.24 (t, J = 9.2 Hz, 1H), 6.72 (s, 1H), 3.63 (d, J = 8.7 Hz, 1H), 3.50 (d, J = 8.9 Hz, 1H), 2.31 (s, 3H), 1.67 (s, 3H) ppm. |
| 659 | 441 | 0.68 | 1H NMR (400 MHz, CDCl3) δ 8.24 (s, 1H), 7.57 (ddd, J = 10.9, 6.8, 2.6 Hz, 1H), 7.46-7.33 (m, 1H), 7.33-7.19 (m, 2H), 6.62 (dd, J = 8.6, 6.4 Hz, 3H), 5.95 (s, 1H), 4.01 (t, J = 6.9 Hz, 2H), 3.82 (t, J = 6.2 Hz, 2H), 3.77-3.72 (m, 2H), 3.71-3.61 (m, 2H), 3.63-3.52 (m, 1H), 2.63 (dd, J = 7.9, 3.6 Hz, 4H), 2.30 (s, 3H), 2.00-1.82 (m, 2H) ppm. |
| 660 | 448.27 | 0.57 | 1H NMR (300 MHz, DMSO-D6) δ 10.03 (s, 1H), 9.21 (s, 1H), 7.62 (dd, J = 8.5, 2.1 Hz, 2H), 7.34-7.22 (m, 1H), 6.98 (d, J = 1.6 Hz, 1H), 6.00 (d, J = 1.6 Hz, 1H), 4.03 (t, J = 7.5 Hz, 2H), 3.81 (dd, J = 8.3, 5.0 Hz, 2H), 3.61 (s, 4H), 2.58-2.54 (m, 1H), 2.37 (s, 4H) ppm. |
| 661 | 475.43 | 0.74 | 1H NMR (300 MHz, DMSO-D6) δ 9.29 (s, 1H), 9.14 (s, 1H), 7.64-7.54 (m, 2H), 7.23 (tt, J = 9.3, 2.3 Hz, 1H), 6.72 (s, 2H), 5.82 (s, 1H), 3.94 (m, 2H), 3.56 (m, 3H), 3.19-3.06 (m, 4H), 2.83 (m, 4H), 2.20 (s, 3H) ppm. |
| 662 | 475.24 | 0.64 | 1H NMR (400 MHz, CDCl3) δ 8.40 (s, 1H), 8.03 (s, 1H), 7.85 (d, J = 7.7 Hz, 1H), 7.69-7.57 (m, 2H), 6.92 (t, J = 2.0 Hz, 1H), 6.77 (s, 1H), 6.71 (t, J = 2.0 Hz, 1H), 6.17 (t, J = 2.1 Hz, 1H), 4.72 (dt, J = 15.5, 6.4 Hz, 4H), 3.86 (s, 3H), 3.59 (p, J = 6.4 Hz, 1H), 3.38-3.24 (m, 4H), 2.59-2.43 (m, 4H) ppm. |
| 663 | 442.33 | 0.75 | 1H NMR (300 MHz, DMSO-D6) δ 9.51 (s, 1H), 9.18 (s, 1H), 7.73 (d, J = 1.8 Hz, 1H), 7.70-7.57 (m, 2H), 7.22 (ddt, J = 18.4, 9.2, 2.0 Hz, 2H), 6.68 (s, 1H), 4.60-4.43 (m, 5H), 3.79 (ddd, J = 9.9, 6.1, 2.1 Hz, 1H), 3.41 (m, 1H), 2.85-2.69 (m, 2H), 2.50 (p, J = 1.9 Hz, 5H), 2.26 (s, 3H), 1.75 (t, J = 10.7 Hz, 1H), 1.63 (t, J = 10.5 Hz, 1H), 1.18 (d, J = 6.2 Hz, 3H) ppm. |

TABLE 3A-continued

Analytical Data

| Cmpd No. in PRV2 | LCMS (M + H) | LC/MS Ret. Time (min) | ¹H-NMR |
|---|---|---|---|
| 664 | 471.64 | 0.61 | 1H NMR (300 MHz, CDCl3) δ 8.35 (s, 1H), 7.51 (d, J = 0.8 Hz, 1H), 7.33 (s, 1H), 7.27 (s, 1H), 7.25 (d, J = 2.2 Hz, 1H), 6.83 (tt, J = 8.7, 2.3 Hz, 1H), 6.70 (d, J = 0.9 Hz, 1H), 6.27 (s, 1H), 4.79-4.57 (m, 4H), 3.74-3.61 (m, 4H), 3.60-3.49 (m, 1H), 3.05 (d, J = 4.9 Hz, 3H), 2.54-2.31 (m, 4H) ppm. |
| 665 | 442.32 | 0.61 | 1H NMR (400 MHz, CDCl3) δ 8.29 (s, 1H), 7.72-7.61 (m, 1H), 7.47-7.39 (m, 1H), 7.34-7.29 (m, 1H), 7.27 (d, J = 1.9 Hz, 1H), 6.92 (s, 1H), 6.76 (s, 1H), 6.41 (t, J = 1.6 Hz, 1H), 4.70-4.57 (m, 4H), 4.46 (tt, J = 8.9, 4.1 Hz, 1H), 3.56 (p, J = 6.5 Hz, 1H), 3.09-3.00 (m, 1H), 2.66 (dd, J = 10.9, 4.1 Hz, 1H), 2.34 (s, 3H), 2.21 (dp, J = 12.1, 3.9, 3.4 Hz, 1H), 2.05-1.93 (m, 2H), 1.89 (dp, J = 15.6, 4.0 Hz, 1H), 1.72 (dtt, J = 17.4, 6.8, 3.9 Hz, 1H), 1.59-1.47 (m, 1H) ppm. |
| 666 | 349.15 | 0.62 | 1H NMR (300 MHz, DMSO-D6) δ 9.94 (s, 1H), 9.26 (s, 1H), 9.09 (s, 1H), 8.69 (d, J = 2.3 Hz, 1H), 8.60 (s, 1H), 7.53 (s, 1H), 7.47 (s, 1H), 6.94 (s, 1H), 3.92-3.63 (m, 4H), 3.20 (d, J = 4.6 Hz, 4H) ppm. |
| 667 | 442.36 | 0.77 | 1H NMR (400 MHz, CDCl3) δ 8.37 (s, 1H), 7.62-7.53 (m, 2H), 7.26 (dt, J = 6.0, 2.1 Hz, 3H), 6.88 (s, 1H), 6.78 (tt, J = 8.7, 2.3 Hz, 1H), 4.80-4.60 (m, 4H), 3.91-3.77 (m, 2H), 3.50 (dd, J = 13.4, 6.9 Hz, 1H), 2.91 (d, J = 11.5 Hz, 1H), 2.38 (d, J = 23.7 Hz, 6H), 1.52 (s, 3H) ppm. |
| 668 | 383.58 | 0.88 | 1H NMR (300 MHz, CDCl3) δ 9.77 (s, 1H), 9.11 (s, 1H), 8.07-7.91 (m, 1H), 7.77-7.61 (m, 2H), 7.50 (s, 1H), 7.42 (s, 1H), 6.91 (s, 1H), 3.87-3.69 (m, 4H), 3.23-3.09 (m, 4H) ppm. |
| 669 | 374.25 | 0.83 | 1H NMR (300 MHz, CDCl3) δ 8.30 (s, 1H), 7.74-7.64 (m, 2H), 7.57-7.47 (m, 3H), 7.42 (s, 1H), 7.40-7.32 (m, 1H), 7.09 (d, J = 1.9 Hz, 1H), 6.69 (s, 1H), 6.62 (s, 1H), 6.22 (s, 1H), 5.12 (s, 1H), 4.53-4.36 (m, 1H), 2.29 (s, 3H), 1.50 (d, J = 6.7 Hz, 6H) ppm. |
| 670 | 441.35 | 0.68 | 1H NMR (300 MHz, DMSO-D6) δ 9.29 (s, 1H), 9.14 (s, 1H), 7.66-7.52 (m, 2H), 7.22 (tt, J = 9.2, 2.3 Hz, 1H), 6.81 (s, 1H), 6.67 (s, 1H), 5.84 (s, 1H), 4.00 (m, 1H), 3.90 (m, 1H), 3.66 (d, J = 11.3 Hz, 1H), 3.53 (m, 5H), 3.21-3.10 (m, 1H), 2.64 (d, J = 11.4 Hz, 1H), 2.41 (m, 1H), 2.19 (s, 3H), 2.12 (m, 1H), 0.91 (d, J = 6.4 Hz, 3H) ppm. |
| 671 | 419.23 | 0.9 | 1H NMR (400 MHz, CDCl3) δ 8.41 (s, 1H), 8.02 (d, J = 2.0 Hz, 1H), 7.88 (dt, J = 7.7, 1.9 Hz, 1H), 7.71-7.58 (m, 2H), 7.26 (t, J = 2.2 Hz, 1H), 6.83 (t, J = 1.6 Hz, 1H), 6.74 (s, 1H), 6.45 (t, J = 1.6 Hz, 1H), 4.68 (d, J = 5.9 Hz, 2H), 4.49 (d, J = 5.9 Hz, 2H), 4.10 (s, 2H), 2.37 (s, 3H), 1.48 (s, 3H) ppm. |
| 672 | 496.53 | 0.71 | 1H NMR (300 MHz, CDCl3) δ 8.37 (s, 1H), 7.59 (s, 1H), 7.41 (s, 1H), 7.28-7.18 (m, 2H), 6.83 (tt, J = 8.7, 2.3 Hz, 1H), 6.44 (s, 1H), 4.05-3.90 (m, 2H), 3.83 (dd, J = 15.9, 8.1 Hz, 1H), 3.72 (dd, J = 8.6, 6.8 Hz, 1H), 3.62 (t, J = 5.1 Hz, 4H), 3.11-2.98 (m, 1H), 2.66 (dt, J = 10.5, 5.1 Hz, 2H), 2.59-2.46 (m, 2H), 2.18-2.03 (m, 1H), 1.93 (ddd, J = 15.6, 12.3, 8.2 Hz, 1H) ppm. |
| 673 | 442.26 | 0.62 | 1H NMR (300 MHz, CDCl3) δ 8.33 (s, 1H), 7.30 (s, 1H), 7.27 (d, J = 2.2 Hz, 1H), 7.20 (d, J = 6.5 Hz, 2H), 6.81 (tt, J = 8.7, 2.2 Hz, 1H), 6.13 (s, 1H), 3.98 (ddd, J = 15.2, 8.5, 5.7 Hz, 2H), 3.83 (dd, J = 15.9, 8.1 Hz, 1H), 3.72 (dd, J = 8.5, 6.9 Hz, 1H), 3.56 (t, J = 5.1 Hz, 4H), 3.09-2.97 (m, 1H), 2.66 (dt, J = 10.3, 5.1 Hz, 2H), 2.59-2.47 (m, 2H), 2.35 (s, 3H), 2.17-2.04 (m, 1H), 1.93 (ddd, J = 15.7, 12.2, 8.2 Hz, 1H) ppm. |

TABLE 3A-continued

Analytical Data

| Cmpd No. in PRV2 | LCMS (M + H) | LC/MS Ret. Time (min) | ¹H-NMR |
|---|---|---|---|
| 674 | 427.54 | 0.97 | 1H NMR (300 MHz, CDCl3) δ 8.37 (s, 1H), 7.64 (s, 1H), 7.37 (s, 1H), 7.28 (s, 1H), 7.25 (d, J = 2.2 Hz, 1H), 6.83 (tt, J = 8.7, 2.3 Hz, 1H), 6.44 (s, 1H), 3.90-3.78 (m, 4H), 3.63-3.50 (m, 4H) ppm. |
| 675 | 417.3 | 3.84 | 1H NMR (300 MHz, CDCl3) δ 8.28 (s, 1H), 7.86 (s, 1H), 7.26-7.18 (m, 3H), 6.83-6.66 (m, 2H), 3.88 (s, 3H), 3.82-3.67 (m, 4H), 3.60-3.40 (m, 4H) ppm. |
| 676 | 347.32 | 0.7 | 1H NMR (300 MHz, MeOD + CDCl3) δ 8.47 (s, 1H), 7.91 (s, 1H), 7.81-7.72 (m, 2H), 7.66 (t, J = 1.8 Hz, 1H), 7.57-7.48 (m, 2H), 7.41-7.33 (m, 1H), 6.96 (s, 1H), 6.89 (s, 1H), 3.84 (s, 3H), 2.37 (s, 3H) ppm. |
| 677 | 387.14 | 0.88 | 1H NMR (400 MHz, CDCl3) δ 8.18 (s, 1H), 7.11 (d, J = 2.3 Hz, 1H), 7.03 (s, 1H), 6.74-6.63 (m, 2H), 6.59 (s, 1H), 6.30 (t, J = 1.7 Hz, 1H), 4.52 (d, J = 5.9 Hz, 2H), 4.35 (d, J = 5.9 Hz, 2H), 3.95 (s, 2H), 2.22 (s, 3H), 1.33 (s, 3H) ppm. |
| 678 | 438.7 | 0.66 | 1H NMR (300 MHz, MeOD + CDCl3) δ 8.63 (s, 1H), 7.50 (t, J = 2.2 Hz, 1H), 7.43-7.29 (m, 3H), 6.84 (tt, J = 8.8, 2.3 Hz, 1H), 6.80-6.73 (m, 1H), 4.73 (dt, J = 12.5, 6.5 Hz, 4H), 3.67-3.54 (m, 1H), 3.34 (d, J = 5.3 Hz, 4H), 2.65-2.45 (m, 4H) ppm. |
| 679 | | | 1H NMR (400 MHz, DMSO-D6) δ 9.59 (s, 1H), 9.18 (s, 1H), 7.71-7.62 (m, 3H), 7.60 (s, 1H), 7.28 (d, J = 10.2 Hz, 1H), 7.27-7.20 (m, 1H), 6.72 (s, 1H), 3.63 (d, J = 8.8 Hz, 1H), 3.50 (d, J = 8.8 Hz, 1H), 2.31 (s, 3H), 1.67 (s, 3H) ppm. |
| 680 | 496.22 | 0.7 | 1H NMR (400 MHz, CDCl3) δ 8.43 (s, 1H), 7.96 (s, 1H), 7.91 (d, J = 7.7 Hz, 1H), 7.73-7.59 (m, 2H), 7.51 (s, 1H), 7.35 (s, 1H), 6.60 (t, J = 56.2 Hz, 2H), 6.39 (s, 1H), 4.72 (dt, J = 14.4, 6.4 Hz, 4H), 3.71-3.61 (m, 3H), 3.61-3.48 (m, 1H), 2.50-2.38 (m, 3H) ppm. |
| 681 | 409.18 | 0.87 | 1H NMR (300 MHz, DMSO-D6) δ 9.35 (s, 2H), 9.08 (s, 2H), 7.97 (s, 1H), 7.91 (d, J = 7.6 Hz, 4H), 7.49 (t, J = 7.9 Hz, 4H), 7.31 (t, J = 7.4 Hz, 2H), 6.92 (d, J = 1.4 Hz, 2H), 2.26 (s, 3H) ppm. |
| 682 | | | 1H NMR (400 MHz, DMSO-D6) δ 9.72 (s, 1H), 9.23 (s, 1H), 9.14 (d, J = 1.3 Hz, 1H), 8.68 (d, J = 2.5 Hz, 1H), 8.58 (dd, J = 2.5, 1.4 Hz, 1H), 7.70 (s, 1H), 7.63 (s, 1H), 7.35 (s, 1H), 6.74 (s, 1H), 3.65 (d, J = 8.6 Hz, 1H), 3.51 (d, J = 8.7 Hz, 1H), 2.32 (s, 3H), 1.68 (s, 3H) ppm. |
| 683 | 441.39 | 0.66 | 1H NMR (300 MHz, DMSO-D6) δ 9.28 (s, 1H), 9.14 (s, 1H), 7.64-7.52 (m, 2H), 7.29-7.15 (m, 1H), 6.73 (s, 1H), 6.69 (s, 1H), 5.82 (s, 1H), 3.54 (m, 8H), 2.38 (m, 4H), 2.19 (s, 3H), 1.33 (s, 3H) ppm. |
| 684 | 447.48 | 0.57 | 1H NMR (300 MHz, CDCl3) δ 9.02 (d, J = 2.5 Hz, 1H), 8.65 (dd, J = 4.8, 1.4 Hz, 1H), 8.44 (s, 1H), 8.05 (ddd, J = 8.3, 2.6, 1.5 Hz, 1H), 7.64 (s, 1H), 7.51 (dd, J = 8.3, 4.8 Hz, 1H), 7.43 (s, 1H), 6.45 (s, 1H), 4.71 (p, J = 6.3 Hz, 4H), 3.72-3.61 (m, 4H), 3.60-3.51 (m, 1H), 2.53-2.38 (m, 4H) ppm. |
| 685 | 478.16 | 0.69 | 1H NMR (300 MHz, CDCl3) δ 8.36 (s, 1H), 7.49 (s, 1H), 7.33 (s, 1H), 7.28-7.22 (m, 2H), 6.82 (tt, J = 8.7, 2.2 Hz, 1H), 6.38 (s, 1H), 4.81-4.60 (m, 4H), 3.63 (dd, J = 11.4, 6.4 Hz, 4H), 3.55 (dd, J = 12.8, 6.4 Hz, 1H), 2.52-2.33 (m, 4H), 1.96 (t, J = 18.3 Hz, 3H) ppm. |
| 686 | 362.28 | 3.74 | 1H NMR (300 MHz, DMSO-D6) δ 9.57 (s, 1H), 9.18 (s, 1H), 7.74-7.60 (m, 2H), 7.27 (ddd, J = 9.3, 5.8, 2.2 Hz, 1H), 6.77-6.59 (m, 3H), 5.84-5.73 (m, 1H), 4.84 (t, J = 6.0 Hz, 2H), 4.56-4.37 (m, 3H) ppm. |

TABLE 3A-continued

Analytical Data

| Cmpd No. in PRV2 | LCMS (M + H) | LC/MS Ret. Time (min) | ¹H-NMR |
|---|---|---|---|
| 687 | 416.33 | 0.57 | 1H NMR (300 MHz, DMSO-D6) δ 9.38 (s, 1H), 9.25 (s, 1H), 8.05 (d, J = 10.5 Hz, 4H), 7.16 (s, 1H), 6.89 (s, 1H), 6.32 (s, 1H), 4.53 (dt, J = 25.3, 6.4 Hz, 4H), 3.45 (d, J = 6.5 Hz, 1H), 3.15 (d, J = 5.7 Hz, 4H), 2.41 (s, 4H), 2.23 (s, 3H) ppm. |
| 688 | 401.08 | 0.69 | |
| 689 | 387.26 | 0.6 | 1H NMR (400 MHz, CDCl3) δ 8.41 (s, 1H), 7.87 (s, 1H), 7.85-7.81 (m, 1H), 7.67 (s, 1H), 7.62 (t, J = 7.9 Hz, 1H), 7.52 (t, J = 8.3 Hz, 1H), 7.24 (s, 1H), 6.75 (t, J = 56.2 Hz, 1H), 5.89 (s, 1H), 4.87 (d, J = 7.1 Hz, 1H), 4.37 (dtt, J = 10.6, 7.1, 3.5 Hz, 1H), 4.00 (dt, J = 14.5, 6.5 Hz, 2H), 3.88 (td, J = 8.4, 5.5 Hz, 1H), 3.74 (dd, J = 9.2, 3.3 Hz, 1H), 2.33 (s, 3H), 2.32-2.24 (m, 1H), 1.96-1.84 (m, 1H) ppm. |
| 690 | 455.4 | 0.77 | 1H NMR (300 MHz, DMSO-D6) δ 9.37 (s, 1H), 9.16 (s, 1H), 7.61 (d, J = 6.4 Hz, 2H), 7.31-7.20 (m, 1H), 6.82 (d, J = 11.2 Hz, 1H), 6.67 (s, 1H), 5.83 (s, 1H), 4.01 (t, J = 7.1 Hz, 2H), 3.91-3.76 (m, 3H), 3.57 (d, J = 4.3 Hz, 4H), 3.47 (s, 2H), 2.90 (d, J = 14.9 Hz, 2H), 2.20 (s, 3H) ppm. |
| 691 | 445.3 | 0.64 | 1H NMR (400 MHz, DMSO-D6) δ 9.17 (s, 1H), 8.86 (d, J = 1.6 Hz, 1H), 7.61 (dd, J = 8.5, 2.2 Hz, 2H), 7.51 (d, J = 5.6 Hz, 1H), 7.26 (tt, J = 9.2, 2.3 Hz, 1H), 6.44 (d, J = 5.9 Hz, 1H), 4.56 (t, J = 6.5 Hz, 2H), 4.47 (t, J = 6.1 Hz, 2H), 3.51-3.40 (m, 1H), 3.02 (s, 4H), 2.39 (s, 4H), 2.27 (s, 3H) ppm. |
| 692 | 398.21 | 0.94 | 1H NMR (300 MHz, DMSO-D6) δ 9.27 (s, 1H), 9.14 (s, 1H), 7.65-7.54 (m, 2H), 7.23 (tt, J = 9.3, 2.3 Hz, 1H), 7.07 (s, 1H), 6.84 (s, 1H), 6.23 (s, 1H), 4.42 (m, 2H), 3.33 (d, J = 11.3 Hz, 2H), 2.83 (dd, J = 11.4, 2.3 Hz, 2H), 2.22 (s, 3H), 1.84 (m, 4H) ppm. |
| 693 | 457.29 | 0.58 | 1H NMR (400 MHz, CDCl3) δ 8.39 (s, 1H), 7.92 (s, 1H), 7.79 (dd, J = 8.1, 1.1 Hz, 1H), 7.61 (t, J = 7.9 Hz, 1H), 7.48 (d, J = 7.7 Hz, 1H), 6.92-6.53 (m, 4H), 6.16 (t, J = 2.1 Hz, 1H), 4.72 (dt, J = 14.3, 6.4 Hz, 4H), 3.86 (s, 3H), 3.64-3.53 (m, 1H), 3.38-3.24 (m, 4H), 2.60-2.45 (m, 4H) ppm. |
| 694 | 384.25 | 0.75 | 1H NMR (400 MHz, DMSO-D6) δ 9.30 (s, 1H), 9.15 (s, 1H), 7.61-7.51 (m, 2H), 7.23 (tt, J = 9.3, 2.3 Hz, 1H), 6.81 (m, 1H), 6.68 (s, 1H), 5.95 (s, 1H), 4.27 (d, J = 10.4 Hz, 2H), 4.20 (d, J = 6.0 Hz, 2H), 3.59 (d, J = 9.1 Hz, 2H), 2.66 (m, 1H), 2.21 (s, 3H), 1.86 (d, J = 7.9 Hz, 1H) ppm. |
| 695 | 423.22 | 0.66 | 1H NMR (300 MHz, CDCl3) δ 8.33 (s, 1H), 7.53-7.40 (m, 3H), 7.12 (s, 1H), 7.06 (ddd, J = 10.3, 5.7, 3.0 Hz, 1H), 6.81 (s, 1H), 6.64 (s, 1H), 6.42 (s, 1H), 4.67 (d, J = 5.5 Hz, 2H), 4.30 (d, J = 5.7 Hz, 2H), 3.41-3.17 (m, 4H), 2.64-2.46 (m, 4H), 2.35 (s, 3H), 1.44 (s, 3H) ppm. |
| 696 | 441.35 | 0.66 | 1H NMR (300 MHz, DMSO-D6) δ 9.28 (s, 1H), 9.14 (s, 1H), 7.65-7.51 (m, 2H), 7.22 (tt, J = 9.3, 2.2 Hz, 1H), 6.74 (s, 1H), 6.69 (s, 1H), 5.82 (s, 1H), 3.89 (t, J = 6.9 Hz, 2H), 3.77 (d, J = 10.0 Hz, 1H), 3.58 (t, J = 6.0 Hz, 2H), 3.48 (m, 2H), 3.28-3.20 (m, 1H), 2.72 (d, J = 11.2 Hz, 1H), 2.64 (d, J = 10.4 Hz, 1H), 2.19 (s, 3H), 1.96 (td, J = 10.9, 8.2 Hz, 1H), 1.66 (t, J = 10.4 Hz, 1H), 1.06 (d, J = 6.2 Hz, 3H) ppm. |
| 697 | 441.34 | 0.68 | 1H NMR (400 MHz, DMSO-D6) δ 9.13 (s, 1H), 8.25 (s, 1H), 7.62-7.49 (m, 2H), 7.33 (s, 1H), 7.23 (tt, J = 9.3, 2.3 Hz, 1H), 6.56 (s, 1H), 4.56 (t, J = 6.5 Hz, 2H), 4.48 (t, J = 6.1 Hz, 2H), 3.54-3.41 (m, 1H), 2.84 (s, 4H), 2.38 (br s, 4H), 2.26 (s, 3H), 2.14 (s, 3H) ppm. |
| 698 | 397.17 | 0.81 | 1H NMR (400 MHz, CDCl3) δ 8.13 (s, 1H), 7.42 (dd, J = 8.9, 2.1 Hz, 3H), 7.26 (d, J = 9.1 Hz, 1H), 7.18 (dd, J = 9.5, 8.2 Hz, 1H), 6.94 (s, 1H), 6.68 (s, 1H), 6.58 (s, 1H), 6.20 (d, J = 2.0 Hz, 1H), 6.13 (t, J = 2.1 Hz, 1H), 4.41 (t, J = 5.3 Hz, |

TABLE 3A-continued

Analytical Data

| Cmpd No. in PRV2 | LCMS (M + H) | LC/MS Ret. Time (min) | $^1$H-NMR |
|---|---|---|---|
| | | | 2H), 4.23 (t, J = 5.3 Hz, 2H), 2.18 (s, 3H) ppm. |
| 699 | 346 | 0.66 | 1H NMR (300 MHz, DMSO-D6) δ 11.58 (s, 1H), 9.10 (s, 1H), 9.03 (s, 1H), 8.04 (s, 1H), 7.87 (d, J = 7.7 Hz, 2H), 7.54 (t, J = 8.0 Hz, 2H), 7.45 (s, 1H), 7.34 (t, J = 7.4 Hz, 1H), 6.65 (s, 2H), 5.75 (d, J = 1.3 Hz, 1H), 2.18 (s, 6H) ppm. |
| 700 | 442.28 | 0.62 | 1H NMR (400 MHz, CDCl3) δ 8.35 (s, 1H), 7.31 (dd, J = 7.8, 2.3 Hz, 2H), 7.06 (s, 1H), 6.84-6.74 (m, 2H), 6.42 (s, 1H), 4.63 (p, J = 6.4 Hz, 5H), 4.46 (tt, J = 8.9, 4.1 Hz, 1H), 3.56 (p, J = 6.5 Hz, 1H), 3.04 (dd, J = 10.8, 3.8 Hz, 1H), 2.66 (dd, J = 10.6, 4.3 Hz, 1H), 2.34 (s, 3H), 2.22 (dp, J = 14.0, 4.7 Hz, 1H), 2.05-1.85 (m, 4H), 1.81-1.64 (m, 1H), 1.61-1.46 (m, 1H) ppm. |
| 701 | 553.43 | 0.56 | 1H NMR (400 MHz, DMSO-D6) δ 9.23 (s, 1H), 9.14 (s, 1H), 7.60-7.56 (m, 2H), 7.23 (m, 1H), 6.61 (s, 1H), 6.39 (s, 1H), 5.56 (s, 1H), 4.57 (t, J = 6.4 Hz, 2H), 4.47 (t, J = 6.0 Hz, 2H), 3.87 (m, 2H), 3.57 (m, 6H), 3.47-3.40 (m, 1H), 3.23 (s, 1H), 3.12 (s, 4H), 2.39 (s, 4H), 2.34 (s, 4H) ppm. |
| 702 | 428.33 | 0.6 | 1H NMR (400 MHz, DMSO-D6) δ 9.37 (s, 1H), 9.18 (s, 1H), 7.69-7.59 (m, 2H), 7.26 (tt, J = 9.2, 2.3 Hz, 1H), 6.92 (s, 1H), 6.13 (s, 1H), 3.46 (s, 4H), 2.56 (dd, J = 13.0, 8.3 Hz, 4H), 2.22 (s, 3H), 1.04 (s, 9H) ppm. |
| 703 | 373.23 | 0.86 | 1H NMR (300 MHz, CDCl3) δ 8.32 (s, 1H), 7.32-7.21 (m, 2H), 7.14 (t, J = 2.3 Hz, 1H), 6.89-6.70 (m, 3H), 6.36 (t, J = 1.7 Hz, 1H), 5.06-4.93 (m, 1H), 4.10-3.87 (m, 4H), 2.35 (s, 3H), 2.32-2.17 (m, 2H) ppm. |
| 704 | 391 | 0.64 | 1H NMR (300 MHz, CDCl3) δ 8.31 (s, 1H), 7.74-7.60 (m, 2H), 7.49 (t, J = 7.9 Hz, 2H), 7.33 (t, J = 7.4 Hz, 1H), 6.74 (s, 1H), 6.71-6.55 (m, 2H), 5.93 (s, 1H), 3.98 (t, J = 7.0 Hz, 2H), 3.75 (t, J = 6.2 Hz, 6H), 3.45-3.23 (m, 1H), 2.46 (d, J = 4.2 Hz, 4H), 2.30 (s, 3H) ppm. |
| 705 | 378.23 | 4.05 | 1H NMR (300 MHz, DMSO-D6) δ 9.59 (s, 1H), 9.19 (s, 1H), 7.66 (dd, J = 8.5, 2.1 Hz, 2H), 7.28 (ddd, J = 9.3, 5.8, 2.3 Hz, 1H), 6.91 (d, J = 1.8 Hz, 1H), 6.82 (t, J = 1.8 Hz, 1H), 6.72 (d, J = 5.7 Hz, 1H), 6.00 (t, J = 1.8 Hz, 1H), 4.85 (t, J = 6.1 Hz, 2H), 4.57-4.38 (m, 3H) ppm. |
| 706 | 407.21 | 0.95 | 1H NMR (400 MHz, CDCl3) δ 8.34 (s, 1H), 7.29 (s, 2H), 7.16 (t, J = 2.2 Hz, 1H), 6.87-6.78 (m, 2H), 6.71 (s, 1H), 6.41 (t, J = 1.7 Hz, 1H), 4.10-4.01 (m, 2H), 2.77 (dddd, J = 13.5, 11.8, 10.0, 8.4 Hz, 3H), 2.61-2.45 (m, 2H), 2.36 (s, 3H) ppm. |
| 707 | 439.27 | 0.62 | 1H NMR (400 MHz, DMSO-D6) δ 10.20 (s, 1H), 9.22 (s, 1H), 7.70-7.57 (m, 3H), 7.33-7.25 (m, 1H), 7.18 (d, J = 2.1 Hz, 1H), 4.57 (t, J = 6.5 Hz, 2H), 4.48 (t, J = 6.1 Hz, 2H), 3.50-3.43 (m, 5H), 2.42-2.38 (m, 4H) ppm. |
| 708 | 442.33 | 0.75 | 1H NMR (300 MHz, DMSO-D6) δ 9.45 (s, 1H), 9.11 (s, 1H), 7.63-7.51 (m, 3H), 7.25-7.11 (m, 2H), 6.70 (s, 1H), 4.54-4.38 (m, 3H), 4.33 (t, J = 6.0 Hz, 1H), 3.60 (dtd, J = 16.5, 8.0, 4.6 Hz, 2H), 3.27 (d, J = 6.4 Hz, 1H), 2.79 (d, J = 11.5 Hz, 1H), 2.24 (s, 4H), 2.19-1.98 (m, 2H), 1.28 (s, 3H) ppm. |
| 709 | 427.29 | 0.67 | 1H NMR (400 MHz, DMSO-D6) δ 9.33 (s, 1H), 9.16 (s, 1H), 7.61 (dd, J = 8.6, 2.2 Hz, 2H), 7.25 (ddd, J = 9.3, 5.7, 2.3 Hz, 1H), 7.14 (s, 1H), 6.85 (s, 1H), 6.30 (s, 1H), 3.16-3.06 (m, 4H), 2.66-2.59 (m, 4H), 2.22 (s, 3H), 1.05 (s, 9H) ppm. |
| 710 | 421.26 | 2.7 | 1H NMR (400 MHz, CDCl3) δ 8.11 (s, 1H), 7.53-7.45 (m, 2H), 7.02 (s, 1H), 6.97-6.88 (m, 2H), 6.71 (s, 1H), 6.50 (s, 1H), 6.30 (s, 1H), 4.68-4.56 (m, 4H), 3.79 (s, 3H), 3.49 (p, J = 6.4 Hz, 1H), 3.24-3.17 (m, 4H), 2.47-2.40 (m, 4H), 2.25 (s, 3H) ppm. |

TABLE 3A-continued

Analytical Data

| Cmpd No. in PRV2 | LCMS (M + H) | LC/MS Ret. Time (min) | ¹H-NMR |
|---|---|---|---|
| 711 | 413.34 | 3.37 | 1H NMR (300 MHz, DMSO-D6) δ 9.31 (s, 1H), 9.15 (s, 1H), 7.64-7.53 (m, 2H), 7.22 (tt, J = 9.2, 2.2 Hz, 1H), 6.79 (s, 1H), 6.70 (s, 1H), 5.84 (s, 1H), 4.02 (m, 2H), 3.82 (m, 3H), 2.90 (s, 3H), 2.84 (s, 3H), 2.20 (s, 3H) ppm. |
| 712 | 448.56 | 0.63 | 1H NMR (300 MHz, CDCl3) δ 9.22 (d, J = 1.4 Hz, 1H), 8.97 (s, 1H), 8.61 (d, J = 2.5 Hz, 1H), 8.42 (dd, J = 2.5, 1.5 Hz, 1H), 7.67 (s, 1H), 7.47 (s, 1H), 6.47 (s, 1H), 4.79-4.63 (m, 4H), 3.73-3.63 (m, 4H), 3.56 (dt, J = 12.8, 6.4 Hz, 1H), 2.53-2.38 (m, 4H) ppm. |
| 713 | 444.24 | 0.59 | 1H NMR (300 MHz, CDCl3) δ 8.28 (s, 1H), 7.58 (ddd, J = 10.8, 6.8, 2.5 Hz, 1H), 7.46-7.37 (m, 1H), 7.33 (dd, J = 10.4, 7.0 Hz, 2H), 7.25 (s, 1H), 6.34 (s, 1H), 4.77-4.65 (m, 6H), 3.72-3.53 (m, 6H), 2.54-2.39 (m, 4H) ppm. |
| 714 | 397.17 | 0.8 | 1H NMR (400 MHz, CDCl3) δ 8.28 (s, 1H), 7.61 (ddd, J = 10.8, 6.8, 2.6 Hz, 1H), 7.48-7.41 (m, 1H), 7.37 (d, J = 2.2 Hz, 1H), 7.32 (dd, J = 9.5, 8.3 Hz, 1H), 7.19 (t, J = 2.2 Hz, 1H), 6.87 (d, J = 1.6 Hz, 1H), 6.73 (s, 1H), 6.50 (t, J = 1.8 Hz, 1H), 6.39 (d, J = 2.2 Hz, 1H), 5.12 (s, 2H), 3.94 (s, 3H), 2.36 (s, 3H) ppm. |
| 715 | 453.33 | 0.65 | 1H NMR (300 MHz, CDCl3) δ 8.29 (s, 1H), 7.73 (d, J = 2.2 Hz, 1H), 7.52-7.31 (m, 2H), 7.22 (t, J = 2.2 Hz, 1H), 6.79 (s, 1H), 6.71 (s, 1H), 6.45 (s, 1H), 4.80-4.66 (m, 4H), 3.59 (p, J = 6.4 Hz, 1H), 3.39-3.28 (m, 5H), 2.64 (q, J = 7.6 Hz, 2H), 2.59-2.49 (m, 5H), 2.43 (s, 3H), 1.28 (t, J = 7.6 Hz, 4H) ppm. |
| 716 | 478.62 | 0.68 | 1H NMR (300 MHz, CDCl3) δ 8.35 (s, 1H), 7.46 (s, 1H), 7.33 (s, 1H), 7.26 (d, J = 2.2 Hz, 2H), 6.90-6.76 (m, 1H), 6.51 (d, J = 56.2 Hz, 1H), 6.39 (s, 1H), 4.67 (d, J = 5.5 Hz, 2H), 4.30 (d, J = 5.7 Hz, 2H), 3.73-3.54 (m, 4H), 2.61-2.41 (m, 4H), 1.40 (s, 3H) ppm. |
| 717 | 453.46 | 0.68 | 1H NMR (300 MHz, DMSO-D6) δ 9.28 (s, 1H), 9.14 (s, 1H), 7.59 (m, 2H), 7.22 (m, 1H), 6.74 (s, 1H), 6.69 (s, 1H), 5.82 (s, 1H), 4.24 (m, 2H), 3.86 (t, J = 7.0 Hz, 2H), 3.56-3.46 (m, 2H), 3.26 (m, 1H), 2.54 (m, 2H), 2.19 (s, 3H), 2.12 (d, J = 9.4 Hz, 2H), 1.86-1.77 (m, 2H), 1.75-1.65 (m, 2H) ppm. |
| 718 | 478.26 | 0.62 | 1H NMR (400 MHz, CDCl3) δ 8.42 (s, 1H), 7.91-7.73 (m, 2H), 7.64 (t, J = 7.9 Hz, 1H), 7.57-7.48 (m, 2H), 7.39 (d, J = 14.7 Hz, 1H), 6.91-6.43 (m, 2H), 6.39 (s, 1H), 4.71 (dq, J = 12.4, 6.4 Hz, 4H), 3.70-3.61 (m, 4H), 3.59-3.48 (m, 1H), 2.51-2.37 (m, 4H) ppm. |
| 719 | 496.3 | 0.65 | 1H NMR (400 MHz, CDCl3) δ 8.42 (s, 1H), 7.96 (s, 1H), 7.91 (d, J = 7.7 Hz, 1H), 7.73-7.60 (m, 2H), 7.52 (s, 1H), 7.37 (s, 1H), 6.59 (t, J = 56.2 Hz, 1H), 6.06 (s, 1H), 4.12 (dd, J = 16.3, 8.5 Hz, 2H), 3.92 (dd, J = 8.3, 5.3 Hz, 2H), 3.83-3.72 (m, 4H), 3.35 (dt, J = 12.2, 6.1 Hz, 1H), 2.47 (s, 4H) ppm. |
| 720 | 427.34 | 0.65 | 1H NMR (300 MHz, DMSO-D6) δ 9.21 (s, 1H), 9.04 (s, 1H), 8.00-7.87 (m, 1H), 7.73-7.58 (m, 2H), 6.70 (s, 2H), 5.80 (s, 1H), 3.88 (t, J = 7.0 Hz, 2H), 3.64-3.52 (m, 6H), 3.28-3.20 (m, 1H), 2.35 (m, 4H), 2.19 (s, 3H) ppm. |
| 721 | 409 | 0.63 | 1H NMR (300 MHz, CDCl3) δ 8.31 (s, 1H), 7.45 (dt, J = 10.3, 2.6 Hz, 3H), 7.09-6.98 (m, 1H), 6.72 (s, 1H), 6.69-6.59 (m, 2H), 5.94 (s, 1H), 3.99 (t, J = 7.0 Hz, 2H), 3.75 (dd, J = 8.1, 4.3 Hz, 6H), 3.43-3.27 (m, 1H), 2.46 (d, J = 4.2 Hz, 4H), 2.30 (s, 3H) ppm. |
| 722 | 398.35 | 0.79 | 1H NMR (300 MHz, DMSO-D6) δ 9.24 (s, 1H), 9.14 (s, 1H), 7.63-7.51 (m, 2H), 7.22 (tt, J = 9.2, 2.3 Hz, 1H), 7.06 (s, 1H), 6.75 (s, 1H), 6.24 (s, 1H), 4.05 (m, 2H), 3.77 (d, J = 10.6 Hz, 2H), 3.45 (d, J = 10.5 Hz, 2H), 2.22 (s, 3H), 1.97-1.86 (m, 4H) ppm. |

TABLE 3A-continued

Analytical Data

| Cmpd No. in PRV2 | LCMS (M + H) | LC/MS Ret. Time (min) | ¹H-NMR |
|---|---|---|---|
| 723 | 447 | 0.68 | 1H NMR (400 MHz, CDCl3) δ 8.30 (s, 1H), 7.35-7.14 (m, 1H), 6.89 (t, J = 1.9 Hz, 1H), 6.79 (tt, J = 8.7, 2.3 Hz, 1H), 6.65 (s, 1H-NH), 6.58 (t, J = 2.0 Hz, 1H), 6.09 (t, J = 1.9 Hz, 1H), 3.99 (t, J = 7.1 Hz, 2H), 3.76 (dd, J = 7.6, 5.3 Hz, 6H), 3.35 (dd, J = 12.7, 6.1 Hz, 1H), 2.45 (m, 4H) ppm. |
| 724 | 414.29 | 0.88 | 1H NMR (300 MHz, DMSO-D6) δ 9.42 (s, 1H), 9.17 (s, 1H), 7.69-7.55 (m, 2H), 7.34-7.19 (m, 2H), 6.87 (s, 1H), 6.40 (s, 1H), 4.47 (dd, J = 21.6, 6.9 Hz, 4H), 3.78-3.68 (m, 2H), 3.08-2.99 (m, 2H), 2.25 (s, 3H) ppm. |
| 725 | 469.3 | 0.56 | 1H NMR (400 MHz, CDCl3) δ 8.39 (s, 1H), 7.92 (s, 1H), 7.79 (ddd, J = 8.1, 2.1, 1.0 Hz, 1H), 7.60 (t, J = 7.9 Hz, 1H), 7.48 (d, J = 7.7 Hz, 1H), 7.26 (t, J = 2.0 Hz, 1H), 6.92-6.56 (m, 3H), 6.43 (s, 1H), 3.84 (d, J = 12.6 Hz, 2H), 3.80-3.72 (m, 4H), 2.80 (td, J = 12.3, 2.2 Hz, 2H), 2.66-2.57 (m, 4H), 2.43-2.34 (m, 1H), 2.34 (d, J = 4.3 Hz, 3H), 1.97 (d, J = 12.5 Hz, 2H), 1.70 (qd, J = 12.2, 3.9 Hz, 2H) ppm. |
| 726 | 554.42 | 0.51 | 1H NMR (400 MHz, DMSO-D6) δ 9.19 (s, 1H), 9.16 (s, 1H), 7.59 (dd, J = 8.6, 2.2 Hz, 2H), 7.29-7.20 (m, 1H), 6.86 (d, J = 1.3 Hz, 1H), 5.78 (s, 1H), 4.57 (td, J = 6.5, 2.0 Hz, 4H), 4.48 (t, J = 6.0 Hz, 4H), 3.54-3.37 (m, 6H), 3.33-3.25 (m, 4H), 2.42-2.35 (m, 4H), 2.35-2.28 (m, 4H) ppm. |
| 727 | 384.21 | 0.87 | 1H NMR (300 MHz, DMSO-D6) δ 9.23 (s, 1H), 9.14 (s, 1H), 7.65-7.51 (m, 2H), 7.22 (tt, J = 9.3, 2.3 Hz, 1H), 6.87 (s, 1H), 6.69 (s, 1H), 6.02 (s, 1H), 4.61 (m, 1H), 4.43 (m, 1H), 3.80-3.69 (m, 2H), 3.55-3.45 (m, 1H), 2.99 (d, J = 9.2 Hz, 1H), 1.94 (dd, J = 9.5, 1.7 Hz, 1H), 1.84 (d, J = 9.4 Hz, 1H) ppm. |
| 728 | 464.16 | 0.68 | 1H NMR (300 MHz, CDCl3) δ 8.38 (s, 1H), 7.65 (s, 1H), 7.48 (dt, J = 4.2, 2.2 Hz, 2H), 7.44 (s, 1H), 7.39 (s, 1H), 7.15-7.02 (m, 1H), 6.44 (s, 1H), 4.71 (p, J = 6.4 Hz, 4H), 3.74-3.60 (m, 4H), 3.56 (dt, J = 12.8, 6.4 Hz, 2H), 2.57-2.38 (m, 4H) ppm. |
| 729 | 451.26 | 0.74 | 1H NMR (400 MHz, CDCl3) δ 8.36 (s, 1H), 7.41 (d, J = 7.7 Hz, 2H), 7.28-7.25 (m, 2H), 6.82 (tt, J = 8.7, 2.3 Hz, 1H), 6.59 (t, J = 56.2 Hz, 1H), 6.41 (s, 1H), 4.37 (d, J = 13.1 Hz, 2H), 3.38 (s, 3H), 3.28 (d, J = 6.2 Hz, 2H), 2.87 (td, J = 12.9, 2.4 Hz, 2H), 1.95-1.79 (m, 3H), 1.28 (qt, J = 14.7, 7.2 Hz, 2H) ppm. |
| 730 | 441.39 | 0.68 | 1H NMR (300 MHz, DMSO-D6) δ 9.35 (s, 1H), 9.16 (s, 1H), 7.66-7.55 (m, 2H), 7.31-7.17 (m, 1H), 6.82 (s, 1H), 6.66 (s, 1H), 5.84 (s, 1H), 4.00 (t, J = 5.8 Hz, 1H), 3.90 (t, J = 5.9 Hz, 1H), 3.66 (d, J = 10.9 Hz, 1H), 3.60-3.44 (m, 5H), 3.16 (dd, J = 10.8, 8.1 Hz, 1H), 2.63 (d, J = 11.5 Hz, 1H), 2.40 (m, 1H), 2.19 (s, 3H), 2.11 (t, J = 8.3 Hz, 1H), 0.91 (d, J = 6.4 Hz, 3H) ppm. |
| 731 | 386.24 | 0.58 | 1H NMR (400 MHz, DMSO-D6) δ 9.36 (s, 1H), 9.16 (s, 1H), 7.62 (dd, J = 8.6, 2.2 Hz, 2H), 7.24 (tt, J = 9.3, 2.3 Hz, 1H), 6.94 (s, 1H), 6.15 (s, 1H), 3.47 (s, 4H), 2.36 (dd, J = 13.0, 8.3 Hz, 4H), 2.21 (s, 3H), 2.20 (s, 3H) ppm. |
| 732 | 464.53 | 0.67 | 1H NMR (300 MHz, MeOD + CDCl3) δ 8.79 (s, 1H), 7.45 (dd, J = 7.0, 5.1 Hz, 3H), 6.87 (t, J = 8.7 Hz, 1H), 6.54 (d, J = 55.9 Hz, 1H), 6.08 (s, 1H), 4.14 (t, J = 7.6 Hz, 2H), 3.93 (dd, J = 8.3, 5.3 Hz, 2H), 3.87-3.65 (m, 4H), 3.38 (s, 1H), 2.51 (s, 4H) ppm. |
| 733 | 448.31 | 0.59 | 1H NMR (400 MHz, DMSO-D6) δ 10.05 (s, 1H), 9.22 (s, 1H), 7.61 (d, J = 6.3 Hz, 3H), 7.46 (d, J = 1.9 Hz, 1H), 7.29 (dd, J = 10.3, 8.1 Hz, 2H), 6.53 (d, J = 1.9 Hz, 1H), 4.57 (t, J = 6.5 Hz, 2H), 4.47 (t, J = 6.0 Hz, 2H), 3.47-3.42 (m, 1H), 3.40 (s, 4H), 2.38 (s, 4H) ppm. |

TABLE 3A-continued

Analytical Data

| Cmpd No. in PRV2 | LCMS (M + H) | LC/MS Ret. Time (min) | ¹H-NMR |
|---|---|---|---|
| 734 | 430.37 | 0.6 | 1H NMR (300 MHz, CDCl3) δ 8.37 (s, 1H), 8.03 (d, J = 1.1 Hz, 1H), 7.95-7.82 (m, 1H), 7.67-7.58 (m, 2H), 7.16 (t, J = 2.0 Hz, 1H), 6.83 (s, 1H), 6.72 (s, 1H), 6.47 (s, 1H), 4.77-4.61 (m, 4H), 3.59 (p, J = 6.4 Hz, 1H), 3.39-3.24 (m, 4H), 2.65 (q, J = 7.6 Hz, 2H), 2.59-2.50 (m, 4H), 1.37-1.20 (m, 3H) ppm. |
| 735 | 439.23 | 2.76 | 1H NMR (400 MHz, CDCl3) δ 8.22 (s, 1H), 7.47 (dd, J = 11.7, 2.6 Hz, 1H), 7.36 (ddd, J = 8.8, 2.6, 1.6 Hz, 1H), 7.06 (t, J = 8.8 Hz, 1H), 6.71-6.61 (m, 2H), 5.94 (s, 1H), 3.97 (d, J = 16.7 Hz, 5H), 3.78-3.70 (m, 6H), 3.47-3.29 (m, 2H), 2.46 (t, J = 4.7 Hz, 4H), 2.29 (s, 3H) ppm. |
| 736 | 455.31 | 0.61 | 1H NMR (400 MHz, CDCl3) δ 8.39 (s, 1H), 7.93 (s, 1H), 7.78 (ddd, J = 8.1, 2.1, 1.0 Hz, 1H), 7.67-7.54 (m, 1H), 7.47 (d, J = 7.7 Hz, 1H), 6.91-6.54 (m, 3H), 6.46 (s, 1H), 4.72 (dt, J = 13.0, 6.4 Hz, 4H), 3.59 (p, J = 6.4 Hz, 1H), 3.39-3.27 (m, 4H), 2.64 (q, J = 7.6 Hz, 2H), 2.61-2.49 (m, 4H), 1.28 (t, J = 7.6 Hz, 3H) ppm. |
| 737 | 365.22 | 0.86 | 1H NMR (300 MHz, MeOD) δ 8.62 (s, 1H), 7.59-7.53 (m, 2H), 7.51-7.44 (m, 3H), 7.17-7.03 (m, 1H), 6.83-6.74 (m, 1H), 3.97-3.84 (m, 4H), 3.31-3.20 (m, 4H) ppm. |
| 738 | 428.94 | 2.69 | |
| 739 | 441.34 | 0.64 | 1H NMR (400 MHz, DMSO-D6) δ 9.27 (s, 1H), 9.15 (s, 1H), 7.61 (dd, J = 8.7, 2.2 Hz, 2H), 7.27-7.18 (m, 1H), 7.09 (d, J = 1.9 Hz, 1H), 6.77 (d, J = 1.8 Hz, 1H), 3.97 (t, J = 6.9 Hz, 2H), 3.59 (t, J = 6.4 Hz, 6H), 3.21-3.12 (m, 1H), 2.33 (s, 4H), 2.16 (s, 3H), 1.97 (s, 3H) ppm. |
| 740 | 442.57 | 0.62 | 1H NMR (300 MHz, CDCl3) δ 8.34 (s, 1H), 7.29 (d, J = 2.2 Hz, 1H), 7.27 (d, J = 2.2 Hz, 1H), 7.21 (s, 2H), 6.81 (tt, J = 8.7, 2.2 Hz, 1H), 6.13 (s, 1H), 3.98 (ddd, J = 15.3, 8.7, 5.6 Hz, 2H), 3.83 (dd, J = 15.9, 8.1 Hz, 1H), 3.73 (d, J = 7.0 Hz, 1H), 3.56 (t, J = 5.1 Hz, 4H), 3.03 (p, J = 7.2 Hz, 1H), 2.75-2.60 (m, 2H), 2.60-2.47 (m, 2H), 2.36 (s, 3H), 2.17-2.04 (m, 1H), 1.93 (ddd, J = 15.9, 12.3, 8.2 Hz, 1H) ppm. |
| 741 | 352.2 | 0.65 | 1H NMR (400 MHz, DMSO-D6) δ 9.73 (s, 1H), 9.23 (s, 1H), 9.14 (s, 1H), 8.68 (s, 1H), 8.58 (s, 1H), 7.70 (s, 1H), 7.63 (s, 1H), 7.35 (s, 1H), 6.74 (s, 1H), 3.65 (d, J = 8.9 Hz, 1H), 3.51 (d, J = 8.8 Hz, 1H), 2.32 (s, 3H), 1.68 (s, 3H) ppm. |
| 742 | 439.46 | 0.67 | 1H NMR (300 MHz, DMSO-D6) δ 9.34 (s, 1H), 9.16 (s, 1H), 7.60 (dd, J = 8.7, 2.2 Hz, 2H), 7.30-7.18 (m, 1H), 6.76 (s, 1H), 6.70 (s, 1H), 5.84 (s, 1H), 4.47 (d, J = 6.1 Hz, 2H), 3.93 (m, 2H), 3.71 (m, 3H), 3.07 (d, J = 11.0 Hz, 2H), 2.86 (dd, J = 13.8, 6.4 Hz, 1H), 2.65 (d, J = 11.1 Hz, 2H), 2.20 (s, 3H), 2.17 (m, 1H) ppm. |
| 743 | 402.03 | 0.91 | 1H NMR (300 MHz, CDCl3) δ 8.42 (s, 1H), 7.54 (d, J = 7.3 Hz, 1H), 7.41 (s, 1H), 7.28-7.25 (m, 2H), 6.86 (tt, J = 8.6, 2.3 Hz, 1H), 6.11-5.90 (m, 1H), 4.89 (s, 4H), 4.21 (d, J = 2.1 Hz, 4H) ppm. |
| 744 | 371.24 | 0.61 | 1H NMR (400 MHz, DMSO-D6) δ 9.64 (s, 1H), 9.20 (s, 1H), 7.72-7.61 (m, 2H), 7.59 (s, 1H), 7.27 (tt, J = 9.3, 2.3 Hz, 1H), 6.61 (s, 1H), 3.01 (d, J = 12.0 Hz, 2H), 2.61-2.53 (m, 3H), 2.32 (s, 3H), 1.74 (d, J = 10.6 Hz, 2H), 1.58 (qd, J = 12.2, 3.9 Hz, 2H) ppm. |
| 745 | 460.87 | 2.54 | 1H NMR (300 MHz, DMSO-D6) δ 9.28 (s, 1H), 9.15 (s, 1H), 7.65-7.54 (m, 2H), 7.30-7.14 (m, 2H), 6.80 (s, 1H), 6.31 (s, 1H), 3.57 (t, J = 12.4 Hz, 5H), 2.80 (t, J = 11.3 Hz, 2H), 2.35 (s, 1H), 2.22 (s, 3H), 1.74 (d, J = 13.5 Hz, 2H), 1.34 (t, J = 10.2 Hz, 2H) ppm. |
| 746 | 453.46 | 0.68 | 1H NMR (300 MHz, DMSO-D6) δ 9.27 (s, 1H), 9.14 (s, 1H), 7.67-7.53 (m, 2H), 7.22 (tt, J = 9.3, 2.3 Hz, 1H), 6.76-6.65 (m, 2H), 5.80 (s, |

TABLE 3A-continued

Analytical Data

| Cmpd No. in PRV2 | LCMS (M + H) | LC/MS Ret. Time (min) | ¹H-NMR |
|---|---|---|---|
| | | | 1H), 3.91 (t, J = 6.7 Hz, 2H), 3.58-3.32 (m, 7H), 3.03 (m, 2H), 2.20 (s, 3H), 1.87-1.70 (m, 4H) ppm. |
| 747 | 455.94 | 2.38 | |
| 748 | 442.32 | 0.62 | 1H NMR (400 MHz, CDCl3) δ 8.26 (s, 1H), 7.23-7.17 (m, 3H), 7.02 (s, 1H), 6.78-6.61 (m, 2H), 6.32 (d, J = 1.7 Hz, 1H), 4.52 (q, J = 6.7 Hz, 4H), 4.36 (tt, J = 8.8, 4.0 Hz, 1H), 3.46 (p, J = 6.5 Hz, 1H), 3.00-2.91 (m, 1H), 2.62-2.53 (m, 1H), 2.24 (s, 3H), 2.12 (dt, J = 13.2, 4.4 Hz, 1H), 1.95-1.75 (m, 3H), 1.63 (ddt, J = 20.8, 10.9, 3.2 Hz, 1H), 1.50-1.38 (m, 1H) ppm. |
| 749 | 444.28 | 0.59 | 1H NMR (300 MHz, CDCl3) δ 8.33 (s, 1H), 7.62-7.50 (m, 2H), 7.43 (dd, J = 8.9, 2.2 Hz, 1H), 7.22 (s, 1H), 7.19 (s, 1H), 6.13 (s, 1H), 4.78-4.63 (m, 4H), 3.72-3.47 (m, 5H), 2.45 (t, J = 5.0 Hz, 4H), 2.35 (s, 3H) ppm. |
| 750 | 442.36 | 0.77 | 1H NMR (400 MHz, CDCl3) δ 8.38 (s, 1H), 7.62 (s, 1H), 7.56 (t, J = 1.9 Hz, 1H), 7.26 (dt, J = 6.1, 2.2 Hz, 3H), 6.88 (s, 1H), 6.78 (tt, J = 8.7, 2.3 Hz, 1H), 4.80-4.69 (m, 1H), 4.72-4.60 (m, 3H), 3.88-3.80 (m, 2H), 3.50 (dd, J = 13.5, 7.1 Hz, 1H), 2.91 (d, J = 11.5 Hz, 1H), 2.38 (d, J = 23.6 Hz, 6H), 1.52 (s, 3H) ppm. |
| 751 | 428.28 | 0.77 | 1H NMR (300 MHz, MeOD) δ 8.85 (s, 1H), 7.62-7.40 (m, 3H), 7.26 (s, 1H), 6.94 (ddd, J = 9.0, 5.6, 2.3 Hz, 1H), 6.76 (s, 1H), 4.67 (dt, J = 12.2, 6.7 Hz, 3H), 4.54 (dd, J = 10.3, 2.1 Hz, 1H), 4.04 (dd, J = 11.5, 2.0 Hz, 1H), 3.85 (td, J = 11.5, 2.4 Hz, 1H), 3.55 (dd, J = 12.7, 6.1 Hz, 1H), 2.86 (d, J = 11.5 Hz, 1H), 2.75 (d, J = 11.4 Hz, 1H), 2.33 (s, 3H), 2.24-1.96 (m, 2H), 1.29-1.11 (m, 1H) ppm. |
| 752 | 442.47 | 0.69 | 1H NMR (300 MHz, DMSO-D6) δ 9.43 (s, 1H), 9.14 (s, 1H), 7.65-7.52 (m, 2H), 7.31-7.18 (m, 1H), 7.06 (s, 1H), 6.90 (s, 1H), 6.17 (s, 1H), 3.58 (t, J = 4.6 Hz, 4H), 2.97-2.84 (m, 1H), 2.45-2.33 (m, 2H), 2.33-2.25 (m, 4H), 2.23 (s, 3H), 2.21-2.10 (m, 2H) ppm. |
| 753 | 413 | 0.61 | 1H NMR (400 MHz, DMSO-D6) δ 9.76 (s, 1H), 9.24 (s, 1H), 9.04 (d, J = 1.3 Hz, 1H), 8.68 (d, J = 2.5 Hz, 1H), 8.59 (dd, J = 2.5, 1.4 Hz, 1H), 6.99 (t, J = 1.8 Hz, 1H), 6.81 (t, J = 1.9 Hz, 1H), 6.00 (t, J = 1.9 Hz, 1H), 3.93 (t, J = 7.2 Hz, 2H), 3.74-3.50 (m, 6H), 3.31-3.19 (m, 1H partially obscured by water peak), 2.36 (s, 4H). |
| 754 | 493.18 | 0.64 | 1H NMR (400 MHz, CDCl3) δ 8.40 (s, 1H), 7.80 (d, J = 1.8 Hz, 1H), 7.62 (dt, J = 9.1, 2.2 Hz, 1H), 7.31 (dt, J = 8.0, 1.9 Hz, 1H), 6.89 (t, J = 2.0 Hz, 1H), 6.81 (s, 1H), 6.70 (t, J = 2.0 Hz, 1H), 6.18 (t, J = 2.2 Hz, 1H), 4.73 (q, J = 5.3, 4.4 Hz, 4H), 3.86 (s, 3H), 3.64 (d, J = 26.2 Hz, 1H), 3.33 (t, J = 4.9 Hz, 4H), 2.55 (s, 4H) ppm. |
| 755 | 387.26 | 0.58 | 1H NMR (400 MHz, CDCl3) δ 8.37 (s, 1H), 7.45-7.29 (m, 2H), 7.14 (s, 1H), 6.81 (tt, J = 8.7, 2.3 Hz, 1H), 6.19 (s, 1H), 3.99-3.87 (m, 1H), 3.77-3.67 (m, 1H), 3.63-3.37 (m, 3H), 2.34 (s, 3H), 1.97-1.80 (m, 2H), 1.79-1.64 (m, 2H) ppm. |
| 756 | 478.26 | 0.61 | 1H NMR (400 MHz, CDCl3) δ 8.38 (d, J = 29.4 Hz, 1H), 7.83 (d, J = 8.9 Hz, 2H), 7.64 (t, J = 8.1 Hz, 1H), 7.57-7.47 (m, 2H), 7.39 (s, 1H), 6.70 (ddd, J = 107.8, 61.5, 35.6 Hz, 2H), 6.07 (d, J = 9.6 Hz, 1H), 4.16-4.07 (m, 2H), 3.91 (dt, J = 16.6, 8.3 Hz, 2H), 3.83-3.71 (m, 4H), 3.35 (ddd, J = 12.1, 6.8, 5.2 Hz, 1H), 2.47 (s, 4H) ppm. |
| 757 | 477.25 | 0.65 | 1H NMR (400 MHz, CDCl3) δ 8.40 (s, 1H), 7.80 (d, J = 1.9 Hz, 1H), 7.62 (dt, J = 9.1, 2.2 Hz, 1H), 7.32 (dt, J = 8.2, 2.0 Hz, 1H), 7.26 (s, 1H), 6.79 (s, 1H), 6.73 (s, 1H), 6.44 (s, 1H), 4.75 (t, J = 6.4 Hz, 2H), 3.65 (d, J = 34.1 Hz, 1H), 3.35 (s, 4H), 2.56 (s, 4H), 2.36 (s, 3H) ppm. |

TABLE 3A-continued

Analytical Data

| Cmpd No. in PRV2 | LCMS (M + H) | LC/MS Ret. Time (min) | ¹H-NMR |
|---|---|---|---|
| 758 | 460.26 | 0.58 | 1H NMR (300 MHz, CDCl3) δ 8.33 (s, 1H), 7.62-7.47 (m, 2H), 7.42 (dd, J = 8.8, 2.4 Hz, 1H), 7.26 (s, 1H), 7.12 (s, 1H), 5.81 (s, 1H), 4.71 (dt, J = 11.6, 6.3 Hz, 4H), 3.91 (s, 3H), 3.62-3.48 (m, 5H), 2.45 (t, J = 5.1 Hz, 4H) ppm. |
| 759 | 416.42 | 0.58 | 1H NMR (300 MHz, CDCl3) δ 8.37 (s, 1H), 8.03 (d, J = 1.1 Hz, 1H), 7.96-7.83 (m, 1H), 7.64 (dd, J = 7.3, 5.9 Hz, 2H), 7.13 (s, 1H), 6.81 (s, 1H), 6.67 (s, 1H), 6.44 (s, 1H), 4.80-4.62 (m, 4H), 3.68-3.51 (m, 1H), 3.39-3.26 (m, 4H), 2.62-2.48 (m, 4H), 2.36 (s, 3H) ppm. |
| 760 | 482.45 | 0.66 | 1H NMR (300 MHz, CDCl3) δ 8.38 (s, 1H), 7.26 (d, J = 2.2 Hz, 1H), 7.23 (d, J = 2.2 Hz, 1H), 7.20 (s, 1H), 7.13 (s, 1H), 7.01 (d, J = 1.5 Hz, 1H), 6.86 (tt, J = 8.6, 2.2 Hz, 1H), 4.86-4.58 (m, 4H), 3.81-3.63 (m, 3H), 3.56 (dt, J = 12.8, 6.4 Hz, 1H), 2.61-2.36 (m, 4H) ppm. |
| 761 | 437.39 | 0.62 | 1H NMR (300 MHz, CDCl3) δ 8.29 (s, 1H), 7.44-7.25 (m, 3H), 7.17 (d, J = 2.2 Hz, 1H), 6.82 (d, J = 2.1 Hz, 2H), 6.44 (d, J = 1.9 Hz, 1H), 4.79-4.66 (m, 4H), 3.59 (p, J = 6.5 Hz, 1H), 3.36-3.26 (m, 4H), 2.64 (q, J = 7.6 Hz, 2H), 2.57-2.48 (m, 4H), 2.33 (d, J = 1.9 Hz, 3H), 1.27 (t, J = 7.6 Hz, 4H) ppm. |
| 762 | 430.33 | 0.59 | 1H NMR (300 MHz, DMSO-D6) δ 9.38 (s, 1H), 9.25 (s, 1H), 8.03 (q, J = 8.5 Hz, 4H), 7.17 (s, 1H), 6.94 (s, 1H), 6.36 (s, 1H), 4.54 (dt, J = 25.6, 6.3 Hz, 4H), 3.46 (q, J = 6.2 Hz, 1H), 3.16 (t, J = 4.7 Hz, 6H), 2.42 (t, J = 4.7 Hz, 6H), 1.18 (t, J = 7.5 Hz, 3H) ppm. |
| 763 | 347.62 | 0.65 | 1H NMR (300 MHz, DMSO-D6) δ 9.86 (s, 1H), 9.22 (s, 1H), 9.11 (d, J = 2.5 Hz, 1H), 8.58 (dd, J = 4.7, 1.3 Hz, 1H), 8.22 (ddd, J = 8.3, 2.6, 1.4 Hz, 1H), 7.63 (dd, J = 8.3, 4.7 Hz, 1H), 7.52 (s, 1H), 7.44 (s, 1H), 6.93 (s, 1H), 3.82-3.69 (m, 4H), 3.24-3.11 (m, 4H) ppm. |
| 764 | 401.21 | 0.63 | 1H NMR (400 MHz, CDCl3) δ 8.37 (s, 1H), 7.52 (d, J = 20.1 Hz, 1H), 7.33-7.26 (m, 2H), 7.16 (s, 1H), 6.86-6.71 (m, 1H), 6.15 (s, 1H), 4.26 (dd, J = 12.6, 3.9 Hz, 1H), 3.96-3.80 (m, 1H), 3.45 (s, 3H), 3.39-3.27 (m, 1H), 3.02 (ddd, J = 19.2, 11.3, 5.9 Hz, 2H), 2.34 (s, 3H), 2.20-1.97 (m, 1H), 1.91-1.77 (m, 1H), 1.64-1.43 (m, 2H) ppm. |
| 765 | 390.01 | 0.91 | 1H NMR (300 MHz, CDCl3) δ 8.44 (s, 1H), 7.41 (s, 2H), 7.30 (d, J = 2.2 Hz, 1H), 6.86 (s, 1H), 6.22 (d, J = 7.2 Hz, 1H), 4.14 (s, 1H), 4.01 (ddd, J = 9.0, 6.4, 3.3 Hz, 2H), 3.90 (td, J = 8.5, 5.4 Hz, 2H), 2.55-2.16 (m, 4H), 1.93 (dd, J = 8.7, 5.2 Hz, 1H) ppm. |
| 766 | 415.37 | 0.86 | 1H NMR (300 MHz, DMSO-D6) δ 9.19 (s, 1H), 8.98 (s, 1H), 6.81 (m, 4H), 6.44-6.26 (m, 2H), 5.84 (s, 1H), 5.58 (m, 0.5H), 5.38 (m, 0.5H), 4.13 (ddd, J = 20.0, 9.2, 5.8 Hz, 2H), 3.84 (ddd, J = 12.1, 9.1, 2.5 Hz, 2H), 3.51 (t, J = 5.5 Hz, 2H), 3.29 (s, 3H), 3.28-3.23 (m, 2H), 2.20 (s, 3H) ppm. |
| 767 | 439.33 | 0.62 | 1H NMR (300 MHz, CDCl3) δ 8.28 (s, 1H), 7.73 (d, J = 2.2 Hz, 1H), 7.46 (dd, J = 8.2, 2.2 Hz, 1H), 7.34 (d, J = 8.3 Hz, 1H), 7.20 (s, 1H), 6.75 (s, 1H), 6.66 (s, 1H), 6.41 (s, 1H), 4.79-4.58 (m, 4H), 3.59 (p, J = 6.4 Hz, 1H), 3.37-3.24 (m, 4H), 2.60-2.48 (m, 4H), 2.44 (s, 3H), 2.34 (s, 3H) ppm. |
| 768 | 442.3 | 0.53 | 1H NMR (400 MHz, CDCl3) δ 8.39 (s, 1H), 7.92-7.75 (m, 2H), 7.66-7.57 (m, 1H), 7.51 (d, J = 7.7 Hz, 1H), 7.25 (s, 2H), 6.92-6.59 (m, 1H), 5.80 (s, 1H), 4.08 (dd, J = 17.9, 10.3 Hz, 2H), 3.87 (dd, J = 8.1, 5.4 Hz, 2H), 3.76 (dd, J = 12.3, 7.7 Hz, 4H), 3.38-3.25 (m, 1H), 2.47 (s, 4H), 2.33 (s, 3H) ppm. |
| 769 | 333.58 | 1.02 | 1H NMR (300 MHz, DMSO-D6) δ 9.49 (s, 1H), 9.12 (s, 1H), 7.82-7.67 (m, 2H), 7.61 (dt, J = 14.8, |

TABLE 3A-continued

Analytical Data

| Cmpd No. in PRV2 | LCMS (M + H) | LC/MS Ret. Time (min) | ¹H-NMR |
|---|---|---|---|
| | | | 7.3 Hz, 1H), 7.41 (s, 2H), 7.28-7.08 (m, 1H), 6.69 (s, 1H), 2.25 (s, 3H), 1.53 (ddd, J = 13.2, 8.3, 5.0 Hz, 1H), 0.90-0.79 (m, 2H), 0.79-0.55 (m, 2H) ppm. |
| 770 | 427.59 | 0.98 | 1H NMR (300 MHz, CDCl3) δ 8.32 (s, 1H), 7.64 (s, 1H), 7.57 (ddd, J = 10.7, 6.8, 2.6 Hz, 1H), 7.48-7.40 (m, 1H), 7.38 (s, 1H), 7.36-7.29 (m, 1H), 6.43 (s, 1H), 3.90-3.78 (m, 4H), 3.63-3.51 (m, 4H) ppm. |
| 771 | 412.97 | 2.72 | 1H NMR (300 MHz, DMSO-D6) δ 10.45 (s, 1H), 9.46 (s, 1H), 9.19 (s, 1H), 7.70-7.57 (m, 2H), 7.37-7.31 (m, 1H), 7.26 (tt, J = 9.3, 2.3 Hz, 1H), 6.83 (s, 1H), 6.39 (s, 1H), 3.64 (dd, J = 20.3, 13.0 Hz, 2H), 3.35 (s, 2H), 3.17-3.01 (m, 1H), 2.97 (d, J = 13.1 Hz, 1H), 2.73 (d, J = 4.8 Hz, 3H), 2.24 (s, 3H), 1.43 (s, 3H), 1.39 (s, 3H) ppm. |
| 772 | 467.94 | 2.27 | |
| 773 | 439.41 | 0.77 | 1H NMR (300 MHz, DMSO-D6) δ 9.31 (s, 1H), 9.14 (s, 1H), 7.64-7.54 (m, 2H), 7.22 (tt, J = 9.3, 2.2 Hz, 1H), 6.79 (s, 1H), 6.69 (s, 1H), 5.83 (s, 1H), 4.06-3.96 (m, 2H), 3.85 (t, J = 6.5 Hz, 2H), 3.72 (m, 1H), 3.33 (m, 4H), 2.20 (s, 3H), 1.93-1.73 (m, 4H) ppm. |
| 774 | 370.21 | 0.84 | 1H NMR (400 MHz, DMSO-D6) δ 9.74 (s, 1H), 9.21 (s, 1H), 8.14 (s, 1H), 7.75-7.52 (m, 3H), 7.37-7.21 (m, 1H), 6.88 (s, 1H), 6.78 (s, 1H), 4.27 (d, J = 2.6 Hz, 2H), 3.82 (t, J = 5.4 Hz, 2H), 3.33 (s, 2H), 2.34 (s, 3H) ppm. |
| 775 | 363.19 | 0.76 | 1H NMR (300 MHz, DMSO-D6) δ 9.93 (s, 1H), 9.22 (s, 1H), 7.84 (s, 1H), 7.72-7.59 (m, 2H), 7.43 (dt, J = 11.6, 2.2 Hz, 1H), 7.27 (tt, J = 9.3, 2.2 Hz, 1H), 6.89 (dd, J = 10.1, 1.4 Hz, 1H), 6.48 (s, 1H), 4.79 (d, J = 6.6 Hz, 2H), 4.66 (d, J = 6.6 Hz, 2H) ppm. |
| 776 | 424 | 0.62 | 1H NMR (400 MHz, CDCl3) δ 8.45 (s, 1H), 8.29 (d, J = 5.6 Hz, 1H), 7.48-7.36 (m, 1H), 7.26 (d, J = 4.0 Hz, 1H), 7.00 (s, 1H), 6.68 (s, 1H), 6.50 (s, 1H), 6.19 (s, 1H), 4.65 (t, J = 6.5 Hz, 2H), 4.58 (t, J = 6.2 Hz, 2H), 3.74-3.55 (m, 5H), 2.68-2.57 (m, 2H), 2.47-2.38 (m, 2H), 2.32 (s, 3H), 2.11-1.98 (m, 2H) ppm. |
| 777 | 449.49 | 0.77 | 1H NMR (400 MHz, CD3CN) δ 8.60 (s, 1H), 7.41 (dt, J = 7.2, 3.6 Hz, 2H), 7.35 (s, 1H), 6.98-6.90 (m, 1H), 6.69 (t, J = 55.9 Hz, 1H), 6.49 (s, 1H), 4.31 (q, J = 5.9 Hz, 4H), 3.83 (s, 2H), 3.49-3.34 (m, 2H), 1.26-1.12 (m, 4H) ppm. |
| 778 | 373.23 | 0.84 | 1H NMR (300 MHz, CDCl3) δ 8.27 (s, 1H), 7.58 (ddd, J = 10.9, 6.8, 2.6 Hz, 1H), 7.45-7.38 (m, 1H), 7.36-7.28 (m, 1H), 7.13 (t, J = 2.3 Hz, 1H), 6.79 (d, J = 3.6 Hz, 2H), 6.34 (t, J = 1.6 Hz, 1H), 5.02-4.92 (m, 1H), 4.09-3.89 (m, 4H), 2.35 (s, 3H), 2.23 (tq, J = 8.4, 4.2, 3.8 Hz, 2H) ppm. |
| 779 | 427.31 | 0.62 | 1H NMR (300 MHz, CDCl3) δ 8.30 (s, 1H), 7.43-7.29 (m, 3H), 7.09 (s, 1H), 6.92 (dd, J = 10.7, 2.2 Hz, 1H), 6.85 (s, 1H), 6.26 (dt, J = 12.0, 2.2 Hz, 1H), 4.81-4.68 (m, 4H), 3.57 (p, J = 6.4 Hz, 1H), 3.35-3.23 (m, 4H), 2.58-2.42 (m, 4H), 2.34 (s, 3H) ppm. |
| 780 | 423.35 | 0.61 | 1H NMR (300 MHz, CDCl3) δ 8.24 (s, 1H), 7.51 (dd, J = 6.5, 2.7 Hz, 1H), 7.45 (dt, J = 7.2, 3.7 Hz, 1H), 7.18-7.07 (m, 2H), 6.81 (s, 1H), 6.72 (s, 1H), 6.41 (s, 1H), 4.71 (p, J = 6.3 Hz, 5H), 3.58 (p, J = 6.4 Hz, 1H), 3.37-3.23 (m, 4H), 2.59-2.45 (m, 4H), 2.37 (d, J = 2.0 Hz, 3H), 2.34 (s, 3H) ppm. |
| 781 | 443.3 | 0.61 | 1H NMR (400 MHz, CDCl3) δ 8.25 (s, 1H), 7.62-7.42 (m, 2H), 7.40-7.35 (m, 1H), 7.12-6.93 (m, 2H), 6.81 (s, 1H), 6.26 (d, J = 11.8 Hz, 1H), 4.72 (p, J = 6.4 Hz, 4H), 3.97 (s, 3H), 3.60 (p, J = 6.5 Hz, 1H), 3.30 (t, J = 4.9 Hz, 4H), 2.54 (t, J = 4.9 Hz, 4H) ppm. |

TABLE 3A-continued

Analytical Data

| Cmpd No. in PRV2 | LCMS (M + H) | LC/MS Ret. Time (min) | ¹H-NMR |
|---|---|---|---|
| 782 | 457.3 | 2.88 | 1H NMR (400 MHz, CDCl3) δ 8.13 (s, 1H), 7.18 (d, J = 8.9 Hz, 2H), 6.59-6.51 (m, 2H), 6.48 (s, 1H), 5.88 (m, 1H), 3.99-3.87 (m, 5H), 3.67 (dd, J = 5.7, 3.8 Hz, 6H), 3.27 (tt, J = 6.7, 5.4 Hz, 1H), 2.38 (t, J = 4.6 Hz, 4H), 2.23 (s, 3H), 1.19 (s, 1H) ppm. |
| 783 | 414 | 0.61 | 1H NMR (400 MHz, Acetone-D6) δ 9.13 (s, 1H), 8.78 (s, 1H), 8.35 (s, 1H), 7.83 (s, 1H), 7.54 (s, 1H), 7.11 (d, J = 12.2 Hz, 2H), 6.33 (d, J = 12.4 Hz, 1H), 4.61 (s, 4H), 4.55 (s, 4H), 3.50 (s, 1H), 3.29 (s, 4H), 2.82 (d, J = 12.9 Hz, 10H), 2.48 (s, 4H) ppm. |
| 784 | 447 | 0.69 | 1H NMR (400 MHz, CDCl3) δ 8.25 (s, 1H), 7.65-7.50 (m, 1H), 7.38 (d, J = 9.0 Hz, 1H), 7.34-7.22 (m, 1H), 6.93 (t, J = 1.8 Hz, 1H), 6.67 (s, 1H), 6.53 (t, J = 1.9 Hz, 1H), 6.08 (t, J = 1.8 Hz, 1H), 3.98 (t, J = 7.1 Hz, 2H), 3.75 (t, J = 4.7 Hz, 6H), 3.35 (dd, J = 11.6, 6.0 Hz, 1H), 2.45 (m, 4H) ppm. |
| 785 | 412 | 0.65 | 1H NMR (400 MHz, CDCl3) δ 8.95 (s, 1H), 8.42 (d, J = 4.0 Hz, 1H), 7.87 (dd, J = 12.2, 4.9 Hz, 1H), 7.81 (d, J = 8.1 Hz, 1H), 7.41-7.17 (m, 2H), 7.04 (s, 1H), 6.96 (s, 1H), 6.52 (s, 1H), 6.08 (s, 1H), 3.99 (t, J = 7.0 Hz, 2H), 3.87-3.67 (m, 6H), 3.48-3.23 (m, 1H) ppm. |
| 786 | 415.25 | 0.65 | 1H NMR (400 MHz, CDCl3) δ 8.36 (s, 1H), 7.40 (s, 1H), 7.32-7.28 (m, 2H), 7.15 (s, 1H), 6.80 (tt, J = 8.7, 2.3 Hz, 1H), 6.17 (s, 1H), 5.05 (d, J = 38.9 Hz, 1H), 4.31-4.05 (m, 2H), 3.38 (s, 3H), 3.34-3.25 (m, 1H), 2.99-2.83 (m, 1H), 2.68 (dd, J = 12.8, 10.1 Hz, 1H), 2.34 (s, 3H), 1.98-1.57 (m, 4H), 1.35-1.20 (m, 1H) ppm. |
| 787 | 496.58 | 0.69 | 1H NMR (300 MHz, CDCl3) δ 8.37 (s, 1H), 7.59 (s, 1H), 7.39 (s, 1H), 7.25 (dd, J = 7.6, 5.4 Hz, 2H), 6.83 (tt, J = 8.7, 2.2 Hz, 1H), 6.44 (s, 1H), 4.05-3.91 (m, 2H), 3.78 (ddd, J = 15.3, 12.2, 7.4 Hz, 2H), 3.62 (t, J = 5.1 Hz, 4H), 3.11-2.96 (m, 1H), 2.66 (dt, J = 10.5, 5.1 Hz, 2H), 2.60-2.46 (m, 2H), 2.18-2.06 (m, 1H), 1.93 (ddd, J = 15.6, 12.2, 8.1 Hz, 1H) ppm. |
| 788 | 439.41 | 0.66 | 1H NMR (300 MHz, DMSO-D6) δ 9.27 (s, 1H), 9.14 (s, 1H), 7.65-7.53 (m, 2H), 7.22 (tt, J = 9.3, 2.3 Hz, 1H), 6.72 (s, 1H), 6.69 (s, 1H), 5.80 (s, 1H), 4.37 (s, 1H), 3.91 (m, 2H), 3.79-3.67 (m, 2H), 3.53 (m, 4H), 2.80-2.68 (m, 1H), 2.58-2.52 (m, 1H), 1.73 (d, J = 8.3 Hz, 1H), 1.58 (d, J = 9.3 Hz, 1H) ppm. |
| 789 | 471.27 | 0.61 | 1H NMR (300 MHz, MeOD + CDCl3) δ 8.69 (s, 1H), 7.78 (ddd, J = 11.1, 6.9, 2.6 Hz, 1H), 7.63-7.59 (m, 1H), 7.50 (d, J = 0.9 Hz, 1H), 7.37 (dd, J = 18.3, 8.8 Hz, 1H), 6.65 (d, J = 0.9 Hz, 1H), 4.80-4.69 (m, 4H), 3.76-3.64 (m, 4H), 3.63-3.51 (m, 1H), 2.96 (s, 3H), 2.56-2.39 (m, 4H) ppm. |
| 790 | 445.04 | 0.68 | |
| 791 | 401.36 | 0.65 | 1H NMR (300 MHz, DMSO-D6) δ 9.32 (s, 1H), 9.16 (s, 1H), 7.66-7.55 (m, 2H), 7.24 (tt, J = 9.3, 2.3 Hz, 1H), 6.75 (s, 1H), 6.68 (s, 1H), 5.81 (s, 1H), 4.51 (s, 1H), 4.00 (t, J = 6.9 Hz, 2H), 3.74-3.62 (m, 1H), 3.48-3.39 (m, 4H), 2.59 (t, J = 5.9 Hz, 2H), 2.19 (s, 3H) ppm. |
| 792 | 441.39 | 0.65 | 1H NMR (300 MHz, DMSO-D6) δ 9.13 (s, 1H), 9.04 (s, 1H), 7.97 (ddd, J = 11.9, 7.1, 2.5 Hz, 1H), 7.77-7.58 (m, 2H), 6.82-6.77 (m, 1H), 6.52 (s, 1H), 5.84 (s, 1H), 5.79 (d, J = 5.2 Hz, 1H), 3.84-3.67 (m, 1H), 3.58 (t, J = 4.6 Hz, 4H), 2.90-2.79 (m, 1H), 2.32-2.16 (m, 6H), 2.14 (s, 3H), 2.02-1.89 (m, 2H) ppm. |

TABLE 3A-continued

Analytical Data

| Cmpd No. in PRV2 | LCMS (M + H) | LC/MS Ret. Time (min) | ¹H-NMR |
|---|---|---|---|
| 793 | 420.2 | 0.65 | 1H NMR (300 MHz, CDCl3) δ 8.36 (s, 1H), 7.56-7.41 (m, 3H), 7.35 (d, J = 1.6 Hz, 2H), 7.15-7.04 (m, 1H), 6.87 (s, 1H), 6.82-6.76 (m, 1H), 4.71 (dt, J = 12.4, 6.4 Hz, 4H), 3.65-3.53 (m, 1H), 3.40-3.24 (m, 4H), 2.63-2.41 (m, 4H) ppm. |
| 794 | 445.32 | 0.6 | 1H NMR (300 MHz, CDCl3) δ 8.40 (s, 1H), 7.90 (s, 1H), 7.80 (dd, J = 8.4, 2.1 Hz, 1H), 7.61 (t, J = 7.9 Hz, 1H), 7.49 (d, J = 7.7 Hz, 1H), 7.07-6.96 (m, 2H), 6.95-6.50 (m, 2H), 6.27 (dt, J = 12.0, 2.2 Hz, 1H), 4.82-4.57 (m, 4H), 3.58 (p, J = 6.4 Hz, 1H), 3.31 (dd, J = 6.3, 3.8 Hz, 4H), 2.52 (dd, J = 6.1, 3.9 Hz, 4H) ppm. |
| 795 | 483.25 | 0.75 | 1H NMR (400 MHz, CDCl3) δ 8.43 (d, J = 6.7 Hz, 1H), 7.96 (s, 1H), 7.91 (d, J = 7.7 Hz, 1H), 7.71-7.60 (m, 2H), 7.45 (s, 1H), 7.34 (s, 1H), 6.59 (t, J = 56.2 Hz, 1H), 6.40 (s, 1H), 4.38 (d, J = 13.1 Hz, 2H), 3.38 (s, 3H), 3.28 (d, J = 6.2 Hz, 2H), 2.88 (td, J = 12.9, 2.4 Hz, 2H), 1.96-1.77 (m, 3H), 1.38-1.18 (m, 2H) ppm. |
| 796 | | | 1H NMR (400 MHz, DMSO-D6) δ 9.61 (s, 1H), 9.19 (s, 1H), 7.71-7.60 (m, 3H), 7.32-7.18 (m, 2H), 6.73 (s, 1H), 3.69 (d, J = 8.8 Hz, 1H), 3.60 (d, J = 8.8 Hz, 1H), 2.77 (s, 3H), 2.31 (s, 3H), 1.68 (s, 3H) ppm. |
| 797 | 441.44 | 0.65 | 1H NMR (300 MHz, DMSO-D6) δ 9.26-9.18 (m, 1H), 9.17-9.10 (m, 1H), 7.73-7.56 (m, 2H), 7.25 (tt, J = 9.3, 2.3 Hz, 1H), 6.50-6.40 (m, 1H), 5.93-5.71 (m, 2H), 3.83-3.66 (m, 1H), 3.66-3.45 (m, 4H), 2.93-2.79 (m, 1H), 2.62-2.54 (m, 1H), 2.36-2.17 (m, 5H), 2.14 (s, 3H), 2.02-1.93 (m, 1H), 1.71-1.55 (m, 1H) ppm. |
| 798 | 351.58 | 1.05 | 1H NMR (300 MHz, DMSO-D6) δ 9.55 (s, 1H), 9.17 (s, 1H), 7.74-7.51 (m, 2H), 7.41 (s, 2H), 7.25 (td, J = 9.3, 2.2 Hz, 1H), 6.70 (s, 1H), 2.26 (s, 3H), 1.53 (tt, J = 8.2, 5.0 Hz, 1H), 1.00-0.80 (m, 2H), 0.80-0.56 (m, 2H) ppm. |
| 799 | 441.44 | 0.64 | 1H NMR (300 MHz, DMSO-D6) δ 9.17-9.09 (m, 1H), 9.09-9.00 (m, 1H), 8.03-7.90 (m, 1H), 7.77-7.58 (m, 2H), 6.80 (s, 1H), 6.56-6.45 (m, 1H), 5.91-5.67 (m, 2H), 3.89-3.67 (m, 1H), 3.64-3.48 (m, 4H), 2.91-2.79 (m, 1H), 2.31-2.18 (m, 5H), 2.14 (s, 3H), 2.00-1.91 (m, 1H), 1.70-1.57 (m, 1H) ppm. |
| 800 | 441.12 | 0.68 | 1H NMR (300 MHz, DMSO-D6) δ 9.29 (s, 1H), 9.14 (s, 1H), 7.59 (dd, J = 8.6, 2.1 Hz, 2H), 7.23 (tt, J = 9.2, 4.6 Hz, 1H), 6.81 (s, 1H), 6.67 (s, 1H), 5.84 (s, 1H), 3.95 (d, J = 30.9 Hz, 2H), 3.66 (m, 1H), 3.53 (m, 5H), 3.21-3.10 (m, 1H), 2.64 (d, J = 12.0 Hz, 1H), 2.41 (m, 1H), 2.23-2.08 (m, 4H), 0.91 (d, J = 6.4 Hz, 3H) ppm. |
| 801 | 427.29 | 0.74 | 1H NMR (400 MHz, DMSO-D6) δ 9.66 (s, 1H), 9.20 (s, 1H), 7.66 (dd, J = 8.5, 2.2 Hz, 2H), 7.58 (s, 1H), 7.27 (ddd, J = 9.3, 5.8, 2.3 Hz, 1H), 6.65 (s, 1H), 4.54 (t, J = 6.5 Hz, 2H), 4.45 (t, J = 6.2 Hz, 2H), 3.43-3.27 (m, 2H), 2.79 (app d, J = 10.9 Hz, 2H), 2.48-2.44 (m, 1H), 2.32 (s, 3H), 1.89-1.72 (m, 6H) ppm. |
| 802 | 437.21 | 0.67 | 1H NMR (300 MHz, CDCl3) δ 8.33 (s, 1H), 7.52-7.41 (m, 3H), 7.14 (t, J = 2.0 Hz, 1H), 7.10-7.00 (m, 1H), 6.85 (s, 1H), 6.66 (s, 1H), 6.46 (s, 1H), 4.67 (d, J = 5.5 Hz, 2H), 4.30 (d, J = 5.7 Hz, 2H), 3.39-3.19 (m, 4H), 2.70-2.52 (m, 6H), 1.44 (s, 3H), 1.28 (t, J = 7.6 Hz, 3H) ppm. |
| 803 | 431 | 0.67 | 1H NMR (400 MHz, Acetone-D6) δ 8.85 (s, 1H), 8.61 (s, 1H), 7.88 (s, 1H), 7.73 (s, 1H), 7.54 (q, J = 9.4 Hz, 1H), 7.11 (s, 2H), 6.29 (d, J = 12.4 Hz, 1H), 4.61 (s, 2H), 4.54 (s, 2H), 3.49 (s, 1H), 3.27 (s, 4H), 2.83 (d, J = 12.9 Hz, 3H), 2.47 (s, 4H) ppm. |

TABLE 3A-continued

Analytical Data

| Cmpd No. in PRV2 | LCMS (M + H) | LC/MS Ret. Time (min) | ¹H-NMR |
|---|---|---|---|
| 804 | 463.41 | 0.67 | 1H NMR (300 MHz, DMSO-D6) δ 9.63 (s, 1H), 9.18 (s, 1H), 7.69-7.54 (m, 2H), 7.24 (tt, J = 9.3, 2.2 Hz, 1H), 7.16-6.67 (m, 3H), 6.14 (s, 1H), 3.95 (t, J = 7.1 Hz, 2H), 3.69-3.54 (m, 6H), 2.36 (m, 4H) ppm. |
| 805 | 428.28 | 0.8 | 1H NMR (400 MHz, CDCl3) δ 8.34 (s, 1H), 7.28-7.25 (m, 2H), 7.23 (t, J = 2.3 Hz, 1H), 6.86-6.74 (m, 4H), 6.42 (t, J = 1.7 Hz, 1H), 4.60 (tt, J = 6.9, 3.5 Hz, 1H), 3.87 (ddd, J = 12.5, 8.1, 3.8 Hz, 1H), 3.76 (ddd, J = 13.6, 8.1, 3.6 Hz, 1H), 3.63 (ddd, J = 13.4, 7.3, 4.0 Hz, 1H), 3.43 (ddd, J = 13.6, 7.4, 3.8 Hz, 1H), 2.36 (s, 3H), 2.15 (s, 3H), 2.07-1.80 (m, 4H) ppm. |
| 806 | 446.21 | 0.66 | 1H NMR (300 MHz, CDCl3) δ 8.37 (s, 1H), 7.61-7.40 (m, 4H), 7.34 (s, 1H), 7.15-7.03 (m, 1H), 6.61 (t, J = 56.1 Hz, 1H), 6.39 (s, 1H), 4.82-4.62 (m, 4H), 3.72-3.61 (m, 4H), 3.56 (dt, J = 12.8, 6.5 Hz, 1H), 2.53-2.38 (m, 4H) ppm. |
| 807 | 483.25 | 0.89 | 1H NMR (400 MHz, CDCl3) δ 8.42 (s, 1H), 7.86-7.82 (m, 2H), 7.64 (t, J = 8.1 Hz, 1H), 7.58 (s, 1H), 7.52 (d, J = 7.7 Hz, 1H), 7.35 (d, J = 15.9 Hz, 1H), 6.75 (t, J = 56.2 Hz, 1H), 6.46 (s, 1H), 4.38 (d, J = 13.1 Hz, 2H), 3.38 (s, 3H), 3.26 (t, J = 18.4 Hz, 2H), 2.89 (td, J = 12.9, 2.4 Hz, 2H), 1.95-1.75 (m, 3H), 1.29 (tt, J = 12.9, 6.3 Hz, 2H) ppm. |
| 808 | 441 | 0.68 | 1H NMR (400 MHz, CDCl3) δ 8.29 (s, 1H), 7.34-7.14 (m, 3H), 6.77 (tt, J = 8.7, 2.3 Hz, 1H), 6.69-6.56 (m, 3H), 5.96 (s, 1H), 4.02 (t, J = 6.9 Hz, 2H), 3.82 (t, J = 6.2 Hz, 2H), 3.79-3.71 (m, 2H), 3.71-3.62 (m, 2H), 3.62-3.48 (m, 1H), 2.63 (dd, J = 7.9, 3.7 Hz, 3H), 2.30 (s, 3H), 1.98-1.82 (m, 2H) ppm. |
| 809 | 442.43 | 0.61 | |
| 810 | 404.01 | 0.84 | 1H NMR (300 MHz, CDCl3) δ 8.51 (s, 1H), 7.79 (d, J = 7.4 Hz, 1H), 7.26 (d, J = 2.2 Hz, 2H), 6.90-6.78 (m, 2H), 6.60-6.50 (m, 1H), 4.09 (d, J = 11.6 Hz, 2H), 3.68-3.22 (m, 3H), 2.39 (s, 3H), 1.77 (qd, J = 11.7, 4.2 Hz, 2H) ppm. |
| 811 | 450 | 0.66 | 1H NMR (400 MHz, CDCl3) δ 8.93 (s, 1H), 8.41 (ddd, J = 4.8, 1.7, 0.7 Hz, 1H), 7.91-7.79 (m, 1H), 7.76 (d, J = 8.2 Hz, 1H), 7.22 (ddd, J = 7.3, 4.9, 1.1 Hz, 1H), 7.16 (d, J = 2.1 Hz, 1H), 6.56 (s, 1H), 5.77 (d, J = 2.0 Hz, 1H), 4.46 (dt, J = 12.1, 6.1 Hz, 1H), 3.99 (t, J = 7.0 Hz, 2H), 3.85-3.69 (m, 6H), 3.38 (dt, J = 11.2, 5.6 Hz, 1H), 2.56-2.43 (m, 4H), 2.12 (s, 3H), 1.33 (d, J = 6.1 Hz, 6H) ppm. |
| 812 | 416.21 | 0.62 | 1H NMR (400 MHz, CDCl3) δ 8.32 (s, 1H), 7.27-7.20 (m, 1H), 7.15 (t, J = 2.2 Hz, 1H), 6.86-6.76 (m, 2H), 6.67 (s, 1H), 6.41 (t, J = 1.6 Hz, 1H), 4.21 (s, 2H), 3.78 (s, 4H), 2.88 (s, 2H), 2.65 (s, 4H), 2.36 (s, 3H). |
| 813 | 414.38 | 0.82 | 1H NMR (300 MHz, DMSO-D6) δ 9.44 (s, 1H), 9.15 (s, 1H), 8.23 (d, J = 7.0 Hz, 1H), 7.61 (dd, J = 8.4, 2.2 Hz, 2H), 7.30-7.19 (m, 1H), 7.02 (s, 1H), 6.95 (s, 1H), 6.17 (s, 1H), 4.85-4.74 (m, 1H), 4.32-4.21 (m, 1H), 2.37 (t, J = 6.3 Hz, 4H), 2.24 (s, 3H), 1.80 (s, 3H) ppm. |
| 814 | 425.9 | 2.63 | |
| 815 | 401.26 | 0.6 | 1H NMR (400 MHz, CDCl3) δ 8.35 (s, 1H), 7.31-7.29 (m, 2H), 7.25 (s, 1H), 7.02 (s, 1H), 6.81 (tt, J = 8.7, 2.3 Hz, 1H), 6.15 (s, 1H), 3.87 (dd, J = 13.2, 3.4 Hz, 1H), 3.79 (ddd, J = 13.0, 6.6, 3.8 Hz, 1H), 3.55 (t, J = 9.2 Hz, 2H), 3.46 (dd, J = 13.2, 7.2 Hz, 1H), 3.34-3.19 (m, 1H), 2.33 (s, 3H), 1.89 (dtd, J = 16.4, 7.5, 3.8 Hz, 2H), 1.73 (dtd, J = 10.6, 7.3, 3.8 Hz, 1H), 1.61-1.50 (m, 1H), 1.39 (ddd, J = 16.5, 8.2, 3.9 Hz, 1H) ppm. |
| 816 | 415.37 | 0.68 | 1H NMR (300 MHz, DMSO-D6) δ 9.33 (s, 1H), 9.16 (s, 1H), 7.66-7.54 (m, 2H), 7.22 (tt, J = 9.3, |

TABLE 3A-continued

Analytical Data

| Cmpd No. in PRV2 | LCMS (M + H) | LC/MS Ret. Time (min) | ¹H-NMR |
|---|---|---|---|
| | | | 2.3 Hz, 1H), 6.78 (s, 1H), 6.67 (s, 1H), 5.80 (s, 1H), 4.00 (t, J = 6.9 Hz, 2H), 3.73-3.61 (m, 1H), 3.47-3.39 (m, 2H), 3.36 (t, J = 5.7 Hz, 2H), 3.25 (s, 3H), 2.67 (t, J = 5.7 Hz, 2H), 2.20 (s, 3H) ppm. |
| 817 | 441.39 | 0.82 | 1H NMR (300 MHz, DMSO-D6) δ 9.31 (s, 1H), 9.15 (s, 1H), 7.58 (m, 2H), 7.22 (tt, J = 9.3, 2.2 Hz, 1H), 6.80 (s, 1H), 6.68 (s, 1H), 5.84 (s, 1H), 4.03 (m, 2H), 3.87-3.75 (m, 3H), 3.27 (m, 4H), 2.20 (s, 3H), 1.11 (t, J = 7.1 Hz, 3H), 1.02 (t, J = 7.1 Hz, 3H) ppm. |
| 818 | 407 | 0.58 | 1H NMR (400 MHz, CDCl3) δ 9.14 (d, J = 1.4 Hz, 1H), 8.90 (s, 1H), 8.54 (d, J = 2.5 Hz, 1H), 8.38 (dd, J = 2.5, 1.5 Hz, 1H), 7.05 (s, 1H), 6.79 (s, 1H), 6.52 (s, 1H), 6.18 (s, 1H), 4.66 (t, J = 6.5 Hz, 2H), 4.58 (t, J = 6.2 Hz, 2H), 3.75-3.55 (m, 5H), 2.68-2.53 (m, 2H), 2.47-2.36 (m, 2H), 2.32 (s, 3H), 2.11-2.00 (m, 2H) ppm. |
| 819 | 430 | 0.63 | 1H NMR (400 MHz, DMSO-D6) δ 9.70 (s, 1H), 9.35 (s, 1H), 8.35 (d, J = 5.6 Hz, 1H), 7.81 (d, J = 5.5 Hz, 1H), 7.57 (s, 1H), 7.01 (s, 1H), 6.82 (s, 1H), 6.00 (s, 1H), 3.97 (t, J = 7.0 Hz, 2H), 3.66 (dd, J = 15.0, 7.8 Hz, 6H), 3.30 (s, 4H), 2.39 (s, 4H) ppm. |
| 820 | 441.29 | 0.63 | 1H NMR (400 MHz, DMSO-D6) δ 9.10 (s, 1H), 8.30 (s, 1H), 7.58-7.48 (m, 2H), 7.22 (tt, J = 9.3, 2.3 Hz, 1H), 6.99 (s, 1H), 6.10 (s, 1H), 3.93 (t, J = 7.0 Hz, 2H), 3.64-3.51 (m, 6H), 3.14 (dd, J = 12.5, 6.2 Hz, 1H), 2.33 (s, 4H), 2.21 (s, 3H), 1.98 (s, 3H) ppm. |
| 821 | 368.18 | 0.61 | 1H NMR (400 MHz, CDCl3) δ 8.34 (s, 1H), 7.32-7.28 (m, 2H), 7.22 (s, 1H), 6.82 (tt, J = 8.7, 2.3 Hz, 1H), 5.81 (s, 1H), 4.25 (ddd, J = 14.2, 12.2, 7.3 Hz, 4H), 3.59 (tt, J = 8.6, 6.4 Hz, 1H), 2.34 (d, J = 14.8 Hz, 3H) ppm. |
| 822 | 384.25 | 0.87 | 1H NMR (300 MHz, DMSO-D6) δ 9.24 (s, 1H), 9.14 (s, 1H), 7.59 (dd, J = 8.6, 2.2 Hz, 2H), 7.23 (tt, J = 9.3, 2.3 Hz, 1H), 6.90-6.80 (m, 1H), 6.69 (s, 1H), 6.02 (s, 1H), 4.65-4.56 (m, 1H), 4.43 (s, 1H), 3.80-3.68 (m, 2H), 3.50 (dd, J = 9.1, 1.6 Hz, 1H), 2.98 (d, J = 9.2 Hz, 1H), 2.21 (s, 3H), 1.97-1.78 (m, 2H) ppm. |
| 823 | 460.25 | 0.66 | 1H NMR (300 MHz, CDCl3) δ 8.37 (s, 1H), 7.52-7.43 (m, 4H), 7.36 (s, 1H), 7.13-7.01 (m, 1H), 6.60 (t, J = 56.2 Hz, 1H), 6.38 (s, 1H), 4.67 (d, J = 5.5 Hz, 2H), 4.30 (d, J = 5.7 Hz, 2H), 3.75-3.50 (m, 4H), 2.57-2.37 (m, 4H), 1.40 (s, 3H) ppm. |
| 824 | 457.38 | 0.76 | 1H NMR (300 MHz, DMSO-D6) δ 9.32 (s, 1H), 9.14 (s, 1H), 7.64-7.53 (m, 2H), 7.23 (m, 1H), 6.79 (m, 1H), 6.70 (s, 1H), 5.84 (s, 1H), 4.01 (m, 2H), 3.84 (m, 3H), 3.45 (m, 4H), 3.28 (s, 1.5H), 3.23 (s, 1.5H), 2.93 (s, 1.5H), 2.86 (s, 1.5H), 2.21 (s, 3H) ppm. |
| 825 | 407 | 0.59 | 1H NMR (400 MHz, CDCl3) δ 9.17 (d, J = 1.4 Hz, 1H), 8.90 (s, 1H), 8.54 (d, J = 2.5 Hz, 1H), 8.38 (dd, J = 2.5, 1.5 Hz, 1H), 6.75 (s, 1H), 6.70 (s, 1H), 6.64 (s, 1H), 5.96 (s, 1H), 4.03 (t, J = 6.9 Hz, 2H), 3.82 (t, J = 6.1 Hz, 2H), 3.79-3.73 (m, 2H), 3.73-3.65 (m, 2H), 3.62-3.53 (m, 1H), 2.64 (t, J = 5.7 Hz, 3H), 2.31 (s, 3H), 2.01-1.86 (m, 2H) ppm. |
| 826 | 441.35 | 0.65 | 1H NMR (300 MHz, DMSO-D6) δ 9.14 (s, 1H), 9.06 (s, 1H), 7.98 (ddd, J = 12.0, 7.0, 2.5 Hz, 1H), 7.79-7.57 (m, 2H), 6.98-6.88 (m, 1H), 6.51-6.43 (m, 1H), 5.89 (s, 1H), 5.71 (d, J = 6.9 Hz, 1H), 3.65-3.45 (m, 5H), 2.65-2.54 (m, 2H), 2.47-2.41 (m, 1H), 2.31-2.17 (m, 4H), 2.13 (s, 3H), 1.71-1.55 (m, 2H) ppm. |
| 827 | 429 | 0.68 | 1H NMR (400 MHz, CDCl3) δ 8.32 (s, 1H), 7.52-7.37 (m, 3H), 7.12-6.96 (m, 1H), 6.92 (t, J = 1.9 Hz, 1H), 6.68 (s, 1H), 6.59 (t, J = 2.0 Hz, 1H), 6.08 (t, J = 1.9 Hz, 1H), 3.99 (t, J = 7.1 Hz, |

TABLE 3A-continued

Analytical Data

| Cmpd No. in PRV2 | LCMS (M + H) | LC/MS Ret. Time (min) | ¹H-NMR |
|---|---|---|---|
| | | | 2H), 3.76 (dd, J = 7.7, 5.2 Hz, 6H), 3.41-3.27 (m, 1H), 2.45 (m, 4H) ppm. |
| 828 | 346.09 | 0.76 | 1H NMR (300 MHz, MeOD + CDCl3) δ 8.37 (s, 1H), 7.58-7.43 (m, 4H), 7.40 (s, 1H), 7.14-7.00 (m, 1H), 6.37 (s, 1H), 4.85-4.56 (m, 4H), 3.63 (dd, J = 11.2, 6.2 Hz, 4H), 3.54 (dd, J = 12.8, 6.4 Hz, 1H), 2.58-2.31 (m, 4H), 1.96 (t, J = 18.3 Hz, 3H) ppm. |
| 829 | 437.39 | 0.63 | 1H NMR (300 MHz, CDCl3) δ 8.24 (s, 1H), 7.56-7.49 (m, 1H), 7.45 (dt, J = 7.4, 3.6 Hz, 1H), 7.18-7.07 (m, 2H), 6.84 (s, 1H), 6.81 (s, 1H), 6.44 (s, 1H), 4.71 (p, J = 6.3 Hz, 4H), 3.58 (p, J = 6.4 Hz, 1H), 3.30 (t, J = 5.0 Hz, 4H), 2.63 (q, J = 7.6 Hz, 2H), 2.53 (t, J = 5.0 Hz, 4H), 2.37 (s, 3H), 1.27 (t, J = 7.6 Hz, 3H) ppm. |
| 830 | 471 | 0.7 | 1H NMR (400 MHz, CDCl3) δ 8.29 (s, 1H), 7.30-7.18 (m, 3H), 6.77 (tt, J = 8.7, 2.2 Hz, 1H), 6.67 (s, 1H), 6.62 (t, J = 1.9 Hz, 1H), 6.25 (t, J = 1.9 Hz, 1H), 5.69 (t, J = 2.0 Hz, 1H), 4.56 (dt, J = 12.1, 6.1 Hz, 1H), 3.97 (t, J = 7.0 Hz, 2H), 3.84-3.67 (m, 6H), 3.40-3.24 (m, 1H), 2.45 (s, 4H), 1.37 (d, J = 6.1 Hz, 6H) ppm. |
| 831 | 447.43 | 0.72 | 1H NMR (300 MHz, DMSO-D6) δ 9.38 (s, 1H), 9.17 (s, 1H), 7.61 (m, 2H), 7.33-7.18 (m, 2H), 6.79 (s, 1H), 6.34 (s, 1H), 3.77 (m, 1H), 3.64 (d, J = 12.0 Hz, 1H), 3.44 (m, 1H), 3.03 (d, J = 10.7 Hz, 1H), 2.79 (td, J = 11.9, 6.0 Hz, 1H), 2.67-2.52 (m, 3H), 2.38 (m, 2H), 2.23 (s, 3H), 2.11-1.89 (m, 1H) ppm. |
| 832 | 397.22 | 0.82 | 1H NMR (400 MHz, CDCl3) δ 8.33 (s, 1H), 7.59 (d, J = 2.2 Hz, 1H), 7.56 (d, J = 1.8 Hz, 1H), 7.29-7.25 (m, 2H), 7.10 (t, J = 2.2 Hz, 1H), 6.85-6.78 (m, 2H), 6.73 (s, 1H), 6.35 (t, J = 1.6 Hz, 1H), 6.29 (t, J = 2.1 Hz, 1H), 4.57 (t, J = 5.3 Hz, 2H), 4.39 (t, J = 5.3 Hz, 2H), 2.34 (s, 3H) ppm. |
| 833 | 441.26 | 0.6 | 1H NMR (400 MHz, CDCl3) δ 8.39 (s, 1H), 7.92 (s, 1H), 7.82-7.70 (m, 1H), 7.61 (t, J = 7.9 Hz, 1H), 7.48 (d, J = 7.7 Hz, 1H), 6.73 (dd, J = 62.6, 49.9 Hz, 3H), 6.42 (s, 1H), 4.79-4.65 (m, 4H), 3.69-3.51 (m, 1H), 3.46-3.23 (m, 4H), 2.53 (dd, J = 11.9, 7.0 Hz, 4H), 2.35 (s, 3H) ppm. |
| 834 | 459.21 | 0.64 | 1H NMR (300 MHz, CDCl3) δ 8.29 (s, 1H), 8.00 (dd, J = 7.8, 1.7 Hz, 1H), 7.60 (ddd, J = 10.7, 6.8, 2.6 Hz, 1H), 7.48-7.39 (m, 1H), 7.34 (dd, J = 9.3, 8.1 Hz, 1H), 6.95 (d, J = 3.9 Hz, 1H), 6.74 (d, J = 4.5 Hz, 1H), 4.75-4.55 (m, 4H), 3.62 (d, J = 1.4 Hz, 2H), 3.58-3.45 (m, 1H), 2.60 (s, 4H), 2.39 (s, 7H) ppm. |
| 835 | 383.58 | 0.88 | 1H NMR (300 MHz, DMSO-D6) δ 9.82 (s, 1H), 9.20 (s, 1H), 7.74-7.57 (m, 2H), 7.52 (d, J = 2.0 Hz, 1H), 7.42 (s, 1H), 7.27 (tt, J = 9.3, 2.3 Hz, 1H), 6.92 (s, 1H), 3.83-3.68 (m, 4H), 3.23-3.11 (m, 4H) ppm. |
| 836 | 423.4 | 0.61 | 1H NMR (300 MHz, CDCl3) δ 8.28 (s, 1H), 7.40 (dd, J = 10.3, 1.7 Hz, 1H), 7.36-7.29 (m, 2H), 7.15 (s, 1H), 6.78 (s, 1H), 6.71 (s, 1H), 6.41 (s, 1H), 4.77-4.63 (m, 4H), 3.59 (p, J = 6.4 Hz, 1H), 3.36-3.24 (m, 4H), 2.61-2.47 (m, 4H), 2.34 (s, 6H) ppm. |
| 837 | 405.22 | 0.63 | 1H NMR (400 MHz, CDCl3) δ 8.42 (d, J = 6.7 Hz, 1H), 7.98 (s, 1H), 7.93-7.83 (m, 1H), 7.76-7.55 (m, 2H), 7.27 (d, J = 3.1 Hz, 2H), 6.12 (s, 1H), 3.89-3.77 (m, 4H), 3.58-3.43 (m, 4H), 2.36 (s, 3H) ppm. |
| 838 | 333 | 0.69 | 1H NMR (300 MHz, MeOD + CDCl3) δ 8.48 (s, 1H), 7.97-7.68 (m, 3H), 7.59-7.30 (m, 5H), 7.08-6.78 (m, 3H), 2.36 (s, 3H) ppm. |
| 839 | 469.21 | 0.94 | 1H NMR (400 MHz, CDCl3) δ 8.22 (s, 1H), 7.38 (d, J = 7.7 Hz, 1H), 7.23 (s, 1H), 7.13-7.10 (m, 2H), 6.68 (ddd, J = 8.7, 5.5, 2.2 Hz, 1H), 6.32 (s, 1H), 4.22 (d, J = 13.0 Hz, 2H), 3.23 (s, |

TABLE 3A-continued

Analytical Data

| Cmpd No. in PRV2 | LCMS (M + H) | LC/MS Ret. Time (min) | ¹H-NMR |
|---|---|---|---|
| | | | 3H), 3.13 (d, J = 6.2 Hz, 2H), 2.74 (td, J = 13.0, 2.4 Hz, 2H), 1.73 (dd, J = 17.9, 7.9 Hz, 3H), 1.19-1.10 (m, 2H) ppm. |
| 840 | 441.63 | 0.65 | 1H NMR (300 MHz, CDCl3) δ 8.28 (s, 1H), 7.62 (ddd, J = 10.8, 6.8, 2.5 Hz, 1H), 7.47-7.37 (m, 1H), 7.33 (t, J = 8.7 Hz, 2H), 7.27 (s, 1H), 6.78 (s, 1H), 6.67 (s, 1H), 4.66 (p, J = 6.4 Hz, 4H), 3.61-3.43 (m, 3H), 2.49 (d, J = 62.8 Hz, 11H) ppm. |
| 841 | 421.26 | 2.73 | 1H NMR (400 MHz, CDCl3) δ 8.10 (s, 1H), 7.53-7.46 (m, 2H), 6.96-6.89 (m, 2H), 6.61-6.52 (m, 2H), 6.42 (s, 1H), 5.85 (s, 1H), 3.90 (t, J = 7.0 Hz, 2H), 3.79 (s, 3H), 3.67 (dd, J = 5.8, 3.6 Hz, 6H), 3.32-3.21 (m, 1H), 2.38 (t, J = 4.5 Hz, 4H), 2.24-2.19 (m, 3H) ppm. |
| 842 | 403.24 | 0.55 | 1H NMR (300 MHz, DMSO-D6) δ 9.78 (s, 1H), 9.20 (s, 1H), 9.10 (d, J = 2.4 Hz, 1H), 8.58 (dd, J = 4.7, 1.4 Hz, 1H), 8.21 (ddd, J = 8.3, 2.6, 1.4 Hz, 1H), 7.62 (dd, J = 8.3, 4.7 Hz, 1H), 7.53 (d, J = 2.0 Hz, 1H), 7.40 (s, 1H), 6.91 (s, 1H), 4.53 (dt, J = 12.1, 6.3 Hz, 4H), 3.45 (dd, J = 12.6, 6.2 Hz, 1H), 3.28-3.14 (m, 4H), 2.46-2.30 (m, 4H) ppm. |
| 843 | 399.28 | 0.6 | 1H NMR (400 MHz, CDCl3) δ 8.33 (s, 1H), 7.31-7.25 (m, 4H), 7.23-7.09 (m, 2H), 6.88-6.73 (m, 1H), 5.87 (d, J = 22.2 Hz, 1H), 4.67 (t, J = 5.2 Hz, 1H), 4.00 (dd, J = 15.1, 7.8 Hz, 1H), 3.88 (td, J = 8.1, 4.9 Hz, 1H), 3.72 (d, J = 11.6 Hz, 1H), 3.66 (dd, J = 10.6, 8.7 Hz, 1H), 3.51 (dd, J = 11.8, 5.2 Hz, 1H), 3.37 (dd, J = 10.7, 5.4 Hz, 1H), 3.07-2.95 (m, 1H), 2.34 (s, 3H), 2.20 (tt, J = 15.5, 7.8 Hz, 1H), 1.91 (dt, J = 12.0, 7.9 Hz, 1H) ppm. |
| 845 | 416.21 | 0.61 | 1H NMR (400 MHz, CDCl3) δ 8.27 (s, 1H), 7.65-7.55 (m, 1H), 7.46-7.38 (m, 1H), 7.37-7.26 (m, 1H), 7.16-7.09 (m, 1H), 6.84 (d, J = 3.1 Hz, 2H), 6.40 (d, J = 2.3 Hz, 1H), 4.18 (t, J = 5.8 Hz, 2H), 3.82-3.71 (m, 4H), 2.85 (t, J = 5.8 Hz, 2H), 2.62 (t, J = 4.7 Hz, 4H), 2.35 (s, 3H) ppm. |
| 846 | 366.16 | 0.69 | 1H NMR (300 MHz, DMSO-D6) δ 9.74 (s, 1H), 9.23 (s, 1H), 9.14 (d, J = 1.3 Hz, 1H), 8.68 (d, J = 2.5 Hz, 1H), 8.58 (dd, J = 2.5, 1.4 Hz, 1H), 7.72 (s, 1H), 7.34 (s, 1H), 6.76 (s, 1H), 3.72 (d, J = 8.8 Hz, 1H), 3.61 (d, J = 8.8 Hz, 1H), 2.78 (s, 3H), 2.32 (s, 3H), 1.69 (s, 3H) ppm. |
| 847 | 432.29 | 0.57 | 1H NMR (400 MHz, DMSO-D6) δ 9.95 (s, 1H), 9.22 (s, 1H), 7.62 (d, J = 7.9 Hz, 2H), 7.39 (s, 1H), 7.29 (t, J = 9.1 Hz, 1H), 6.14 (s, 1H), 4.57 (t, J = 6.3 Hz, 2H), 4.48 (t, J = 5.9 Hz, 2H), 3.50-3.37 (m, 5H), 2.39 (s, 4H) ppm. |
| 848 | 442.3 | 0.55 | 1H NMR (400 MHz, CDCl3) δ 8.40 (s, 1H), 7.87 (s, 1H), 7.82 (ddd, J = 8.1, 2.1, 1.0 Hz, 1H), 7.62 (t, J = 7.9 Hz, 1H), 7.50 (d, J = 7.7 Hz, 1H), 7.27 (s, 1H), 7.25 (s, 1H), 6.91-6.59 (m, 1H), 6.13 (s, 1H), 4.76-4.67 (m, 4H), 3.64-3.50 (m, 5H), 2.47 (dd, J = 15.6, 10.6 Hz, 4H), 2.34 (d, J = 8.6 Hz, 3H) ppm. |
| 849 | 478.66 | 0.68 | 1H NMR (300 MHz, CDCl3) δ 8.30 (s, 1H), 7.58 (ddd, J = 10.7, 6.8, 2.6 Hz, 1H), 7.47 (s, 1H), 7.46-7.38 (m, 1H), 7.38-7.29 (m, 2H), 6.59 (t, J = 56.2 Hz, 1H), 6.38 (s, 1H), 4.67 (d, J = 5.5 Hz, 2H), 4.30 (d, J = 5.7 Hz, 2H), 3.71-3.56 (m, 4H), 2.55-2.40 (m, 4H), 1.40 (s, 3H) ppm. |
| 850 | 442.94 | 2.72 | 1H NMR (300 MHz, DMSO-D6) δ 10.36 (s, 1H), 9.44 (s, 1H), 9.18 (s, 1H), 7.69-7.57 (m, 2H), 7.27 (tt, J = 9.2, 2.3 Hz, 1H), 7.13 (s, 1H), 6.97 (s, 1H), 6.39 (s, 1H), 3.75 (d, J = 10.9 Hz, 2H), 3.59 (d, J = 10.1 Hz, 2H), 3.41 (t, J = 5.9 Hz, 2H), 3.26 (s, 3H), 3.23-2.99 (m, 6H), 2.25 (s, 3H), 2.06-1.90 (m, 2H) ppm. |

TABLE 3A-continued

Analytical Data

| Cmpd No. in PRV2 | LCMS (M + H) | LC/MS Ret. Time (min) | ¹H-NMR |
|---|---|---|---|
| 851 | 426.1 | 0.69 | |
| 852 | 401.41 | 0.79 | 1H NMR (300 MHz, DMSO-D6) δ 9.19 (s, 1H), 8.97 (s, 1H), 6.94-6.61 (m, 4H), 6.45-6.21 (m, 2H), 5.83 (s, 1H), 5.58 (m, 0.5H), 5.39 (m, 0.5H), 4.73 (t, J = 5.4 Hz, 1H), 4.22-4.01 (m, 2H), 3.91-3.74 (m, 2H), 3.58 (q, J = 5.8 Hz, 2H), 3.21-3.11 (m, 2H), 2.20 (s, 3H) ppm. |
| 853 | 439.37 | 0.66 | 1H NMR (300 MHz, CDCl3) δ 8.68 (s, 1H), 7.53 (s, 1H), 7.47-7.31 (m, 2H), 6.86 (s, 1H), 6.50 (s, 1H), 4.72 (dt, J = 18.6, 6.3 Hz, 4H), 3.64 (t, J = 16.6 Hz, 5H), 2.48 (d, J = 4.8 Hz, 4H) ppm. |
| 854 | 487.3 | 0.61 | 1H NMR (400 MHz, CDCl3) δ 8.40 (s, 1H), 8.05 (s, 1H), 7.92-7.75 (m, 1H), 7.75-7.52 (m, 2H), 7.30 (t, J = 1.9 Hz, 1H), 6.72 (s, 1H), 6.68 (s, 1H), 6.44 (s, 1H), 3.84 (d, J = 12.6 Hz, 2H), 3.80-3.72 (m, 4H), 2.80 (td, J = 12.3, 2.2 Hz, 2H), 2.66-2.59 (m, 4H), 2.38 (ddd, J = 14.0, 7.0, 3.2 Hz, 1H), 2.34 (s, 3H), 1.98 (s, 1H), 1.69 (dq, J = 12.2, 8.2 Hz, 2H) ppm. |
| 855 | 429 | 0.7 | 1H NMR (400 MHz, CDCl3) δ 8.32 (s, 1H), 7.43-7.18 (m, 4H), 7.12 (s, 1H), 6.78 (tt, J = 8.7, 2.2 Hz, 1H), 6.13 (s, 1H), 4.28 (d, J = 12.9 Hz, 2H), 3.45 (t, J = 6.5 Hz, 2H), 3.35 (s, 3H), 2.77 (td, J = 12.7, 2.2 Hz, 2H), 2.32 (s, 3H), 1.77 (d, J = 12.4 Hz, 2H), 1.63 (dd, J = 10.2, 7.3 Hz, 2H), 1.55 (dd, J = 13.1, 6.5 Hz, 2H), 1.34-1.19 (m, 3H) ppm. |
| 856 | 390.96 | 0.92 | |
| 857 | 455.4 | 0.7 | 1H NMR (300 MHz, DMSO-D6) δ 9.29 (s, 1H), 9.14 (s, 1H), 7.66-7.51 (m, 2H), 7.23 (tt, J = 9.3, 2.3 Hz, 1H), 6.75 (s, 1H), 6.68 (s, 1H), 5.81 (s, 1H), 3.89 (t, J = 7.0 Hz, 2H), 3.56 (m, 4H), 3.28-3.18 (m, 1H), 2.71 (d, J = 10.3 Hz, 2H), 2.19 (s, 3H), 1.58 (t, J = 10.6 Hz, 2H), 1.06 (d, J = 6.2 Hz, 5H) ppm. |
| 858 | 415.37 | 0.67 | 1H NMR (300 MHz, DMSO-D6) δ 9.35 (s, 1H), 9.17 (s, 1H), 7.76-7.63 (m, 2H), 7.24 (tt, J = 9.3, 2.3 Hz, 1H), 7.08 (s, 1H), 6.67 (s, 2H), 6.14 (s, 1H), 3.90 (s, 4H), 3.51 (t, J = 6.4 Hz, 2H), 3.45-3.19 (m, 6H), 2.20 (s, 3H). |
| 859 | 480.24 | 0.64 | 1H NMR (300 MHz, CDCl3) δ 8.30 (s, 1H), 7.77 (dd, J = 6.2, 2.6 Hz, 1H), 7.64-7.51 (m, 1H), 7.48 (s, 1H), 7.37 (s, 1H), 7.31 (t, J = 7.5 Hz, 1H), 6.60 (t, J = 56.1 Hz, 1H), 6.38 (s, 1H), 4.71 (p, J = 6.3 Hz, 4H), 3.64 (t, J = 5.1 Hz, 4H), 3.55 (p, J = 6.4 Hz, 1H), 2.45 (t, J = 5.1 Hz, 4H) ppm. |
| 860 | 460.07 | 0.67 | 1H NMR (300 MHz, MeOD + CDCl3) δ 8.37 (s, 1H), 7.58-7.43 (m, 4H), 7.40 (s, 1H), 7.14-7.00 (m, 1H), 6.37 (s, 1H), 4.85-4.56 (m, 4H), 3.63 (dd, J = 11.2, 6.2 Hz, 4H), 3.54 (dd, J = 12.8, 6.4 Hz, 1H), 2.58-2.31 (m, 4H), 1.96 (t, J = 18.3 Hz, 3H) ppm. |
| 861 | 441.39 | 0.65 | 1H NMR (300 MHz, DMSO-D6) δ 9.22 (s, 1H), 9.15 (s, 1H), 7.69-7.61 (m, 2H), 7.24 (tt, J = 9.3, 2.4 Hz, 1H), 7.01 (s, 1H), 6.42 (s, 1H), 5.90 (s, 1H), 5.75 (d, J = 6.8 Hz, 1H), 3.65-3.45 (m, 5H), 2.63-2.54 (m, 2H), 2.48-2.41 (m, 1H), 2.31-2.18 (m, 4H), 2.13 (s, 3H), 1.65 (t, J = 9.4 Hz, 2H) ppm. |
| 862 | 450 | 0.66 | 1H NMR (400 MHz, CDCl3) δ 8.94 (s, 1H), 8.42 (ddd, J = 4.8, 1.8, 0.8 Hz, 1H), 7.85 (ddd, J = 8.2, 7.4, 1.8 Hz, 1H), 7.80-7.68 (m, 1H), 7.61 (d, J = 2.2 Hz, 1H), 7.31-7.16 (m, 2H), 6.58 (s, 1H), 6.24 (d, J = 2.2 Hz, 1H), 4.79-4.64 (m, 4H), 4.47 (dt, J = 12.1, 6.1 Hz, 1H), 3.67-3.51 (m, 1H), 3.39-3.19 (m, 4H), 2.61-2.45 (m, 4H), 2.14 (s, 3H), 1.34 (d, J = 6.1 Hz, 6H) ppm. |
| 863 | 413 | 0.59 | |
| 864 | 455.67 | 0.64 | 1H NMR (300 MHz, CDCl3) δ 8.33 (s, 1H), 7.48 (s, 1H), 7.30 (d, J = 5.1 Hz, 1H), 7.27-7.17 (m, 2H), 6.91-6.71 (m, 3H), 4.65 (dt, J = 12.4, |

TABLE 3A-continued

Analytical Data

| Cmpd No. in PRV2 | LCMS (M + H) | LC/MS Ret. Time (min) | ¹H-NMR |
|---|---|---|---|
| | | | 6.4 Hz, 4H), 3.84 (s, 2H), 3.53 (dt, J = 12.7, 6.3 Hz, 3H), 2.41 (s, 7H) ppm. |
| 865 | 387.14 | 0.86 | 1H NMR (400 MHz, CDCl3) δ 8.16 (s, 1H), 7.45 (ddd, J = 10.9, 6.8, 2.6 Hz, 1H), 7.31-7.22 (m, 1H), 7.20-7.13 (m, 1H), 6.97 (t, J = 2.2 Hz, 1H), 6.68 (d, J = 1.6 Hz, 1H), 6.24 (t, J = 1.6 Hz, 1H), 3.88-3.73 (m, 4H), 3.72-3.63 (m, 1H), 3.59 (dd, J = 8.8, 5.3 Hz, 1H), 2.64 (tq, J = 13.5, 6.7, 6.2 Hz, 1H), 2.20 (s, 3H), 2.00 (dtd, J = 13.5, 8.2, 5.6 Hz, 1H), 1.70-1.56 (m, 1H) ppm. |
| 866 | 441.35 | 0.67 | 1H NMR (300 MHz, DMSO-D6) δ 9.29 (s, 1H), 9.14 (s, 1H), 7.70-7.52 (m, 2H), 7.31-7.15 (m, 1H), 6.75 (s, 1H), 6.65 (s, 1H), 5.77 (s, 1H), 3.91 (t, J = 7.3 Hz, 2H), 3.62-3.51 (m, 4H), 3.44 (t, J = 6.3 Hz, 2H), 3.00-2.81 (m, 1H), 2.56 (d, J = 7.4 Hz, 2H), 2.37 (s, 4H), 2.18 (s, 3H) ppm. |
| 867 | 441.22 | 0.8 | 1H NMR (400 MHz, CDCl3) δ 8.44 (s, 1H), 7.97 (s, 1H), 7.91 (d, J = 7.6 Hz, 1H), 7.75-7.60 (m, 2H), 7.55 (s, 1H), 7.37 (s, 1H), 6.61 (t, J = 56.1 Hz, 1H), 6.38 (s, 1H), 3.92-3.81 (m, 4H), 3.61-3.49 (m, 4H) ppm. |
| 868 | 553.43 | 0.52 | 1H NMR (300 MHz, DMSO-D6) δ 9.17 (s, 1H), 9.12 (s, 1H), 7.60-7.56 (m, 2H), 7.25-7.17 (m, 1H), 6.21 (d, J = 1.7 Hz, 2H), 5.09 (s, 1H), 3.86 (t, J = 6.9 Hz, 4H), 3.65-3.50 (m, 12H), 3.26-3.17 (m, 2H), 2.34 (s, 8H) ppm. |
| 869 | 390.01 | 0.9 | 1H NMR (300 MHz, CDCl3) δ 8.41 (s, 1H), 7.50-7.35 (m, 2H), 7.32-7.29 (m, 1H), 7.27 (d, J = 1.9 Hz, 1H), 6.85 (tt, J = 8.7, 2.3 Hz, 1H), 6.02-5.73 (m, 1H), 4.89 (d, J = 6.0 Hz, 2H), 4.61 (d, J = 6.0 Hz, 2H), 2.35 (d, J = 1.0 Hz, 2H), 1.73 (s, 3H) ppm. |

TABLE 3B

Analytical Data

| Cmpd No. in US | LCMS (M + H) | LC/MS Ret. Time (min) | ¹H-NMR |
|---|---|---|---|
| 870 | 445.09 | 0.67 | 1H NMR (300 MHz, DMSO-d6) δ 9.18 (s, 1H), 8.89 (s, 1H), 7.59 (d, J = 7.6 Hz, 2H), 7.16 (s, 1H), 5.89 (s, 1H), 3.90 (t, J = 6.8 Hz, 2H), 3.59 (d, J = 5.8 Hz, 5H), 2.34 (s, 4H), 2.17 (d, J = 2.2 Hz, 3H) ppm. |
| 871 | 455.22 | 0.7 | |
| 872 | 442.94 | 2.73 | 1H NMR (400 MHz, DMSO-d6) δ 9.30 (s, 1H), 9.16 (s, 1H), 7.69-7.62 (m, 2H), 7.30-7.20 (m, 1H), 6.97 (s, 1H), 6.63 (s, 1H), 6.04 (s, 1H), 3.94 (t, J = 15.1 Hz, 2H), 3.83-3.78 (m, 1H), 3.47-3.40 (m, 4H), 3.36-3.23 (m, 3H), 2.20 (s, 3H), 1.84-1.79 (m, 1H), 1.62-1.57 (m, 1H), 0.92 (t, J = 7.5 Hz, 3H) ppm. |
| 873 | 431.35 | 0.68 | |
| 874 | 414.24 | 0.66 | 1H NMR (400 MHz, DMSO-d6) δ 9.76 (s, 1H), 9.21 (s, 1H), 7.74-7.47 (m, 3H), 7.28-7.06 (m, 2H), 6.82 (s, 1H), 3.49 (t, J = 6.4 Hz, 2H), 3.33-3.10 (m, 3H), 2.31 (s, 3H), 1.89 (d, J = 13.2 Hz, 2H), 1.83-1.68 (m, 2H), 1.46 (dd, J = 18.0, 11.4 Hz, 4H) ppm. |
| 875 | 455.32 | 0.64 | |
| 876 | 416.31 | 0.71 | 1H NMR (300 MHz, DMSO-d6) δ 9.60 (s, 1H), 9.19 (s, 1H), 7.69-7.52 (m, 2H), 7.44 (s, 1H), 7.30-7.13 (m, 2H), 7.12-6.67 (m, 1H), 6.63 (s, 1H) ppm. |
| 877 | 428.31 | 0.61 | |
| 878 | 469.37 | 2.75 | |
| 879 | 469.34 | 2.34 | |

TABLE 3B-continued

Analytical Data

| Cmpd No. in US | LCMS (M + H) | LC/MS Ret. Time (min) | ¹H-NMR |
|---|---|---|---|
| 880 | 484.35 | 0.63 | 1H NMR (400 MHz, DMSO-d6) δ 9.32 (s, 1H), 9.16 (s, 1H), 7.74-7.58 (m, 2H), 7.25 (td, J = 9.1, 4.6 Hz, 1H), 6.94 (s, 1H), 6.63 (s, 1H), 5.95 (s, 1H), 4.20-4.09 (m, 2H), 3.66-2.84 (m, 16H), 2.19 (s, 3H), 2.08-1.95 (m, 1H) ppm. |
| 881 | 413.3 | 2.61 | |
| 882 | 457.57 | 1.84 | |
| 883 | 501.23 | 0.95 | 1H NMR (300 MHz, DMSO-d6) δ 9.79 (d, J = 12.5 Hz, 1H), 9.21 (s, 1H), 7.66-7.56 (m, 2H), 7.47 (d, J = 19.4 Hz, 2H), 7.32-7.21 (m, 1H), 6.77 (s, 1H), 2.08-1.94 (m, 1H), 0.75 (t, J = 6.7 Hz, 4H) ppm. |
| 884 | 455.31 | 0.69 | 1H NMR (300 MHz, DMSO-d6) δ 9.13 (d, J = 2.8 Hz, 1H), 7.69-7.59 (m, 2H), 6.94 (s, 1H), 6.66 (s, 1H), 6.15 (s, 1H), 4.13 (d, J = 12.5 Hz, 1H), 3.94 (d, J = 16.7 Hz, 2H), 3.70 (dd, J = 12.5, 6.5 Hz, 2H), 3.61 (s, 1H), 3.30 (s, 3H), 2.48 (d, J = 2.6 Hz, 26H), 2.19 (s, 3H), 1.91 (s, 5H), 1.56 (s, 2H) ppm. |
| 885 | 479.39 | 0.69 | 1H NMR (300 MHz, DMSO-d6) δ 9.28 (s, 1H), 9.14 (s, 1H), 7.60 (d, J = 8.4 Hz, 2H), 7.32-7.17 (m, 1H), 7.14 (d, J = 2.3 Hz, 1H), 6.85 (s, 1H), 6.30 (s, 1H), 3.73-3.46 (m, 5H), 3.25-3.17 (m, 1H), 2.36-2.32 (m, 1H), 2.23 (s, 3H), 1.25 (d, J = 5.2 Hz, 2H) ppm. |
| 886 | 373.05 | 0.9 | 1H NMR (300 MHz, CDCl3) δ 8.28 (s, 1H), 7.80-7.57 (m, 1H), 7.48-7.32 (m, 3H), 7.08 (d, J = 3.7 Hz, 1H), 7.03-6.91 (m, 1H), 6.28 (dd, J = 7.3, 1.9 Hz, 1H), 4.89 (tt, J = 4.7, 2.5 Hz, 1H), 4.04-3.66 (m, 4H), 2.29 (d, J = 1.0 Hz, 3H), 2.25-1.99 (m, 2H) ppm. |
| 887 | 427.4 | 2.38 | |
| 888 | 442.29 | 0.8 | 1H NMR (400 MHz, DMSO-d6) δ 9.37 (s, 1H), 9.16 (s, 1H), 7.67-7.55 (m, 2H), 7.23 (s, 2H), 6.83 (s, 1H), 6.31 (s, 1H), 3.99-3.89 (m, 1H), 3.76 (q, J = 6.8 Hz, 2H), 3.70-3.58 (m, 3H), 3.51-3.40 (m, 2H), 2.68 (td, J = 11.6, 3.2 Hz, 1H), 2.49-2.40 (m, 1H), 2.23 (s, 3H), 2.01-1.89 (m, 1H), 1.89-1.73 (m, 3H) ppm. |
| 889 | 396.9 | 2.65 | |
| 890 | 411.9 | 3.07 | 1H NMR (400 MHz, DMSO-d6) δ 9.34 (s, 1H), 9.15 (s, 1H), 7.64-7.56 (m, 2H), 7.24 (tt, J = 9.1, 2.1 Hz, 1H), 6.72 (d, J = 12.4 Hz, 2H), 5.82 (s, 1H), 3.90 (dt, J = 10.5, 7.5 Hz, 2H), 3.77 (dd, J = 9.0, 6.4 Hz, 2H), 3.64 (q, J = 7.6 Hz, 2H), 3.34 (dd, J = 8.4, 5.9 Hz, 2H), 2.72-2.60 (m, 1H), 2.20 (s, 3H), 2.07-1.94 (m, 1H), 1.57-1.43 (m, 1H) ppm. |
| 891 | 469.44 | 0.65 | 1H NMR (400 MHz, DMSO-d6) δ 9.44 (s, 1H), 9.27 (d, J = 4.5 Hz, 1H), 9.15 (s, 1H), 7.71-7.60 (m, 2H), 7.25 (tt, J = 9.3, 4.7 Hz, 1H), 7.00 (s, 1H), 6.55 (d, J = 9.3 Hz, 1H), 6.04 (s, 1H), 4.28-4.18 (m, 1H), 3.87-3.80 (m, 2H), 3.77-3.70 (m, 4H), 3.15-3.06 (m, 2H), 2.17 (s, 4H), 2.11-1.99 (m, 2H), 1.93-1.49 (m, 6H) ppm. |
| 892 | 468.41 | 0.63 | 1H NMR (400 MHz, DMSO-d6) δ 9.95 (s, 2H), 9.41 (s, 1H), 9.16 (s, 1H), 7.70-7.55 (m, 2H), 7.26 (tt, J = 9.2, 2.3 Hz, 1H), 7.14 (s, 1H), 6.94 (s, 1H), 6.38 (s, 1H), 3.37-3.03 (m, 8H), 2.96-2.74 (m, 4H), 2.25 (s, 3H), 2.14-1.92 (m, 2H), 1.74-1.47 (m, 3H) ppm. |
| 893 | 429.42 | 0.64 | 1H NMR (400 MHz, DMSO-d6) δ 9.73 (s, 1H), 9.27 (s, 1H), 9.16 (s, 1H), 7.74-7.58 (m, 2H), 7.24 (tt, J = 9.3, 2.3 Hz, 1H), 7.04 (s, 1H), 6.52 (s, 1H), 5.99 (s, 1H), 4.07 (dd, J = 12.7, 3.4 Hz, 1H), 3.94-3.83 (m, 1H), 3.44 (d, J = 12.3 Hz, 2H), 3.21 (ddd, J = 19.5, 13.1, 5.7 Hz, 4H), 2.84 (q, J = 10.8 Hz, 1H), 2.16 (s, 3H), 1.21 (t, J = 7.3 Hz, 3H) ppm. |
| 894 | 429.33 | 0.67 | 1H NMR (400 MHz, DMSO-d6) δ 9.86 (s, 2H), 9.30 (s, 1H), 9.15 (s, 1H), 7.76-7.54 (m, 2H), 7.25 (tt, J = 9.4, 2.3 Hz, 1H), 6.90 (d, J = 17.2 Hz, 1H), 6.63 (d, J = 11.7 Hz, 1H), 5.95 (s, 1H), |

TABLE 3B-continued

Analytical Data

| Cmpd No. in US | LCMS (M + H) | LC/MS Ret. Time (min) | ¹H-NMR |
|---|---|---|---|
| | | | 4.21-4.04 (m, 1H), 3.73-3.61 (m, 3H), 3.45-3.39 (m, 3H), 3.32 (d, J = 8.6 Hz, 3H), 3.23-3.08 (m, 1H), 2.19 (s, 2H), 2.08-1.84 (m, 2H) ppm. |
| 895 | 469.41 | 0.64 | |
| 896 | 457.3 | 0.65 | |
| 897 | 413.36 | 0.64 | |
| 898 | 392.13 | 0.64 | 1H NMR (300 MHz, CDCl3) δ 8.32 (d, J = 2.3 Hz, 1H), 7.69 (dd, J = 7.5, 1.2 Hz, 2H), 7.51 (dd, J = 11.3, 4.7 Hz, 2H), 7.36 (t, J = 7.4 Hz, 1H), 7.17 (s, 1H), 6.82 (s, 1H), 6.63 (s, 1H), 6.42 (s, 1H), 4.74 (s, 4H), 3.36 (s, 4H), 2.61 (s, 4H), 2.35 (s, 3H) ppm. |
| 899 | 483.19 | 2.14 | |
| 900 | 473.36 | 0.69 | |
| 901 | 398.29 | 3.76 | |
| 902 | 429.37 | 0.68 | 1H NMR (400 MHz, DMSO-d6) δ 9.45 (s, 1H), 9.17 (s, 1H), 7.70-7.56 (m, 2H), 7.36-7.20 (m, 2H), 6.85 (s, 1H), 6.39 (d, J = 16.1 Hz, 1H), 5.45 (s, 1H), 3.89-3.63 (m, 4H), 3.51 (d, J = 10.4 Hz, 2H), 3.30-3.18 (m, 2H), 3.18-3.09 (m, 1H), 3.04 (t, J = 12.3 Hz, 1H), 2.92 (t, J = 12.0 Hz, 1H), 2.25 (s, 3H), 1.49-1.32 (m, 3H) ppm. |
| 903 | 457.29 | 0.68 | |
| 904 | 443.42 | 0.69 | 1H NMR (400 MHz, DMSO-d6) δ 9.43 (s, 2H), 9.17 (s, 1H), 7.69-7.57 (m, 2H), 7.26 (tt, J = 9.3, 2.3 Hz, 1H), 7.13 (d, J = 2.3 Hz, 1H), 6.96 (s, 1H), 6.39 (s, 1H), 5.50 (s, 1H), 3.88 (dd, J = 13.2, 2.7 Hz, 1H), 3.77 (s, 2H), 3.70 (dd, J = 13.1, 4.6 Hz, 1H), 3.43-3.15 (m, 4H), 3.07 (q, J = 11.1 Hz, 2H), 2.25 (s, 3H), 1.87-1.63 (m, 2H), 0.96 (t, J = 7.4 Hz, 3H) ppm. |
| 905 | 453.34 | 0.88 | |
| 906 | 456.39 | 0.69 | 1H NMR (400 MHz, DMSO-d6) δ 9.44 (s, 1H), 9.16 (s, 1H), 7.67-7.56 (m, 2H), 7.32-7.19 (m, 2H), 6.78 (s, 1H), 6.36 (s, 1H), 3.76 (d, J = 6.0 Hz, 3H), 3.64-3.57 (m, 7H), 2.23 (s, 3H), 1.96 (t, J = 4.7 Hz, 2H), 1.67 (d, J = 13.5 Hz, 2H), 1.50 (ddd, J = 14.1, 9.4, 5.4 Hz, 2H) ppm. |
| 907 | 355 | 0.89 | 1H NMR (300 MHz, DMSO-d6) δ 9.07 (s, 1H), 8.90-8.72 (m, 1H), 7.91-7.78 (m, 2H), 7.66-7.47 (m, 3H), 7.43-7.26 (m, 1H), 6.52 (dd, J = 7.2, 2.0 Hz, 1H), 5.03 (tt, J = 3.8, 1.9 Hz, 1H), 3.99-3.67 (m, 4H), 2.28 (d, J = 2.4 Hz, 3H), 2.24-2.10 (m, 1H), 2.00 (dt, J = 12.1, 5.2 Hz, 1H) ppm. |
| 908 | 410.08 | 0.62 | 1H NMR (300 MHz, CDCl3) δ 8.98 (s, 1H), 8.44 (ddd, J = 4.8, 1.7, 0.9 Hz, 1H), 7.96-7.76 (m, 3H), 7.28-7.19 (m, 1H), 6.98 (d, J = 4.0 Hz, 1H), 6.42 (dd, J = 7.7, 1.5 Hz, 1H), 4.72 (d, J = 6.5 Hz, 4H), 3.64 (s, 1H), 3.19 (s, 4H), 2.58 (s, 4H), 2.39 (s, 3H) ppm. |
| 909 | | | 1H NMR (300 MHz, DMSO-d6) δ 9.14 (s, 1H), 8.34 (s, 1H), 7.67-7.49 (m, 2H), 7.35 (d, J = 2.6 Hz, 1H), 7.29-7.11 (m, 1H), 6.49 (d, J = 2.7 Hz, 1H), 4.81-4.60 (m, 2H), 4.49-4.31 (m, 2H), 4.18 (d, J = 6.8 Hz, 2H), 3.49-3.24 (m, 3H), 2.23 (s, 3H), 2.10 (s, 3H) ppm. |
| 910 | 363.01 | 0.81 | 1H NMR (300 MHz, MeOD + CDCl3) δ 8.67 (s, 1H), 7.77 (d, J = 7.5 Hz, 2H), 7.52 (d, J = 8.3 Hz, 2H), 7.40 (dd, J = 14.3, 6.9 Hz, 2H), 7.06 (s, 1H), 6.83 (s, 1H), 4.28-4.21 (m, 1H), 2.33 (s, 5H), 1.89 (dd, J = 10.2, 7.7 Hz, 2H), 1.71 (dd, J = 11.9, 4.8 Hz, 2H) ppm. |
| 911 | 455.32 | 0.63 | |
| 912 | 455.31 | 0.7 | |
| 913 | 373 | 0.9 | 1H NMR (300 MHz, DMSO-d6) δ 9.13 (s, 1H), 8.90 (d, J = 1.9 Hz, 1H), 7.83-7.65 (m, 2H), 7.66-7.47 (m, 2H), 7.20 (tdd, J = 8.5, 2.5, 1.0 Hz, 1H), 6.54 (dd, J = 7.2, 2.0 Hz, 1H), 5.04 (ddt, J = 6.2, 4.1, 1.8 Hz, 1H), 3.98-3.60 (m, 4H), 2.29 (s, 3H), 2.25-2.10 (m, 1H), 2.01 (ddq, J = 12.1, 5.4, 3.6, 2.6 Hz, 1H) ppm. |

TABLE 3B-continued

Analytical Data

| Cmpd No. in US | LCMS (M + H) | LC/MS Ret. Time (min) | ¹H-NMR |
|---|---|---|---|
| 914 | 455.4 | 0.71 | 1H NMR (300 MHz, DMSO-d6) δ 9.15 (s, 1H), 7.66-7.57 (m, 2H), 7.30-7.19 (m, 1H), 7.16 (s, 1H), 6.95 (s, 1H), 6.39 (s, 1H), 4.31-4.24 (m, 1H), 3.94-3.82 (m, 1H), 3.82-3.69 (m, 3H), 3.66-3.59 (m, 1H), 3.35-3.30 (m, 2H), 3.30-2.96 (m, 5H), 2.25 (s, 3H), 2.16-1.99 (m, 1H), 1.94-1.84 (m, 2H), 1.57-1.51 (m, 1H) ppm. |
| 915 | 375.93 | 0.89 | 1H NMR (300 MHz, CDCl3) δ 8.34 (s, 1H), 7.49 (d, J = 7.3 Hz, 1H), 6.88 (d, J = 17.8 Hz, 1H), 5.93 (d, J = 7.6 Hz, 1H), 5.03 (t, J = 6.3 Hz, 2H), 4.81-4.46 (m, 3H), 4.31 (s, 1H), 2.07 (d, J = 1.5 Hz, 3H) ppm. |
| 916 | 379.25 | 0.68 | 1H NMR (300 MHz, DMSO-d6) δ 9.30 (s, 1H), 9.15 (s, 1H), 7.61 (dd, J = 6.8, 4.0 Hz, 2H), 7.30-7.19 (m, 1H), 7.16 (d, J = 3.0 Hz, 1H), 6.83 (s, 1H), 6.29 (s, 1H), 5.79-5.72 (m, 1H), 2.23 (s, 3H) ppm. |
| 917 | 443.39 | 0.65 | |
| 918 | 426.21 | 1.93 | |
| 919 | 455.31 | 0.71 | 1H NMR (400 MHz, DMSO-d6) δ 9.73 (s, 1H), 9.31 (s, 1H), 9.14 (s, 1H), 7.68-7.56 (m, 2H), 7.25 (tt, J = 9.2, 2.4 Hz, 1H), 6.84 (s, 1H), 6.73 (s, 1H), 6.04 (s, 1H), 4.16 (d, J = 6.2 Hz, 1H), 3.99-3.71 (m, 5H), 3.10 (d, J = 7.7 Hz, 3H), 2.25 (s, 3H), 2.19-2.11 (m, 1H), 2.09-1.90 (m, 3H) ppm. |
| 920 | 455.4 | 0.7 | 1H NMR (300 MHz, DMSO-d6) δ 9.13 (d, J = 2.3 Hz, 1H), 7.69-7.53 (m, 2H), 7.22 (tt, J = 8.7, 8.1, 4.1 Hz, 1H), 7.14 (s, 1H), 6.60 (d, J = 10.7 Hz, 1H), 6.04 (d, J = 15.5 Hz, 1H), 4.17-3.63 (m, 7H), 3.43-3.14 (m, 3H), 2.23 (s, 3H), 1.93-1.77 (m, 1H), 1.27 (dd, J = 26.9, 5.8 Hz, 3H) ppm. |
| 921 | 381.32 | 2.41 | |
| 922 | 423.38 | 0.67 | 1H NMR (300 MHz, DMSO-d6) δ 9.28 (s, 1H), 9.14 (s, 1H), 7.64-7.55 (m, 2H), 7.23 (t, J = 8.7 Hz, 1H), 7.17-7.10 (m, 1H), 6.85 (s, 1H), 6.30 (s, 1H), 4.39 (s, 1H), 3.62-3.42 (m, 2H), 2.45-2.41 (m, 2H), 2.23 (s, 3H) ppm. |
| 923 | 547 | 0.71 | 1H NMR (300 MHz, CDCl3) δ 8.35 (s, 1H), 7.75 (d, J = 6.7 Hz, 1H), 7.29 (s, 1H), 7.26 (d, J = 2.1 Hz, 1H), 7.14 (s, 1H), 6.82 (tt, J = 8.7, 2.2 Hz, 1H), 6.41 (d, J = 7.1 Hz, 1H), 4.58-3.96 (m, 4H), 3.57-2.53 (m, 9H), 2.38 (s, 3H), 2.12 (s, 9H) ppm. |
| 924 | 412.31 | 0.71 | 1H NMR (400 MHz, DMSO-d6) δ 9.33 (s, 1H), 9.16 (s, 1H), 7.66-7.57 (m, 2H), 7.22 (tt, J = 9.3, 2.4 Hz, 1H), 7.11 (s, 1H), 6.52 (s, 1H), 5.77 (s, 1H), 3.87 (dd, J = 11.5, 4.5 Hz, 2H), 3.65 (t, J = 7.2 Hz, 2H), 3.33 (t, J = 11.8 Hz, 3H), 2.32 (td, J = 12.5, 4.6 Hz, 2H), 2.17 (d, J = 2.9 Hz, 4H), 1.66 (d, J = 12.5 Hz, 2H) ppm. |
| 925 | 481.87 | 2.39 | |
| 926 | 463.41 | 0.7 | 1H NMR (300 MHz, DMSO-d6) δ 9.27 (s, 1H), 9.14 (s, 1H), 7.64-7.54 (m, 2H), 7.29-7.17 (m, 1H), 7.11 (s, 1H), 6.85 (s, 1H), 6.29 (s, 1H), 3.99-3.87 (m, 1H), 3.74 (d, J = 11.1 Hz, 1H), 3.24-3.13 (m, 2H), 2.53-2.44 (m, 12H), 2.22 (s, 3H), 1.96 (d, J = 11.2 Hz, 1H), 1.72-1.61 (m, 1H), 1.58-1.28 (m, 1H) ppm. |
| 927 | 443.9 | 3.56 | |
| 928 | 429.33 | 0.68 | |
| 929 | 378.13 | 0.66 | 1H NMR (300 MHz, CDCl3) δ 8.32 (s, 1H), 7.69 (dd, J = 7.6, 1.2 Hz, 2H), 7.51 (dd, J = 11.2, 4.6 Hz, 2H), 7.36 (t, J = 7.4 Hz, 1H), 7.13 (s, 1H), 6.82 (s, 1H), 6.60 (s, 1H), 6.41 (s, 1H), 3.35 (s, 4H), 2.78 (s, 4H), 2.34 (s, 3H), 1.16 (s, 6H) ppm. |
| 930 | 443.33 | 0.63 | 1H NMR (400 MHz, DMSO-d6) δ 9.44 (s, 1H), 9.28 (s, 1H), 9.15 (s, 1H), 7.71-7.57 (m, 2H), 7.25 (tt, J = 9.3, 2.3 Hz, 1H), 7.00 (d, J = 9.5 Hz, 1H), 6.56 (d, J = 8.1 Hz, 1H), 6.05 (s, 1H), 3.44 (d, J = 11.5 Hz, 5H), 3.32 (d, J = 3.0 Hz, 3H), |

TABLE 3B-continued

Analytical Data

| Cmpd No. in US | LCMS (M + H) | LC/MS Ret. Time (min) | ¹H-NMR |
|---|---|---|---|
| | | | 3.27 (q, J = 4.9 Hz, 2H), 3.16-3.02 (m, 2H), 2.17 (s, 3H), 2.03 (s, 2H), 1.67 (q, J = 12.4, 11.9 Hz, 2H) ppm. |
| 931 | 429.28 | 0.67 | |
| 932 | 402.17 | 1.93 | |
| 933 | 457.33 | 0.61 | 1H NMR (400 MHz, DMSO-d6) δ 9.46 (s, 1H), 9.38 (s, 1H), 9.18 (s, 1H), 7.69-7.54 (m, 2H), 7.34 (s, 1H), 7.25 (tt, J = 9.3, 2.3 Hz, 1H), 6.90 (s, 1H), 6.45 (s, 1H), 3.75 (t, J = 5.0 Hz, 4H), 3.29 (q, J = 5.1 Hz, 3H), 3.04 (t, J = 10.8 Hz, 2H), 2.81 (d, J = 4.7 Hz, 6H), 2.25 (s, 3H), 2.07-1.94 (m, 2H), 1.66 (d, J = 9.5 Hz, 2H) ppm. |
| 934 | 443.37 | 1.87 | |
| 935 | 443.24 | 0.7 | 1H NMR (300 MHz, DMSO-d6) δ 9.29 (s, 1H), 9.14 (s, 1H), 7.64-7.54 (m, 2H), 7.29-7.17 (m, 1H), 7.14 (d, J = 2.1 Hz, 1H), 6.86 (s, 1H), 6.44-5.92 (m, 2H), 2.79 (td, J = 15.9, 4.2 Hz, 2H), 2.23 (s, 3H) ppm. |
| 936 | 455.04 | 0.65 | 1H NMR (400 MHz, DMSO-d6) δ 9.63 (s, 1H), 9.43 (s, 1H), 9.17 (s, 1H), 7.67-7.51 (m, 2H), 7.26 (tt, J = 9.3, 2.3 Hz, 1H), 7.14 (d, J = 2.1 Hz, 1H), 6.96 (s, 1H), 6.40 (s, 1H), 3.85 (t, J = 7.9 Hz, 1H), 3.82-3.71 (m, 2H), 3.71-3.52 (m, 3H), 3.48-3.40 (m, 2H), 3.30-3.10 (m, 3H), 3.10-3.01 (m, 2H), 2.75-2.60 (m, 1H), 2.25 (s, 3H), 2.18-2.04 (m, 1H), 1.70-1.56 (m, 1H) ppm. |
| 937 | 400.27 | 1.99 | |
| 938 | 455.33 | 2.08 | |
| 939 | 469.4 | 0.8 | 1H NMR (400 MHz, DMSO-d6) δ 9.33 (s, 1H), 9.16 (d, J = 2.2 Hz, 1H), 7.70-7.58 (m, 2H), 7.25 (tt, J = 9.3, 2.2 Hz, 1H), 7.07 (s, 1H), 6.62 (s, 1H), 6.15 (s, 1H), 4.04-3.80 (m, 3H), 3.80-3.66 (m, 2H), 3.44-3.05 (m, 6H), 2.19 (s, 3H), 2.11 (d, J = 12.1 Hz, 1H), 1.92-1.76 (m, 1H), 1.70-1.47 (m, 2H), 1.40-1.09 (m, 3H) ppm. |
| 940 | 447.17 | 1.65 | |
| 941 | 457.38 | 0.69 | |
| 942 | 356.17 | 1.83 | |
| 943 | 457.14 | 0.71 | 1H NMR (300 MHz, Chloroform-d) δ 8.38 (s, 1H), 7.44 (s, 1H), 7.41-7.28 (m, 2H), 6.97-6.70 (m, 1H), 6.35-6.04 (m, 1H), 3.90-3.61 (m, 1H), 3.61-3.21 (m, 2H), 2.96-2.45 (m, 9H), 2.47-2.14 (m, 4H), 2.14-1.86 (m, 2H) ppm. |
| 944 | 468.38 | 0.58 | |
| 945 | 482.38 | 0.58 | |
| 946 | 445.31 | 0.61 | 1H NMR (400 MHz, DMSO-d6) δ 9.28 (d, J = 3.3 Hz, 1H), 9.15 (s, 1H), 7.71-7.59 (m, 2H), 7.24 (t, J = 9.3 Hz, 1H), 6.97 (d, J = 15.4 Hz, 1H), 6.56 (d, J = 15.2 Hz, 1H), 5.99 (d, J = 7.5 Hz, 1H), 4.36 (s, 1H), 4.14-3.97 (m, 3H), 3.90-3.79 (m, 1H), 3.67-3.60 (m, 3H), 3.24 (d, J = 6.6 Hz, 2H), 2.17 (s, 3H) ppm. |
| 947 | 407.35 | 0.69 | 1H NMR (300 MHz, DMSO-d6) δ 9.28 (s, 1H), 9.14 (s, 1H), 7.66-7.53 (m, 2H), 7.23 (t, J = 8.5 Hz, 1H), 7.15 (s, 1H), 6.85 (s, 1H), 6.30 (s, 1H), 2.37 (q, J = 7.2 Hz, 2H), 2.23 (s, 3H), 1.04 (t, J = 7.2 Hz, 3H) ppm. |
| 948 | 413.23 | 0.58 | 1H NMR (400 MHz, Methanol-d4) δ 8.96 (s, 1H), 8.05 (d, J = 2.0 Hz, 1H), 7.71-7.60 (m, 2H), 7.39 (dd, J = 2.0, 0.9 Hz, 1H), 7.12 (d, J = 1.7 Hz, 1H), 6.98 (tt, J = 9.0, 2.3 Hz, 1H), 3.90 (s, 2H), 3.89-3.73 (m, 1H), 2.99 (s, 6H), 2.66 (s, 1H), 2.61-2.47 (m, 1H), 2.51 (s, 4H), 2.43 (s, 3H) ppm. |

TABLE 3B-continued

Analytical Data

| Cmpd No. in US | LCMS (M + H) | LC/MS Ret. Time (min) | ¹H-NMR |
|---|---|---|---|
| 949 | 470.91 | 2.68 | |
| 950 | 432.39 | 0.68 | 1H NMR (400 MHz, DMSO-d6) δ 9.61 (s, 1H), 9.19 (s, 1H), 7.70-7.58 (m, 2H), 7.46 (s, 1H), 7.26 (tt, J = 9.2, 2.3 Hz, 1H), 7.06 (s, 1H), 6.62 (s, 1H), 4.64-4.56 (m, 1H), 4.52-4.45 (m, 1H), 3.62-3.52 (m, 4H), 3.27-3.07 (m, 2H), 2.28 (s, 3H), 2.10-1.98 (m, 2H), 1.81-1.65 (m, 2H) ppm. |
| 951 | 441.37 | 0.64 | |
| 952 | 356.98 | 0.8 | 1H NMR (300 MHz, DMSO-d6) δ 9.22 (s, 1H), 9.17-9.00 (m, 2H), 8.68 (d, J = 2.6 Hz, 1H), 8.59 (dd, J = 2.6, 1.4 Hz, 1H), 7.56 (dd, J = 6.9, 1.9 Hz, 1H), 6.57 (dd, J = 7.3, 2.0 Hz, 1H), 5.04 (tt, J = 4.0, 2.1 Hz, 1H), 3.97-3.61 (m, 4H), 2.31 (s, 3H), 2.27-2.11 (m, 1H), 2.01 (dt, J = 12.5, 5.5 Hz, 1H) ppm. |
| 953 | 390.01 | 0.72 | 1H NMR (300 MHz, DMSO-d6) δ 9.18 (d, J = 2.2 Hz, 1H), 8.70 (d, J = 2.6 Hz, 1H), 7.66 (dd, J = 8.4, 2.6 Hz, 2H), 7.32 (dd, J = 6.8, 2.9 Hz, 1H), 7.24 (tt, J = 7.0, 3.3 Hz, 1H), 5.99 (dd, J = 5.6, 2.9 Hz, 1H), 5.66 (d, J = 5.2 Hz, 1H), 4.01-3.78 (m, 3H), 3.63-3.34 (m, 1H), 2.15 (t, J = 2.3 Hz, 4H), 1.80 (d, J = 5.5 Hz, 1H) ppm. |
| 954 | 484.35 | 0.62 | 1H NMR (400 MHz, DMSO-d6) δ 9.42 (s, 1H), 9.17 (s, 1H), 7.67-7.57 (m, 2H), 7.29-7.19 (m, 2H), 6.84 (s, 1H), 6.34 (s, 1H), 4.01-3.93 (m, 2H), 3.89 (d, J = 7.6 Hz, 2H), 3.70-3.61 (m, 8H), 2.89 (s, 2H), 2.79 (s, 3H), 2.71 (td, J = 12.1, 3.5 Hz, 2H), 2.46 (d, J = 10.8 Hz, 1H), 2.24 (s, 3H) ppm. |
| 955 | 427.04 | 0.66 | 1H NMR (300 MHz, CDCl3) δ 8.35 (s, 1H), 7.80 (d, J = 6.7 Hz, 1H), 7.53-7.43 (m, 3H), 7.14-7.02 (m, 1H), 6.92 (d, J = 3.9 Hz, 1H), 6.42 (d, J = 6.1 Hz, 1H), 4.74 (s, 4H), 3.67 (s, 1H), 3.22 (s, 4H), 2.60 (s, 3H), 2.38 (s, 3H) ppm. |
| 956 | 467.94 | 2.38 | |
| 957 | 443.42 | 0.66 | 1H NMR (400 MHz, DMSO-d6) δ 9.51 (s, 1H), 9.42 (s, 1H), 9.16 (s, 1H), 7.66-7.55 (m, 2H), 7.25 (tt, J = 9.3, 2.3 Hz, 1H), 7.15 (s, 1H), 6.94 (s, 1H), 6.39 (s, 1H), 5.51 (s, 1H), 3.93-3.81 (m, 1H), 3.74 (dd, J = 21.8, 12.5 Hz, 2H), 3.65-3.52 (m, 2H), 3.29-3.12 (m, 4H), 3.06 (t, J = 11.9 Hz, 2H), 2.25 (s, 3H), 1.51-1.36 (m, 2H), 0.91 (t, J = 7.4 Hz, 3H) ppm. |
| 958 | 416.34 | 2.77 | |
| 959 | 424.33 | 0.71 | 1H NMR (300 MHz, DMSO-d6) δ 9.32 (s, 1H), 9.15 (s, 1H), 7.65-7.56 (m, 2H), 7.23 (t, J = 8.6 Hz, 1H), 7.14 (s, 1H), 6.90 (s, 1H), 6.33 (s, 1H), 2.24 (s, 3H) ppm. |
| 960 | 443.37 | 0.7 | 1H NMR (400 MHz, DMSO-d6) δ 9.28 (s, 1H), 9.14 (s, 1H), 7.68-7.58 (m, 2H), 7.25 (tt, J = 9.4, 2.3 Hz, 1H), 6.94 (s, 1H), 6.61 (s, 1H), 6.08 (s, 1H), 3.89-3.74 (m, 5H), 3.36-3.16 (m, 6H), 2.18 (s, 3H), 1.56 (dq, J = 14.3, 7.3 Hz, 2H), 0.90 (t, J = 7.4 Hz, 3H) ppm. |
| 961 | 447.34 | 0.76 | 1H NMR (300 MHz, DMSO-d6) δ 9.32 (s, 1H), 9.15 (s, 1H), 7.66-7.55 (m, 2H), 7.24 (tt, J = 9.2, 2.3 Hz, 1H), 7.20-7.08 (m, 1H), 6.90 (s, 1H), 6.35 (s, 1H), 2.25 (s, 3H), 2.07-1.95 (m, 1H), 0.81-0.67 (m, 4H) ppm. |
| 962 | 458.37 | 0.69 | 1H NMR (400 MHz, DMSO-d6) δ 9.49 (s, 1H), 9.08 (s, 1H), 7.58-7.47 (m, 2H), 7.35 (s, 1H), 7.16 (td, J = 9.2, 4.7 Hz, 1H), 6.94 (s, 1H), 6.50 (s, 1H), 3.52-3.43 (m, 9H), 3.11-3.00 (m, 2H), 2.17 (s, 3H), 1.97-1.86 (m, 2H), 1.59 (d, J = 11.8 Hz, 2H), 0.99 (t, J = 7.0 Hz, 3H) ppm. |
| 963 | 461.06 | 0.7 | 1H NMR (300 MHz, CDCl3) δ 8.44 (s, 1H), 7.46 (d, J = 7.9 Hz, 3H), 6.85 (t, J = 9.3 Hz, 1H), 6.17 (d, J = 7.4 Hz, 1H), 4.01 (s, 4H), 3.71 (s, 3H), 2.34 (s, 3H), 1.04 (s, 4H) ppm. |
| 964 | 429.35 | 2.62 | |
| 965 | | | 1H NMR (300 MHz, DMSO-d6) δ 9.14 (s, 1H), 8.31 (s, 1H), 7.73-7.52 (m, 2H), 7.41-7.31 (m, |

TABLE 3B-continued

Analytical Data

| Cmpd No. in US | LCMS (M + H) | LC/MS Ret. Time (min) | ¹H-NMR |
|---|---|---|---|
| | | | 1H), 7.29-7.11 (m, 1H), 6.46 (s, 1H), 4.64 (s, 2H), 3.62-3.39 (m, 5H), 3.31 (t, J = 6.8 Hz, 2H), 2.22 (s, 3H), 2.10 (s, 3H), 1.96-1.61 (m, 4H) ppm. |
| 966 | 390.15 | 0.56 | 1H NMR (300 MHz, CDCl3) δ 9.02 (d, J = 2.6 Hz, 1H), 8.63 (dt, J = 4.8, 1.3 Hz, 1H), 8.37 (d, J = 1.0 Hz, 1H), 8.02 (ddt, J = 8.2, 2.6, 1.3 Hz, 1H), 7.50 (dd, J = 8.3, 4.7 Hz, 1H), 6.81-6.50 (m, 3H), 5.94 (s, 1H), 3.99 (s, 4H), 3.37 (s, 4H), 0.99-0.66 (m, 6H) ppm. |
| 967 | 391.14 | 0.61 | 1H NMR (300 MHz, CDCl3) δ 9.19 (d, J = 1.5 Hz, 1H), 9.03-8.71 (m, 1H), 8.57 (s, 1H), 8.48-8.16 (m, 1H), 7.28 (d, J = 1.7 Hz, 1H), 6.74 (dd, J = 4.2, 2.1 Hz, 2H), 6.63 (s, 1H), 5.96 (s, 1H), 4.00 (s, 4H), 3.38 (s, 4H), 2.46-2.09 (m, 4H), 0.96 (dd, J = 6.0, 4.1 Hz, 6H) ppm. |
| 968 | 441.37 | 0.62 | |
| 969 | 390.01 | 0.91 | 1H NMR (300 MHz, CDCl3) δ 8.35 (s, 1H), 7.74 (d, J = 7.3 Hz, 1H), 6.96 (s, 1H), 6.82 (s, 1H), 6.07 (d, J = 7.5 Hz, 1H), 4.82 (t, J = 6.6 Hz, 2H), 4.69 (t, J = 6.3 Hz, 2H), 4.55-4.39 (m, 1H), 2.82 (s, 3H), 2.35 (s, 2H) ppm. |
| 970 | 414.21 | 1.89 | |
| 971 | 414.46 | 3.65 | 1H NMR (300 MHz, DMSO-d6) δ 9.15 (s, 1H), 8.38 (s, 1H), 7.82-7.47 (m, 2H), 7.39-7.07 (m, 2H), 6.51-6.22 (m, 1H), 5.06-4.85 (m, 1H), 4.61-4.43 (m, 1H), 4.34-4.17 (m, 1H), 4.16-4.02 (m, 1H), 3.87-3.67 (m, 1H), 2.23 (s, 3H), 2.10 (s, 3H), 1.78 (s, 3H) ppm. |
| 972 | 442.25 | 0.81 | 1H NMR (400 MHz, DMSO-d6) δ 9.40 (s, 1H), 9.16 (s, 1H), 7.70-7.51 (m, 2H), 7.33-7.15 (m, 2H), 6.83 (s, 1H), 6.37 (s, 1H), 3.96 (dd, J = 11.2, 3.0 Hz, 1H), 3.83 (q, J = 6.5 Hz, 1H), 3.77-3.69 (m, 2H), 3.55-3.50 (m, 2H), 3.46 (d, J = 11.7 Hz, 2H), 2.71 (td, J = 12.0, 3.4 Hz, 1H), 2.62 (t, J = 11.1 Hz, 1H), 2.24 (s, 3H), 1.98-1.62 (m, 4H) ppm. |
| 973 | 443.3 | 0.64 | |
| 974 | 456.91 | 2.8 | 1H NMR (400 MHz, DMSO-d6) δ 9.29 (s, 1H), 9.16 (s, 1H), 7.74-7.56 (m, 2H), 7.25 (t, J = 9.5 Hz, 1H), 6.97 (d, J = 3.7 Hz, 1H), 6.62 (d, J = 7.0 Hz, 1H), 6.04 (d, J = 13.3 Hz, 1H), 4.01-3.77 (m, 3H), 3.48-3.15 (m, 6H), 3.02-2.90 (m, 1H), 2.20 (s, 3H), 1.93-1.76 (m, 1H), 1.76-1.61 (m, 1H), 1.14 (t, J = 6.7 Hz, 3H), 0.93 (dt, J = 19.3, 7.4 Hz, 3H) ppm. |
| 975 | 440.4 | 0.63 | 1H NMR (400 MHz, DMSO-d6) δ 9.35 (s, 1H), 9.15 (s, 1H), 7.64-7.55 (m, 2H), 7.24 (tt, J = 9.3, 2.4 Hz, 1H), 6.77-6.66 (m, 2H), 5.82 (s, 1H), 3.93 (t, J = 7.1 Hz, 2H), 3.77-3.54 (m, 5H), 3.12-2.92 (m, 4H), 2.79 (s, 3H), 2.36-2.23 (m, 2H), 2.20 (s, 3H) ppm. |
| 976 | 414.31 | 0.65 | |
| 977 | 425.15 | 0.68 | 1H NMR (300 MHz, CDCl3) δ 8.25 (d, J = 1.8 Hz, 1H), 7.55 (ddd, J = 10.9, 6.8, 2.6 Hz, 1H), 7.47-7.28 (m, 2H), 6.73-6.53 (m, 3H), 5.93 (t, J = 1.9 Hz, 1H), 3.97 (d, J = 1.9 Hz, 4H), 3.37 (s, 4H), 2.41-2.08 (m, 4H), 0.96 (dd, J = 6.3, 1.8 Hz, 6H) ppm. |
| 978 | 391 | 0.91 | 1H NMR (300 MHz, DMSO-d6) δ 9.07 (s, 1H), 8.89 (d, J = 1.7 Hz, 1H), 7.96 (ddd, J = 12.0, 7.2, 2.1 Hz, 1H), 7.77-7.59 (m, 2H), 7.51 (dd, J = 7.0, 1.9 Hz, 1H), 6.53 (dd, J = 7.2, 2.0 Hz, 1H), 5.03 (ddt, J = 6.2, 4.0, 1.7 Hz, 1H), 3.98-3.58 (m, 4H), 2.28 (s, 3H), 2.25-2.10 (m, 1H), 2.09-1.86 (m, 1H) ppm. |
| 979 | 435.45 | 0.66 | 1H NMR (300 MHz, DMSO-d6) δ 9.30 (s, 1H), 9.14 (s, 1H), 7.60 (d, J = 7.8 Hz, 2H), 7.23 (t, J = 9.3 Hz, 1H), 7.13 (s, 1H), 6.87 (s, 1H), 6.31 (s, 1H), 4.57 (t, J = 6.5 Hz, 2H), 4.47 (t, J = 6.0 Hz, 2H), 3.46 (t, J = 6.2 Hz, 1H), 2.23 (s, 3H) ppm. |
| 980 | 357.97 | 0.9 | 1H NMR (300 MHz, DMSO-d6) δ 9.68 (s, 1H), 9.19 (d, J = 2.1 Hz, 1H), 7.79-7.46 (m, 2H), |

TABLE 3B-continued

Analytical Data

| Cmpd No. in US | LCMS (M + H) | LC/MS Ret. Time (min) | ¹H-NMR |
|---|---|---|---|
| | | | 7.35-7.21 (m, 1H), 7.17 (s, 1H), 6.14 (s, 1H), 4.11 (dd, J = 6.9, 2.1 Hz, 2H), 2.27 (s, 3H), 1.38-1.19 (m, 1H), 0.62-0.44 (m, 2H), 0.39-0.23 (m, 2H) ppm. |
| 981 | 412.35 | 0.69 | 1H NMR (400 MHz, DMSO-d6) δ 9.40 (s, 1H), 9.17 (s, 1H), 7.64-7.55 (m, 2H), 7.38 (s, 1H), 7.24 (tt, J = 9.3, 2.4 Hz, 1H), 6.78 (s, 1H), 6.40 (s, 1H), 4.39 (q, J = 6.9 Hz, 1H), 3.90 (t, J = 7.8 Hz, 1H), 3.85 (dd, J = 8.3, 5.7 Hz, 1H), 3.65 (dd, J = 8.3, 3.3 Hz, 1H), 2.95 (d, J = 10.9 Hz, 1H), 2.40-2.31 (m, 1H), 2.23 (s, 3H), 1.88-1.72 (m, 2H), 1.64-1.43 (m, 2H) ppm. |
| 982 | 380.24 | 0.74 | 1H NMR (300 MHz, DMSO-d6) δ 9.31 (s, 1H), 9.15 (s, 1H), 7.60 (d, J = 8.2 Hz, 2H), 7.30-7.17 (m, 1H), 7.14 (d, J = 2.1 Hz, 1H), 6.90 (s, 1H), 6.32 (s, 1H), 2.24 (s, 3H) ppm. |
| 983 | 455.35 | 0.68 | 1H NMR (400 MHz, DMSO-d6) δ 9.78 (s, 1H), 9.30 (s, 1H), 9.15 (s, 1H), 7.61 (h, J = 5.5 Hz, 2H), 7.25 (tt, J = 9.3, 2.2 Hz, 1H), 6.89 (d, J = 2.1 Hz, 1H), 6.66 (s, 1H), 5.94 (s, 1H), 3.99 (d, J = 12.5 Hz, 2H), 3.71 (t, J = 12.0 Hz, 4H), 3.37 (td, J = 8.3, 3.3 Hz, 2H), 3.29 (dd, J = 12.5, 7.5 Hz, 3H), 3.20-3.01 (m, 3H), 2.79 (q, J = 7.5 Hz, 1H), 2.21 (s, 4H), 1.86-1.72 (m, 1H) ppm. |
| 984 | 469.34 | 2.27 | |
| 985 | 443.32 | 2.74 | |
| 986 | 425.41 | 0.69 | 1H NMR (400 MHz, DMSO-d6) δ 9.15 (s, 1H), 7.66-7.58 (m, 2H), 7.24 (tt, J = 9.2, 2.2 Hz, 1H), 7.03 (t, J = 2.1 Hz, 1H), 6.67 (s, 1H), 6.03 (s, 1H), 4.09-4.00 (m, 1H), 3.72-3.58 (m, 3H), 3.54-3.42 (m, 3H), 3.28 (q, J = 8.2 Hz, 1H), 3.23-3.13 (m, 2H), 2.23 (s, 3H), 2.19 (dd, J = 12.8, 8.0 Hz, 1H), 2.12-2.02 (m, 2H), 1.95-1.84 (m, 2H) ppm. |
| 987 | 469.94 | 2.41 | |
| 988 | 469.37 | 0.59 | |
| 989 | 462.99 | 0.66 | 1H NMR (300 MHz, DMSO) δ 9.16 (s, 1H), 8.82 (s, 1H), 7.76-7.55 (m, 2H), 7.50 (d, J = 7.1 Hz, 1H), 7.33-7.14 (m, 1H), 6.43 (d, J = 6.5 Hz, 1H), 4.62-4.35 (m, 2H), 3.72-3.41 (m, 3H), 3.30-2.53 (m, 9H), 2.47-2.37 (m, 1H), 2.30 (d, J = 17.9 Hz, 3H) ppm. |
| 990 | 429.35 | 2.6 | |
| 991 | 482.87 | 2.97 | 1H NMR (400 MHz, DMSO-d6) δ 9.41 (s, 1H), 9.17 (s, 1H), 7.67-7.58 (m, 2H), 7.31-7.23 (m, 1H), 7.20 (s, 1H), 6.92 (s, 1H), 6.38 (s, 1H), 3.71-3.66 (m, 3H), 3.65-3.60 (m, 2H), 3.40 (td, J = 11.4, 2.6 Hz, 2H), 3.14 (d, J = 17.0 Hz, 4H), 2.98-2.87 (m, 1H), 2.25 (s, 3H), 1.68-1.51 (m, 4H) ppm. |
| 992 | 449.2 | 1.73 | |
| 993 | 413.43 | 2.26 | |
| 994 | 433.38 | 0.71 | 1H NMR (300 MHz, DMSO-d6) δ 9.28 (s, 1H), 9.14 (s, 1H), 7.60 (d, J = 7.9 Hz, 2H), 7.23 (t, J = 9.2 Hz, 1H), 7.14 (s, 1H), 6.85 (s, 1H), 6.30 (s, 1H), 2.81-2.69 (m, 1H), 2.22 (s, 3H), 1.99 (d, J = 7.8 Hz, 2H), 1.82 (t, J = 9.5 Hz, 2H), 1.66 (d, J = 9.7 Hz, 2H) ppm. |
| 995 | 429.35 | 2.63 | 1H NMR (400 MHz, DMSO-d6) δ 9.57 (s, 1H), 9.43 (s, 1H), 9.17 (s, 1H), 7.68-7.56 (m, 2H), 7.26 (tt, J = 9.3, 2.3 Hz, 1H), 7.15 (s, 1H), 6.94 (s, 1H), 6.39 (s, 1H), 5.55 (s, 1H), 4.18-4.06 (m, 1H), 3.73 (dd, J = 21.3, 12.6 Hz, 2H), 3.59 (d, J = 11.5 Hz, 2H), 3.27-3.11 (m, 4H), 3.11-3.01 (m, 2H), 2.25 (s, 3H), 1.14 (d, J = 6.1 Hz, 3H) ppm. |
| 996 | 411.29 | 0.64 | |
| 997 | 436.18 | 0.67 | 1H NMR (300 MHz, CDCl3) δ 8.32 (s, 1H), 7.26 (d, J = 6.8 Hz, 2H), 7.12 (s, 1H), 6.80 (s, 2H), 6.67 (s, 1H), 6.43 (s, 1H), 4.74 (s, 4H), 2.36 (s, 3H) ppm. |
| 998 | 445.04 | 0.68 | 1H NMR (300 MHz, CDCl3) δ 8.28 (s, 1H), 7.76 (d, J = 6.0 Hz, 1H), 7.59 (ddd, J = 10.8, 6.8, |

TABLE 3B-continued

Analytical Data

| Cmpd No. in US | LCMS (M + H) | LC/MS Ret. Time (min) | ¹H-NMR |
|---|---|---|---|
| | | | 2.6 Hz, 1H), 7.47-7.38 (m, 1H), 7.33 (dd, J = 9.3, 8.1 Hz, 1H), 6.94 (d, J = 4.0 Hz, 1H), 6.42 (dd, J = 7.7, 1.6 Hz, 1H), 4.73 (d, J = 4.8 Hz, 4H), 3.65 (t, J = 10.4 Hz, 1H), 3.20 (s, 4H), 2.59 (s, 4H), 2.38 (s, 3H) ppm. |
| 999 | 388.08 | 0.91 | 1H NMR (300 MHz, DMSO-d6) δ 9.75 (d, J = 2.1 Hz, 1H), 9.20 (d, J = 2.1 Hz, 1H), 7.75-7.60 (m, 2H), 7.33-7.19 (m, 1H), 7.12 (s, 1H), 6.12 (s, 1H), 5.13-4.98 (m, 1H), 4.03-3.89 (m, 1H), 3.75-3.61 (m, 1H), 3.55-3.36 (m, 2H), 2.26 (s, 3H), 2.14-1.99 (m, 1H), 1.85-1.48 (m, 3H) ppm. |
| 1001 | 456.94 | 2.75 | |
| 1002 | 355.05 | 0.89 | 1H NMR (300 MHz, CDCl3) δ 8.27 (s, 1H), 7.86-7.67 (m, 1H), 7.68-7.57 (m, 2H), 7.44 (dd, J = 8.6, 7.1 Hz, 2H), 7.37-7.22 (m, 1H), 6.99 (s, 1H), 6.26 (dd, J = 7.3, 1.9 Hz, 1H), 4.89 (dq, J = 4.9, 2.6 Hz, 1H), 3.98-3.71 (m, 4H), 2.28 (s, 3H), 2.16-2.00 (m, 2H) ppm. |
| 1003 | 443.39 | 0.64 | |
| 1004 | 399.14 | 2.04 | |
| 1005 | 457.37 | 2.85 | |
| 1006 | 399.94 | 2.68 | |
| 1007 | 473.12 | 0.72 | 1H NMR (300 MHz, CDCl3) δ 8.29 (s, 1H), 7.42 (d, J = 6.8 Hz, 1H), 6.11 (d, J = 7.3 Hz, 1H), 4.12 (d, J = 5.6 Hz, 1H), 3.94 (s, 4H), 3.56 (s, 2H), 3.21 (q, J = 8.6 Hz, 1H), 2.89 (s, 3H), 2.46 (s, 1H), 2.24 (d, J = 2.2 Hz, 3H), 2.14-1.76 (m, 4H) ppm. |
| 1008 | 400.31 | 2.1 | |
| 1009 | 391.05 | 0.91 | 1H NMR (300 MHz, CDCl3) δ 8.22 (s, 1H), 7.68-7.59 (m, 1H), 7.51 (ddd, J = 10.8, 6.8, 2.6 Hz, 1H), 7.39-7.29 (m, 1H), 7.29-7.21 (m, 1H), 7.10 (d, J = 3.5 Hz, 1H), 6.28 (dd, J = 7.3, 1.9 Hz, 1H), 4.89 (tt, J = 4.9, 2.6 Hz, 1H), 4.03-3.67 (m, 4H), 2.29 (d, J = 1.0 Hz, 3H), 2.19-2.04 (m, 2H) ppm. |
| 1010 | 441.3 | 0.67 | 1H NMR (400 MHz, DMSO-d6) δ 10.28 (s, 1H), 9.37 (s, 1H), 9.15 (s, 1H), 7.69-7.54 (m, 2H), 7.23 (tt, J = 9.2, 2.3 Hz, 1H), 7.01 (s, 1H), 6.66 (s, 1H), 6.08-5.94 (m, 2H), 4.54 (d, J = 6.9 Hz, 1H), 3.79 (d, J = 5.6 Hz, 2H), 3.75-3.65 (m, 2H), 3.65-3.55 (m, 2H), 3.25 (s, 2H), 3.11 (dd, J = 9.6, 6.5 Hz, 1H), 2.22 (s, 3H), 1.98 (d, J = 61.0 Hz, 4H) ppm. |
| 1011 | 443.37 | 0.69 | 1H NMR (400 MHz, DMSO-d6) δ 9.62 (s, 1H), 9.46 (s, 1H), 9.18 (s, 1H), 7.70-7.54 (m, 2H), 7.37-7.19 (m, 2H), 6.86 (d, J = 11.0 Hz, 1H), 6.39 (d, J = 16.7 Hz, 1H), 3.87-3.57 (m, 5H), 3.52 (s, 2H), 3.35 (s, 3H), 3.26 (d, J = 10.8 Hz, 2H), 3.07-2.96 (m, 1H), 2.93-2.84 (m, 1H), 2.25 (s, 3H), 1.38 (d, J = 6.3 Hz, 2H) ppm. |
| 1012 | 455.31 | 0.71 | 1H NMR (400 MHz, DMSO-d6) δ 9.30 (s, 1H), 9.13 (s, 1H), 7.73-7.51 (m, 3H), 7.25 (tt, J = 9.2, 2.5 Hz, 2H), 6.84 (s, 1H), 6.73 (s, 1H), 6.04 (s, 1H), 4.16 (q, J = 6.5 Hz, 2H), 4.02-3.67 (m, 7H), 3.18-3.03 (m, 4H), 2.25 (s, 3H), 2.19-2.12 (m, 1H), 2.07-1.92 (m, 3H) ppm. |
| 1014 | 456.3 | 0.68 | 1H NMR (400 MHz, DMSO-d6) δ 9.62 (s, 1H), 9.19 (s, 1H), 7.71-7.58 (m, 2H), 7.46 (s, 1H), 7.27 (tt, J = 9.4, 2.2 Hz, 1H), 7.07 (s, 1H), 6.63 (s, 1H), 4.35-4.24 (m, 1H), 3.70-3.56 (m, 7H), 3.28-3.05 (m, 2H), 2.28 (s, 3H), 2.07-1.92 (m, 3H), 1.78-1.59 (m, 2H) ppm. |
| 1015 | 443.33 | 0.61 | |
| 1016 | 390.06 | 0.78 | 1H NMR (300 MHz, DMSO-d6) δ 9.18 (d, J = 2.0 Hz, 1H), 8.75 (d, J = 2.4 Hz, 1H), 7.74-7.50 (m, 2H), 7.25 (tt, J = 9.3, 2.3 Hz, 1H), 7.11 (dd, J = 6.8, 2.9 Hz, 1H), 5.90 (s, 1H), 5.82 (dd, J = 5.6, 2.8 Hz, 1H), 4.65 (d, J = 5.6 Hz, 2H), 4.45 (dd, J = 5.7, 1.9 Hz, 2H), 2.14 (t, J = 2.3 Hz, 3H), 1.62 (d, J = 2.2 Hz, 3H) ppm. |

TABLE 3B-continued

Analytical Data

| Cmpd No. in US | LCMS (M + H) | LC/MS Ret. Time (min) | ¹H-NMR |
|---|---|---|---|
| 1017 | 457.35 | 0.65 | |
| 1018 | 429.3 | 0.61 | |
| 1019 | 427.94 | 2.87 | |
| 1020 | 441.37 | 0.63 | |
| 1021 | 404.1 | 0.67 | 1H NMR (300 MHz, DMSO-d6) δ 9.18 (d, J = 1.7 Hz, 1H), 8.68 (d, J = 2.1 Hz, 1H), 7.74-7.55 (m, 2H), 7.35 (dd, J = 7.0, 2.8 Hz, 1H), 7.33-7.13 (m, 1H), 6.03 (dd, J = 5.8, 2.8 Hz, 1H), 5.33 (d, J = 7.7 Hz, 1H), 3.89 (d, J = 11.5 Hz, 2H), 3.52-3.32 (m, 4H), 2.13 (d, J = 2.3 Hz, 3H), 1.94 (d, J = 13.0 Hz, 2H), 1.51-1.27 (m, 2H) ppm. |
| 1022 | 410.03 | 0.55 | 1H NMR (300 MHz, CDCl3) δ 9.04 (d, J = 2.4 Hz, 1H), 8.64 (dd, J = 4.7, 1.4 Hz, 1H), 8.40 (s, 1H), 8.03 (ddd, J = 8.3, 2.6, 1.5 Hz, 1H), 7.80 (d, J = 7.0 Hz, 1H), 7.48 (dd, J = 8.3, 4.8 Hz, 1H), 7.05 (s, 1H), 6.42 (d, J = 7.6 Hz, 1H), 4.72 (d, J = 6.5 Hz, 4H), 3.65 (d, J = 5.7 Hz, 1H), 3.19 (s, 4H), 2.58 (s, 4H), 2.38 (s, 3H) ppm. |
| 1023 | 469.32 | 0.6 | |
| 1024 | 457.33 | 2.63 | |
| 1025 | 482.38 | 0.57 | |
| 1026 | 429.36 | 2.78 | 1H NMR (400 MHz, Methanol-d4) δ 9.15 (s, 1H), 9.10-8.95 (m, 1H), 7.62-7.44 (m, 3H), 7.22-7.09 (m, 0H), 7.01 (tt, J = 9.0, 2.3 Hz, 2H), 4.32 (s, 0H), 4.25-4.20 (m, 1H), 4.01 (s, 1H), 3.89-3.72 (m, 3H), 3.66 (s, 6H), 3.61 (s, 1H), 3.45 (s, 1H), 3.35 (s, 2H), 3.38-3.29 (m, 1H), 3.18-3.03 (m, 2H), 3.06-2.98 (m, 6H), 2.66 (s, 7H), 2.46-2.29 (m, 3H), 2.33 (s, 4H), 2.18 (s, 2H), 2.08 (s, 3H) ppm. |
| 1027 | 455.37 | 0.64 | |
| 1028 | 391.05 | 0.93 | 1H NMR (300 MHz, CDCl3) δ 8.27 (s, 1H), 7.74-7.60 (m, 1H), 7.27-7.19 (m, 1H), 7.04 (d, J = 3.7 Hz, 1H), 6.73 (tt, J = 8.7, 2.3 Hz, 1H), 6.29 (dd, J = 7.3, 2.0 Hz, 1H), 4.90 (tt, J = 4.9, 2.6 Hz, 1H), 3.99-3.76 (m, 4H), 2.30 (d, J = 1.0 Hz, 3H), 2.22-1.97 (m, 2H) ppm. |
| 1029 | 400.26 | 2.14 | |
| 1030 | 429.9 | 3.22 | |
| 1031 | 413.3 | 0.65 | 1H NMR (400 MHz, DMSO-d6) δ 9.40 (s, 1H), 9.17 (s, 1H), 7.69-7.62 (m, 2H), 7.30-7.19 (m, 2H), 7.17 (s, 1H), 6.67 (s, 1H), 6.15 (s, 1H), 4.17 (t, J = 8.3 Hz, 2H), 3.54 (dd, J = 9.6, 5.3 Hz, 2H), 2.88-2.80 (m, 1H), 2.19 (s, 3H), 1.72 (s, 3H) ppm. |
| 1032 | 434.23 | 0.82 | 1H NMR (300 MHz, DMSO-d6) δ 9.74 (s, 1H), 9.21 (d, J = 1.2 Hz, 1H), 7.93-7.06 (m, 5H), 6.77-6.55 (m, 1H) ppm. |
| 1033 | 459.33 | 2.6 | |
| 1034 | 389.16 | 0.66 | 1H NMR (300 MHz, CDCl3) δ 8.32 (d, J = 2.0 Hz, 1H), 7.79-7.63 (m, 2H), 7.53 (td, J = 7.9, 2.0 Hz, 2H), 7.47-7.33 (m, 1H), 6.78-6.68 (m, 2H), 6.67-6.48 (m, 1H), 5.92 (d, J = 1.9 Hz, 1H), 3.98 (d, J = 2.1 Hz, 4H), 3.37 (d, J = 2.1 Hz, 4H), 2.39-2.12 (m, 4H), 0.97 (dd, J = 6.2, 2.1 Hz, 6H) ppm. |
| 1035 | 398.24 | 0.72 | 1H NMR (400 MHz, Methanol-d4) δ 8.94 (s, 1H), 8.02 (s, 1H), 7.62-7.55 (m, 3H), 7.38 (s, 1H), 7.10 (s, 1H), 7.00 (t, J = 9.1 Hz, 2H), 4.19-4.12 (m, 3H), 3.83 (d, J = 4.4 Hz, 5H), 2.99 (s, 0H), 2.65 (s, 1H), 2.44 (s, 4H), 1.08 (t, J = 3.6 Hz, 3H), 0.96-0.88 (m, 3H) ppm. |
| 1036 | 415.34 | 2.6 | 1H NMR (400 MHz, DMSO-d6) δ 9.62 (s, 1H), 9.42 (s, 1H), 9.16 (s, 1H), 7.72-7.56 (m, 2H), 7.30-7.19 (m, 1H), 7.15 (s, 1H), 6.95 (s, 1H), 6.39 (s, 1H), 5.44 (s, 1H), 3.88-3.67 (m, 4H), 3.59 (d, J = 12.0 Hz, 2H), 3.30-3.15 (m, 4H), 3.07 (t, J = 12.5 Hz, 2H), 2.25 (s, 3H) ppm. |
| 1037 | 420.31 | 1.93 | |
| 1038 | 438.67 | 4.68 | |
| 1039 | 406.17 | 0.65 | 1H NMR (300 MHz, CDCl3) δ 8.32 (s, 1H), 7.76-7.64 (m, 2H), 7.51 (t, J = 7.9 Hz, 2H), |

TABLE 3B-continued

Analytical Data

| Cmpd No. in US | LCMS (M + H) | LC/MS Ret. Time (min) | ¹H-NMR |
|---|---|---|---|
| | | | 7.36 (t, J = 7.4 Hz, 1H), 7.13 (s, 1H), 6.81 (s, 1H), 6.62 (s, 1H), 6.40 (s, 1H), 4.08-3.73 (m, 4H), 3.33 (s, 4H), 2.72 (d, J = 29.0 Hz, 4H), 2.34 (s, 3H), 2.20-1.92 (m, 2H) ppm. |
| 1040 | 441.32 | 2.64 | 1H NMR (400 MHz, DMSO-d6) δ 10.46 (s, 2H), 9.38 (s, 1H), 9.17 (s, 1H), 7.73-7.52 (m, 3H), 7.25 (t, J = 9.3 Hz, 1H), 7.03 (d, J = 13.4 Hz, 1H), 6.65 (d, J = 20.3 Hz, 1H), 6.00 (d, J = 12.0 Hz, 1H), 5.61 (s, 1H), 4.55-4.36 (m, 2H), 4.15-3.98 (m, 2H), 3.78-3.60 (m, 3H), 3.31-3.07 (m, 3H), 2.35-2.09 (m, 5H) ppm. |
| 1041 | 483.31 | 0.86 | 1H NMR (300 MHz, DMSO-d6) δ 9.64 (d, J = 12.7 Hz, 1H), 9.23-9.11 (m, 1H), 7.63 (d, J = 7.9 Hz, 1H), 7.50-7.07 (m, 4H), 6.95-6.78 (m, 1H), 6.68 (s, 1H), 2.11-1.89 (m, 0H), 0.86-0.51 (m, 4H) ppm. |
| 1042 | 449.5 | 0.69 | 1H NMR (300 MHz, DMSO-d6) δ 9.28 (s, 1H), 9.14 (s, 1H), 7.60 (d, J = 8.4 Hz, 2H), 7.26-7.20 (m, 1H), 7.12 (s, 1H), 6.87 (s, 1H), 6.30 (s, 1H), 3.87-3.74 (m, 2H), 3.66 (q, J = 8.0 Hz, 1H), 3.58-3.47 (m, 1H), 2.98-2.87 (m, 1H), 2.23 (s, 3H), 2.04-1.93 (m, 1H), 1.79-1.73 (m, 1H) ppm. |
| 1043 | 433.03 | 0.67 | 1H NMR (300 MHz, CDCl3) δ 8.43-8.19 (m, 1H), 7.75 (d, J = 7.4 Hz, 1H), 7.27 (s, 1H), 6.96 (d, J = 4.1 Hz, 1H), 6.81 (dt, J = 7.1, 4.6 Hz, 1H), 6.43 (d, J = 7.6 Hz, 1H), 3.69 (t, J = 5.3 Hz, 2H), 3.15 (t, J = 4.7 Hz, 4H), 2.74 (t, J = 4.8 Hz, 4H), 2.65 (t, J = 5.4 Hz, 2H), 2.39 (s, 3H) ppm. |
| 1044 | 421.4 | 0.71 | 1H NMR (300 MHz, DMSO-d6) δ 9.32 (s, 1H), 9.15 (s, 1H), 7.61 (d, J = 8.0 Hz, 2H), 7.33-7.19 (m, 1H), 7.15 (d, J = 2.2 Hz, 1H), 6.90 (s, 1H), 6.34 (s, 1H), 2.24 (s, 3H), 2.04 (s, 3H) ppm. |
| 1045 | 469.41 | 0.59 | |
| 1046 | 483.4 | 0.64 | |
| 1047 | 482.38 | 0.58 | |
| 1048 | 441.99 | 2.07 | |
| 1049 | 347.08 | 0.67 | 1H NMR (300 MHz, CDCl3) δ 8.41 (s, 1H), 7.81 (s, 1H), 7.78-7.69 (m, 2H), 7.56-7.46 (m, 2H), 7.40-7.32 (m, 1H), 7.21 (s, 1H), 6.95 (s, 1H), 6.82 (s, 1H), 6.57 (d, J = 1.3 Hz, 1H), 3.51 (s, 1H), 2.37 (s, 3H), 2.27 (d, J = 1.3 Hz, 3H) ppm. |
| 1050 | 443.33 | 0.68 | 1H NMR (400 MHz, DMSO-d6) δ 9.51 (s, 1H), 9.25 (s, 1H), 9.14 (s, 1H), 7.66 (dt, J = 7.3, 3.5 Hz, 2H), 7.24 (tt, J = 9.3, 2.5 Hz, 1H), 6.95 (d, J = 11.7 Hz, 1H), 6.54 (s, 1H), 6.00 (s, 1H), 3.76-3.61 (m, 3H), 3.35-3.05 (m, 6H), 2.94-2.80 (m, 1H), 2.63 (q, J = 10.4 Hz, 1H), 2.18 (s, 3H), 1.99 (dd, J = 34.4, 13.6 Hz, 2H), 1.79 (d, J = 14.3 Hz, 2H), 1.49-1.29 (m, 1H) ppm. |
| 1051 | 448.31 | 2.45 | |
| 1052 | 355.05 | 0.88 | 1H NMR (300 MHz, CDCl3) δ 8.27 (s, 1H), 7.81-7.69 (m, 1H), 7.68-7.58 (m, 2H), 7.55-7.38 (m, 2H), 7.37-7.29 (m, 1H), 7.01 (d, J = 3.7 Hz, 1H), 6.26 (dd, J = 7.4, 1.9 Hz, 1H), 4.89 (tt, J = 4.7, 2.5 Hz, 1H), 4.03-3.70 (m, 4H), 2.29 (d, J = 1.0 Hz, 3H), 2.19-1.95 (m, 2H) ppm. |
| 1053 | 391.09 | 0.93 | 1H NMR (300 MHz, CDCl3) δ 8.36 (s, 1H), 7.74 (dd, J = 7.1, 2.0 Hz, 1H), 7.32-7.28 (m, 1H), 7.14 (d, J = 3.7 Hz, 1H), 6.82 (tt, J = 8.7, 2.3 Hz, 1H), 6.38 (dd, J = 7.3, 1.9 Hz, 1H), 4.99 (tt, J = 5.0, 2.7 Hz, 1H), 2.39 (s, 3H), 2.33-2.09 (m, 2H) ppm. |

TABLE 3B-continued

Analytical Data

| Cmpd No. in US | LCMS (M + H) | LC/MS Ret. Time (min) | ¹H-NMR |
|---|---|---|---|
| 1054 | 469.32 | 0.58 | 1H NMR (400 MHz, Methanol-d4) δ 8.95 (s, 1H), 8.04 (d, J = 9.9 Hz, 1H), 7.69-7.61 (m, 2H), 7.38 (d, J = 2.0 Hz, 1H), 7.10 (s, 0H), 7.03-6.93 (m, 1H), 4.27 (s, 1H), 3.89 (s, 2H), 3.84 (d, J = 4.3 Hz, 1H), 3.67-3.55 (m, 1H), 3.51 (s, 1H), 3.24 (dd, J = 20.5, 11.6 Hz, 1H), 2.66 (s, 1H), 2.54 (s, 2H), 2.52 (s, 0H), 2.43 (s, 3H), 2.36-2.24 (m, 1H), 2.13 (s, 1H), 1.95-1.82 (m, 2H), 1.75 (t, J = 13.3 Hz, 1H) ppm. |
| 1055 | 391.05 | 0.91 | 1H NMR (300 MHz, CDCl3) δ 8.21 (s, 1H), 7.72-7.61 (m, 1H), 7.51 (ddd, J = 10.8, 6.8, 2.6 Hz, 1H), 7.33 (dddd, J = 8.9, 4.0, 2.6, 1.5 Hz, 1H), 7.30-7.21 (m, 1H), 7.09 (d, J = 3.7 Hz, 1H), 6.28 (dd, J = 7.3, 1.9 Hz, 1H), 4.89 (tt, J = 5.0, 2.6 Hz, 1H), 4.06-3.69 (m, 4H), 2.29 (d, J = 1.0 Hz, 3H), 2.21-2.00 (m, 2H) ppm. |
| 1056 | 457.38 | 0.7 | 1H NMR (400 MHz, DMSO-d6) δ 9.45 (s, 1H), 9.17 (s, 1H), 7.68-7.56 (m, 2H), 7.33-7.16 (m, 2H), 6.85 (s, 1H), 6.43-6.29 (m, 1H), 5.55 (s, 1H), 4.20-3.98 (m, 2H), 3.82-3.64 (m, 2H), 3.32-3.17 (m, 2H), 3.17-3.01 (m, 2H), 2.25 (s, 3H), 2.12-1.83 (m, 2H), 1.82-1.67 (m, 1H), 1.17 (d, J = 6.1 Hz, 3H), 1.03 (q, J = 7.5 Hz, 3H) ppm. |
| 1057 | 398.3 | 0.71 | |
| 1058 | 333.99 | 0.82 | 1H NMR (300 MHz, DMSO-d6) δ 10.03 (s, 1H), 9.33 (s, 1H), 9.06 (s, 1H), 7.95-7.84 (m, 2H), 7.75 (s, 1H), 7.54 (t, J = 8.0 Hz, 2H), 7.35 (t, J = 7.4 Hz, 1H), 7.05 (d, J = 1.9 Hz, 2H), 2.23 (s, 3H), 1.88-1.75 (m, 1H), 0.77 (m, 4H) ppm. |
| 1059 | 370.43 | 2.42 | |
| 1060 | 425.27 | 0.68 | |
| 1061 | 373.05 | 0.9 | 1H NMR (300 MHz, CDCl3) δ 8.37 (s, 1H), 7.78 (ddd, J = 7.2, 2.0, 0.8 Hz, 1H), 7.49 (ddt, J = 6.4, 2.8, 1.5 Hz, 3H), 7.19 (d, J = 3.7 Hz, 1H), 7.14-6.97 (m, 1H), 6.37 (dd, J = 7.4, 2.0 Hz, 1H), 4.98 (tt, J = 4.8, 2.5 Hz, 1H), 4.00-3.80 (m, 1H), 2.39 (d, J = 1.0 Hz, 3H), 2.31-2.09 (m, 2H) ppm. |
| 1062 | 415.37 | 2.64 | |
| 1063 | 457.38 | 0.71 | 1H NMR (400 MHz, DMSO-d6) δ 9.68 (s, 1H), 9.45 (s, 1H), 9.17 (s, 1H), 7.72-7.53 (m, 2H), 7.35-7.16 (m, 2H), 6.84 (s, 1H), 6.39 (s, 1H), 3.90-3.68 (m, 4H), 3.53 (q, J = 7.0 Hz, 3H), 3.30 (s, 2H), 3.05 (d, J = 12.9 Hz, 1H), 2.89 (t, J = 11.9 Hz, 1H), 2.24 (s, 3H), 1.38 (d, J = 6.2 Hz, 3H), 1.16 (t, J = 7.0 Hz, 3H) ppm. |
| 1064 | 454.91 | 2.44 | 1H NMR (400 MHz, DMSO-d6) δ 9.71 (s, 1H), 9.28 (s, 1H), 9.16 (s, 1H), 7.66 (d, J = 7.2 Hz, 2H), 7.28-7.23 (m, 1H), 7.02 (s, 1H), 6.56 (d, J = 14.8 Hz, 1H), 6.05 (s, 1H), 4.07 (d, J = 10.5 Hz, 1H), 3.96-3.91 (m, 2H), 3.55-3.40 (m, 5H), 3.29-3.24 (m, 1H), 3.19-3.08 (m, 2H), 2.17 (s, 4H), 2.03-1.98 (m, 1H), 1.65-1.60 (m, 1H) ppm. |
| 1065 | 400.19 | 2.05 | |
| 1066 | 380.33 | 0.73 | 1H NMR (300 MHz, DMSO-d6) δ 9.23 (s, 1H), 9.05 (s, 1H), 7.94 (dd, J = 11.4, 7.0 Hz, 1H), 7.66 (dd, J = 8.8, 6.4 Hz, 2H), 7.12 (s, 1H), 6.89 (s, 1H), 6.30 (s, 1H), 2.23 (s, 3H) ppm. |
| 1067 | 443.32 | 3.57 | |
| 1068 | 482.87 | 2.44 | |
| 1069 | 373.99 | 0.85 | 1H NMR (300 MHz, CDCl3) δ 8.36 (d, J = 2.1 Hz, 1H), 7.50-7.42 (m, 1H), 7.34-7.22 (m, 3H), 6.90-6.75 (m, 1H), 6.23 (s, 1H), 4.89 (ddd, J = 7.9, 6.1, 2.1 Hz, 2H), 4.60 (td, J = 6.1, 2.3 Hz, 2H), 4.52 (dd, J = 6.9, 2.3 Hz, 2H), 3.46 (p, J = 7.1 Hz, 1H), 2.39 (s, 3H) ppm. |

TABLE 3B-continued

Analytical Data

| Cmpd No. in US | LCMS (M + H) | LC/MS Ret. Time (min) | ¹H-NMR |
|---|---|---|---|
| 1070 | 439.32 | 0.65 | |
| 1071 | 407.16 | 0.67 | 1H NMR (300 MHz, DMSO-d6) δ 9.22 (s, 1H), 9.10 (s, 1H), 7.85-7.65 (m, 2H), 7.60 (td, J = 8.4, 6.3 Hz, 1H), 7.18 (tdd, J = 8.4, 2.4, 1.2 Hz, 1H), 6.84-6.58 (m, 2H), 3.81 (s, 4H), 3.22 (s, 4H), 2.19 (s, 4H), 0.84 (d, J = 6.1 Hz, 6H) ppm. |
| 1072 | 443.15 | 0.72 | 1H NMR (300 MHz, CDCl3) δ 8.35 (d, J = 1.9 Hz, 1H), 7.55 (d, J = 6.9 Hz, 1H), 7.33-7.28 (m, 1H), 7.25 (s, 1H), 7.02 (s, 1H), 6.83 (ddd, J = 8.6, 6.1, 3.3 Hz, 1H), 5.97 (d, J = 7.9 Hz, 1H), 4.65 (d, J = 10.4 Hz, 2H), 4.22 (s, 2H), 4.09 (d, J = 2.9 Hz, 2H), 3.87 (d, J = 10.5 Hz, 2H), 3.20 (s, 1H), 1.33 (dd, J = 6.5, 1.9 Hz, 6H) ppm. |
| 1073 | 402.31 | 0.7 | |
| 1074 | 483.4 | 0.6 | 1H NMR (400 MHz, DMSO-d6) δ 9.61 (s, 1H), 9.48 (s, 1H), 9.18 (s, 1H), 7.67-7.57 (m, 2H), 7.37 (s, 1H), 7.25 (tt, J = 9.2, 2.4 Hz, 1H), 6.92 (s, 1H), 6.48 (s, 1H), 3.74 (t, J = 5.0 Hz, 3H), 3.36 (q, J = 5.3 Hz, 3H), 3.12-3.02 (m, 4H), 2.25 (s, 3H), 2.06-1.96 (m, 4H), 1.92-1.81 (m, 2H), 1.79-1.56 (m, 3H) ppm. |
| 1075 | 371.18 | 1.69 | |
| 1076 | 381.16 | 2.08 | |
| 1077 | 469.35 | 0.71 | 1H NMR (400 MHz, DMSO-d6) δ 9.35 (s, 1H), 9.13 (s, 1H), 8.78 (s, 2H), 7.69-7.53 (m, 2H), 7.26 (tt, J = 9.4, 2.5 Hz, 1H), 6.78 (d, J = 11.3 Hz, 2H), 6.00 (s, 1H), 4.12-3.98 (m, 2H), 3.99-3.85 (m, 2H), 3.80 (dd, J = 12.3, 3.6 Hz, 1H), 3.64 (dd, J = 12.2, 6.2 Hz, 2H), 3.17-3.01 (m, 2H), 2.24 (s, 3H), 2.17-1.89 (m, 6H), 1.89-1.61 (m, 3H) ppm. |
| 1078 | 472.38 | 2.36 | |
| 1079 | 390.28 | 3.55 | |
| 1080 | 428.12 | 0.67 | 1H NMR (300 MHz, Methanol-d4) δ 7.55-7.43 (m, 2H), 7.19 (t, J = 2.2 Hz, 1H), 6.98-6.89 (m, 1H), 6.88 (s, 1H), 6.41 (t, J = 1.7 Hz, 1H), 4.69 (dt, J = 23.9, 6.4 Hz, 4H), 3.62-3.50 (m, 1H), 3.28-3.17 (m, 4H), 2.60-2.46 (m, 4H), 2.30 (s, 3H) ppm. |
| 1081 | 425.11 | 0.69 | |
| 1082 | 429.33 | 0.68 | 1H NMR (400 MHz, DMSO-d6) δ 9.30 (s, 1H), 9.15 (s, 1H), 7.72-7.60 (m, 2H), 7.25 (tt, J = 9.4, 2.3 Hz, 1H), 6.96 (d, J = 2.0 Hz, 1H), 6.63 (s, 1H), 6.04 (s, 1H), 3.97-3.86 (m, 2H), 3.81-3.73 (m, 2H), 3.52-3.37 (m, 5H), 3.32-3.19 (m, 2H), 2.19 (s, 3H), 1.23 (d, J = 5.6 Hz, 3H) ppm. |
| 1083 | 426.31 | 0.86 | 1H NMR (400 MHz, DMSO-d6) δ 9.28 (d, J = 3.4 Hz, 1H), 9.16 (s, 1H), 7.66-7.52 (m, 2H), 7.27-7.17 (m, 1H), 6.99 (d, J = 12.7 Hz, 1H), 6.54 (s, 1H), 5.91 (s, 1H), 3.86-3.73 (m, 2H), 3.68-3.58 (m, 2H), 3.33-3.28 (m, 1H), 3.27-3.17 (m, 2H), 2.22-2.10 (m, 5H), 2.09-1.96 (m, 2H), 1.68-1.55 (m, 2H) ppm. |
| 1084 | 471.1 | 2.12 | |
| 1085 | | | 1H NMR (300 MHz, CDCl3) δ 8.34 (s, 1H), 7.83 (dd, J = 7.3, 1.4 Hz, 1H), 7.75-7.66 (m, 2H), 7.58-7.47 (m, 2H), 7.42-7.34 (m, 1H), 6.96 (d, J = 4.0 Hz, 1H), 6.40 (dd, J = 7.7, 1.5 Hz, 1H), 4.72 (d, J = 6.6 Hz, 4H), 3.75-3.53 (m, 1H), 3.19 (s, 4H), 2.58 (s, 4H), 2.38 (s, 3H) ppm. |
| 1086 | 384.16 | 0.66 | 1H NMR (300 MHz, MeOD + CDCl3) δ 8.48 (s, 1H), 7.80-7.65 (m, 2H), 7.53 (d, J = 7.5 Hz, 2H), 7.37 (t, J = 7.4 Hz, 1H), 7.16 (s, 1H), 6.92 (s, 1H), 6.42 (s, 1H), 3.30 (s, 4H), 2.79 (s, 4H), 2.33 (s, 3H) ppm. |
| 1087 | 456.3 | 0.83 | 1H NMR (400 MHz, DMSO-d6) δ 9.39 (s, 1H), 9.15 (s, 1H), 7.66-7.55 (m, 2H), 7.24 (tt, J = 6.8, 3.4 Hz, 2H), 6.84 (s, 1H), 6.34 (s, 1H), 3.94 (dd, J = 11.5, 2.7 Hz, 1H), 3.77-3.69 (m, 1H), 3.65 (td, J = 11.4, 2.5 Hz, 1H), 3.59-3.46 (m, 5H), 3.26 (dd, J = 6.9, 1.5 Hz, 2H), 2.71 (s, 1H), 2.69 (td, J = 11.8, 3.4 Hz, 1H), 2.23 (s, 3H), |

TABLE 3B-continued

Analytical Data

| Cmpd No. in US | LCMS (M + H) | LC/MS Ret. Time (min) | ¹H-NMR |
|---|---|---|---|
| | | | 1.04-0.89 (m, 1H), 0.44 (dt, J = 8.1, 2.9 Hz, 2H), 0.18-0.09 (m, 2H) ppm. |
| 1088 | 465.06 | 0.68 | 1H NMR (300 MHz, DMSO-d6) δ 9.75 (s, 1H), 7.97 (t, J = 9.5 Hz, 1H), 7.80-7.57 (m, 2H), 7.28 (s, 1H), 6.93 (t, J = 55.7 Hz, 1H), 6.44 (s, 1H), 4.68-4.40 (m, 4H), 3.69-3.51 (m, 4H), 3.50-3.36 (m, 1H), 2.43-2.25 (m, 4H) ppm. |
| 1089 | 483.06 | 0.7 | 1H NMR (300 MHz, DMSO-d6) δ 9.99 (d, J = 2.2 Hz, 1H), 8.02-7.86 (m, 1H), 7.77-7.60 (m, 2H), 7.34 (s, 1H), 6.54 (s, 1H), 4.68-4.40 (m, 4H), 3.63 (s, 4H), 3.46 (d, J = 5.9 Hz, 1H), 2.35 (t, J = 4.9 Hz, 4H) ppm. |
| 1090 | 465.02 | 0.69 | 1H NMR (300 MHz, CDCl3) δ 7.48 (s, 1H), 7.34 (s, 1H), 7.31-7.20 (m, 2H), 6.89-6.75 (m, 1H), 6.51 (d, J = 56.2 Hz, 1H), 6.40 (s, 1H), 4.70 (dt, J = 9.7, 5.2 Hz, 4H), 3.71-3.60 (m, 4H), 3.55 (q, J = 6.4 Hz, 1H), 2.51-2.37 (m, 4H) ppm. |
| 1091 | 460.11 | 0.69 | 1H NMR (300 MHz, CDCl3) δ 8.04 (s, 1H), 7.94-7.76 (m, 1H), 7.73-7.51 (m, 2H), 7.41-7.17 (m, 1H), 6.87-6.63 (m, 2H), 6.43 (s, 1H), 4.73 (d, J = 6.5 Hz, 4H), 3.74-3.50 (m, 1H), 3.46-3.22 (m, 4H), 2.73-2.46 (m, 4H), 2.35 (s, 3H) ppm. |
| 1092 | 401.08 | 0.7 | 1H NMR (300 MHz, DMSO-d6) δ 9.25 (s, 1H), 7.68-7.52 (m, 2H), 7.21 (tt, J = 9.3, 2.4 Hz, 1H), 6.75 (s, 1H), 6.65 (s, 1H), 5.79 (s, 1H), 4.37 (s, 1H), 3.84-3.58 (m, 4H), 2.71 (q, J = 7.4 Hz, 1H), 2.20 (s, 3H), 1.07 (s, 6H) ppm. |
| 1093 | 400.05 | 0.67 | 1H NMR (300 MHz, DMSO-d6) δ 9.75 (s, 1H), 7.71-7.55 (m, 2H), 7.26 (tt, J = 9.2, 2.4 Hz, 1H), 6.90 (s, 1H), 6.82 (s, 1H), 3.83-3.59 (m, 4H), 3.44-3.32 (m, 4H), 1.97-1.77 (m, 1H), 0.92-0.70 (m, 4H) ppm. |
| 1094 | 444.2 | 3.72 | 1H NMR (300 MHz, CD3OD) δ 8.96 (s, 1H), 7.63-7.40 (m, 3H), 7.06-6.88 (m, 1H), 6.55 (d, J = 2.6 Hz, 1H), 3.77-3.50 (m, 9H), 2.27 (s, 4H), 2.15 (s, 4H) ppm. |
| 1095 | 434.28 | 0.81 | 1H NMR (300 MHz, DMSO-d6) δ 9.67 (s, 1H), 9.11 (d, J = 1.9 Hz, 1H), 7.93 (dd, J = 12.1, 7.3 Hz, 1H), 7.76-7.60 (m, 2H), 7.57-7.44 (m, 1H), 7.33 (s, 1H), 6.68 (s, 1H) ppm. |
| 1096 | 483.31 | 0.88 | 1H NMR (300 MHz, DMSO-d6) δ 9.59 (s, 1H), 9.09 (s, 1H), 7.97 (dd, J = 11.5, 7.1 Hz, 1H), 7.75-7.60 (m, 2H), 7.38 (s, 1H), 7.32 (s, 1H), 6.81 (t, J = 56.0 Hz, 1H), 6.67 (s, 1H), 2.07-1.93 (m, 1H), 0.86-0.60 (m, 6H) ppm. |
| 1097 | 435.49 | 0.7 | 1H NMR (300 MHz, DMSO-d6) δ 9.28 (s, 1H), 9.14 (s, 1H), 7.66-7.51 (m, 2H), 7.22 (s, 1H), 6.71 (d, J = 12.2 Hz, 2H), 5.82 (s, 1H), 3.89 (t, J = 7.0 Hz, 2H), 3.58 (t, J = 6.4 Hz, 2H), 3.30-3.25 (m, 1H), 2.19 (s, 3H) ppm. |
| 1098 | 435.49 | 0.7 | 1H NMR (300 MHz, DMSO-d6) δ 9.21 (s, 1H), 9.05 (s, 1H), 7.94 (dd, J = 12.0, 7.1 Hz, 1H), 7.75-7.56 (m, 2H), 6.71 (s, 2H), 5.81 (s, 1H), 3.89 (t, J = 7.0 Hz, 2H), 3.58 (t, J = 6.3 Hz, 2H), 3.28-3.22 (m, 0H), 2.20 (s, 3H) ppm. |
| 1099 | 416.4 | 0.75 | 1H NMR (300 MHz, DMSO-d6) δ 9.52 (s, 1H), 9.09 (s, 1H), 7.95 (dd, J = 11.9, 7.0 Hz, 1H), 7.73-7.56 (m, 2H), 7.40 (s, 1H), 7.22 (s, 1H), 6.88 (t, J = 56.4 Hz, 1H), 6.62 (s, 1H) ppm. |
| 1100 | 501.36 | 0.95 | 1H NMR (300 MHz, DMSO-d6) δ 9.74 (s, 1H), 9.12 (s, 1H), 7.95 (dd, J = 11.8, 7.0 Hz, 1H), 7.73-7.60 (m, 2H), 7.53-7.46 (m, 1H), 7.43 (s, 1H), 6.75 (s, 1H), 2.10-1.95 (m, 1H), 0.84-0.66 (m, 4H) ppm. |
| 1101 | 416.31 | 0.85 | 1H NMR (300 MHz, DMSO-d6) δ 9.68 (s, 1H), 9.17 (s, 1H), 7.77-7.51 (m, 4H), 7.34 (s, 1H), 7.28-7.14 (m, 1H), 6.68 (s, 1H) ppm. |
| 1102 | 398.44 | 0.73 | 1H NMR (300 MHz, DMSO-d6) δ 9.54 (s, 1H), 9.15 (s, 1H), 7.78-7.66 (m, 2H), 7.60 (td, J = 8.6, 3.9 Hz, 1H), 7.44 (s, 1H), 7.27-7.12 (m, 2H), 7.10-6.67 (m, 1H), 6.62 (s, 1H) ppm. |

TABLE 3B-continued

Analytical Data

| Cmpd No. in US | LCMS (M + H) | LC/MS Ret. Time (min) | ¹H-NMR |
|---|---|---|---|
| 1103 | 483.36 | 0.94 | 1H NMR (300 MHz, DMSO-d6) δ 9.75 (s, 1H), 9.18 (s, 1H), 7.78-7.67 (m, 2H), 7.67-7.56 (m, 1H), 7.51 (d, J = 2.1 Hz, 1H), 7.46 (d, J = 2.0 Hz, 1H), 7.27-7.14 (m, 1H), 6.76 (s, 1H), 2.09-1.97 (m, 1H), 0.84-0.61 (m, 4H) ppm. |
| 1104 | 465.44 | 0.88 | 1H NMR (300 MHz, DMSO-d6) δ 9.61 (s, 1H), 9.16 (s, 1H), 7.80-7.67 (m, 2H), 7.67-7.55 (m, 1H), 7.41 (s, 1H), 7.34 (s, 1H), 7.25-7.15 (m, 1H), 7.13-6.72 (m, 1H), 6.71-6.60 (m, 1H), 2.13-1.90 (m, 1H), 0.87-0.55 (m, 4H) ppm. |
| 1105 | 400.09 | 0.7 | 1H NMR (300 MHz, DMSO-d6) δ 9.85 (s, 1H), 9.25 (s, 1H), 9.01 (s, 1H), 8.72-8.63 (m, 1H), 8.63-8.50 (m, 1H), 7.54 (s, 1H), 7.38 (s, 1H), 6.71 (s, 1H) ppm. |
| 1106 | 382.09 | 0.63 | 1H NMR (300 MHz, DMSO-d6) δ 9.71 (s, 1H), 9.23 (s, 1H), 9.12-9.00 (m, 1H), 8.68 (d, J = 2.4 Hz, 1H), 8.63-8.54 (m, 1H), 7.41 (s, 1H), 7.30 (s, 1H), 7.13-6.71 (m, 1H), 6.65 (s, 1H) ppm. |
| 1107 | 449.14 | 0.76 | 1H NMR (300 MHz, DMSO-d6) δ 9.78 (s, 1H), 9.25 (s, 1H), 9.10 (s, 1H), 8.69 (d, J = 2.5 Hz, 1H), 8.60 (s, 1H), 7.40 (s, 2H), 7.11-6.77 (m, 1H), 6.71 (s, 1H), 2.11-1.93 (m, 0H), 0.80-0.70 (m, 4H) ppm. |
| 1108 | 396.13 | 0.64 | |
| 1109 | 409.99 | 1.02 | 1H NMR (300 MHz, CDCl3) δ 8.34 (s, 1H), 7.51-7.22 (m, 9H), 6.80 (t, J = 8.6 Hz, 1H), 6.27 (s, 1H), 4.41 (s, 2H), 2.32 (s, 3H) ppm. |
| 1110 | 428.49 | 0.7 | 1H NMR (300 MHz, CDCl3) δ 8.31 (s, 1H), 7.25 (dd, J = 7.8, 2.0 Hz, 2H), 7.12 (s, 1H), 6.87-6.73 (m, 2H), 6.66 (s, 1H), 6.43 (s, 1H), 4.80-4.61 (m, 4H), 3.40-3.21 (m, 4H), 2.64-2.48 (m, 4H), 2.35 (s, 3H) ppm. |
| 1111 | 357.29 | 0.63 | 1H NMR (300 MHz, MeOD) δ 8.78 (s, 1H), 7.83-7.74 (m, 2H), 7.52 (t, J = 7.9 Hz, 2H), 7.36 (t, J = 7.4 Hz, 1H), 7.19 (s, 1H), 6.91 (s, 1H), 6.40 (s, 1H), 2.49 (s, 3H), 2.29 (s, 3H) ppm. |
| 1112 | 501.1 | 0.88 | 1H NMR (300 MHz, CDCl₃) δ 8.39 (s, 1H), 7.70 (d, J = 7.5 Hz, 1H), 7.39-7.27 (m, 1H), 7.23 (s, 1H), 6.88-6.69 (m, 1H), 6.48-6.23 (m, 1H), 4.12-3.90 (m, 2H), 3.71 (d, J = 26.9 Hz, 4H), 3.54-3.26 (m, 3H), 2.83 (dd, J = 22.2, 9.2 Hz, 9H), 2.32 (d, J = 6.4 Hz, 3H), 2.03-1.80 (m, 2H) ppm. |
| 1113 | 500.2 | 0.64 | 1H NMR (300 MHz, CDCl₃) δ 8.36 (s, 1H), 7.71 (s, 1H), 7.40-7.27 (m, 1H), 7.20 (d, J = 5.1 Hz, 1H), 6.75 (s, 1H), 6.32 (d, J = 7.3 Hz, 1H), 3.98 (s, 2H), 3.80-3.26 (m, 9H), 3.12 (d, J = 12.1 Hz, 4H), 2.31 (d, J = 17.6 Hz, 6H), 1.41 (d, J = 6.3 Hz, 3H) ppm. |
| 1114 | 461.15 | 0.72 | 1H NMR (300 MHz, CDCl₃) δ 8.35 (s, 1H), 7.38 (s, 2H), 7.20 (d, J = 6.0 Hz, 1H), 6.05 (d, J = 8.0 Hz, 1H), 4.03-3.80 (m, 2H), 3.80-3.40 (m, 5H), 3.38-3.26 (m, 2H), 2.82 (s, 1H), 2.51 (s, 1H), 2.37-2.10 (m, 3H), 1.03-0.69 (m, 3H) ppm. |
| 1115 | 487.11 | 0.7 | 1H NMR (300 MHz, CDCl₃) δ 8.35 (s, 1H), 7.35 (d, J = 7.8 Hz, 1H), 7.23-7.14 (m, 2H), 6.72 (tt, J = 8.7, 2.3 Hz, 1H), 6.08 (d, J = 7.5 Hz, 1H), 3.98-3.76 (m, 2H), 3.69 (q, J = 7.7 Hz, 2H), 3.41 (dd, J = 8.8, 6.2 Hz, 2H), 3.06 (td, J = 12.8, 6.6 Hz, 3H), 2.61 (dq, J = 15.7, 8.7, 7.9 Hz, 2H), 2.35-2.05 (m, 6H), 1.90 (s, 2H), 1.63 (dq, J = 14.7, 7.5 Hz, 1H) ppm. |
| 1116 | 487.16 | 0.72 | 1H NMR (300 MHz, CDCl₃) δ 8.33 (d, J = 7.2 Hz, 1H), 7.35 (s, 1H), 7.26 (d, J = 7.6 Hz, 1H), 7.19 (d, J = 5.8 Hz, 1H), 6.73 (s, 1H), 6.09 (s, 1H), 4.19 (s, 1H), 3.81 (d, 3H), 3.47 (s, 2H), 3.31 (s, 2H), 2.24 (t, J = 4.4 Hz, 6H), 1.46 (s, 1H) ppm. |

TABLE 3B-continued

Analytical Data

| Cmpd No. in US | LCMS (M + H) | LC/MS Ret. Time (min) | ¹H-NMR |
|---|---|---|---|
| 1117 | 458.18 | 0.68 | 1H NMR (300 MHz, CDCl₃) δ 7.40 (d, J = 6.9 Hz, 1H), 7.24 (s, 1H), 7.20 (dd, J = 7.2, 2.3 Hz, 1H), 5.86 (d, J = 8.0 Hz, 1H), 4.01 (s, 2H), 3.69 (s, 2H), 3.60-3.16 (m, 5H), 2.75 (d, J = 3.8 Hz, 4H) ppm. |
| 1118 | 459.12 | 0.71 | 1H NMR (300 MHz, CDCl₃) δ 8.36 (s, 1H), 7.31 (d, J = 6.9 Hz, 1H), 7.22-7.11 (m, 2H), 6.72 (tt, J = 8.8, 2.4 Hz, 1H), 4.10-3.78 (m, 3H), 3.54 (dd, J = 24.9, 12.1 Hz, 2H), 3.30 (dq, J = 5.9, 4.2 Hz, 2H), 3.19 (dd, J = 13.4, 5.2 Hz, 2H), 3.05-2.76 (m, 3H), 2.38 (dq, J = 7.3, 3.9 Hz, 1H), 1.19 (dq, J = 5.7, 3.8, 3.0 Hz, 2H), 0.89-0.66 (m, 2H) ppm. |
| 1119 | 447.07 | 0.71 | 1H NMR (300 MHz, CDCl₃) δ 8.35 (s, 1H), 7.37 (s, 2H), 6.71 (dd, J = 12.3, 5.4 Hz, 1H), 4.11-3.79 (m, 4H), 3.62-3.24 (m, 4H), 2.24 (t, J = 8.1 Hz, 3H), 1.15 (t, J = 5.7 Hz, 3H) ppm. |
| 1120 | 462.09 | 1.03 | 1H NMR (300 MHz, CDCl₃) δ 7.38 (s, 1H), 7.12 (s, 2H), 6.57 (s, 1H), 4.14 (s, 1H), 3.62 (d, J = 29.6 Hz, 2H), 3.44-3.15 (m, 3H), 2.90 (s, 1H), 2.58 (s, 1H), 2.21-1.85 (m, 3H), 0.93 (dd, J = 30.1, 9.2 Hz, 8H) ppm. |
| 1121 | 459.12 | 0.71 | 1H NMR (300 MHz, CDCl₃) δ 8.35 (s, 1H), 7.39 (s, 2H), 7.24 (s, 2H), 7.20 (d, J = 6.3 Hz, 2H), 6.29-5.59 (m, 1H), 3.80 (p, J = 6.2, 5.3 Hz, 4H), 3.49-3.25 (m, 7H), 1.35 (t, J = 9.1 Hz, 2H), 0.83 (t, J = 6.4 Hz, 2H) ppm. |
| 1122 | 430.1 | 0.95 | 1H NMR (300 MHz, CDCl₃) δ 8.33 (s, 1H), 7.38 (d, J = 7.0 Hz, 1H), 7.23-7.14 (m, 2H), 6.78-6.62 (m, 1H), 3.98 (td, J = 7.6, 2.3 Hz, 2H), 3.88-3.75 (m, 2H), 3.71 (td, J = 8.6, 8.0, 5.9 Hz, 1H), 3.56 (dd, J = 13.6, 6.7 Hz, 2H), 3.39 (dd, J = 8.6, 5.7 Hz, 1H), 2.71-2.40 (m, 2H), 2.24 (d, J = 2.9 Hz, 3H), 1.51 (dt, J = 13.6, 7.0 Hz, 1H) ppm. |
| 1123 | 475.1 | 0.71 | 1H NMR (300 MHz, CDCl₃) δ 8.36 (s, 1H), 7.68 (d, J = 7.9 Hz, 1H), 7.24 (s, 1H), 7.19 (d, J = 2.5 Hz, 1H), 6.86-6.60 (m, 1H), 6.32 (d, J = 7.9 Hz, 1H), 3.28 (tt, J = 5.9, 3.3 Hz, 7H), 2.90 (s, 1H), 1.38 (dd, J = 33.4, 7.4 Hz, 8H) ppm. |

Assays for Detecting and Measuring Remyelination Properties of Compounds

In Vivo Mouse Cuprizone Assay:

Cuprizone Feeding Protocol:

2 month old female C57BL/6 mice (Stock Number: 000664) were purchased from Jackson Labs and fed for 4-10 months with a 0.2% cuprizone chow (provided by Research Diets, Product # D10020701R, Description AIN-76A Rodent Diet with 0.2% cuprizone) using cuprizone purchased from Sigma (Cat #14690-100G). Chow was provided ad libitum, and refreshed every 4 days to ensure stability of the cuprizone. Mice were maintained on this diet for 4-10 months before initiation of the experiments.

Dosing and PK:

1) 24 hours prior to the start of dosing, 6 to 10 mice were switched from cuprizone chow to normal chow (Picolab rodent diet 20 EXT IRR 5053, irradiated) without added cuprizone. These mice were maintained on normal chow throughout the course of dosing.

2) 6 to 10 mice per group were randomized into new cages such that mice that were housed in one cage during the cuprizone diet were not housed together in one dose group during the study.

3) Mice were dosed with compound in one of two regimens: Regimen A: mice were dosed QD or BID for 14 days via oral gavage. Regimen B: mice were dosed QD or BID for 14 days via IP injection. However, other dosing schedules and/or routes of administration may also be used.

4) On the last day of dosing, dried blood spots were collected at multiple time points following the last dose. Often this was 30 minutes, 2, 6 and 24 hours following the final dose on day 14 via the tail vein.

Perfusion and Sectioning:

1) The day after the last day of dosing, mice were transcardially perfused with 12 ml of PBS (Sigma, P4417) followed by 20 ml of 3.2% paraformaldehyde in PBS (Electron Microscopy Sciences #15714-S). The brains were removed via standard dissection techniques and each was postfixed in 3.2% paraformaldehyde (20 ml) for 24-48 hours at room temperature in sealed scintillation vials.

2) Serial 50 micron sections were collected through the anterior posterior extent of the brain, from just behind the olfactory bulb, through visual cortex using a vibrating microtome, the V-STAR (described in International Publication No. WO 2013/012799 and U.S. Pat. No. 8,967,024 both of which are incorporated herein by reference in their entirety). Sections were collected in phosphate buffered saline (PBS). Vibratome speed was set to 1.1 mm/s and amplitude was set to 0.8 mm.

3) A series of every 24th section was removed for staining yielding 5 sections per brain.

Staining:

1) Tissue sections were stained using an automated system for processing blots (hereinafter the "blotinator") (described in WO2011/087646 and U.S. Pat. Nos. 8,337,754 and 8,679,406 each of which is incorporated herein by reference in its entirety). Brain sections were placed in the blotinator plate and bathed in PBS. The blotinator applied primary antibodies (MOG and MBP together) and Hoechst nuclear stain for 12 hours at room temperature with constant shaking.

The following stains were diluted in blocking buffer (described below):

Hoechst nuclear stain (0.5 mg/ml)(bisBenzimide H 33342 trihydrochloride Sigma #33342).

Myelin basic Protein (MBP) antibody (Abcam Cat # ab7349) was diluted at a 1:750 ratio in blocking buffer).

Myelin Oligodendrocyte Glycoprotein (MOG) (R&D systems Cat # AF2439) was diluted at a 1:250 ratio in blocking buffer.

Antibodies were diluted in blocking buffer, which consisted of 0.3% Triton X-100 (Sigma Cat #234729), 0.02% Sodium Azide (Sigma Cat # S2002) and 8% fetal bovine serum in PBS (Sigma Cat # F2442).

2) The blotinator washed the samples 4 times for 5 minutes each with a wash buffer (0.2% Triton X-100 in PBS).

3) The blotinator applied secondary antibodies diluted in blocking buffer and incubated them for 2 hours with constant shaking.

Alexa 488 donkey anti-rat secondary (Life technologies Cat # A-21208) was diluted at 1:1000 in blocking buffer.

Alexa 568 donkey anti-goat secondary (Life technologies Cat # A-11057) was diluted at 1:1000 in blocking buffer.

Antibodies were also diluted in blocking buffer described above.

4) The samples were then washed 4 times for 5 minutes each with wash buffer (0.2% Triton X-100 in PBS).

5) All 5 sections were mounted on a slide (Fisherbrand Superfrost Plus microscope slide Cat #12-550-15) and coverslip with 50 microliters Fluormount (Sigma cat # F4680-25 ml) in preparation for scanning.

Scanning:

Images were scanned using an Olympus CS120 fluorescent scanning microscope. Entire sections were scanned at 10× magnification, with 500 millisecond exposures for the 488 and 568 nanometer fluorescent channels. The Hoechst signal was detected using a 100 millisecond exposure.

In Vivo Myelin Detection Software:

A custom algorithm was developed in house and was used to quantify the amount of new myelin in mice that had been demyelinated with cuprizone and subsequently treated with compounds. Conceptually, the software subtracted a mature myelin marker from a pan-myelin (young and old myelin) marker, and measured the area of the remaining "new" myelin. Myelin oligodendrocyte glycoprotein ("MOG") is specific to old myelin, while myelin basic protein ("MBP") is a pan myelin marker, expressed in more immature myelin as well as more mature myelin. This process accounted for the variability inherent in the demyelination process, in which some animals experience more demyelination than others. It more accurately measured myelin generated in response to compound treatment.

The algorithm was written using Definiens Tissue Studio and Definiens Developer XD. There are several steps to the algorithm, each of which are discussed below.

Three channels of information for each sample was loaded. The intensity levels of the three images were summed, and the resulting image was used to determine the "tissue" area. Subsequent analyses was done exclusively on the tissue area.

The MOG channel was loaded and the Definiens "Auto Threshold" function was used to distinguish MOG positive regions from background. Regions of putative white matter with areas <50 pixels were returned to the tissue class. Thus, remaining white matter tracts that resisted demyelination from cuprizone were excluded from subsequent analyses.

The ratio of MBP signal to MOG signal was calculated. This consisted of the mean MBP intensity value divided by the mean MOG intensity value over the entirety of the image. This MBP:MOG ratio was used to normalize the intensity between the MBP and MOG channels. The normalized MOG signal multiplied by 0.5 was subtracted from the MBP signal, creating a new image, "MBP-MOG". The "Auto Threshold" function was used on the MBP-MOG image, and the 'new' myelin consisting of pixels with intensities above the threshold was delineated. Regions of putative new myelin with areas <2 pixels were returned to the tissue class, and the number of pixels positive for "new" myelin was measured.

The algorithm returned the area of the tissue and the MBP positive, MOG negative 'new' myelin. Each section was normalized by area relative to its comparable tissue (e.g., the first). Most anterior sections were normalized relative to other first anterior sections. The 5 normalized MBP+/MOG− areas were summed, yielding a total positive area per sample. This yielded a representation of myelin synthesis over the whole extent of the brain, excluding the olfactory bulb and the cerebellum.

Compounds 33, 48, 107, 195, 215, 247, 331, 406, 485, 512, 524 and 691 were tested in the in vivo Mouse Cuprizone assay described above using Regimen A at various doses (milligrams per kilogram or "mpk") and all had a positive effect (measured as new myelin generated in response to compound treatment compared to control with no added compound). Compound 33 showed a positive effect at 10, 25 and 50 mpk. Compound 48 showed a positive effect at 30, 50 and 100 mpk. Compound 195 showed a positive effect at 60 and 100 mpk. Compound 215 showed a positive effect at 30 and 90 mpk. Compound 406 showed a positive effect at 25 and 50 mpk. Compound 331 showed a positive effect at 20, 30 and 40 mpk. Compound 485 showed a positive effect at 20 and 30 mpk. Compound 512 showed a positive effect at 50 mpk. Compound 524 showed a positive effect at 10, 20 and 30 mpk. Compound 691 showed a positive effect at 8, 10 and 20 mpk. Compound 107 showed a positive effect at 30 and 90 mpk. Compound 247 showed a positive effect at 10, 25 and 50 mpk.

In Vitro Myelination Assay

Compounds were screened for their ability to induce myelination using a primary rat mixed cortical cell culture assay, which contains neurons, oligodendrocyte precursor cells, oligodendrocytes, astrocytes and microglia. The assay quantifies myelination by measuring myelin basic protein (MBP) immunofluorescent positive myelin strands from images taken using a Cellomics Array Scan (model Arrayscan VTI HCS Reader) or a Molecular Devices Image Xpress (model IXM XL) high content imager. The myelin strands were quantitated using a custom created myelin detection software program. Test compounds were dissolved in DMSO to make a 10 mM initial stock solution. Dilutions were made in myelination medium to obtain the final solutions for the assay and were tested in primary rat mixed cortical cells at selected doses.

Primary rat mixed cortical cells were prepared from harvested cerebral cortices from postnatal day 1 (P1) rats (P1 Rat CD® IGS pups) were purchased from Charles River) in Complete Dissociation Medium, wherein the meninges were removed and the cortical tissue chopped with a razor blade into ~1 mm$^3$ pieces. Tissue from 1-3 pups was collected and placed into 15 ml conical tubes in a total volume of 5 ml of Complete Dissociation Medium. Activated papain (3 ml) was added to each 15 ml conical tube and tissue was incubated at 37° C. for 30 minutes. After the 30 minute incubation, DNase (Sigma D4527; 75 µl of a 1 mg/ml stock) was added to each tube, followed by mechanical trituration using a 2 ml serological pipette and autopipettor to gently dissociate the tissue. Following trituration, larger tissue pieces were allowed to settle by gravity, and the supernatant containing dissociated cells was transferred to a 50 ml conical tube with 4 ml of trypsin inhibitor. Cells were pelleted by centrifugation, resuspended in myelination medium and filtered through a 40 µm filter. Cells were then seeded in 96-well plates (BD Biosciences, Black, PDL-coated, Cat. No. 356640) at 87,500-95,000 cells/well in a final volume of 200 µl of Myelination Medium in the presence or absence of compound and cultured for 14 days in a humidified 37° C. incubator with 5% $CO_2$. Half the medium was removed and replaced with fresh medium containing 1× compound on days 6 and 10. Using a Biotek automatic plate washer (model Biomek® FXP Laboratory Automation Workstation), cells were fixed with 4% paraformaldehyde on day 14, washed with PBS and blocked in 5% normal goat serum (Vector Laboratories, S-1000) in 0.1% PBS-TritonX-100 (PBST) for 1 hour. Cells were stained with 1:500 anti-MBP (Covance, cat # SMI99) primary antibody in 1% normal goat serum in 0.1% PBST for 2 hours at room temperature followed by 2 washes with PBST. A final incubation in secondary antibody (1:1000, Invitrogen, Alexa-488 anti-mouse IgG2b) and 1:10,000 Hoechst dye in 1% normal goat serum in 0.1% PBST was performed for 2 hours at room temperature. Plates were washed with PBS and then scanned on a Cellomics Array Scan using a 10× objective (25 images per well) or the Image Xpress using a 10× objective (9 image per well). Images were analyzed using Vertex myelin detection software (described below) to quantify total MBP myelin pixels per well. Fold myelin pixels above background at two concentrations (1.0 µM and 10.0 µM) relative to baseline of no added compound are reported below in Table 4. Standard deviation for each compound concentration was calculated using all replicates and using a standard deviation formula commonly used in the art.

One of skill in the art would recognize that for this type of primary neuronal mixed cell assay variability between different assay runs is to be expected even though the protocol is the same for each assay run. For instance, variability may be due to small differences in cell viability, cell density, age of the animals, etc.

Vertex Myelin Detection Software:

The Vertex myelin detection software was used to quantify the amount of myelin wrapping axons in a digital image that was obtained from our in-house microscope. Conceptually, the software identified and traced MBP positive ridge like structures in the image that were indicative of myelinating axons. A confounding factor in the analysis was the large debris fields typically occurring in the images. These fields resulted from the assay conditions required to achieve myelination. Special care was taken to ensure that noise in the image induced by the debris field was appropriately suppressed so that the signal that arose from the myelination could be recovered. The software was written in the Jython programming language and made significant utilization of the Fiji image analysis toolkits (see, Schindelin, J.; Arganda-Carreras, I. & Frise, E. et al., "Fiji: an open-source platform for biological-image analysis", *Nature Methods* 9(7): 676-682, 2012). There were several steps to the algorithm, each of which are discussed below.

Initially the image was loaded and converted to a 256-bit grey scale representation. Image contrast was enhanced by performing standard histogram stretching. The saturation parameter for the enhancement was set at 0.35, meaning the upper and lower 3.5% of the distribution of the gray scale values present in the image were removed prior to enhancement. The Frangi[2] vesselness measure, which computes the likelihood of a pixel belonging to a ridge-like structure, was applied to the resulting image (see, Frangi A F, Niessen W J, Vincken K L, Viergever M A "Multiscale vessel enhancement filtering", *Proceedings of Medical Image Computer-Assisted Intervention (MICCAI)*, Lecture notes in computer science 1496: 130-137, 1998). The Frangi process created a "vessel likeness image" which was then converted to a binary image mask. The threshold of the Frangi measure for conversion to the mask was adjusted so that appropriate regions of the input image were selected. Once the mask was created, morphological closing was applied to remove small holes. Small structures were removed from the mask by deleting regions containing less than 40 connected pixels. The resulting mask overlaps regions of the original image that had a high likelihood of containing myelin strands.

Morphological skeletonization was applied to the binary mask and the resulting image was then converted to a graph data structure. Each node of the graph represented a pixel of the image. Owing to the skeletonization process, each node was connected to at most 4 neighboring pixels. Nodes connected to one other node indicated the end of a myelin strand ("end nodes"); nodes connected to exactly two other nodes indicated a pixel contained in a myelin strand ("myelin node"); while nodes connected to 3 or 4 other nodes indicated regions where myelin strands intersect ("join nodes"). Neighboring 'myelin nodes' that were adjacent to the same "join node" were merged into longer strands of myelin. This process was done in a greedy fashion. The longest strand of myelin originating from an "end node" in the graph were identified. If this strand terminated in an end node the strand was extracted from the graph. If the strand terminated at a "join node" then it was joined with one of the other myelin strands adjacent to the same join node. The largest angle between the growing strand and all other strands adjacent to the join node was determined. If this angle was greater or equal to 140 degrees, then the growing strand and the strand that made this large angle were merged into one strand. The two strands that were merged were removed from being adjacent to the "join node". If the angle was less than 140 degrees, the growing strand was extracted from the graph and removed as being adjacent to the join node. The entire process was repeated until all strands were removed from the graph. Various geometric properties of the strand such as length and maximum curvature were computed from the number of pixels in the strand and the connectivity of the graph.

Before a putative myelin strand was quantified as myelin it was subjected to several quality control measures. The strand needed to be of a sufficient length (at least greater than 40 pixels). To ensure the strand was not overly curved, the ratio of the geometric distance between strand endpoints to the length of the strand needed to be greater than or equal to 0.8. Finally, to ensure the strand was not overly thick, the gray scale gradient at each point on the strand in the directions orthogonal to the strand direction needed to decay sufficiently rapidly. Specifically, the gray scale needed to decrease by 25% from the gray scale value of pixel intersected by the orthogonal line and the putative myelin strand. This decrease needed to occur within 5 pixels. If a strand passes all quality checks it was quantified as myelin.

Reagent and Media Preparation and Animal Source for the In Vitro Myelination Assay 10× Dissociation Media (DM):

10×DM was prepared on a 1 liter scale by combining 900 mM Na2SO4, 300 mM K2SO4, 58 mM MgCl2, 2.5 mM CaCl2, 10 mM HEPES and 20 mL of a phenol red solution (0.5%). The pH was adjusted with 0.1N NaOH by eye until orange-red. The solution was then sterilized by filtration through a 0.2 uM filter (prewashed with 100 ml of deionized sterile water which was discarded prior to filtration of the DM media solution.

10×KyMg Stock:

KyMg stock was prepared on a 200 mL scale as follows. To a 250 mL flask was added 190 mL of water, 1 mL of phenol red (Sigma P0290), stock, 1.75 mL of 1N NaOH, 378 mg of kynurenic acid, and 2 mL 500 mM HEPES. The mixture was then sonicated to dissolve the kynurenate and then MgCl2 (4.1 ml of a 4.9 M solution) was added. The pH was adjusted to 7.4 by adding up to 1 ml of 0.1N NaOH and the mixture sterilized by filtration through a prewashed nylon filter (0.2 μm pore).

Complete Dissociation Medium (DM):

5 mL Ky Mg to 45 mL 1×DM media

Papain Enzyme Solution (Worthington Biochemical, LK003178):

A 10 units/mL stock solution was made fresh the day of dissection by adding 1 mL of 10 mM NaOH and Complete Dissociation Medium to one vial of papain (~100 units) to give a 10 units/mL final concentration. The papain was activated at 37° C. for 10-15 minutes prior to use.

Trypsin Inhibitor Solution:

9.6 mL of Complete Dissociation Medium was added to 100 mg of trypsin inhibitor (type II-O; Sigma T-9253) and the mixture was sonicated. The pH was adjusted to ~5.75 using 1N NaOH and pH strips. Aliquots (4 mL) were measured out and and stored at –20° C.

DNase I Solution 1 mg/mL):

Added 25 mL DMEM/F12 medium (Corning, 10-092-CM) to 20 KU DNAse I (Sigma D4527) and aliquoted into one time use aliquots stored at –20° C.

Myelination Medium:
DMEM (Invitrogen, Cat #11960-051)
1:50 B27 (Invitrogen, Cat #17504-044)
1% FBS (HyClone)
2 mM Glutamax (1:100) (Cat # Gibco 25030081)
Pen Strep (1:100) 10,000 units/mL (Cat # Gibco 15140122)
PDGF/FGF 0.3 ng/mL each (3 uL per 100 mL; PeproTech, cat #100-13A and cat #100-18B Myelination medium was made fresh the day of use from a stock bottle of DMEM containing penicillin/streptomycin and Glutamax, which was stored at 4° C. for up to one month. On the day of use, 1:50 B27, 1% FBS and 0.3 ng/mL of PDGF and FGF were added to the DMEM containing penicillin/streptomycin and Glutamax.

Other in vitro and in vivo assays and models known in the art may also be used to show induction of remyelination in response to treatment with compounds such as those of the present invention (see, Nalm, F. J. et al., Nature (Letter), published online 20 Apr. 2015, doi:10.1038/nature14335 and Macklin, W. B. et al., *Developmental Cell*, 32, pp 447-458 (2015))

TABLE 4

Remyelination in vitro data. The activities of the compounds below were determined by testing groups of compounds in different test batches. Compounds with no asterisk were part of one or more in vitro assay testing batches. Compound numbers indicated with an asterisk were all part of the same in vitro assay test batch. Compound numbers with a double asterisk were part of a different in vitro assay test batch. Compound numbers with a # symbol were part of a different in vitro assay batch. Compounds in Table 4 below have between less than 1 fold to greater than 10,000 fold myelin pixels above background at two concentrations (1.0 μM and 10.0 μM) relative to baseline of no added compound.

| Cmpd No. | 10.0 μM | 1.0 μM |
| --- | --- | --- |
| 1 | +++ | ++++ |
| 2 | +++ | +++ |
| 3 | ++++ | +++ |
| 4 | – | + |
| 5 | – | ++++ |
| 6 | ++ | +++ |
| 7 | ++++ | ++++ |
| 8 | + | +++ |
| 9 | +++ | ++++ |
| 10 | – | + |
| 11 | ++++ | ++++ |
| 12 | + | +++ |
| 13 | – | +++ |
| 14 | – | ++++ |
| 15 | ++ | +++ |
| 16 | ++ | +++ |
| 17 | – | +++ |
| 18 | + | ++++ |
| 19 | + | ++ |
| 20 | +++ | ++ |
| 21 | – | ++ |
| 22 | +++ | +++ |
| 23 | ++ | ++ |
| 24 | +++ | ++ |
| 25 | ++++ | ++++ |
| 26 | – | +++ |
| 27 | +++ | ++++ |
| 28 | – | – |
| 29 | – | – |
| 30 | +++ | – |
| 31 | +++ | +++ |
| 32 | +++ | ++++ |
| 33 | – | +++ |
| 34 | – | +++ |
| 35 | ++ | +++ |
| 36 | – | ++++ |
| 37 | – | +++ |
| 38 | ++ | ++ |
| 39 | – | ++++ |
| 40 | ++ | ++++ |
| 41 | – | ++ |
| 42 | +++ | ++ |
| 43 | +++ | +++ |
| 44 | ++++ | ++++ |
| 45 | +++ | ++++ |
| 46 | + | ++++ |
| 47 | – | +++ |
| 48 | +++ | +++ |
| 49 | ++ | – |
| 50 | ++++ | – |
| 51 | +++ | +++ |
| 52 | – | ++++ |
| 53 | – | ++ |
| 54 | +++ | ++ |
| 55 | – | +++ |
| 56 | +++ | +++ |
| 57 | – | +++ |
| 58 | +++ | +++ |
| 59 | +++ | +++ |

TABLE 4-continued

| | | |
|---|---|---|
| 60 | − | ++++ |
| 61 | − | ++++ |
| 62 | − | ++++ |
| 63 | + | ++ |
| 64 | − | ++ |
| 65 | + | ++++ |
| 66 | ++ | ++ |
| 67 | ++ | + |
| 68 | ++++ | +++ |
| 69 | ++ | ++++ |
| 70 | ++ | − |
| 71 | − | ++++ |
| 72 | + | ++ |
| 73 | − | +++ |
| 74 | +++ | +++ |
| 75 | +++ | − |
| 76 | +++ | +++ |
| 77 | − | +++ |
| 78 | − | +++ |
| 79 | − | ++ |
| 80 | ++++ | ++ |
| 81 | − | + |
| 82 | +++ | ++++ |
| 83 | ++ | − |
| 84 | ++ | ++++ |
| 85 | +++ | +++ |
| 86 | +++ | +++ |
| 87 | +++ | +++ |
| 88 | ++++ | ++++ |
| 89 | +++ | ++++ |
| 90 | + | +++ |
| 91 | +++ | − |
| 92 | +++ | ++++ |
| 93 | +++ | ++ |
| 94 | + | +++ |
| 95 | − | ++ |
| 96 | +++ | +++ |
| 97 | +++ | +++ |
| 98 | − | ++ |
| 99 | − | − |
| 100 | +++ | +++ |
| 101 | + | ++++ |
| 102 | + | +++ |
| 103 | − | +++ |
| 104 | +++ | ++ |
| 105 | + | +++ |
| 106 | + | − |
| 107 | ++++ | ++++ |
| 108 | − | ++ |
| 109 | − | ++ |
| 110 | + | +++ |
| 111 | +++ | ++ |
| 112 | +++ | ++++ |
| 113 | − | ++++ |
| 114 | ++ | ++ |
| 115 | +++ | +++ |
| 116 | − | − |
| 117 | − | ++++ |
| 118 | ++ | +++ |
| 119 | ++ | +++ |
| 120 | − | ++++ |
| 121 | − | +++ |
| 122 | ++++ | ++ |
| 123 | − | + |
| 124 | − | ++++ |
| 125 | + | ++ |
| 127 | + | ++++ |
| 128 | ++ | ++ |
| 129 | − | − |
| 130 | +++ | ++++ |
| 131 | ++++ | ++ |
| 132 | + | + |
| 133 | − | ++++ |
| 134 | ++ | +++ |
| 135 | − | ++++ |
| 136 | ++ | + |
| 137 | +++ | ++++ |
| 138 | +++ | ++ |
| 139 | + | +++ |
| 140 | + | + |
| 141 | − | +++ |
| 142 | +++ | ++++ |
| 143 | ++++ | ++++ |
| 144 | − | +++ |
| 145 | ++ | ++ |
| 146 | +++ | ++++ |
| 147 | ++ | ++++ |
| 148 | +++ | +++ |
| 149 | ++ | ++++ |
| 150 | − | ++++ |
| 151 | − | ++ |
| 152 | − | − |
| 153 | ++ | +++ |
| 154 | +++ | +++ |
| 155 | +++ | +++ |
| 156 | − | ++++ |
| 157 | ++++ | ++++ |
| 158 | +++ | ++ |
| 159 | − | ++++ |
| 160 | − | ++++ |
| 161 | ++ | ++ |
| 162 | − | − |
| 163 | − | +++ |
| 164 | + | + |
| 165 | ++ | +++ |
| 166 | ++ | +++ |
| 167 | +++ | − |
| 168 | ++++ | ++++ |
| 169 | + | ++ |
| 170 | +++ | ++ |
| 171 | +++ | ++ |
| 172 | + | ++++ |
| 173 | ++ | +++ |
| 174 | ++ | + |
| 175 | − | ++++ |
| 176 | +++ | +++ |
| 177 | − | − |
| 178 | + | ++++ |
| 179 | − | +++ |
| 180 | − | +++ |
| 181 | +++ | − |
| 182 | + | ++++ |
| 183 | ++ | +++ |
| 184 | + | ++ |
| 185 | + | +++ |
| 186 | ++ | ++ |
| 187 | − | +++ |
| 188 | − | +++ |
| 189 | − | +++ |
| 190 | − | + |
| 191 | + | − |
| 192 | − | +++ |
| 193 | +++ | +++ |
| 194 | − | ++++ |
| 195 | +++ | +++ |
| 196 | − | − |
| 197 | +++ | +++ |
| 198 | ++ | +++ |
| 199 | +++ | +++ |
| 200 | +++ | +++ |
| 201 | − | ++++ |
| 202 | ++ | +++ |
| 203 | − | +++ |
| 204 | − | − |
| 205 | − | +++ |
| 206 | +++ | +++ |
| 207 | − | ++ |
| 208 | − | +++ |
| 209 | +++ | +++ |
| 210 | +++ | − |
| 211 | +++ | ++ |
| 212 | − | − |
| 213 | − | +++ |
| 214 | ++++ | ++ |
| 215 | ++ | ++ |
| 216 | ++ | + |
| 217 | ++ | ++ |
| 218 | − | +++ |
| 219 | + | +++ |
| 220 | − | ++ |

TABLE 4-continued

| | | |
|---|---|---|
| 221 | +++ | + |
| 222 | + | +++ |
| 223 | ++ | ++ |
| 224 | ++ | +++ |
| 225 | +++ | +++ |
| 226 | − | +++ |
| 227 | ++ | +++ |
| 228 | +++ | ++ |
| 229 | +++ | +++ |
| 230 | − | ++++ |
| 231 | +++ | +++ |
| 232 | ++ | ++ |
| 233 | − | − |
| 234 | +++ | + |
| 235 | ++ | ++ |
| 236 | − | − |
| 237 | +++ | ++++ |
| 238 | +++ | ++++ |
| 239 | − | ++++ |
| 240 | + | +++ |
| 241 | − | − |
| 242 | − | ++ |
| 243 | − | +++ |
| 244 | ++ | + |
| 245 | ++ | + |
| 246 | +++ | ++ |
| 247 | − | +++ |
| 248 | + | +++ |
| 249 | − | ++ |
| 250 | ++ | +++ |
| 251 | + | +++ |
| 252 | ++ | ++++ |
| 253 | ++ | ++++ |
| 254 | +++ | − |
| 255 | +++ | +++ |
| 257 | − | +++ |
| 258 | + | +++ |
| 259 | − | ++++ |
| 260 | − | ++++ |
| 261 | ++ | ++ |
| 262 | +++ | ++ |
| 263 | +++ | ++ |
| 264 | ++ | ++ |
| 265 | +++ | +++ |
| 266 | +++ | ++ |
| 267 | − | ++ |
| 268 | ++++ | +++ |
| 269 | ++ | + |
| 270 | +++ | +++ |
| 271 | − | − |
| 272 | − | ++ |
| 273 | − | ++++ |
| 274 | + | ++++ |
| 275 | +++ | ++ |
| 276 | + | − |
| 277 | +++ | ++ |
| 278 | + | +++ |
| 279 | +++ | +++ |
| 280 | ++ | ++++ |
| 281 | − | + |
| 282 | ++ | ++ |
| 283 | − | − |
| 284 | + | + |
| 285 | ++ | + |
| 286 | +++ | +++ |
| 287 | +++ | +++ |
| 288 | ++++ | ++++ |
| 289 | + | ++++ |
| 290 | ++++ | ++++ |
| 291 | + | − |
| 292 | ++ | +++ |
| 293 | ++ | ++ |
| 294 | ++++ | ++++ |
| 295 | + | ++ |
| 296 | ++ | +++ |
| 297 | ++ | ++ |
| 298 | +++ | ++++ |
| 299 | ++ | +++ |
| 300 | − | +++ |
| 301 | +++ | ++++ |
| 302 | ++++ | ++++ |
| 303 | + | + |
| 304 | − | +++ |
| 305 | − | +++ |
| 306 | − | − |
| 307 | ++ | + |
| 308 | − | ++++ |
| 309 | − | ++++ |
| 310 | +++ | ++++ |
| 311 | − | − |
| 312 | + | + |
| 313 | +++ | + |
| 314 | ++ | ++ |
| 315 | +++ | +++ |
| 316 | − | +++ |
| 317 | ++ | +++ |
| 318 | − | ++ |
| 319 | − | + |
| 320 | +++ | ++ |
| 321 | − | + |
| 322 | + | + |
| 323 | +++ | ++++ |
| 324 | ++ | + |
| 325 | ++ | ++ |
| 326 | − | ++++ |
| 327 | +++ | +++ |
| 328 | +++ | +++ |
| 329 | ++ | + |
| 330 | − | ++++ |
| 331 | ++ | + |
| 332 | ++ | +++ |
| 333 | − | ++++ |
| 334 | ++++ | +++ |
| 335 | ++ | ++++ |
| 336 | − | + |
| 337 | − | +++ |
| 338 | ++ | + |
| 339 | ++ | +++ |
| 340 | − | +++ |
| 341 | + | − |
| 342 | ++ | ++++ |
| 343 | +++ | − |
| 344 | ++ | +++ |
| 345 | + | ++ |
| 346 | ++++ | ++++ |
| 347 | − | − |
| 348 | +++ | ++++ |
| 349 | +++ | ++ |
| 350 | − | − |
| 351 | − | ++ |
| 352 | +++ | − |
| 353 | +++ | ++++ |
| 354 | +++ | + |
| 355 | +++ | ++ |
| 356 | ++ | − |
| 357 | + | + |
| 358 | ND | ND |
| 359 | − | ++++ |
| 360 | ++ | ++ |
| 361 | − | +++ |
| 362 | − | +++ |
| 363 | +++ | ++++ |
| 364 | ++ | + |
| 365 | − | ++ |
| 366 | ++++ | ++++ |
| 367 | +++ | +++ |
| 368 | + | ++ |
| 369 | − | ++++ |
| 370 | +++ | ++++ |
| 371 | +++ | + |
| 372 | ++ | + |
| 373 | +++ | +++ |
| 374 | +++ | +++ |
| 375 | ++ | ++++ |
| 376 | + | +++ |
| 377 | ++ | +++ |
| 378 | ++ | + |
| 379 | +++ | ++ |
| 380 | ++ | +++ |
| 381 | +++ | + |

TABLE 4-continued

| | | |
|---|---|---|
| 382 | + | ++++ |
| 383# | + | ++ |
| 384 | +++ | +++ |
| 385 | +++ | +++ |
| 386 | ++++ | +++ |
| 387 | +++ | ++ |
| 388 | − | ++ |
| 389 | − | ++++ |
| 390 | ++ | ++ |
| 391 | +++ | ++++ |
| 392 | ++ | +++ |
| 393 | − | +++ |
| 394 | − | + |
| 395 | − | ++ |
| 396 | ++ | ++ |
| 397 | +++ | ++++ |
| 398 | +++ | ++++ |
| 399 | + | ++ |
| 400 | − | ++++ |
| 401 | +++ | +++ |
| 402 | ++ | +++ |
| 403 | ++ | ++++ |
| 404 | +++ | +++ |
| 405 | ++++ | +++ |
| 406 | − | ++++ |
| 407 | − | ++++ |
| 408 | ++ | +++ |
| 409 | +++ | ++++ |
| 410 | − | ++ |
| 411 | − | +++ |
| 412 | − | ++++ |
| 413 | +++ | − |
| 414 | +++ | + |
| 415 | − | +++ |
| 416 | ++ | +++ |
| 417 | ++++ | +++ |
| 418 | ++ | − |
| 419 | − | ++ |
| 420 | + | + |
| 421 | +++ | +++ |
| 422 | +++ | − |
| 423 | − | +++ |
| 424 | − | +++ |
| 425 | +++ | + |
| 426 | ++++ | ++++ |
| 427 | +++ | +++ |
| 428 | ++ | + |
| 429 | − | ++++ |
| 430 | − | +++ |
| 431 | − | + |
| 432 | + | +++ |
| 433 | +++ | +++ |
| 434 | ++++ | ++++ |
| 435 | +++ | +++ |
| 436 | +++ | ++++ |
| 437 | ++ | ++ |
| 438 | − | ++ |
| 439 | + | + |
| 440 | ++ | ++ |
| 441 | − | + |
| 442 | ++ | ++ |
| 443 | − | ++++ |
| 444 | + | − |
| 445 | ++ | ++ |
| 446 | ++++ | + |
| 447 | ++ | ++ |
| 448 | + | +++ |
| 449 | − | +++ |
| 450 | − | − |
| 451 | +++ | + |
| 452 | − | ++ |
| 453 | ++++ | ++ |
| 454 | + | − |
| 455 | ++ | − |
| 456 | +++ | ++++ |
| 457 | ++++ | ++++ |
| 458 | +++ | ++++ |
| 459 | − | ++ |
| 460 | ++ | +++ |
| 461 | − | ++++ |
| 462 | − | +++ |
| 463 | − | + |
| 464 | +++ | ++ |
| 465 | − | +++ |
| 466 | − | +++ |
| 467 | ++ | +++ |
| 468 | + | +++ |
| 469 | ++ | +++ |
| 470 | +++ | ++ |
| 471 | − | + |
| 472 | − | +++ |
| 473 | + | +++ |
| 475 | ++++ | +++ |
| 476 | ++ | ++ |
| 477 | − | ++ |
| 478 | + | + |
| 479 | − | +++ |
| 480 | − | ++ |
| 481 | +++ | +++ |
| 482 | +++ | ++ |
| 483 | − | − |
| 484 | − | − |
| 485 | + | ++ |
| 486 | − | +++ |
| 487 | + | +++ |
| 488 | − | − |
| 489 | ++ | ++ |
| 490 | ++ | ++ |
| 491 | − | +++ |
| 492 | ++++ | ++++ |
| 493 | − | ND |
| 494 | ++ | +++ |
| 495 | − | + |
| 496 | + | +++ |
| 497 | − | − |
| 498 | +++ | +++ |
| 499 | ++ | +++ |
| 500 | + | +++ |
| 501 | − | + |
| 502 | − | + |
| 503 | − | + |
| 504 | ++ | ++ |
| 505 | − | ++ |
| 506 | + | +++ |
| 507 | +++ | ++ |
| 508 | ++ | +++ |
| 509 | +++ | +++ |
| 510 | ++ | + |
| 511 | +++ | +++ |
| 512 | +++ | +++ |
| 513 | +++ | +++ |
| 514 | +++ | ++ |
| 515 | + | − |
| 516 | ++ | ++ |
| 517 | ++ | ++ |
| 518 | ++ | ++ |
| 519 | − | +++ |
| 520 | − | +++ |
| 521 | +++ | +++ |
| 522 | +++ | +++ |
| 523 | − | +++ |
| 524 | +++ | +++ |
| 525 | ++ | +++ |
| 526 | ++ | +++ |
| 527 | +++ | +++ |
| 528 | +++ | +++ |
| 529 | − | + |
| 530 | +++ | +++ |
| 531 | +++ | +++ |
| 532 | ++ | ++ |
| 533 | + | ++ |
| 534 | − | + |
| 535 | + | + |
| 536 | +++ | +++ |
| 537 | − | + |
| 538 | + | + |
| 539 | ++ | ++ |
| 540 | +++ | ++ |
| 541 | + | − |
| 542 | ++ | ++ |

TABLE 4-continued

| | | |
|---|---|---|
| 543 | + | + |
| 544 | ++ | + |
| 545 | ++ | ++ |
| 546 | ++ | + |
| 547 | ++ | +++ |
| 548 | + | + |
| 549 | ++ | + |
| 550 | ++ | ++ |
| 551 | ++ | +++ |
| 552 | ++ | ++ |
| 553 | ++ | +++ |
| 554 | ++ | ++ |
| 555 | +++ | ++ |
| 556 | + | + |
| 557 | − | − |
| 558 | − | ++ |
| 559 | ++ | +++ |
| 560 | +++ | ++ |
| 561 | ++ | +++ |
| 562 | + | + |
| 563 | + | − |
| 564 | − | − |
| 565 | − | − |
| 566 | ++ | +++ |
| 567 | − | − |
| 568 | − | + |
| 569 | ++ | + |
| 570 | + | − |
| 571 | + | − |
| 572 | + | − |
| 573 | + | + |
| 574 | ++ | +++ |
| 575* | − | ++ |
| 576* | ++ | ++ |
| 577* | ++ | ++ |
| 578* | ++ | + |
| 579** | + | + |
| 580* | + | − |
| 581** | − | ++ |
| 582# | ++ | + |
| 583* | ++ | ++ |
| 584* | + | ++ |
| 585* | + | ++ |
| 586* | ++ | ++ |
| 587* | ++ | + |
| 588* | − | ++ |
| 589# | − | ++ |
| 590* | + | ++ |
| 591* | ++ | ++ |
| 592** | − | + |
| 593# | − | + |
| 594** | + | + |
| 595** | − | + |
| 596* | ++ | ++ |
| 597** | − | + |
| 598** | + | + |
| 599* | ++ | ++ |
| 600* | ++ | + |
| 601** | − | + |
| 602** | + | + |
| 603* | ++ | ++ |
| 604* | − | ++ |
| 605* | ++ | ++ |
| 606** | + | + |
| 607* | ++ | ++ |
| 608** | + | ++ |
| 609* | +++ | +++ |
| 610** | + | + |
| 611* | + | ++ |
| 612* | ++ | − |
| 613** | + | ++ |
| 614** | + | + |
| 615* | ++ | ++ |
| 616** | − | + |
| 617* | ++ | ++ |
| 618* | ++ | ++ |
| 619** | + | + |
| 620* | + | ++ |
| 621** | + | ++ |
| 622** | + | + |
| 623* | + | ++ |
| 624# | − | ++ |
| 625** | ++ | + |
| 626* | − | ++ |
| 627# | ++ | + |
| 628* | + | ++ |
| 629** | − | ++ |
| 630** | + | + |
| 631* | + | + |
| 632* | − | ++ |
| 633* | ++ | ++ |
| 634* | ++ | ++ |
| 635* | + | ++ |
| 636* | + | + |
| 637* | − | +++ |
| 638* | ++ | ++ |
| 639** | + | + |
| 640* | + | ++ |
| 641* | + | ++ |
| 642* | ++ | + |
| 643* | − | ++ |
| 644* | ++ | + |
| 645* | ++ | + |
| 646# | + | ++ |
| 647** | − | + |
| 648* | ++ | ++ |
| 649* | − | ++ |
| 650* | + | ++ |
| 651** | + | ++ |
| 652** | − | ++ |
| 653* | − | ++ |
| 654** | + | + |
| 655* | − | ++ |
| 656** | − | + |
| 657* | − | + |
| 658** | − | ++ |
| 659* | ++ | ++ |
| 660** | − | − |
| 661* | + | ++ |
| 662* | − | ++ |
| 663** | − | ++ |
| 664* | + | + |
| 665* | + | ++ |
| 666** | + | ++ |
| 667* | + | ++ |
| 668** | + | + |
| 669* | − | ++ |
| 670* | ++ | ++ |
| 671* | + | ++ |
| 672** | + | + |
| 673* | +++ | ++ |
| 674* | + | + |
| 675** | + | + |
| 676* | − | ++ |
| 677* | − | +++ |
| 678* | + | ++ |
| 679* | + | ++ |
| 680* | ++ | ++ |
| 681** | + | ++ |
| 682* | ++ | ++ |
| 683** | ++ | ++ |
| 684** | ++ | ++ |
| 685# | + | ++ |
| 686** | + | + |
| 687** | + | + |
| 688# | − | + |
| 689** | + | + |
| 690* | ++ | + |
| 691* | ++ | ++ |
| 692* | ++ | ++ |
| 693** | − | + |
| 694** | − | ++ |
| 695** | + | + |
| 696* | + | ++ |
| 697* | ++ | + |
| 698* | ++ | ++ |
| 699# | − | + |
| 700* | − | ++ |
| 701* | − | ++ |
| 702* | ++ | ++ |

TABLE 4-continued

| | | |
|---|---|---|
| 703* | + | ++ |
| 704** | − | ++ |
| 705** | + | ++ |
| 706* | + | + |
| 707* | − | − |
| 708** | − | + |
| 709** | + | + |
| 710# | − | ++ |
| 711* | + | ++ |
| 712* | + | + |
| 713* | ++ | ++ |
| 714* | ++ | ++ |
| 715** | + | ++ |
| 716* | +++ | + |
| 717* | ++ | + |
| 718* | +++ | ++ |
| 719* | − | + |
| 720** | ++ | + |
| 721** | − | ++ |
| 722* | ++ | ++ |
| 723** | +++ | ++ |
| 724** | + | + |
| 725* | ++ | ++ |
| 726* | + | + |
| 727* | − | ++ |
| 728** | − | ++ |
| 729* | ++ | − |
| 730* | ++ | ++ |
| 731* | − | ++ |
| 732** | + | + |
| 733* | + | + |
| 734** | − | + |
| 735# | + | + |
| 736* | − | ++ |
| 737** | ++ | ++ |
| 738# | − | ++ |
| 739* | ++ | ++ |
| 740** | ++ | ++ |
| 741** | + | ++ |
| 742** | − | ++ |
| 743# | ++ | + |
| 744* | − | + |
| 745# | − | ++ |
| 746* | ++ | ++ |
| 747# | − | − |
| 748* | − | ++ |
| 749** | ++ | ++ |
| 750* | ++ | + |
| 751** | − | ++ |
| 752* | + | ++ |
| 753* | +++ | ++ |
| 754* | + | ++ |
| 755** | ++ | + |
| 756* | ++ | + |
| 757* | ++ | ++ |
| 758** | ++ | ++ |
| 759** | + | + |
| 760** | − | + |
| 761** | − | + |
| 762** | − | − |
| 763* | ++ | ++ |
| 764** | + | + |
| 765# | + | ++ |
| 766** | − | + |
| 767** | ++ | + |
| 768* | + | − |
| 769** | − | + |
| 770* | ++ | ++ |
| 771# | − | ++ |
| 772# | − | + |
| 773* | − | ++ |
| 774* | ++ | + |
| 775** | ++ | + |
| 776* | − | ++ |
| 777* | ++ | + |
| 778* | + | ++ |
| 779** | + | + |
| 780** | + | + |
| 781# | − | + |
| 782# | + | ++ |

TABLE 4-continued

| | | |
|---|---|---|
| 783** | + | − |
| 784* | ++ | ++ |
| 785* | +++ | ++ |
| 786** | − | + |
| 787** | ++ | + |
| 788** | + | ++ |
| 789** | − | + |
| 790# | ++ | ++ |
| 791** | − | ++ |
| 792* | − | ++ |
| 793** | − | + |
| 794** | − | + |
| 795** | + | + |
| 796** | − | ++ |
| 797* | − | + |
| 798** | + | + |
| 799* | − | ++ |
| 800* | ++ | ++ |
| 801* | + | + |
| 802* | − | ++ |
| 803* | − | ++ |
| 804** | − | ++ |
| 805* | + | ++ |
| 806** | − | + |
| 807** | + | + |
| 808* | − | ++ |
| 809# | − | + |
| 810# | + | + |
| 811* | ++ | + |
| 812* | ++ | ++ |
| 813* | + | ++ |
| 814# | + | ++ |
| 815** | ++ | + |
| 816** | + | + |
| 817* | ++ | ++ |
| 818* | +++ | ++ |
| 819* | + | ++ |
| 820* | ++ | + |
| 821** | ++ | − |
| 822* | − | ++ |
| 823** | ++ | ++ |
| 824* | + | ++ |
| 825* | ++ | ++ |
| 826* | − | ++ |
| 827* | + | ++ |
| 828# | − | + |
| 829** | − | + |
| 830* | ++ | +++ |
| 831* | ++ | ++ |
| 832* | ++ | ++ |
| 833** | − | + |
| 834** | + | + |
| 835 | ++ | + |
| 836** | + | + |
| 837* | ++ | + |
| 838# | − | − |
| 839* | − | + |
| 840* | ++ | ++ |
| 841# | ++ | + |
| 842** | − | + |
| 843** | + | + |
| 845* | + | ++ |
| 846** | + | ++ |
| 847** | + | + |
| 848* | ++ | ++ |
| 849** | ++ | ++ |
| 850# | − | ++ |
| 851# | ++ | + |
| 852** | − | + |
| 853* | ++ | + |
| 854* | ++ | +++ |
| 855** | + | + |
| 856# | − | ++ |
| 857* | ++ | ++ |
| 858# | − | ++ |
| 859** | + | + |
| 860* | + | ++ |
| 861* | − | ++ |
| 862* | ++ | + |
| 863* | ++ | ++ |

TABLE 4-continued

| | | |
|---|---|---|
| 864* | ++ | ++ |
| 865** | + | + |
| 866** | ++ | + |
| 867* | ++ | ++ |
| 868** | + | + |
| 869# | + | ++ |
| 870# | + | + |
| 871# | + | + |
| 872# | − | ++ |
| 873# | − | + |
| 874# | − | ++ |
| 875# | − | ++ |
| 876# | ++ | ++ |
| 877# | + | + |
| 878# | − | ++ |
| 879# | − | − |
| 880# | − | + |
| 881# | − | ++ |
| 882# | + | + |
| 883# | + | ++ |
| 884# | − | + |
| 885# | − | ++ |
| 886# | + | ++ |
| 887# | ++ | ++ |
| 888# | + | + |
| 889# | − | ++ |
| 890# | ++ | + |
| 891# | − | + |
| 892# | − | + |
| 893# | − | + |
| 894# | − | ++ |
| 895# | + | ++ |
| 896# | + | + |
| 897# | − | + |
| 898# | − | ++ |
| 899# | + | + |
| 900# | − | + |
| 901# | − | + |
| 902# | − | + |
| 903# | + | ++ |
| 904# | − | − |
| 905# | ++ | + |
| 906# | + | ++ |
| 907# | +++ | ++ |
| 908# | ++ | + |
| 909# | ++ | + |
| 910# | ++ | + |
| 911# | + | + |
| 912# | + | + |
| 913# | ++ | ++ |
| 914# | − | ++ |
| 915# | − | + |
| 916# | − | ++ |
| 917# | − | ++ |
| 918# | − | + |
| 919# | − | ++ |
| 920# | − | ++ |
| 921# | + | ++ |
| 922# | − | + |
| 923# | + | ++ |
| 924 | ND | ND |
| 925# | − | + |
| 926# | + | ++ |
| 927# | + | ++ |
| 928# | − | ++ |
| 929# | − | ++ |
| 930# | − | ++ |
| 931# | − | ++ |
| 932# | − | + |
| 933# | − | + |
| 934# | − | ++ |
| 935# | ND | ++ |
| 936# | − | ++ |
| 937# | − | + |
| 938# | − | + |
| 939# | − | + |
| 940# | + | ++ |
| 941# | + | + |
| 942# | − | + |
| 943 | ND | ND |

TABLE 4-continued

| | | |
|---|---|---|
| 944# | − | + |
| 945# | − | + |
| 946# | − | − |
| 947# | − | + |
| 948# | − | ++ |
| 949# | ++ | ++ |
| 950# | + | ++ |
| 951# | − | + |
| 952# | + | + |
| 953# | + | + |
| 954# | − | + |
| 955# | + | ++ |
| 956# | − | − |
| 957# | − | ++ |
| 958# | − | ++ |
| 959# | − | + |
| 960# | − | + |
| 961# | + | + |
| 962# | + | + |
| 963 | ND | ND |
| 964# | − | − |
| 965# | ++ | ++ |
| 966# | − | + |
| 967# | − | ++ |
| 968# | + | + |
| 969# | − | + |
| 970# | − | ++ |
| 971# | + | + |
| 972# | + | − |
| 973# | − | ++ |
| 974# | − | ++ |
| 975# | − | + |
| 976# | ++ | + |
| 977# | − | + |
| 978# | + | ++ |
| 979# | − | +++ |
| 980# | + | + |
| 981# | ++ | + |
| 982# | − | ++ |
| 983# | + | + |
| 984# | − | ++ |
| 985# | + | + |
| 986# | − | + |
| 987# | − | + |
| 988# | + | ++ |
| 989# | − | − |
| 990# | − | − |
| 991# | + | ++ |
| 992# | + | + |
| 993# | ++ | + |
| 994# | + | + |
| 995# | − | ++ |
| 996# | − | + |
| 997# | − | +++ |
| 998# | + | ++ |
| 999# | − | + |
| 1001# | + | ++ |
| 1002# | ++ | +++ |
| 1003# | − | ++ |
| 1004# | + | + |
| 1005# | − | + |
| 1006# | + | ++ |
| 1007# | ++ | + |
| 1008# | + | ++ |
| 1009# | + | ++ |
| 1010# | − | + |
| 1011# | − | ++ |
| 1012# | − | + |
| 1013# | − | ++ |
| 1014# | + | + |
| 1015# | − | − |
| 1016# | + | ++ |
| 1017# | − | ++ |
| 1018# | − | ++ |
| 1019# | ++ | + |
| 1020# | + | ++ |
| 1021# | − | + |
| 1022# | ++ | + |
| 1023# | ++ | + |
| 1024# | − | ++ |

TABLE 4-continued

| | | |
|---|---|---|
| 1025# | ++ | + |
| 1026# | + | + |
| 1027# | − | + |
| 1028# | + | ++ |
| 1029# | ++ | ++ |
| 1030# | + | ++ |
| 1031# | − | ++ |
| 1032# | + | ++ |
| 1033# | − | + |
| 1034# | − | ++ |
| 1035# | + | + |
| 1036# | − | − |
| 1037# | − | ++ |
| 1038# | ++ | + |
| 1039# | − | ++ |
| 1040# | − | ++ |
| 1041# | + | + |
| 1042# | − | ++ |
| 1043# | − | ++ |
| 1044# | + | + |
| 1045# | − | + |
| 1046# | − | + |
| 1047# | − | + |
| 1048# | − | ++ |
| 1049# | ++ | + |
| 1050# | − | ++ |
| 1051# | + | ++ |
| 1052# | ++ | ++ |
| 1053# | + | ++ |
| 1054# | − | − |
| 1055# | + | ++ |
| 1056# | − | + |
| 1057# | − | + |
| 1058# | ++ | ++ |
| 1059# | − | ++ |
| 1060# | − | + |
| 1061# | ++ | ++ |
| 1062# | − | ++ |
| 1063# | − | ++ |
| 1064# | − | ++ |
| 1065# | + | ++ |
| 1066# | − | ++ |
| 1067# | − | + |
| 1068# | ++ | ++ |
| 1069# | + | + |
| 1070# | − | ++ |
| 1071# | − | ++ |
| 1072# | − | + |
| 1073# | − | ++ |
| 1074# | − | + |
| 1075# | − | + |
| 1076# | − | ++ |
| 1077# | − | + |
| 1078# | − | + |
| 1079# | − | ++ |
| 1080# | ++ | ++ |
| 1081# | + | + |
| 1082# | − | ++ |
| 1083# | − | + |
| 1084# | + | ++ |
| 1085# | ++ | ++ |
| 1086# | − | ++ |
| 1087# | + | + |
| 1110 | + | ++++ |
| 1111 | − | +++ |

| Fold relative to baseline | Activity |
|---|---|
| ND | not determined |
| ≤1 | − |
| >1 to 10x | + |
| >10 to 100x | ++ |
| >100 to 1000x | +++ |
| >1000 to 10,000x | ++++ |

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

We claim:

1. A method of treating or reducing the severity of one or more symptoms of multiple sclerosis comprising administering to a patient in need thereof a therapeutically effective amount of a compound of formula (I'), or a pharmaceutically acceptable salt thereof,

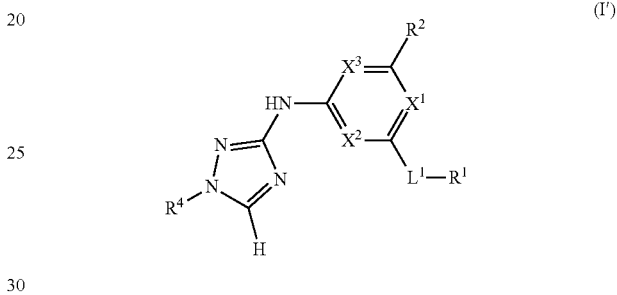

(I')

wherein:
$X^1$ is CH;
$X^2$ is $CR^{X2}$;
$X^3$ is $CR^3$;
where $R^3$ and $R^{X2}$ are each independently selected from the group consisting of hydrogen, halogen, $C_{1-4}$alkyl, $C_{1-4}$haloalkyl, —$OC_{1-4}$alkyl, and cyano;
$L^1$ is a bond, —O—, —$NR^5$—, —$NR^5$—$C_{1-4}$alkylene-, —O—$C_{1-4}$alkylene-, —$C_{1-4}$alkylene-, —C(O)—, —$NR^5$C(O)—, —OC(O)—, —$NR^5$C(O)$NR^5$—, —$NR^5$C(O)O—, —$NR^5$—$C_{1-4}$alkylene-C(O)—, —O—$C_{1-4}$alkylene-C(O)—, —$C_{1-4}$alkylene-C(O)—, —$NR^5$C(O)—$C_{1-4}$alkylene-, —OC(O)—$C_{1-4}$alkylene-, —$NR^5$C(O)$NR^5$—$C_{1-4}$alkylene-, —$NR^5$C(O)O—$C_{1-4}$alkylene-, or —$NR^5$—$C_{1-4}$alkylene-O—, wherein each $R^5$ is independently hydrogen or $C_{1-4}$alkyl, and the $C_{1-4}$alkylene of —$NR^5$—$C_{1-4}$alkylene-, —O—$C_{1-4}$alkylene-, —$C_{1-4}$alkylene-, $NR^5$—$C_{1-4}$alkylene-C(O)—, —O—$C_{1-4}$alkylene-C(O)—, —$C_{1-4}$alkylene-C(O)—, —$NR^5$C(O)—$C_{1-4}$alkylene-, —OC(O)—$C_{1-4}$alkylene-, —$NR^5$C(O)$NR^5$—$C_{1-4}$alkylene-, —$NR^5$C(O)O—$C_{1-4}$alkylene-, or —$NR^5$—$C_{1-4}$alkylene-O— is optionally substituted with 1-6 halogens;
$R^1$ is -$G^1$-$L^2$-$R^6$, -$G^1$-$L^2$-$R^7$, $G^2$, $G^3$, $G^4$, $G^6$, or -≡-$G^5$;
$G^1$ is
  i) a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms, $G^1$ being optionally substituted with 1-4 substituents independently selected from the group consisting of $C_{1-4}$alkyl, $C_{1-4}$haloalkyl, halogen, hydroxyl, and oxo; or
  ii) a 3- to 8-membered cycloalkyl optionally substituted with 1-4 substituents independently selected from the group consisting of $C_{1-4}$alkyl, $C_{1-4}$haloalkyl, halogen, hydroxyl, and oxo;

$L^2$ is a bond, a —$C_{1-6}$alkylene-, —C(O)—, —O—, or —$NR^{5'}$—, wherein the —$C_{1-6}$alkylene- is optionally substituted with 1-6 halogens and 1-2 $C_1$alkylene units of the —$C_{1-6}$alkylene- are optionally replaced with —C(O)—, —O—, or —$NR^{5'}$—, wherein each $R^{5'}$ is independently hydrogen or $C_{1-4}$alkyl;

$R^6$ is
- a) a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms and being optionally substituted with 1-4 substituents independently selected from the group consisting of $C_{1-4}$alkyl, $C_{1-4}$haloalkyl, —$CH_2S(O)_2$phenyl, halogen, hydroxyl, oxo, —$OC_{1-4}$alkyl, —$C_{1-6}$alkylene-$OC_{1-4}$alkyl, and —$C_{1-6}$alkylene-OH;
- b) a 5- or 6-membered monocyclic heteroaryl containing 1-3 heteroatoms independently selected from nitrogen, oxygen, and sulfur, the monocyclic heteroaryl being optionally substituted with 1-3 substituents independently selected from the group consisting of $C_{1-4}$alkyl, $C_{1-4}$haloalkyl, halogen, hydroxyl, —$OC_{1-4}$alkyl, —$C_{1-6}$alkylene-$OC_{1-4}$alkyl, and —$C_{1-6}$alkylene-OH;
- c) a 7- to 12-membered spiro heterocycle comprising a first ring and a second ring, the first ring being a 4- to 8-membered monocyclic heterocycle containing 1-2 heteroatoms independently selected from nitrogen and oxygen and being attached to $L^2$, the second ring being a $C_{3-8}$cycloalkyl or a 4- to 8-membered monocyclic heterocycle containing 1-2 oxygen atoms wherein two atoms of the second ring are attached to one carbon of the first ring to form a spirocycle optionally substituted with 1-4 substituents independently selected from the group consisting of $C_{1-4}$alkyl, $C_{1-4}$haloalkyl, halogen, hydroxyl, oxo, —$OC_{1-4}$alkyl, —$C_{1-6}$alkylene-$OC_{1-4}$alkyl, and —$C_{1-6}$alkylene-OH; or
- d) a 7- to 12-membered fused bicyclic heterocycle containing 1-3 heteroatoms independently selected from oxygen, nitrogen, and sulfur and being optionally substituted with 1-4 substituents independently selected from the group consisting of $C_{1-4}$alkyl, $C_{1-4}$haloalkyl, halogen, hydroxyl, oxo, —$OC_{1-4}$alkyl, —$C_{1-6}$alkylene-$OC_{1-4}$alkyl, and —$C_{1-6}$alkylene-OH;

$R^7$ is
- a) a 3- to 8-membered cycloalkyl optionally substituted with 1-4 substituents independently selected from the group consisting of $C_{1-4}$alkyl, $C_{1-4}$haloalkyl, halogen, hydroxyl, —$C(O)OC_{1-4}$alkyl, —C(O)OH, oxo, —$OC_{1-4}$alkyl, —$C_{1-6}$alkylene-$OC_{1-4}$alkyl, and —$C_{1-6}$alkylene-OH; or
- b) phenyl optionally substituted with 1-4 substituents independently selected from the group consisting of $C_{1-4}$alkyl, $C_{1-4}$haloalkyl, halogen, hydroxyl, —$C(O)OC_{1-4}$alkyl, —C(O)OH, —$OC_{1-4}$alkyl, —$C_{1-6}$alkylene-$OC_{1-4}$alkyl, and —$C_{1-6}$alkylene-OH;

$G^2$ is a 4- to 8-membered monocyclic heterocycle containing 1-3 heteroatoms independently selected from oxygen, nitrogen, and sulfur, the monocyclic heterocycle optionally containing one double bond and/or a $C_{1-3}$alkylene bridge between two non-adjacent ring atoms, $G^2$ being optionally substituted with 1-4 substituents independently selected from the group consisting of $C_{1-4}$alkyl, $C_{1-4}$haloalkyl, halogen, hydroxyl, oxo, cyano, —$C_{1-6}$alkylene-cyano, —$C(O)C_{1-4}$alkyl, —C(O)—$C_{1-6}$alkylene-$OC_{1-4}$alkyl, —C(O)—$C_{1-6}$alkylene-OH, —$C(O)C_{3-6}$cycloalkyl, —$C(O)OC_{1-4}$alkyl, —$C(O)OC_{1-4}$haloalkyl, —$C(O)NH_2$, —$C(O)NH(C_{1-4}$alkyl), —$C(O)N(C_{1-4}$alkyl)($C_{1-4}$alkyl), —C(O)NH(—$C_{1-6}$alkylene-$OC_{1-4}$alkyl), —$C(O)N(C_{1-4}$alkyl)(—$C_{1-6}$alkylene-$OC_{1-4}$alkyl), —C(O)NH(—$C_{1-6}$alkylene-OH), —$C(O)N(C_{1-4}$alkyl)(—$C_{1-6}$alkylene-OH), —NH(—$C_{1-6}$alkylene-$OC_{1-4}$alkyl), —$N(C_{1-4}$alkyl)(—$C_{1-6}$alkylene-$OC_{1-4}$alkyl), —NH(—$C_{1-6}$alkylene-OH), —$N(C_{1-4}$alkyl)(—$C_{1-6}$alkylene-OH), —$C(O)C_{1-4}$haloalkyl, —$OC_{1-4}$alkyl, —$OC_{1-4}$haloalkyl, —$C_{1-6}$alkylene-$OC_{1-4}$alkyl, —$C_{1-6}$alkylene-OH, —$C_{1-6}$alkylene-$NH_2$, —$C_{1-6}$alkylene-$NH(C_{1-4}$alkyl), —$C_{1-6}$alkylene-$N(C_{1-4}$alkyl)($C_{1-4}$alkyl), —O—$C_{1-6}$alkylene-$NH_2$, —O—$C_{1-6}$alkylene-$NH(C_{1-4}$alkyl), —O—$C_{1-6}$alkylene-$N(C_{1-4}$alkyl)($C_{1-4}$alkyl), —O—$C_{1-6}$alkylene-$OC_{1-4}$alkyl, —O—$C_{1-6}$alkylene-OH, —$C_{1-4}$alkylene-O—$C_{1-4}$alkylene-$OC_{1-4}$alkyl, —$C_{1-4}$alkylene-O—$C_{1-4}$alkylene-OH, —$C_{1-4}$alkylene-C(O)$OC_{1-4}$alkyl, —$C_{1-4}$alkylene-C(O)OH, —NHC(O)($C_{1-4}$alkyl), —$N(C_{1-4}$alkyl)C(O)($C_{1-4}$alkyl), —$NH_2$, —$NH(C_{1-4}$alkyl), —$N(C_{1-4}$alkyl)($C_{1-4}$alkyl), —$S(O)_{1-2}C_{1-4}$alkyl, —$C_{1-6}$alkylene-$S(O)_{1-2}C_{1-4}$alkyl, and a —$C_{1-6}$alkylene substituted by 2 groups independently selected from hydroxyl, —$OC(O)C_{1-4}$alkyl, —$OC_{1-4}$alkyl, —$NH_2$, —$NH(C_{1-4}$alkyl), and —$N(C_{1-4}$alkyl)($C_{1-4}$alkyl);

$G^3$ is a 7- to 12-membered spiro heterocycle comprising a first ring and a second ring, the first ring being a 4- to 8-membered monocyclic heterocycle containing 1-2 heteroatoms independently selected from nitrogen and oxygen and being attached to $L^1$, the second ring being a $C_{3-8}$cycloalkyl or a 4- to 8-membered monocyclic heterocycle containing 1-2 oxygen atoms wherein two atoms of the second ring are attached to one carbon of the first ring to form a spirocycle, and wherein $G^3$ is optionally substituted with 1-4 substituents independently selected from the group consisting of $C_{1-4}$alkyl, $C_{1-4}$haloalkyl, halogen, hydroxyl, and oxo;

$G^4$ is a 7- to 12-membered fused bicyclic heterocycle containing 1-3 heteroatoms independently selected from oxygen, nitrogen, and sulfur, $G^4$ being optionally substituted with 1-4 substituents independently selected from the group consisting of $C_{1-4}$alkyl, $C_{1-4}$haloalkyl, halogen, hydroxyl, and oxo;

$G^5$ is 3- to 8-membered cycloalkyl optionally substituted with 1-4 substituents independently selected from the group consisting of $C_{1-4}$alkyl, $C_{1-4}$haloalkyl, halogen, hydroxyl, oxo, cyano, —$C(O)C_{1-4}$alkyl, —$C(O)C_{3-6}$cycloalkyl, —$C(O)OC_{1-4}$alkyl, —$C(O)OC_{1-4}$haloalkyl, —$C(O)NH_2$, —$C(O)NH(C_{1-4}$alkyl), —$C(O)N(C_{1-4}$alkyl)($C_{1-4}$alkyl), —C(O)NH(—$C_{1-6}$alkylene-$OC_{1-4}$alkyl), —$C(O)N(C_{1-4}$alkyl)(—$C_{1-6}$alkylene-$OC_{1-4}$alkyl), —C(O)NH(—$C_{1-6}$alkylene-OH), —$C(O)N(C_{1-4}$alkyl)(—$C_{1-6}$alkylene-OH), —NH(—$C_{1-6}$alkylene-$OC_{1-4}$alkyl), —$N(C_{1-4}$alkyl)(—$C_{1-6}$alkylene-$OC_{1-4}$alkyl), —NH(—$C_{1-6}$alkylene-OH), —N($C_{1-4}$alkyl)(—$C_{1-6}$alkylene-OH), —C(O)$C_{1-4}$haloalkyl, —O$C_{1-4}$alkyl, —$C_{1-4}$alkylene-O$C_{1-4}$alkyl, —$C_{1-6}$alkylene-OH, —$C_{1-6}$alkylene substituted by 2 groups independently selected from hydroxyl and —OC(O)$C_{1-4}$alkyl, —$C_{1-4}$alkylene-C(O)O$C_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —$NH_2$, —NH($C_{1-4}$alkyl), and —N($C_{1-4}$alkyl)($C_{1-4}$alkyl);

$G^6$ is a monocyclic or bicyclic heteroaryl containing 1-4 heteroatoms independently selected from oxygen, nitrogen, and sulfur, $G^6$ being optionally substituted with 1-4 substituents independently selected from the group consisting of $C_{1-4}$alkyl, $C_{1-4}$haloalkyl, halogen, hydroxyl, cyano, phenyl, —C(O)$C_{1-4}$alkyl, —C(O)$C_{3-6}$cycloalkyl, —C(O)O$C_{1-4}$alkyl, —C(O)O$C_{1-4}$haloalkyl, —C(O)$NH_2$, —C(O)NH($C_{1-4}$alkyl), —C(O)N($C_{1-4}$alkyl)($C_{1-4}$alkyl), —C(O)NH(—$C_{1-6}$alkylene-O$C_{1-4}$alkyl), —C(O)N($C_{1-4}$alkyl)(—$C_{1-6}$alkylene-O$C_{1-4}$alkyl), —C(O)NH(—$C_{1-6}$alkylene-OH), —C(O)N($C_{1-4}$alkyl)(—$C_{1-6}$alkylene-OH), —NH(—$C_{1-6}$alkylene-O$C_{1-4}$alkyl), —N($C_{1-4}$alkyl)(—$C_{1-6}$alkylene-O$C_{1-4}$alkyl), —NH(—$C_{1-6}$alkylene-OH), —N($C_{1-4}$alkyl)(—$C_{1-6}$alkylene-OH), —C(O)$C_{1-4}$haloalkyl, —O$C_{1-4}$alkyl, —$C_{1-4}$alkylene-O$C_{1-4}$alkyl, —$C_{1-6}$alkylene-OH, —$C_{1-6}$alkylene substituted by 2 groups independently selected from hydroxyl and —OC(O)$C_{1-4}$alkyl, —$C_{1-4}$alkylene-C(O)O$C_{1-4}$alkyl, —$C_{1-4}$alkylene-C(O)OH, —NHC(O)($C_{1-4}$alkyl), —N($C_{1-4}$alkyl)C(O)($C_{1-4}$alkyl), —$NH_2$, —NH($C_{1-4}$alkyl), and —N($C_{1-4}$alkyl)($C_{1-4}$alkyl);

$R^2$ is $C_{1-4}$alkyl, $C_{1-4}$haloalkyl, halogen, hydroxyl, cyano, —S(O)$_2C_{1-4}$alkyl, —S(O)$C_{1-4}$alkyl, —S$C_{1-4}$alkyl, —O$C_{1-4}$alkyl, —O$C_{1-4}$haloalkyl, —C(O)$C_{1-4}$alkyl, —C(O)O$C_{1-4}$alkyl, —C(O)$NH_2$, —C(O)NH($C_{1-4}$alkyl), —C(O)N($C_{1-4}$alkyl)($C_{1-4}$alkyl), —$C_{1-4}$alkylene-O$C_{1-4}$alkyl, —$C_{1-4}$alkylene-OH, or $G^{10}$, $G^{10}$ being a $C_{3-6}$cycloalkyl, $C_{5-6}$cycloalkenyl, or a 4- to 8-membered monocyclic heterocycle containing 1 to 2 heteroatoms independently selected from nitrogen and oxygen and optionally containing 1 double bond, $G^{10}$ being optionally substituted with 1-2 substituents independently selected from oxo, halogen, $C_{1-4}$alkyl, $C_{1-4}$haloalkyl, and $G^{20}$, $G^{20}$ being a $C_{3-6}$cycloalkyl or a 4- to 8-membered monocyclic heterocycle containing 1 to 2 heteroatoms independently selected from nitrogen and oxygen, $G^{20}$ being optionally substituted with 1-4 substituents independently selected from the group consisting of $C_{1-4}$alkyl, $C_{1-4}$haloalkyl, halogen, hydroxyl, and oxo; and $R^4$ is phenyl or a 6-membered heteroaryl containing 1-3 nitrogen atoms, $R^4$ being optionally substituted with 1-3 substituents independently selected from the group consisting of halogen, hydroxyl, cyano, —S(O)$_2C_{1-4}$alkyl, —S(O)$C_{1-4}$alkyl, —S$C_{1-4}$alkyl, $C_{1-4}$alkyl, $C_{1-4}$haloalkyl, —O$C_{1-4}$alkyl, —O$C_{1-4}$haloalkyl, —$C_{1-4}$alkylene-O$C_{1-4}$alkyl, —$C_{1-4}$alkylene-N($C_{1-4}$alkyl)($C_{1-4}$alkyl), —NH($C_{1-4}$alkylene-O$C_{1-4}$alkyl), —NH($C_{1-4}$alkylene-OH), —N($C_{1-4}$alkyl)($C_{1-4}$alkylene-O$C_{1-4}$alkyl), —N($C_{1-4}$alkyl)($C_{1-4}$alkylene-OH), —$NH_2$, —NH($C_{1-4}$alkyl), —N($C_{1-4}$alkyl)($C_{1-4}$alkyl), $C_{3-6}$cycloalkyl, $C_{5-6}$cycloalkenyl, or a 4- to 8-membered monocyclic heterocycle containing 1-2 nitrogen atoms, the $C_{3-6}$cycloalkyl, the $C_{5-6}$cycloalkenyl, and the 4- to 8-membered monocyclic heterocycle being independently optionally substituted with 1-2 substituents independently selected from the group consisting of halogen, hydroxyl, —O$C_{1-4}$alkyl, $C_{1-4}$alkyl, $C_{1-4}$haloalkyl, —$C_{1-4}$alkylene-O$C_{1-4}$alkyl, and —$C_{1-4}$alkylene-OH.

2. The method of claim 1, wherein the compound is a compound of formula (I'), or a pharmaceutically acceptable salt thereof, wherein $R^1$ is -$G^1$-$L^2$-$R^6$.

3. The method of claim 2, wherein the compound is a compound of formula (I'), or a pharmaceutically acceptable salt thereof, wherein $R^6$ is oxetanyl, tetrahydrofuranyl, tetrahydropyranyl, morpholinyl, pyrrolidinyl, or thietanyl, each being optionally substituted with 1-4 substituents independently selected from $C_{1-4}$alkyl and oxo.

4. The method of claim 2, wherein the compound is a compound of formula (I'), or a pharmaceutically acceptable salt thereof, wherein $R^6$ is oxetan-3-yl or 3-methyloxetan-3-yl.

5. The method of claim 2, wherein the compound is a compound of formula (I'), or a pharmaceutically acceptable salt thereof, wherein $R^6$ is a 4- to 8-membered monocyclic heterocycle containing 1-2 heteroatoms independently selected from oxygen, nitrogen, and sulfur, the monocyclic heterocycle optionally containing one double bond and/or a $C_{1-3}$alkylene bridge between two non-adjacent ring atoms and being optionally substituted with 1-4 substituents independently selected from the group consisting of $C_{1-4}$alkyl, $C_{1-4}$haloalkyl, —$CH_2$S(O)$_2$phenyl, halogen, hydroxyl, and oxo.

6. The method of claim 2, wherein the compound is a compound of formula (I'), or a pharmaceutically acceptable salt thereof, wherein $R^6$ is a 5- or 6-membered monocyclic heteroaryl containing 1-3 heteroatoms independently selected from nitrogen, oxygen, and sulfur, the monocyclic heteroaryl being optionally substituted with 1-3 substituents independently selected from $C_{1-4}$alkyl, $C_{1-4}$haloalkyl, halogen, and hydroxyl.

7. The method of claim 2, wherein the compound is a compound of formula (I'), or a pharmaceutically acceptable salt thereof, wherein $R^6$ is a 7- to 12-membered spiro heterocycle comprising a first ring and a second ring, the first ring being a 4- to 8-membered monocyclic heterocycle containing 1-2 heteroatoms independently selected from nitrogen and oxygen and being attached to $L^2$, the second ring being a $C_{3-8}$cycloalkyl or a 4- to 8-membered monocyclic heterocycle containing 1-2 oxygen atoms wherein two atoms of the second ring are attached to one carbon of the first ring to form a spirocycle optionally substituted with 1-4 substituents independently selected from the group consisting of $C_{1-4}$alkyl, $C_{1-4}$haloalkyl, halogen, hydroxyl, and oxo.

8. The method of claim 2, wherein the compound is a compound of formula (I'), or a pharmaceutically acceptable salt thereof, wherein $R^6$ is a 7- to 12-membered fused bicyclic heterocycle containing 1-3 heteroatoms independently selected from oxygen, nitrogen, and sulfur and being optionally substituted with 1-4 substituents independently selected from the group consisting of $C_{1-4}$alkyl, $C_{1-4}$haloalkyl, halogen, hydroxyl, and oxo.

9. The method of claim 1, wherein the compound is a compound of formula (I'), or a pharmaceutically acceptable salt thereof, wherein $R^1$ is -$G^1$-$L^2$-$R^7$.

10. The method of claim 3, wherein the compound is a compound of formula (I'), or a pharmaceutically acceptable salt thereof, wherein $G^1$ is piperazinyl, homopiperazinyl, azetidinyl, pyrrolidinyl, piperidinyl, azepanyl, 2,5-diazabicyclo[2.2.1]heptanyl, 2,5-dihydro-1H-pyrrolyl, or 1,2,3,6-tetrahydropyridinyl, G$^1$ being optionally substituted with 1-4 substituents independently selected from 1 hydroxyl, 1-2 halogen, 1 oxo, and 1-4 C$_{1-4}$alkyl groups.

11. The method of claim 10, wherein the compound is a compound of formula (I'), or a pharmaceutically acceptable salt thereof, wherein the pyrrolidinyl and piperidinyl are optionally substituted with 1-4 substituents independently selected from 1 hydroxyl, 1-2 halogen, and 1 oxo, and the piperazinyl is optionally substituted with oxo.

12. The method of claim 1, wherein the compound is a compound of formula (I'), or a pharmaceutically acceptable salt thereof, wherein G$^1$ is a 3- to 8-membered cycloalkyl optionally substituted with 1-4 substituents independently selected from the group consisting of C$_{1-4}$alkyl, C$_{1-4}$haloalkyl, halogen, hydroxyl, and oxo.

13. The method of claim 10, wherein the compound is a compound of formula (I'), or a pharmaceutically acceptable salt, wherein L$^2$ is a bond.

14. The method of claim 1, wherein the compound is a compound of formula (I'), or a pharmaceutically acceptable salt thereof, wherein R$^1$ is G$^2$.

15. The method of claim 1, wherein the compound is a compound of formula (I'), or a pharmaceutically acceptable salt thereof, wherein R$^1$ is G$^3$.

16. The method of claim 1, wherein the compound is a compound of formula (I'), or a pharmaceutically acceptable salt thereof, wherein R$^1$ is G$^4$.

17. The method of claim 1, wherein the compound is a compound of formula (I'), or a pharmaceutically acceptable salt thereof, wherein R$^1$ is G$^6$.

18. The method of claim 1, wherein the compound is a compound of formula (I'), or a pharmaceutically acceptable salt thereof, wherein R$^1$ is -=-G$^5$.

19. The method of any of claim 13, wherein the compound is a compound of formula (I'), or a pharmaceutically acceptable salt thereof, wherein L$^1$ is a bond.

20. The method of claim 3, wherein the compound is a compound of formula (I'), or a pharmaceutically acceptable salt thereof, wherein R$^4$ is
 a) phenyl,
  the phenyl being optionally substituted with one substituent selected from the group consisting of halogen, cyano, —S(O)$_2$C$_{1-4}$alkyl, —S(O)C$_{1-4}$alkyl, —SC$_{1-4}$alkyl, C$_{1-4}$alkyl, C$_{1-4}$haloalkyl, —OC$_{1-4}$haloalkyl, —OC$_{1-4}$haloalkyl, —C$_{1-4}$alkylene-OC$_{1-4}$alkyl, —C$_{1-4}$alkylene-N(C$_{1-4}$alkyl)(C$_{1-4}$alkyl), —N(C$_{1-4}$alkyl)(C$_{1-4}$alkylene-OC$_{1-4}$alkyl), or a 4- to 8-membered monocyclic heterocycle containing 1-2 nitrogen atoms, the 4- to 8-membered monocyclic heterocycle being independently optionally substituted with 1-2 substituents independently selected from the group consisting of halogen, —OC$_{1-4}$alkyl, C$_{1-4}$alkyl, —C$_{1-4}$alkylene-OC$_{1-4}$alkyl, and —C$_{1-4}$alkylene-OH,
  the phenyl being further optionally substituted with 1-2 substituents independently selected from the group consisting of halogen and C$_{1-4}$alkyl;
 b) pyrazinyl,
  the pyrazinyl being optionally substituted with 1-3 C$_{1-4}$alkyl groups;
 c) pyrimidinyl,
  the pyrimidinyl being optionally substituted with one substituent selected from halogen, —S(O)$_2$C$_{1-4}$alkyl, —S(O)C$_{1-4}$alkyl, —SC$_{1-4}$alkyl, C$_{1-4}$alkyl, —OC$_{1-4}$alkyl, or —C$_{1-4}$alkylene-OC$_{1-4}$alkyl, the pyrimidinyl being further optionally substituted with C$_{1-4}$alkyl;
 d) pyridazinyl; or
 e) pyridinyl,
  the pyridinyl being optionally substituted with one substituent selected from the group consisting of halogen, hydroxyl, C$_{1-4}$alkyl, and a 4- to 8-membered monocyclic heterocycle containing 1-2 nitrogen atoms,
  the pyridinyl being further optionally substituted with 1-2 substituents selected from halogen and C$_{1-4}$alkyl.

21. The method of claim 1, wherein R$^2$ is C$_{1-4}$alkyl, C$_{1-4}$haloalkyl, or C$_{3-6}$cycloalkyl.

22. The method of claim 1, wherein the compound is a compound or a pharmaceutically acceptable salt thereof, selected from the following table:

| | |
|---|---|
| 2. | 1-(3,5-difluorophenyl)-N-[3-(3-methoxyazetidin-1-yl)-5-methyl-phenyl]-1,2,4-triazol-3-amine |
| 4. | 1-[4-[3-[[1-(3,5-difluorophenyl)-1,2,4-triazol-3-yl]amino]-5-(trifluoromethyl)phenyl]piperazin-2-yl]cyclobutanol |
| 5. | N-[3-chloro-5-[4-(oxetan-3-yl)piperazin-1-yl]phenyl]-1-(3,5-difluorophenyl)-1,2,4-triazol-3-amine |
| 6. | 3-methyl-1-[3-methyl-5-[(1-phenyl-1,2,4-triazol-3-yl)amino]phenyl]pyrrolidin-3-ol |
| 7. | N-[3-methyl-5-(6-oxa-2-azaspiro[3.3]heptan-2-yl)phenyl]-1-phenyl-1,2,4-triazol-3-amine |
| 8. | N3-[1-(3,5-difluorophenyl)-1,2,4-triazol-3-yl]-5-methyl-N1-tetrahydrofuran-3-yl-benzene-1,3-diamine |
| 10. | N-[3,5-di(tetrahydropyran-4-yl)phenyl]-1-phenyl-1,2,4-triazol-3-amine |
| 11. | N-[3-methyl-5-(2-oxa-7-azaspiro[3.5]nonan-7-yl)phenyl]-1-phenyl-1,2,4-triazol-3-amine |
| 12. | methyl 4-[3-methyl-5-[(1-phenyl-1,2,4-triazol-3-yl)amino]phenyl]piperidine-1-carboxylate |
| 13. | N-[3-(4-methylpiperazin-1-yl)-5-(trifluoromethyl)phenyl]-1-(4-pyridyl)-1,2,4-triazol-3-amine |
| 14. | N-[3-ethyl-5-[4-(oxetan-3-yl)piperazin-1-yl]phenyl]-1-(4-fluorophenyl)-1,2,4-triazol-3-amine |
| 15. | N-[3-ethyl-5-(3-morpholinoazetidin-1-yl)phenyl]-1-(3-fluorophenyl)-1,2,4-triazol-3-amine |
| 16. | N-[3-ethyl-5-[4-(oxetan-3-yl)piperazin-1-yl]phenyl]-1-(2-fluoro-4-pyridyl)-1,2,4-triazol-3-amine |
| 17. | N-[3-tert-butyl-5-[4-(oxetan-3-yl)piperazin-1-yl]phenyl]-1-(3,5-difluorophenyl)-1,2,4-triazol-3-amine |
| 18. | N-[3-[3-fluoro-1-(oxetan-3-yl)pyrrolidin-3-yl]-5-methyl-phenyl]-1-phenyl-1,2,4-triazol-3-amine |
| 19. | 1-(3,5-difluorophenyl)-N-[3-(6,8-dihydro-5H-imidazo[1,2-a]pyrazin-7-yl)-5-methyl-phenyl]-1,2,4-triazol-3-amine |
| 20. | N-[3-(4-cyclopropylpiperazin-1-yl)-5-methyl-phenyl]-1-pyrazin-2-yl-1,2,4-triazol-3-amine |
| 21. | N-[3-(2,5-dimethylpiperazin-1-yl)-5-methyl-phenyl]-1-phenyl-1,2,4-triazol-3-amine |
| 23. | 1-(3,5-difluorophenyl)-N-[3-(3-fluoro-1-methyl-pyrrolidin-3-yl)-5-methyl-phenyl]-1,2,4-triazol-3-amine |
| 24. | 1-(5-fluoro-3-pyridyl)-N-[3-methyl-5-[4-(oxetan-3-yl)piperazin-1-yl]phenyl]-1,2,4-triazol-3-amine |
| 25. | 1-(3,5-difluorophenyl)-N-[3-methyl-5-[1-(oxetan-3-yl)pyrrolidin-3-yl]phenyl]-1,2,4-triazol-3-amine |
| 26. | N-[3-(difluoromethyl)-5-[4-(oxetan-3-yl)piperazin-1-yl]phenyl]-1-phenyl-1,2,4-triazol-3-amine |
| 27. | 1-(3-fluorophenyl)-N-(3-methyl-5-morpholino-phenyl)-1,2,4-triazol-3-amine |
| 28. | 1-(2,4-difluorophenyl)-N-[3-fluoro-5-(4-methyl-1,4-diazepan-1-yl)phenyl]-1,2,4-triazol-3-amine |
| 29. | N-[3-[(8aR)-4-isobutyl-3,4,6,7,8,8a-hexahydro-1H-pyrrolo[1,2-a]pyrazin-2-yl]-5-methyl-phenyl]-1-(3,5-difluorophenyl)-1,2,4-triazol-3-amine |
| 30. | 1-(2-methoxypyrimidin-4-yl)-N-[3-methyl-5-[4-(oxetan-3-yl)piperazin-1-yl]phenyl]-1,2,4-triazol-3-amine |
| 31. | N-[3-ethyl-5-[4-(oxetan-3-yl)piperazin-1-yl]phenyl]-1-(p-tolyl)-1,2,4-triazol-3-amine |

| | |
|---|---|
| 32. | 1-(3-chloro-5-fluoro-phenyl)-N-[3-methyl-5-[4-(oxetan-3-yl)piperazin-1-yl]phenyl]-1,2,4-triazol-3-amine |
| 33. | 1-(3,5-difluorophenyl)-N-[3-methyl-5-[4-(oxetan-3-yl)piperazin-1-yl]phenyl]-1,2,4-triazol-3-amine |
| 34. | 1-(3,5-difluorophenyl)-N-[3-methyl-5-[(1S,4S)-2-(oxetan-3-yl)-2,5-diazabicyclo[2.2.1]heptan-5-yl]phenyl]-1,2,4-triazol-3-amine |
| 36. | 1-(3-fluorophenyl)-N-[3-methyl-5-[1-(oxetan-3-yl)azetidin-3-yl]phenyl]-1,2,4-triazol-3-amine |
| 37. | 1-(3,5-difluorophenyl)-N-[3-methyl-5-(4-methylpiperazin-1-yl)phenyl]-1,2,4-triazol-3-amine |
| 38. | N3-[1-(3,5-difluorophenyl)-1,2,4-triazol-3-yl]-5-methyl-N1-[1-(oxetan-3-yl)-4-piperidyl]benzene-1,3-diamine |
| 39. | N-(3-methyl-5-pyrrolidin-3-yl-phenyl)-1-phenyl-1,2,4-triazol-3-amine |
| 40. | 1-(2-fluoro-4-pyridyl)-N-[3-methyl-5-[4-(oxetan-3-yl)piperazin-1-yl]phenyl]-1,2,4-triazol-3-amine |
| 41. | 1-[3-[2-(ethoxymethyl)pyrrolidin-1-yl]-5-fluoro-phenyl]-N-[3-methyl-5-[4-(oxetan-3-yl)piperazin-1-yl]phenyl]-1,2,4-triazol-3-amine |
| 42. | 1-(2-chloro-4-pyridyl)-N-(3-methyl-5-pyrrolidin-1-yl-phenyl)-1,2,4-triazol-3-amine |
| 43. | 1-(3,4-difluorophenyl)-N-(3-methyl-5-morpholino-phenyl)-1,2,4-triazol-3-amine |
| 45. | N-(3-methyl-5-morpholino-phenyl)-1-phenyl-1,2,4-triazol-3-amine |
| 46. | 1-(3,4-difluorophenyl)-N-[3-methyl-5-[(3R)-1-(oxetan-3-yl)pyrrolidin-3-yl]oxy-phenyl]-1,2,4-triazol-3-amine |
| 47. | N-[3-cyclopropyl-5-[4-(oxetan-3-yl)piperazin-1-yl]phenyl]-1-phenyl-1,2,4-triazol-3-amine |
| 48. | N-[3-ethyl-5-[4-(oxetan-3-yl)piperazin-1-yl]phenyl]-1-pyrazin-2-yl-1,2,4-triazol-3-amine |
| 49. | N-(3-fluoro-5-morpholino-phenyl)-1-(2-fluorophenyl)-1,2,4-triazol-3-amine |
| 50. | N-[3-ethyl-5-[4-(oxetan-3-yl)piperazin-1-yl]phenyl]-1-(5-fluoropyrimidin-4-yl)-1,2,4-triazol-3-amine |
| 51. | N-[3-[1-[3-(benzenesulfonylmethyl)oxetan-3-yl]-4-piperidyl]-5-methyl-phenyl]-1-phenyl-1,2,4-triazol-3-amine |
| 52. | 1-(3,4-difluorophenyl)-N-[3-methyl-5-[(3S)-1-(oxetan-3-yl)pyrrolidin-3-yl]oxy-phenyl]-1,2,4-triazol-3-amine |
| 53. | [4-[3-[[1-(3,5-difluorophenyl)-1,2,4-triazol-3-yl]amino]-5-methyl-phenyl]-1-methyl-piperazin-2-yl]methanol |
| 54. | N-[3-methyl-5-[4-(oxetan-3-yl)piperazin-1-yl]phenyl]-1-(4-methyl-2-pyridyl)-1,2,4-triazol-3-amine |
| 55. | 1-(3-chlorophenyl)-N-[3-cyclopropyl-5-[4-(oxetan-3-yl)piperazin-1-yl]phenyl]-1,2,4-triazol-3-amine |
| 56. | 1-(3-fluoro-5-methoxy-phenyl)-N-[3-methyl-5-[4-(oxetan-3-yl)piperazin-1-yl]phenyl]-1,2,4-triazol-3-amine |
| 58. | N-[3-ethyl-5-[4-(oxetan-3-yl)piperazin-1-yl]phenyl]-1-(6-methylpyrimidin-4-yl)-1,2,4-triazol-3-amine |
| 59. | [4-[3-methyl-5-[(1-phenyl-1,2,4-triazol-3-yl)amino]phenyl]piperazin-2-yl]methanol |
| 60. | N-[3-methyl-5-(1-methyl-3-piperidyl)phenyl]-1-phenyl-1,2,4-triazol-3-amine |
| 61. | 1-(3,5-difluorophenyl)-N-[3-methyl-5-[1-(oxetan-3-yl)-3,6-dihydro-2H-pyridin-4-yl]phenyl]-1,2,4-triazol-3-amine |
| 62. | N-[3-(difluoromethyl)-5-piperazin-1-yl-phenyl]-1-phenyl-1,2,4-triazol-3-amine |
| 63. | 1-(3,5-difluorophenyl)-N-[3-(4-methylpiperazin-1-yl)-5-(trifluoromethyl)phenyl]-1,2,4-triazol-3-amine |
| 64. | N-[3-methyl-5-[4-(oxetan-3-yl)piperazin-1-yl]phenyl]-1-(2-methylsulfanylpyrimidin-4-yl)-1,2,4-triazol-3-amine |
| 65. | N-[3-methyl-5-[1-(oxetan-3-yl)azetidin-3-yl]phenyl]-1-phenyl-1,2,4-triazol-3-amine |
| 66. | 2,5-difluoro-4-[3-[3-methyl-5-[4-(oxetan-3-yl)piperazin-1-yl]anilino]-1,2,4-triazol-1-yl]benzonitrile |
| 67. | 1-[3-[[1-(3,5-difluorophenyl)-1,2,4-triazol-3-yl]amino]-5-methyl-phenyl]-4-(oxetan-3-yl)piperazin-2-one |
| 68. | N-[3-methyl-5-(4-methylpiperazin-1-yl)phenyl]-1-pyrazin-2-yl-1,2,4-triazol-3-amine |
| 69. | 1-(3,4-difluorophenyl)-N-[3-ethyl-5-[4-(oxetan-3-yl)piperazin-1-yl]phenyl]-1,2,4-triazol-3-amine |
| 70. | N-[3-methyl-5-[4-(oxetan-3-yl)piperazin-1-yl]phenyl]-1-(p-tolyl)-1,2,4-triazol-3-amine |
| 71. | N-[3-methyl-5-[1-(oxetan-3-yl)-4-piperidyl]phenyl]-1-phenyl-1,2,4-triazol-3-amine |
| 72. | ethyl 2-[4-[3-[[1-(3,5-difluorophenyl)-1,2,4-triazol-3-yl]amino]-5-methyl-phenyl]piperazin-1-yl]acetate |
| 73. | N-[3-cyclopropyl-5-[4-(oxetan-3-yl)piperazin-1-yl]phenyl]-1-(3-fluoro-5-methyl-phenyl)-1,2,4-triazol-3-amine |
| 74. | N-[3-methyl-5-[1-(oxetan-3-yl)-3-piperidyl]phenyl]-1-pyrazin-2-yl-1,2,4-triazol-3-amine |
| 75. | N-[3-[4-(3,3-difluorocyclobutyl)piperazin-1-yl]-5-methyl-phenyl]-1-pyrazin-2-yl-1,2,4-triazol-3-amine |
| 76. | 1-methyl-4-[3-methyl-5-[(1-phenyl-1,2,4-triazol-3-yl)amino]phenyl]piperazin-2-one |
| 77. | 1-(3,5-difluorophenyl)-N-(3-methyl-5-piperazin-1-yl-phenyl)-1,2,4-triazol-3-amine |
| 78. | N-[3-[(1S,4S)-2-cyclopropyl-2,5-diazabicyclo[2.2.1]heptan-5-yl]-5-methyl-phenyl]-1-(3,5-difluorophenyl)-1,2,4-triazol-3-amine |
| 79. | 2-[4-[3-[[1-(3,5-difluorophenyl)-1,2,4-triazol-3-yl]amino]-5-methyl-phenyl]piperazin-1-yl]propane-1,3-diol |
| 80. | N-(3-fluoro-5-morpholino-phenyl)-1-phenyl-1,2,4-triazol-3-amine |
| 81. | 4-[3-[3-methyl-5-(4-methylpiperazin-1-yl)anilino]-1,2,4-triazol-1-yl]benzonitrile |
| 82. | N-[3-(difluoromethyl)-5-[4-(oxetan-3-yl)piperazin-1-yl]phenyl]-1-(3,5-difluorophenyl)-1,2,4-triazol-3-amine |
| 83. | 1-(2-fluorophenyl)-N-(3-fluoro-5-pyrrolidin-1-yl-phenyl)-1,2,4-triazol-3-amine |
| 84. | N-(3-methyl-5-morpholino-phenyl)-1-(4-pyridyl)-1,2,4-triazol-3-amine |
| 85. | N-[3-(difluoromethyl)-5-morpholino-phenyl]-1-(2-fluoro-4-pyridyl)-1,2,4-triazol-3-amine |
| 86. | 1-(3-methoxyphenyl)-N-[3-methyl-5-[4-(oxetan-3-yl)piperazin-1-yl]phenyl]-1,2,4-triazol-3-amine |
| 87. | N-[3-(4-cyclopentylpiperazin-1-yl)-5-methyl-phenyl]-1-phenyl-1,2,4-triazol-3-amine |
| 88. | N-[3-(1,1-dioxo-1,4-thiazinan-4-yl)-5-methyl-phenyl]-1-phenyl-1,2,4-triazol-3-amine |
| 90. | 1-[4-[3-[[1-(3,5-difluorophenyl)-1,2,4-triazol-3-yl]amino]-5-methyl-phenyl]-1-piperidyl]ethanone |
| 91. | N-[3-ethyl-5-[4-(oxetan-3-yl)piperazin-1-yl]phenyl]-1-(2-methylpyrimidin-4-yl)-1,2,4-triazol-3-amine |
| 92. | 1-(3,5-difluorophenyl)-N-[3-methyl-5-[(3S)-1-(oxetan-3-yl)pyrrolidin-3-yl]phenyl]-1,2,4-triazol-3-amine |
| 93. | 1-[3-[[1-(3,5-difluorophenyl)-1,2,4-triazol-3-yl]amino]-5-methyl-phenyl]piperazin-2-one |
| 94. | 1-(3-methoxyphenyl)-N-[3-methyl-5-(4-methylpiperazin-1-yl)phenyl]-1,2,4-triazol-3-amine |
| 95. | 1-(3,5-difluorophenyl)-N-[3-methyl-5-[4-(thietan-3-yl)piperazin-1-yl]phenyl]-1,2,4-triazol-3-amine |
| 96. | N-[3-(4-methylpiperazin-1-yl)-5-(trifluoromethyl)phenyl]-1-pyrimidin-4-yl-1,2,4-triazol-3-amine |
| 97. | N-[3-tert-butyl-5-[4-(oxetan-3-yl)piperazin-1-yl]phenyl]-1-(3-fluorophenyl)-1,2,4-triazol-3-amine |
| 98. | N-[3-fluoro-5-(4-methyl-1,4-diazepan-1-yl)phenyl]-1-(3-fluorophenyl)-1,2,4-triazol-3-amine |
| 99. | 1-(3,4-difluorophenyl)-N-(3-fluoro-5-pyrrolidin-1-yl-phenyl)-1,2,4-triazol-3-amine |
| 101. | (3S)-3-[3-[[1-(3,5-difluorophenyl)-1,2,4-triazol-3-yl]amino]-5-methyl-phenyl]-1-(oxetan-3-yl)pyrrolidin-3-ol |
| 102. | 1-(4-fluorophenyl)-N-[3-methoxy-5-[4-(oxetan-3-yl)piperazin-1-yl]phenyl]-1,2,4-triazol-3-amine |
| 103. | 1-[3-(2-ethylpyrrolidin-1-yl)-5-fluoro-phenyl]-N-[3-methyl-5-[4-(oxetan-3-yl)piperazin-1-yl]phenyl]-1,2,4-triazol-3-amine |
| 104. | N-[3-methyl-5-[4-(oxetan-3-yl)piperazin-1-yl]phenyl]-1-(2-pyridyl)-1,2,4-triazol-3-amine |
| 107. | 1-(3,5-difluorophenyl)-N-[3-ethyl-5-[4-(oxetan-3-yl)piperazin-1-yl]phenyl]-1,2,4-triazol-3-amine |
| 108. | 1-(3,5-difluorophenyl)-N-[3-methyl-5-(4-piperidyl)phenyl]-1,2,4-triazol-3-amine |

| | |
|---|---|
| 109. | N-[3-[3-(dimethylamino)pyrrolidin-1-yl]-5-fluoro-phenyl]-1-(3-fluorophenyl)-1,2,4-triazol-3-amine |
| 110. | N-(3-methyl-5-pyrrolidin-1-yl-phenyl)-1-phenyl-1,2,4-triazol-3-amine |
| 111. | N-[3-methyl-5-[4-(oxetan-3-yl)piperazin-1-yl]phenyl]-1-(6-methylpyrimidin-4-yl)-1,2,4-triazol-3-amine |
| 112. | 1-(3,5-difluorophenyl)-N-[3-fluoro-5-[4-(oxetan-3-yl)piperazin-1-yl]phenyl]-1,2,4-triazol-3-amine |
| 113. | N3-[1-(3,4-difluorophenyl)-1,2,4-triazol-3-yl]-5-methyl-N1-[1-(oxetan-3-yl)pyrrolidin-3-yl]benzene-1,3-diamine |
| 114. | 1-[1-[3-[[1-(3,5-difluorophenyl)-1,2,4-triazol-3-yl]amino]-5-methyl-phenyl]-3-piperidyl]pyrrolidin-2-one |
| 115. | 1-[3-[3-methyl-5-[(1-phenyl-1,2,4-triazol-3-yl)amino]anilino]-1-piperidyl]ethanone |
| 116. | 1-(3,5-difluorophenyl)-N-[3-[3-(methoxymethyl)azetidin-1-yl]-5-methyl-phenyl]-1,2,4-triazol-3-amine |
| 117. | 1-[3-[3-methyl-5-[(1-phenyl-1,2,4-triazol-3-yl)amino]phenyl]-1-piperidyl]ethanone |
| 118. | N-[3-methyl-5-[4-(oxetan-3-yl)piperazin-1-yl]phenyl]-1-phenyl-1,2,4-triazol-3-amine |
| 119. | 1-(3,5-difluorophenyl)-N-[3-(3,4-dimethylpiperazin-1-yl)-5-methyl-phenyl]-1,2,4-triazol-3-amine |
| 120. | N-[3-(1-cyclopropyl-4-piperidyl)-5-methyl-phenyl]-1-phenyl-1,2,4-triazol-3-amine |
| 121. | N-[3-cyclopropyl-5-[4-(oxetan-3-yl)piperazin-1-yl]phenyl]-1-(2,6-difluoro-4-pyridyl)-1,2,4-triazol-3-amine |
| 122. | 1-(2-fluoro-4-pyridyl)-N-[3-[4-(methoxymethyl)-1-piperidyl]-5-methyl-phenyl]-1,2,4-triazol-3-amine |
| 123. | 2-[(2S)-4-[3-[[1-(3,5-difluorophenyl)-1,2,4-triazol-3-yl]amino]-5-(trifluoromethyl)phenyl]piperazin-2-yl]propan-2-ol |
| 124. | N-(3-ethyl-5-piperazin-1-yl-phenyl)-1-pyrazin-2-yl-1,2,4-triazol-3-amine |
| 125. | 2-[4-[3-[[1-(3,5-difluorophenyl)-1,2,4-triazol-3-yl]amino]-5-methyl-phenyl]piperazin-1-yl]acetic acid |
| 126. | N-[3-[4-(3-deuteriooxetan-3-yl)piperazin-1-yl]-5-methyl-phenyl]-1-(3-fluorophenyl)-1,2,4-triazol-3-amine |
| 127. | N-[3-methyl-5-[4-(2-methyltetrahydrofuran-3-yl)piperazin-1-yl]phenyl]-1-phenyl-1,2,4-triazol-3-amine |
| 128. | N-[3-[(8aR)-3,4,6,7,8,8a-hexahydro-1H-pyrrolo[1,2-a]pyrazin-2-yl]-5-methyl-phenyl]-1-(3,5-difluorophenyl)-1,2,4-triazol-3-amine |
| 129. | N-[3-cyclopropyl-5-[4-(oxetan-3-yl)piperazin-1-yl]phenyl]-1-(2,6-dimethylpyrimidin-4-yl)-1,2,4-triazol-3-amine |
| 130. | 1-(3,5-difluorophenyl)-N-[3-[4-(oxetan-3-yl)piperazin-1-yl]-5-(trifluoromethyl)phenyl]-1,2,4-triazol-3-amine |
| 131. | 1-(3,5-difluorophenyl)-N-[3-methyl-5-(oxetan-3-yl)phenyl]-1,2,4-triazol-3-amine |
| 132. | N-[3-ethyl-5-[4-(oxetan-3-yl)piperazin-1-yl]phenyl]-1-(2-methylsulfanylpyrimidin-4-yl)-1,2,4-triazol-3-amine |
| 133. | N-[3-(3,4-dimethylpiperazin-1-yl)-5-methyl-phenyl]-1-phenyl-1,2,4-triazol-3-amine |
| 134. | 1-(5-chloro-3-pyridyl)-N-[3-cyclopropyl-5-[4-(oxetan-3-yl)piperazin-1-yl]phenyl]-1,2,4-triazol-3-amine |
| 136. | N-[3-methyl-5-[4-(3-methyloxetan-3-yl)piperazin-1-yl]phenyl]-1-pyrazin-2-yl-1,2,4-triazol-3-amine |
| 137. | 1-(3,5-difluorophenyl)-N-[3-methyl-5-(4-tetrahydrofuran-3-ylpiperazin-1-yl)phenyl]-1,2,4-triazol-3-amine |
| 138. | N-[3-methyl-5-(4-methylpiperazin-1-yl)phenyl]-1-(2-pyridyl)-1,2,4-triazol-3-amine |
| 139. | 1-(3,5-difluorophenyl)-N-[3-methyl-5-[4-(oxetan-3-yl)-4-oxido-piperazin-4-ium-1-yl]phenyl]-1,2,4-triazol-3-amine |
| 140. | 2-fluoro-4-[3-[3-methyl-5-[4-(oxetan-3-yl)piperazin-1-yl]anilino]-1,2,4-triazol-1-yl]benzonitrile |
| 141. | 1-(3-chlorophenyl)-N-[3-methyl-5-(4-methylpiperazin-1-yl)phenyl]-1,2,4-triazol-3-amine |
| 142. | 1-[3-methyl-5-[(1-phenyl-1,2,4-triazol-3-yl)amino]phenyl]piperidine-4-carbonitrile |
| 143. | methyl 3-[3-methyl-5-[(1-phenyl-1,2,4-triazol-3-yl)amino]phenyl]piperidine-1-carboxylate |
| 144. | 1-[4-[3-(difluoromethyl)-5-[(1-phenyl-1,2,4-triazol-3-yl)amino]phenyl]piperazin-1-yl]ethanone |
| 146. | 1-[3-methyl-5-[(1-phenyl-1,2,4-triazol-3-yl)amino]phenyl]piperidine-3-carbonitrile |
| 147. | 1-(3-fluorophenyl)-N-[3-methyl-5-(oxetan-3-yl)phenyl]-1,2,4-triazol-3-amine |
| 148. | N-[3-[4-(2-methoxyethyl)-1-piperidyl]-5-methyl-phenyl]-1-phenyl-1,2,4-triazol-3-amine |
| 149. | N-[3-(4-cyclopropylpiperazin-1-yl)-5-methyl-phenyl]-1-phenyl-1,2,4-triazol-3-amine |
| 151. | 1-(3,5-difluorophenyl)-N-[3-methyl-5-(1-methyl-4-piperidyl)phenyl]-1,2,4-triazol-3-amine |
| 152. | N-[3-[(8aR)-4-isobutyl-3,4,6,7,8,8a-hexahydro-1H-pyrrolo[1,2-a]pyrazin-2-yl]-5-methyl-phenyl]-1-phenyl-1,2,4-triazol-3-amine |
| 153. | N-[3-(4-cyclopropylpiperazin-1-yl)-5-(difluoromethyl)phenyl]-1-(2-fluoro-4-pyridyl)-1,2,4-triazol-3-amine |
| 154. | 1-(6-fluoro-2-pyridyl)-N-[3-methyl-5-[4-(oxetan-3-yl)piperazin-1-yl]phenyl]-1,2,4-triazol-3-amine |
| 155. | 4-[3-(3-methyl-5-morpholino-anilino)-1,2,4-triazol-1-yl]pyridin-2-ol |
| 157. | N-[3-[(8aR)-3,4,6,7,8,8a-hexahydro-1H-pyrrolo[1,2-a]pyrazin-2-yl]-5-methyl-phenyl]-1-phenyl-1,2,4-triazol-3-amine |
| 158. | N-(3-fluoro-5-morpholino-phenyl)-1-(3-fluorophenyl)-1,2,4-triazol-3-amine |
| 159. | N-(3-methyl-5-piperazin-1-yl-phenyl)-1-phenyl-1,2,4-triazol-3-amine |
| 160. | N-[3-methyl-5-[1-(oxetan-3-yl)-2,5-dihydropyrrol-3-yl]phenyl]-1-phenyl-1,2,4-triazol-3-amine |
| 161. | 1-[1-[3-[[1-(3,5-difluorophenyl)-1,2,4-triazol-3-yl]amino]-5-methyl-phenyl]-4-piperidyl]pyrrolidin-2-one |
| 162. | 1-(3,5-difluorophenyl)-N-[3-[4-(methoxymethyl)-1-piperidyl]-5-methyl-phenyl]-1,2,4-triazol-3-amine |
| 163. | 4-[3-[3-(difluoromethyl)-5-[4-(oxetan-3-yl)piperazin-1-yl]anilino]-1,2,4-triazol-1-yl]-1H-pyridin-2-one |
| 164. | 1-(3,5-difluorophenyl)-N-[3-(3-methoxypyrrolidin-1-yl)-5-methyl-phenyl]-1,2,4-triazol-3-amine |
| 165. | N-(3-morpholino-5-tetrahydrofuran-3-yl-phenyl)-1-phenyl-1,2,4-triazol-3-amine |
| 166. | N-[3-fluoro-5-(1,4-oxazepan-4-yl)phenyl]-1-(3-fluorophenyl)-1,2,4-triazol-3-amine |
| 167. | 1-(4-fluorophenyl)-N-(3-fluoro-5-pyrrolidin-1-yl-phenyl)-1,2,4-triazol-3-amine |
| 168. | N-(3-bromo-5-morpholino-phenyl)-1-phenyl-1,2,4-triazol-3-amine |
| 169. | 1-(3,4-difluorophenyl)-N-[3-methyl-5-[4-(oxetan-3-yl)-1-piperidyl]phenyl]-1,2,4-triazol-3-amine |
| 171. | 1-(3,5-difluorophenyl)-N-[3-methyl-5-(6-oxa-2-azaspiro[3.3]heptan-2-yl)phenyl]-1,2,4-triazol-3-amine |
| 172. | N-[3-methyl-5-(4-tetrahydropyran-3-ylpiperazin-1-yl)phenyl]-1-phenyl-1,2,4-triazol-3-amine |
| 173. | 1-(3,5-difluorophenyl)-N-[3-ethyl-5-(3-morpholinoazetidin-1-yl)phenyl]-1,2,4-triazol-3-amine |
| 174. | N-[3-methyl-5-[4-(oxetan-3-yl)piperazin-1-yl]phenyl]-1-pyrimidin-4-yl-1,2,4-triazol-3-amine |
| 175. | 1-(3-fluorophenyl)-N-[3-[4-(oxetan-3-yl)piperazin-1-yl]-5-(trifluoromethyl)phenyl]-1,2,4-triazol-3-amine |

| # | Name |
|---|---|
| 176. | N-[3-(4-cyclopropylpiperazin-1-yl)-5-methyl-phenyl]-1-pyrimidin-4-yl-1,2,4-triazol-3-amine |
| 177. | N1-(azetidin-3-yl)-N3-[1-(2,4-difluorophenyl)-1,2,4-triazol-3-yl]-5-fluoro-benzene-1,3-diamine |
| 178. | 1-(3,5-difluorophenyl)-N-[3-[(3R)-1-(oxetan-3-yl)pyrrolidin-3-yl]oxy-phenyl]-1,2,4-triazol-3-amine |
| 179. | N-[3-methyl-5-(4-methyl-1,4-diazepan-1-yl)phenyl]-1-phenyl-1,2,4-triazol-3-amine |
| 180. | N-[3-methyl-5-[1-(oxetan-3-yl)-3-piperidyl]phenyl]-1-pyrimidin-4-yl-1,2,4-triazol-3-amine |
| 181. | N-(3-fluoro-5-morpholino-phenyl)-1-[3-(trifluoromethyl)phenyl]-1,2,4-triazol-3-amine |
| 182. | N1-[1-(3-methoxypropyl)-4-piperidyl]-5-methyl-N3-(1-phenyl-1,2,4-triazol-3-yl)benzene-1,3-diamine |
| 183. | 1-(3,4-difluorophenyl)-N-[3-methoxy-5-[4-(oxetan-3-yl)piperazin-1-yl]phenyl]-1,2,4-triazol-3-amine |
| 184. | N-[3-cyclopropyl-5-[4-(oxetan-3-yl)piperazin-1-yl]phenyl]-1-(2-fluoro-4-pyridyl)-1,2,4-triazol-3-amine |
| 185. | 1-(3,5-difluorophenyl)-N-[3-methyl-5-[(1R,4R)-2-(oxetan-3-yl)-2,5-diazabicyclo[2.2.1]heptan-5-yl]phenyl]-1,2,4-triazol-3-amine |
| 186. | 4-[3-(3-methyl-5-pyrrolidin-1-yl-anilino)-1,2,4-triazol-1-yl]benzonitrile |
| 187. | 1-[3-[[ethyl(methyl)amino]methyl]-5-fluoro-phenyl]-N-[3-methyl-5-[4-(oxetan-3-yl)piperazin-1-yl]phenyl]-1,2,4-triazol-3-amine |
| 188. | N3-[1-(3-fluorophenyl)-1,2,4-triazol-3-yl]-5-methyl-N1-[1-(oxetan-3-yl)pyrrolidin-3-yl]benzene-1,3-diamine |
| 189. | N-[3-(difluoromethyl)-5-[4-(oxetan-3-yl)piperazin-1-yl]phenyl]-1-(2-fluoro-4-pyridyl)-1,2,4-triazol-3-amine |
| 190. | N-(3-methyl-5-pyrrolidin-1-yl-phenyl)-1-[3-(trifluoromethyl)phenyl]-1,2,4-triazol-3-amine |
| 191. | N-[3-methyl-5-[4-(oxetan-3-yl)piperazin-1-yl]phenyl]-1-[4-(trifluoromethyl)phenyl]-1,2,4-triazol-3-amine |
| 192. | N3-[1-(3-fluorophenyl)-1,2,4-triazol-3-yl]-5-methyl-N1-[1-(oxetan-3-yl)-4-piperidyl]benzene-1,3-diamine |
| 193. | 1-(3,5-difluorophenyl)-N-[3-[3-fluoro-1-(oxetan-3-yl)pyrrolidin-3-yl]-5-methyl-phenyl]-1,2,4-triazol-3-amine |
| 194. | 1-[4-[3-methyl-5-[(1-phenyl-1,2,4-triazol-3-yl)amino]phenyl]-1-piperidyl]ethanone |
| 195. | N-[3-methyl-5-[4-(oxetan-3-yl)piperazin-1-yl]phenyl]-1-pyrazin-2-yl-1,2,4-triazol-3-amine |
| 196. | ethyl 4-[3-[[1-(3,5-difluorophenyl)-1,2,4-triazol-3-yl]amino]-5-methyl-phenyl]piperazine-1-carboxylate |
| 197. | N3-[1-(3,5-difluorophenyl)-1,2,4-triazol-3-yl]-N1,5-dimethyl-N1-(oxetan-3-yl)benzene-1,3-diamine |
| 198. | 1-(3,4-difluorophenyl)-N-[3-ethyl-5-(3-morpholinoazetidin-1-yl)phenyl]-1,2,4-triazol-3-amine |
| 199. | 1-(3,5-difluorophenyl)-N-[3-methyl-5-(4-tetrahydropyran-3-ylpiperazin-1-yl)phenyl]-1,2,4-triazol-3-amine |
| 200. | 7-[3-[[1-(3,5-difluorophenyl)-1,2,4-triazol-3-yl]amino]-5-methyl-phenyl]-5,6,8,8a-tetrahydro-1H-oxazolo[3,4-a]pyrazin-3-one |
| 201. | 1-(4-fluorophenyl)-N-[3-methyl-5-[[1-(oxetan-3-yl)-4-piperidyl]oxy]phenyl]-1,2,4-triazol-3-amine |
| 203. | N-[3-fluoro-5-(4-methylpiperazin-1-yl)phenyl]-1-(3-fluorophenyl)-1,2,4-triazol-3-amine |
| 204. | 1-(2-ethoxypyrimidin-4-yl)-N-[3-methyl-5-[4-(oxetan-3-yl)piperazin-1-yl]phenyl]-1,2,4-triazol-3-amine |
| 205. | 1-(3-fluoro-5-isopropoxy-phenyl)-N-[3-methyl-5-(4-methylpiperazin-1-yl)phenyl]-1,2,4-triazol-3-amine |
| 206. | 1-(3-ethyl-5-fluoro-phenyl)-N-[3-methyl-5-[4-(oxetan-3-yl)piperazin-1-yl]phenyl]-1,2,4-triazol-3-amine |
| 207. | N-[3-methyl-5-[1-(oxetan-3-yl)-3-piperidyl]phenyl]-1-(2-pyridyl)-1,2,4-triazol-3-amine |
| 208. | 1-(3,5-difluorophenyl)-N-[3-[(3S,4R)-3-fluoro-1-(oxetan-3-yl)-4-piperidyl]-5-methyl-phenyl]-1,2,4-triazol-3-amine; 1-(3,5-difluorophenyl)-N-[3-[(3R,4S)-3-fluoro-1-(oxetan-3-yl)-4-piperidyl]-5-methyl-phenyl]-1,2,4-triazol-3-amine |
| 209. | N-[3-(difluoromethyl)-5-[4-(oxetan-3-yl)piperazin-1-yl]phenyl]-1-(3-pyridyl)-1,2,4-triazol-3-amine |
| 211. | N-[3-[4-(methoxymethyl)-1-piperidyl]-5-methyl-phenyl]-1-(2-pyridyl)-1,2,4-triazol-3-amine |
| 212. | 2-[3-(3-methyl-5-pyrrolidin-1-yl-anilino)-1,2,4-triazol-1-yl]benzonitrile |
| 213. | N-[3-fluoro-5-(4-methylpiperazin-1-yl)phenyl]-1-phenyl-1,2,4-triazol-3-amine |
| 214. | 1-cyclopropyl-4-[3-methyl-5-[(1-phenyl-1,2,4-triazol-3-yl)amino]phenyl]piperazin-2-one |
| 215. | 1-(3,5-difluorophenyl)-N-[3-methyl-5-[4-(3-methyloxetan-3-yl)piperazin-1-yl]phenyl]-1,2,4-triazol-3-amine |
| 216. | 1-(3,5-difluorophenyl)-N-[3-methyl-5-[4-(oxetan-3-yl)-1-piperidyl]phenyl]-1,2,4-triazol-3-amine |
| 217. | 1-(5-chloro-3-pyridyl)-N-[3-methyl-5-[4-(oxetan-3-yl)piperazin-1-yl]phenyl]-1,2,4-triazol-3-amine |
| 218. | N-[3-ethyl-5-[4-(oxetan-3-yl)piperazin-1-yl]phenyl]-1-[3-(trifluoromethyl)phenyl]-1,2,4-triazol-3-amine |
| 219. | N-[3-methyl-5-[(1S,4S)-2-(oxetan-3-yl)-2,5-diazabicyclo[2.2.1]heptan-5-yl]phenyl]-1-phenyl-1,2,4-triazol-3-amine |
| 220. | 1-(3-chloro-5-fluoro-phenyl)-N-[3-methyl-5-(4-methylpiperazin-1-yl)phenyl]-1,2,4-triazol-3-amine |
| 221. | 1-(3,5-difluorophenyl)-N-[3-methyl-5-[1-(oxetan-3-yl)-4-piperidyl]phenyl]-1,2,4-triazol-3-amine |
| 223. | 1-(2-fluorophenyl)-N-[3-methyl-5-[4-(oxetan-3-yl)piperazin-1-yl]phenyl]-1,2,4-triazol-3-amine |
| 224. | N-[3-methyl-5-[4-(oxetan-3-yl)piperazin-1-yl]phenyl]-1-(4-pyridyl)-1,2,4-triazol-3-amine |
| 225. | N-[3-cyclopropyl-5-[4-(oxetan-3-yl)piperazin-1-yl]phenyl]-1-(2-fluoropyridyl)-1,2,4-triazol-3-amine |
| 226. | 1-(2-fluoro-4-pyridyl)-N-[3-(4-methylpiperazin-1-yl)-5-(trifluoromethyl)phenyl]-1,2,4-triazol-3-amine |
| 227. | 7-[3-methyl-5-[(1-phenyl-1,2,4-triazol-3-yl)amino]phenyl]-5,6,8,8a-tetrahydro-1H-oxazolo[3,4-a]pyrazin-3-one |
| 228. | 1-(3,5-difluorophenyl)-N-[3-[4-(1,1-dioxothietan-3-yl)piperazin-1-yl]-5-methyl-phenyl]-1,2,4-triazol-3-amine |
| 229. | 1-(3,5-difluorophenyl)-N-[3-methyl-5-[1-(oxetan-3-yl)azetidin-3-yl]phenyl]-1,2,4-triazol-3-amine |
| 230. | N-[3-fluoro-5-[1-(oxetan-3-yl)pyrrolidin-3-yl]phenyl]-1-(3-fluorophenyl)-1,2,4-triazol-3-amine |
| 231. | 1-(3,4-difluorophenyl)-N-[3-methyl-5-[4-(2,2,2-trifluoroethyl)piperazin-1-yl]phenyl]-1,2,4-triazol-3-amine |
| 232. | 1-(2,6-difluoro-4-pyridyl)-N-[3-methyl-5-[4-(oxetan-3-yl)piperazin-1-yl]phenyl]-1,2,4-triazol-3-amine |
| 233. | 1-[2-(methoxymethyl)phenyl]-N-[3-methyl-5-[4-(oxetan-3-yl)piperazin-1-yl]phenyl]-1,2,4-triazol-3-amine |
| 234. | N-[3,5-bis(2,5-dihydrofuran-3-yl)phenyl]-1-phenyl-1,2,4-triazol-3-amine |
| 235. | N-[3-[3,3-difluoro-1-(oxetan-3-yl)-4-piperidyl]-5-methyl-phenyl]-1-(3,5-difluorophenyl)-1,2,4-triazol-3-amine |
| 236. | N-[3-[4-(oxetan-3-yl)piperazin-1-yl]-5-propyl-phenyl]-1-pyrazin-2-yl-1,2,4-triazol-3-amine |
| 237. | N-[2,3-dimethyl-5-[4-(oxetan-3-yl)piperazin-1-yl]phenyl]-1-phenyl-1,2,4-triazol-3-amine |
| 238. | 1-[3-[[1-(3,5-difluorophenyl)-1,2,4-triazol-3-yl]amino]-5-methyl-phenyl]piperidin-4-ol |
| 239. | N-[3-methyl-5-[(3S)-1-(oxetan-3-yl)pyrrolidin-3-yl]oxy-phenyl]-1-phenyl-1,2,4-triazol-3-amine |

| | |
|---|---|
| 240. | N3-[1-(3,5-difluorophenyl)-1,2,4-triazol-3-yl]-5-methyl-N1-(oxetan-3-yl)benzene-1,3-diamine |
| 241. | N-(3-fluoro-5-pyrrolidin-1-yl-phenyl)-1-[3-(trifluoromethyl)phenyl]-1,2,4-triazol-3-amine |
| 242. | 3-[3-[[1-(3,5-difluorophenyl)-1,2,4-triazol-3-yl]amino]-5-methyl-phenyl]-1-methyl-pyrrolidin-3-ol |
| 243. | 1-(3,5-difluorophenyl)-N-[3-methyl-5-(4-tetrahydropyran-4-ylpiperazin-1-yl)phenyl]-1,2,4-triazol-3-amine |
| 246. | N-[3-chloro-5-[4-(methoxymethyl)-1-piperidyl]phenyl]-1-phenyl-1,2,4-triazol-3-amine |
| 247. | N-[3-methyl-5-(4-methylpiperazin-1-yl)phenyl]-1-phenyl-1,2,4-triazol-3-amine |
| 248. | N-[3-methyl-5-[1-(oxetan-3-y1)-3-piperidyl]phenyl]-1-phenyl-1,2,4-triazol-3-amine |
| 249. | N3-[1-(2-fluoro-4-pyridyl)-1,2,4-triazol-3-yl]-5-methyl-N1-[1-(oxetan-3-yl)pyrrolidin-3-yl]benzene-1,3-diamine |
| 250. | N-[3,5-di(tetrahydropyran-4-yl)phenyl]-1-(3-pyridyl)-1,2,4-triazol-3-amine |
| 251. | N-(3-morpholino-5-tetrahydropyran-4-yl-phenyl)-1-phenyl-1,2,4-triazol-3-amine |
| 252. | N-[3-methyl-5-[4-(oxetan-3-yl)piperazin-1-yl]phenyl]-1-[3-(trifluoromethoxy)phenyl]-1,2,4-triazol-3-amine |
| 253. | N-[3-[4-(2-methoxyethyl)piperazin-1-yl]-5-methyl-phenyl]-1-phenyl-1,2,4-triazol-3-amine |
| 254. | 1-(6-methoxypyrimidin-4-yl)-N-[3-methyl-5-[4-(oxetan-3-yl)piperazin-1-yl]phenyl]-1,2,4-triazol-3-amine |
| 255. | 1-(3-ethyl-5-fluoro-phenyl)-N-[3-methyl-5-(4-methylpiperazin-1-yl)phenyl]-1,2,4-triazol-3-amine |
| 256. | N-[3-[4-(3-deuteriooxetan-3-yl)piperazin-1-yl]-5-methyl-phenyl]-1-(3,5-difluorophenyl)-1,2,4-triazol-3-amine |
| 257. | 1-(3-fluorophenyl)-N-[3-(4-methylpiperazin-1-yl)-5-(trifluoromethyl)phenyl]-1,2,4-triazol-3-amine |
| 258. | 1-(3-fluorophenyl)-N-[3-methoxy-5-[4-(oxetan-3-yl)piperazin-1-yl]phenyl]-1,2,4-triazol-3-amine |
| 259. | N-[3-methyl-5-(3-methylpiperazin-1-yl)phenyl]-1-phenyl-1,2,4-triazol-3-amine |
| 260. | N-[3-methyl-5-[1-(oxetan-3-yl)pyrrolidin-3-yl]phenyl]-1-phenyl-1,2,4-triazol-3-amine |
| 261. | N-[3-(1-cyclopropyl-4-piperidyl)-5-methyl-phenyl]-1-(3,5-difluorophenyl)-1,2,4-triazol-3-amine |
| 262. | 1-(5-chloro-3-pyridyl)-N-[3-methyl-5-(4-methylpiperazin-1-yl)phenyl]-1,2,4-triazol-3-amine |
| 264. | 1-(3,5-difluorophenyl)-N-[3-ethyl-5-[4-(3-methyloxetan-3-yl)piperazin-1-yl]phenyl]-1,2,4-triazol-3-amine |
| 266. | 1-[3-[3-[[1-(3,5-difluorophenyl)-1,2,4-triazol-3-yl]amino]-5-methyl-phenyl]-1-piperidyl]ethanone |
| 267. | 1-(3,5-difluorophenyl)-N-[3-methyl-5-[3-(methylamino)pyrrolidin-1-yl]phenyl]-1,2,4-triazol-3-amine |
| 268. | 1-(3,5-difluorophenyl)-N-[3-fluoro-5-[1-(oxetan-3-yl)pyrrolidin-3-yl]phenyl]-1,2,4-triazol-3-amine |
| 269. | 1-(4-fluorophenyl)-N-(3-methyl-5-pyrrolidin-1-yl-phenyl)-1,2,4-triazol-3-amine |
| 270. | N-[3-methyl-5-(oxetan-3-yl)phenyl]-1-(3-pyridyl)-1,2,4-triazol-3-amine |
| 271. | N-[3-methyl-5-[4-(oxetan-3-yl)piperazin-1-yl]phenyl]-1-(6-methylpyrazin-2-yl)-1,2,4-triazol-3-amine |
| 272. | 1-(3-fluorophenyl)-N-(3-methyl-5-pyrrolidin-1-yl-phenyl)-1,2,4-triazol-3-amine |
| 273. | N-[3-[1-(2,2-difluoroethyl)pyrrolidin-3-yl]-5-methyl-phenyl]-1-phenyl-1,2,4-triazol-3-amine |
| 274. | N-[3-(4-ethylpiperazin-1-yl)-5-methyl-phenyl]-1-phenyl-1,2,4-triazol-3-amine |
| 275. | N-[3-methyl-5-[4-(oxetan-3-yl)piperazin-1-yl]phenyl]-1-(3-pyridyl)-1,2,4-triazol-3-amine |
| 276. | 1-(2,3-difluorophenyl)-N-[3-ethyl-5-[4-(oxetan-3-yl)piperazin-1-yl]phenyl]-1,2,4-triazol-3-amine |
| 277. | N-[3-cyclopropyl-5-[4-(oxetan-3-yl)piperazin-1-yl]phenyl]-1-(2-methoxypyrimidin-4-yl)-1,2,4-triazol-3-amine |
| 278. | N3-[1-(3,4-difluorophenyl)-1,2,4-triazol-3-yl]-5-methyl-N1-[1-(oxetan-3-yl)-4-piperidyl]benzene-1,3-diamine |
| 279. | 1-(3,5-difluorophenyl)-N-[3-methyl-5-(2-oxa-7-azaspiro[3.5]nonan-7-yl)phenyl]-1,2,4-triazol-3-amine |
| 280. | 1-[4-[3-methyl-5-[(1-phenyl-1,2,4-triazol-3-yl)amino]phenyl]-1,4-diazepan-1-yl]ethanone |
| 281. | 3-[3-(3-methyl-5-pyrrolidin-1-yl-anilino)-1,2,4-triazol-1-yl]benzonitrile |
| 282. | (3R,4R)-4-[3-[[1-(3,5-difluorophenyl)-1,2,4-triazol-3-yl]amino]-5-methyl-phenyl]-1-(oxetan-3-yl)piperidin-3-ol; (3S,4S)-4-[3-[[1-(3,5-difluorophenyl)-1,2,4-triazol-3-yl]amino]-5-methyl-phenyl]-1-(oxetan-3-yl)piperidin-3-ol |
| 283. | N-[3-(3-aminoazetidin-1-yl)-5-fluoro-phenyl]-1-(2,4-difluorophenyl)-1,2,4-triazol-3-amine |
| 284. | 1-(3,5-difluorophenyl)-N-[3-methyl-5-(3-morpholinopyrrolidin-1-yl)phenyl]-1,2,4-triazol-3-amine |
| 285. | N-[3-cyclopropyl-5-[4-(oxetan-3-yl)piperazin-1-yl]phenyl]-1-(3-fluoro-5-isopropoxy-phenyl)-1,2,4-triazol-3-amine |
| 286. | N-[3-cyclopropyl-5-[4-(oxetan-3-yl)piperazin-1-yl]phenyl]-1-(2-ethoxypyrimidin-4-yl)-1,2,4-triazol-3-amine |
| 287. | N-[3-methyl-5-[4-(oxetan-3-yl)piperazin-1-yl]phenyl]-1-[3-(trifluoromethyl)phenyl]-1,2,4-triazol-3-amine |
| 288. | N-[3-tert-butyl-5-[4-(oxetan-3-yl)piperazin-1-yl]phenyl]-1-pyrazin-2-yl-1,2,4-triazol-3-amine |
| 289. | N-[3-methyl-5-(4-tetrahydropyran-4-ylpiperazin-1-yl)phenyl]-1-phenyl-1,2,4-triazol-3-amine |
| 290. | N-[3-(4-cyclobutylpiperazin-1-yl)-5-methyl-phenyl]-1-phenyl-1,2,4-triazol-3-amine |
| 291. | 1-(5-fluoropyrimidin-4-yl)-N-[3-methyl-5-[4-(oxetan-3-yl)piperazin-1-yl]phenyl]-1,2,4-triazol-3-amine |
| 292. | N-[3-[(1S,4S)-2-cyclopropyl-2,5-diazabicyclo[2.2.1]heptan-5-yl]-5-methyl-phenyl]-1-phenyl-1,2,4-triazol-3-amine |
| 293. | 1-(3,5-difluorophenyl)-N-[3-(3-methoxy-1-piperidyl)-5-methyl-phenyl]-1,2,4-triazol-3-amine |
| 294. | N-[3-methyl-5-[1-(3-methyloxetan-3-yl)-4-piperidyl]phenyl]-1-phenyl-1,2,4-triazol-3-amine |
| 295. | 5-[3-[[1-(3,5-difluorophenyl)-1,2,4-triazol-3-yl]amino]-5-methyl-phenyl]oxazolidin-2-one |
| 297. | N-[3-methyl-5-(4-methylpiperazin-1-yl)phenyl]-1-(3-pyridyl)-1,2,4-triazol-3-amine |
| 298. | 1-(3,5-difluorophenyl)-N-[3-(2,5-dihydrofuran-3-yl)-5-morpholino-phenyl]-1,2,4-triazol-3-amine |
| 299. | 1-(3,4-difluorophenyl)-N-[3-[4-(methoxymethyl)-1-piperidyl]-5-methyl-phenyl]-1,2,4-triazol-3-amine |
| 300. | 1-[3-[3-methyl-5-[(1-pyrazin-2-yl-1,2,4-triazol-3-yl)amino]phenyl]-1-piperidyl]ethanone |
| 301. | 1-(3,4-difluorophenyl)-N-[3-methyl-5-[1-(oxetan-3-yl)azetidin-3-yl]phenyl]-1,2,4-triazol-3-amine |
| 302. | N-[3-cyclopropyl-5-[4-(oxetan-3-yl)piperazin-1-yl]phenyl]-1-(6-methylpyrimidin-4-yl)-1,2,4-triazol-3-amine |
| 303. | N-[3-ethyl-5-[4-(oxetan-3-yl)piperazin-1-yl]phenyl]-1-[4-(trifluoromethoxy)phenyl]-1,2,4-triazol-3-amine |
| 304. | 1-(3,5-difluorophenyl)-N-[3-methyl-5-[(3S)-1-(oxetan-3-yl)pyrrolidin-3-yl]oxy-phenyl]-1,2,4-triazol-3-amine |
| 305. | N-(3-cyclopropyl-5-morpholino-phenyl)-1-phenyl-1,2,4-triazol-3-amine |
| 306. | N-[3-(2,6-dimethylmorpholin-4-yl)-5-methyl-phenyl]-1-phenyl-1,2,4-triazol-3-amine |
| 307. | N-(2-fluoro-3-methyl-5-morpholino-phenyl)-1-(2-pyridyl)-1,2,4-triazol-3-amine |
| 308. | N-[3-methyl-5-(4-piperidyl)phenyl]-1-phenyl-1,2,4-triazol-3-amine |
| 309. | 5-methyl-N1-[1-(oxetan-3-yl)pyrrolidin-3-yl]-N3-(1-phenyl-1,2,4-triazol-3-yl)benzene-1,3-diamine |

| | |
|---|---|
| 310. | 1-(3,5-difluorophenyl)-N-[3-methoxy-5-[4-(oxetan-3-yl)piperazin-1-yl]phenyl]-1,2,4-triazol-3-amine |
| 311. | 2-[4-[3-[[1-(3,5-difluorophenyl)-1,2,4-triazol-3-yl]amino]-5-methyl-phenyl]piperazin-1-yl]-2-methyl-propane-1,3-diol |
| 312. | 1-(2,6-dimethylpyrimidin-4-yl)-N-[3-methyl-5-[4-(oxetan-3-yl)piperazin-1-yl]phenyl]-1,2,4-triazol-3-amine |
| 313. | 1-(3,5-difluorophenyl)-N-[3-(oxetan-3-yl)-5-[4-(oxetan-3-yl)piperazin-1-yl]phenyl]-1,2,4-triazol-3-amine |
| 314. | N-[3-ethyl-5-[4-(oxetan-3-yl)piperazin-1-yl]phenyl]-1-(2-methoxypyrimidin-4-yl)-1,2,4-triazol-3-amine |
| 315. | N-[3,5-bis(3,6-dihydro-2H-pyran-4-yl)phenyl]-1-phenyl-1,2,4-triazol-3-amine |
| 316. | N-[3-methyl-5-(3-piperidyl)phenyl]-1-phenyl-1,2,4-triazol-3-amine |
| 317. | 1-(3,4-difluorophenyl)-N-[3-methyl-5-(4-methylpiperazin-1-yl)phenyl]-1,2,4-triazol-3-amine |
| 318. | 2-[(3R)-1-[3-fluoro-5-[3-[5-[4-(oxetan-3-yl)piperazin-1-yl]anilino]-1,2,4-triazol-1-yl]phenyl]pyrrolidin-3-yl]propan-2-ol |
| 320. | 1-(5-fluoro-3-pyridyl)-N-(3-methyl-5-pyrrolidin-1-yl-phenyl)-1,2,4-triazol-3-amine |
| 321. | 1-(2,4-difluorophenyl)-N-(3-fluoro-5-morpholino-phenyl)-1,2,4-triazol-3-amine |
| 322. | N-[3-ethyl-5-[4-(oxetan-3-yl)piperazin-1-yl]phenyl]-1-[4-(trifluoromethyl)phenyl]-1,2,4-triazol-3-amine |
| 323. | 1-(3-fluoro-5-methyl-phenyl)-N-[3-methyl-5-[4-(oxetan-3-yl)piperazin-1-yl]phenyl]-1,2,4-triazol-3-amine |
| 324. | 1-(3,5-difluorophenyl)-N-[3-methyl-5-(4-morpholino-1-piperidyl)phenyl]-1,2,4-triazol-3-amine |
| 325. | 1-(3,5-difluorophenyl)-N-[3-[2-(methoxymethyl)morpholin-4-yl]-5-methyl-phenyl]-1,2,4-triazol-3-amine |
| 326. | N-[3-(4-isopropylpiperazin-1-yl)-5-methyl-phenyl]-1-phenyl-1,2,4-triazol-3-amine |
| 328. | 1-(3,5-difluorophenyl)-N-[3-methyl-5-(1-methyl-3-piperidyl)phenyl]-1,2,4-triazol-3-amine |
| 329. | 1-(4,6-difluoro-2-pyridyl)-N-[3-methyl-5-[4-(oxetan-3-yl)piperazin-1-yl]phenyl]-1,2,4-triazol-3-amine |
| 330. | N-[3-ethyl-5-[4-(oxetan-3-yl)piperazin-1-yl]phenyl]-1-phenyl-1,2,4-triazol-3-amine |
| 333. | N-[3-methyl-5-(1-methyl-4-piperidyl)phenyl]-1-phenyl-1,2,4-triazol-3-amine |
| 334. | 5-methyl-N1-[1-(oxetan-3-yl)-4-piperidyl]-N3-(1-phenyl-1,2,4-triazol-3-yl)benzene-1,3-diamine |
| 335. | N-(3-chloro-5-morpholino-phenyl)-1-phenyl-1,2,4-triazol-3-amine |
| 336. | N-(3-fluoro-5-pyrrolidin-1-yl-phenyl)-1-phenyl-1,2,4-triazol-3-amine |
| 337. | N-[3-(4-cyclopropyl-1,4-diazepan-1-yl)-5-methyl-phenyl]-1-phenyl-1,2,4-triazol-3-amine |
| 338. | N-[3-ethyl-5-[4-(oxetan-3-yl)piperazin-1-yl]phenyl]-1-(2-fluoro-5-methyl-phenyl)-1,2,4-triazol-3-amine |
| 339. | N-[3-cyclopropyl-5-[4-(oxetan-3-yl)piperazin-1-yl]phenyl]-1-(5-fluoro-3-pyridyl)-1,2,4-triazol-3-amine |
| 340. | N-[3-(1-cyclopropyl-3-piperidyl)-5-methyl-phenyl]-1-phenyl-1,2,4-triazol-3-amine |
| 341. | N-[3-ethyl-5-(3-morpholinoazetidin-1-yl)phenyl]-1-pyrazin-2-yl-1,2,4-triazol-3-amine |
| 342. | 5-methyl-N1-[1-(oxetan-3-yl)-4-piperidyl]-N3-[1-(3-pyridyl)-1,2,4-triazol-3-yl]benzene-1,3-diamine |
| 343. | 1-(2,4-difluorophenyl)-N-[3-fluoro-5-(1,4-oxazepan-4-yl)phenyl]-1,2,4-triazol-3-amine |
| 344. | 1-(3,5-difluorophenyl)-N-[3-methylsulfonyl-5-[4-(oxetan-3-yl)piperazin-1-yl]phenyl]-1,2,4-triazol-3-amine |
| 346. | N-(3-bromo-5-morpholino-phenyl)-1-(3,5-difluorophenyl)-1,2,4-triazol-3-amine |
| 347. | 1-(2,4-difluorophenyl)-N-[3-[3-(dimethylamino)pyrrolidin-1-yl]-5-fluoro-phenyl]-1,2,4-triazol-3-amine |
| 348. | N-[3-(4-cyclopropylpiperazin-1-yl)-5-(difluoromethyl)phenyl]-1-phenyl-1,2,4-triazol-3-amine |
| 349. | 1-(3,5-difluorophenyl)-N-[3-methyl-5-(9-methyl-2-oxa-6,9-diazaspiro[3.5]nonan-6-yl)phenyl]-1,2,4-triazol-3-amine |
| 350. | 2,2,2-trifluoroethyl4-[3-[[1-(3,5-difluorophenyl)-1,2,4-triazol-3-yl]amino]-5-methyl-phenyl]piperazine-1-carboxylate |
| 351. | N1-(azetidin-3-yl)-5-fluoro-N3-[1-(3-fluorophenyl)-1,2,4-triazol-3-yl]benzene-1,3-diamine |
| 352. | 1-[4-[3-[[1-(3,5-difluorophenyl)-1,2,4-triazol-3-yl]amino]-5-methyl-phenyl]piperazin-1-yl]-2,2,2-trifluoro-ethanone |
| 353. | N-[3-cyclopropyl-5-[4-(oxetan-3-yl)piperazin-1-yl]phenyl]-1-[6-(methoxymethyl)pyrimidin-4-yl]-1,2,4-triazol-3-amine |
| 355. | 1-[3-[[1-(3,5-difluorophenyl)-1,2,4-triazol-3-yl]amino]-5-methyl-phenyl]azetidin-3-ol |
| 356. | N-(3-methyl-5-pyrrolidin-1-yl-phenyl)-1-[4-(trifluoromethyl)phenyl]-1,2,4-triazol-3-amine |
| 357. | N-[3-morpholino-5-(trifluoromethyl)phenyl]-1-pyrazin-2-yl-1,2,4-triazol-3-amine |
| 358. | N-[3-(3,3a,4,5,7,7a-hexahydro-2H-furo[2,3-c]pyridin-6-yl)-5-methyl-phenyl]-1-phenyl-1,2,4-triazol-3-amine |
| 359. | 1-(3,5-difluorophenyl)-N-[3-isopropyl-5-[4-(oxetan-3-yl)piperazin-1-yl]phenyl]-1,2,4-triazol-3-amine |
| 360. | 4-[3-[[1-(3,5-difluorophenyl)-1,2,4-triazol-3-yl]amino]-5-methyl-phenyl]-1-methyl-piperazin-2-one |
| 361. | 1-(3-fluorophenyl)-N-[3-methylsulfonyl-5-[4-(oxetan-3-yl)piperazin-1-yl]phenyl]-1,2,4-triazol-3-amine |
| 362. | 1-(3,5-difluorophenyl)-N-[3-methyl-5-(3-methylpiperazin-1-yl)phenyl]-1,2,4-triazol-3-amine |
| 363. | N-[3-methyl-5-(oxetan-3-yl)phenyl]-1-phenyl-1,2,4-triazol-3-amine |
| 364. | 1-[6-(methoxymethyl)pyrimidin-4-yl]-N-[3-methyl-5-[4-(oxetan-3-yl)piperazin-1-yl]phenyl]-1,2,4-triazol-3-amine |
| 366. | N-[3-morpholino-5-(trifluoromethyl)phenyl]-1-phenyl-1,2,4-triazol-3-amine |
| 368. | tert-butyl 4-[3-ethyl-5-[(1-pyrazin-2-yl-1,2,4-triazol-3-yl)amino]phenyl]piperazine-1-carboxylate |
| 369. | N-[3-[(3aR,6aR)-1-methyl-2,3,3a,4,6,6a-hexahydropyrrolo[2,3-c]pyrrol-5-yl]-5-methyl-phenyl]-1-phenyl-1,2,4-triazol-3-amine |
| 370. | 1-[4-[3-[[1-(3,5-difluorophenyl)-1,2,4-triazol-3-yl]amino]-5-methyl-phenyl]piperazin-1-yl]ethanone |
| 371. | N-(3-fluoro-5-morpholino-phenyl)-1-(5-fluoro-3-pyridyl)-1,2,4-triazol-3-amine |
| 372. | N-(3-methyl-5-pyrrolidin-1-yl-phenyl)-1-(p-tolyl)-1,2,4-triazol-3-amine |
| 373. | 1-[3-fluoro-5-[2-methoxyethyl(methyl)amino]phenyl]-N-[3-methyl-5-[4-(oxetan-3-yl)piperazin-1-yl]phenyl]-1,2,4-triazol-3-amine |
| 374. | 1-(3,5-difluorophenyl)-N-(3-methyl-5-morpholino-phenyl)-1,2,4-triazol-3-amine |
| 375. | 1-(3-fluorophenyl)-N-[3-methyl-5-[4-(3-methyloxetan-3-yl)piperazin-1-yl]phenyl]-1,2,4-triazol-3-amine |
| 376. | N-[3-tert-butyl-5-[4-(oxetan-3-yl)piperazin-1-yl]phenyl]-1-phenyl-1,2,4-triazol-3-amine |
| 377. | N-[3-cyclopropyl-5-[4-(oxetan-3-yl)piperazin-1-yl]phenyl]-1-(6-methoxypyrimidin-4-yl)-1,2,4-triazol-3-amine |
| 379. | 1-(3,5-difluorophenyl)-N-[3-methyl-5-(3-pyrazol-1-ylazetidin-1-yl)phenyl]-1,2,4-triazol-3-amine |
| 380. | N-(3-chloro-5-pyrrolidin-1-yl-phenyl)-1-phenyl-1,2,4-triazol-3-amine |
| 381. | N-[3-methyl-5-(4-methylpiperazin-1-yl)phenyl]-1-pyrimidin-5-yl-1,2,4-triazol-3-amine |
| 382. | 1-(3-fluorophenyl)-N-[3-methyl-5-[1-(oxetan-3-yl)pyrrolidin-3-yl]phenyl]-1,2,4-triazol-3-amine |

| # | Name |
|---|---|
| 383. | 1-(2,5-difluorophenyl)-N-[3-methyl-5-[4-(oxetan-3-yl)-1-piperidyl]phenyl]-1,2,4-triazol-3-amine |
| 384. | 1-(3,4-difluorophenyl)-N-[3-methyl-5-[[1-(oxetan-3-yl)-4-piperidyl]oxy]phenyl]-1,2,4-triazol-3-amine |
| 385. | N-[3-[4-(methoxymethyl)-1-piperidyl]-5-methyl-phenyl]-1-(4-pyridyl)-1,2,4-triazol-3-amine |
| 386. | 1-(3,4-difluorophenyl)-N-[3-methyl-5-[4-(oxetan-3-yl)piperazin-1-yl]phenyl]-1,2,4-triazol-3-amine |
| 387. | 1-(5-fluoro-3-pyridyl)-N-[3-methyl-5-(4-methylpiperazin-1-yl)phenyl]-1,2,4-triazol-3-amine |
| 388. | N-[3-cyclopropyl-5-[4-(oxetan-3-yl)piperazin-1-yl]phenyl]-1-(3-fluoro-5-methoxy-phenyl)-1,2,4-triazol-3-amine |
| 389. | N-[3-cyclopropyl-5-[4-(oxetan-3-yl)piperazin-1-yl]phenyl]-1-(3,5-difluorophenyl)-1,2,4-triazol-3-amine |
| 390. | 1-[3-[[ethyl(methyl)amino]methyl]-5-fluoro-phenyl]-N-[3-methyl-5-(4-methylpiperazin-1-yl)phenyl]-1,2,4-triazol-3-amine |
| 391. | N-[3-methyl-5-[(3R)-1-(oxetan-3-yl)pyrrolidin-3-yl]oxy-phenyl]-1-phenyl-1,2,4-triazol-3-amine |
| 392. | N-[3-(difluoromethyl)-5-morpholino-phenyl]-1-phenyl-1,2,4-triazol-3-amine |
| 394. | N-(3-fluoro-5-morpholino-phenyl)-1-(4-fluorophenyl)-1,2,4-triazol-3-amine |
| 395. | 1-(3-fluoro-5-methoxy-phenyl)-N-[3-methyl-5-(4-methylpiperazin-1-yl)phenyl]-1,2,4-triazol-3-amine |
| 396. | 1-(3,5-difluorophenyl)-N-[3-[4-(oxetan-3-yl)piperazin-1-yl]-5-propyl-phenyl]-1,2,4-triazol-3-amine |
| 397. | 1-(3-chlorophenyl)-N-[3-methyl-5-[4-(oxetan-3-yl)piperazin-1-yl]phenyl]-1,2,4-triazol-3-amine |
| 398. | N-[3-methyl-5-[4-(2,2,2-trifluoroethyl)piperazin-1-yl]phenyl]-1-phenyl-1,2,4-triazol-3-amine |
| 399. | N-[3-methyl-5-(4-methylpiperazin-1-yl)phenyl]-1-pyridazin-4-yl-1,2,4-triazol-3-amine |
| 400. | 1-(3-chloro-5-fluoro-phenyl)-N-[3-cyclopropyl-5-[4-(oxetan-3-yl)piperazin-1-yl]phenyl]-1,2,4-triazol-3-amine |
| 401. | N-[3-ethyl-5-[4-(oxetan-3-yl)piperazin-1-yl]phenyl]-1-(6-methylpyrazin-2-yl)-1,2,4-triazol-3-amine |
| 402. | 1-[4-[3-methyl-5-[(1-phenyl-1,2,4-triazol-3-yl)amino]anilino]-1-piperidyl]ethanone |
| 403. | 1-(2-fluoro-4-pyridyl)-N-(3-methyl-5-morpholino-phenyl)-1,2,4-triazol-3-amine |
| 404. | N-[3-methyl-5-(oxetan-3-yl)phenyl]-1-(2-pyridyl)-1,2,4-triazol-3-amine |
| 406. | 1-(3-fluorophenyl)-N-[3-methyl-5-[4-(oxetan-3-yl)piperazin-1-yl]phenyl]-1,2,4-triazol-3-amine |
| 408. | 1-(3,5-difluorophenyl)-N-[3-methyl-5-[1-(oxetan-3-yl)-3-piperidyl]phenyl]-1,2,4-triazol-3-amine |
| 409. | 1-(4-fluorophenyl)-N-[3-methyl-5-(oxetan-3-yl)phenyl]-1,2,4-triazol-3-amine |
| 410. | N-[3-methyl-5-[[1-(oxetan-3-yl)-4-piperidyl]oxy]phenyl]-1-phenyl-1,2,4-triazol-3-amine |
| 411. | 1-(3-fluorophenyl)-N-[3-methyl-5-[1-(oxetan-3-yl)-3-piperidyl]phenyl]-1,2,4-triazol-3-amine |
| 412. | 1-(3,4-difluorophenyl)-N-[3-(4-methylpiperazin-1-yl)-5-(trifluoromethyl)phenyl]-1,2,4-triazol-3-amine |
| 413. | N-[3-methyl-5-[4-(oxetan-3-yl)piperazin-1-yl]phenyl]-1-(2,4,5-trifluorophenyl)-1,2,4-triazol-3-amine |
| 414. | N-[3-methyl-5-[4-(oxetan-3-yl)piperazin-1-yl]phenyl]-1-(o-tolyl)-1,2,4-triazol-3-amine |
| 415. | 1-(3-fluoro-5-isopropoxy-phenyl)-N-[3-methyl-5-[4-(oxetan-3-yl)piperazin-1-yl]phenyl]-1,2,4-triazol-3-amine |
| 416. | 3-[3-[[1-(3,5-difluorophenyl)-1,2,4-triazol-3-yl]amino]-5-methyl-phenyl]-1-(oxetan-3-yl)pyrrolidin-3-ol |
| 417. | 1-(2,5-difluorophenyl)-N-[3-ethyl-5-[4-(oxetan-3-yl)piperazin-1-yl]phenyl]-1,2,4-triazol-3-amine |
| 418. | N-[3-methyl-5-[4-(oxetan-3-yl)piperazin-1-yl]phenyl]-1-(2-methylpyrimidin-4-yl)-1,2,4-triazol-3-amine |
| 419. | N-[3-methyl-5-(2,4,5-trimethylpiperazin-1-yl)phenyl]-1-phenyl-1,2,4-triazol-3-amine |
| 420. | N-[3-(4-cyclopropylpiperazin-1-yl)-5-methyl-phenyl]-1-(6-methylpyrazin-2-yl)-1,2,4-triazol-3-amine |
| 421. | 1-(3,5-difluorophenyl)-N-[3-methyl-5-[4-(2,2,2-trifluoroethyl)piperazin-1-yl]phenyl]-1,2,4-triazol-3-amine |
| 422. | methyl 4-[3-[[1-(3,5-difluorophenyl)-1,2,4-triazol-3-yl]amino]-5-methyl-phenyl]piperazine-1-carboxylate |
| 423. | N-[3-methyl-5-[(3R,5S)-3,4,5-trimethylpiperazin-1-yl]phenyl]-1-phenyl-1,2,4-triazol-3-amine |
| 424. | 1-(3-fluoro-5-methyl-phenyl)-N-[3-methyl-5-(4-methylpiperazin-1-yl)phenyl]-1,2,4-triazol-3-amine |
| 425. | 1-(3,5-difluorophenyl)-N-[2,3-dimethyl-5-[4-(oxetan-3-yl)piperazin-1-yl]phenyl]-1,2,4-triazol-3-amine |
| 426. | N-(3-chloro-5-morpholino-phenyl)-1-(3,5-difluorophenyl)-1,2,4-triazol-3-amine |
| 427. | 1-(5-fluoro-3-pyridyl)-N-(3-methyl-5-morpholino-phenyl)-1,2,4-triazol-3-amine |
| 428. | 1-(2-chlorophenyl)-N-[3-methyl-5-(4-methylpiperazin-1-yl)phenyl]-1,2,4-triazol-3-amine |
| 429. | 1-(3,5-difluorophenyl)-N-[3-methyl-5-(3-piperidyl)phenyl]-1,2,4-triazol-3-amine |
| 431. | N-[3-methyl-5-[4-[(3-methyloxetan-3-yl)methyl]piperazin-1-yl]phenyl]-1-phenyl-1,2,4-triazol-3-amine |
| 432. | N-[3-ethyl-5-[4-(oxetan-3-yl)piperazin-1-yl]phenyl]-1-(3-methoxyphenyl)-1,2,4-triazol-3-amine |
| 433. | 1-(3,5-difluorophenyl)-N-[3-methyl-5-[[1-(oxetan-3-yl)-4-piperidyl]oxy]phenyl]-1,2,4-triazol-3-amine |
| 434. | N-[3-methyl-5-(4-tetrahydrofuran-3-ylpiperazin-1-yl)phenyl]-1-phenyl-1,2,4-triazol-3-amine |
| 435. | 1-(3-fluorophenyl)-N-(3-fluoro-5-pyrrolidin-1-yl-phenyl)-1,2,4-triazol-3-amine |
| 436. | N-[3-methyl-5-[4-(3-methyloxetan-3-yl)piperazin-1-yl]phenyl]-1-phenyl-1,2,4-triazol-3-amine |
| 437. | 1-(2,5-difluorophenyl)-N-[3-methyl-5-[4-(oxetan-3-yl)piperazin-1-yl]phenyl]-1,2,4-triazol-3-amine |
| 438. | 4-[3-[[1-(3,5-difluorophenyl)-1,2,4-triazol-3-yl]amino]-5-methyl-phenyl]piperidin-3-ol |
| 439. | N-[3-methyl-5-[4-(oxetan-3-yl)piperazin-1-yl]phenyl]-1-(3-methylsulfanylphenyl)-1,2,4-triazol-3-amine |
| 440. | 1-(3,4-difluorophenyl)-N-(3-fluoro-5-morpholino-phenyl)-1,2,4-triazol-3-amine |
| 441. | N-(3-fluoro-5-pyrrolidin-1-yl-phenyl)-1-[4-(trifluoromethyl)phenyl]-1,2,4-triazol-3-amine |
| 442. | 3-[3-[3-[[1-(3,5-difluorophenyl)-1,2,4-triazol-3-yl]amino]-5-methyl-phenyl]-1-piperidyl]cyclobutanecarboxylic acid |
| 443. | 1-[3-[3-methyl-5-[(1-phenyl-1,2,4-triazol-3-yl)amino]phenyl]pyrrolidin-1-yl]ethanone |
| 444. | 1-(3,5-difluorophenyl)-N-[3-methyl-5-(2-oxa-7-azaspiro[3.4]octan-7-yl)phenyl]-1,2,4-triazol-3-amine |
| 445. | 1-(2,3-difluorophenyl)-N-[3-methyl-5-[4-(oxetan-3-yl)piperazin-1-yl]phenyl]-1,2,4-triazol-3-amine |
| 446. | 1-(2-chlorophenyl)-N-[3-methyl-5-[4-(oxetan-3-yl)piperazin-1-yl]phenyl]-1,2,4-triazol-3-amine |
| 447. | 1-(5-fluoro-3-pyridyl)-N-[3-methyl-5-(oxetan-3-yl)phenyl]-1,2,4-triazol-3-amine |
| 448. | N1-cyclopropyl-N3-[1-(3,5-difluorophenyl)-1,2,4-triazol-3-yl]-5-methyl-benzene-1,3-diamine |
| 449. | 1-[3-[3-methyl-5-[(1-pyrimidin-4-yl-1,2,4-triazol-3-yl)amino]phenyl]-1-piperidyl]ethanone |
| 450. | 1-(2,4-difluorophenyl)-N-[3-fluoro-5-(4-methylpiperazin-1-yl)phenyl]-1,2,4-triazol-3-amine |
| 451. | N-(2-fluoro-3-methyl-5-morpholino-phenyl)-1-(3-pyridyl)-1,2,4-triazol-3-amine |

| | |
|---|---|
| 452. | N-(3-fluoro-5-pyrrolidin-3-yl-phenyl)-1-phenyl-1,2,4-triazol-3-amine |
| 453. | N-[3-[4-(3,3-difluorocyclobutyl)piperazin-1-yl]-5-methyl-phenyl]-1-(3,5-difluorophenyl)-1,2,4-triazol-3-amine |
| 454. | N-[3-cyclopropyl-5-[4-(oxetan-3-yl)piperazin-1-yl]phenyl]-1-(2-methylpyrimidin-4-yl)-1,2,4-triazol-3-amine |
| 455. | N-[3-[4-(2-fluorophenyl)piperazin-1-yl]-5-methyl-phenyl]-1-phenyl-1,2,4-triazol-3-amine |
| 456. | 1-(3,5-difluorophenyl)-N-(3-morpholino-5-tetrahydrofuran-3-yl-phenyl)-1,2,4-triazol-3-amine |
| 458. | cyclopropyl-[4-[3-[[1-(3,5-difluorophenyl)-1,2,4-triazol-3-yl]amino]-5-methyl-phenyl]piperazin-1-yl]methanone |
| 459. | 1-(3,5-difluorophenyl)-N-[3-methyl-5-[(1R,4R)-5-methyl-2,5-diazabicyclo[2.2.1]heptan-2-yl]phenyl]-1,2,4-triazol-3-amine |
| 461. | 2-methyl-1-[4-[3-methyl-5-[(1-phenyl-1,2,4-triazol-3-yl)amino]phenyl]piperazin-1-yl]propan-2-ol |
| 462. | N-[3-cyclopropyl-5-[4-(oxetan-3-yl)piperazin-1-yl]phenyl]-1-(3-fluorophenyl)-1,2,4-triazol-3-amine |
| 463. | N-[3-ethyl-5-[4-(oxetan-3-yl)piperazin-1-yl]phenyl]-1-(3-methylsulfanylphenyl)-1,2,4-triazol-3-amine |
| 464. | N-[3-[4-(methoxymethyl)-1-piperidyl]-5-methyl-phenyl]-1-pyrimidin-4-yl-1,2,4-triazol-3-amine |
| 465. | N-[3-(2,5-dihydrofuran-3-yl)-5-morpholino-phenyl]-1-phenyl-1,2,4-triazol-3-amine |
| 466. | N-[3-(1-cyclopropyl-3-piperidyl)-5-methyl-phenyl]-1-(3,5-difluorophenyl)-1,2,4-triazol-3-amine |
| 467. | 1-[3-fluoro-5-[(3R)-3-fluoropyrrolidin-1-yl]phenyl]-N-[3-methyl-5-[4-(oxetan-3-yl)piperazin-1-yl]phenyl]-1,2,4-triazol-3-amine |
| 468. | N-[3-ethyl-5-[4-(oxetan-3-yl)piperazin-1-yl]phenyl]-1-(3-fluorophenyl)-1,2,4-triazol-3-amine |
| 469. | 1-(2,5-difluorophenyl)-N-[3-methyl-5-[4-(3-methyloxetan-3-yl)piperazin-1-yl]phenyl]-1,2,4-triazol-3-amine |
| 470. | N-[2,3-dimethyl-5-[4-(oxetan-3-yl)piperazin-1-yl]phenyl]-1-pyrazin-2-yl-1,2,4-triazol-3-amine |
| 471. | N-[2-methoxy-3-methyl-5-[4-(oxetan-3-yl)piperazin-1-yl]phenyl]-1-pyrazin-2-yl-1,2,4-triazol-3-amine |
| 472. | N3-[1-(3,5-difluorophenyl)-1,2,4-triazol-3-yl]-5-methyl-N1-[1-(oxetan-3-yl)pyrrolidin-3-yl]benzene-1,3-diamine |
| 473. | 1-(3,5-difluorophenyl)-N-[3-methyl-5-[(3R)-1-(oxetan-3-yl)pyrrolidin-3-yl]phenyl]-1,2,4-triazol-3-amine |
| 474. | N-[3-methyl-5-(2,2,3,3,5,5,6,6-octadeuterio-4-methyl-piperazin-1-yl)phenyl]-1-phenyl-1,2,4-triazol-3-amine |
| 475. | 1-(3,5-difluorophenyl)-N-[3-morpholino-5-(trifluoromethyl)phenyl]-1,2,4-triazol-3-amine |
| 476. | 1-(2-fluoro-5-methyl-phenyl)-N-[3-methyl-5-[4-(oxetan-3-yl)piperazin-1-yl]phenyl]-1,2,4-triazol-3-amine |
| 478. | N-[3-methyl-5-[4-(oxetan-3-yl)piperazin-1-yl]phenyl]-1-[4-(trifluoromethoxy)phenyl]-1,2,4-triazol-3-amine |
| 479. | N-[3-methyl-5-[(1S,4S)-5-methyl-2,5-diazabicyclo[2.2.1]heptan-2-yl]phenyl]-1-phenyl-1,2,4-triazol-3-amine |
| 480. | [1-[3-fluoro-5-[3-[3-methyl-5-[4-(oxetan-3-yl)piperazin-1-yl]anilino]-1,2,4-triazol-1-yl]phenyl]pyrrolidin-3-yl]methanol |
| 481. | N-[3-[4-(methoxymethyl)-1-piperidyl]-5-methyl-phenyl]-1-phenyl-1,2,4-triazol-3-amine |
| 482. | N-[3-(4-cyclopropylpiperazin-1-yl)-5-methyl-phenyl]-1-(3,5-difluorophenyl)-1,2,4-triazol-3-amine |
| 483. | N-[3-methyl-5-[1-[(3-methyloxetan-3-yl)methyl]-4-piperidyl]phenyl]-1-phenyl-1,2,4-triazol-3-amine |
| 484. | N-[3-methyl-5-[4-(oxetan-3-yl)piperazin-1-yl]phenyl]-1-(2,3,5-trifluorophenyl)-1,2,4-triazol-3-amine |
| 485. | 1-(3,5-difluorophenyl)-N-[3-methyl-5-(3-morpholinoazetidin-1-yl)phenyl]-1,2,4-triazol-3-amine |
| 486. | N-[3-(4-methylpiperazin-1-yl)-5-(trifluoromethyl)phenyl]-1-phenyl-1,2,4-triazol-3-amine |
| 487. | (3R)-3-[3-[[1-(3,5-difluorophenyl)-1,2,4-triazol-3-yl]amino]-5-methyl-phenyl]-1-(oxetan-3-yl)pyrrolidin-3-ol |
| 488. | 1-(6-chloro-2-pyridyl)-N-(3-methyl-5-pyrrolidin-1-yl-phenyl)-1,2,4-triazol-3-amine |
| 489. | N-[3-ethyl-5-[4-(3-methyloxetan-3-yl)piperazin-1-yl]phenyl]-1-pyrazin-2-yl-1,2,4-triazol-3-amine |
| 490. | N1-[1-(3,5-difluorophenyl)-1,2,4-triazol-3-yl]-5-methyl-N3-[(2-methyltetrahydrofuran-2-yl)methyl]benzene-1,3-diamine |
| 491. | 1-[3-fluoro-5-[(2R)-2-(methoxymethyl)pyrrolidin-1-yl]phenyl]-N-[3-methyl-5-[4-(oxetan-3-yl)piperazin-1-yl]phenyl]-1,2,4-triazol-3-amine |
| 493. | [1-[3-[[1-(3,5-difluorophenyl)-1,2,4-triazol-3-yl]amino]-5-methyl-phenyl]azetidin-3-yl]methanol |
| 494. | N-[3-cyclopropyl-5-[4-(oxetan-3-yl)piperazin-1-yl]phenyl]-1-[3-fluoro-5-(3-methoxyazetidin-1-yl)phenyl]-1,2,4-triazol-3-amine |
| 495. | 1-[2-(azepan-1-yl)-4-pyridyl]-N-[3-methyl-5-(4-methylpiperazin-1-yl)phenyl]-1,2,4-triazol-3-amine |
| 496. | N1-[1-(3,5-difluorophenyl)-1,2,4-triazol-3-yl]-5-methyl-N3-(2-tetrahydrofuran-2-ylethyl)benzene-1,3-diamine |
| 497. | 1-(2,4-difluorophenyl)-N-(3-fluoro-5-pyrrolidin-1-yl-phenyl)-1,2,4-triazol-3-amine |
| 499. | 3-[3-[3-methyl-5-(4-methylpiperazin-1-yl)anilino]-1,2,4-triazol-1-yl]benzonitrile |
| 500. | N-[1-[3-[[1-(3,5-difluorophenyl)-1,2,4-triazol-3-yl]amino]-5-methyl-phenyl]pyrrolidin-3-yl]-N-methyl-acetamide |
| 505. | [3-acetoxy-2-[4-[3-[[1-(3,5-difluorophenyl)-1,2,4-triazol-3-yl]amino]-5-methyl-phenyl]piperazin-1-yl]-2-methyl-propyl]acetate |
| 506. | 1-(3,5-difluorophenyl)-N-[3-methyl-5-[3-(oxetan-3-yl)azetidin-1-yl]phenyl]-1,2,4-triazol-3-amine |
| 507. | N-[3-[4-(oxetan-3-yl)-1-piperidyl]-5-(trifluoromethyl)phenyl]-1-pyrazin-2-yl-1,2,4-triazol-3-amine |
| 508. | 1-(3,5-difluorophenyl)-N-[3-methyl-5-(3-oxa-6-azaspiro[3.3]heptan-6-yl)phenyl]-1,2,4-triazol-3-amine |
| 509. | 2-[4-[3-[[1-(3,5-difluorophenyl)-1,2,4-triazol-3-yl]amino]-5-methyl-phenyl]piperazin-1-yl]-2-methyl-propanoic acid |
| 510. | 1-(3,5-difluorophenyl)-N-[3-methyl-5-(3-pyrrolidin-1-ylazetidin-1-yl)phenyl]-1,2,4-triazol-3-amine |
| 511. | N-[3-isopropyl-5-[4-(oxetan-3-yl)piperazin-1-yl]phenyl]-1-pyrimidin-4-yl-1,2,4-triazol-3-amine |
| 513. | N-[3-(6-oxa-3-azabicyclo[3.1.1]heptan-3-yl)-5-(trifluoromethyl)phenyl]-1-pyrazin-2-yl-1,2,4-triazol-3-amine |
| 514. | N-[3-[4-(oxetan-3-yl)piperazin-1-yl]-5-(trifluoromethyl)phenyl]-1-pyrazin-2-yl-1,2,4-triazol-3-amine |
| 515. | 1-(3,5-difluorophenyl)-N-[3-[4-fluoro-1-(oxetan-3-yl)-4-piperidyl]-5-methyl-phenyl]-1,2,4-triazol-3-amine |
| 516. | 4-[3-[[1-(3,5-difluorophenyl)-1,2,4-triazol-3-yl]amino]-5-methyl-phenyl]-1-(oxetan-3-yl)piperidin-4-ol |
| 517. | 3-[3-[[1-(3,5-difluorophenyl)-1,2,4-triazol-3-yl]amino]-5-methyl-phenyl]oxazolidin-2-one |
| 518. | 1-[3-[[1-(3,5-difluorophenyl)-1,2,4-triazol-3-yl]amino]-5-methyl-phenyl]-3-isopropyl-azetidin-3-ol |
| 519. | 2-[1-[3-[[1-(3,5-difluorophenyl)-1,2,4-triazol-3-yl]amino]-5-methyl-phenyl]azetidin-3-yl]propan-2-ol |
| 520. | N3-[1-(3,5-difluorophenyl)-1,2,4-triazol-3-yl]-N1-(3-methoxycyclobutyl)-5-methyl-benzene-1,3-diamine |
| 521. | N-[3-methyl-5-[4-(oxetan-3-yl)-1-piperidyl]phenyl]-1-pyrazin-2-yl-1,2,4-triazol-3-amine |
| 522. | 1-(3-fluorophenyl)-N-[3-methyl-5-[4-(oxetan-3-yl)-1-piperidyl]phenyl]-1,2,4-triazol-3-amine |

-continued

| | |
|---|---|
| 523. | 1-(3-fluorophenyl)-N-[3-isopropyl-5-[4-(oxetan-3-yl)piperazin-1-yl]phenyl]-1,2,4-triazol-3-amine |
| 527. | 1-(3,5-difluorophenyl)-N-[3-methyl-5-(6-oxa-3-azabicyclo[3.1.1]heptan-3-yl)phenyl]-1,2,4-triazol-3-amine |
| 528. | N-[3-(3,3a,4,6,7,7a-hexahydro-2H-furo[3,2-c]pyridin-5-yl)-5-methyl-phenyl]-1-(3,5-difluorophenyl)-1,2,4-triazol-3-amine |
| 530. | 1-(3,5-difluorophenyl)-N-[3-methyl-5-[4-[(3S)-tetrahydrofuran-3-yl]piperazin-1-yl]phenyl]-1,2,4-triazol-3-amine |
| 531. | 1-(3,5-difluorophenyl)-N-[3-methyl-5-[4-[(3R)-tetrahydrofuran-3-yl]piperazin-1-yl]phenyl]-1,2,4-triazol-3-amine |
| 533. | tert-butyl 4-[6-[[1-(3,5-difluorophenyl)-1,2,4-triazol-3-yl]amino]-4-methyl-2-pyridyl]piperazine-1-carboxylate |
| 534. | [2-[4-[3-[[1-(3,5-difluorophenyl)-1,2,4-triazol-3-yl]amino]-5-methyl-phenyl]piperazin-1-yl]-3-hydroxy-2-methyl-propyl]acetate |
| 535. | N-[3-methyl-5-[4-(oxetan-3-yl)piperazin-1-yl]phenyl]-1-pyrimidin-5-yl-1,2,4-triazol-3-amine |
| 536. | N-[3-isopropyl-5-[4-(oxetan-3-yl)piperazin-1-yl]phenyl]-1-pyrazin-2-yl-1,2,4-triazol-3-amine |
| 539. | N-[3-cyclopropyl-5-(3-morpholinoazetidin-1-yl)phenyl]-1-pyrazin-2-yl-1,2,4-triazol-3-amine |
| 541. | 1-(3,5-difluorophenyl)-N-[3-methyl-5-(2-oxa-8-azaspiro[3.5]nonan-8-yl)phenyl]-1,2,4-triazol-3-amine |
| 542. | 1-[1-[3-[[1-(3,5-difluorophenyl)-1,2,4-triazol-3-yl]amino]-5-methyl-phenyl]azetidin-3-yl]pyrrolidin-2-one |
| 543. | 1-(3,5-difluorophenyl)-N-[3-methyl-5-(9-oxa-6-azaspiro[3.5]nonan-6-yl)phenyl]-1,2,4-triazol-3-amine |
| 544. | N-[3-ethyl-5-(3-morpholinoazetidin-1-yl)phenyl]-1-pyrimidin-5-yl-1,2,4-triazol-3-amine |
| 549. | N-[3-ethyl-5-[4-(oxetan-3-yl)piperazin-1-yl]phenyl]-1-pyrimidin-5-yl-1,2,4-triazol-3-amine |
| 550. | N-[3-tert-butyl-5-[4-(oxetan-3-yl)piperazin-1-yl]phenyl]-1-pyrimidin-5-yl-1,2,4-triazol-3-amine |
| 551. | 1-[3-[[1-(3,5-difluorophenyl)-1,2,4-triazol-3-yl]amino]-5-methyl-phenyl]-3-methyl-azetidin-3-ol |
| 552. | 1-(3,5-difluorophenyl)-N-[3-methyl-5-[3-(trifluoromethyl)piperazin-1-yl]phenyl]-1,2,4-triazol-3-amine |
| 553. | 1-[3-[[1-(3,5-difluorophenyl)-1,2,4-triazol-3-yl]amino]-5-methyl-phenyl]-3-ethyl-azetidin-3-ol |
| 557. | tert-butyl 4-[6-[[1-(3,5-difluorophenyl)-1,2,4-triazol-3-yl]amino]-4-(trifluoromethyl)-2-pyridyl]piperazine-1-carboxylate |
| 558. | 1-(2,5-difluorophenyl)-N-(3-methyl-5-piperazin-1-yl-phenyl)-1,2,4-triazol-3-amine |
| 559. | 1-(3,4-difluorophenyl)-N-[3-[4-(oxetan-3-yl)piperazin-1-yl]-5-propyl-phenyl]-1,2,4-triazol-3-amine |
| 561. | 2-[3-[[1-(3,5-difluorophenyl)-1,2,4-triazol-3-yl]amino]-5-methyl-phenyl]-1,3,4,7,8,8a-hexahydropyrrolo[1,2-a]pyrazin-6-one |
| 566. | N-[3-(3,4,6,7,9,9a-hexahydro-1H-pyrazino[2,1-c][1,4]oxazin-8-yl)-5-methyl-phenyl]-1-(3,5-difluorophenyl)-1,2,4-triazol-3-amine |
| 569. | 1-[6-[[1-(3,5-difluorophenyl)-1,2,4-triazol-3-yl]amino]-4-methyl-2-pyridyl]-4-methyl-piperidin-4-ol |
| 573. | N-[3,5-bis(4-tert-butylpiperazin-1-yl)phenyl]-1-(3,5-difluorophenyl)-1,2,4-triazol-3-amine |
| 574. | N-[3,5-bis[4-(oxetan-3-yl)piperazin-1-yl]phenyl]-1-(3,5-difluorophenyl)-1,2,4-triazol-3-amine |
| 575. | N-[3-methyl-5-(2-morpholinoethoxy)phenyl]-1-[3-(trifluoromethyl)phenyl]-1,2,4-triazol-3-amine |
| 577. | 1-(3,4-difluorophenyl)-N-[3-ethyl-5-[4-(3-methyloxetan-3-yl)piperazin-1-yl]phenyl]-1,2,4-triazol-3-amine |
| 581. | 1-(3,5-difluorophenyl)-N-[3-methyl-5-[4-(oxetan-3-yl)morpholin-2-yl]phenyl]-1,2,4-triazol-3-amine |
| 582. | [4-[3-[[1-(3,5-difluorophenyl)-1,2,4-triazol-3-yl]amino]-5-methyl-phenyl]piperazin-1-yl]-morpholino-methanone |
| 583. | N-[3-methyl-5-[[4-(oxetan-3-yl)piperazin-1-yl]methyl]phenyl]-1-pyrazin-2-yl-1,2,4-triazol-3-amine |
| 584. | 1-[3-[[1-(3,5-difluorophenyl)-1,2,4-triazol-3-yl]amino]-5-methyl-phenyl]-N-[(1S)-2-methoxy-1-methyl-ethyl]azetidine-3-carboxamide |
| 585. | N-[3-methyl-5-[4-(3-methyloxetan-3-yl)piperazin-1-yl]phenyl]-1-(3-pyridyl)-1,2,4-triazol-3-amine |
| 586. | 1-(3,5-difluorophenyl)-N-[3-methyl-5-[3-(4-oxa-7-azaspiro[2.5]octan-7-yl)azetidin-1-yl]phenyl]-1,2,4-triazol-3-amine |
| 587. | 1-(3,5-difluorophenyl)-N-[2-fluoro-3-methyl-5-[4-(oxetan-3-yl)piperazin-1-yl]phenyl]-1,2,4-triazol-3-amine |
| 588. | 5-methyl-N1-(5-methylthiazol-2-yl)-N3-(1-phenyl-1,2,4-triazol-3-yl)benzene-1,3-diamine |
| 589. | [1-[3-[[1-(3,5-difluorophenyl)-1,2,4-triazol-3-yl]amino]-5-methyl-phenyl]-4-piperidyl]-morpholino-methanone |
| 590. | 1-(3,4-difluorophenyl)-N-[3-methyl-5-[[1-(oxetan-3-yl)-3-piperidyl]oxy]phenyl]-1,2,4-triazol-3-amine |
| 591. | 1-(3,5-difluorophenyl)-N-[3-isopropoxy-2-methyl-5-[4-(oxetan-3-yl)piperazin-1-yl]phenyl]-1,2,4-triazol-3-amine |
| 592. | 3-[4-(oxetan-3-yl)piperazin-1-yl]-5-[(1-phenyl-1,2,4-triazol-3-yl)amino]benzonitrile |
| 593. | 1-(3,5-difluorophenyl)-N-[3-methyl-5-[4-(2-morpholinoethyl)piperazin-1-yl]phenyl]-1,2,4-triazol-3-amine |
| 594. | N-[3-fluoro-5-[4-(oxetan-3-yl)piperazin-1-yl]phenyl]-1-(3-fluorophenyl)-1,2,4-triazol-3-amine |
| 595. | 1-[3-(difluoromethyl)phenyl]-N-[3-methyl-5-(3-morpholinoazetidin-1-yl)phenyl]-1,2,4-triazol-3-amine |
| 596. | 1-(3,5-difluorophenyl)-N-[3-methyl-5-[[4-(oxetan-3-yl)piperazin-1-yl]methyl]phenyl]-1,2,4-triazol-3-amine |
| 597. | 1-(3-chloro-4-fluoro-phenyl)-N-[3-methyl-5-[4-(oxetan-3-yl)piperazin-1-yl]phenyl]-1,2,4-triazol-3-amine |
| 598. | N-[3-fluoro-5-[4-(oxetan-3-yl)piperazin-1-yl]phenyl]-1-pyrazin-2-yl-1,2,4-triazol-3-amine |
| 602. | 1-(3,5-difluorophenyl)-N-[3-[3-(2,2-dimethylmorpholin-4-yl)azetidin-1-yl]-5-methyl-phenyl]-1,2,4-triazol-3-amine |
| 603. | (5S)-5-methyl-3-[3-methyl-5-[(1-pyrazin-2-yl-1,2,4-triazol-3-yl)amino]phenyl]oxazolidin-2-one |
| 604. | N1-(1-ethyl-1,2,4-triazol-3-yl)-5-methyl-N3-(1-phenyl-1,2,4-triazol-3-yl)benzene-1,3-diamine |
| 605. | 1-(3,5-difluorophenyl)-N-[3-methyl-5-[(1-methylpyrazol-3-yl)methoxy]phenyl]-1,2,4-triazol-3-amine |
| 606. | 1-(4-fluorophenyl)-N-[3-methyl-5-(3-morpholinoazetidin-1-yl)phenyl]-1,2,4-triazol-3-amine |
| 608. | 3-morpholino-5-[(1-phenyl-1,2,4-triazol-3-yl)amino]benzonitrile |
| 609. | N-[3-methyl-5-[4-(oxetan-3-yl)-1,4-diazepan-1-yl]phenyl]-1-(2-pyridyl)-1,2,4-triazol-3-amine |
| 611. | (5S)-5-[3-[[1-(3,5-difluorophenyl)-1,2,4-triazol-3-yl]amino]-5-methyl-phenyl]-3,5-dimethyl-oxazolidin-2-one |
| 613. | 5-[3-[[1-(3,5-difluorophenyl)-1,2,4-triazol-3-yl]amino]-5-methyl-phenyl]-3,5-dimethyl-oxazolidin-2-one |
| 615. | 1-(3,4-difluorophenyl)-N-[3-methyl-5-[(3-methyloxetan-3-yl)methoxy]phenyl]-1,2,4-triazol-3-amine |
| 617. | 1-(3,5-difluorophenyl)-N-[3-[3-(4-fluoro-1-piperidyl)azetidin-1-yl]-5-methyl-phenyl]-1,2,4-triazol-3-amine |
| 618. | 1-(3,5-difluorophenyl)-N-[3-[3-[(2R,6S)-2,6-dimethylmorpholin-4-yl]azetidin-1-yl]-5-methyl-phenyl]-1,2,4-triazol-3-amine |
| 620. | 1-(3,5-difluorophenyl)-N-[3-methyl-5-[[1-(oxetan-3-yl)-3-piperidyl]oxy]phenyl]-1,2,4-triazol-3-amine |
| 622. | 1-(4-fluorophenyl)-N-[3-methyl-5-[4-(oxetan-3-yl)piperazin-1-yl]phenyl]-1,2,4-triazol-3-amine |

| | |
|---|---|
| 623. | 1-(3,5-difluorophenyl)-N-[3-methyl-5-[(2S)-4-(oxetan-3-yl)morpholin-2-yl]phenyl]-1,2,4-triazol-3-amine |
| 624. | 1-(3-fluoro-4-methoxy-phenyl)-N-[3-methyl-5-[4-(oxetan-3-yl)piperazin-1-yl]phenyl]-1,2,4-triazol-3-amine |
| 626. | 1-[4-[3-[[1-(3,4-difluorophenyl)-1,2,4-triazol-3-yl]amino]-5-methyl-phenoxy]-1-piperidyl]ethanone |
| 627. | 1-(3,4-difluorophenyl)-N-[3-methyl-5-(tetrahydropyran-4-ylmethoxy)phenyl]-1,2,4-triazol-3-amine |
| 628. | 1-(3,5-difluorophenyl)-N-[3-methyl-5-[(1R,4R)-2-oxa-5-azabicyclo[2.2.1]heptan-5-yl]phenyl]-1,2,4-triazol-3-amine |
| 629. | 1-(3,5-difluorophenyl)-N-[3-methyl-5-[5-methyl-4-(oxetan-3-yl)morpholin-2-yl]phenyl]-1,2,4-triazol-3-amine |
| 630. | 1-(3,5-difluorophenyl)-N-[2-fluoro-5-methyl-3-[[4-(oxetan-3-yl)piperazin-1-yl]methyl]phenyl]-1,2,4-triazol-3-amine |
| 632. | 1-(3,4-difluorophenyl)-N-[3-methyl-5-[[(3S)-1-(oxetan-3-yl)-3-piperidyl]oxy]phenyl]-1,2,4-triazol-3-amine |
| 633. | 1-(3,4-difluorophenyl)-N-[3-methyl-5-[4-(3-methyloxetan-3-yl)piperazin-1-yl]phenyl]-1,2,4-triazol-3-amine |
| 634. | 1-(3,5-difluorophenyl)-N-[3-methyl-5-[3-(1-piperidyl)azetidin-1-yl]phenyl]-1,2,4-triazol-3-amine |
| 635. | 1-(3,5-difluorophenyl)-N-(3-methyl-5-tetrahydropyran-3-yloxy-phenyl)-1,2,4-triazol-3-amine |
| 637. | 1-(3,5-difluorophenyl)-N-[3-methyl-5-[4-(oxetan-3-yl)-1,4-diazepan-1-yl]phenyl]-1,2,4-triazol-3-amine |
| 638. | 1-(3,4-difluorophenyl)-N-(3-methyl-5-tetrahydropyran-3-yloxy-phenyl)-1,2,4-triazol-3-amine |
| 640. | N-[3-[(3,3-difluorocyclobutyl)methoxy]-5-methyl-phenyl]-1-(3,4-difluorophenyl)-1,2,4-triazol-3-amine |
| 641. | 1-(3,5-difluorophenyl)-N-[3-isopropoxy-2-methyl-5-(3-morpholinoazetidin-1-yl)phenyl]-1,2,4-triazol-3-amine |
| 642. | N-[3-fluoro-5-[4-(oxetan-3-yl)piperazin-1-yl]phenyl]-1-(2-pyridyl)-1,2,4-triazol-3-amine |
| 643. | 5-methyl-N3-(1-phenyl-1,2,4-triazol-3-yl)-N1-thiazol-2-yl-benzene-1,3-diamine |
| 644. | N-[3-methyl-5-(2-pyrazol-1-ylethoxy)phenyl]-1-[3-(trifluoromethyl)phenyl]-1,2,4-triazol-3-amine |
| 646. | 1-(3,5-difluoro-4-methoxy-phenyl)-N-[3-methyl-5-[4-(oxetan-3-yl)piperazin-1-yl]phenyl]-1,2,4-triazol-3-amine |
| 647. | 1-(4-fluoro-3-methyl-phenyl)-N-[3-fluoro-5-[4-(oxetan-3-yl)piperazin-1-yl]phenyl]-1,2,4-triazol-3-amine |
| 648. | 1-(3,5-difluorophenyl)-N-[3-methyl-5-(tetrahydrofuran-3-ylmethoxy)phenyl]-1,2,4-triazol-3-amine |
| 649. | N1-[1-(3,5-difluorophenyl)-1,2,4-triazol-3-yl]-5-methyl-N3-(3-morpholinocyclobutyl)benzene-1,3-diamine |
| 651. | N-[3-methyl-5-(3-morpholinoazetidin-1-yl)phenyl]-1-[3-(trifluoromethyl)phenyl]-1,2,4-triazol-3-amine |
| 652. | 1-(3,5-difluorophenyl)-N-[3-methyl-5-[3-(5-oxa-2-azabicyclo[4.1.0]heptan-2-yl)azetidin-1-yl]phenyl]-1,2,4-triazol-3-amine |
| 653. | 1-(3,5-difluorophenyl)-N-[3-isopropoxy-5-[4-(oxetan-3-yl)piperazin-1-yl]phenyl]-1,2,4-triazol-3-amine |
| 655. | (5R)-5-[3-[[1-(3,5-difluorophenyl)-1,2,4-triazol-3-yl]amino]-5-methyl-phenyl]-5-methyl-oxazolidin-2-one |
| 656. | 3-[[1-(3,4-difluorophenyl)-1,2,4-triazol-3-yl]amino]-5-[4-(oxetan-3-yl)piperazin-1-yl]benzonitrile |
| 657. | N-[3,5-bis(4-methylpiperazin-1-yl)phenyl]-1-(3,5-difluorophenyl)-1,2,4-triazol-3-amine |
| 658. | 5-[3-[[1-(3,5-difluorophenyl)-1,2,4-triazol-3-yl]amino]-5-methyl-phenyl]-5-methyl-oxazolidin-2-one |
| 659. | 1-(3,4-difluorophenyl)-N-[3-methyl-5-[3-(1,4-oxazepan-4-yl)azetidin-1-yl]phenyl]-1,2,4-triazol-3-amine |
| 661. | 1-(3,5-difluorophenyl)-N-[3-[3-(1,1-dioxo-1,4-thiazinan-4-yl)azetidin-1-yl]-5-methyl-phenyl]-1,2,4-triazol-3-amine |
| 662. | N-[3-methoxy-5-[4-(oxetan-3-yl)piperazin-1-yl]phenyl]-1-[3-(trifluoromethyl)phenyl]-1,2,4-triazol-3-amine |
| 663. | 1-(3,5-difluorophenyl)-N-[3-methyl-5-[6-methyl-4-(oxetan-3-yl)morpholin-2-yl]phenyl]-1,2,4-triazol-3-amine |
| 665. | 1-(3,4-difluorophenyl)-N-[3-methyl-5-[[(3R)-1-(oxetan-3-yl)-3-piperidyl]oxy]phenyl]-1,2,4-triazol-3-amine |
| 666. | 3-morpholino-5-[(1-pyrazin-2-yl-1,2,4-triazol-3-yl)amino]benzonitrile |
| 667. | 1-(3,5-difluorophenyl)-N-[3-methyl-5-[(2S)-2-methyl-4-(oxetan-3-yl)morpholin-2-yl]phenyl]-1,2,4-triazol-3-amine |
| 668. | 3-[[1-(3,4-difluorophenyl)-1,2,4-triazol-3-yl]amino]-5-morpholino-benzonitrile |
| 669. | N3-(1-isopropylpyrazol-3-yl)-5-methyl-N1-(1-phenyl-1,2,4-triazol-3-yl)benzene-1,3-diamine |
| 670. | 1-(3,5-difluorophenyl)-N-[3-methyl-5-[3-[(3R)-3-methylmorpholin-4-yl]azetidin-1-yl]phenyl]-1,2,4-triazol-3-amine |
| 671. | N-[3-methyl-5-[(3-methyloxetan-3-yl)methoxy]phenyl]-1-[3-(trifluoromethyl)phenyl]-1,2,4-triazol-3-amine |
| 676. | 5-methyl-N3-(1-methyl-1,2,4-triazol-3-yl)-N1-(1-phenyl-1,2,4-triazol-3-yl)benzene-1,3-diamine |
| 677. | 1-(3,5-difluorophenyl)-N-[3-methyl-5-[(3-methyloxetan-3-yl)methoxy]phenyl]-1,2,4-triazol-3-amine |
| 678. | 3-[[1-(3,5-difluorophenyl)-1,2,4-triazol-3-yl]amino]-5-[4-(oxetan-3-yl)piperazin-1-yl]benzonitrile |
| 679. | (5S)-5-[3-[[1-(3,5-difluorophenyl)-1,2,4-triazol-3-yl]amino]-5-methyl-phenyl]-5-methyl-oxazolidin-2-one |
| 681. | 5-methyl-N1,N3-bis(1-phenyl-1,2,4-triazol-3-yl)benzene-1,3-diamine |
| 682. | (5R)-5-methyl-5-[3-methyl-5-[(1-pyrazin-2-yl-1,2,4-triazol-3-yl)amino]phenyl]oxazolidin-2-one |
| 683. | 1-(3,5-difluorophenyl)-N-[3-methyl-5-(3-methyl-3-morpholino-azetidin-1-yl)phenyl]-1,2,4-triazol-3-amine |
| 686. | N3-[1-(3,5-difluorophenyl)-1,2,4-triazol-3-yl]-5-fluoro-N1-(oxetan-3-yl)benzene-1,3-diamine |
| 687. | 4-[3-[3-methyl-5-[4-(oxetan-3-yl)piperazin-1-yl]anilino]-1,2,4-triazol-1-yl]benzonitrile |
| 688. | N-[3-(2,6-diazaspiro[3.3]heptan-2-yl)-2-fluoro-5-methyl-phenyl]-1-(3,5-difluorophenyl)-1,2,4-triazol-3-amine |
| 690. | [1-[3-[[1-(3,5-difluorophenyl)-1,2,4-triazol-3-yl]amino]-5-methyl-phenyl]azetidin-3-yl]-morpholino-methanone |
| 691. | 1-(3,5-difluorophenyl)-N-[2-fluoro-5-methyl-3-[4-(oxetan-3-yl)piperazin-1-yl]phenyl]-1,2,4-triazol-3-amine |
| 692. | 1-(3,5-difluorophenyl)-N-[3-methyl-5-(8-oxa-3-azabicyclo[3.2.1]octan-3-yl)phenyl]-1,2,4-triazol-3-amine |
| 693. | 1-[3-(difluoromethyl)phenyl]-N-[3-methoxy-5-[4-(oxetan-3-yl)piperazin-1-yl]phenyl]-1,2,4-triazol-3-amine |
| 694. | 1-(3,5-difluorophenyl)-N-[3-methyl-5-(3-oxa-6-azabicyclo[3.1.1]heptan-6-yl)phenyl]-1,2,4-triazol-3-amine |
| 695. | 1-(4-fluorophenyl)-N-[3-methyl-5-[4-(3-methyloxetan-3-yl)piperazin-1-yl]phenyl]-1,2,4-triazol-3-amine |
| 696. | 1-(3,5-difluorophenyl)-N-[3-methyl-5-[3-[(2R)-2-methylmorpholin-4-yl]azetidin-1-yl]phenyl]-1,2,4-triazol-3-amine |
| 697. | 1-(3,5-difluorophenyl)-N-[2,5-dimethyl-3-[4-(oxetan-3-yl)piperazin-1-yl]phenyl]-1,2,4-triazol-3-amine |

| # | Name |
|---|---|
| 698. | 1-(3,4-difluorophenyl)-N-[3-methyl-5-(2-pyrazol-1-ylethoxy)phenyl]-1,2,4-triazol-3-amine |
| 699. | 5-methyl-N3-(5-methyl-1H-pyrazol-3-yl)-N1-(1-phenyl-1,2,4-triazol-3-yl)benzene-1,3-diamine |
| 700. | 1-(3,5-difluorophenyl)-N-[3-methyl-5-[[(3S)-1-(oxetan-3-yl)-3-piperidyl]oxy]phenyl]-1,2,4-triazol-3-amine |
| 701. | 1-(3,5-difluorophenyl)-N-[3-(3-morpholinoazetidin-1-yl)-5-[4-(oxetan-3-yl)piperazin-1-yl]phenyl]-1,2,4-triazol-3-amine |
| 703. | 1-(3,5-difluorophenyl)-N-(3-methyl-5-tetrahydrofuran-3-yloxy-phenyl)-1,2,4-triazol-3-amine |
| 704. | N-[3-methyl-5-(3-morpholinoazetidin-1-yl)phenyl]-1-phenyl-1,2,4-triazol-3-amine |
| 705. | 5-chloro-N3-[1-(3,5-difluorophenyl)-1,2,4-triazol-3-yl]-N1-(oxetan-3-yl)benzene-1,3-diamine |
| 706. | N-[3-[(3,3-difluorocyclobutyl)methoxy]-5-methyl-phenyl]-1-(3,5-difluorophenyl)-1,2,4-triazol-3-amine |
| 708. | 1-(3,5-difluorophenyl)-N-[3-methyl-5-[2-methyl-4-(oxetan-3-yl)morpholin-2-yl]phenyl]-1,2,4-triazol-3-amine |
| 709. | N-[3-(4-tert-butylpiperazin-1-yl)-5-methyl-phenyl]-1-(3,5-difluorophenyl)-1,2,4-triazol-3-amine |
| 710. | 1-(4-methoxyphenyl)-N-[3-methyl-5-[4-(oxetan-3-yl)piperazin-1-yl]phenyl]-1,2,4-triazol-3-amine |
| 711. | 1-[3-[[1-(3,5-difluorophenyl)-1,2,4-triazol-3-yl]amino]-5-methyl-phenyl]-N,N-dimethyl-azetidine-3-carboxamide |
| 714. | 1-(3,4-difluorophenyl)-N-[3-methyl-5-[(1-methylpyrazol-3-yl)methoxy]phenyl]-1,2,4-triazol-3-amine |
| 715. | 1-(3-chloro-4-methyl-phenyl)-N-[3-ethyl-5-[4-(oxetan-3-yl)piperazin-1-yl]phenyl]-1,2,4-triazol-3-amine |
| 716. | |
| 717. | 1-(3,5-difluorophenyl)-N-[3-methyl-5-[3-(8-oxa-3-azabicyclo[3.2.1]octan-3-yl)azetidin-1-yl]phenyl]-1,2,4-triazol-3-amine |
| 720. | 1-(3,4-difluorophenyl)-N-[3-methyl-5-(3-morpholinoazetidin-1-yl)phenyl]-1,2,4-triazol-3-amine |
| 721. | 1-(3-fluorophenyl)-N-[3-methyl-5-(3-morpholinoazetidin-1-yl)phenyl]-1,2,4-triazol-3-amine |
| 722. | 1-(3,5-difluorophenyl)-N-[3-methyl-5-(3-oxa-8-azabicyclo[3.2.1]octan-8-yl)phenyl]-1,2,4-triazol-3-amine |
| 723. | N-[3-chloro-5-(3-morpholinoazetidin-1-yl)phenyl]-1-(3,5-difluorophenyl)-1,2,4-triazol-3-amine |
| 724. | 1-(3,5-difluorophenyl)-N-[3-(2,5-dioxa-8-azaspiro[3.5]nonan-8-yl)-5-methyl-phenyl]-1,2,4-triazol-3-amine |
| 725. | 1-[3-(difluoromethyl)phenyl]-N-[3-methyl-5-(4-morpholino-1-piperidyl)phenyl]-1,2,4-triazol-3-amine |
| 727. | 1-(3,5-difluorophenyl)-N-[3-methyl-5-(2-oxa-5-azabicyclo[2.2.1]heptan-5-yl)phenyl]-1,2,4-triazol-3-amine |
| 730. | 1-(3,5-difluorophenyl)-N-[3-methyl-5-[3-[(2S)-2-methylmorpholin-4-yl]azetidin-1-yl]phenyl]-1,2,4-triazol-3-amine |
| 734. | 3-[3-[3-ethyl-5-[4-(oxetan-3-yl)piperazin-1-yl]anilino]-1,2,4-triazol-1-yl]benzonitrile |
| 735. | 1-(3-fluoro-4-methoxy-phenyl)-N-[3-methyl-5-(3-morpholinoazetidin-1-yl)phenyl]-1,2,4-triazol-3-amine |
| 736. | 1-[3-(difluoromethyl)phenyl]-N-[3-ethyl-5-[4-(oxetan-3-yl)piperazin-1-yl]phenyl]-1,2,4-triazol-3-amine |
| 737. | 3-[[1-(3-fluorophenyl)-1,2,4-triazol-3-yl]amino]-5-morpholino-benzonitrile |
| 738. | N3-[1-(3,5-difluorophenyl)-1,2,4-triazol-3-yl]-N1,5-dimethyl-N1-(2-morpholinoethyl)benzene-1,3-diamine |
| 739. | 1-(3,5-difluorophenyl)-N-[2,3-dimethyl-5-(3-morpholinoazetidin-1-yl)phenyl]-1,2,4-triazol-3-amine |
| 741. | 5-methyl-5-[3-methyl-5-[(1-pyrazin-2-yl-1,2,4-triazol-3-yl)amino]phenyl]oxazolidin-2-one |
| 742. | 1-(3,5-difluorophenyl)-N-[3-methyl-5-[3-(6-oxa-3-azabicyclo[3.1.1]heptan-3-yl)azetidin-1-yl]phenyl]-1,2,4-triazol-3-amine |
| 743. | 1-(3,5-difluorophenyl)-N-[2-fluoro-5-methyl-3-(2-oxa-6-azaspiro[3.3]heptan-6-yl)phenyl]-1,2,4-triazol-3-amine |
| 745. | N-[3-[4-(3,3-difluoroazetidin-1-yl)-1-piperidyl]-5-methyl-phenyl]-1-(3,5-difluorophenyl)-1,2,4-triazol-3-amine |
| 746. | 1-(3,5-difluorophenyl)-N-[3-methyl-5-[3-(3-oxa-8-azabicyclo[3.2.1]octan-8-yl)azetidin-1-yl]phenyl]-1,2,4-triazol-3-amine |
| 747. | 1-(3,5-difluorophenyl)-N-[3-[4-[3-(dimethylamino)propyl]piperazin-1-yl]-5-methyl-phenyl]-1,2,4-triazol-3-amine |
| 748. | 1-(3,5-difluorophenyl)-N-[3-methyl-5-[[(3R)-1-(oxetan-3-yl)-3-piperidyl]oxy]phenyl]-1,2,4-triazol-3-amine |
| 750. | 1-(3,5-difluorophenyl)-N-[3-methyl-5-[(2R)-2-methyl-4-(oxetan-3-yl)morpholin-2-yl]phenyl]-1,2,4-triazol-3-amine |
| 751. | 1-(3,5-difluorophenyl)-N-[3-methyl-5-[(2R)-4-(oxetan-3-yl)morpholin-2-yl]phenyl]-1,2,4-triazol-3-amine |
| 752. | 1-(3,5-difluorophenyl)-N-[3-methyl-5-(3-morpholinocyclobutoxy)phenyl]-1,2,4-triazol-3-amine |
| 753. | N-[3-chloro-5-(3-morpholinoazetidin-1-yl)phenyl]-1-pyrazin-2-yl-1,2,4-triazol-3-amine |
| 754. | 1-[3-fluoro-5-(trifluoromethyl)phenyl]-N-[3-methoxy-5-[4-(oxetan-3-yl)piperazin-1-yl]phenyl]-1,2,4-triazol-3-amine |
| 755. | 1-[6-[[1-(3,5-difluorophenyl)-1,2,4-triazol-3-yl]amino]-4-methyl-2-pyridyl]piperidin-3-ol |
| 757. | 1-[3-fluoro-5-(trifluoromethyl)phenyl]-N-[3-methyl-5-[4-(oxetan-3-yl)piperazin-1-yl]phenyl]-1,2,4-triazol-3-amine |
| 759. | 3-[3-[3-methyl-5-[4-(oxetan-3-yl)piperazin-1-yl]anilino]-1,2,4-triazol-1-yl]benzonitrile |
| 760. | |
| 761. | N-[3-ethyl-5-[4-(oxetan-3-yl)piperazin-1-yl]phenyl]-1-(3-fluoro-4-methyl-phenyl)-1,2,4-triazol-3-amine |
| 762. | 4-[3-[3-ethyl-5-[4-(oxetan-3-yl)piperazin-1-yl]anilino]-1,2,4-triazol-1-yl]benzonitrile |
| 763. | 3-morpholino-5-[[1-(3-pyridyl)-1,2,4-triazol-3-yl]amino]benzonitrile |
| 765. | N3-[1-(3,5-difluorophenyl)-1,2,4-triazol-3-yl]-2-fluoro-5-methyl-N1-tetrahydrofuran-3-yl-benzene-1,3-diamine |
| 766. | N-[3-(3-fluoroazetidin-1-yl)-5-methyl-phenyl]-1-[3-fluoro-5-(2-methoxyethylamino)phenyl]-1,2,4-triazol-3-amine |
| 767. | 1-(3-chloro-4-methyl-phenyl)-N-[3-methyl-5-[4-(oxetan-3-yl)piperazin-1-yl]phenyl]-1,2,4-triazol-3-amine |
| 769. | N-[3-(2-cyclopropylethynyl)-5-methyl-phenyl]-1-(3-fluorophenyl)-1,2,4-triazol-3-amine |
| 771. | 1-(3,5-difluorophenyl)-N-[3-methyl-5-(3,3,4-trimethylpiperazin-1-yl)phenyl]-1,2,4-triazol-3-amine |
| 772. | 1-(3,5-difluorophenyl)-N-[3-methyl-5-[4-(4-methylpiperazin-1-yl)-1-piperidyl]phenyl]-1,2,4-triazol-3-amine |
| 773. | [1-[3-[[1-(3,5-difluorophenyl)-1,2,4-triazol-3-yl]amino]-5-methyl-phenyl]azetidin-3-yl]-pyrrolidin-1-yl-methanone |
| 775. | 3-[3-[[1-(3,5-difluorophenyl)-1,2,4-triazol-3-yl]amino]-5-fluoro-phenyl]oxetan-3-ol |
| 776. | 1-(2-fluoro-4-pyridyl)-N-[3-methyl-5-[4-(oxetan-3-yl)-1,4-diazepan-1-yl]phenyl]-1,2,4-triazol-3-amine |
| 778. | 1-(3,4-difluorophenyl)-N-(3-methyl-5-tetrahydrofuran-3-yloxy-phenyl)-1,2,4-triazol-3-amine |
| 779. | 1-(3-fluoro-4-methoxy-phenyl)-N-[3-fluoro-5-[4-(oxetan-3-yl)piperazin-1-yl]phenyl]-1,2,4-triazol-3-amine |
| 780. | 1-(4-fluoro-3-methyl-phenyl)-N-[3-methyl-5-[4-(oxetan-3-yl)piperazin-1-yl]phenyl]-1,2,4-triazol-3-amine |

| | |
|---|---|
| 781. | 1-(3-fluoro-4-methoxy-phenyl)-N-[3-fluoro-5-[4-(oxetan-3-yl)piperazin-1-yl]phenyl]-1,2,4-triazol-3-amine |
| 782. | 1-(3,5-difluoro-4-methoxy-phenyl)-N-[3-methyl-5-(3-morpholinoazetidin-1-yl)phenyl]-1,2,4-triazol-3-amine |
| 783. | N-[3-fluoro-5-[4-(oxetan-3-yl)piperazin-1-yl]phenyl]-1-(2-fluoro-4-pyridyl)-1,2,4-triazol-3-amine |
| 784. | N-[3-chloro-5-(3-morpholinoazetidin-1-yl)phenyl]-1-(3,4-difluorophenyl)-1,2,4-triazol-3-amine |
| 785. | N-[3-chloro-5-(3-morpholinoazetidin-1-yl)phenyl]-1-(2-pyridyl)-1,2,4-triazol-3-amine |
| 788. | 1-(3,5-difluorophenyl)-N-[3-methyl-5-[3-(2-oxa-5-azabicyclo[2.2.1]heptan-5-yl)azetidin-1-yl]phenyl]-1,2,4-triazol-3-amine |
| 790. | 1-(3,5-difluorophenyl)-N-[2-fluoro-5-methyl-3-(3-morpholinoazetidin-1-yl)phenyl]-1,2,4-triazol-3-amine |
| 791. | 2-[[1-[3-[[1-(3,5-difluorophenyl)-1,2,4-triazol-3-yl]amino]-5-methyl-phenyl]azetidin-3-yl]amino]ethanol |
| 792. | N1-[1-(3,4-difluorophenyl)-1,2,4-triazol-3-yl]-5-methyl-N3-(3-morpholinocyclobutyl)benzene-1,3-diamine |
| 793. | 3-[[1-(3-fluorophenyl)-1,2,4-triazol-3-yl]amino]-5-[4-(oxetan-3-yl)piperazin-1-yl]benzonitrile |
| 794. | 1-[3-(difluoromethyl)phenyl]-N-[3-fluoro-5-[4-(oxetan-3-yl)piperazin-1-yl]phenyl]-1,2,4-triazol-3-amine |
| 796. | (5R)-5-[3-[[1-(3,5-difluorophenyl)-1,2,4-triazol-3-yl]amino]-5-methyl-phenyl]-3,5-dimethyl-oxazolidin-2-one |
| 797. | N3-[1-(3,5-difluorophenyl)-1,2,4-triazol-3-yl]-5-methyl-N1-(3-morpholinocyclobutyl)benzene-1,3-diamine |
| 798. | N-[3-(2-cyclopropylethynyl)-5-methyl-phenyl]-1-(3,5-difluorophenyl)-1,2,4-triazol-3-amine |
| 799. | N3-[1-(3,4-difluorophenyl)-1,2,4-triazol-3-yl]-5-methyl-N1-(3-morpholinocyclobutyl)benzene-1,3-diamine |
| 800. | 1-(3,5-difluorophenyl)-N-[3-methyl-5-[3-[(3S)-3-methylmorpholin-4-yl]azetidin-1-yl]phenyl]-1,2,4-triazol-3-amine |
| 802. | N-[3-ethyl-5-[4-(3-methyloxetan-3-yl)piperazin-1-yl]phenyl]-1-(4-fluorophenyl)-1,2,4-triazol-3-amine |
| 803. | 1-(3,4-difluorophenyl)-N-[3-fluoro-5-[4-(oxetan-3-yl)piperazin-1-yl]phenyl]-1,2,4-triazol-3-amine |
| 804. | N-[3-(difluoromethyl)-5-(3-morpholinoazetidin-1-yl)phenyl]-1-(3,5-difluorophenyl)-1,2,4-triazol-3-amine |
| 805. | 1-[4-[3-[[1-(3,5-difluorophenyl)-1,2,4-triazol-3-yl]amino]-5-methyl-phenoxy]-1-piperidyl]ethanone |
| 808. | 1-(3,5-difluorophenyl)-N-[3-methyl-5-[3-(1,4-oxazepan-4-yl)azetidin-1-yl]phenyl]-1,2,4-triazol-3-amine |
| 809. | 1-(3,5-difluorophenyl)-N-[3-[4-[2-(dimethylamino)ethyl]piperazin-1-yl]-5-methyl-phenyl]-1,2,4-triazol-3-amine |
| 810. | N3-[1-(3,5-difluorophenyl)-1,2,4-triazol-3-yl]-2-fluoro-5-methyl-N1-tetrahydropyran-4-yl-benzene-1,3-diamine |
| 811. | N-[3-isopropoxy-2-methyl-5-(3-morpholinoazetidin-1-yl)phenyl]-1-(2-pyridyl)-1,2,4-triazol-3-amine |
| 812. | 1-(3,5-difluorophenyl)-N-[3-methyl-5-(2-morpholinoethoxy)phenyl]-1,2,4-triazol-3-amine |
| 813. | N-[3-[3-[[1-(3,5-difluorophenyl)-1,2,4-triazol-3-yl]amino]-5-methyl-phenoxy]cyclobutyl]acetamide |
| 814. | 1-(3,5-difluorophenyl)-N-[3-methyl-5-(2-oxa-8-azaspiro[4.5]decan-8-yl)phenyl]-1,2,4-triazol-3-amine |
| 815. | [1-[6-[[1-(3,5-difluorophenyl)-1,2,4-triazol-3-yl]amino]-4-methyl-2-pyridyl]-3-piperidyl]methanol |
| 816. | 1-(3,5-difluorophenyl)-N-[3-[3-(2-methoxyethylamino)azetidin-1-yl]-5-methyl-phenyl]-1,2,4-triazol-3-amine |
| 817. | 1-[3-[[1-(3,5-difluorophenyl)-1,2,4-triazol-3-yl]amino]-5-methyl-phenyl]-N,N-diethyl-azetidine-3-carboxamide |
| 818. | N-[3-methyl-5-[4-(oxetan-3-yl)-1,4-diazepan-1-yl]phenyl]-1-pyrazin-2-yl-1,2,4-triazol-3-amine |
| 819. | N-[3-chloro-5-(3-morpholinoazetidin-1-yl)phenyl]-1-(2-fluoro-4-pyridyl)-1,2,4-triazol-3-amine |
| 820. | 1-(3,5-difluorophenyl)-N-[2,5-dimethyl-3-(3-morpholinoazetidin-1-yl)phenyl]-1,2,4-triazol-3-amine |
| 821. | 1-[6-[[1-(3,5-difluorophenyl)-1,2,4-triazol-3-yl]amino]-4-methyl-2-pyridyl]azetidine-3-carbonitrile |
| 822. | 1-(3,5-difluorophenyl)-N-[3-methyl-5-[(1S,4S)-2-oxa-5-azabicyclo[2.2.1]heptan-5-yl]phenyl]-1,2,4-triazol-3-amine |
| 824. | 1-[3-[[1-(3,5-difluorophenyl)-1,2,4-triazol-3-yl]amino]-5-methyl-phenyl]-N-(2-methoxyethyl)-N-methyl-azetidine-3-carboxamide |
| 825. | N-[3-methyl-5-[3-(1,4-oxazepan-4-yl)azetidin-1-yl]phenyl]-1-pyrazin-2-yl-1,2,4-triazol-3-amine |
| 826. | N1-[1-(3,4-difluorophenyl)-1,2,4-triazol-3-yl]-5-methyl-N3-(3-morpholinocyclobutyl)benzene-1,3-diamine |
| 827. | N-[3-chloro-5-(3-morpholinoazetidin-1-yl)phenyl]-1-(3-fluorophenyl)-1,2,4-triazol-3-amine |
| 828. | 5-methyl-N3-(1-methylpyrazol-3-yl)-N1-(1-phenyl-1,2,4-triazol-3-yl)benzene-1,3-diamine |
| 829. | N-[3-ethyl-5-[4-(oxetan-3-yl)piperazin-1-yl]phenyl]-1-(4-fluoro-3-methyl-phenyl)-1,2,4-triazol-3-amine |
| 830. | 1-(3,5-difluorophenyl)-N-[3-isopropoxy-5-(3-morpholinoazetidin-1-yl)phenyl]-1,2,4-triazol-3-amine |
| 831. | N-[3-[(8aS)-7,7-difluoro-1,3,4,6,8,8a-hexahydropyrrolo[1,2-a]pyrazin-2-yl]-5-methyl-phenyl]-1-(3,5-difluorophenyl)-1,2,4-triazol-3-amine |
| 832. | 1-(3,5-difluorophenyl)-N-[3-methyl-5-(2-pyrazol-1-ylethoxy)phenyl]-1,2,4-triazol-3-amine |
| 833. | 1-[3-(difluoromethyl)phenyl]-N-[3-methyl-5-[4-(oxetan-3-yl)piperazin-1-yl]phenyl]-1,2,4-triazol-3-amine |
| 834. | 1-(3,4-difluorophenyl)-N-[2-fluoro-5-methyl-3-[[4-(oxetan-3-yl)piperazin-1-yl]methyl]phenyl]-1,2,4-triazol-3-amine |
| 835. | 3-[[1-(3,5-difluorophenyl)-1,2,4-triazol-3-yl]amino]-5-morpholino-benzonitrile |
| 836. | 1-(3-fluoro-4-methyl-phenyl)-N-[3-methyl-5-[4-(oxetan-3-yl)piperazin-1-yl]phenyl]-1,2,4-triazol-3-amine |
| 838. | 5-methyl-N1-oxazol-2-yl-N3-(1-phenyl-1,2,4-triazol-3-yl)benzene-1,3-diamine |
| 840. | 1-(3,4-difluorophenyl)-N-[3-methyl-5-[[4-(oxetan-3-yl)piperazin-1-yl]methyl]phenyl]-1,2,4-triazol-3-amine |
| 841. | 1-(4-methoxyphenyl)-N-[3-methyl-5-(3-morpholinoazetidin-1-yl)phenyl]-1,2,4-triazol-3-amine |
| 842. | 3-[4-(oxetan-3-yl)piperazin-1-yl]-5-[[1-(3-pyridyl)-1,2,4-triazol-3-yl]amino]benzonitrile |
| 844. | 1-(3,4-difluorophenyl)-N-[3-methyl-5-(2-morpholinoethoxy)phenyl]-1,2,4-triazol-3-amine |
| 845. | 3,5-dimethyl-5-[3-methyl-5-[(1-pyrazin-2-yl-1,2,4-triazol-3-yl)amino]phenyl]oxazolidin-2-one |
| 849. | 1-(3,5-difluorophenyl)-N-[3-[4-(3-methoxypropyl)piperazin-1-yl]-5-methyl-phenyl]-1,2,4-triazol-3-amine |
| 850. | 1-(3,5-difluorophenyl)-N-[3-methyl-5-(1-oxa-8-azaspiro[4.5]decan-8-yl)phenyl]-1,2,4-triazol-3-amine |
| 851. | 2-[3-fluoro-5-[3-(3-fluoroazetidin-1-yl)-5-methyl-anilino]-1,2,4-triazol-1-yl]anilino]ethanol |
| 853. | N-[3-methyl-5-(4-morpholino-1-piperidyl)phenyl]-1-[3-(trifluoromethyl)phenyl]-1,2,4-triazol-3-amine |
| 855. | 1-(3,5-difluorophenyl)-N-[2-fluoro-5-methyl-3-tetrahydrofuran-3-yloxy-phenyl]-1,2,4-triazol-3-amine |
| 856. | 1-(3,5-difluorophenyl)-N-[3-[3-[(2R,6R)-2,6-dimethylmorpholin-4-yl]azetidin-1-yl]-5-methyl-phenyl]-1,2,4-triazol-3-amine |

| | |
|---|---|
| 857. | N1-[1-(3,5-difluorophenyl)-1,2,4-triazol-3-yl]-5-methyl-N3-(2-morpholinoethyl)benzene-1,3-diamine |
| 860. | N1-[1-(3,5-difluorophenyl)-1,2,4-triazol-3-yl]-5-methyl-N3-(3-morpholinocyclobutyl)benzene-1,3-diamine |
| 861. | N-[3-isopropoxy-2-methyl-5-[4-(oxetan-3-yl)piperazin-1-yl]phenyl]-1-(2-pyridyl)-1,2,4-triazol-3-amine |
| 862. | N-[3-chloro-5-(3-morpholinoazetidin-1-yl)phenyl]-1-pyrimidin-4-yl-1,2,4-triazol-3-amine |
| 863. | [3-[[1-(3,5-difluorophenyl)-1,2,4-triazol-3-yl]amino]-5-methyl-phenyl]-[4-(oxetan-3-yl)piperazin-1-yl]methanone |
| 864. | 1-(3,4-difluorophenyl)-N-[3-methyl-5-(tetrahydrofuran-3-ylmethoxy)phenyl]-1,2,4-triazol-3-amine |
| 865. | 1-(3,5-difluorophenyl)-N-[3-methyl-5-[3-(morpholinomethyl)azetidin-1-yl]phenyl]-1,2,4-triazol-3-amine |
| 867. | N-[3,5-bis(3-morpholinoazetidin-1-yl)phenyl]-1-(3,5-difluorophenyl)-1,2,4-triazol-3-amine |
| 868. | N3-[1-(3,5-difluorophenyl)-1,2,4-triazol-3-yl]-2-fluoro-5-methyl-N1-(3-methyloxetan-3-yl)benzene-1,3-diamine |
| 869. | 1-(3,5-difluorophenyl)-N-[2-fluoro-3-methyl-5-(3-morpholinoazetidin-1-yl)phenyl]-1,2,4-triazol-3-amine |
| 870. | 1-(3,5-difluorophenyl)-N-[3-methyl-5-(3-methyl-4-morpholino-pyrrolidin-1-yl)phenyl]-1,2,4-triazol-3-amine |
| 871. | N3-[1-(3,5-difluorophenyl)-1,2,4-triazol-3-yl]-N1-[2-(3-ethylmorpholin-4-yl)ethyl]-5-methyl-benzene-1,3-diamine |
| 872. | N3-[1-(3,5-difluorophenyl)-1,2,4-triazol-3-yl]-N1-[1-(2-fluoroethyl)-3-piperidyl]-5-methyl-benzene-1,3-diamine |
| 873. | 2-[1-[3-[[1-(3,5-difluorophenyl)-1,2,4-triazol-3-yl]amino]-5-methyl-phenyl]-4-piperidyl]ethanol |
| 874. | 2-[4-[3-[[1-(3,5-difluorophenyl)-1,2,4-triazol-3-yl]amino]-5-methyl-phenyl]piperazin-1-yl]cyclopentanol |
| 875. | N-[3-(2,2,3,3,4,4,5,5,6,6-decadeuterio-1-piperidyl)-5-(difluoromethyl)phenyl]-1-(3,5-difluorophenyl)-1,2,4-triazol-3-amine |
| 876. | 3-[1-[3-[[1-(3,5-difluorophenyl)-1,2,4-triazol-3-yl]amino]-5-methyl-phenyl]-4-piperidyl]propan-1-ol |
| 877. | 2-[4-[3-[[1-(3,5-difluorophenyl)-1,2,4-triazol-3-yl]amino]-5-methyl-phenyl]piperazin-1-yl]cyclohexanol |
| 878. | 1-[1-[3-[[1-(3,5-difluorophenyl)-1,2,4-triazol-3-yl]amino]-5-methyl-phenyl]-4-piperidyl]piperidin-4-ol |
| 879. | N3-[1-(3,5-difluorophenyl)-1,2,4-triazol-3-yl]-5-methyl-N1-[1-(2-morpholinoethyl)pyrrolidin-3-yl]benzene-1,3-diamine |
| 880. | N3-[1-(3,5-difluorophenyl)-1,2,4-triazol-3-yl]-5-methyl-N1-[1-(oxetan-3-yl)azetidin-3-yl]benzene-1,3-diamine |
| 881. | N1-[1-(3,5-difluorophenyl)-1,2,4-triazol-3-yl]-N3-[2-(2,6-dimethylmorpholin-4-yl)propyl]-5-methyl-benzene-1,3-diamine |
| 882. | cyclopropyl-[2,2,3,3,5,5,6,6-octadeuterio-4-[3-[[1-(3,5-difluorophenyl)-1,2,4-triazol-3-yl]amino]-5-(trifluoromethyl)phenyl]piperazin-1-yl]methanone |
| 883. | N3-[1-(3,5-difluorophenyl)-1,2,4-triazol-3-yl]-5-methyl-N1-(3-pyrrolidin-1-yltetrahydropyran-4-yl)benzene-1,3-diamine |
| 884. | 1-(3,5-difluorophenyl)-N-[3-methyl-5-[2,2,3,3,5,5,6,6-octadeuterio-4-(1,4-dioxan-2-ylmethyl)piperazin-1-yl]phenyl]-1,2,4-triazol-3-amine |
| 885. | N-(2-fluoro-5-methyl-3-tetrahydrofuran-3-yloxy-phenyl)-1-(3-fluorophenyl)-1,2,4-triazol-3-amine |
| 886. | 1-[3-[[1-(3,5-difluorophenyl)-1,2,4-triazol-3-yl]amino]-5-methyl-anilino]-N,N-dimethyl-cyclobutanecarboxamide |
| 887. | 1-(3,5-difluorophenyl)-N-[3-methyl-5-(2-tetrahydrofuran-2-ylmorpholin-4-yl)phenyl]-1,2,4-triazol-3-amine |
| 888. | N-[3-(1,4-diazabicyclo[3.2.1]octan-4-yl)-5-methyl-phenyl]-1-(3,5-difluorophenyl)-1,2,4-triazol-3-amine |
| 889. | 1-(3,5-difluorophenyl)-N-[3-methyl-5-(3-tetrahydrofuran-3-ylazetidin-1-yl)phenyl]-1,2,4-triazol-3-amine |
| 890. | N3-[1-(3,5-difluorophenyl)-1,2,4-triazol-3-yl]-5-methyl-N1-[1-(tetrahydrofuran-2-ylmethyl)-4-piperidyl]benzene-1,3-diamine |
| 891. | 1-(3,5-difluorophenyl)-N-[3-methyl-5-[4-(1-methyl-3-piperidyl)piperazin-1-yl]phenyl]-1,2,4-triazol-3-amine |
| 892. | N3-[1-(3,5-difluorophenyl)-1,2,4-triazol-3-yl]-N1-[(4-ethylmorpholin-2-yl)methyl]-5-methyl-benzene-1,3-diamine |
| 893. | N3-[1-(3,5-difluorophenyl)-1,2,4-triazol-3-yl]-N1-[1-(2-methoxyethyl)pyrrolidin-3-yl]-5-methyl-benzene-1,3-diamine |
| 894. | N1-[1-(3,5-difluorophenyl)-1,2,4-triazol-3-yl]-5-methyl-N3-[(2-morpholinocyclopentyl)methyl]benzene-1,3-diamine |
| 895. | 1-(3,5-difluorophenyl)-N-[3-[4-(3-methoxypropyl)-1,4-diazepan-1-yl]-5-methyl-phenyl]-1,2,4-triazol-3-amine |
| 896. | N3-[1-(3,5-difluorophenyl)-1,2,4-triazol-3-yl]-N1-(1-ethyl-3-piperidyl)-5-methyl-benzene-1,3-diamine |
| 897. | N-[3-[4-(3-deuteriooxetan-3-yl)piperazin-1-yl]-5-methyl-phenyl]-1-phenyl-1,2,4-triazol-3-amine |
| 898. | N1-[1-(3,5-difluorophenyl)-1,2,4-triazol-3-yl]-5-methyl-N3-(3,3,3-trifluoro-2-morpholino-propyl)benzene-1,3-diamine |
| 899. | 1-[4-[3-[[1-(3,5-difluorophenyl)-1,2,4-triazol-3-yl]amino]-5-methyl-phenyl]piperazin-1-yl]-3-ethoxy-propan-2-ol |
| 900. | 1-(3,5-difluorophenyl)-N-[3-methyl-5-(1-oxa-7-azaspiro[3.4]octan-7-yl)phenyl]-1,2,4-triazol-3-amine |
| 901. | 2-[4-[3-[[1-(3,5-difluorophenyl)-1,2,4-triazol-3-yl]amino]-5-methyl-phenyl]-2-methyl-piperazin-1-yl]ethanol |
| 902. | N1-[1-(3,5-difluorophenyl)-1,2,4-triazol-3-yl]-N3-[(4-isobutylmorpholin-2-yl)methyl]-5-methyl-benzene-1,3-diamine |
| 903. | 2-[4-[3-[[1-(3,5-difluorophenyl)-1,2,4-triazol-3-yl]amino]-5-methyl-phenyl]piperazin-1-yl]butan-1-ol |
| 904. | 1-cyclopentyl-4-[3-[[1-(3,5-difluorophenyl)-1,2,4-triazol-3-yl]amino]-5-methyl-phenyl]piperazin-2-one |
| 905. | 1-(3,5-difluorophenyl)-N-[3-(3,7-dioxa-10-azaspiro[5.6]dodecan-10-yl)-5-methyl-phenyl]-1,2,4-triazol-3-amine |
| 906. | N-(2-fluoro-5-methyl-3-tetrahydrofuran-3-yloxy-phenyl)-1-phenyl-1,2,4-triazol-3-amine |
| 907. | N-[2-fluoro-5-methyl-3-[4-(oxetan-3-yl)piperazin-1-yl]phenyl]-1-(2-pyridyl)-1,2,4-triazol-3-amine |
| 908. | 1-(3,5-difluorophenyl)-N-[2,3-dimethyl-5-(oxetan-3-ylmethoxy)phenyl]-1,2,4-triazol-3-amine |
| 909. | 1-cyclobutyl-3-[3-methyl-5-[(1-phenyl-1,2,4-triazol-3-yl)amino]phenyl]urea |
| 910. | 1-(3,5-difluorophenyl)-N-[3-methyl-5-(3-morpholino-1-piperidyl)phenyl]-1,2,4-triazol-3-amine |
| 911. | N3-[1-(3,5-difluorophenyl)-1,2,4-triazol-3-yl]-5-methyl-N1-(2-morpholinocyclopentyl)benzene-1,3-diamine |
| 912. | N-(2-fluoro-5-methyl-3-tetrahydrofuran-3-yloxy-phenyl)-1-(3-fluorophenyl)-1,2,4-triazol-3-amine |
| 913. | 1-(3,5-difluorophenyl)-N-[3-methyl-5-[4-(tetrahydrofuran-2-ylmethyl)piperazin-1-yl]phenyl]-1,2,4-triazol-3-amine |
| 914. | N3-[1-(3,5-difluorophenyl)-1,2,4-triazol-3-yl]-2-fluoro-5-methyl-N1-(oxetan-3-yl)benzene-1,3-diamine |
| 915. | 1-(3,5-difluorophenyl)-N-[3-methyl-5-(2,2,3,3,5,5,6,6-octadeuteriopiperazin-1-yl)phenyl]-1,2,4-triazol-3-amine |
| 916. | N3-[1-(3,5-difluorophenyl)-1,2,4-triazol-3-yl]-N1-[2-(2-ethylmorpholin-4-yl)ethyl]-5-methyl-benzene-1,3-diamine |

| # | Name |
|---|---|
| 917. | N1-(2-cyclopropyltetrahydropyran-4-yl)-N3-[1-(3,5-difluorophenyl)-1,2,4-triazol-3-yl]-5-methyl-benzene-1,3-diamine |
| 918. | 1-(3,5-difluorophenyl)-N-[3-methyl-5-[(2S)-2-(morpholinomethyl)pyrrolidin-1-yl]phenyl]-1,2,4-triazol-3-amine |
| 919. | 1-(3,5-difluorophenyl)-N-[3-methyl-5-(2-methyl-4-morpholino-pyrrolidin-1-yl)phenyl]-1,2,4-triazol-3-amine |
| 920. | 2-[1-[3-[[1-(3,5-difluorophenyl)-1,2,4-triazol-3-yl]amino]-5-methyl-phenyl]azetidin-3-yl]acetonitrile |
| 921. | 2-[2,2,3,3,5,5,6,6-octadeuterio-4-[3-[[1-(3,5-difluorophenyl)-1,2,4-triazol-3-yl]amino]-5-methyl-phenyl]piperazin-1-yl]ethanol |
| 922. | [3-acetoxy-2-[4-[3-[[1-(3,5-difluorophenyl)-1,2,4-triazol-3-yl]amino]-2-fluoro-5-methyl-phenyl]piperazin-1-yl]propyl]acetate |
| 923. | 1-(3,5-difluorophenyl)-N-[3-methyl-5-(7-oxa-1-azaspiro[3.5]nonan-1-yl)phenyl]-1,2,4-triazol-3-amine |
| 924. | 1-(3,5-difluorophenyl)-N-[3-methyl-5-[3-methyl-4-(1-methyl-4-piperidyl)piperazin-1-yl]phenyl]-1,2,4-triazol-3-amine |
| 925. | 1-(3,5-difluorophenyl)-N-[3-methyl-5-(2,2,3,3,5,5,6,6-octadeuterio-4-tetrahydropyran-3-yl-piperazin-1-yl)phenyl]-1,2,4-triazol-3-amine |
| 926. | 1-(3,5-difluorophenyl)-N-[3-[2-(isopropoxymethyl)morpholin-4-yl]-5-methyl-phenyl]-1,2,4-triazol-3-amine |
| 927. | N1-[1-(3,5-difluorophenyl)-1,2,4-triazol-3-yl]-5-methyl-N3-[2-(2-methylmorpholin-4-yl)ethyl]benzene-1,3-diamine |
| 928. | N-[3-[4-(1-deuterio-1-methyl-ethyl)piperazin-1-yl]-5-methyl-phenyl]-1-phenyl-1,2,4-triazol-3-amine |
| 929. | N3-[1-(3,5-difluorophenyl)-1,2,4-triazol-3-yl]-N1-[1-(2-methoxyethyl)-4-piperidyl]-5-methyl-benzene-1,3-diamine |
| 930. | N3-[1-(3,5-difluorophenyl)-1,2,4-triazol-3-yl]-5-methyl-N1-(1-methyl-2-morpholino-ethyl)benzene-1,3-diamine |
| 931. | N1-[1-(3,5-difluorophenyl)-1,2,4-triazol-3-yl]-N3-(1,4-dioxan-2-ylmethyl)-5-methyl-benzene-1,3-diamine |
| 932. | 1-(3,5-difluorophenyl)-N-[3-[4-[2-(dimethylamino)ethoxy]-1-piperidyl]-5-methyl-phenyl]-1,2,4-triazol-3-amine |
| 933. | 4-[3-[[1-(3,5-difluorophenyl)-1,2,4-triazol-3-yl]amino]-5-methyl-anilino]-1-(2-methoxyethyl)pyrrolidin-2-one |
| 934. | 1-(3,5-difluorophenyl)-N-[3-methyl-5-[2,2,3,3,5,5,6,6-octadeuterio-4-(2,2-difluoroethyl)piperazin-1-yl]phenyl]-1,2,4-triazol-3-amine |
| 935. | 1-(3,5-difluorophenyl)-N-[3-methyl-5-[4-(tetrahydrofuran-3-ylmethyl)piperazin-1-yl]phenyl]-1,2,4-triazol-3-amine |
| 936. | N1-[1-(3,5-difluorophenyl)-1,2,4-triazol-3-yl]-N3-[[1-(methoxymethyl)cyclopropyl]methyl]-5-methyl-benzene-1,3-diamine |
| 937. | 1-[[3-[[1-(3,5-difluorophenyl)-1,2,4-triazol-3-yl]amino]-5-methyl-anilino]methyl]-N,N-dimethyl-cyclopentanecarboxamide |
| 938. | N3-[1-(3,5-difluorophenyl)-1,2,4-triazol-3-yl]-5-methyl-N1-(2-morpholinocyclohexyl)benzene-1,3-diamine |
| 939. | N1-[1-(3,5-difluorophenyl)-1,2,4-triazol-3-yl]-5-methyl-N3-[2-(1-oxo-1,4-thiazinan-4-yl)ethyl]benzene-1,3-diamine |
| 940. | 1-[4-[3-[[1-(3,5-difluorophenyl)-1,2,4-triazol-3-yl]amino]-5-methyl-phenyl]-2-methyl-piperazin-1-yl]-2-methyl-propan-2-ol |
| 941. | N3-(cyclopropylmethyl)-N1-[1-(3,5-difluorophenyl)-1,2,4-triazol-3-yl]-5-methyl-benzene-1,3-diamine |
| 942. | N1-(1-cyclobutyl-4-piperidyl)-N3-[1-(3,5-difluorophenyl)-1,2,4-triazol-3-yl]-2-fluoro-5-methyl-benzene-1,3-diamine |
| 943. | 1-(3,5-difluorophenyl)-N-[3-methyl-5-[4-(2-pyrrolidin-1-ylethyl)piperazin-1-yl]phenyl]-1,2,4-triazol-3-amine |
| 944. | 1-(3,5-difluorophenyl)-N-[3-methyl-5-[4-(3-pyrrolidin-1-ylpropyl)piperazin-1-yl]phenyl]-1,2,4-triazol-3-amine |
| 945. | 2-[3-[[3-[[1-(3,5-difluorophenyl)-1,2,4-triazol-3-yl]amino]-5-methyl-anilino]methyl]azetidin-1-yl]propane-1,3-diol |
| 946. | 1-(3,5-difluorophenyl)-N-[3-methyl-5-(2,2,3,3,5,5,6,6-octadeuterio-4-ethyl-piperazin-1-yl)phenyl]-1,2,4-triazol-3-amine |
| 947. | 1-[3-[[1-(3,5-difluorophenyl)-1,2,4-triazol-3-yl]amino]-5-methyl-phenyl]-N,N-dimethyl-piperidin-4-amine |
| 948. | 1-(3,5-difluorophenyl)-N-[3-[4-(1,4-dioxan-2-ylmethyl)piperazin-1-yl]-5-methyl-phenyl]-1,2,4-triazol-3-amine |
| 949. | 1-(3,5-difluorophenyl)-N-[3-[4-(2-fluoroethoxy)-1-piperidyl]-5-methyl-phenyl]-1,2,4-triazol-3-amine |
| 950. | N1-[1-(3,5-difluorophenyl)-1,2,4-triazol-3-yl]-5-methyl-N3-[(1-morpholinocyclopropyl)methyl]benzene-1,3-diamine |
| 951. | N-(2-fluoro-5-methyl-3-tetrahydrofuran-3-yloxy-phenyl)-1-pyrazin-2-yl-1,2,4-triazol-3-amine |
| 952. | N3-[1-(3,5-difluorophenyl)-1,2,4-triazol-3-yl]-4-fluoro-5-methyl-N1-tetrahydrofuran-3-yl-benzene-1,3-diamine |
| 953. | 1-(3,5-difluorophenyl)-N-[3-methyl-5-[2-[(4-methylpiperazin-1-yl)methyl]morpholin-4-yl]phenyl]-1,2,4-triazol-3-amine |
| 954. | N-[2-fluoro-5-methyl-3-[4-(oxetan-3-yl)piperazin-1-yl]phenyl]-1-(3-fluorophenyl)-1,2,4-triazol-3-amine |
| 955. | 1-(3,5-difluorophenyl)-N-[3-methyl-5-[4-(1-methyl-4-piperidyl)piperazin-1-yl]phenyl]-1,2,4-triazol-3-amine |
| 956. | 1-[4-[3-[[1-(3,5-difluorophenyl)-1,2,4-triazol-3-yl]amino]-5-methyl-phenyl]piperazin-1-yl]butan-2-ol |
| 957. | 2-[4-[3-[[1-(3,5-difluorophenyl)-1,2,4-triazol-3-yl]amino]-5-methyl-phenyl]morpholin-2-yl]ethanol |
| 958. | 2,2,2-trideuterio-1-[2,2,3,3,5,5,6,6-octadeuterio-4-[3-[[1-(3,5-difluorophenyl)-1,2,4-triazol-3-yl]amino]-5-methyl-phenyl]piperazin-1-yl]ethanone |
| 959. | N3-[1-(3,5-difluorophenyl)-1,2,4-triazol-3-yl]-5-methyl-N1-[1-(morpholinomethyl)propyl]benzene-1,3-diamine |
| 960. | cyclopropyl-[2,2,3,3,5,5,6,6-octadeuterio-4-[3-[[1-(3,5-difluorophenyl)-1,2,4-triazol-3-yl]amino]-5-methyl-phenyl]piperazin-1-yl]methanone |
| 961. | 1-(3,5-difluorophenyl)-N-[3-[4-(2-ethoxyethoxy)-1-piperidyl]-5-methyl-phenyl]-1,2,4-triazol-3-amine |
| 962. | N3-[1-(3,5-difluorophenyl)-1,2,4-triazol-3-yl]-N1-[2-(3-ethylmorpholin-4-yl)ethyl]-2-fluoro-5-methyl-benzene-1,3-diamine |
| 963. | 2-[4-[3-[[1-(3,5-difluorophenyl)-1,2,4-triazol-3-yl]amino]-5-methyl-phenyl]piperazin-1-yl]propan-1-ol |
| 964. | 2-[3-[[1-(3,5-difluorophenyl)-1,2,4-triazol-3-yl]amino]-4,5-dimethyl-phenoxy]-1-pyrrolidin-1-yl-ethanone |
| 965. | N-[3-(2-isopropyl-2,6-diazaspiro[3.3]heptan-6-yl)-5-methyl-phenyl]-1-(3-pyridyl)-1,2,4-triazol-3-amine |
| 966. | N-[3-(2-isopropyl-2,6-diazaspiro[3.3]heptan-6-yl)-5-methyl-phenyl]-1-pyrazin-2-yl-1,2,4-triazol-3-amine |
| 967. | N3-[(4-cyclopropylmorpholin-2-yl)methyl]-N1-[1-(3,5-difluorophenyl)-1,2,4-triazol-3-yl]-5-methyl-benzene-1,3-diamine |
| 968. | N3-[1-(3,5-difluorophenyl)-1,2,4-triazol-3-yl]-2-fluoro-N1,5-dimethyl-N1-(oxetan-3-yl)benzene-1,3-diamine |
| 969. | N3-[1-(3,5-difluorophenyl)-1,2,4-triazol-3-yl]-N1-(2,2-dimethyltetrahydropyran-4-yl)-5-methyl-benzene-1,3-diamine |
| 970. | 1-[3-[3-[[1-(3,5-difluorophenyl)-1,2,4-triazol-3-yl]amino]-4,5-dimethyl-phenoxy]azetidin-1-yl]ethanone |

| | |
|---|---|
| 971. | 1-(3,5-difluorophenyl)-N-[3-methyl-5-(2-tetrahydrofuran-2-ylmorpholin-4-yl)phenyl]-1,2,4-triazol-3-amine |
| 972. | 1-(3,5-difluorophenyl)-N-[3-[4-(2-ethoxyethyl)piperazin-1-yl]-5-methyl-phenyl]-1,2,4-triazol-3-amine |
| 973. | N3-[1-(3,5-difluorophenyl)-1,2,4-triazol-3-yl]-N1-[2-(5-ethyl-2-methyl-morpholin-4-yl)ethyl]-5-methyl-benzene-1,3-diamine |
| 974. | 1-(3,5-difluorophenyl)-N-[3-methyl-5-[3-(4-methylpiperazin-1-yl)azetidin-1-yl]phenyl]-1,2,4-triazol-3-amine |
| 975. | 1-(3,5-difluorophenyl)-N-[3-(4-ethoxy-1-piperidyl)-5-methyl-phenyl]-1,2,4-triazol-3-amine |
| 976. | 1-(3,4-difluorophenyl)-N-[3-(2-isopropyl-2,6-diazaspiro[3.3]heptan-6-yl)-5-methyl-phenyl]-1,2,4-triazol-3-amine |
| 977. | 1-(3,4-difluorophenyl)-N-(2-fluoro-5-methyl-3-tetrahydrofuran-3-yloxy-phenyl)-1,2,4-triazol-3-amine |
| 978. | 1-(3,5-difluorophenyl)-N-[3-methyl-5-[2,2,3,3,5,5,6,6-octadeuterio-4-(oxetan-3-yl)piperazin-1-yl]phenyl]-1,2,4-triazol-3-amine |
| 980. | N-[3-(3,4,4a,5,7,7a-hexahydro-2H-furo[3,4-b]pyridin-1-yl)-5-methyl-phenyl]-1-(3,5-difluorophenyl)-1,2,4-triazol-3-amine |
| 981. | 1-(3,5-difluorophenyl)-N-[3-methyl-5-(2,2,3,3,5,5,6,6-octadeuteriomorpholin-4-yl)phenyl]-1,2,4-triazol-3-amine |
| 982. | 1-(3,5-difluorophenyl)-N-[3-methyl-5-[3-(morpholinomethyl)pyrrolidin-1-yl]phenyl]-1,2,4-triazol-3-amine |
| 983. | 1-(3,5-difluorophenyl)-N-[3-methyl-5-[4-(morpholinomethyl)-1-piperidyl]phenyl]-1,2,4-triazol-3-amine |
| 984. | N3-[1-(3,5-difluorophenyl)-1,2,4-triazol-3-yl]-5-methyl-N1-(2-morpholinobutyl)benzene-1,3-diamine |
| 985. | 1-(3,5-difluorophenyl)-N-[3-methyl-5-[(3S)-3-pyrrolidin-1-ylpyrrolidin-1-yl]phenyl]-1,2,4-triazol-3-amine |
| 986. | N-[3-[4-[2-(diethylamino)ethyl]piperazin-1-yl]-5-methyl-phenyl]-1-(3,5-difluorophenyl)-1,2,4-triazol-3-amine |
| 987. | 1-(3,5-difluorophenyl)-N-[3-methyl-5-[4-(3-methylmorpholin-4-yl)-1-piperidyl]phenyl]-1,2,4-triazol-3-amine |
| 988. | 2-[4-[3-[[1-(3,5-difluorophenyl)-1,2,4-triazol-3-yl]amino]-2-fluoro-5-methyl-phenyl]piperazin-1-yl]propane-1,3-diol |
| 989. | 3-[4-[3-[[1-(3,5-difluorophenyl)-1,2,4-triazol-3-yl]amino]-5-methyl-phenyl]piperazin-1-yl]propan-1-ol |
| 990. | [4-[3-[[1-(3,5-difluorophenyl)-1,2,4-triazol-3-yl]amino]-5-methyl-phenyl]piperazin-1-yl]-tetrahydropyran-4-yl-methanone |
| 991. | N1-[1-(2,2-difluoroethyl)-4-piperidyl]-N3-[1-(3,5-difluorophenyl)-1,2,4-triazol-3-yl]-5-methyl-benzene-1,3-diamine |
| 992. | 2-[3-[[1-(3,5-difluorophenyl)-1,2,4-triazol-3-yl]amino]-5-methyl-anilino]-1-pyrrolidin-1-yl-ethanone |
| 993. | N-[3-(4-cyclobutyl-2,2,3,3,5,5,6,6-octadeuterio-piperazin-1-y1)-5-methyl-phenyl]-1-(3,5-difluorophenyl)-1,2,4-triazol-3-amine |
| 994. | 1-[4-[3-[[1-(3,5-difluorophenyl)-1,2,4-triazol-3-yl]amino]-5-methyl-phenyl]piperazin-1-yl]propan-2-ol |
| 995. | 1-(3,5-difluorophenyl)-N-[3-(5-ethyl-2,5-diazabicyclo[2.2.1]heptan-2-yl)-5-methyl-phenyl]-1,2,4-triazol-3-amine |
| 996. | 1-(3,5-difluorophenyl)-N-[3-methyl-5-[2,2,3,3,5,5,6,6-octadeuterio-4-(3-deuteriooxetan-3-yl)piperazin-1-yl]phenyl]-1,2,4-triazol-3-amine |
| 997. | 1-(3,4-difluorophenyl)-N-[2-fluoro-5-methyl-3-[4-(oxetan-3-yl)piperazin-1-yl]phenyl]-1,2,4-triazol-3-amine |
| 1000. | 1-(3,5-difluorophenyl)-N-[3-[4-(4-methoxybutyl)piperazin-1-yl]-5-methyl-phenyl]-1,2,4-triazol-3-amine |
| 1001. | N-(2-fluoro-5-methyl-3-tetrahydrofuran-3-yloxy-phenyl)-1-phenyl-1,2,4-triazol-3-amine |
| 1002. | N1-[1-(3,5-difluorophenyl)-1,2,4-triazol-3-yl]-N3-[2-(2,5-dimethylmorpholin-4-yl)ethyl]-5-methyl-benzene-1,3-diamine |
| 1003. | N1-[1-(3,5-difluorophenyl)-1,2,4-triazol-3-yl]-5-methyl-N3-[(3-methyl-4,5-dihydroisoxazol-5-yl)methyl]benzene-1,3-diamine |
| 1004. | 1-(3,5-difluorophenyl)-N-[3-[4-(2-isopropoxyethyl)piperazin-1-yl]-5-methyl-phenyl]-1,2,4-triazol-3-amine |
| 1005. | 1-(3,5-difluorophenyl)-N-[3-(4-methoxy-1-piperidyl)-5-methyl-phenyl]-1,2,4-triazol-3-amine |
| 1006. | N3-[1-(3,5-difluorophenyl)-1,2,4-triazol-3-yl]-2-fluoro-5-methyl-N1-(2-morpholinocyclopentyl)benzene-1,3-diamine |
| 1007. | N3-[2-(cyclobutoxy)ethyl]-N1-[1-(3,5-difluorophenyl)-1,2,4-triazol-3-yl]-5-methyl-benzene-1,3-diamine |
| 1008. | 1-(3,4-difluorophenyl)-N-(2-fluoro-5-methyl-3-tetrahydrofuran-3-yloxy-phenyl)-1,2,4-triazol-3-amine |
| 1009. | 1-[3-[[1-(3,5-difluorophenyl)-1,2,4-triazol-3-yl]amino]-5-methyl-phenyl]-4-pyrrolidin-1-yl-pyrrolidin-3-ol |
| 1010. | 1-(3,5-difluorophenyl)-N-[3-[4-(2-methoxyethyl)-3-methyl-piperazin-1-yl]-5-methyl-phenyl]-1,2,4-triazol-3-amine |
| 1011. | 1-(3,5-difluorophenyl)-N-[3-methyl-5-[2-(morpholinomethyl)pyrrolidin-1-yl]phenyl]-1,2,4-triazol-3-amine |
| 1012. | N3-[1-(3,5-difluorophenyl)-1,2,4-triazol-3-yl]-5-methyl-N1-(1-tetrahydropyran-4-yl-4-piperidyl)benzene-1,3-diamine |
| 1013. | 1-(3,5-difluorophenyl)-N-[3-methyl-5-(4-tetrahydrofuran-3-yloxy-1-piperidyl)phenyl]-1,2,4-triazol-3-amine |
| 1014. | 2-[[1-[3-[[1-(3,5-difluorophenyl)-1,2,4-triazol-3-yl]amino]-5-methyl-phenyl]-4-piperidyl]-methyl-amino]ethanol |
| 1015. | N3-[1-(3,5-difluorophenyl)-1,2,4-triazol-3-yl]-4-fluoro-5-methyl-N1-(3-methyloxetan-3-yl)benzene-1,3-diamine |
| 1016. | N-[3-[2-(diethylaminomethyl)morpholin-4-yl]-5-methyl-phenyl]-1-(3,5-difluorophenyl)-1,2,4-triazol-3-amine |
| 1017. | 1-(3,5-difluorophenyl)-N-[3-[2-[(dimethylamino)methyl]morpholin-4-yl]-5-methyl-phenyl]-1,2,4-triazol-3-amine |
| 1018. | 1-(3,5-difluorophenyl)-N-[3-(4-isopropoxy-1-piperidyl)-5-methyl-phenyl]-1,2,4-triazol-3-amine |
| 1019. | N1-[1-(3,5-difluorophenyl)-1,2,4-triazol-3-yl]-5-methyl-N3-[(3-pyrrolidin-1-yloxetan-3-yl)methyl]benzene-1,3-diamine |
| 1020. | N3-[1-(3,5-difluorophenyl)-1,2,4-triazol-3-yl]-4-fluoro-5-methyl-N1-tetrahydropyran-4-yl-benzene-1,3-diamine |
| 1021. | N-[2-fluoro-5-methyl-3-[4-(oxetan-3-yl)piperazin-1-yl]phenyl]-1-(3-pyridyl)-1,2,4-triazol-3-amine |
| 1022. | 1-(3,5-difluorophenyl)-N-[3-methyl-5-[4-(2-methylmorpholin-4-yl)-1-piperidyl]phenyl]-1,2,4-triazol-3-amine |
| 1023. | 1-[4-[3-[[1-(3,5-difluorophenyl)-1,2,4-triazol-3-yl]amino]-5-methyl-phenyl]-3-methyl-piperazin-1-yl]-2-methyl-propan-2-ol |
| 1024. | 1-(3,5-difluorophenyl)-N-[3-[4-(4-ethylpiperazin-1-yl)-1-piperidyl]-5-methyl-phenyl]-1,2,4-triazol-3-amine |
| 1025. | 2-[4-[3-[[1-(3,5-difluorophenyl)-1,2,4-triazol-3-yl]amino]-5-methyl-phenyl]-1-methyl-piperazin-2-yl]ethanol |
| 1026. | 1-(3,5-difluorophenyl)-N-[3-methyl-5-[2-(pyrrolidin-1-ylmethyl)morpholin-4-yl]phenyl]-1,2,4-triazol-3-amine |
| 1027. | 1-(3,5-difluorophenyl)-N-(2-fluoro-5-methyl-3-tetrahydrofuran-3-yloxy-phenyl)-1,2,4-triazol-3-amine |

| | |
|---|---|
| 1028. | N1-[1-(3,5-difluorophenyl)-1,2,4-triazol-3-yl]-N3-[(1-methoxycyclobutyl)methyl]-5-methyl-benzene-1,3-diamine |
| 1029. | 1-(3,5-difluorophenyl)-N-[3-[2-(2-methoxyethyl)morpholin-4-yl]-5-methyl-phenyl]-1,2,4-triazol-3-amine |
| 1030. | 1-[3-[[3-[[1-(3,5-difluorophenyl)-1,2,4-triazol-3-yl]amino]-5-methyl-anilino]methyl]azetidin-1-yl]ethanone |
| 1031. | N-[3-(2,2,3,3,4,4,5,5,6,6-decadeuterio-1-piperidyl)-5-(trifluoromethyl)phenyl]-1-(3,5-difluorophenyl)-1,2,4-triazol-3-amine |
| 1032. | 2-[2-[4-[3-[[1-(3,5-difluorophenyl)-1,2,4-triazol-3-yl]amino]-5-methyl-phenyl]piperazin-1-yl]ethoxy]ethanol |
| 1033. | N-[3-(2-isopropyl-2,6-diazaspiro[3.3]heptan-6-yl)-5-methyl-phenyl]-1-phenyl-1,2,4-triazol-3-amine |
| 1034. | 1-(3,5-difluorophenyl)-N-[3-methyl-5-(4-oxa-7-azaspiro[2.5]octan-7-yl)phenyl]-1,2,4-triazol-3-amine |
| 1035. | 2-[4-[3-[[1-(3,5-difluorophenyl)-1,2,4-triazol-3-yl]amino]-5-methyl-phenyl]piperazin-1-yl]ethanol |
| 1036. | 1-(3,5-difluorophenyl)-N-[3-methyl-5-(3-methylsulfonylazetidin-1-yl)phenyl]-1,2,4-triazol-3-amine |
| 1037. | 1-(3,5-difluorophenyl)-N-[3-methyl-5-(4-pyrrolidin-1-yl-1-piperidyl)phenyl]-1,2,4-triazol-3-amine |
| 1038. | N-[3-[4-(3-deuteriotetrahydrofuran-3-yl)piperazin-1-yl]-5-methyl-phenyl]-1-phenyl-1,2,4-triazol-3-amine |
| 1039. | 1-[1-[3-[[1-(3,5-difluorophenyl)-1,2,4-triazol-3-yl]amino]-5-methyl-phenyl]pyrrolidin-3-yl]pyrrolidin-3-ol |
| 1040. | cyclopropyl-[2,2,3,3,5,5,6,6-octadeuterio-4-[3-(difluoromethyl)-5-[[1-(3,5-difluorophenyl)-1,2,4-triazol-3-yl]amino]phenyl]piperazin-1-yl]methanone |
| 1041. | 1-(3,5-difluorophenyl)-N-[3-methyl-5-(2,2,3,3,5,5,6,6-octadeuterio-4-tetrahydrofuran-3-yl-piperazin-1-yl)phenyl]-1,2,4-triazol-3-amine |
| 1042. | 2-[4-[3-[[1-(3,5-difluorophenyl)-1,2,4-triazol-3-yl]amino]-2-fluoro-5-methyl-phenyl]piperazin-1-yl]ethanol |
| 1043. | 1-[2,2,3,3,5,5,6,6-octadeuterio-4-[3-[[1-(3,5-difluorophenyl)-1,2,4-triazol-3-yl]amino]-5-methyl-phenyl]piperazin-1-yl]ethanone |
| 1044. | N3-[1-(3,5-difluorophenyl)-1,2,4-triazol-3-yl]-5-methyl-N1-[1-(tetrahydrofuran-3-ylmethyl)-4-piperidyl]benzene-1,3-diamine |
| 1045. | N1-[1-(3,5-difluorophenyl)-1,2,4-triazol-3-yl]-5-methyl-N3-[(1-tetrahydropyran-4-yl-4-piperidyl)methyl]benzene-1,3-diamine |
| 1046. | 1-(3,5-difluorophenyl)-N-[3-methyl-5-[4-[(1-methyl-3-piperidyl)methyl]piperazin-1-yl]phenyl]-1,2,4-triazol-3-amine |
| 1047. | N3-[1-(3,5-difluorophenyl)-1,2,4-triazol-3-yl]-N1-(2,6-dioxaspiro[4.5]decan-9-yl)-5-methyl-benzene-1,3-diamine |
| 1048. | 5-methyl-N1-(5-methyloxazol-2-yl)-N3-(1-phenyl-1,2,4-triazol-3-yl)benzene-1,3-diamine |
| 1049. | N3-[1-(3,5-difluorophenyl)-1,2,4-triazol-3-yl]-N1-[1-(2-methoxyethyl)-3-piperidyl]-5-methyl-benzene-1,3-diamine |
| 1050. | 1-(3,5-difluorophenyl)-N-[3-methyl-5-[2-(methylsulfonylmethyl)pyrrolidin-1-yl]phenyl]-1,2,4-triazol-3-amine |
| 1051. | N-(2-fluoro-5-methyl-3-tetrahydrofuran-3-yloxy-phenyl)-1-phenyl-1,2,4-triazol-3-amine |
| 1052. | 1-(3,5-difluorophenyl)-N-(2-fluoro-5-methyl-3-tetrahydrofuran-3-yloxy-phenyl)-1,2,4-triazol-3-amine |
| 1053. | 1-[1-[3-[[1-(3,5-difluorophenyl)-1,2,4-triazol-3-yl]amino]-5-methyl-phenyl]-4-piperidyl]piperidin-3-ol |
| 1054. | 1-(3,4-difluorophenyl)-N-(2-fluoro-5-methyl-3-tetrahydrofuran-3-yloxy-phenyl)-1,2,4-triazol-3-amine |
| 1055. | 1-[4-[3-[[1-(3,5-difluorophenyl)-1,2,4-triazol-3-yl]amino]-5-methyl-phenyl]-2-ethyl-piperazin-1-yl]propan-2-ol |
| 1056. | 1-(3,5-difluorophenyl)-N-[3-methyl-5-(8-oxa-4-azabicyclo[4.2.0]octan-4-yl)phenyl]-1,2,4-triazol-3-amine |
| 1057. | N-[3-methyl-5-[(1-phenyl-1,2,4-triazol-3-yl)amino]phenyl]cyclopropanecarboxamide |
| 1058. | N1-(1-cyclopropylethyl)-N3-[1-(3,5-difluorophenyl)-1,2,4-triazol-3-yl]-5-methyl-benzene-1,3-diamine |
| 1059. | 1-(3,5-difluorophenyl)-N-[3-methyl-5-(3-pyrrolidin-1-ylpyrrolidin-1-yl)phenyl]-1,2,4-triazol-3-amine |
| 1060. | N-(2-fluoro-5-methyl-3-tetrahydrofuran-3-yloxy-phenyl)-1-(3-fluorophenyl)-1,2,4-triazol-3-amine |
| 1061. | N1-[1-(3,5-difluorophenyl)-1,2,4-triazol-3-yl]-5-methyl-N3-[(4-methylmorpholin-3-yl)methyl]benzene-1,3-diamine |
| 1062. | 1-(3,5-difluorophenyl)-N-[3-[4-(2-ethoxyethyl)-3-methyl-piperazin-1-yl]-5-methyl-phenyl]-1,2,4-triazol-3-amine |
| 1063. | N3-[1-(3,5-difluorophenyl)-1,2,4-triazol-3-yl]-5-methyl-N1-(1-tetrahydrofuran-3-yl-4-piperidyl)benzene-1,3-diamine |
| 1064. | N3-[1-(3,5-difluorophenyl)-1,2,4-triazol-3-yl]-N1-(2-methoxycyclopentyl)-5-methyl-benzene-1,3-diamine |
| 1065. | 1-(3,4-difluorophenyl)-N-[3-methyl-5-(2,2,3,3,5,5,6,6-octadeuteriomorpholin-4-yl)phenyl]-1,2,4-triazol-3-amine |
| 1066. | 4-[3-[[1-(3,5-difluorophenyl)-1,2,4-triazol-3-yl]amino]-5-methyl-phenyl]-1-(2-methoxyethyl)piperazin-2-one |
| 1067. | 1-(3,5-difluorophenyl)-N-[3-[4-(4-methoxy-1-piperidyl)-1-piperidyl]-5-methyl-phenyl]-1,2,4-triazol-3-amine |
| 1069. | N1-(1-cyclobutyl-4-piperidyl)-N3-[1-(3,5-difluorophenyl)-1,2,4-triazol-3-yl]-5-methyl-benzene-1,3-diamine |
| 1070. | 1-(3-fluorophenyl)-N-[3-(2-isopropyl-2,6-diazaspiro[3.3]heptan-6-yl)-5-methyl-phenyl]-1,2,4-triazol-3-amine |
| 1071. | 1-(3,5-difluorophenyl)-N-[2-fluoro-3-(2-isopropyl-2,6-diazaspiro[3.3]heptan-6-yl)-5-methyl-phenyl]-1,2,4-triazol-3-amine |
| 1072. | [4-[3-[[1-(3,5-difluorophenyl)-1,2,4-triazol-3-yl]amino]-5-methyl-phenyl]morpholin-2-yl]methanol |
| 1073. | 1-(3,5-difluorophenyl)-N-[3-methyl-5-[4-(2-pyrrolidin-1-ylethoxy)-1-piperidyl]phenyl]-1,2,4-triazol-3-amine |
| 1074. | 1-[3-[3-[[1-(3,5-difluorophenyl)-1,2,4-triazol-3-yl]amino]-5-methyl-anilino]-3-methyl-azetidin-1-yl]-2-methoxy-ethanone |
| 1075. | 1-[3-[[1-(3,5-difluorophenyl)-1,2,4-triazol-3-yl]amino]-5-methyl-phenyl]-3-methyl-azetidine-3-carbonitrile |
| 1076. | [1-[[1-[3-[[1-(3,5-difluorophenyl)-1,2,4-triazol-3-yl]amino]-5-methyl-phenyl]pyrrolidin-2-yl]methyl]pyrrolidin-2-yl]methanol |
| 1077. | 1-[4-[3-[[1-(3,5-difluorophenyl)-1,2,4-triazol-3-yl]amino]-5-methyl-phenyl]piperazin-1-yl]-3-(dimethylamino)propan-2-ol |
| 1078. | [1-[3-[[1-(3,5-difluorophenyl)-1,2,4-triazol-3-yl]amino]-5-methyl-phenyl]-3-fluoro-azetidin-3-yl]methanol |
| 1079. | 5-deuterio-1-(3,5-difluorophenyl)-N-[3-methyl-5-[4-(oxetan-3-yl)piperazin-1-yl]phenyl]-1,2,4-triazol-3-amine |
| 1080. | 1-(3,5-difluorophenyl)-N-[3-(2-isopropyl-2,6-diazaspiro[3.3]heptan-6-yl)-5-methyl-phenyl]-1,2,4-triazol-3-amine |
| 1081. | N1-[1-(3,5-difluorophenyl)-1,2,4-triazol-3-yl]-5-methyl-N3-[2-(3-methylmorpholin-4-yl)ethyl]benzene-1,3-diamine |
| 1082. | 1-(3,5-difluorophenyl)-N-[3-methyl-5-(3-tetrahydrofuran-3-ylpyrrolidin-1-yl)phenyl]-1,2,4-triazol-3-amine |
| 1083. | tert-butyl 3-[[3-[[1-(3,5-difluorophenyl)-1,2,4-triazol-3-yl]amino]-5-methyl-anilino]methyl]azetidine-1-carboxylate |
| 1084. | N-[2-fluoro-5-methyl-3-[4-(oxetan-3-yl)piperazin-1-yl]phenyl]-1-phenyl-1,2,4-triazol-3-amine |

| | |
|---|---|
| 1085. | N-[3-methyl-5-[4-[1,2,2,2-tetradeuterio-1-(trideuteriomethyl)ethyl]piperazin-1-yl]phenyl]-1-phenyl-1,2,4-triazol-3-amine |
| 1086. | N-[3-[2-(cyclopropylmethoxymethyl)morpholin-4-yl]-5-methyl-phenyl]-1-(3,5-difluorophenyl)-1,2,4-triazol-3-amine |
| 1090. | 5-deuterio-N-[3-methyl-5-[4-(oxetan-3-yl)piperazin-1-yl]phenyl]-1-[3-(trifluoromethyl)phenyl]-1,2,4-triazol-3-amine |
| 1091. | 2-[1-[3-[[5-deuterio-1-(3,5-difluorophenyl)-1,2,4-triazol-3-yl]amino]-5-methyl-phenyl]azetidin-3-yl]propan-2-ol |
| 1093. | 2-[3-[[1-(3,5-difluorophenyl)-1,2,4-triazol-3-yl]amino]-4,5-dimethyl-phenoxy]-1-morpholino-ethanone |
| 1094. | N-[3-(2,2,3,3,4,4,5,5,6,6-decadeuterio-1-piperidyl)-5-(trifluoromethyl)phenyl]-1-(3,4-difluorophenyl)-1,2,4-triazol-3-amine |
| 1095. | cyclopropyl-[2,2,3,3,5,5,6,6-octadeuterio-4-[3-(difluoromethyl)-5-[[1-(3,4-difluorophenyl)-1,2,4-triazol-3-yl]amino]phenyl]piperazin-1-yl]methanone |
| 1096. | 1-(3,5-difluorophenyl)-N-[3-methyl-5-[3-(2,2,3,3,5,5,6,6-octadeuteriomorpholin-4-yl)azetidin-1-yl]phenyl]-1,2,4-triazol-3-amine |
| 1097. | 1-(3,4-difluorophenyl)-N-[3-methyl-5-[3-(2,2,3,3,5,5,6,6-octadeuteriomorpholin-4-yl)azetidin-1-yl]phenyl]-1,2,4-triazol-3-amine |
| 1098. | N-[3-(2,2,3,3,4,4,5,5,6,6-decadeuterio-1-piperidyl)-5-(difluoromethyl)phenyl]-1-(3,4-difluorophenyl)-1,2,4-triazol-3-amine |
| 1099. | cyclopropyl-[2,2,3,3,5,5,6,6-octadeuterio-4-[3-[[1-(3,4-difluorophenyl)-1,2,4-triazol-3-yl]amino]-5-(trifluoromethyl)phenyl]piperazin-1-yl]methanone |
| 1100. | N-[3-(2,2,3,3,4,4,5,5,6,6-decadeuterio-1-piperidyl)-5-(trifluoromethyl)phenyl]-1-(3-fluorophenyl)-1,2,4-triazol-3-amine |
| 1101. | N-[3-(2,2,3,3,4,4,5,5,6,6-decadeuterio-1-piperidyl)-5-(difluoromethyl)phenyl]-1-(3-fluorophenyl)-1,2,4-triazol-3-amine |
| 1102. | cyclopropyl-[2,2,3,3,5,5,6,6-octadeuterio-4-[3-[[1-(3-fluorophenyl)-1,2,4-triazol-3-yl]amino]-5-(trifluoromethyl)phenyl]piperazin-1-yl]methanone |
| 1103. | cyclopropyl-[2,2,3,3,5,5,6,6-octadeuterio-4-[3-(difluoromethyl)-5-[[1-(3-fluorophenyl)-1,2,4-triazol-3-yl]amino]phenyl]piperazin-1-yl]methanone |
| 1104. | N-[3-(2,2,3,3,4,4,5,5,6,6-decadeuterio-1-piperidyl)-5-(trifluoromethyl)phenyl]-1-pyrazin-2-yl-1,2,4-triazol-3-amine |
| 1105. | N-[3-(2,2,3,3,4,4,5,5,6,6-decadeuterio-1-piperidyl)-5-(difluoromethyl)phenyl]-1-pyrazin-2-yl-1,2,4-triazol-3-amine |
| 1106. | cyclopropyl-[2,2,3,3,5,5,6,6-octadeuterio-4-[3-(difluoromethyl)-5-[(1-pyrazin-2-yl-1,2,4-triazol-3-yl)amino]phenyl]piperazin-1-yl]methanone |
| 1107. | N-[3-methyl-5-[4-(oxetan-3-yl)piperazin-1-yl]phenyl]-1-(2,3,4,5,6-pentadeuteriophenyl)-1,2,4-triazol-3-amine |
| 1108. | N3-benzyl-N1-[1-(3,5-difluorophenyl)-1,2,4-triazol-3-yl]-2-fluoro-5-methyl-benzene-1,3-diamine |
| 1109. | N-[3-[4-(3-deuteriooxetan-3-yl)piperazin-1-yl]-5-methyl-phenyl]-1-(3,5-difluorophenyl)-1,2,4-triazol-3-amine |
| 1110. | N-[3-methyl-5-(2,2,3,3,5,5,6,6-octadeuterio-4-methyl-piperazin-1-yl)phenyl]-1-phenyl-1,2,4-triazol-3-amine |
| 1111. | [4-[3-[[1-(3,5-difluorophenyl)-1,2,4-triazol-3-yl]amino]-2-fluoro-5-methyl-phenyl]piperazin-1-yl]-tetrahydropyran-4-yl-methanone |
| 1112. | 1-(3,5-difluorophenyl)-N-[2-fluoro-5-methyl-3-[3-methyl-4-(1-methyl-4-piperidyl)piperazin-1-yl]phenyl]-1,2,4-triazol-3-amine |
| 1113. | N3-[1-(3,5-difluorophenyl)-1,2,4-triazol-3-yl]-N1-[2-(2-ethylmorpholin-4-yl)ethyl]-2-fluoro-5-methyl-benzene-1,3-diamine |
| 1114. | N3-[1-(3,5-difluorophenyl)-1,2,4-triazol-3-yl]-2-fluoro-5-methyl-N1-[1-(tetrahydrofuran-3-ylmethyl)-4-piperidyl]benzene-1,3-diamine |
| 1115. | N3-[1-(3,5-difluorophenyl)-1,2,4-triazol-3-yl]-2-fluoro-5-methyl-N1-[1-(tetrahydrofuran-2-ylmethyl)-4-piperidyl]benzene-1,3-diamine |
| 1116. | 1-(3,5-difluorophenyl)-N-[2-fluoro-5-methyl-3-[3-(4-methylpiperazin-1-yl)azetidin-1-yl]phenyl]-1,2,4-triazol-3-amine |
| 1117. | N3-[(4-cyclopropylmorpholin-2-yl)methyl]-N1-[1-(3,5-difluorophenyl)-1,2,4-triazol-3-yl]-2-fluoro-5-methyl-benzene-1,3-diamine |
| 1118. | N3-[1-(3,5-difluorophenyl)-1,2,4-triazol-3-yl]-2-fluoro-5-methyl-N1-(1-methyl-2-morpholino-ethyl)benzene-1,3-diamine |
| 1119. | 1-(3,5-difluorophenyl)-N-[2-fluoro-3-[2-(isopropoxymethyl)morpholin-4-yl]-5-methyl-phenyl]-1,2,4-triazol-3-amine |
| 1120. | N1-[1-(3,5-difluorophenyl)-1,2,4-triazol-3-yl]-2-fluoro-5-methyl-N3-[(1-morpholinocyclopropyl)methyl]benzene-1,3-diamine |
| 1121. | 1-(3,5-difluorophenyl)-N-[2-fluoro-5-methyl-3-(3-tetrahydrofuran-3-ylazetidin-1-yl)phenyl]-1,2,4-triazol-3-amine |
| 1122. | 1-[4-[3-[[1-(3,5-difluorophenyl)-1,2,4-triazol-3-yl]amino]-2-fluoro-5-methyl-phenyl]-2-methyl-piperazin-1-yl]-2-methyl-propan-2-ol. |

\* \* \* \* \*